United States Patent
Shim et al.

(10) Patent No.: US 11,130,747 B2
(45) Date of Patent: Sep. 28, 2021

(54) PLURALITY OF HOST MATERIALS AND AN ORGANIC ELECTROLUMINESCENCE DEVICE COMPRISING THE SAME

(71) Applicant: Rohm and Haas Electronic Materials Korea Ltd., Cheonan (KR)

(72) Inventors: Jae-Hoon Shim, Seoul (KR); Kyoung-Jin Park, Seongnam (KR); Yoo-Jin Doh, Seoul (KR); Bitnari Kim, Cheonan (KR)

(73) Assignee: Rohm and Haas Electronic Materials Korea Ltd, Seoul (KR)

( * ) Notice: Subject to any disclaimer, the term of this patent is extended or adjusted under 35 U.S.C. 154(b) by 0 days.

(21) Appl. No.: 15/525,077

(22) PCT Filed: Nov. 11, 2015

(86) PCT No.: PCT/KR2015/012119
§ 371 (c)(1),
(2) Date: May 8, 2017

(87) PCT Pub. No.: WO2016/076629
PCT Pub. Date: May 19, 2016

(65) Prior Publication Data
US 2017/0342057 A1    Nov. 30, 2017

(30) Foreign Application Priority Data

Nov. 11, 2014 (KR) .......... 10-2014-0156301
Nov. 10, 2015 (KR) .......... 10-2015-0157677

(51) Int. Cl.
| H01L 51/50 | (2006.01) |
| C07D 403/10 | (2006.01) |
| C07D 403/14 | (2006.01) |
| C07D 405/14 | (2006.01) |
| C07D 409/14 | (2006.01) |
| C07D 487/04 | (2006.01) |
| C07D 495/04 | (2006.01) |
| C07F 7/08 | (2006.01) |
| C09K 11/06 | (2006.01) |
| H01L 51/00 | (2006.01) |
| H05B 33/14 | (2006.01) |

(52) U.S. Cl.
CPC ......... *C07D 403/10* (2013.01); *C07D 403/14* (2013.01); *C07D 405/14* (2013.01); *C07D 409/14* (2013.01); *C07D 487/04* (2013.01); *C07D 495/04* (2013.01); *C07F 7/0812* (2013.01); *C09K 11/06* (2013.01); *H01L 51/0067* (2013.01); *H01L 51/0071* (2013.01); *H01L 51/0072* (2013.01); *H01L 51/0073* (2013.01); *H01L 51/0085* (2013.01); *H05B 33/14* (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| 9,126,970 | B2 | 9/2015 | Pflumm et al. |
| 2010/0096982 | A1 | 4/2010 | Eum et al. |
| 2014/0077179 | A1 | 3/2014 | Shin et al. |
| 2014/0364625 | A1 | 12/2014 | Ahn et al. |
| 2015/0105563 | A1 | 4/2015 | Ahn et al. |
| 2015/0218441 | A1 | 8/2015 | Cho et al. |
| 2015/0337197 | A1 | 11/2015 | Jatsch et al. |

FOREIGN PATENT DOCUMENTS

| JP | 3139321 B2 | 2/2001 | |
| JP | 2013-183036 A | 9/2013 | |
| KR | 2012-0013173 A | 2/2012 | |
| KR | 101170666 B1 | 8/2012 | |
| WO | 2009/060757 A1 | 5/2009 | |
| WO | WO 2011/025282 * | 3/2011 | ............ C09K 11/06 |
| WO | 2013/112557 A1 | 8/2013 | |
| WO | 2013/154325 A1 | 10/2013 | |
| WO | 2013/168688 A1 | 11/2013 | |
| WO | 2014/129869 A1 | 8/2014 | |
| WO | 2014204464 A1 | 12/2014 | |
| WO | 2015/099507 A1 | 7/2015 | |
| WO | 2015167259 A1 | 11/2015 | |

* cited by examiner

*Primary Examiner* — Gregory D Clark
(74) *Attorney, Agent, or Firm* — S. Matthew Cairns

(57) ABSTRACT

The present invention relates to a plurality of host materials and an organic electroluminescent device comprising the same. By comprising a specific combination of a plurality of host compounds, the organic electroluminescent device according to the present invention provides high efficiency and long lifespan.

10 Claims, No Drawings

PLURALITY OF HOST MATERIALS AND AN ORGANIC ELECTROLUMINESCENCE DEVICE COMPRISING THE SAME

TECHNICAL FIELD

The present invention relates to a plurality of host materials and an organic electroluminescence device comprising the same.

BACKGROUND ART

An electroluminescence device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

An organic EL device (OLED) is a device changing electrical energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, luminescent organic compounds reach an excited state, and light emission occurs by emitting light from energy due to the excited state of the luminescent organic compounds returning to a ground state.

The most important factor determining luminous efficiency in an organic EL device is light-emitting materials. A light-emitting material must have high quantum efficiency, high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material, which acts as a solvent in a solid state and transfers energy, needs to have high purity and a molecular weight appropriate for vacuum deposition. Furthermore, the host material needs to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

A light-emitting material can be used as a combination of a host and a dopant to improve color purity, luminous efficiency, and stability. Generally, an EL device having excellent characteristics has a structure comprising a light-emitting layer formed by doping a dopant to a host. Since host materials greatly influence the efficiency and lifespan of the EL device when using a dopant/host material system as a light-emitting material, their selection is important.

International Publication No. WO 2013/168688 A1, Japanese Patent No. 3139321, Korean Patent No. 10-1170666, Korean Patent Application Laying-Open No. 10-2012-0013173, International Publication Nos. WO 2013/112557 A1 and WO 2009/060757 A1, and Japanese Patent Application Laying-Open No. 2013-183036 A disclose an organic electroluminescent device comprising a dopant/host material system, and use a compound of biscarbazole structure as a host. However, the aforementioned references fail to disclose an organic electroluminescent device using plural hosts comprising a biscarbazole compound fused with indene, indole, benzofuran, or benzothiophene, and a carbazole derivative comprising a nitrogen-containing heteroaryl.

DISCLOSURE OF THE INVENTION

Problems to be Solved

The objective of the present invention is to provide an organic electroluminescent device having high efficiency and long lifespan.

Solution to Problems

The present inventors found that the above objective can be achieved by an organic electroluminescent device comprising at least one light-emitting layer between an anode and a cathode, wherein the light-emitting layer comprises a host and a phosphorescent dopant, the host comprises plural host compounds, at least a first host compound of the plural host compounds is represented by the following formula 1, and a second host compound is represented by the following formula 2:

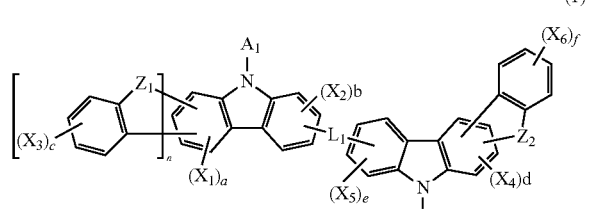

(1)

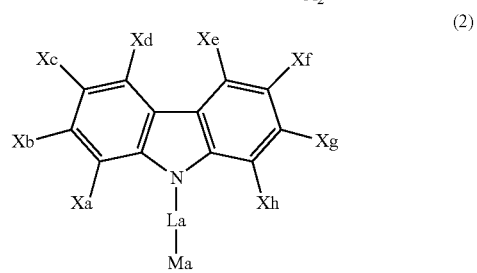

(2)

wherein $A_1$ and $A_2$ each independently represent a substituted or unsubstituted (C6-C30)aryl;

n represents an integer of 0 or 1;

where n is 1, a 5-membered ring including $Z_1$ is fused with the phenyl ring of carbazole;

a 5-membered ring including $Z_2$ is fused with the phenyl ring of carbazole;

$L_1$ and La each independently represent a single bond, or a substituted or unsubstituted (C6-C30)arylene;

$Z_1$ and $Z_2$ each independently represent $CR_1R_2$, $NR_3$, O, or S;

$X_1$ to $X_6$, and $R_1$ to $R_3$ each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur;

Ma represents a substituted or unsubstituted 5- to 30-membered nitrogen-containing heteroaryl;

Xa to Xh each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur;

a and d each independently represent an integer of 1 to 2, b and e each independently represent an integer of 1 to 3, c and f each independently represent an integer of 1 to 4, where a, b, c, d, e, or f is an integer of 2 or more, each of $X_1$, each of $X_2$, each of $X_3$, each of $X_4$, each of $X_5$, and each of $X_6$ may be the same or different; and the heteroaryl contains at least one hetero atom selected from B, N, O, S, Si, and P.

Effects of the Invention

According to the present invention, an organic electroluminescent device having high efficiency and long lifespan is provided, and a display device or a lighting device using the organic electroluminescent device can be manufactured.

EMBODIMENTS OF THE INVENTION

Hereinafter, the present invention will be described in detail. However, the following description is intended to explain the invention, and is not meant in any way to restrict the scope of the invention.

The compound represented by formula 1 can be represented by one of the following formulas 3 to 6:

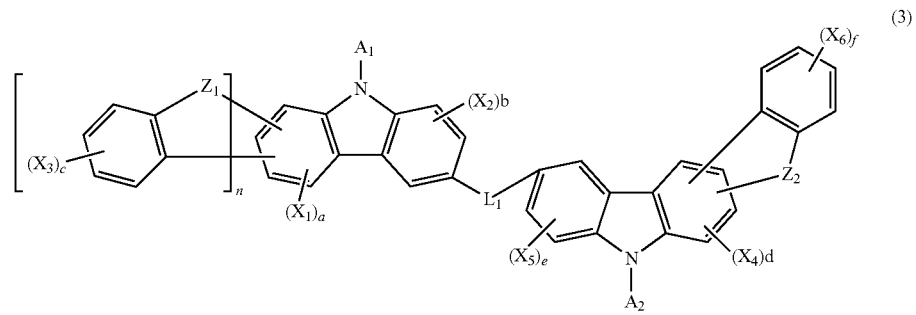

(3)

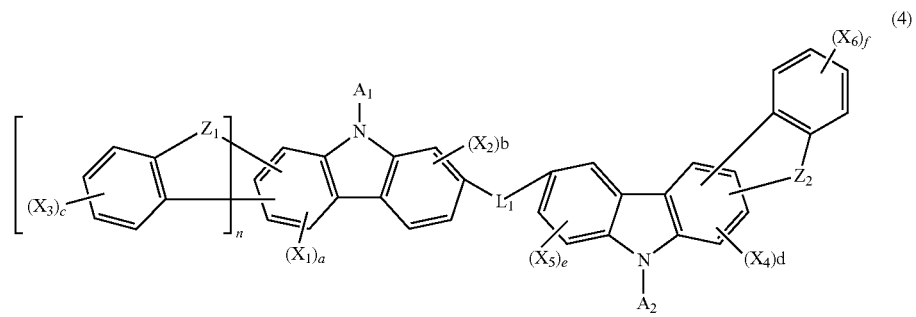

(4)

(5)

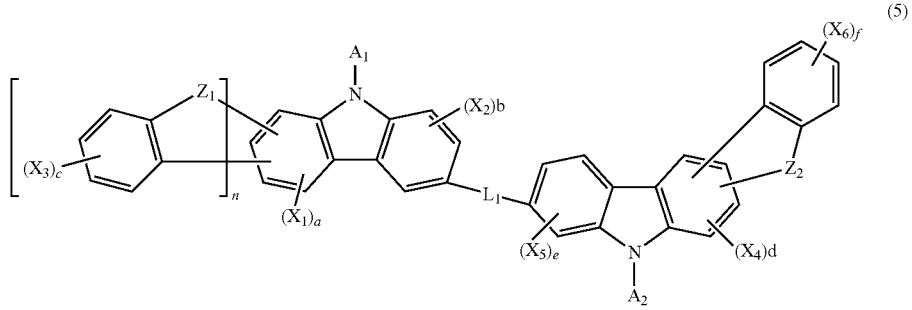

(6)

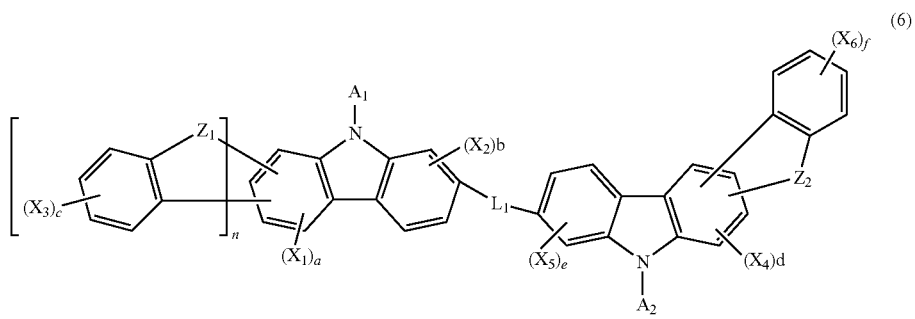

wherein $A_1$, $A_2$, $Z_1$, $Z_2$, $L_1$, $X_1$ to $X_6$, and a to f are as defined in formula 1.

In formula 1 above, $A_1$ and $A_2$ each independently represent a substituted or unsubstituted (C6-C30)aryl; preferably each independently represent a substituted or unsubstituted (C6-C18)aryl; more preferably each independently represent a (C6-C18)aryl unsubstituted or substituted with a cyano, a (C1-C6)alkyl, a (C6-C12)aryl, or a tri(C6-C12)arylsilyl; and even more preferably each independently represent phenyl, biphenyl, terphenyl, naphthyl, naphthylphenyl, fluorenyl, phenanthrenyl, anthracenyl, indenyl, triphenylenyl, pyrenyl, tetracenyl, perylenyl, chrysenyl, naphthacenyl, or fluoranthenyl.

In formula 1 above, $X_1$ to $X_6$, and $R_1$ to $R_3$ each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur; preferably each independently represent hydrogen, a substituted or unsubstituted (C6-C20)aryl, a substituted or unsubstituted tri(C6-C12)arylsilyl, or a substituted or unsubstituted 3- to 15-membered heteroaryl; and more preferably each independently represent hydrogen, a substituted or unsubstituted (C6-C18)aryl, an unsubstituted triphenylsilyl, a substituted or unsubstituted dibenzothiophene, or a substituted or unsubstituted dibenzofuran.

The compound represented by formula 1 can be preferably represented by one of the following formulas 7 to 36:

(7)

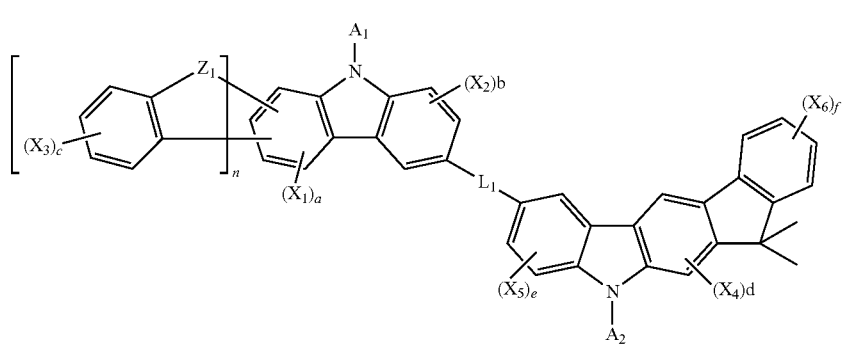

(8)
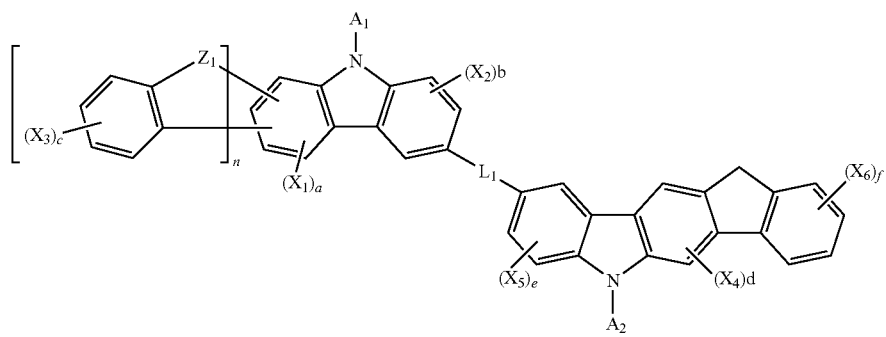
(9)
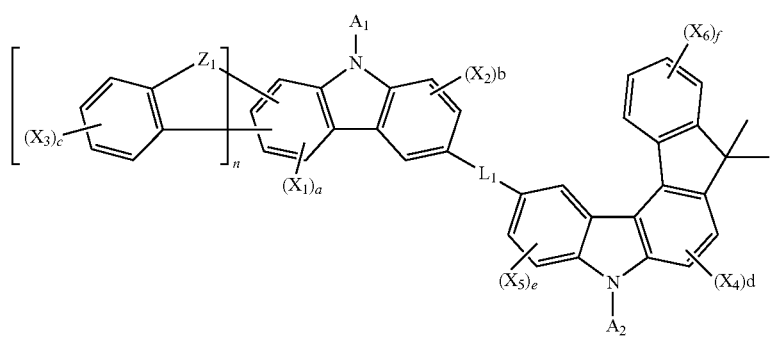
(10)
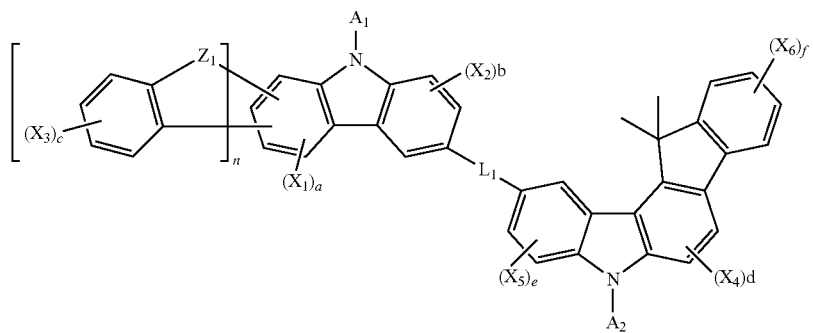
(11)
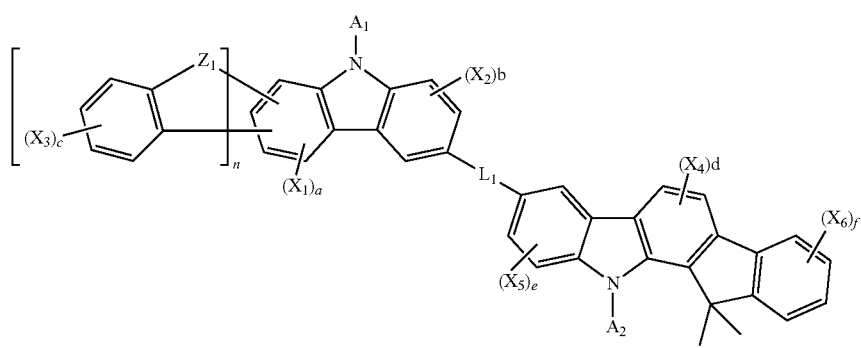

(12)
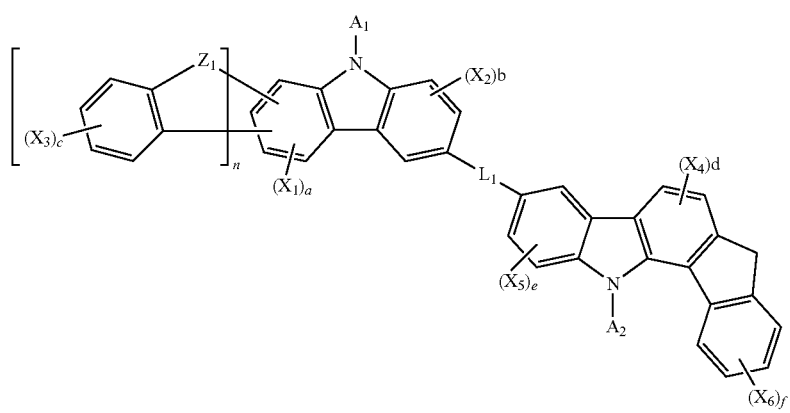
(13)
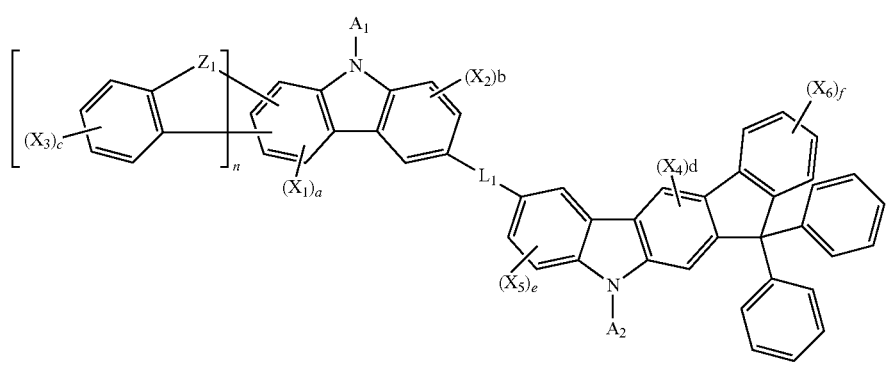
(14)
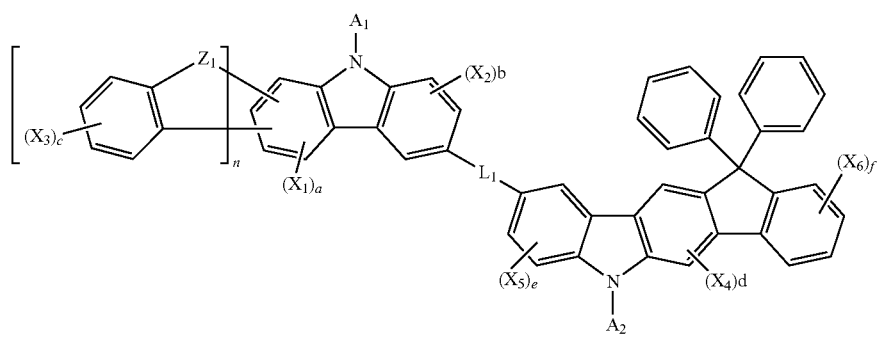
(15)
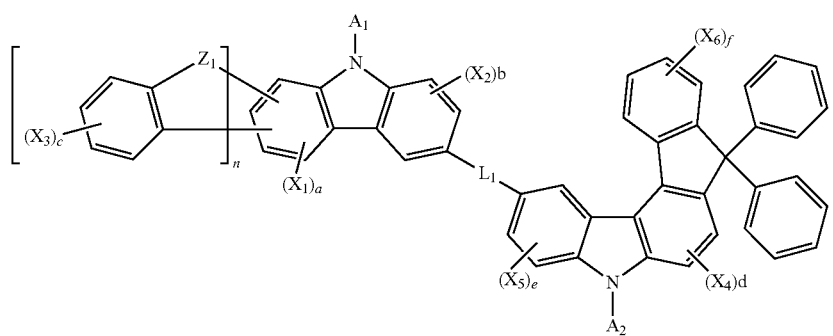

-continued
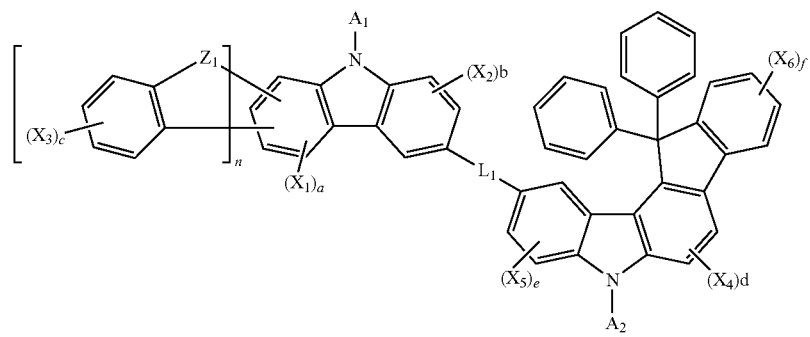
(16)
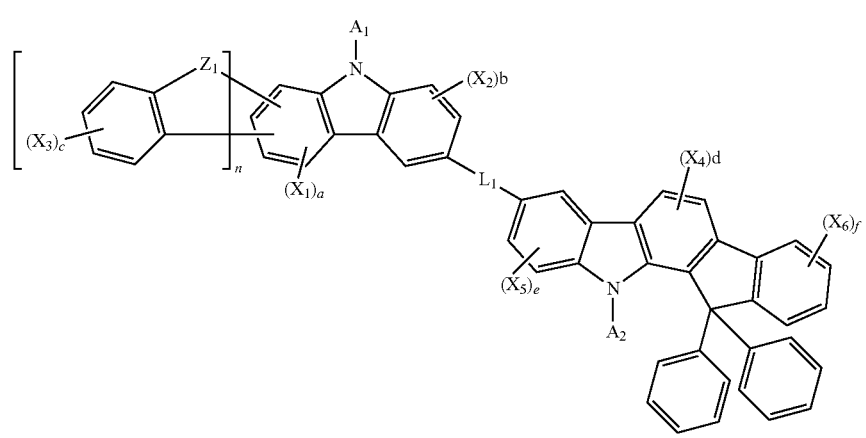
(17)
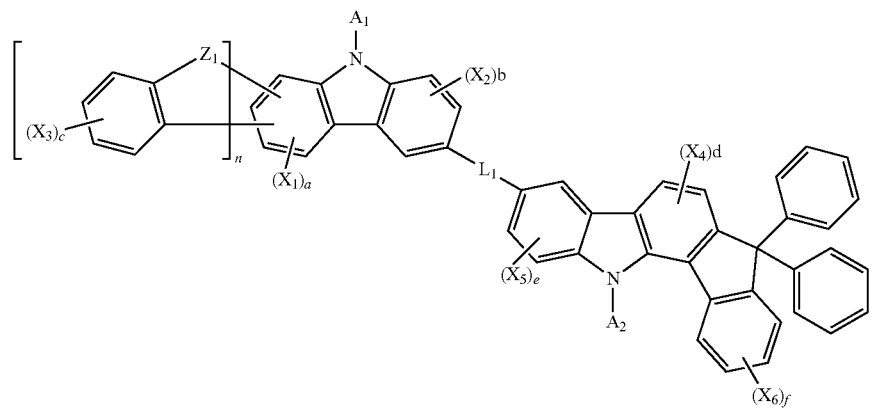
(18)
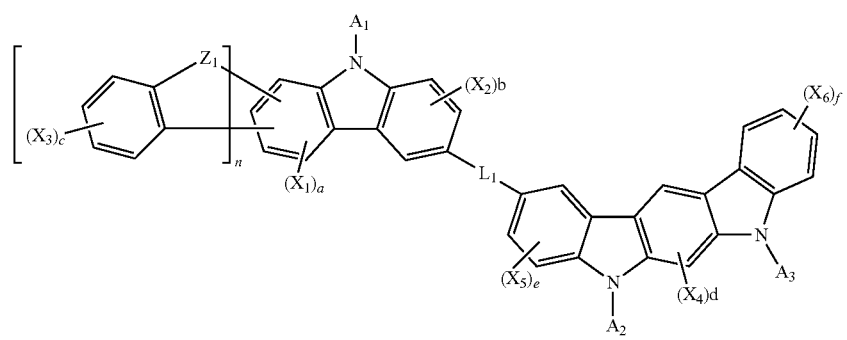
(19)

(20)
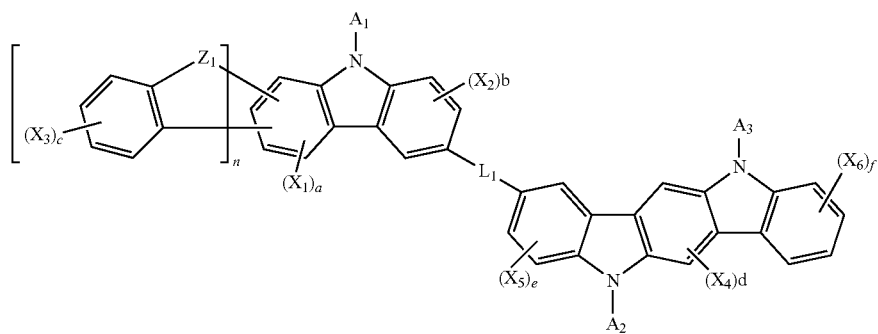
(21)
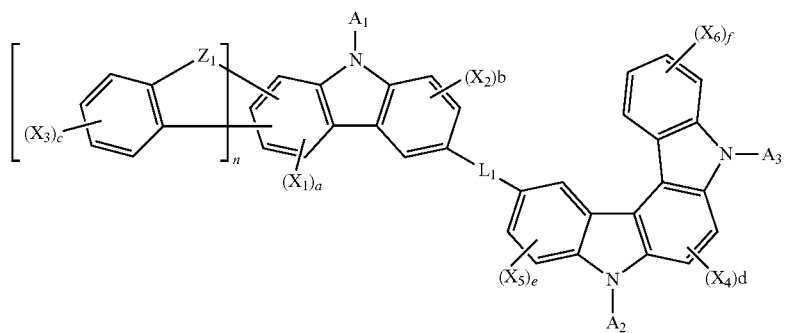
(22)
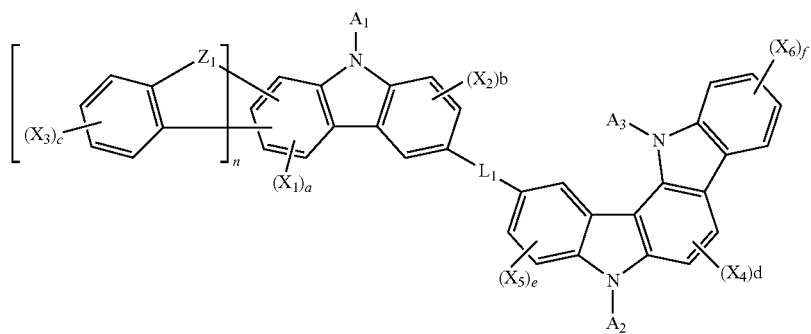
(23)
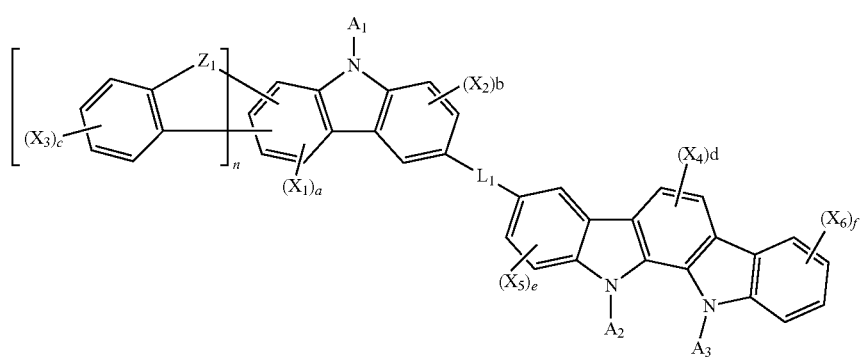

(24)
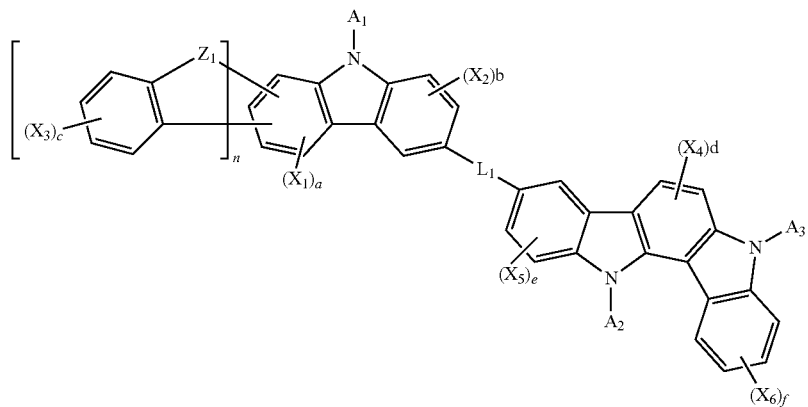
(25)
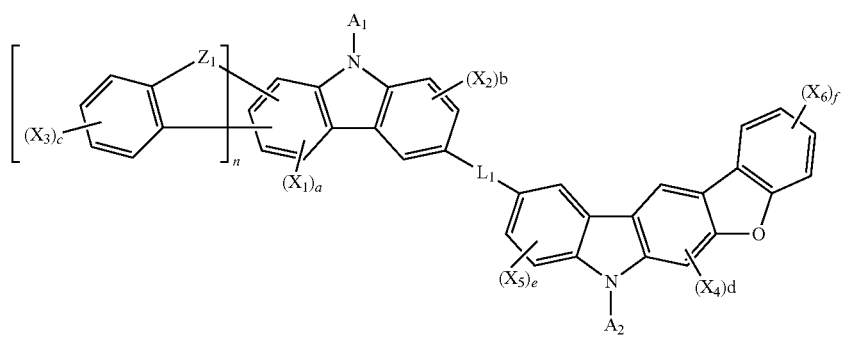
(26)
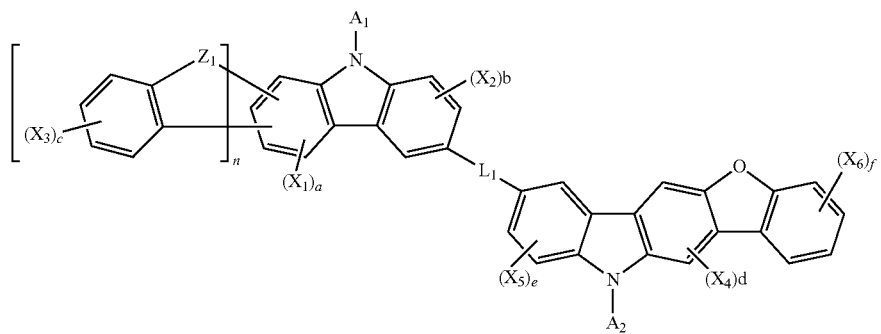
(27)
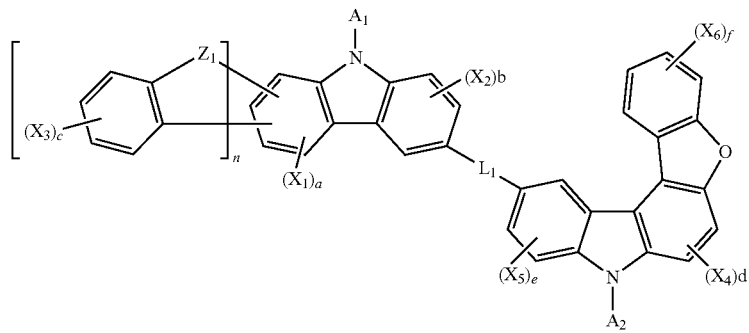

(28)
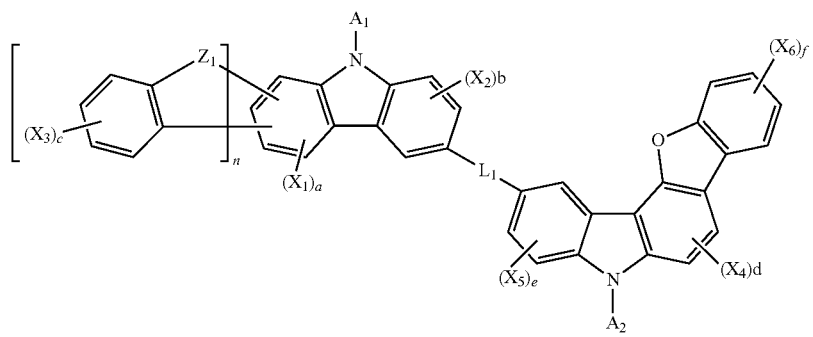
(29)
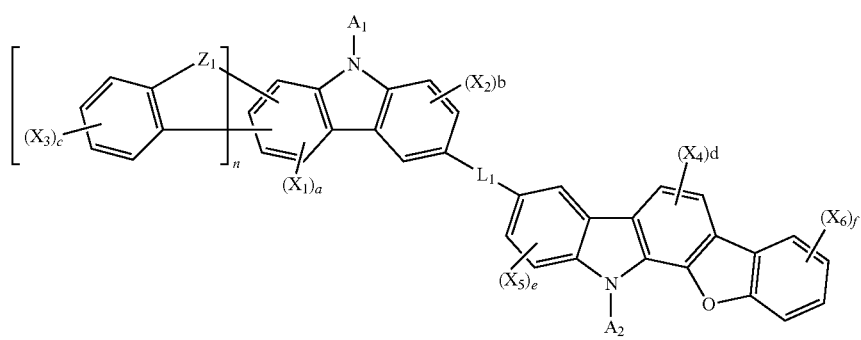
(30)
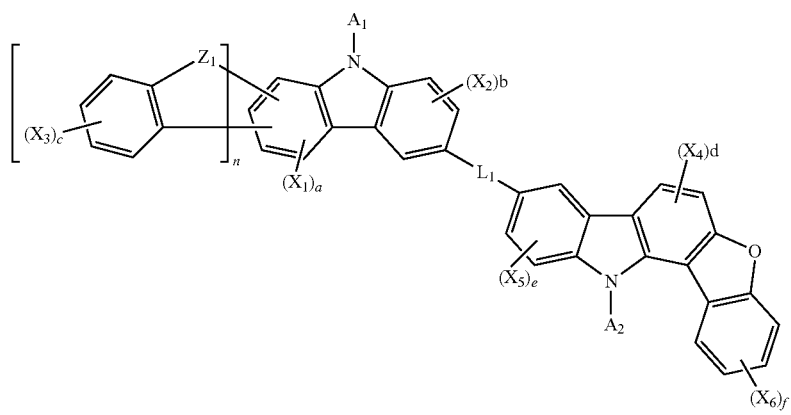
(31)
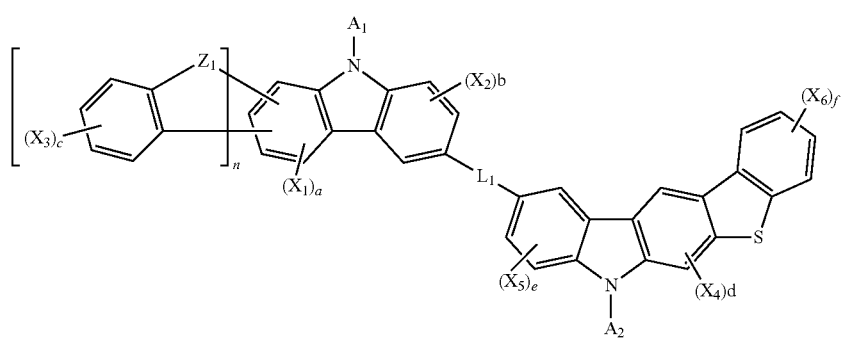

(32)
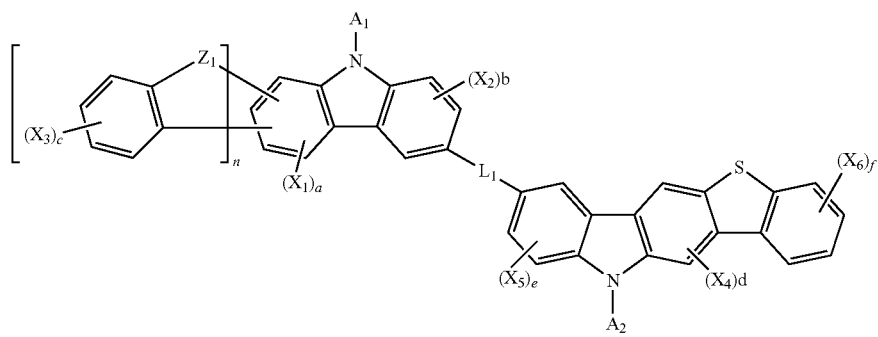
(33)
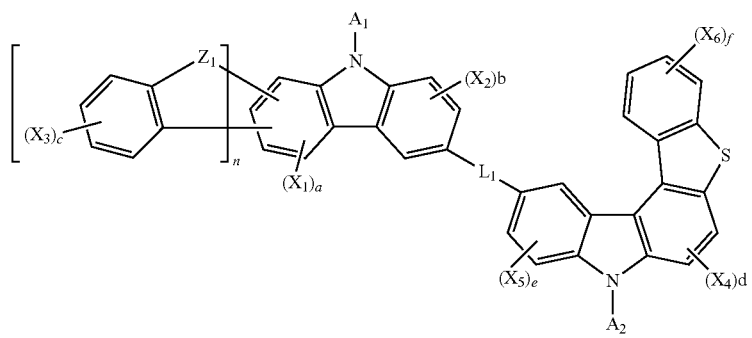
(34)
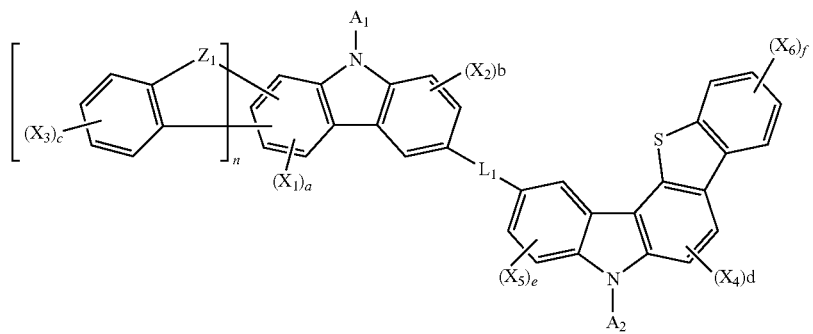
(35)
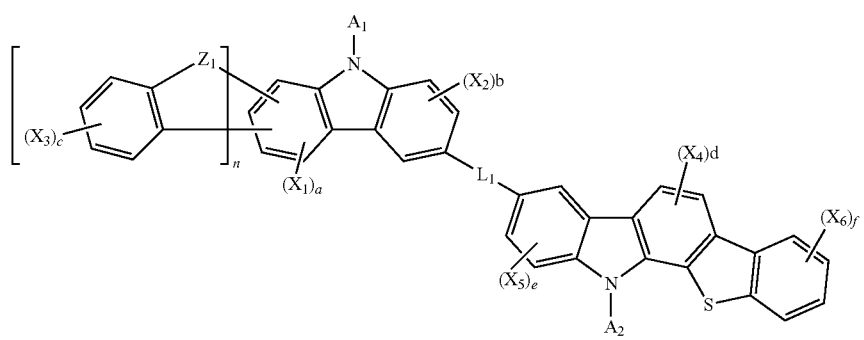

-continued (36)

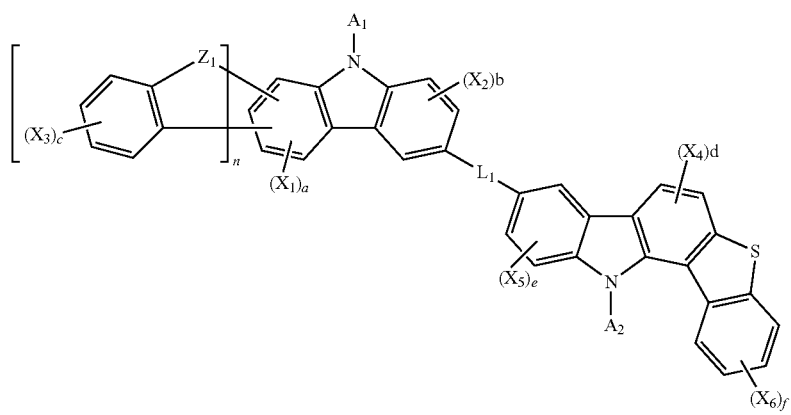

wherein $A_1$, $A_2$, $Z_1$, $L_1$, $X_1$ to $X_6$, and a to f are as defined in formula 1.

In formulas 1 and 2 above, $L_1$ and La each independently represent a single bond or a substituted or unsubstituted (C6-C30)arylene; preferably each independently represent a single bond or a substituted or unsubstituted (C6-C12) arylene; and more preferably each independently represent a single bond, or a (C6-C12)arylene unsubstituted or substituted with a tri(C6-C10)arylsilyl or a (C6-C12)aryl.

In addition, $L_1$ and La may each independently represent a single bond, or one of the following formulas 37 to 49:

(37)

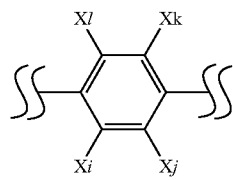

(38)

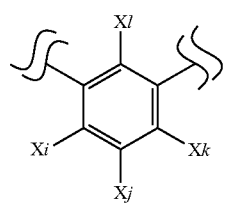

(39)

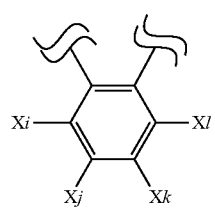

-continued (40)

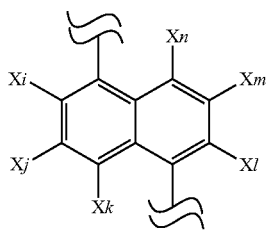

(41)

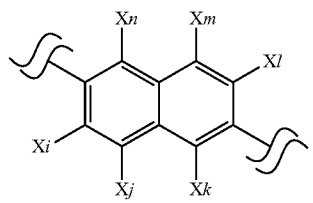

(42)

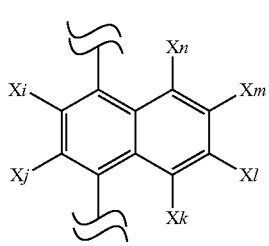

(43)

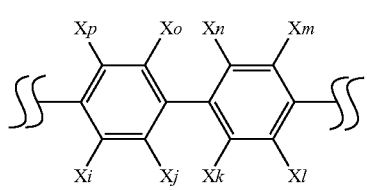

(44)

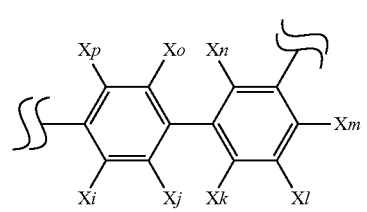

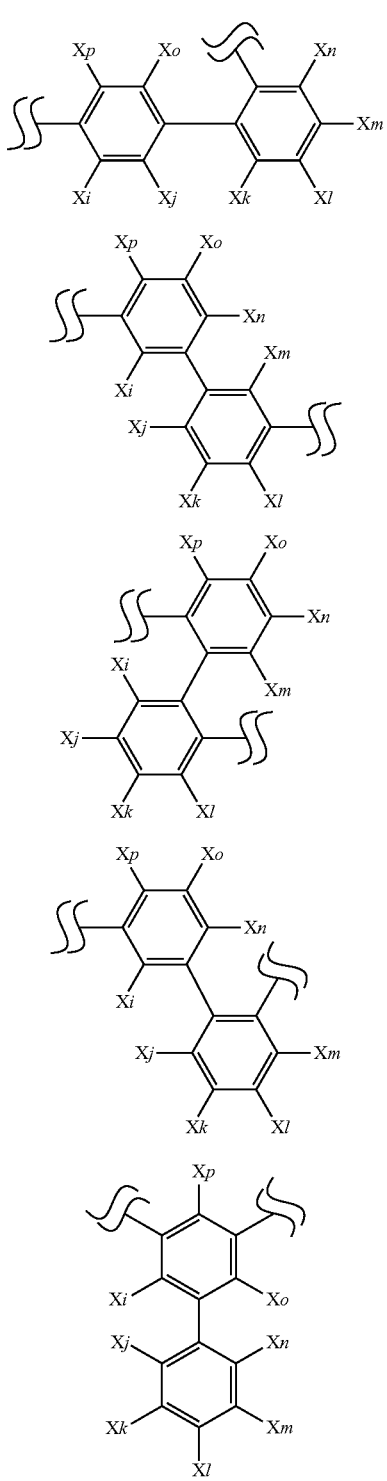

stituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted, mono- or polycyclic, (C3-C30) alicyclic or aromatic ring, whose carbon atom(s) may be replaced with at least one hetero atom selected from nitrogen, oxygen, and sulfur; preferably each independently represent hydrogen, a cyano, a substituted or unsubstituted (C6-C15)aryl, a substituted or unsubstituted 10- to 20-membered heteroaryl, or a substituted or unsubstituted tri(C6-C10)arylsilyl; and more preferably each independently represent hydrogen, a cyano, a (C6-C15)aryl unsubstituted or substituted with a tri(C6-C10)arylsilyl, or a 10- to 20-membered heteroaryl unsubstituted or substituted with a (C6-C15)aryl.

In formula 2 above, Ma represents a substituted or unsubstituted 5- to 30-membered nitrogen-containing heteroaryl; preferably represents a substituted or unsubstituted 6- to 15-membered nitrogen-containing heteroaryl; and more preferably represents a 6- to 15-membered nitrogen-containing heteroaryl substituted with a substituent selected from the group consisting of an unsubstituted (C6-C18)aryl, a (C6-C12)aryl substituted with a cyano, a (C6-C12)aryl substituted with a (C1-C6)alkyl, a (C6-C12)aryl substituted with a tri(C6-C12)arylsilyl, an unsubstituted 6- to 15-membered heteroaryl, and a 6- to 15-membered heteroaryl substituted with a (C6-C12)aryl.

In addition, Ma may represent a monocyclic ring-type heteroaryl such as a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, a substituted or unsubstituted pyridazinyl, etc., or a fused ring-type heteroaryl such as a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, a substituted or unsubstituted quinoxalinyl, a substituted or unsubstituted carbazolyl, a substituted or unsubstituted phenanthridinyl, etc. Preferably, Ma may represent a substituted or unsubstituted triazinyl, a substituted or unsubstituted pyrimidinyl, a substituted or unsubstituted pyridyl, a substituted or unsubstituted quinolyl, a substituted or unsubstituted isoquinolyl, a substituted or unsubstituted quinazolinyl, a substituted or unsubstituted naphthyridinyl, or a substituted or unsubstituted quinoxalinyl.

In formula 2 above, Xa to Xh each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or wherein Xi to Xp each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsuba substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur; and preferably each independently represent hydrogen, a cyano, a substituted or unsubstituted (C6-C15)aryl, a substituted or unsubstituted 10- to 20-membered heteroaryl, or a substituted or unsubstituted tri(C6-C10)arylsilyl; or adjacent substituents may be linked to each other to form a substituted or unsubstituted mono- or polycyclic, (C6-C20) aromatic ring, whose carbon atom(s) may be replaced with at least one hetero atom selected from nitrogen, oxygen, and sulfur. More preferably, Xa to Xh each independently represent hydrogen; a cyano; a (C6-C15)aryl unsubstituted or substituted with a 10- to 20-membered heteroaryl or a tri(C6-C10)arylsilyl; a 10- to 20-membered heteroaryl unsubstituted or substituted with a (C6-C12)aryl or a cyano(C6-C12)aryl; or an unsubstituted tri(C6-C10) arylsilyl; or adjacent substituents may be linked to each other to form a substituted or unsubstituted benzene, a substituted or unsubstituted indole, a substituted or unsubstituted benzoindole, a substituted or unsubstituted indene, a substituted or unsubstituted benzofuran, or a substituted or unsubstituted benzothiophene, Herein, "(C1-C30)alkyl (ene)" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc.; "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc.; "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc.; "(C3-C30) cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "3- to 7-membered heterocycloalkyl" is a cycloalkyl having 3 to 7 ring backbone atoms, preferably 5 to 7, including at least one heteroatom selected from B, N, O, S, Si, and P, preferably O, S, and N, and includes tetrahydrofuran, pyrrolidine, thiolan, tetrahydropyran, etc.; "(C6-C30)aryl(ene)" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; "3- to 30-membered heteroaryl(ene)" is an aryl having 3 to 30 ring backbone atoms, preferably 3 to 20 ring backbone atoms, and more preferably 3 to 15 ring backbone atoms, including at least one, preferably 1 to 4 heteroatoms selected from the group consisting of B, N, O, S, Si, and P; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.; "nitrogen-containing 5- to 30-membered heteroaryl(ene)" is an aryl having 5 to 30 ring backbone atoms, preferably 5 to 20, and more preferably 5 to 15, including at least one heteroatom, N; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including pyrrolyl, imidazolyl, pyrazolyl, triazinyl, tetrazinyl, triazolyl, tetrazolyl, pyridyl, pyrazinyl, pyrimidinyl, pyridazinyl, etc., and a fused ring-type heteroaryl including benzimidazolyl, isoindolyl, indolyl, indazolyl, benzothiadiazolyl, quinolyl, isoquinolyl, cinnolinyl, quinazolinyl, quinoxalinyl, carbazolyl, phenanthridinyl, etc. Further, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl(ene), the substituted alkenyl, the substituted alkynyl, the substituted cycloalkyl, the substituted aryl(ene), the substituted heteroaryl, the substituted trialkylsilyl, the substituted triarylsilyl, the substituted dialkylarylsilyl, the substituted alkyldiarylsilyl, the substituted mono- or di-alkylamino, the substituted mono- or di-arylamino, or the substituted mono- or polycyclic, (C3-C30) alicyclic or aromatic ring in the formulas each independently are at least one selected from the group consisting of deuterium, a halogen, a cyano, a carboxyl, a nitro, a hydroxyl, a (C1-C30)alkyl, a halo(C1-C30) alkyl, a (C2-C30) alkenyl, a (C2-C30) alkynyl, a (C1-C30) alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a cyano, a 3- to 30-membered heteroaryl, or a tri(C6-C30)arylsilyl, a tri(C1-C30)alkylsilyl, a tri(C6-C30)arylsilyl, a di(C1-C30) alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl, and preferably are at least one selected from the group consisting of a cyano; a (C1-C6)alkyl; a 5- to 15-membered heteroaryl; a (C6-C18)aryl unsubstituted or substituted with a cyano or a tri(C6-C12)arylsilyl; a tri(C6-C12)arylsilyl; and a (C1-C6)alkyl(C6-C12)aryl.

The first host compound represented by formula 1 includes the following compounds, but is not limited thereto:

F-1
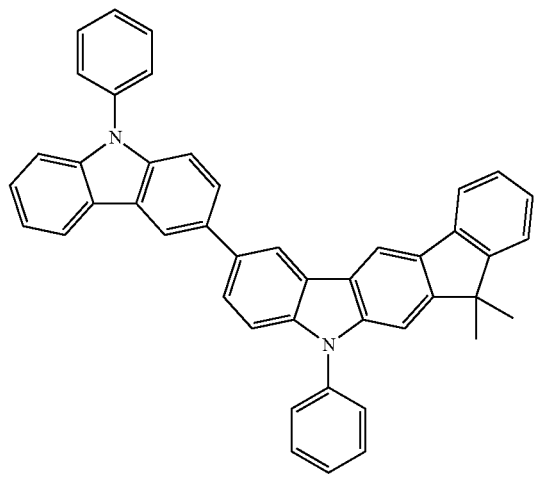
F-2
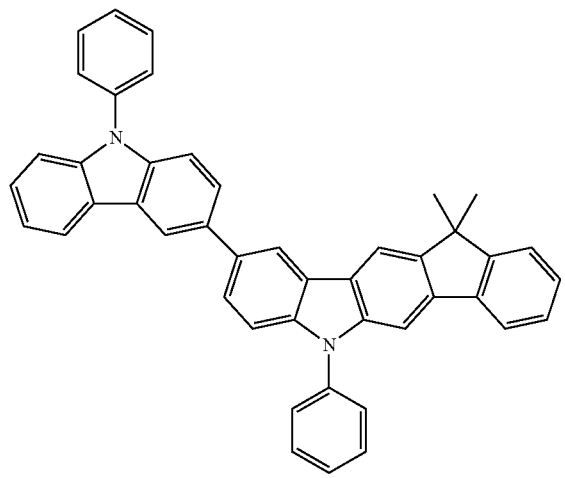
F-3
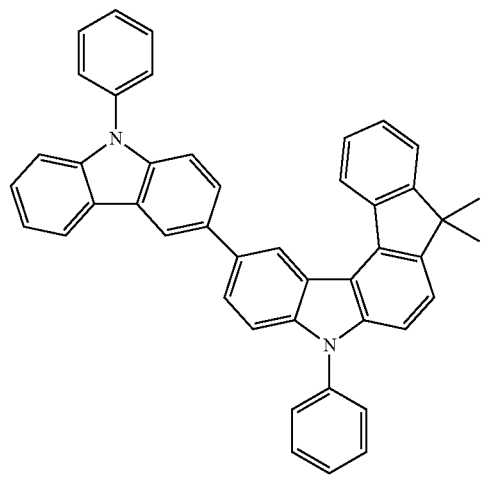
F-4
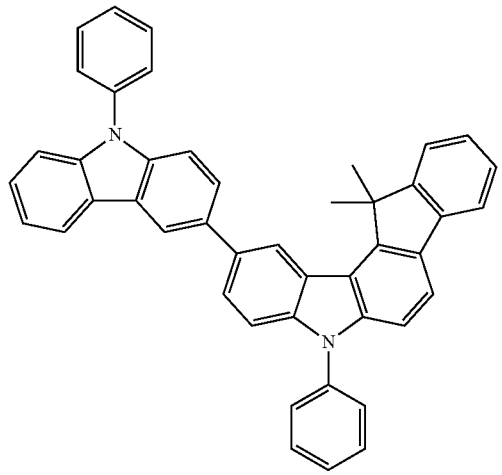
F-5
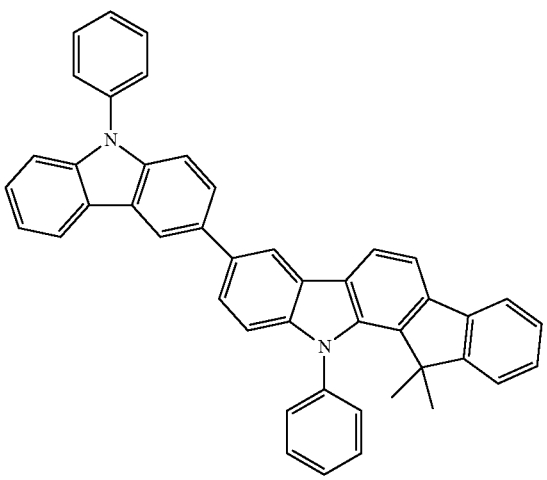
F-6
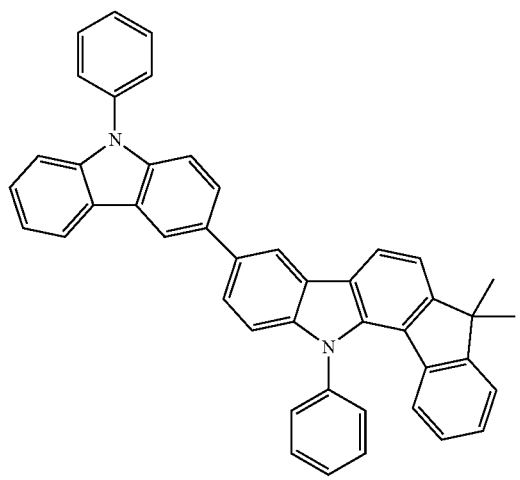

F-7
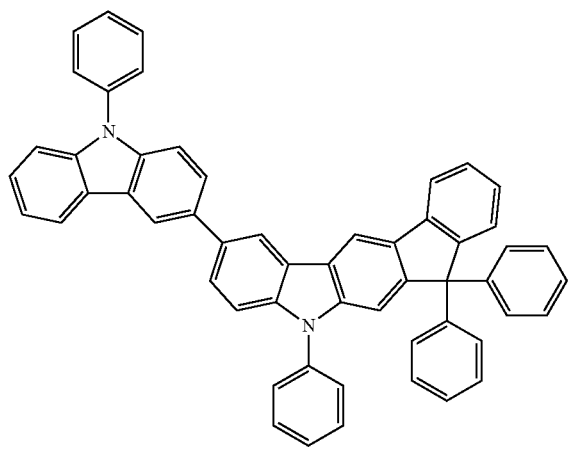
F-8
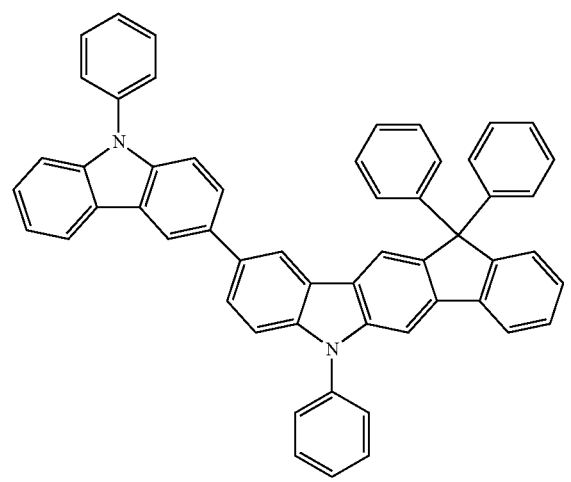
F-9
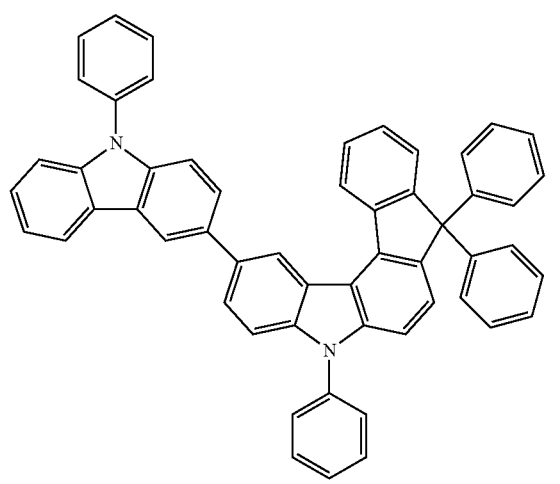
F-10
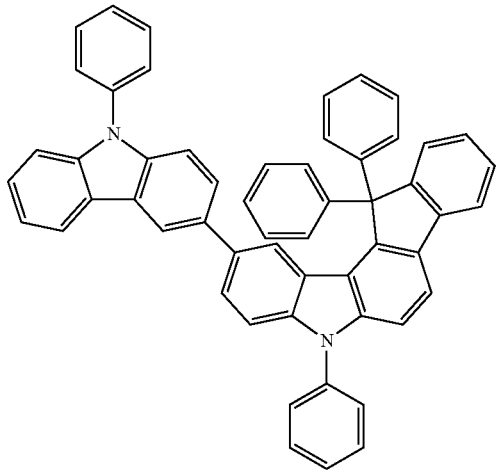
F-11
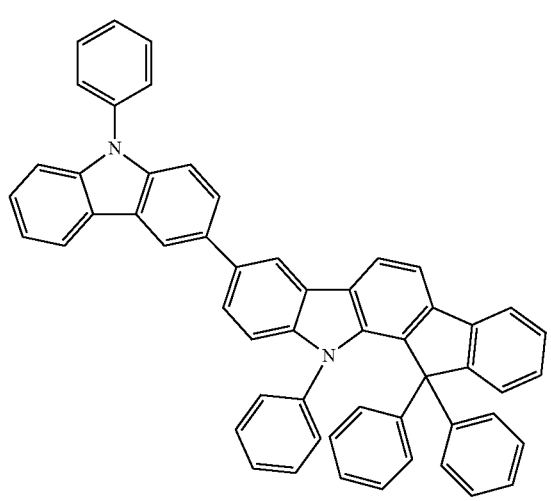
F-12
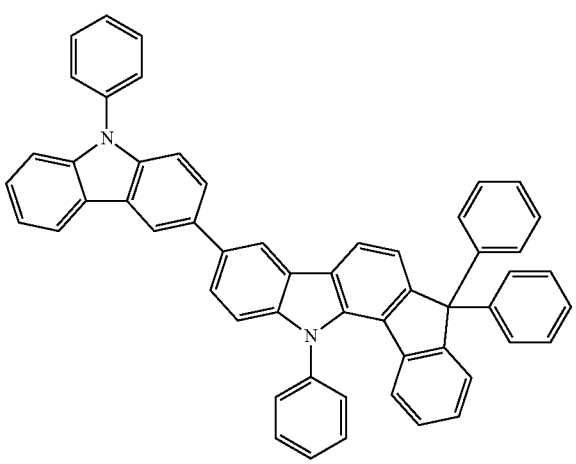

F-13
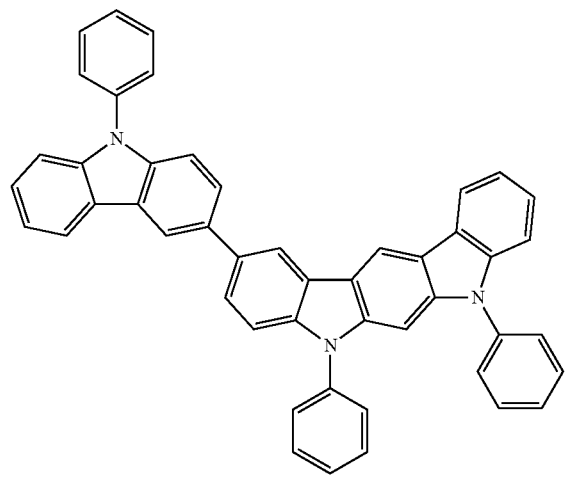
F-14
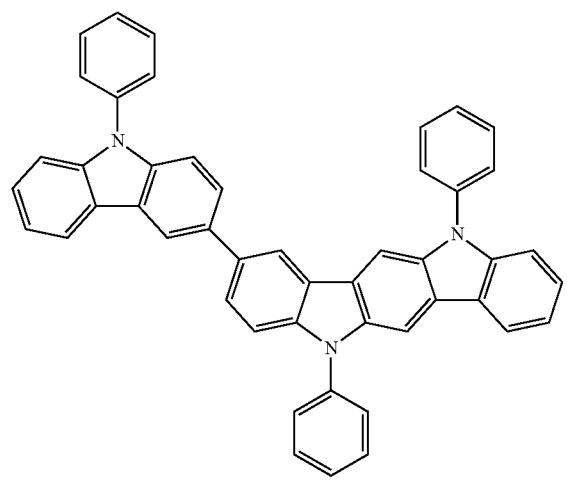
F-15
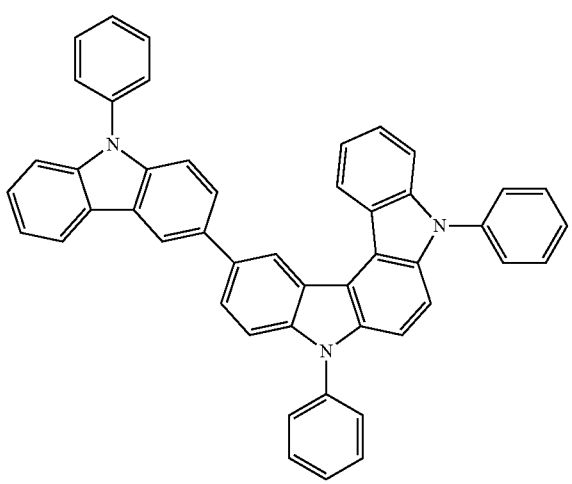
F-16
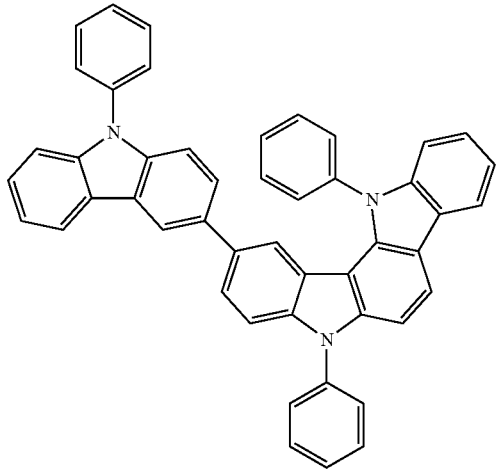
F-17
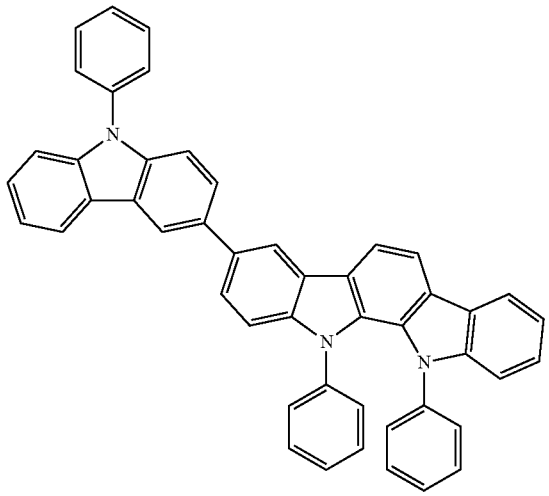
F-18
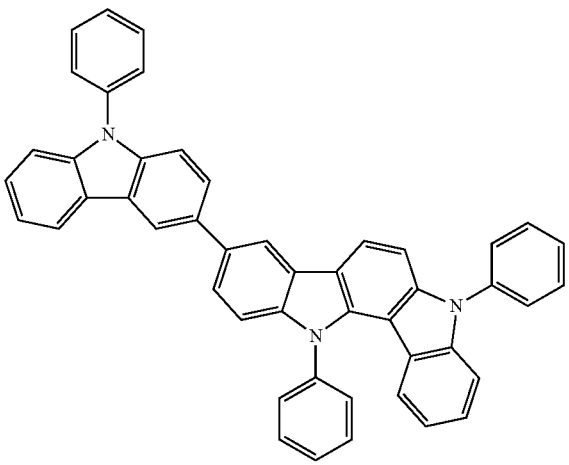

F-19
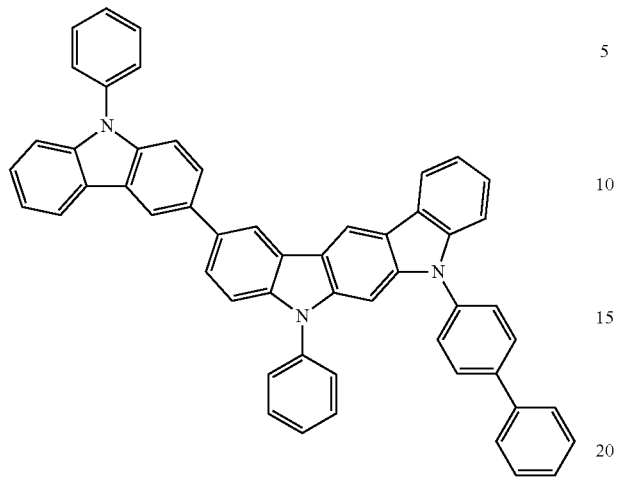
F-22
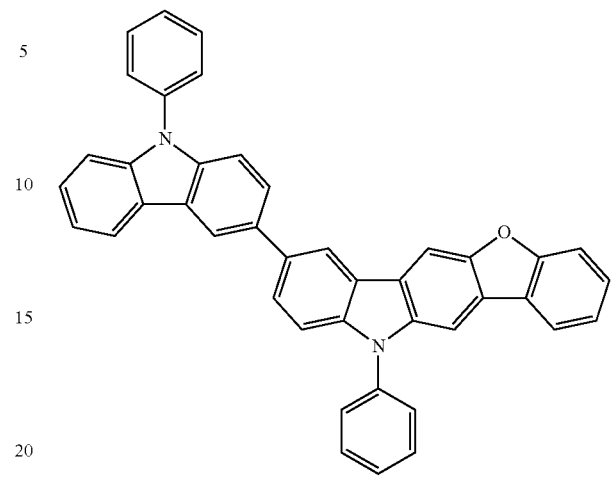
F-20
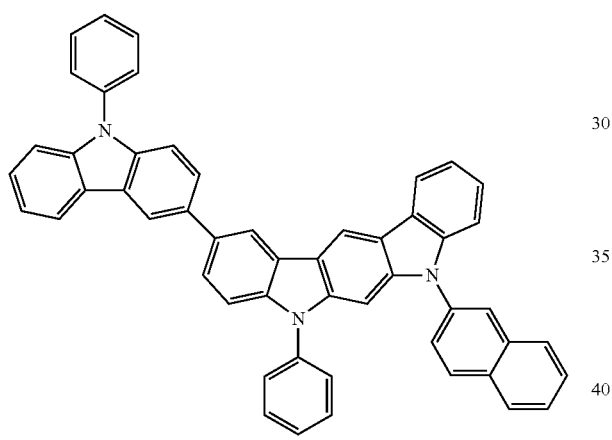
F-23
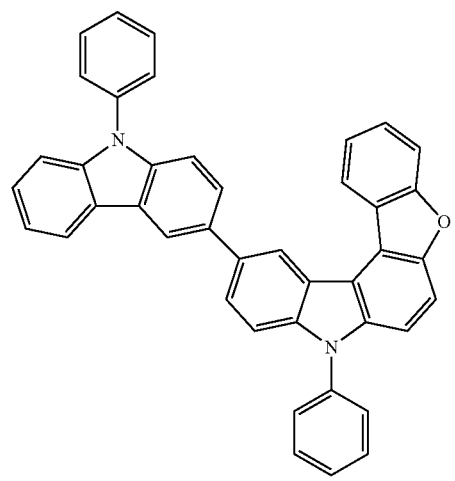
F-21
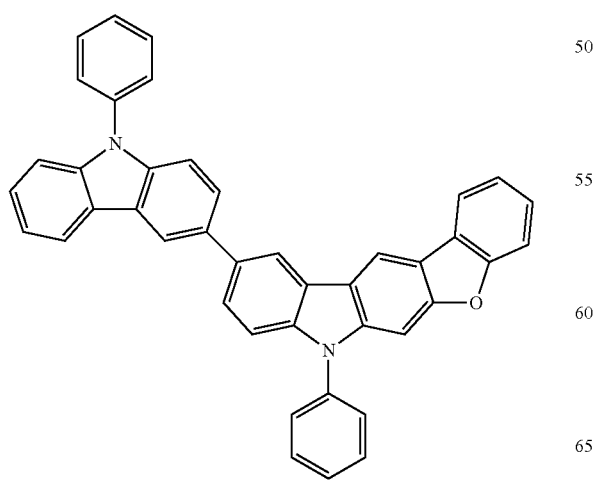
F-24
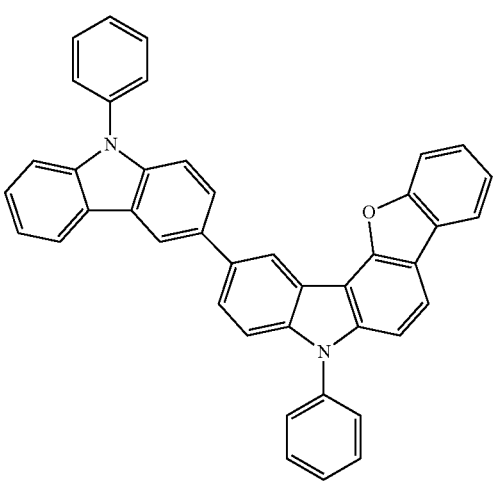

F-25
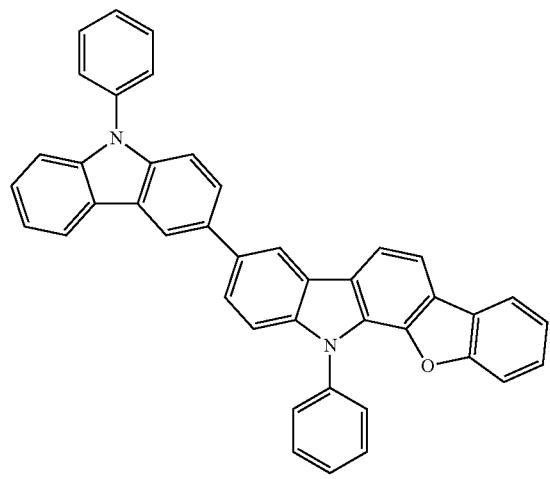
F-26
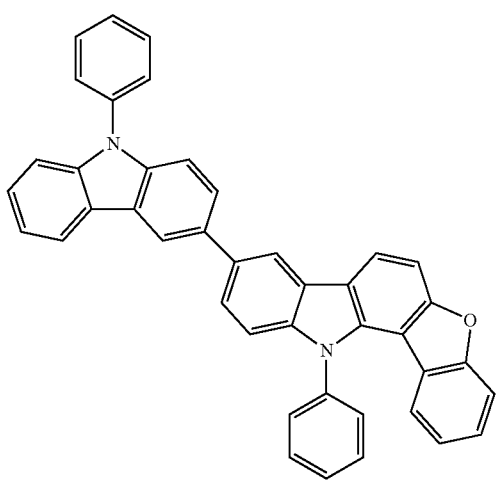
F-27
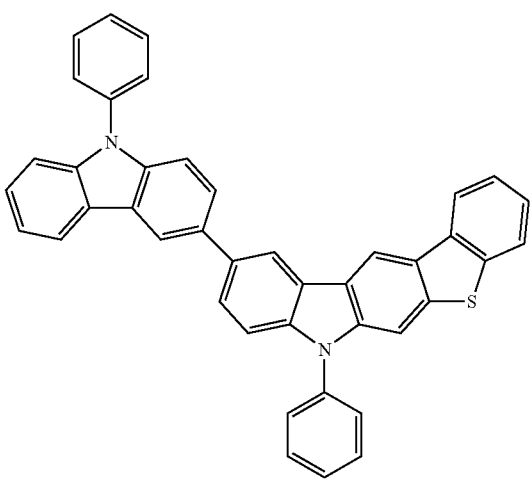
F-28
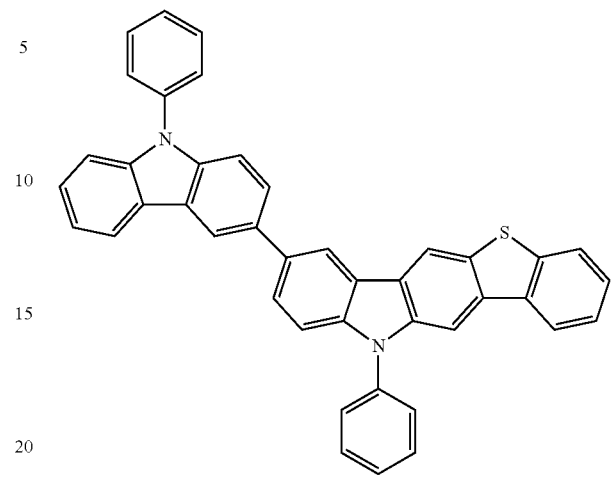
F-29
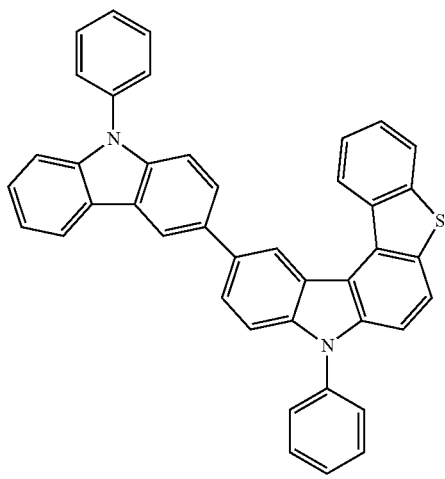
F-30
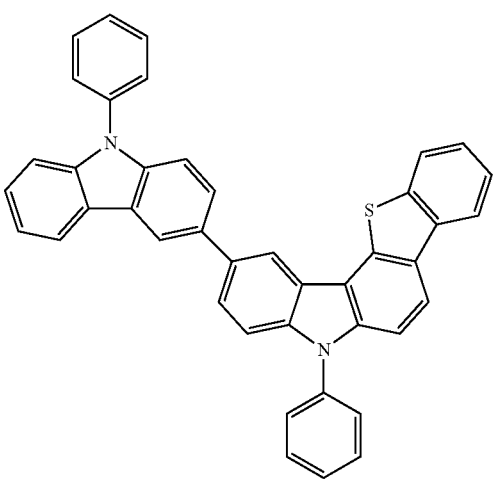

F-31
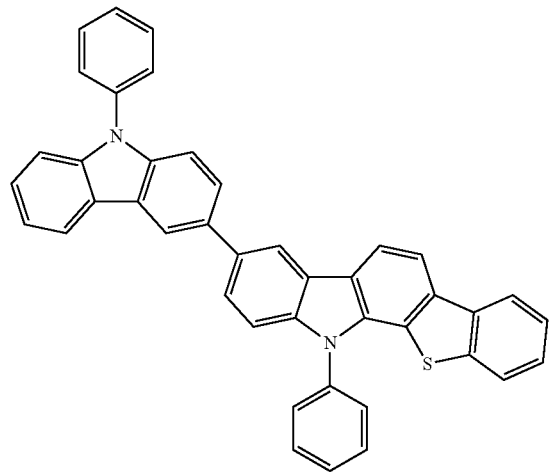
F-32
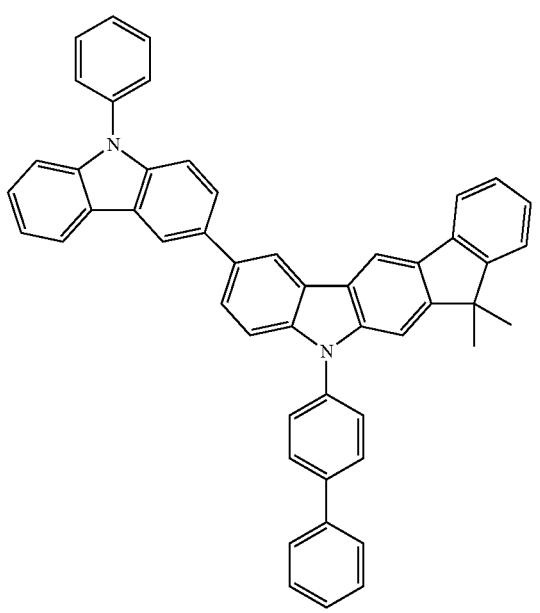
F-34
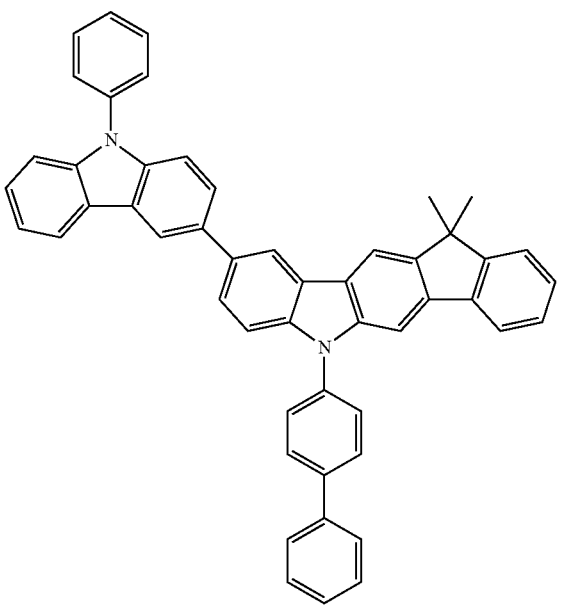
F-33
F-35
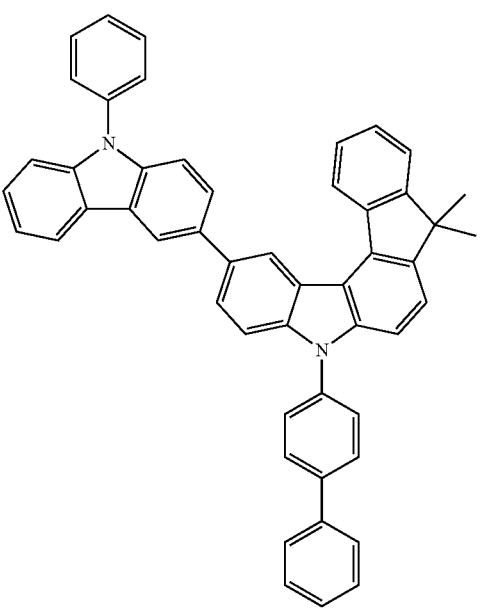
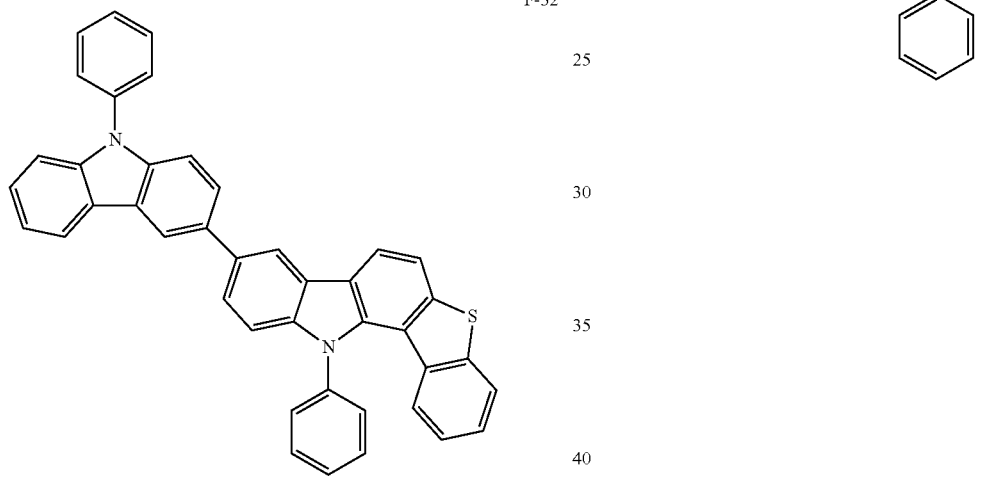

F-36
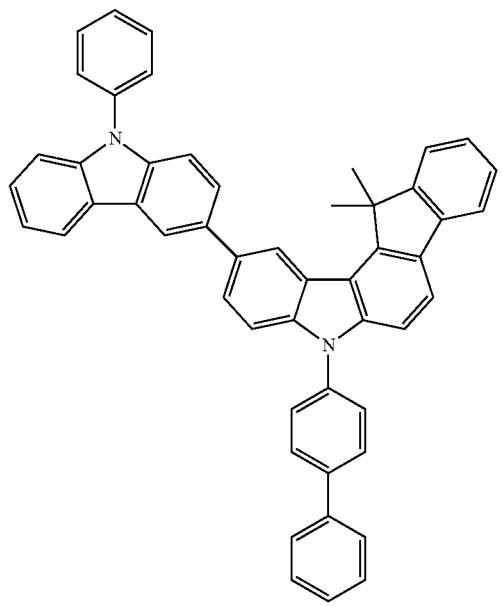
F-38
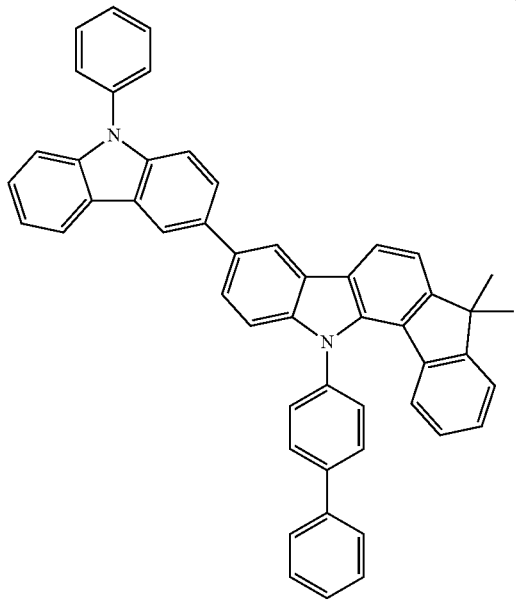
F-37
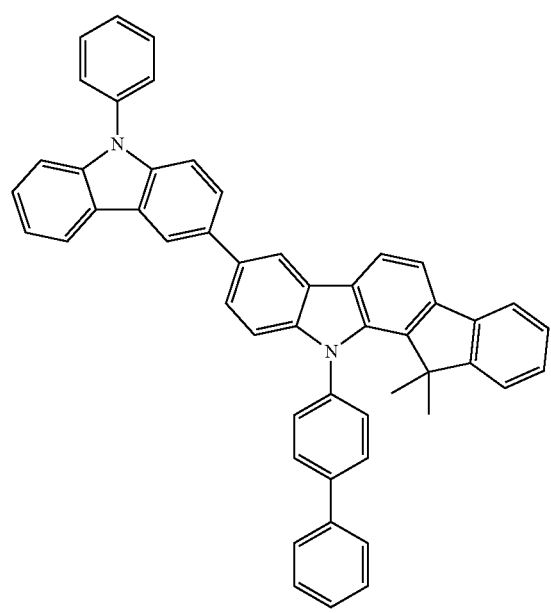
F-39
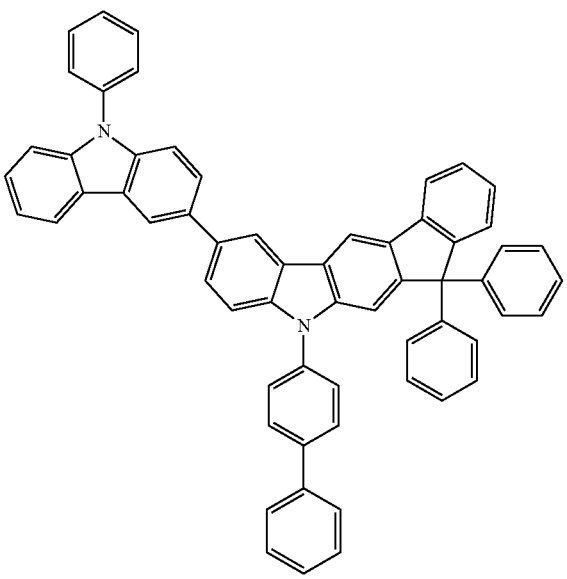

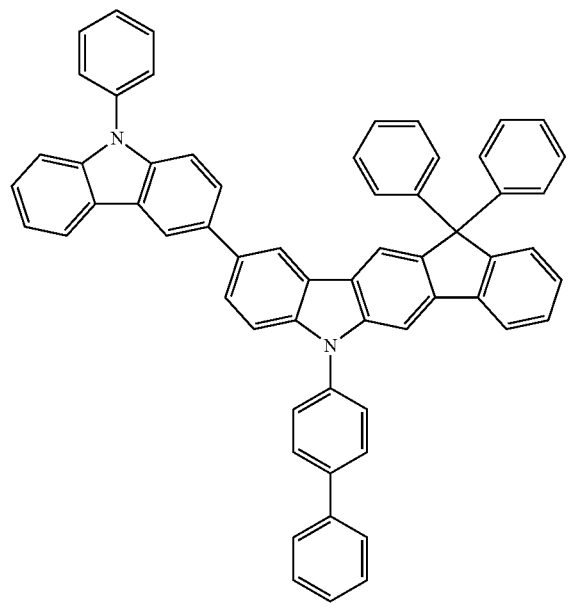
F-40
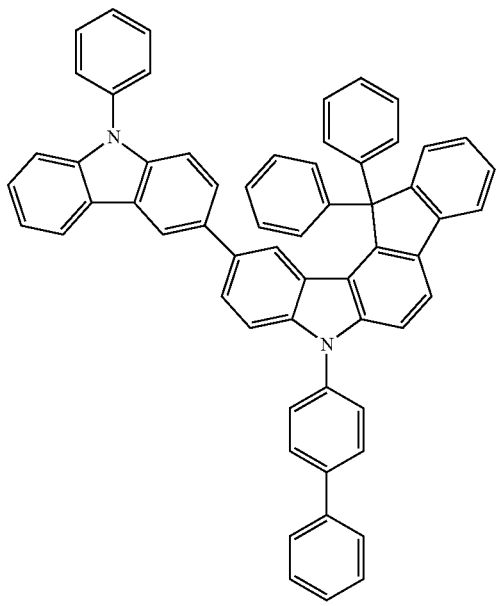
F-42
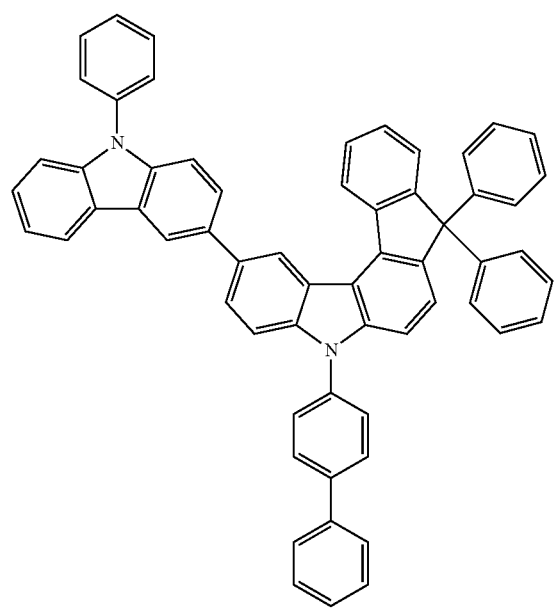
F-41
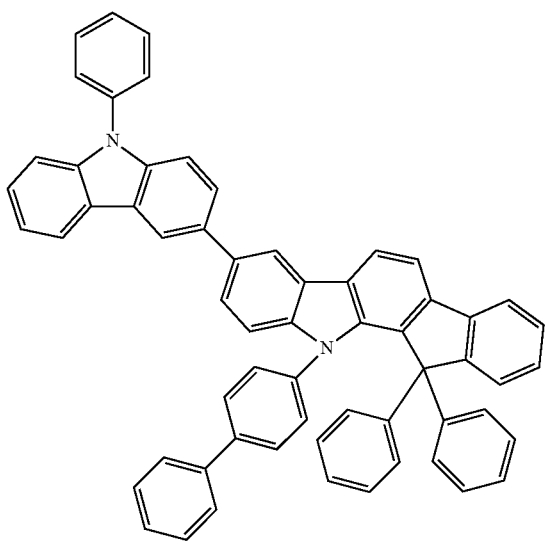
F-43

F-44
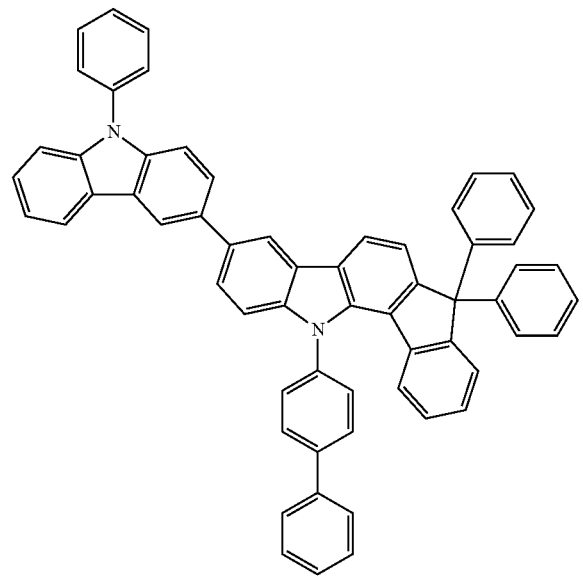
F-45
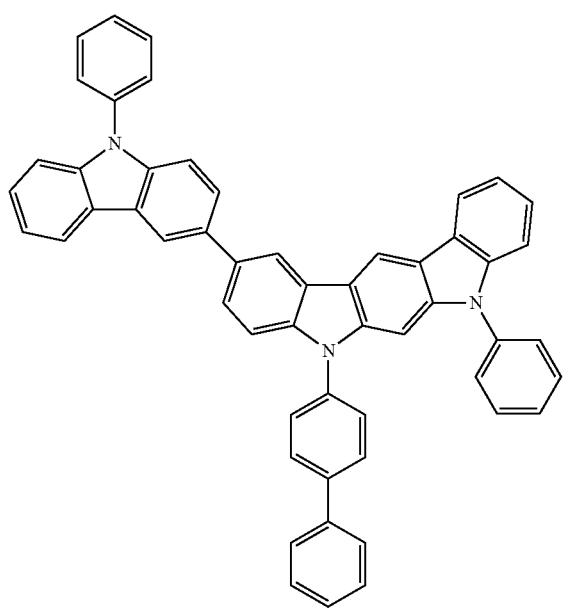
F-46
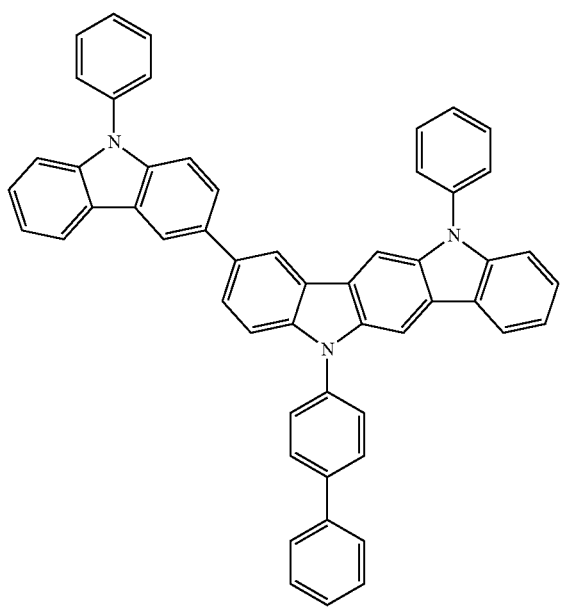
F-47

F-48
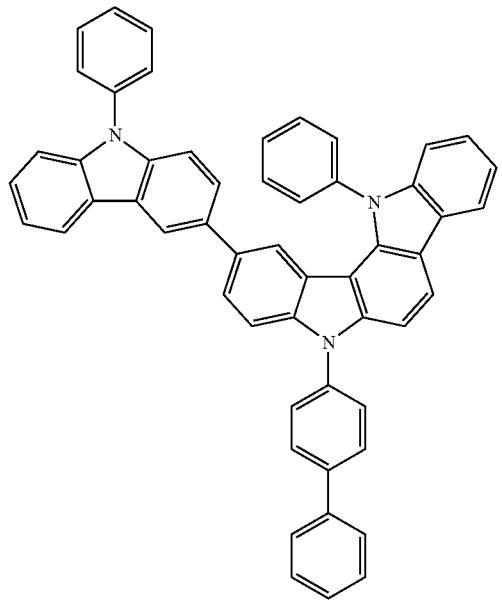
F-50
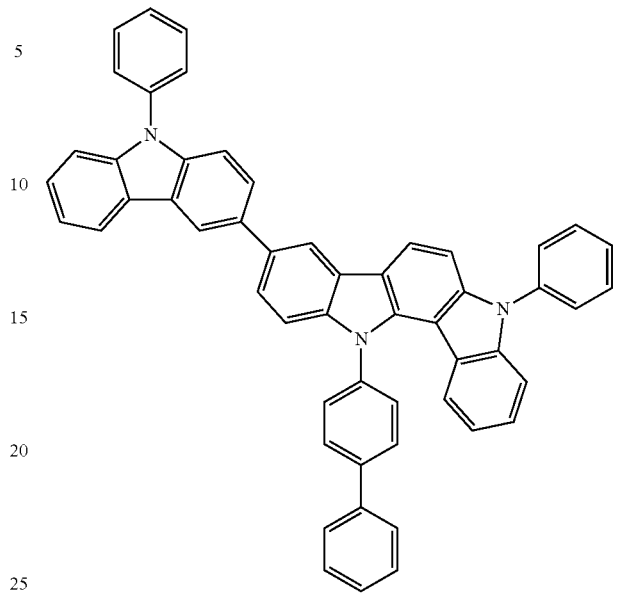
F-49
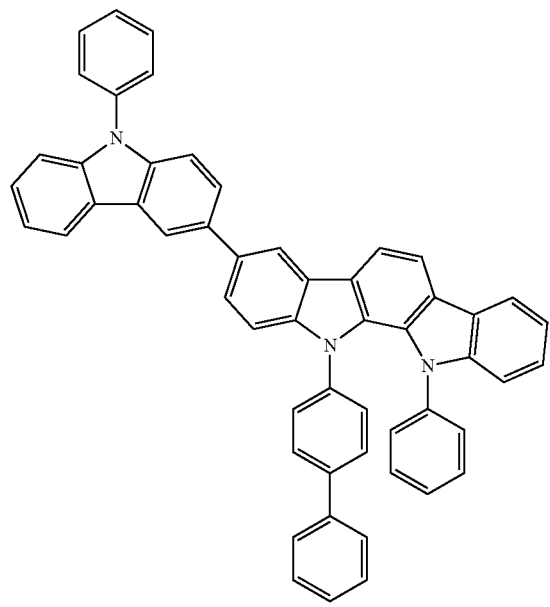
F-51
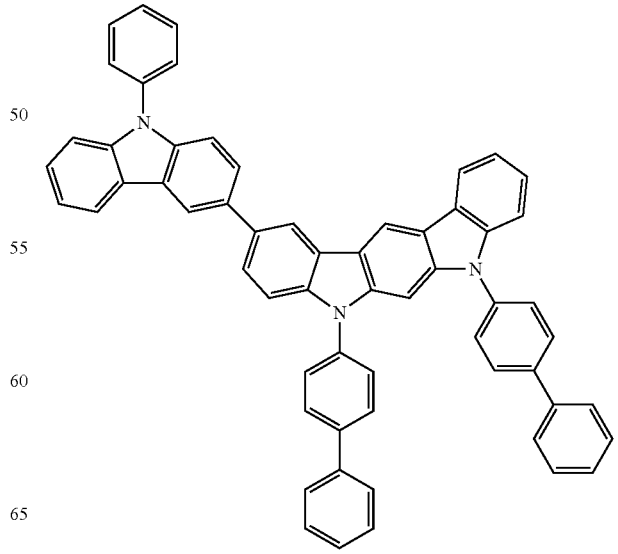

F-52
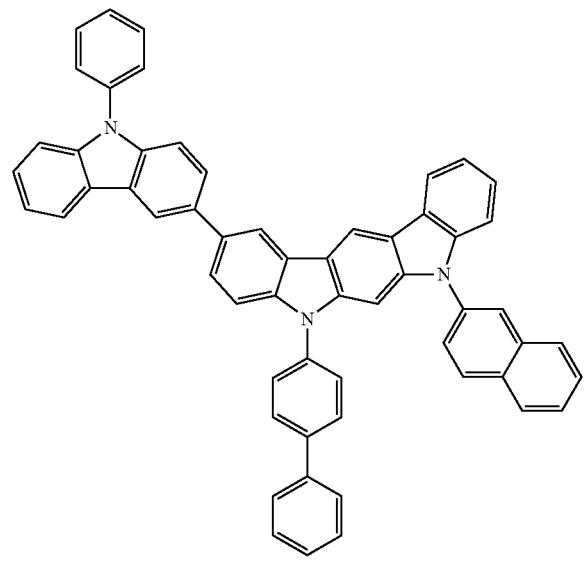
F-54
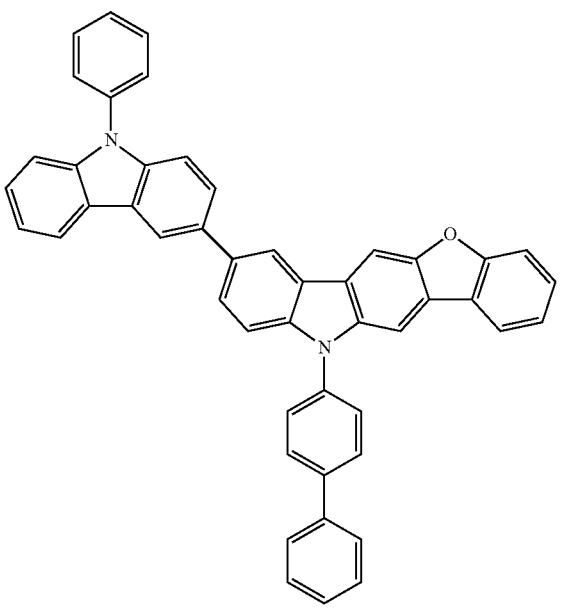
F-53
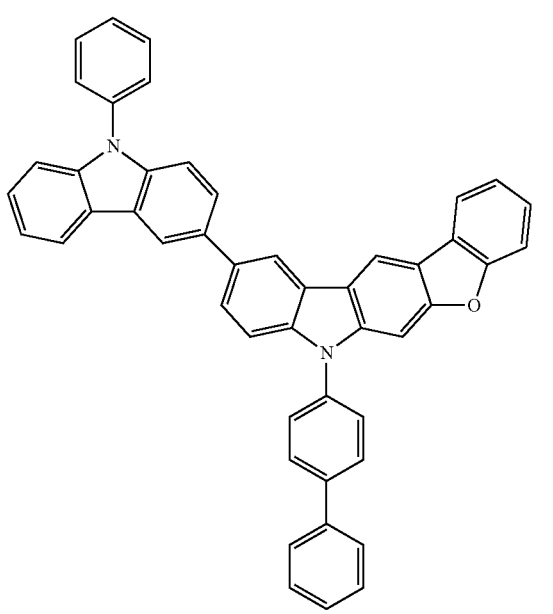
F-55
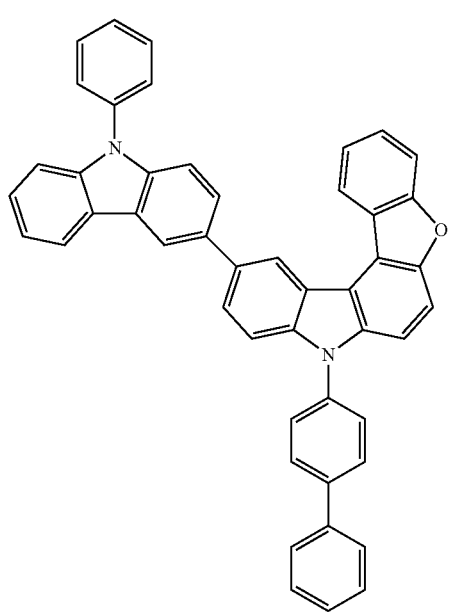

F-56
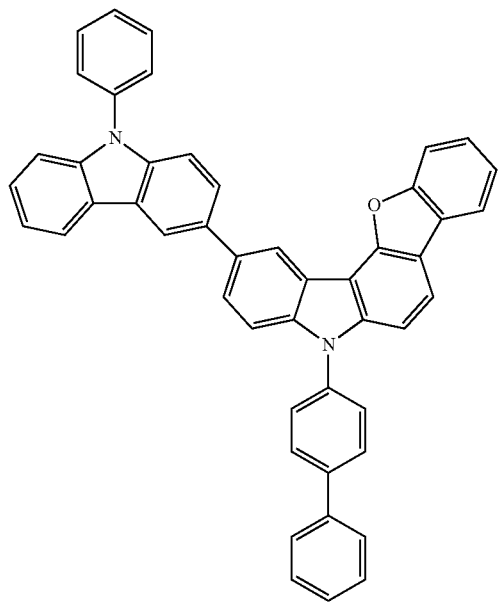
F-57
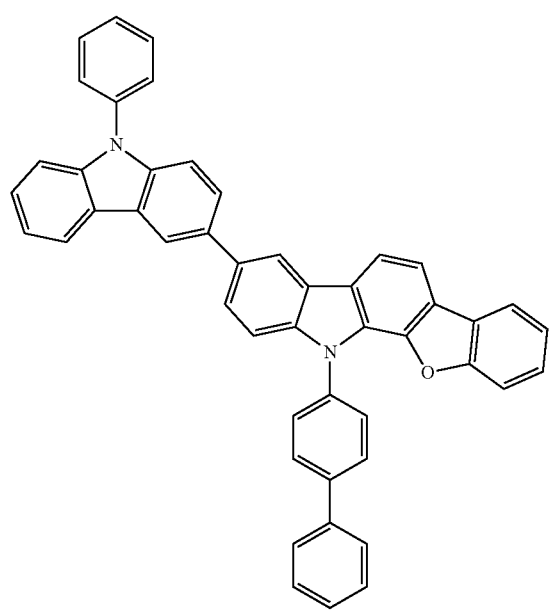
F-58
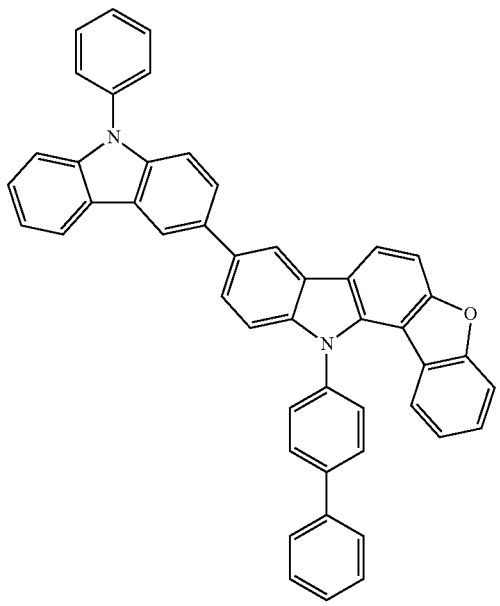
F-59
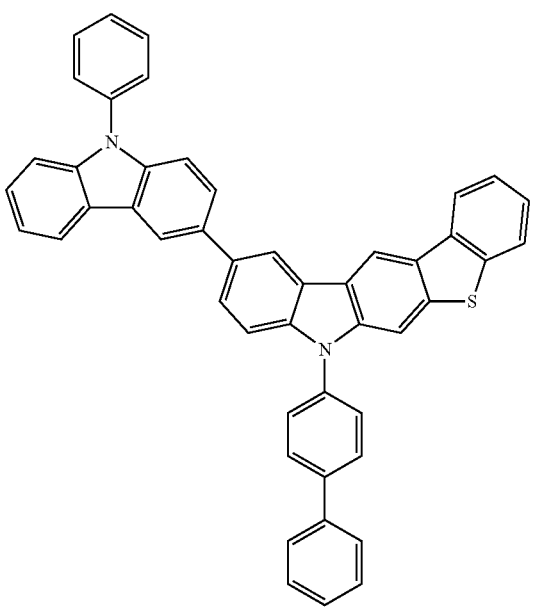

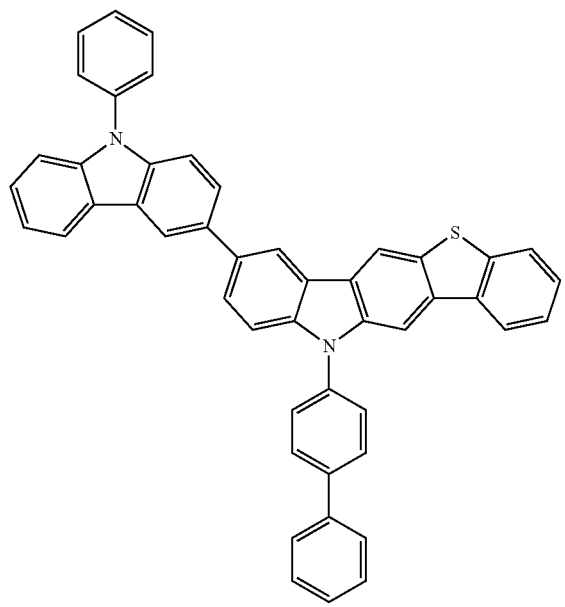
F-60
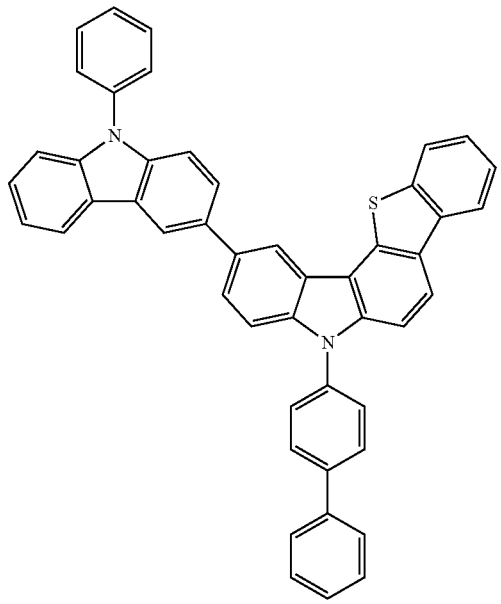
F-62
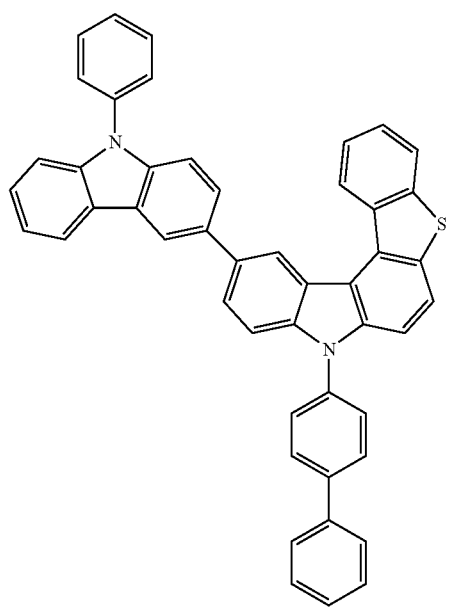
F-61
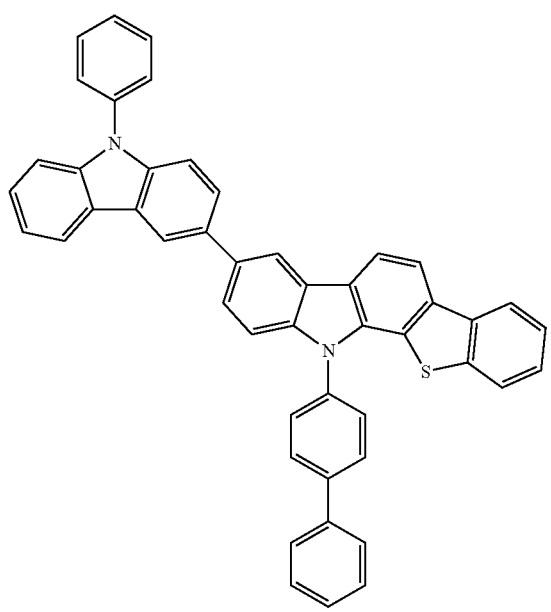
F-63

F-64
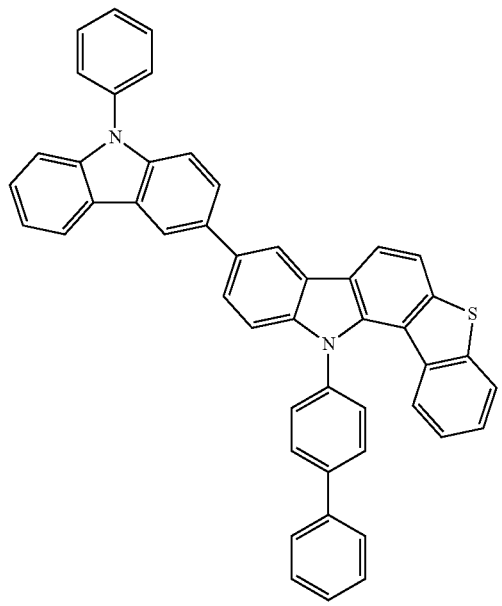
F-66
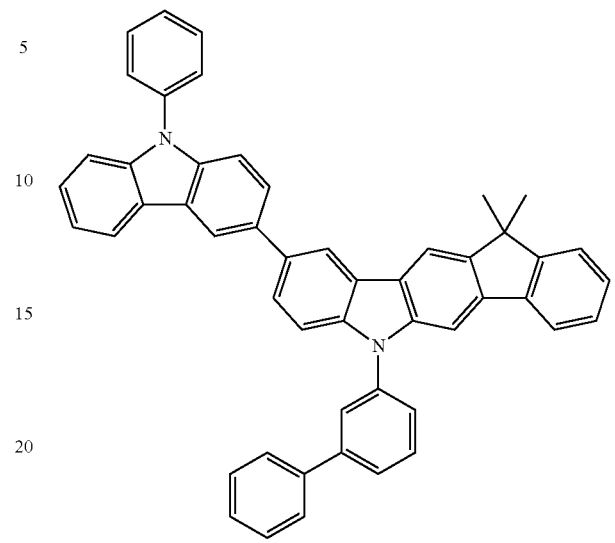
F-67
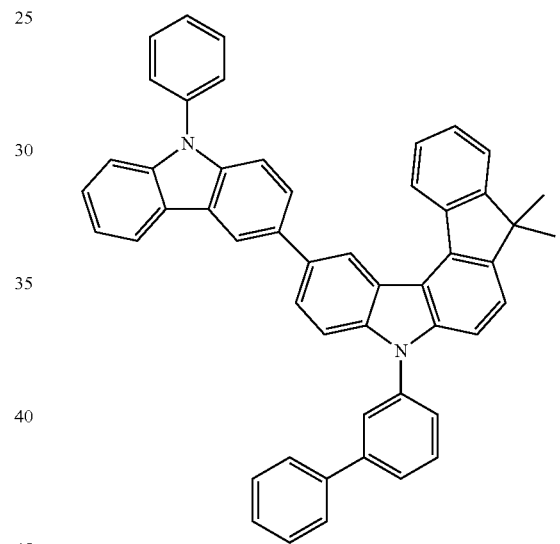
F-65
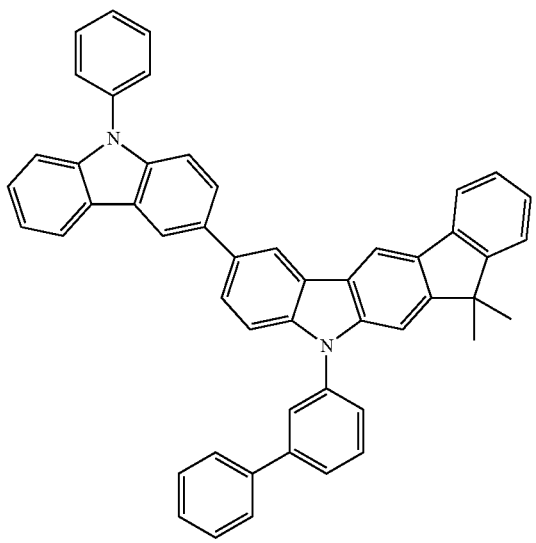
F-68
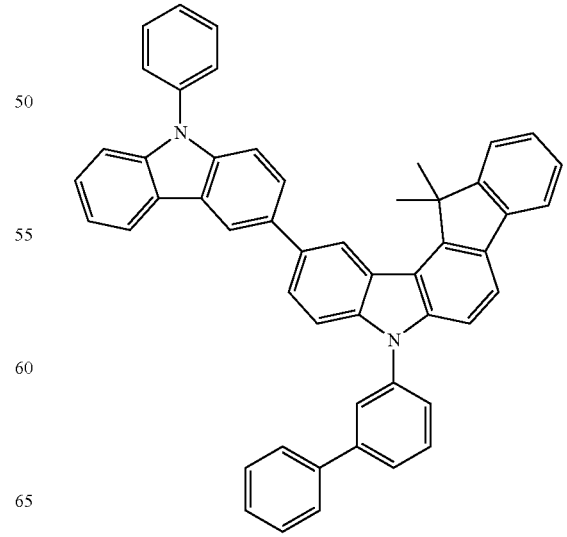

F-69
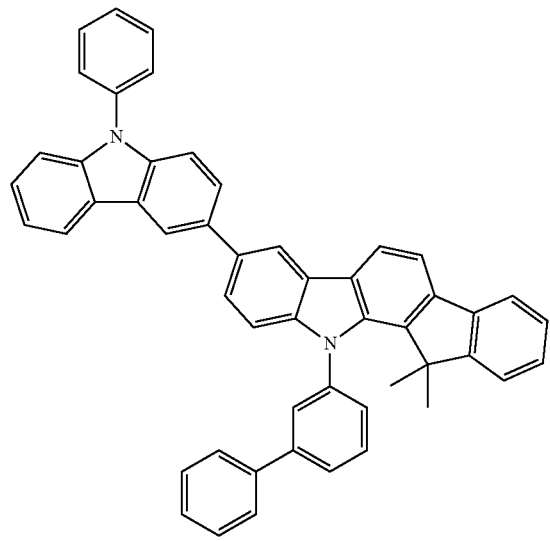
F-70
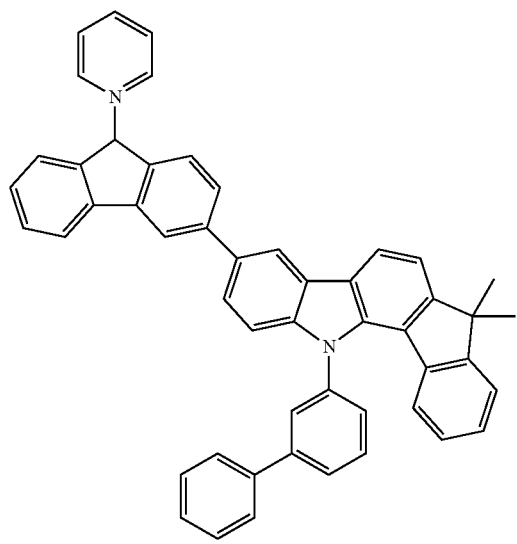
F-71
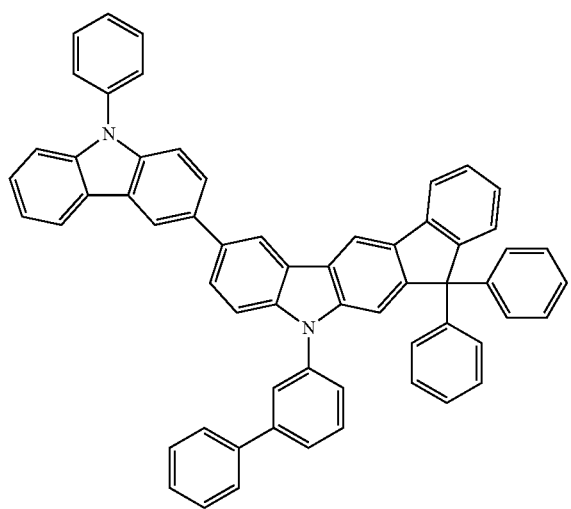
F-72
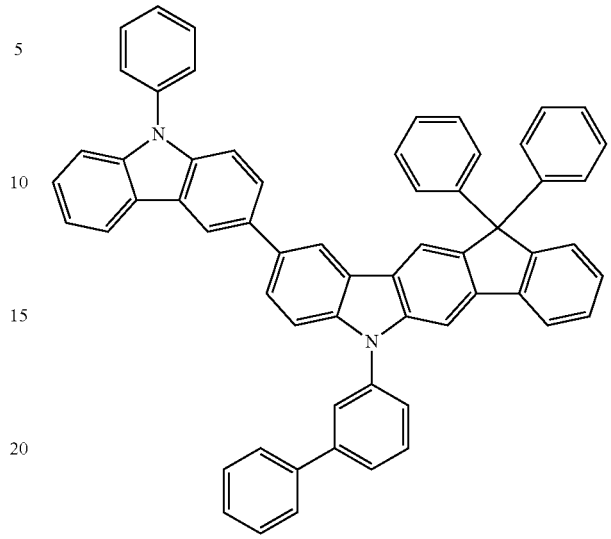
F-73
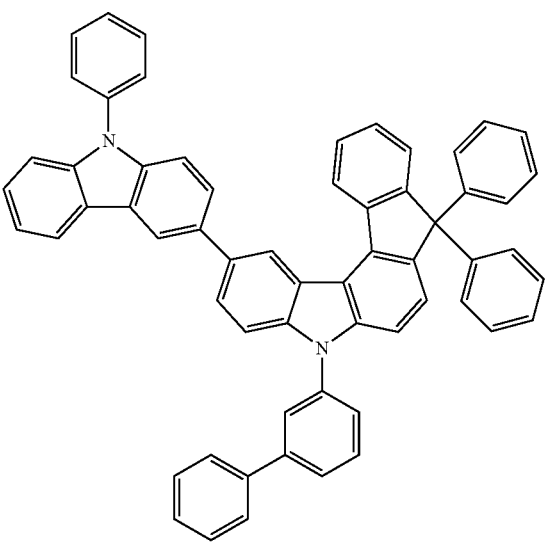
F-74
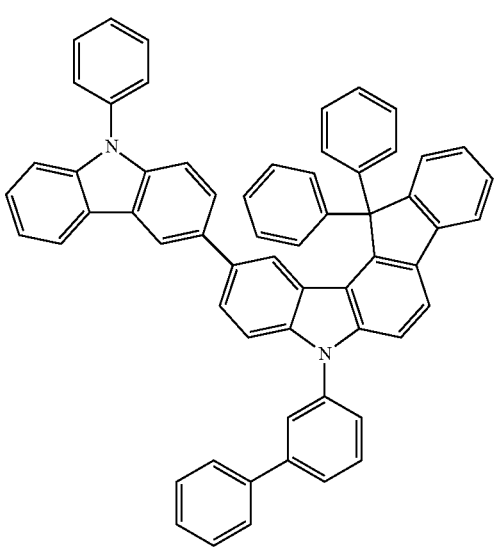

F-75
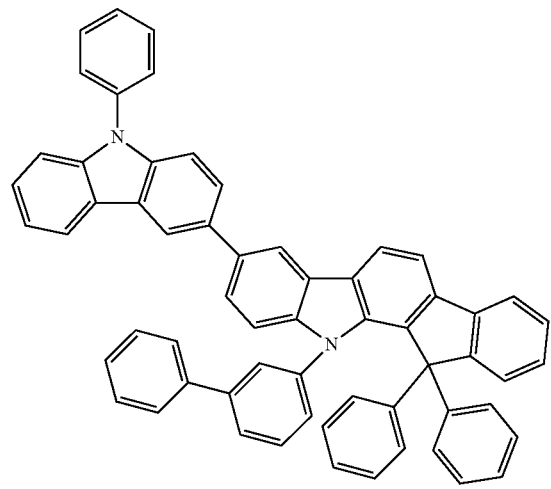
F-76
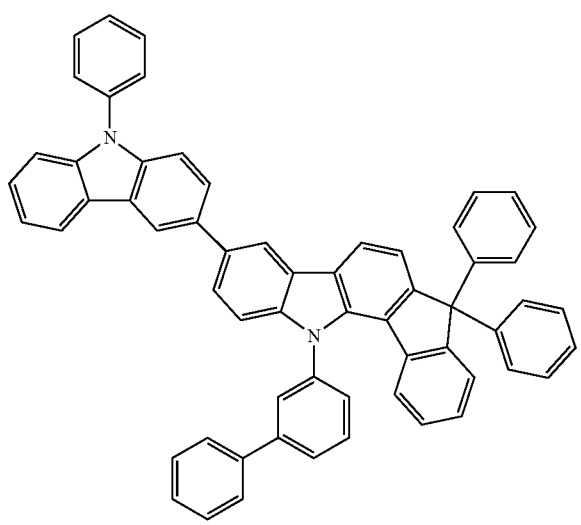
F-77
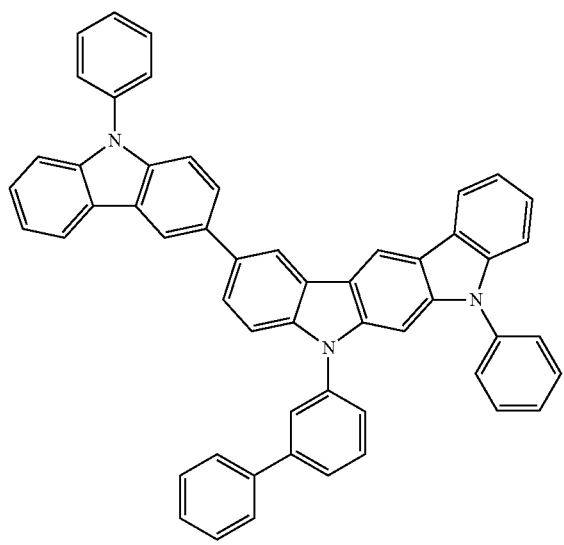
F-78
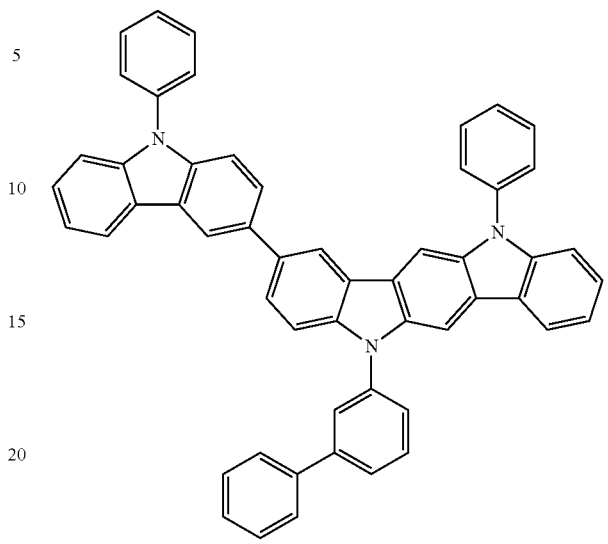
F-79
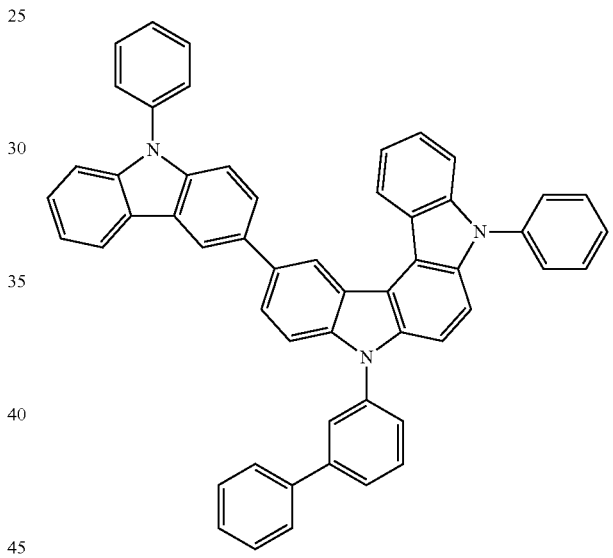
F-80
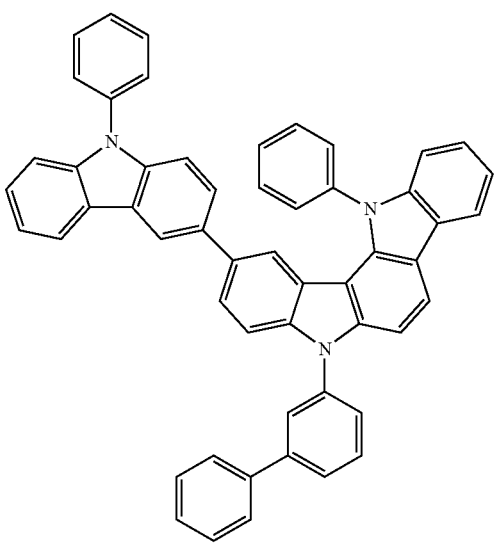

F-81
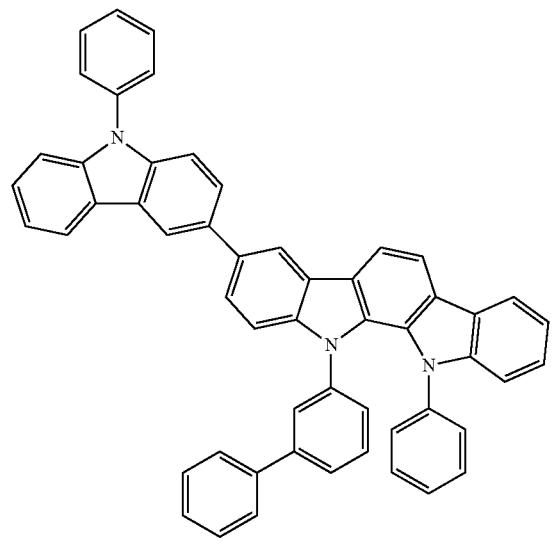
F-82
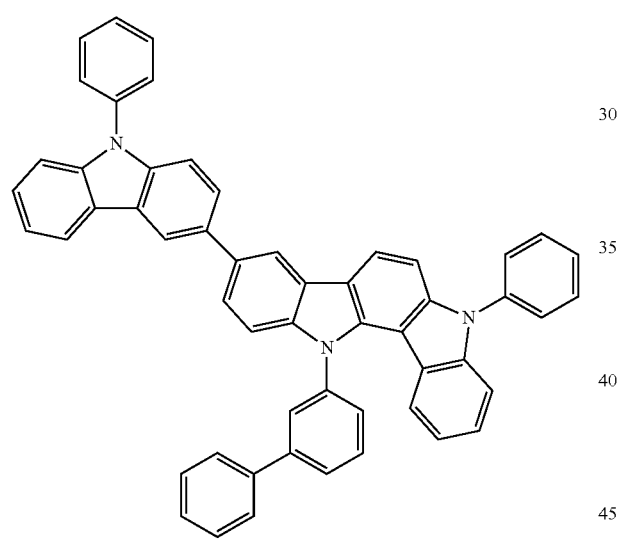
F-83
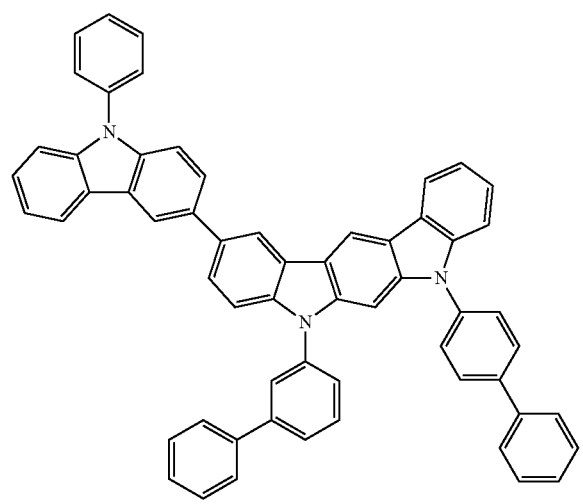
F-84
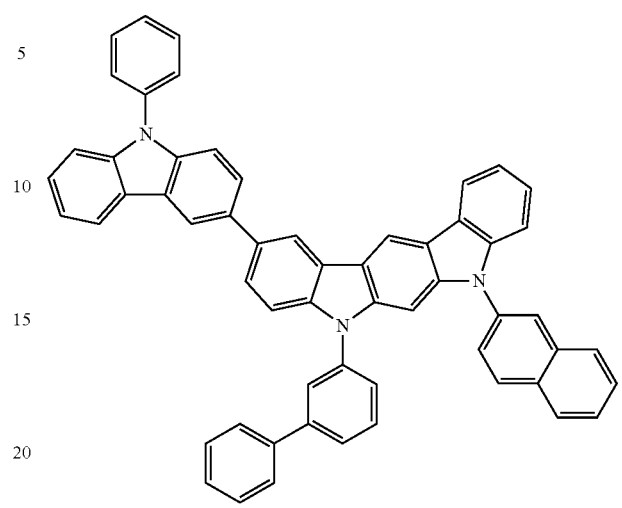
F-85
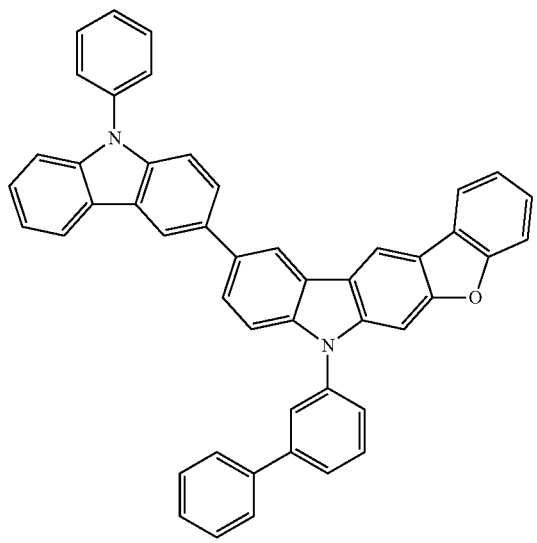
F-86
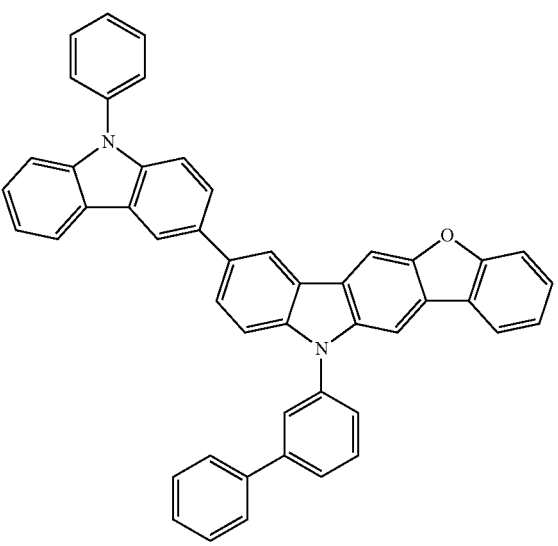

F-87
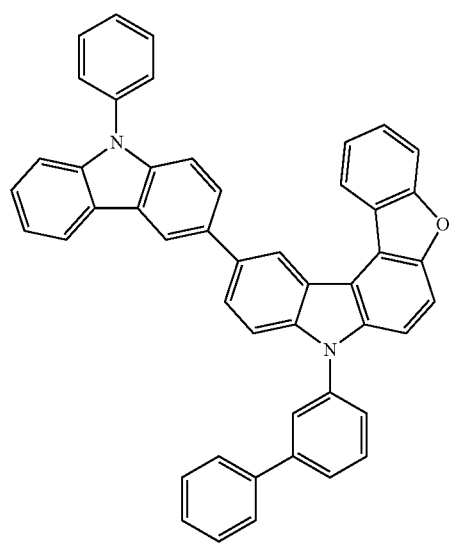
F-88
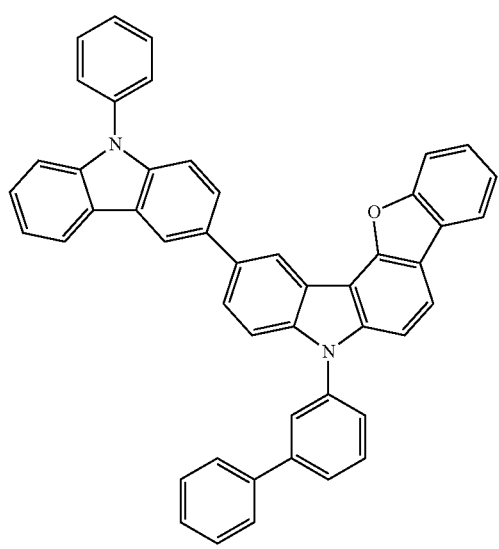
F-89
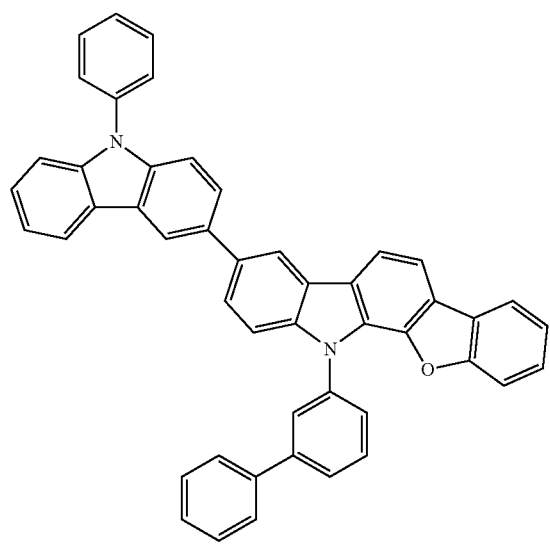
F-90
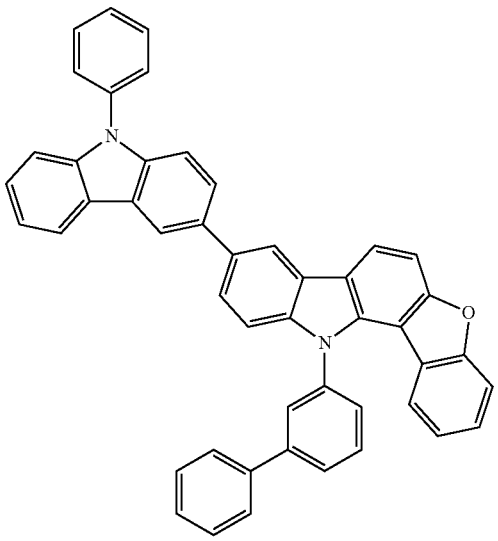
F-91
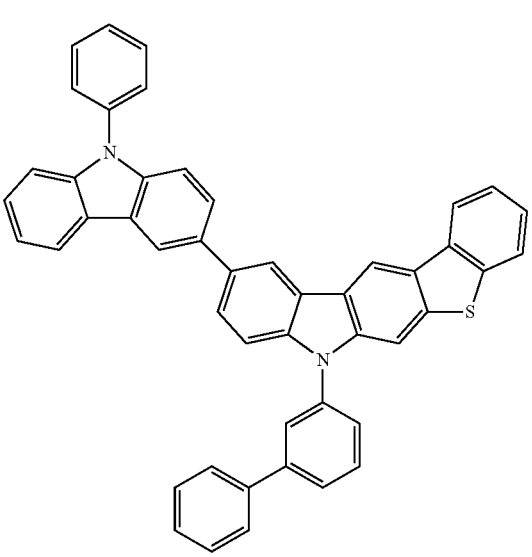
F-92
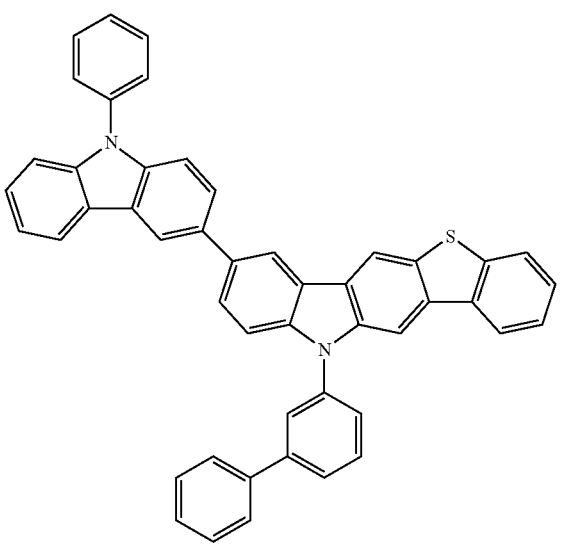

F-93
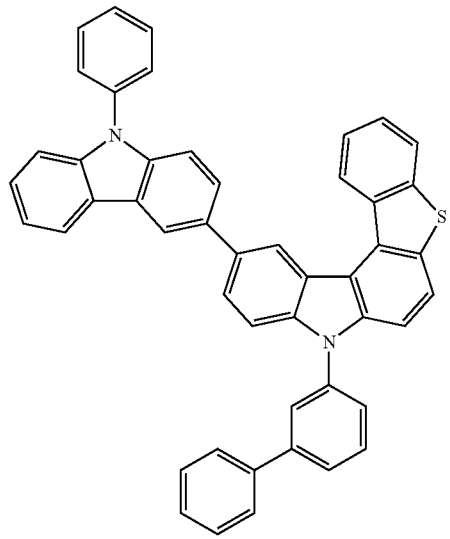
F-94
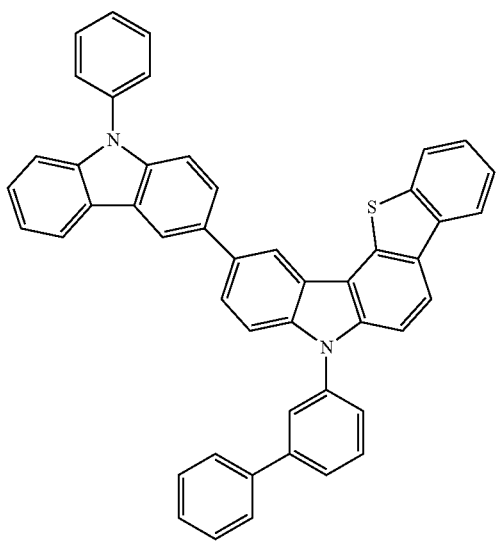
F-95
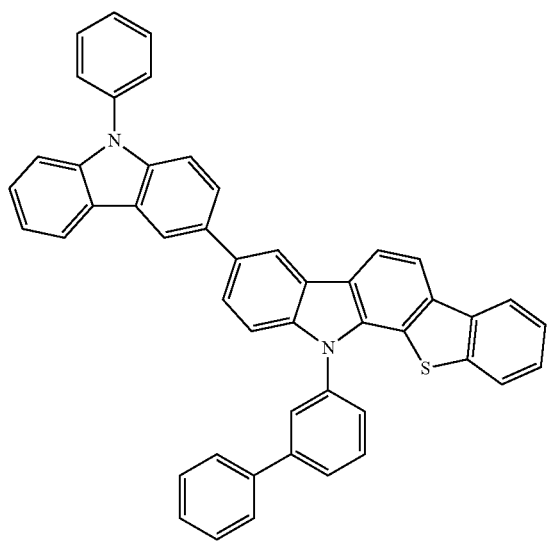
F-96
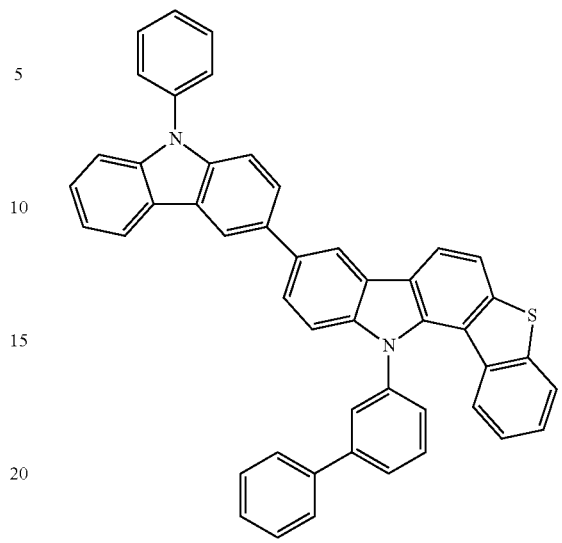
F-97
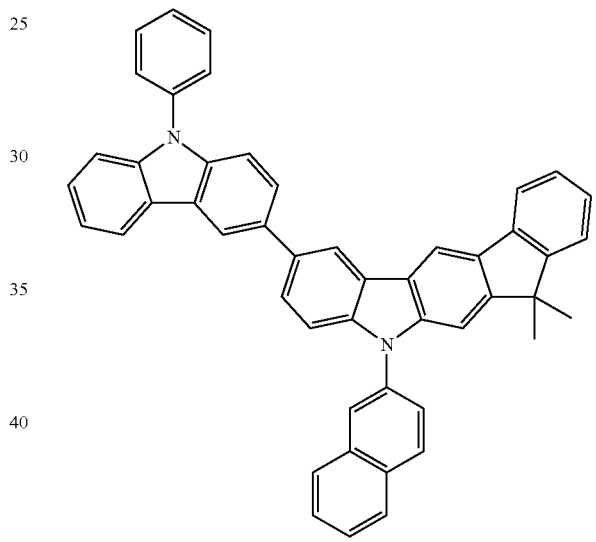
F-98
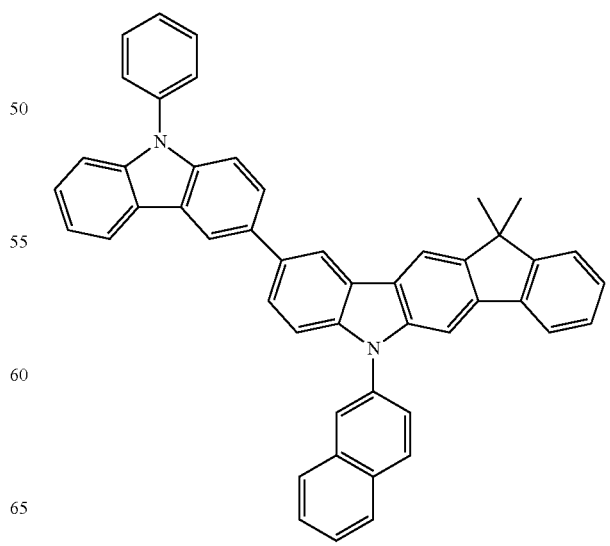

F-99
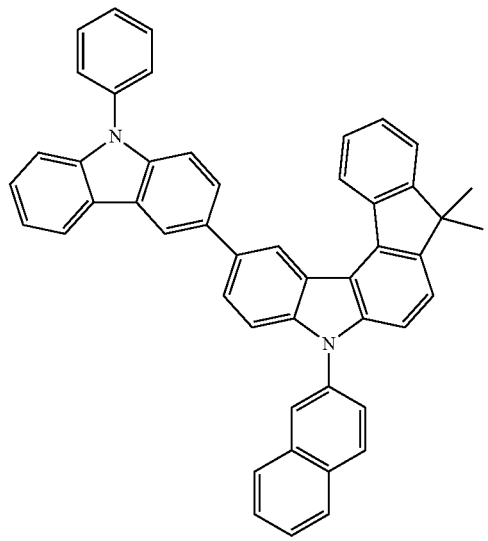
F-100
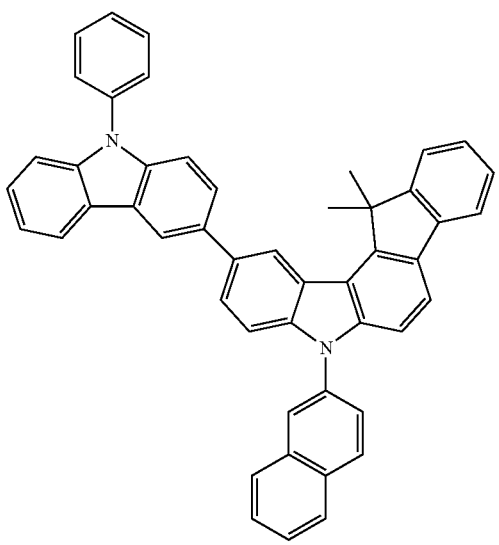
F-101
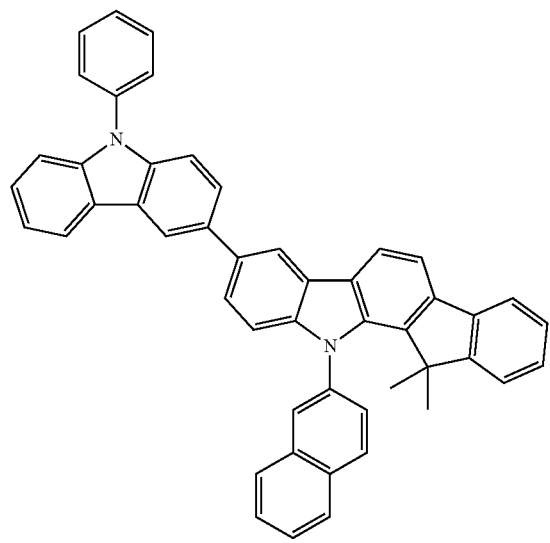
F-102
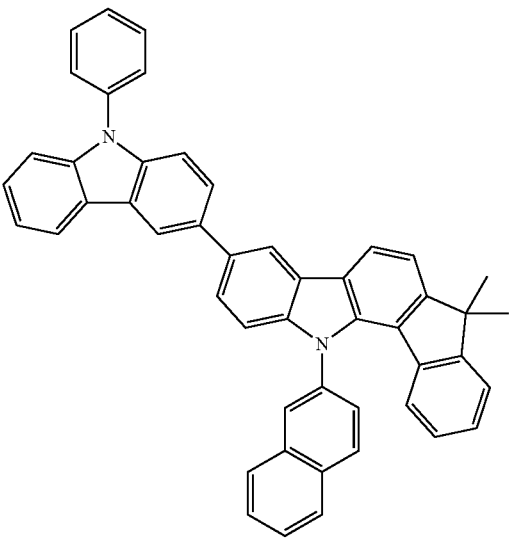
F-103
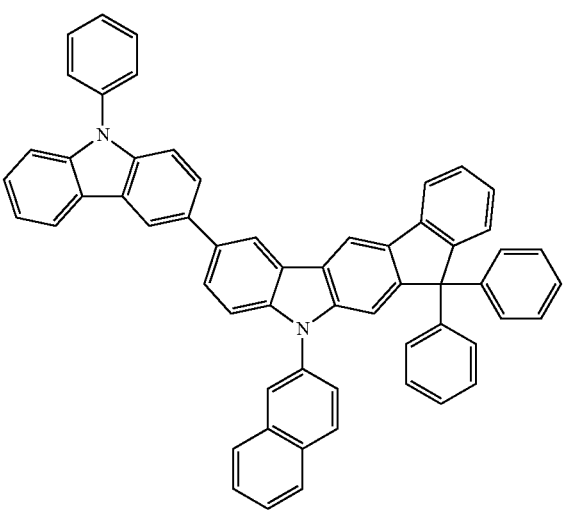
F-104
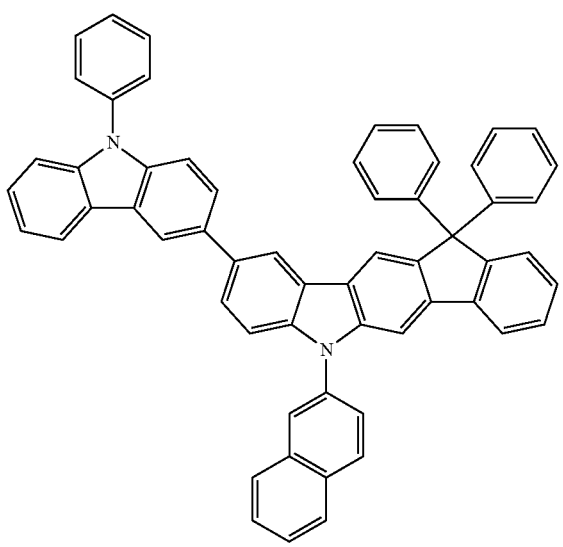

F-105
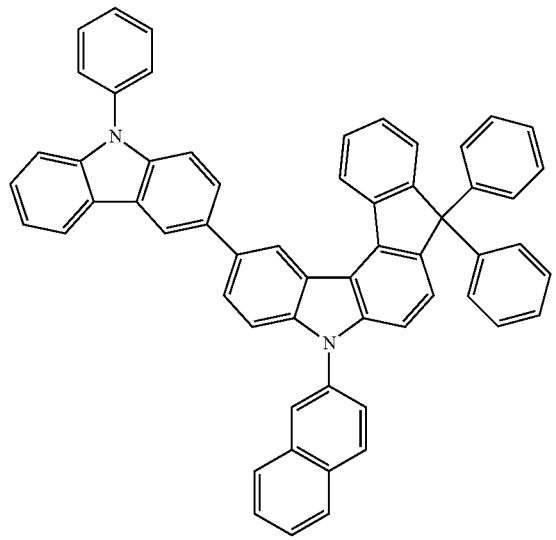
F-106
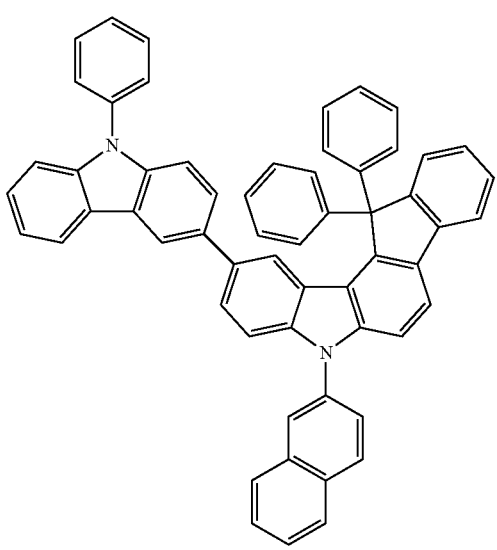
F-107
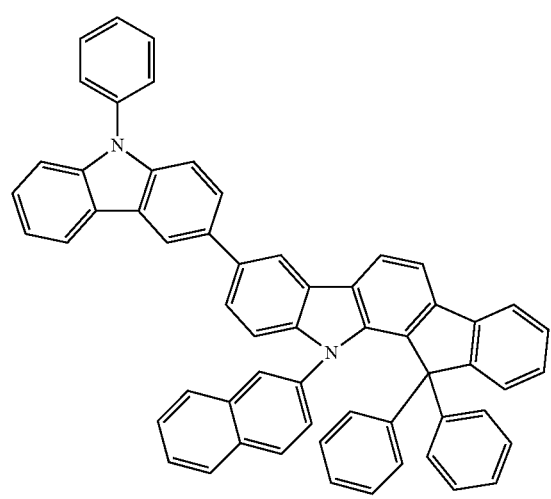
F-108
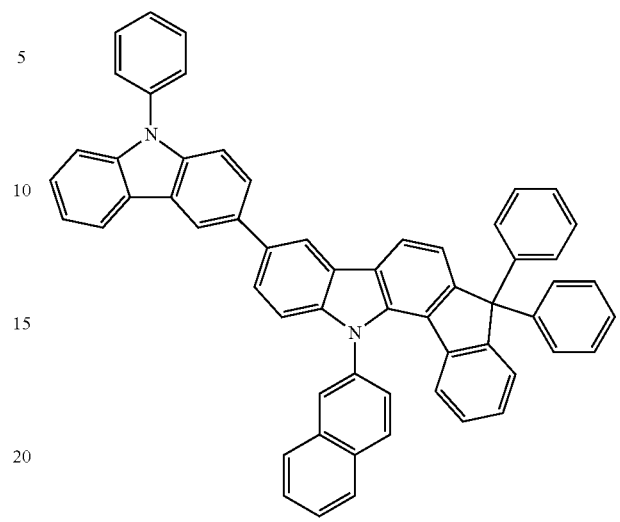
F-109
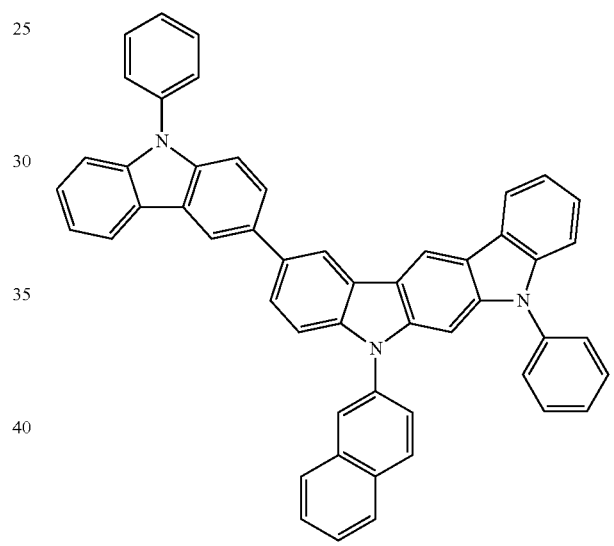
F-110
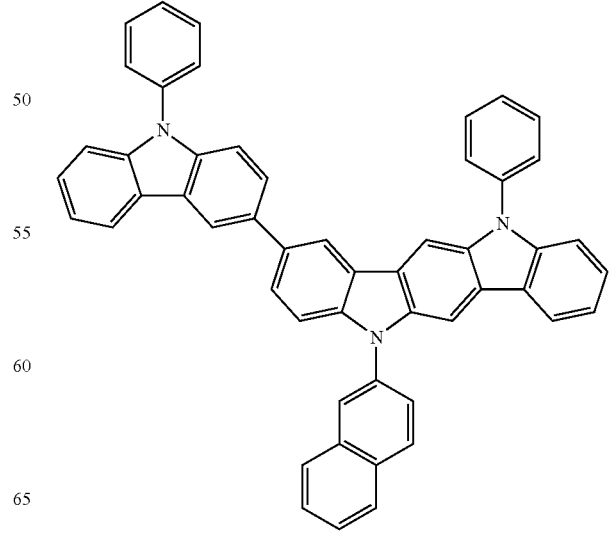

F-111
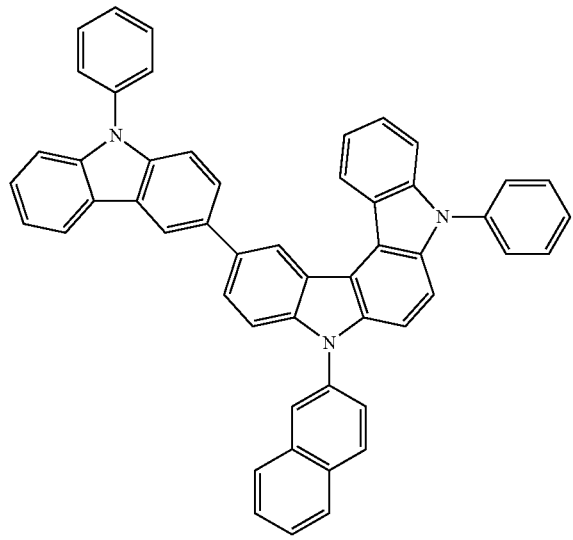
F-112
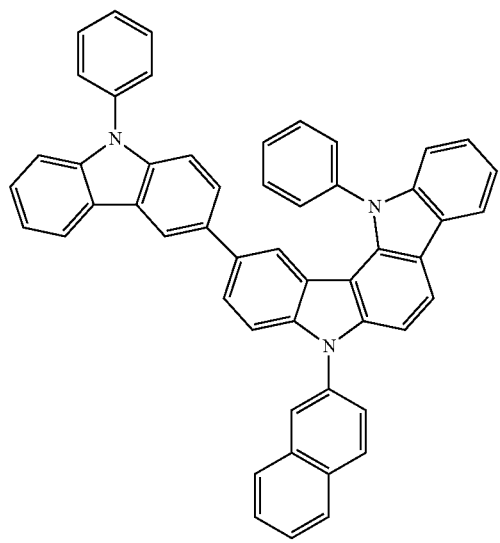
F-113
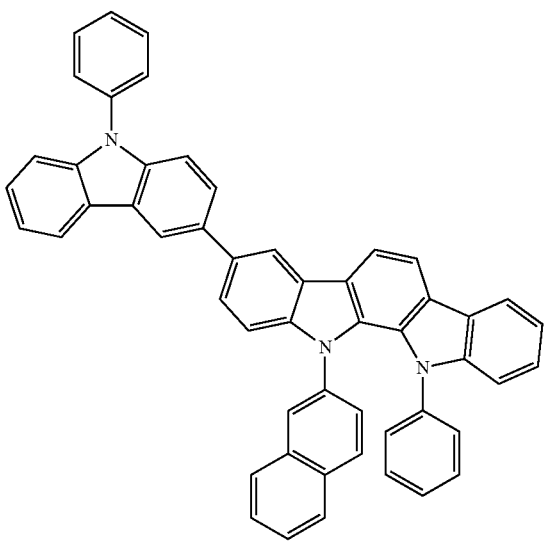
F-114
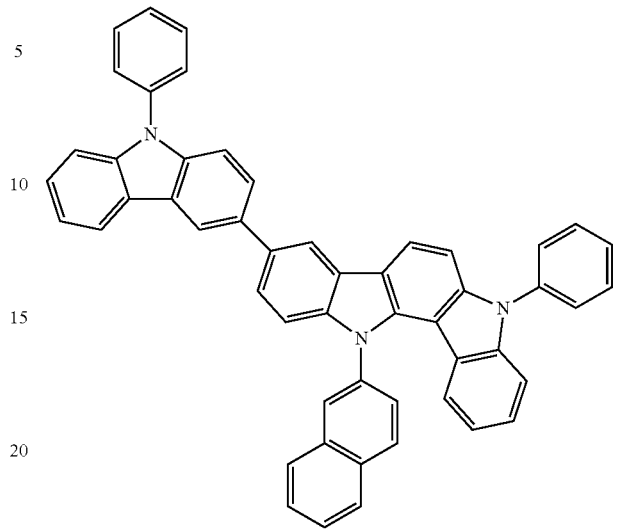
F-115
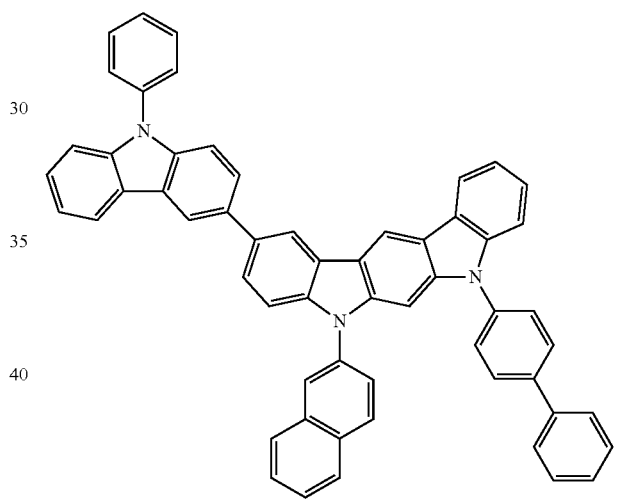
F-116
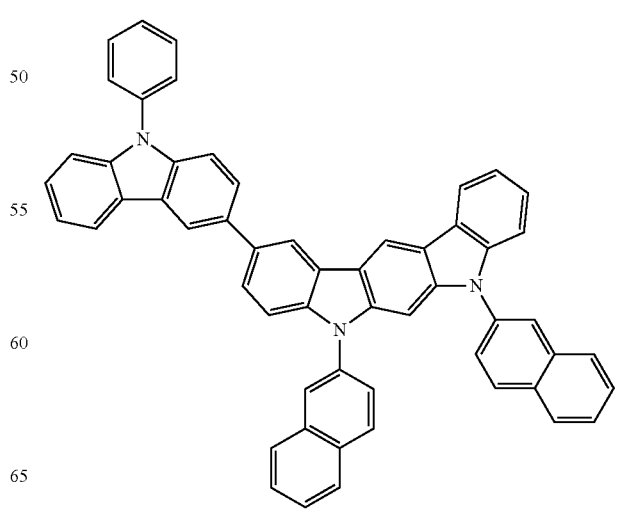

-continued
F-117
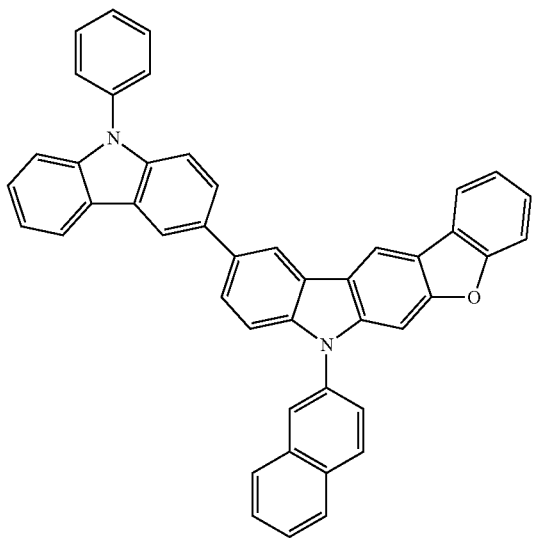
F-118
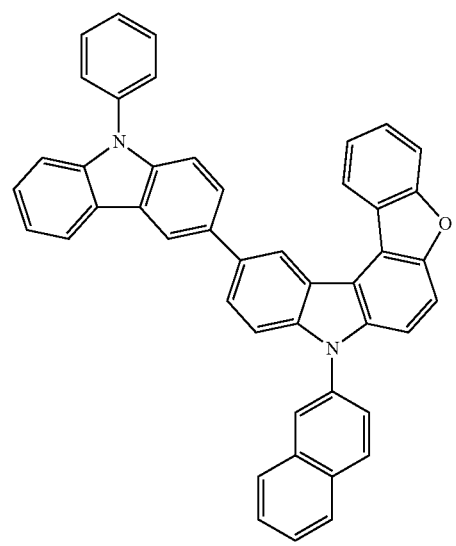
F-120
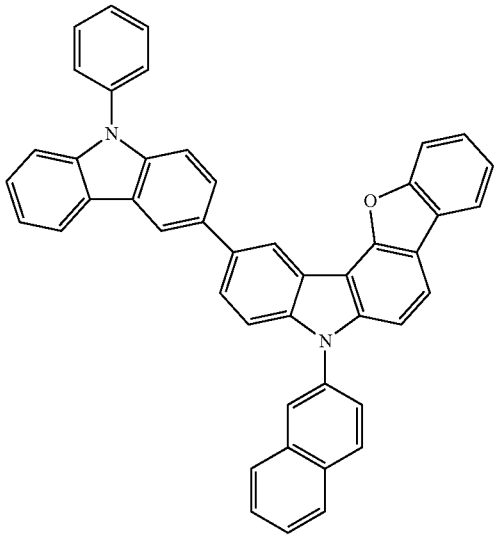
F-121
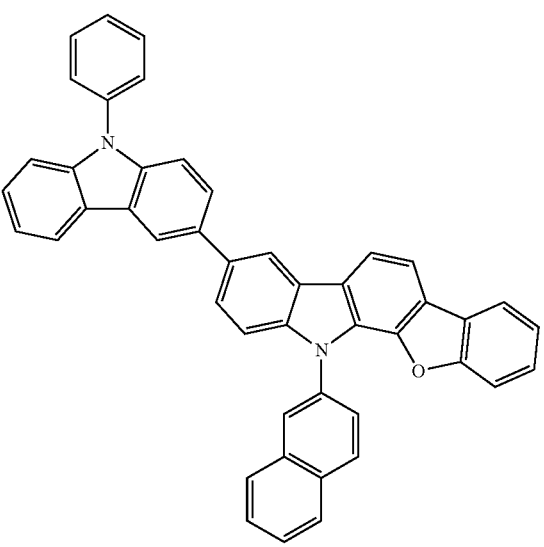
F-119
F-122
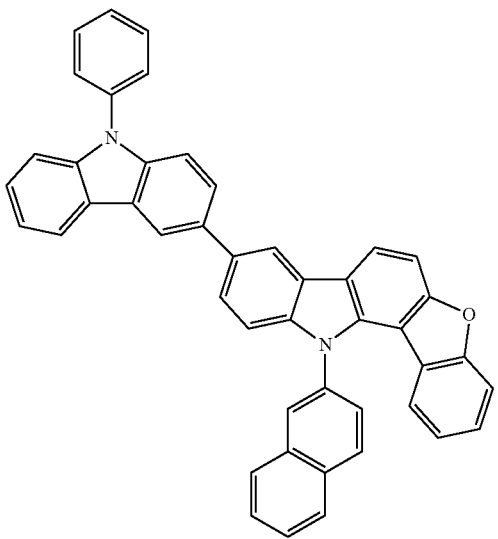

-continued
F-123
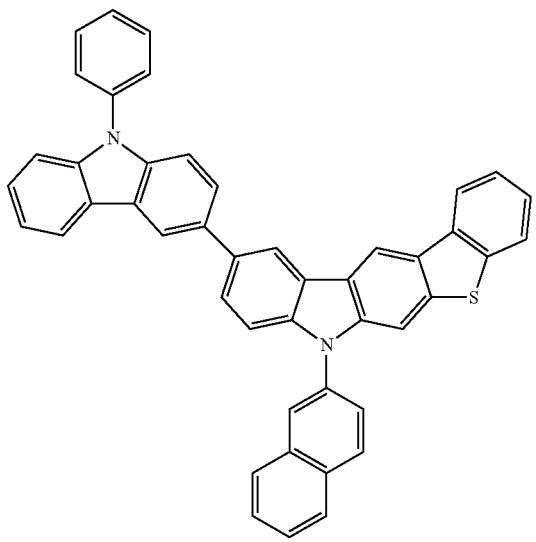
F-124
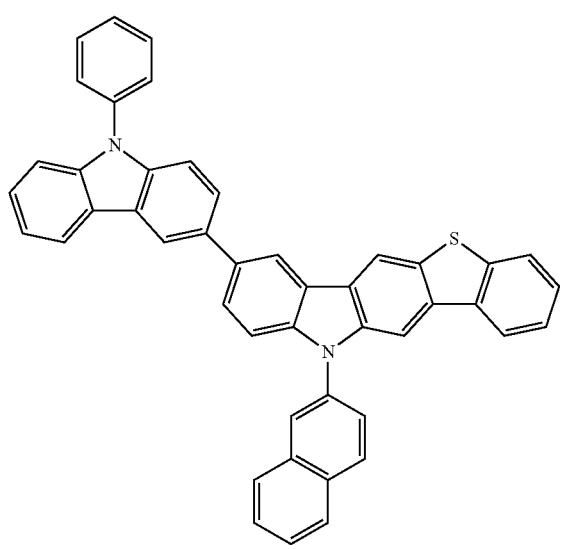
F-125
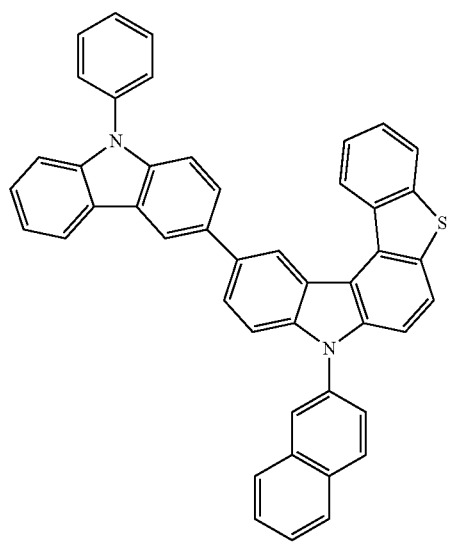
F-126
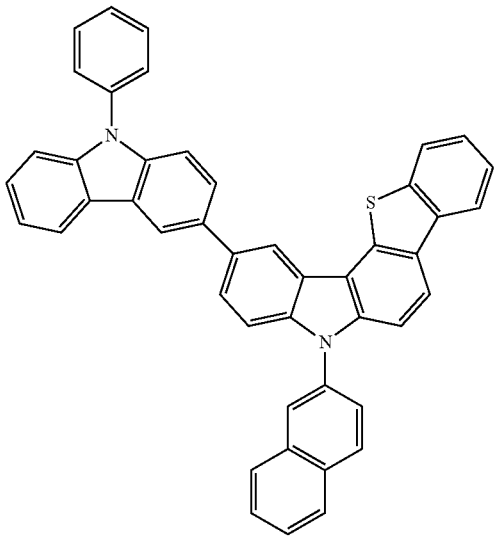
F-127
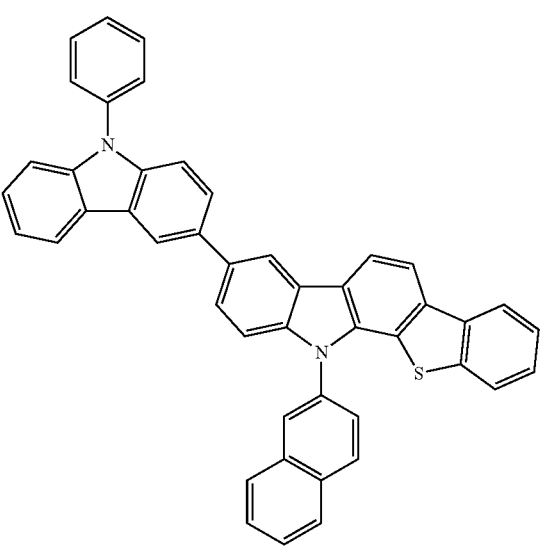
F-128
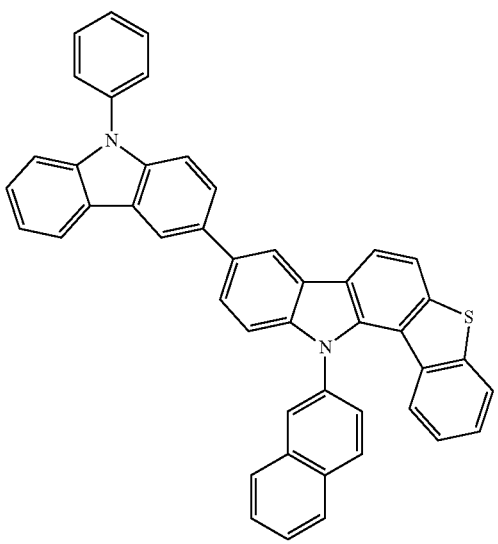

F-129
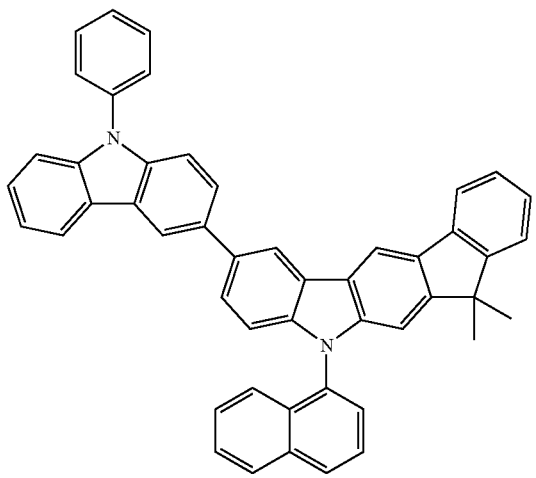
F-130
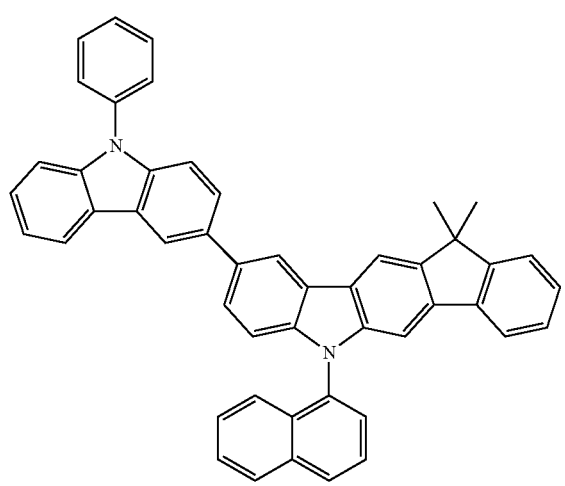
F-131
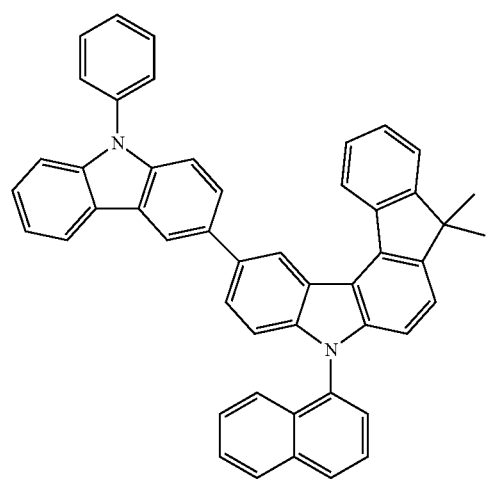
F-132
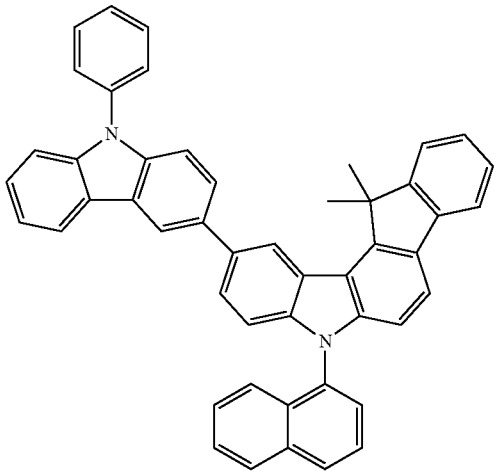
F-133
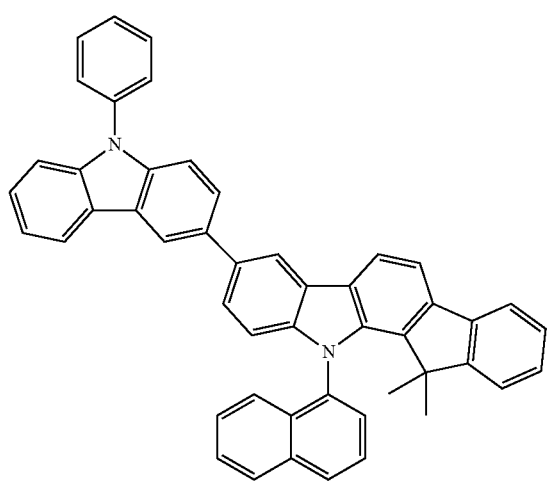
F-134
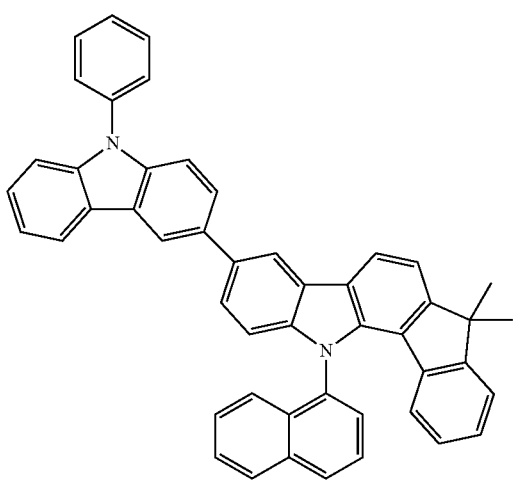

F-135
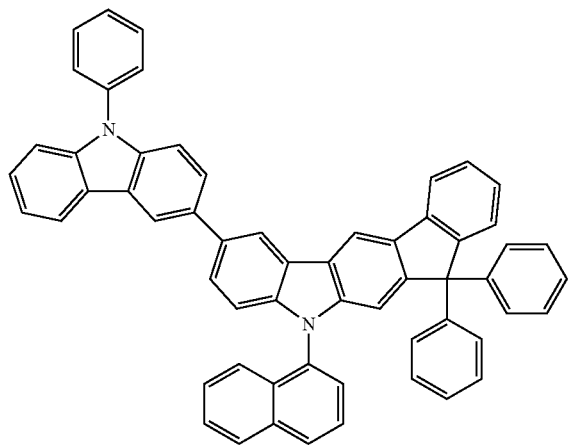
F-136
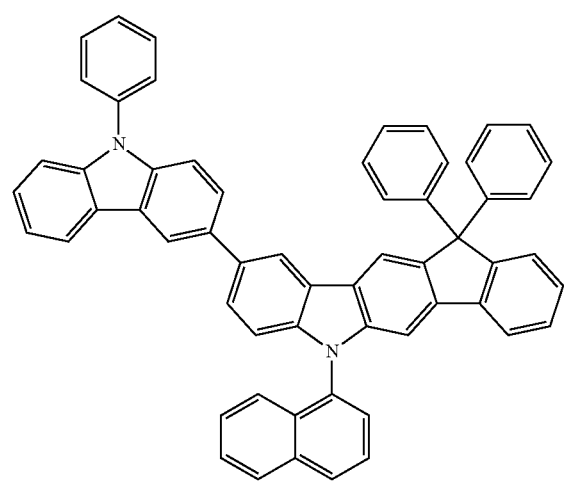
F-137
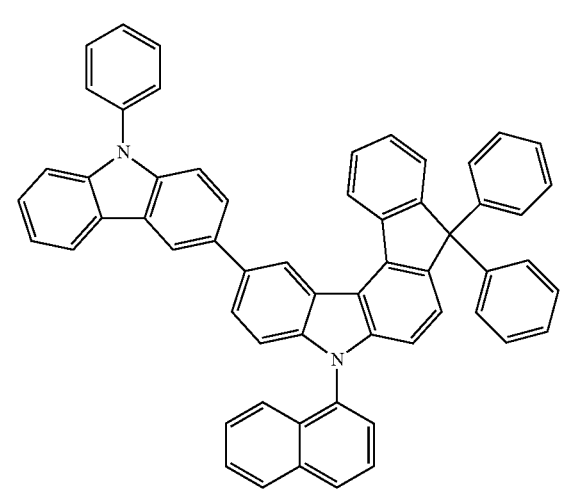
F-138
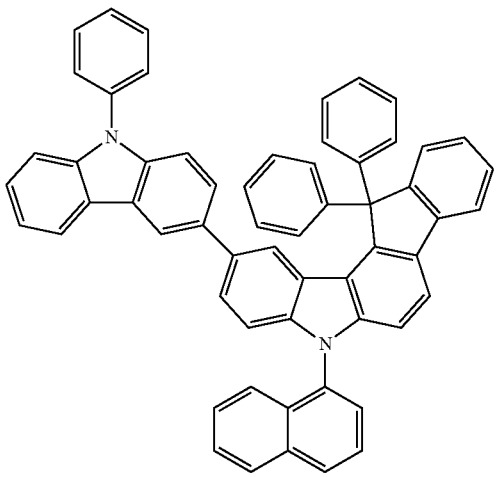
F-139
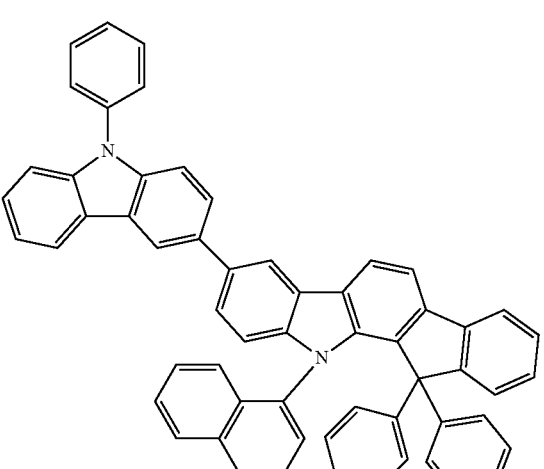
F-140
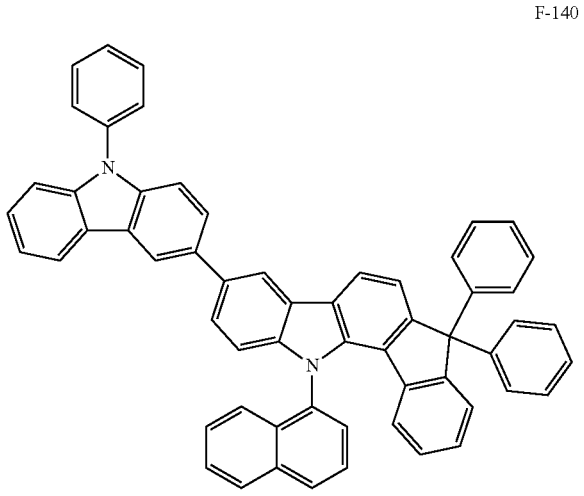

-continued
F-141
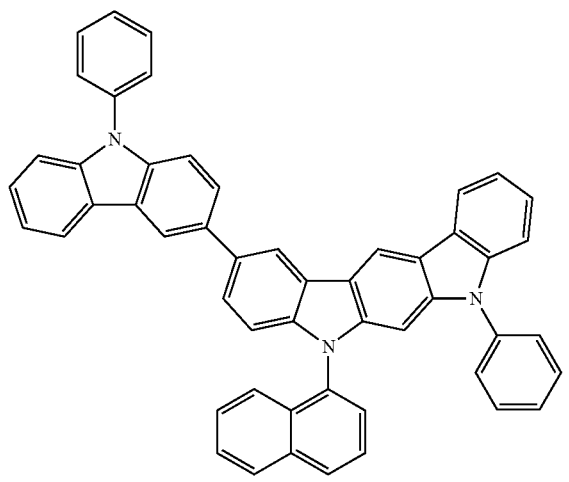
F-142
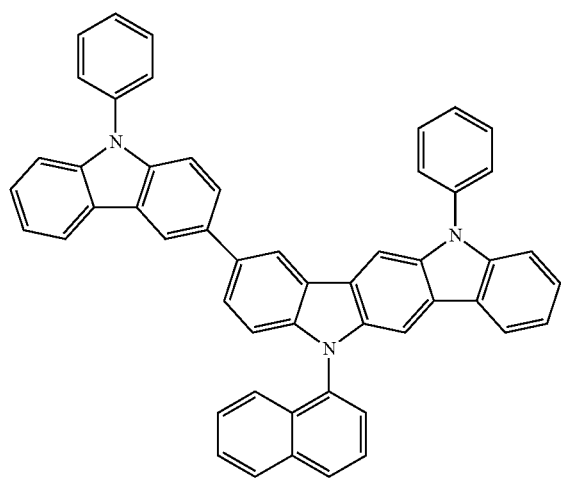
F-143
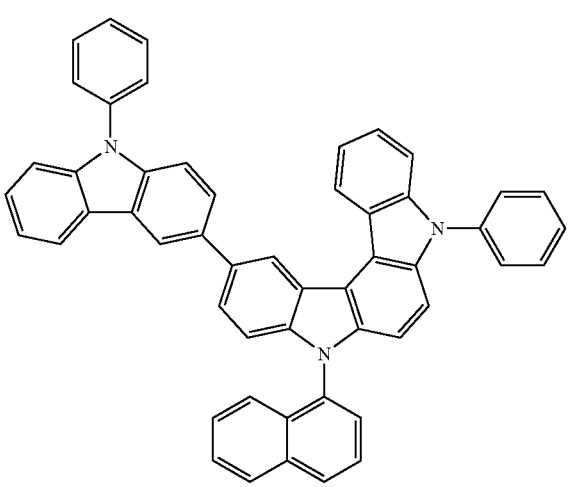
-continued
F-144
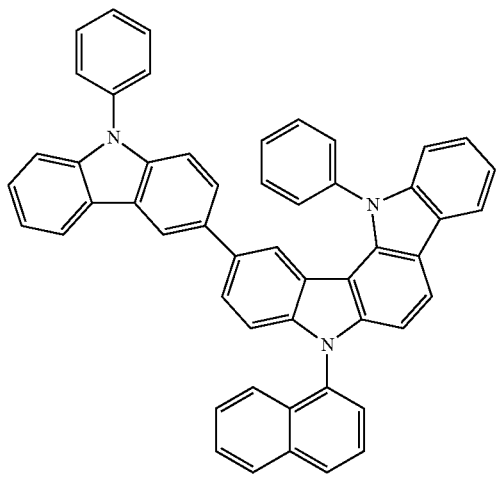
F-145
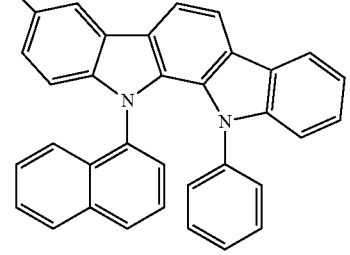
F-146
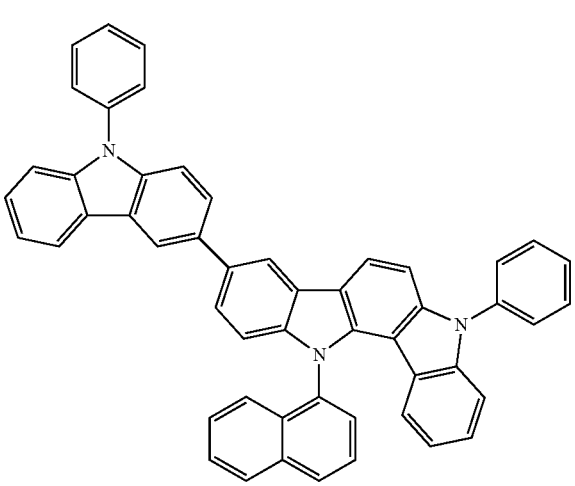

-continued
F-147
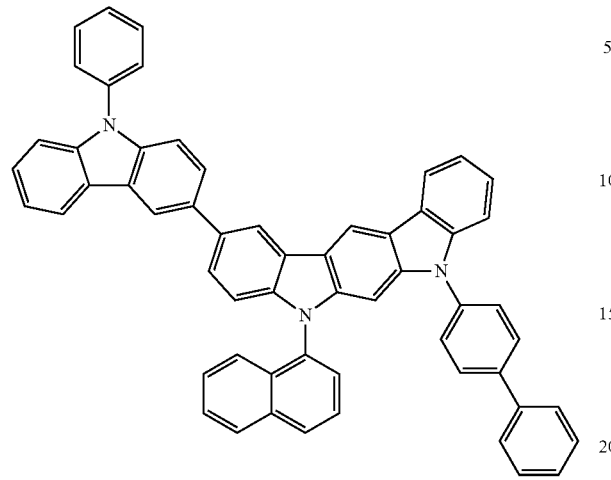
F-150
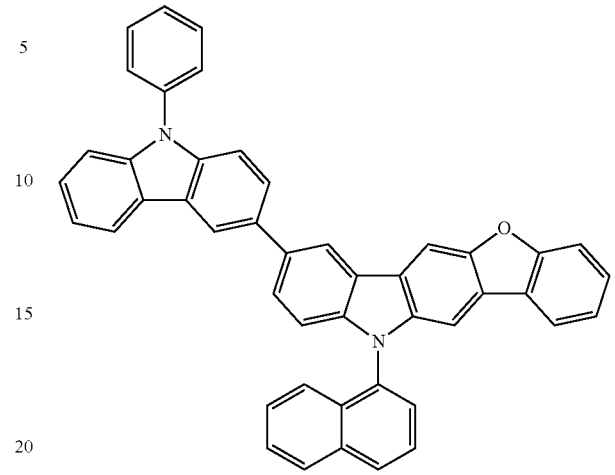
F-148
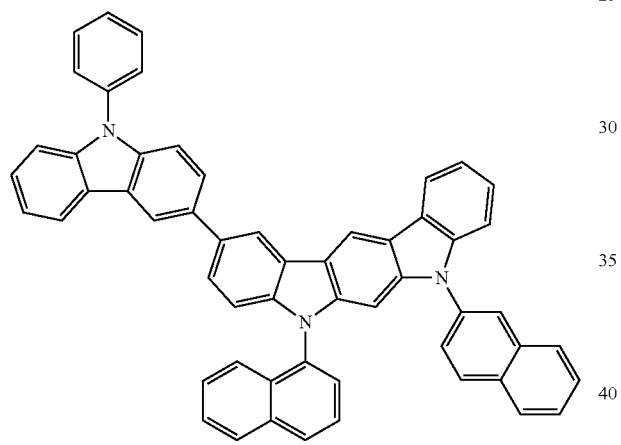
F-151
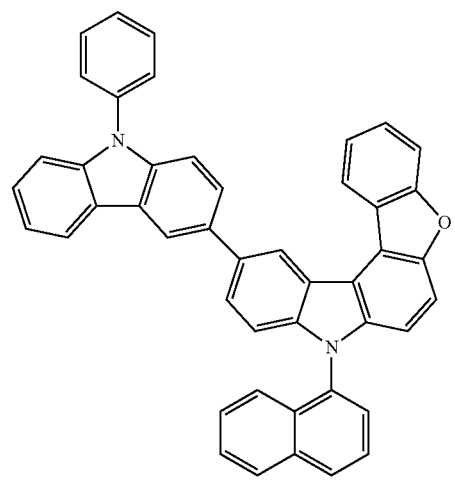
F-149
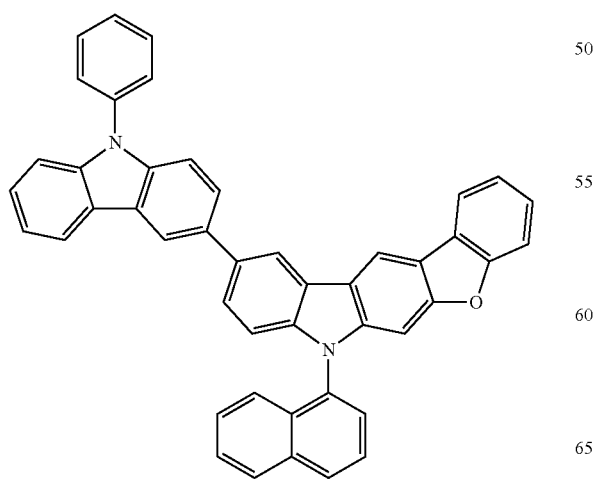
F-152
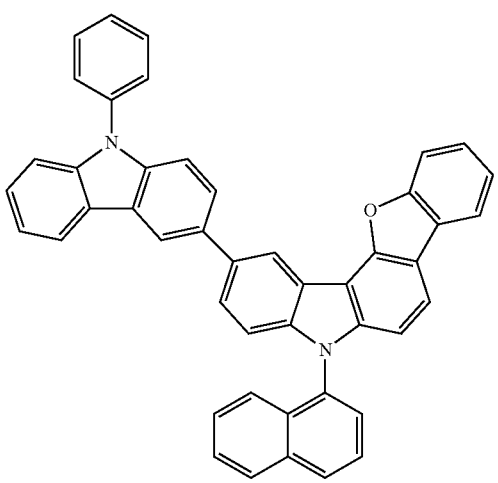

F-153
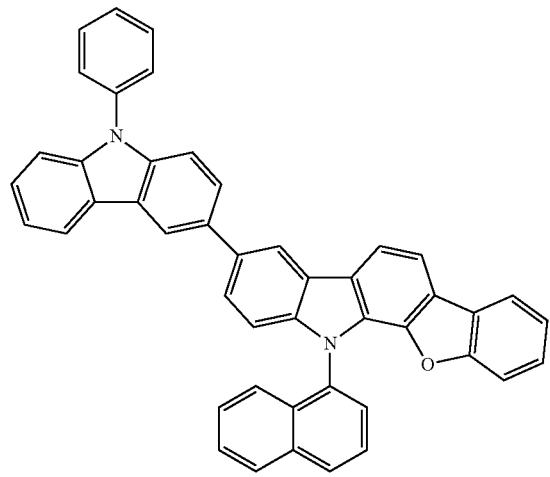
F-154
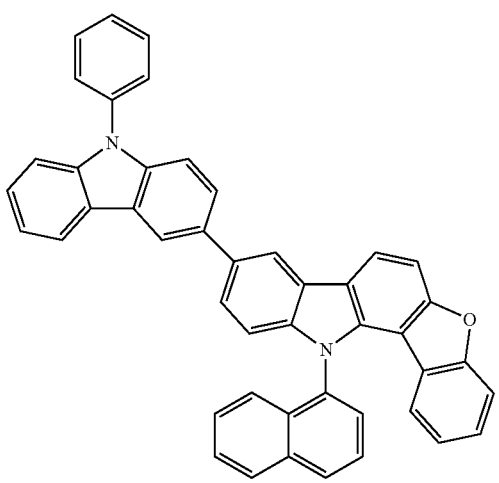
F-155
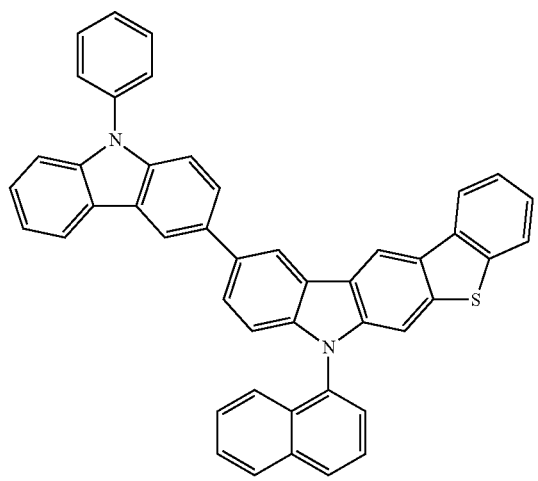
F-156
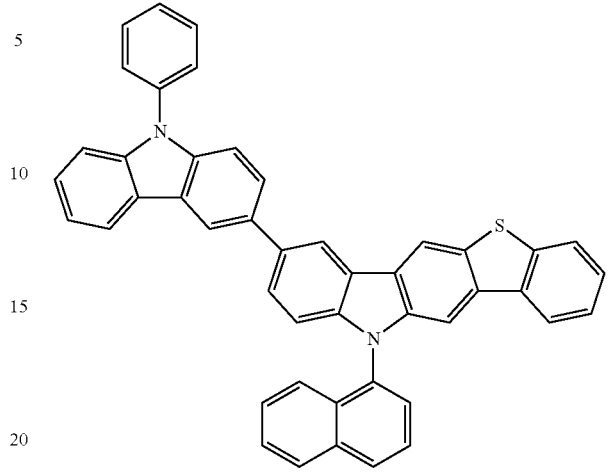
F-157
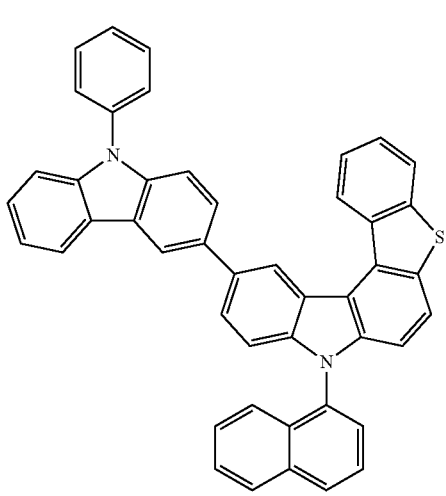
F-158
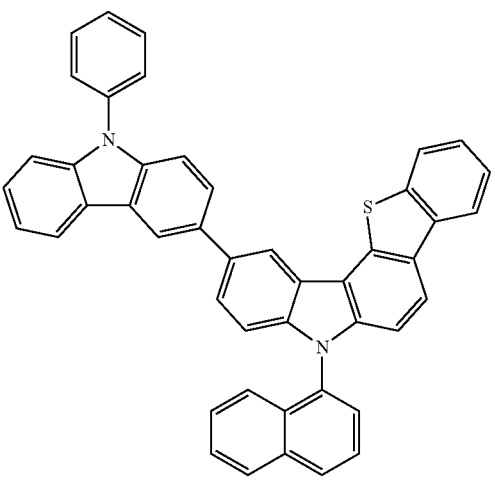

F-159
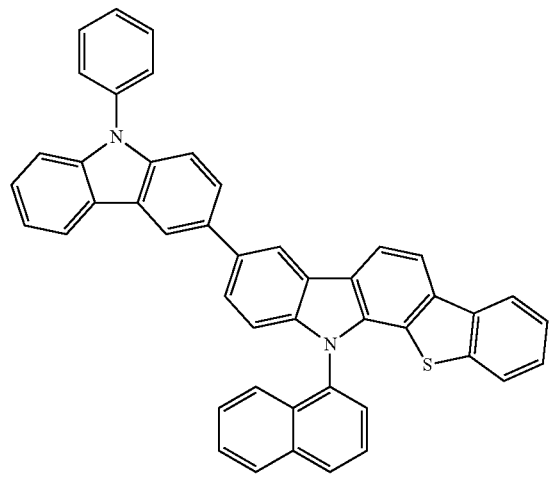
F-160
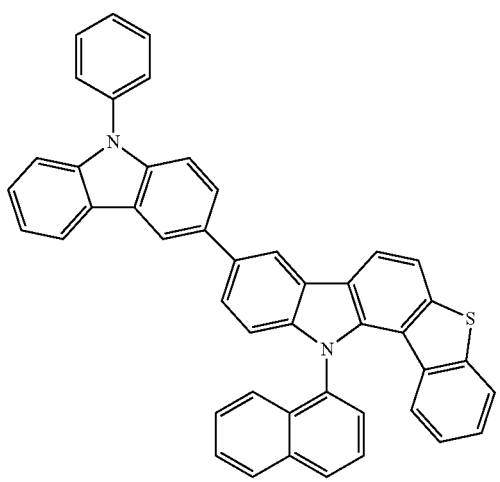
F-161
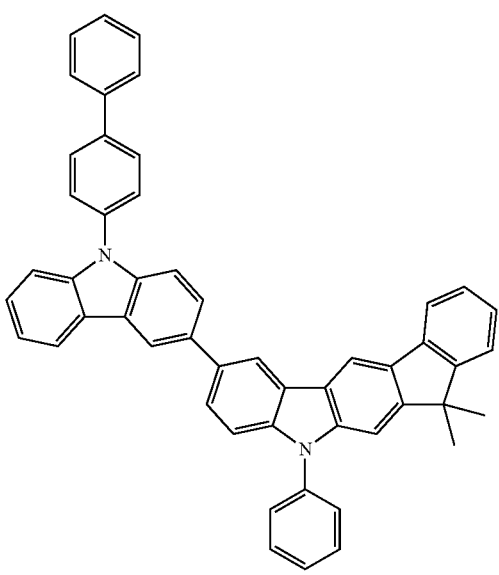
F-162
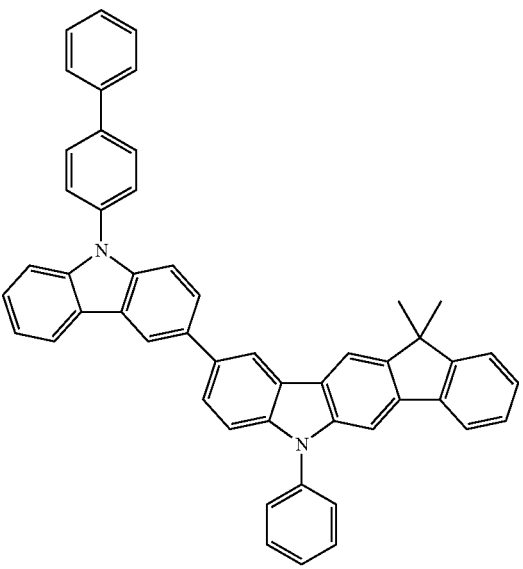
F-163
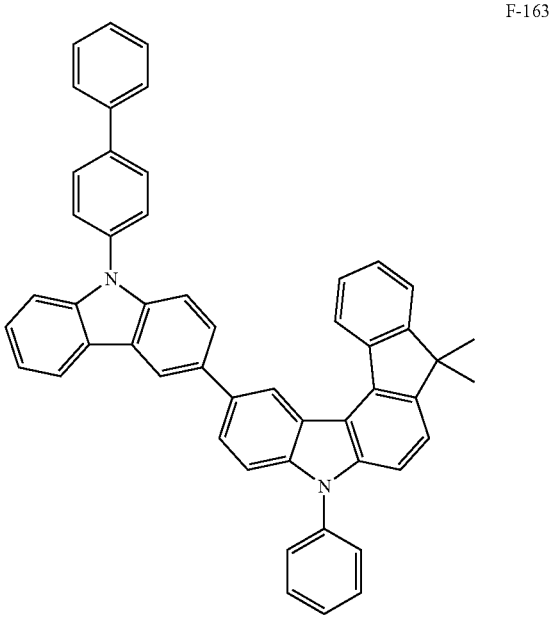

F-164
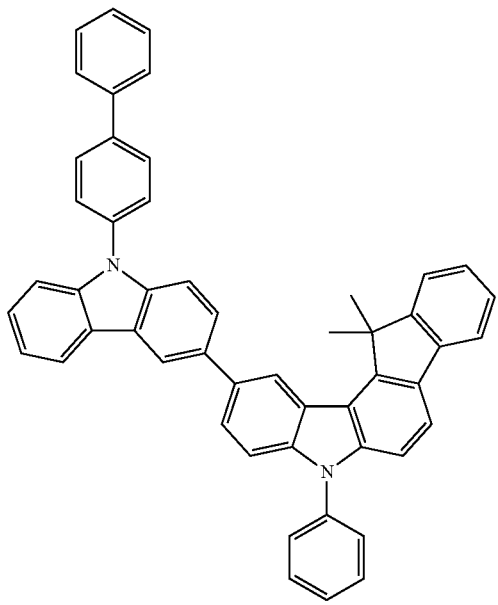
F-166
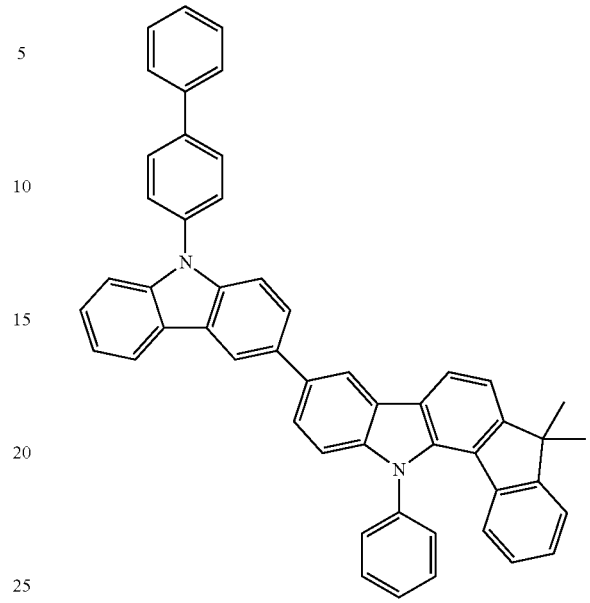
F-165
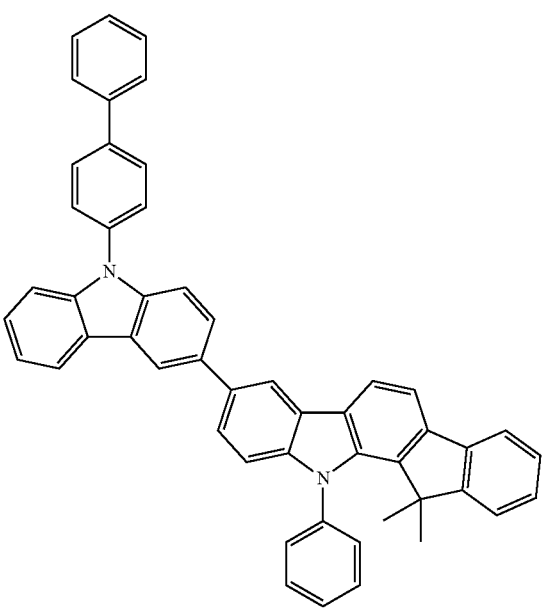
F-167
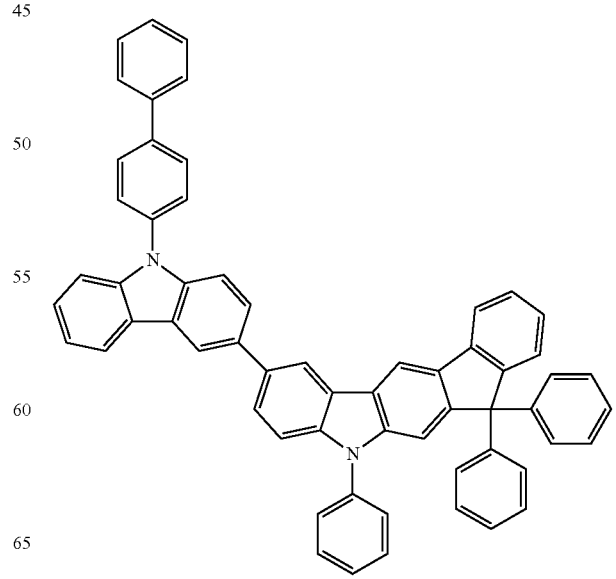

F-168
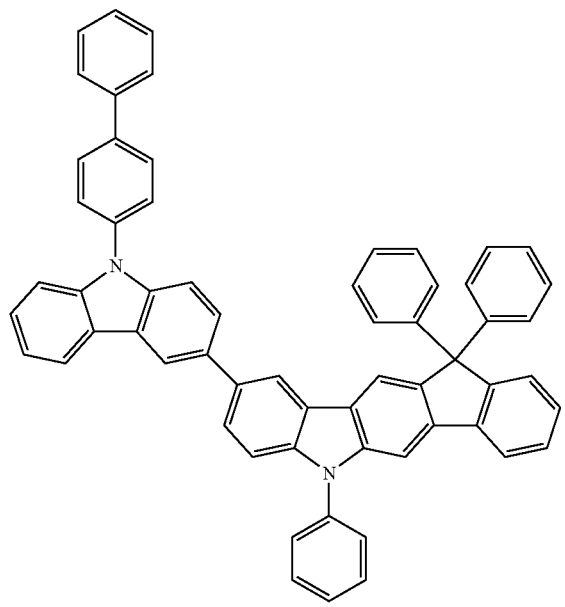
F-170
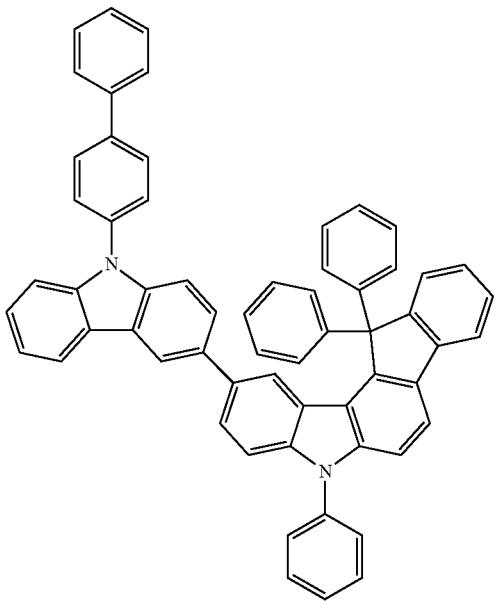
F-169
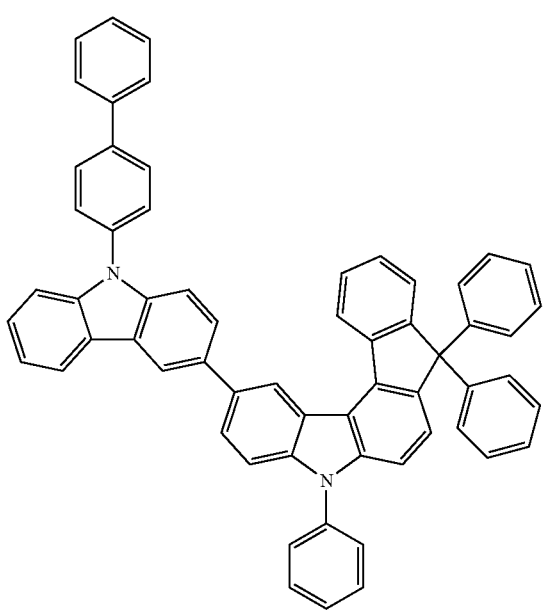
F-171
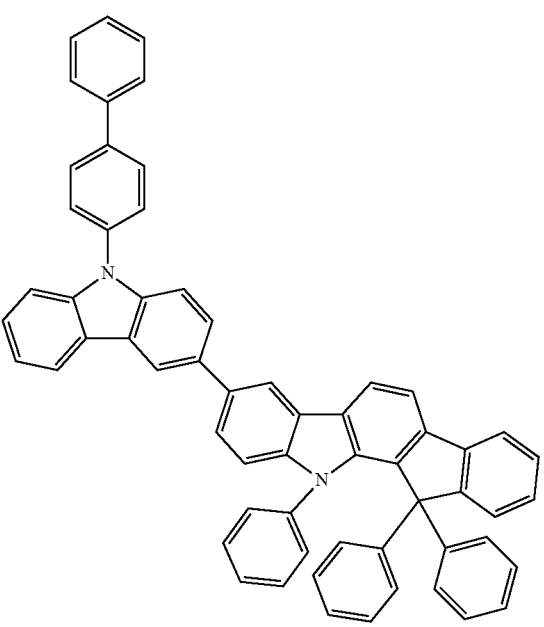

F-172
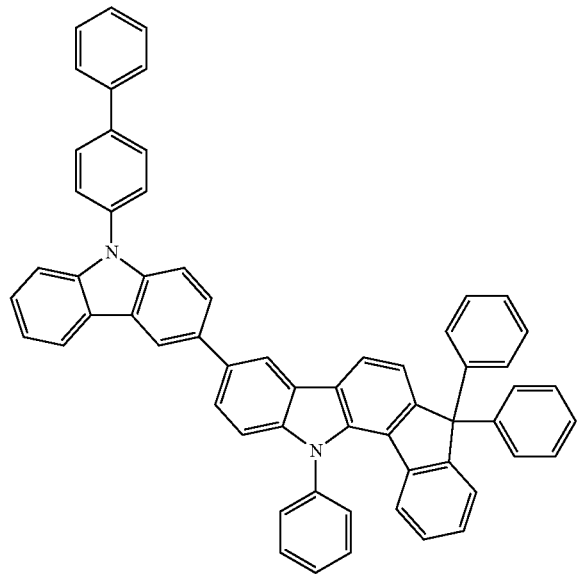
F-174
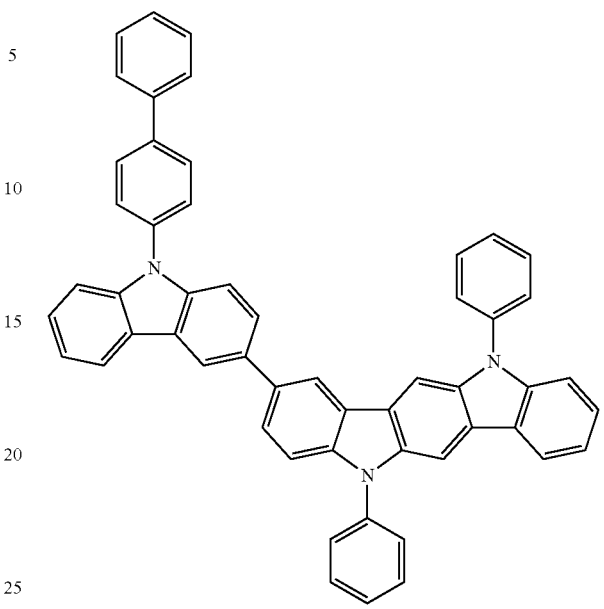
F-173
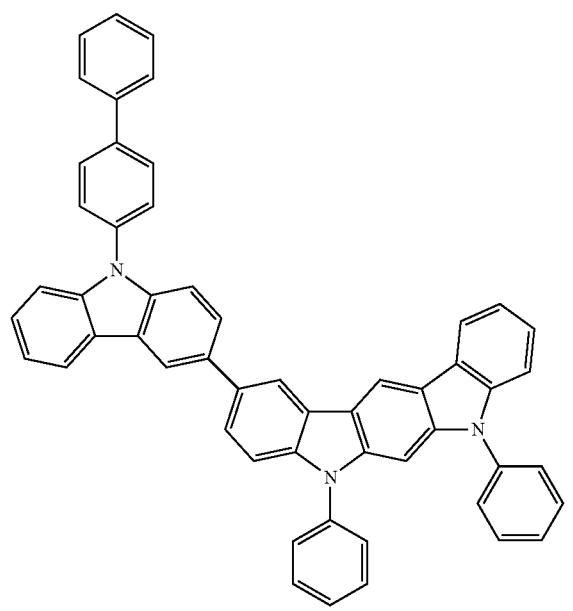
F-175
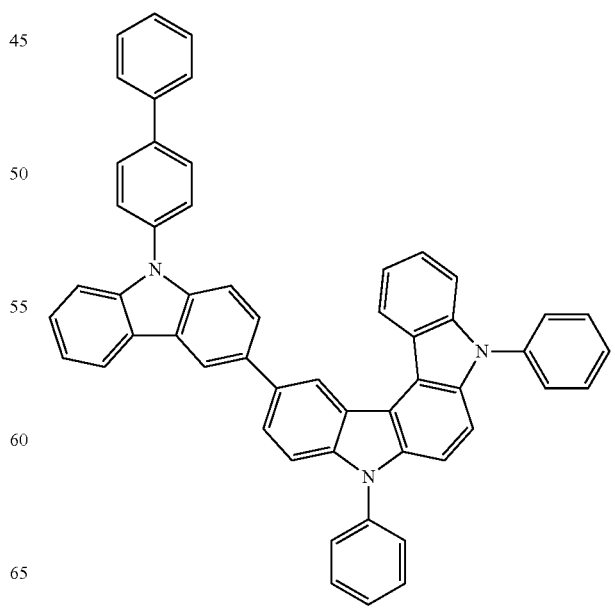

F-176
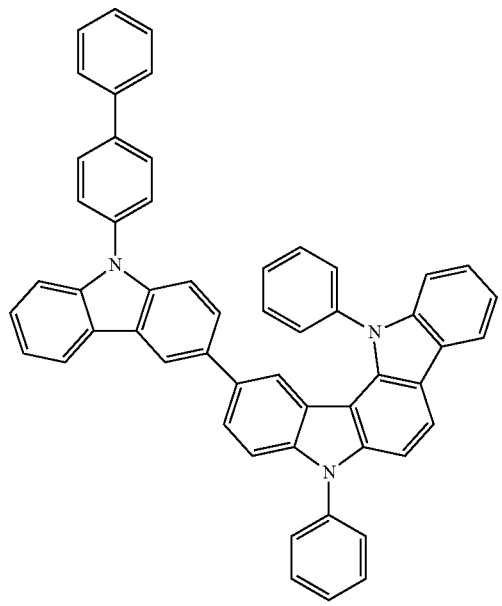
F-178
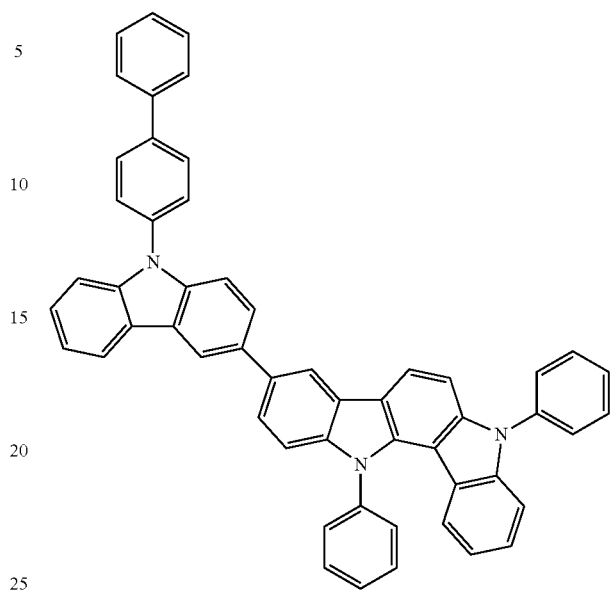
F-177
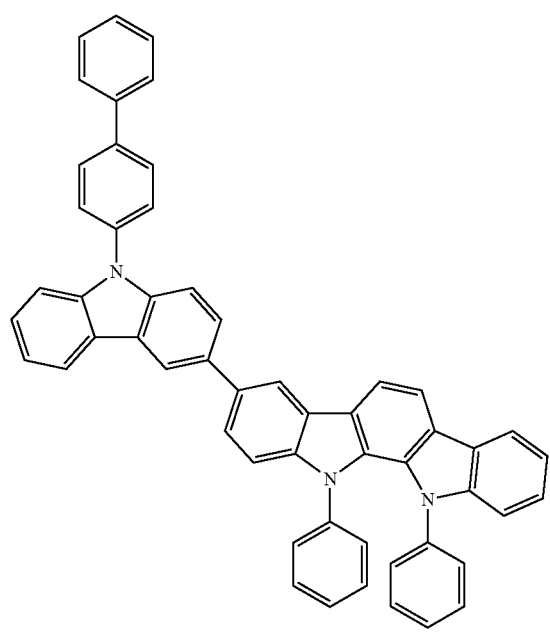
F-179
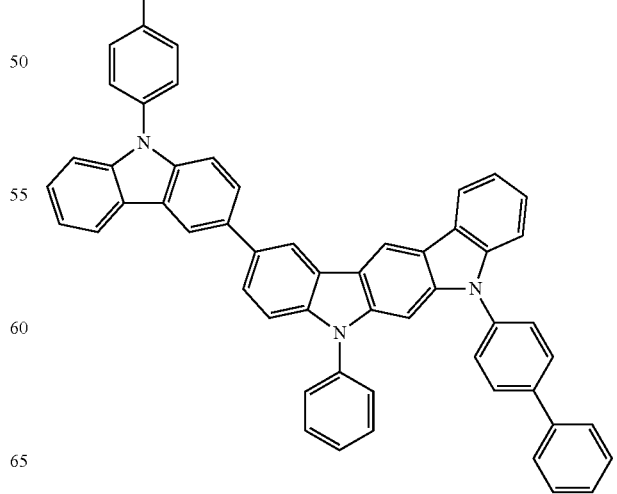

F-180
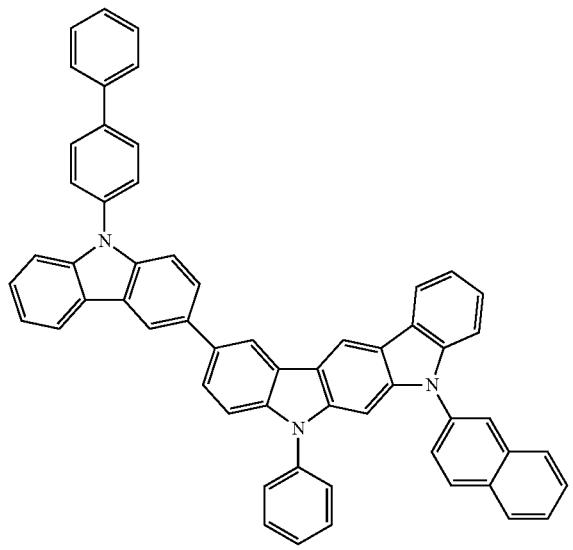
F-181
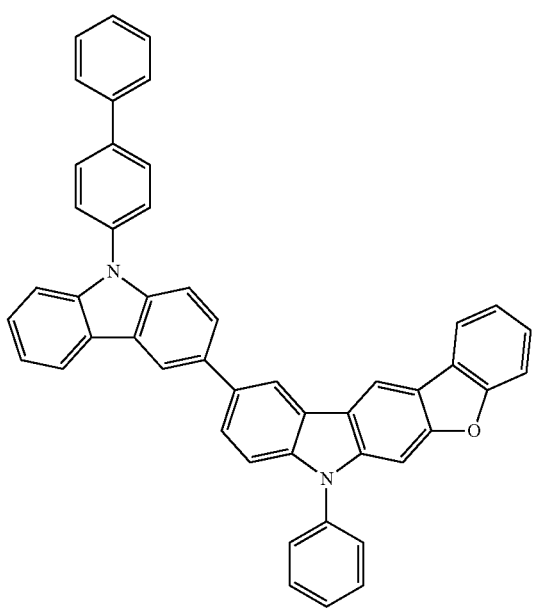
F-182
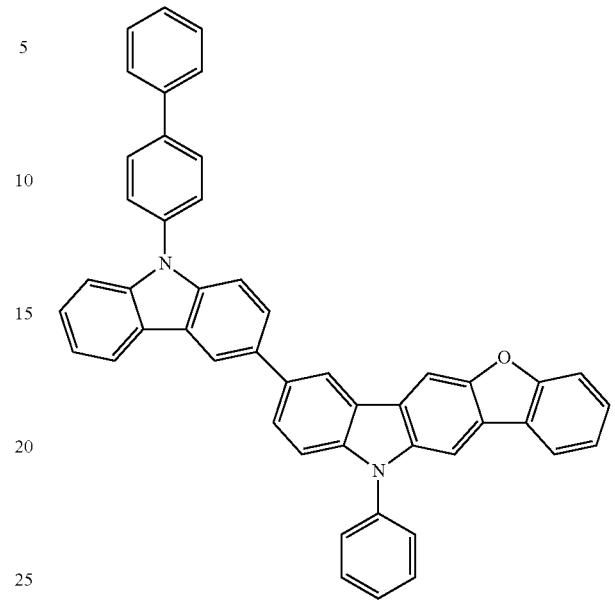
F-183
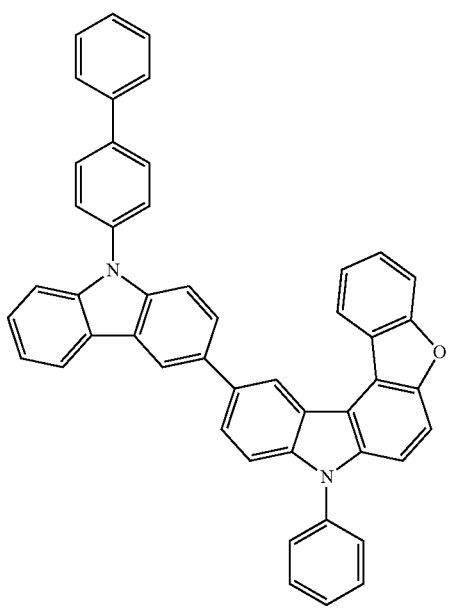

F-184
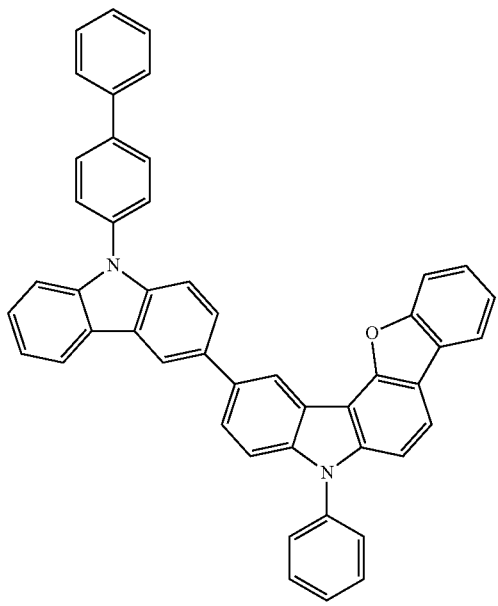
F-186
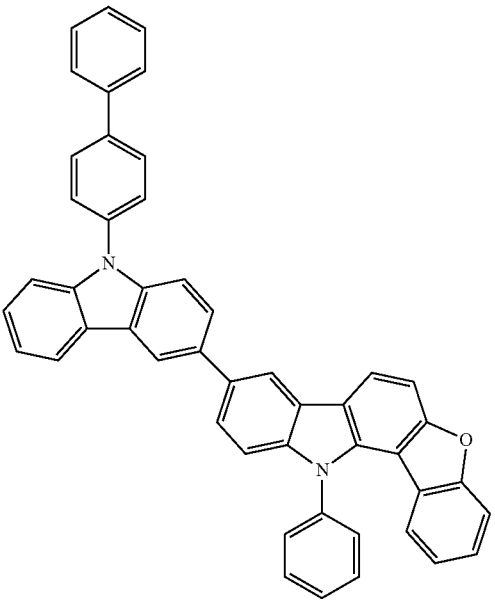
F-185
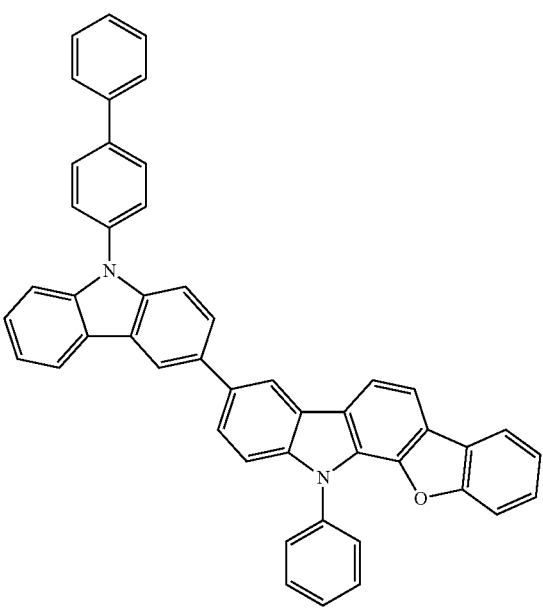
F-187
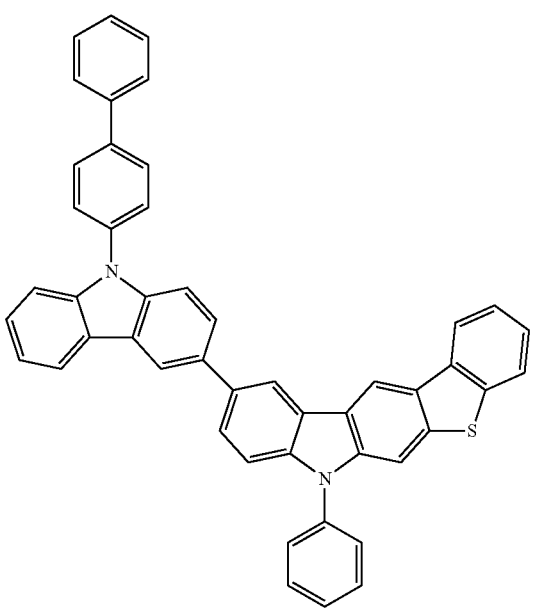

F-188
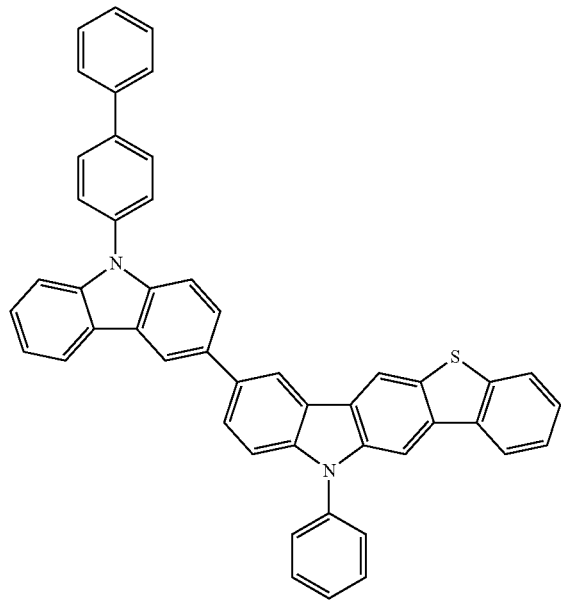
F-190
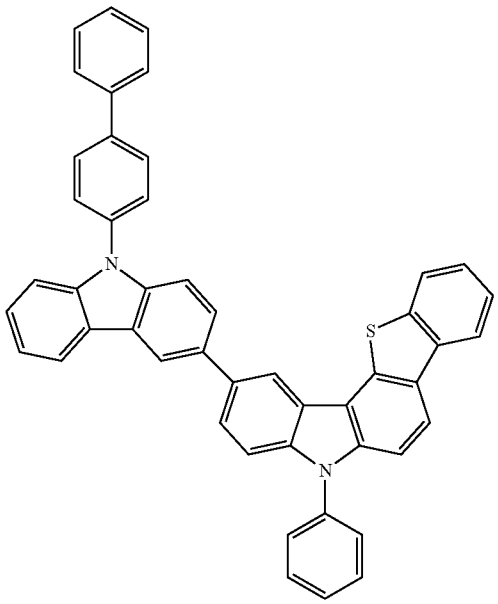
F-189
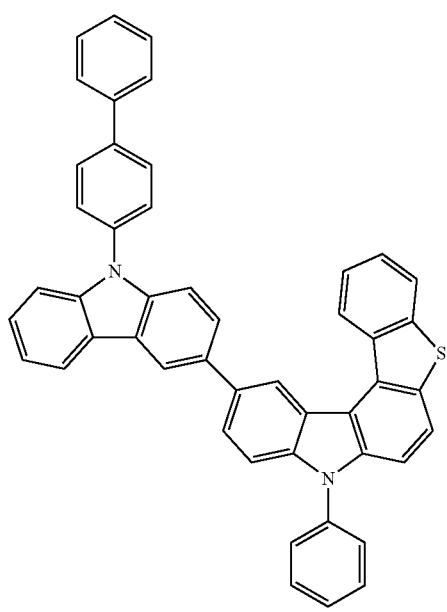
F-191
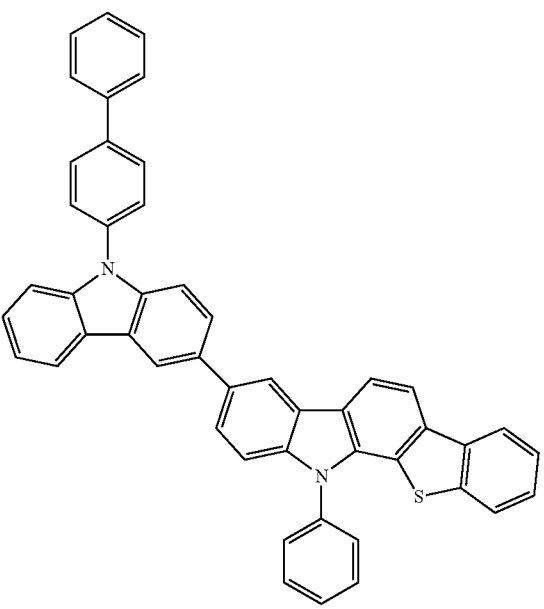

F-192
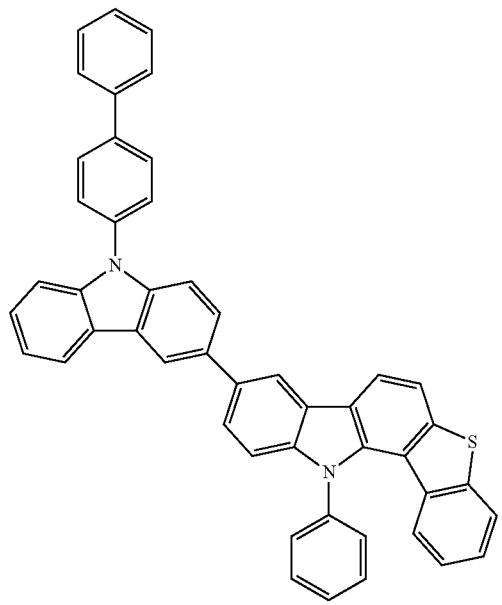
F-194
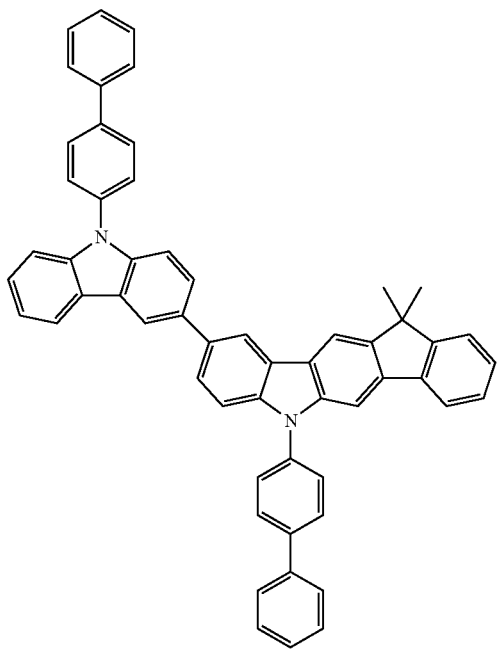
F-193
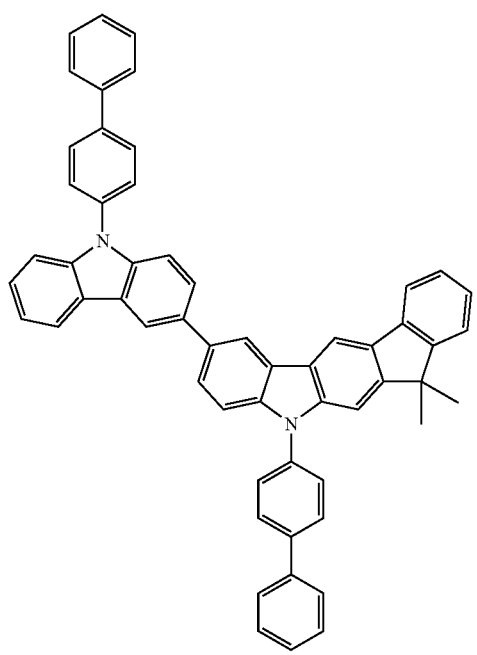
F-195
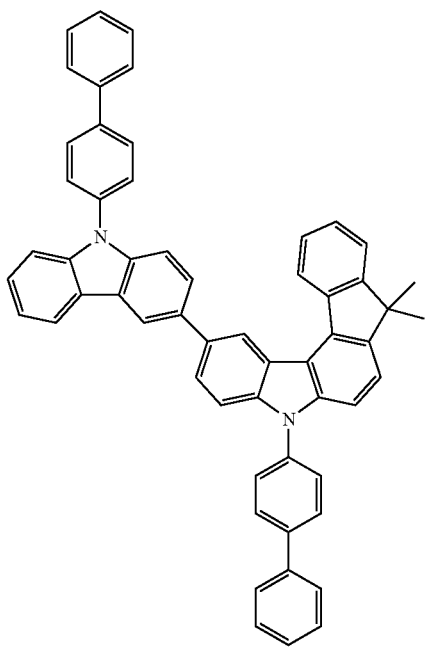

F-196
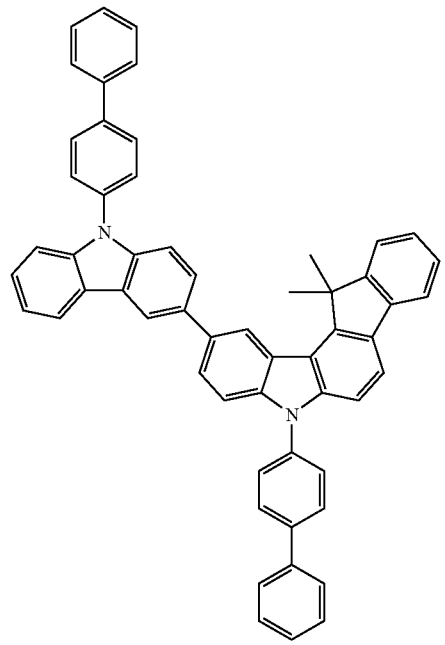
F-197
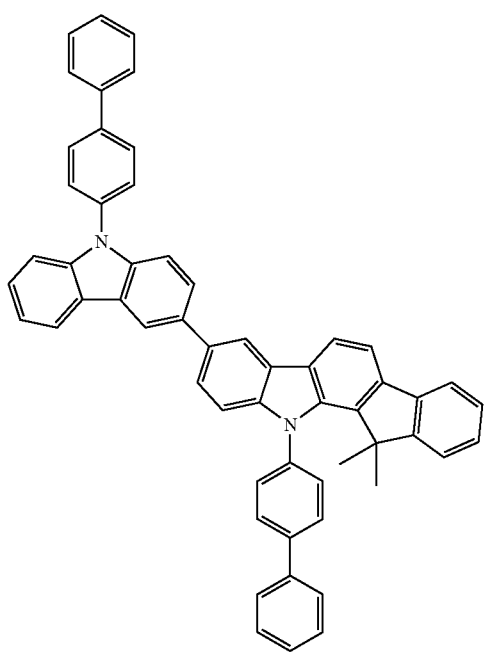
F-198
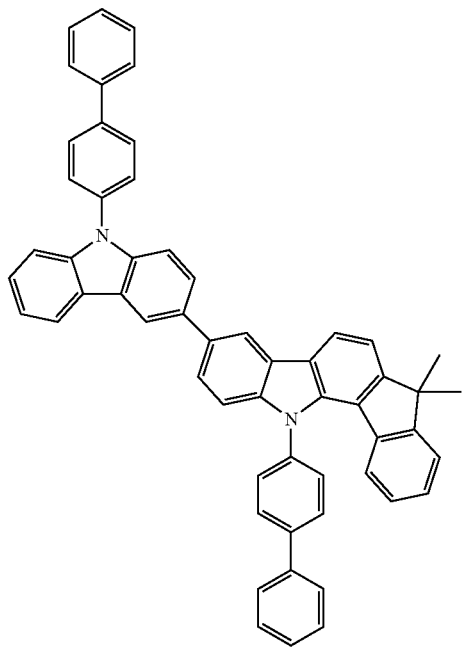
F-199
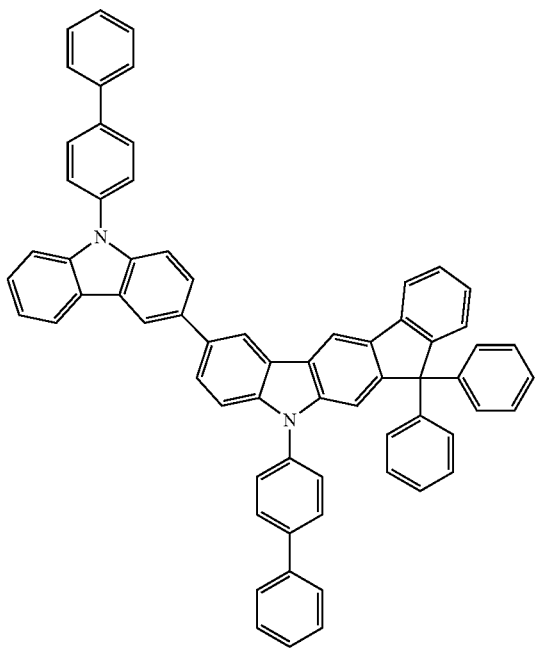

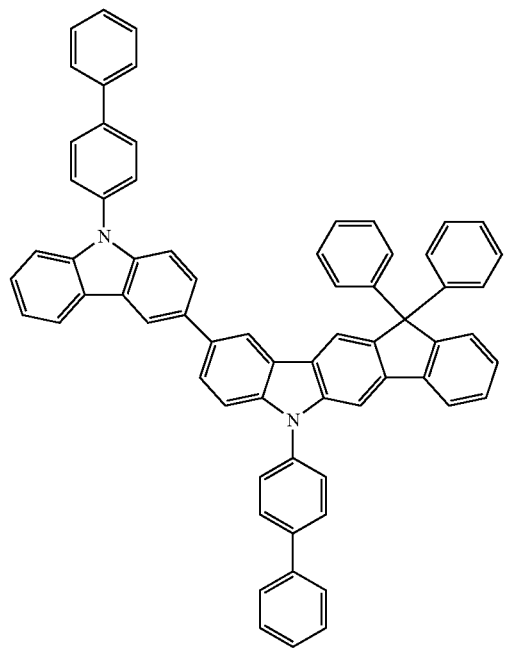
F-200
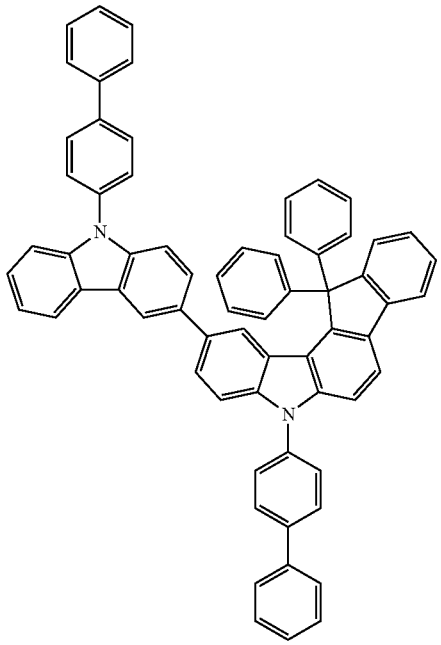
F-202
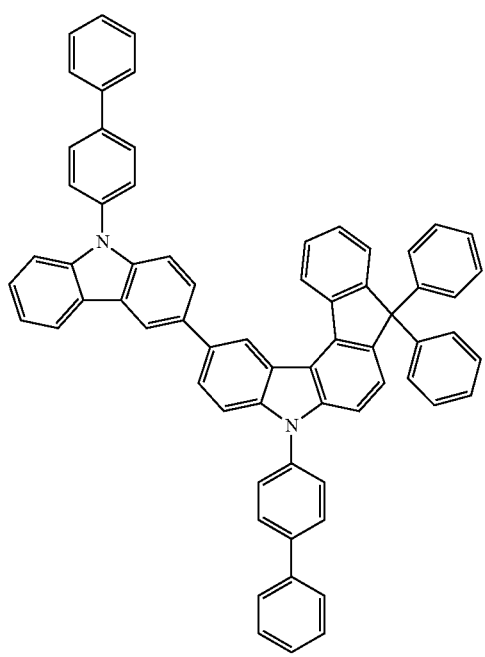
F-201
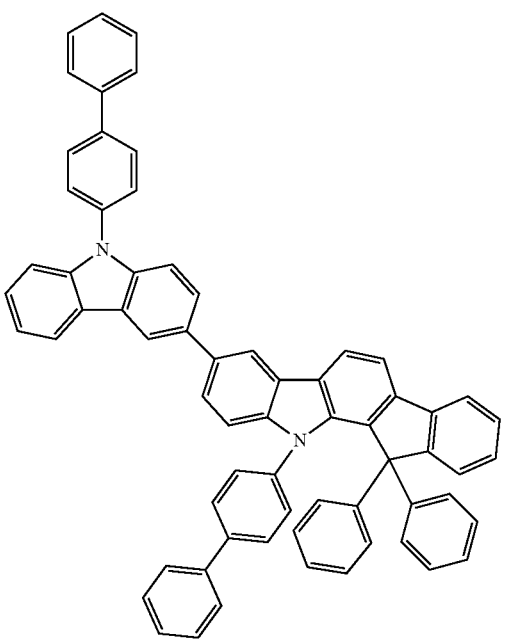
F-203

-continued
F-204
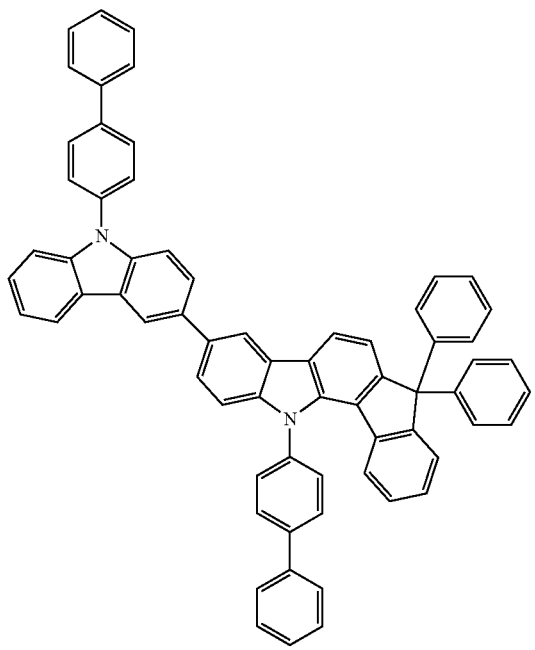
F-206
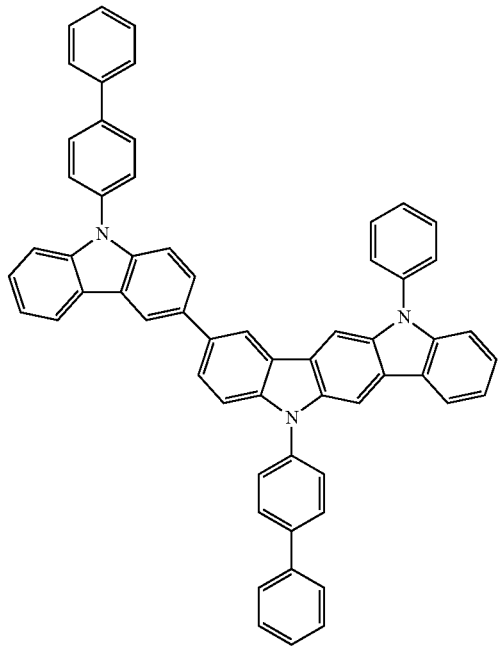
F-205
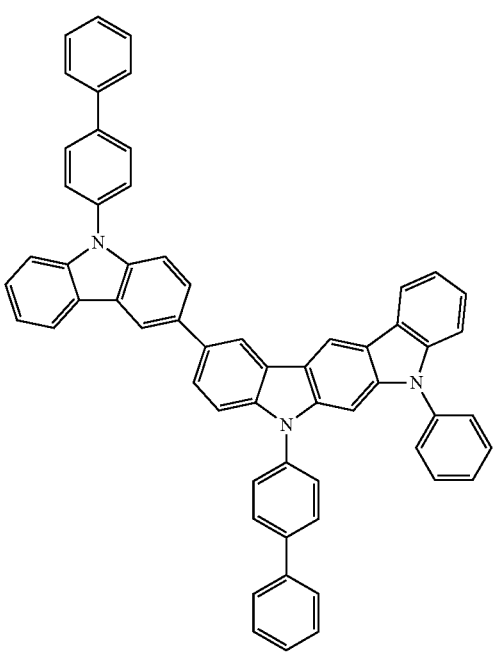
F-207
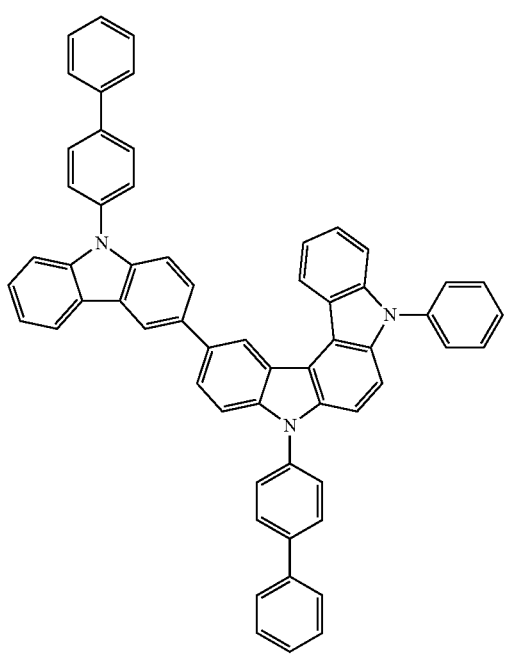

F-208
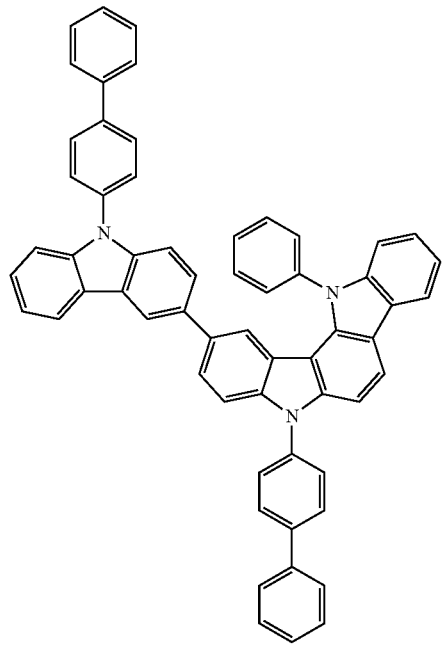
F-210
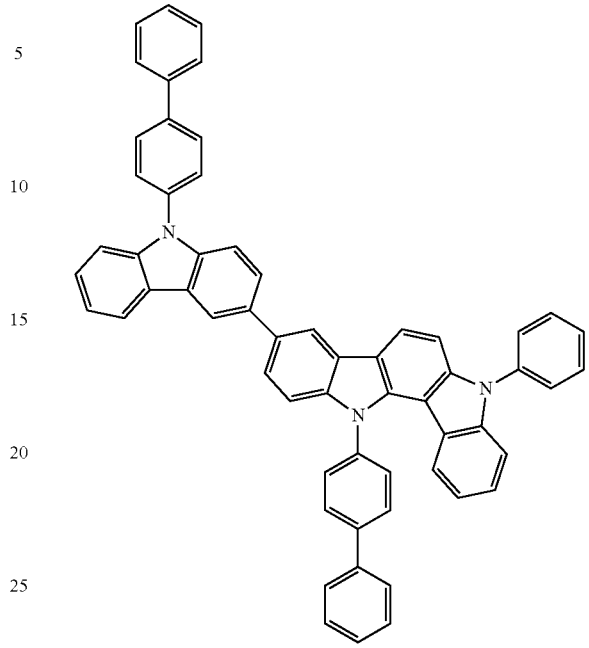
F-209
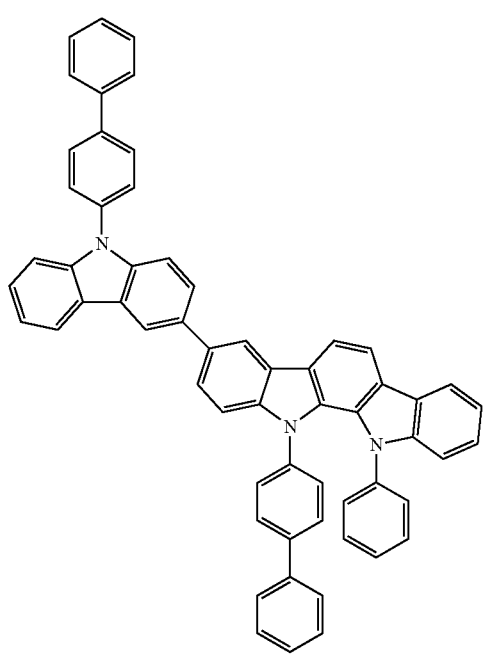
F-211
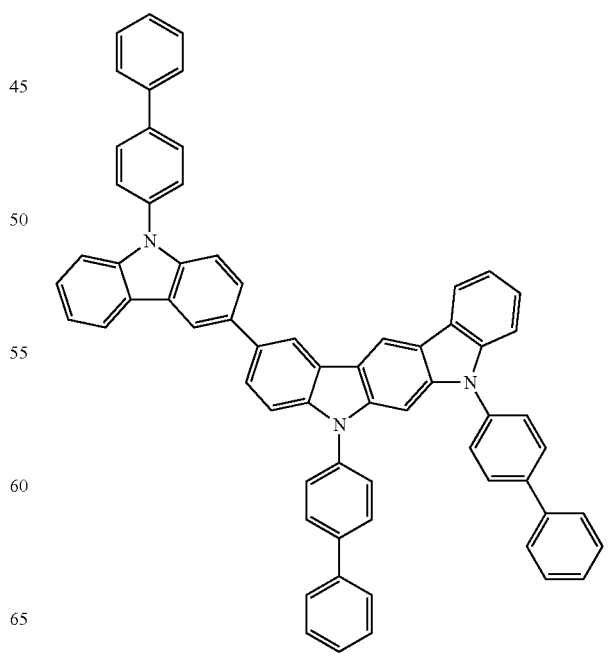

-continued
F-212
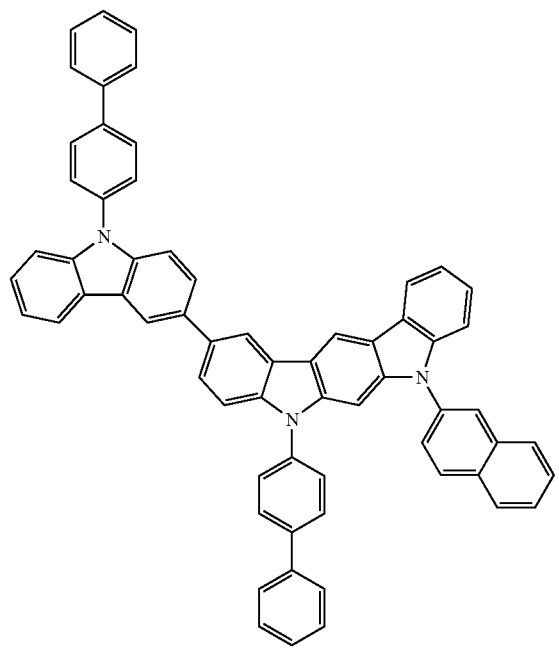
F-214
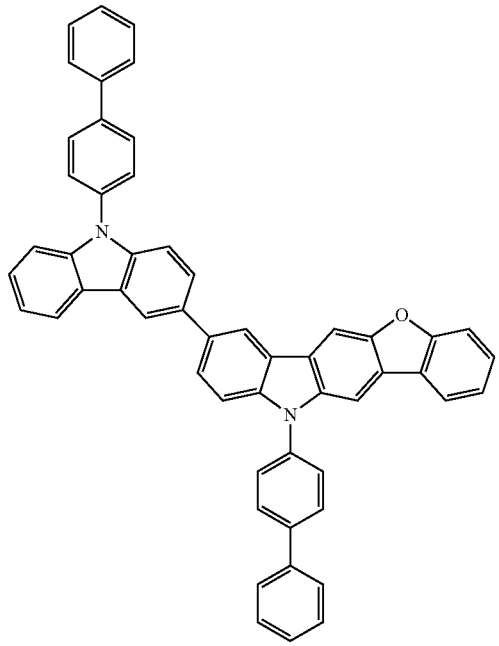
F213
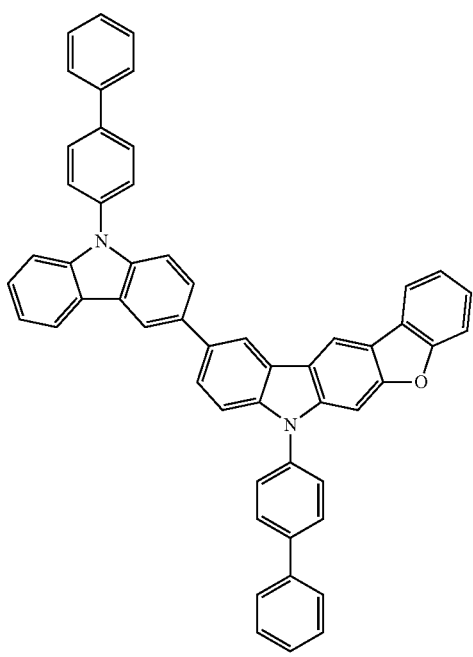
F-215
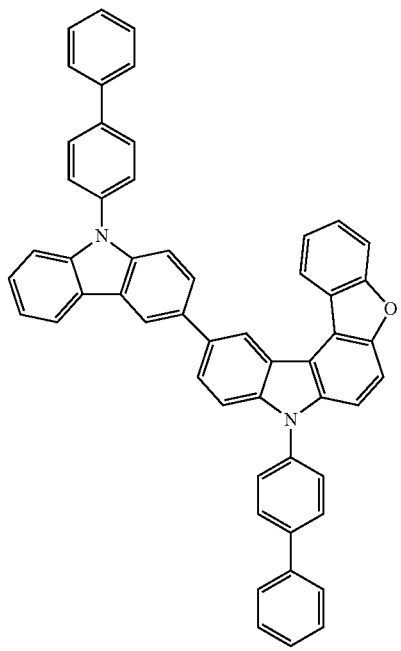

-continued
F-216
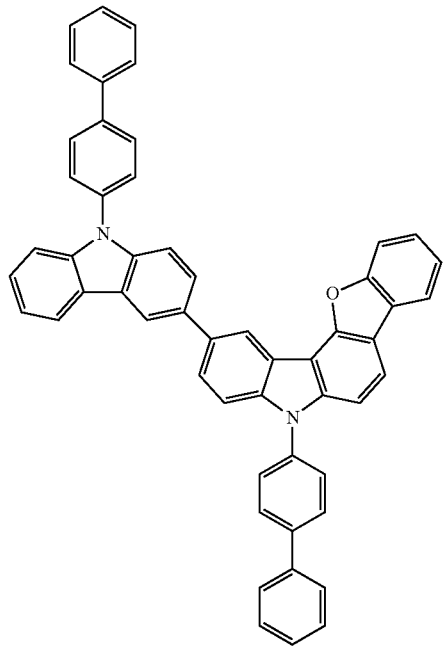
F-217
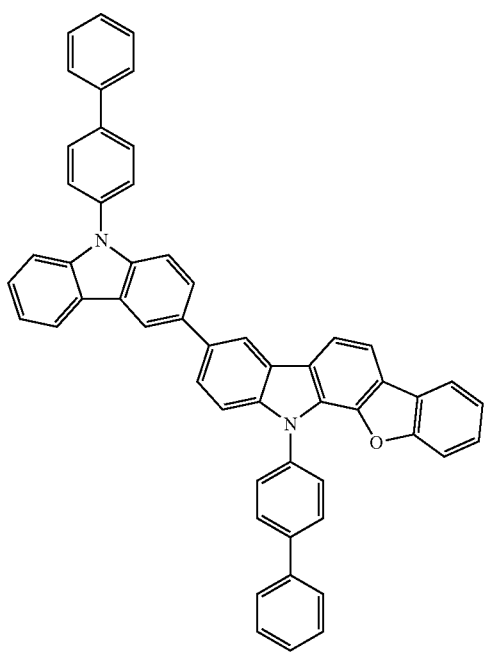
-continued
F-218
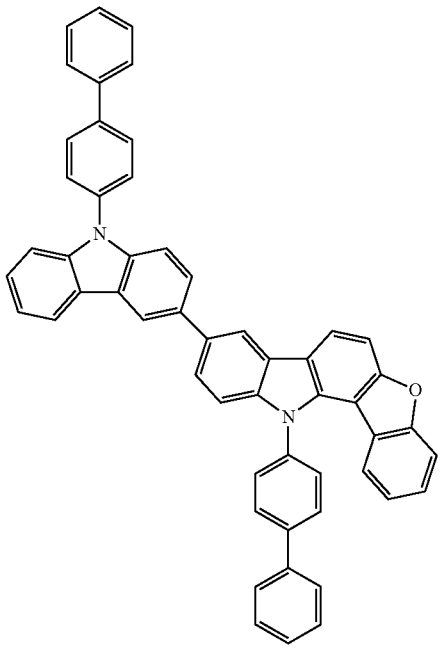
F219
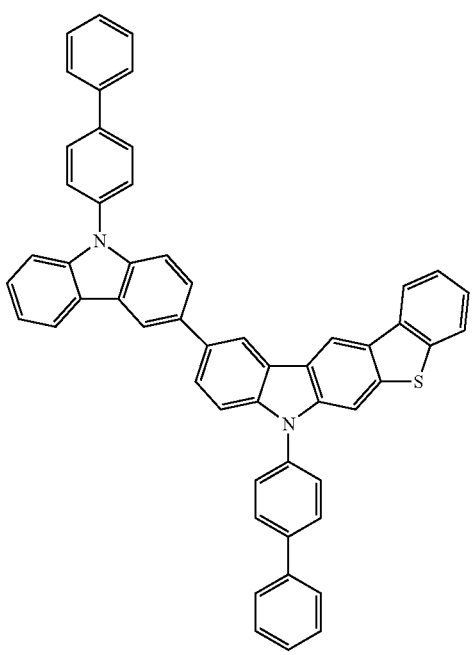

F-220
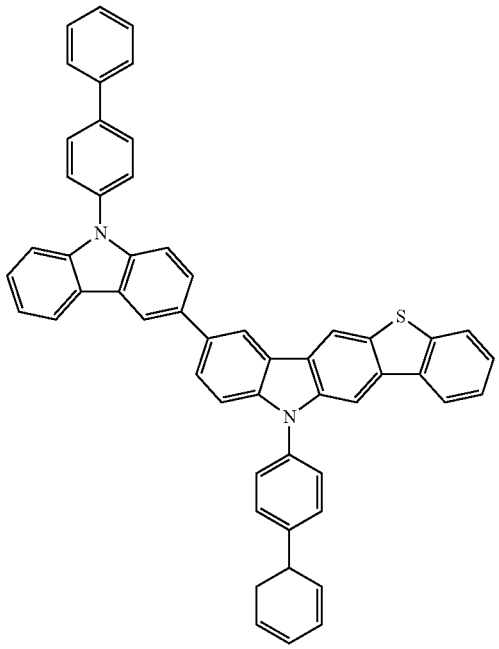
F-221
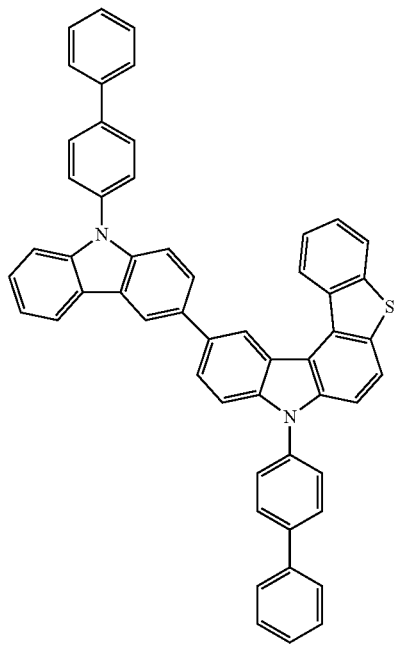
F-222
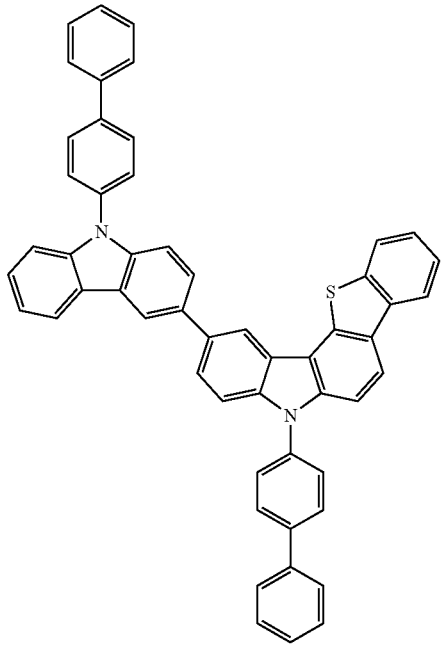
F-223
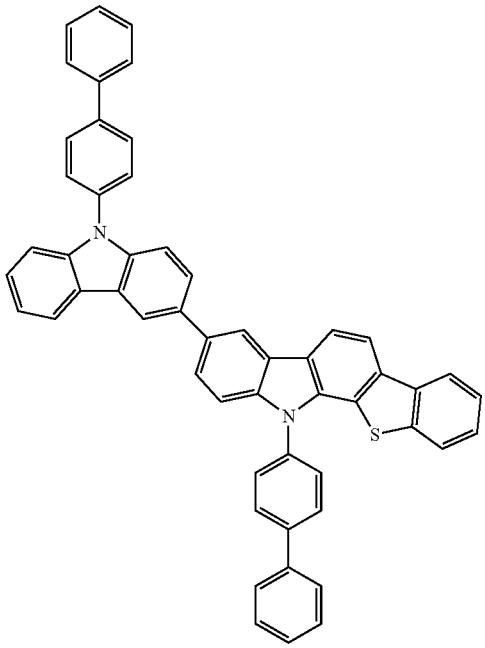

F-224
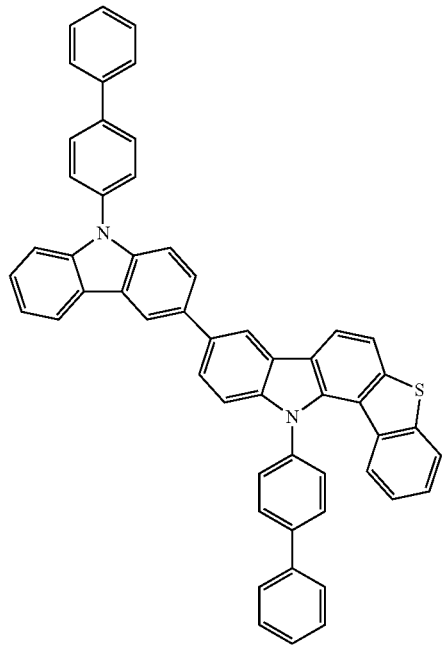
F-226
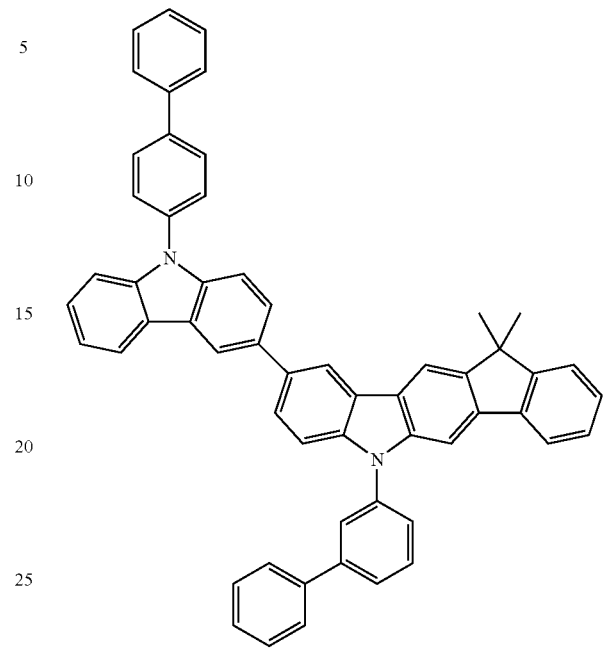
F-225
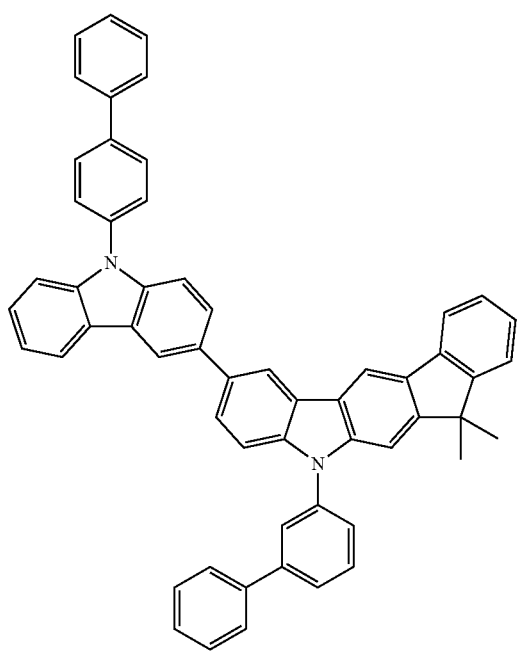
F-227
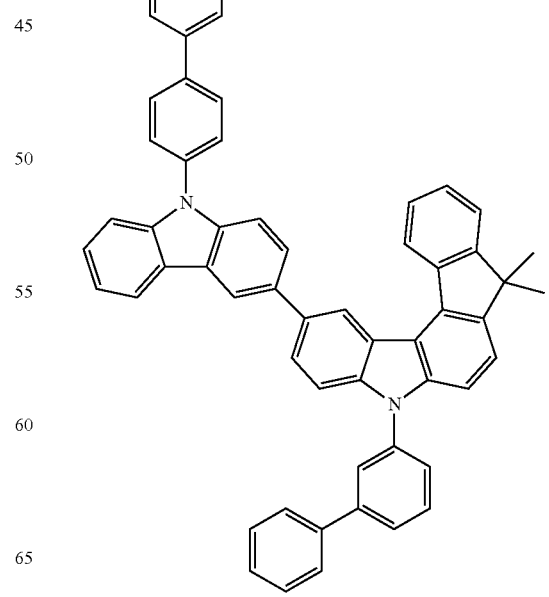

F-228
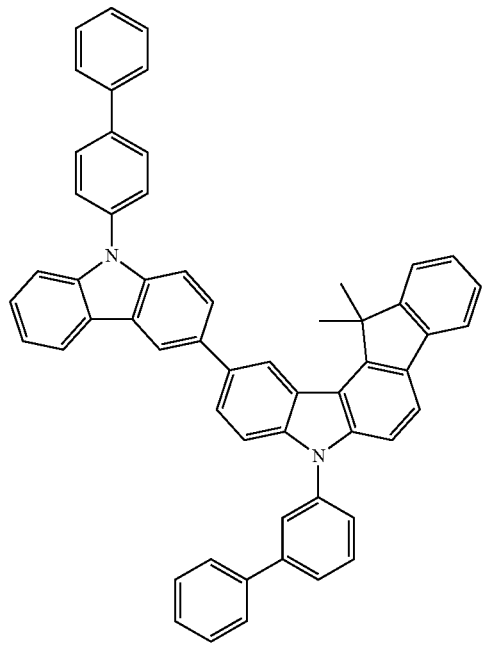
F-230
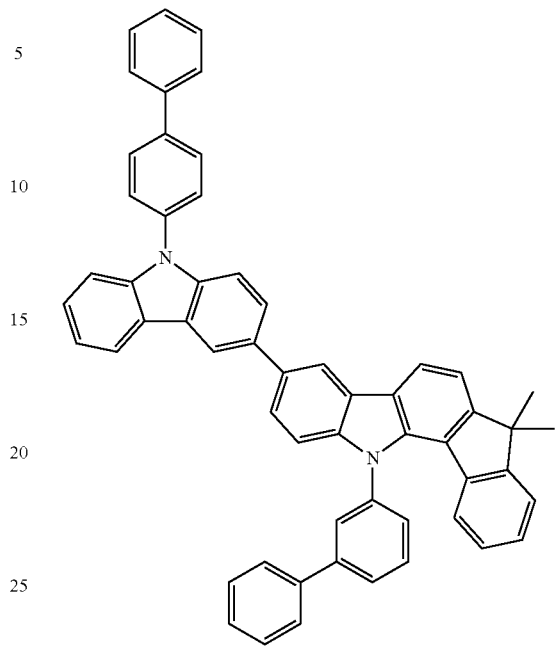
F-229
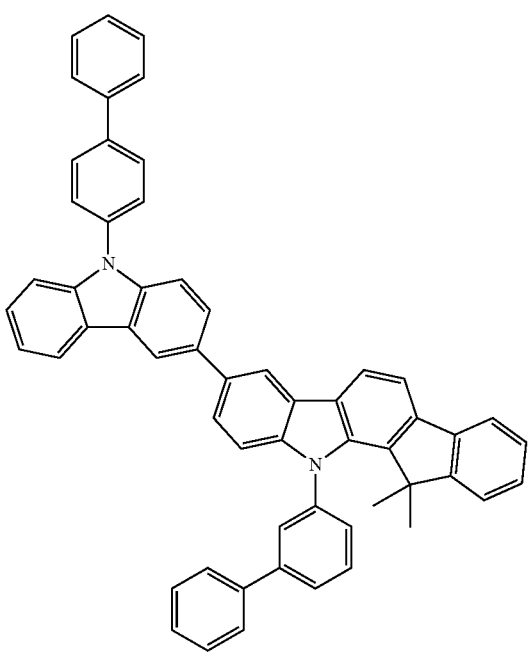
F-231
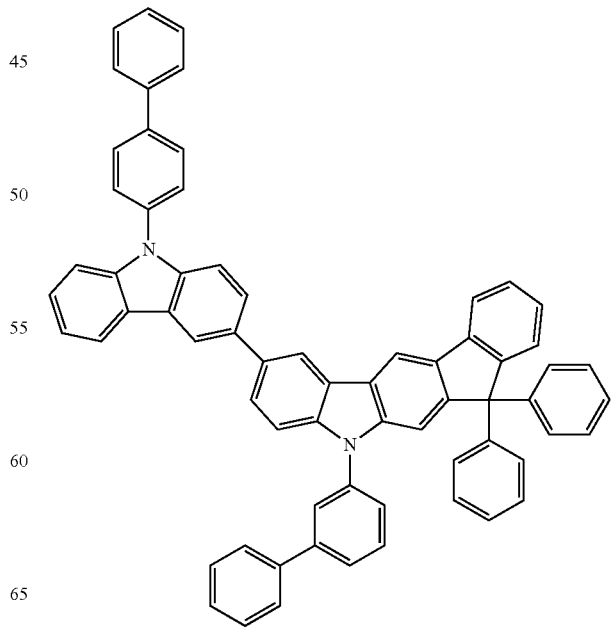

F-232
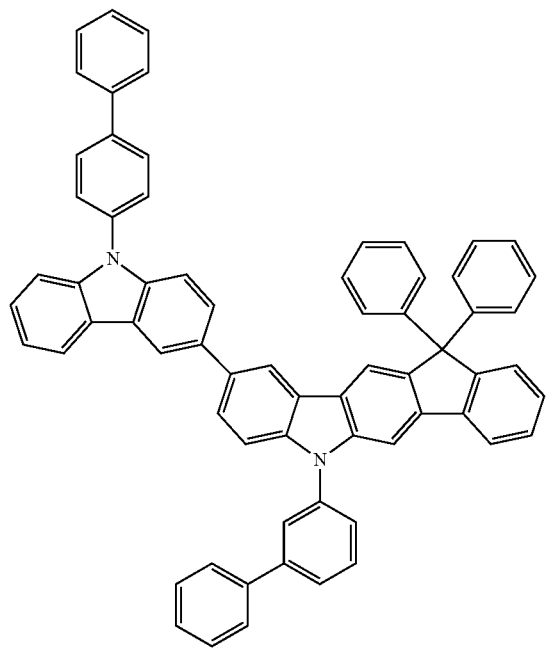
F-234
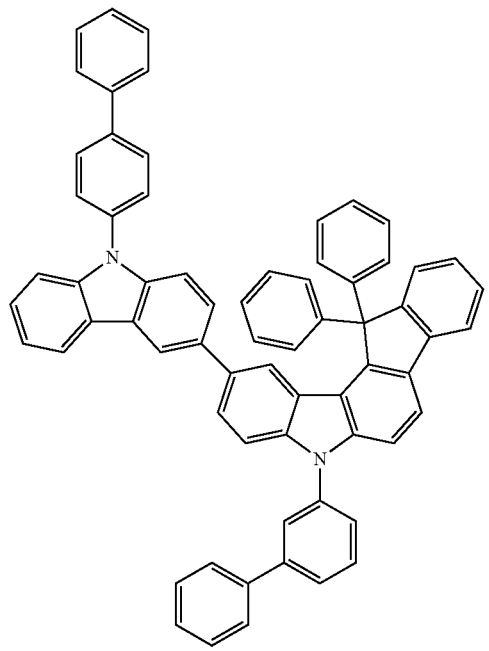
F-233
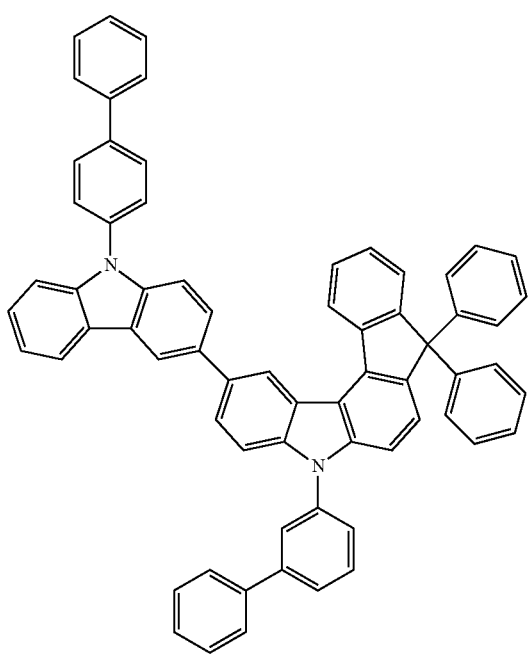
F-235
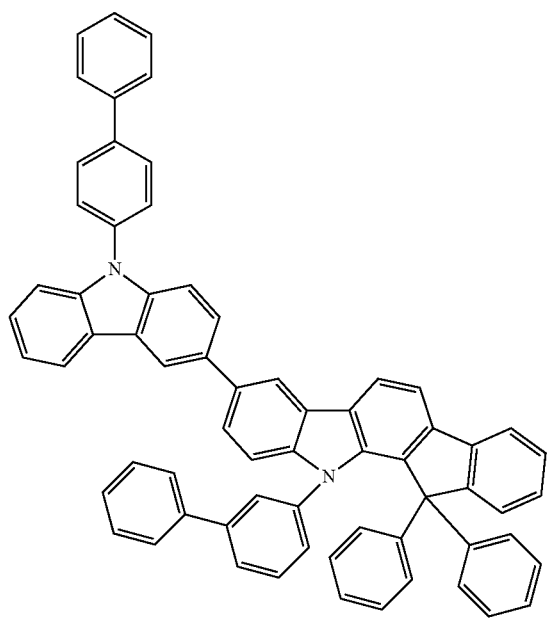

-continued
F-236
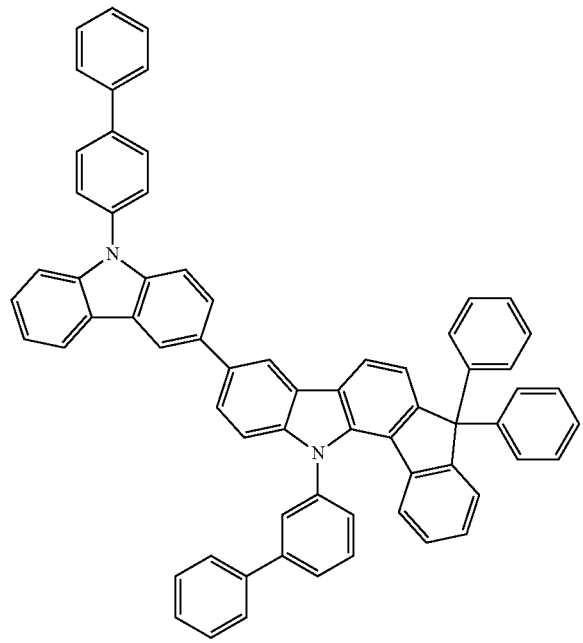
F-237
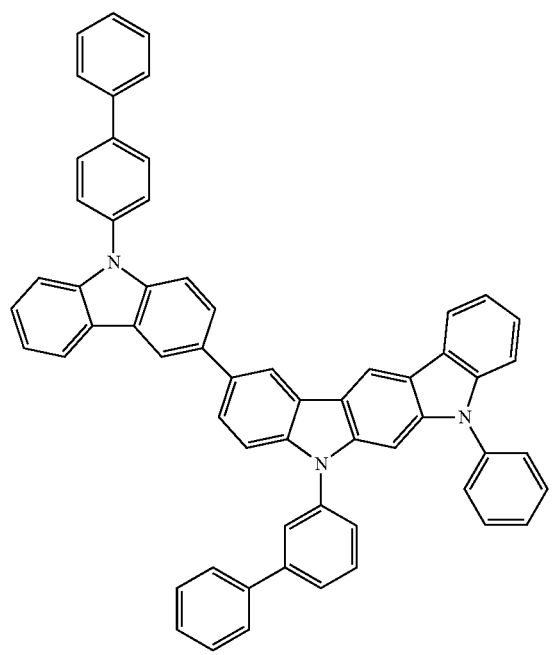
F-238
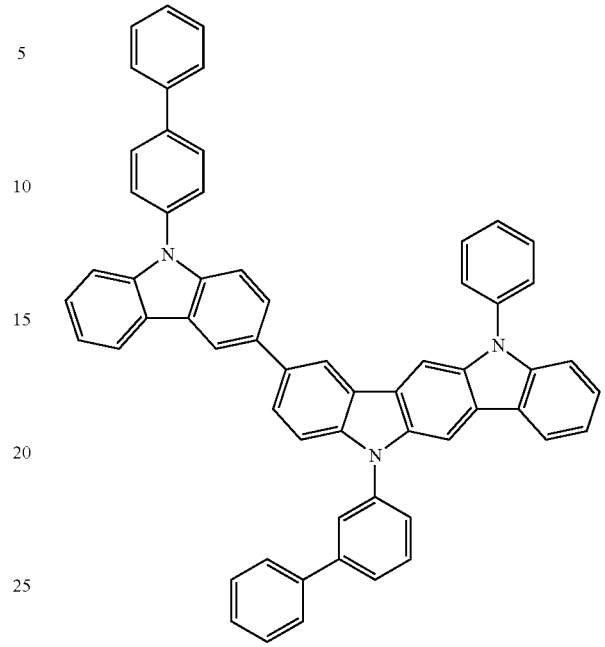
F-239
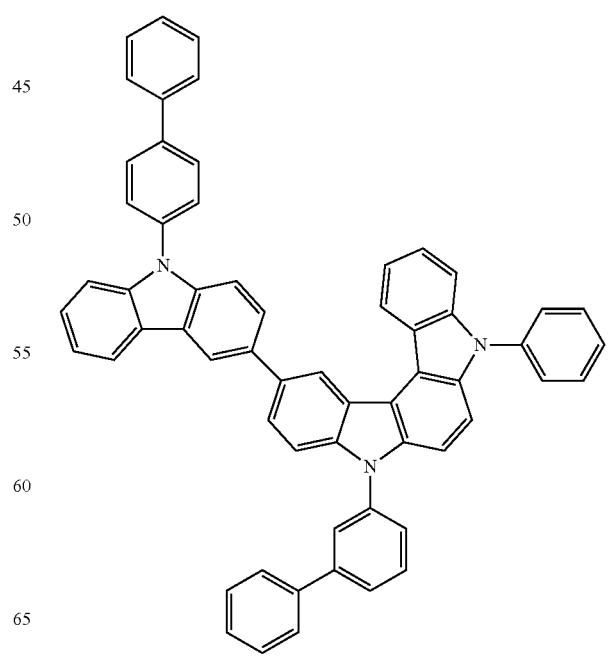

F-240
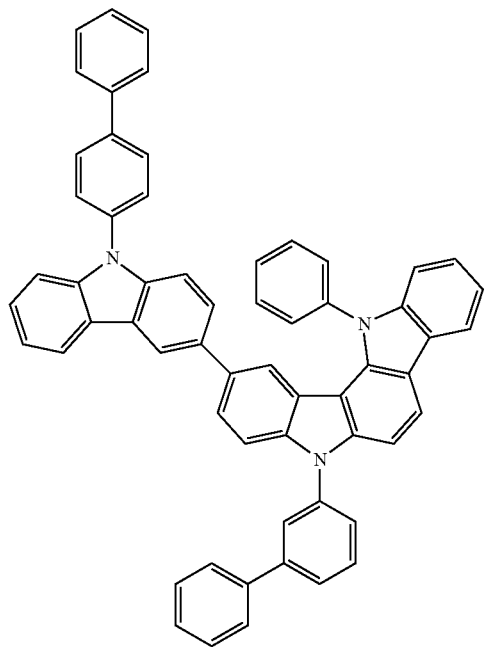
F-242
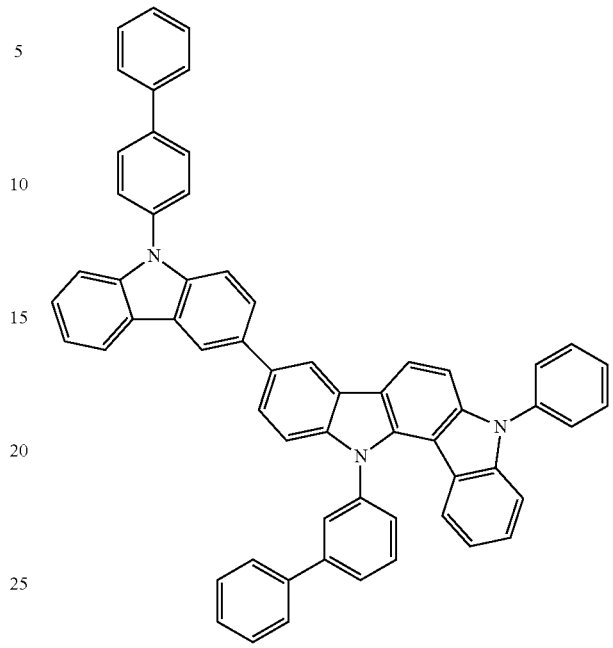
F-241
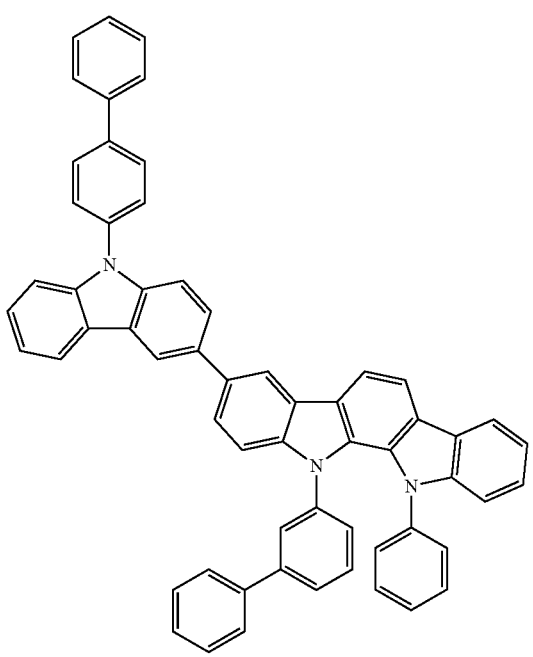
F-243
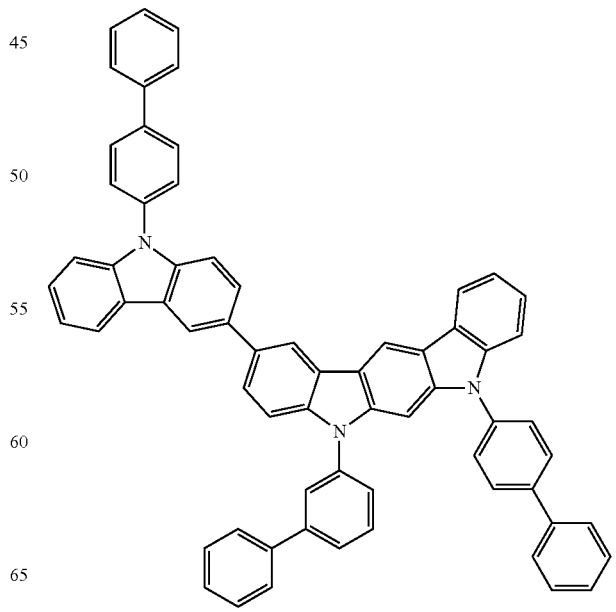

F-244
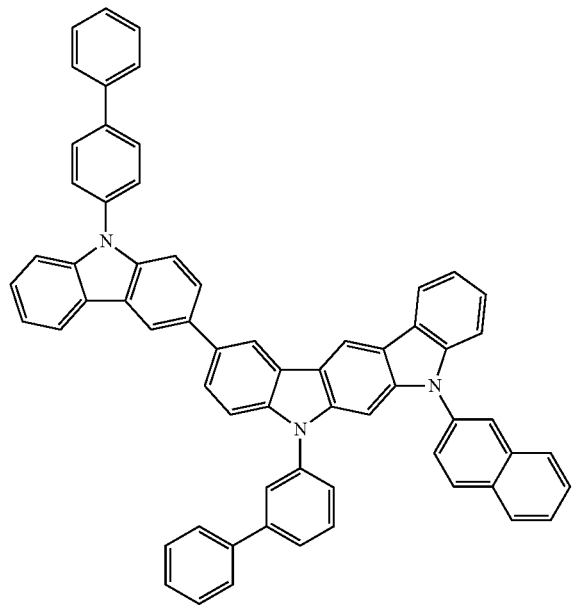
F-245
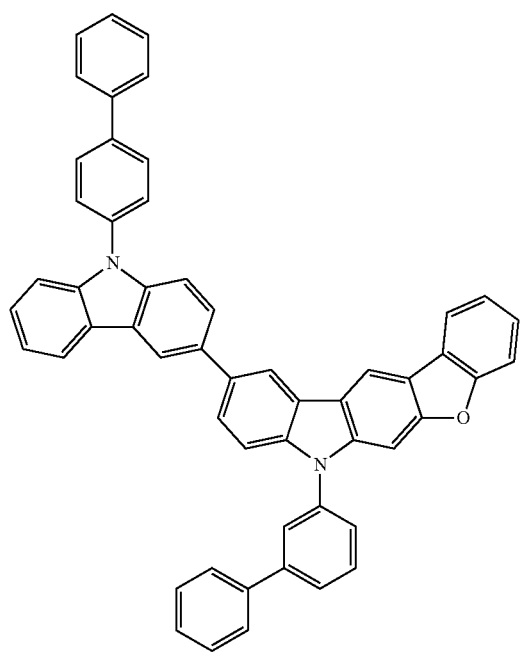
F-246
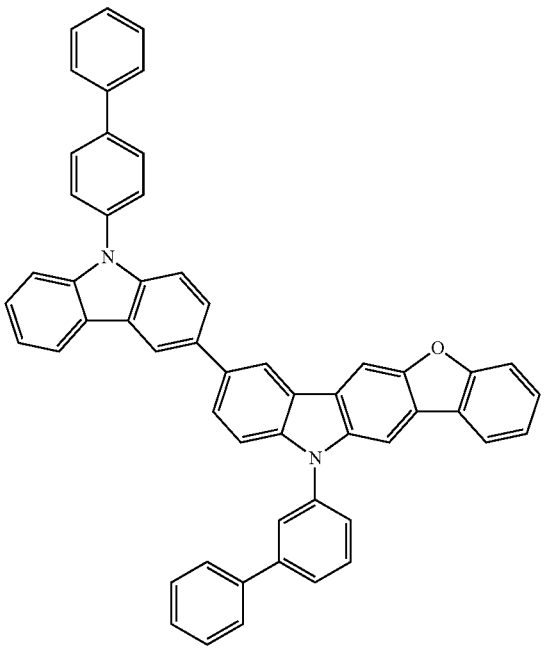
F-247
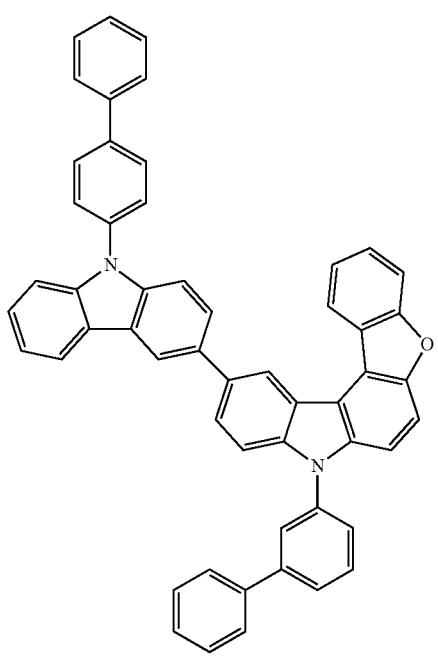

F-248
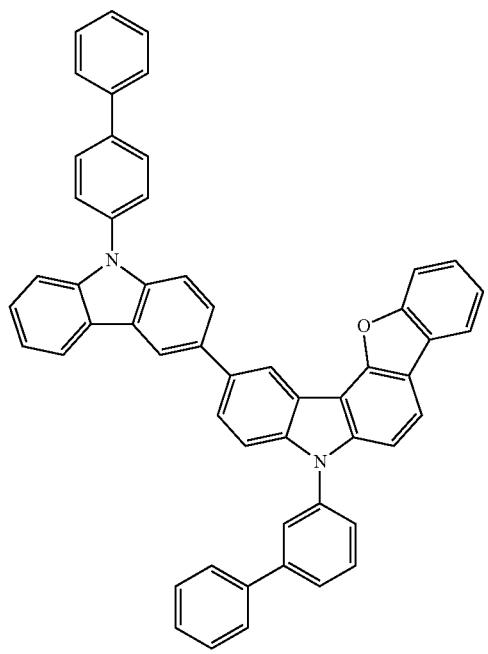
F-250
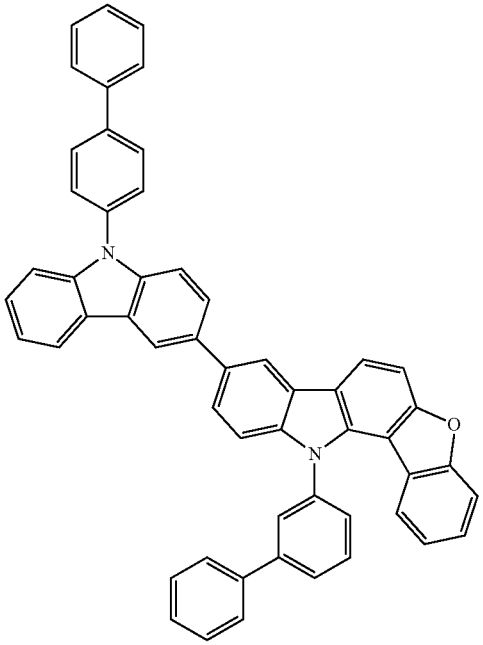
F-249
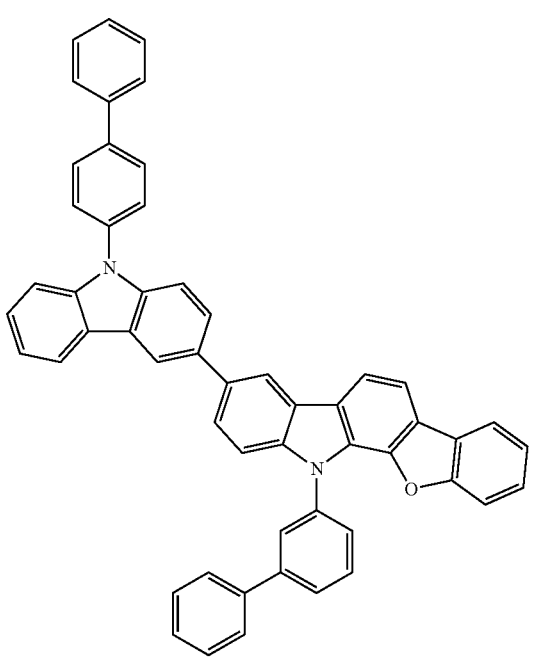
F-251
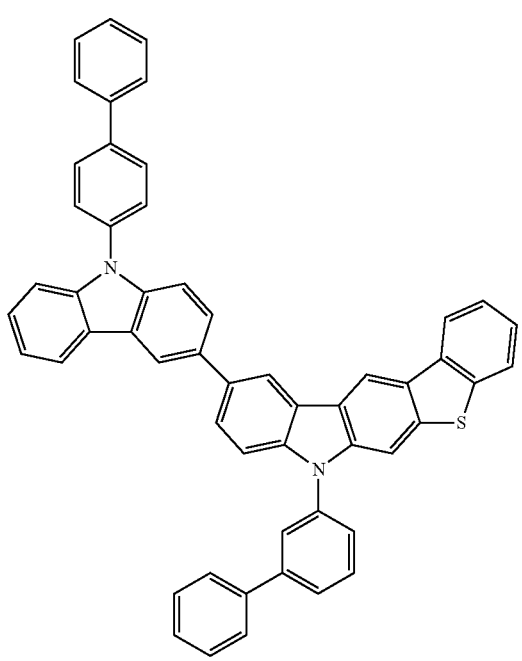

F-252
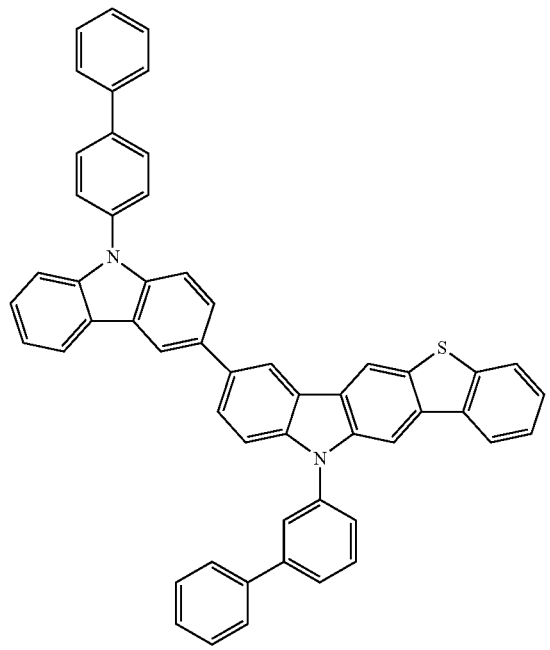
F-254
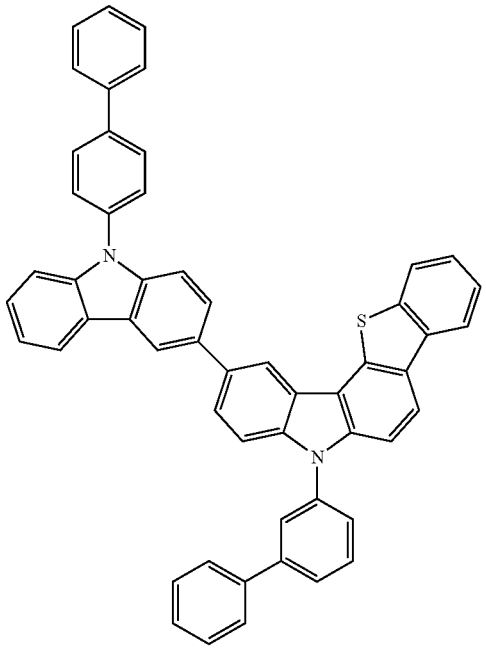
F-253
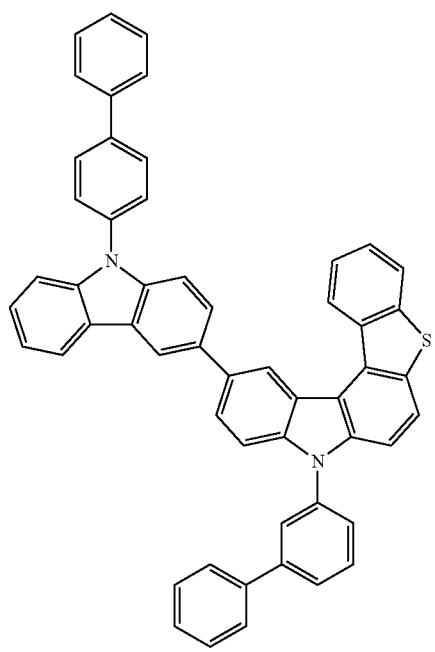
F-255
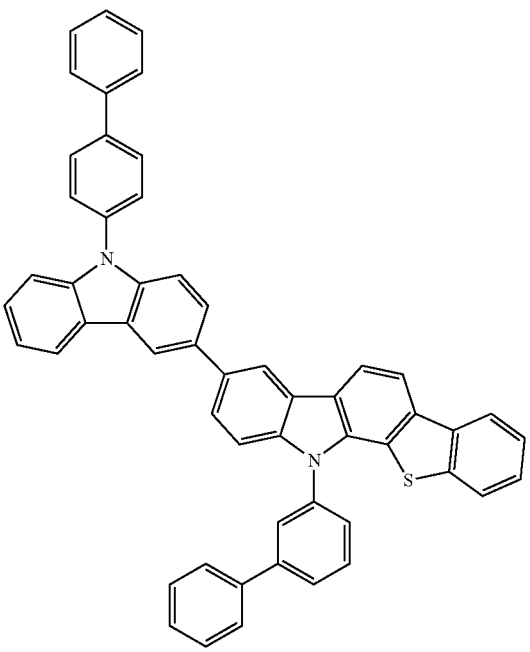

-continued
F-256
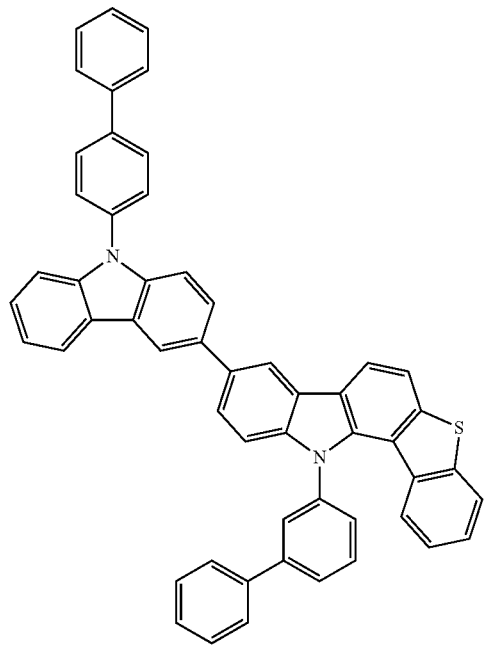
F-258
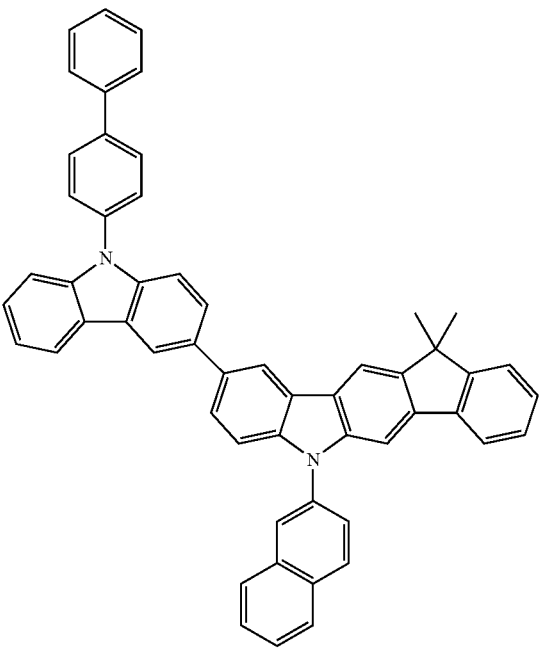
F-257
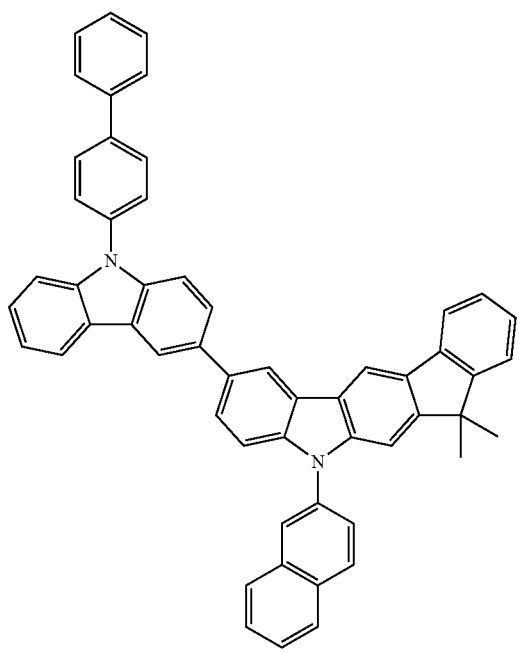
F-259
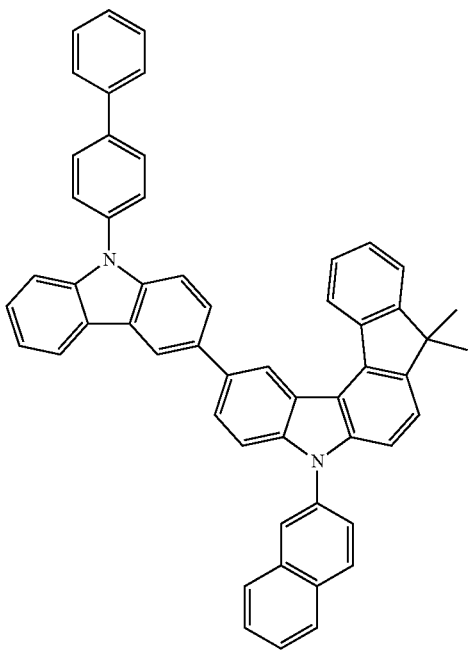

F-260
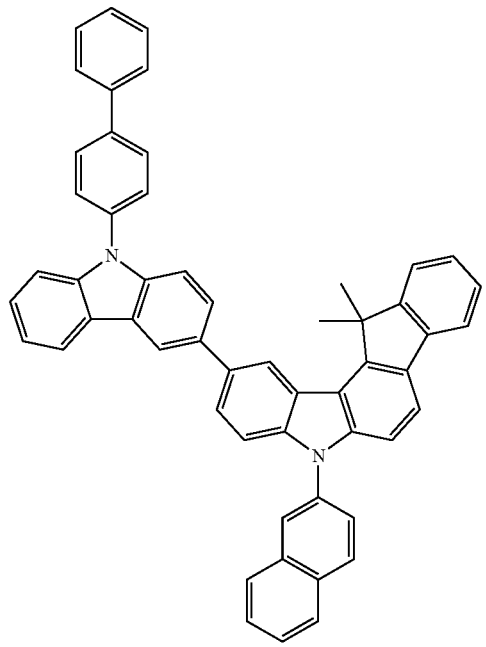
F-262
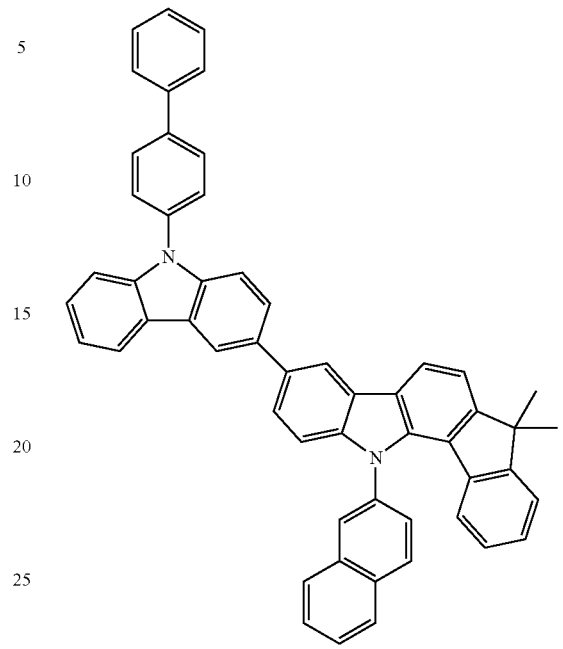
F-261
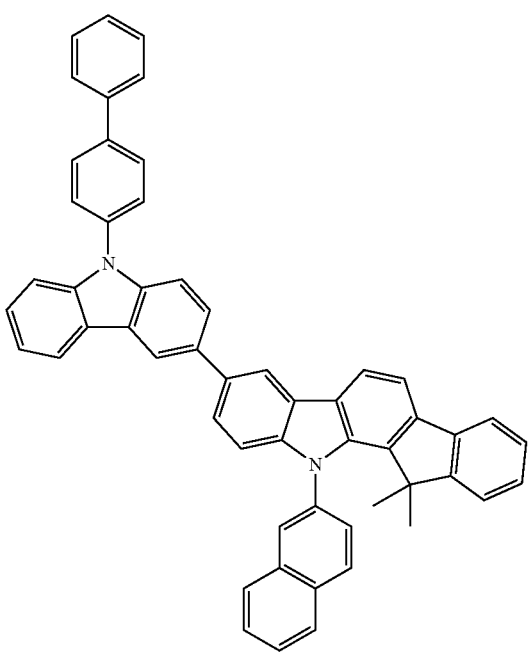
F-263
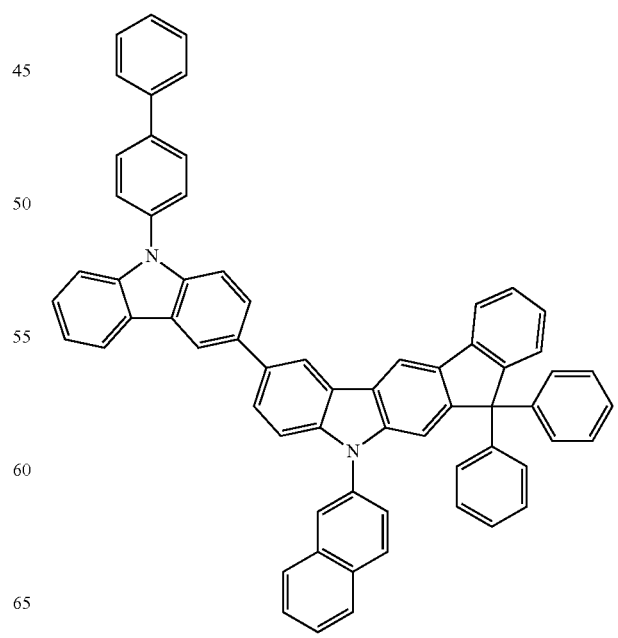

F-264
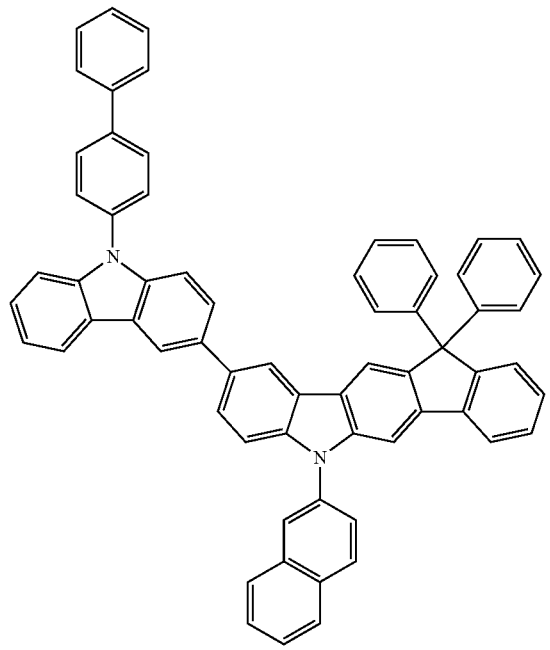
F-266
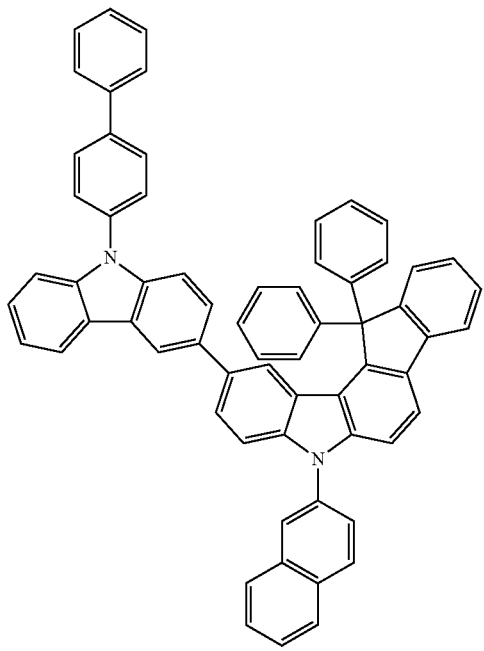
F-265
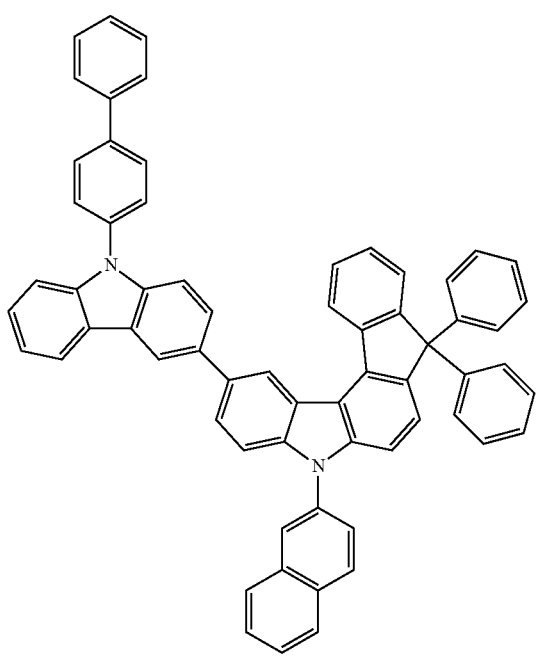
F-267
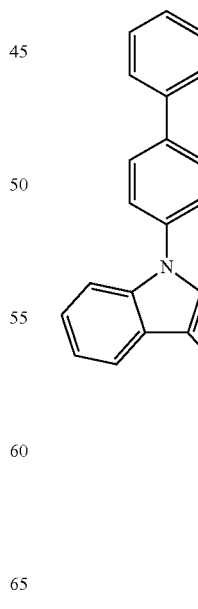

-continued
F-268
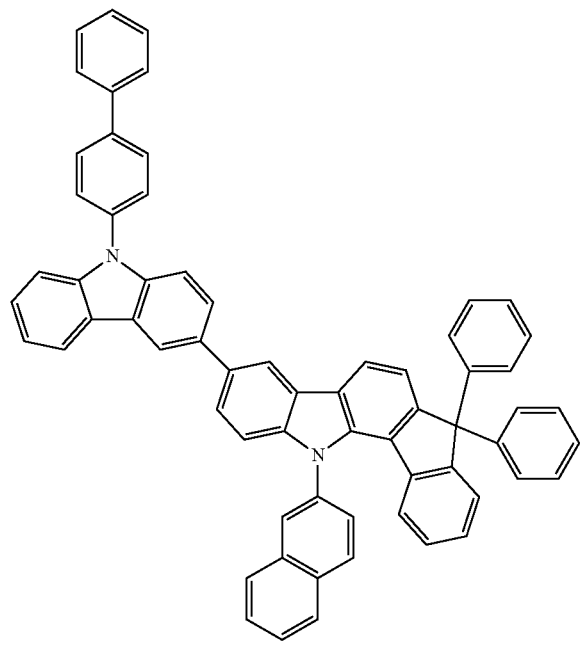
F-269
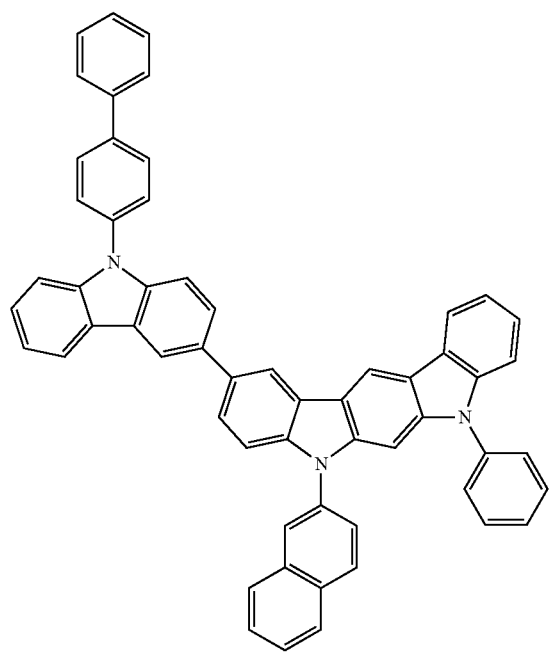
F-270
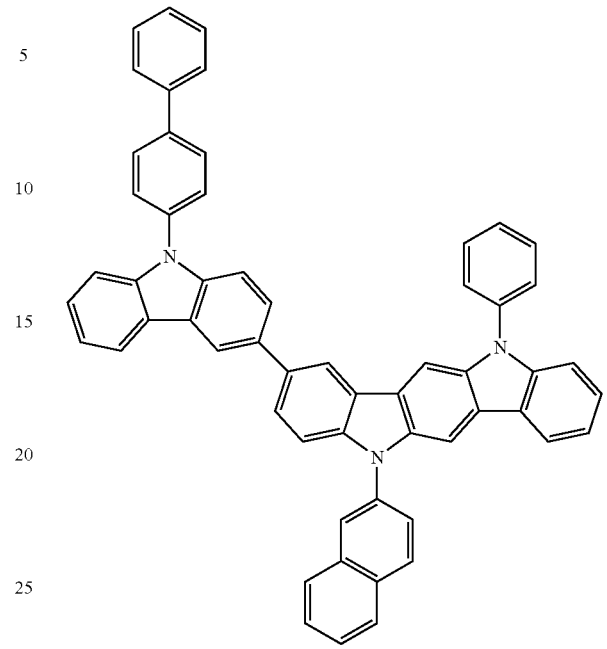
F-271
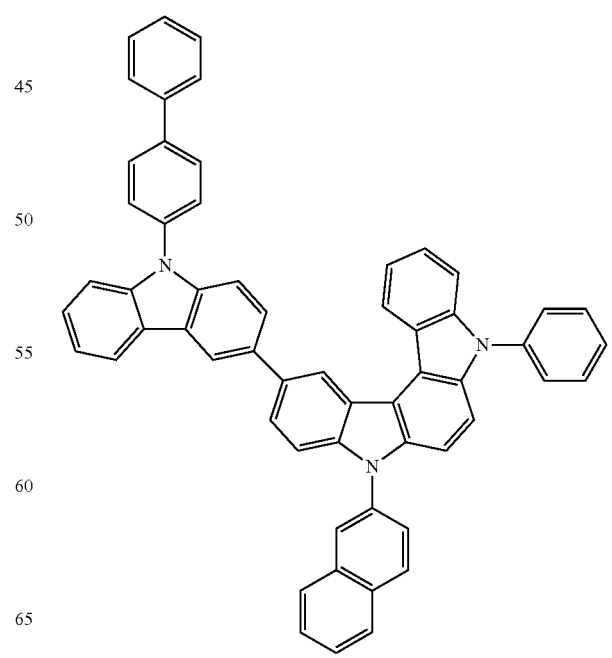

F-272
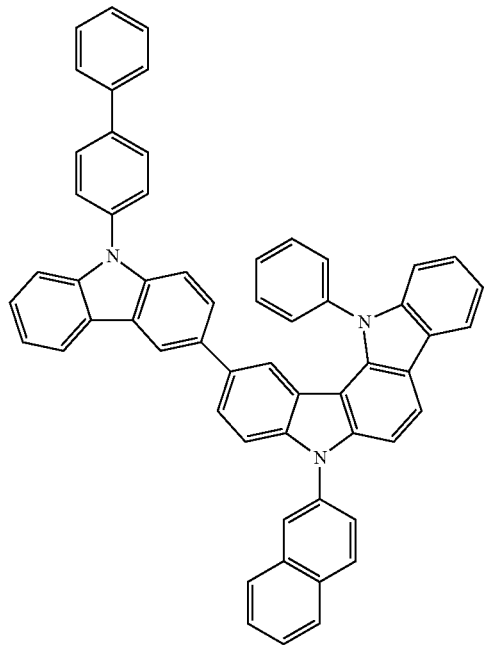
F-274
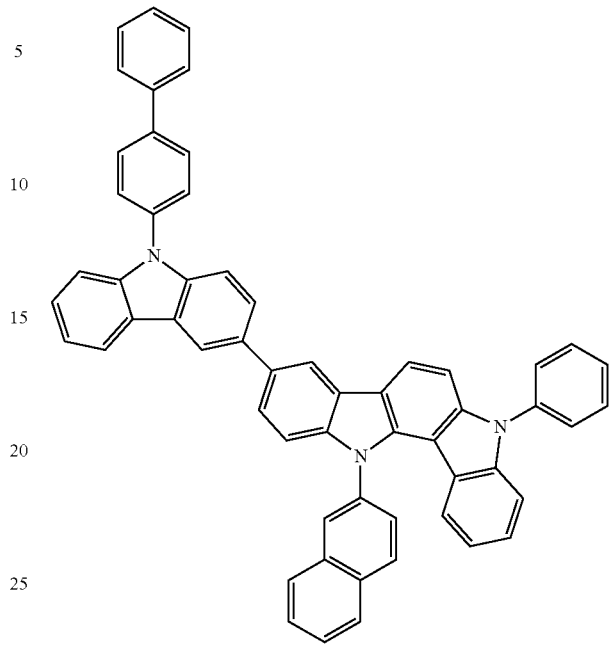
F-273
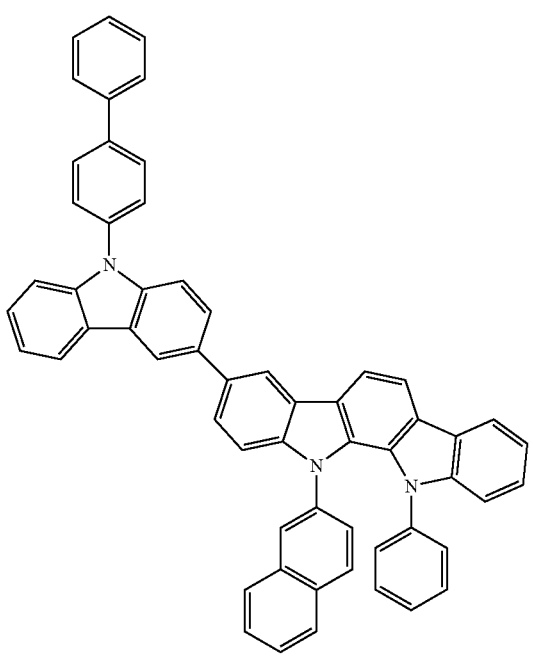
F-275

F-276
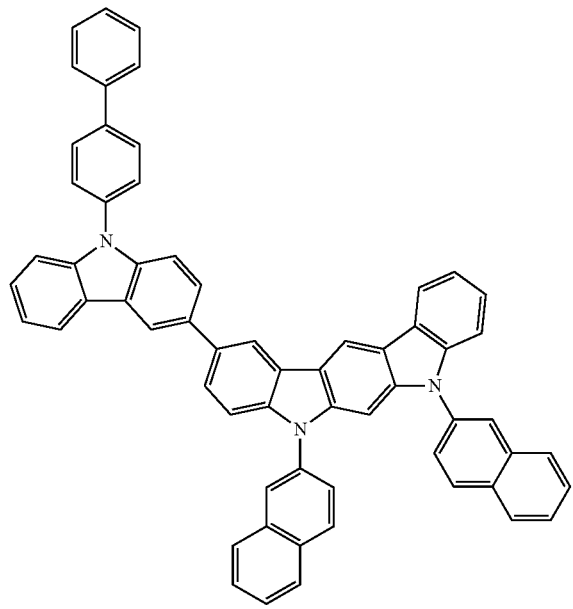
F-277
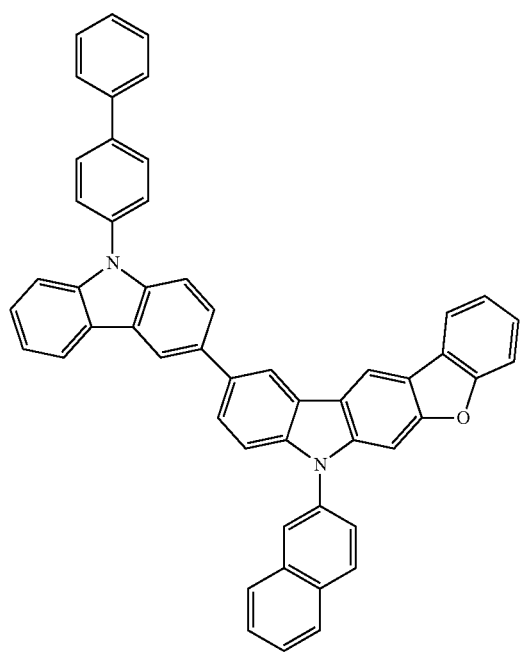
F-278
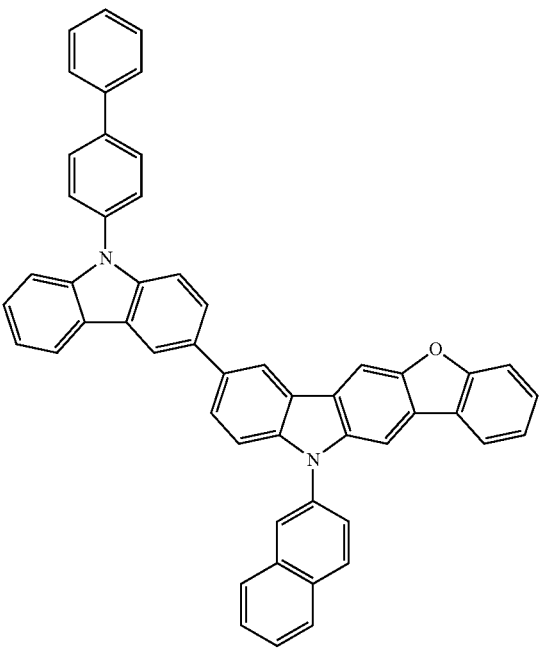
F-279
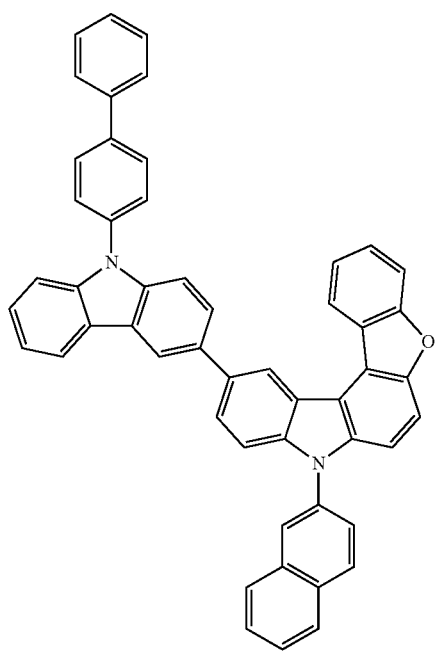

F-280
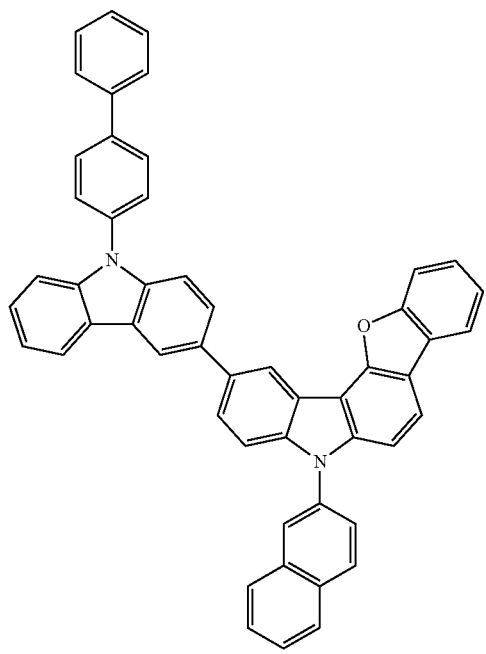
F-282
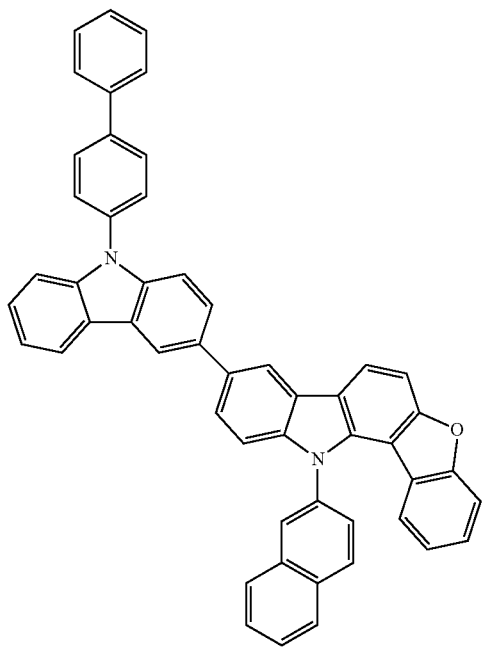
F-281
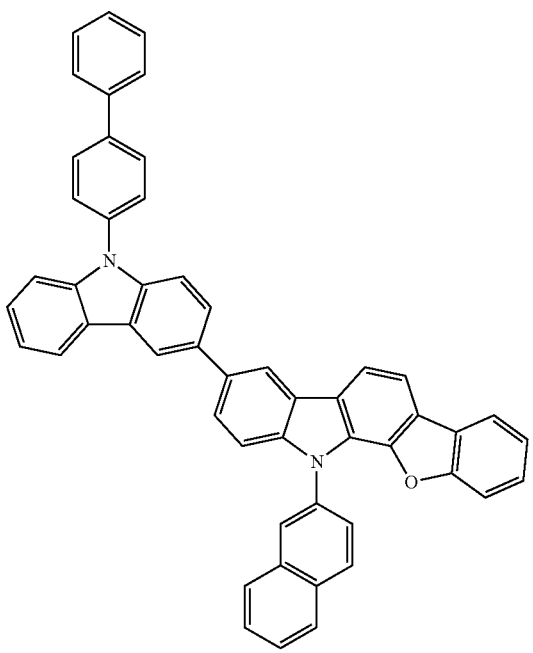
F-283
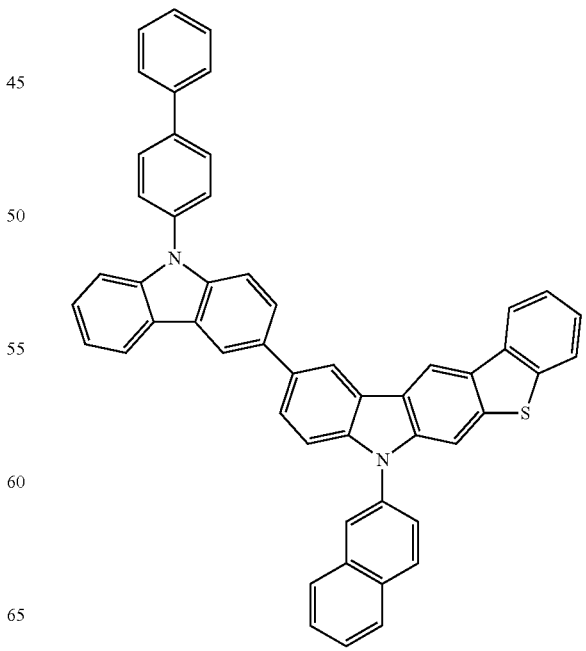

F-284
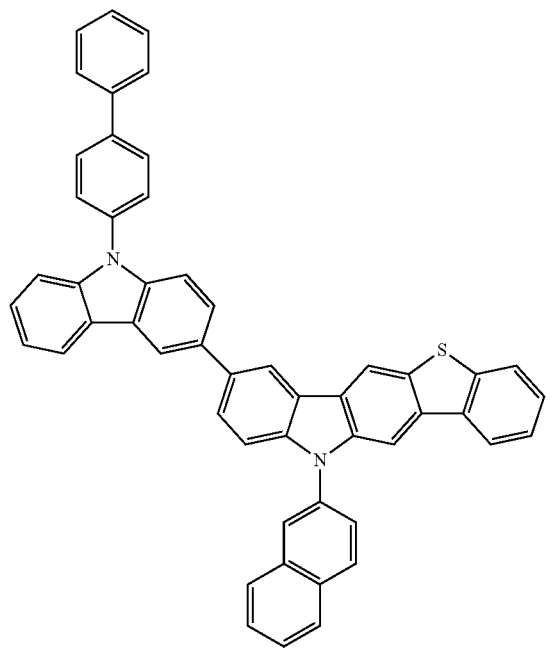
F-285
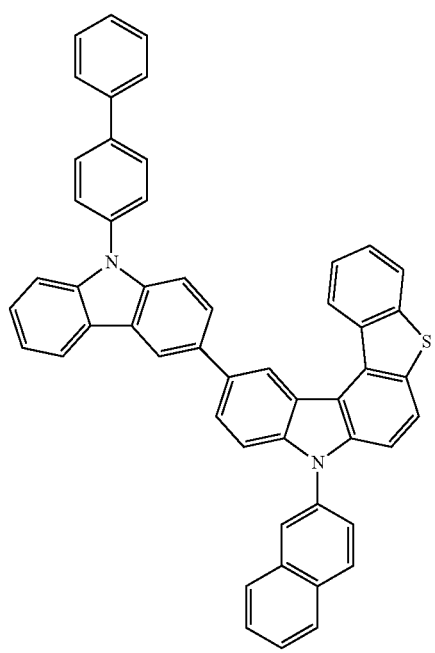
F-286
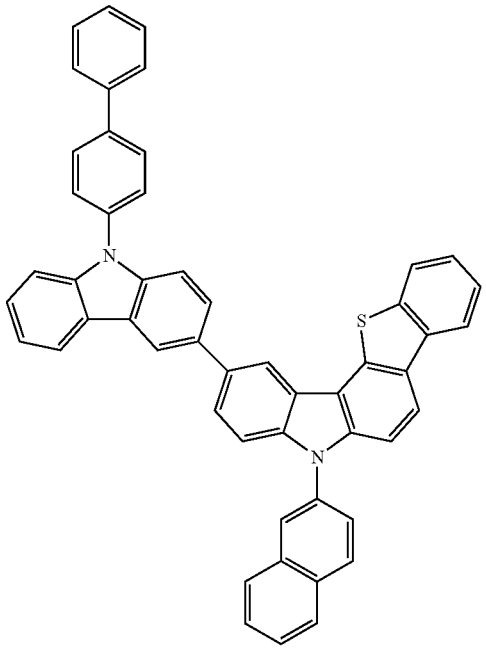
F-287
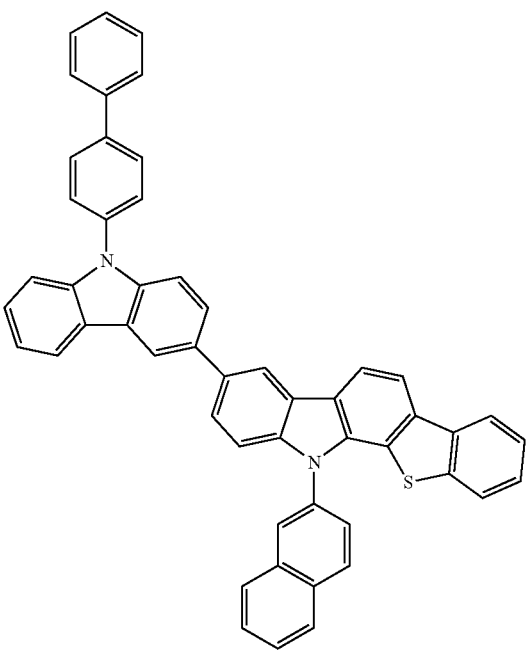

F-288
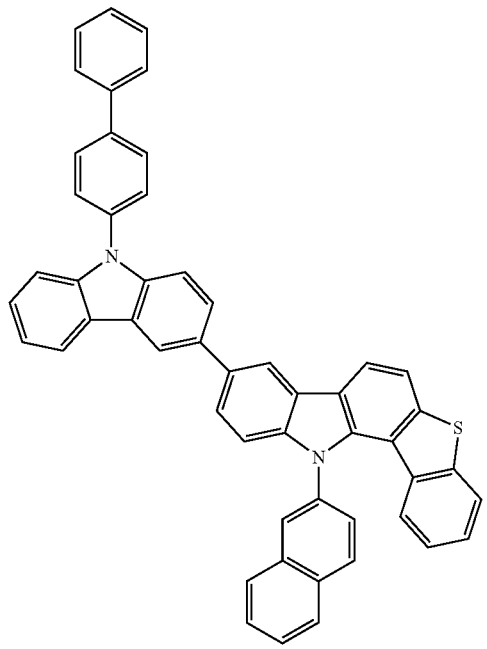
F-290
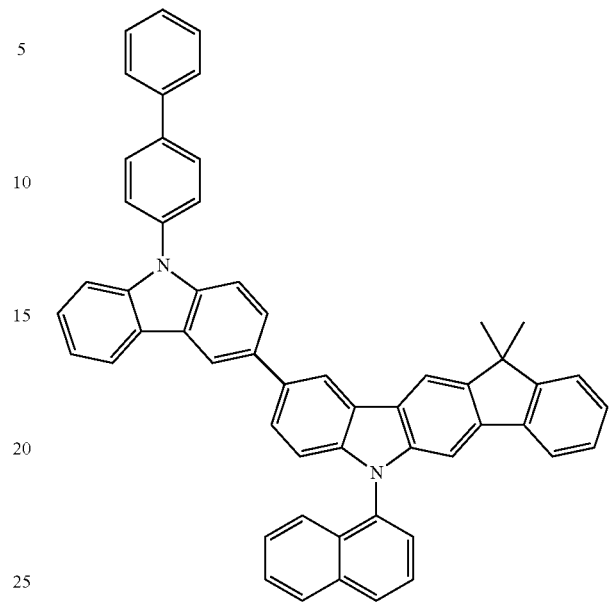
F-289
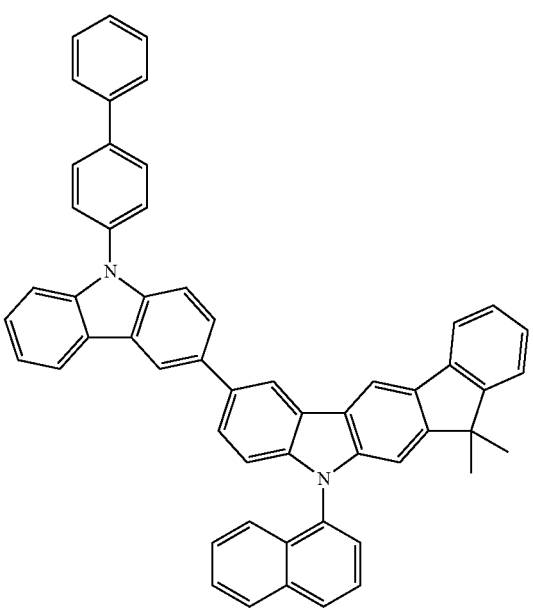
F-291
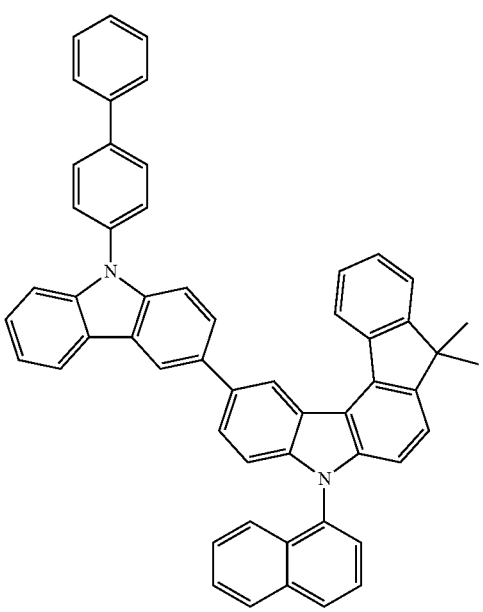

F-292
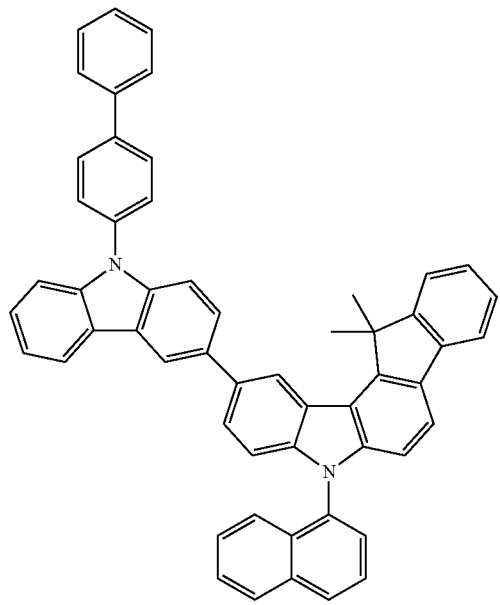
F-294
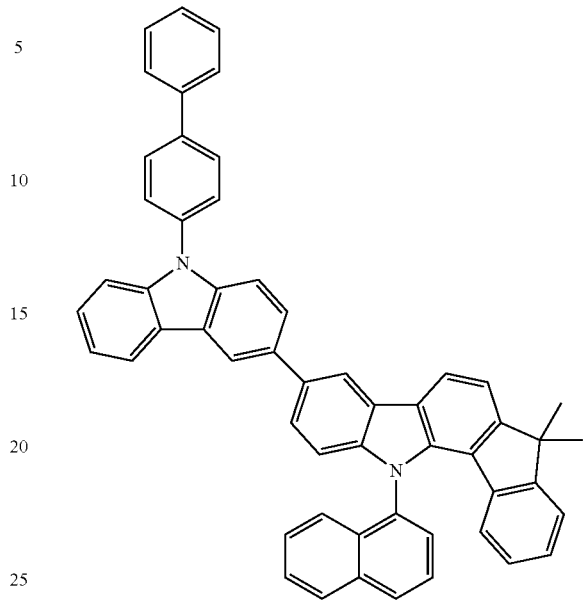
F-293
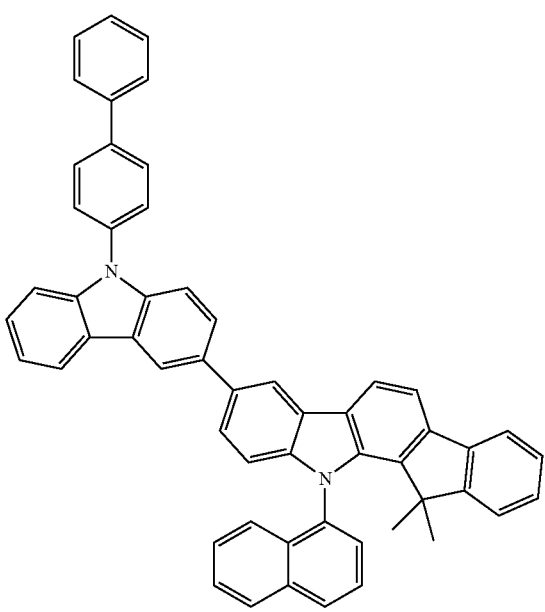
F-295
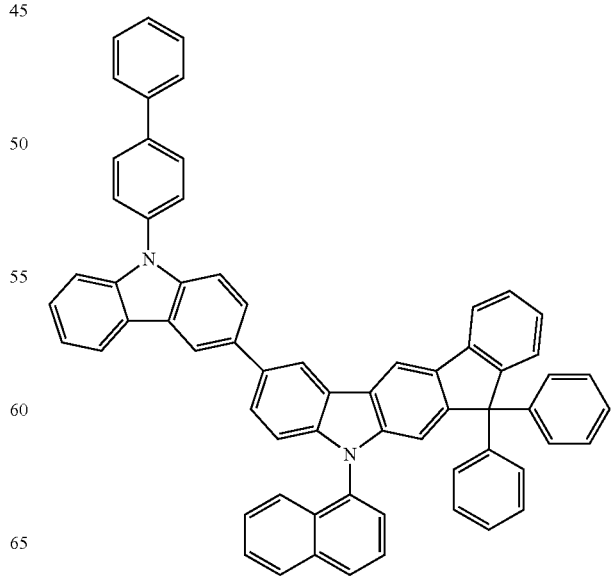

F-296
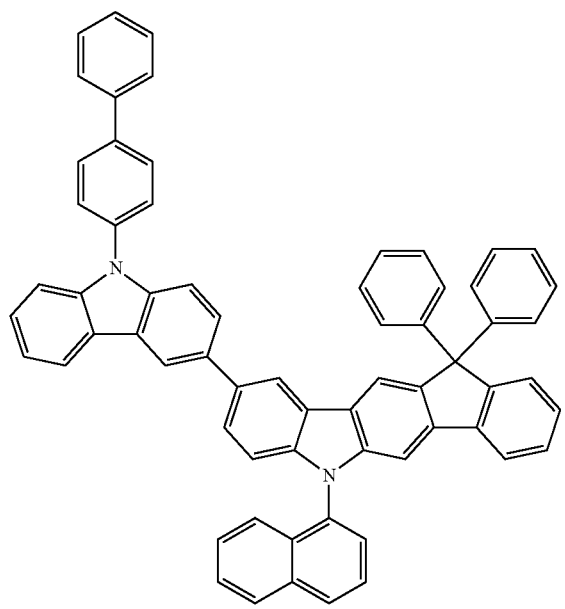
F-298
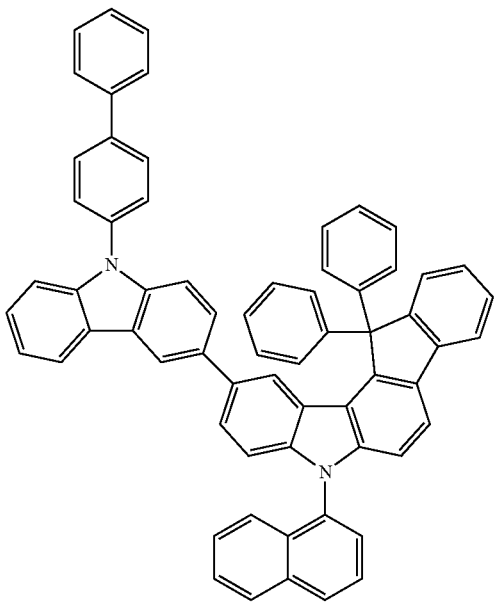
F-297
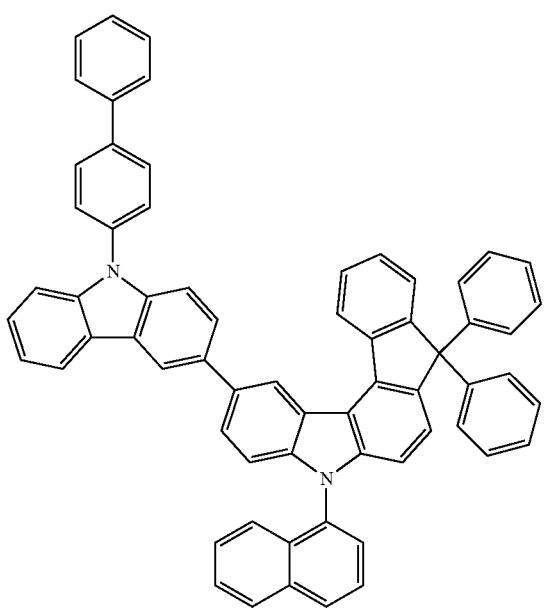
F-299
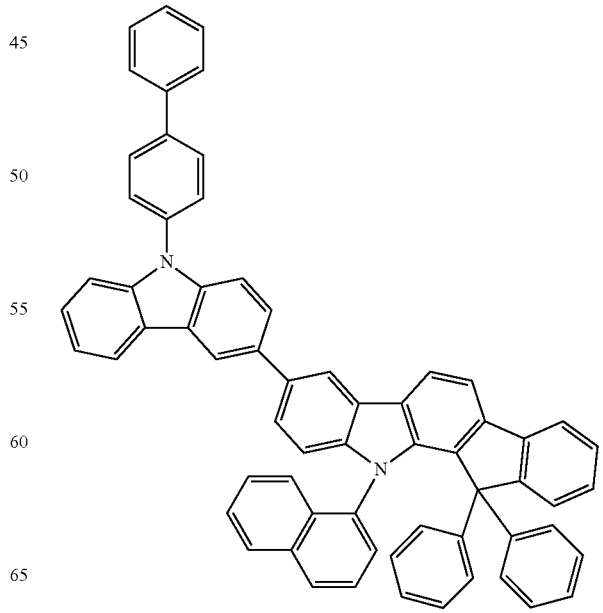

F-300
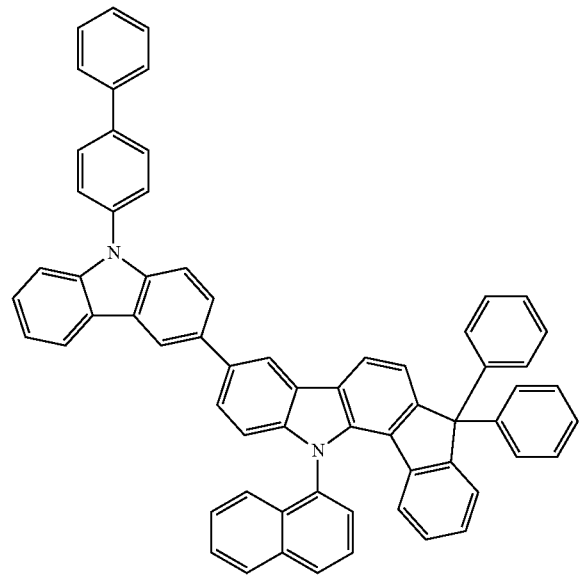
F-302
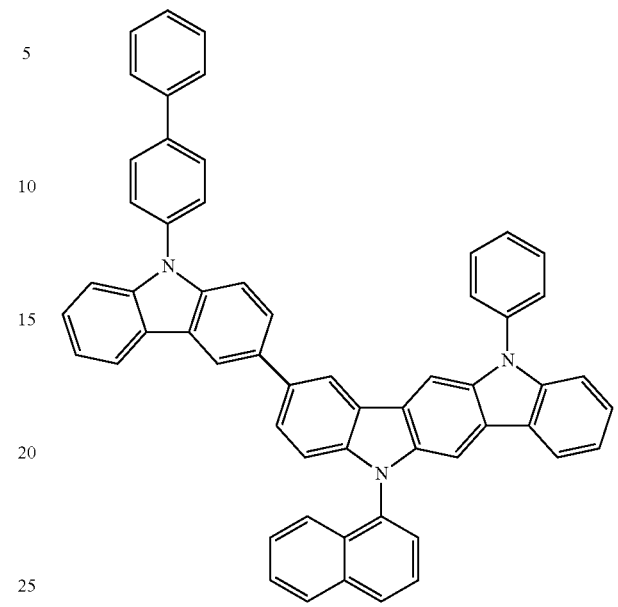
F-301
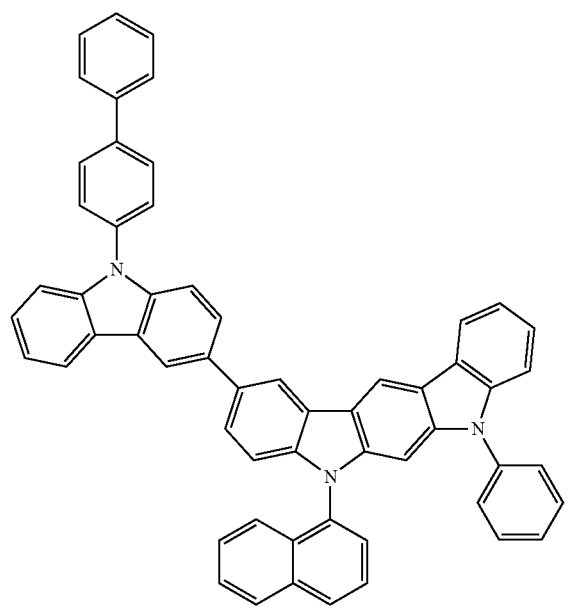
F-303
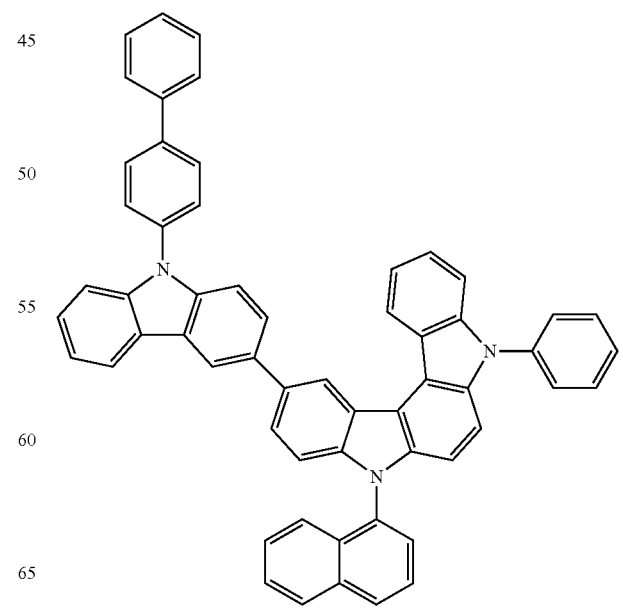

F-304
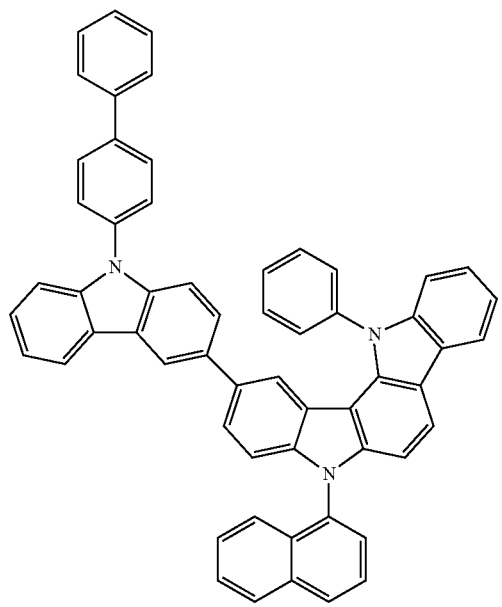
F-306
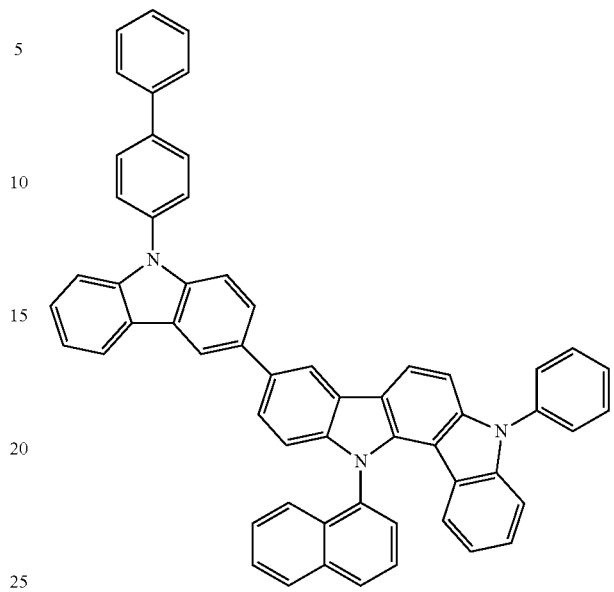
F-305
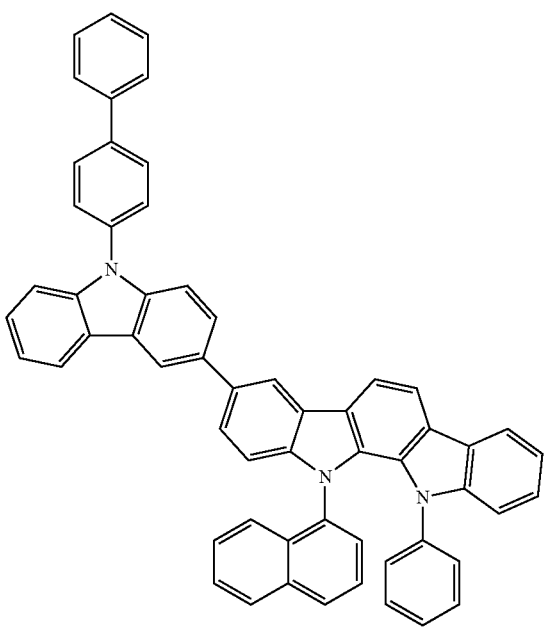
F-307
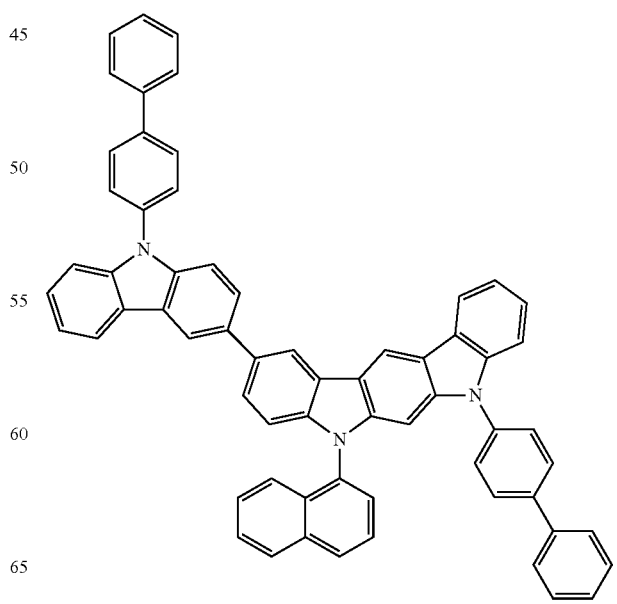

F-308
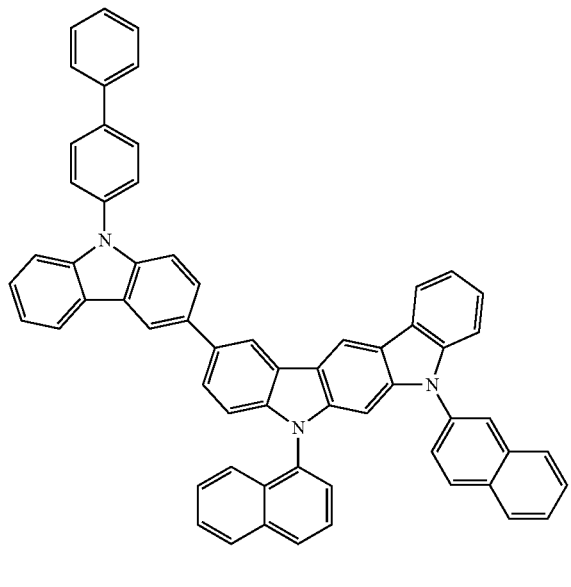
F-310
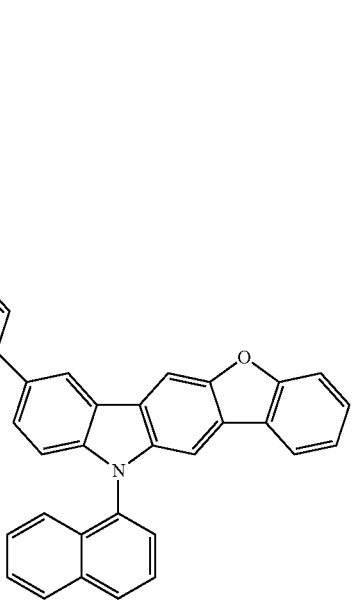
F-309
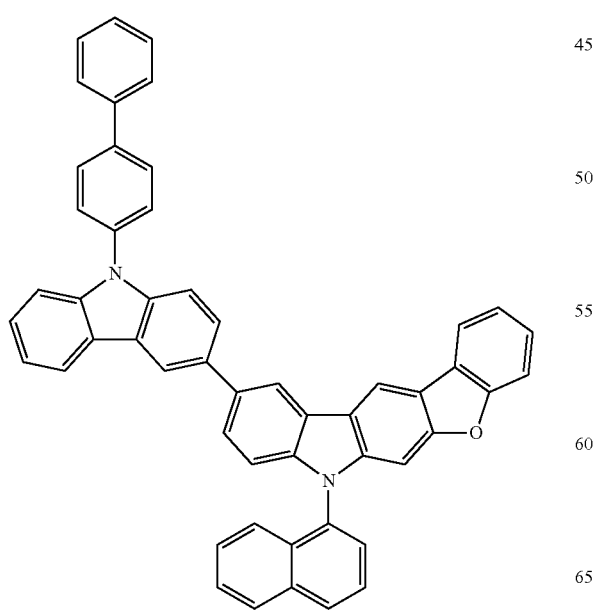
F-311
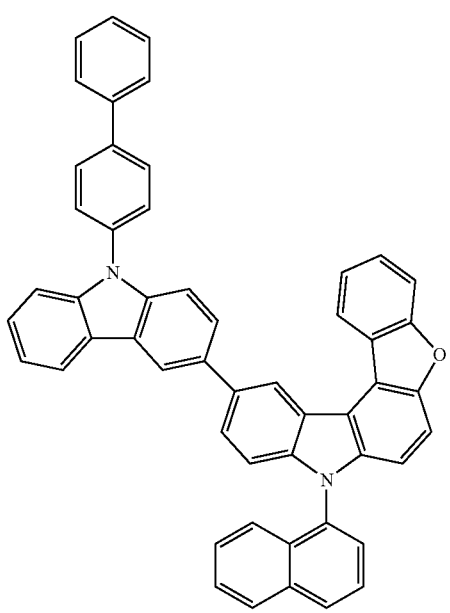

F-312
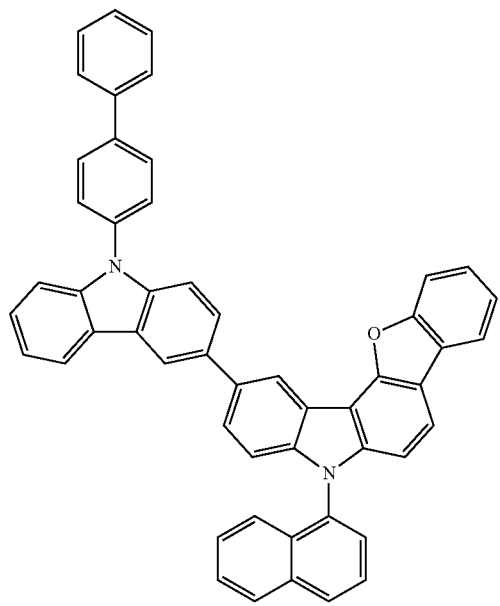
F-314
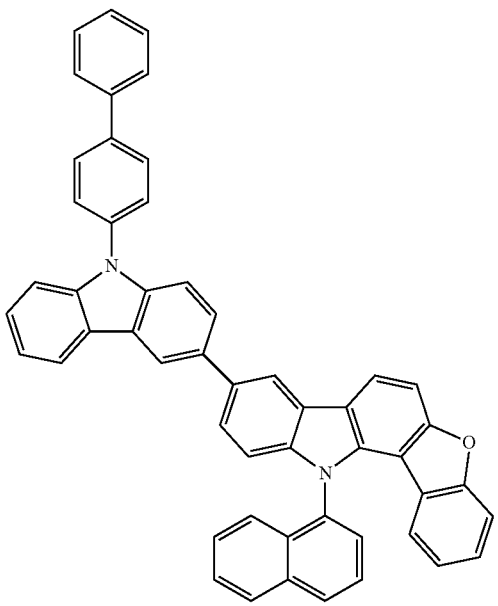
F-313
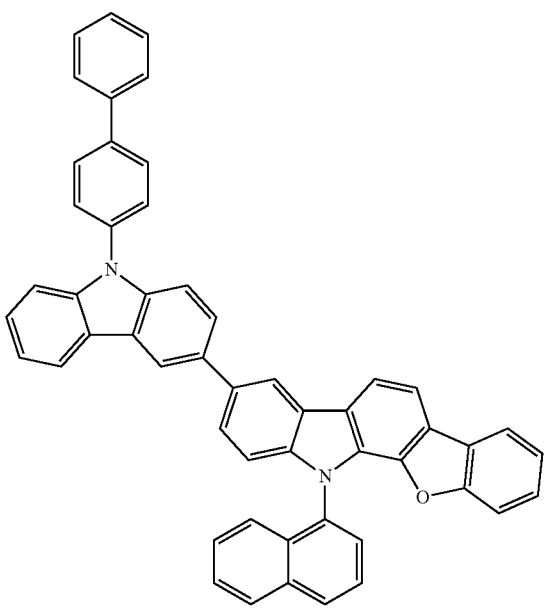
F-315
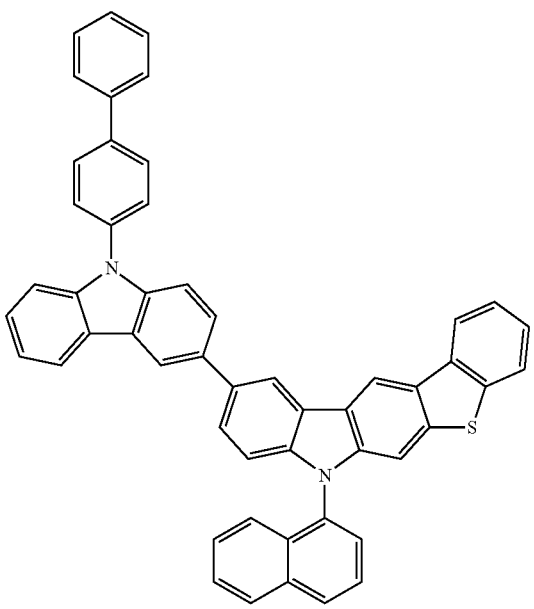

F-316
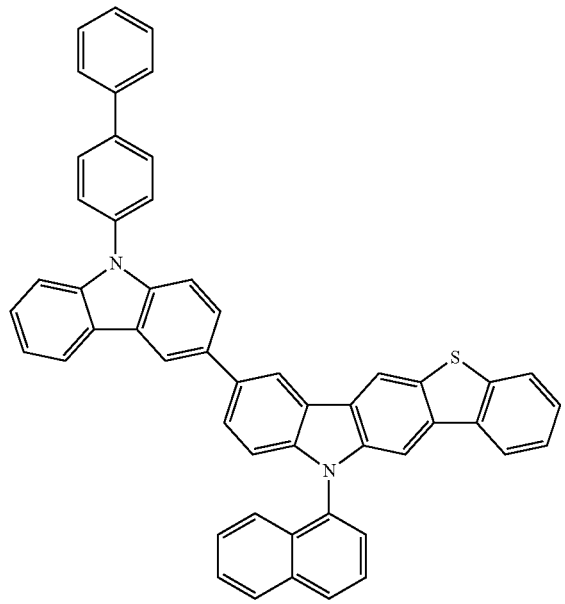
F-318
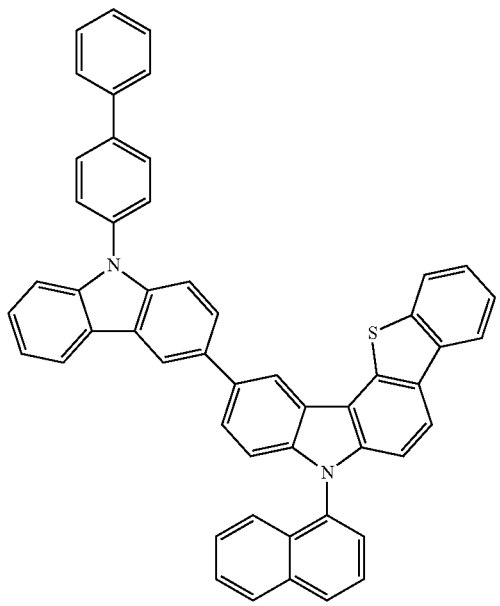
F-317
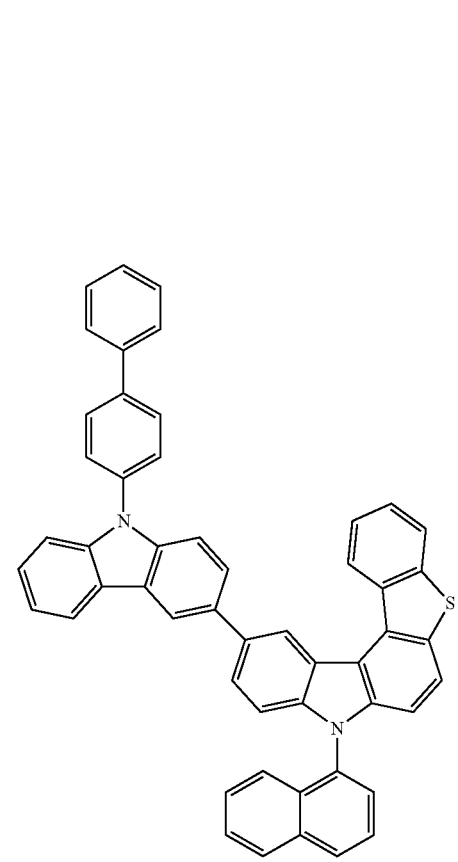
F-319
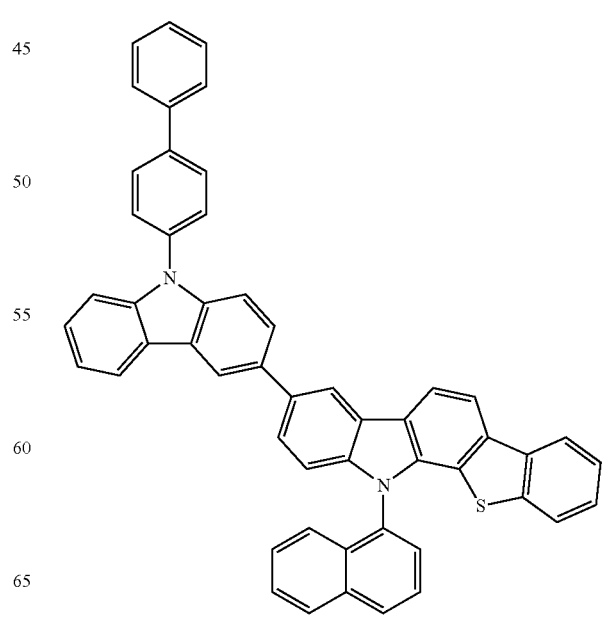

F-320
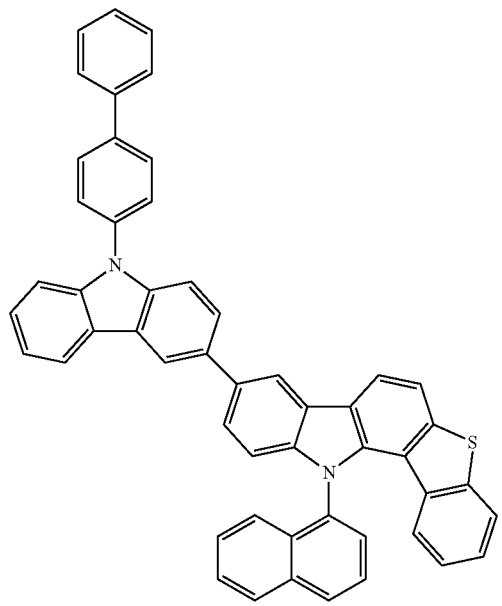
F-321
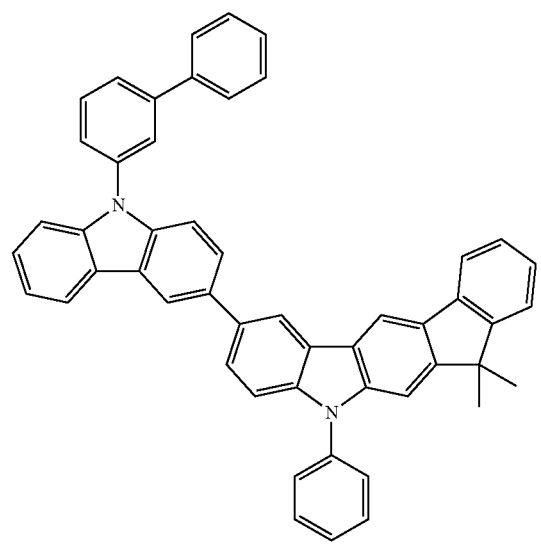
F-322
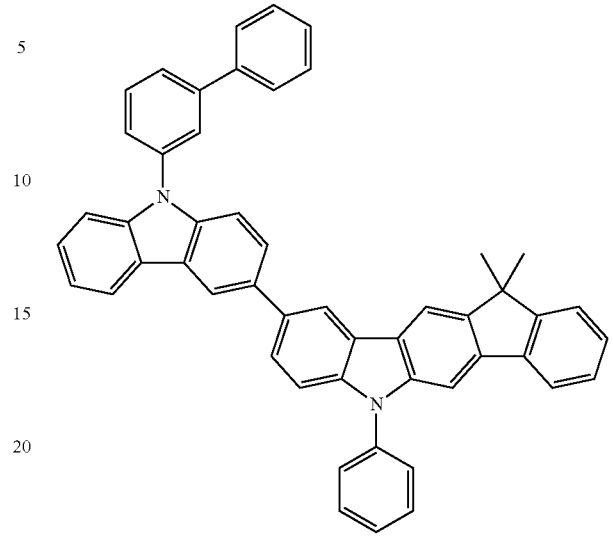
F-323
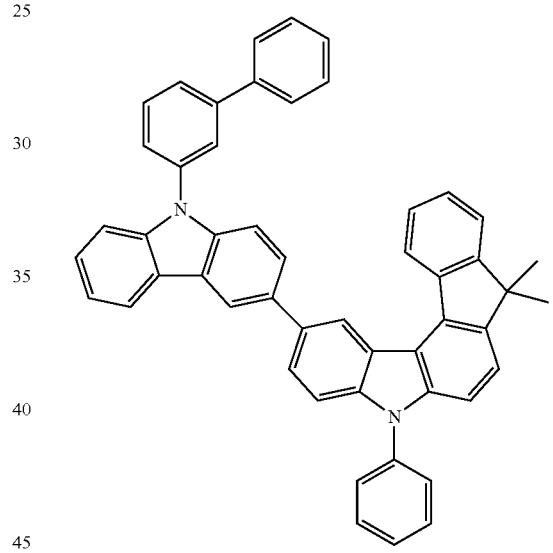
F-324
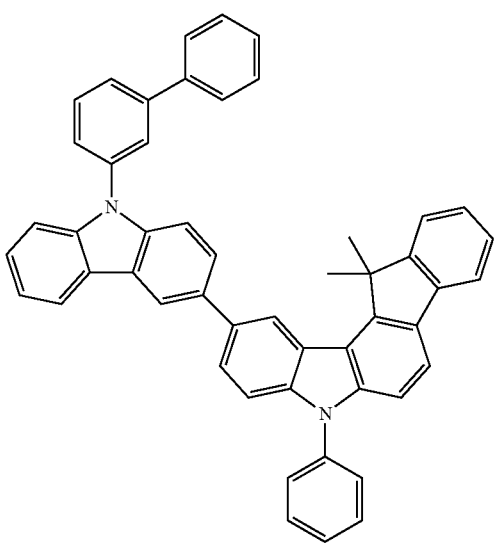

F-325
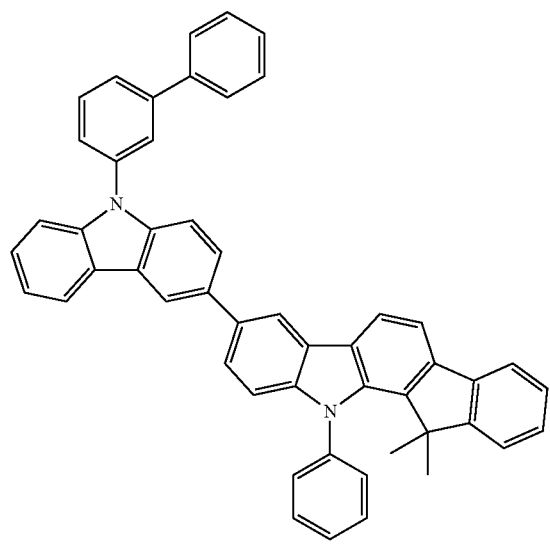
F-326
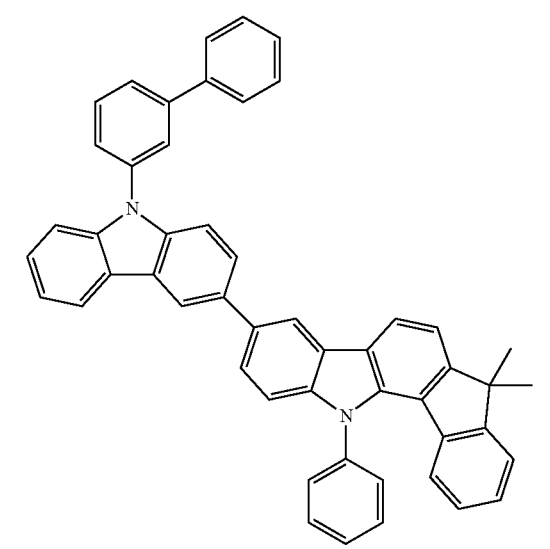
F-327
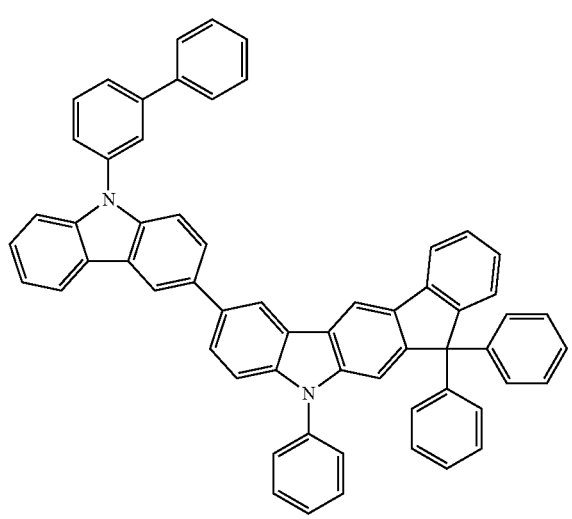
F-328
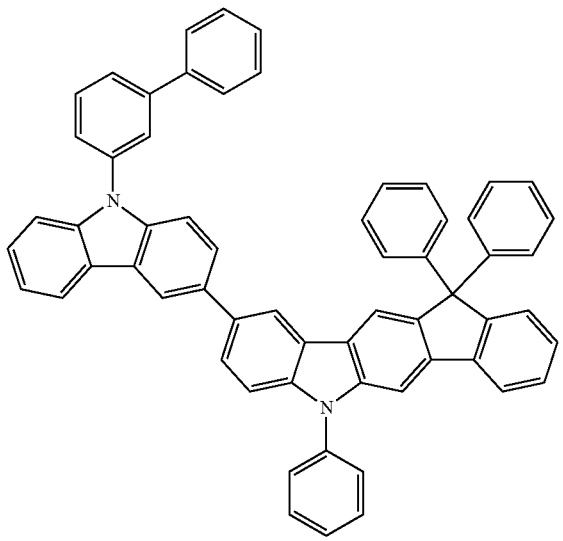
F-329
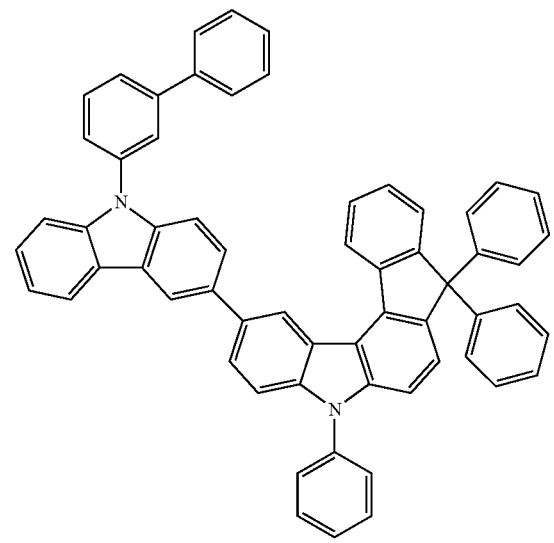
F-330
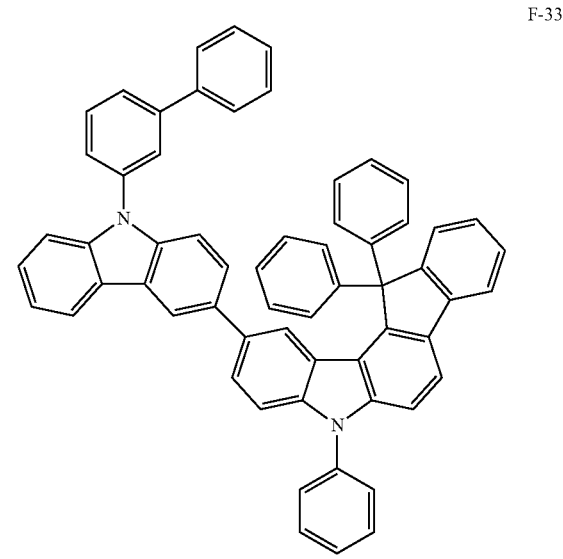

F-331
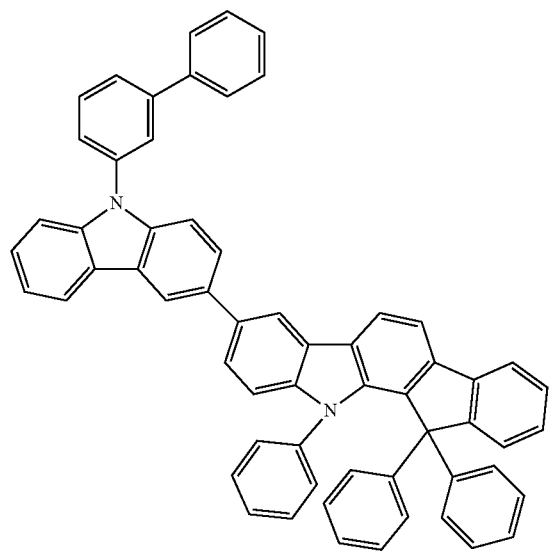
F-332
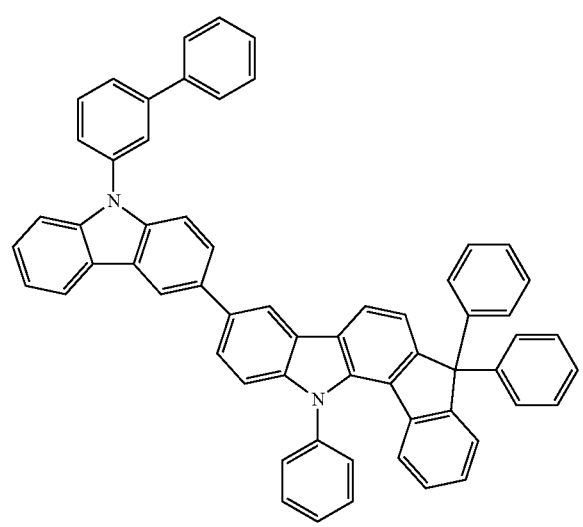
F-333
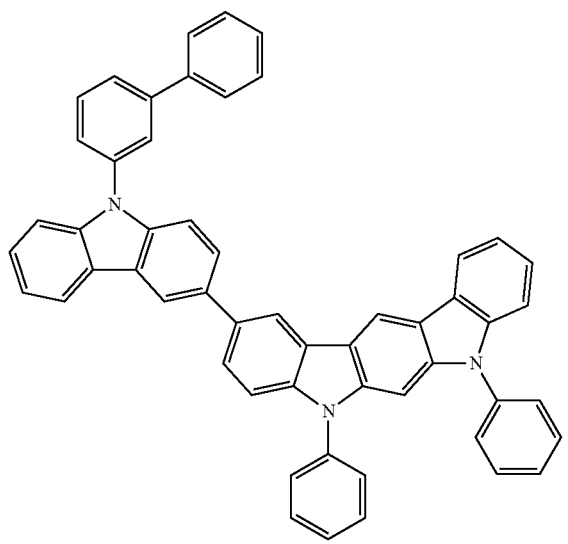
F-334
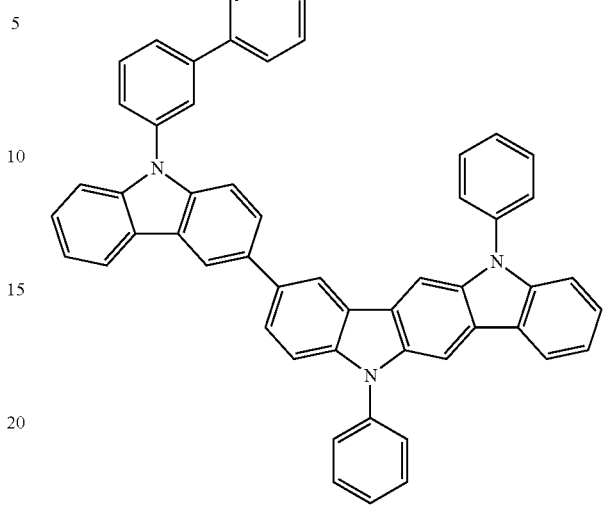
F-335
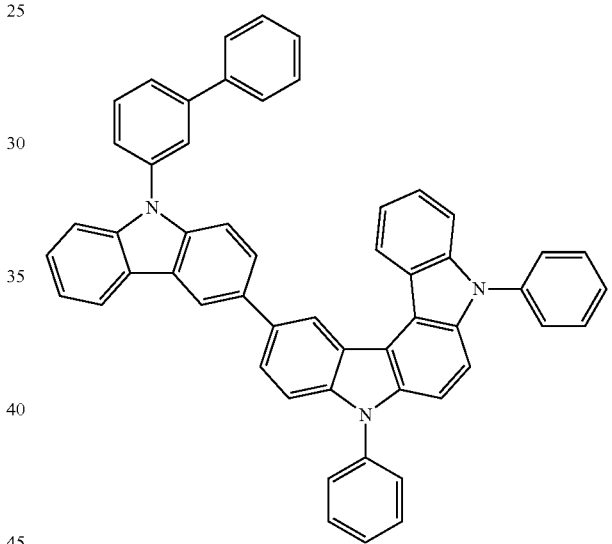
F-336
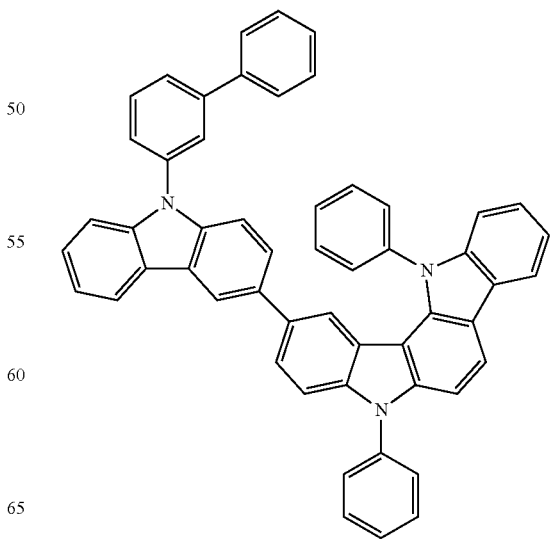

F-337
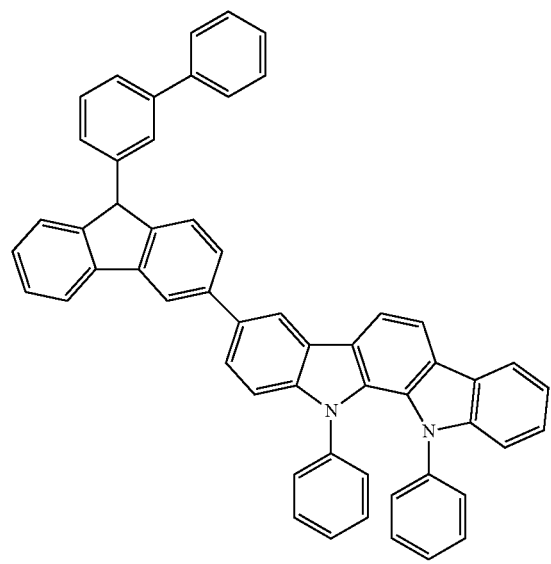
F-338
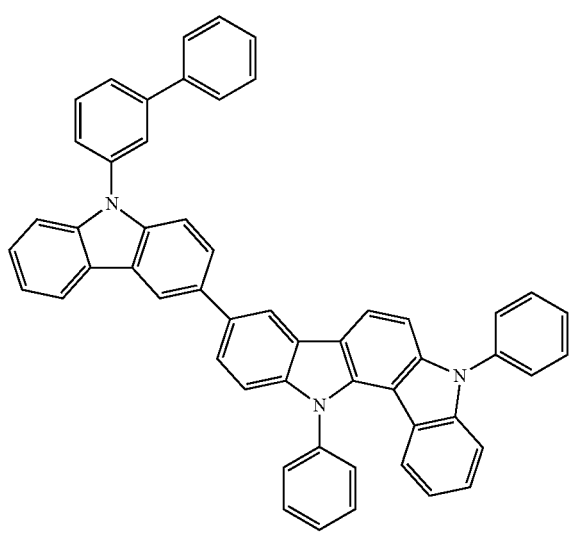
F-339
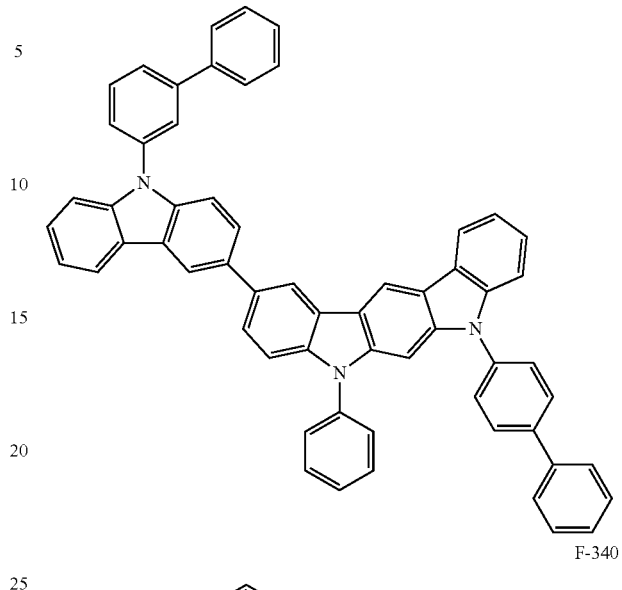
F-340
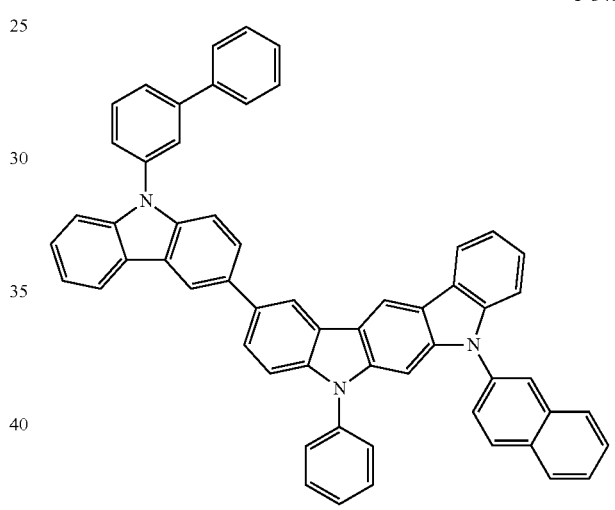
F-341
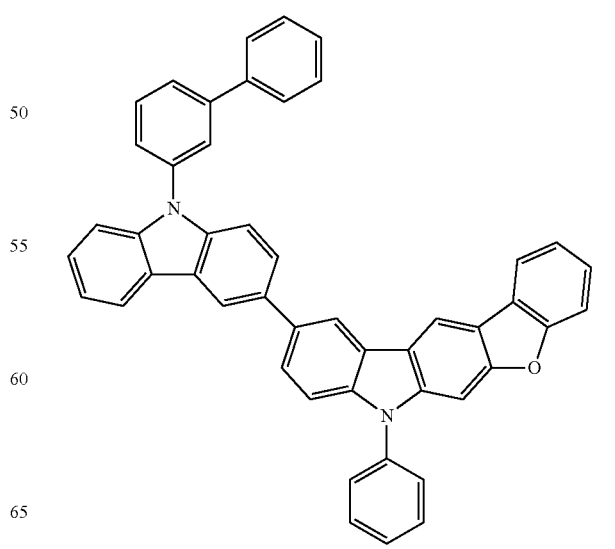

F-342
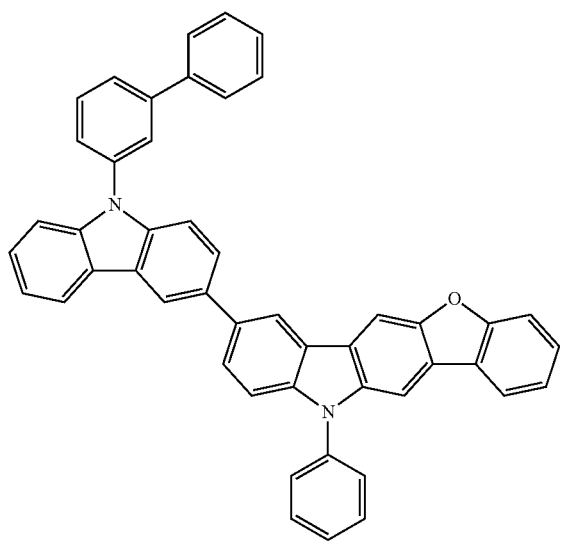
F-343
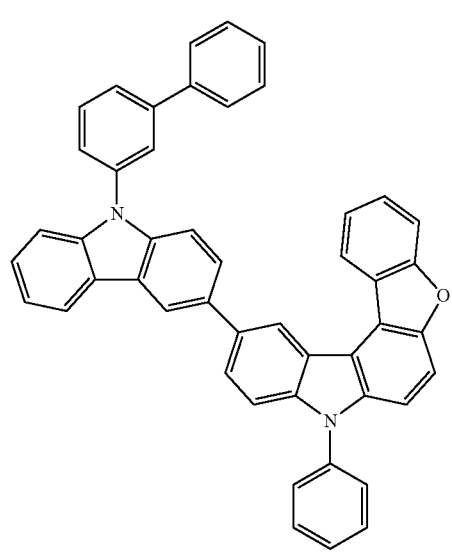
F-344
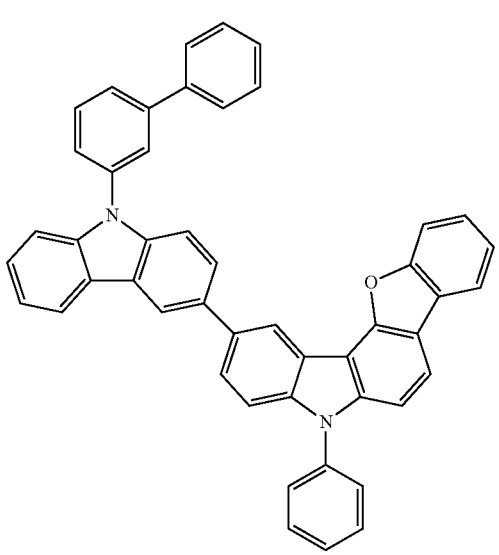
F-345
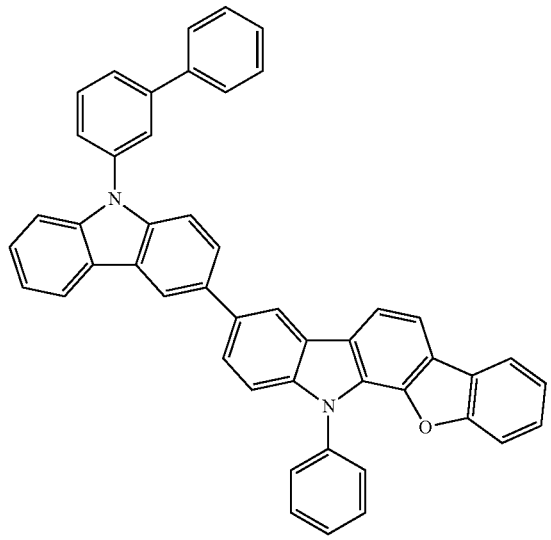
F-346
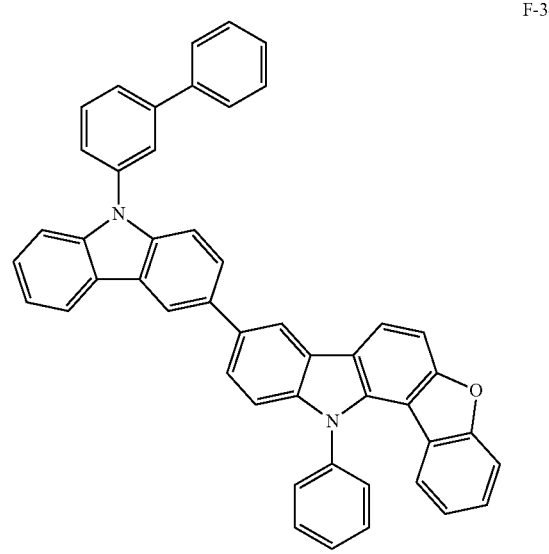
F-347
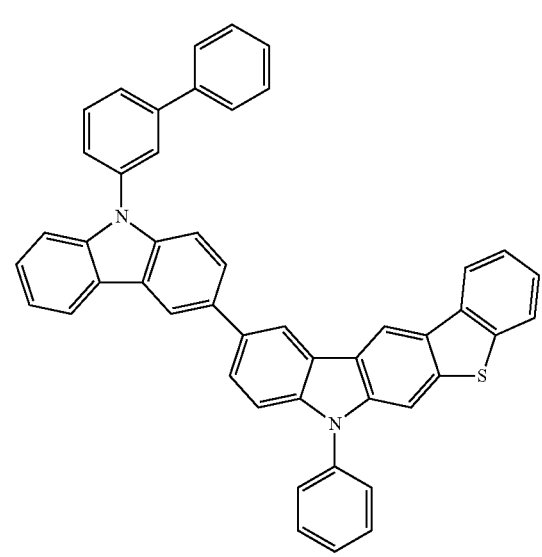

-continued
F-348
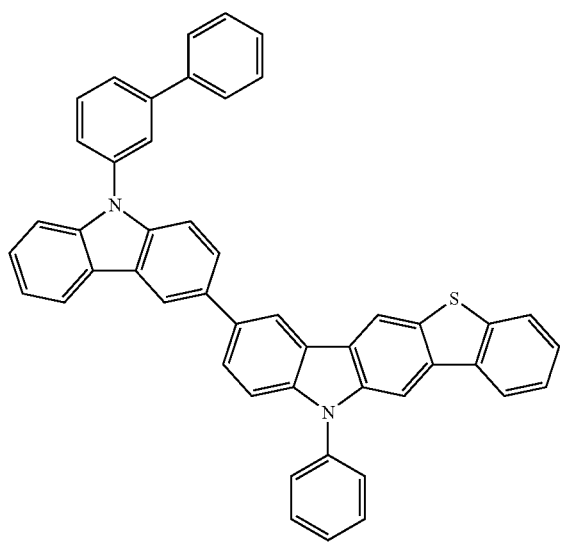
F-349
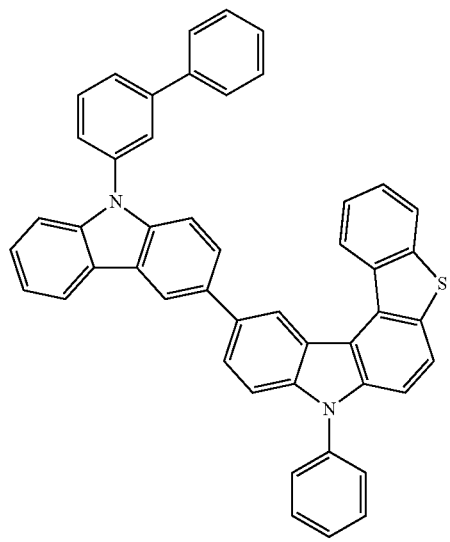
F-350
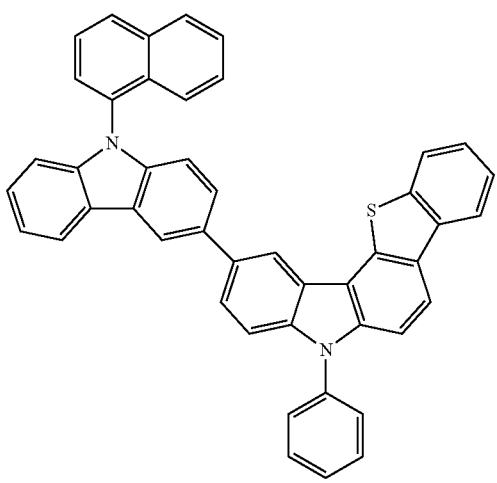
-continued
F-351
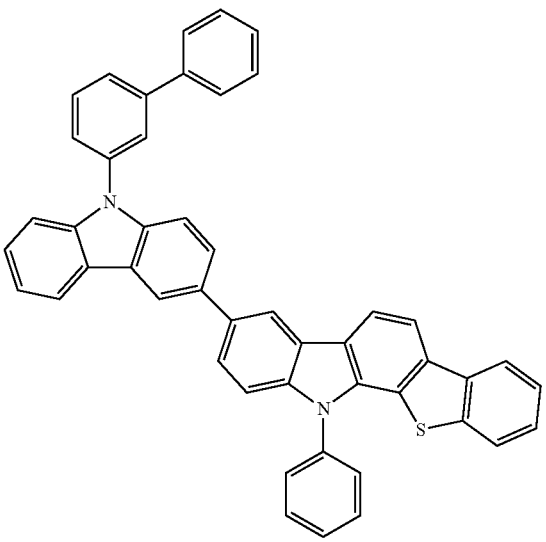
F-352
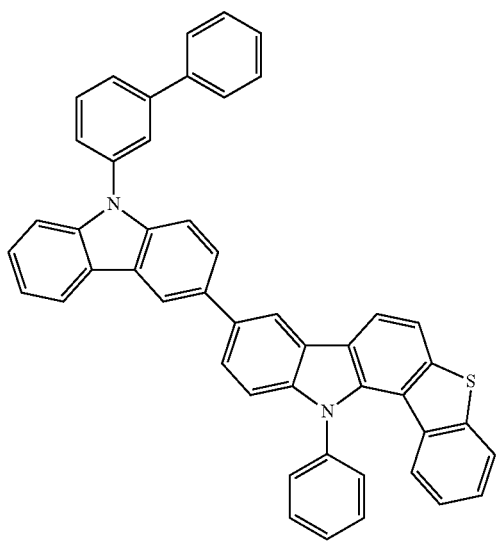

F-353
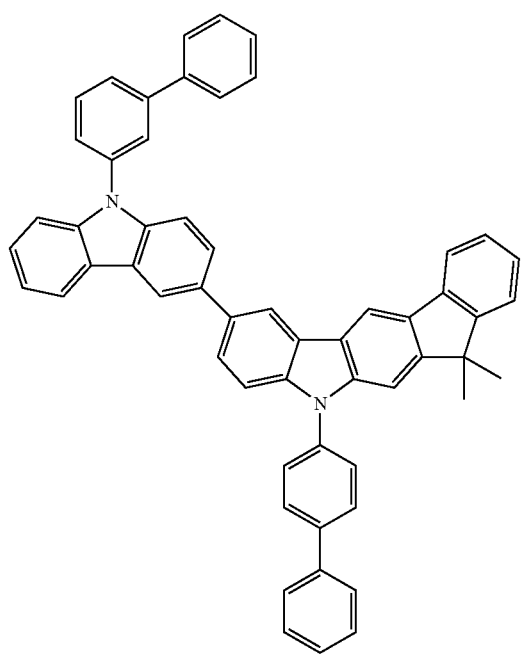
F-355
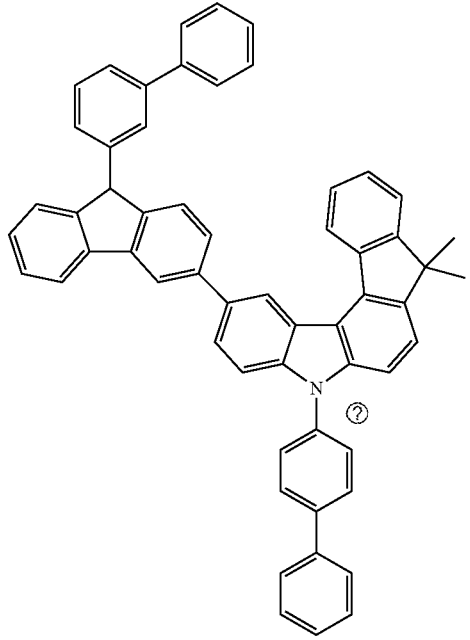
F-354
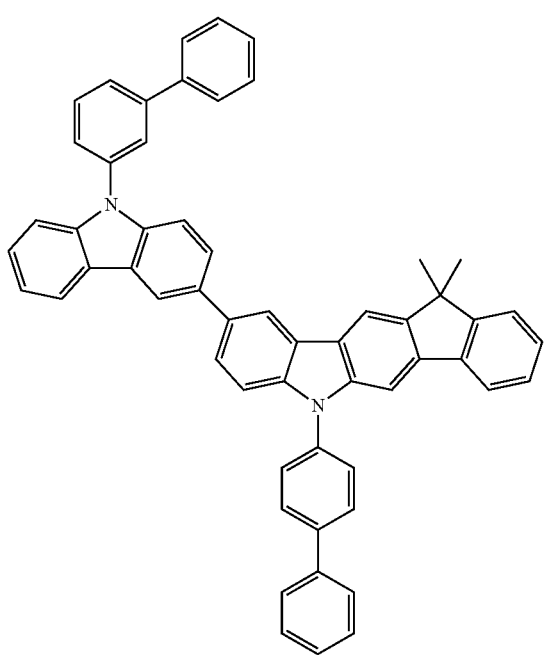
F-356
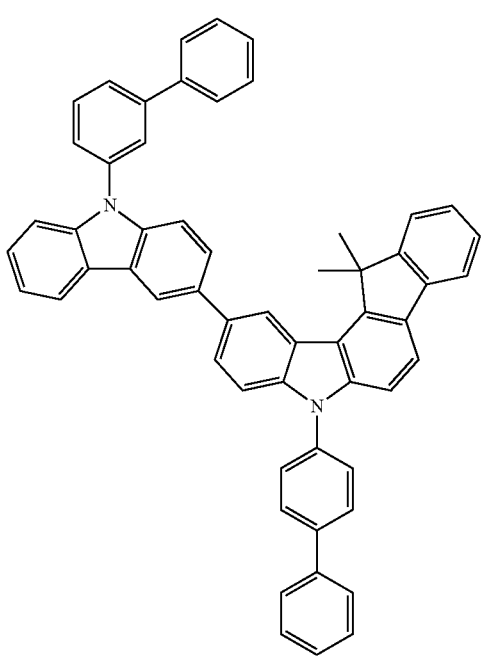

F-357
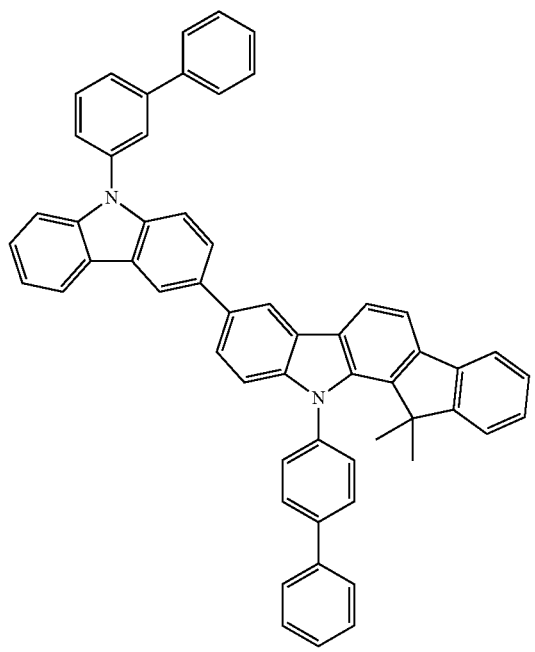
F-358
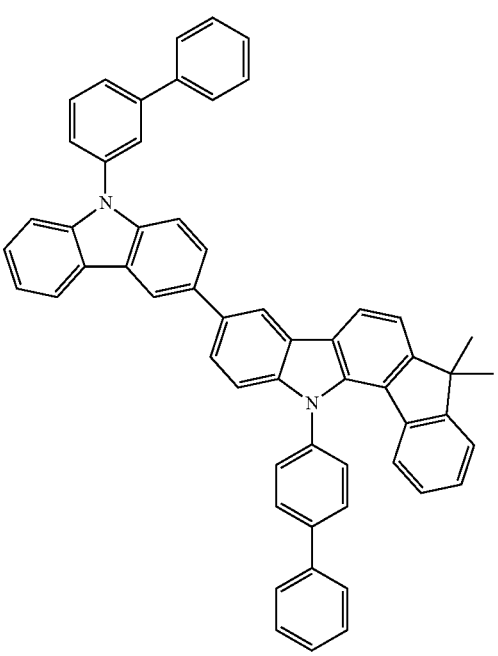
F-359
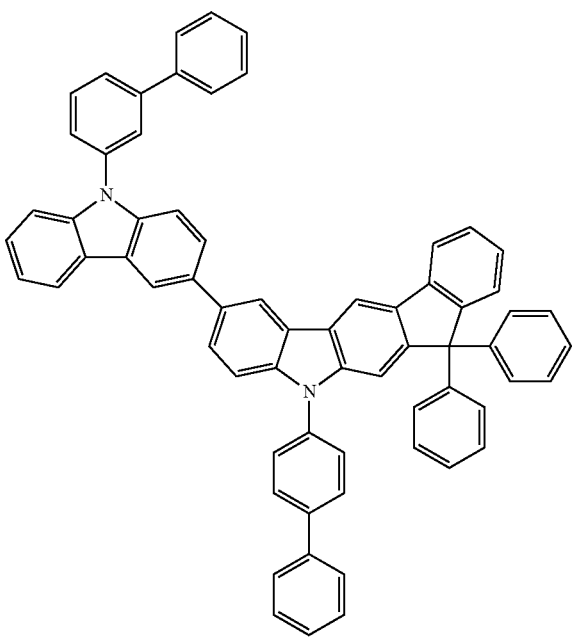
F-360
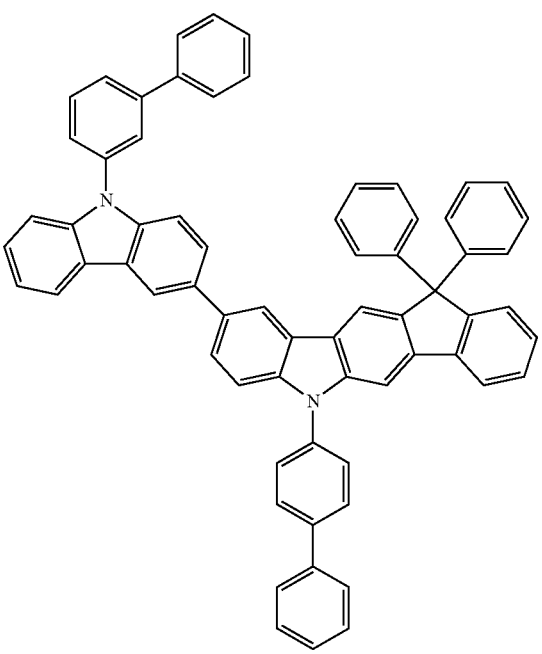

F-361
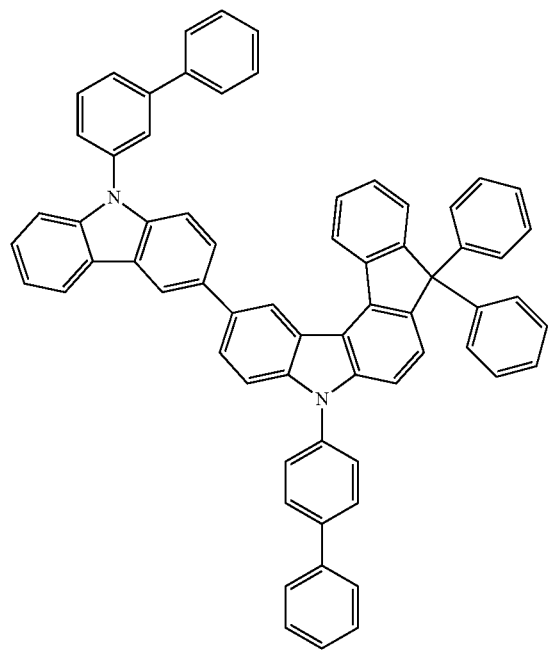
F-363
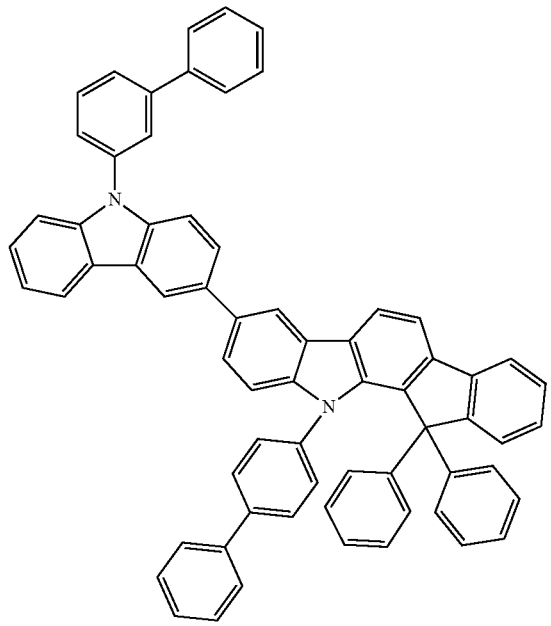
F-362
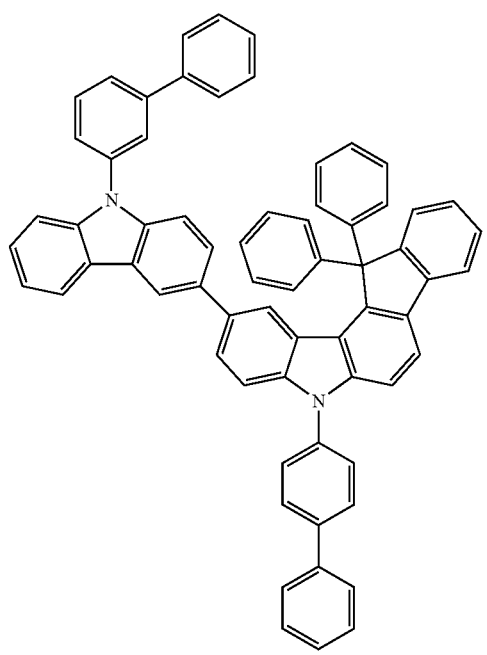
F-364
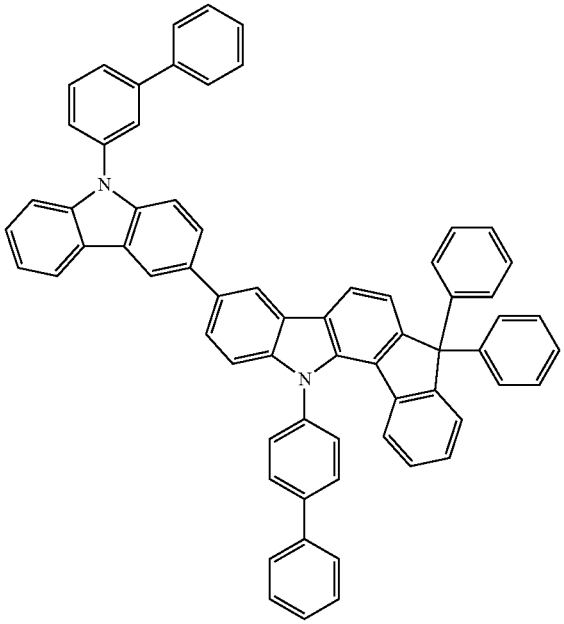

F-365
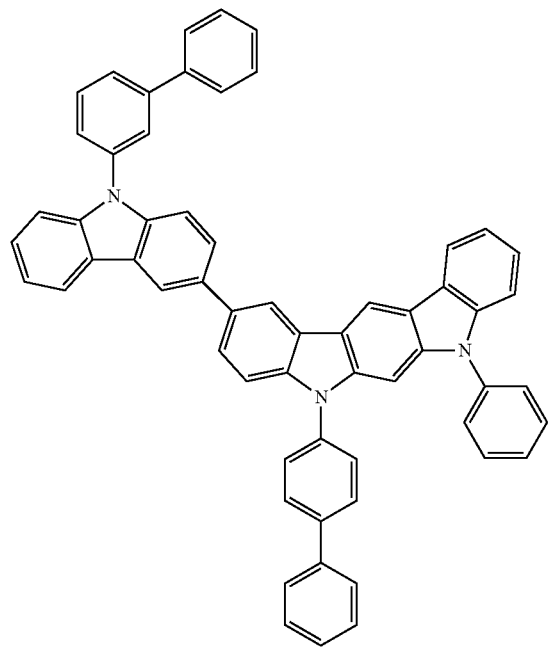
F-367
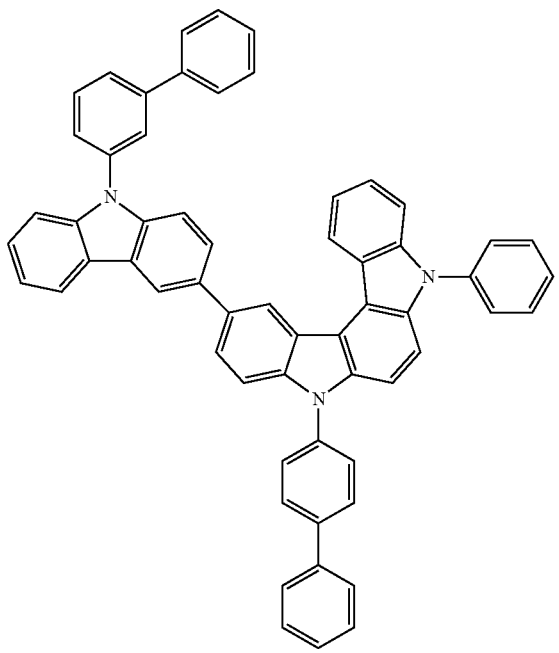
F-366
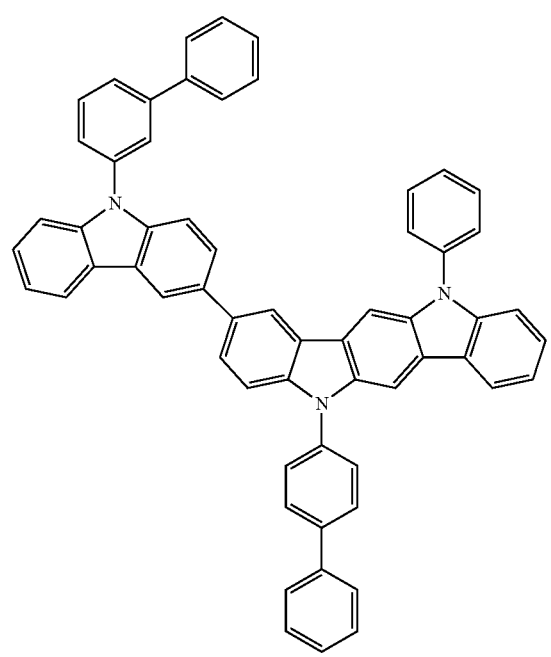
F-368
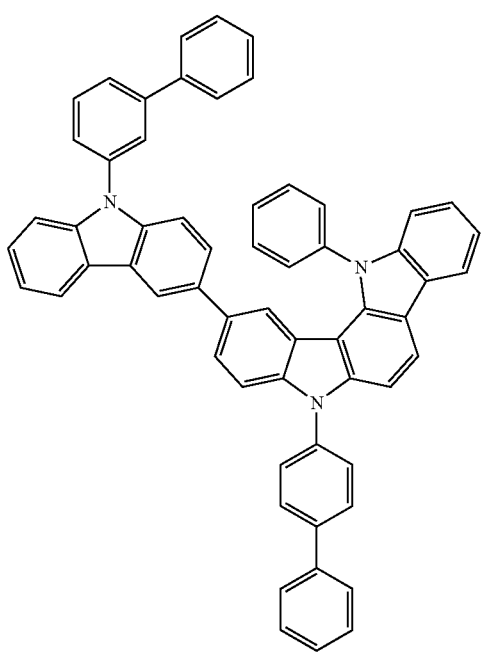

F-369
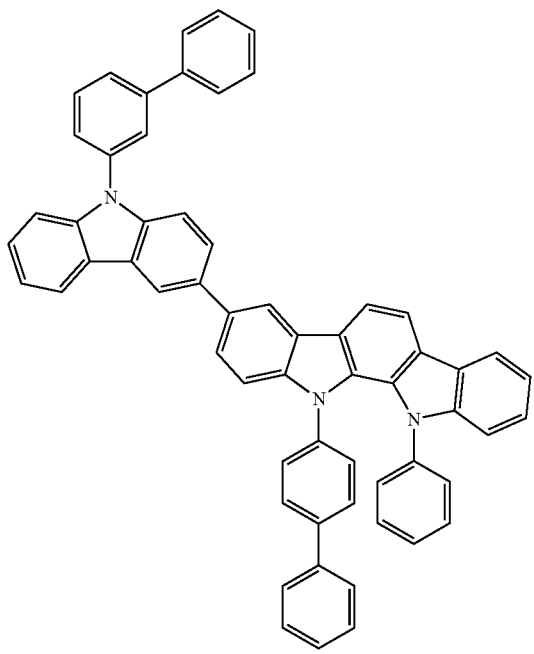
F-370
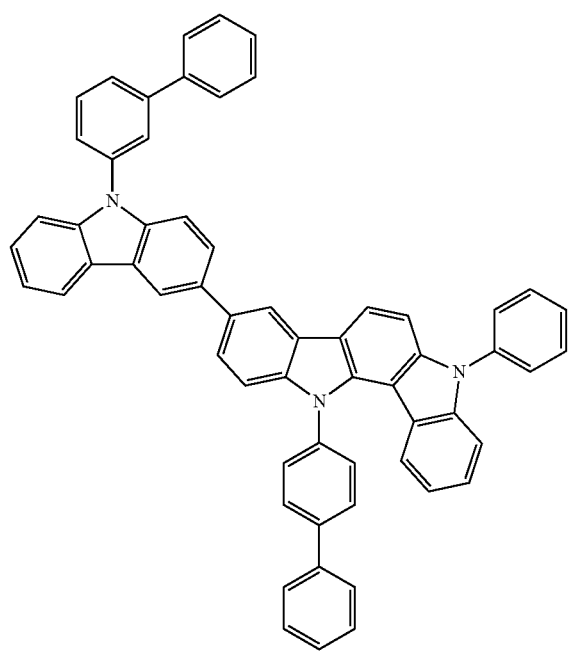
F-371
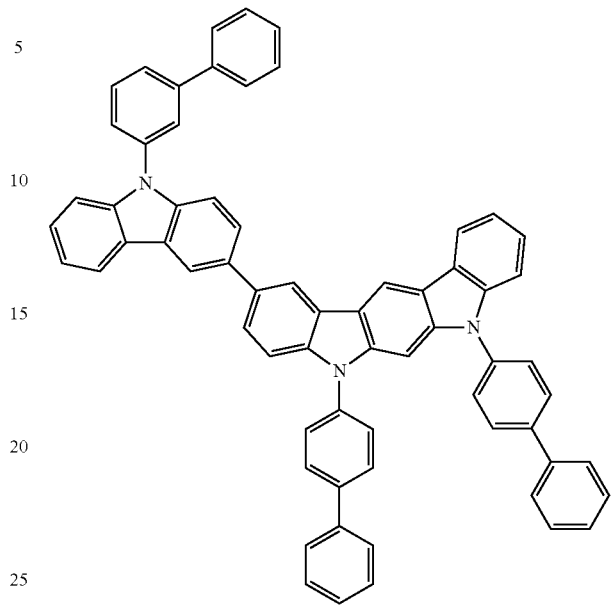
F-372
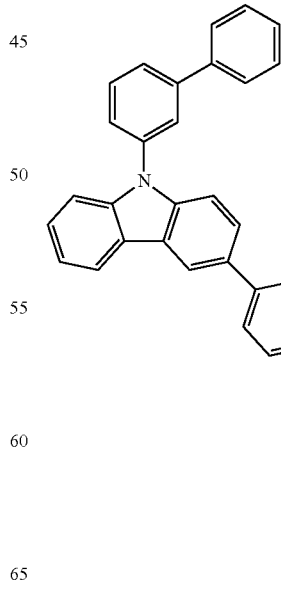

-continued
F-373
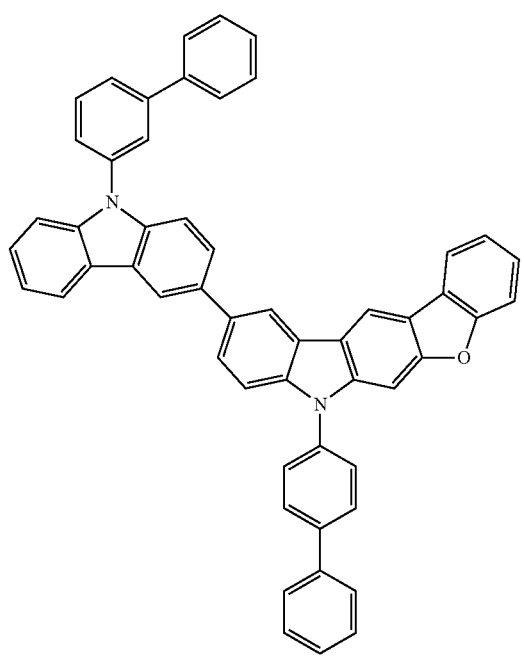
F-374
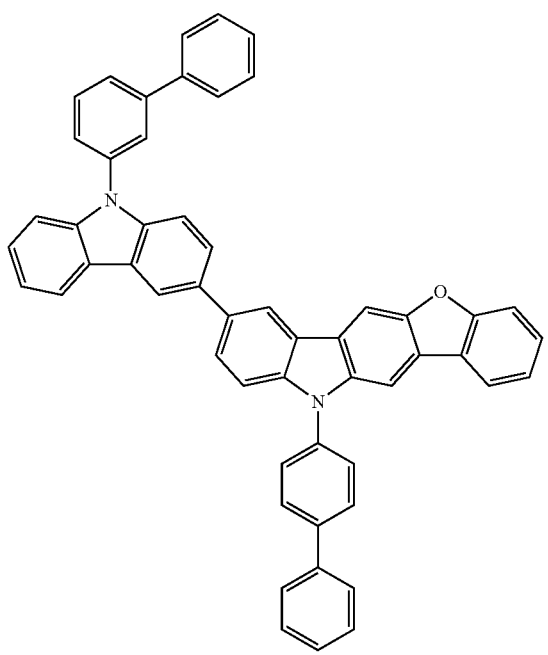
F-375
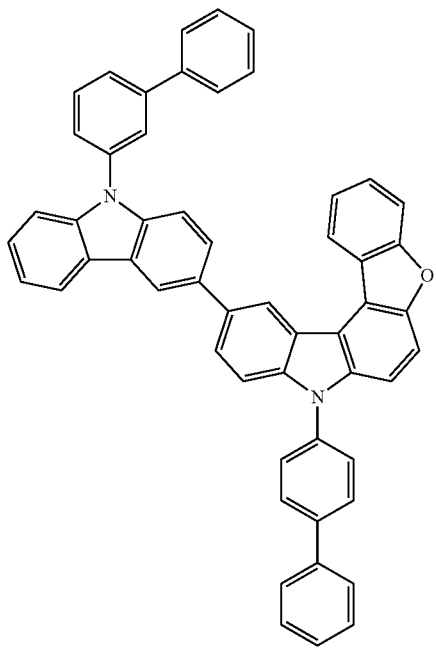
F-376
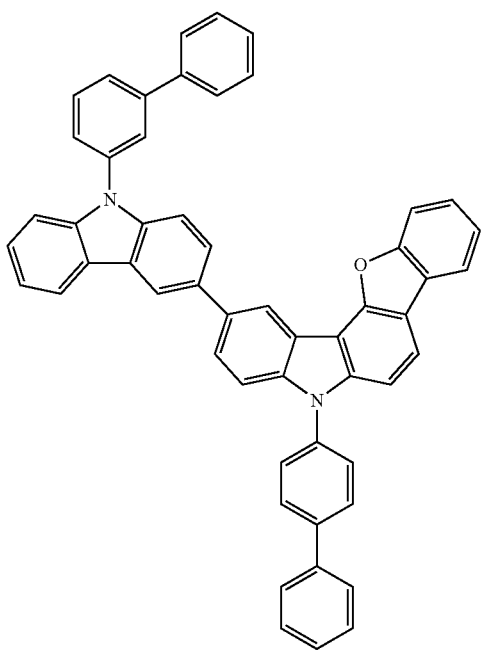

F-377
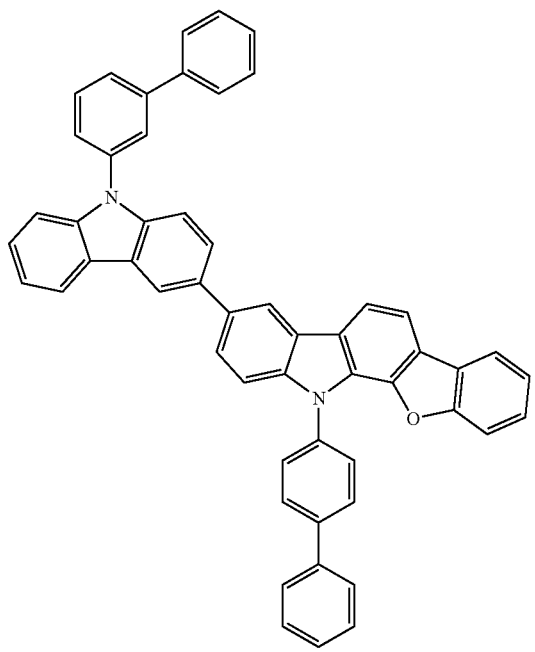
F-379
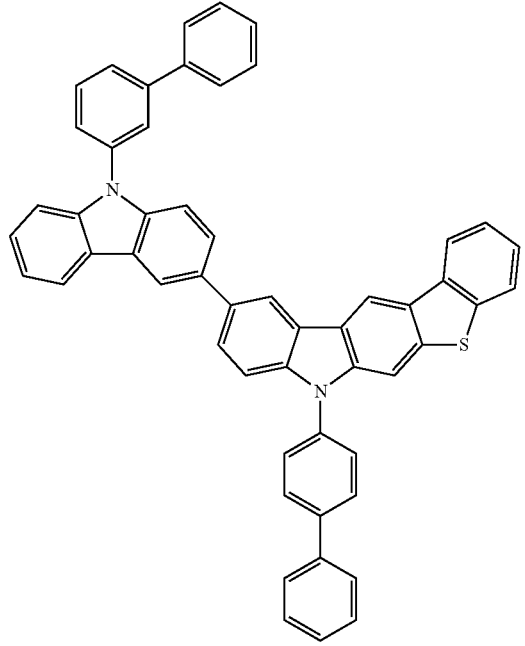
F-378
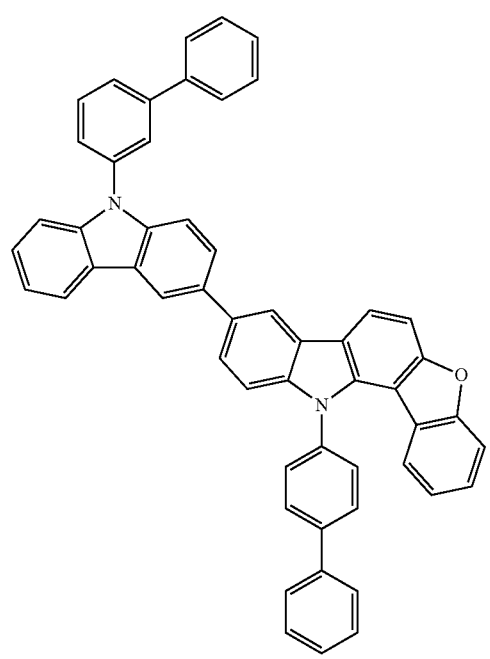
F-380
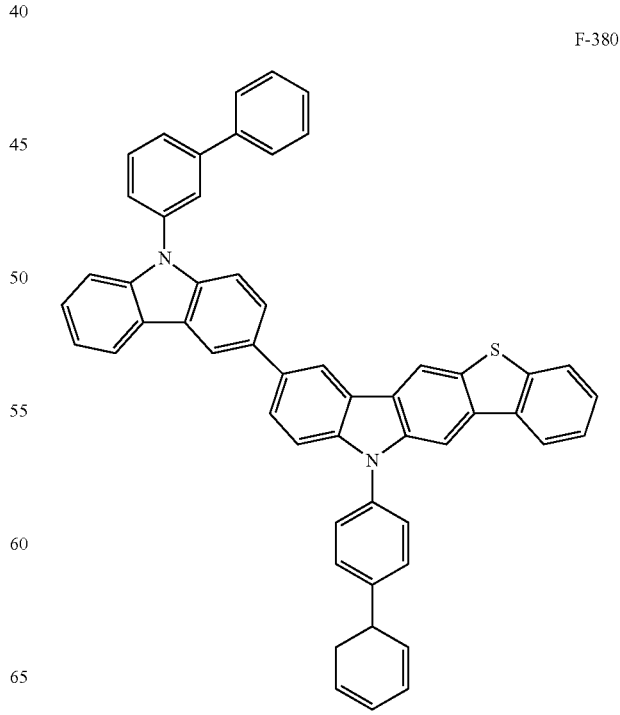

F-381
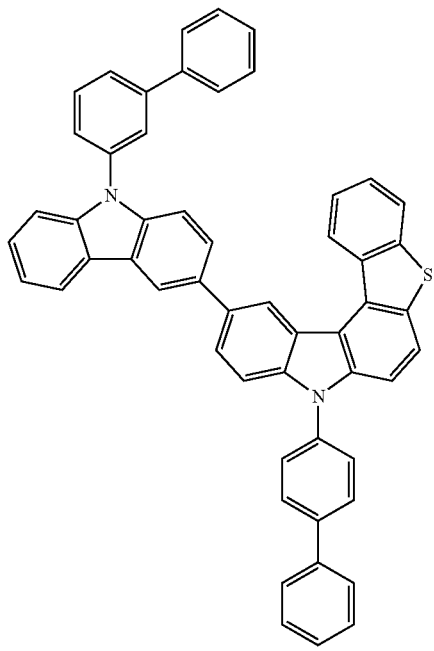
F-382
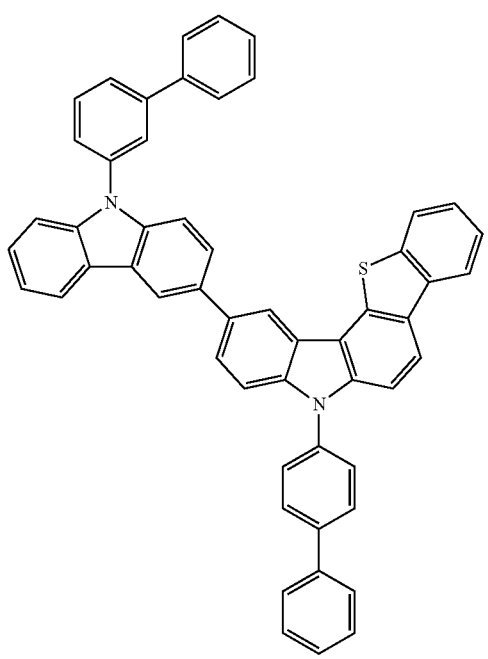
F-383
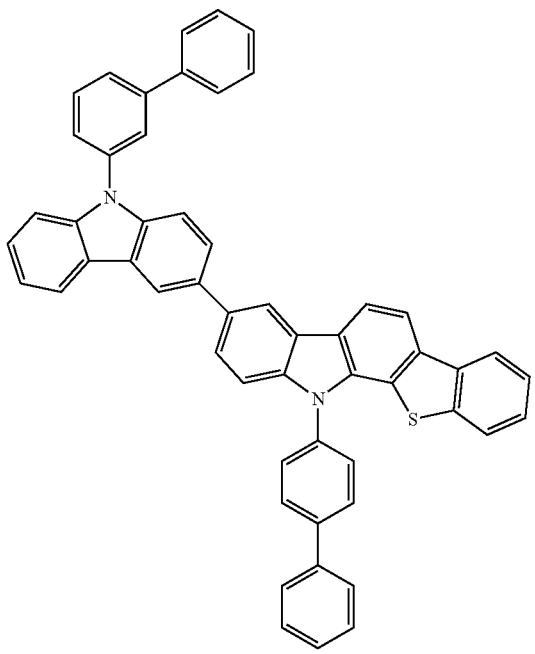
F-384
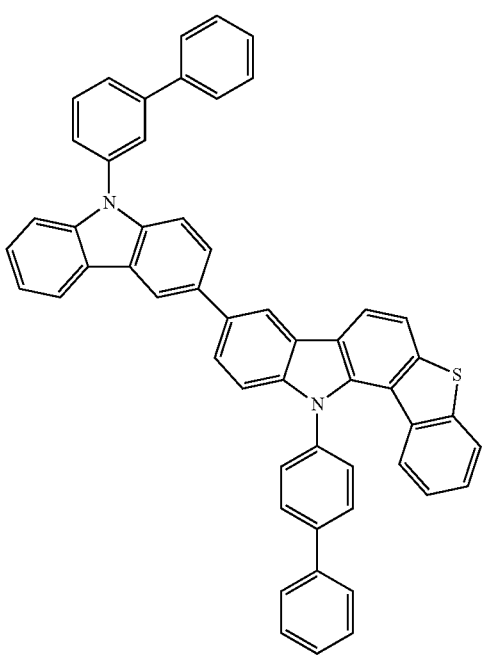

F-385
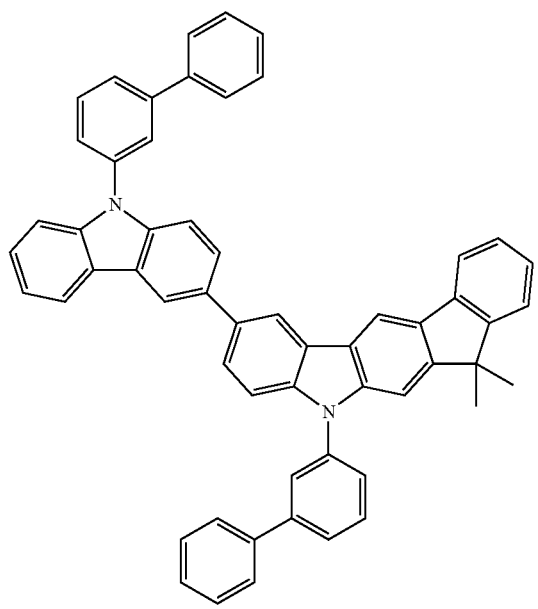
F-387
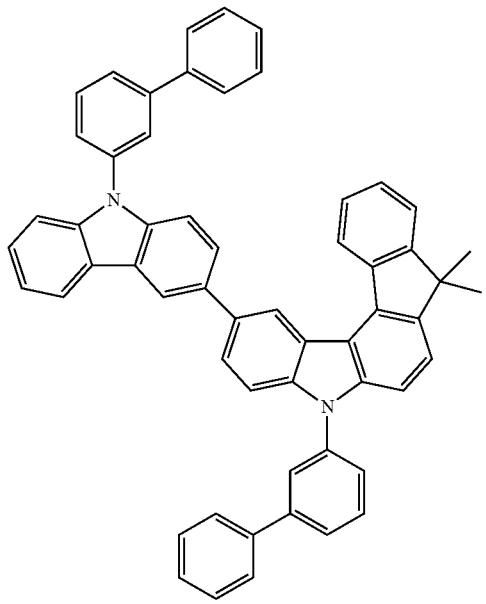
F-386
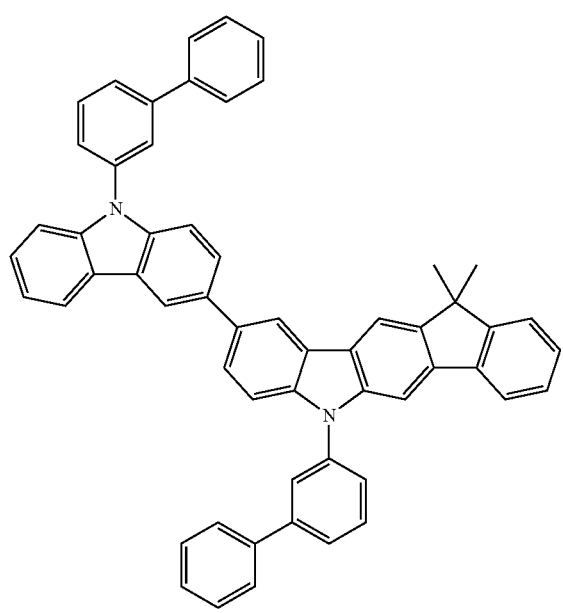
F-388
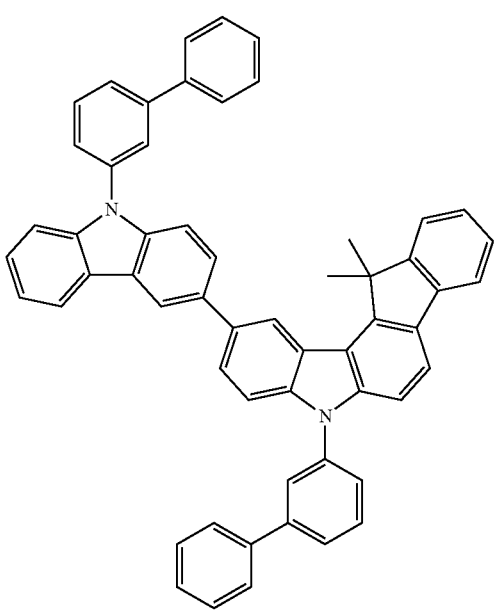

F-389
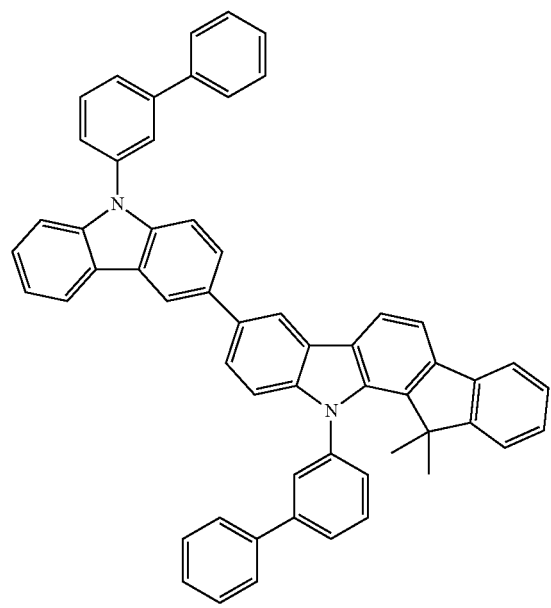
F-391
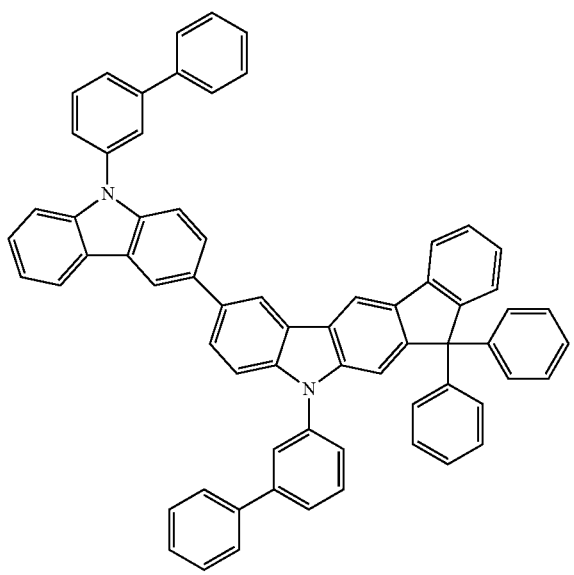
F-390
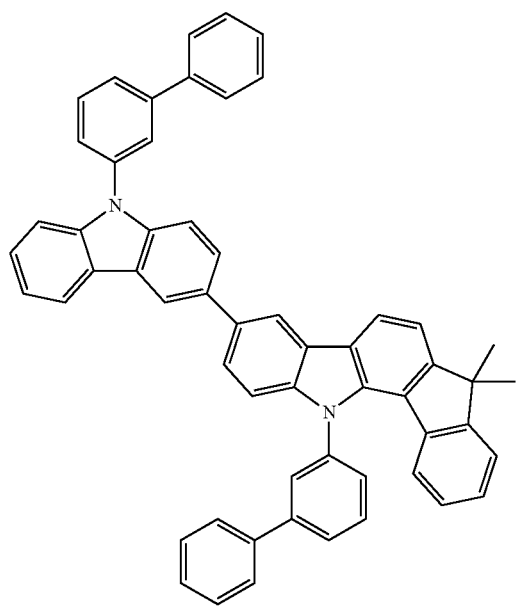
F-392
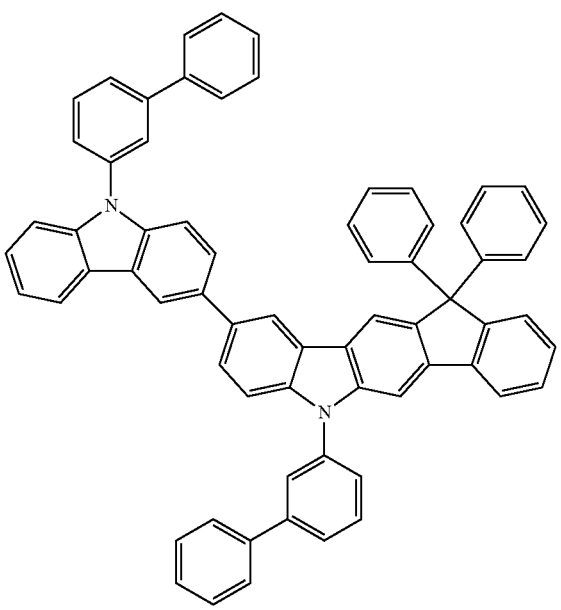

F-393
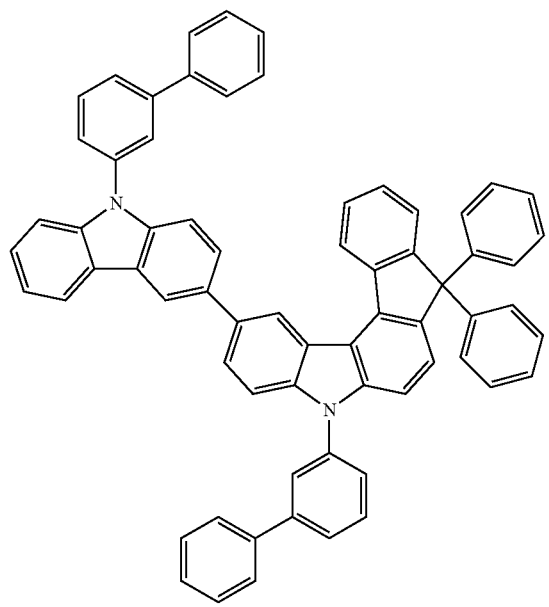
F-395
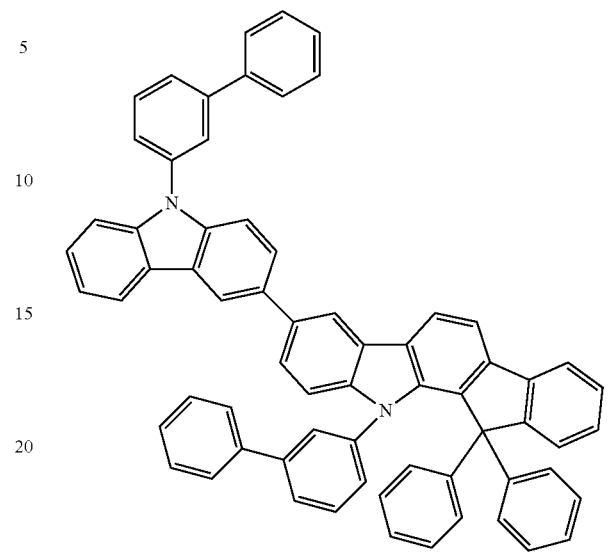
F-394
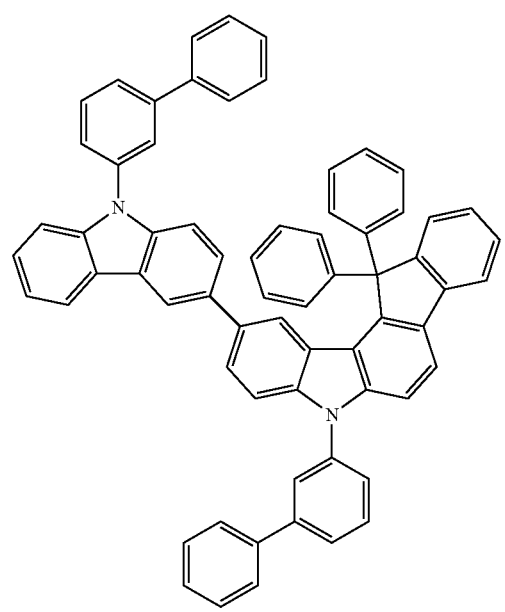
F-396
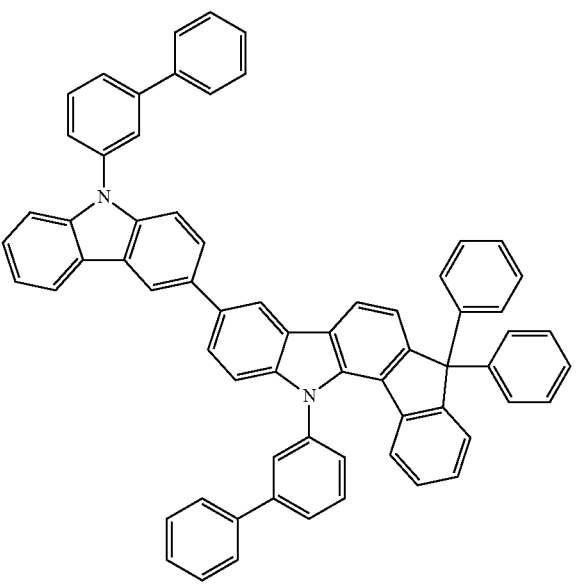

F-397
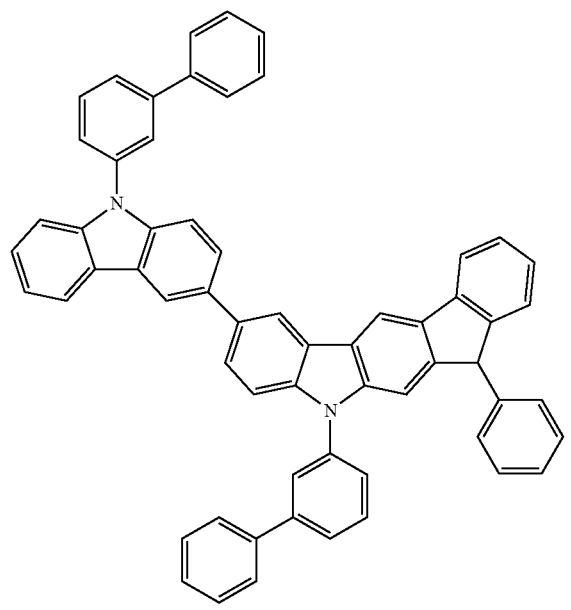
F-398
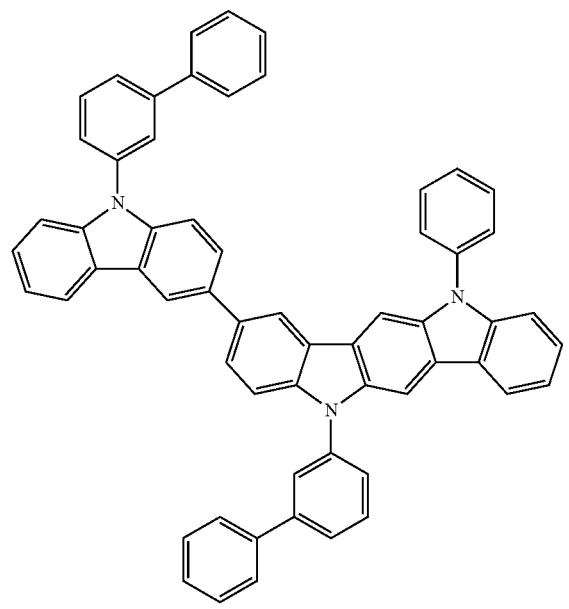
F-399
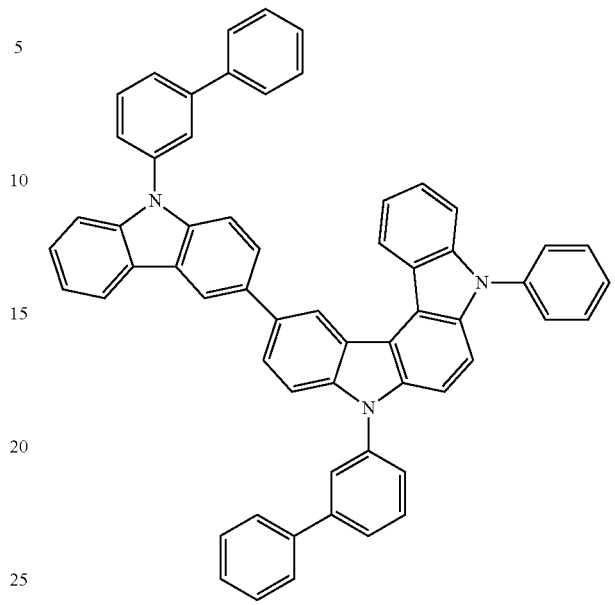
F-400
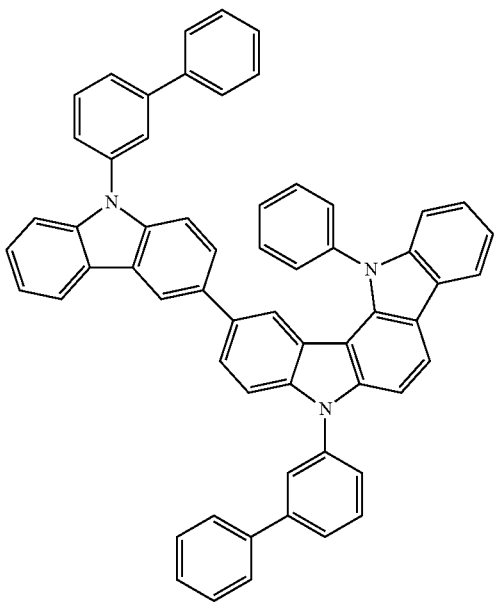

F-401
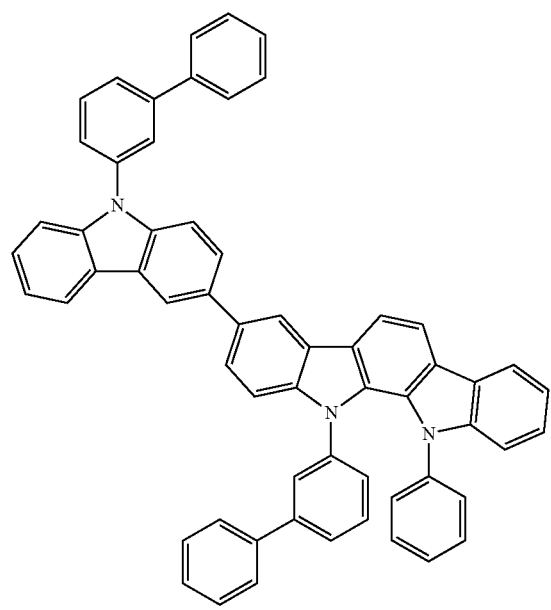
F-402
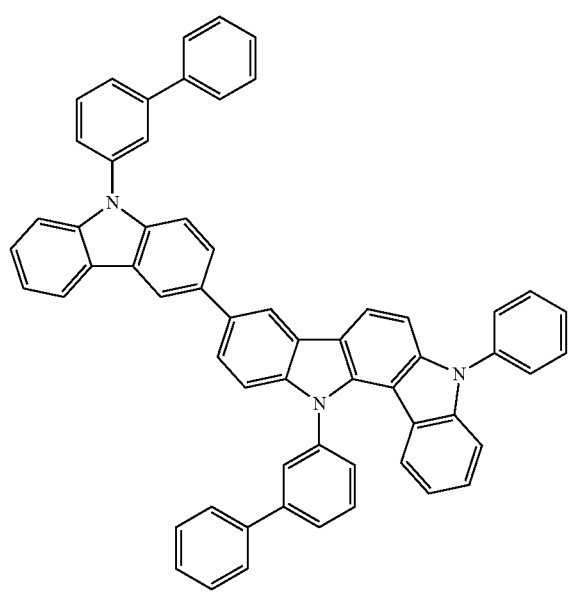
F-403
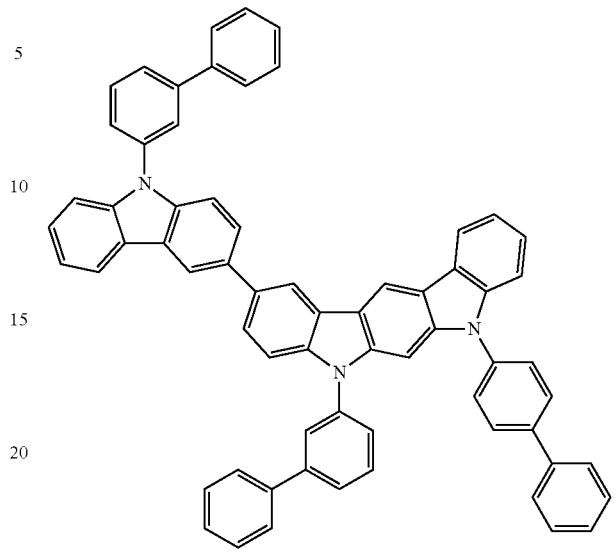
F-404
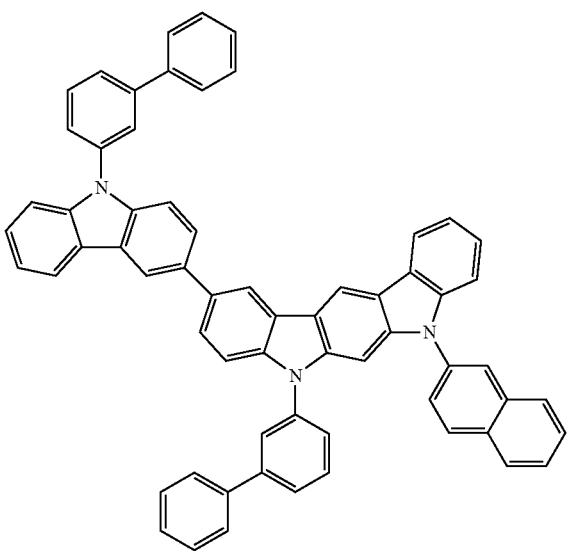

F-405
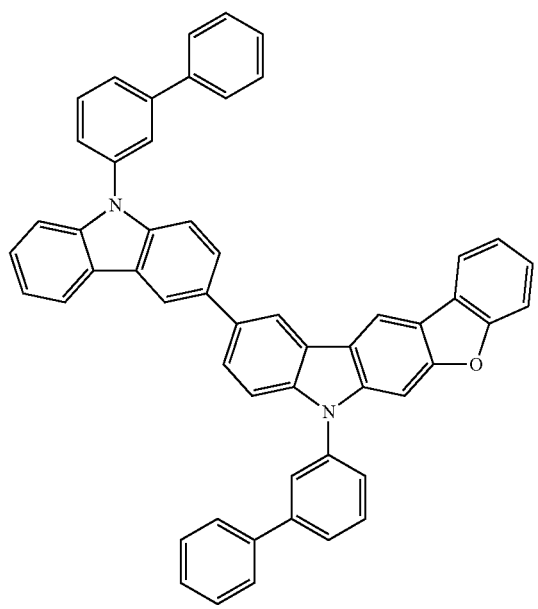
F-406
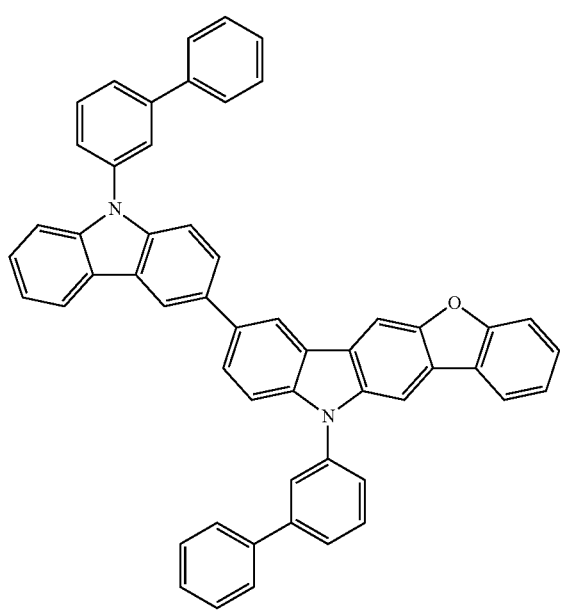
F-407
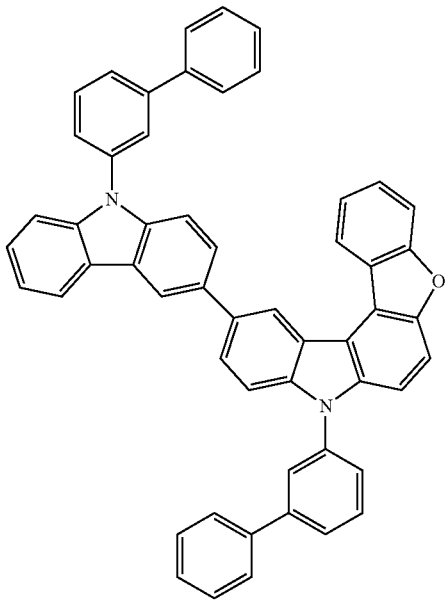
F-408
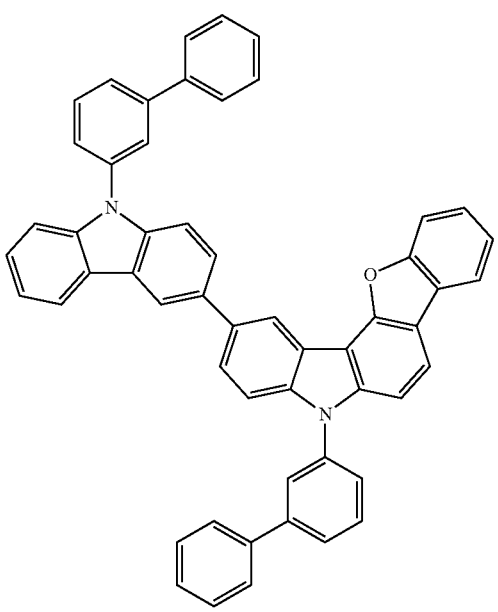

F-409
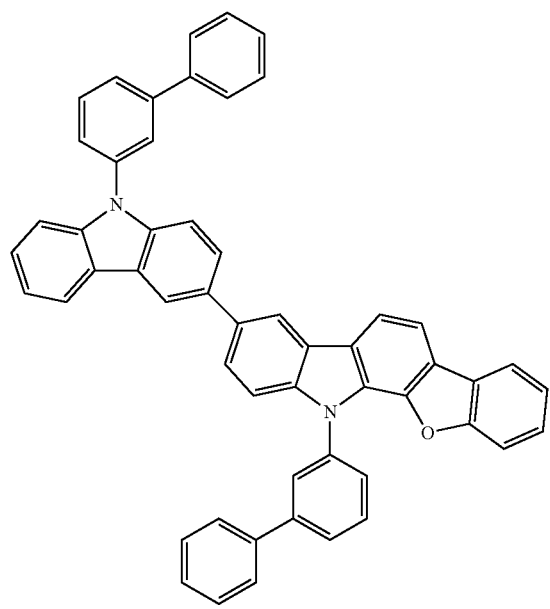
F-410
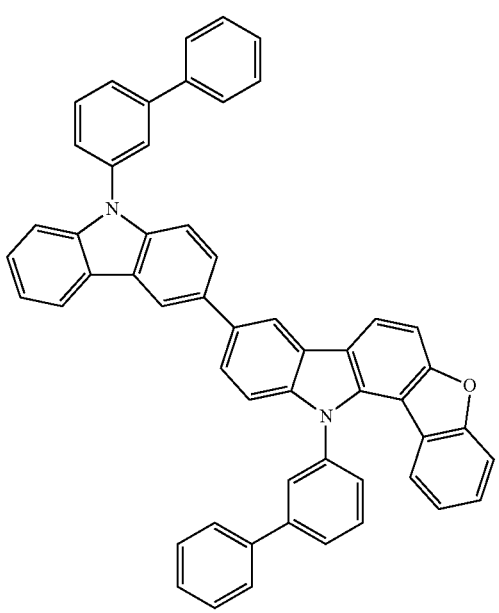
F-411
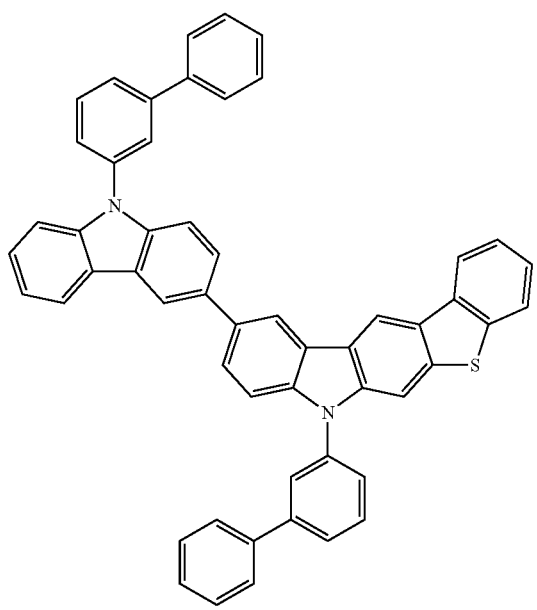
F-412
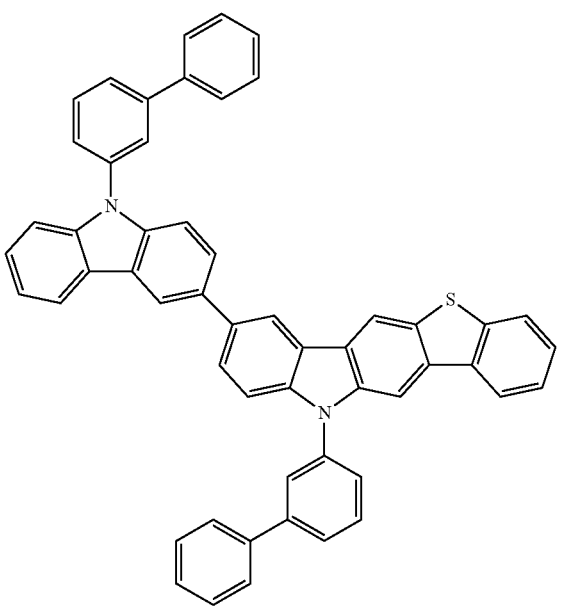

F-413
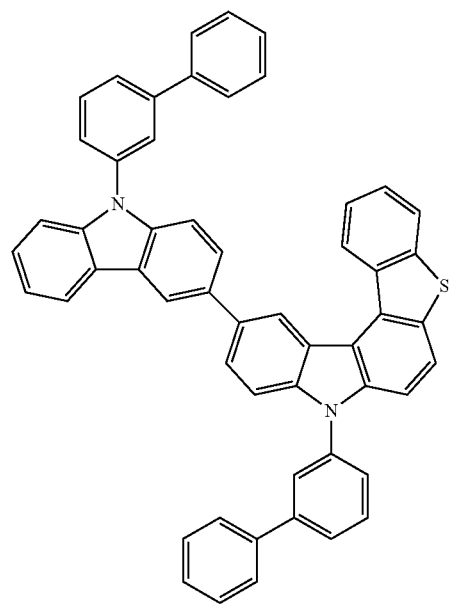
F-414
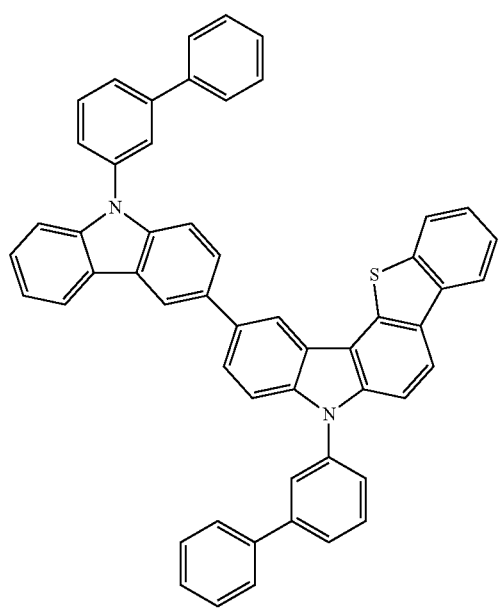
F-415
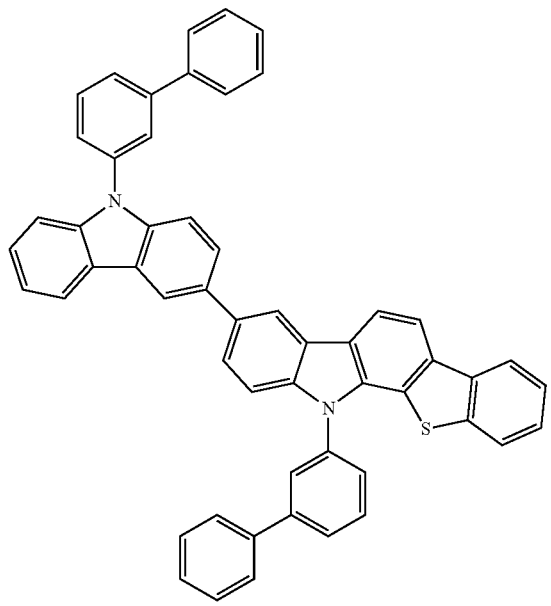
F-416
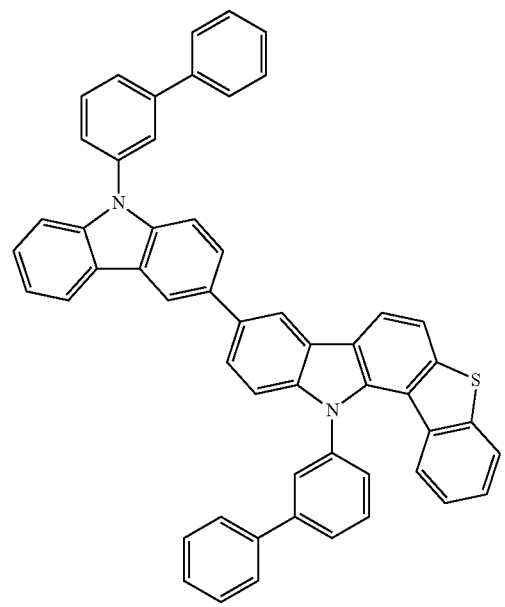

F-417
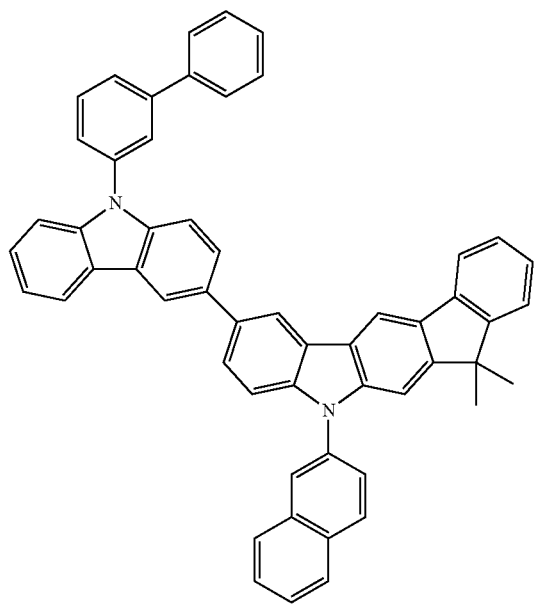
F-418
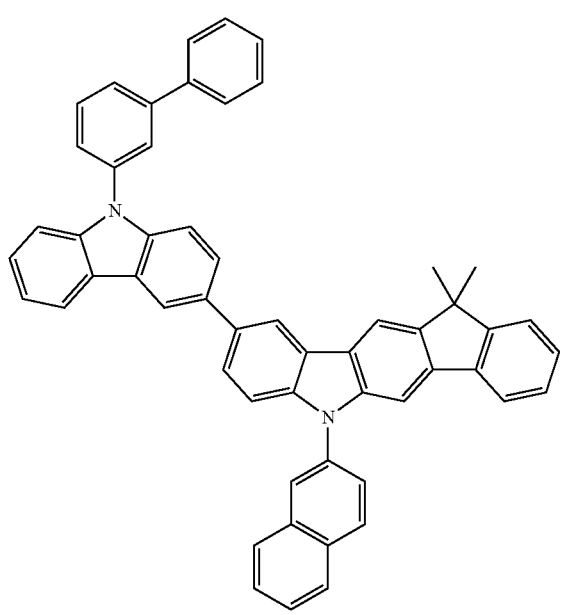
F-419
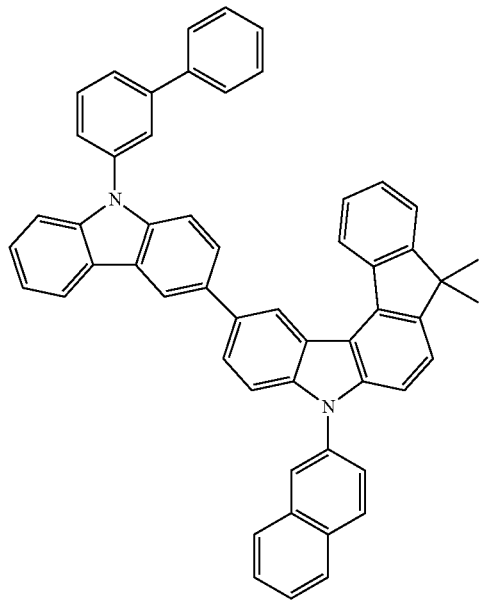
F-420
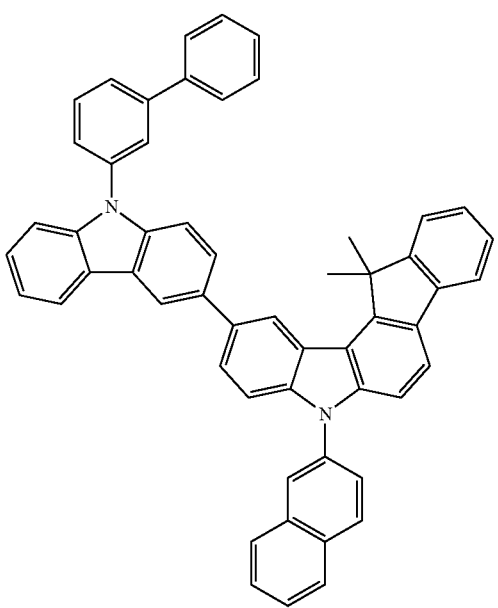

F-421
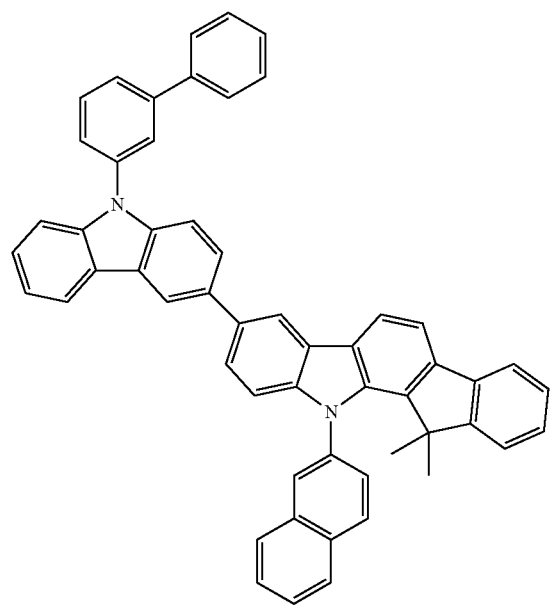
F-422
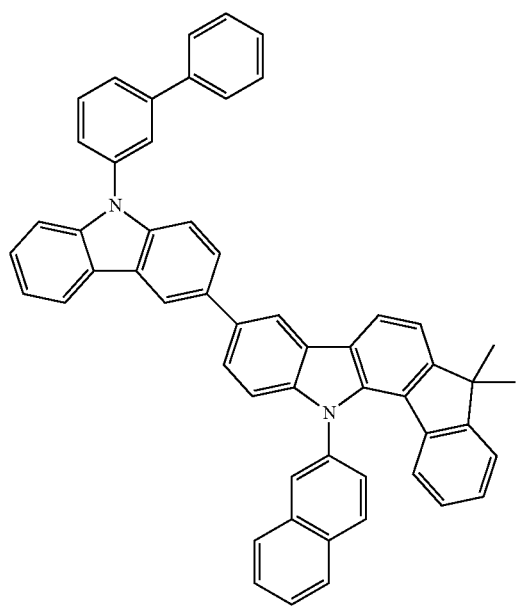
F-423
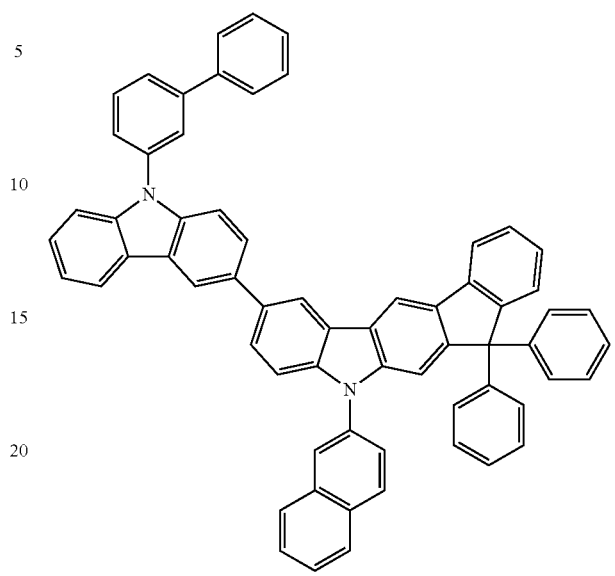
F-424
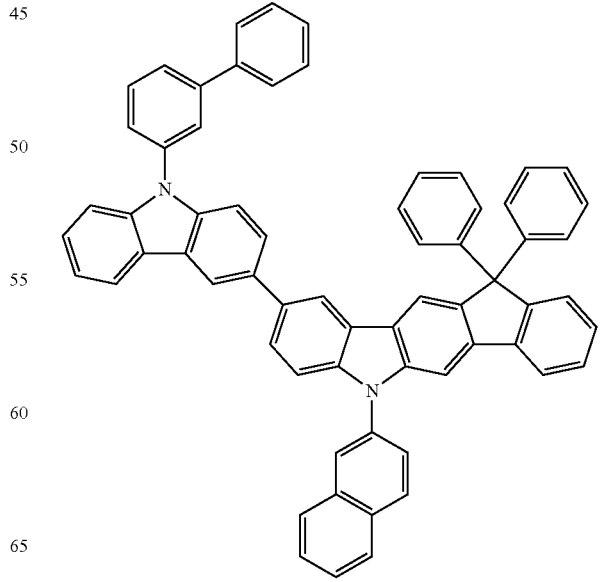

F-425
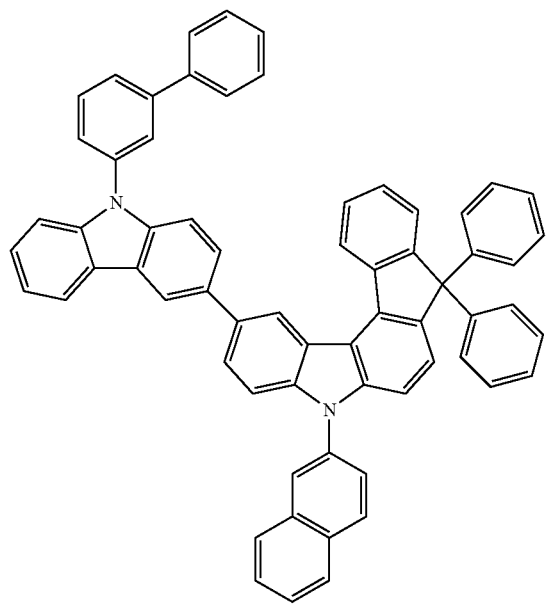
F-427
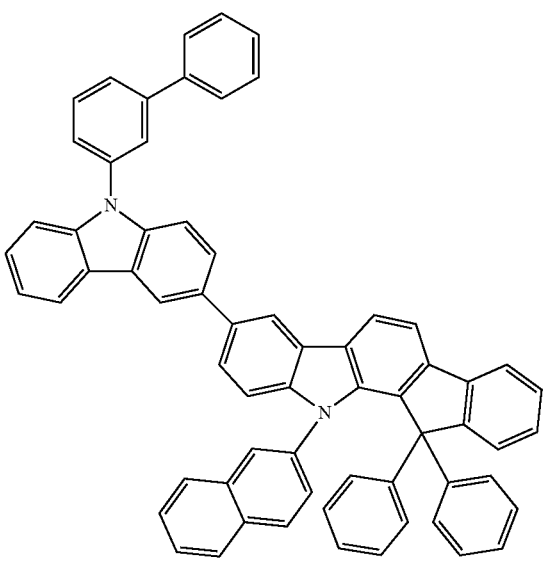
F-426
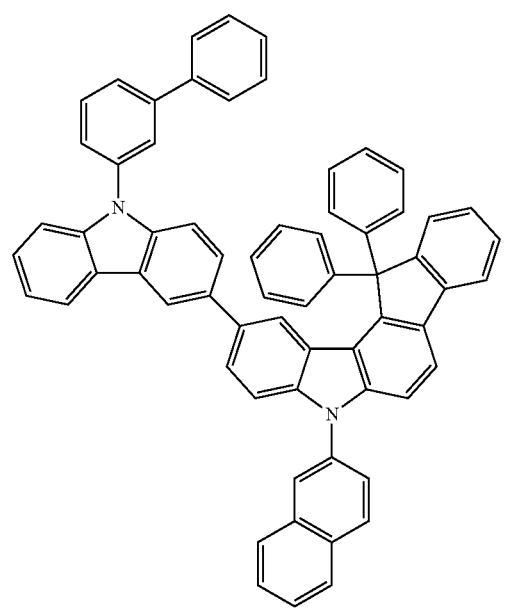
F-428

F-429
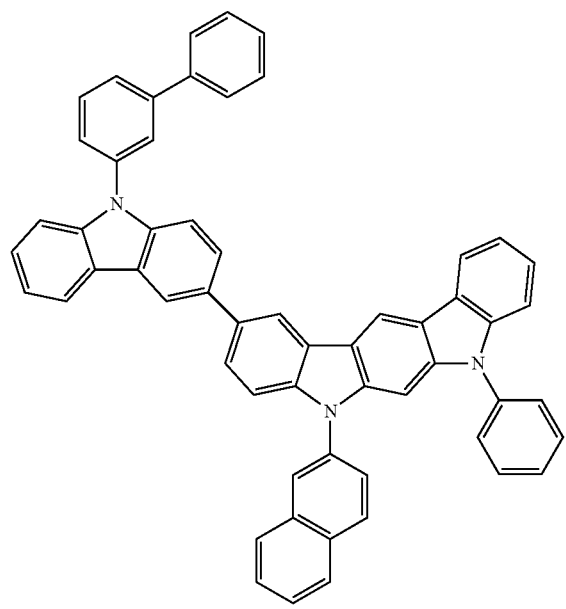
F-431
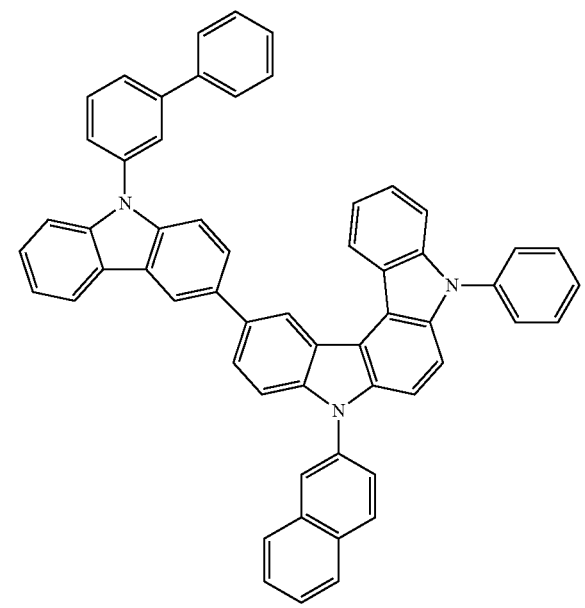
F-430
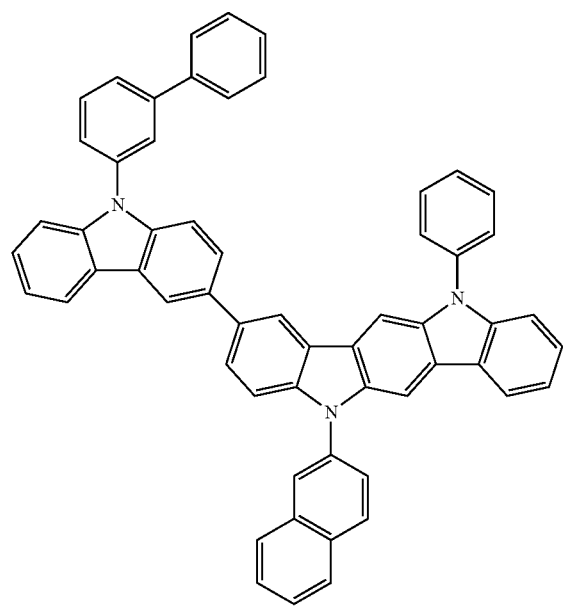
F-432
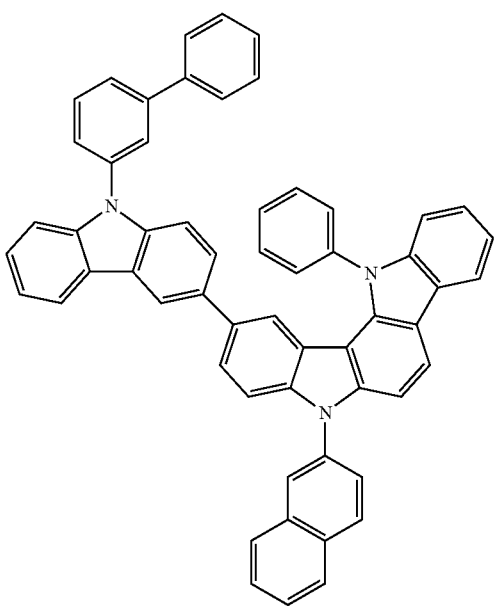

F-401
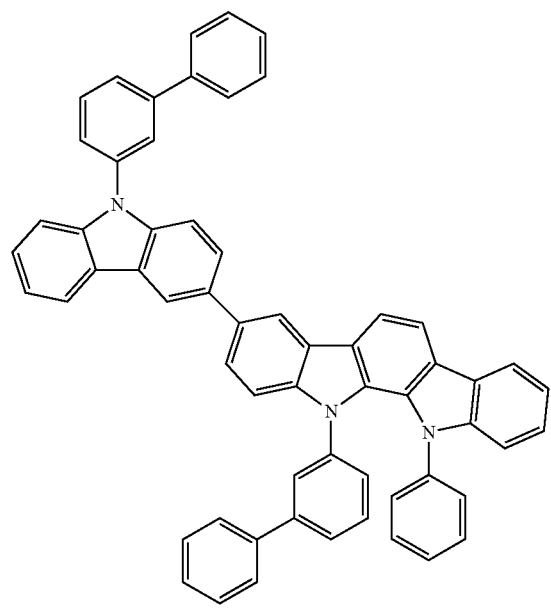
F-402
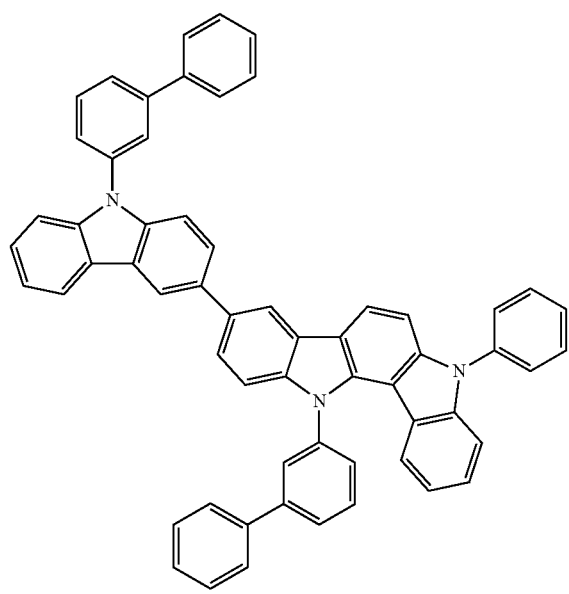
F-403
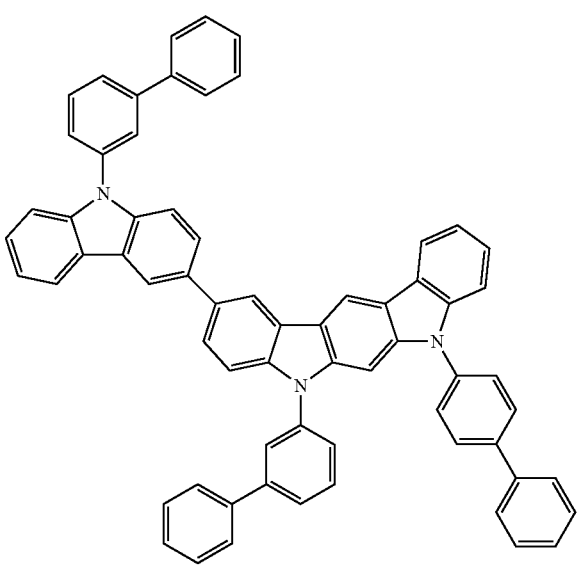
F-404
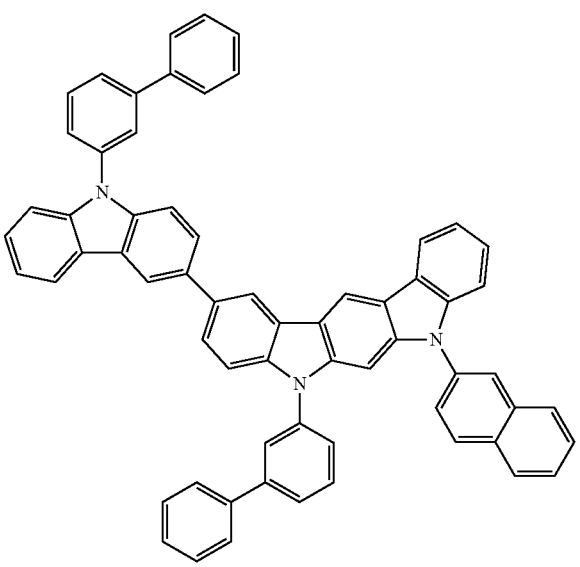

F-405
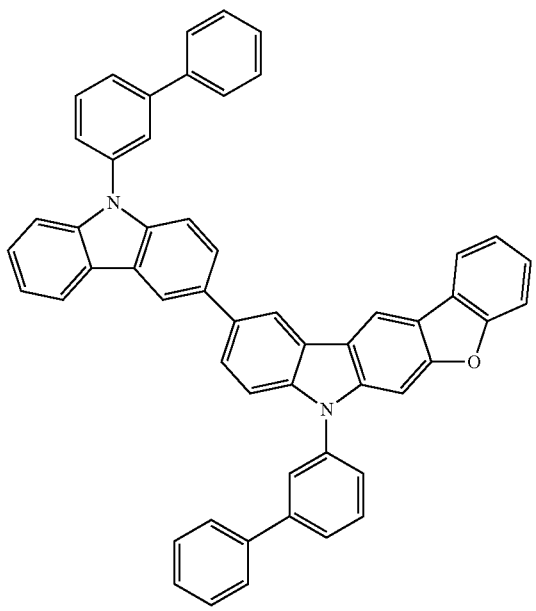
F-406
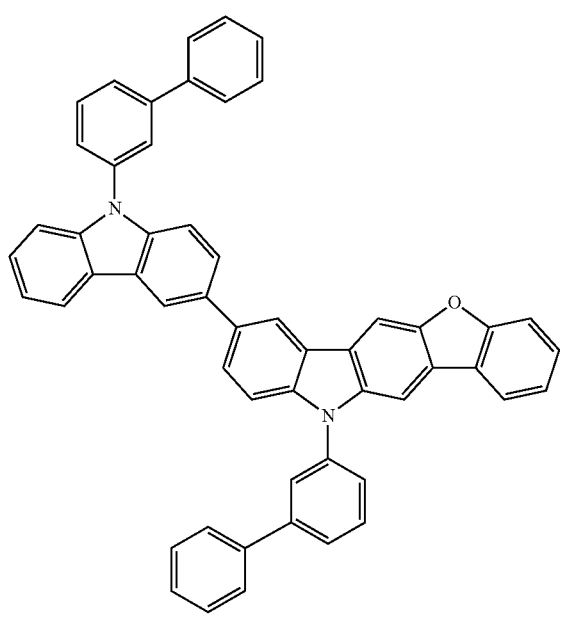
F-407
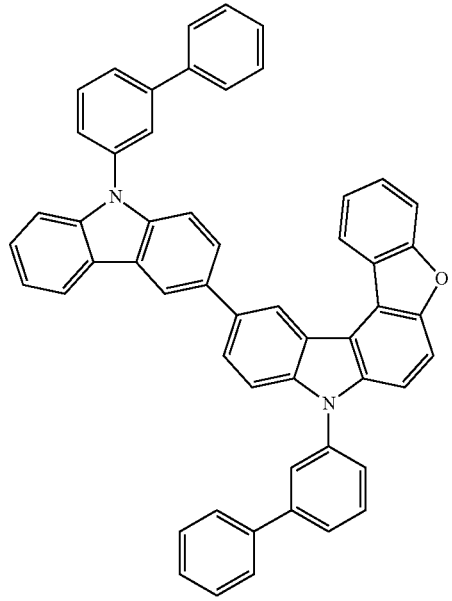
F-408
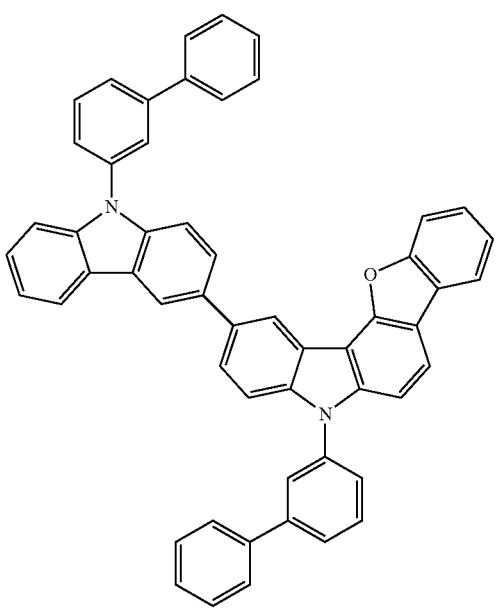

F-409
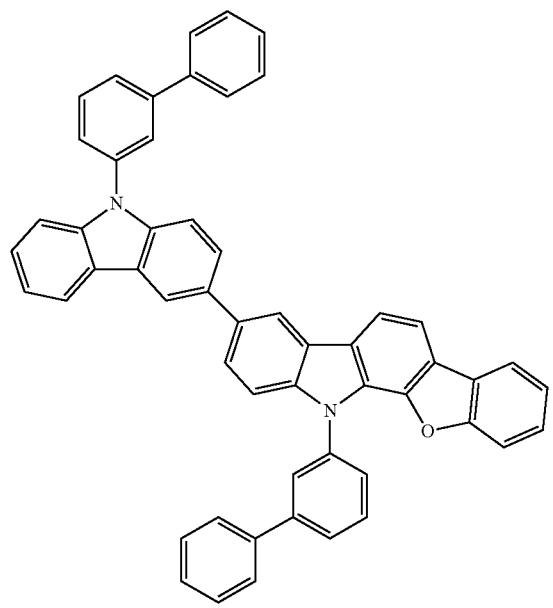
F-411
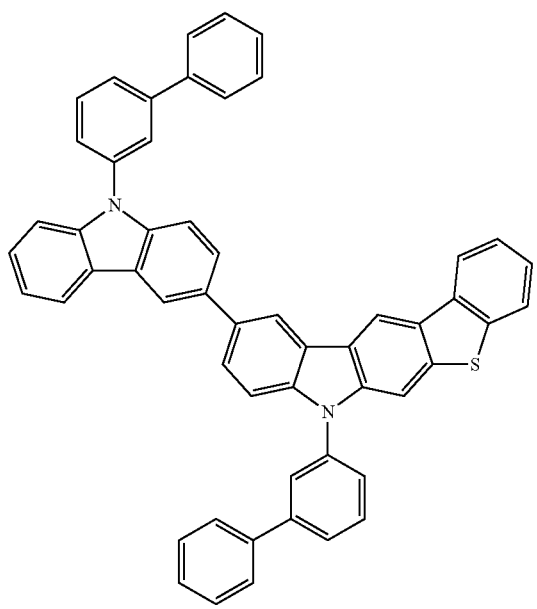
F-410
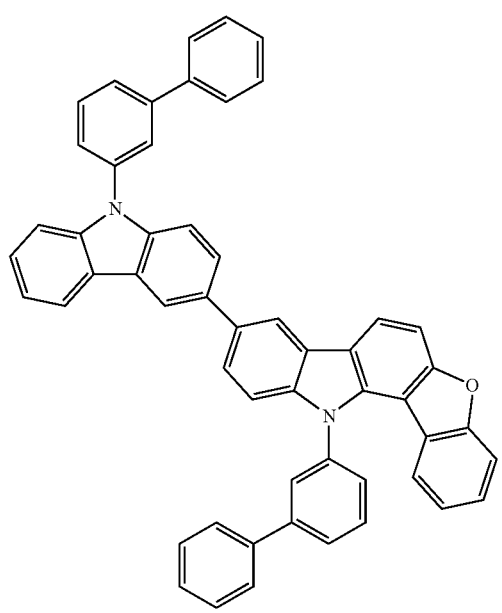
F-412

-continued
F-413
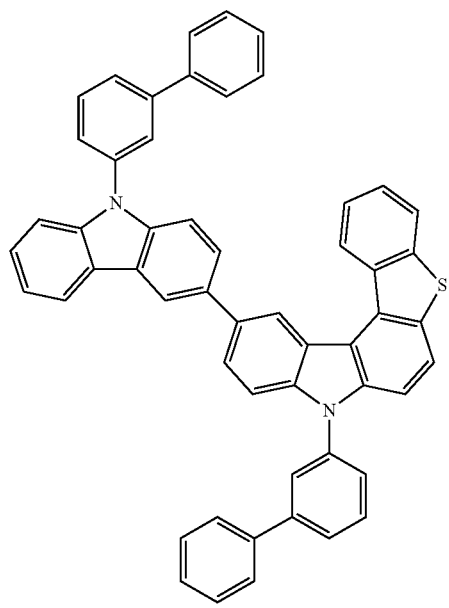
F-415
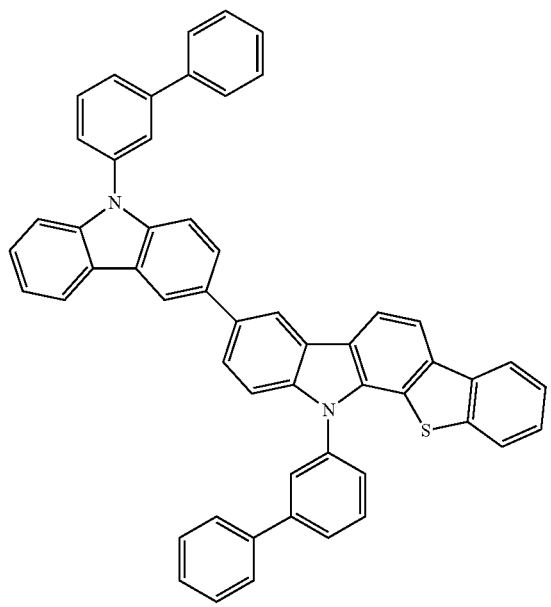
F-414
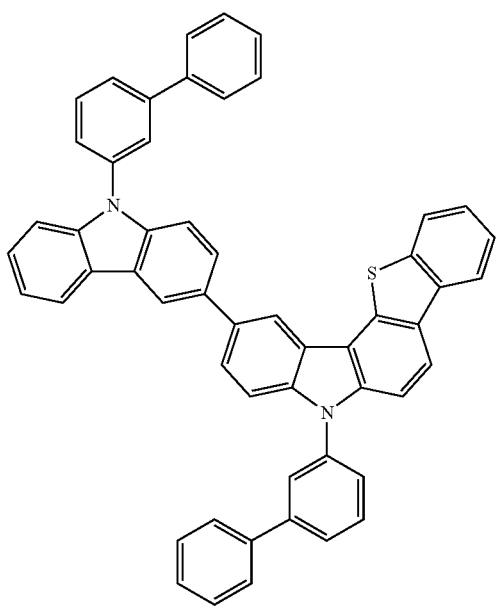
F-416
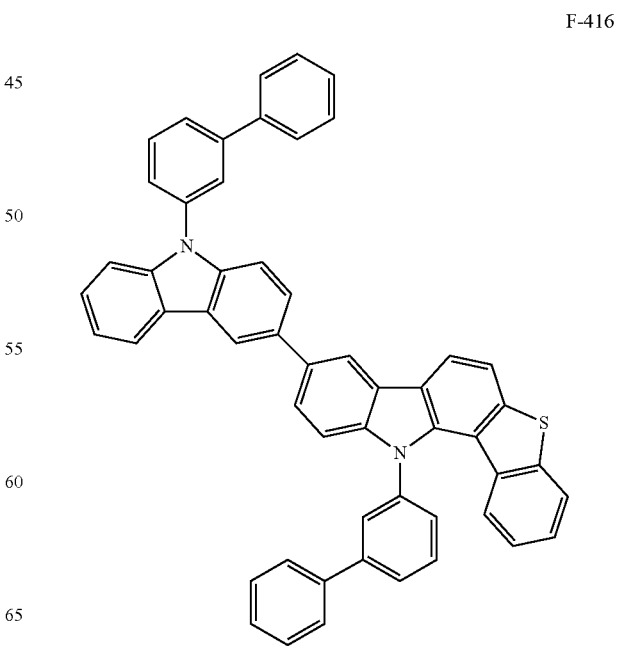

F-449
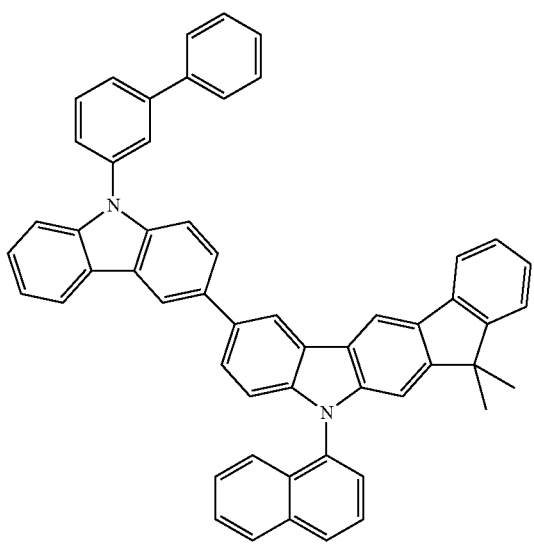
F-450
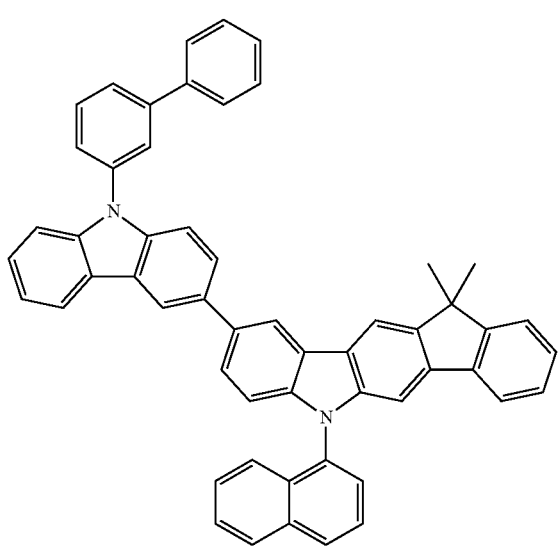
F-451
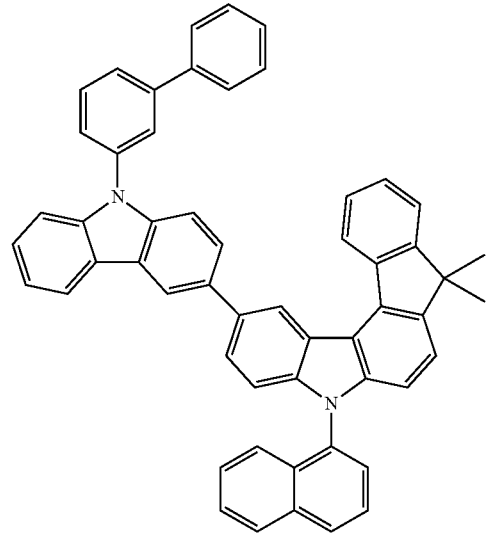
F-452
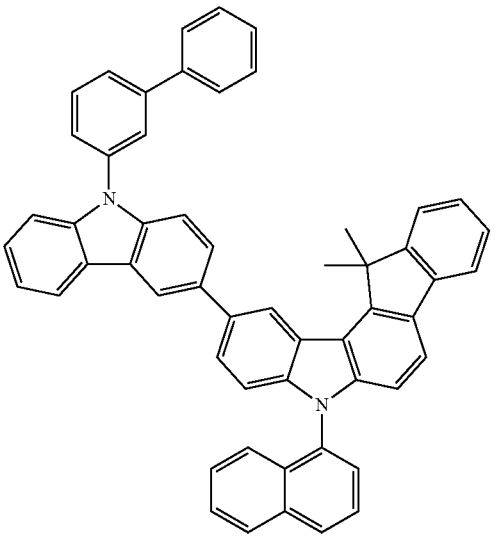
F-453
F-454
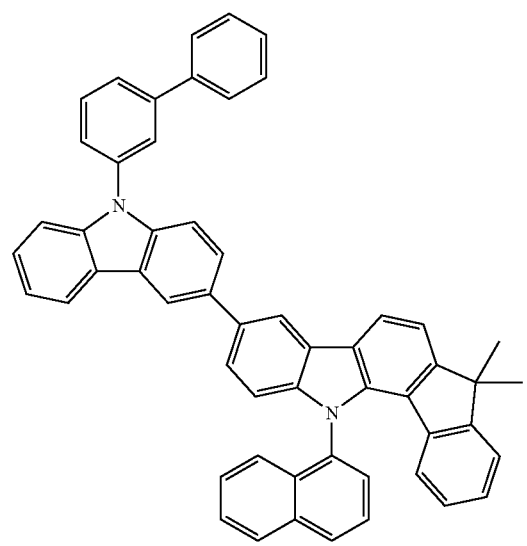

-continued
F-455
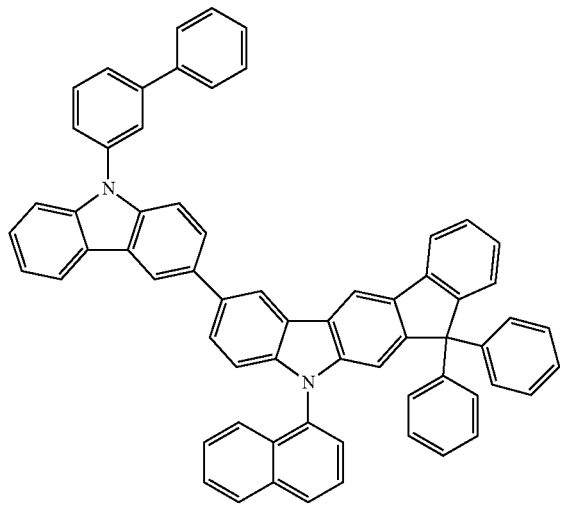
F-456
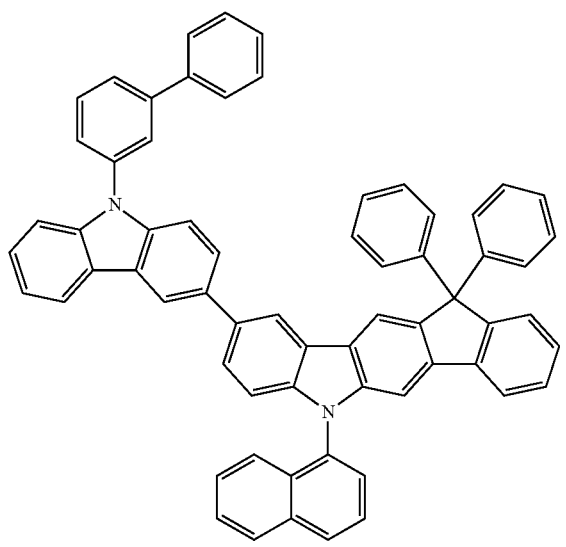
F-457
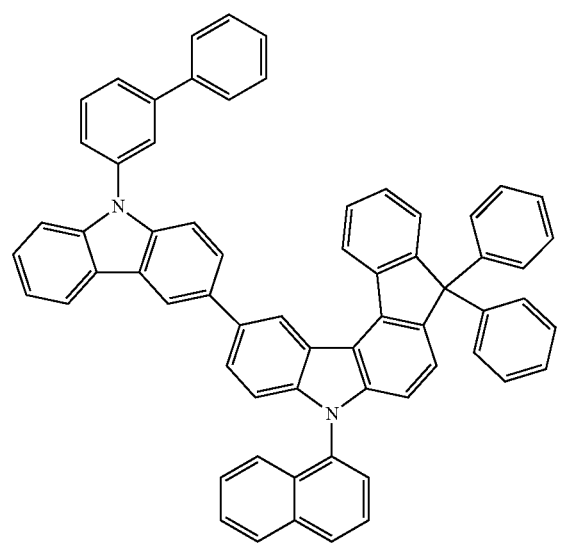
-continued
F-458
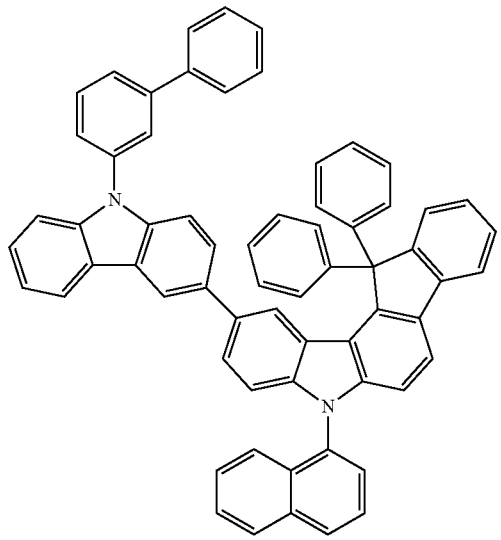
F-459
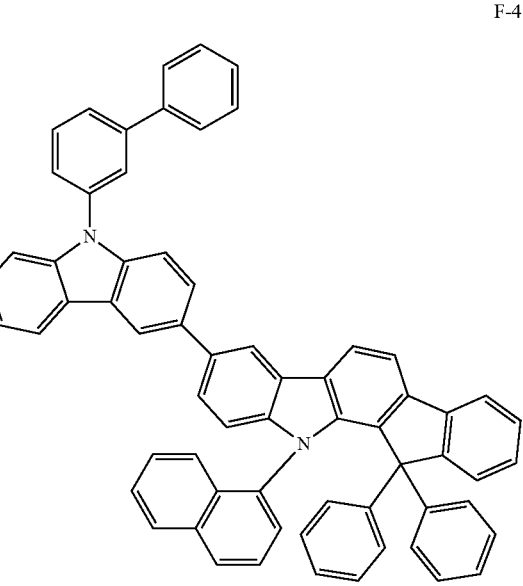
F-460
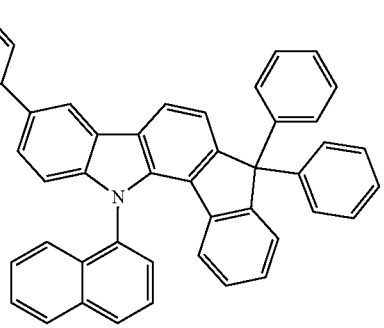

F-461
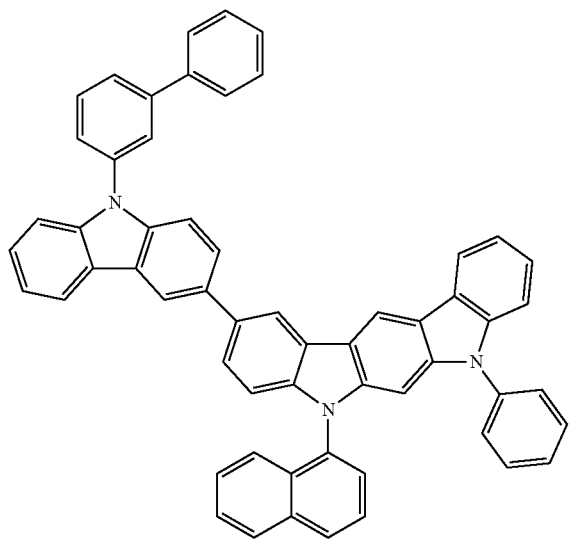
F-462
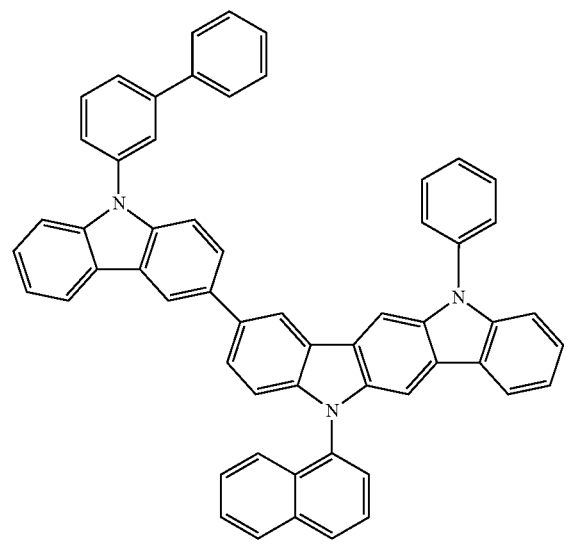
F-463
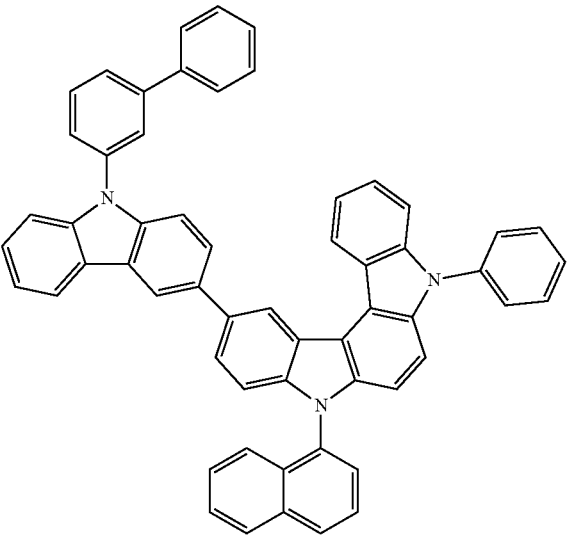
F-464
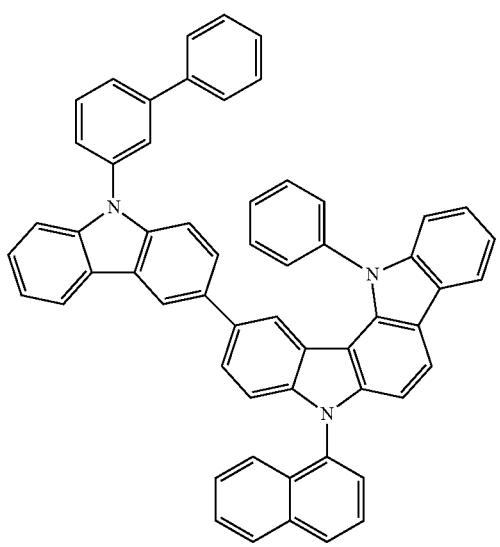

F-465
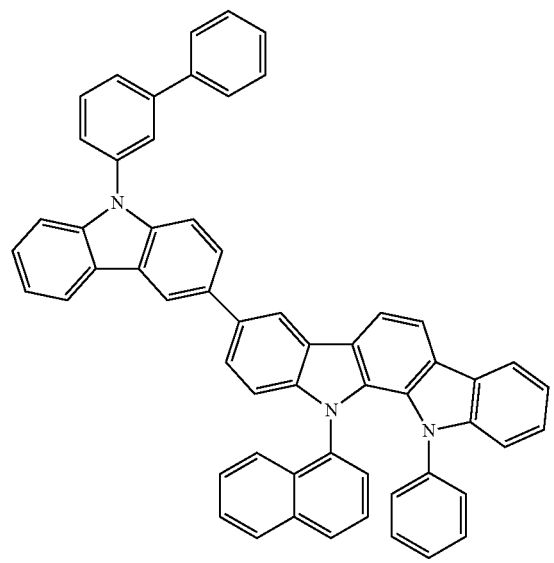
F-466
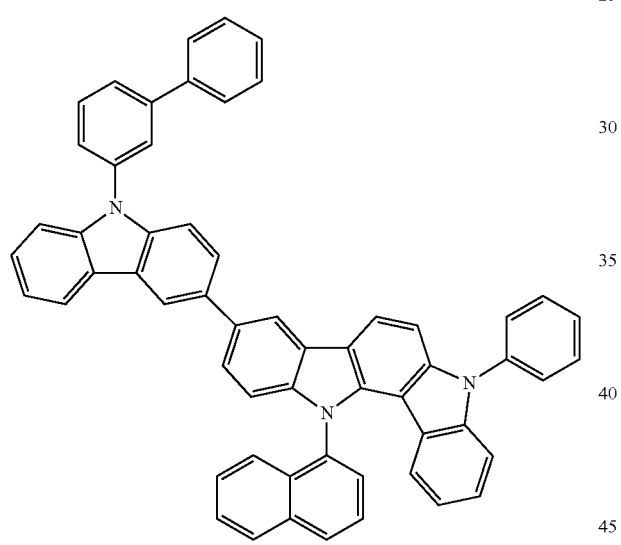
F-467
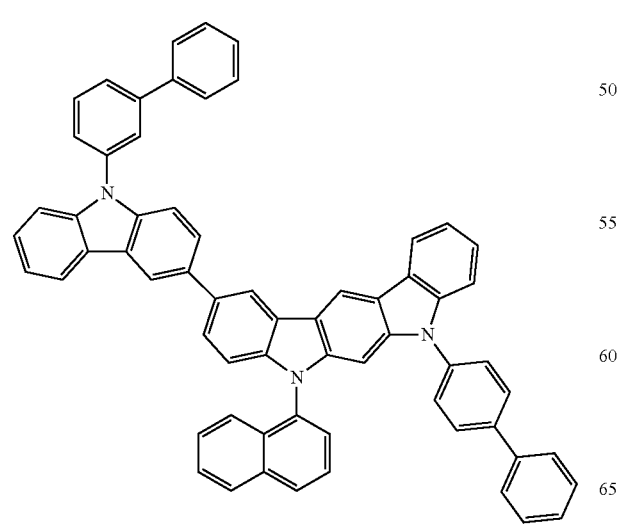
F-468
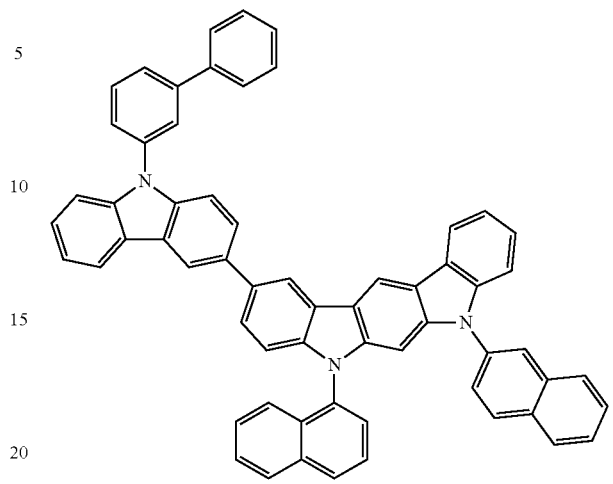
F-469
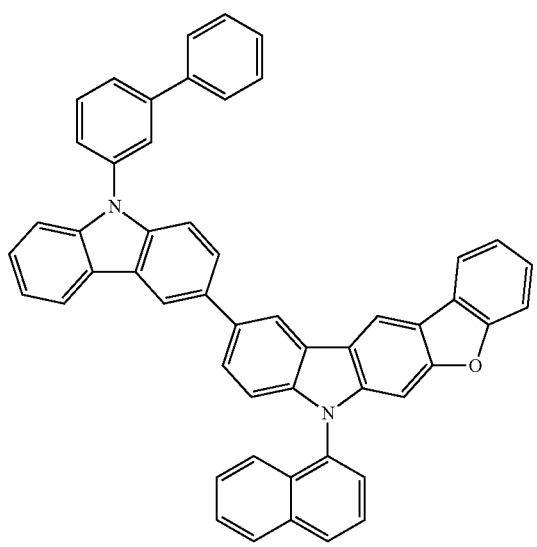
F-470
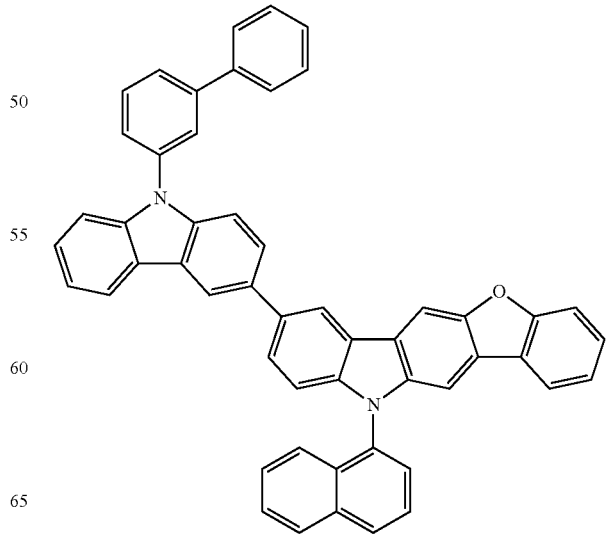

F-471
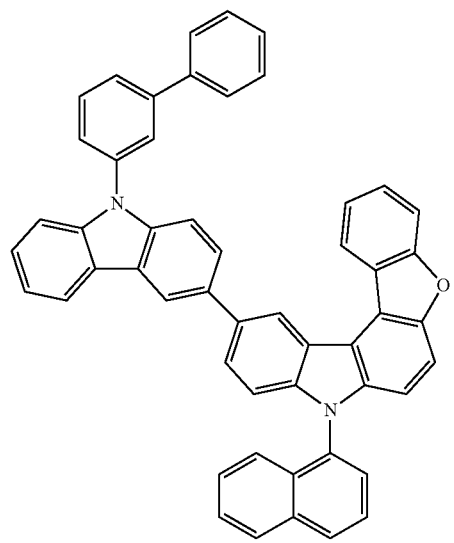
F-473
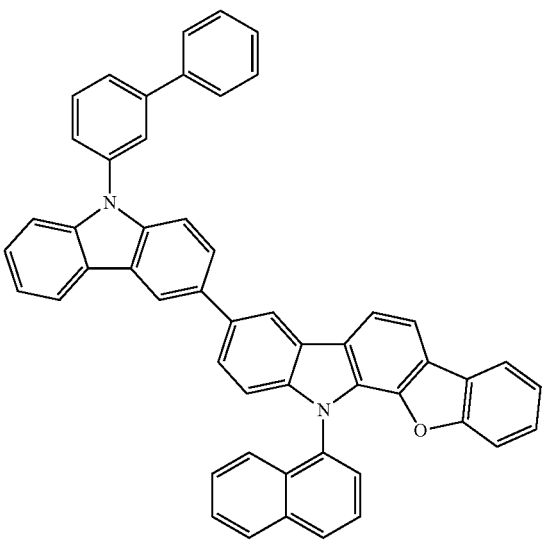
F-472
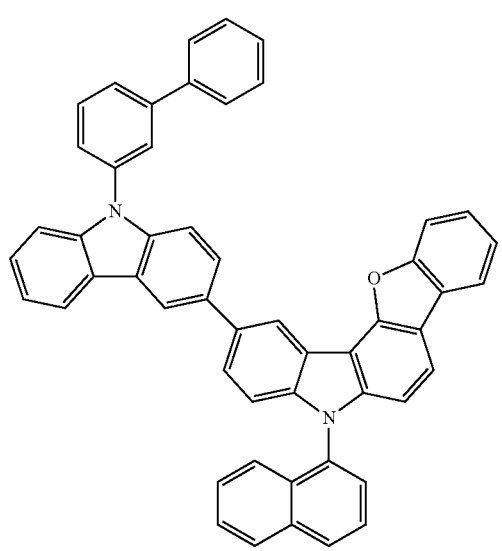
F-474
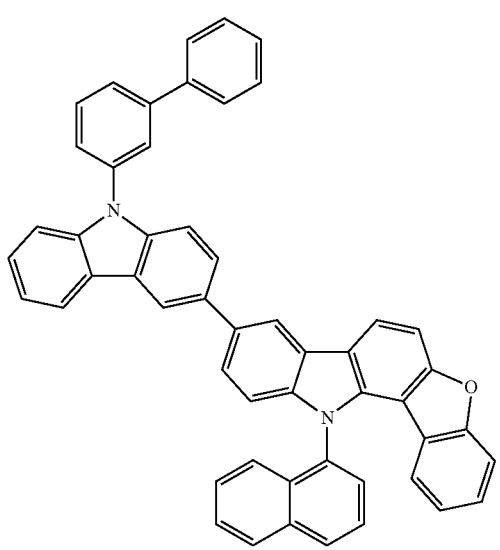

F-475
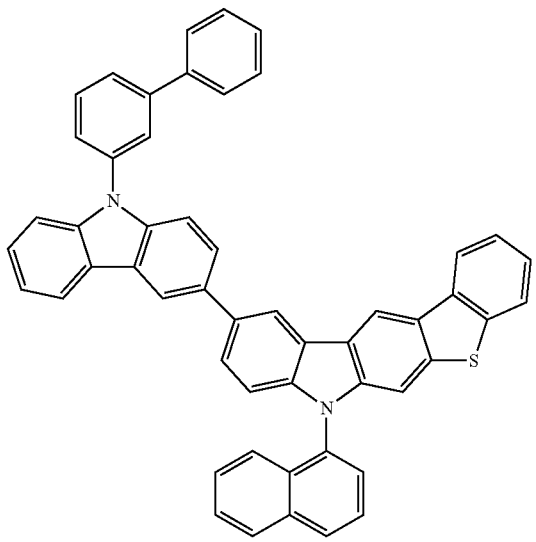
F-476
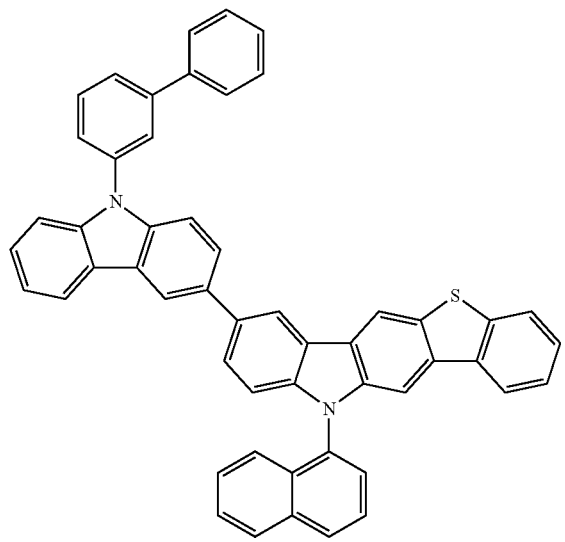
F-477
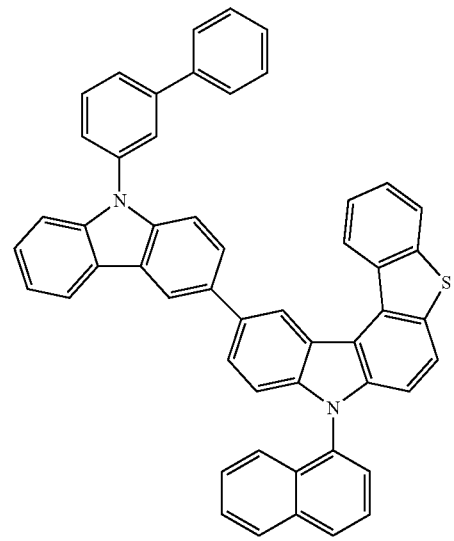
F-478
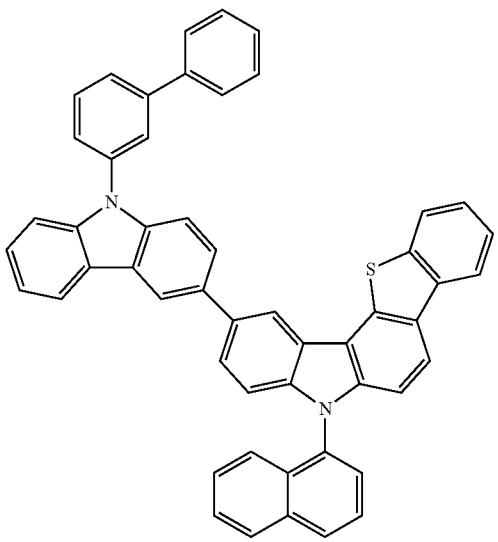
F-479
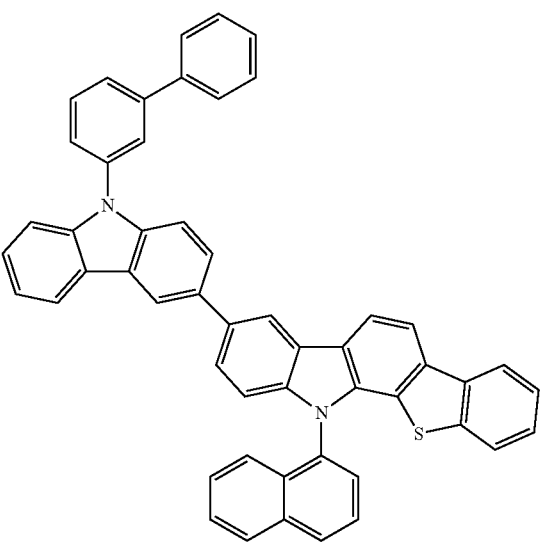
F-480
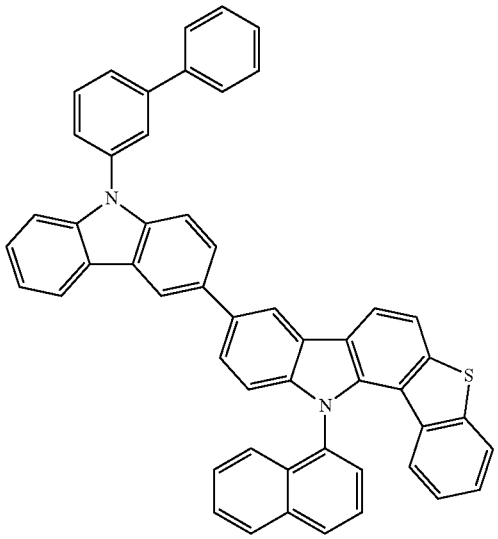

F-481
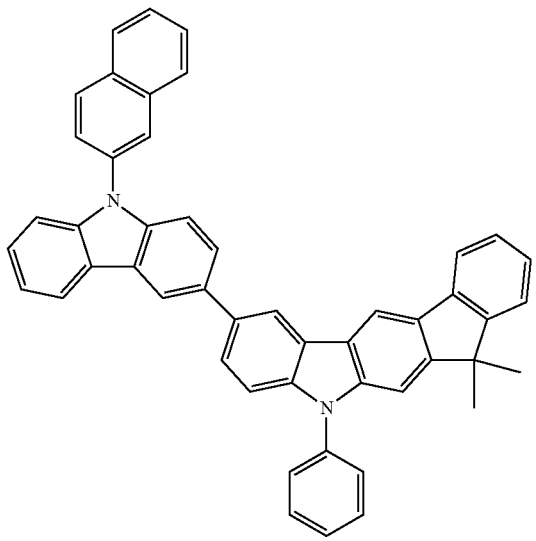
F-483
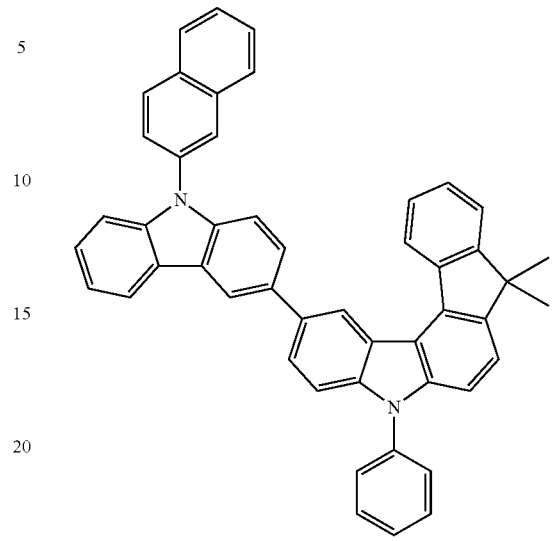
F-482
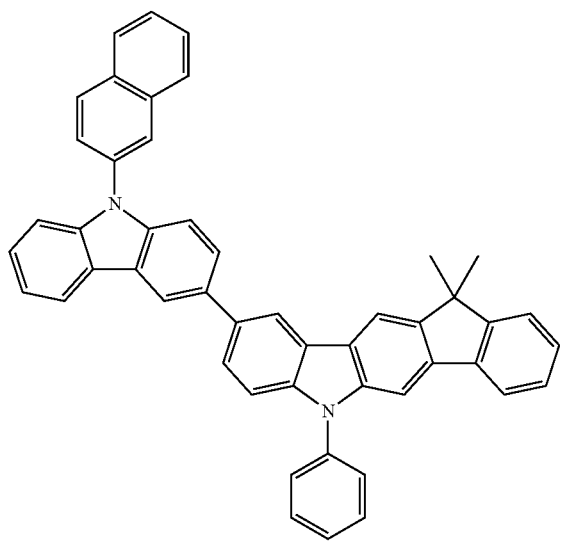
F-484
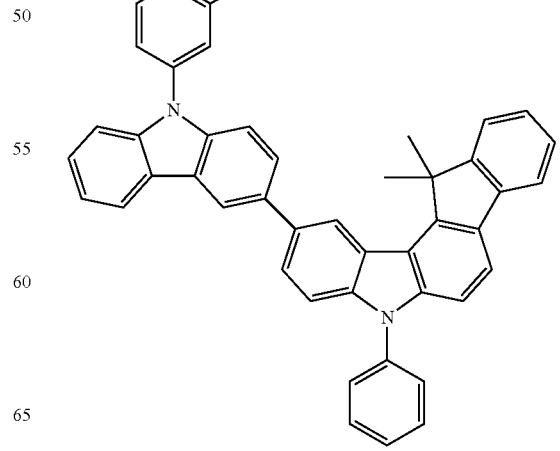

F-485
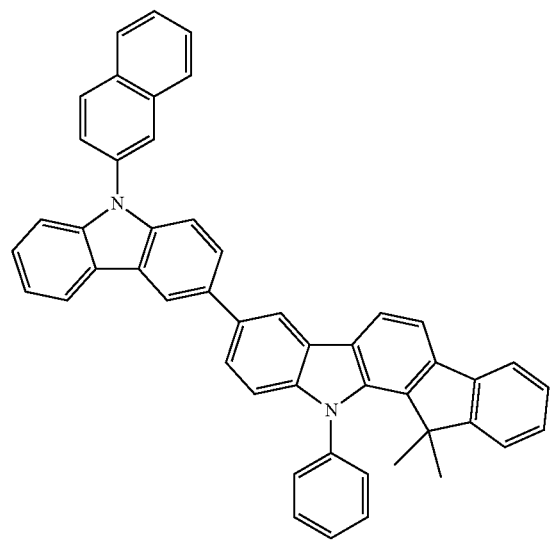
F-486
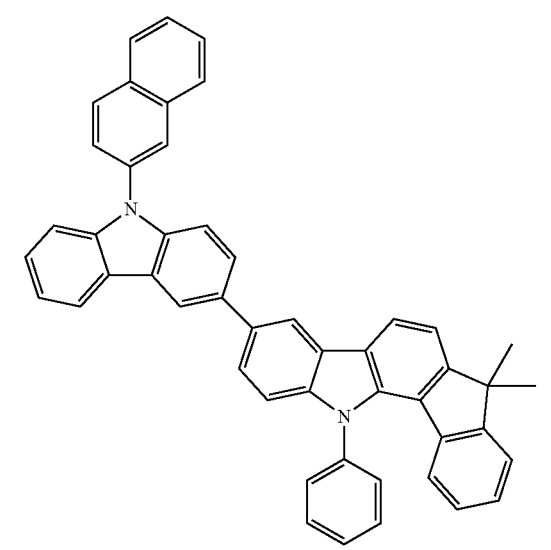
F-487
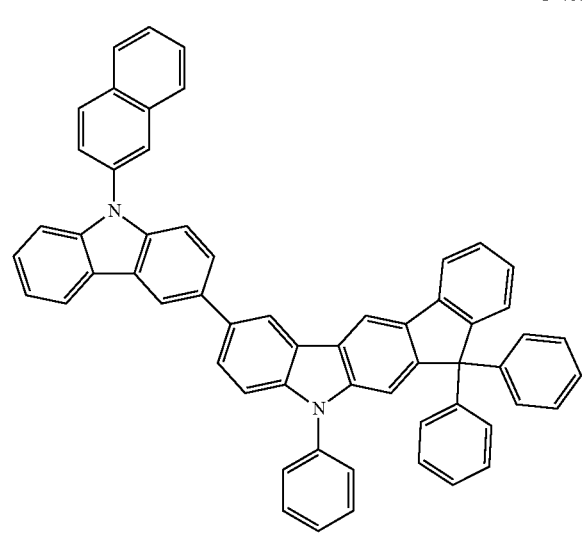
F-488
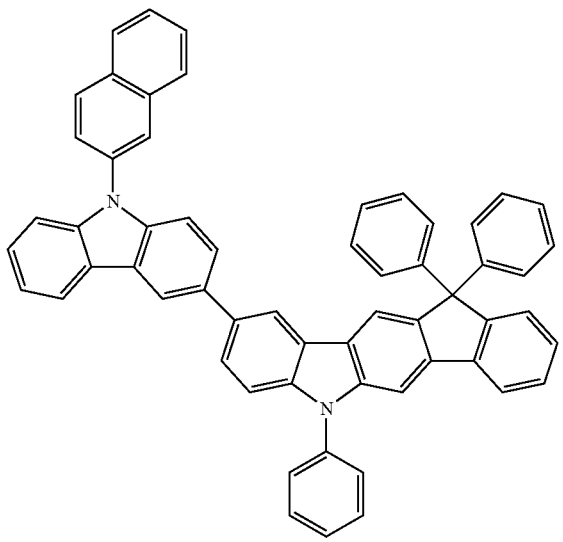
F-489
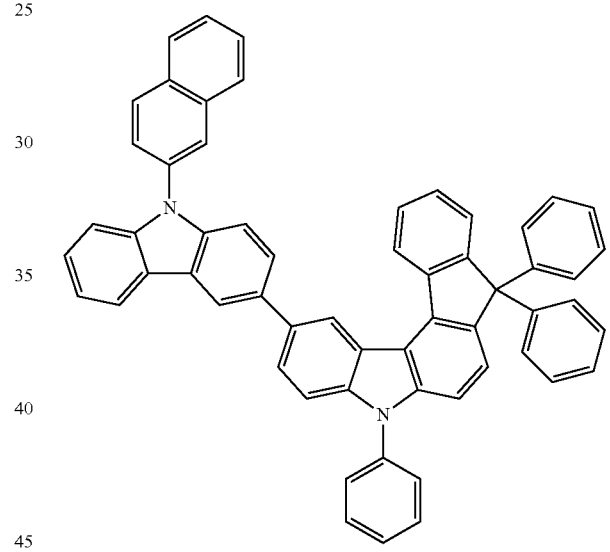
F-490
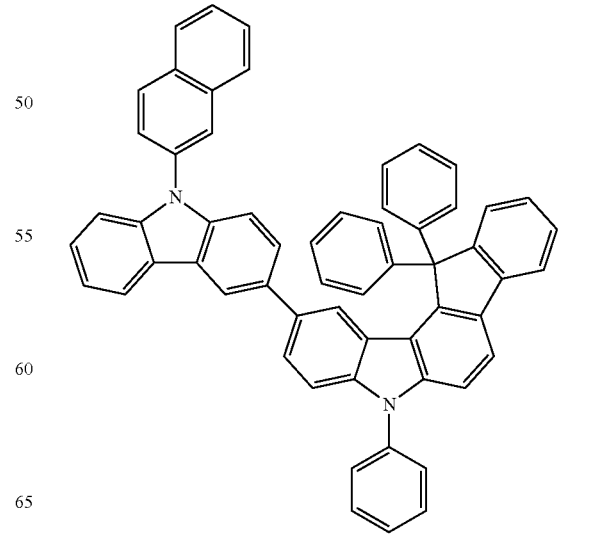

F-491
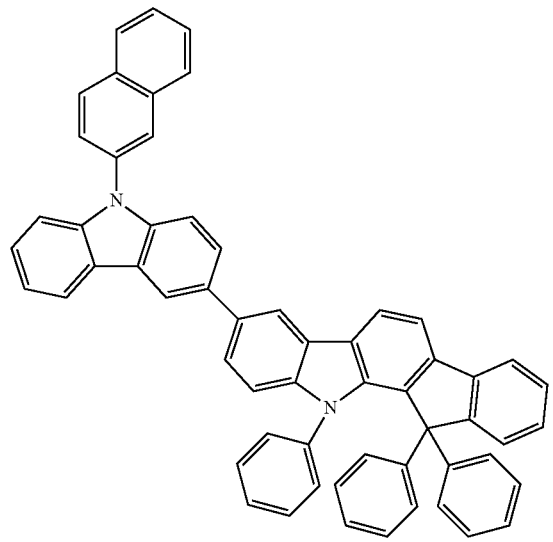
F-492
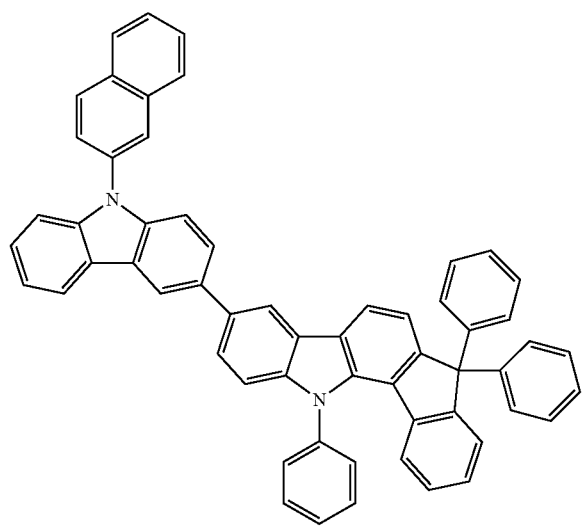
F-493
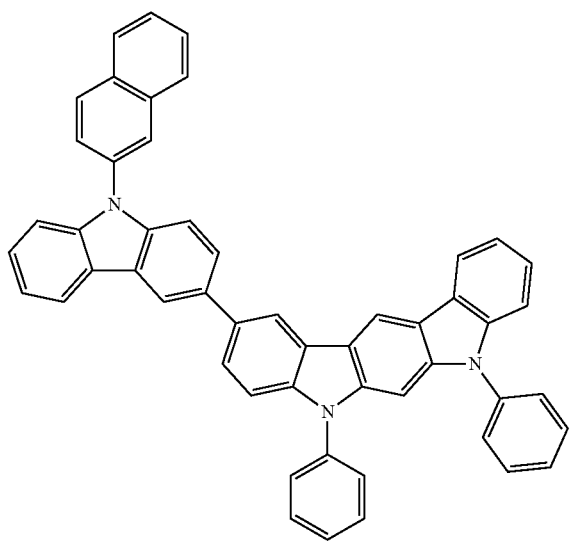
F-494
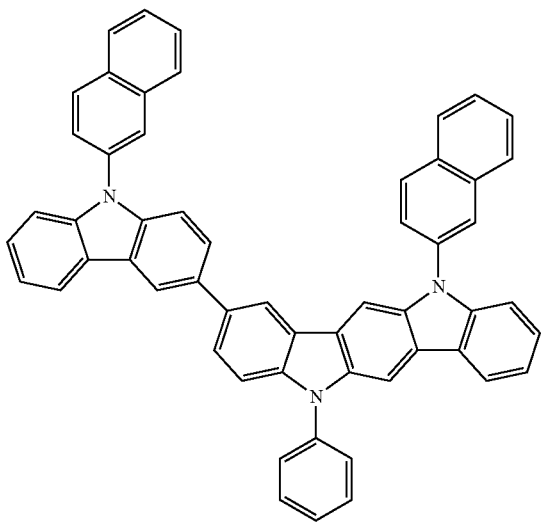
F-495
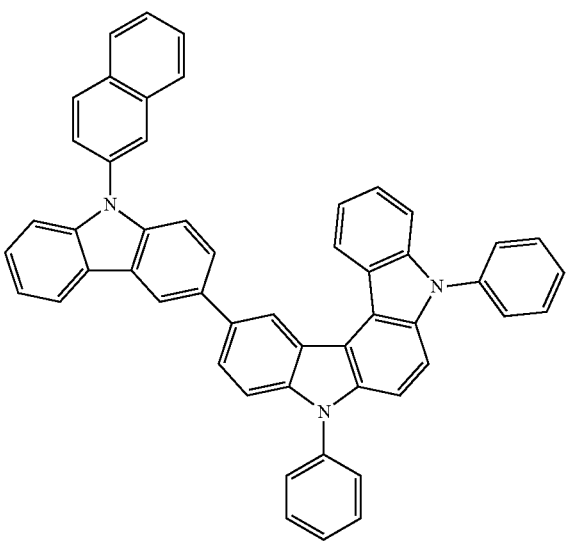
F-496
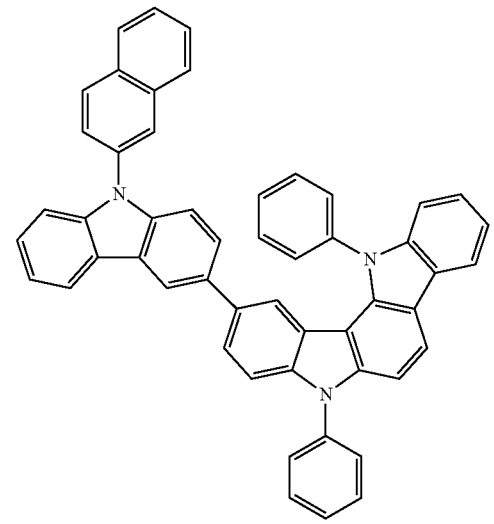

F-497
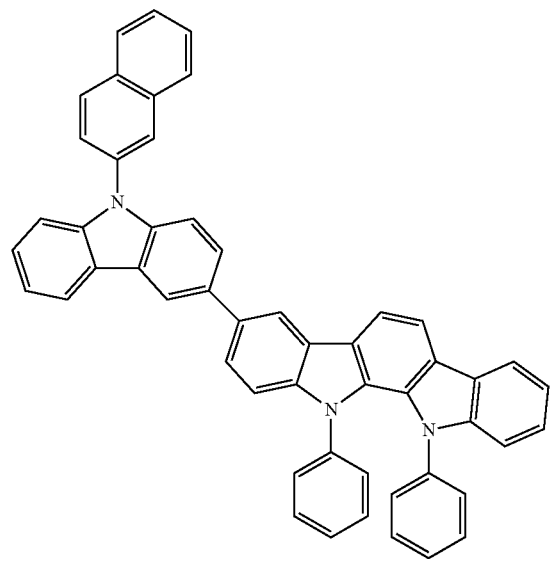
F-500
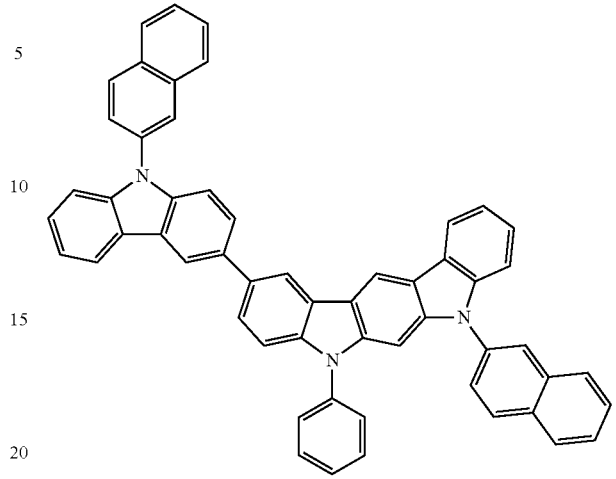
F-498
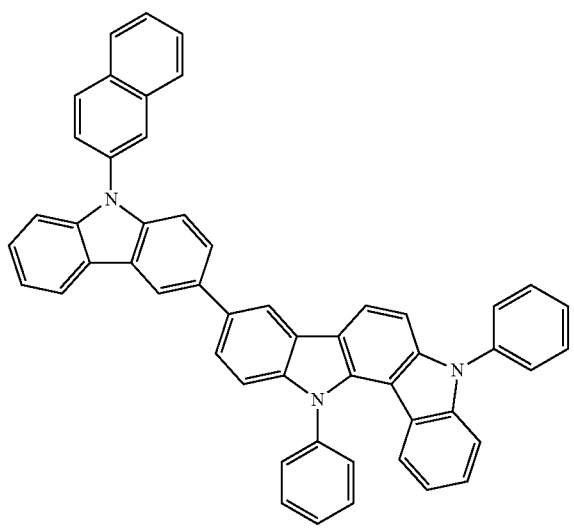
F-501
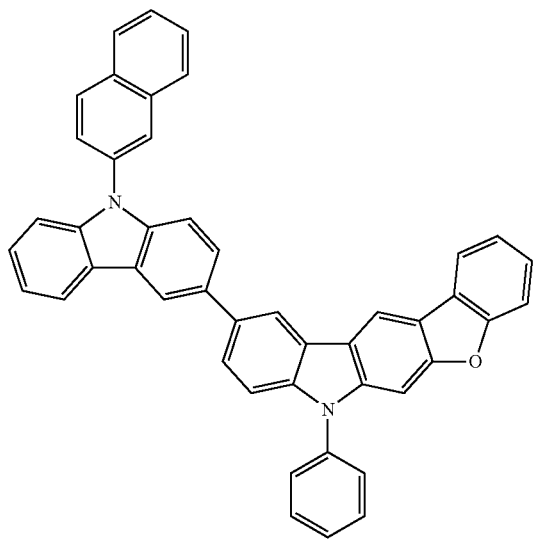
F-499
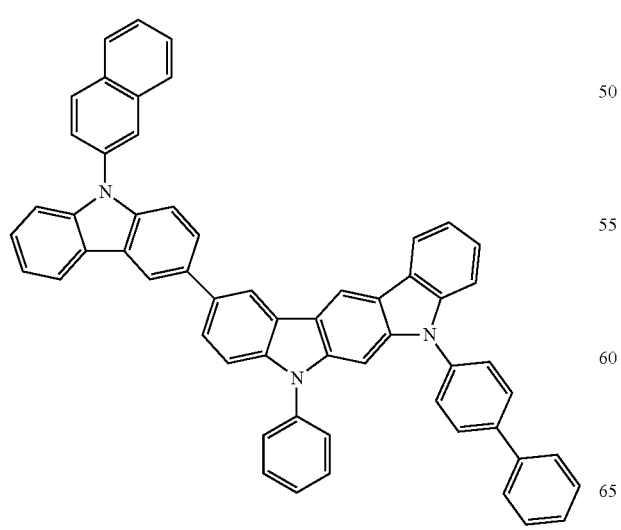
F-502
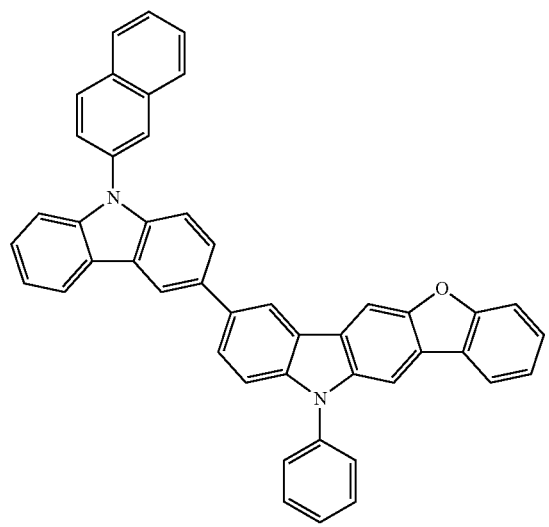

F-503
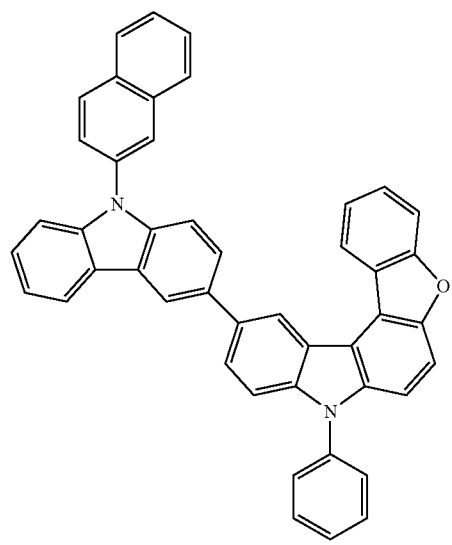
F-504
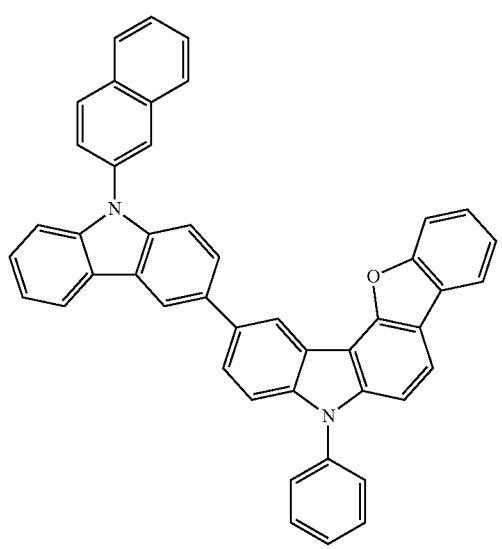
F-505
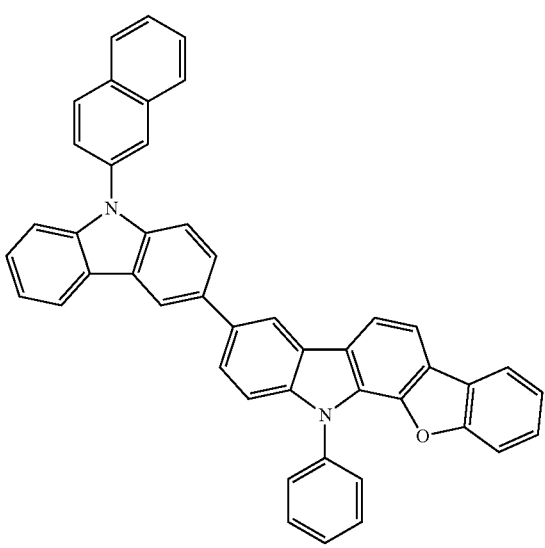
F-506
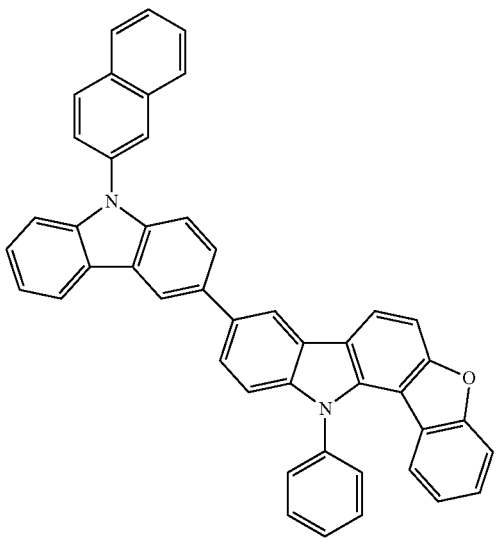
F-507
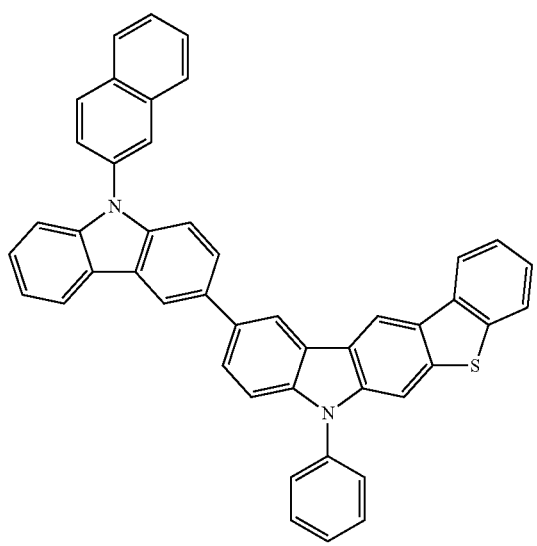

F-508
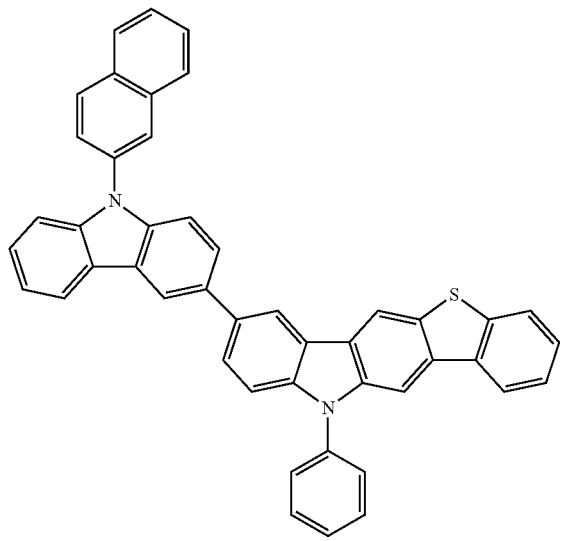
F-511
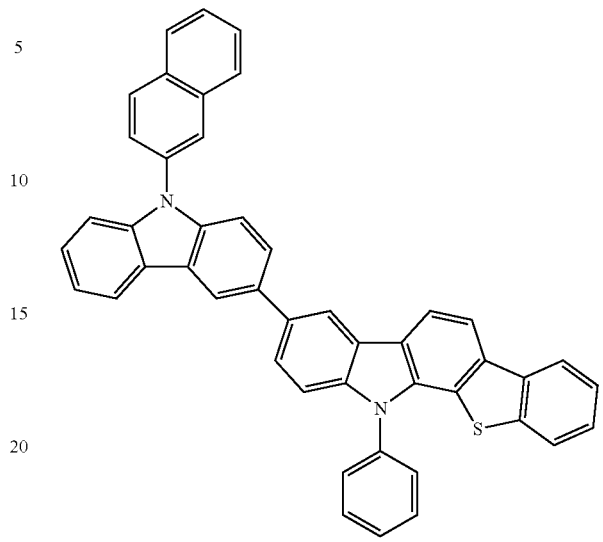
F-509
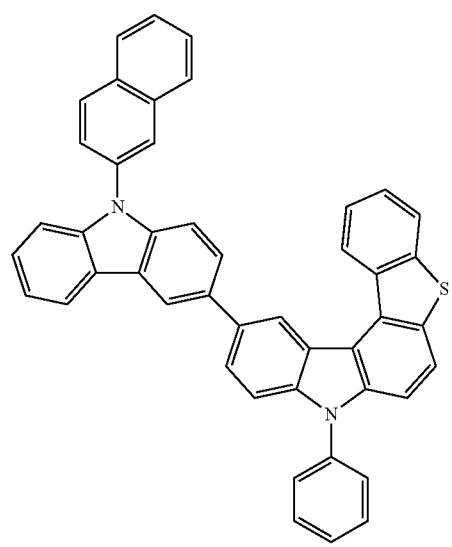
F-510
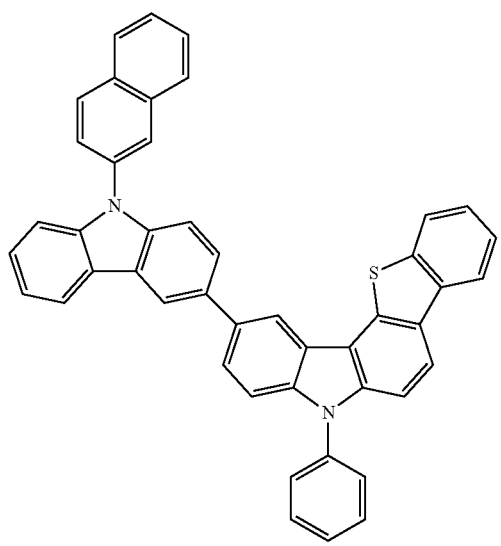
F-512
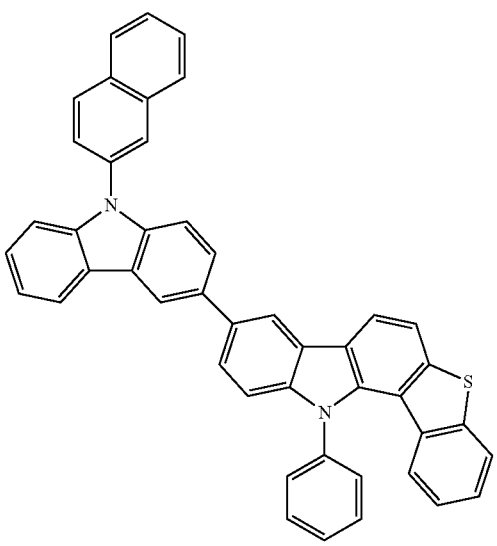

F-513
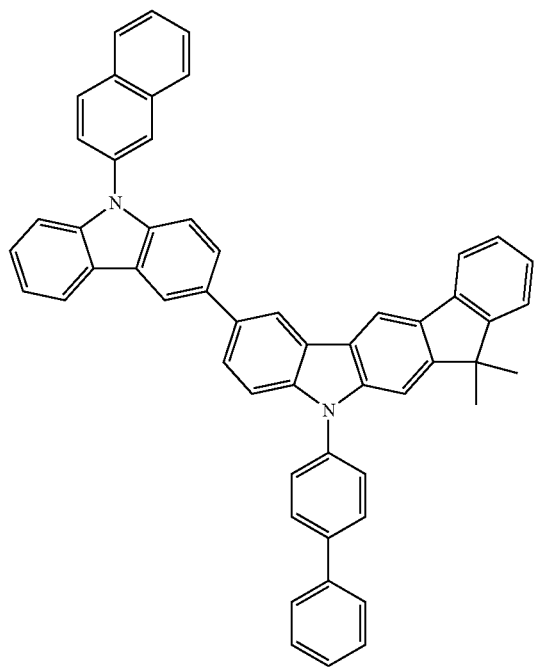
F-515
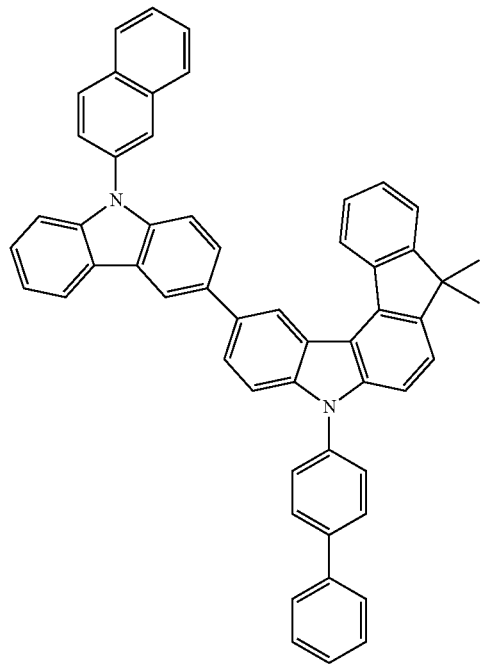
F-514
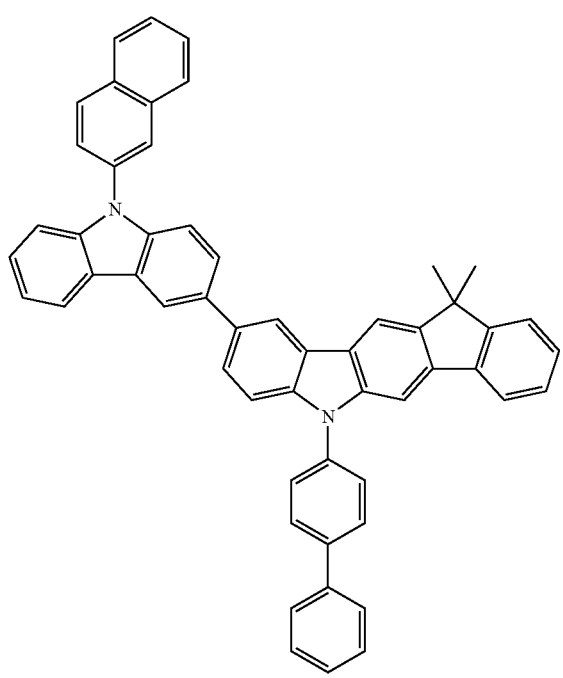
F-516
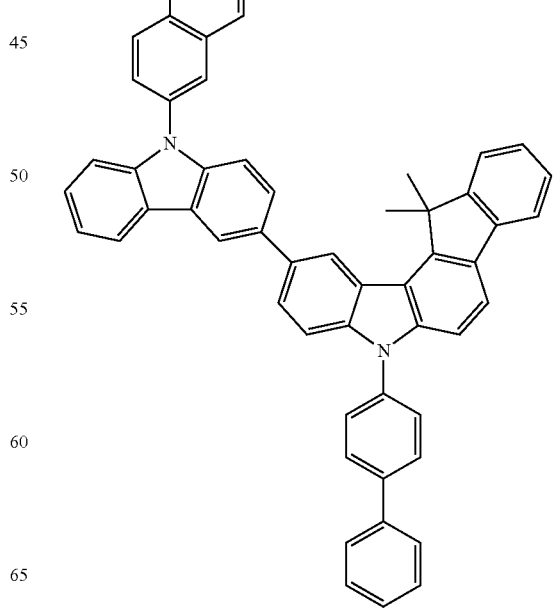

F-517
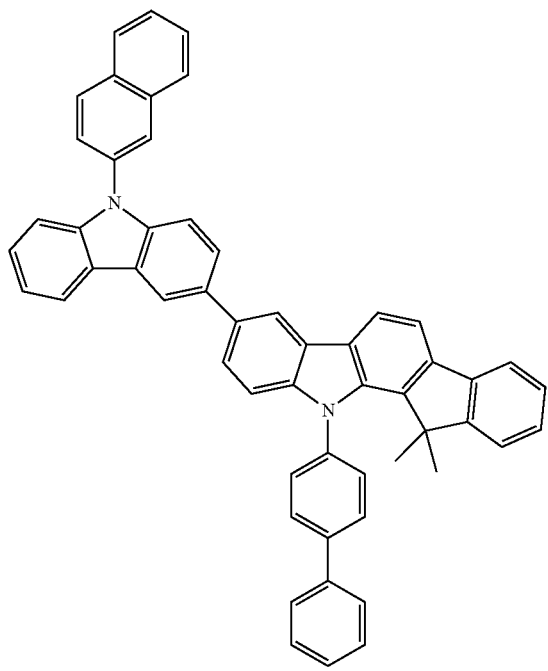
F-519
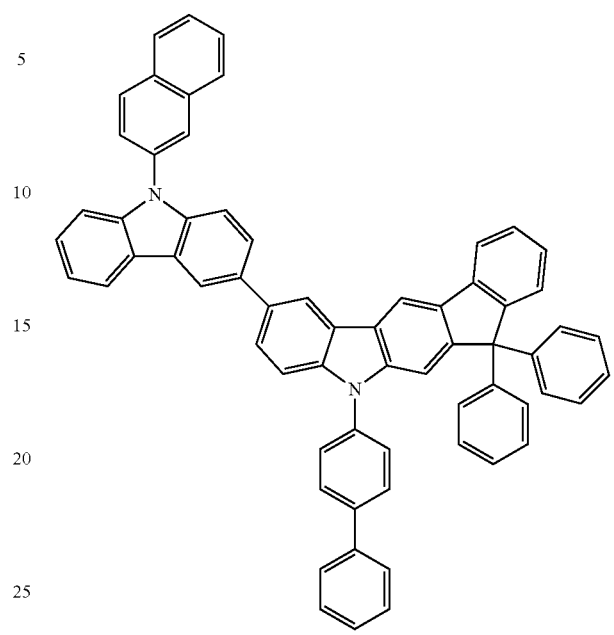
F-518
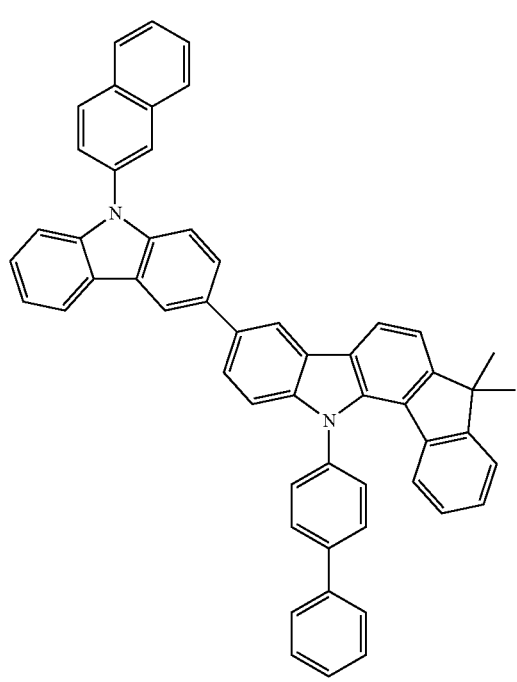
F-520
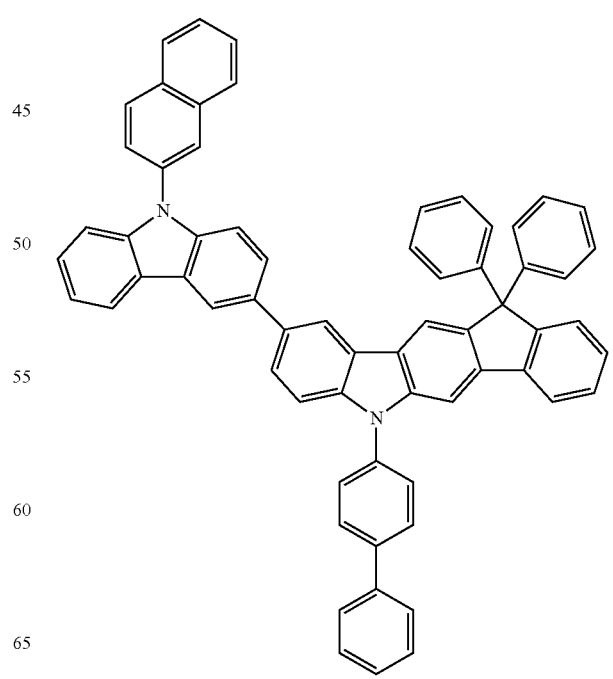

F-521
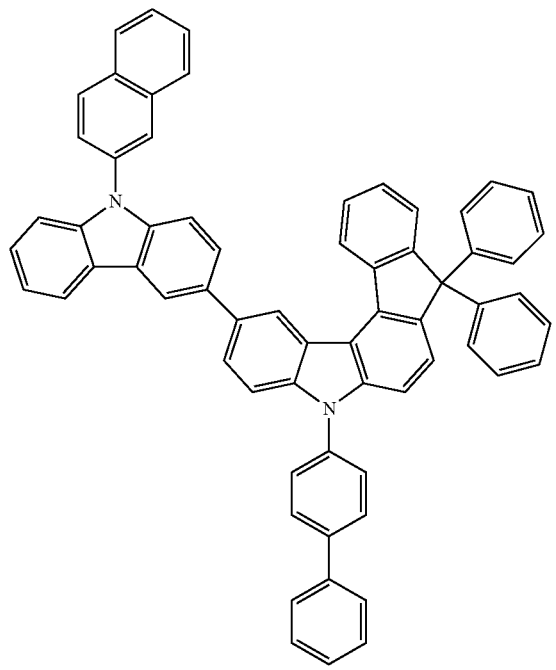
F-523
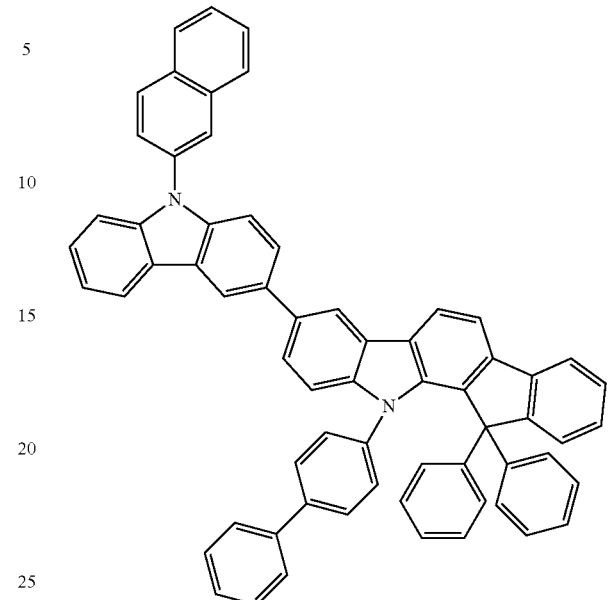
F-522
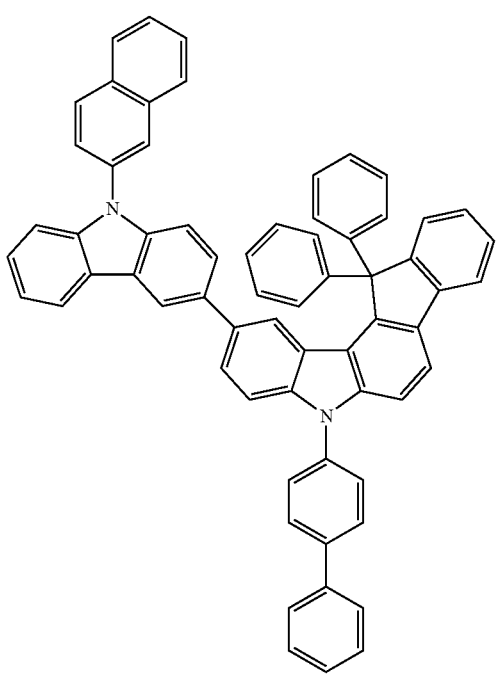
F-524
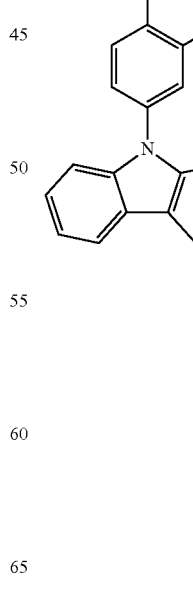

-continued
F-525
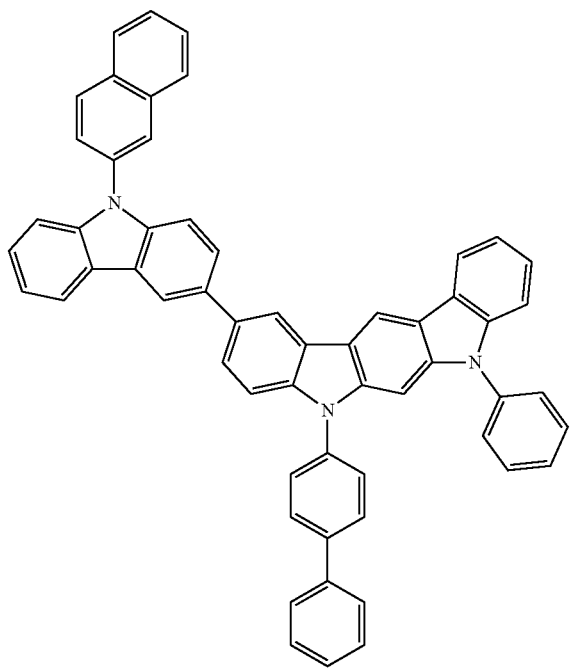
F-526
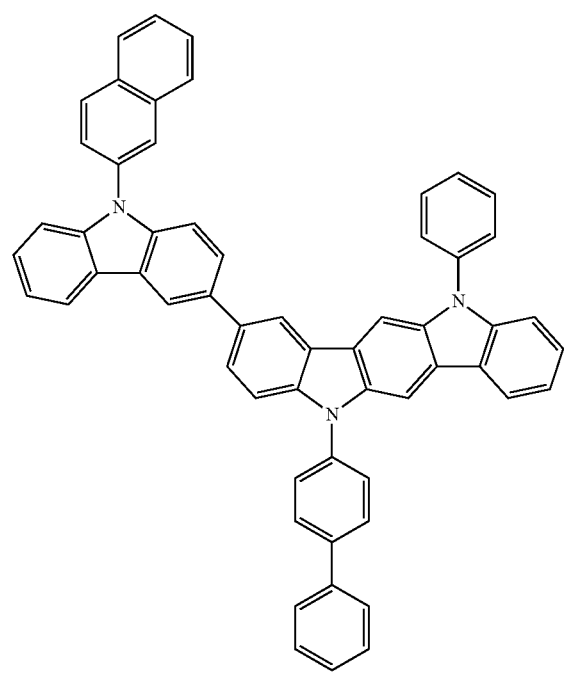
F-527
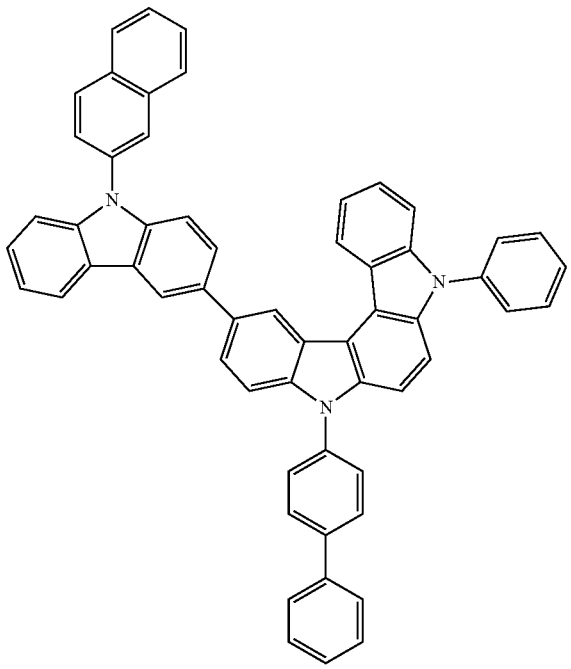
F-528
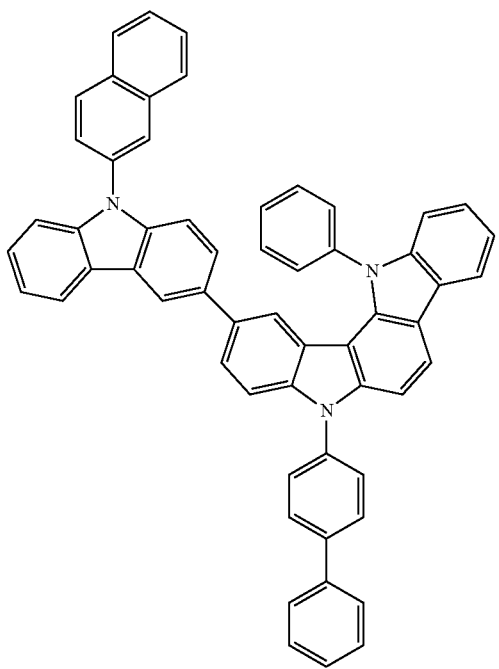

F-529
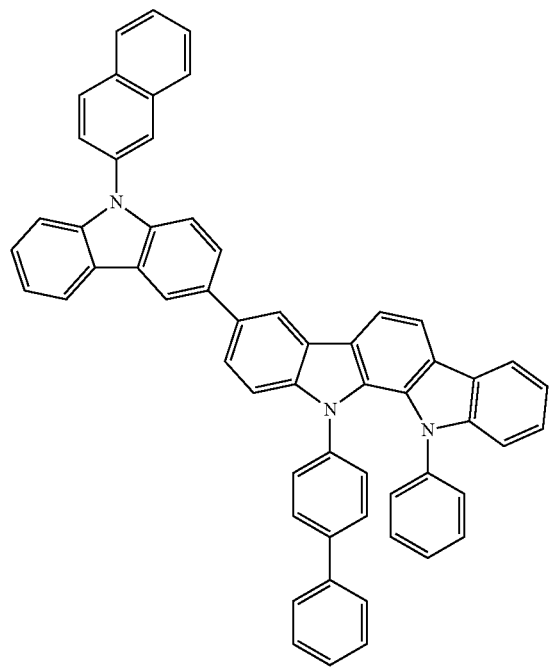
F-531
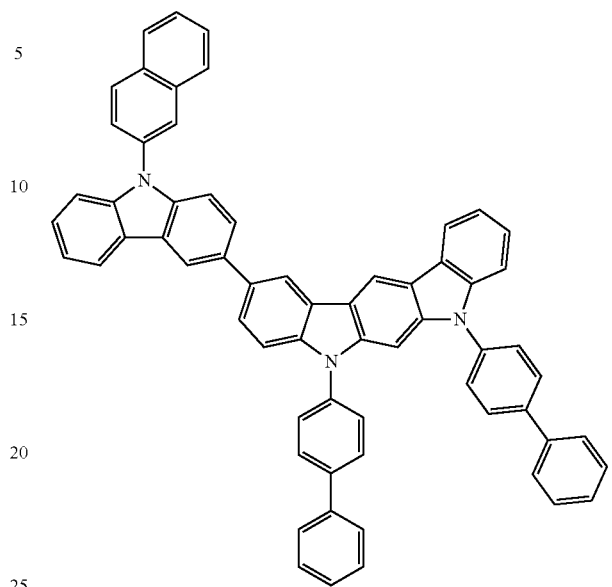
F-530
F-532
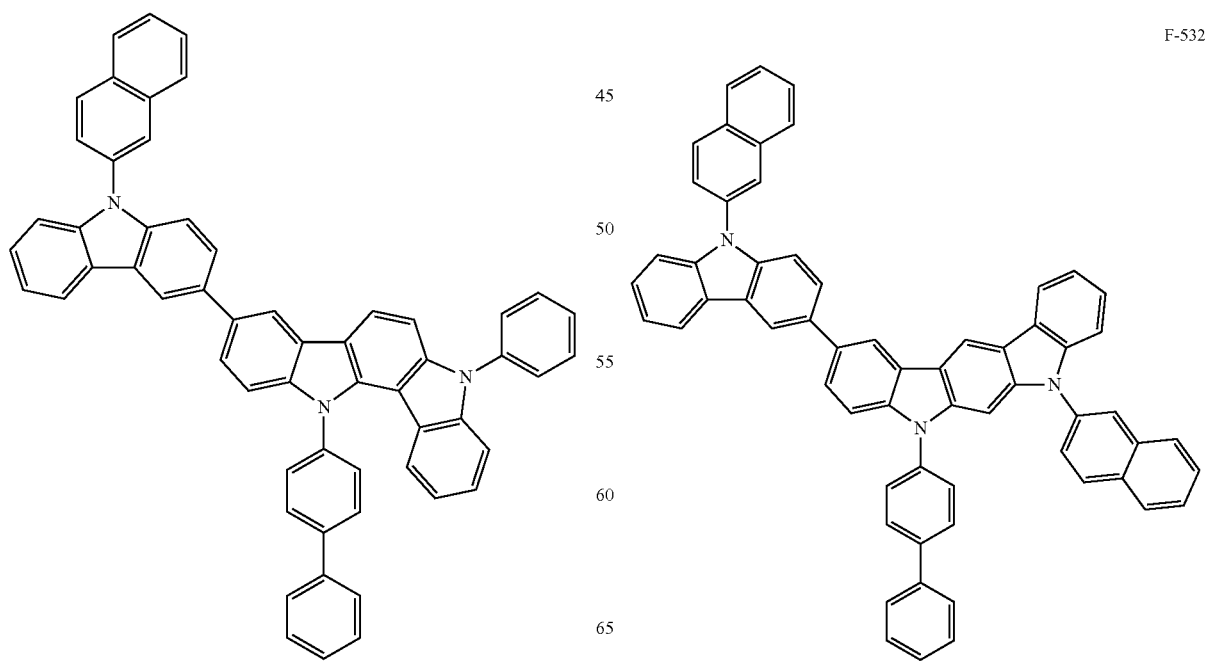

-continued
F-533
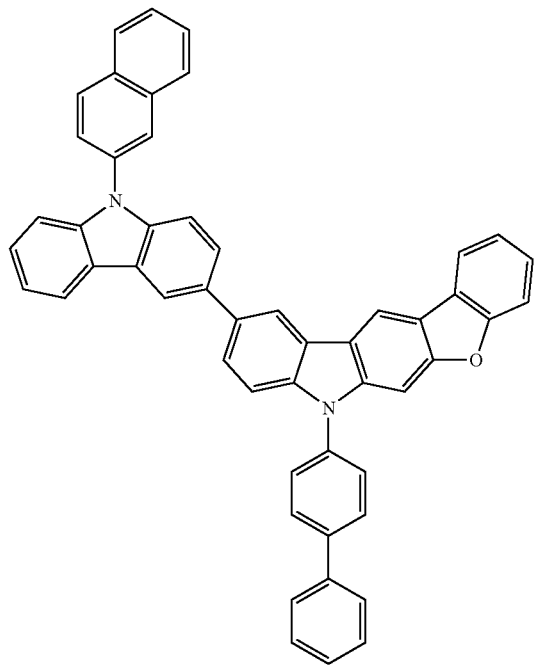
F-534
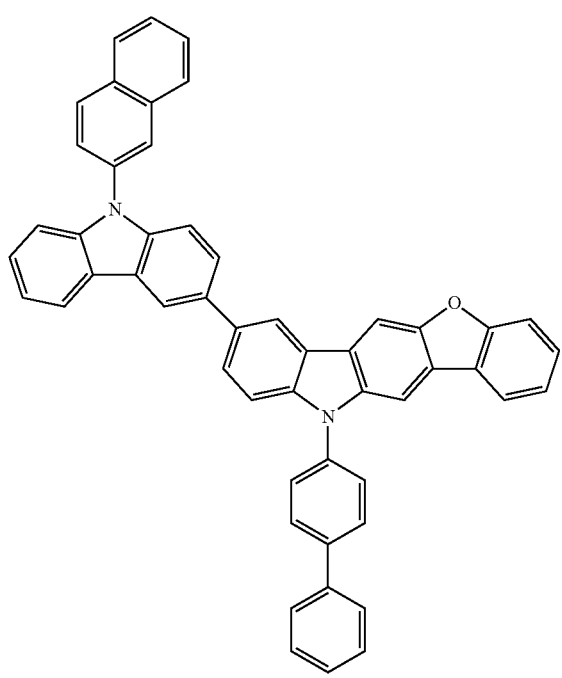
-continued
F-535
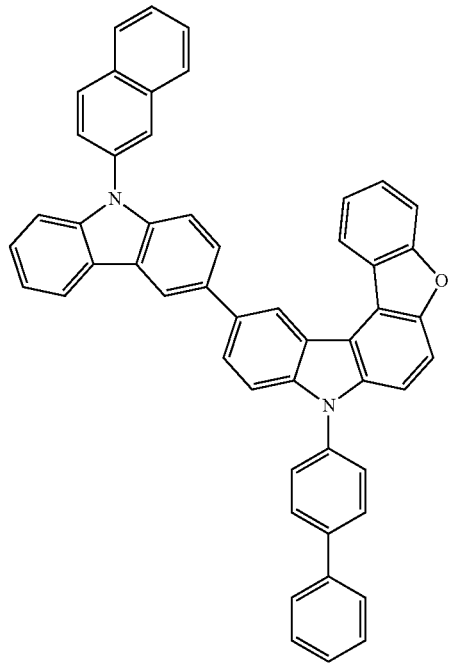
F-536
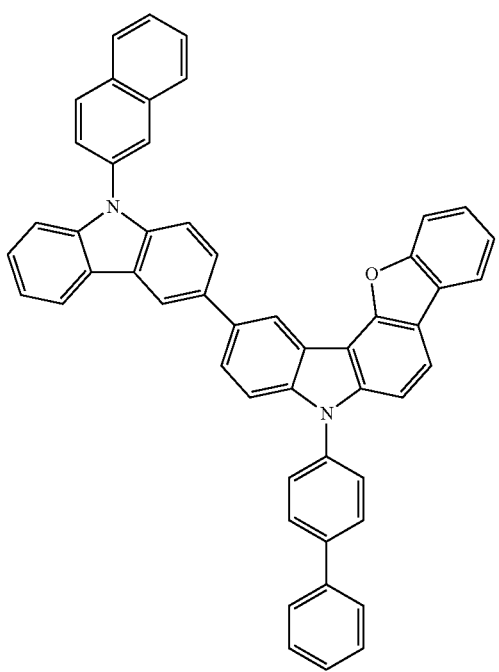

F-537
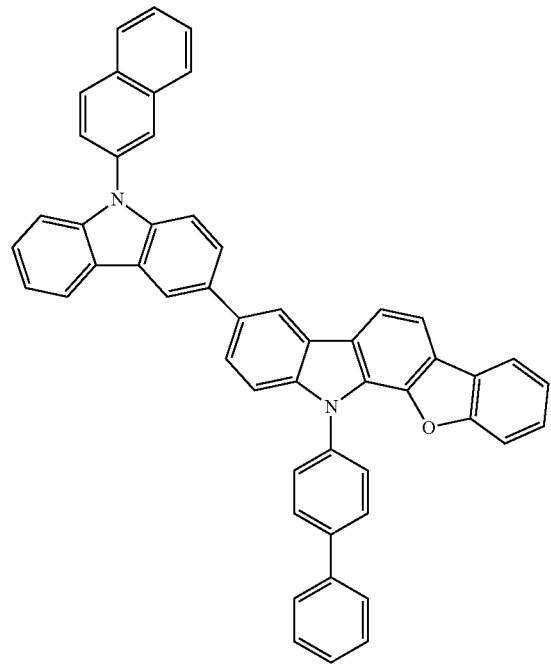
F-539
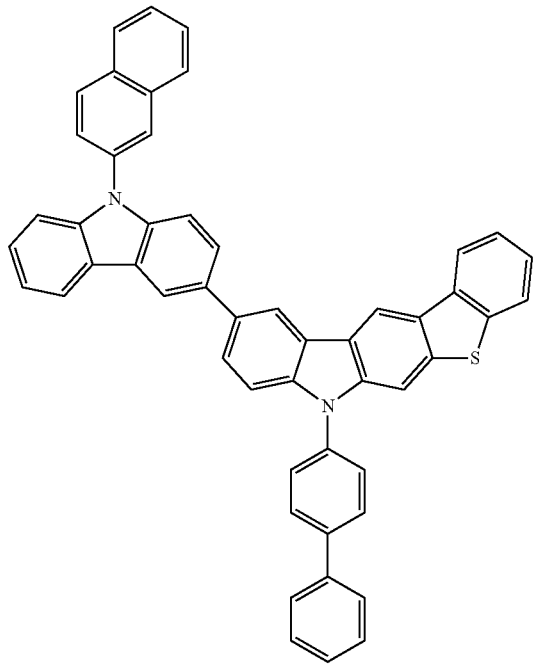
F-538
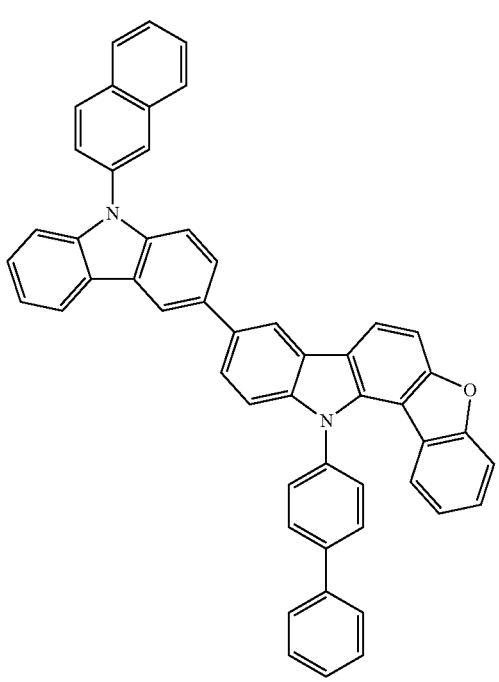
F-540
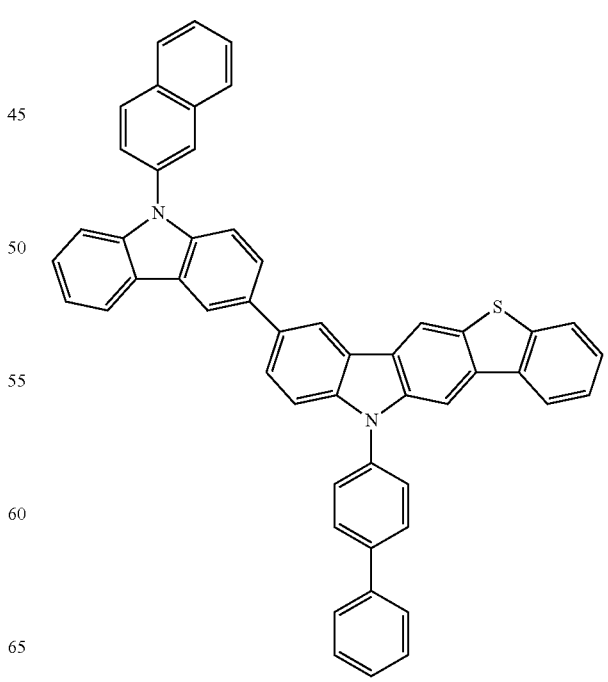

F-541
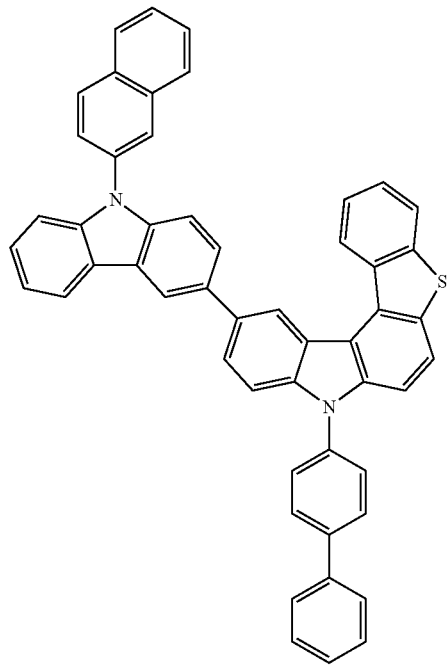
F-542
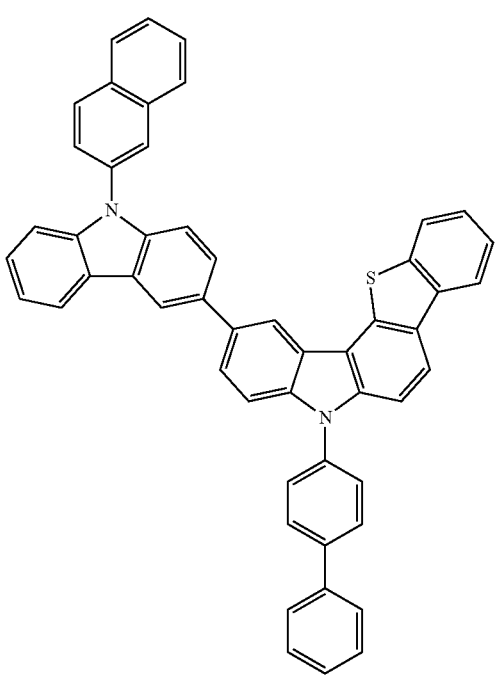
F-543
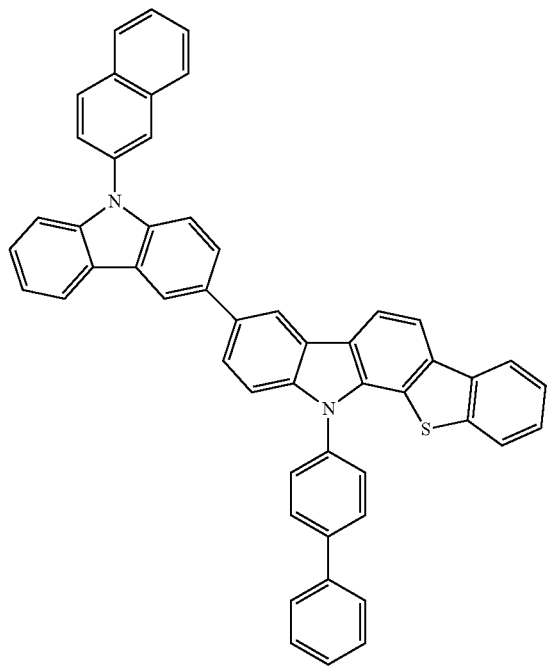
F-544
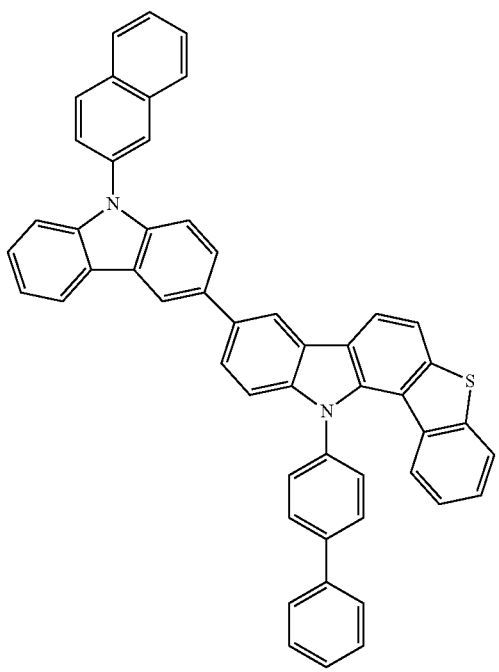

F-545
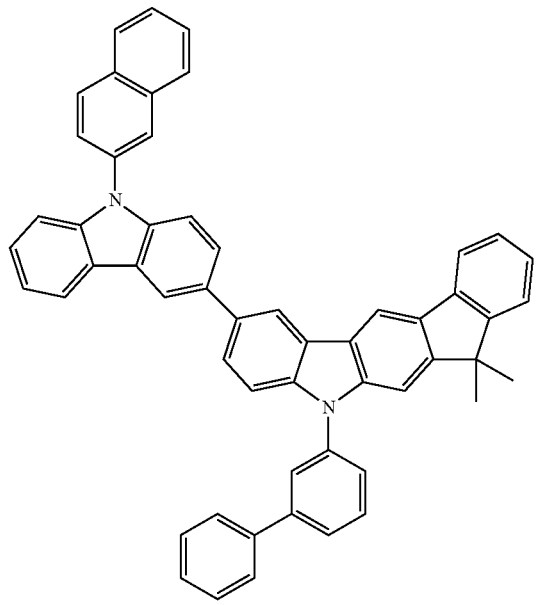
F-547
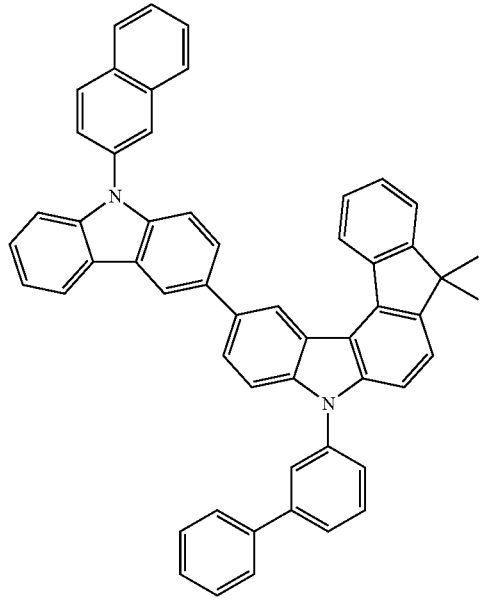
F-546
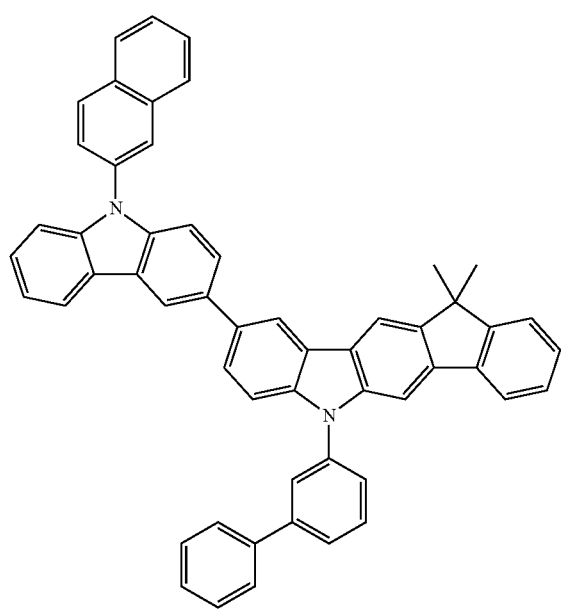
F-548
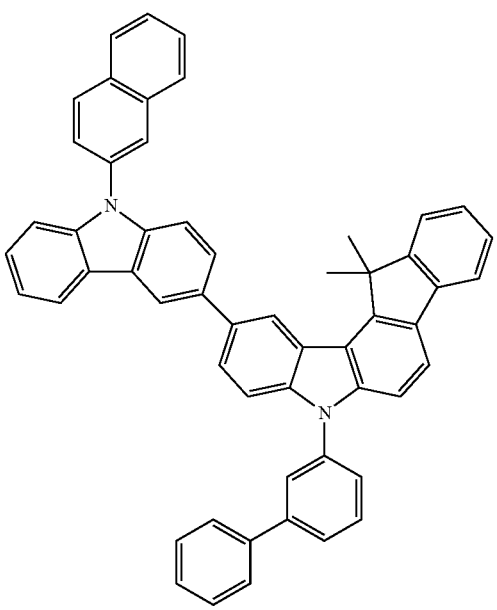

-continued
F-549
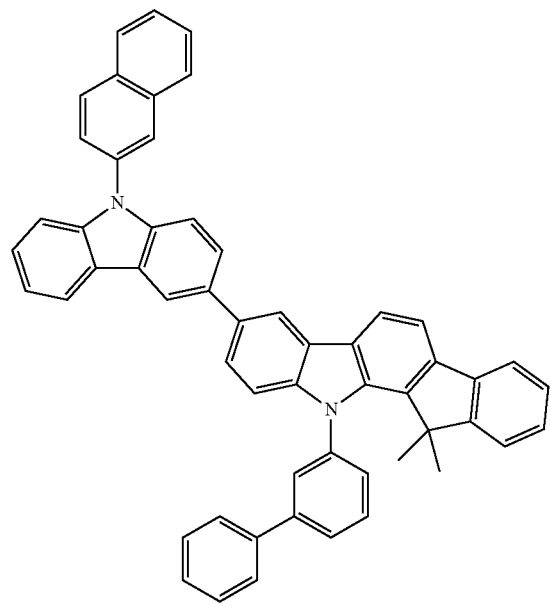
F-550
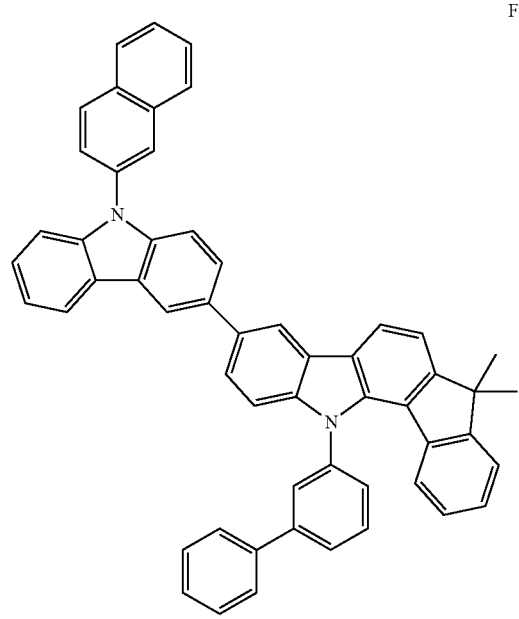
-continued
F-551
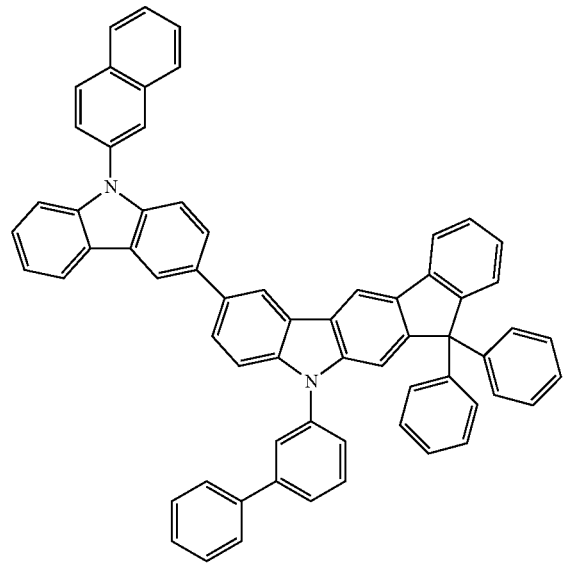
F-552

F-553
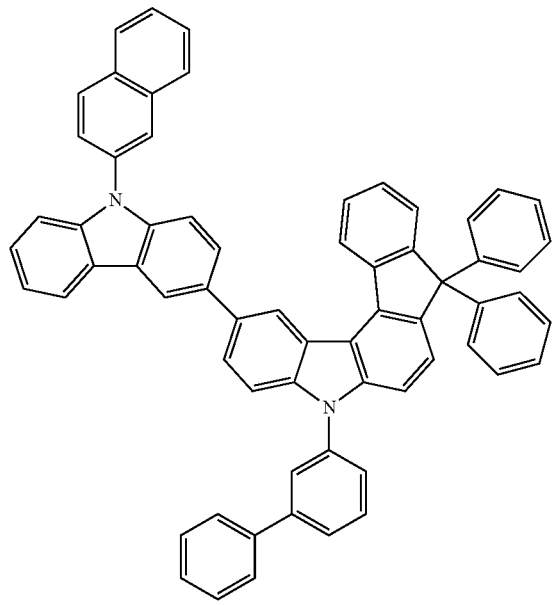
F-555
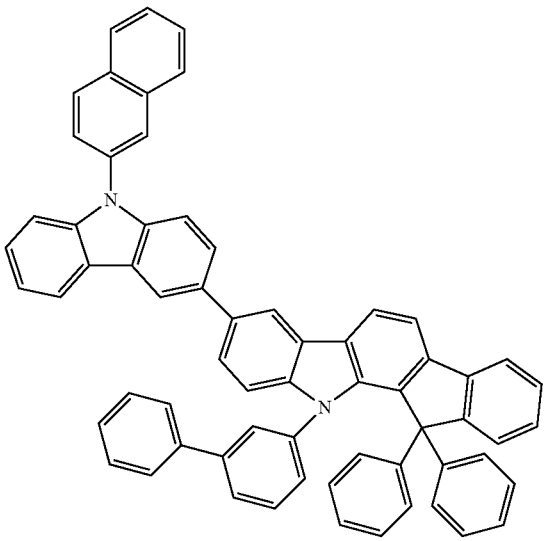
F-554
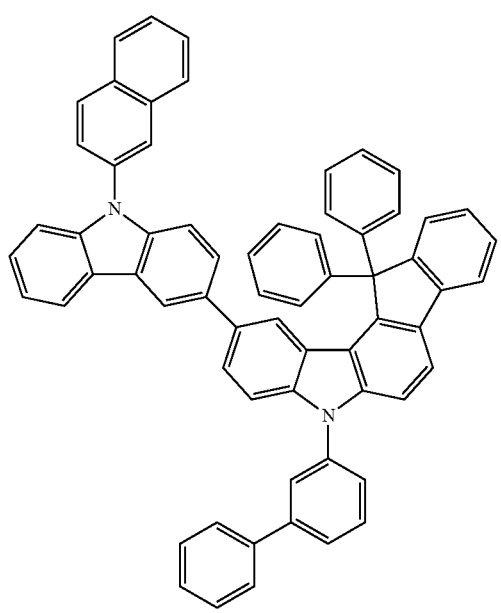
F-556
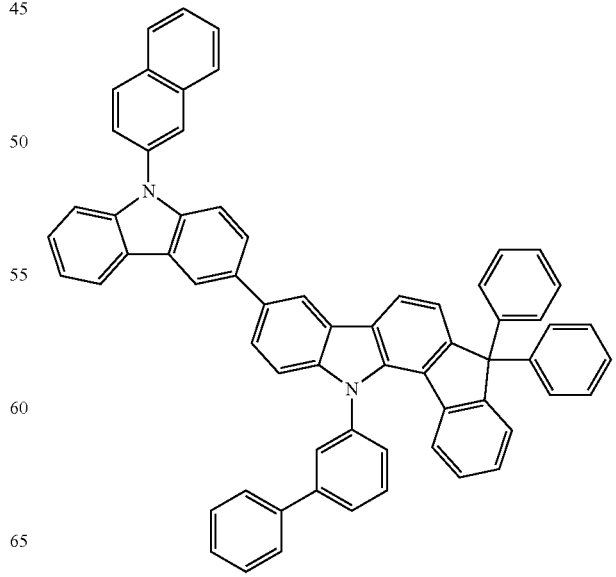

F-557
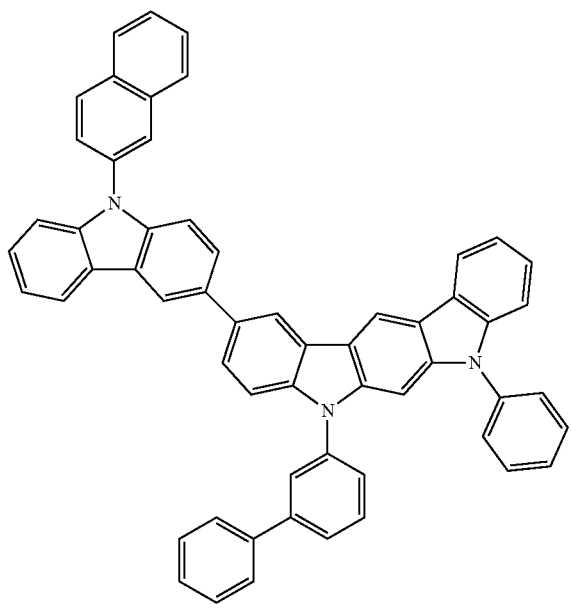
F-559
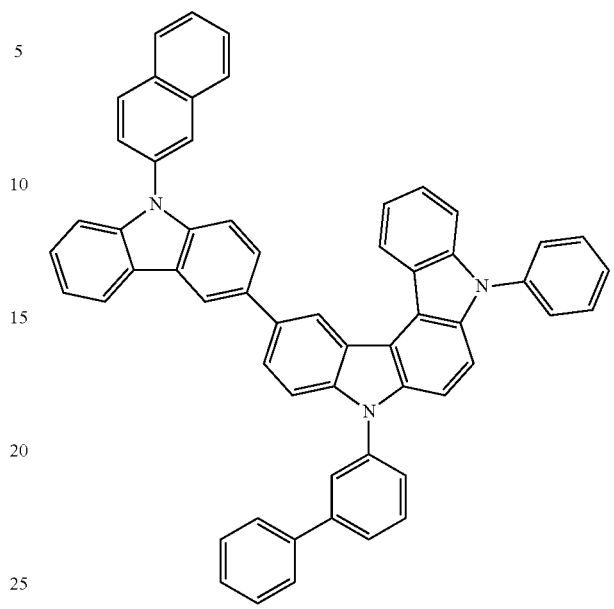
F-558
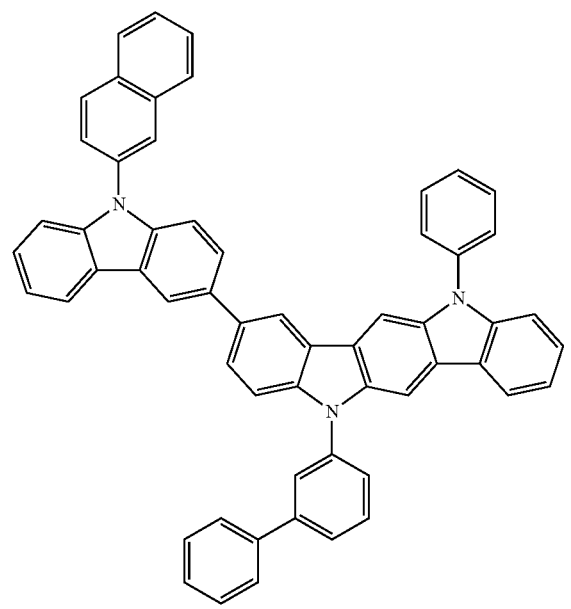
F-560
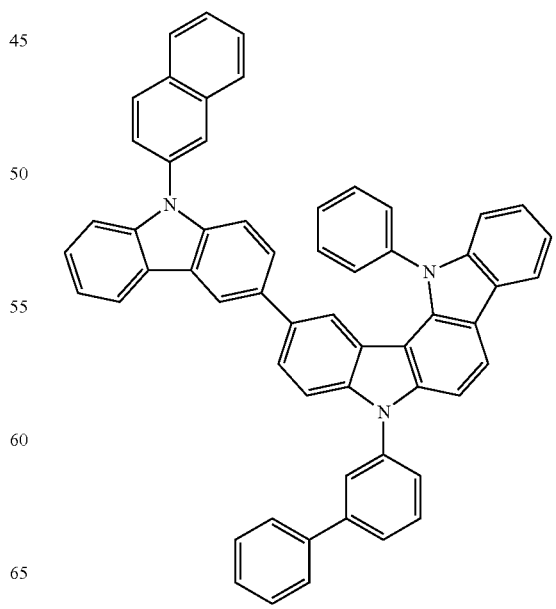

-continued
F-561
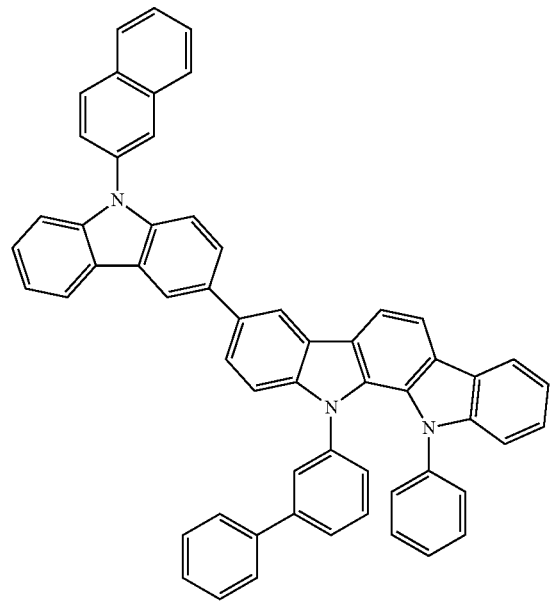
F-562
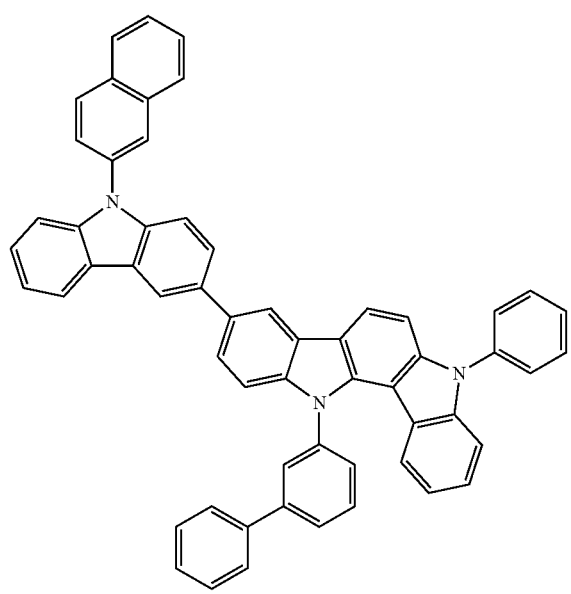
-continued
F-563
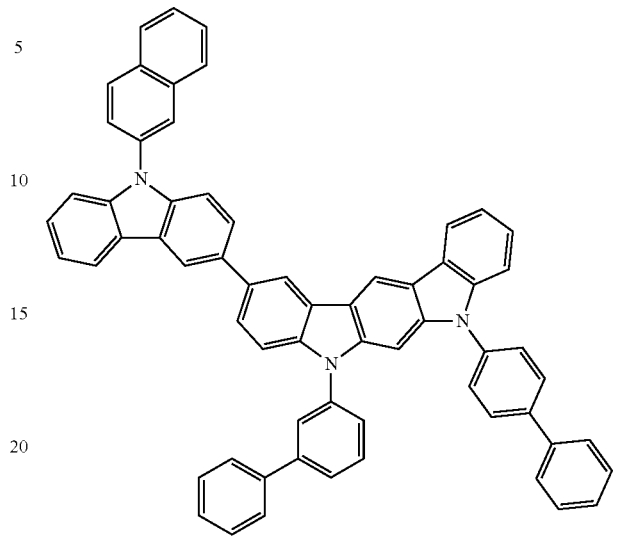
F-564
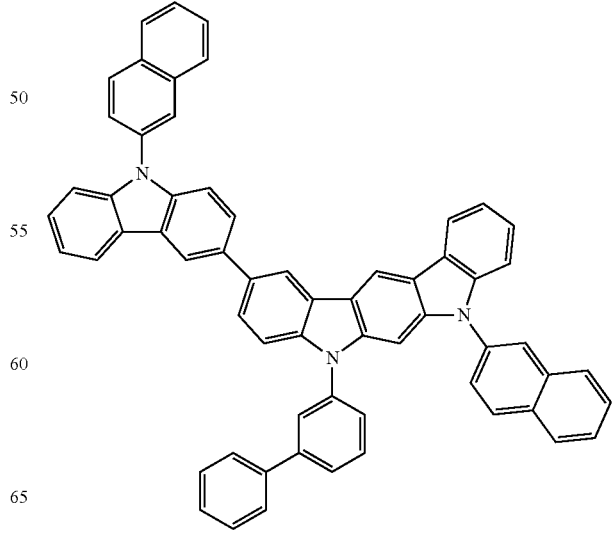

F-565
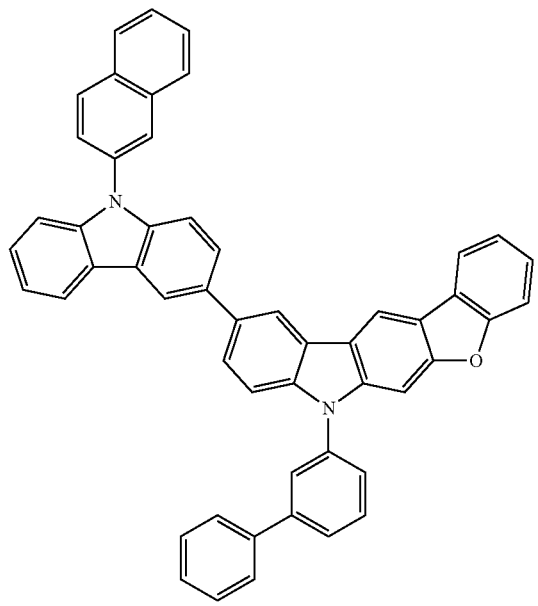
F-567
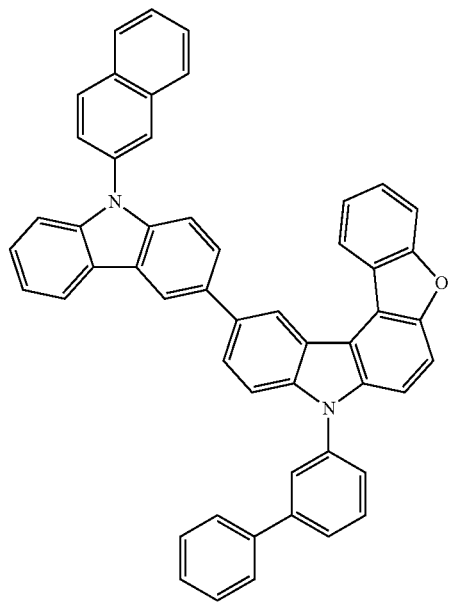
F-566
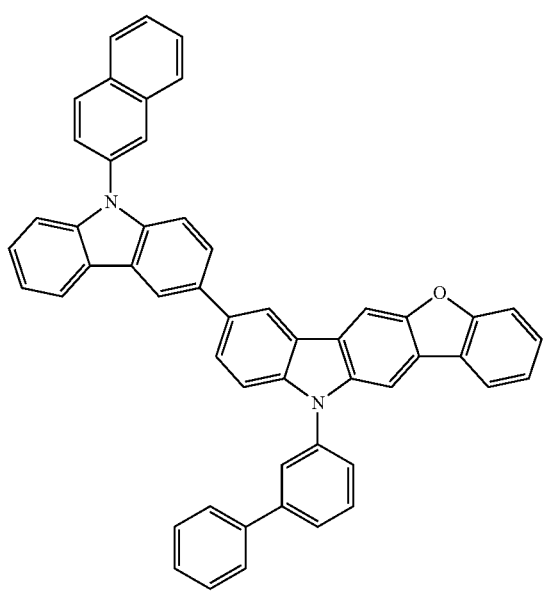
F-568
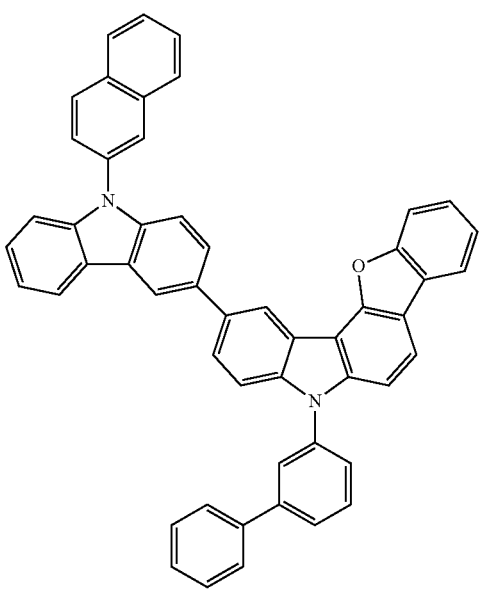

F-569
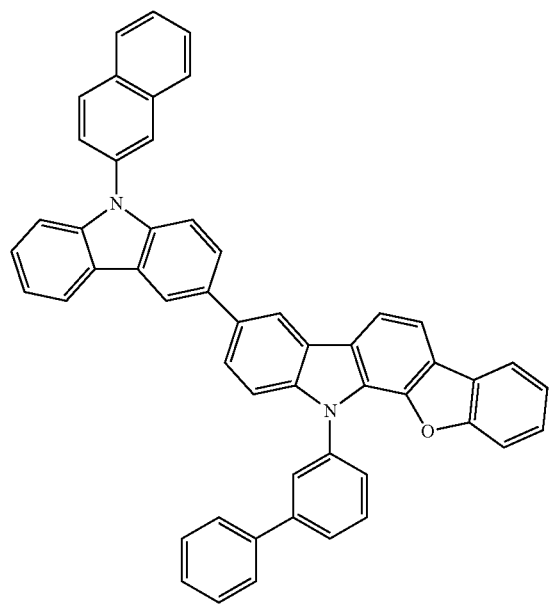
F-570
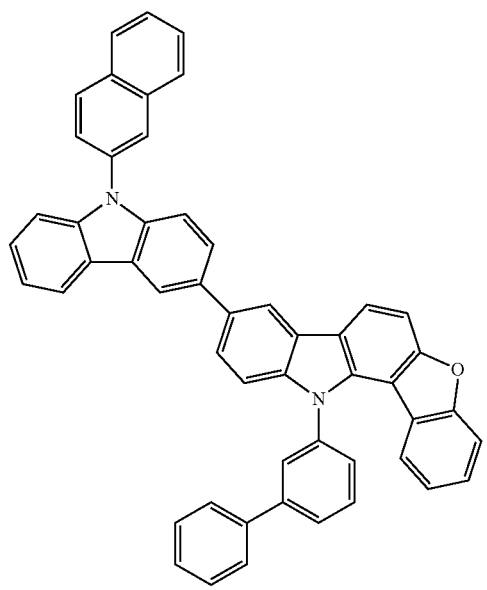
F-571
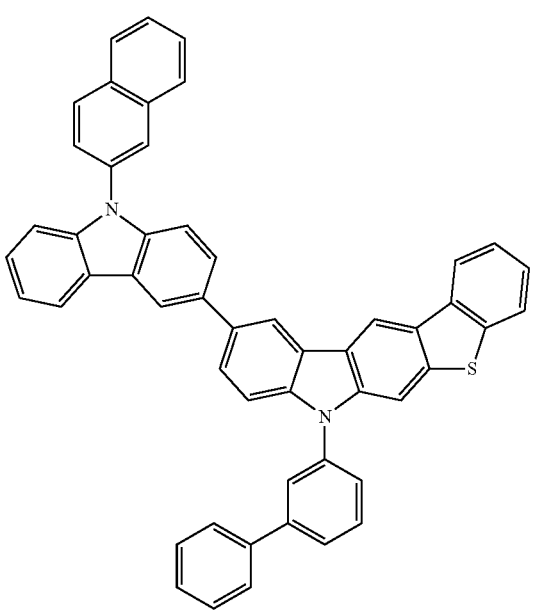
F-572

F-573
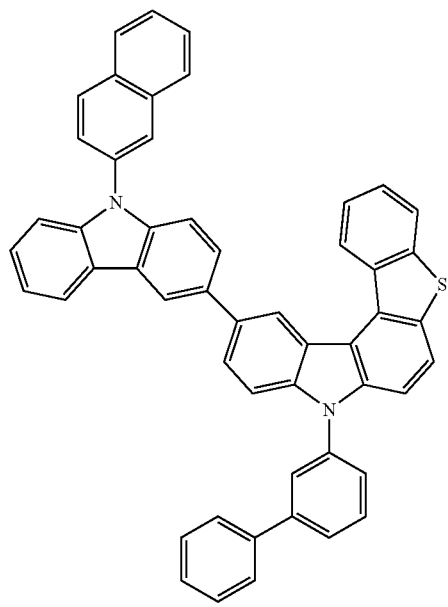
F-575
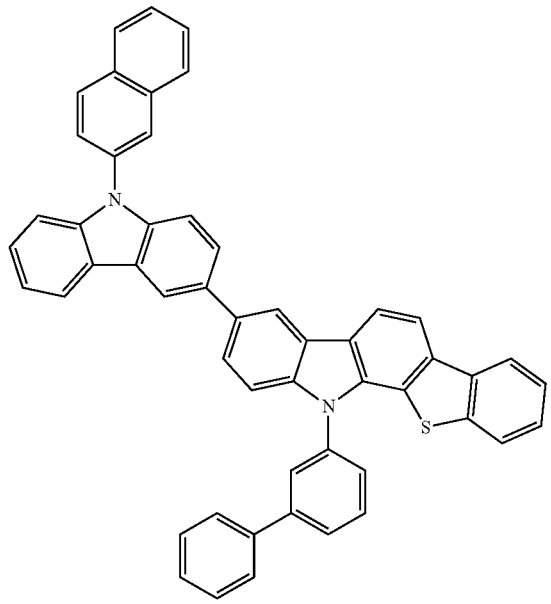
F-574
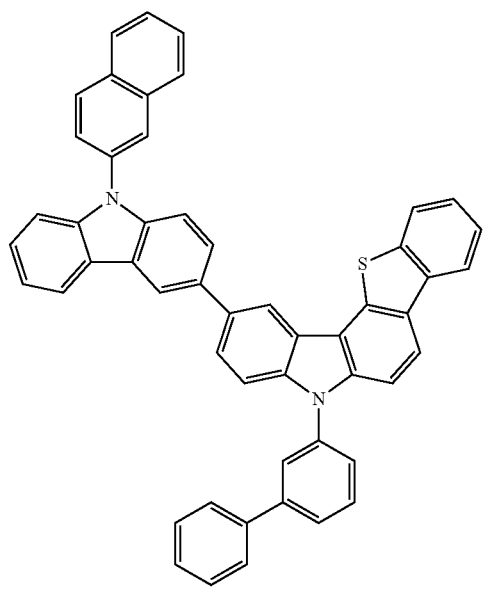
F-576
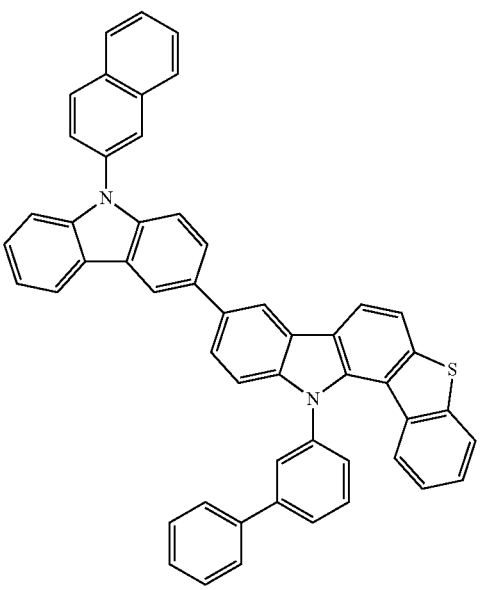

F-577
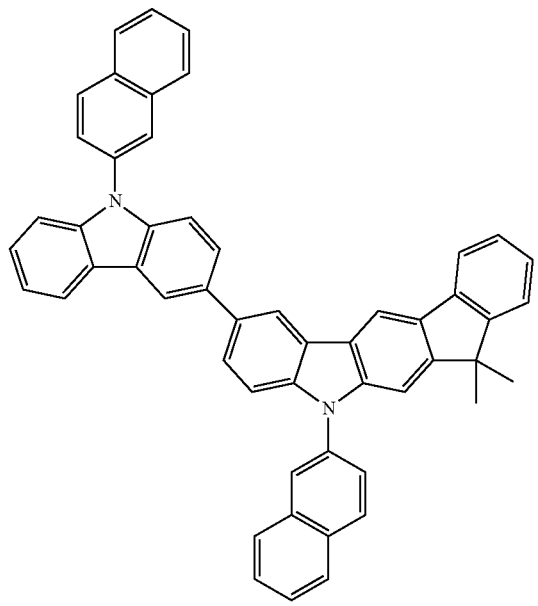
F-579
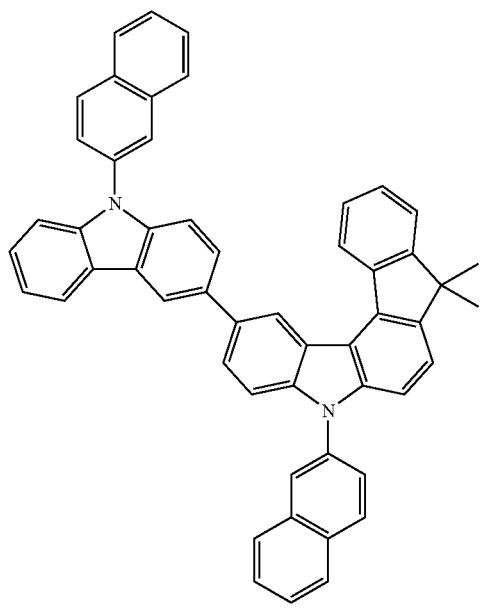
F-578
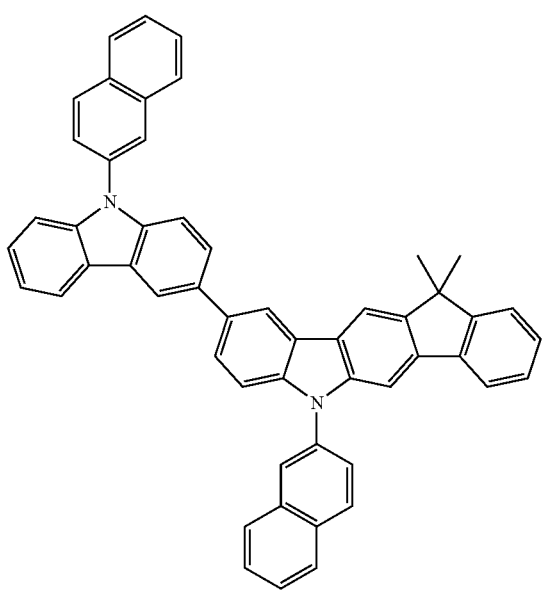
F-580
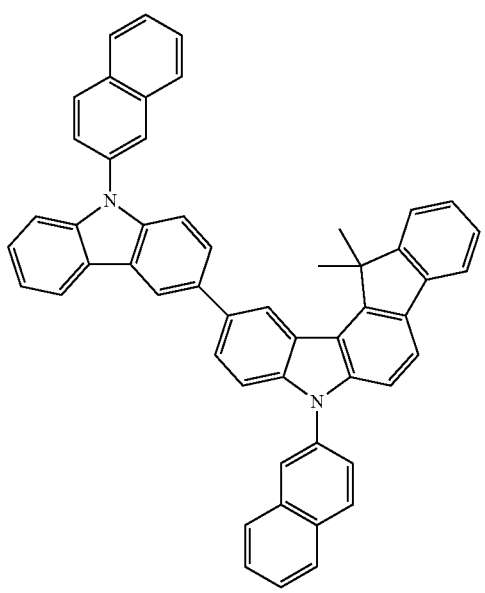

F-581
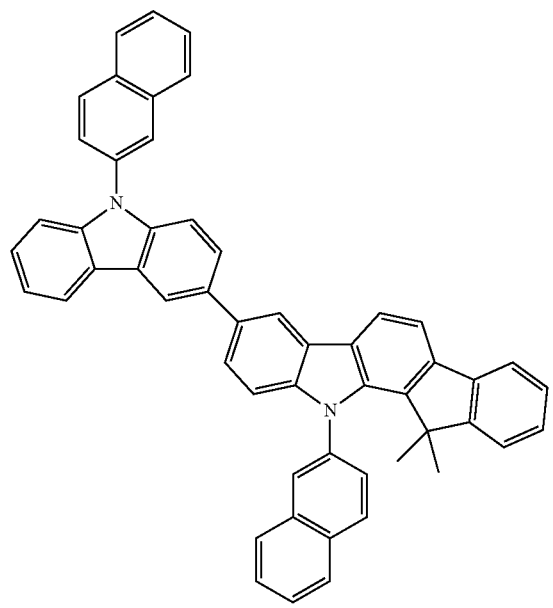
F-582
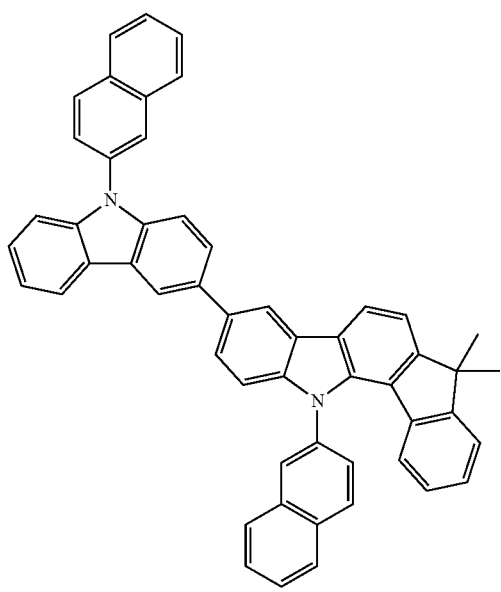
F-583
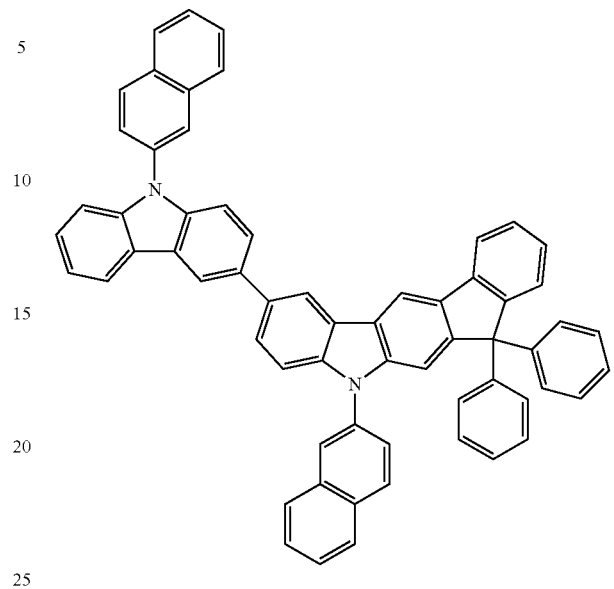
F-584

F-585
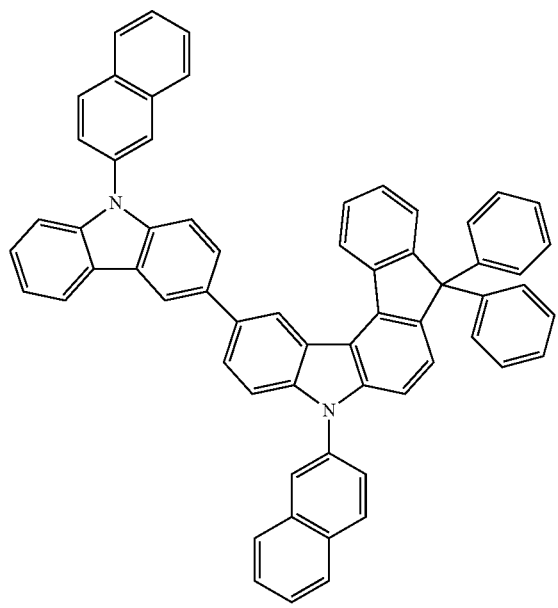
F-587
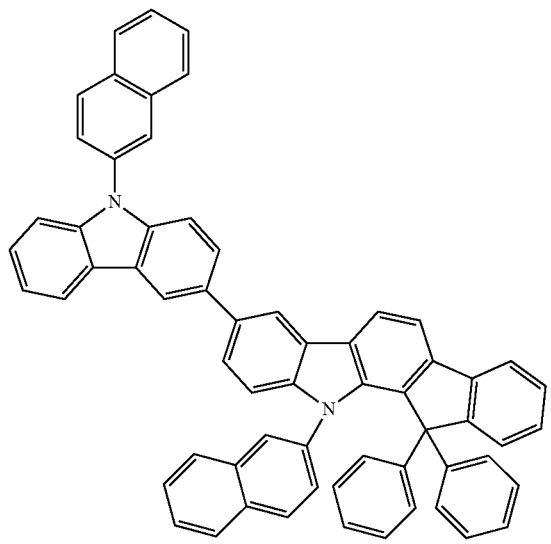
F-586
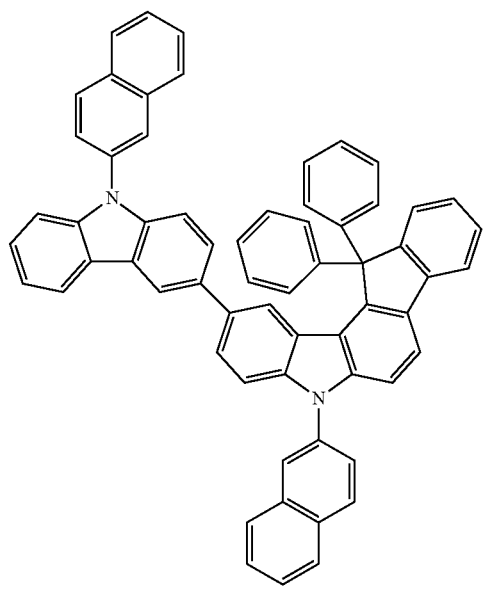
F-588
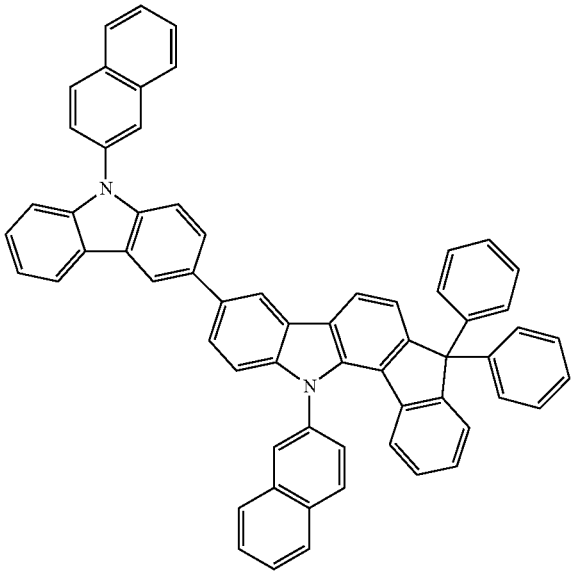

F-589
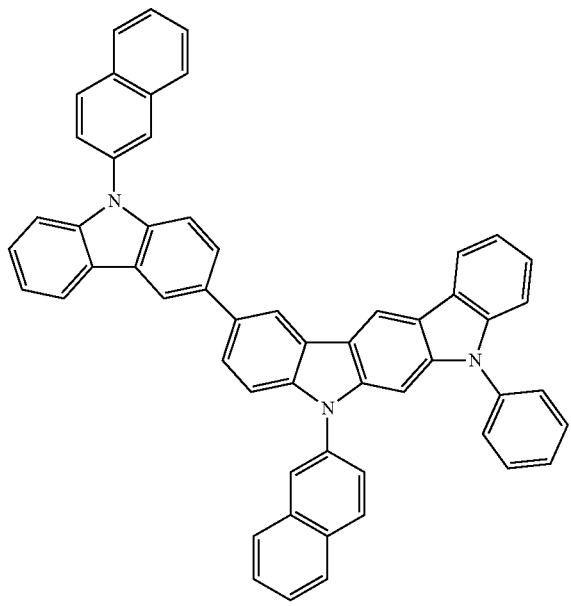
F-591
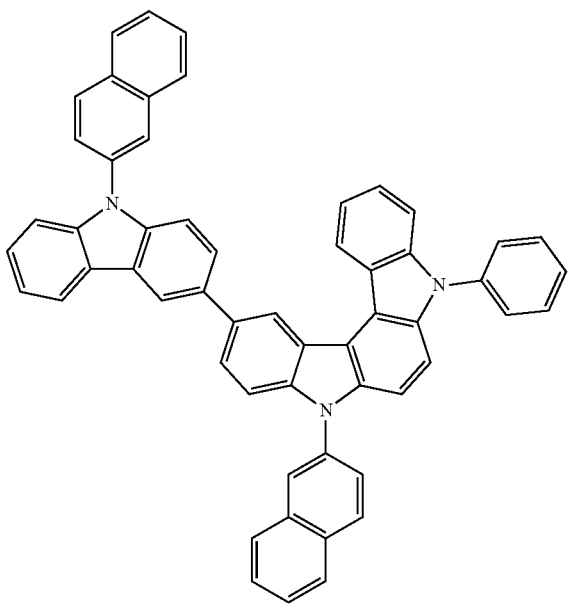
F-590
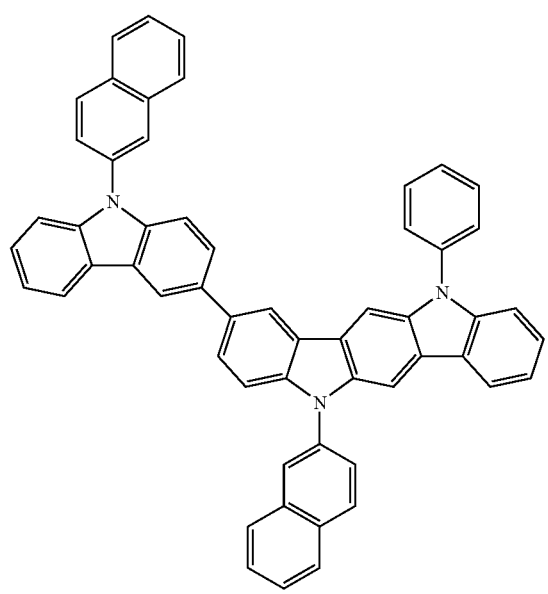
F-592
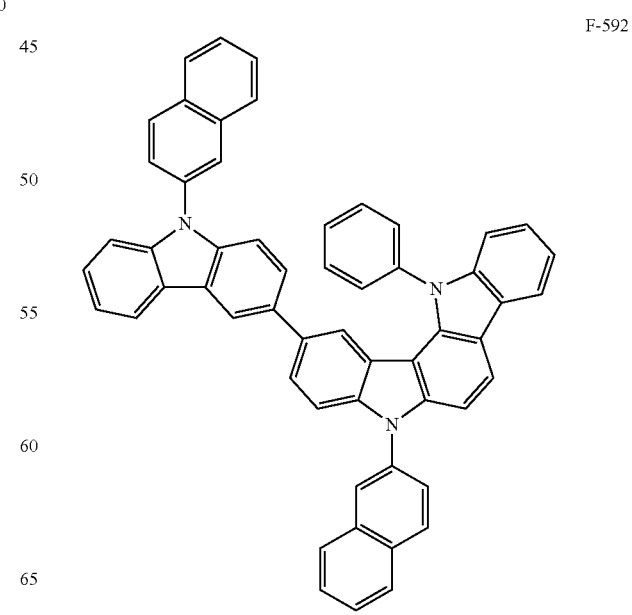

F-593
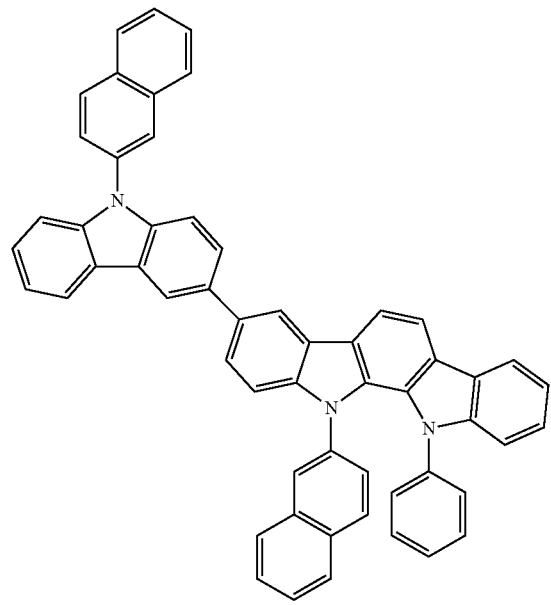
F-594
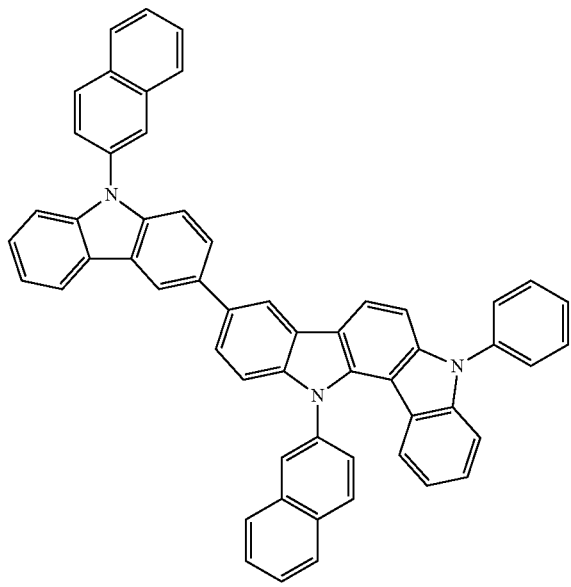
F-595
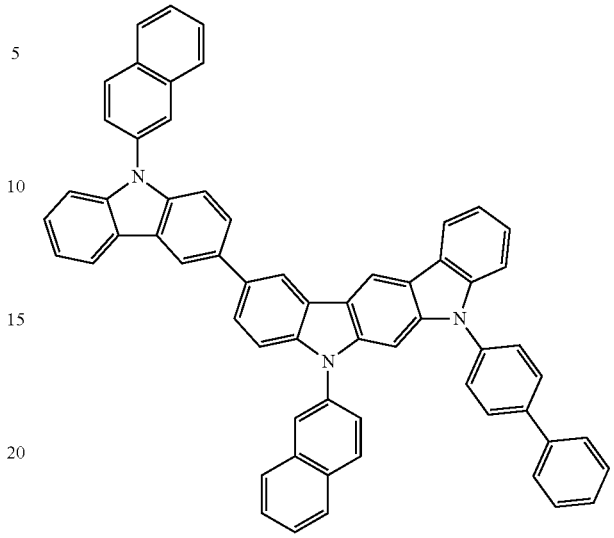
F-596
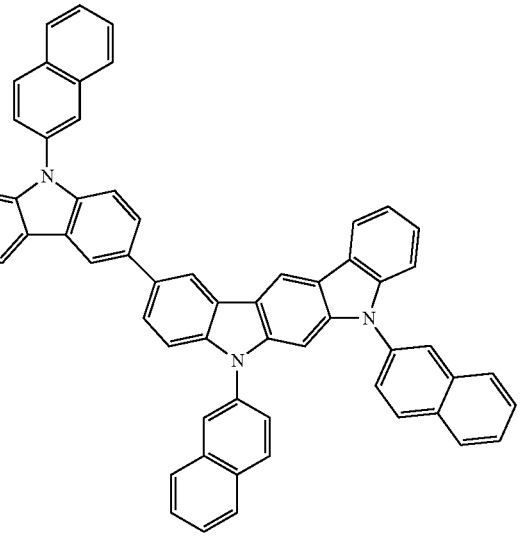

F-597
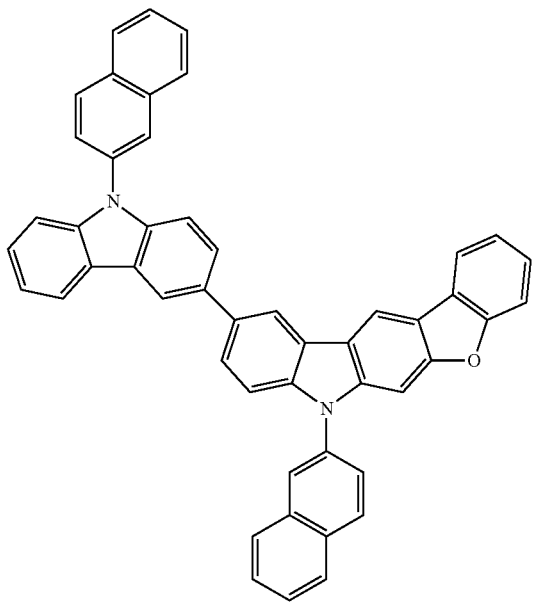
F-599
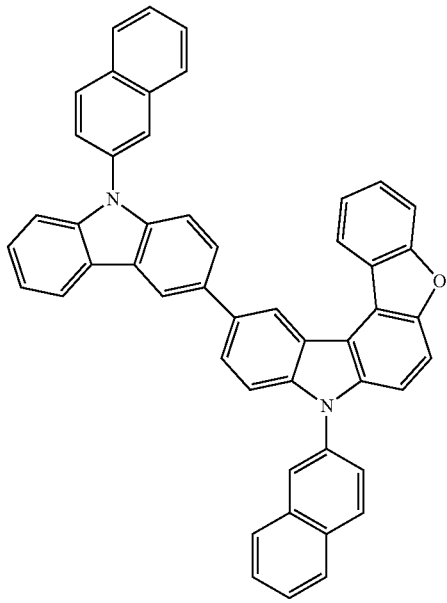
F-598
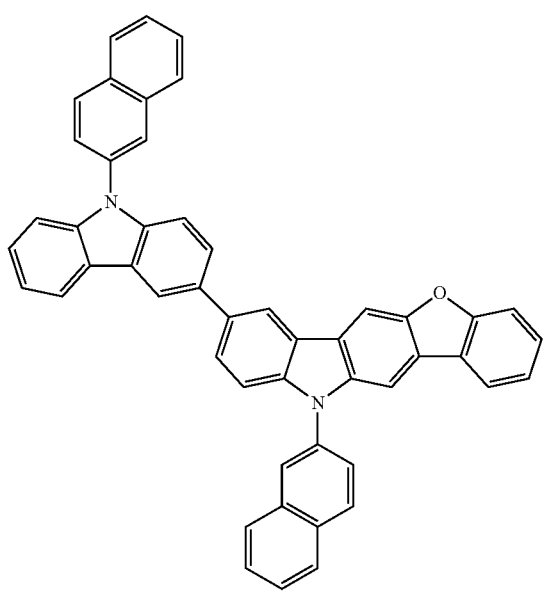
F-600
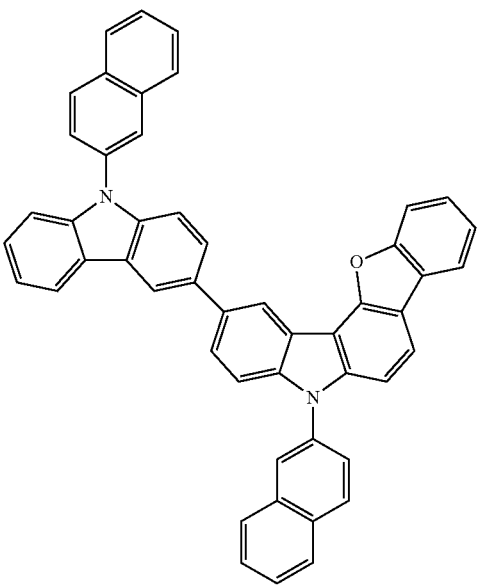

F-601
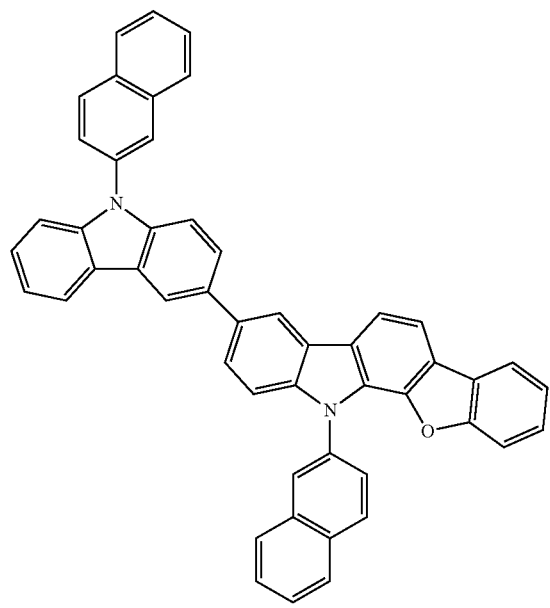
F-603
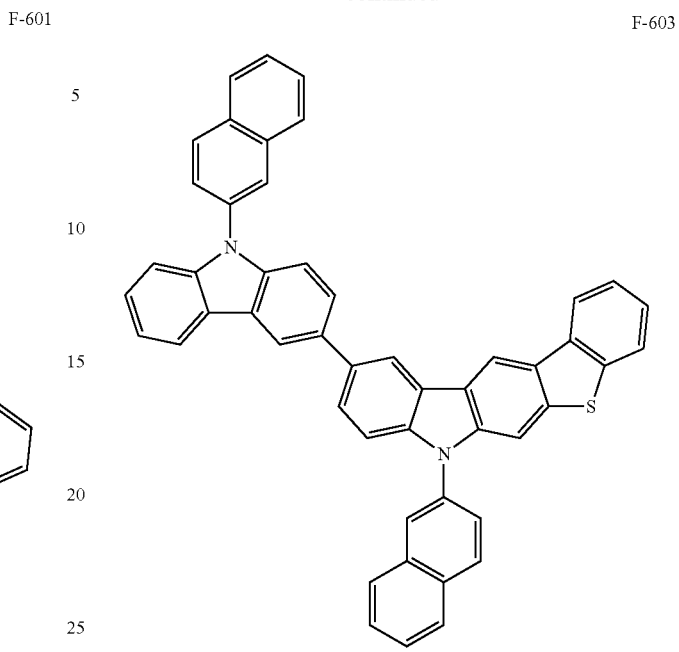
F-602
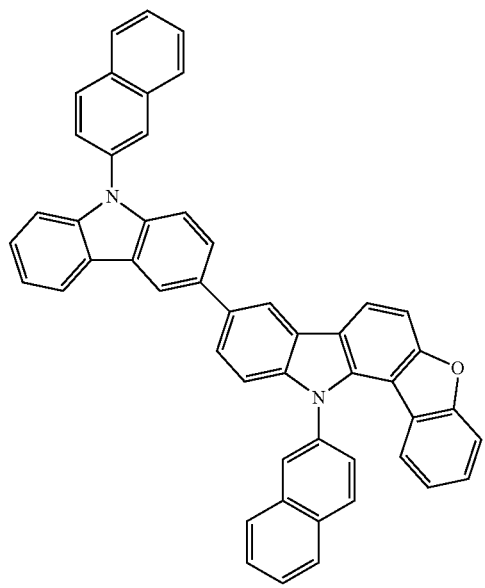
F-604
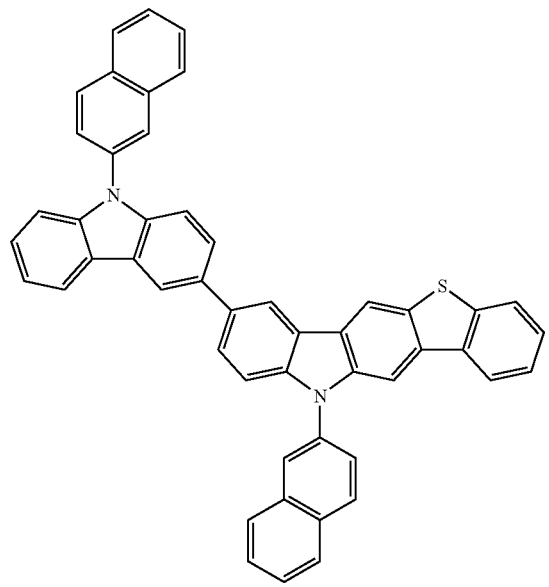

F-605
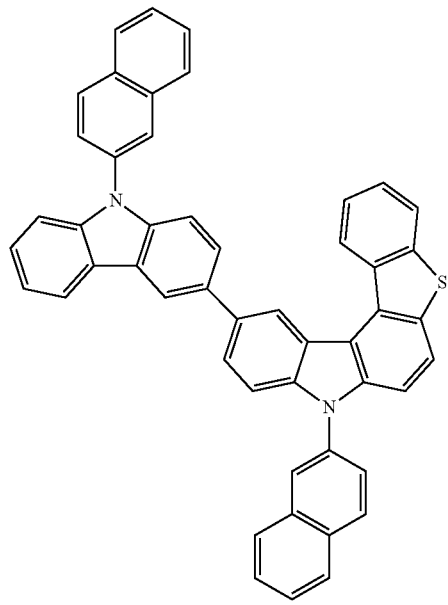
F-607
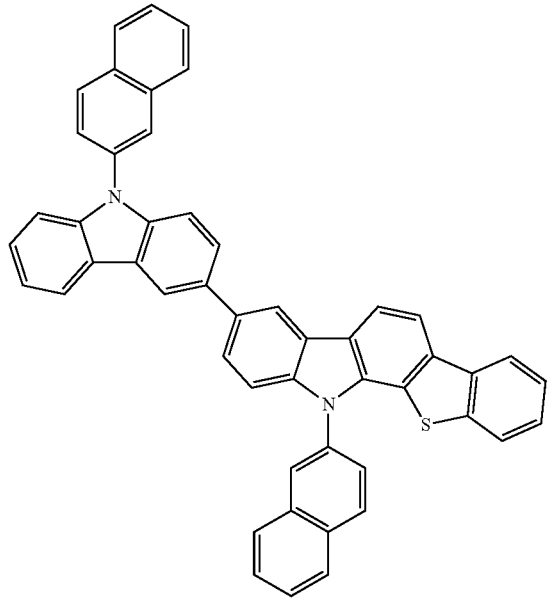
F-606
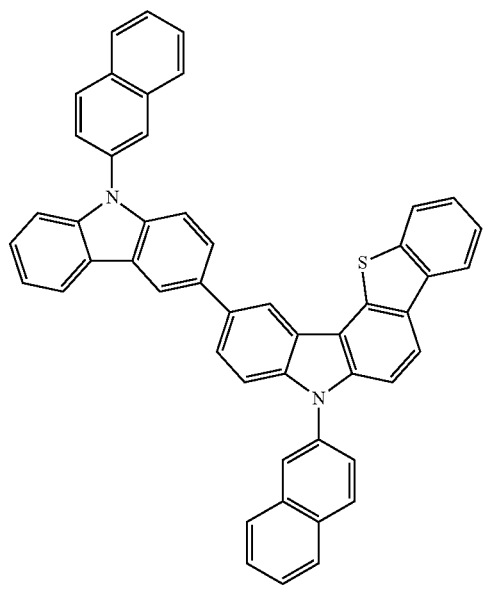
F-608
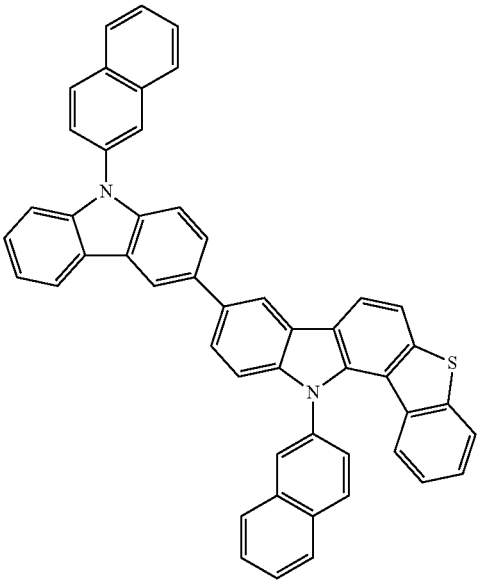

F-609
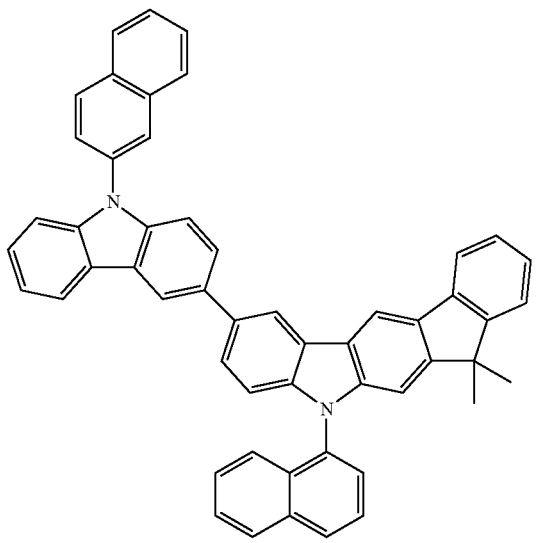
F-610
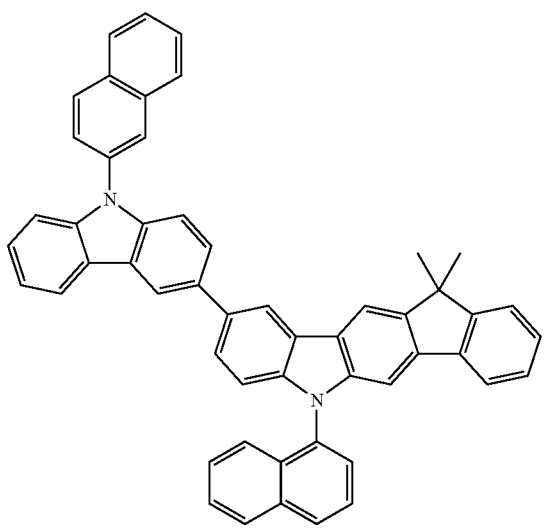
F-611
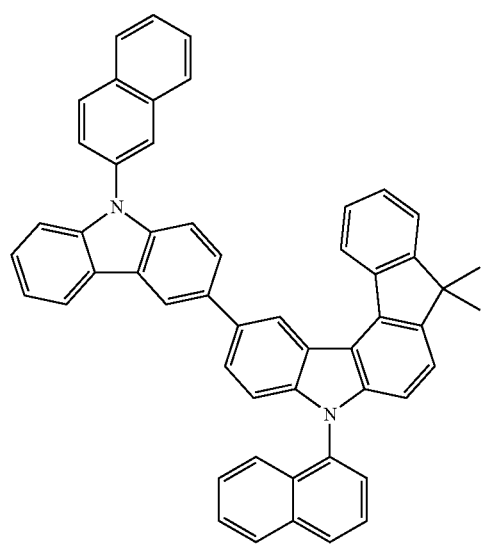
F-612
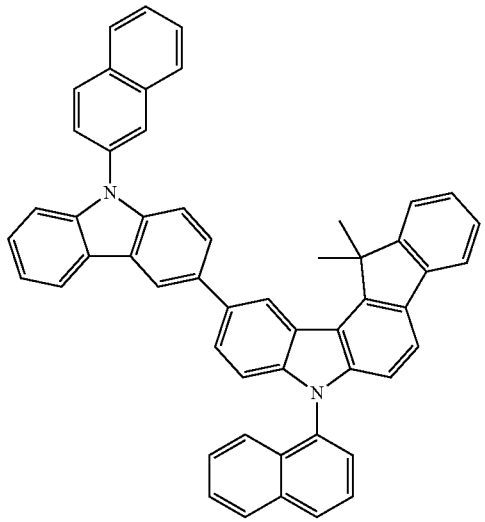
F-613
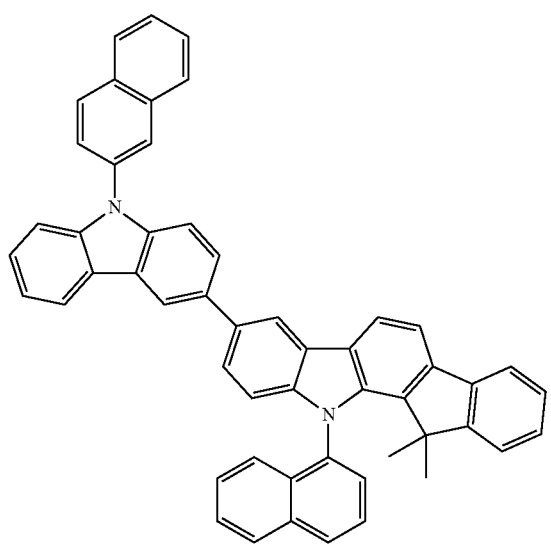
F-614
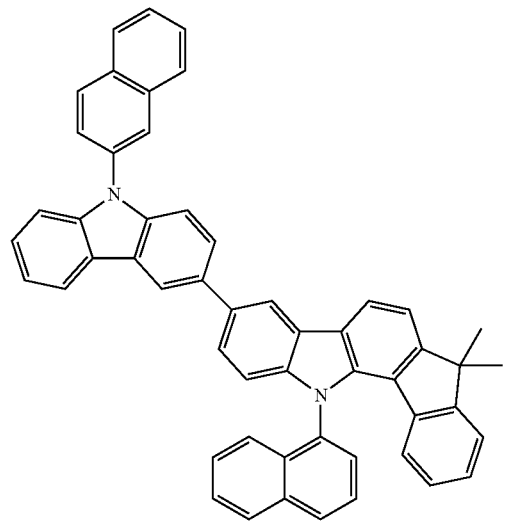

-continued
F-615
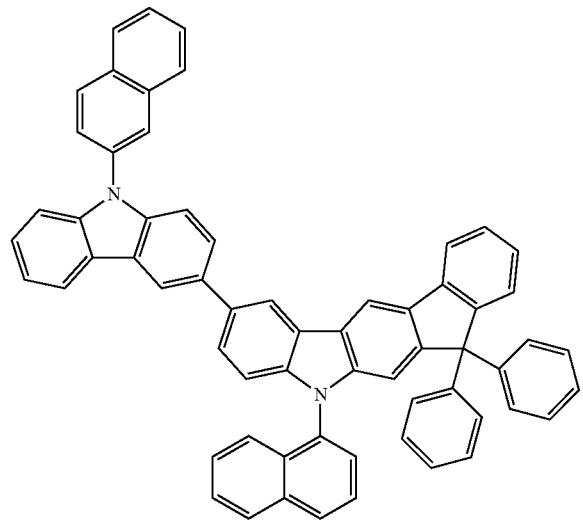
F-616
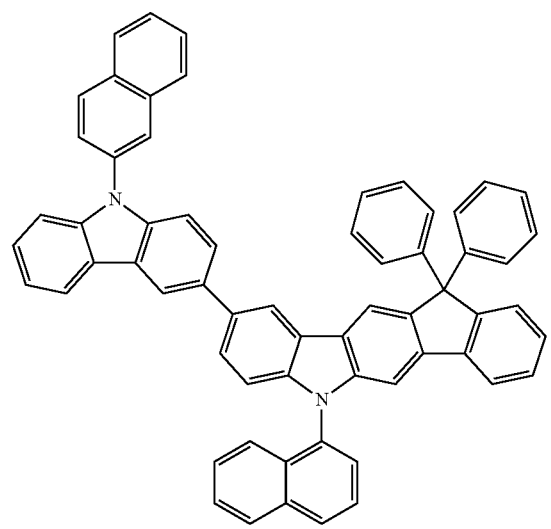
F-617
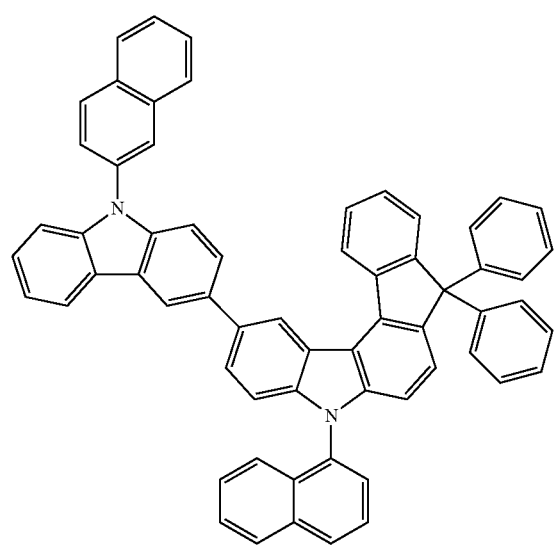
-continued
F-618
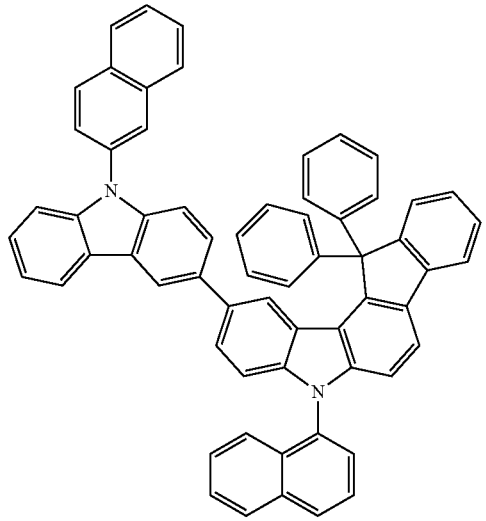
F-619
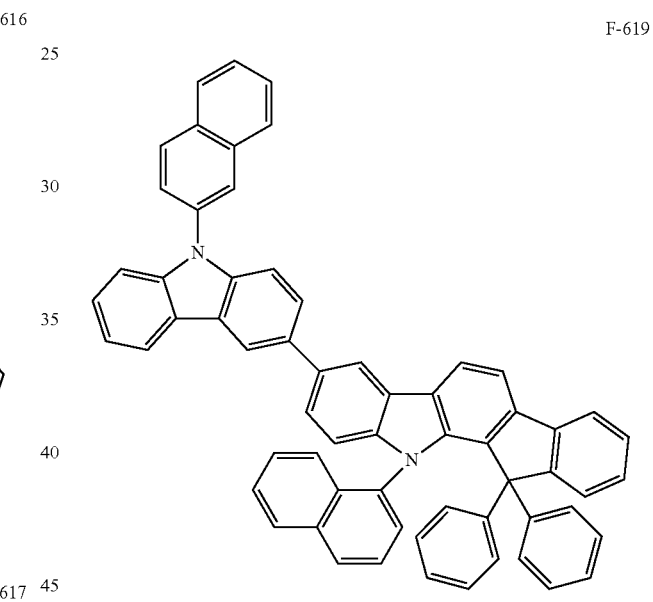
F-620
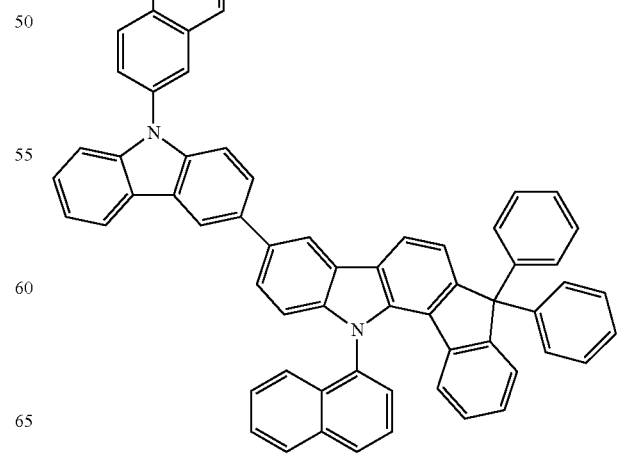

F-621
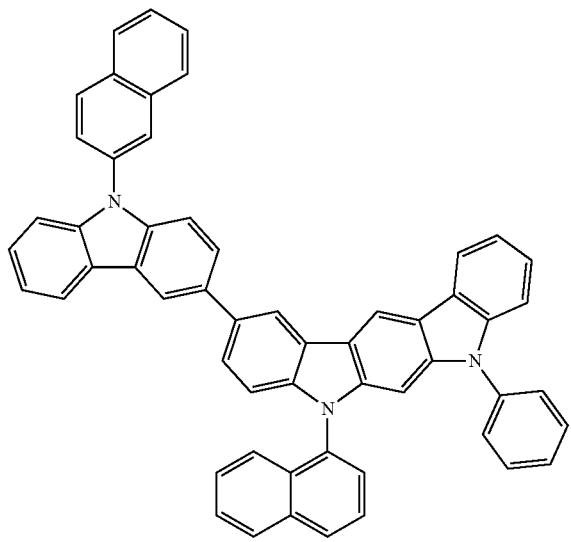
F-622
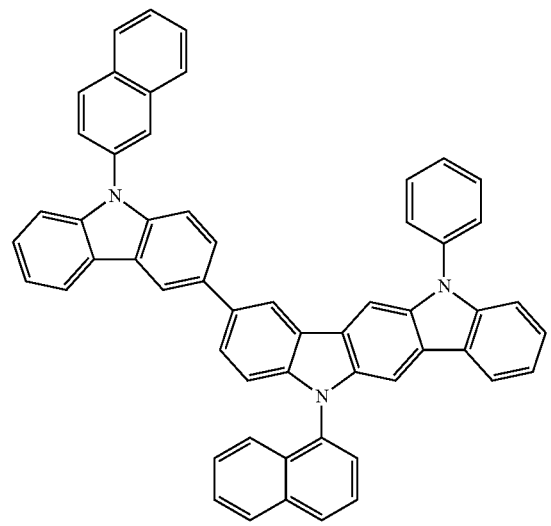
F-623
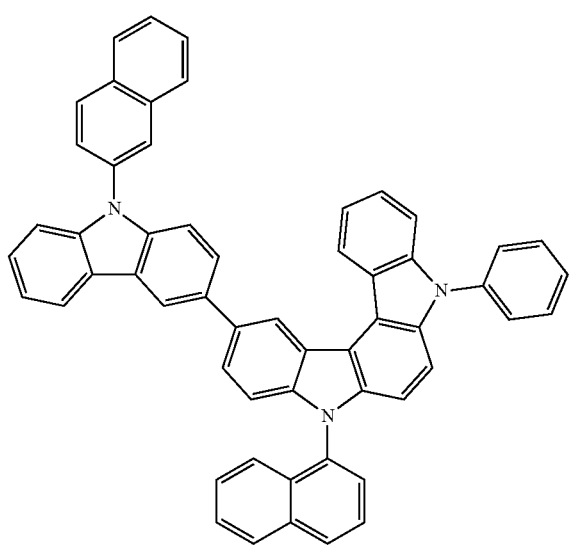
F-624
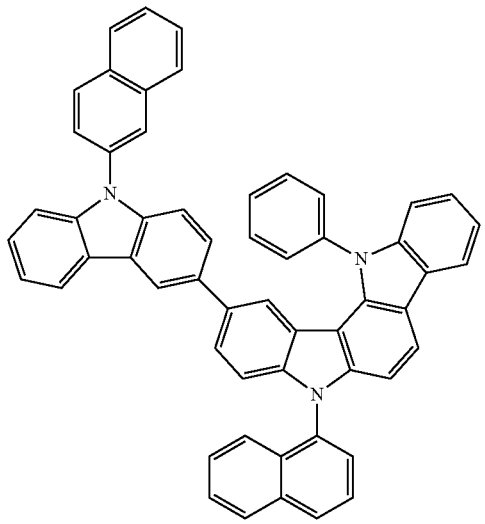
F-625
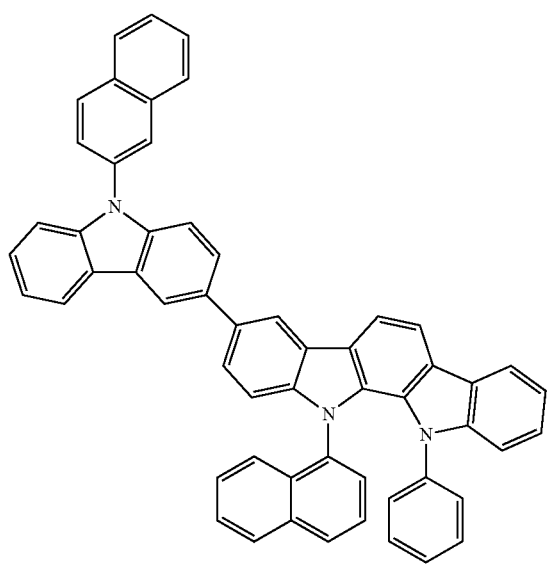
F-626
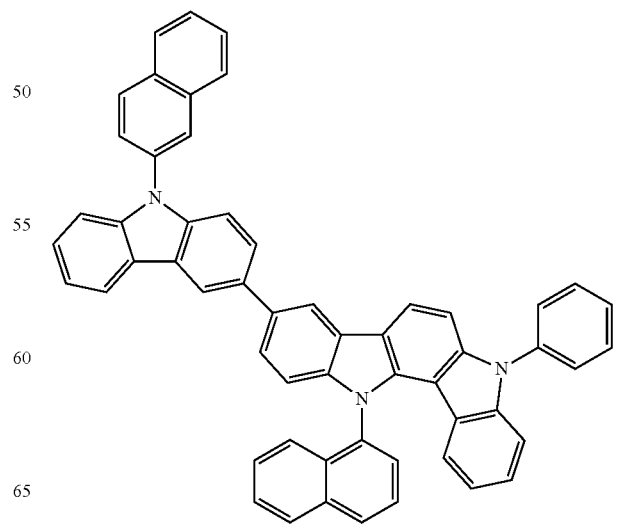

F-627
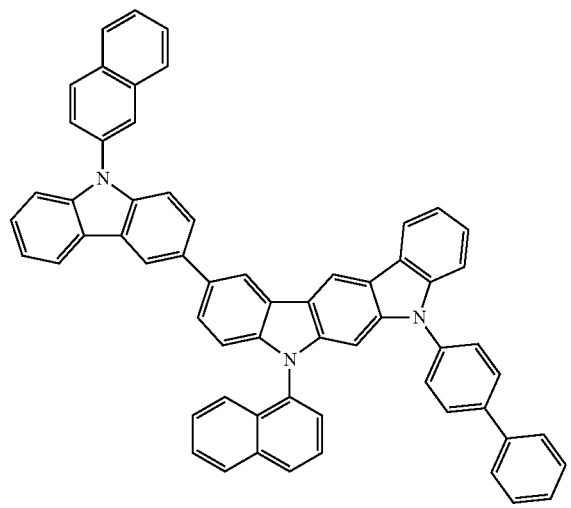
F-628
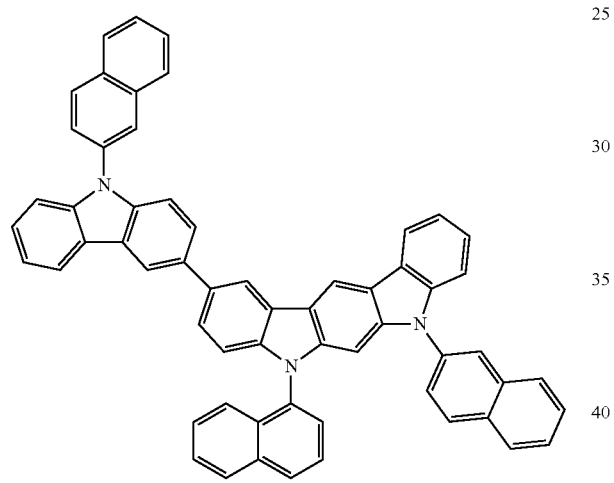
F-629
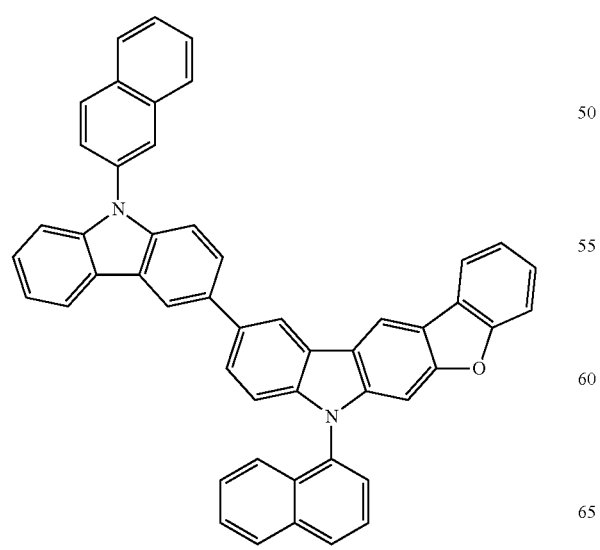
F-630
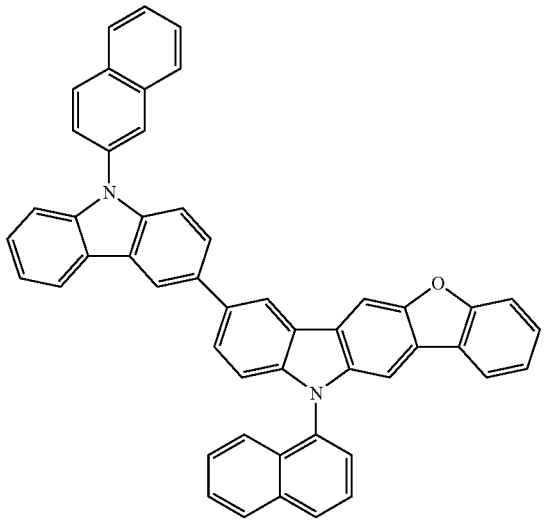
F-631
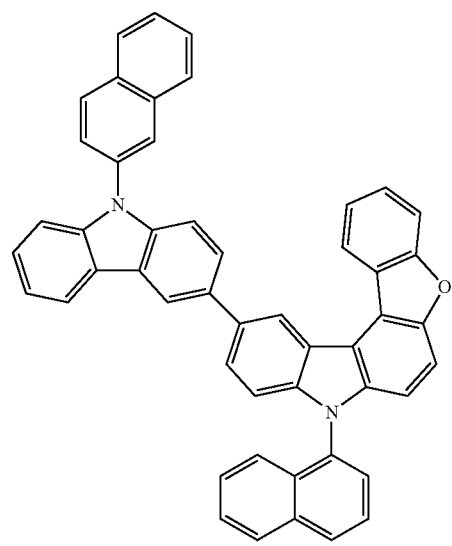
F-632
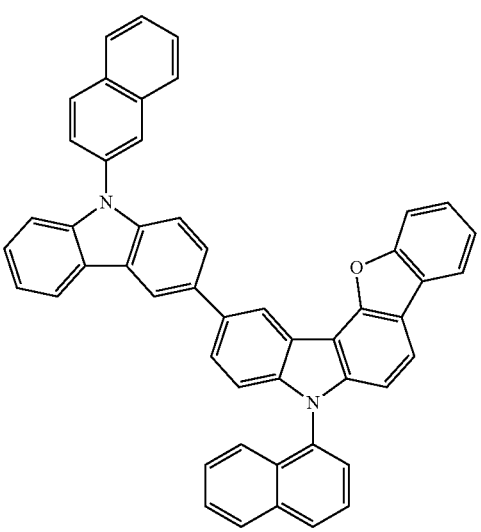

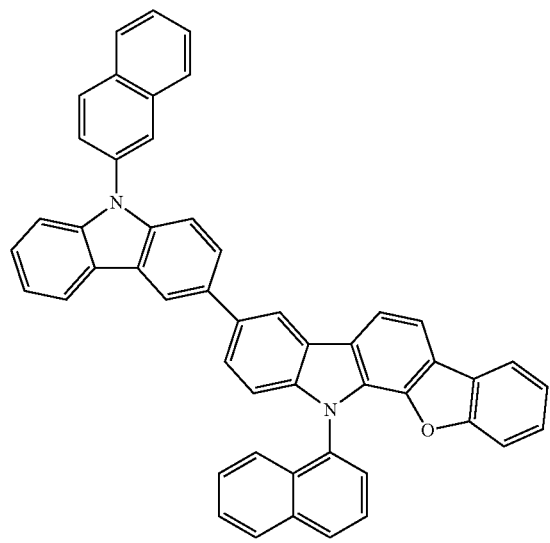
F-633
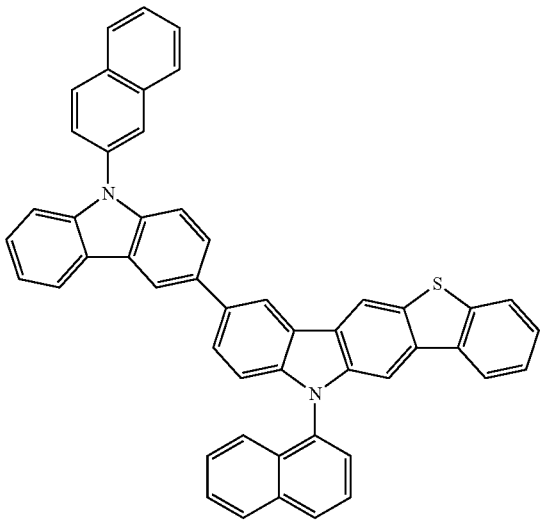
F-636
F-634
F-637
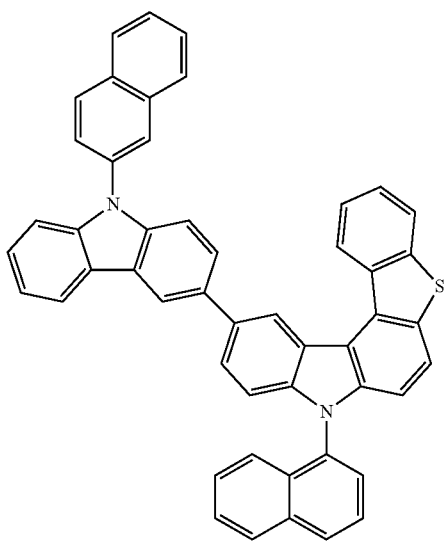
F-635
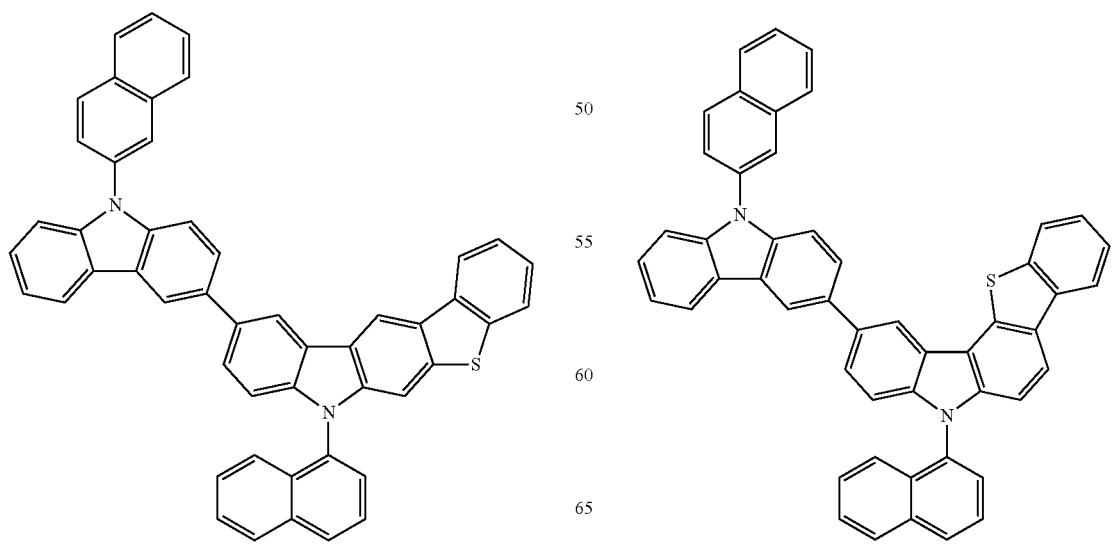
F-638

F-639
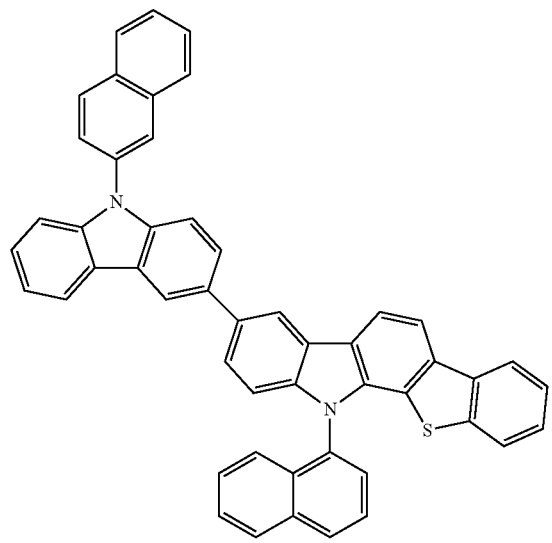
F-640
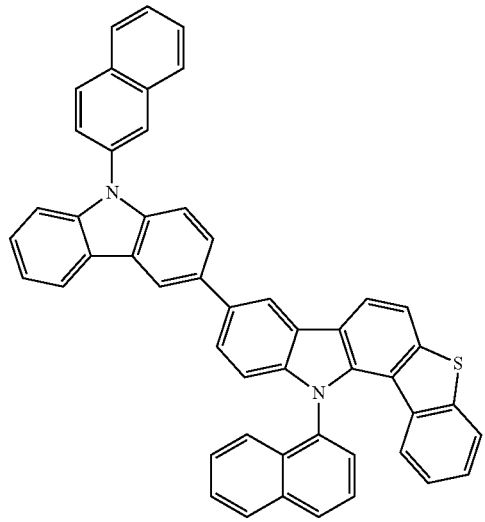
F-641
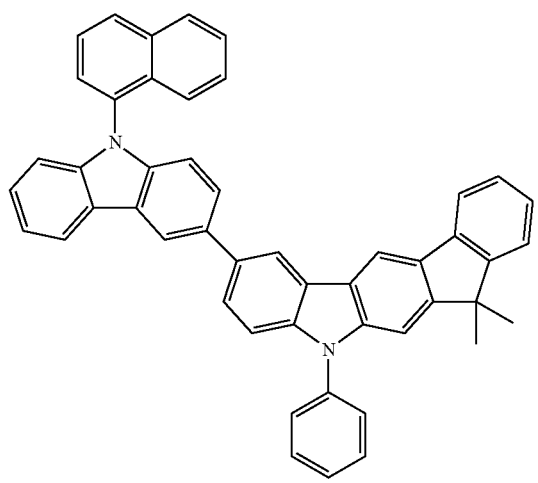
F-642
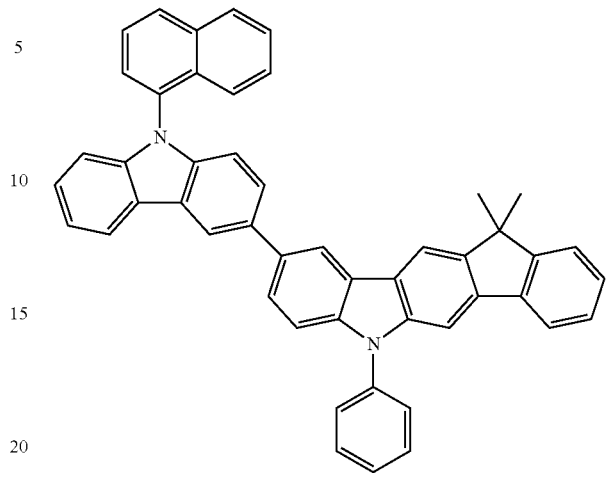
F-643
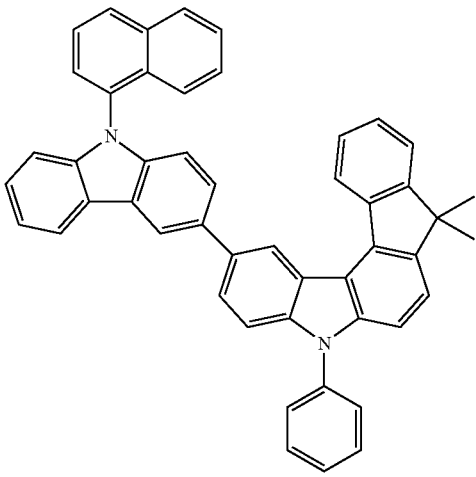
F-644
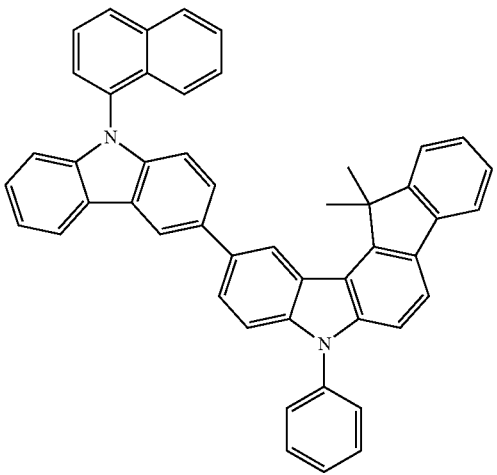

F-645
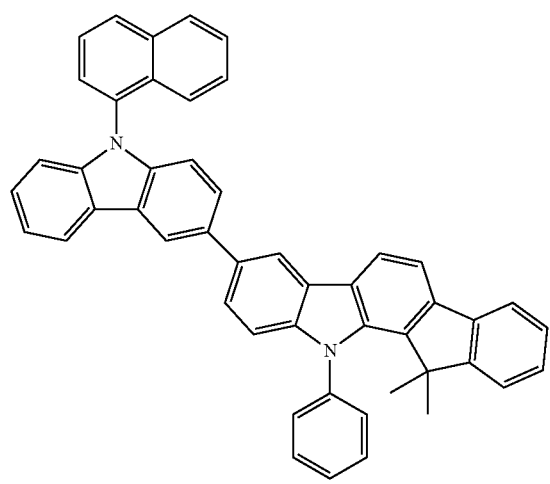
F-648
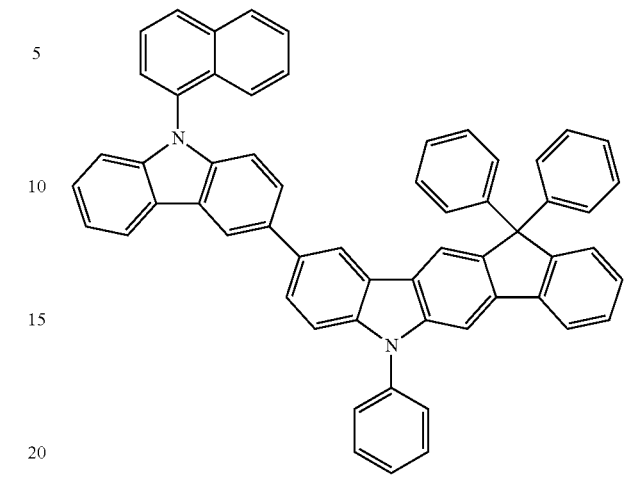
F-646
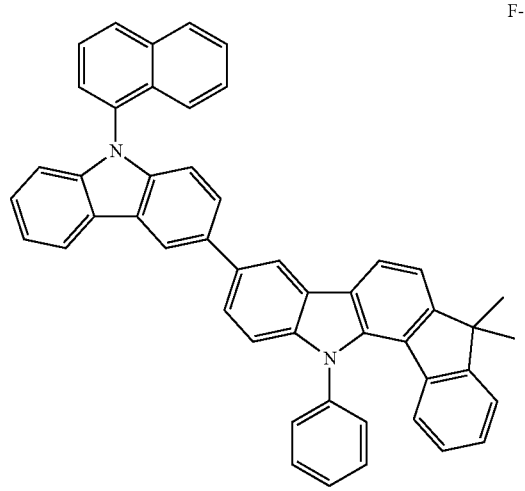
F-649
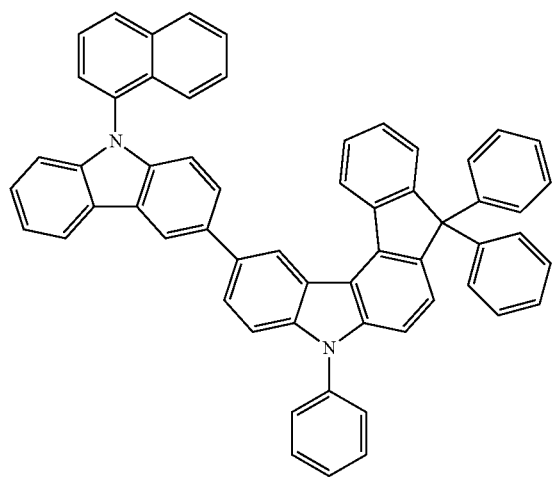
F-647
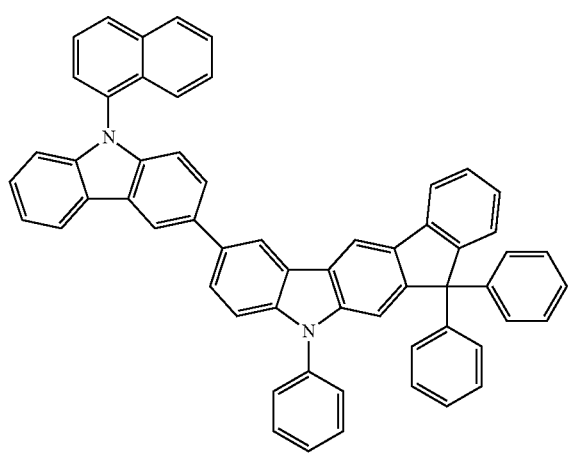
F-650
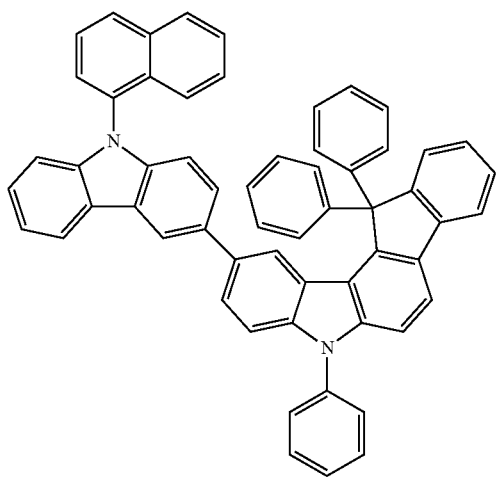

-continued
F-651
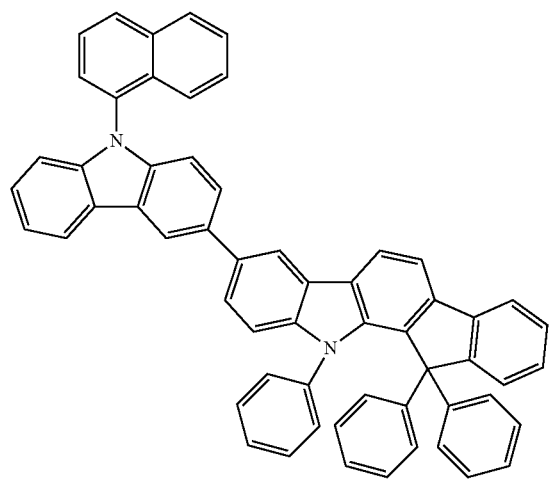
F-654
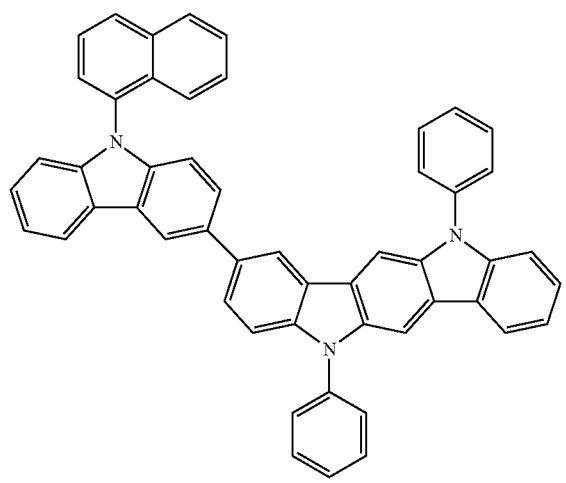
F-652
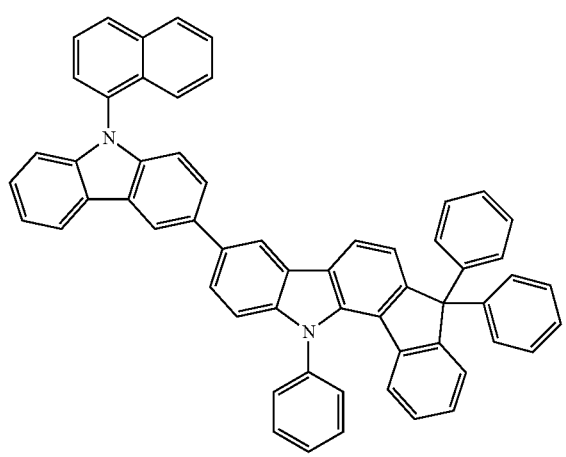
F-655
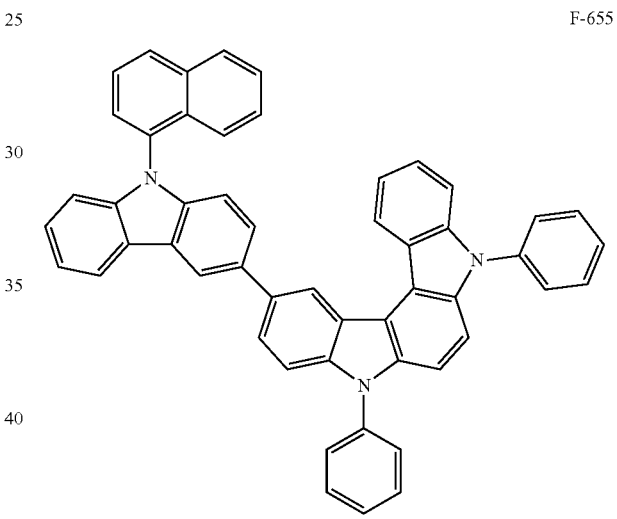
F-653
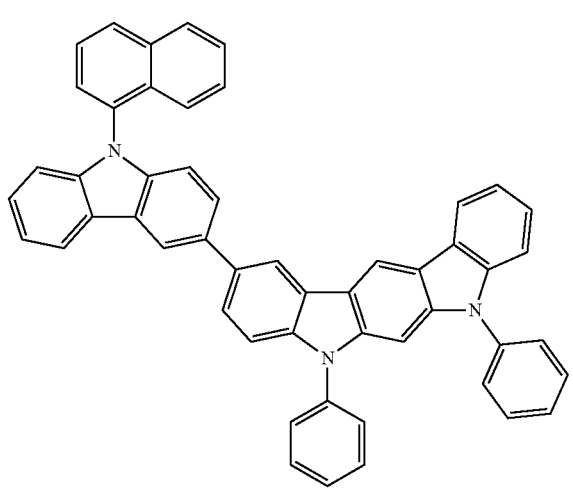
F-656
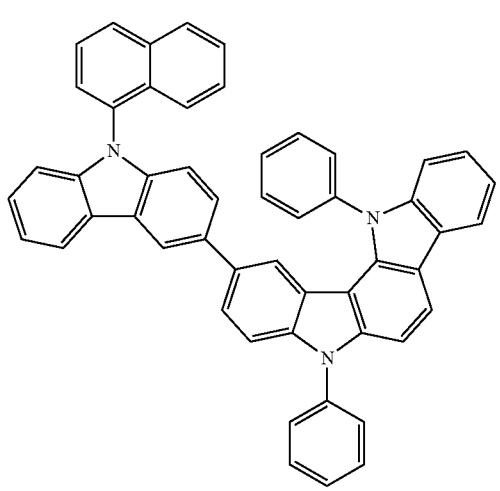

F-657
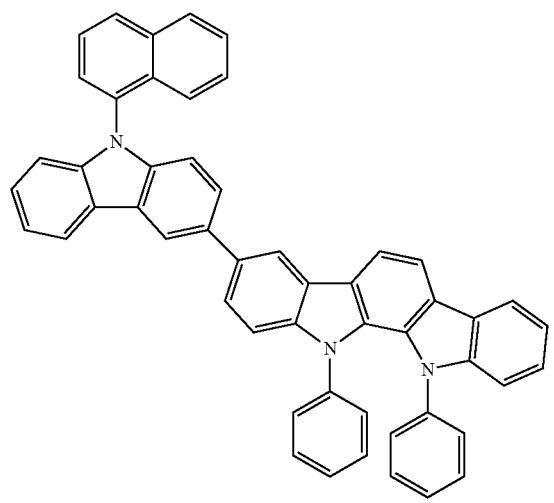
F-658
F-660
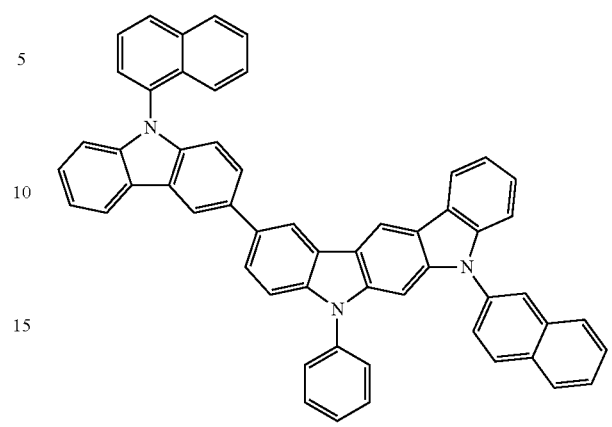
F-661
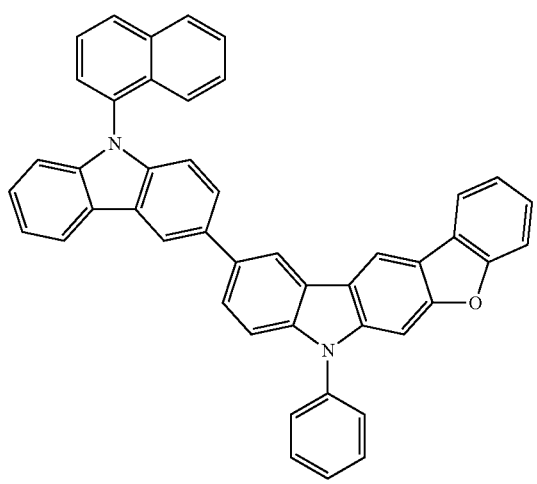
F-659
F-662
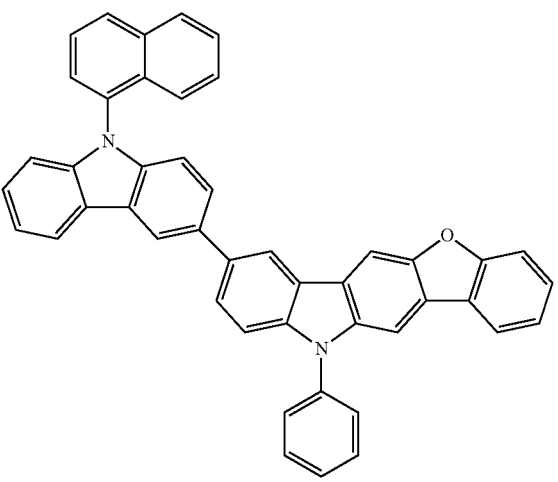

F-663
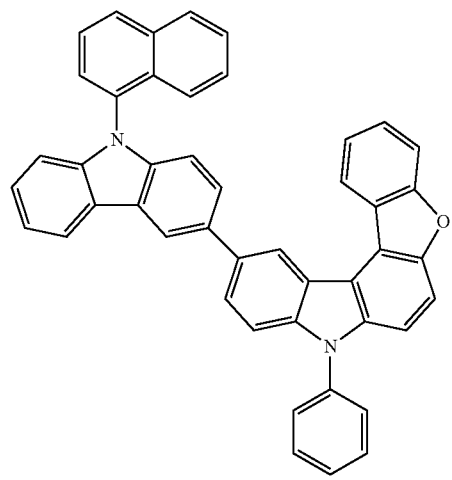
F-664
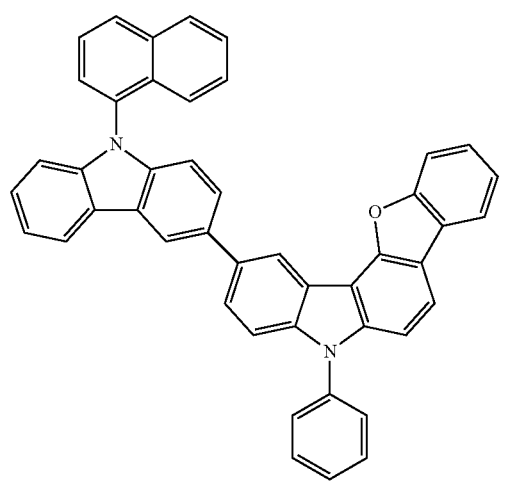
F-665
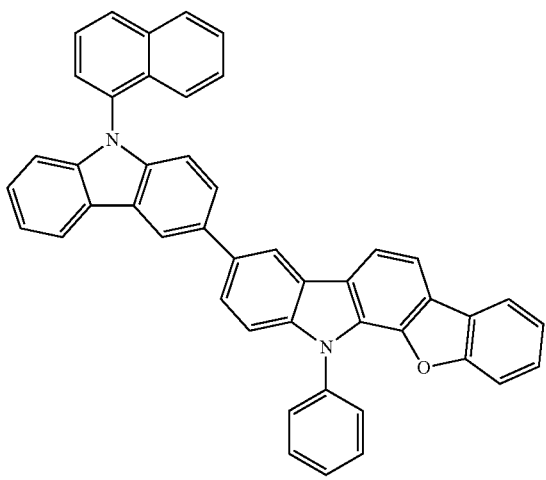
F-666
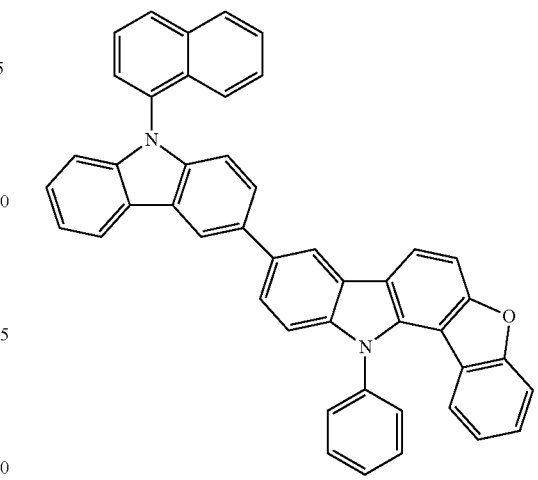
F-667
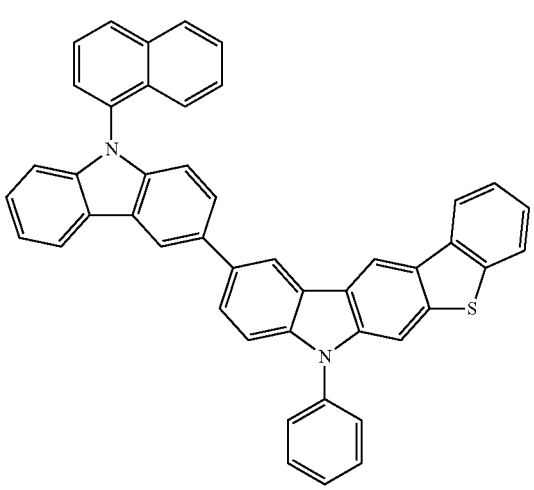
F-668
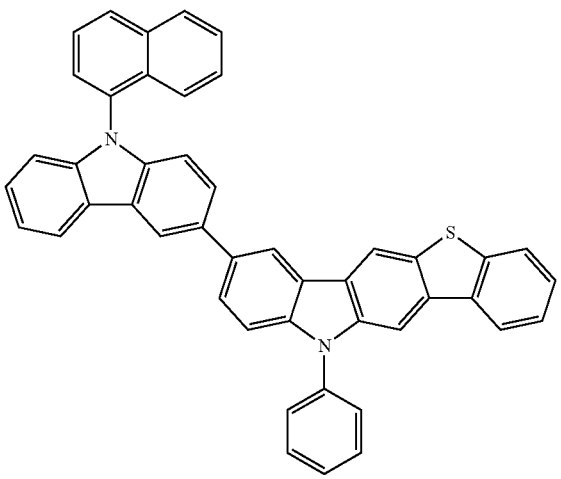

F-669
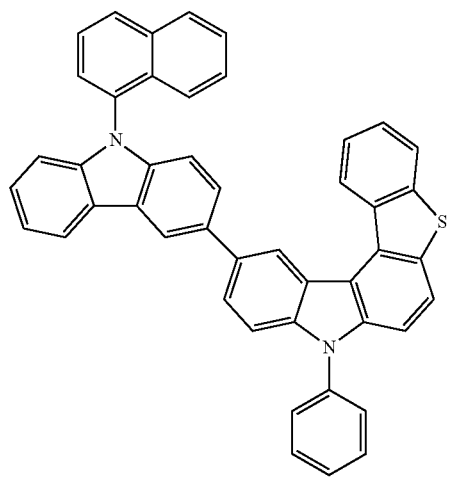
F-670
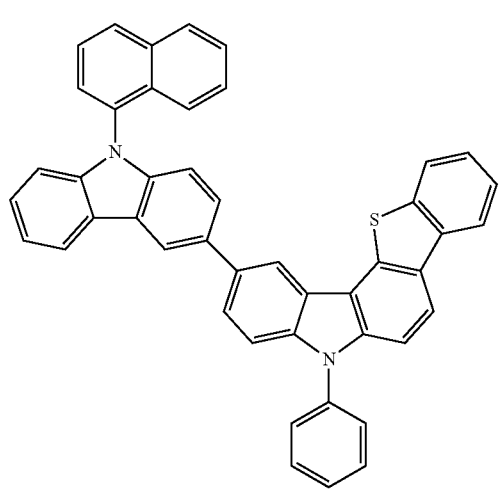
F-671
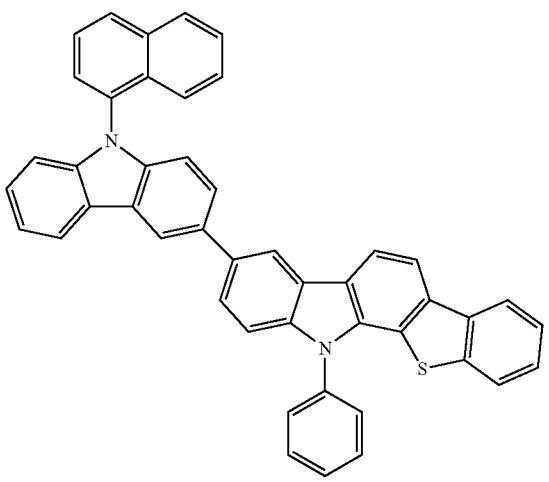
F-672
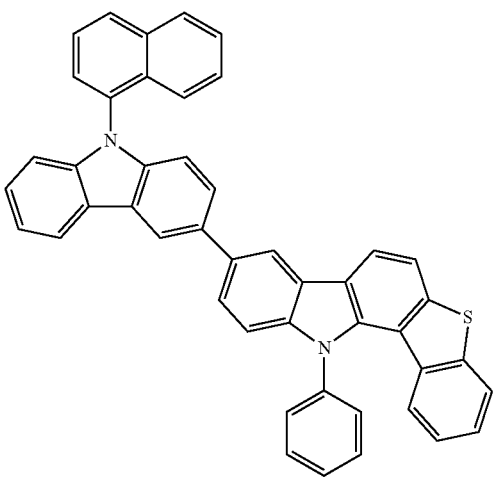
F-673
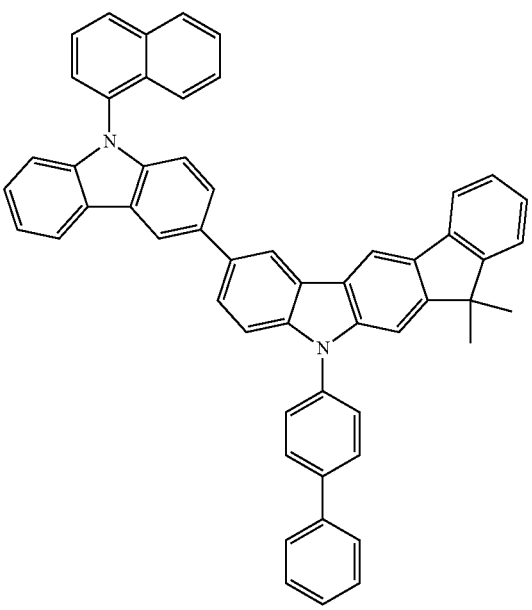

F-674
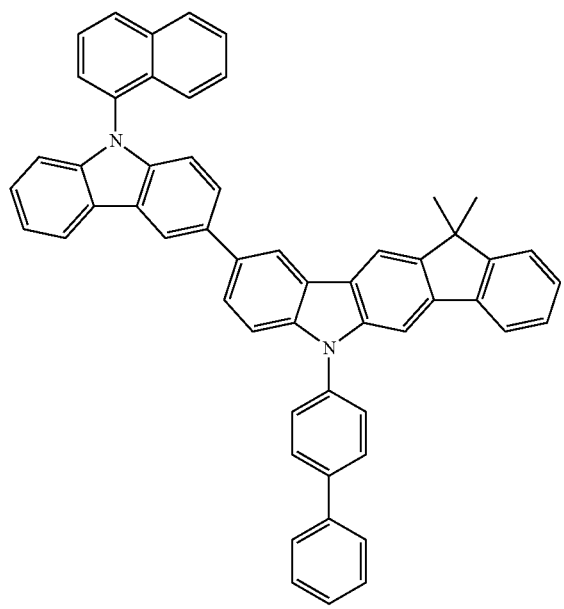
F-676
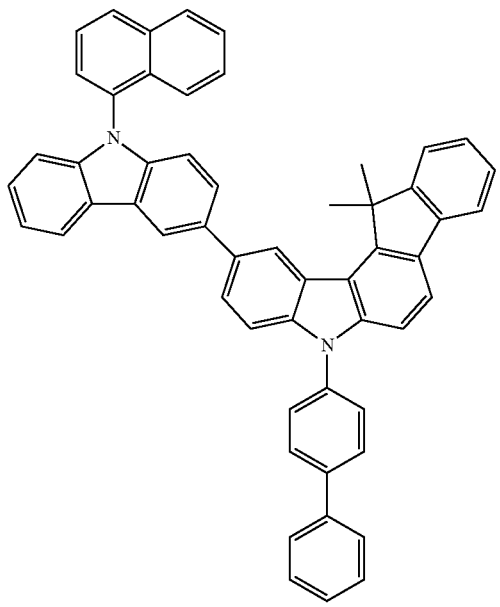
F-675
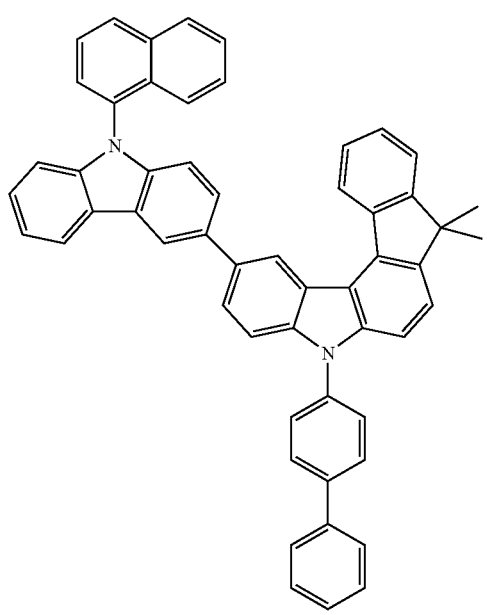
F-677
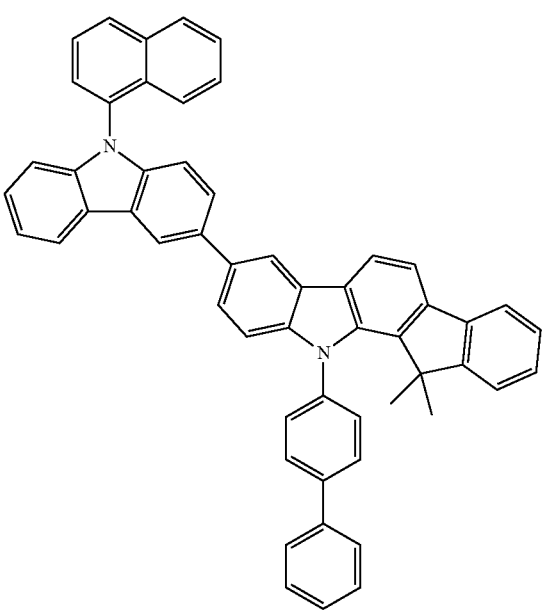

F-678
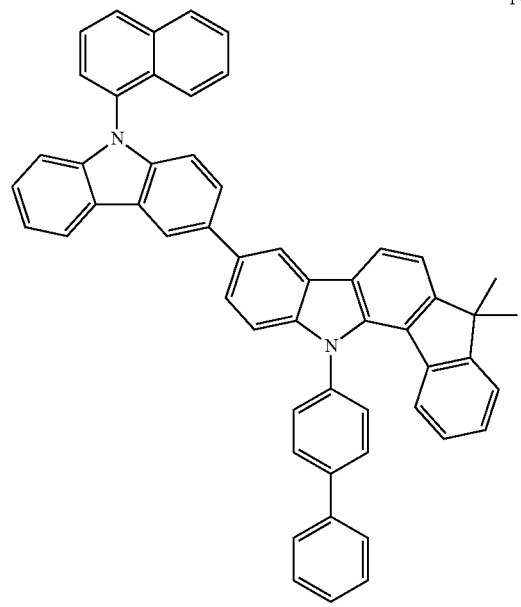
F-680
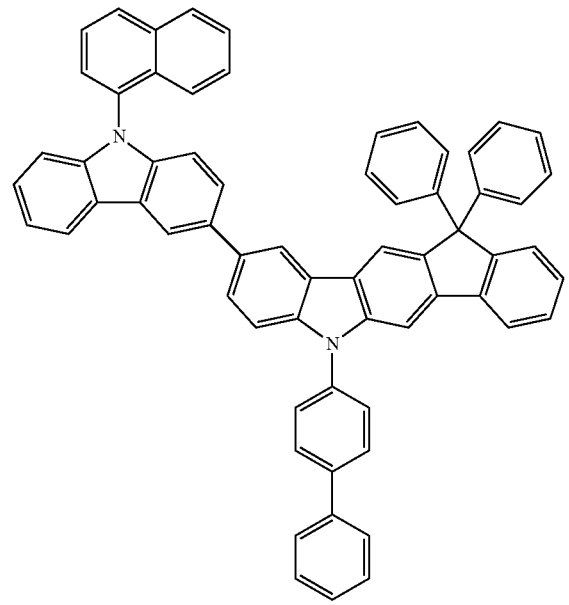
F-679
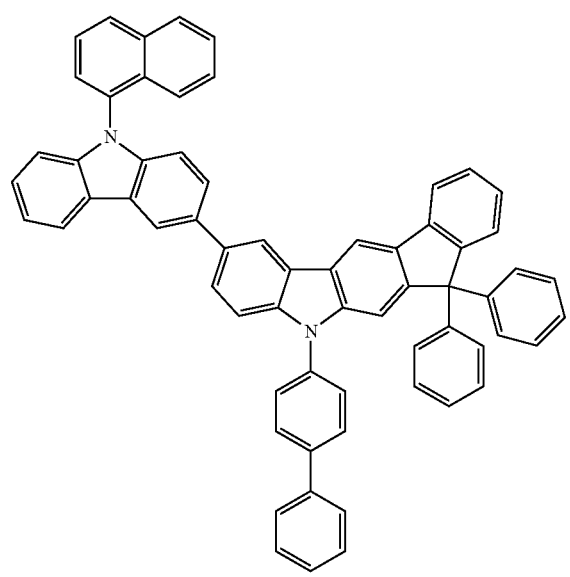
F-681
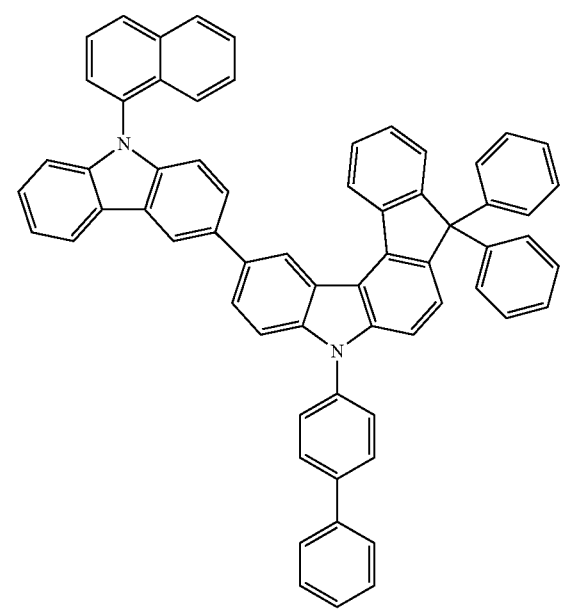

F-682
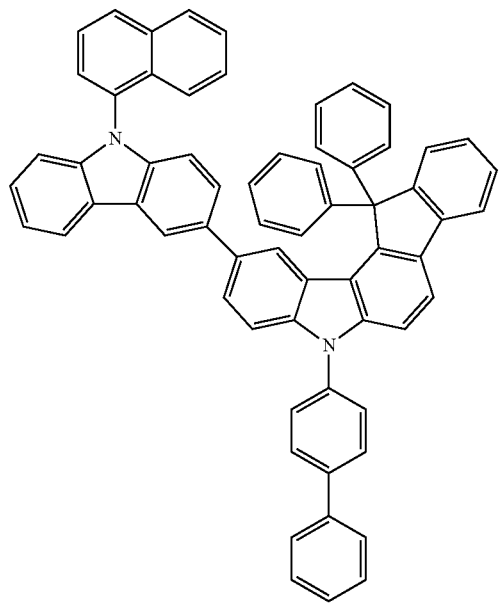
F-684
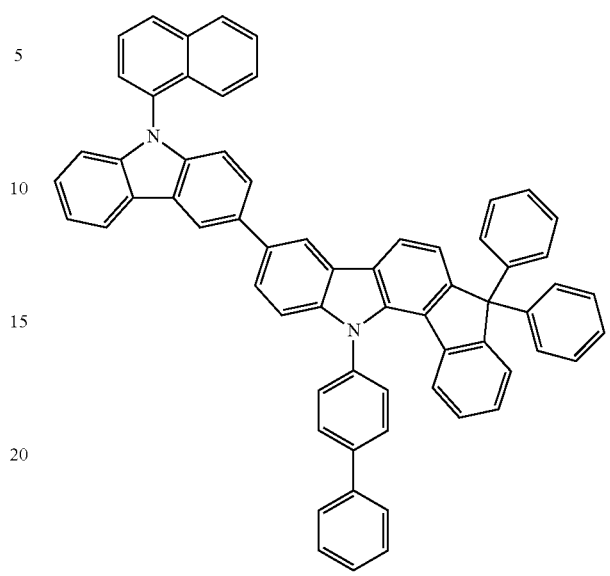
F-683
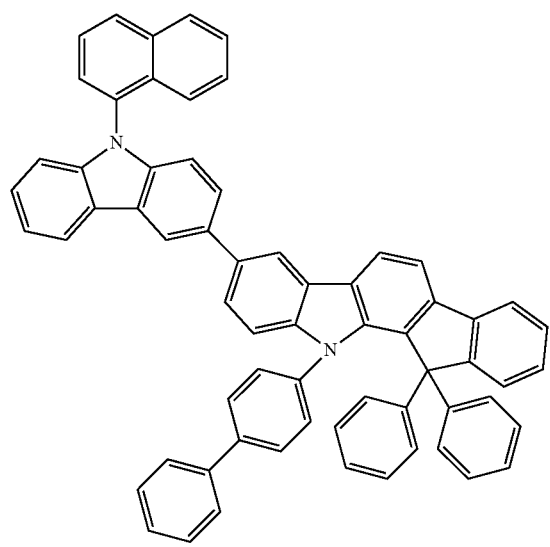
F-685
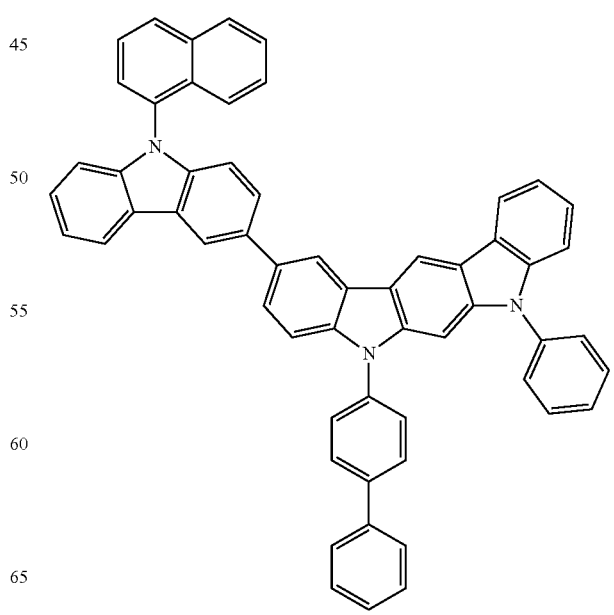

F-686
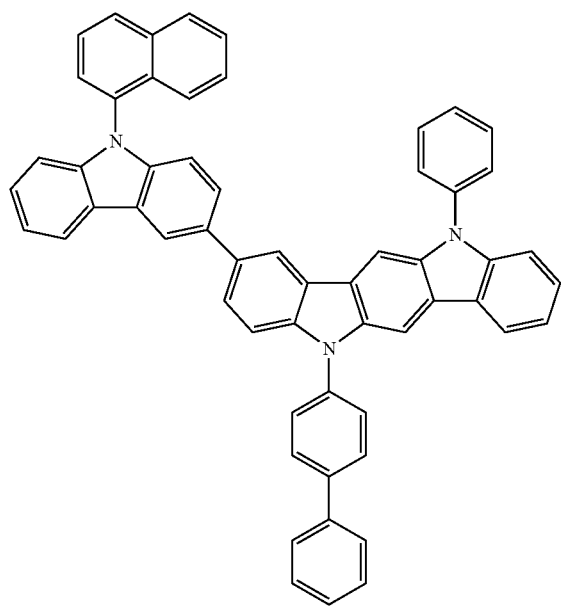
F-688
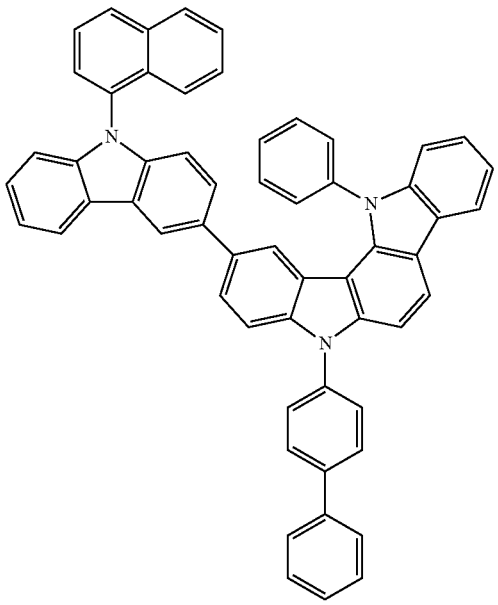
F-687
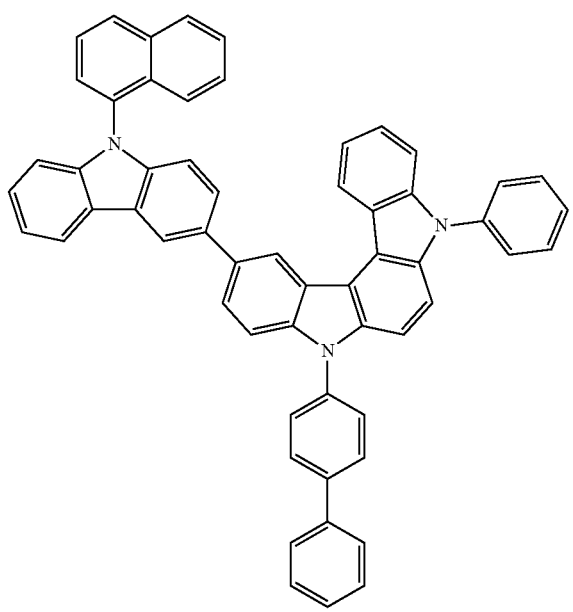
F-689
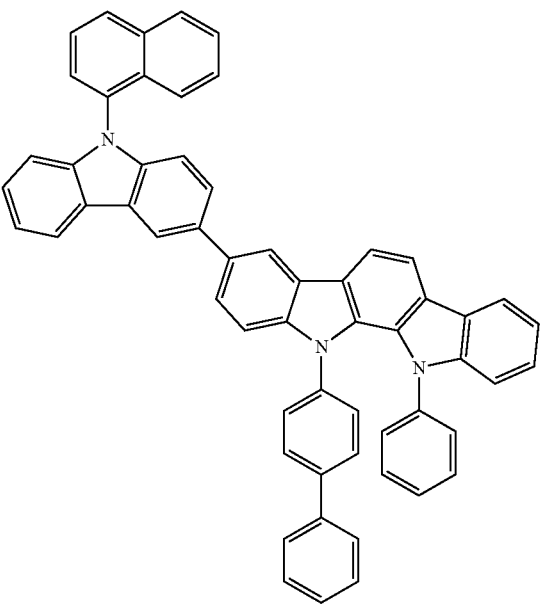

F-690
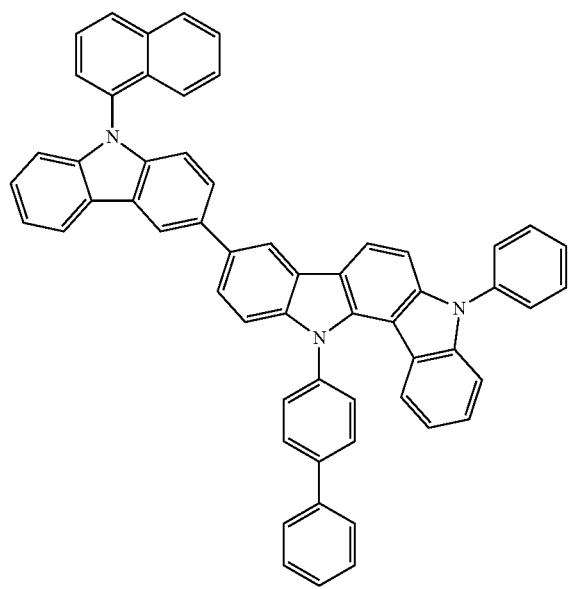
F-691
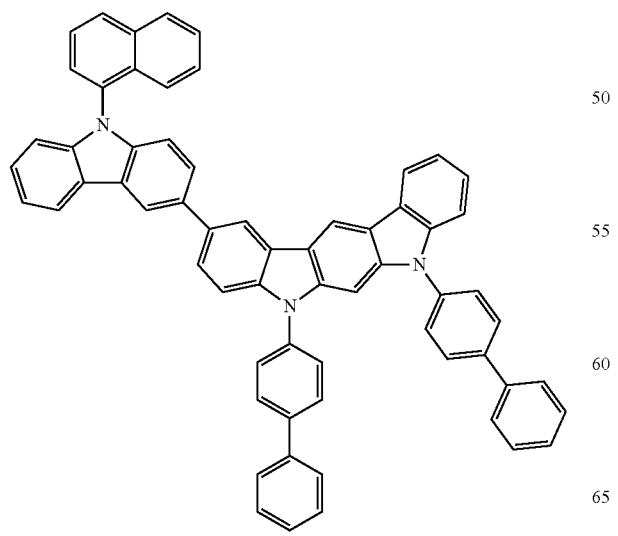
F-692
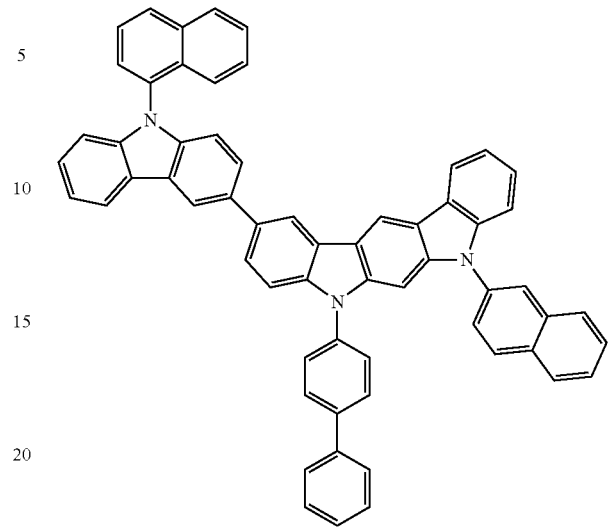
F-693
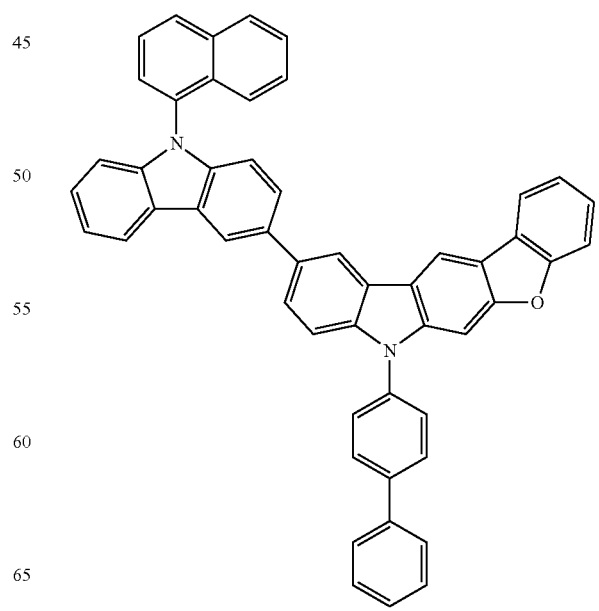

F-694
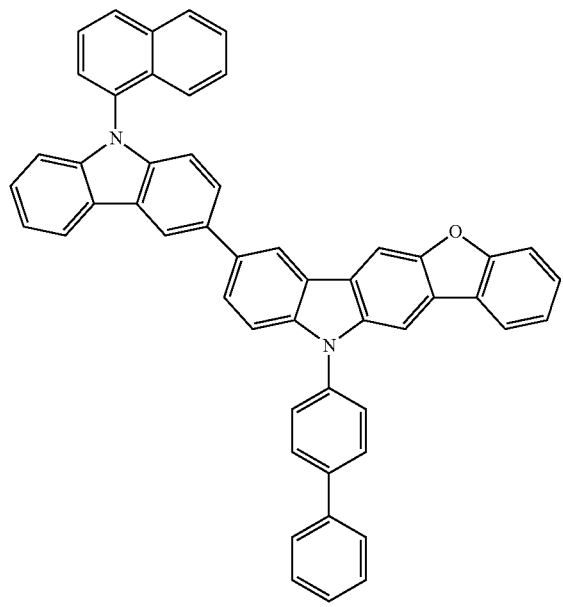
F-696
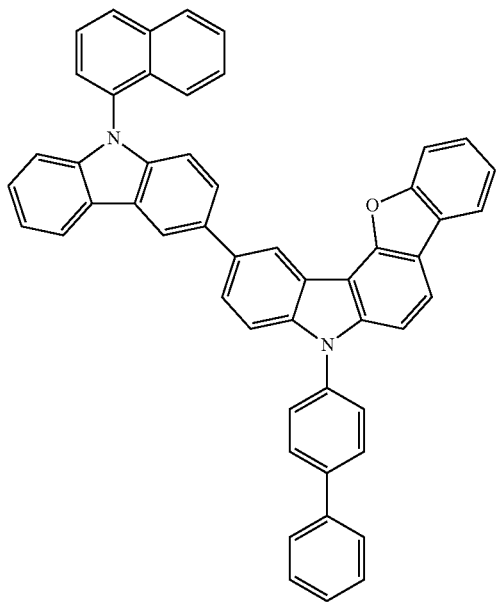
F-695
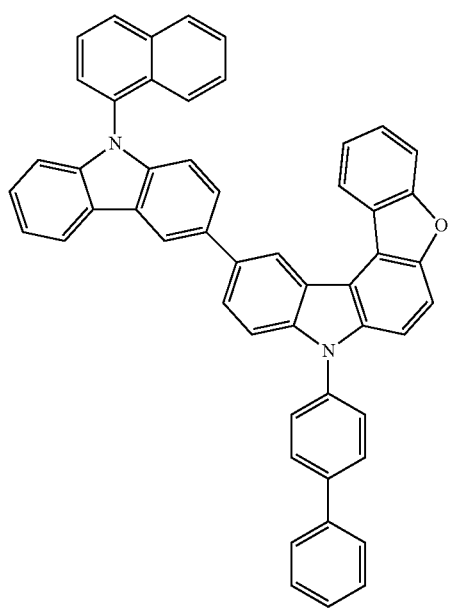
F-697
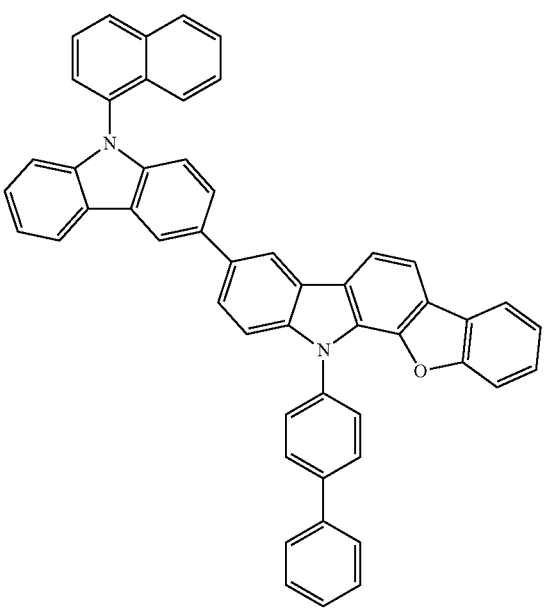

F-698
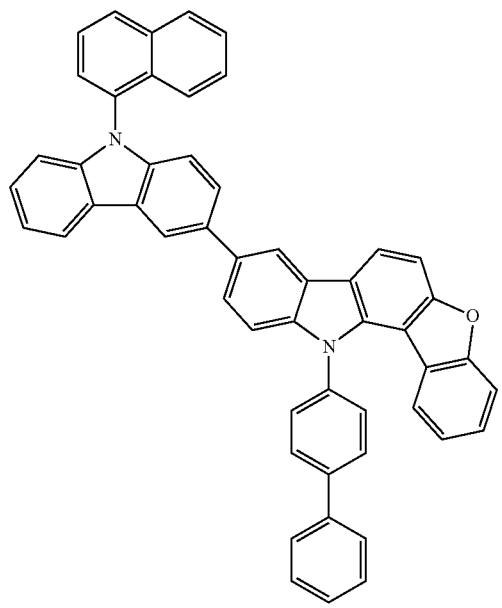
F-700
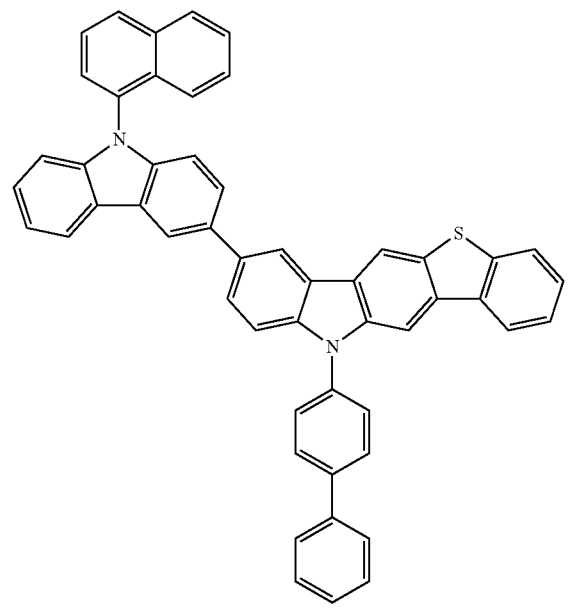
F-699
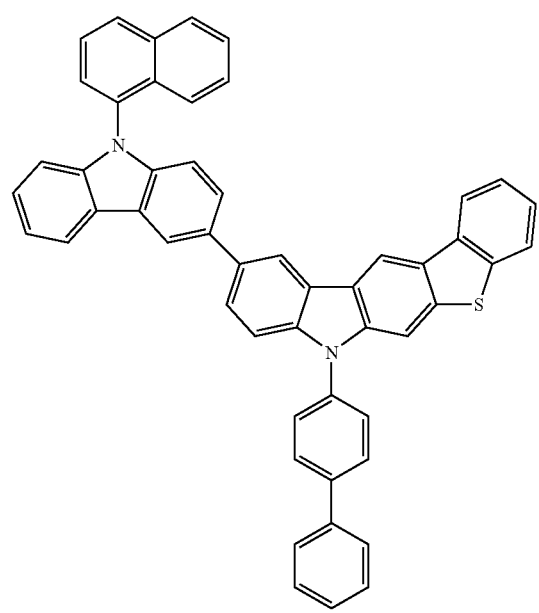
F-701
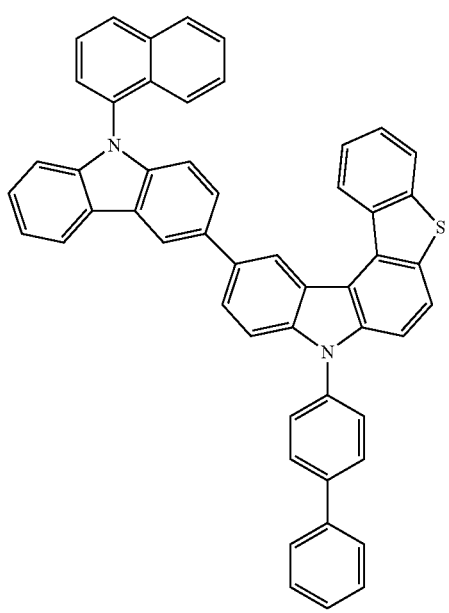

F-702
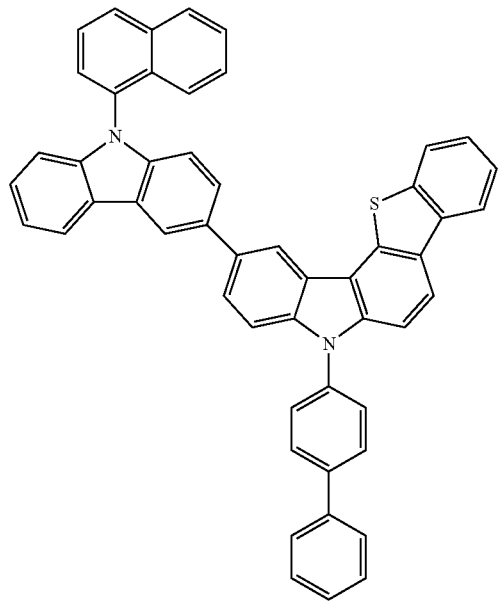
F-704
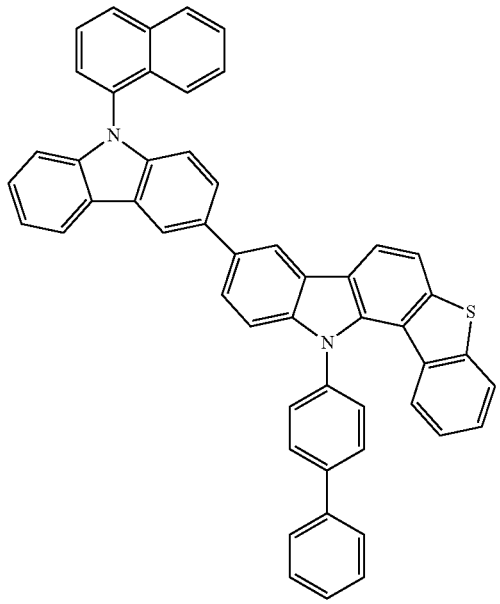
F-703
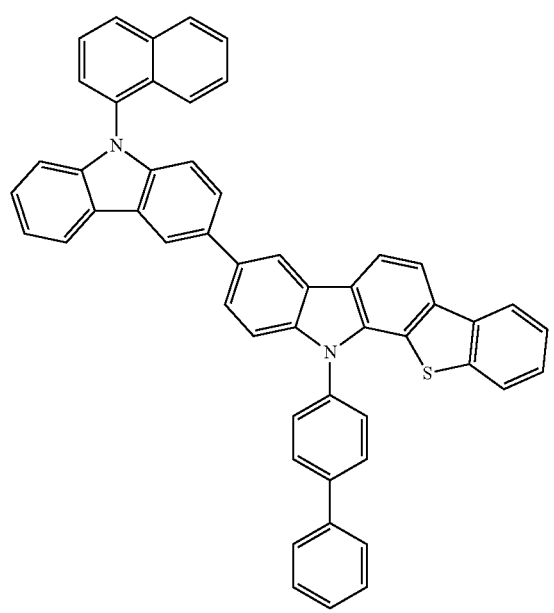
F-705
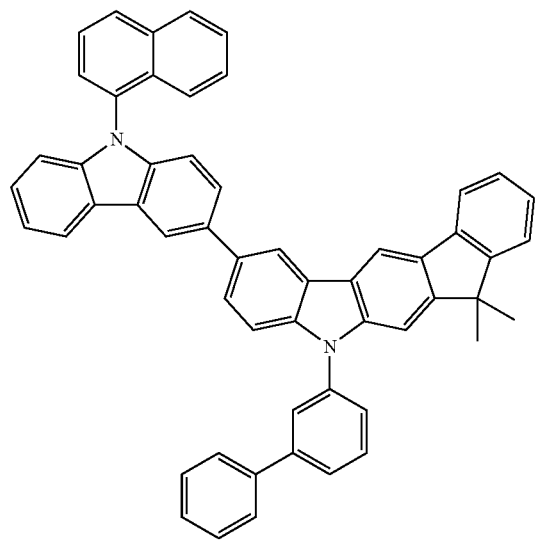

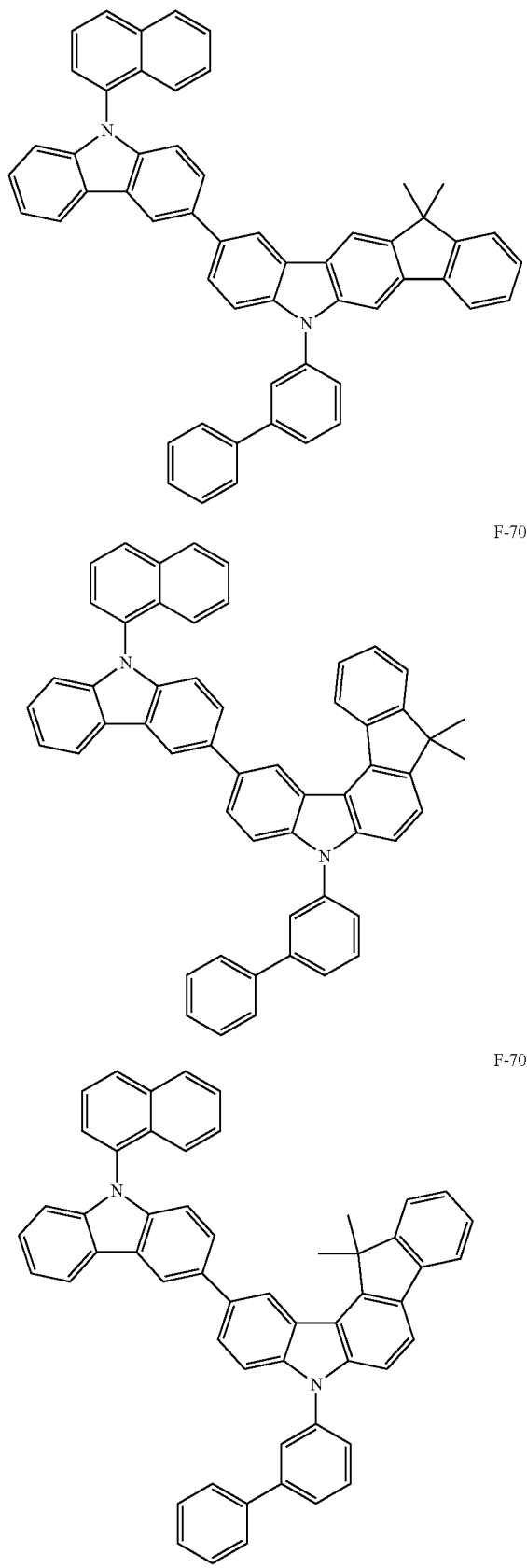
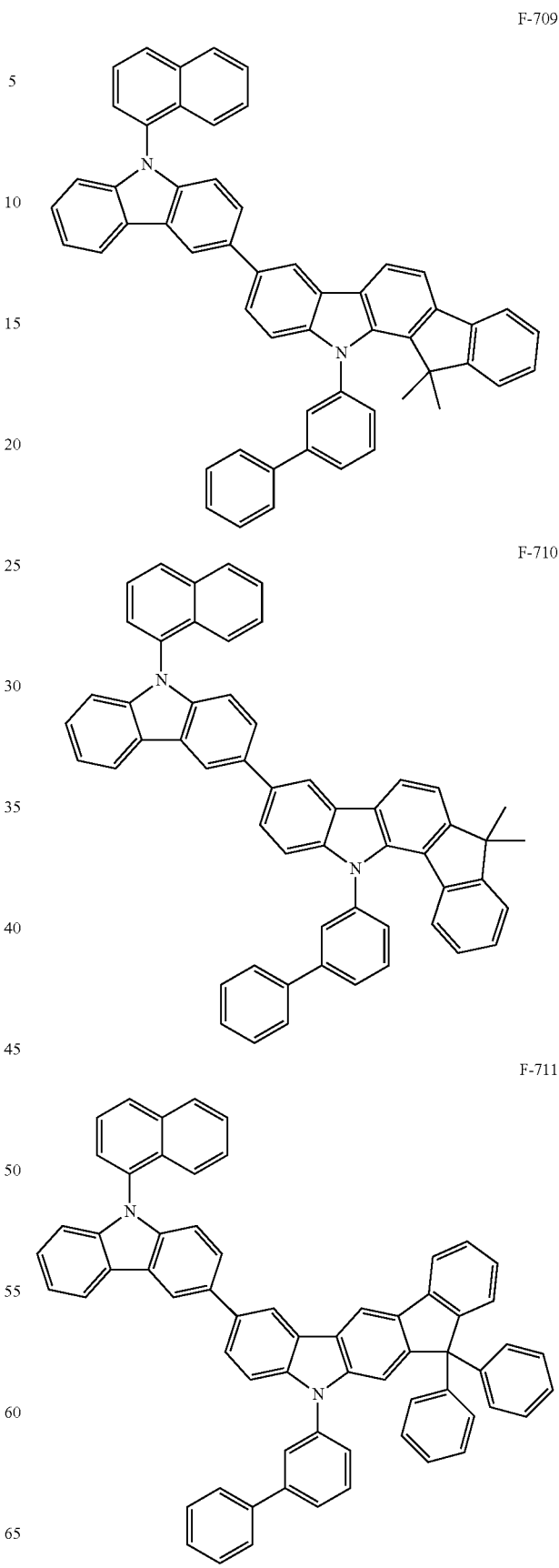

-continued
F-712
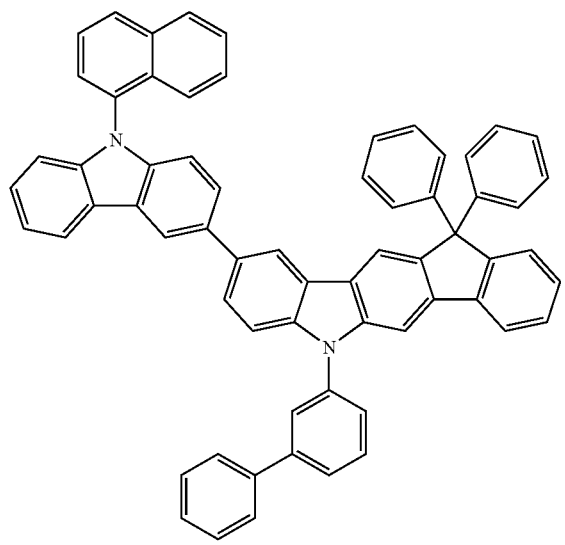
F-713
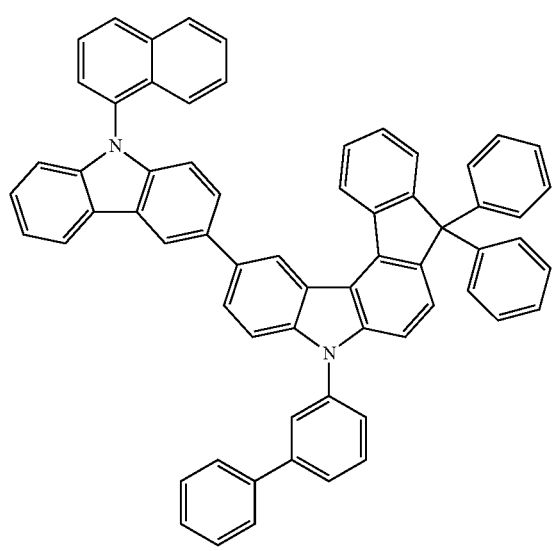
F-714
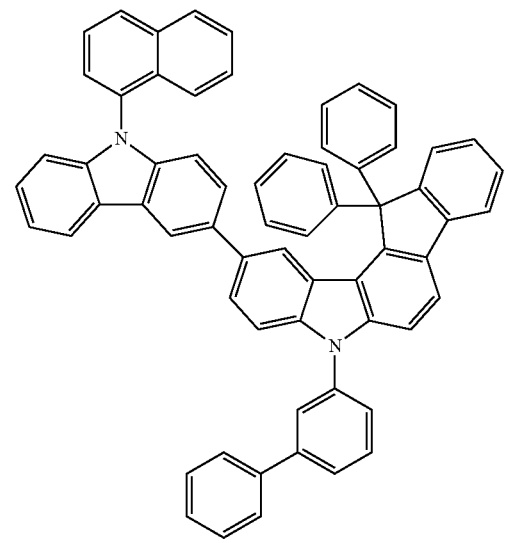
-continued
F-715
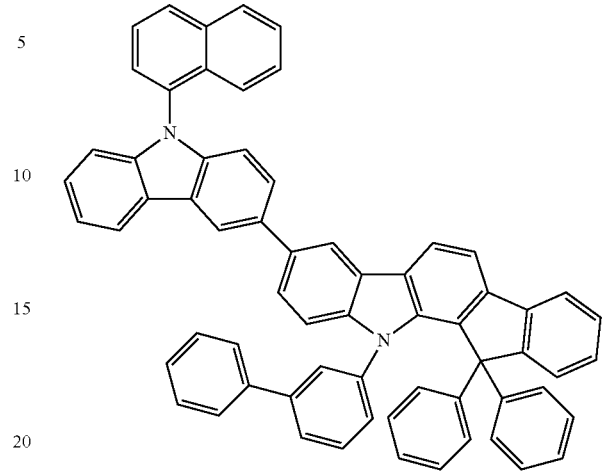
F-716
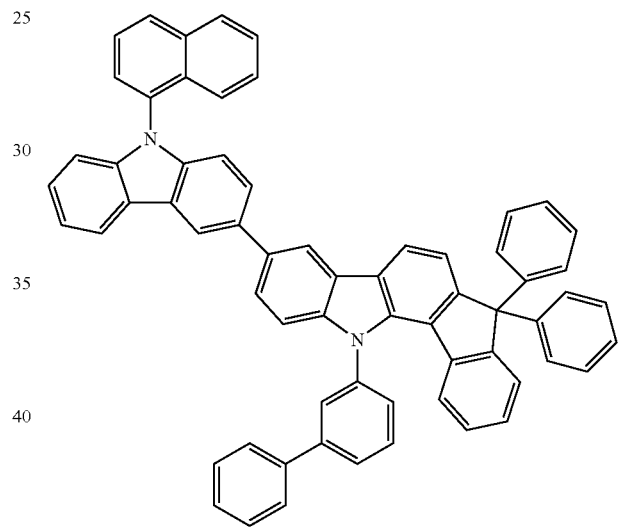
F-717
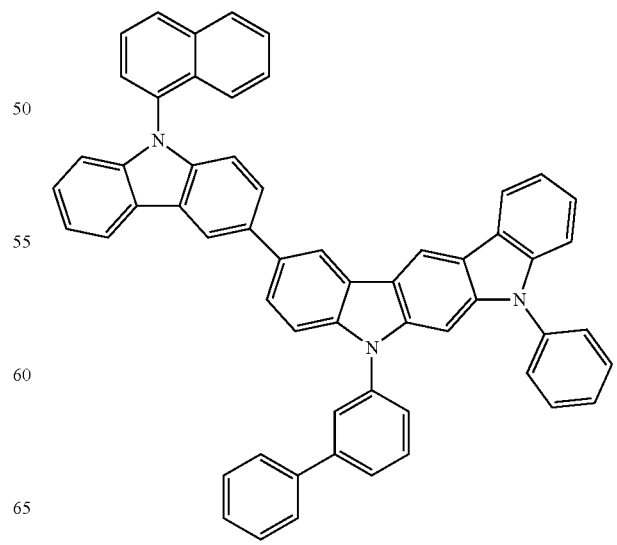

-continued
F-718
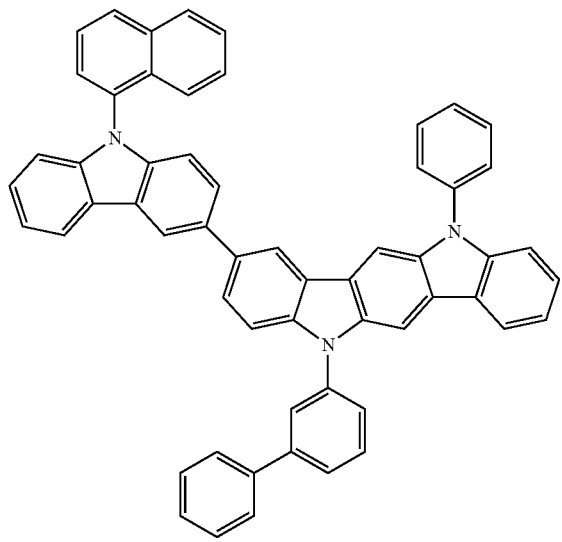
F-719
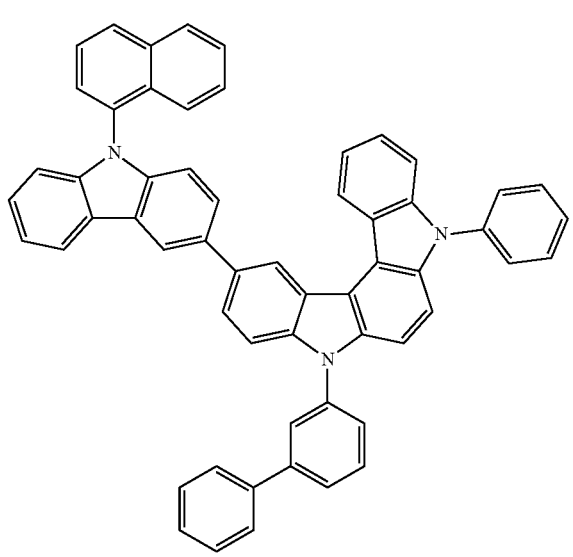
F-720
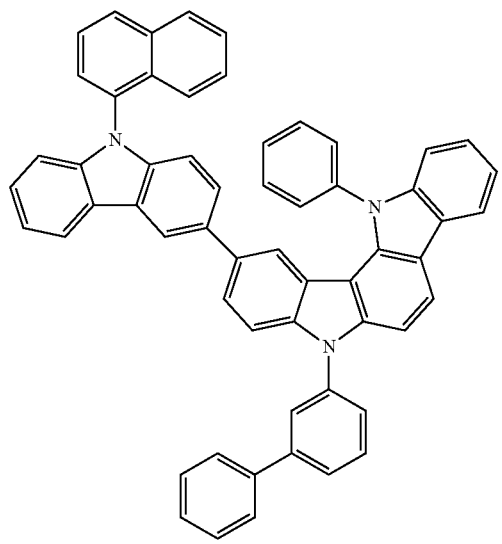
-continued
F-721
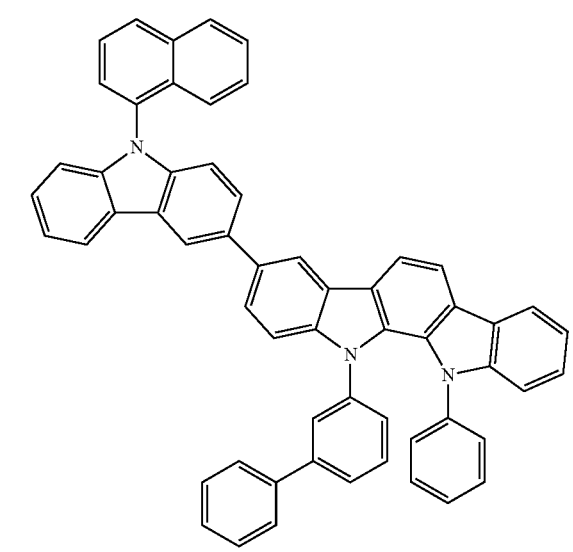
F-722
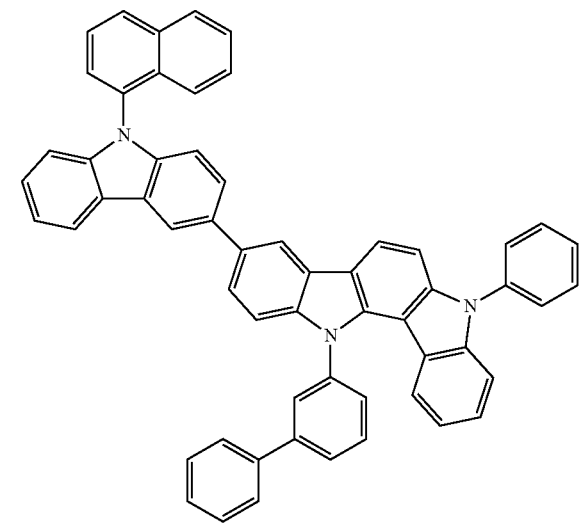
F-723
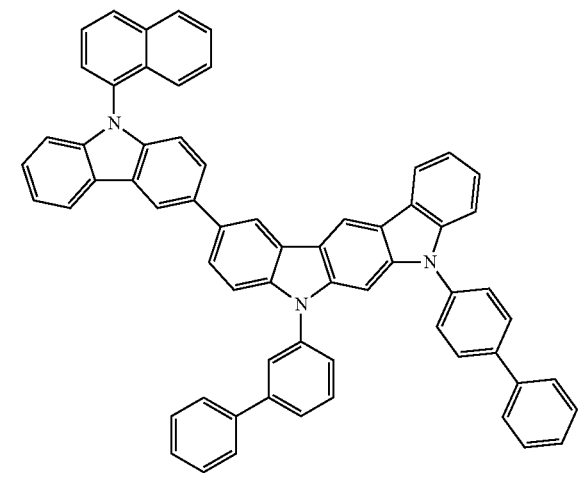

F-724
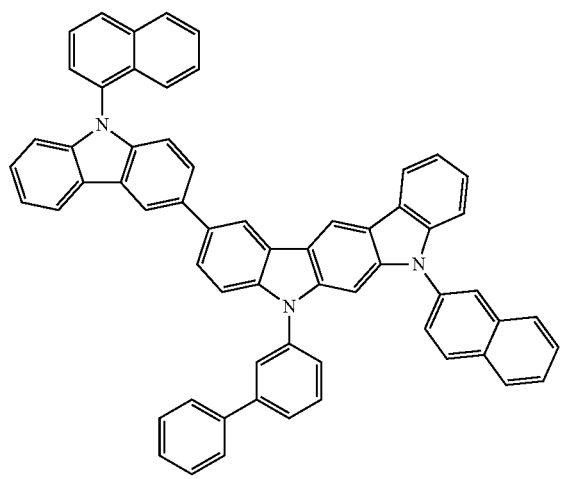
F-725
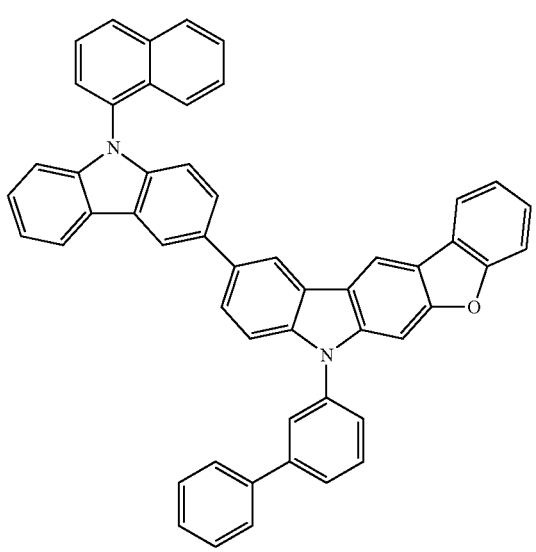
F-726
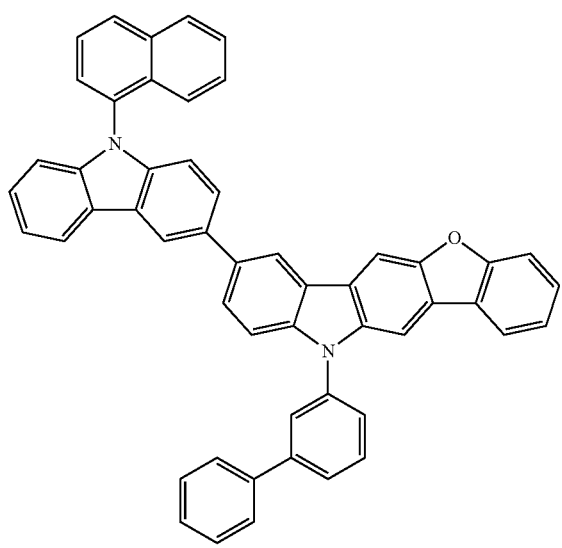
F-727
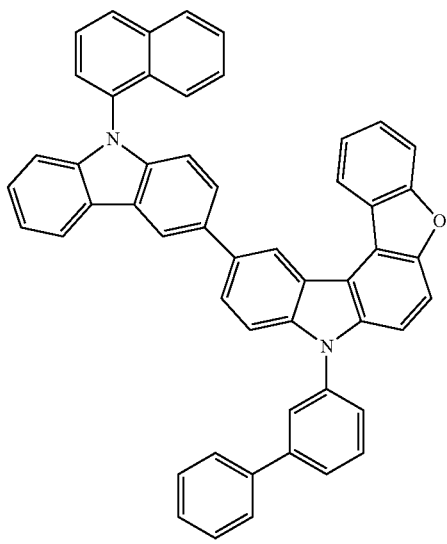
F-728
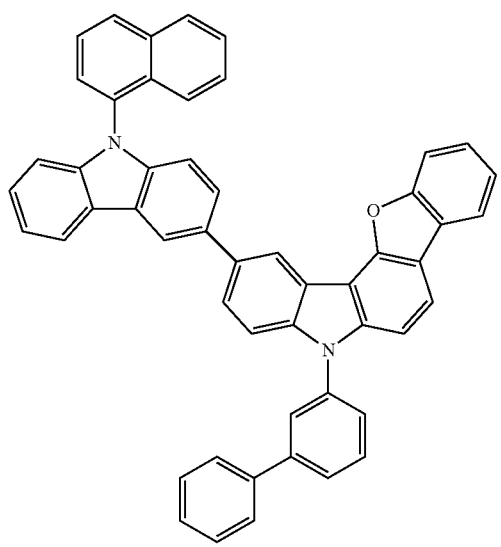
F-729
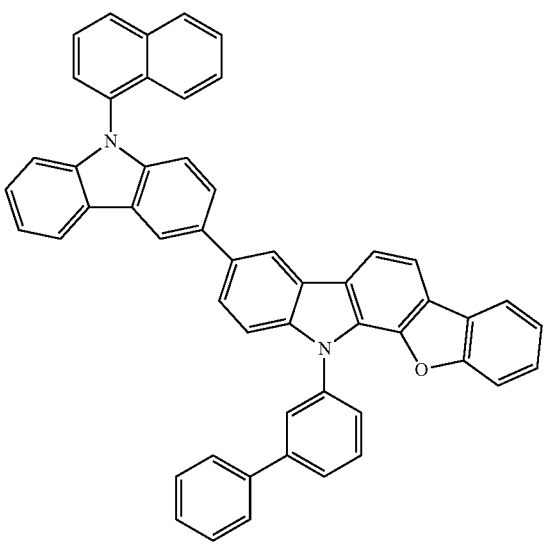

F-730
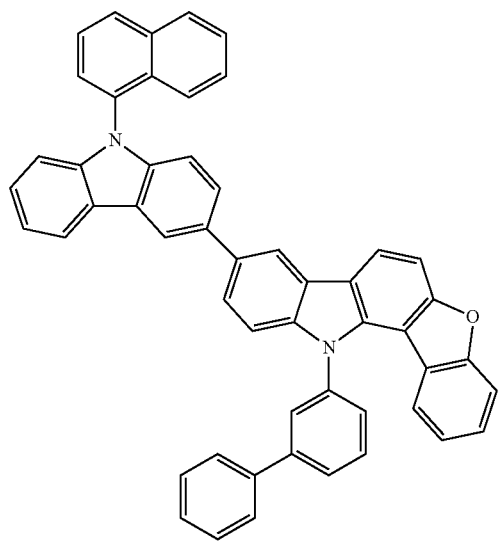
F-731
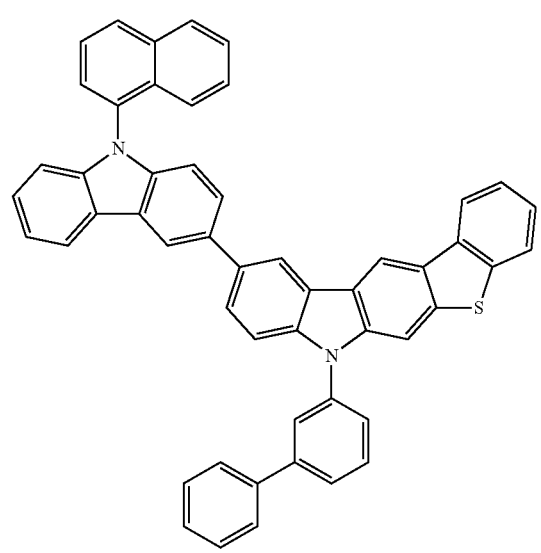
F-732
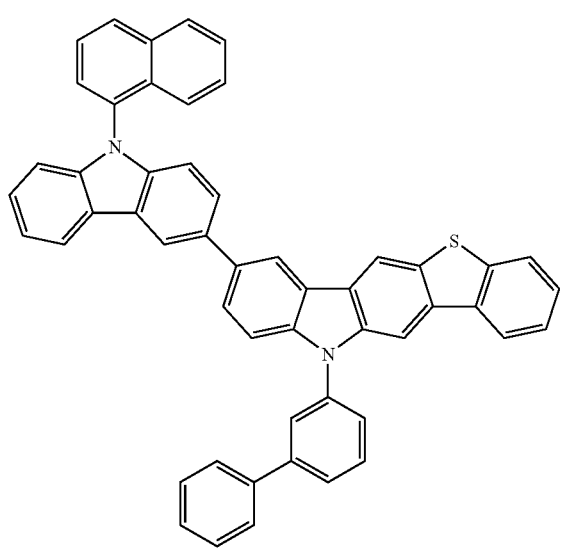
F-733
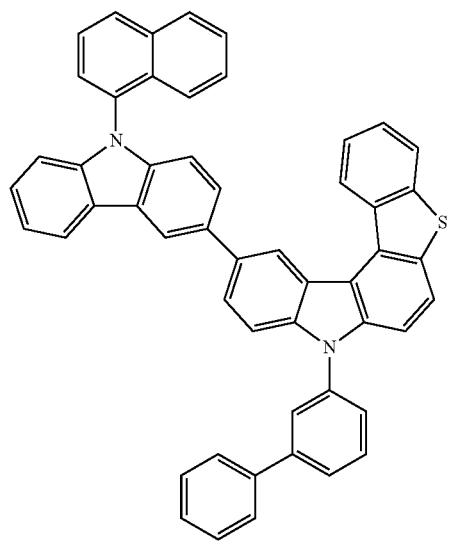
F-734
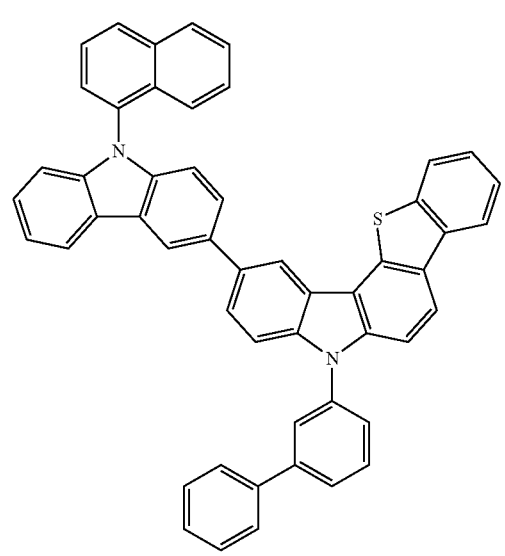
F-735
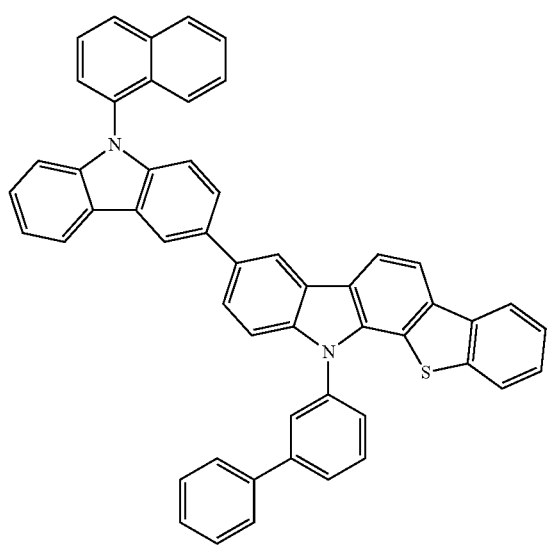

F-736
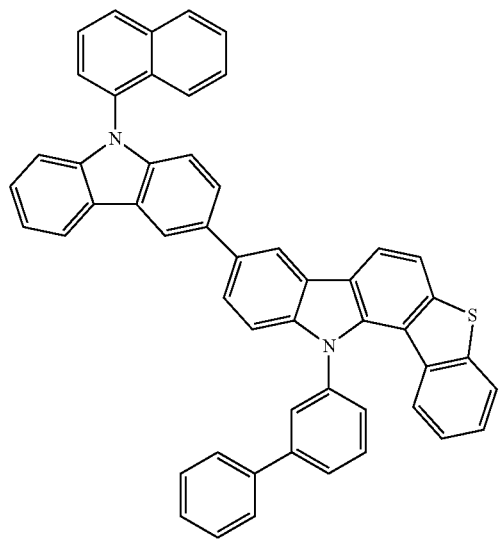
F-737
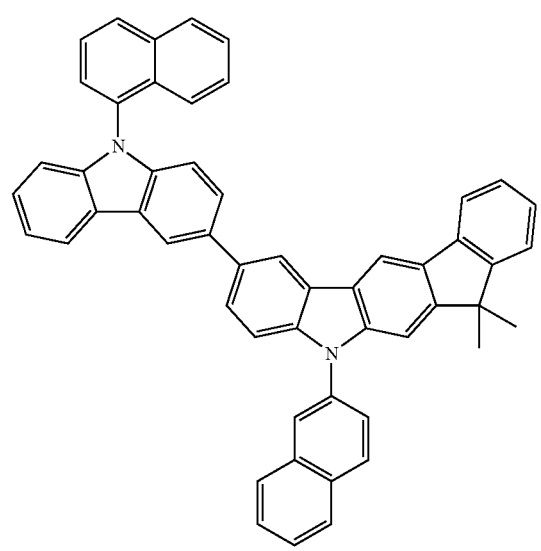
F-738
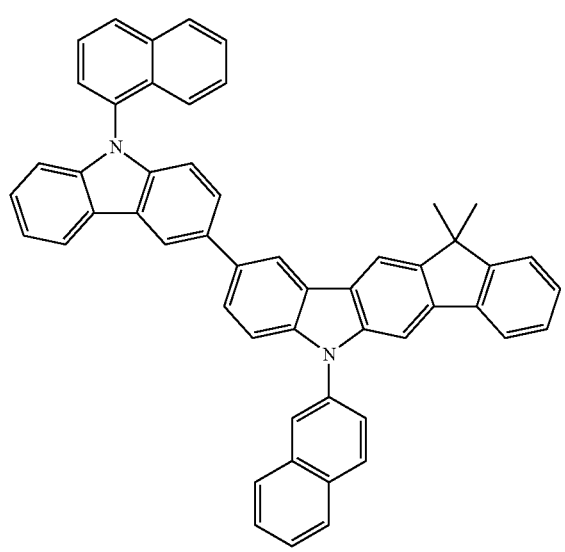
F-739
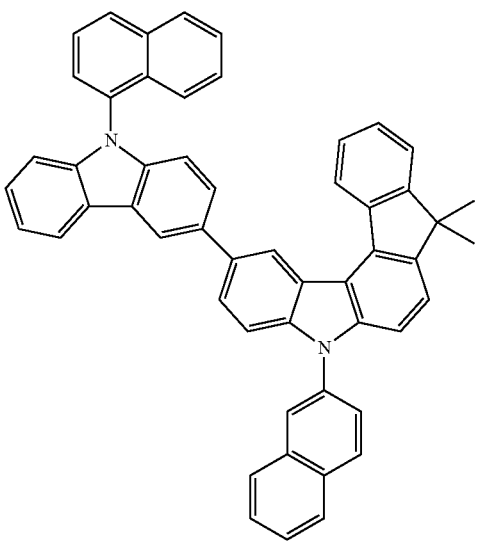
F-740
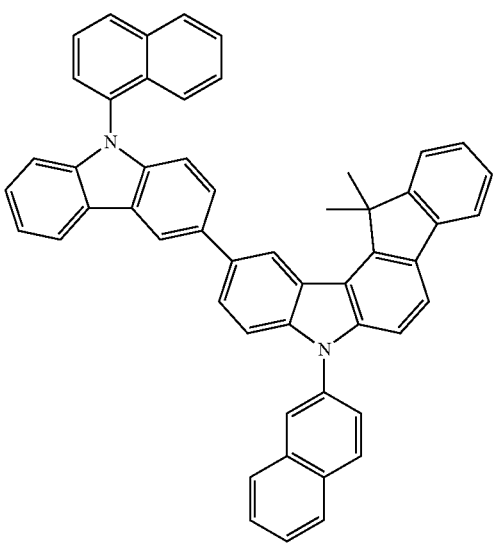
F-741
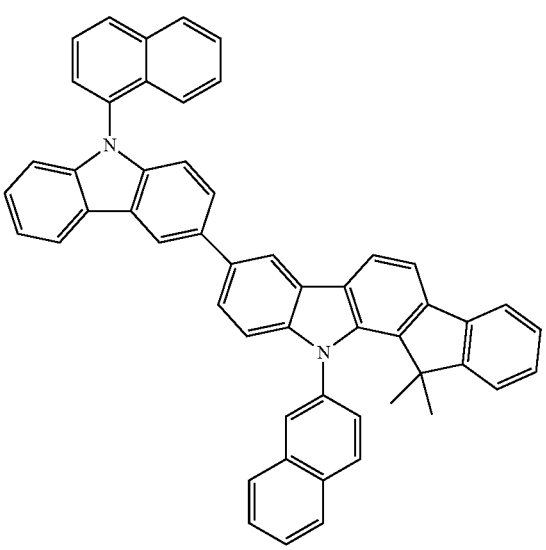

-continued
F-742
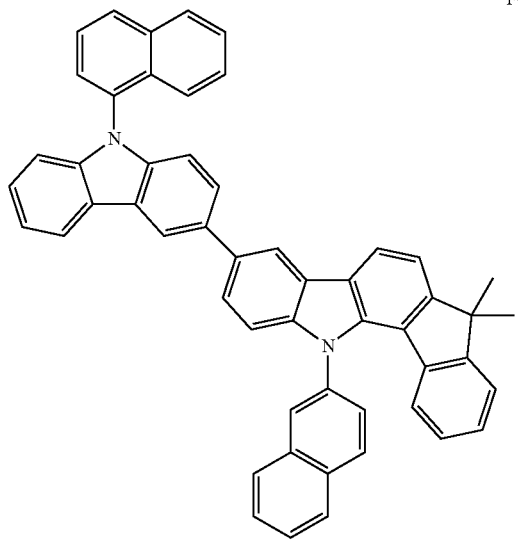
F-743
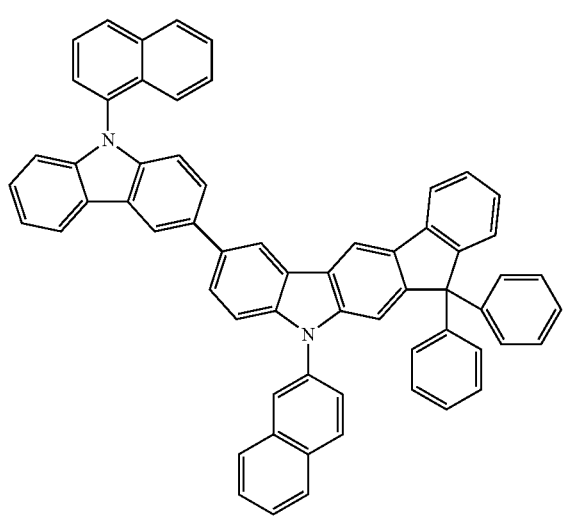
F-744
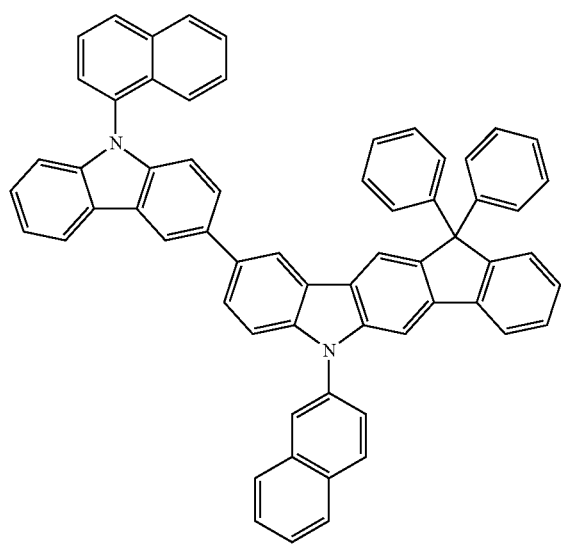
-continued
F-745
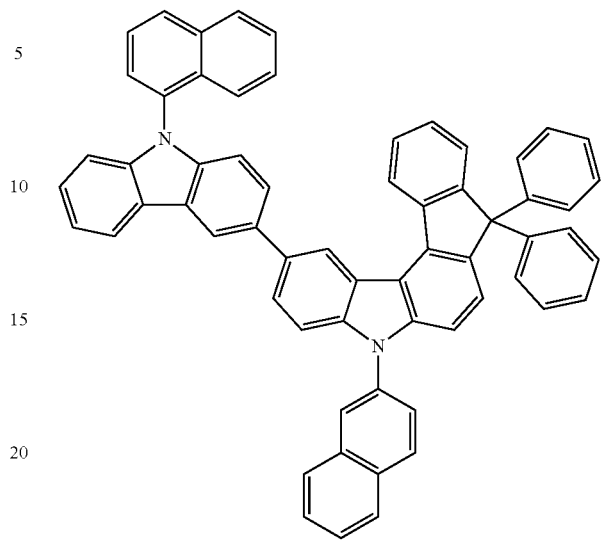
F-746
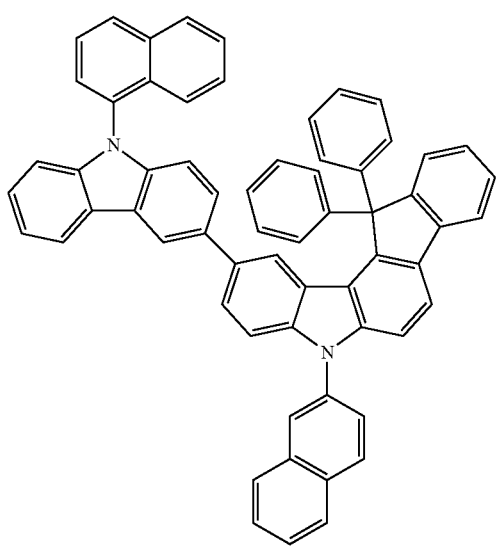
F-747
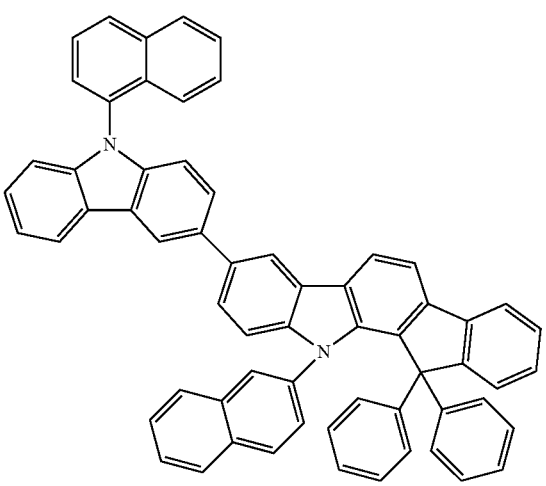

-continued
F-748
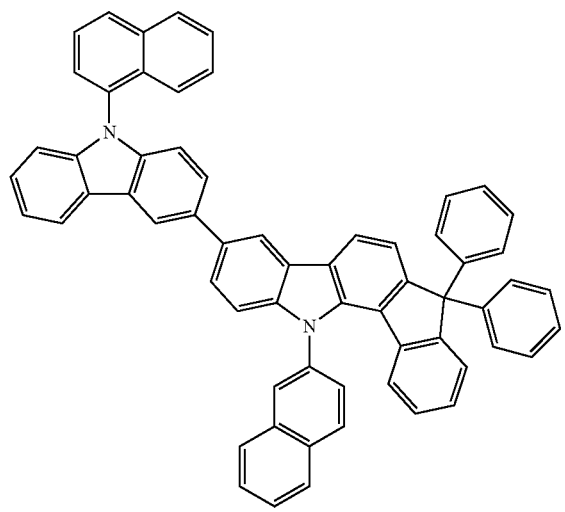
F-749
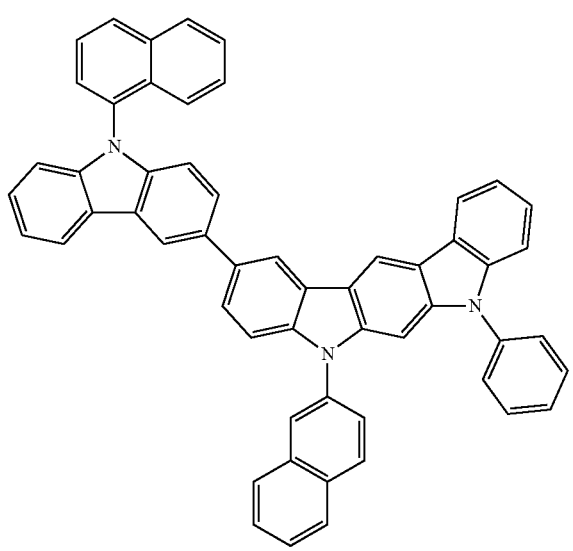
F-750
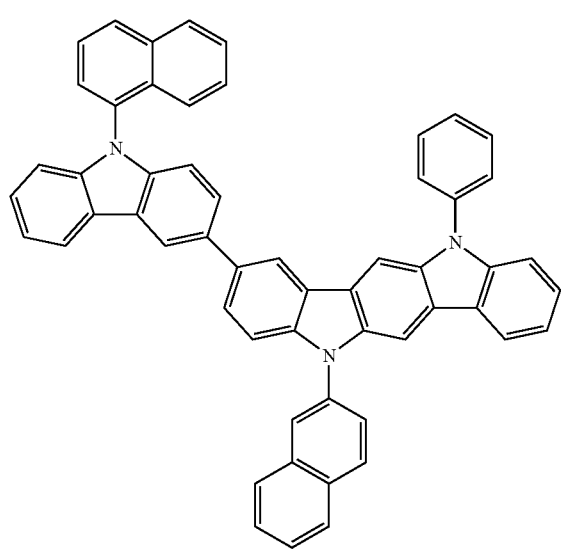
-continued
F-751
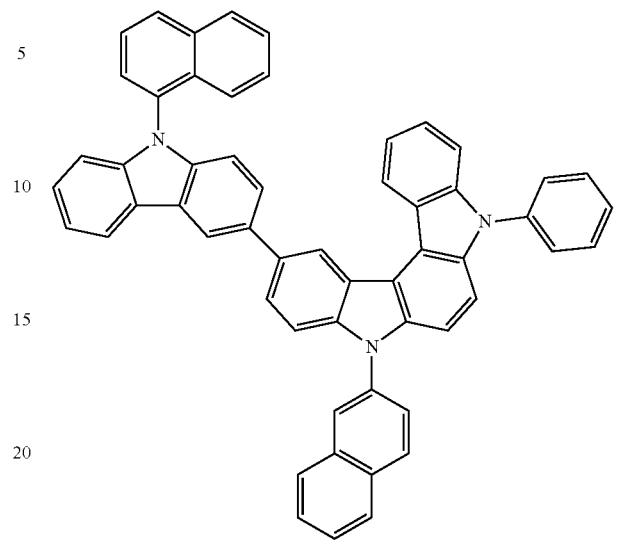
F-752
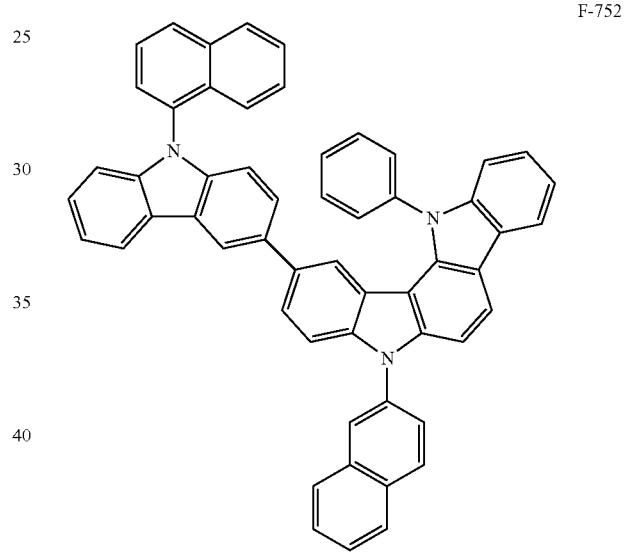
F-753
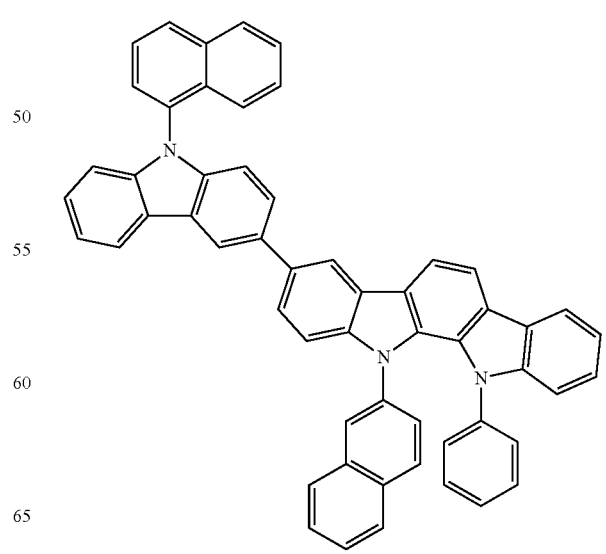

F-754
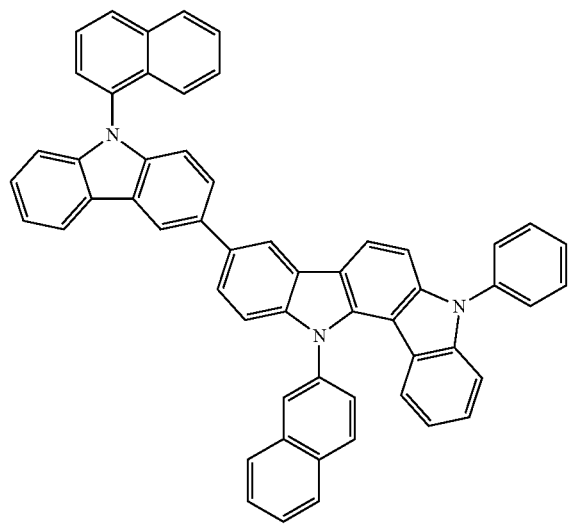
F-757
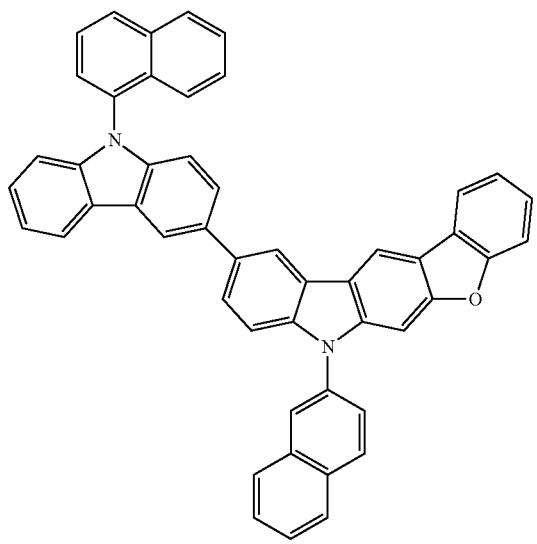
F-755
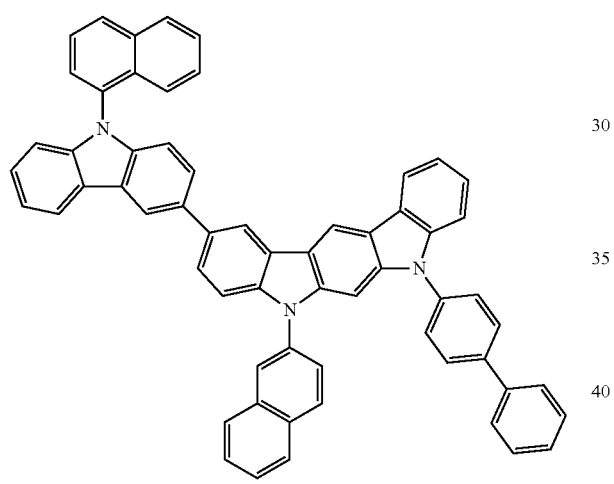
F-758
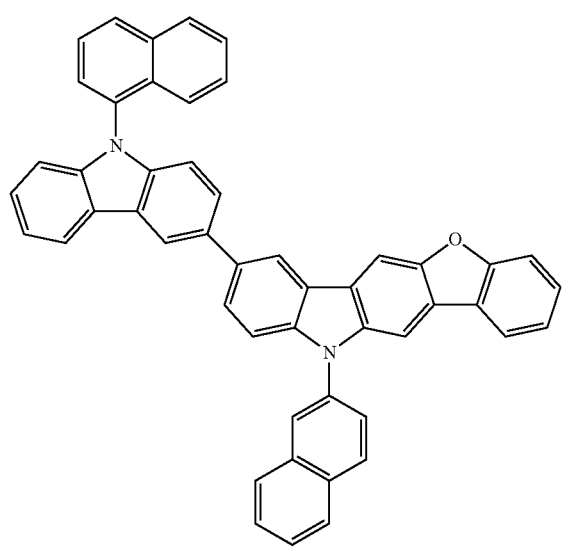
F-756
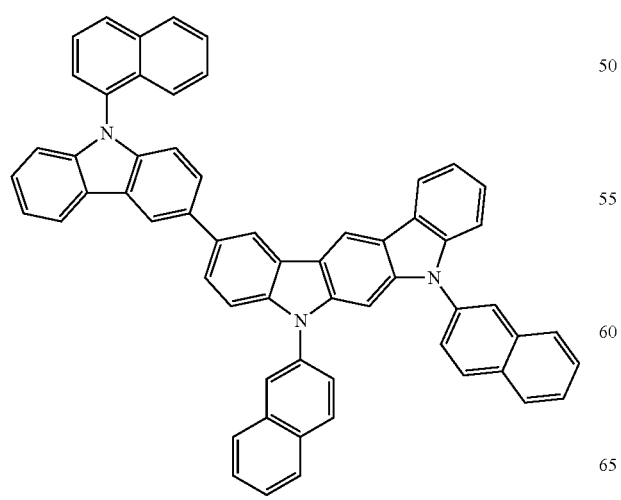
F-759
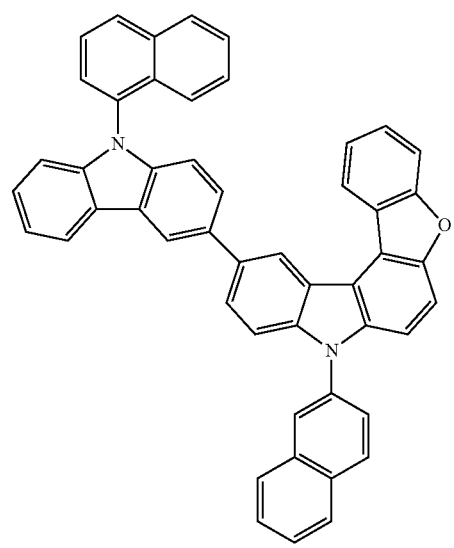

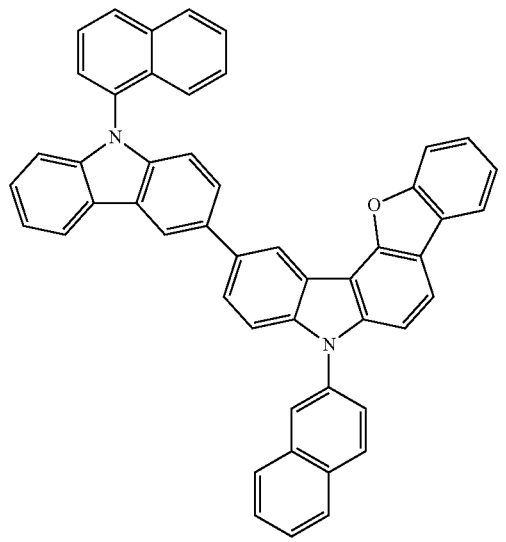
F-760
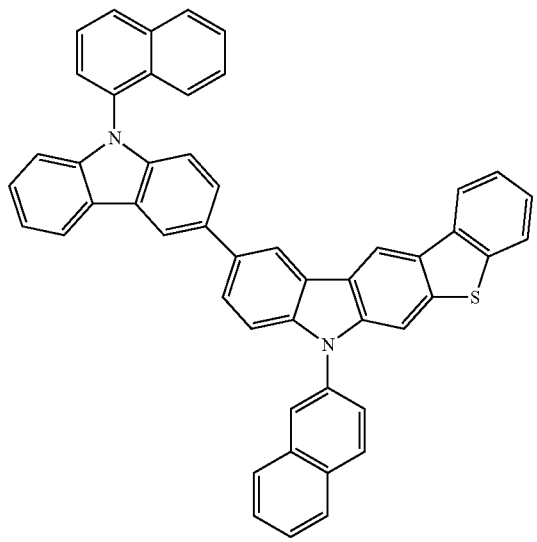
F-763
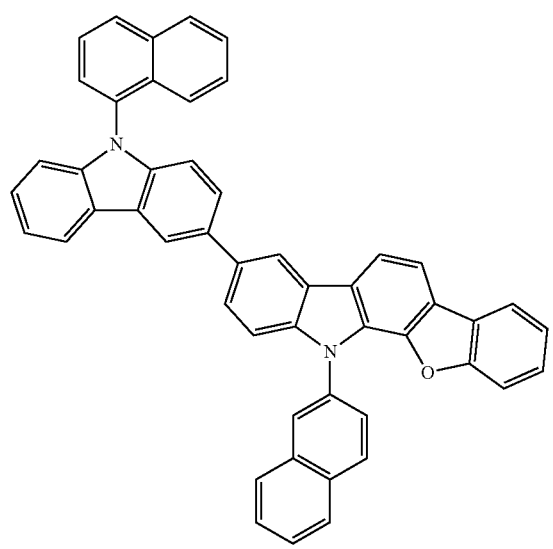
F-761
F-764
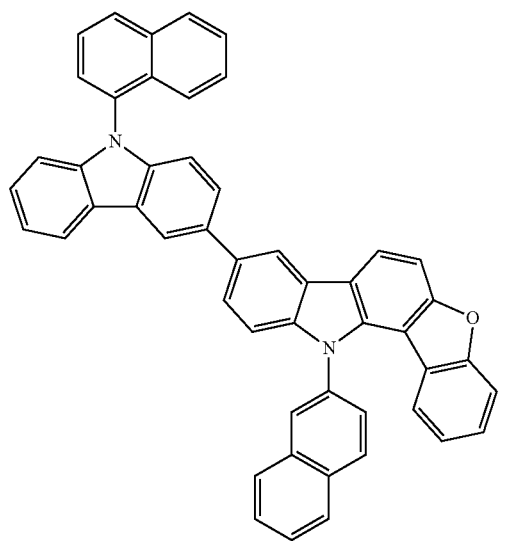
F-762
F-765

-continued
F-766
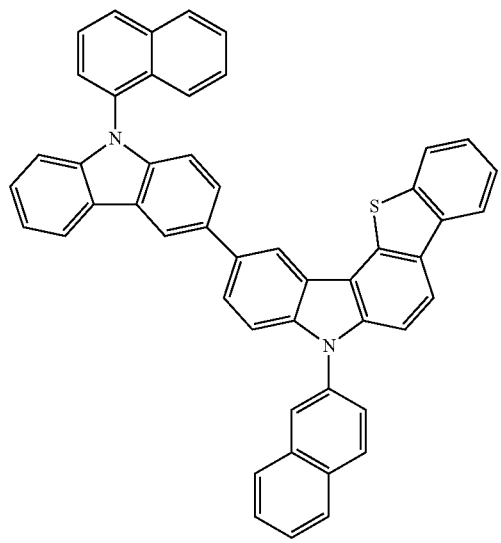
F-767
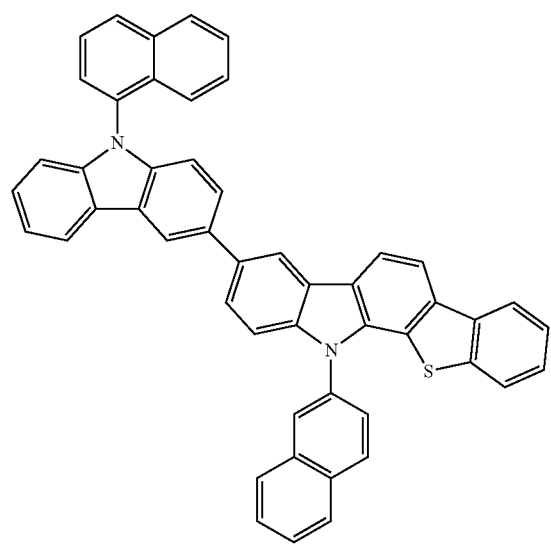
F-768
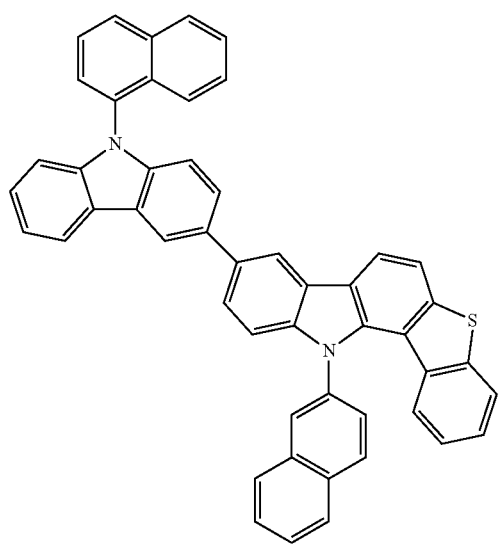
-continued
F-769
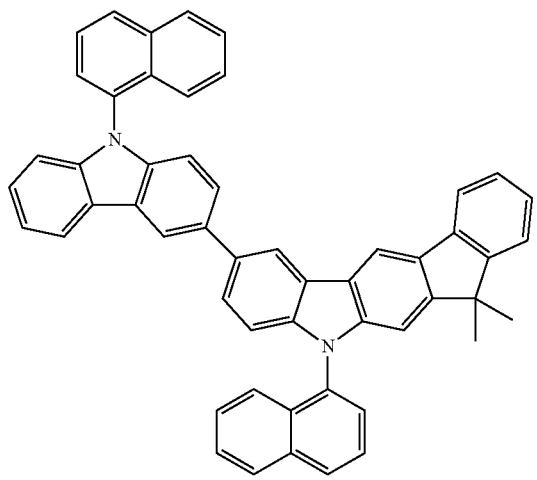
F-770
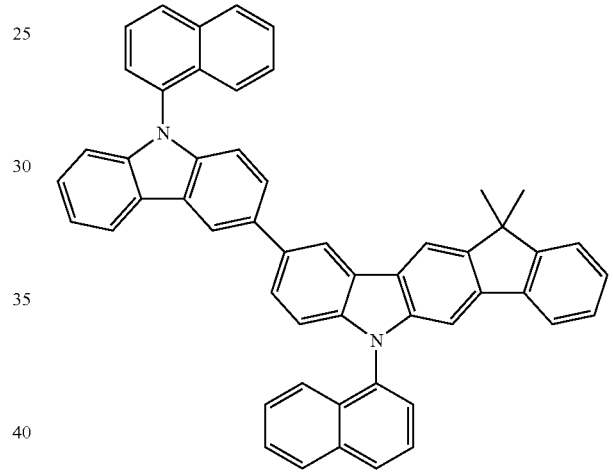
F-771
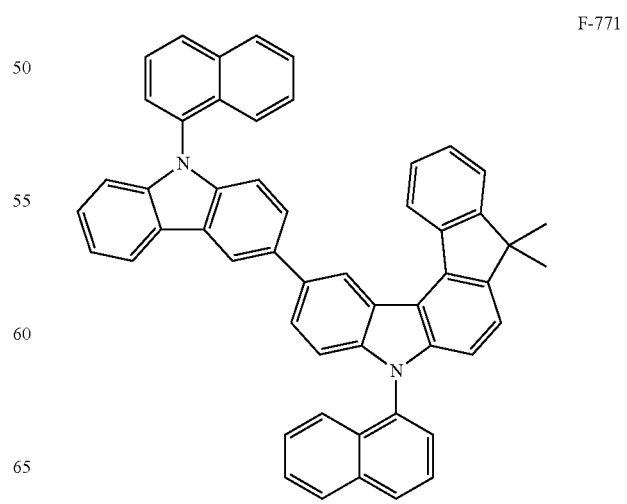

F-772
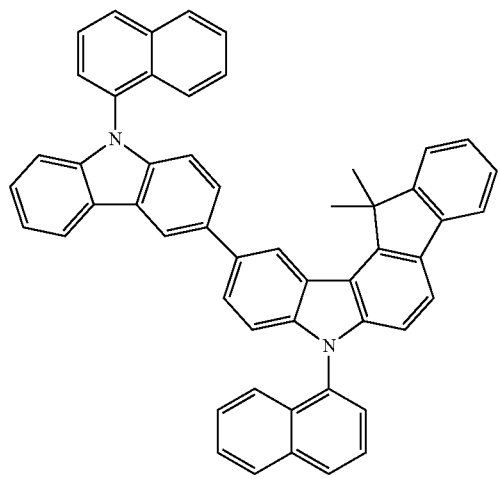
F-775
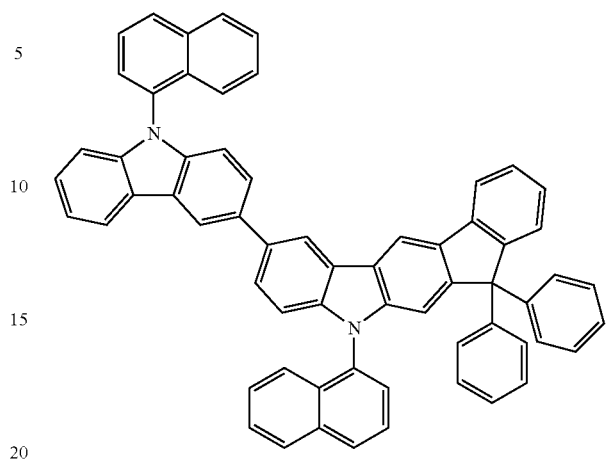
F-773
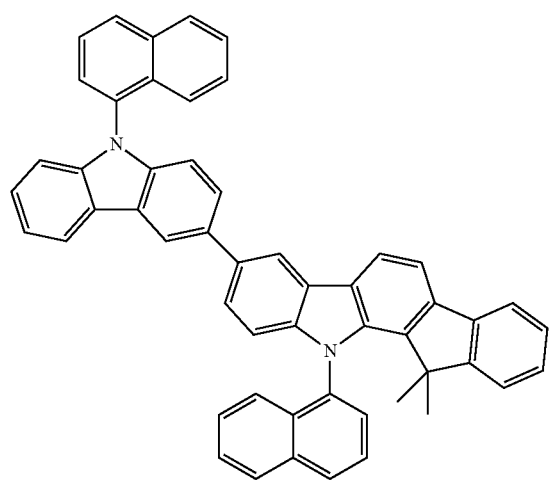
F-776
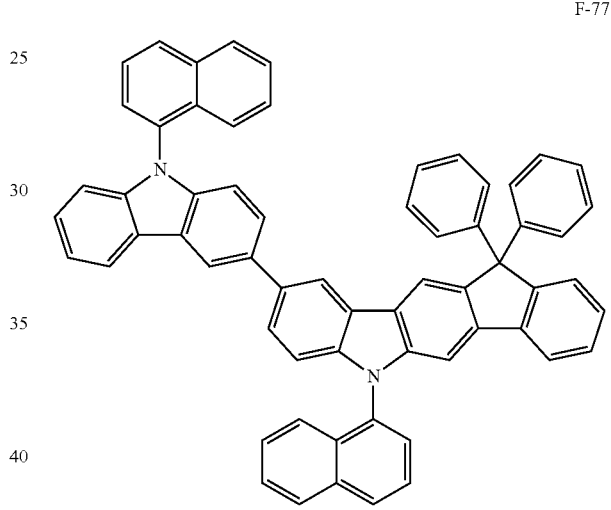
F-774
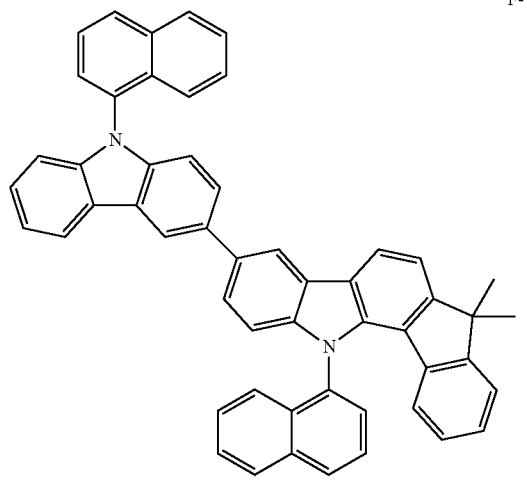
F-777
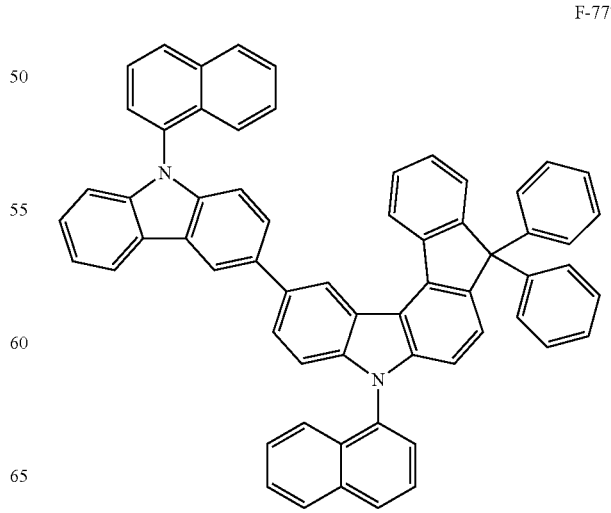

F-778
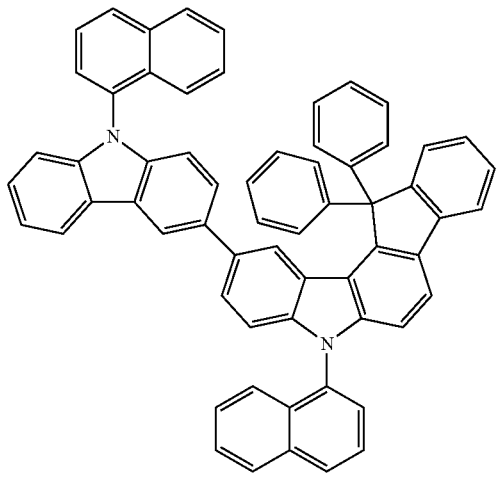
F-781
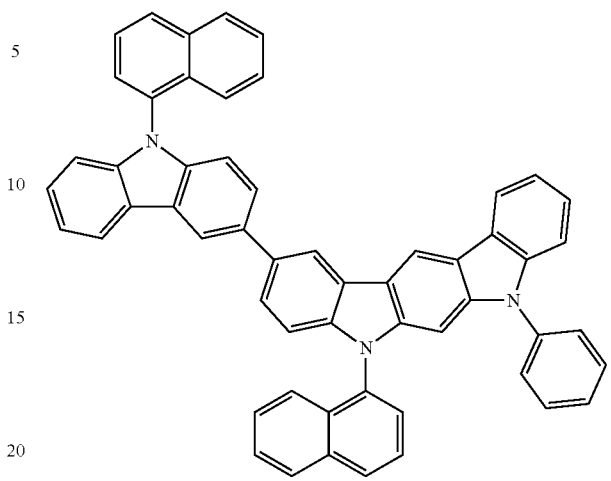
F-779
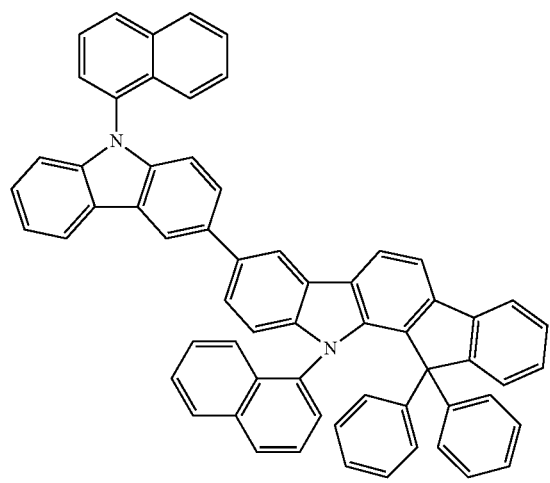
F-782
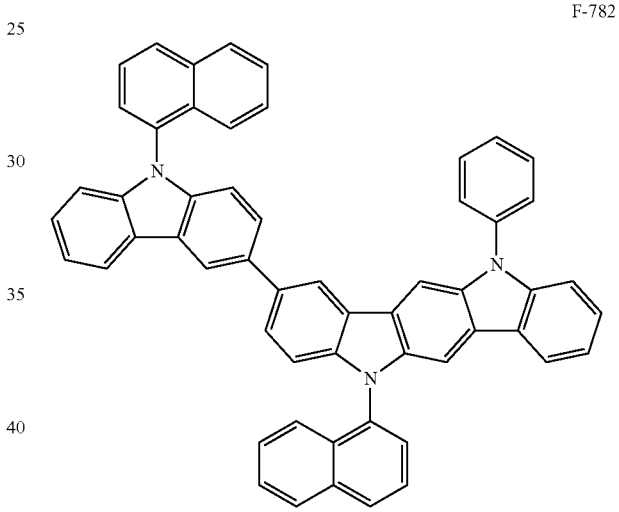
F-780
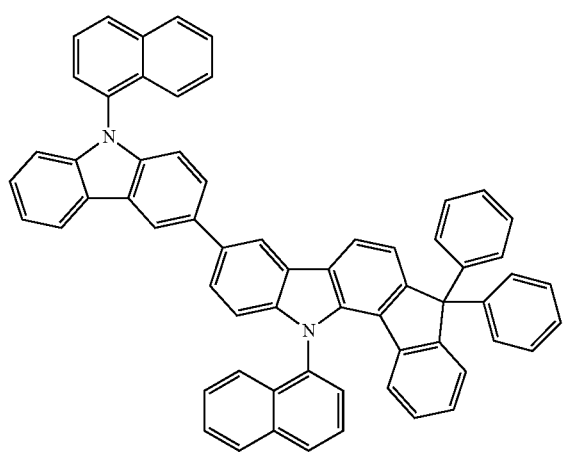
F-783
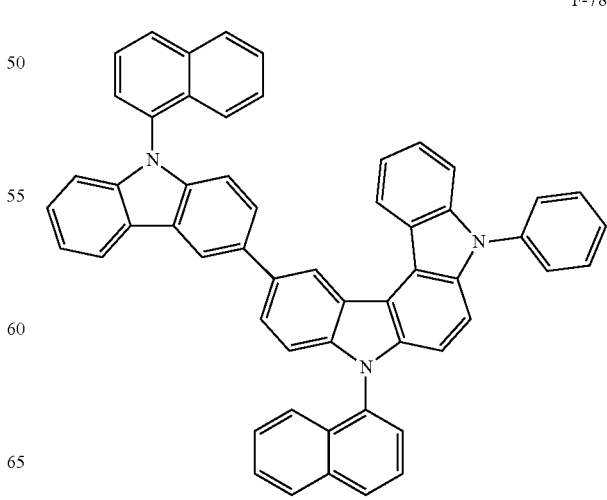

F-784
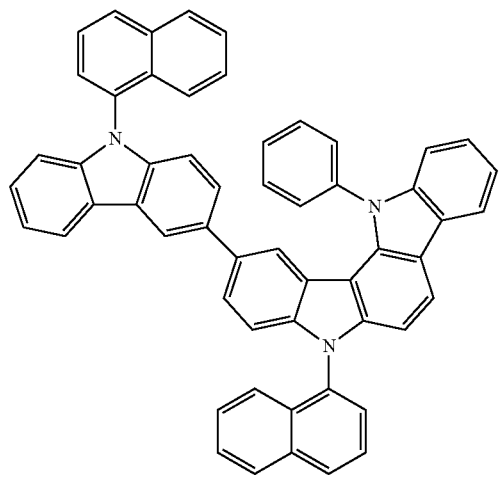
F-785
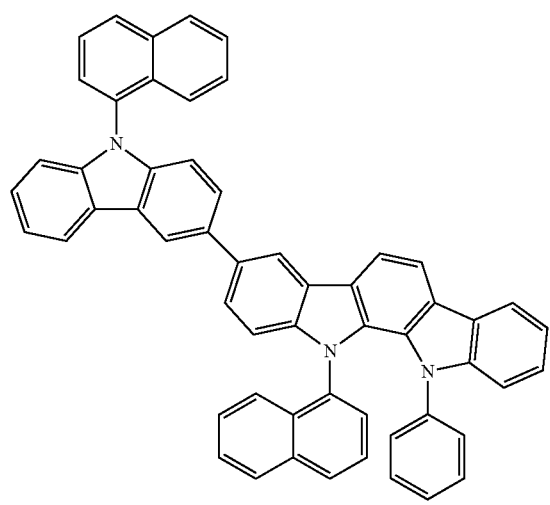
F-786
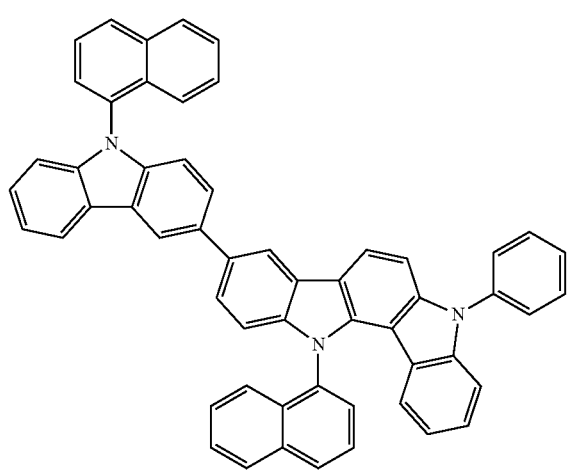
F-787
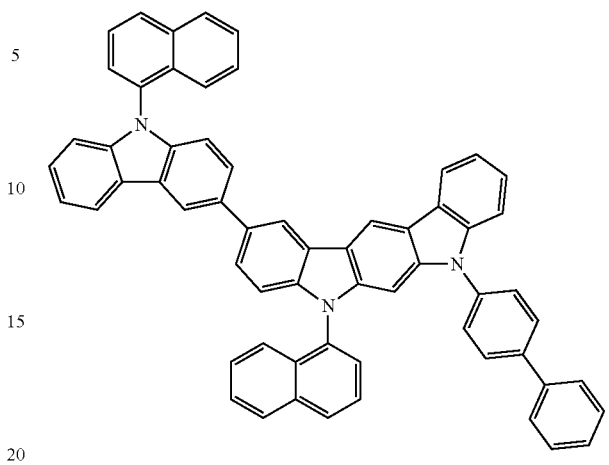
F-788
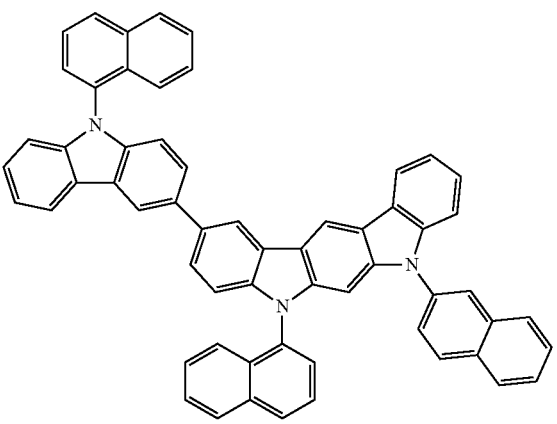
F-789
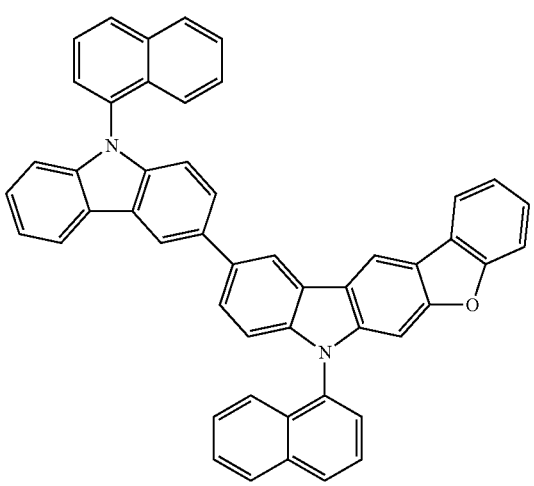

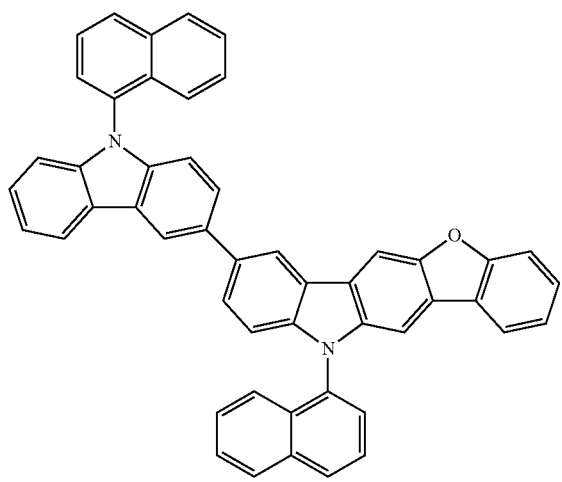
F-790
F-791
F-792
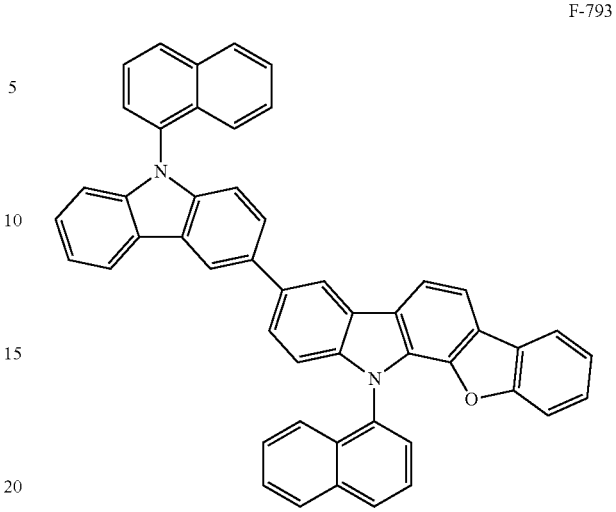
F-793
F-794
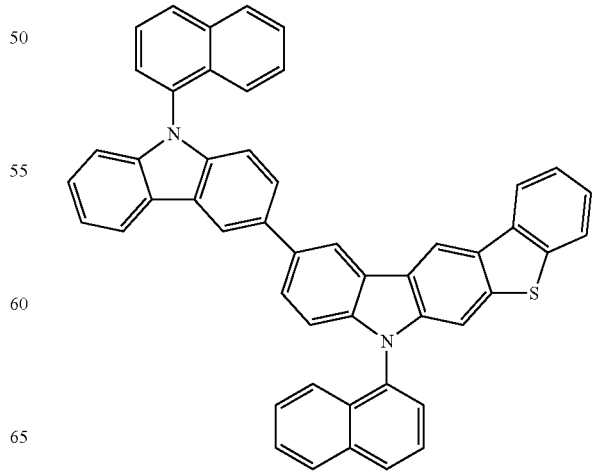
F-795

F-796
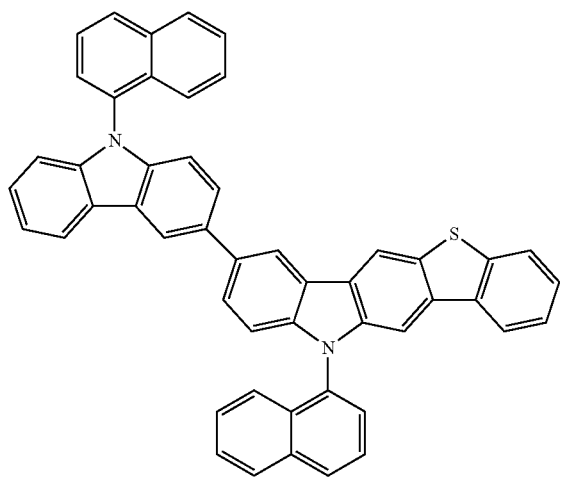
F-799
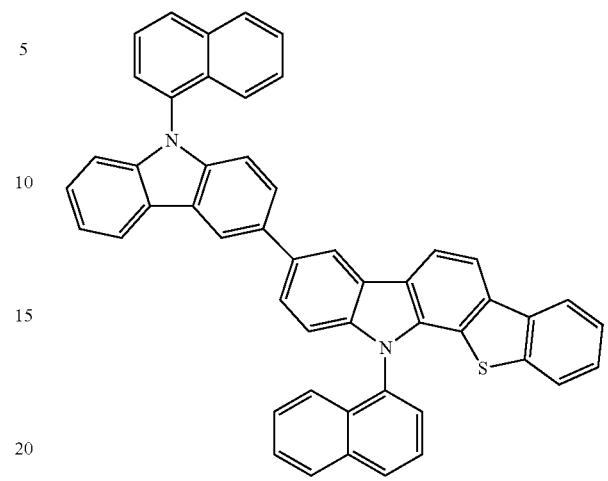
F-797
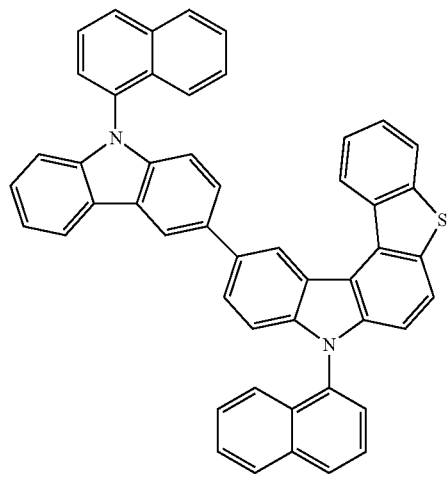
F-800
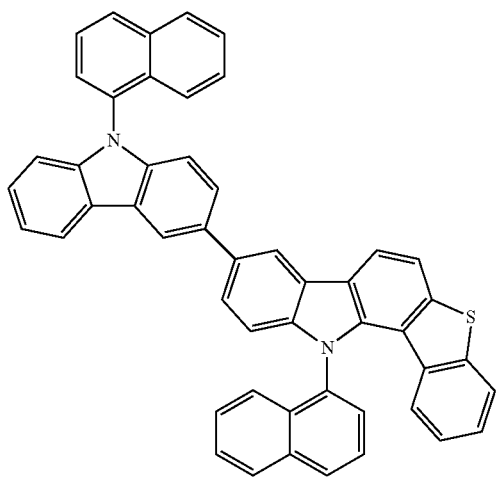
F-798
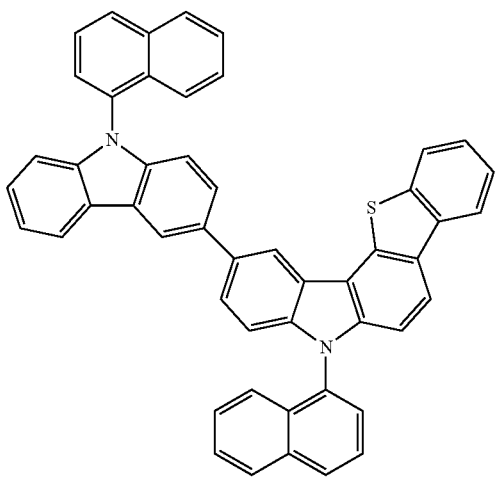
F-801
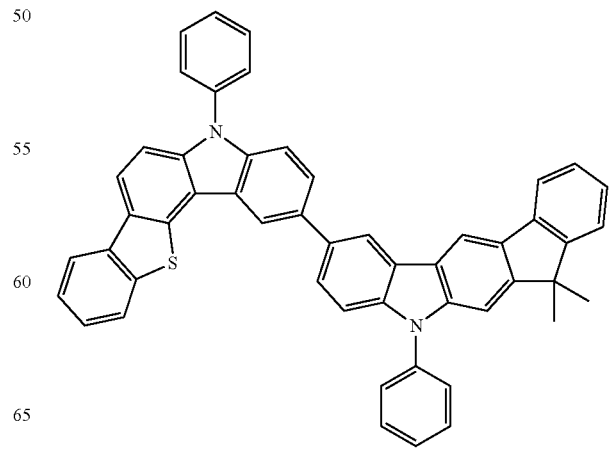

-continued
F-802
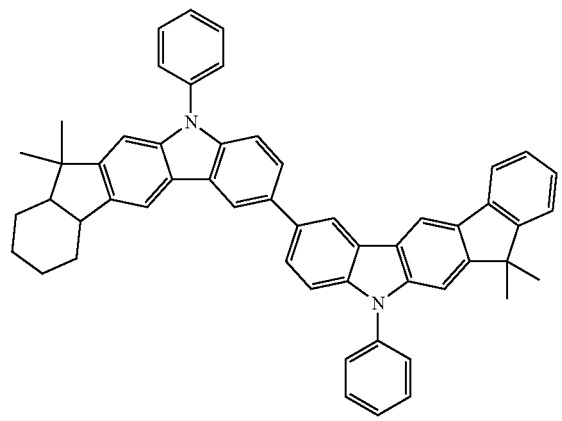
F-803
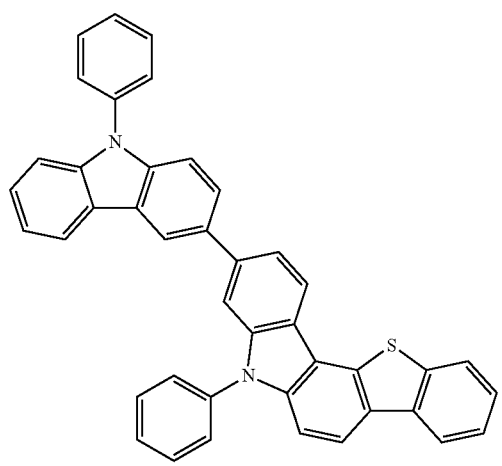
F-804
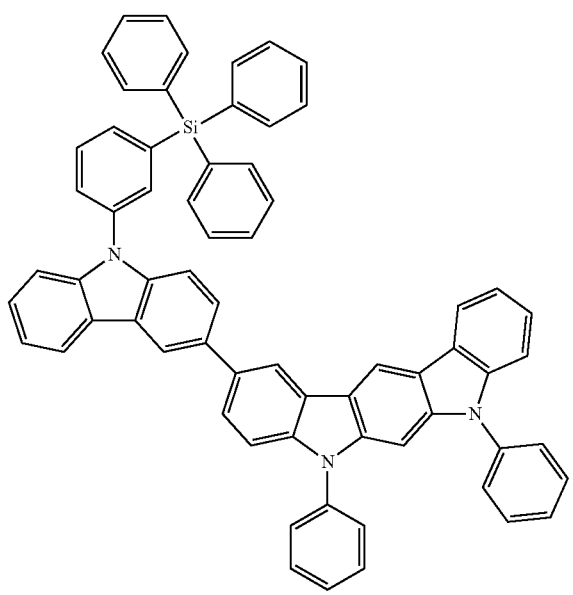
-continued
F-805
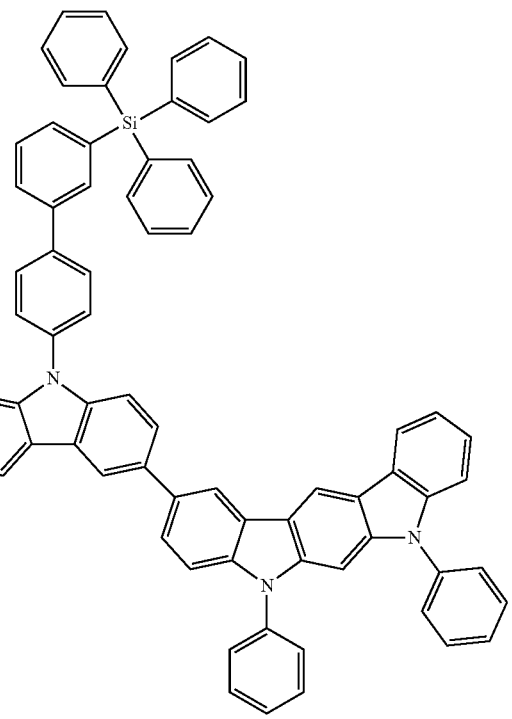
F-806
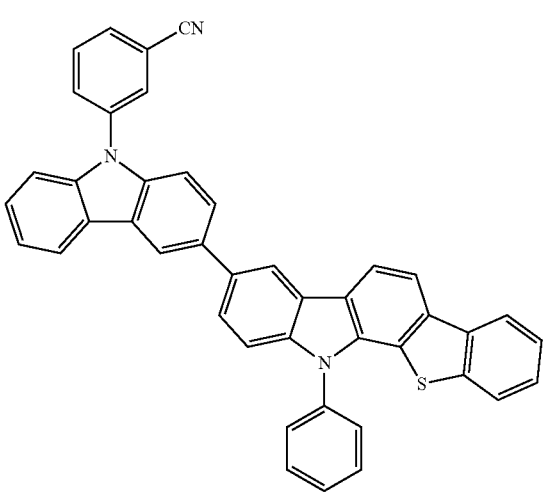

F-807
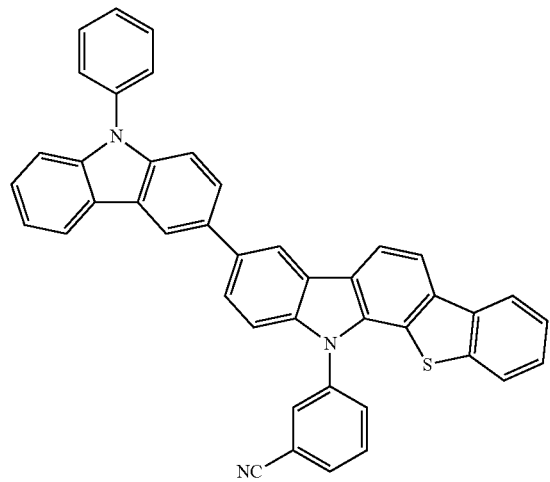
F-808
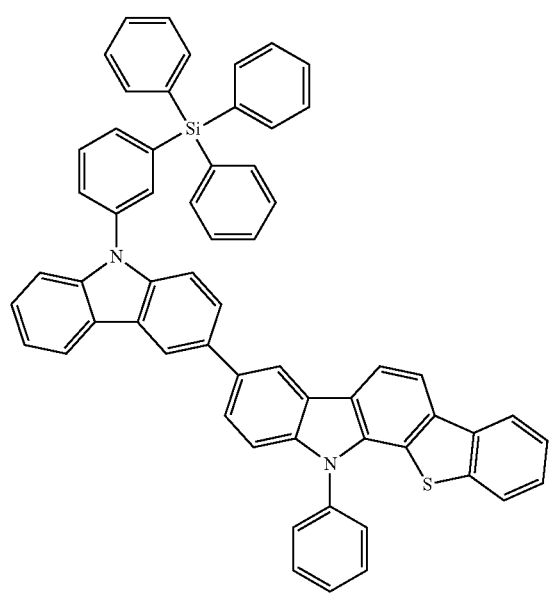
F-809
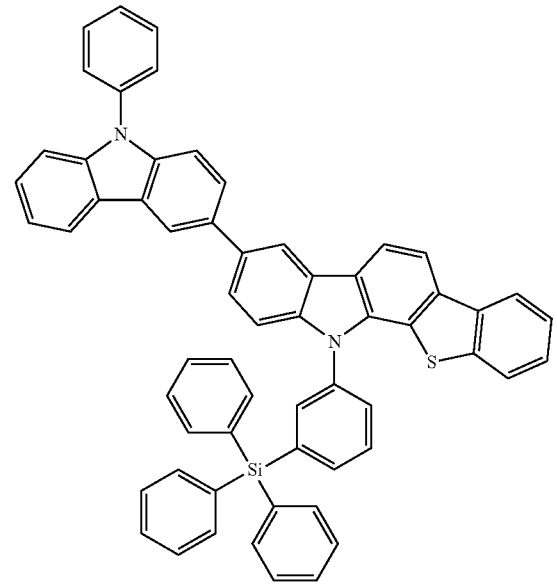
F-810
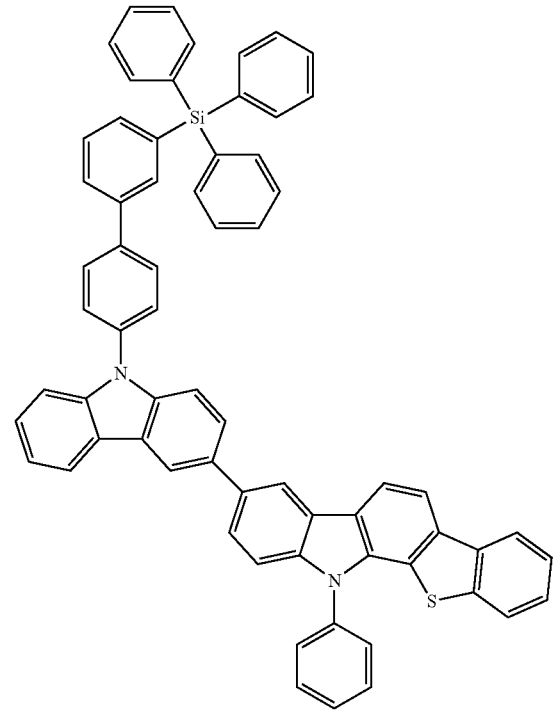

F-811
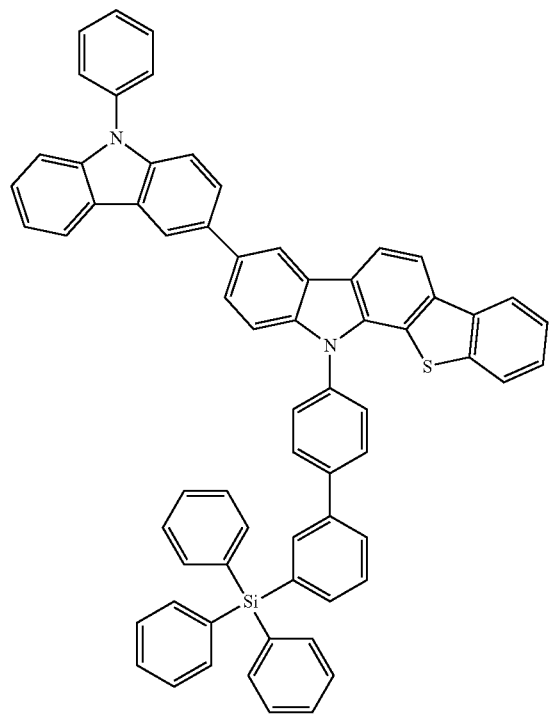
F-812
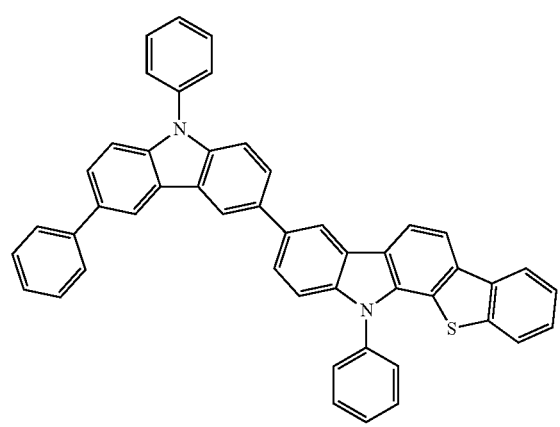
F-813
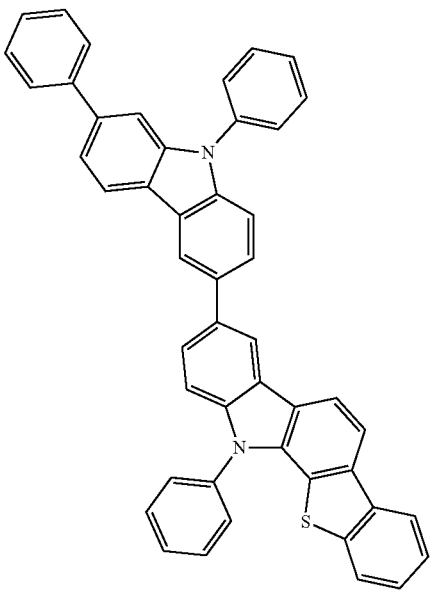
F-814
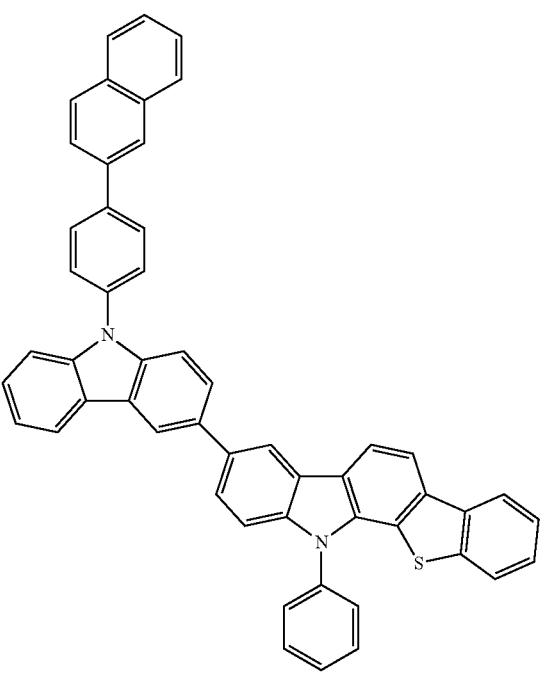

F-815
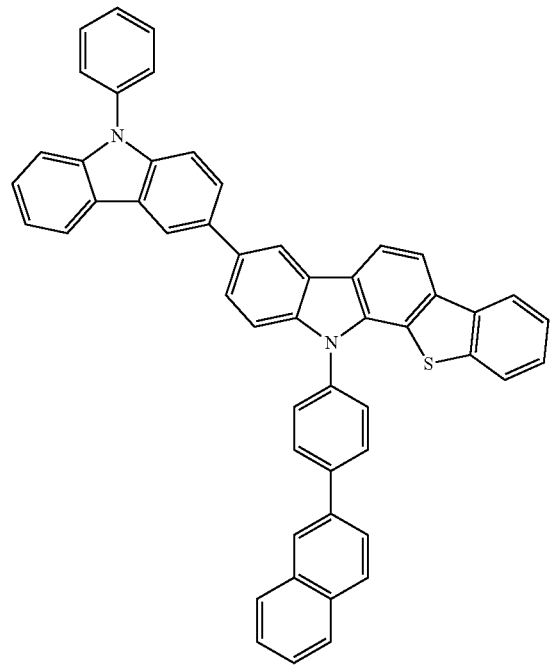
F-816
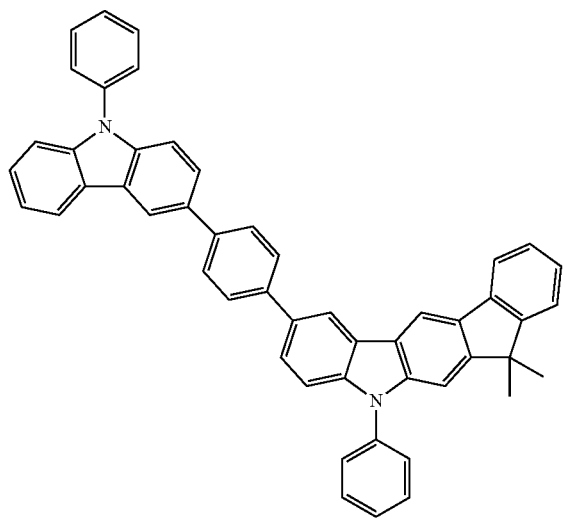
F-817
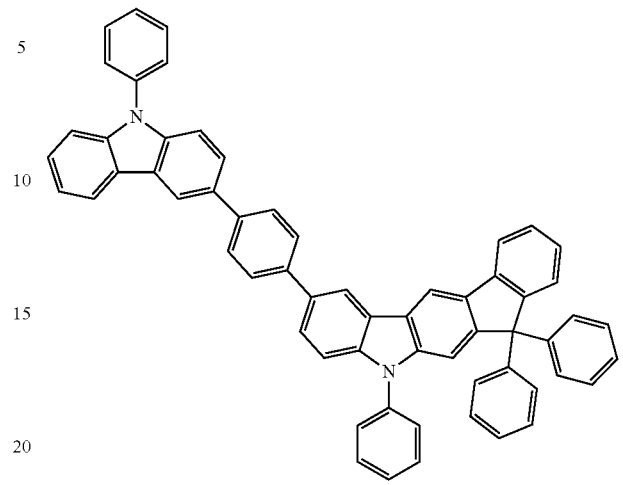
F-818
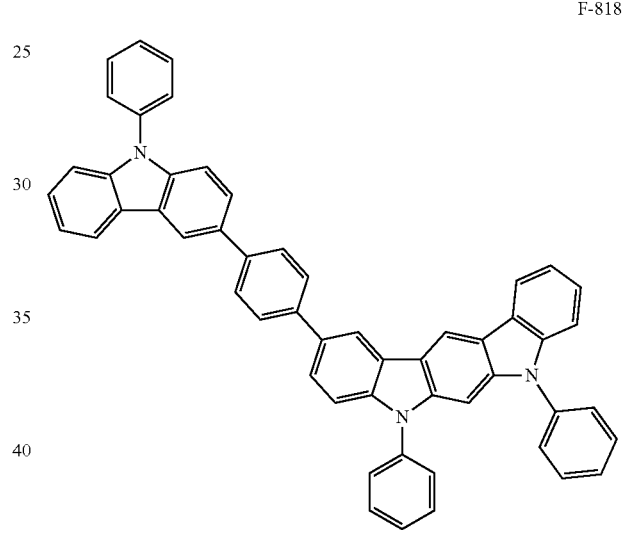
F-819
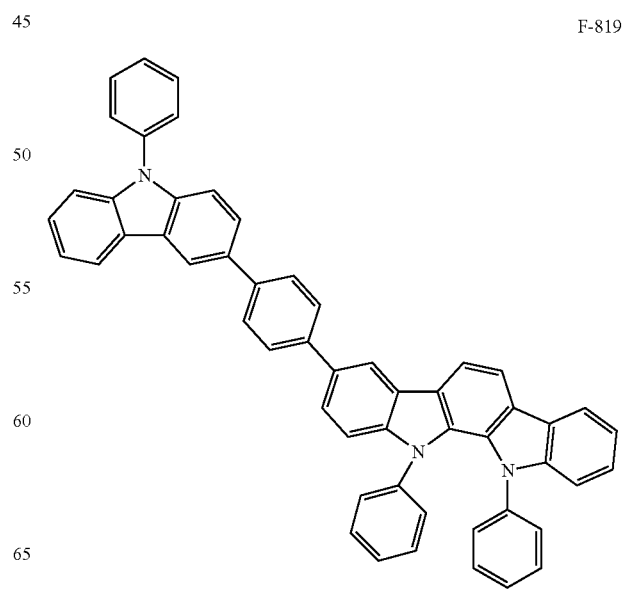

-continued
F-820
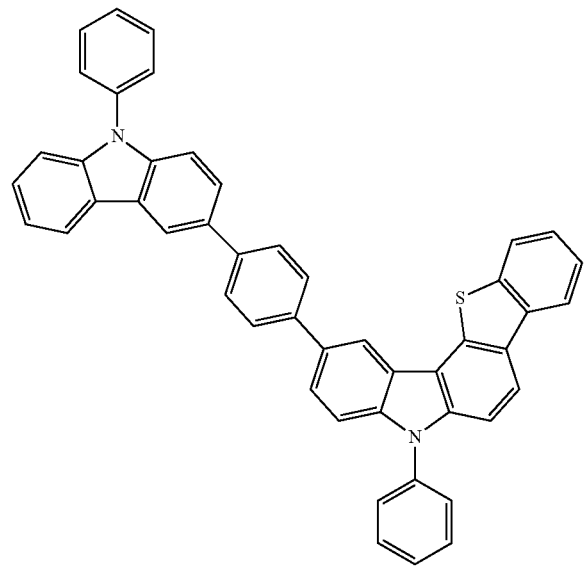
F-822
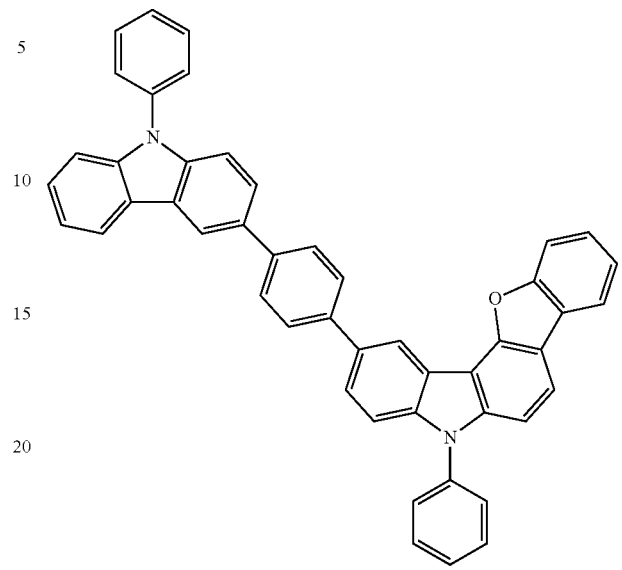
F-821
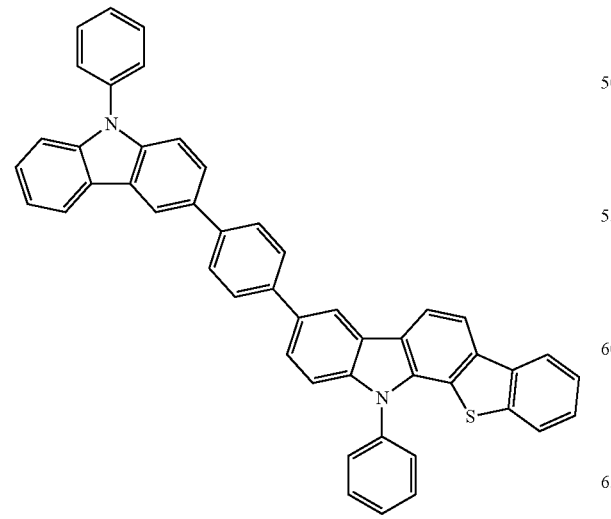
F-823
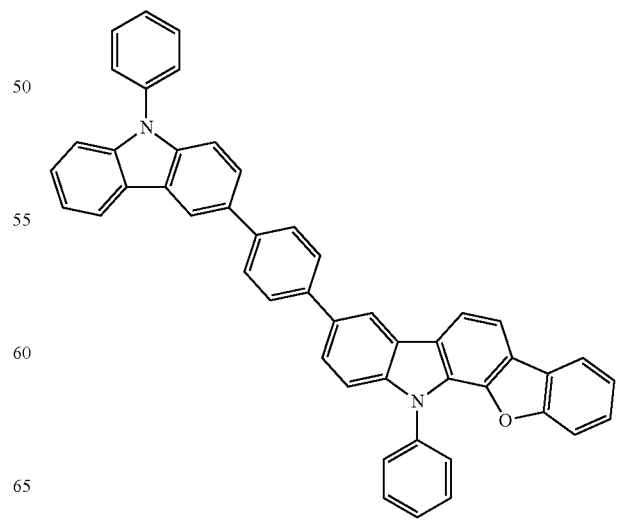

F-824
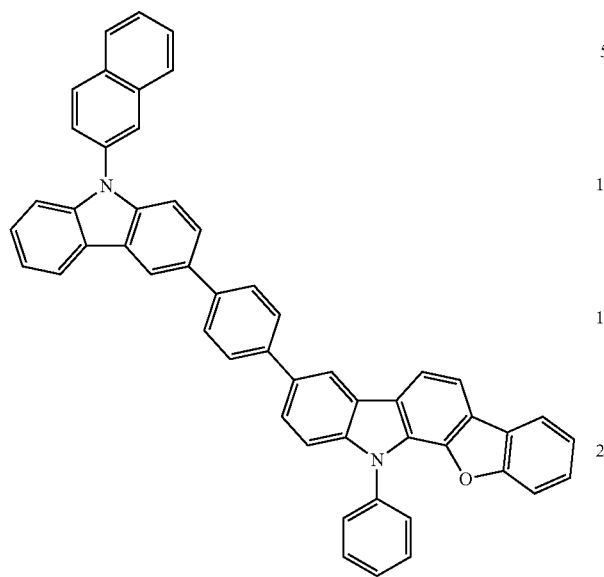
The second host compound represented by formula 2 includes the following compounds, but is not limited thereto:
H2-1
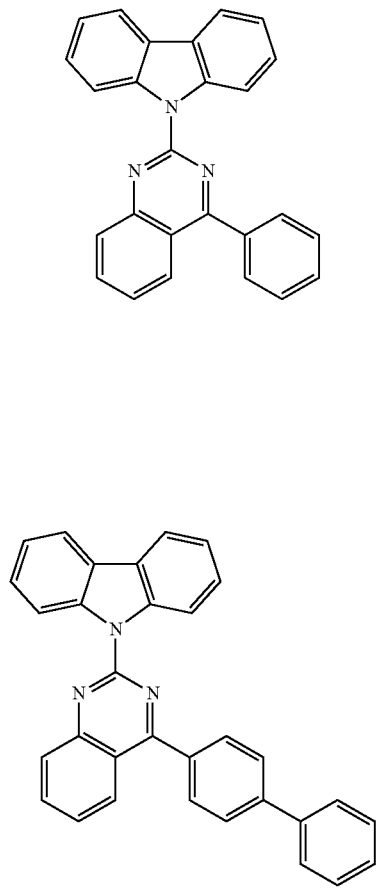
H2-2
H2-3
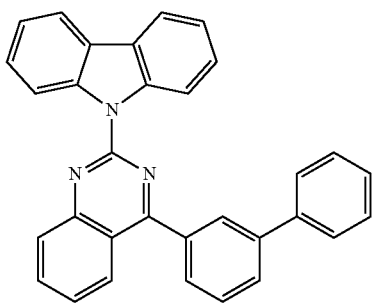
H2-4
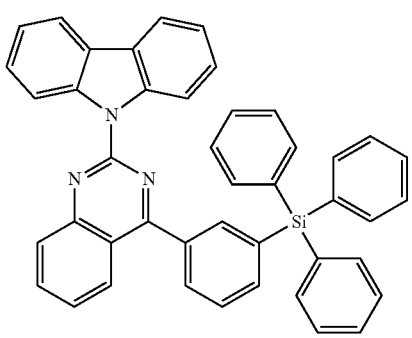
H2-5
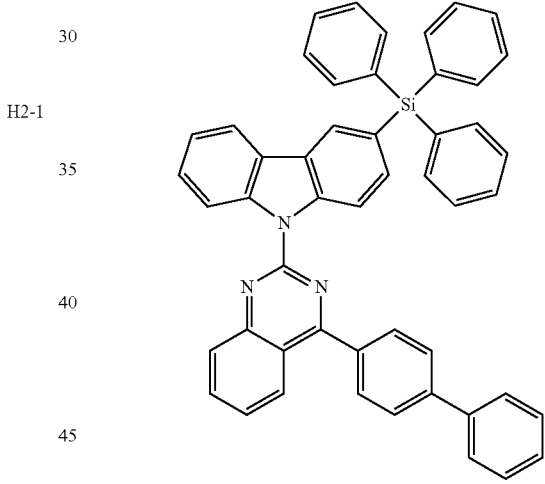
H2-6
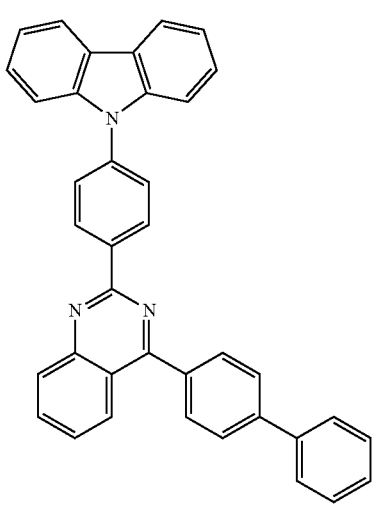

H2-7
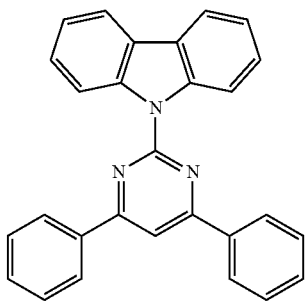
H2-8
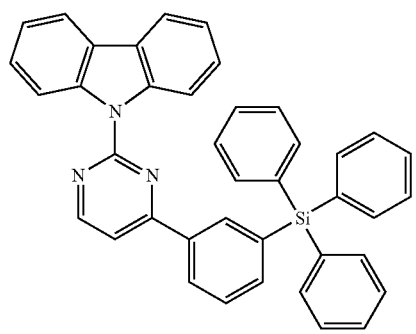
H2-9
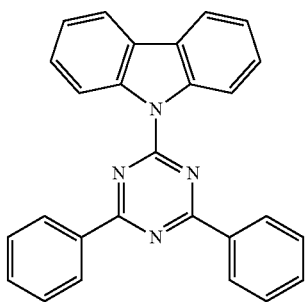
H2-10
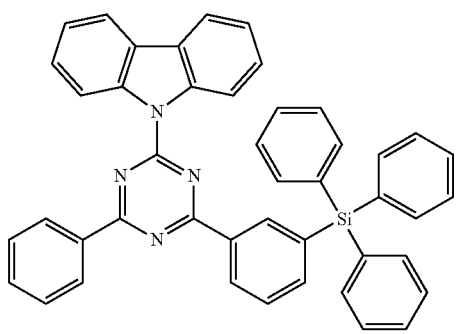
H2-11
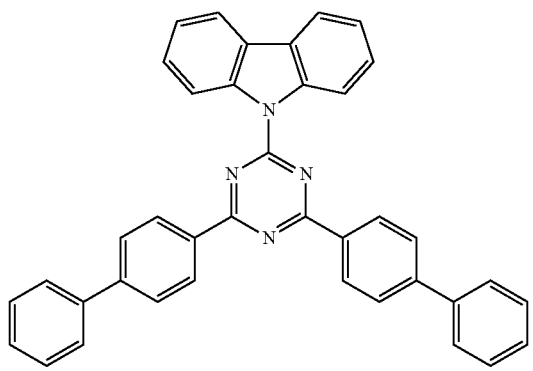
H2-12
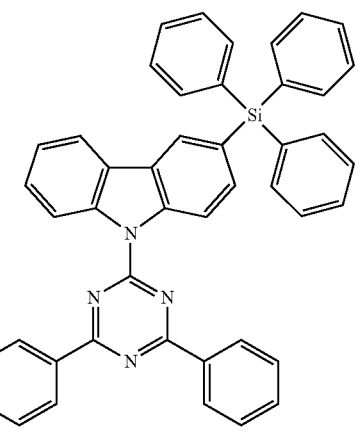
H2-13
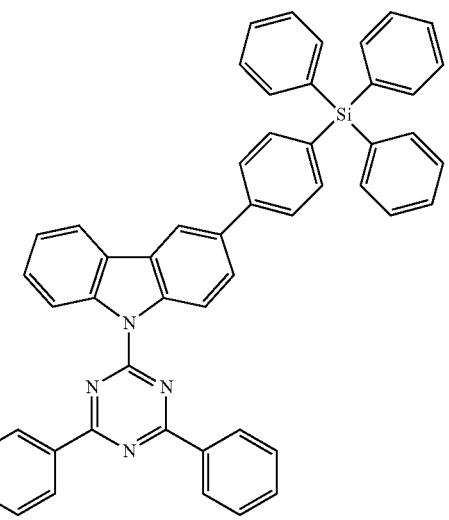

-continued
H2-14
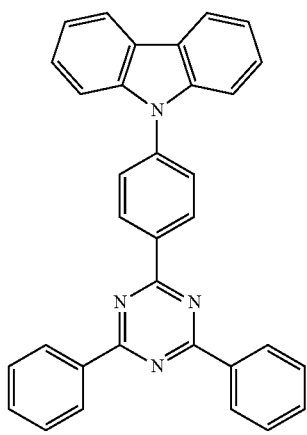
H2-15
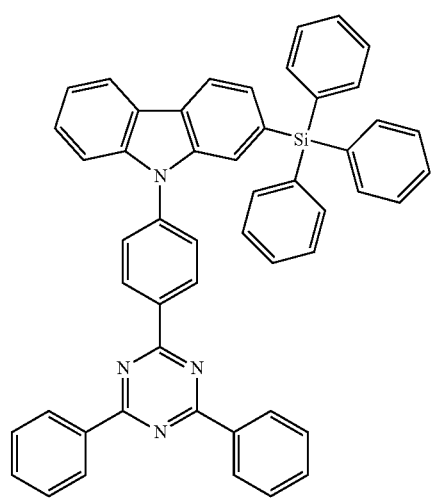
H2-16
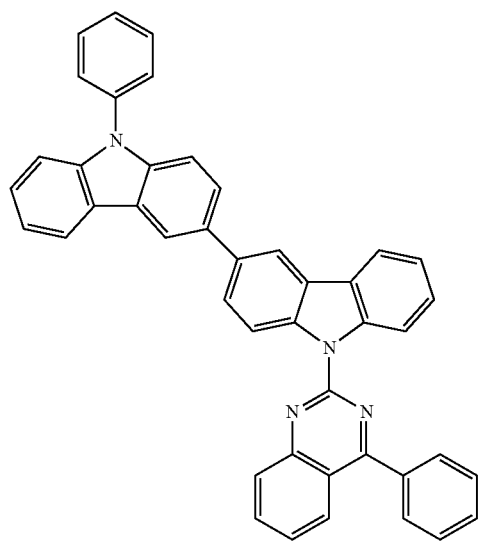
-continued
H2-17
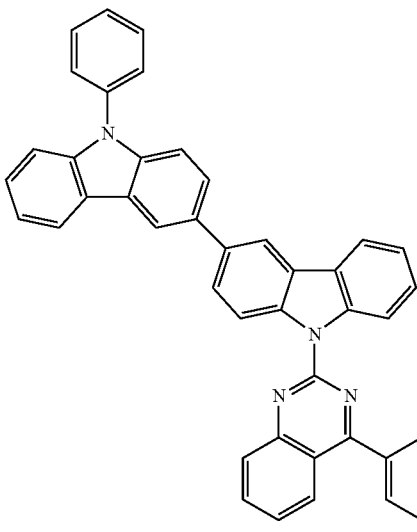
H2-18
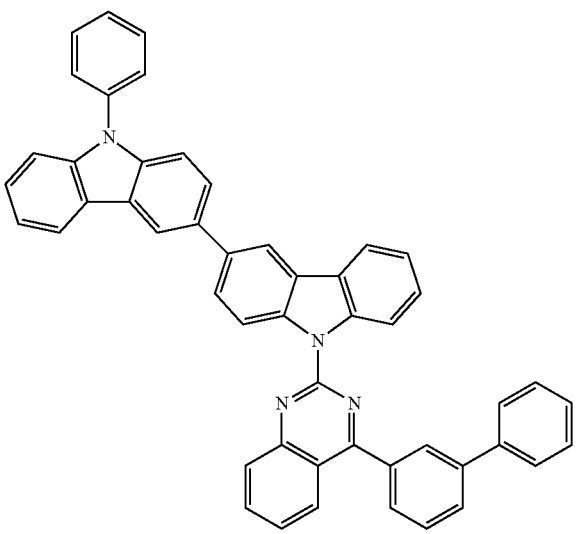

H2-19
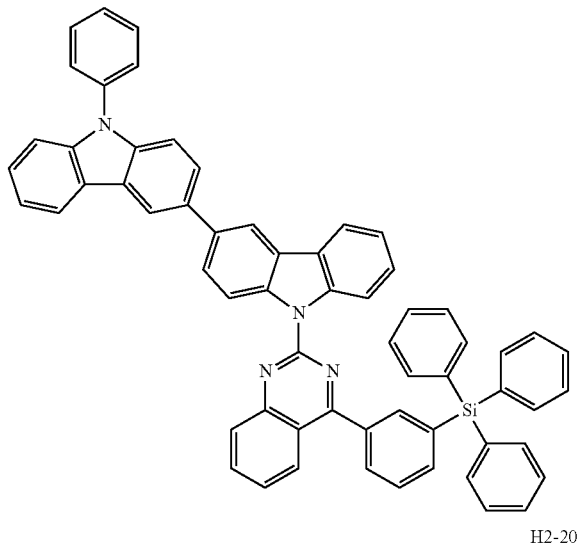
H2-22
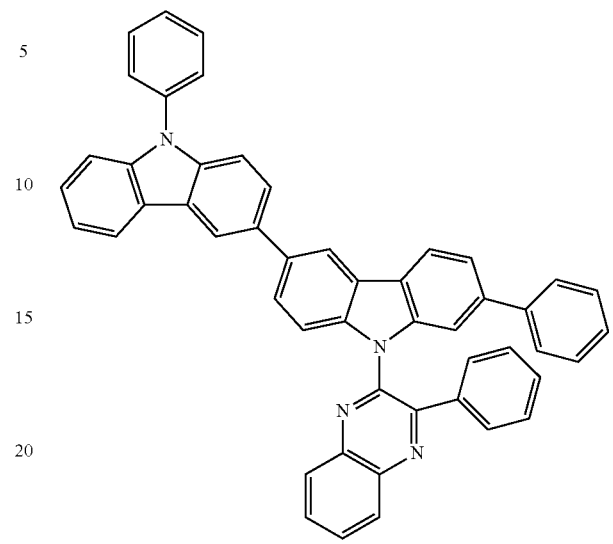
H2-20
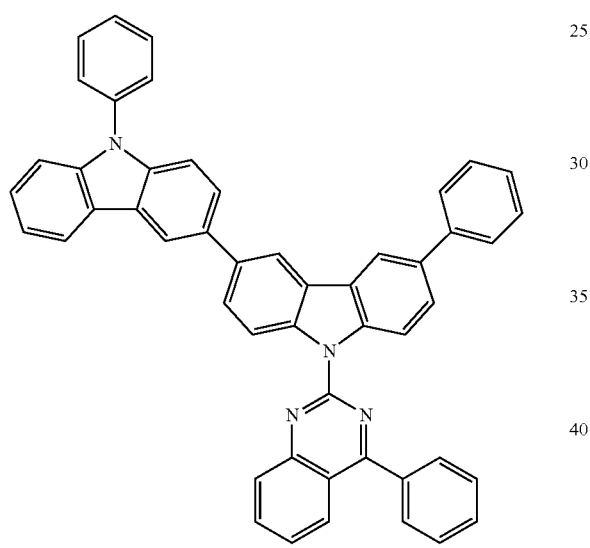
H2-21
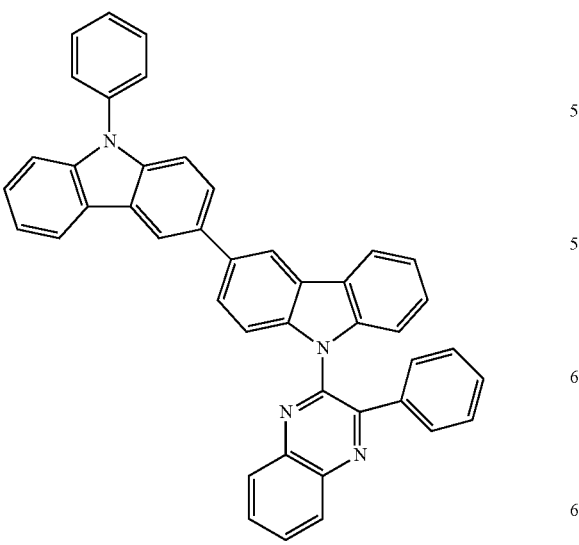
H2-23
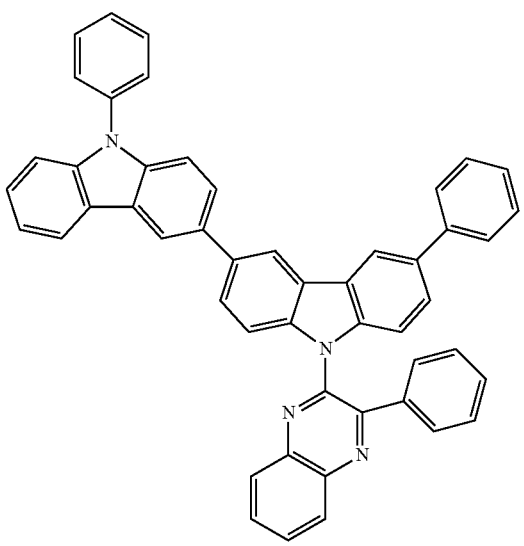

H2-24
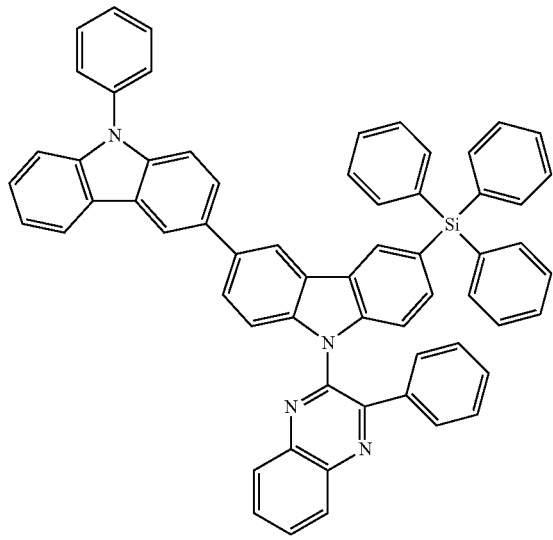
H2-25
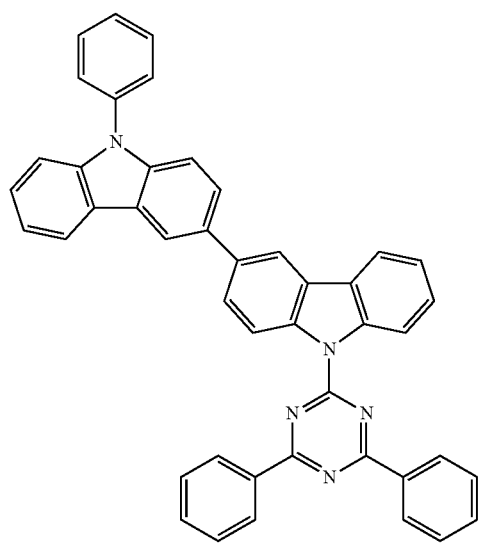
H2-26
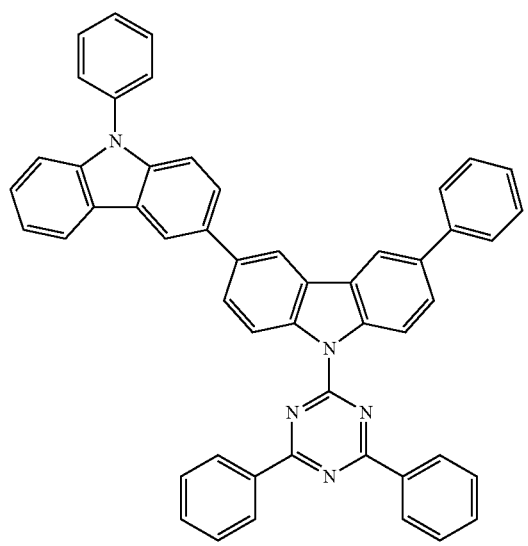
H2-27
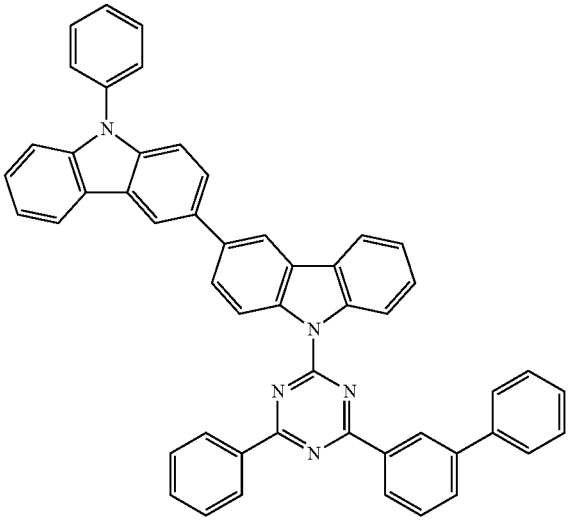
H2-28

H2-29
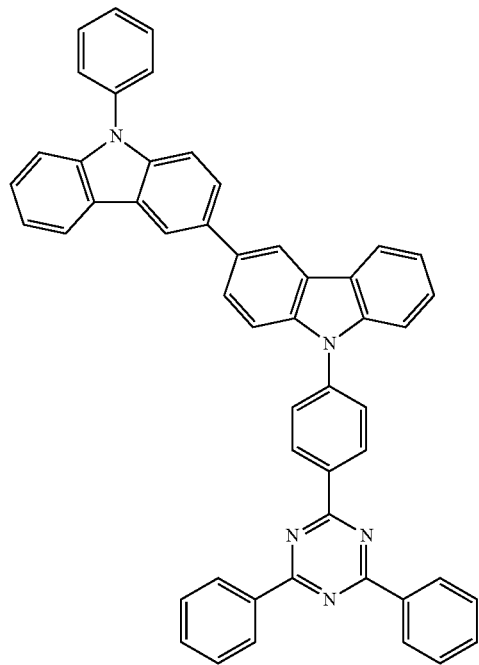
H2-30
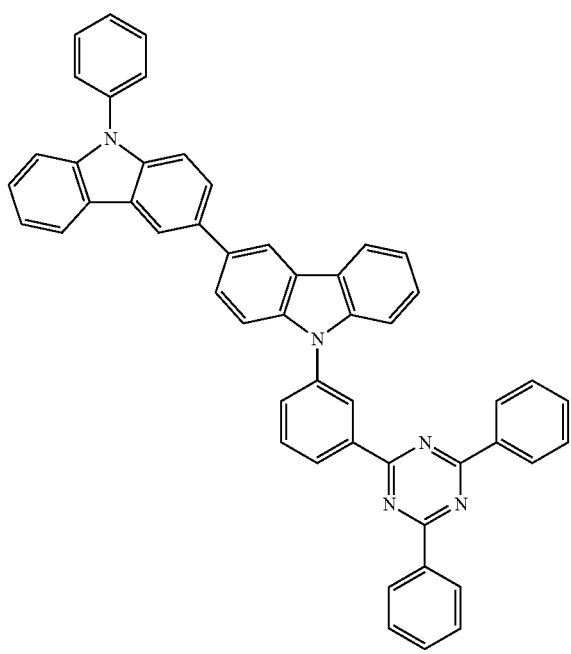
H2-31
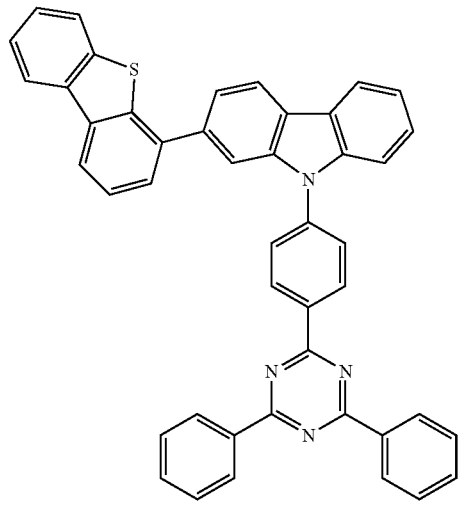
H2-32
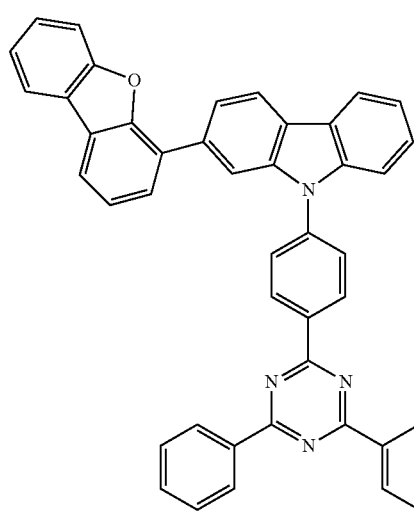
H2-33
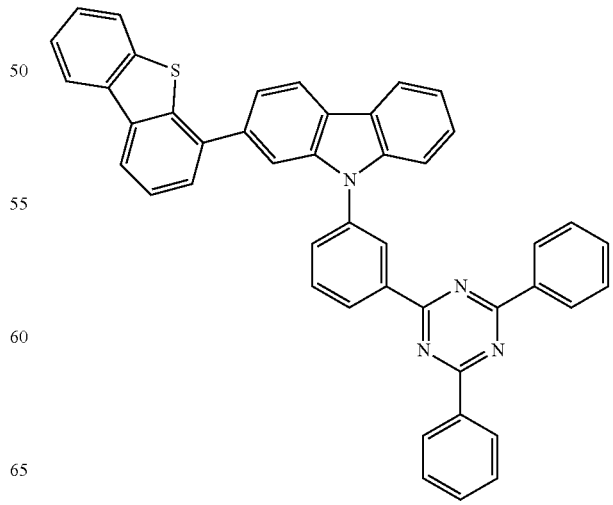

H2-34
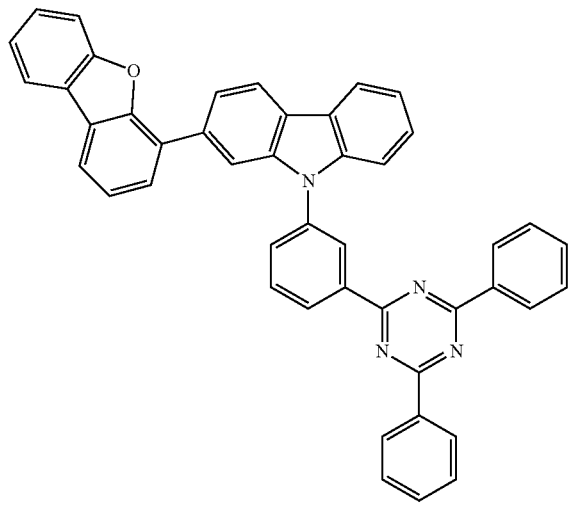
H2-35
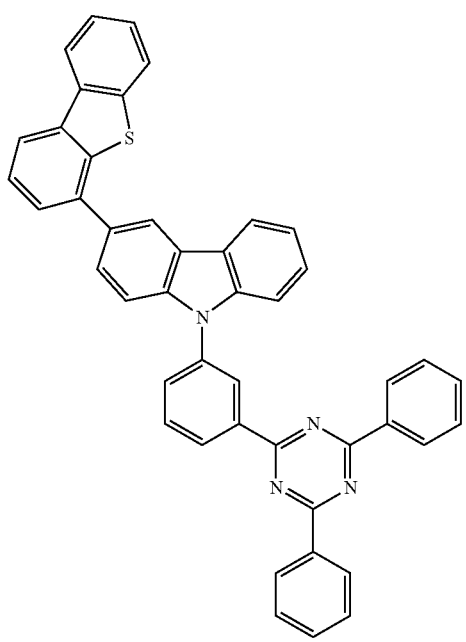
H2-36
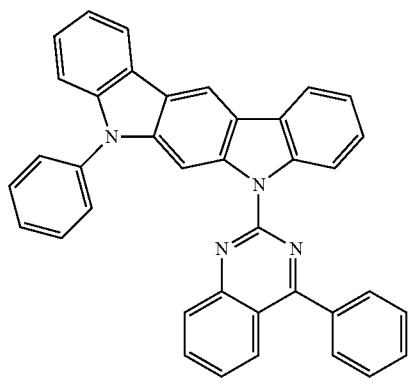
H2-37
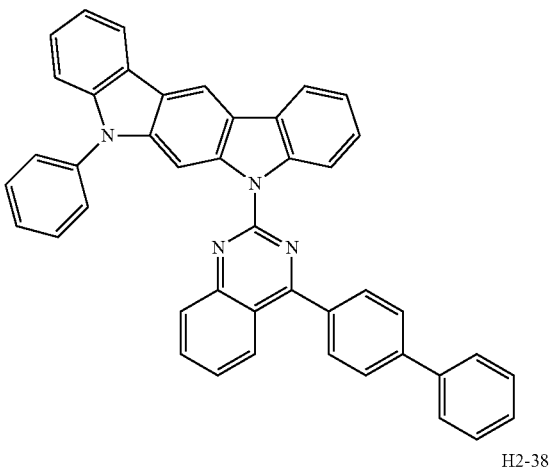
H2-38
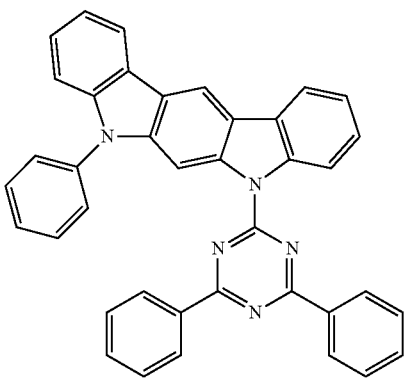
H2-39
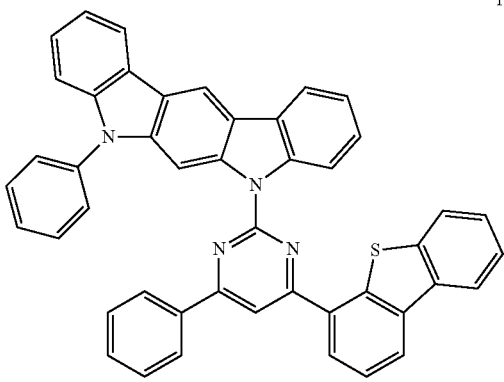
H2-40
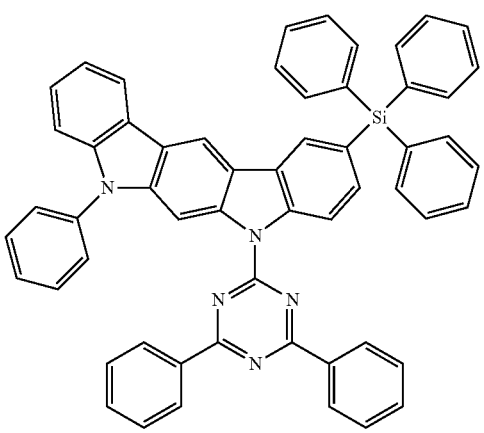

H2-41
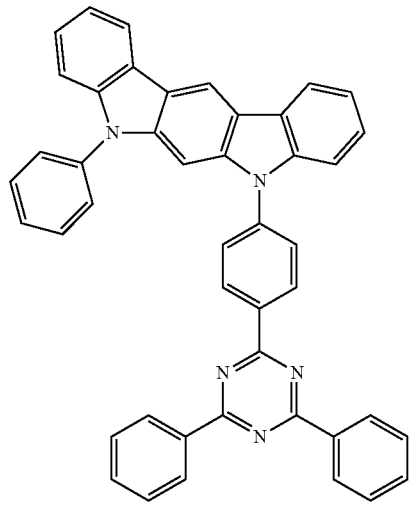
H2-42
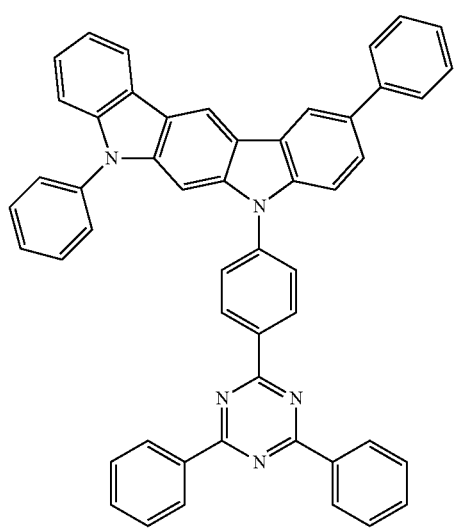
H2-43
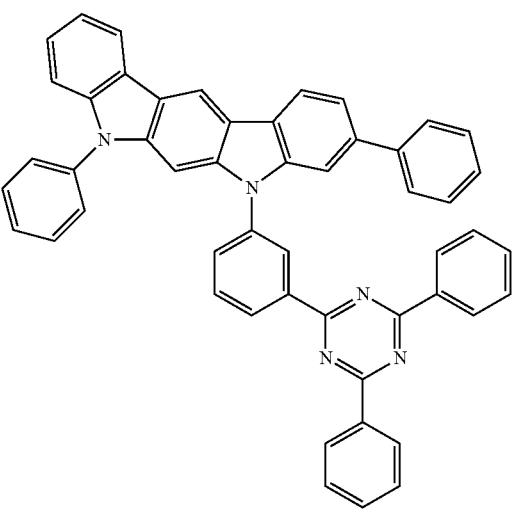
H2-44
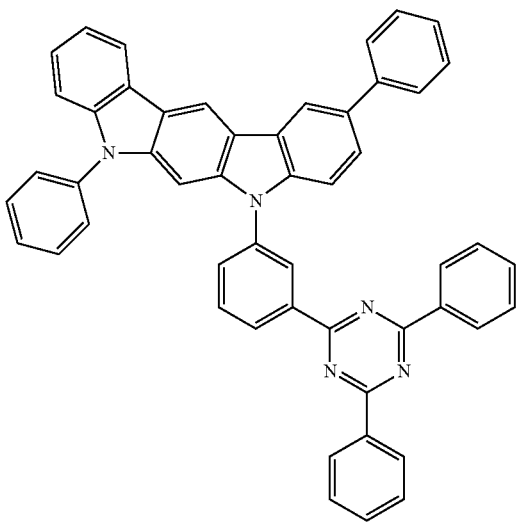
H2-45
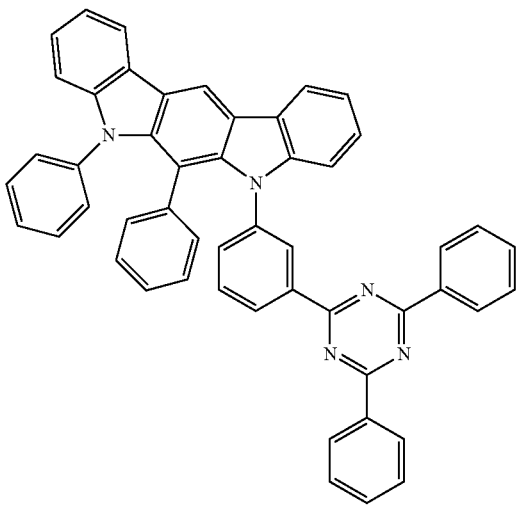
H2-46
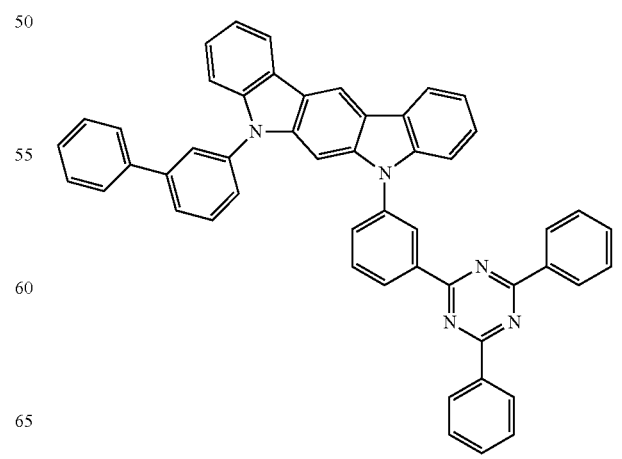

H2-47
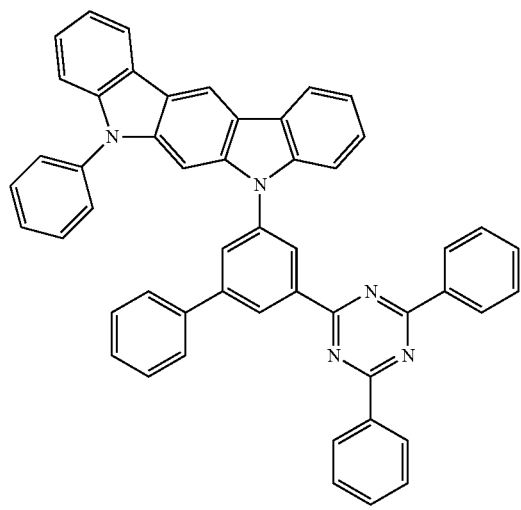
H2-49
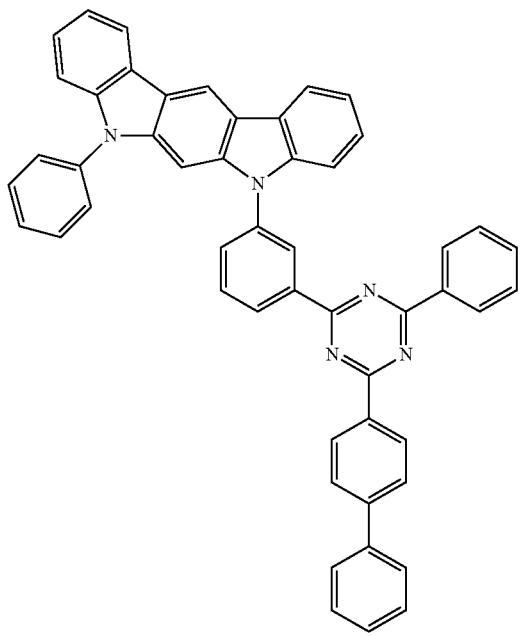
H2-48
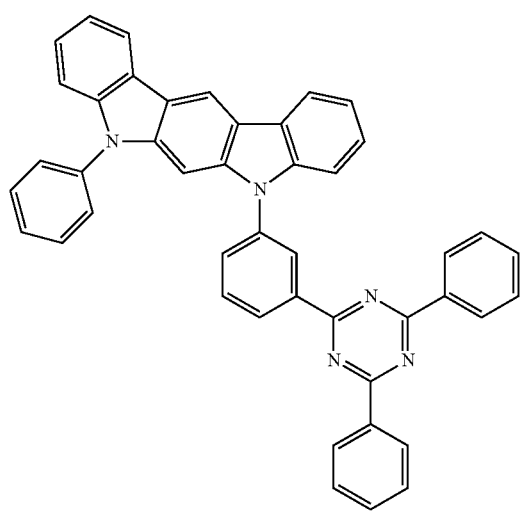
H2-50
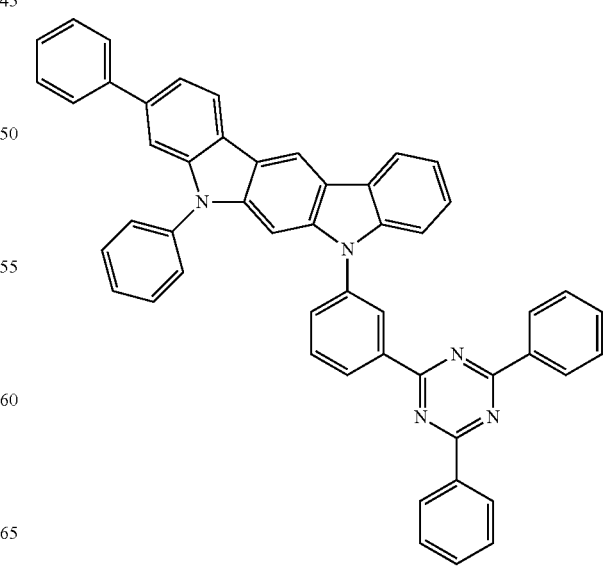

H2-51
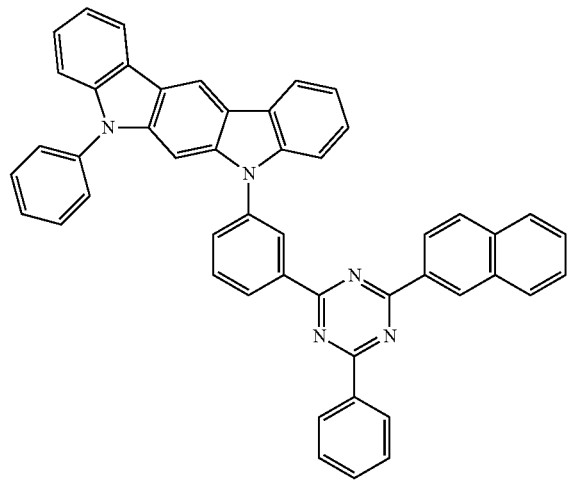
H2-53
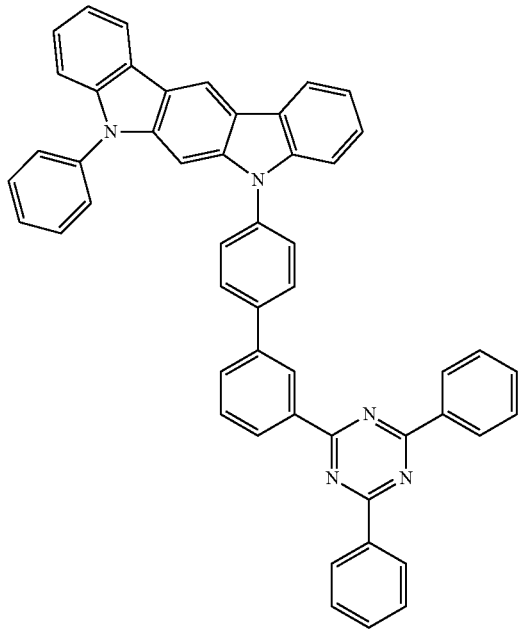
H2-52
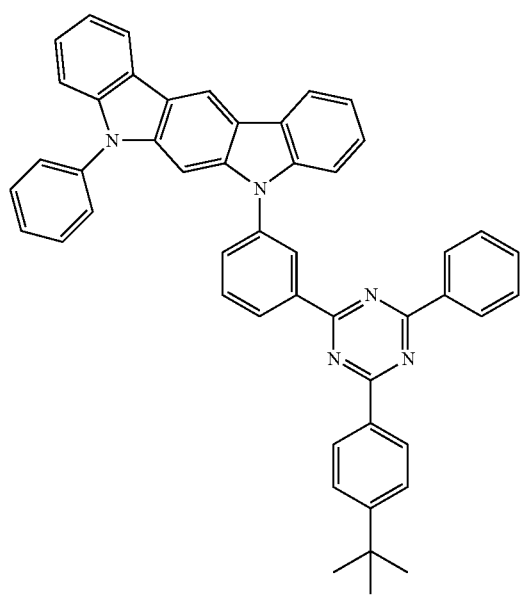
H2-54
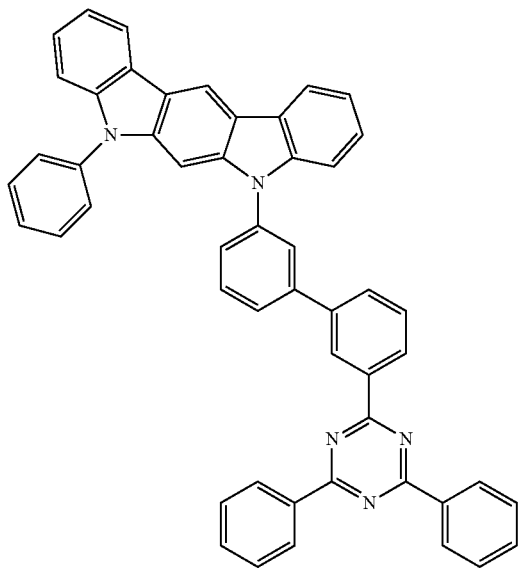

-continued
H2-55
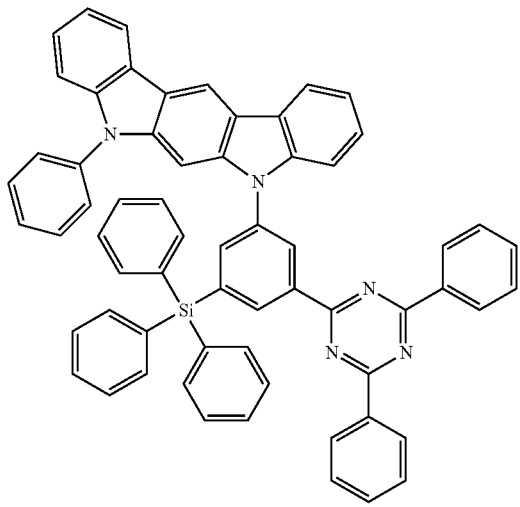
H2-56
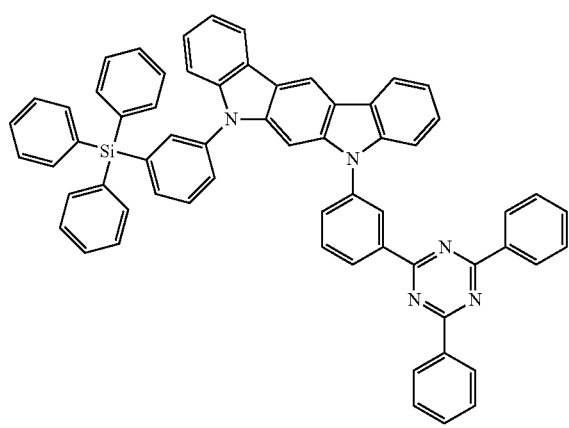
H2-57
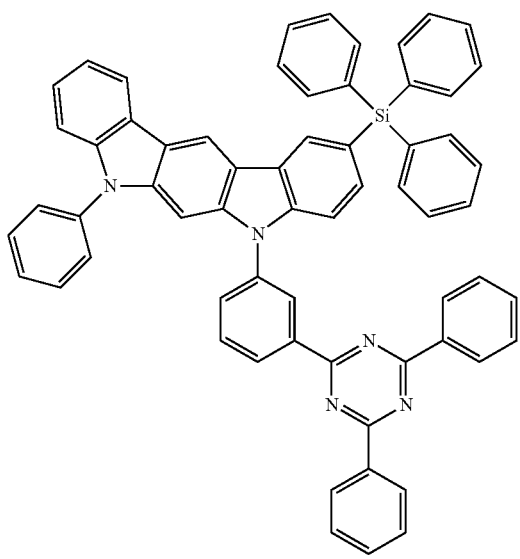
-continued
H2-58
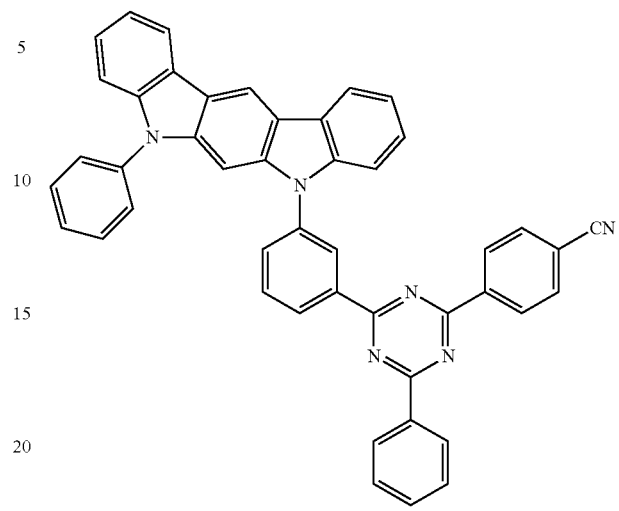
H2-59
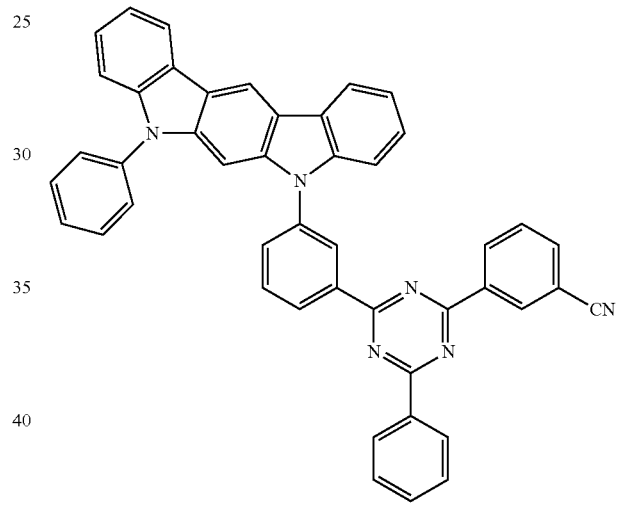
H2-60
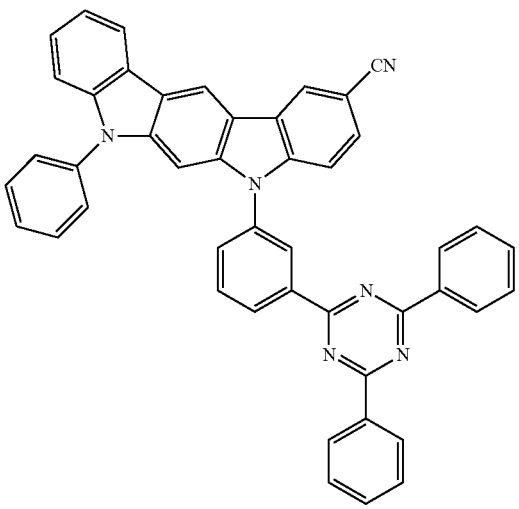

H2-61
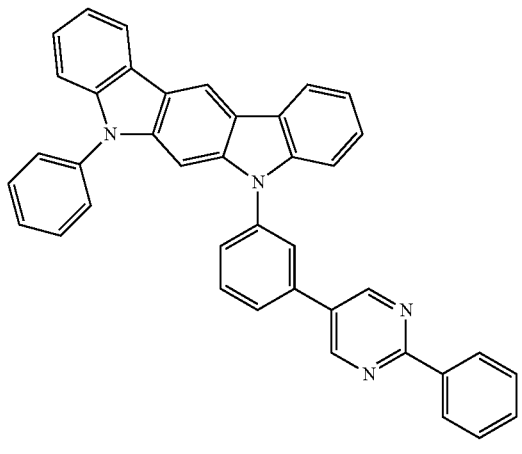
H2-64
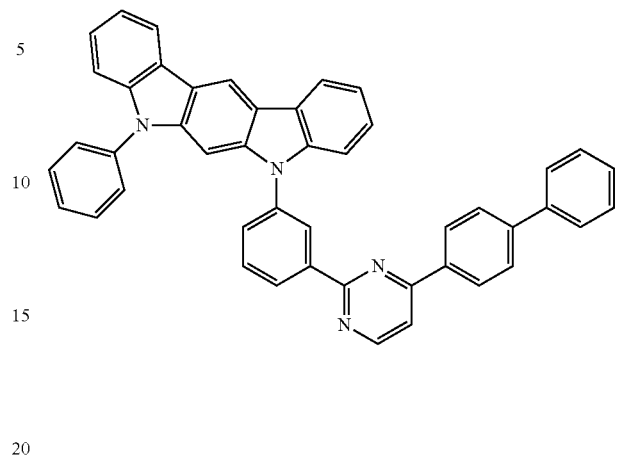
H2-62
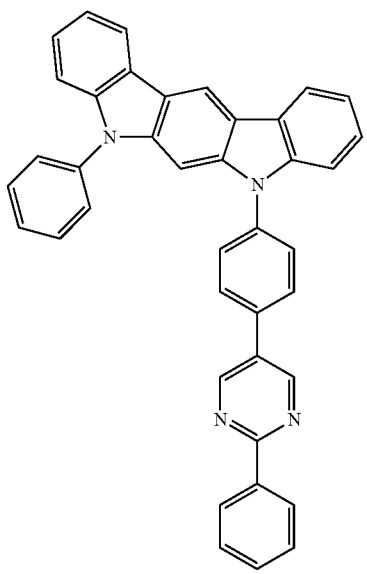
H2-65
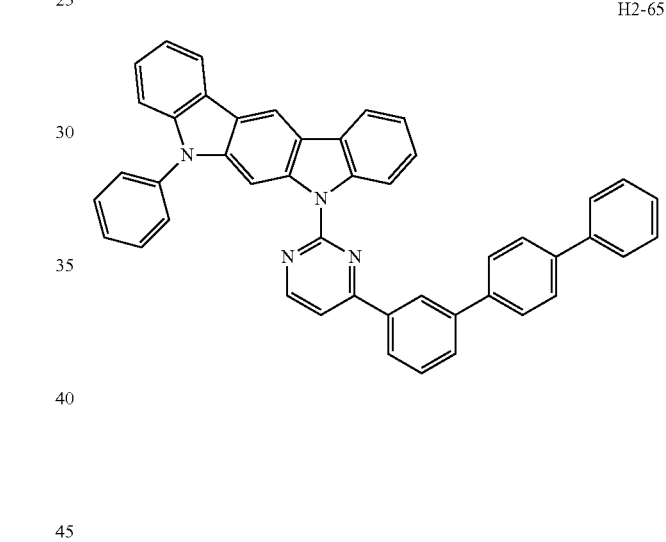
H2-63
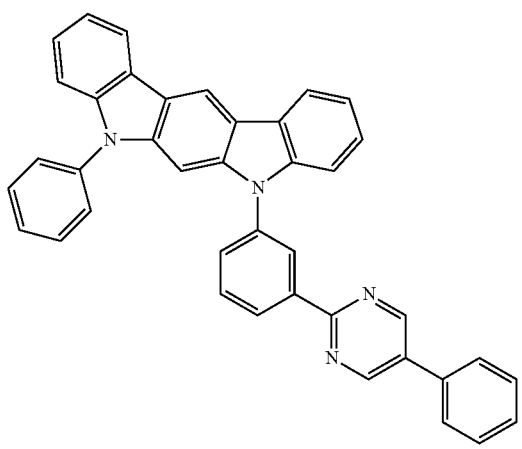
H2-66
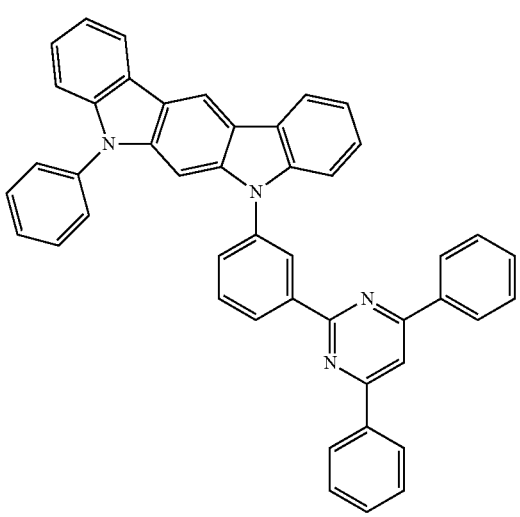

H2-67
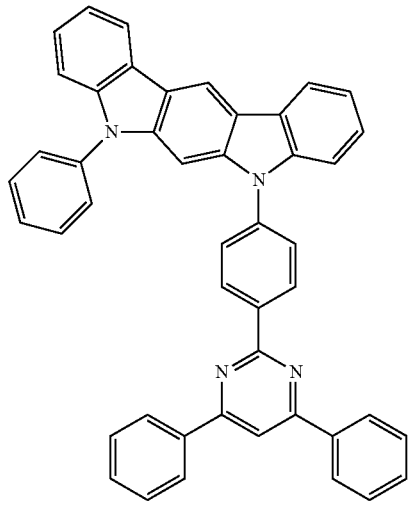
H2-68
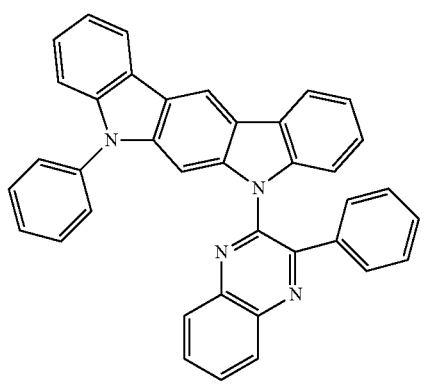
H2-69
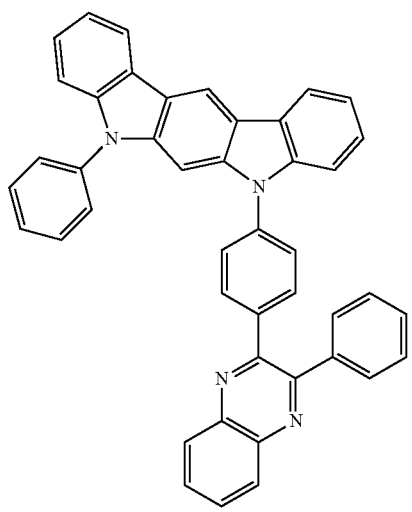
H2-70
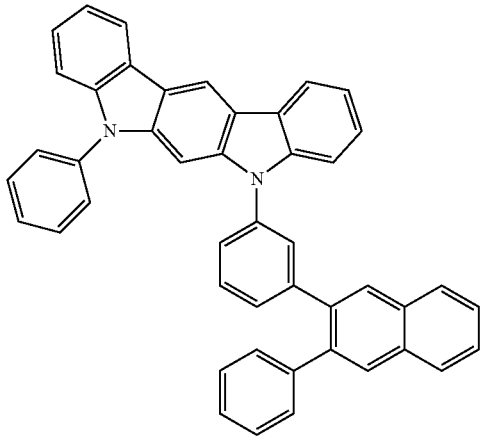
H2-71
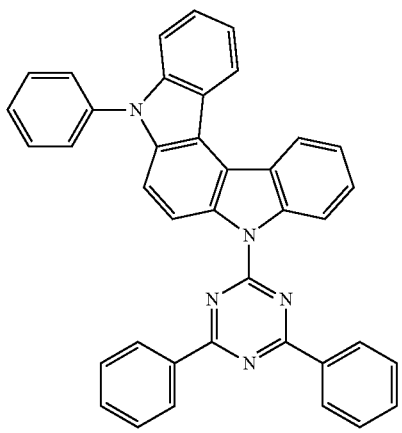
H2-72
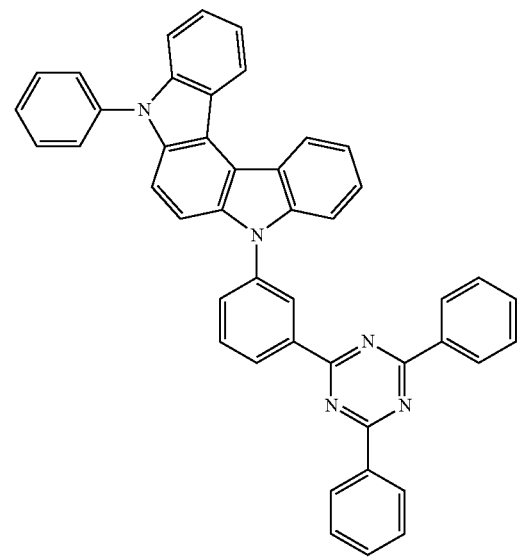

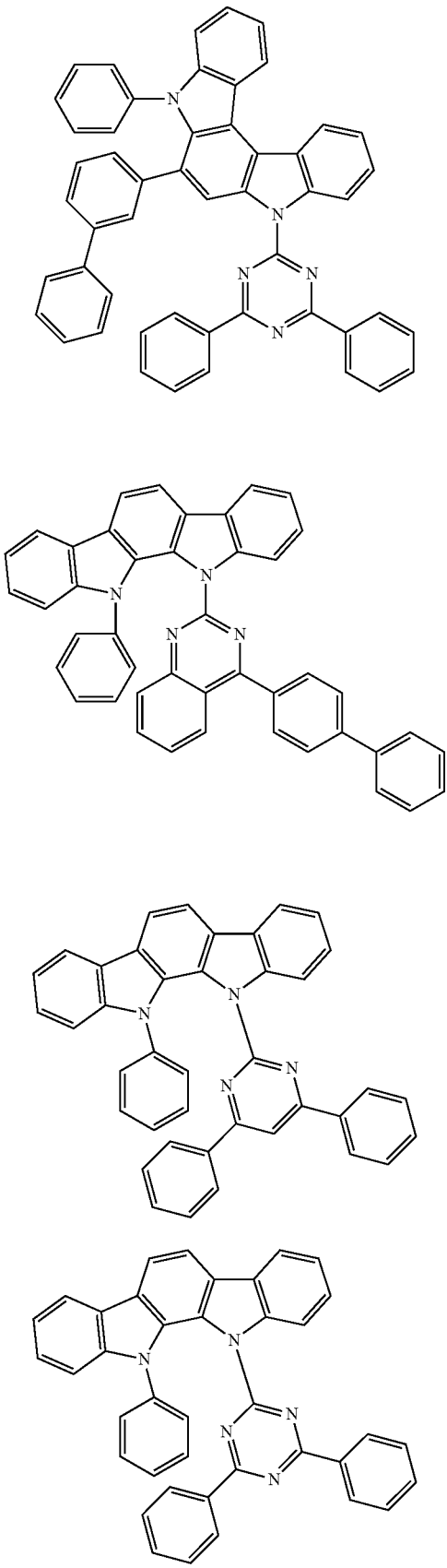
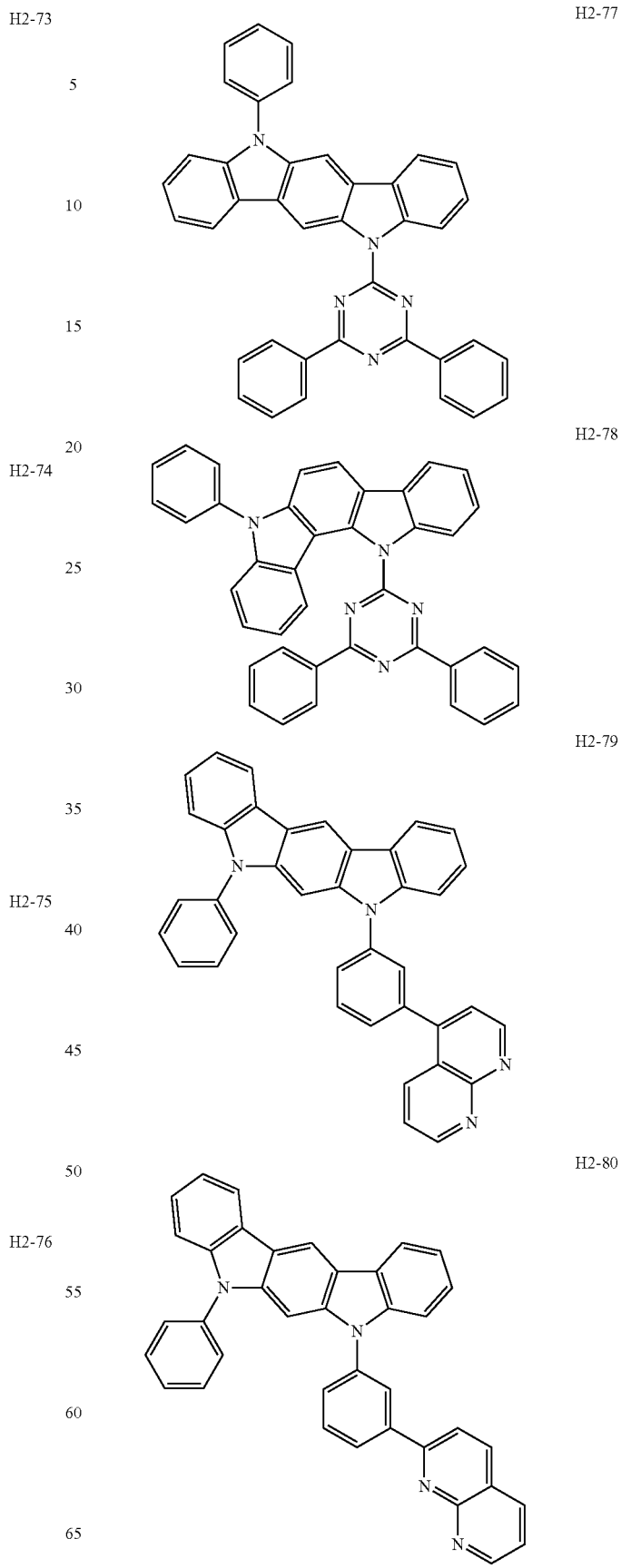

H2-81
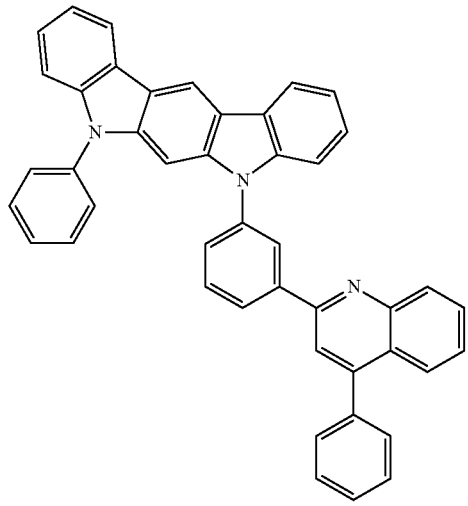
H2-84
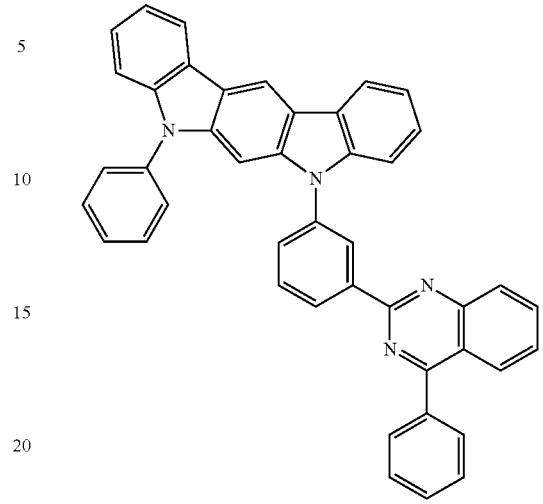
H2-82
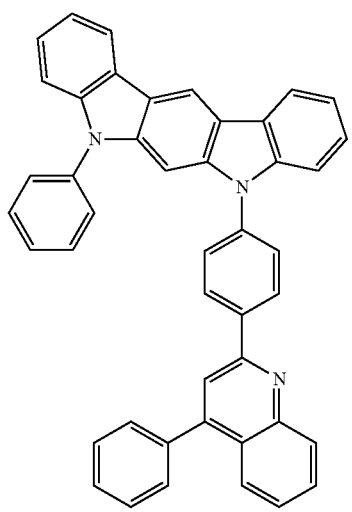
H2-85
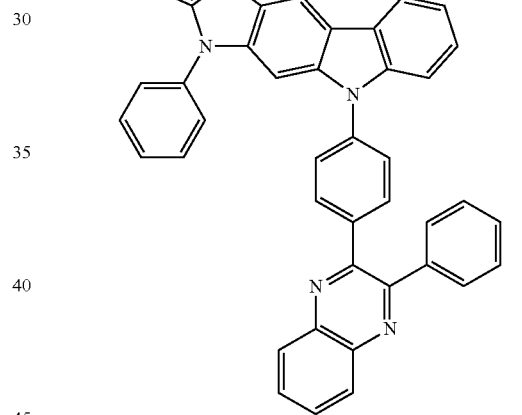
H2-83
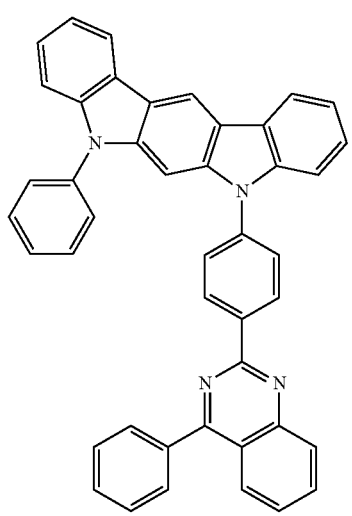
H2-86
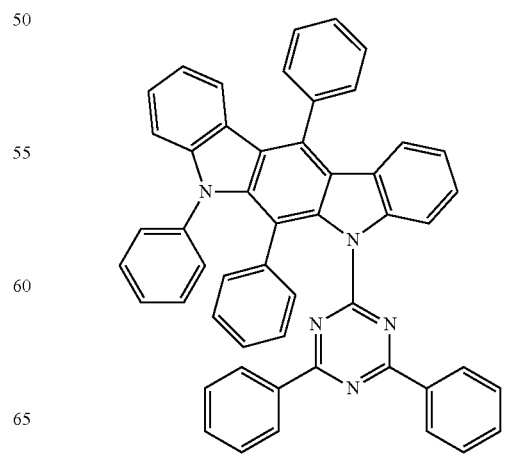

H2-87
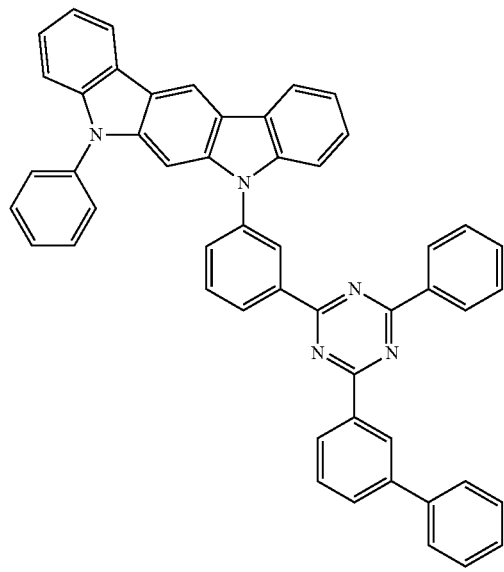
H2-88
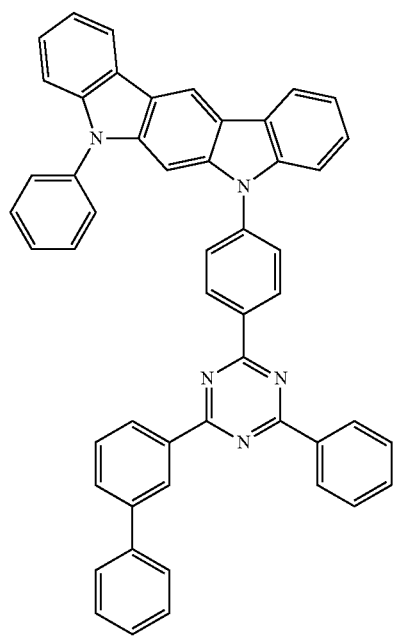
H2-89
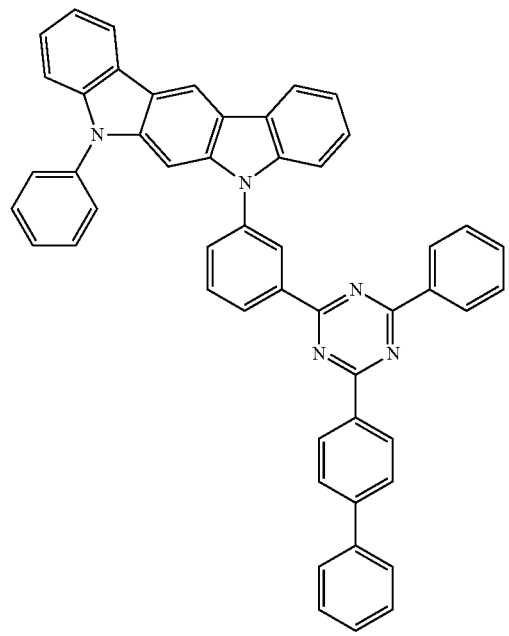
H2-90
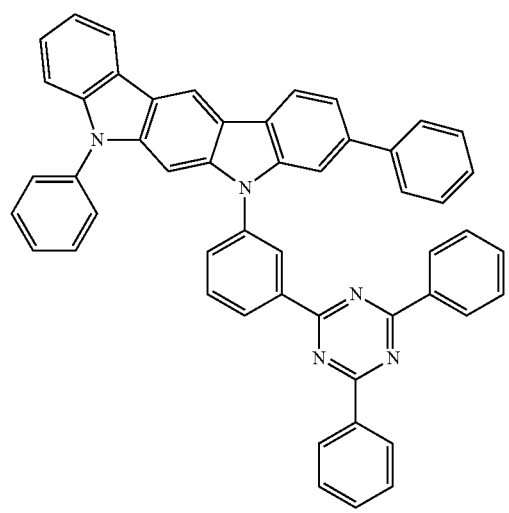

-continued
H2-91
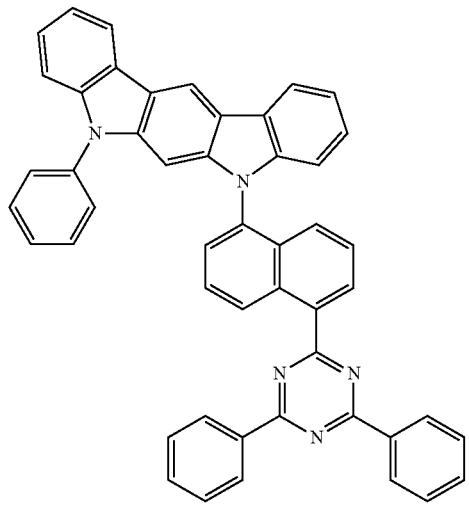
H2-92
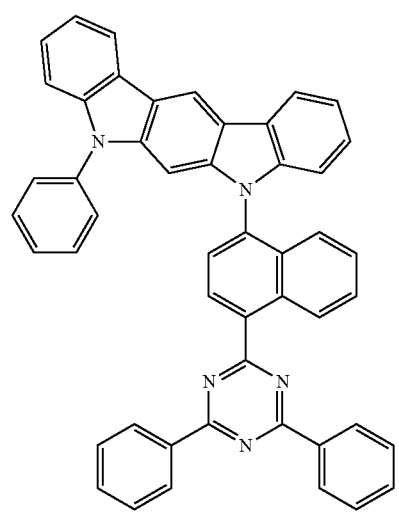
H2-93
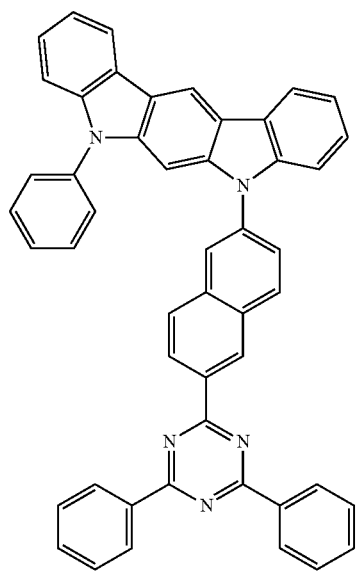
-continued
H2-94
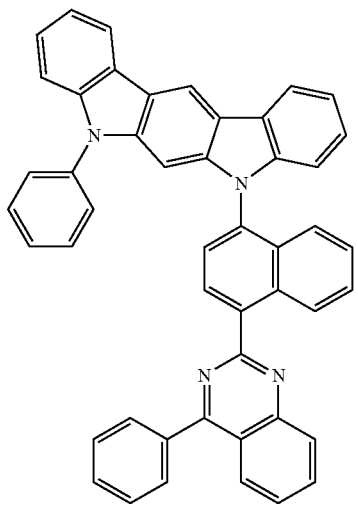
H2-95
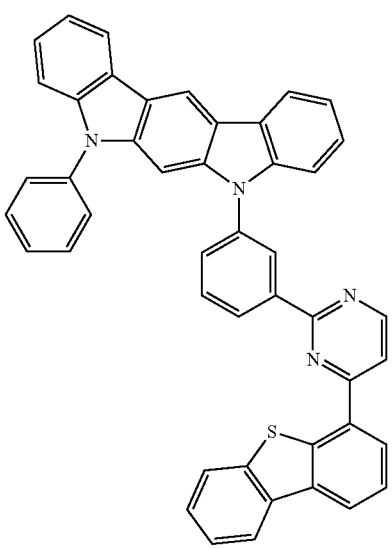
H2-96
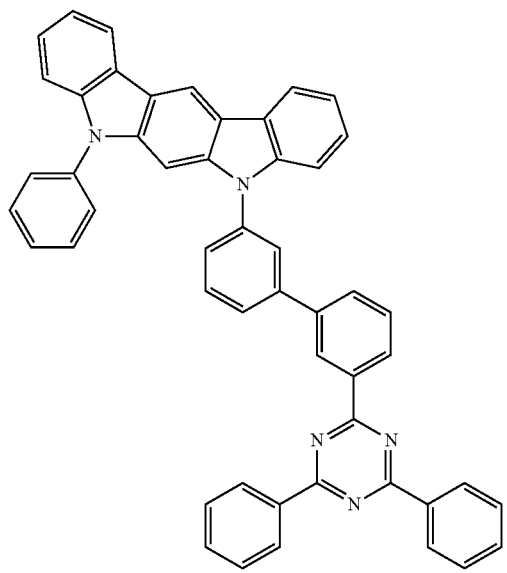

H2-97
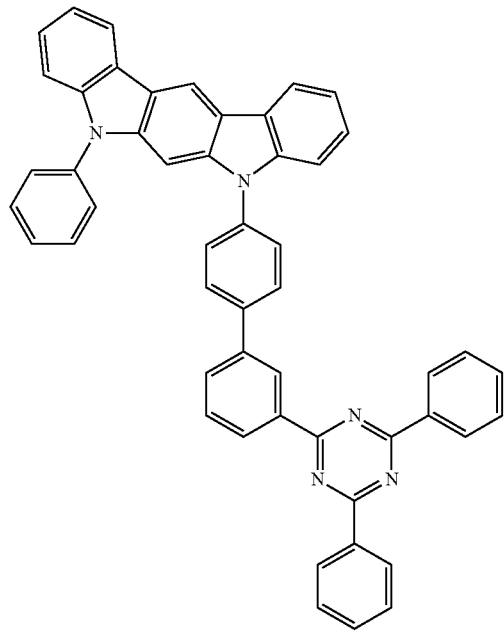
H2-98
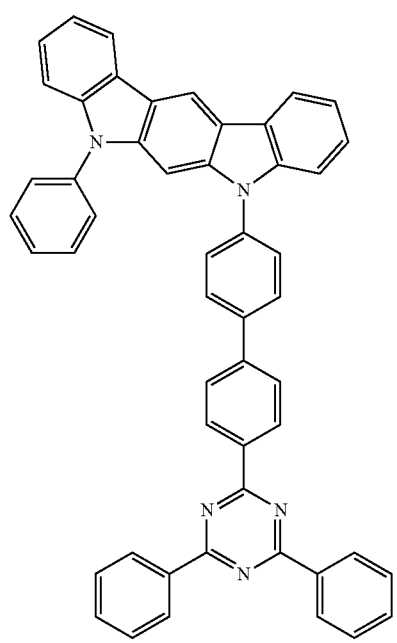
H2-99
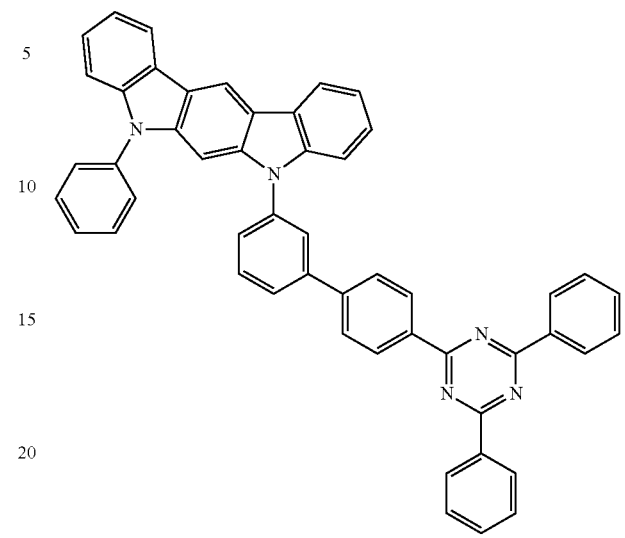
H2-100
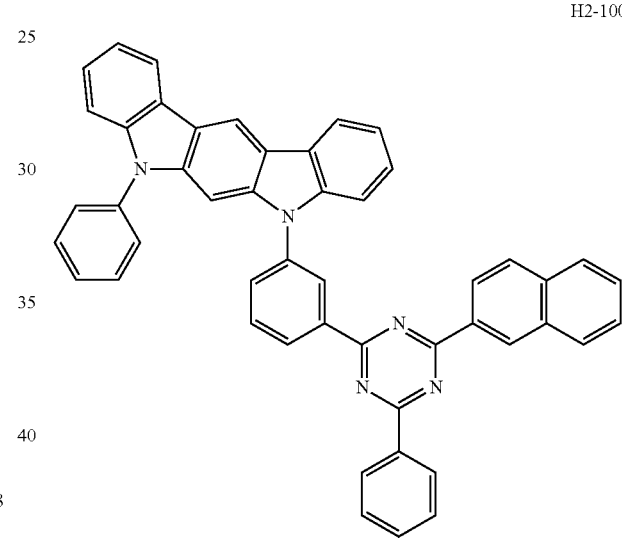
H2-101
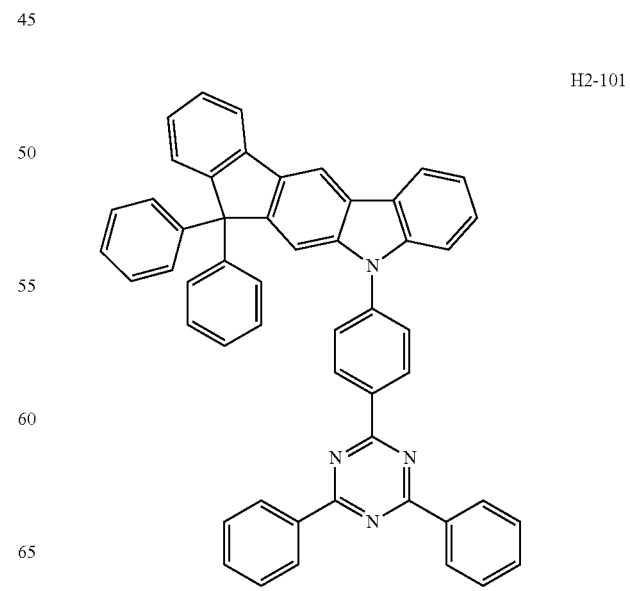

H2-102
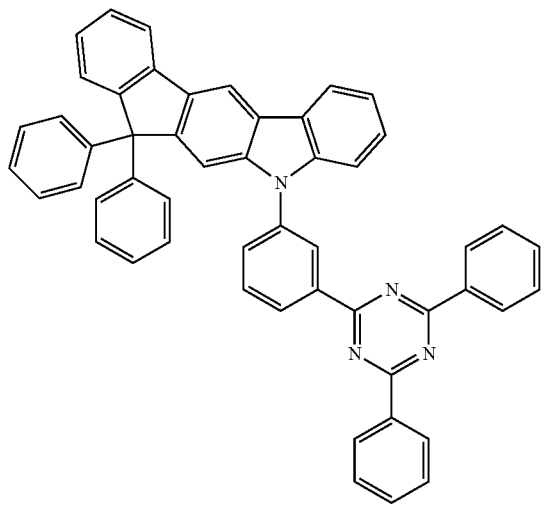
H2-105
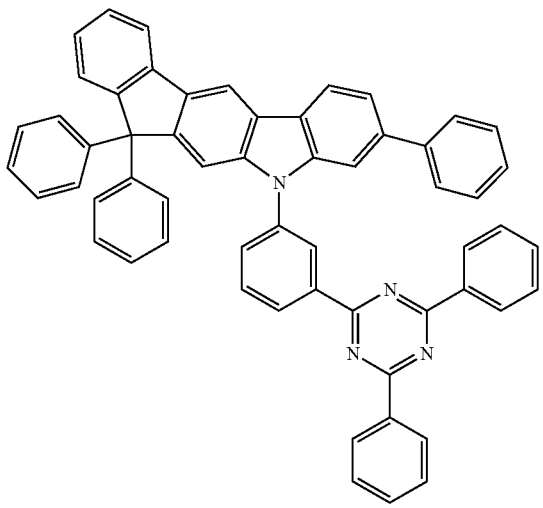
H2-103
H2-106
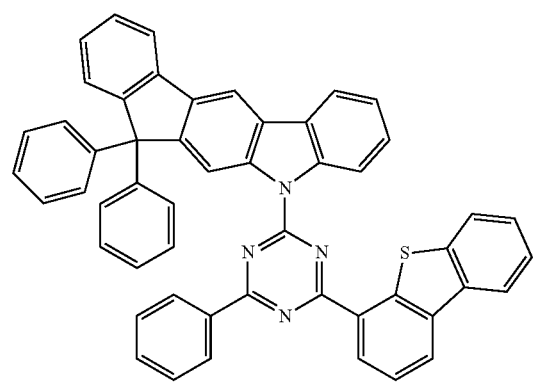
H2-104
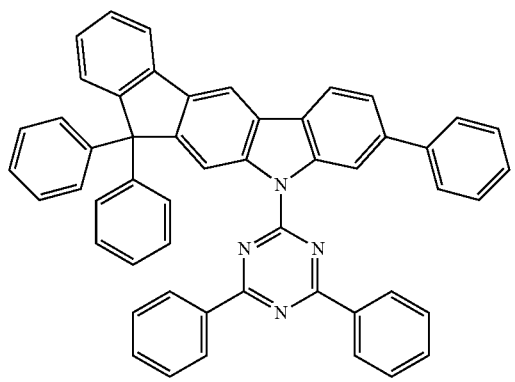
H2-107
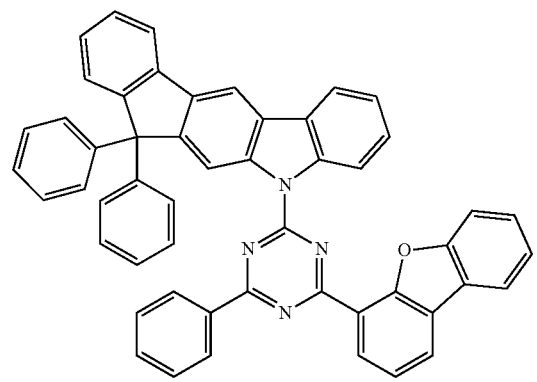

H2-108
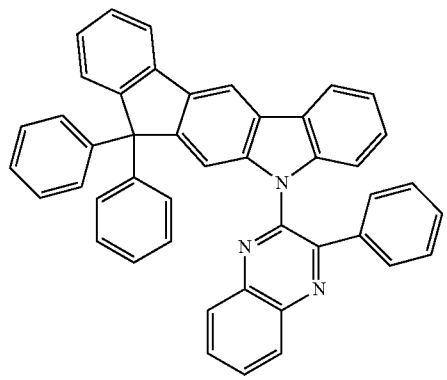
H2-109
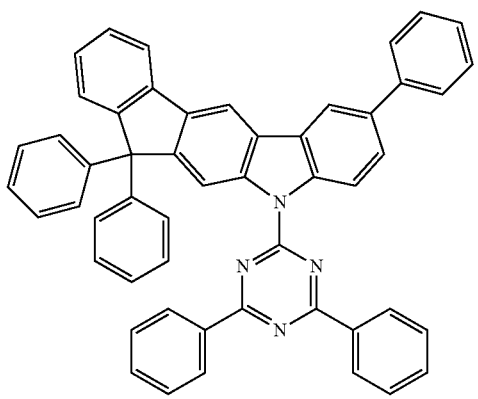
H2-110
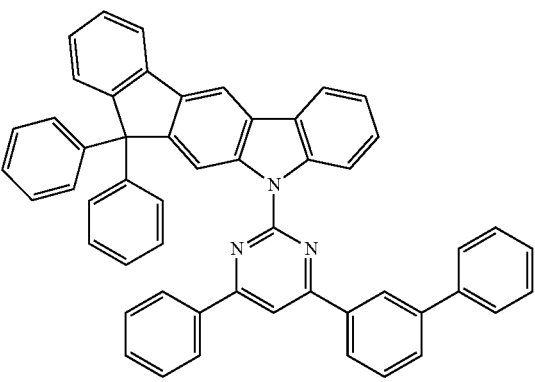
H2-111
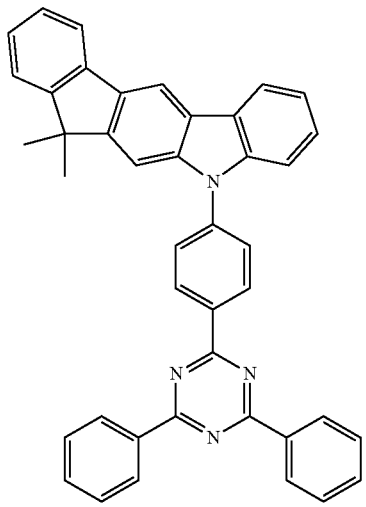
H2-112
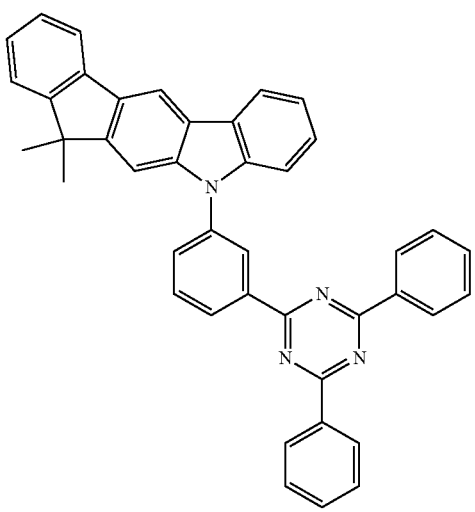
H2-113
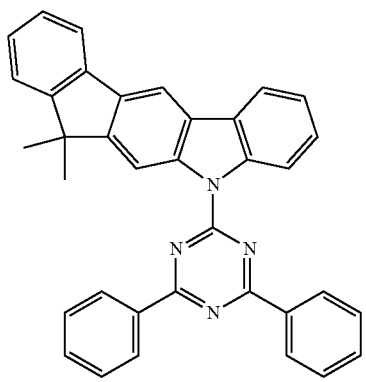

H2-114
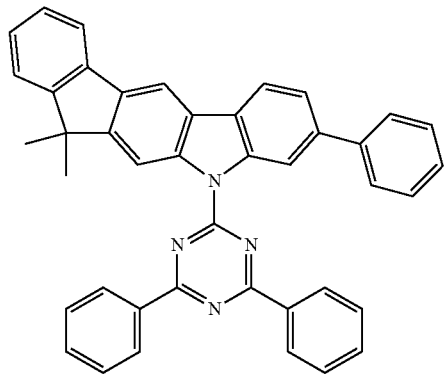
H2-117
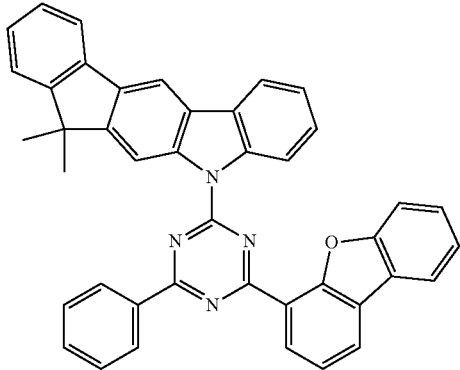
H2-115
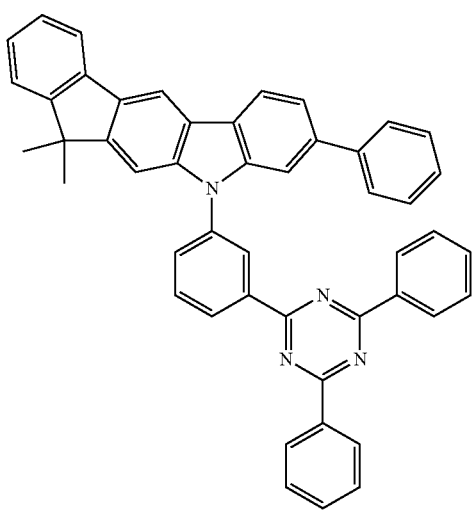
H2-118
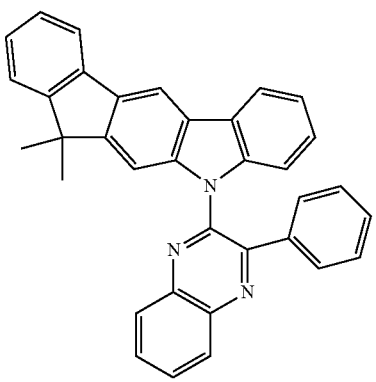
H2-119
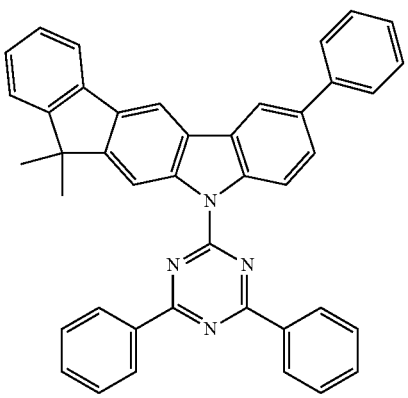
H2-116
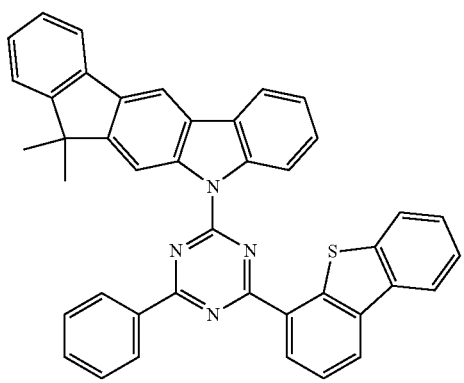
H2-120
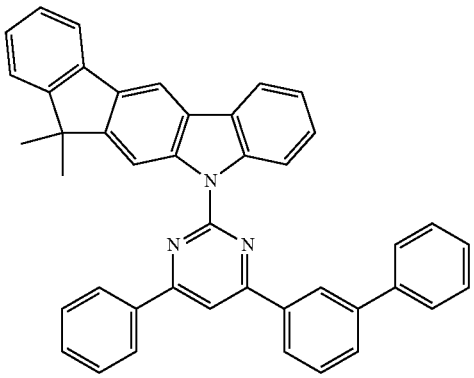

H2-121
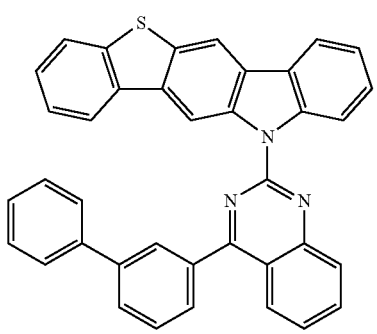
H2-122
H2-123
H2-124
H2-125
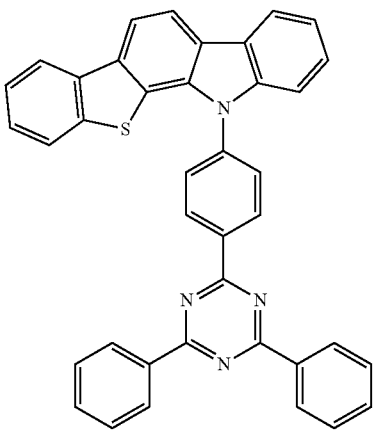
H2-126
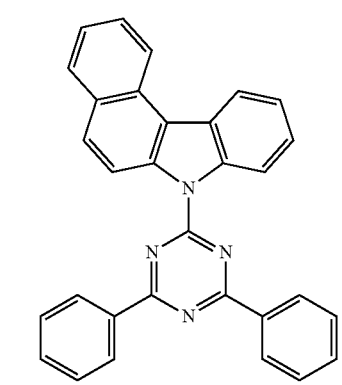
H2-127
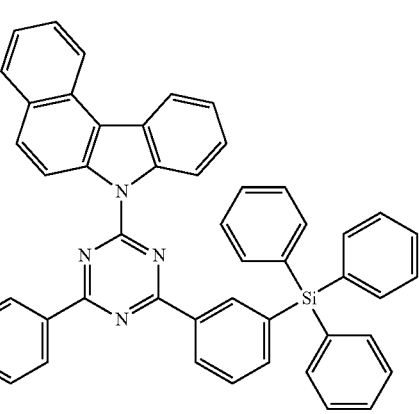

H2-128
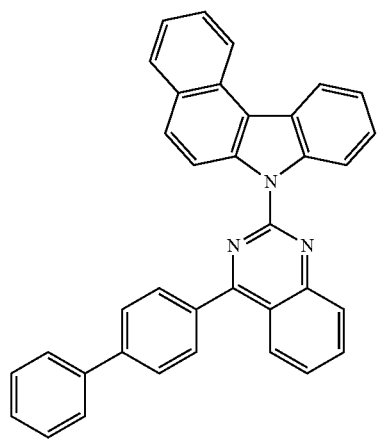
H2-129
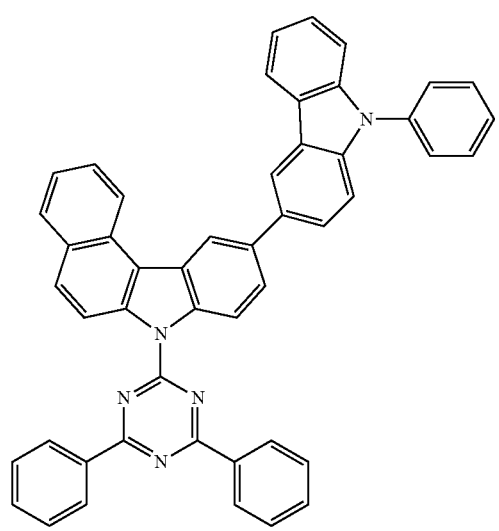
H2-130
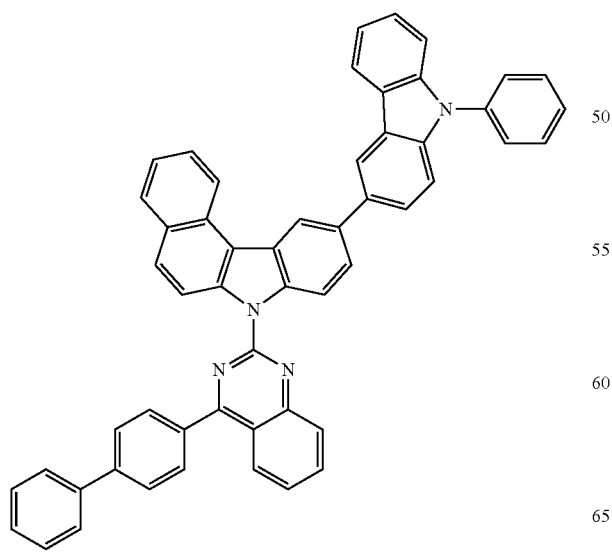
H2-131
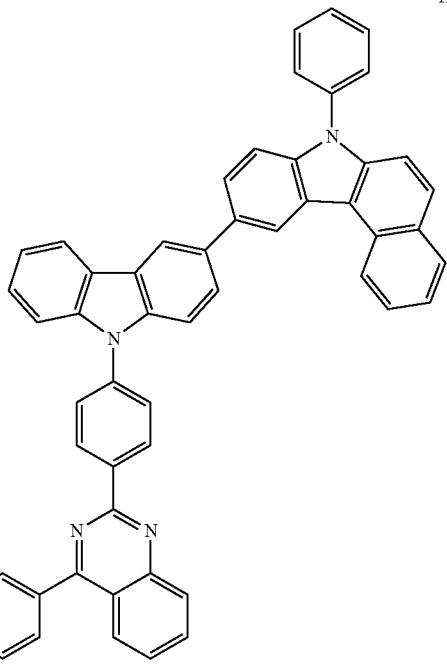
H2-132

H2-133
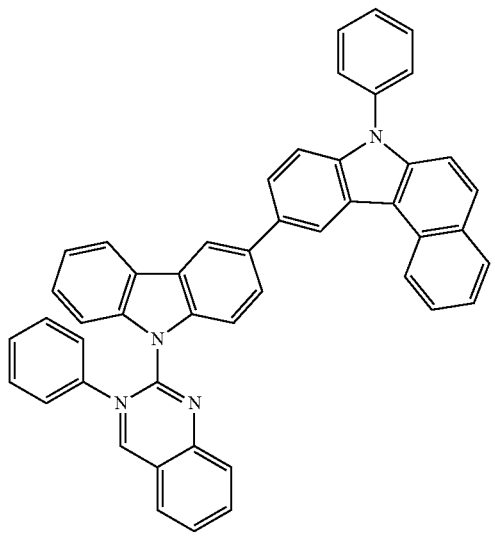
H2-135
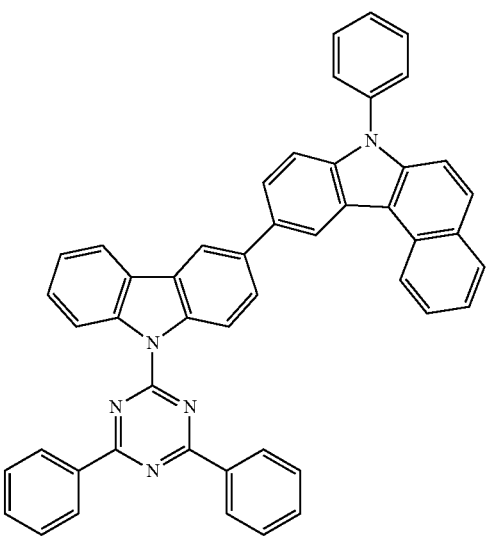
H2-136
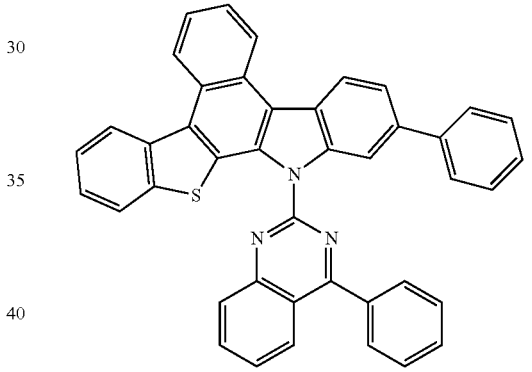
H2-134
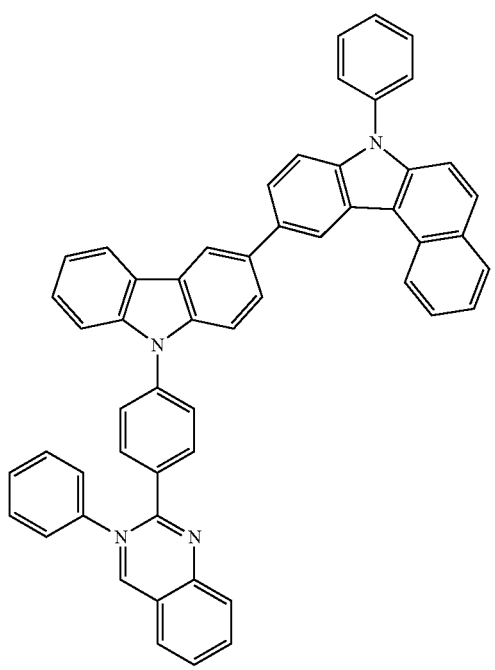
H2-137
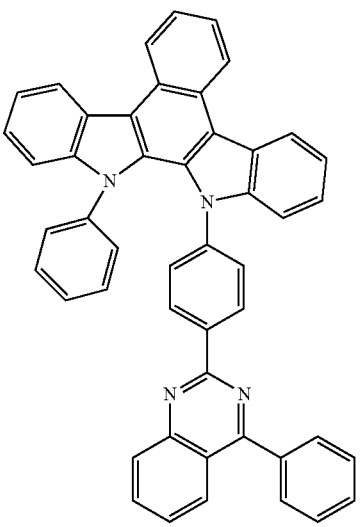

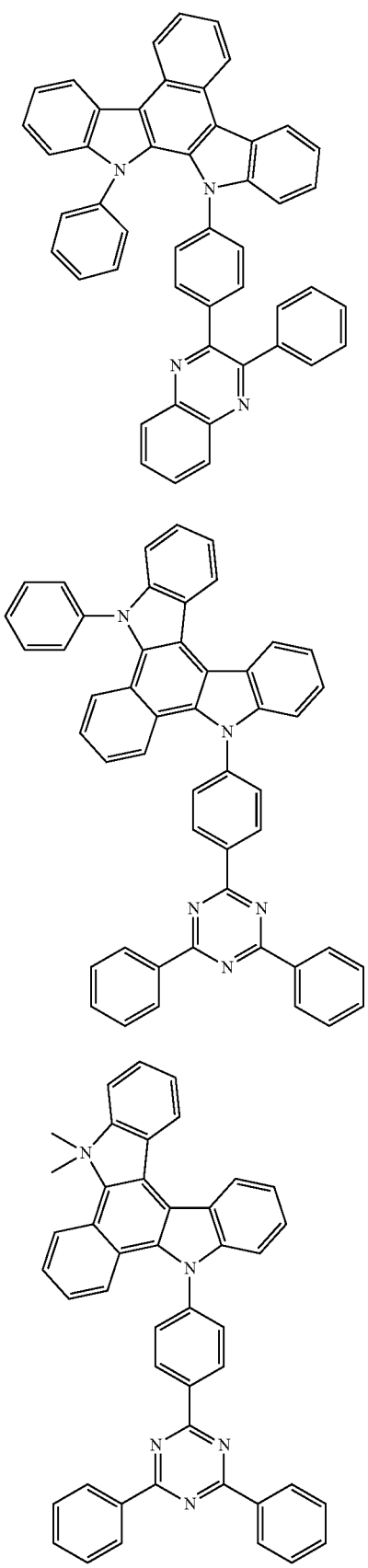
H2-138
H2-139
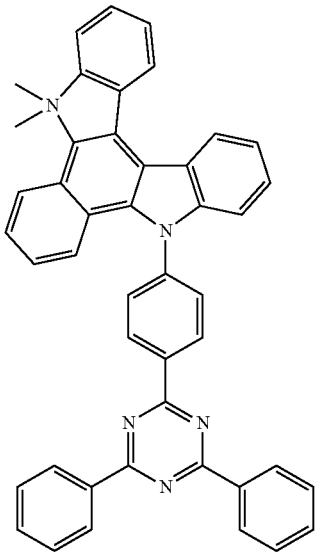
H2-139
H2-140
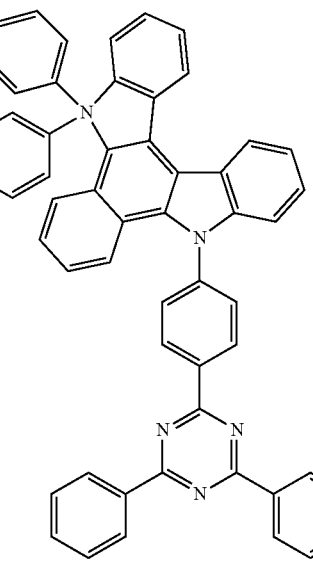
H2-140
H2-141

-continued
H2-142
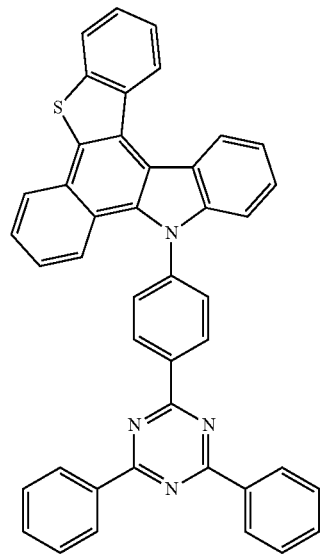
H2-143
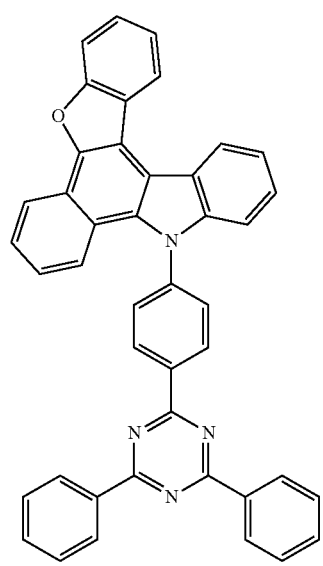
H2-144
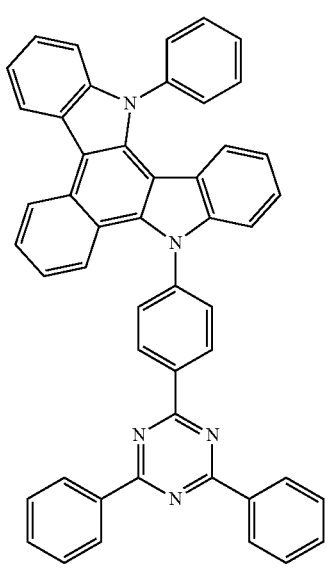
-continued
H2-145
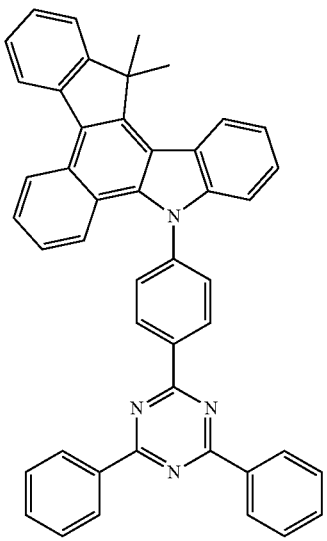
H2-146
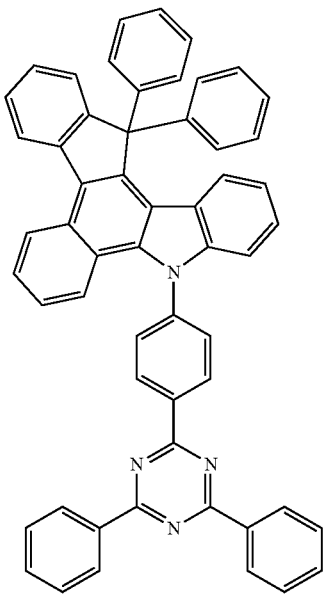
H2-147
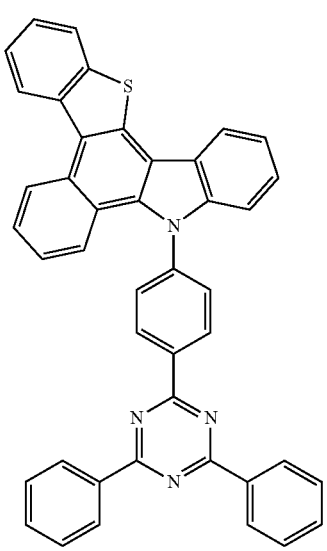

| 429 -continued | 430 -continued |
|---|---|
| H2-148 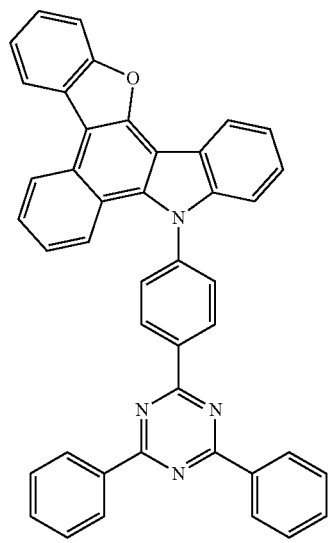 | H2-151 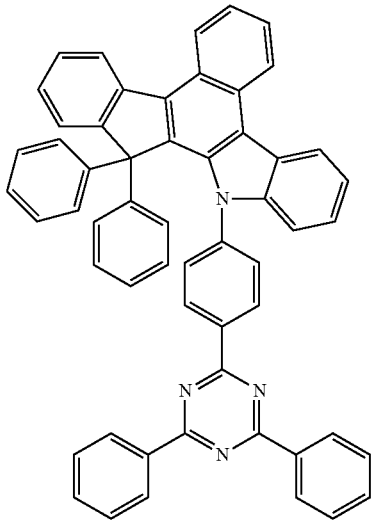 |
| H2-149 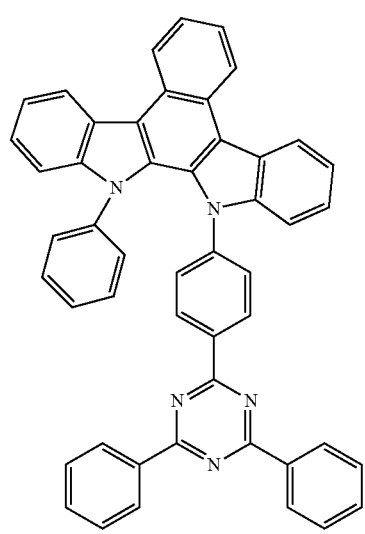 | H2-152 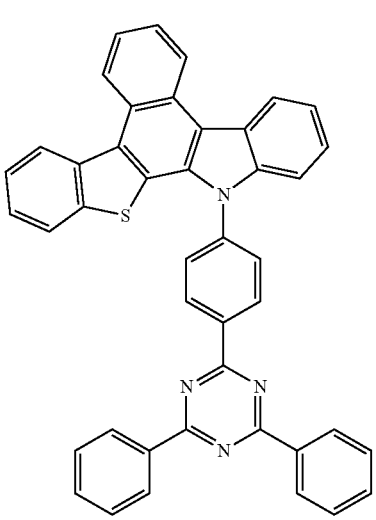 |
| H2-150 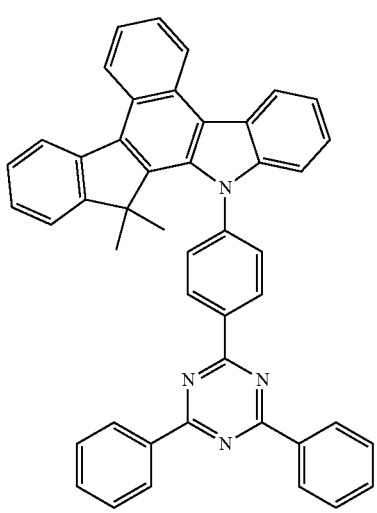 | H2-153 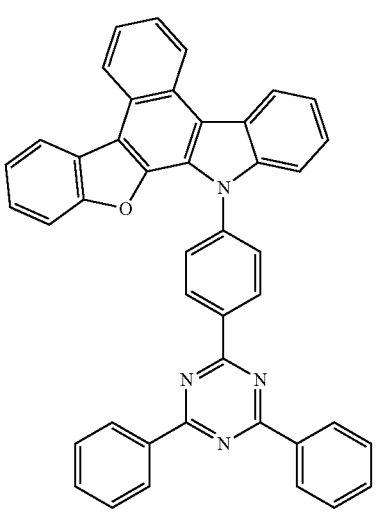 |

-continued
H2-154
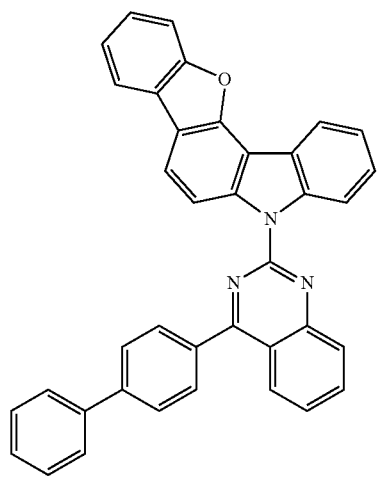
H2-155
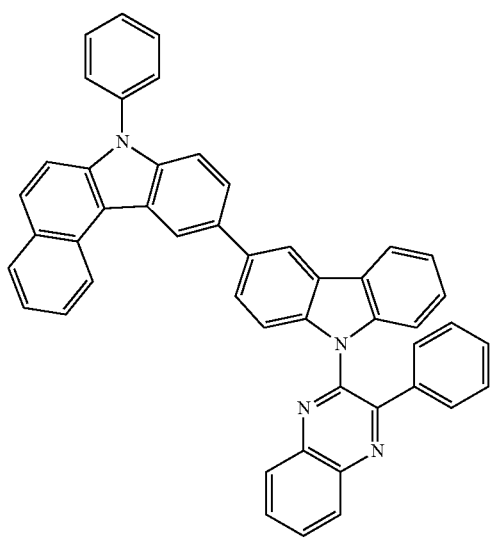
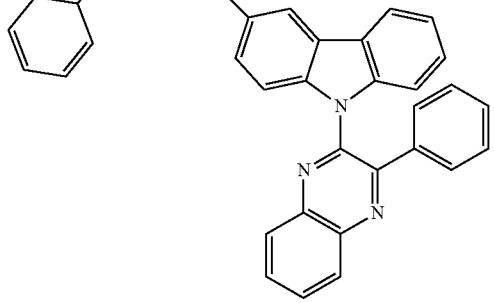
H2-156
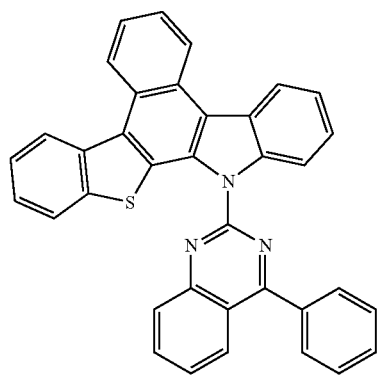
-continued
H2-157
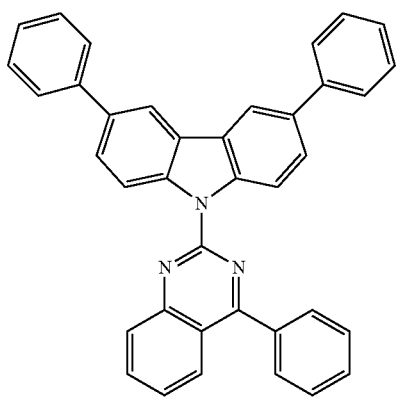
H2-158
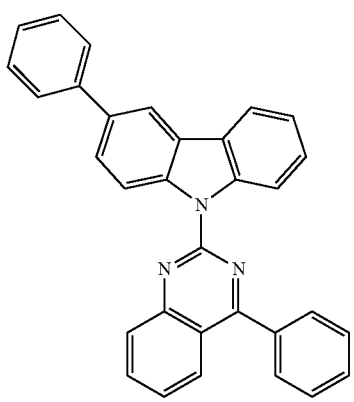
H2-159
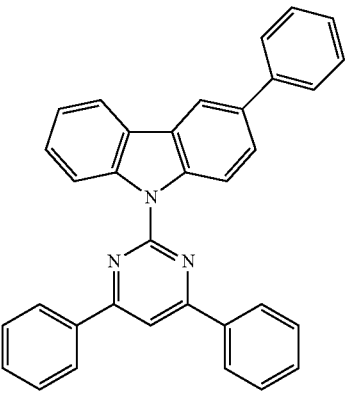
H2-160
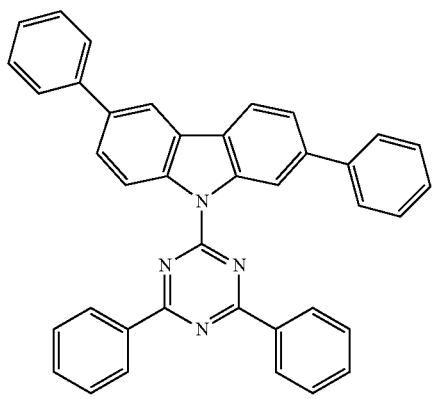

H2-161
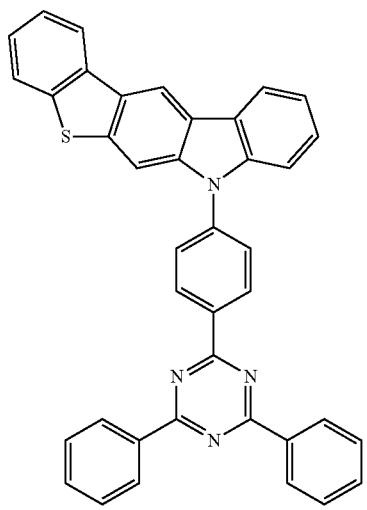
H2-162
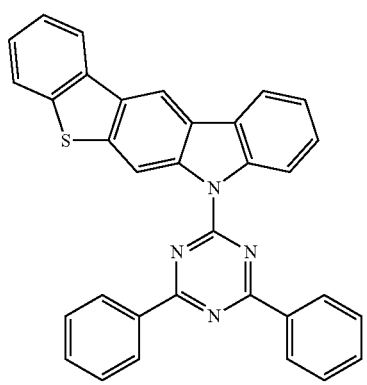
H2-163
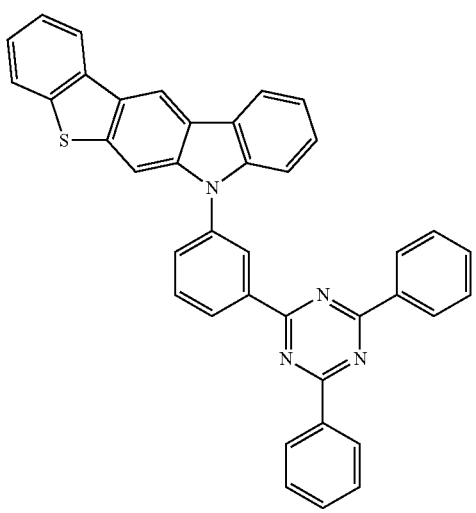
H2-164
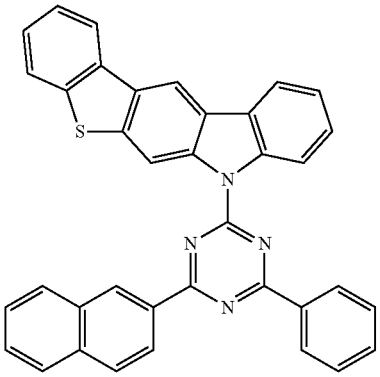
H2-165
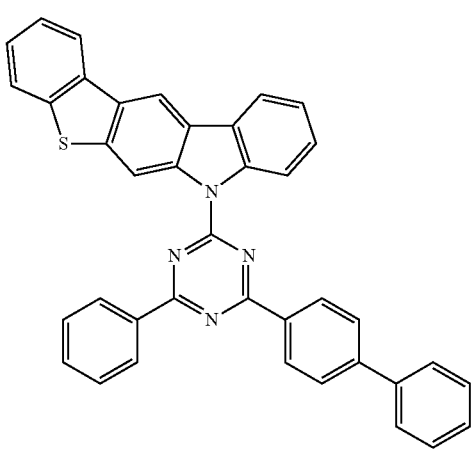
H2-166
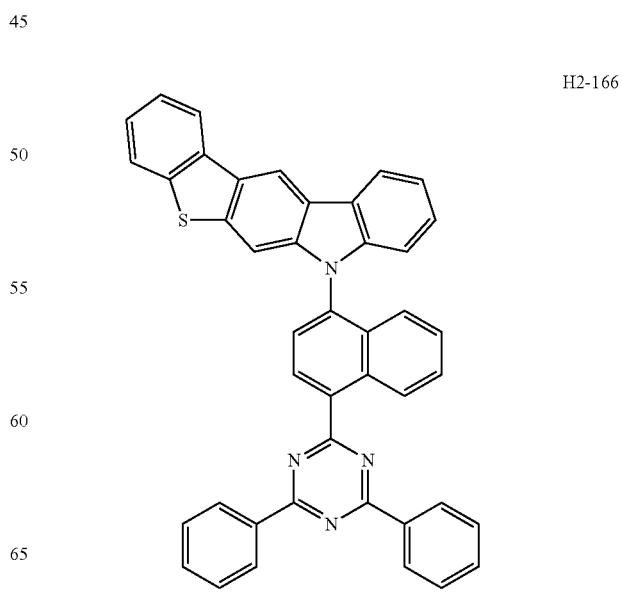

H2-167
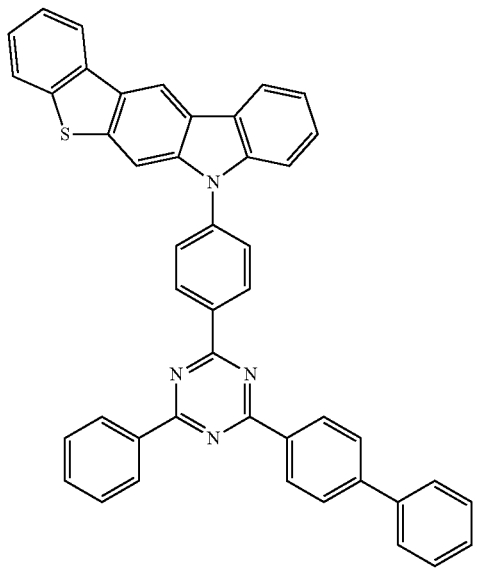
H2-168
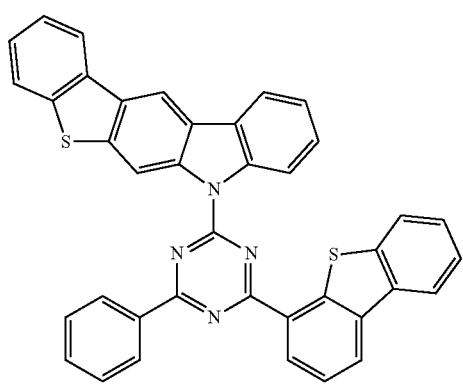
H2-169
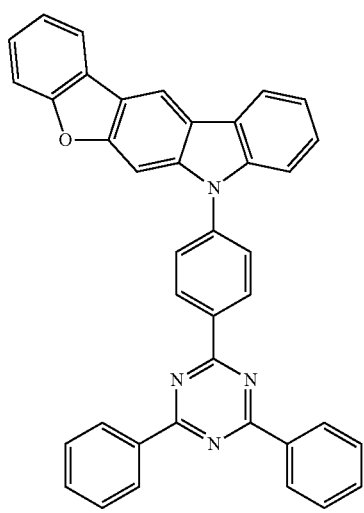
H2-170
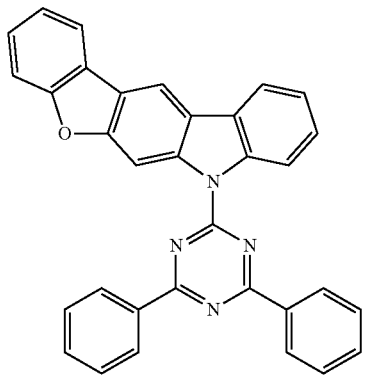
H2-171
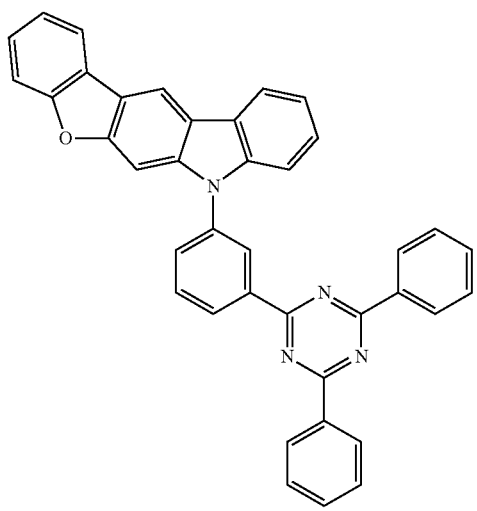
H2-172
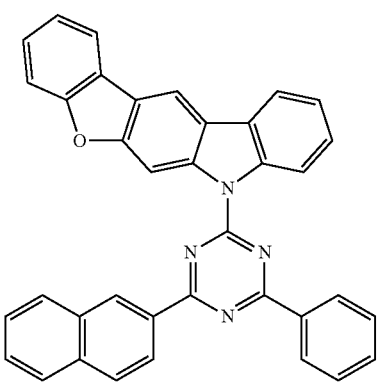

-continued
H2-173
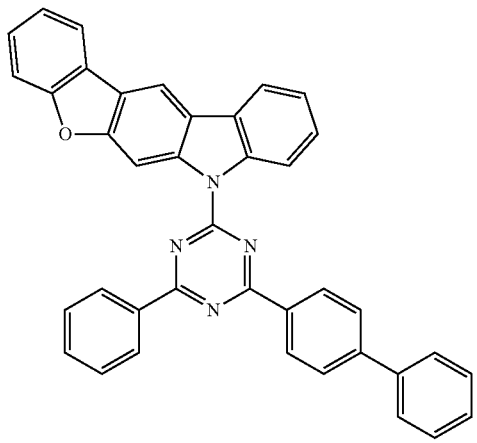
H2-174
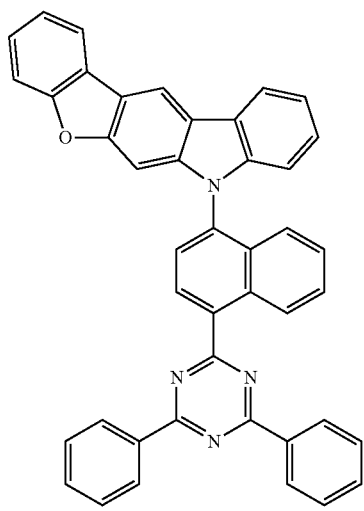
H2-175
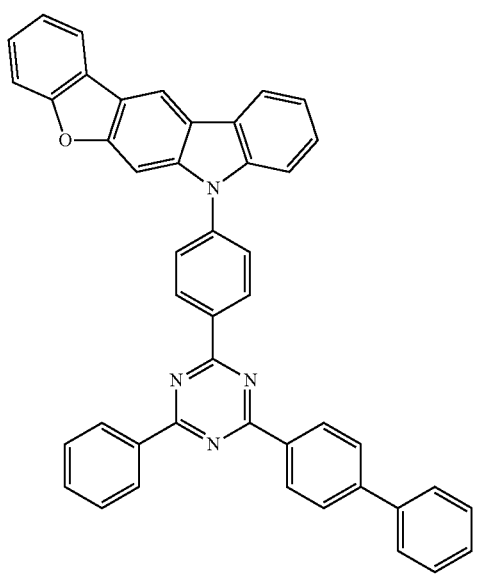
-continued
H2-176
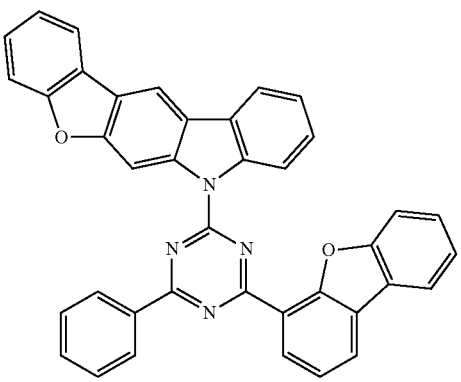
H2-177
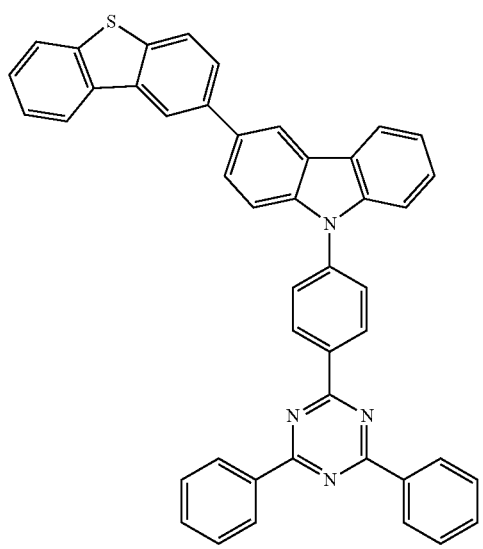
H2-178
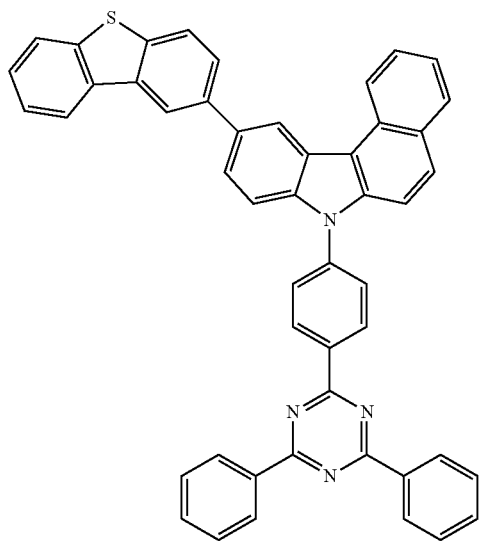

H2-179
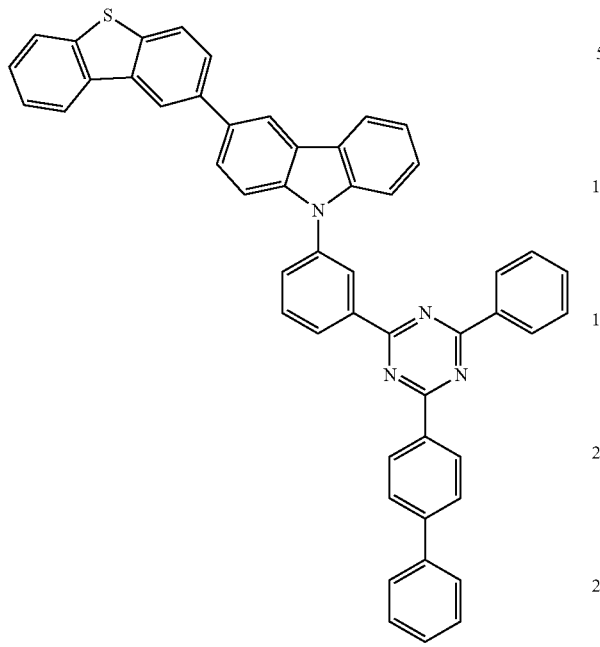
H2-180
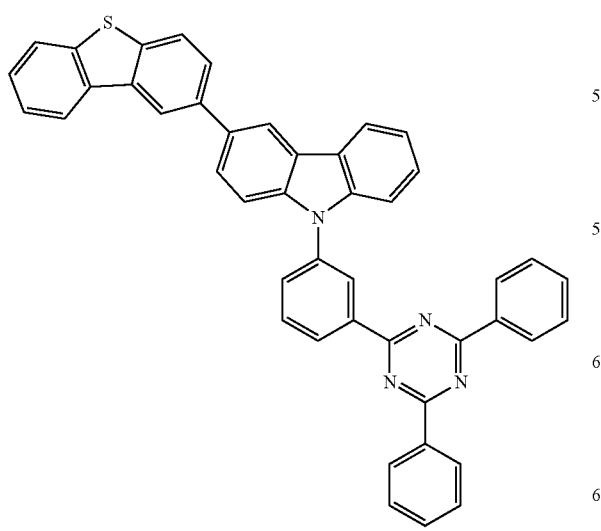
H2-181
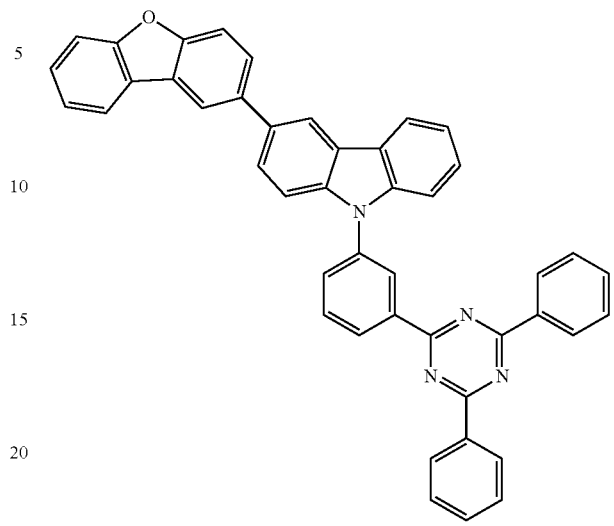
H2-182
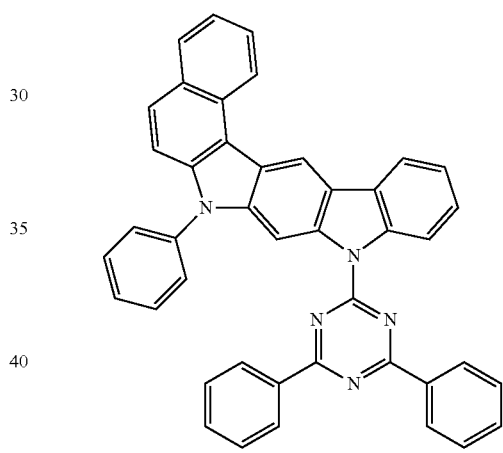
H2-183
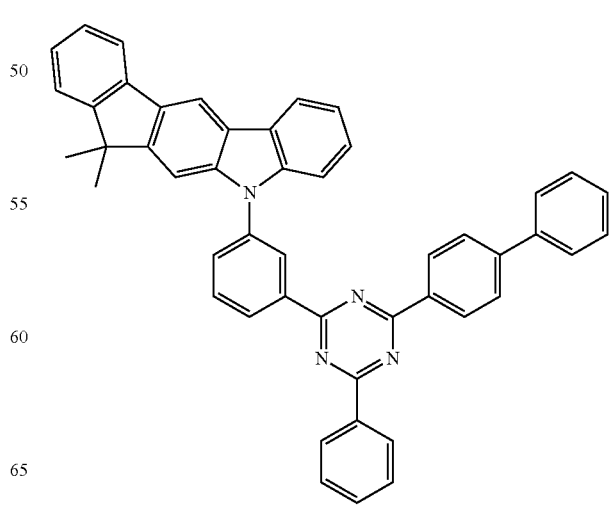

H2-184
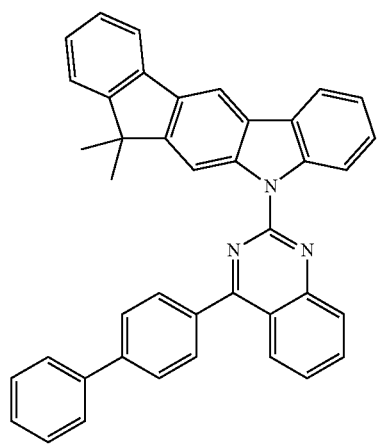
H2-187
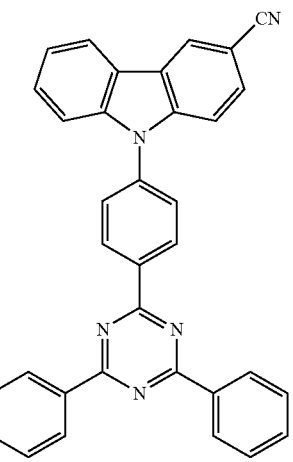
H2-185
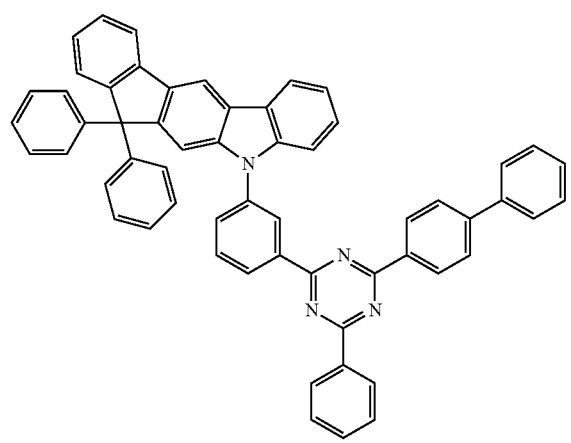
H2-188
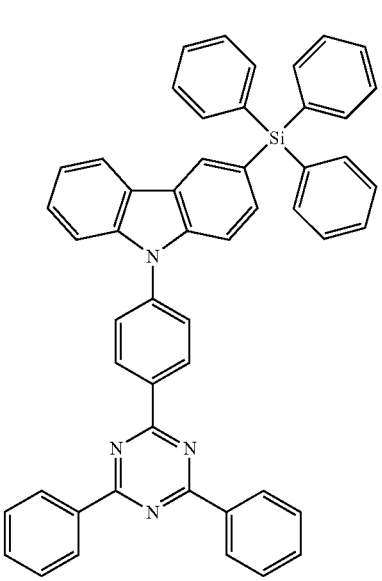
H2-186
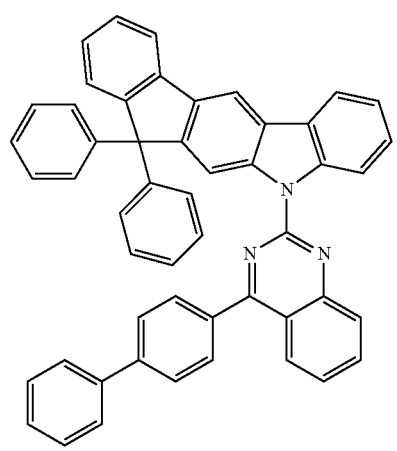
H2-189
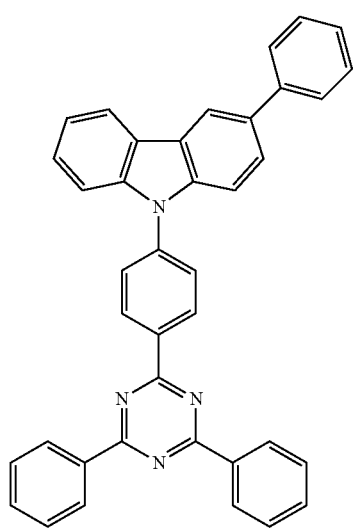

H2-190
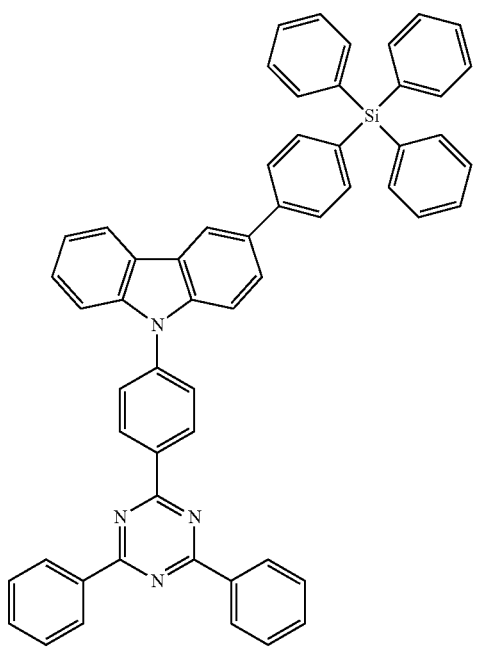
H2-191
H2-192
H2-193
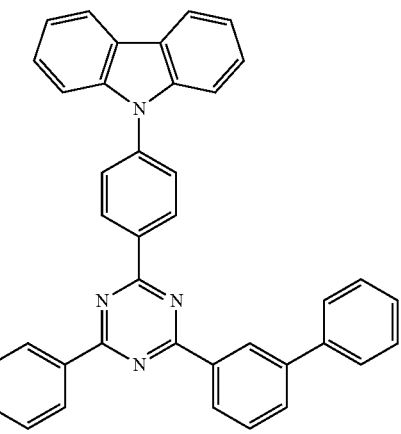
H2-194
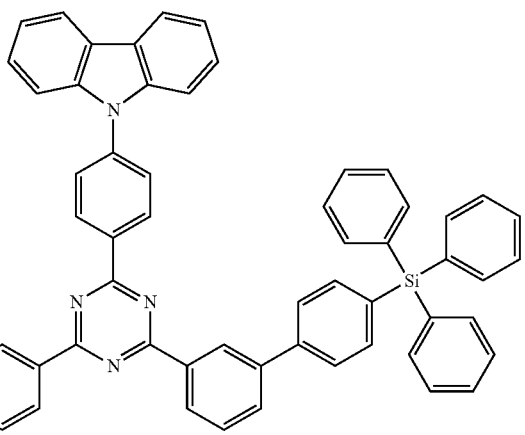
H2-195
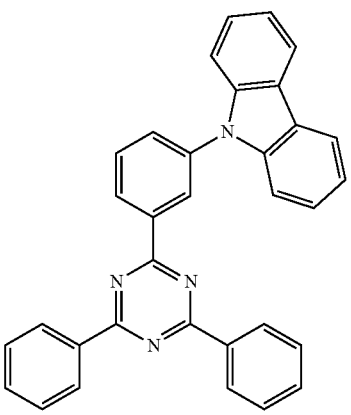

H2-196
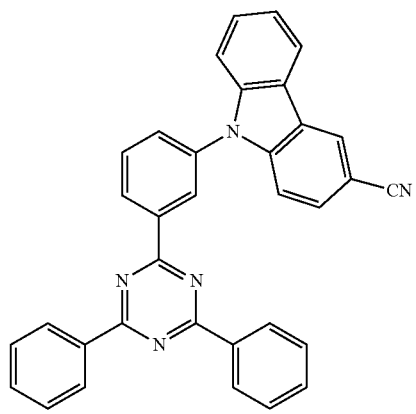
H2-197
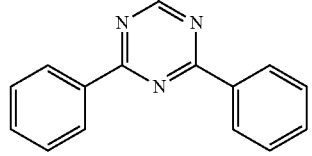
H2-198
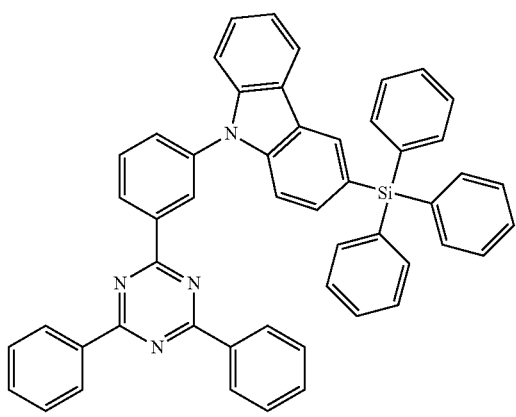
H2-199
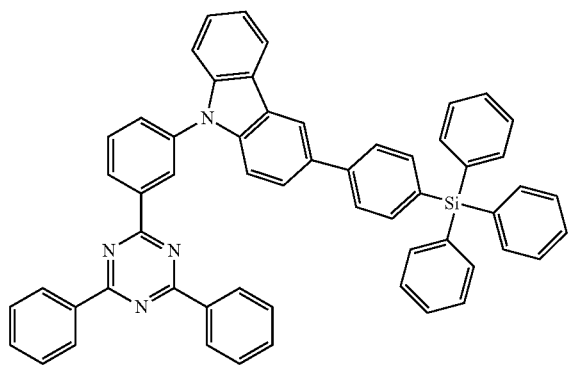
H2-200
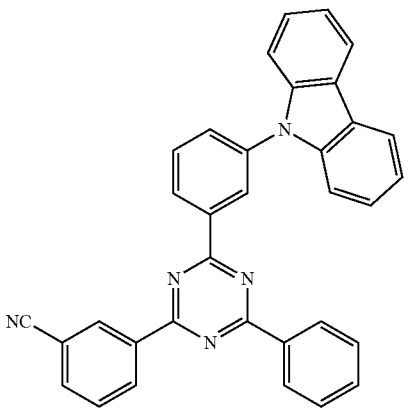
H2-201
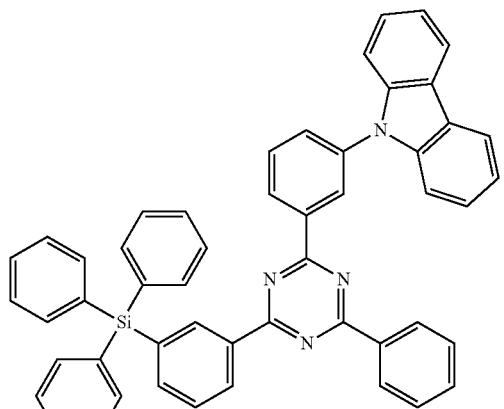
H2-202
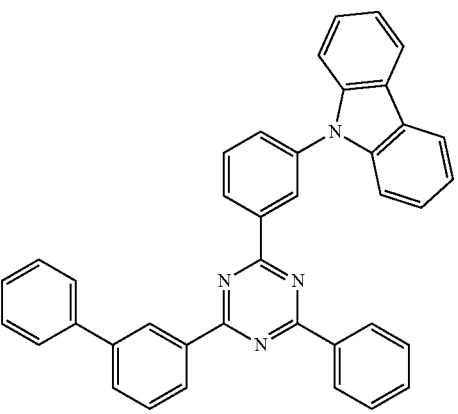

H2-203
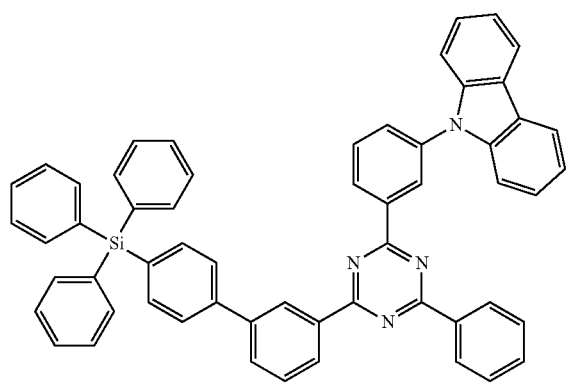
H2-204
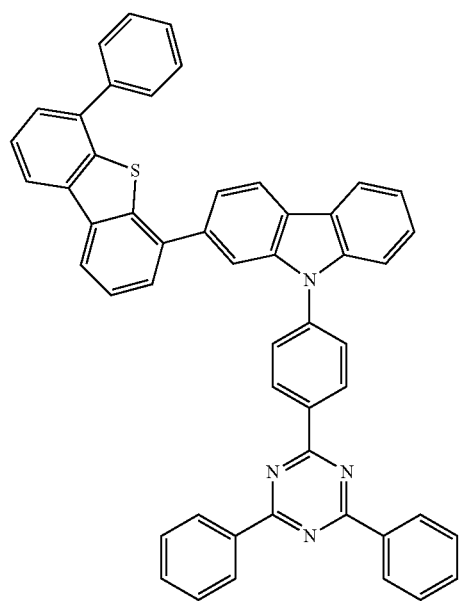
H2-205
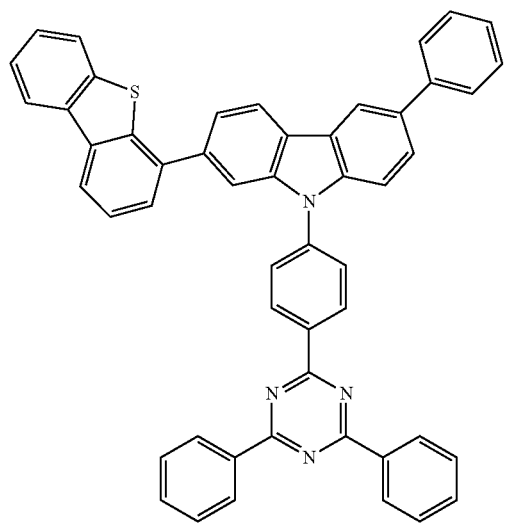
H2-206
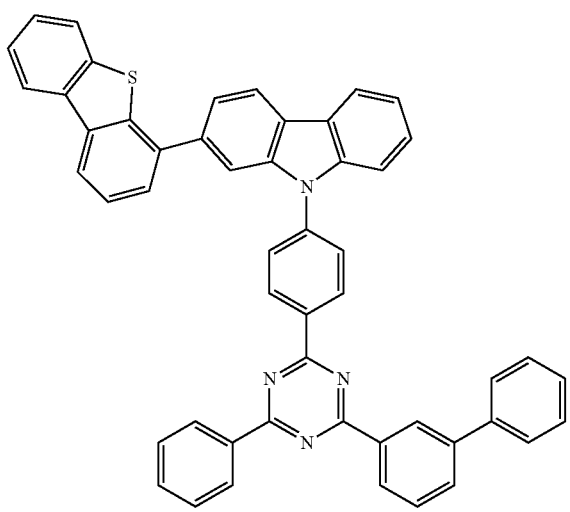
H2-207
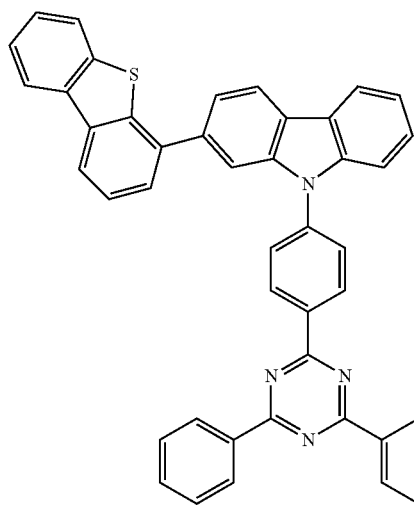
H2-208
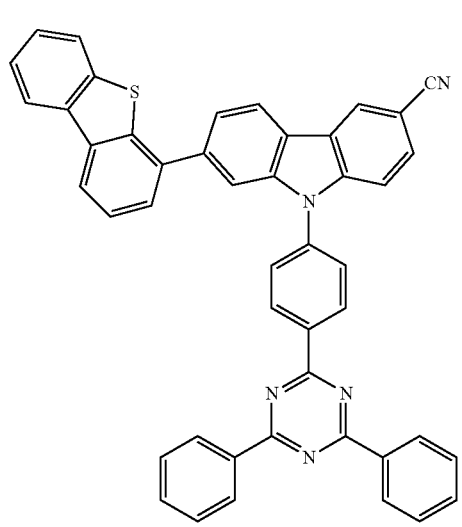

H2-209
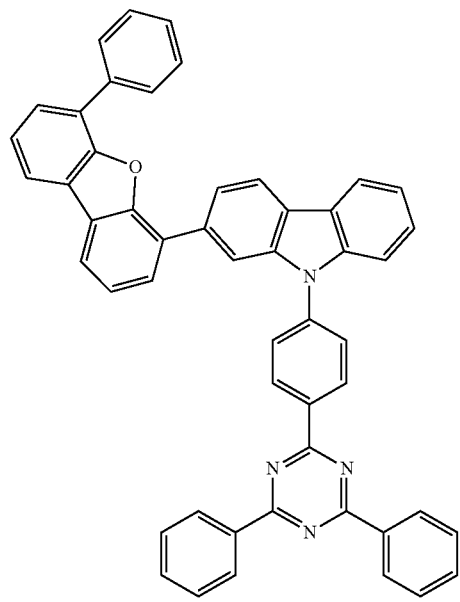
H2-210
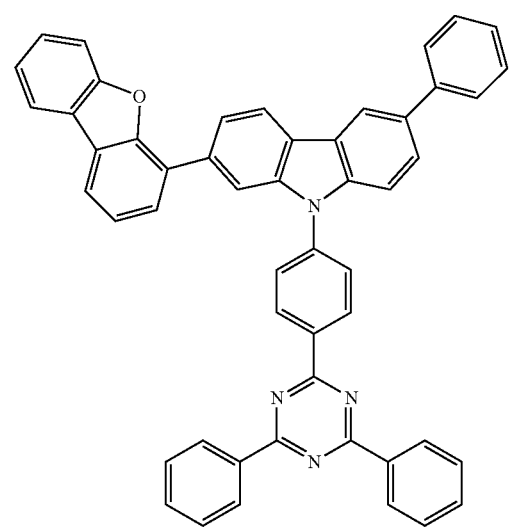
H2-211
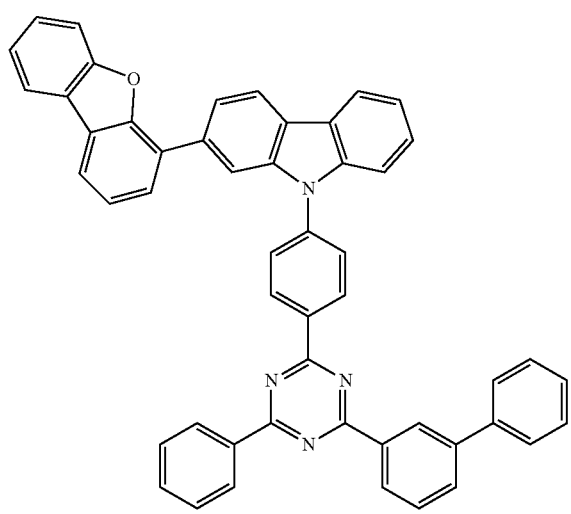
H2-212
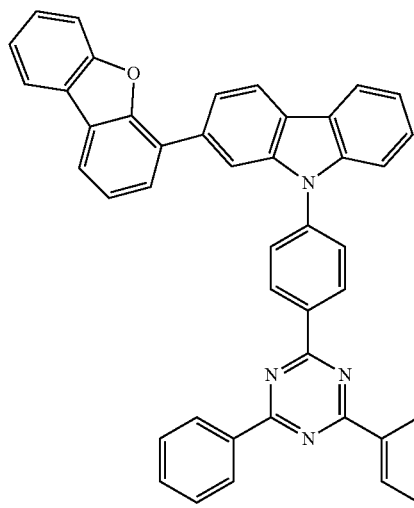
H2-213
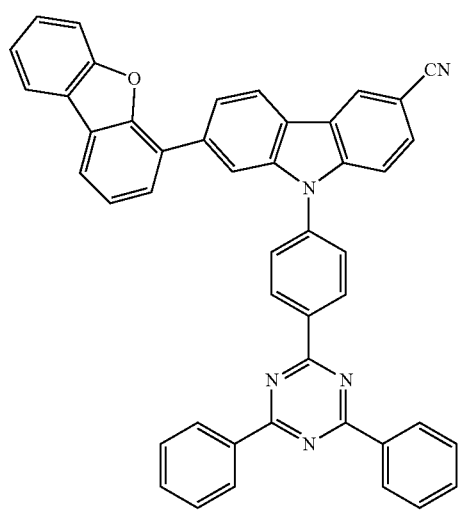
H2-214
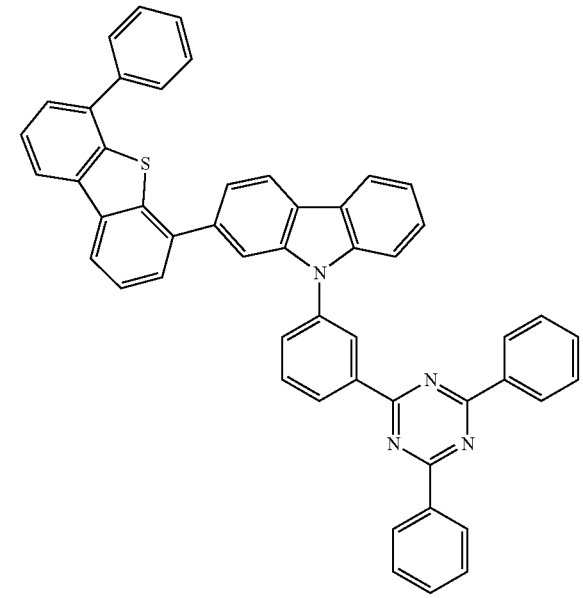

H2-215
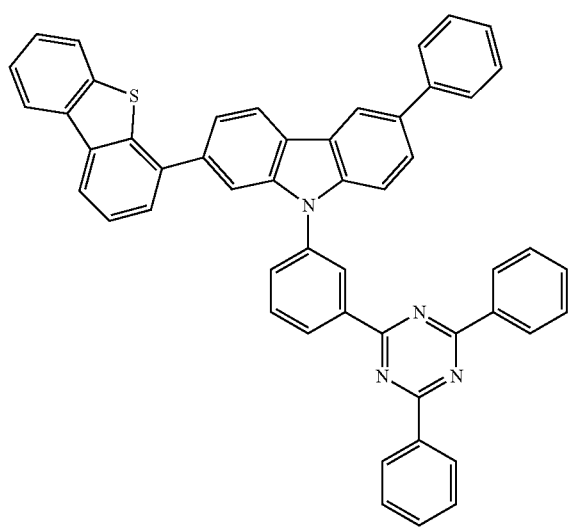
H2-216
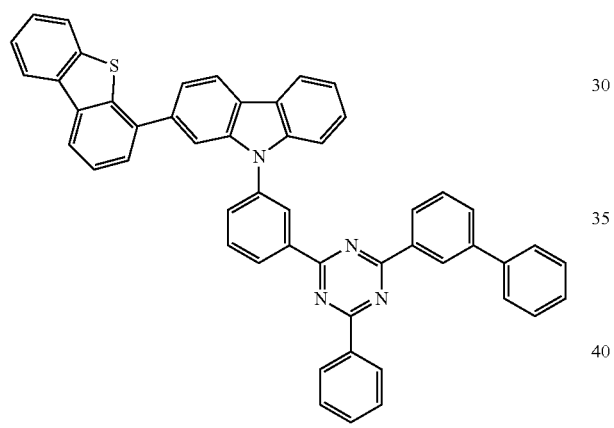
H2-217
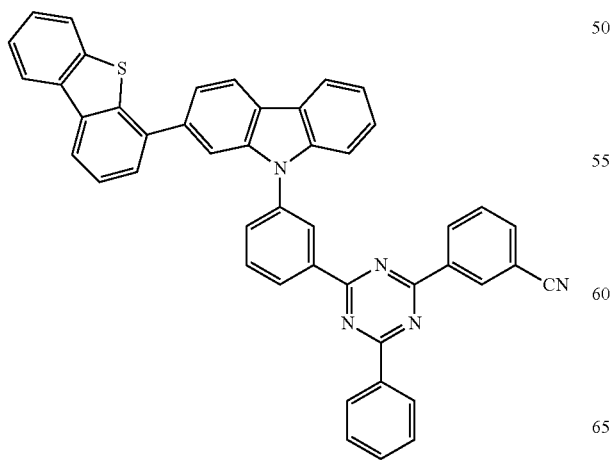
H2-218
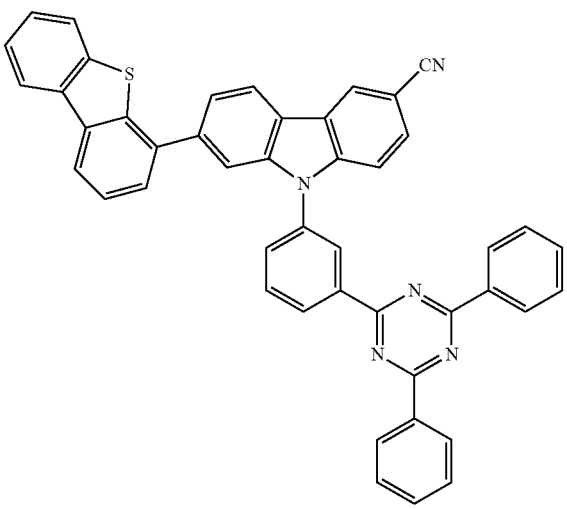
H2-219
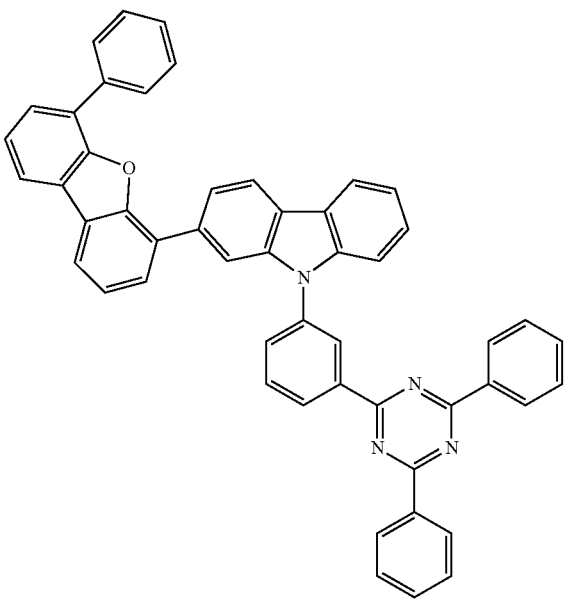

-continued
H2-220
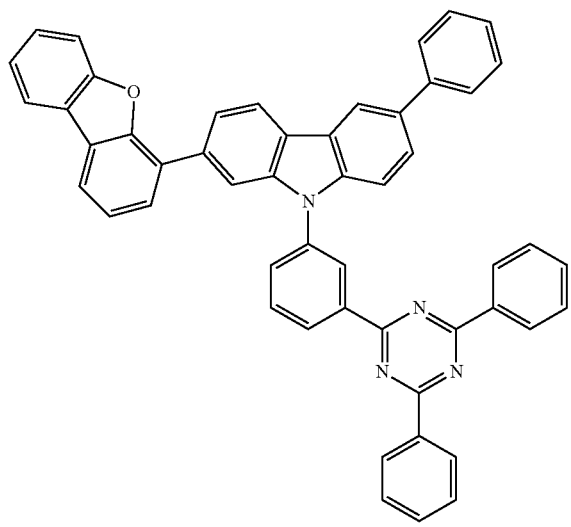
H2-221
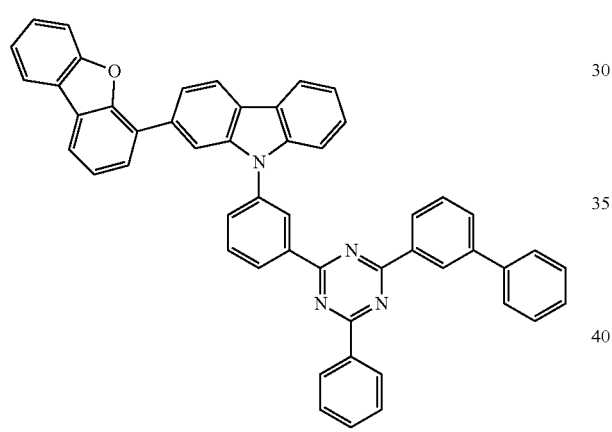
H2-222
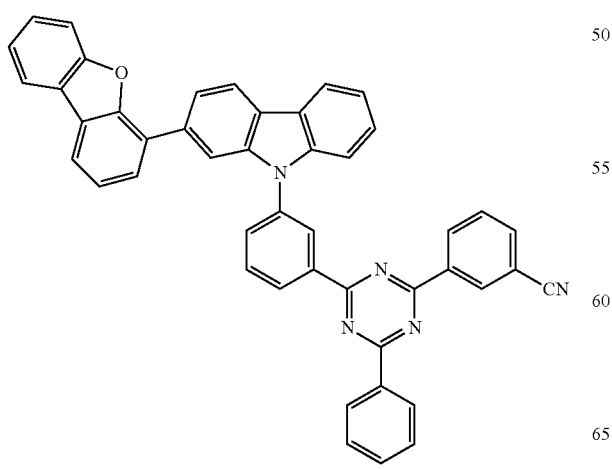
-continued
H2-223
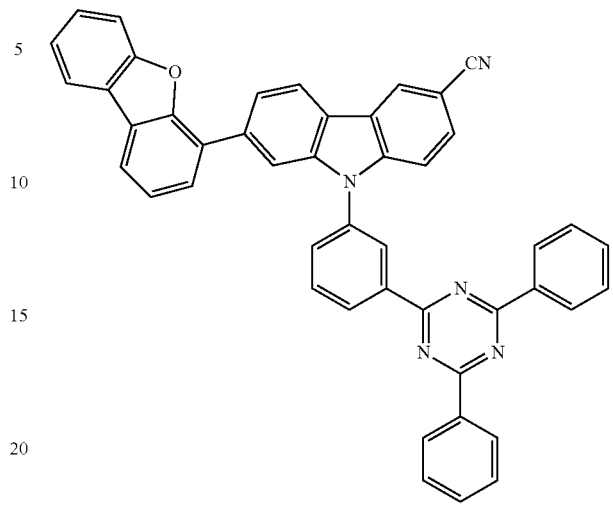
H2-224
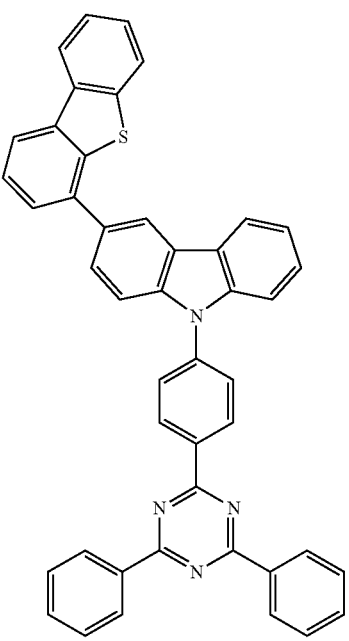

H2-225
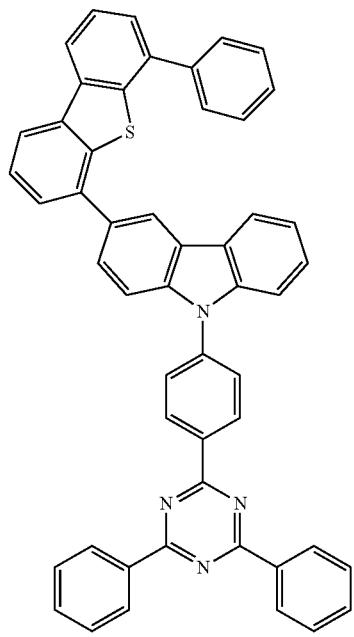
H2-226
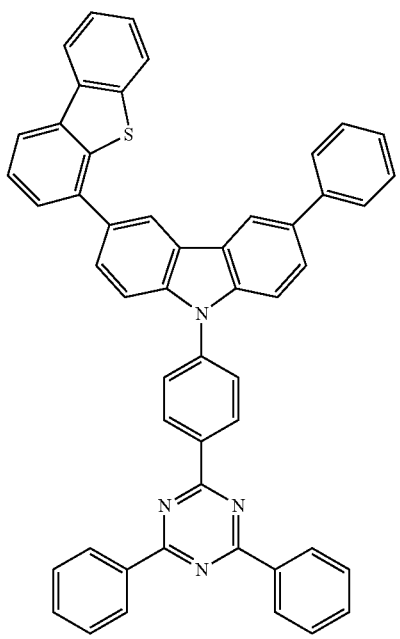
H2-227
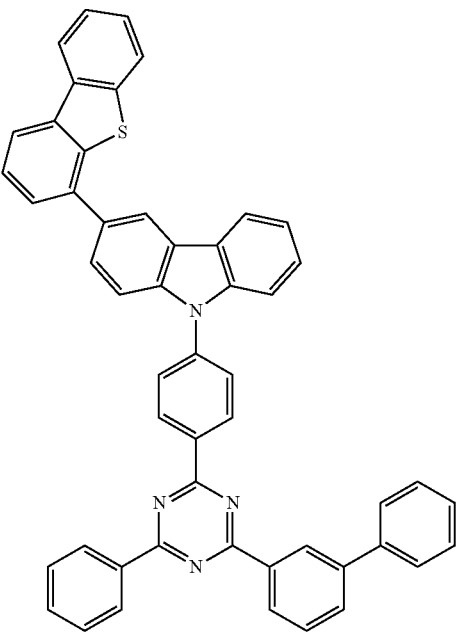
H2-228
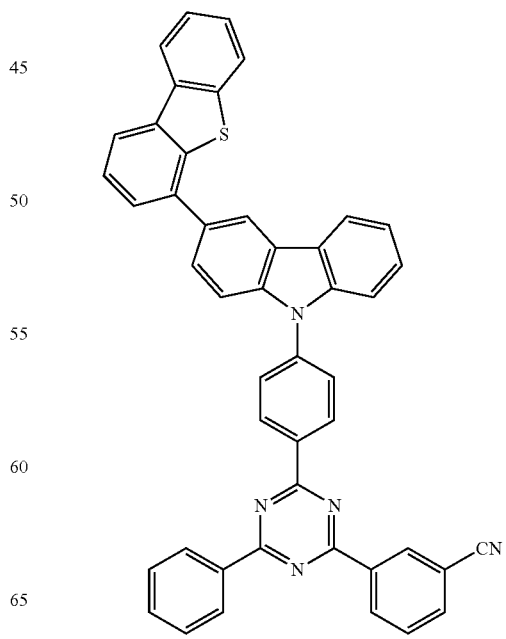

457
-continued
H2-229
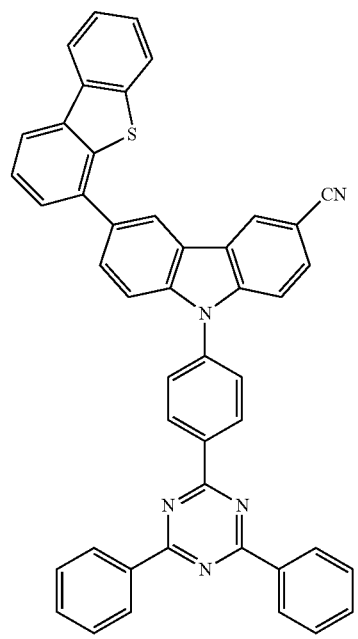
H2-230
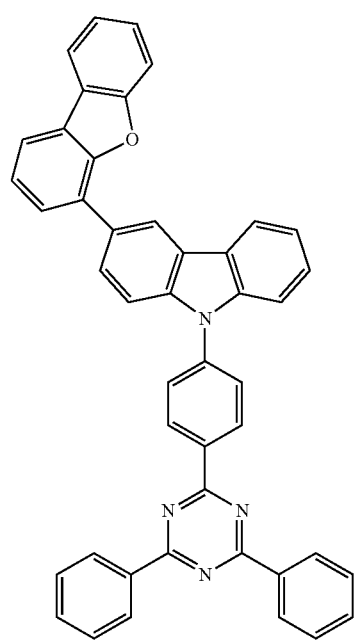
458
-continued
H2-231
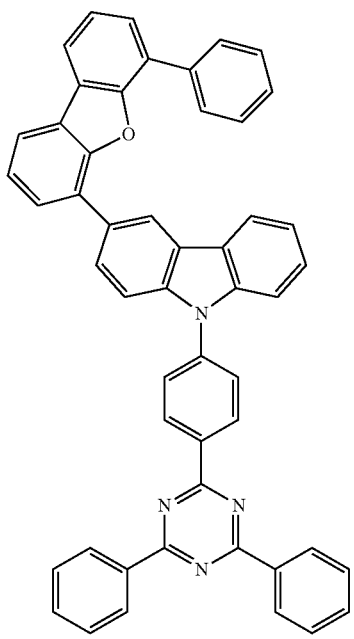
H2-232
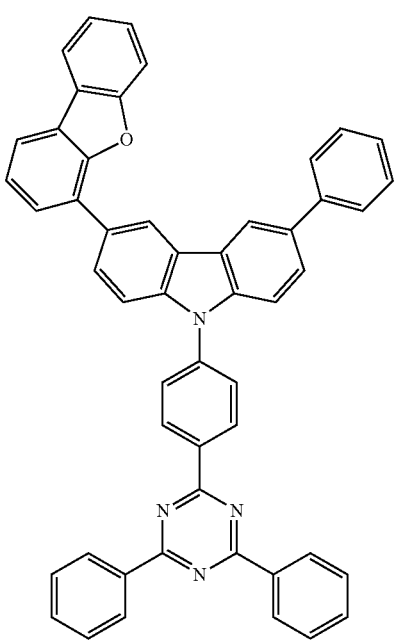

H2-233
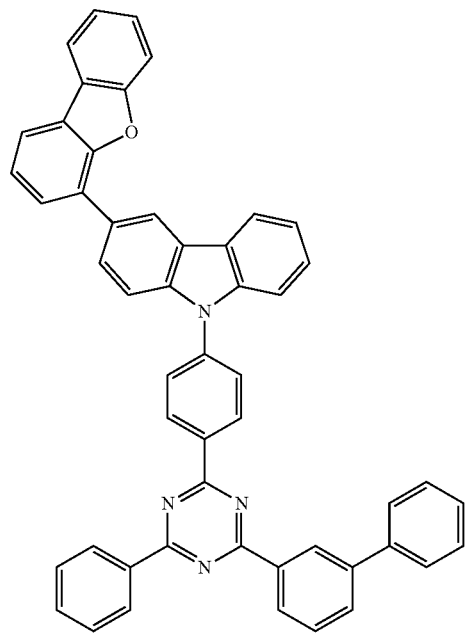
H2-234
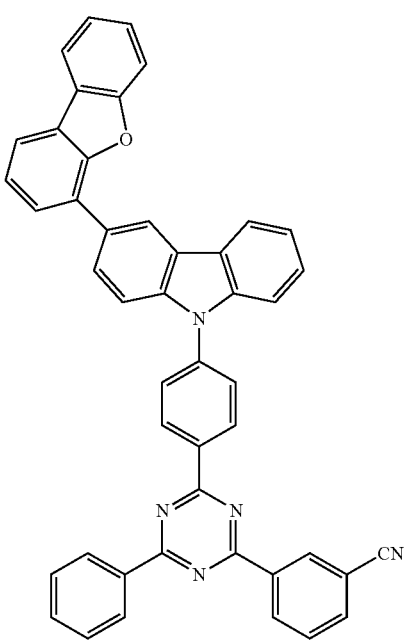
H2-235
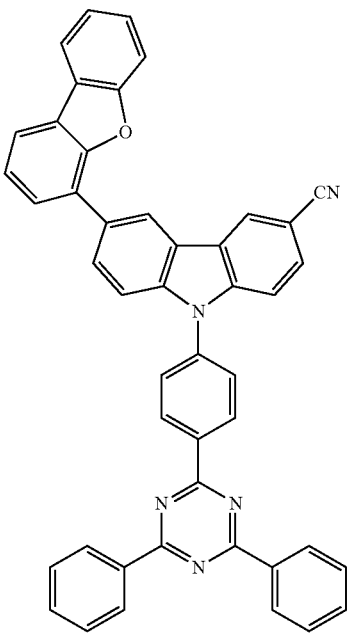
H2-236
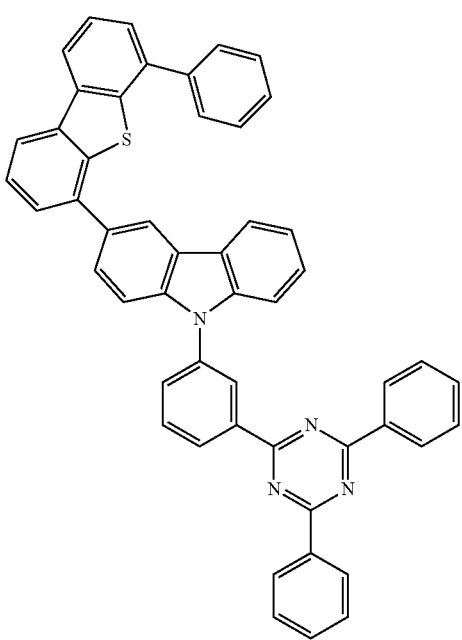

H2-237
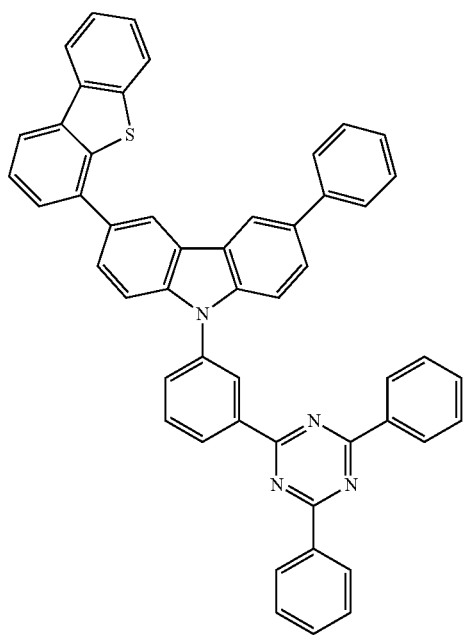
H2-239
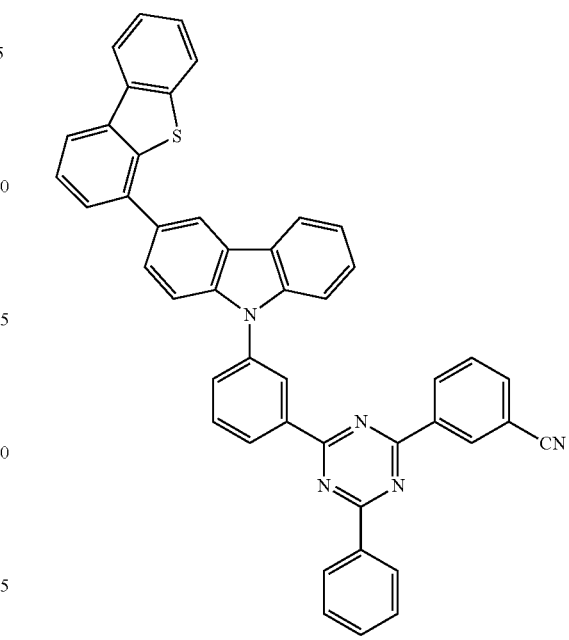
H2-238
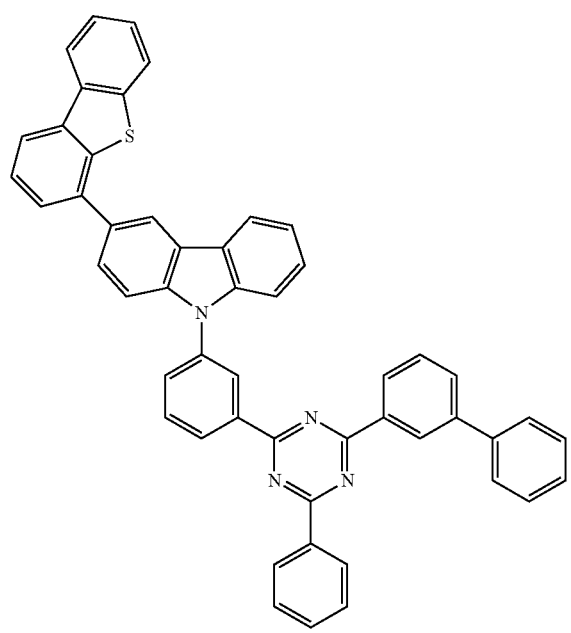
H2-240
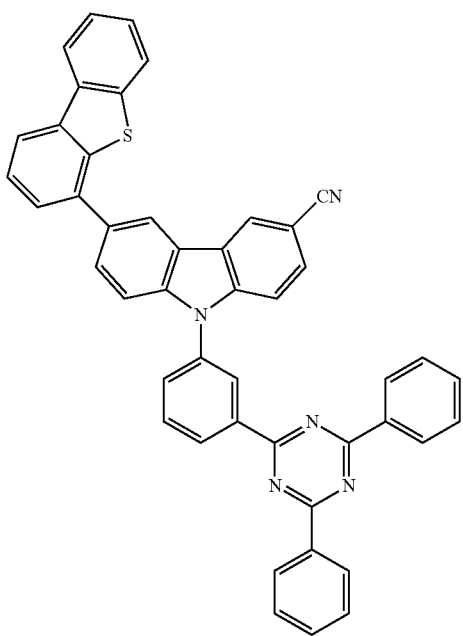

H2-241
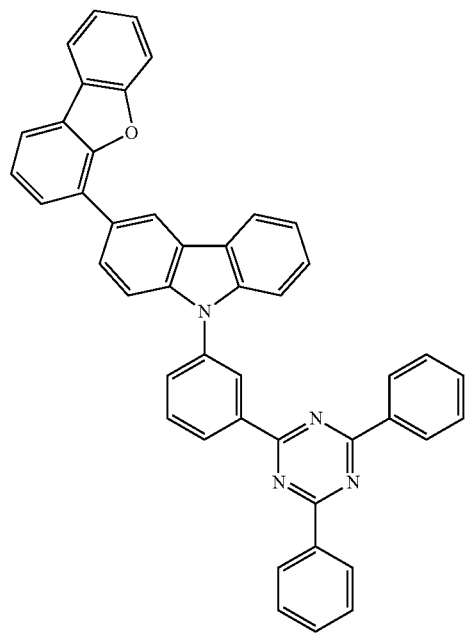
H2-242
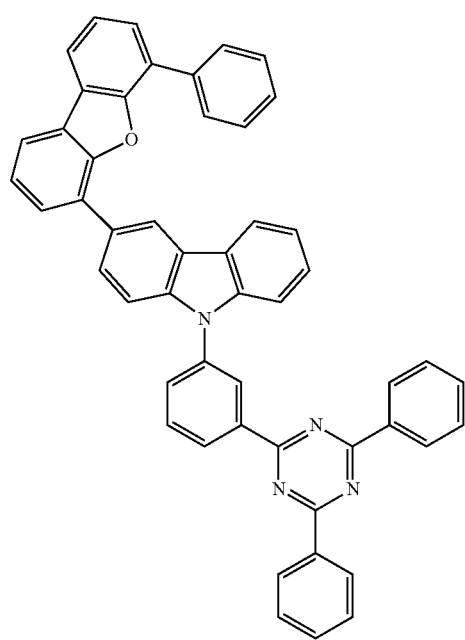
H2-243
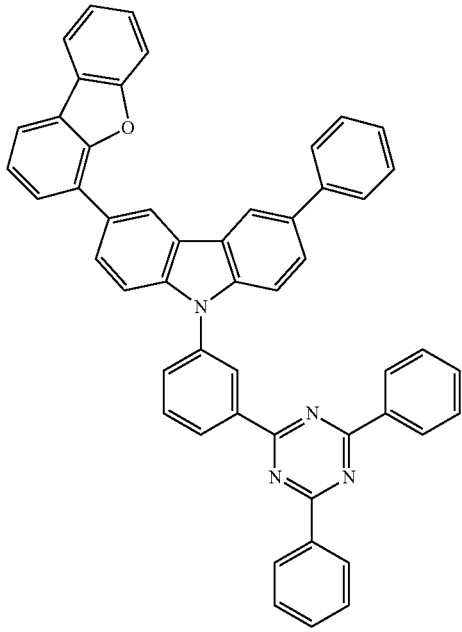
H2-244
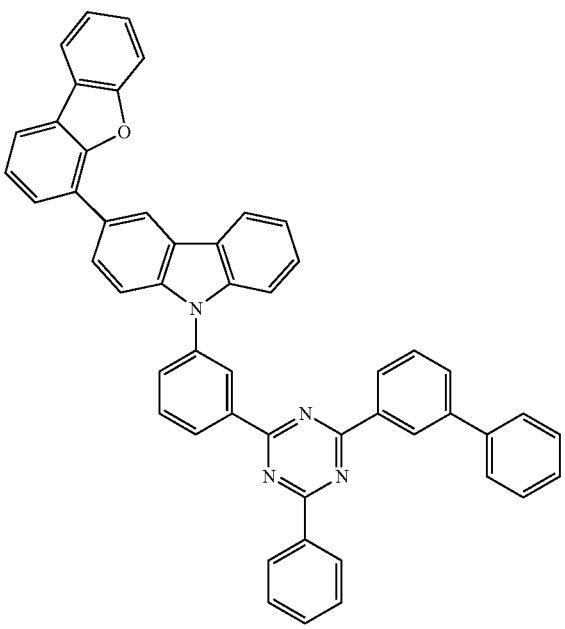

H2-245
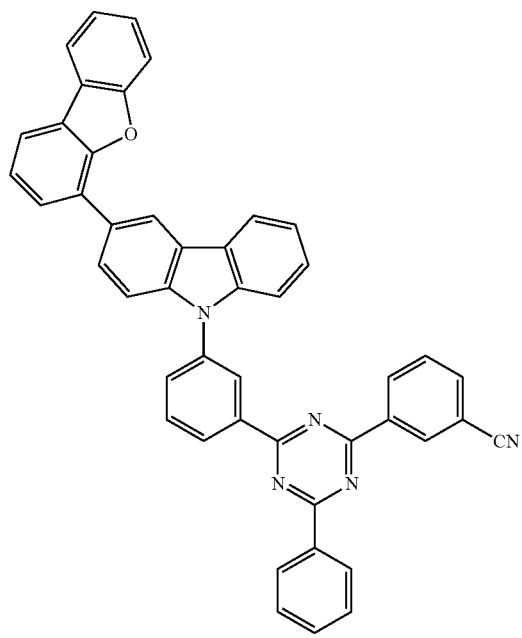
H2-246
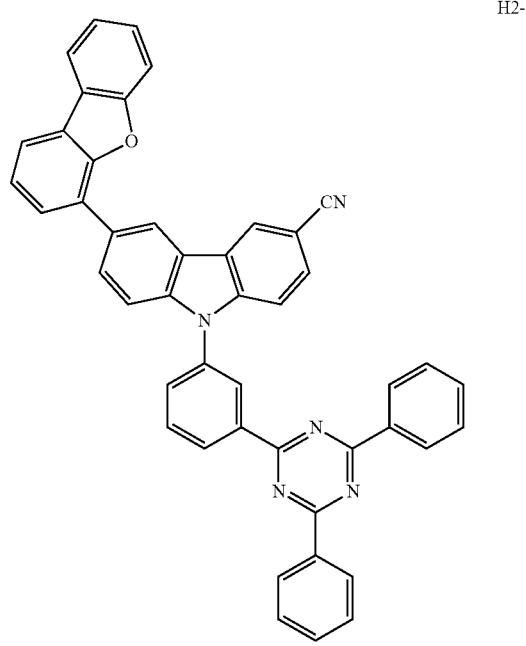
H2-247
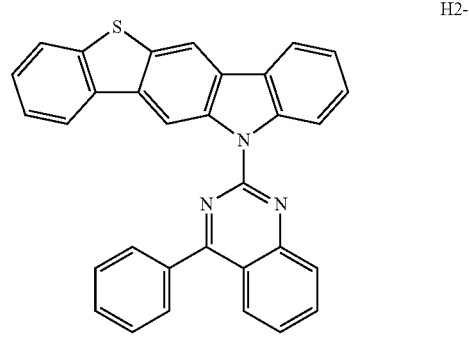
H2-248
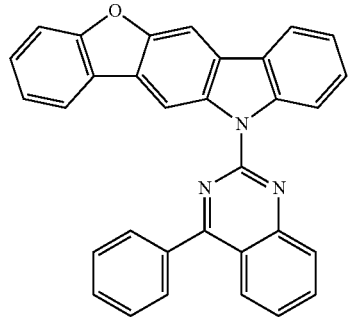
H2-249
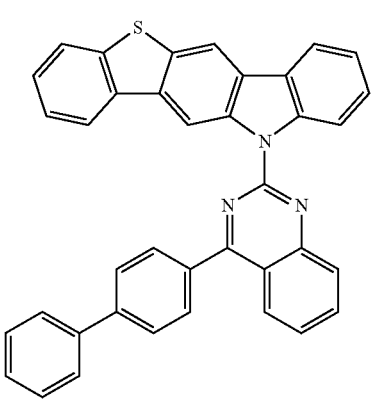
H2-250
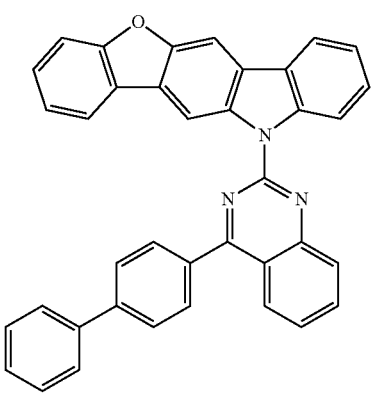
H2-251
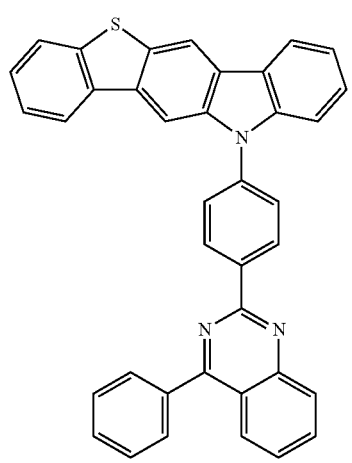

467
-continued
H2-252
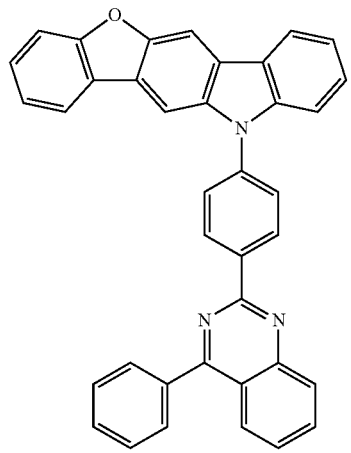
H2-253
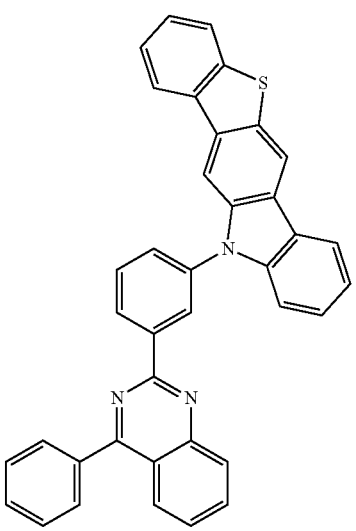
H2-254
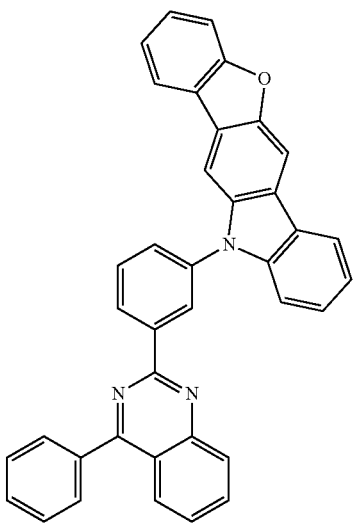
468
-continued
H2-255
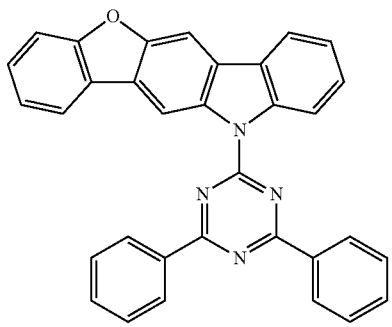
H2-256
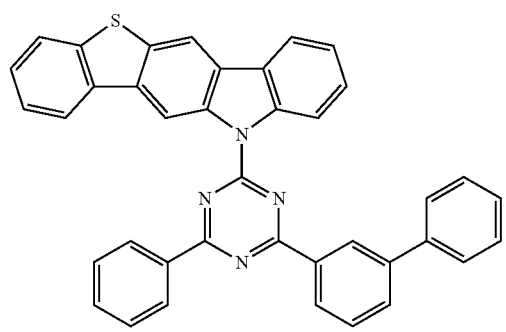
H2-257
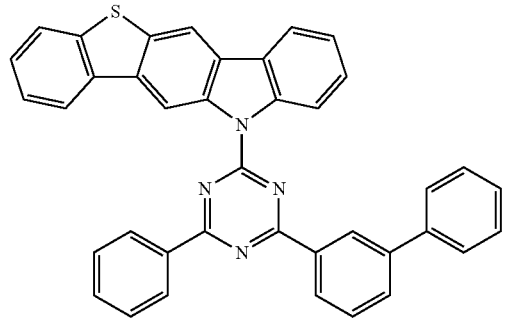
H2-258
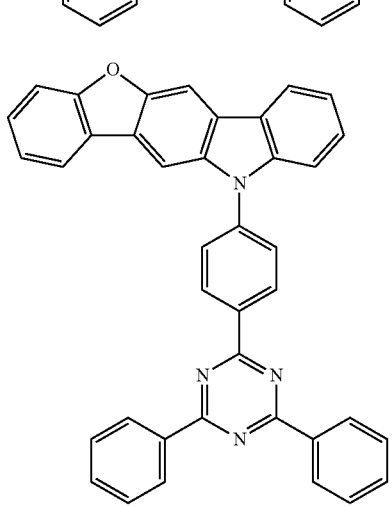

-continued
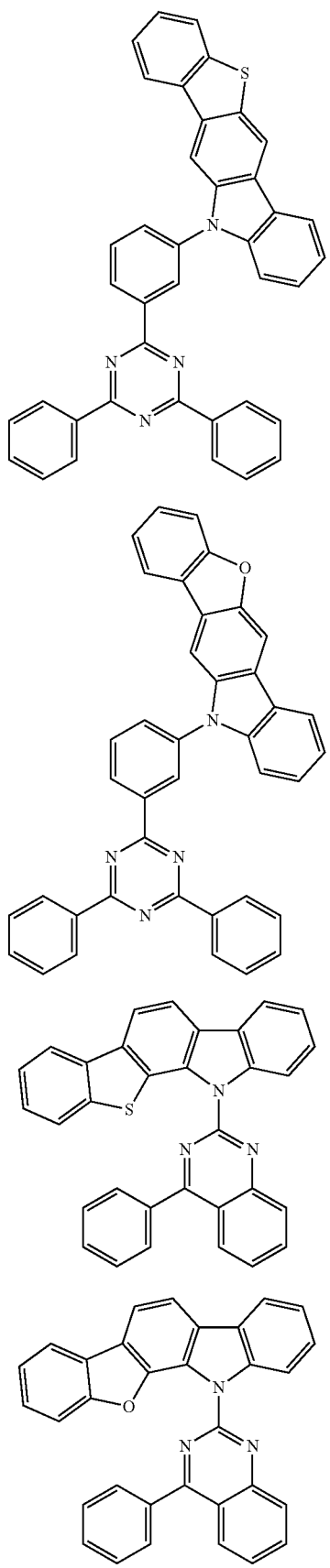
H2-259
H2-260
H2-261
H2-262
-continued
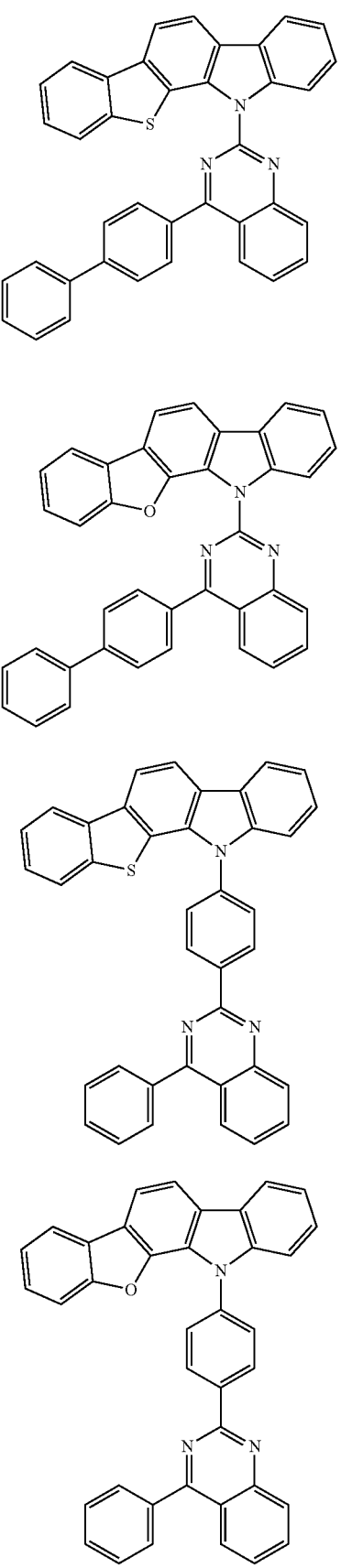
H2-263
H2-264
H2-265
H2-266

-continued
H2-267
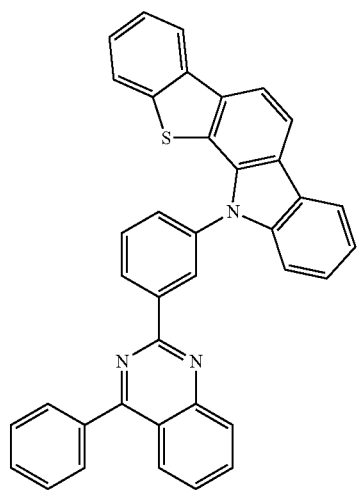
H2-268
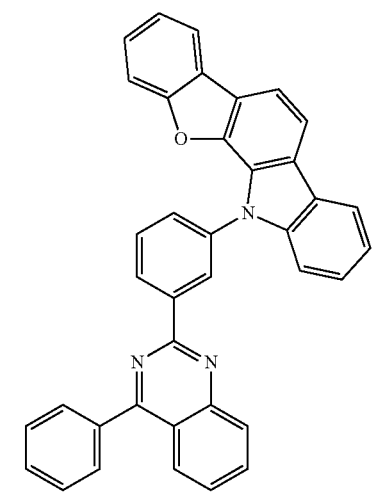
H2-269
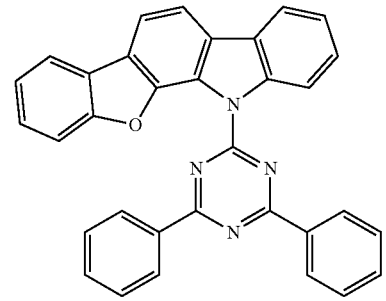
H2-270
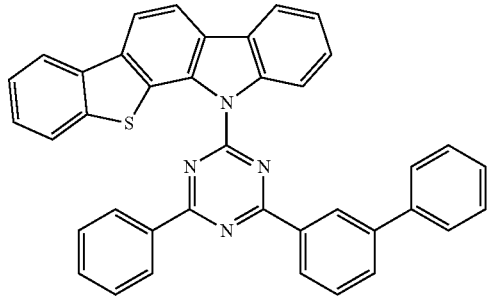
-continued
H2-271
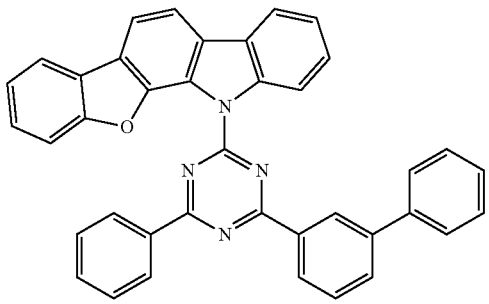
H2-272
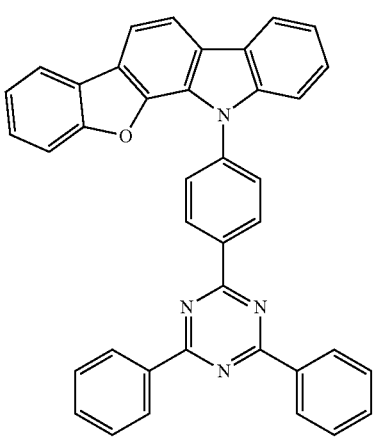
H2-273
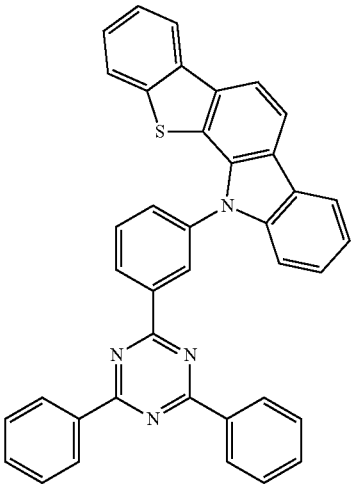

H2-274
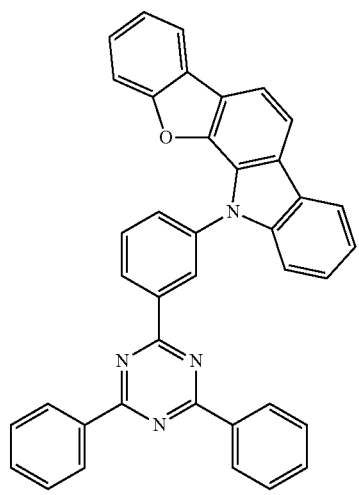
H2-275
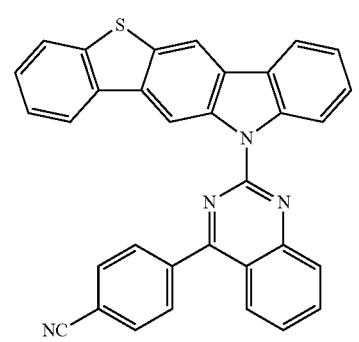
H2-276
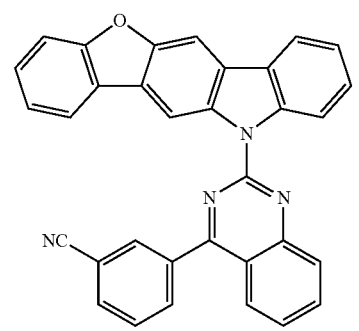
H2-277
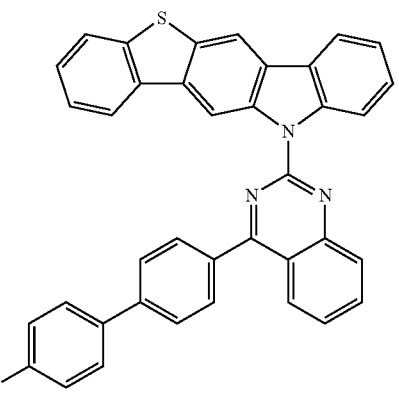
H2-278
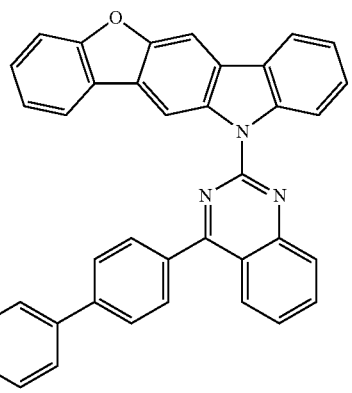
H2-279
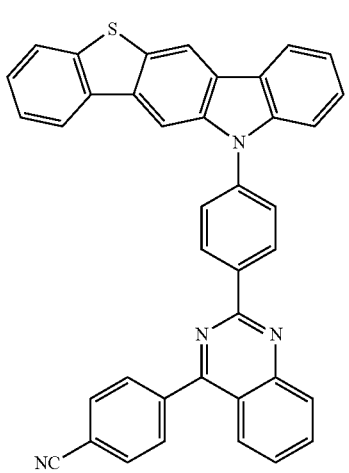
H2-280
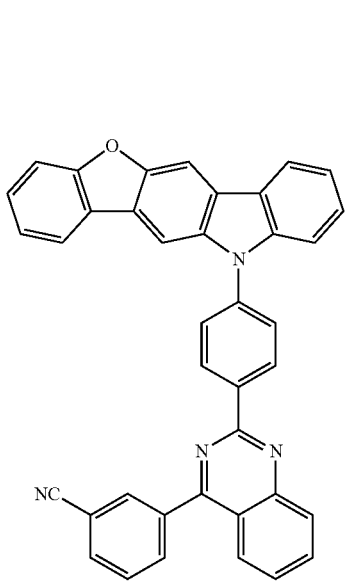

H2-281
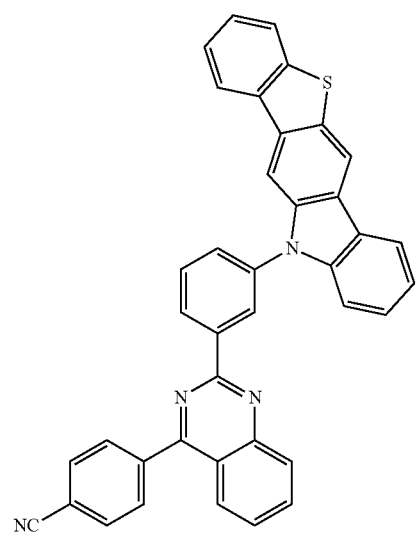
H2-284
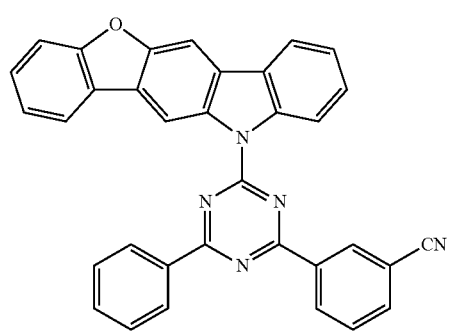
H2-285
H2-282
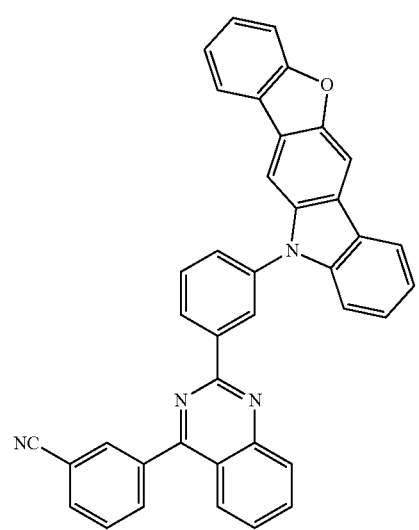
H2-286
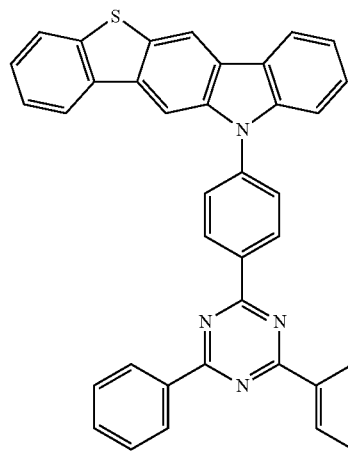
H2-283
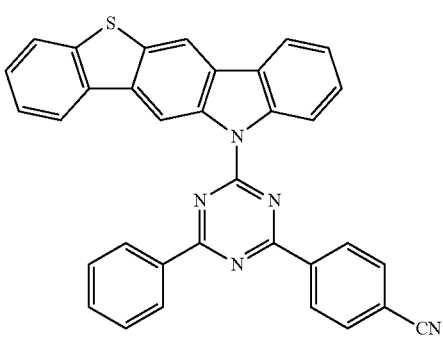
H2-287

-continued
H2-288
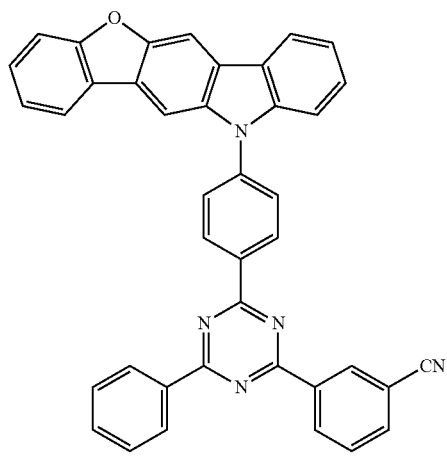
H2-289
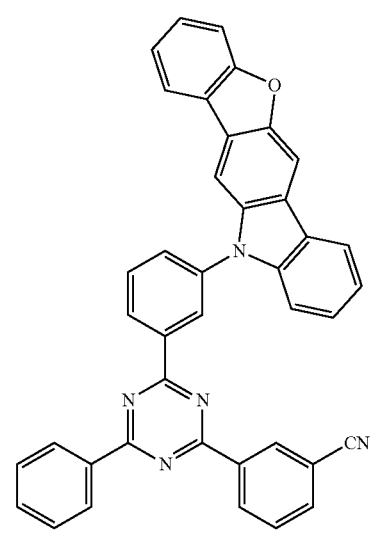
H2-290
-continued
H2-291
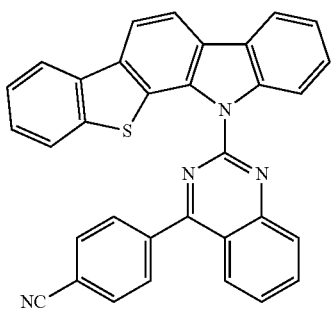
H2-292
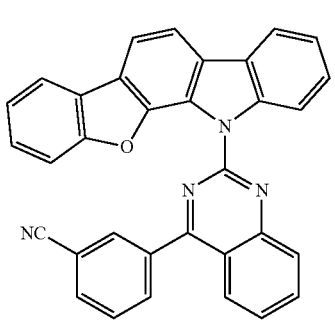
H2-293
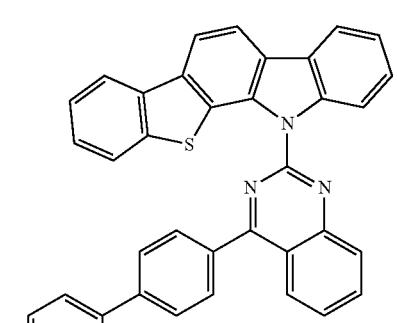
H2-294
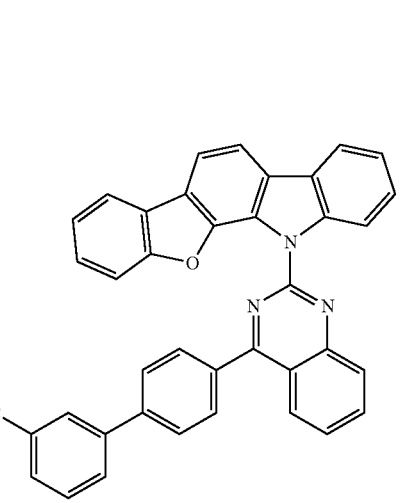

-continued
H2-195
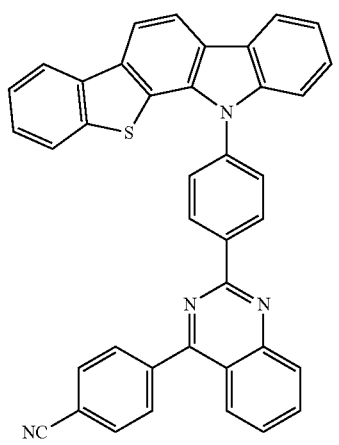
H2-296
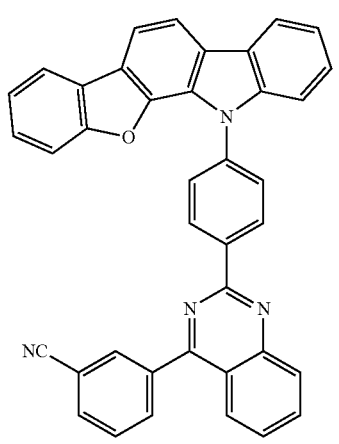
H2-297
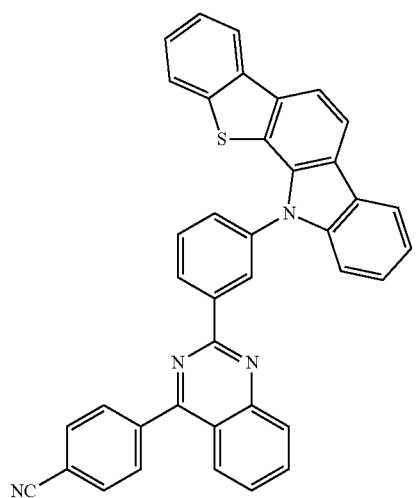
-continued
H2-298
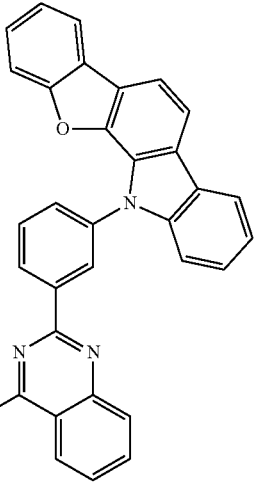
H2-299
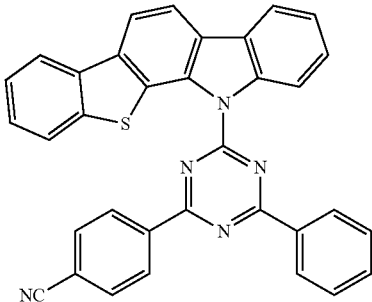
H2-300
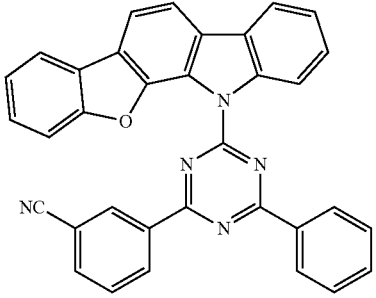
H2-301
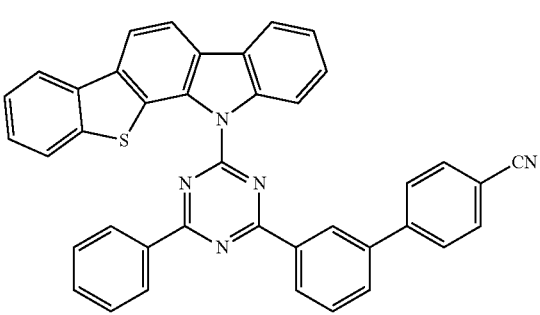

-continued
H2-302
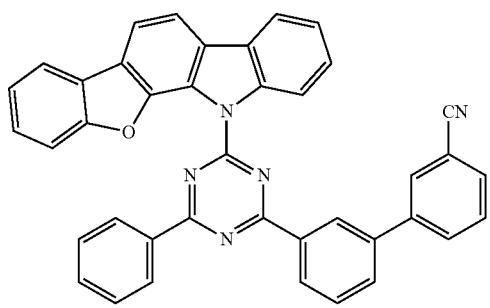
H2-303
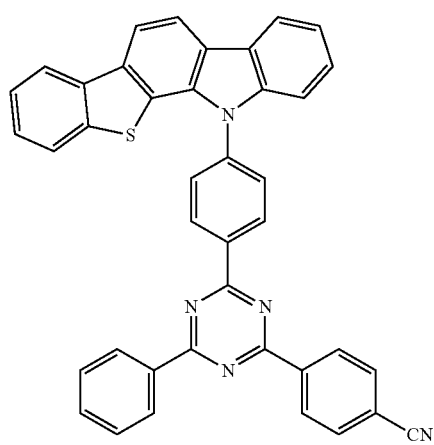
H2-304
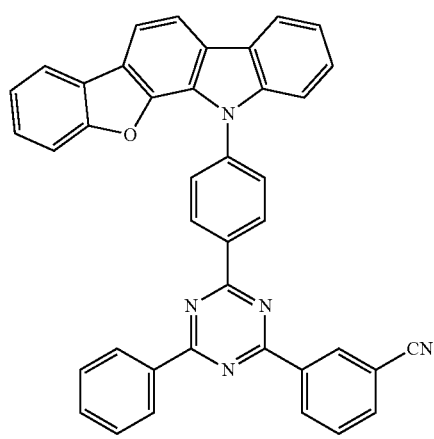
-continued
H2-305
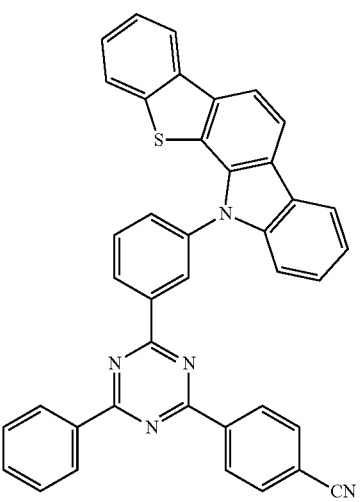
H2-306
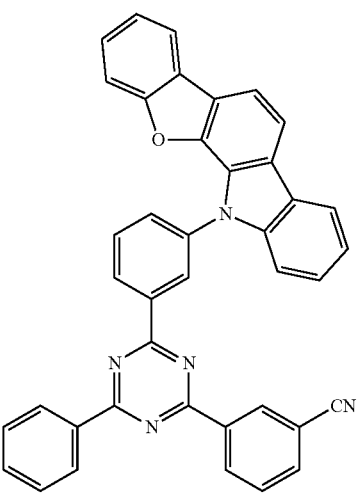
H2-307
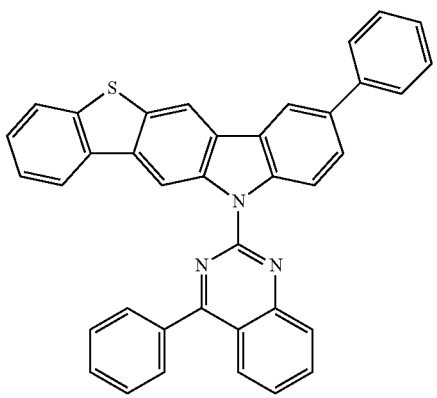

-continued
H2-308
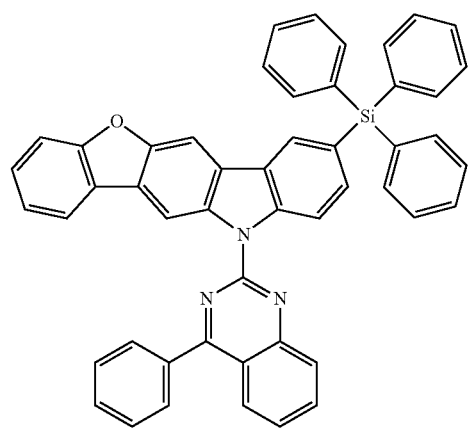
H2-309
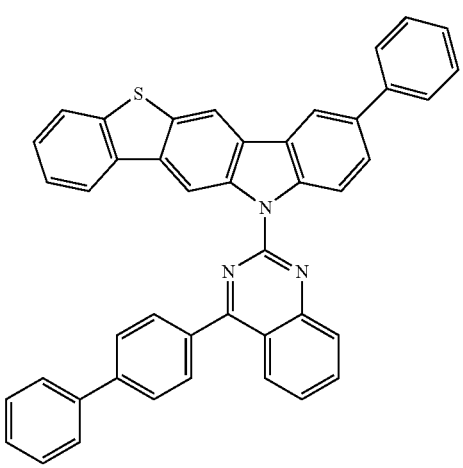
H2-310
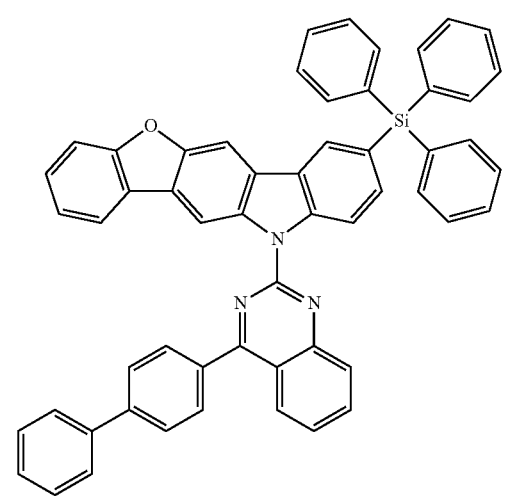
-continued
H2-311
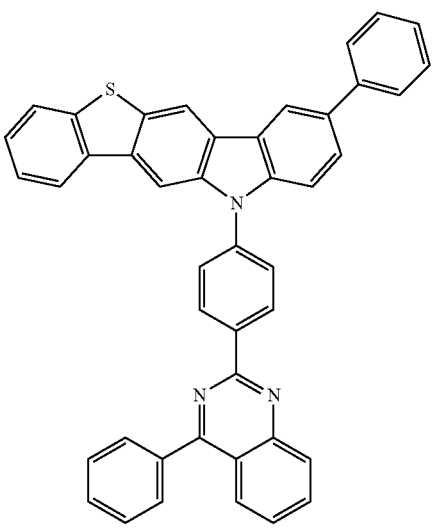
H2-312
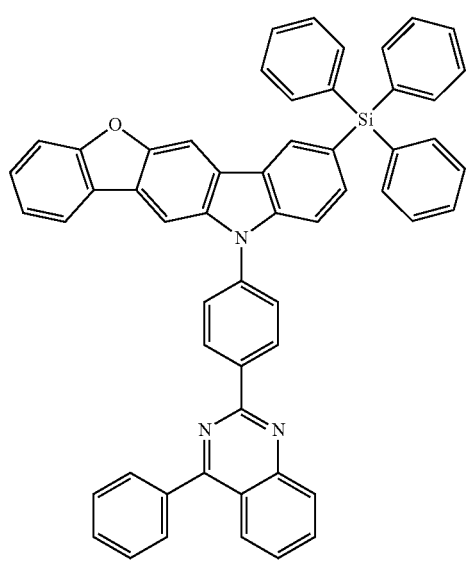
H2-313
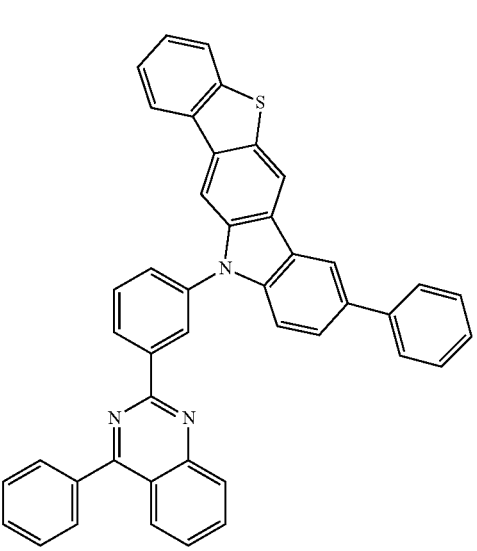

-continued
H2-314
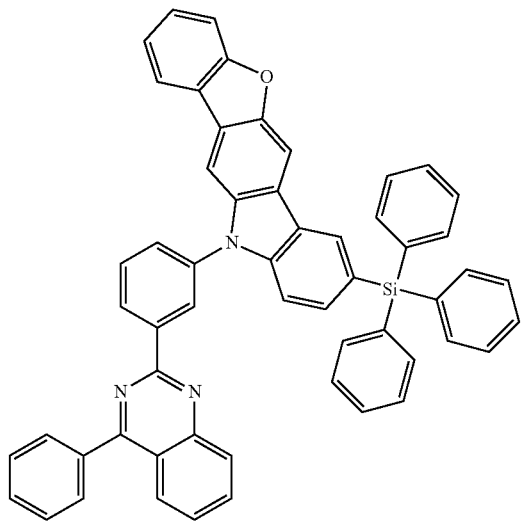
H2-315
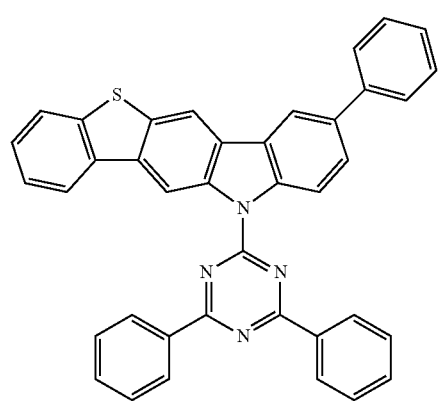
H2-316
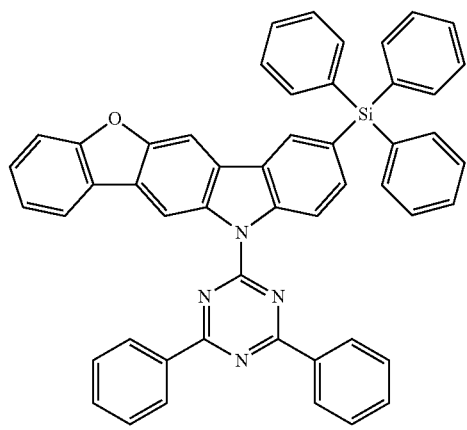
-continued
H2-317
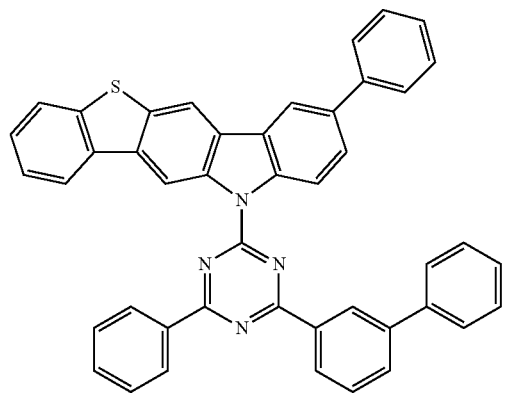
H2-318
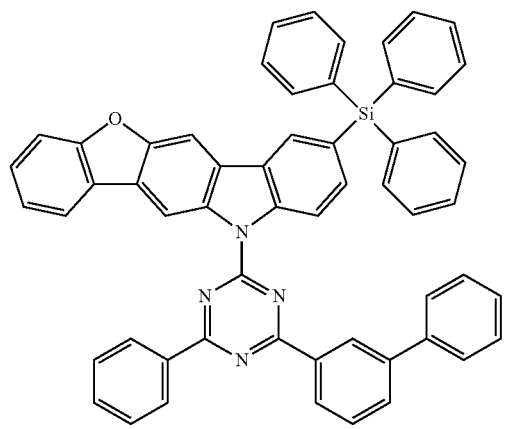
H2-319
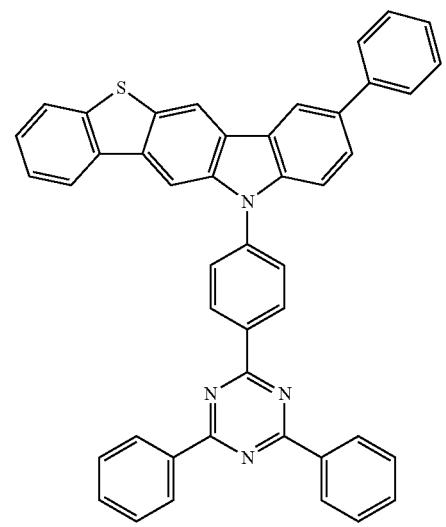

H2-320
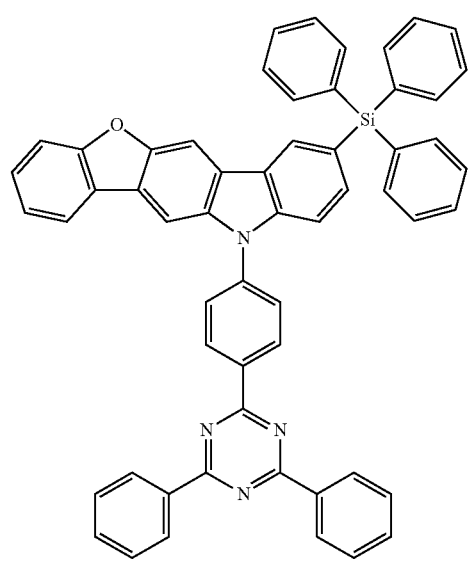
H2-321
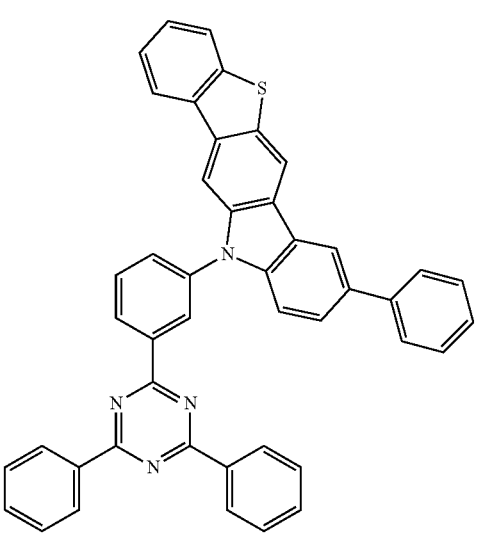
H2-322
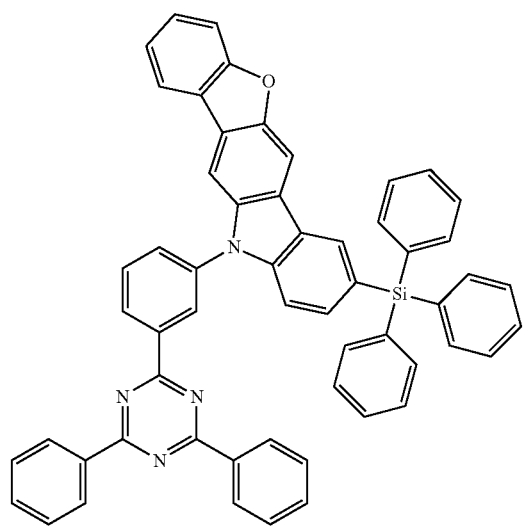
H2-323
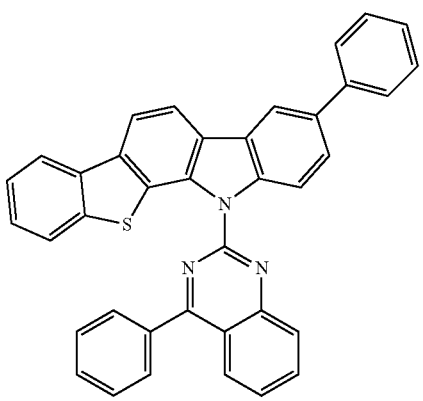
H2-324
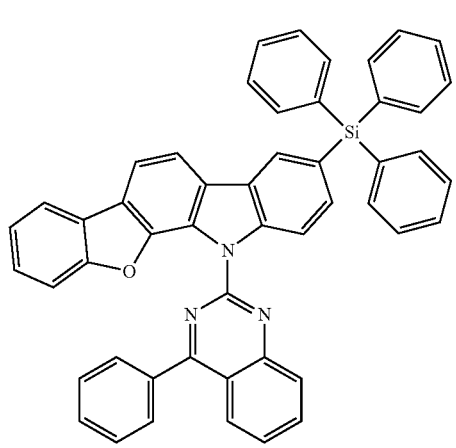
H2-325
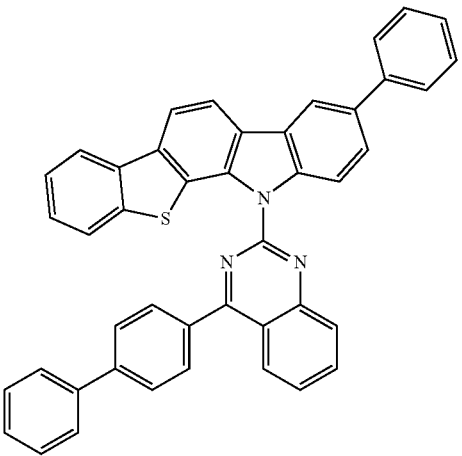

-continued
H2-326
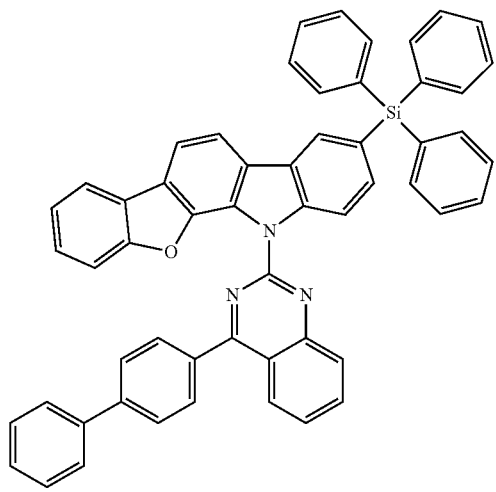
H2-327
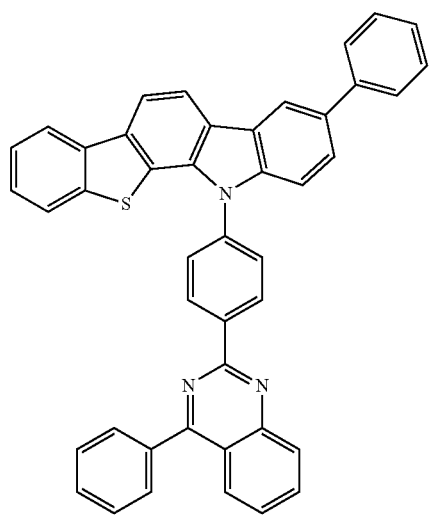
H2-328
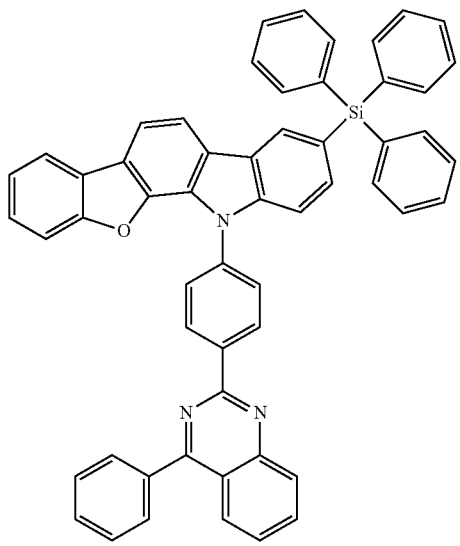
-continued
H2-329
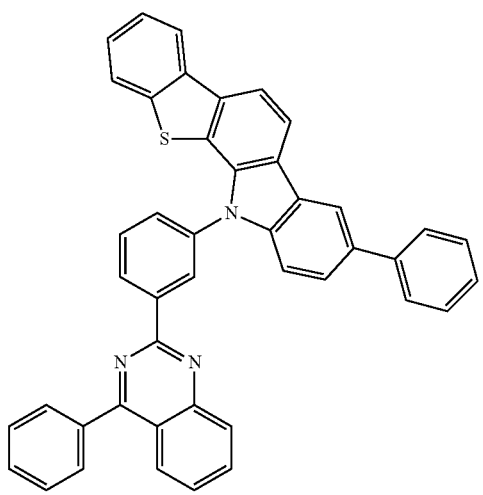
H2-330
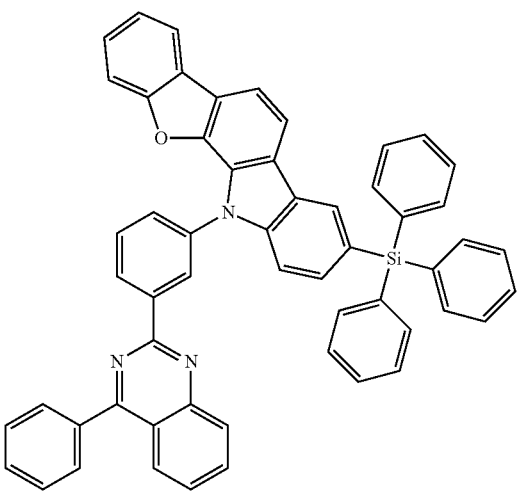
H2-331
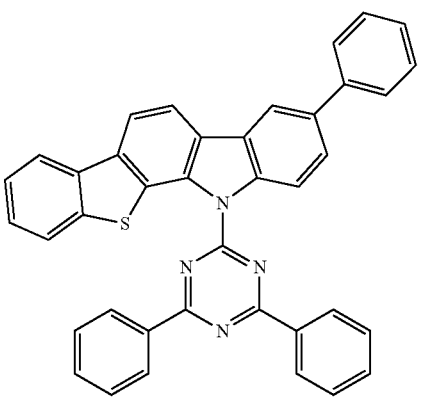

H2-332
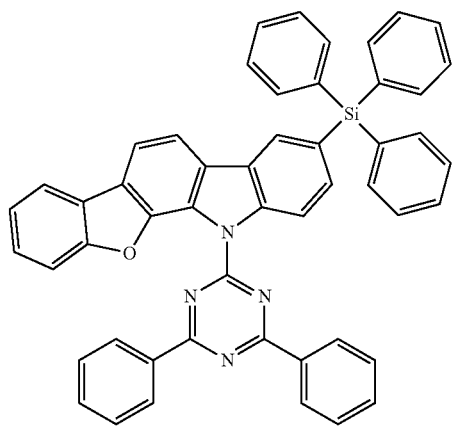
H2-335
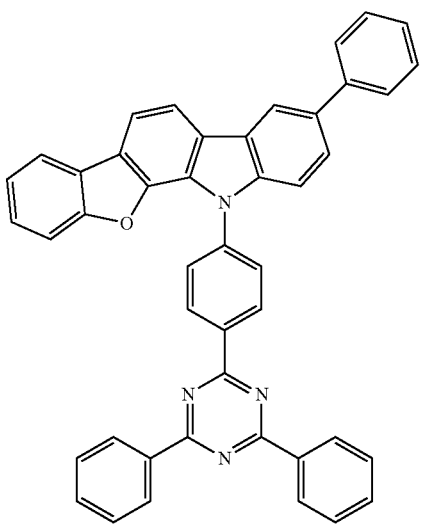
H2-333
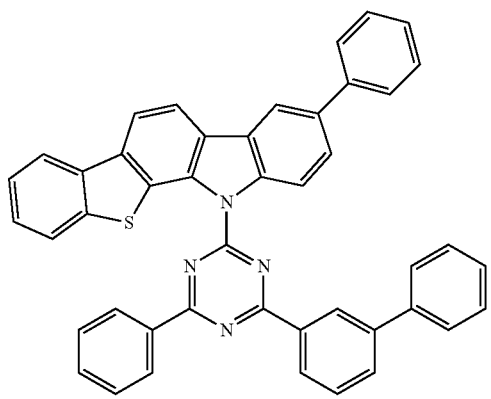
H2-336
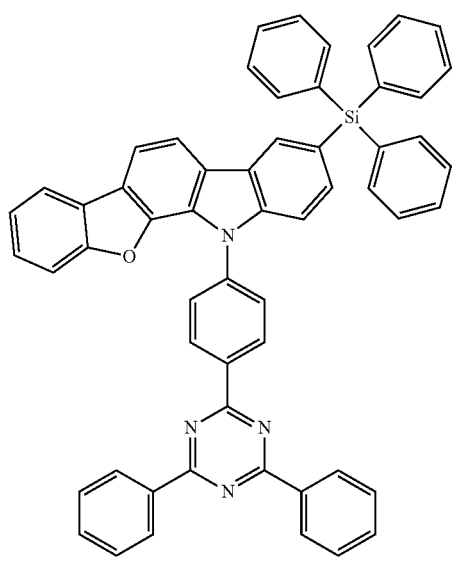
H2-334
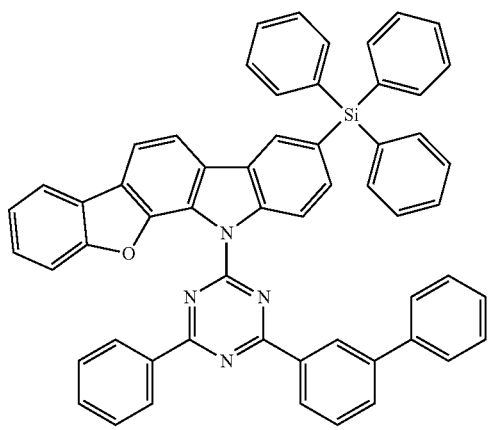
H2-337
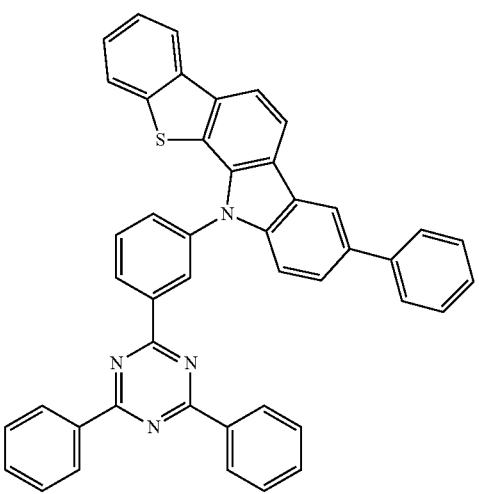

H2-338
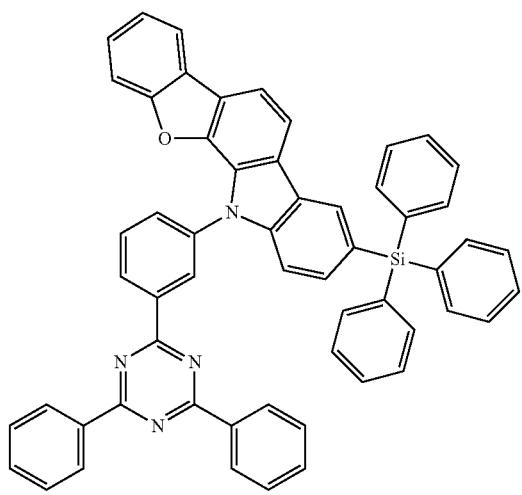
H2-341
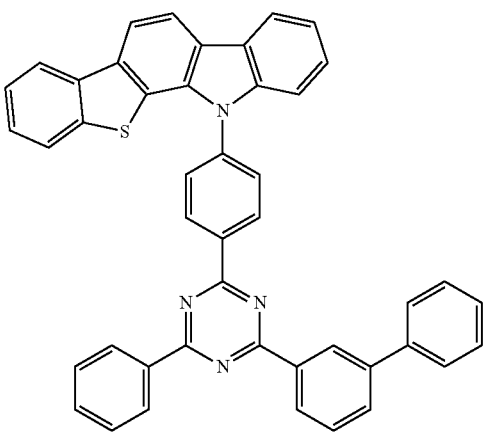
H2-339
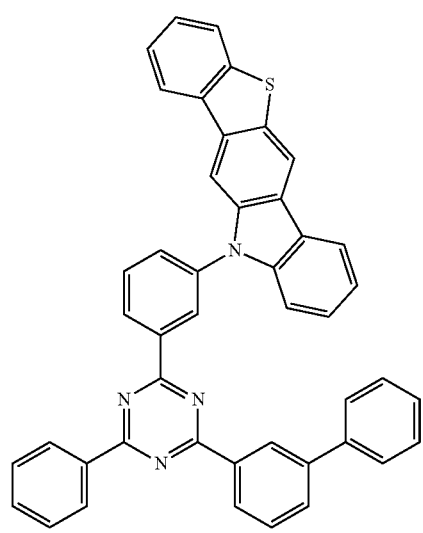
H2-342
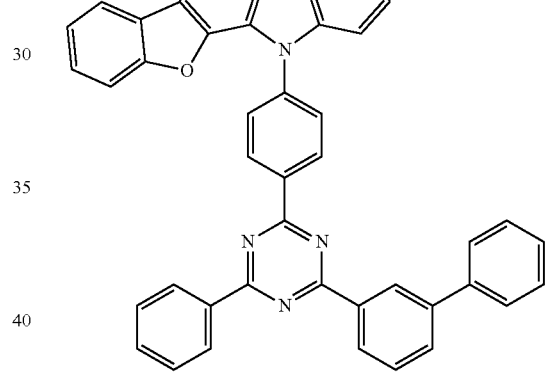
H2-340
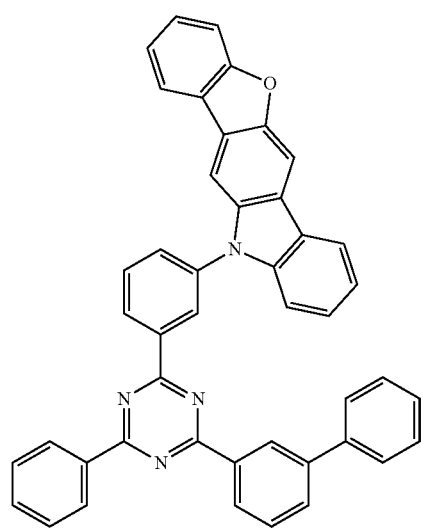
H2-343
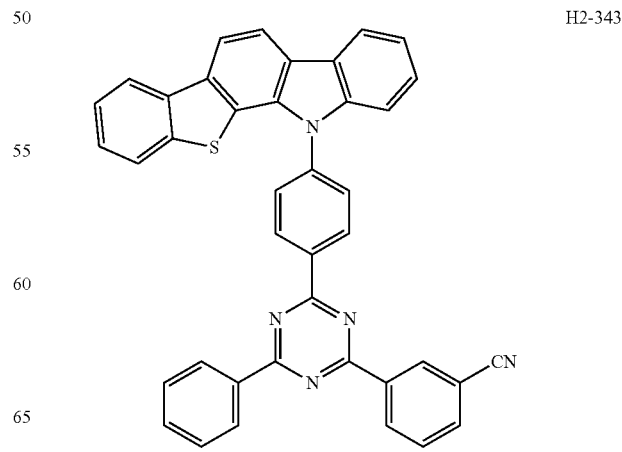

| 495 | 496 |
|---|---|
| -continued | -continued |
| H2-344 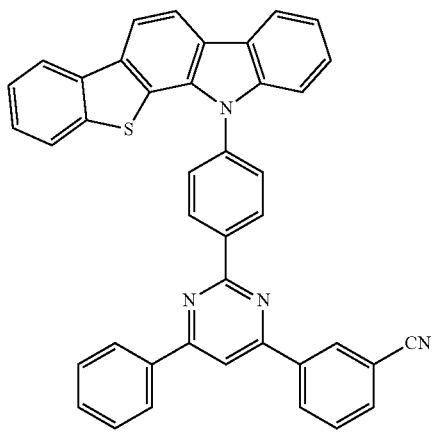 | H2-347 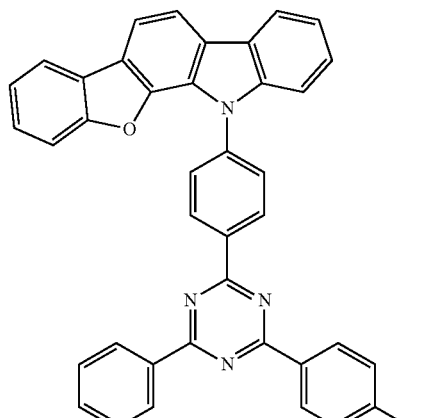 |
| H2-345 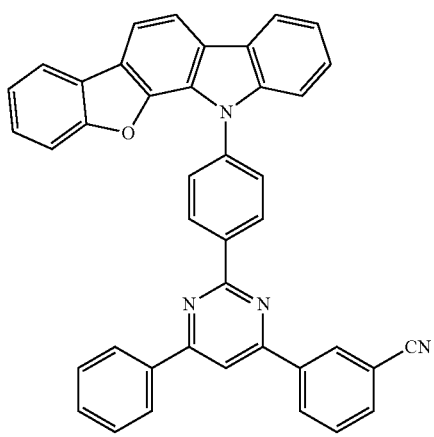 | H2-348 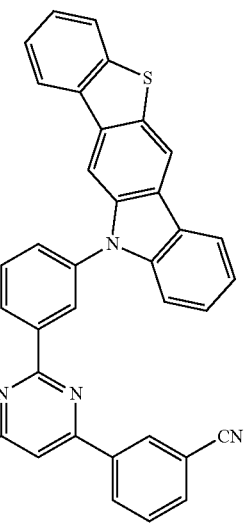 |
| H2-346 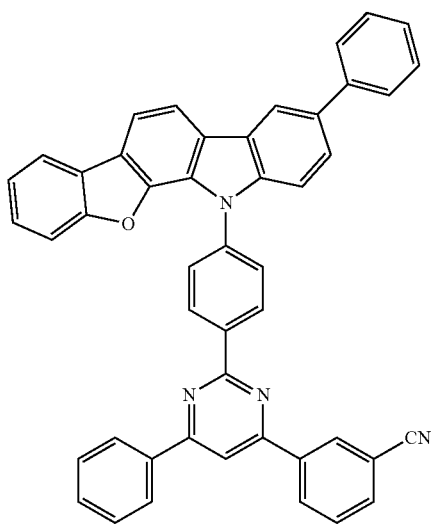 | H2-349 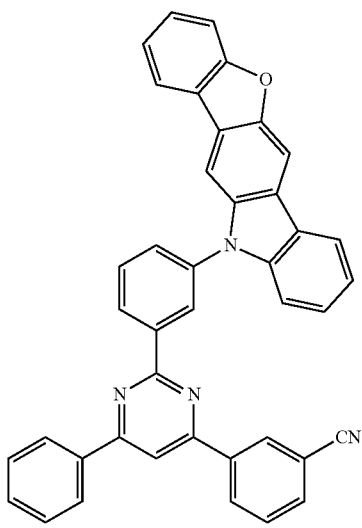 |

-continued
H2-350
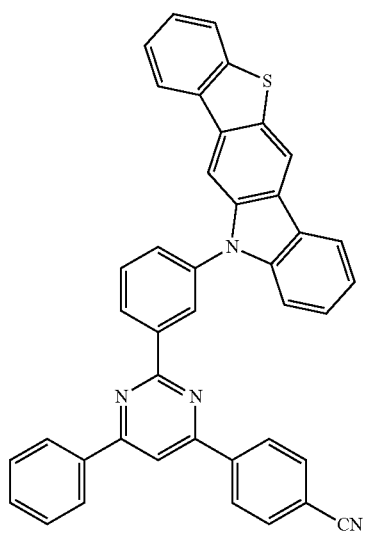
H2-353
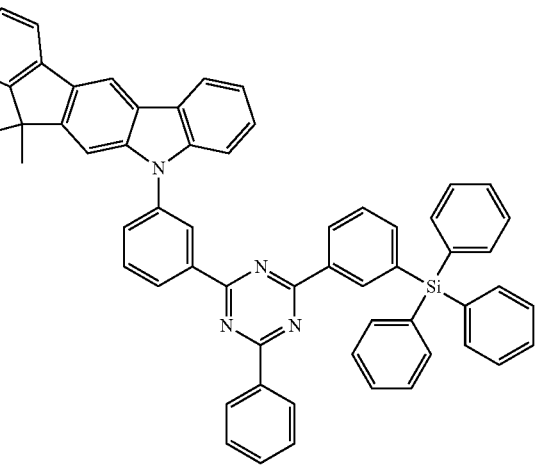
H2-351
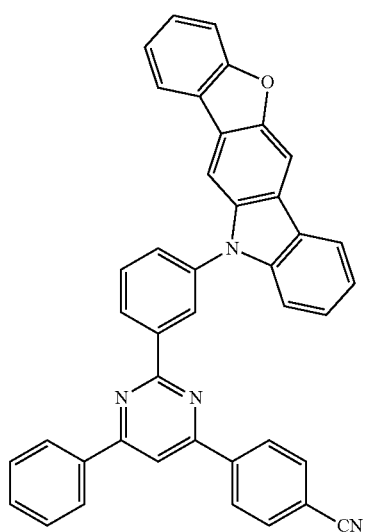
H2-354
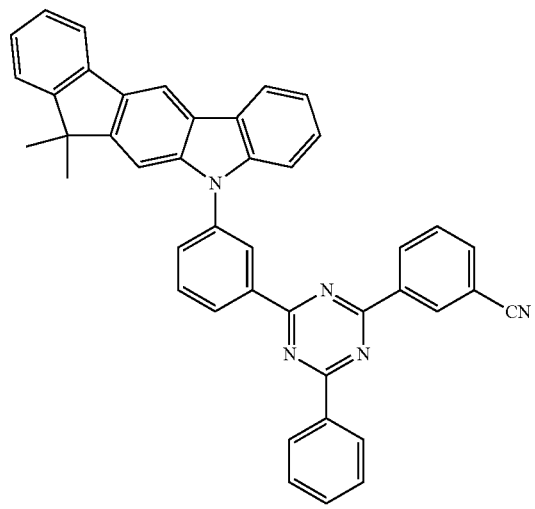
H2-352
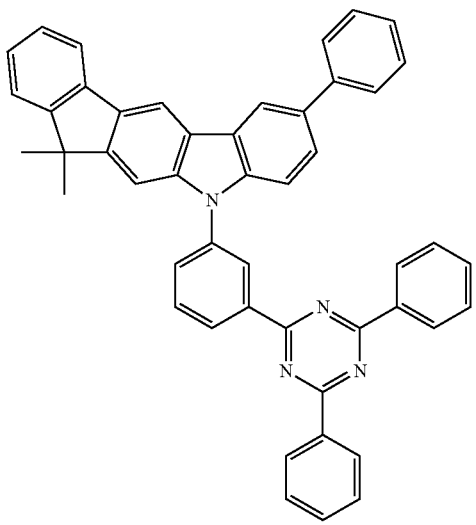
H2-355
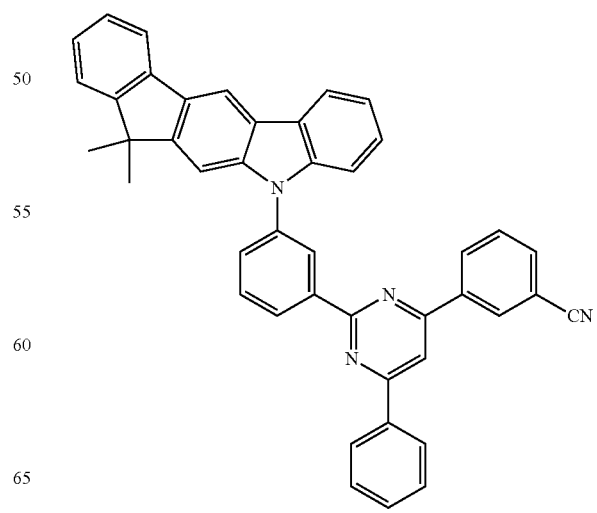

H2-356
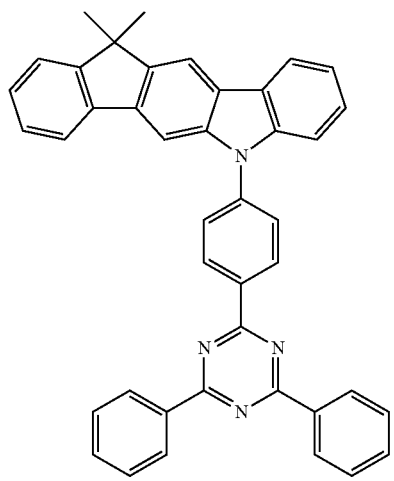
H2-359
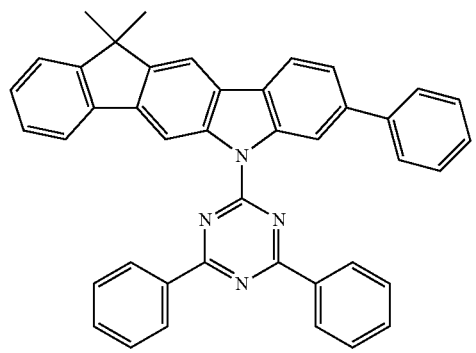
H2-357
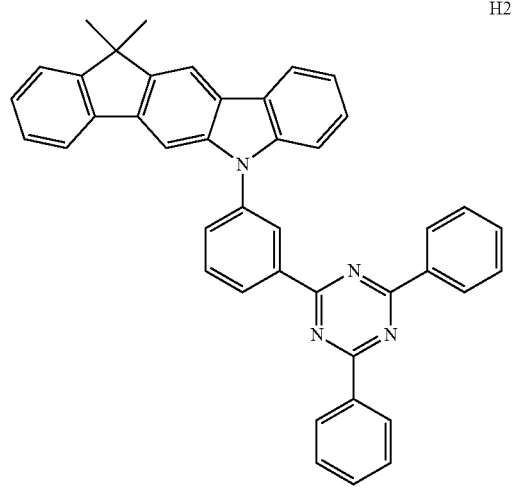
H2-360
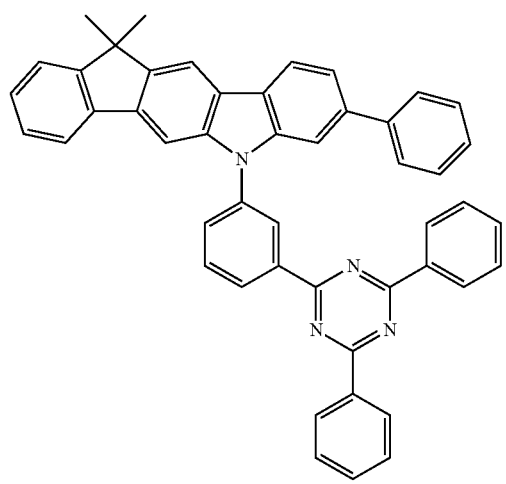
H2-361
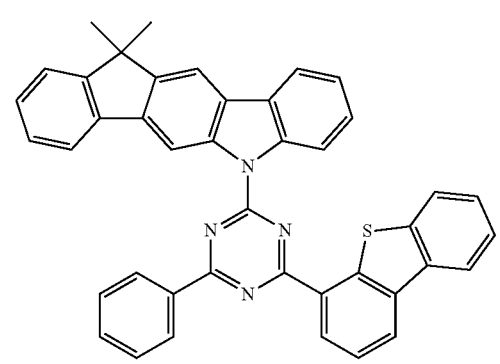
H2-358
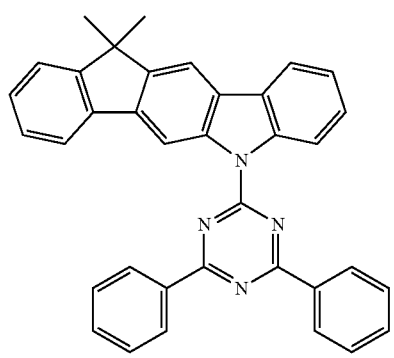
H2-362
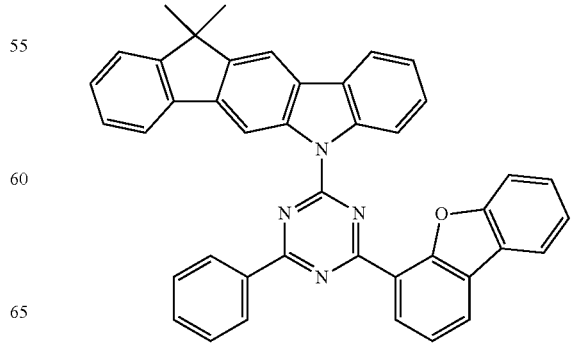

501
-continued
H2-363
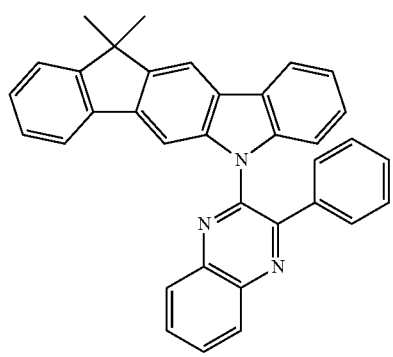
H2-364
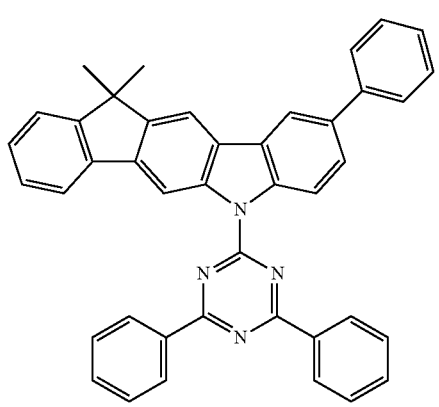
H2-365
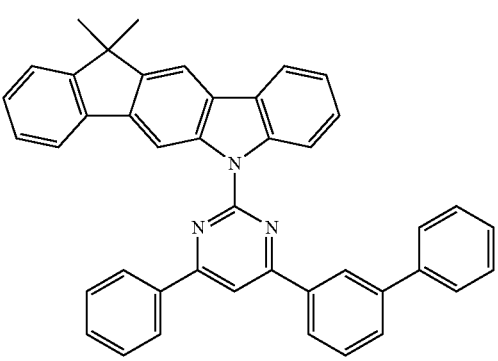
H2-366
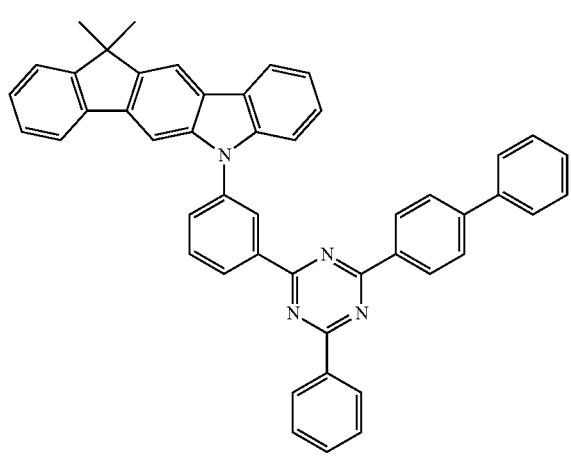
502
-continued
H2-367
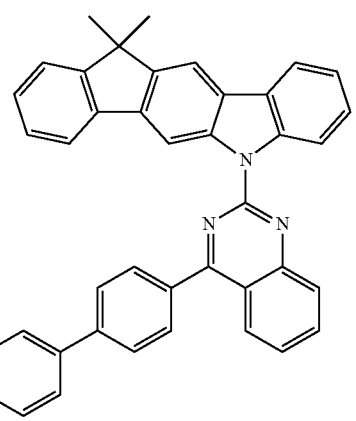
H2-368
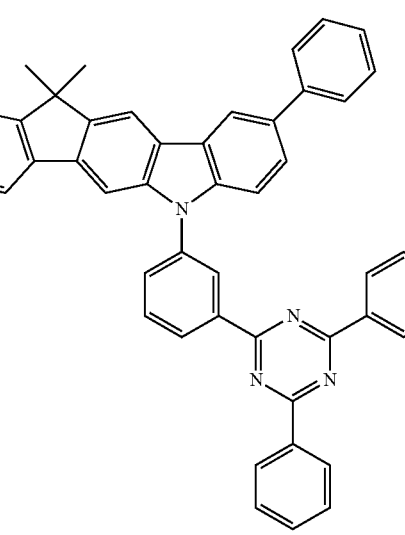
H2-369
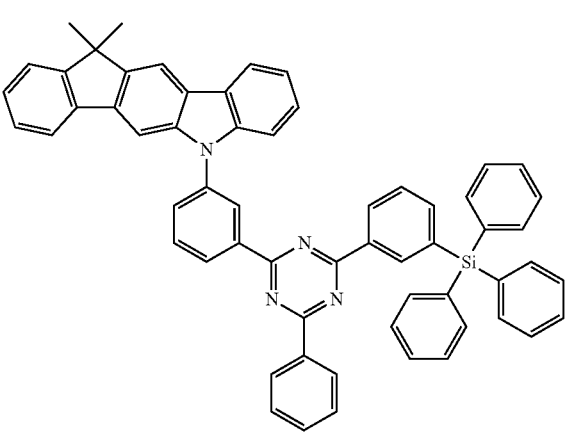

H2-370
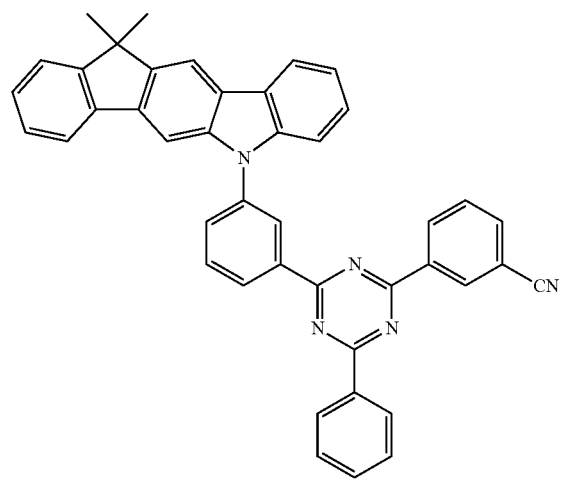
H2-371
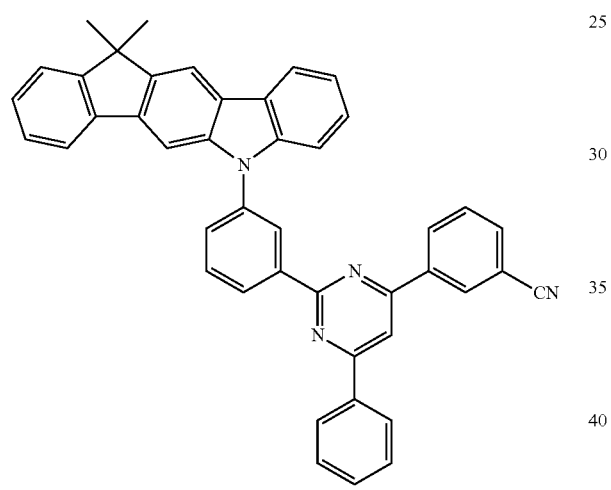
H2-372
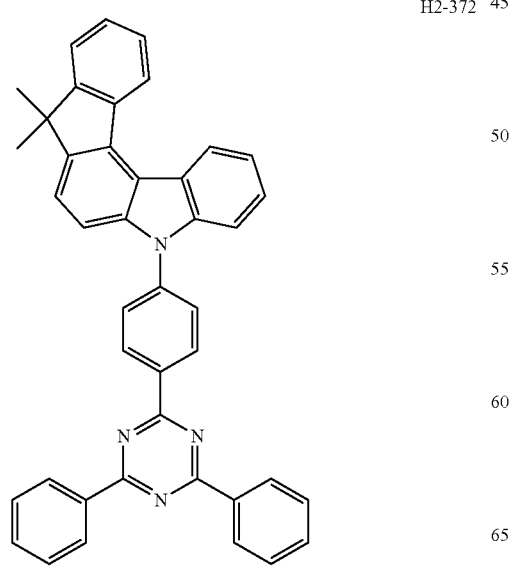
H2-373
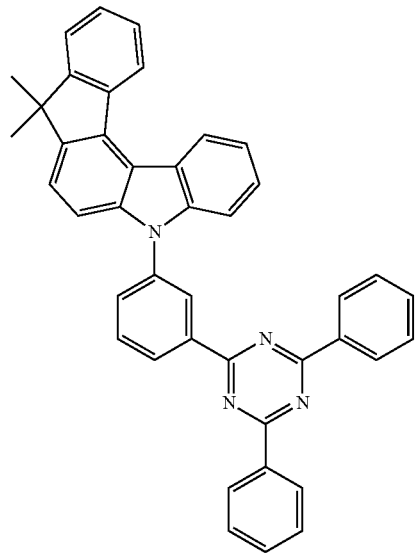
H2-374
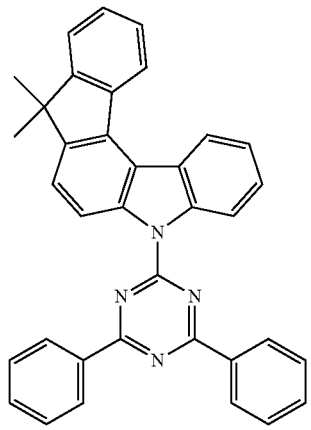
H2-375
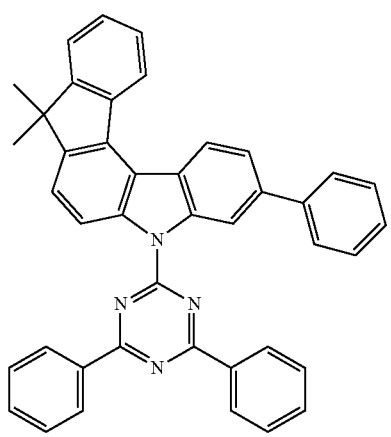

505
-continued
H2-376
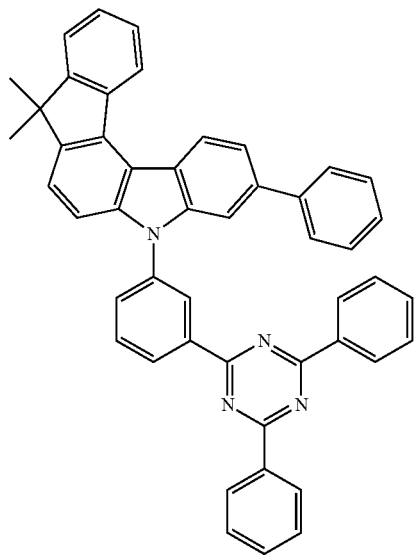
H2-377
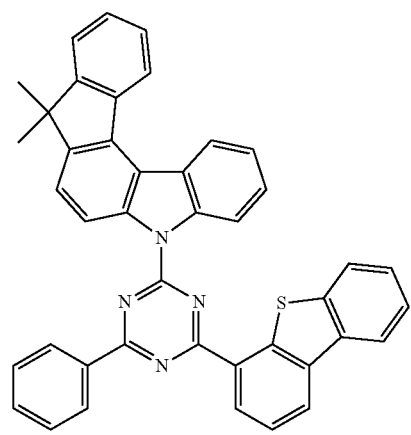
H2-378
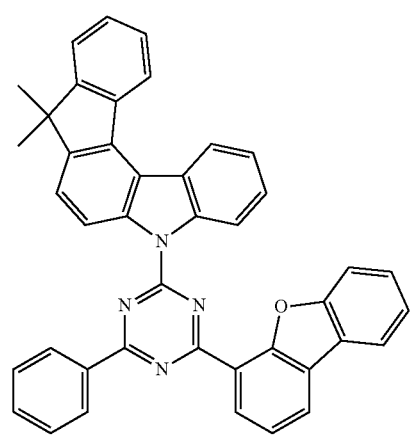
506
-continued
H2-379
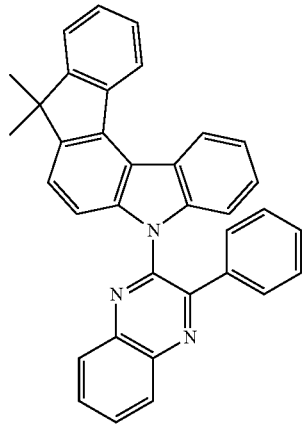
H2-380
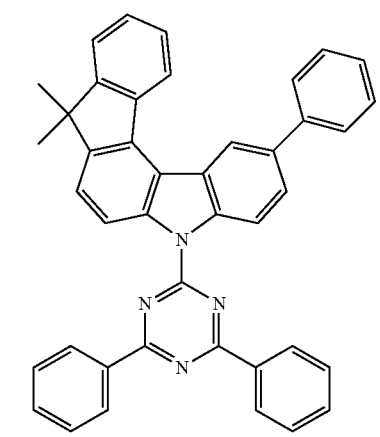
H2-381
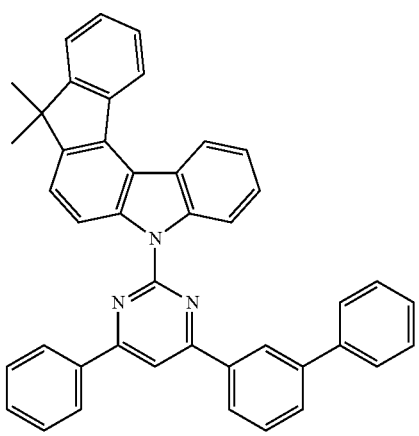

H2-382
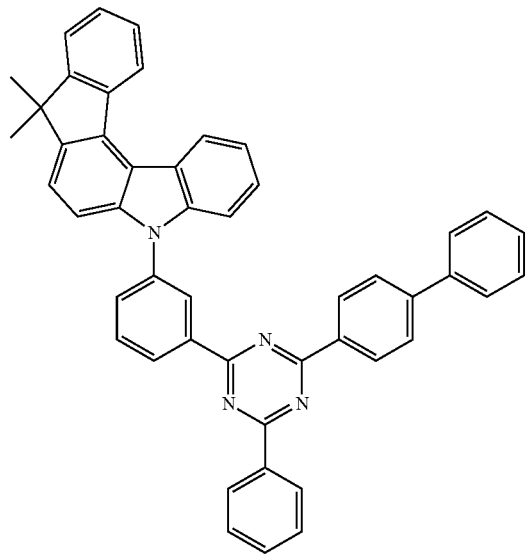
H2-385
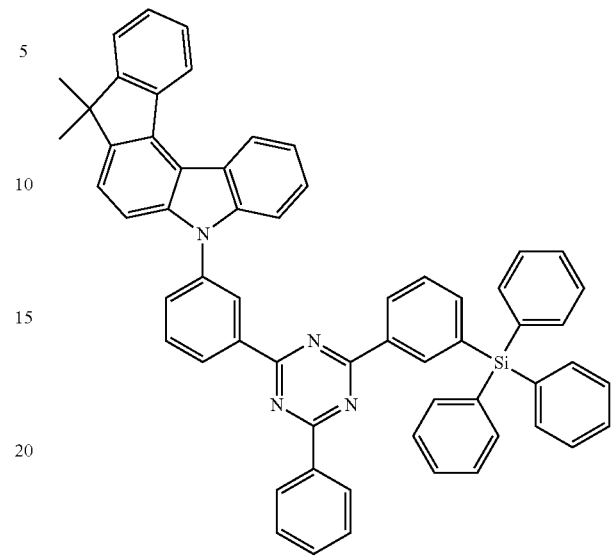
H2-383
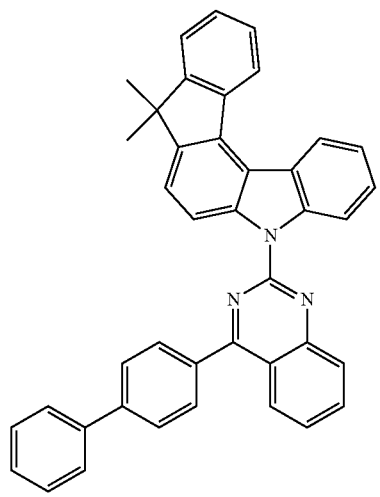
H2-384
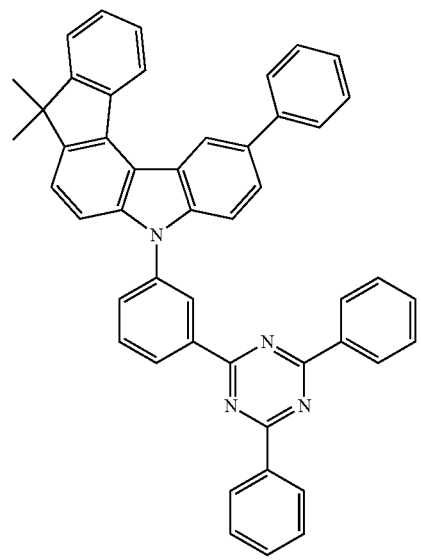
H2-386
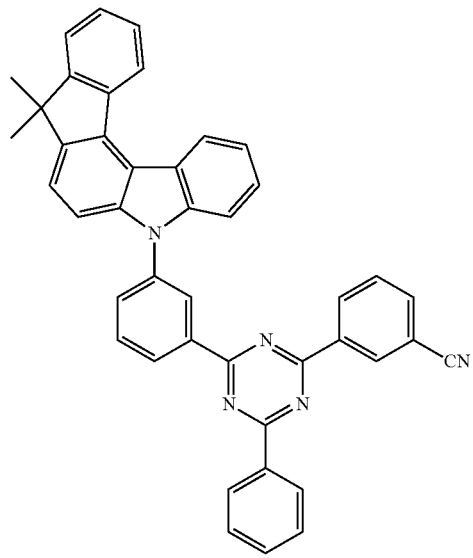

H2-387
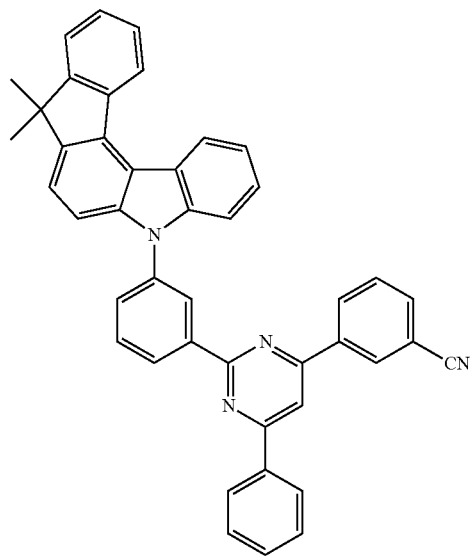
H2-388
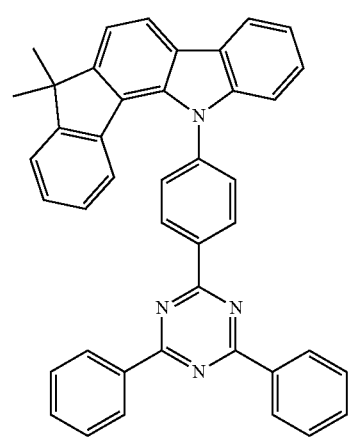
H2-389
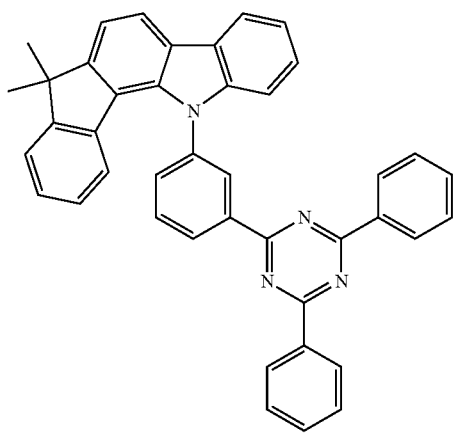
H2-390
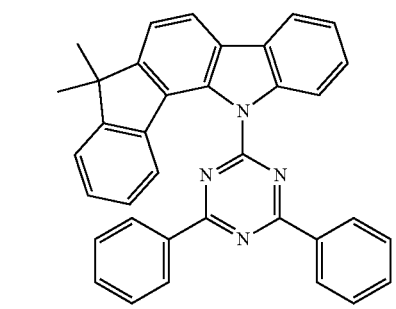
H2-391
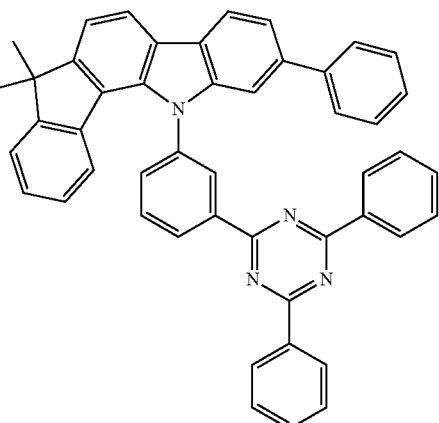
H2-392
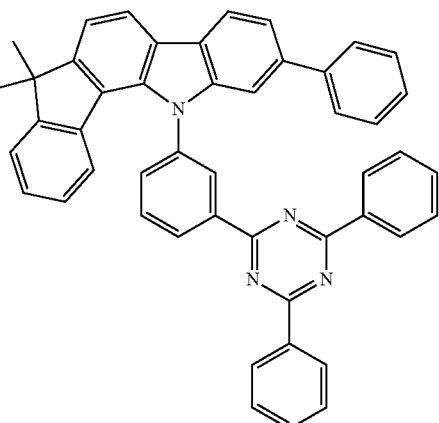
H2-393
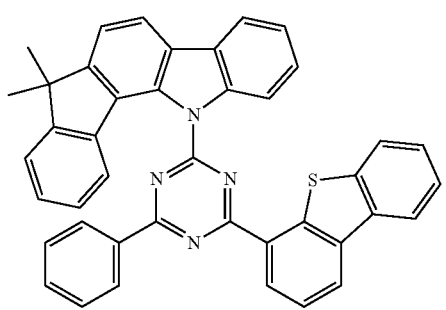

511
-continued
H2-394
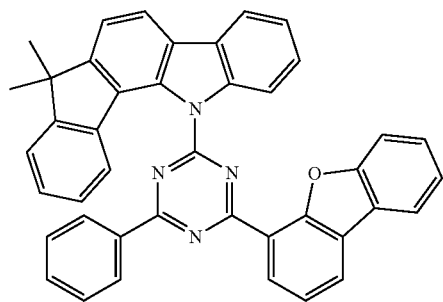
H2-395
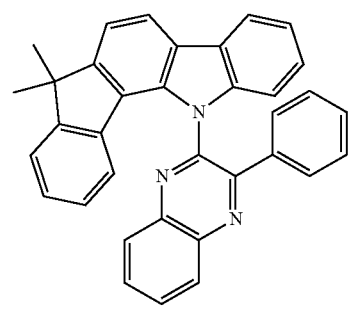
H2-396
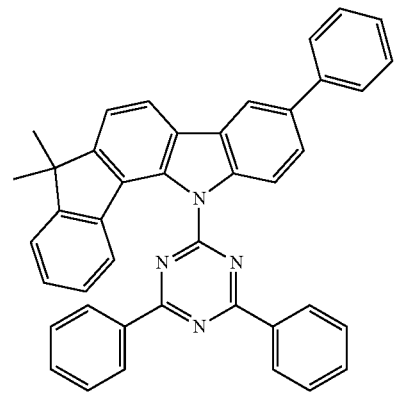
H2-397
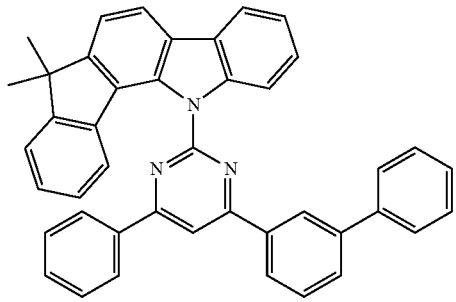
512
-continued
H2-398
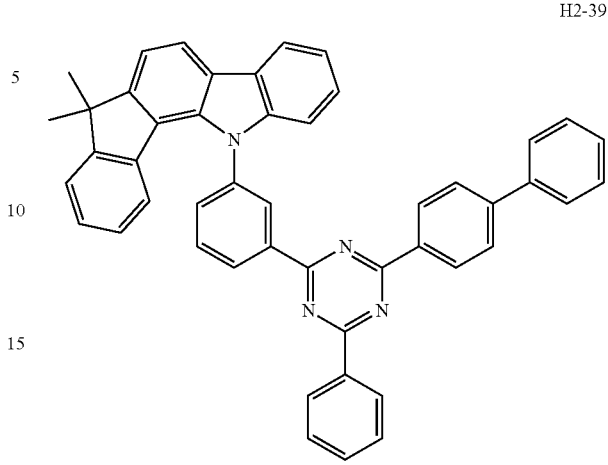
H2-399
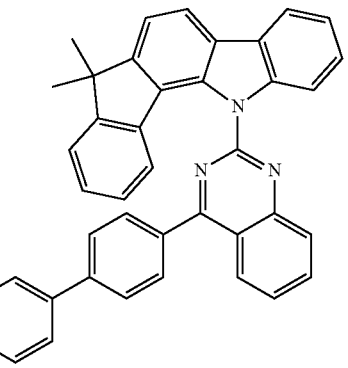
H2-400
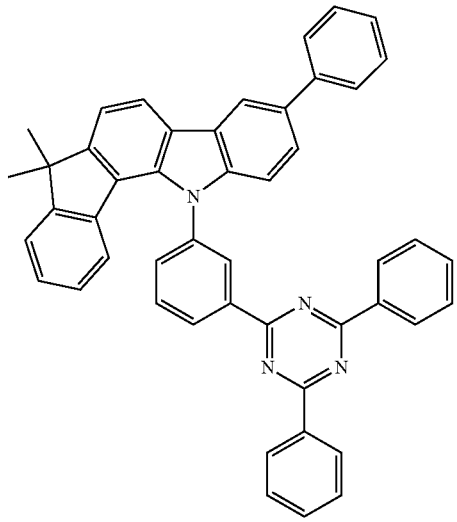

H2-401
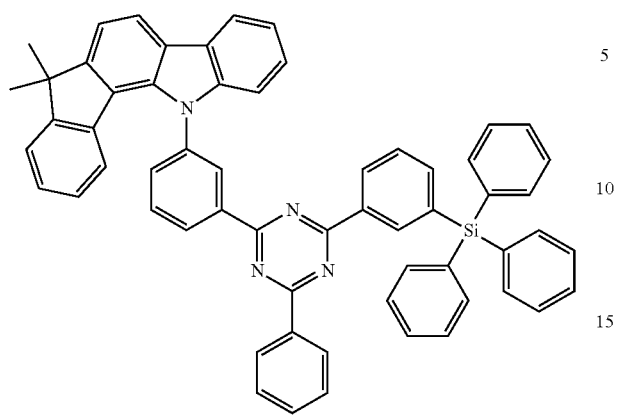
H2-402
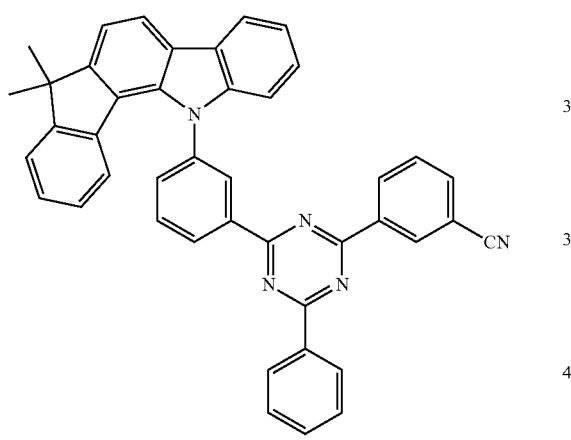
H2-403

H2-404
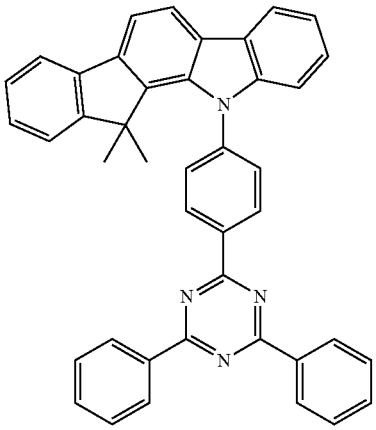
H2-405
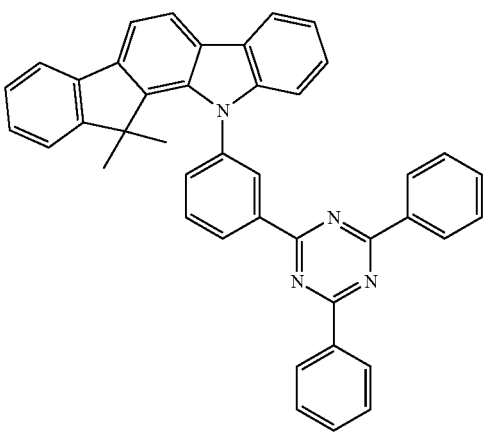
H2-406
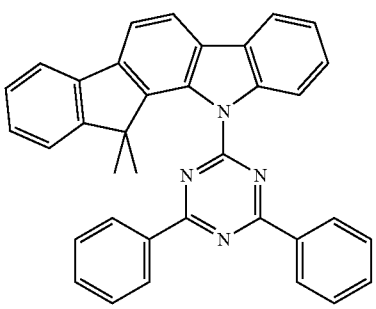
H2-407
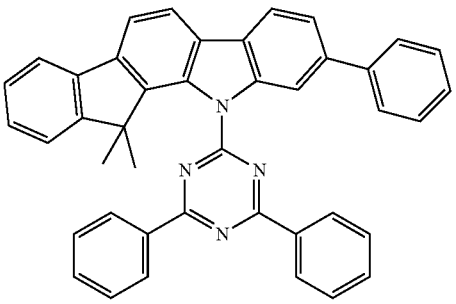

H2-408
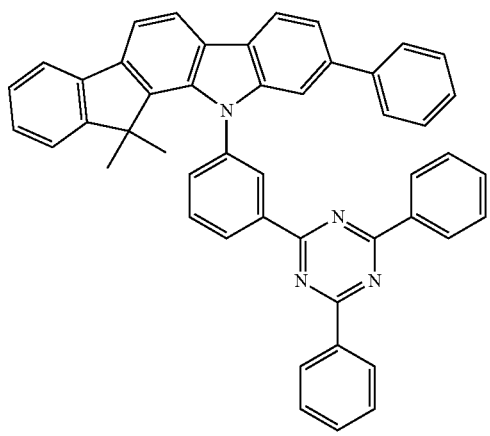
H2-409
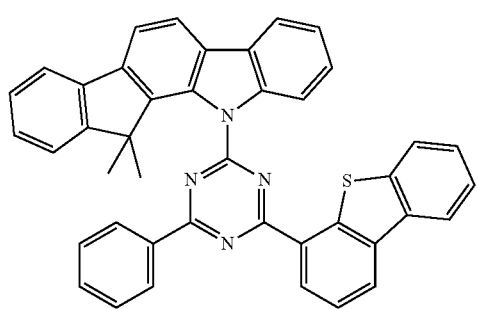
H2-410
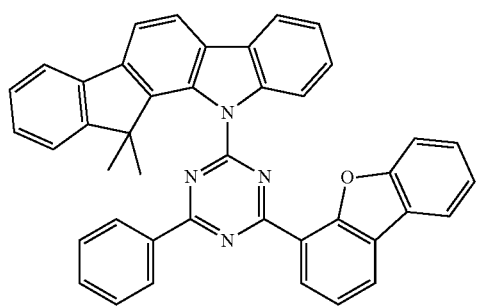
H2-411
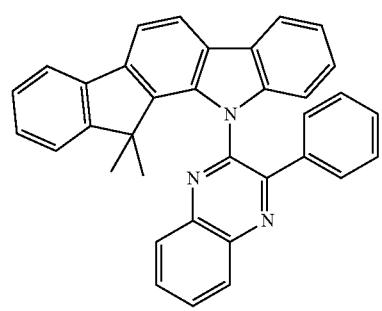
H2-412
H2-413
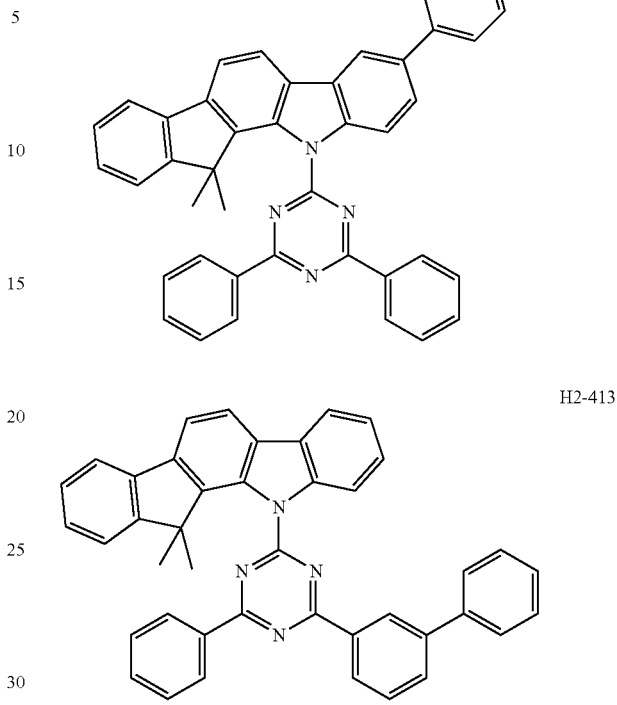
H2-414
H2-415
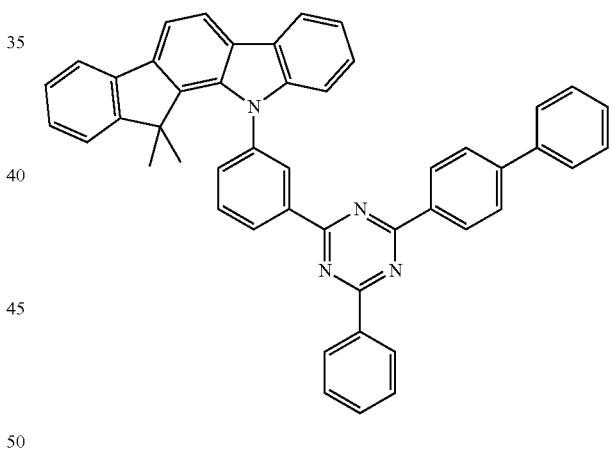
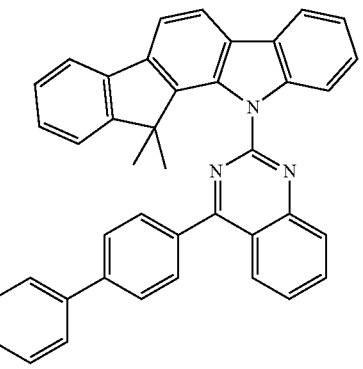

H2-416
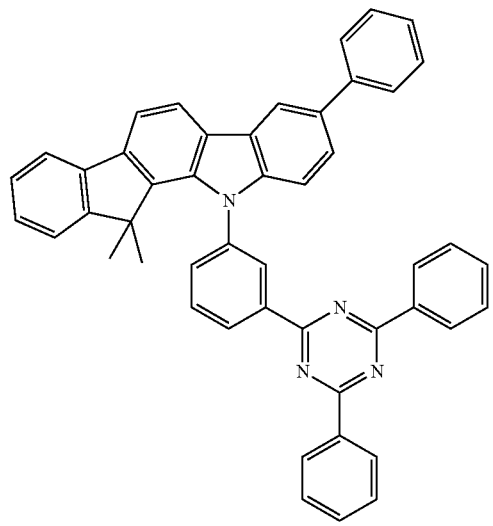
H2-417
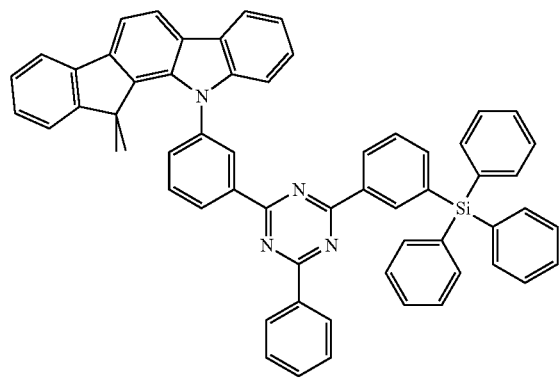
H2-418
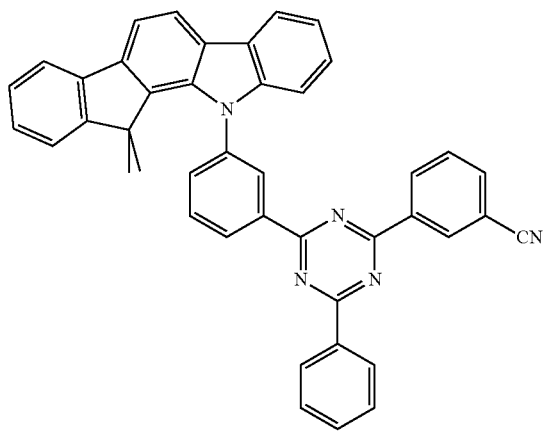
H2-419
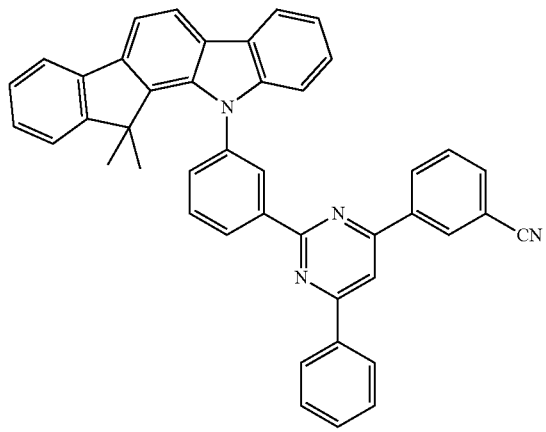
H2-420
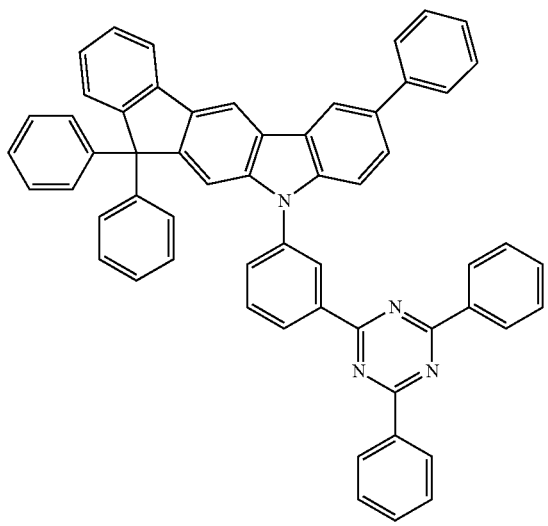
H2-421
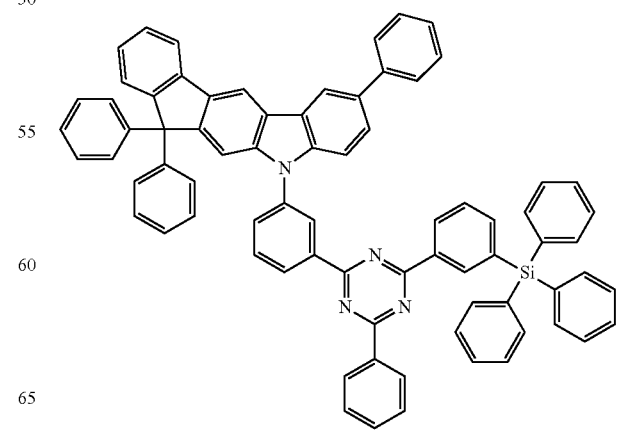

H2-422
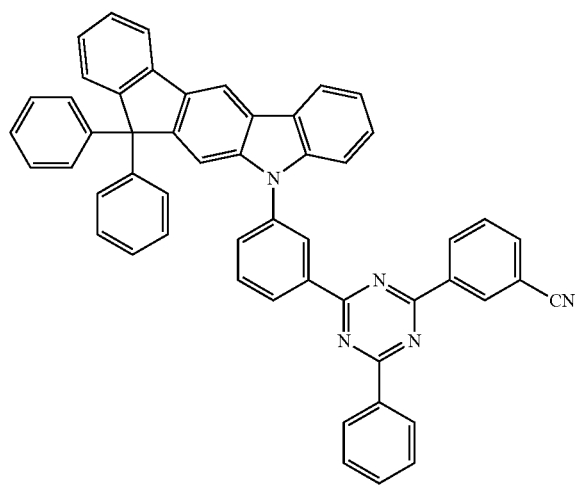
H2-423
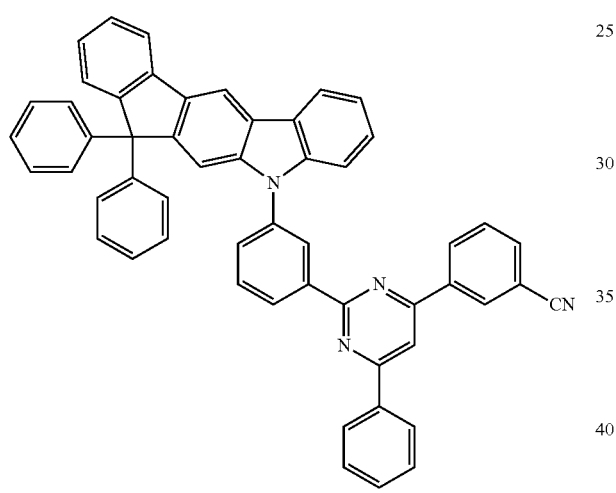
H2-424
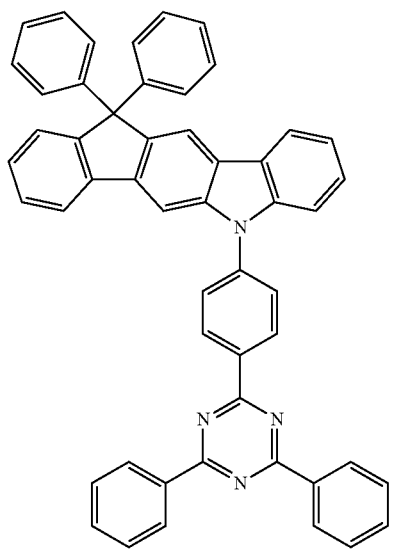
H2-425
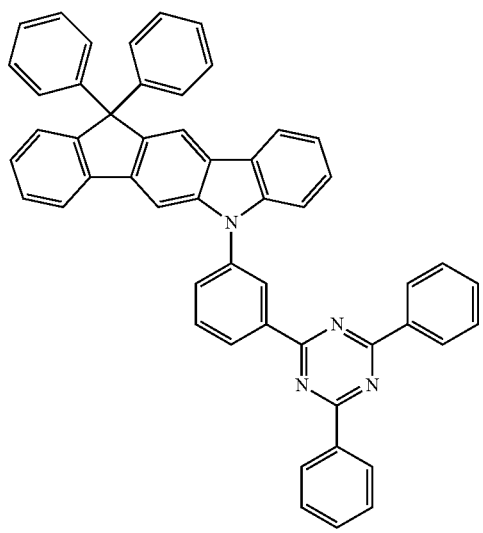
H2-426
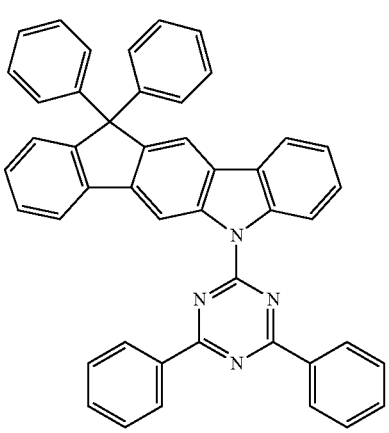
H2-427
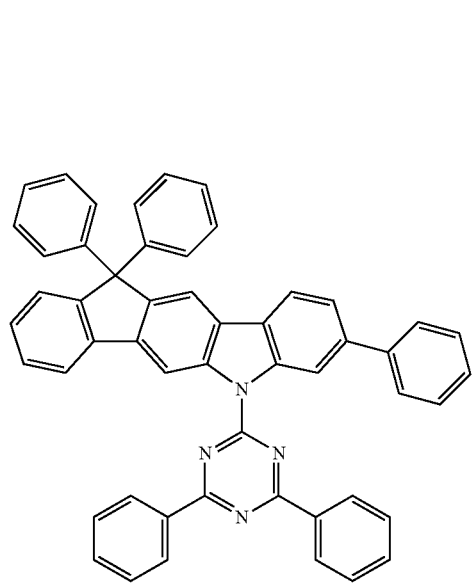

H2-428
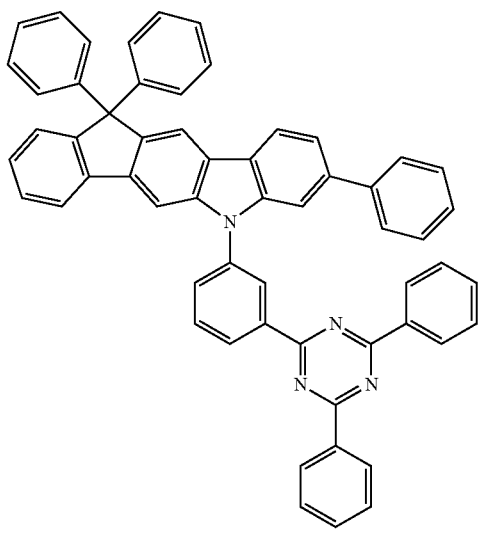
H2-431
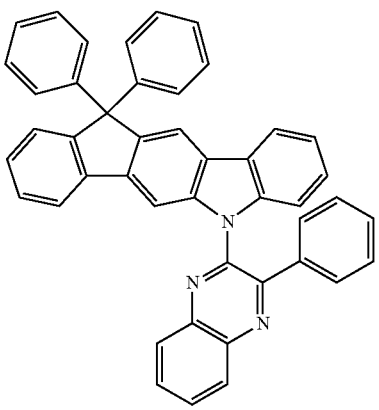
H2-429
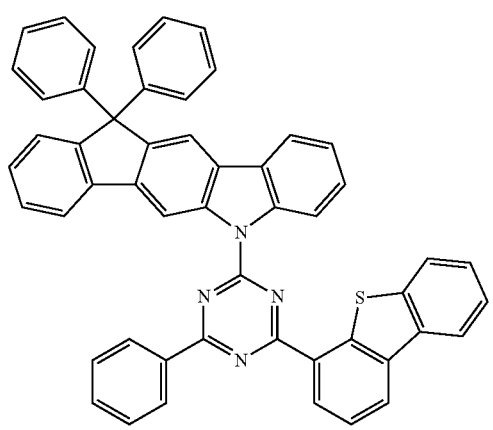
H2-432
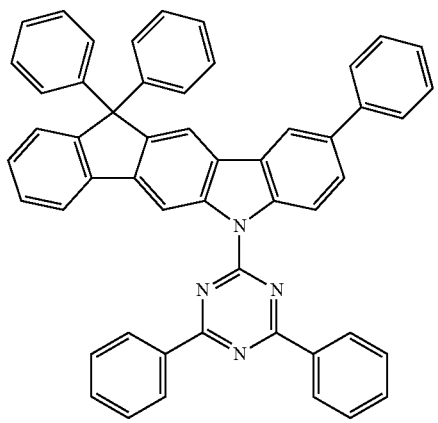
H2-430
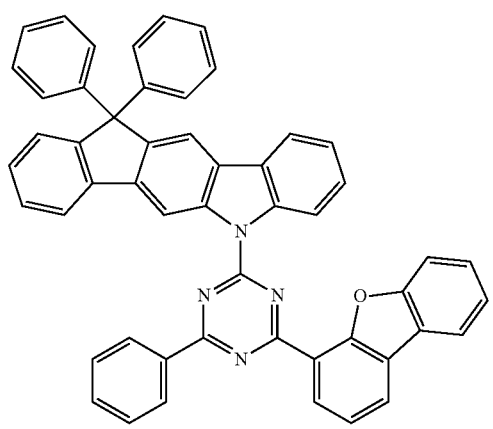
H2-433
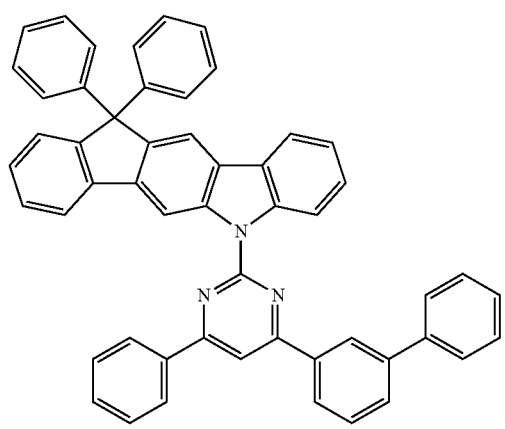

H2-434
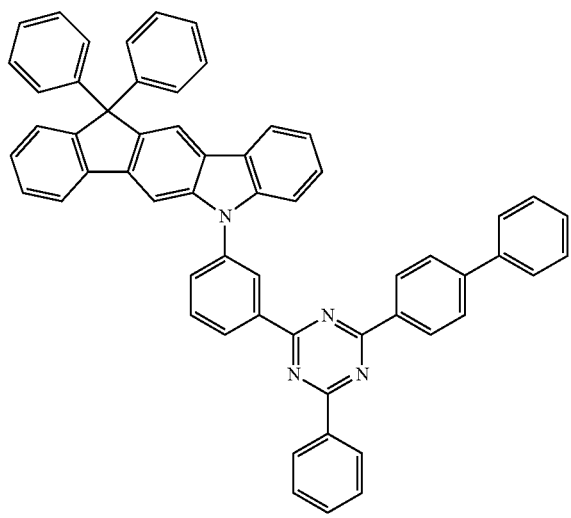
H2-435
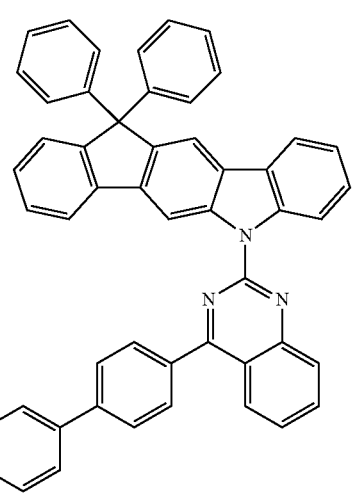
H2-436
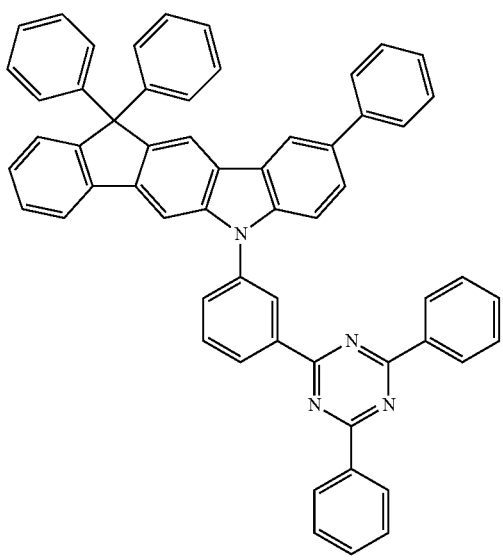
H2-437
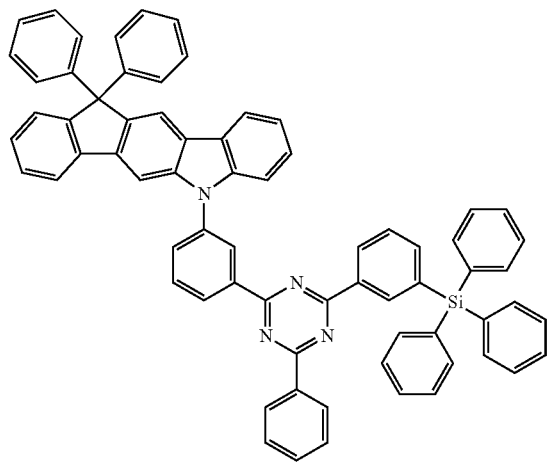
H2-438
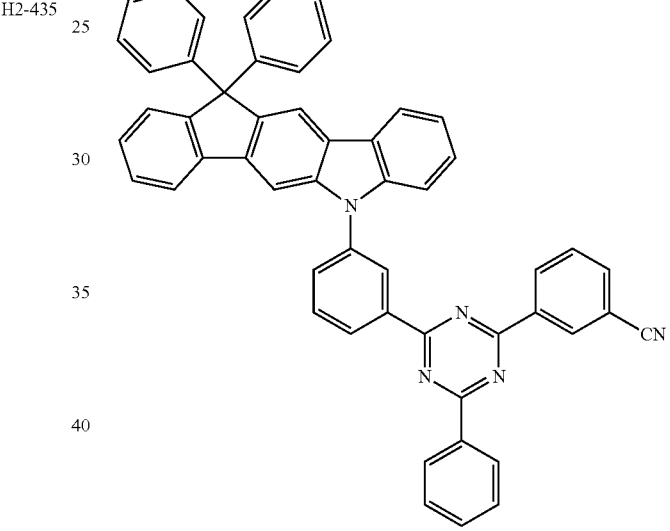
H2-439
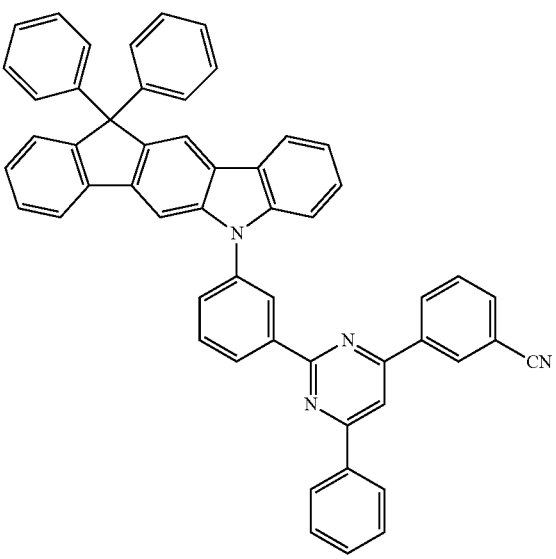

H2-440
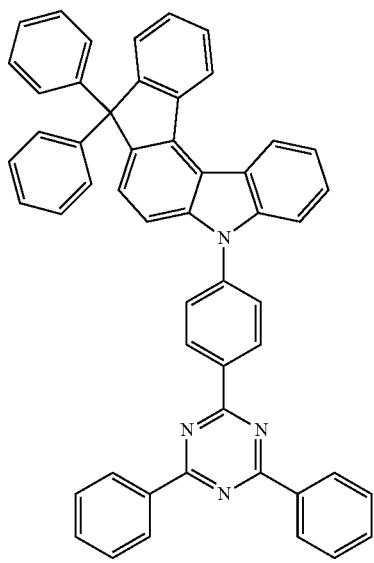
H2-443
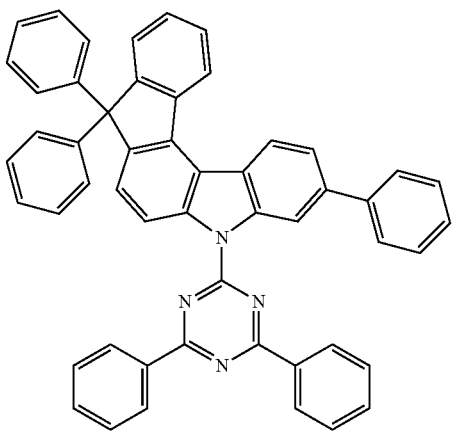
H2-441
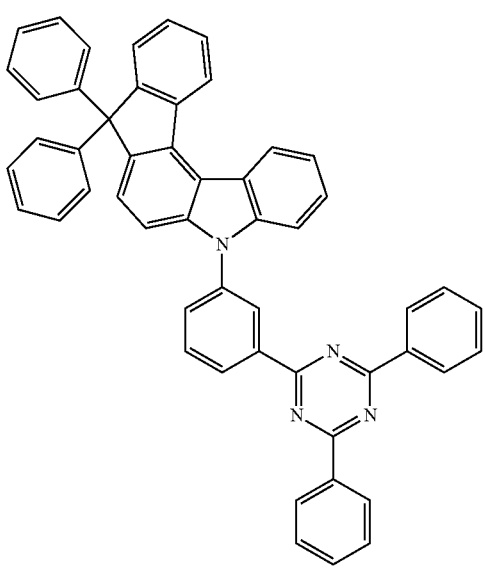
H2-444
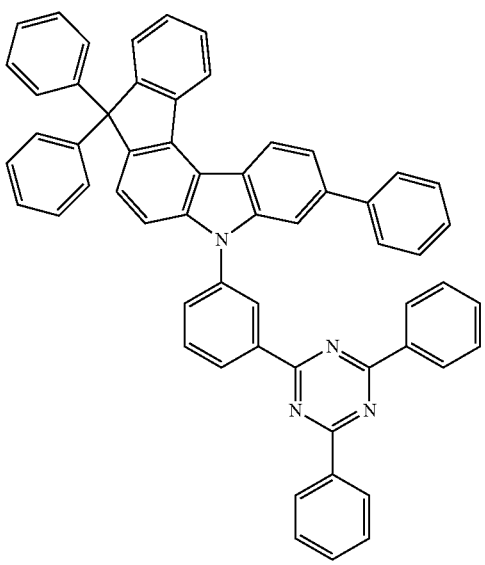
H2-442
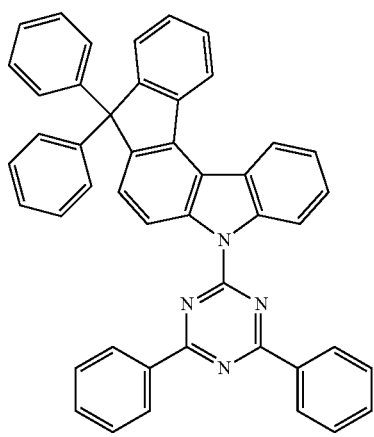
H2-445
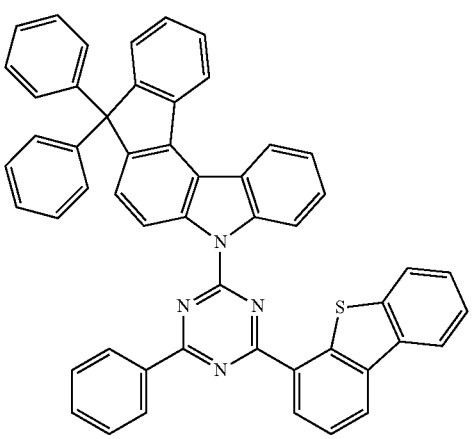

-continued
H2-446
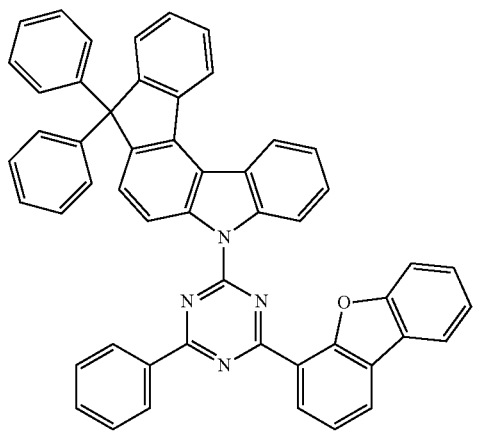
H2-447
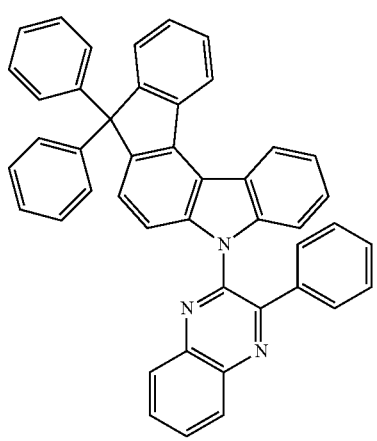
H2-448
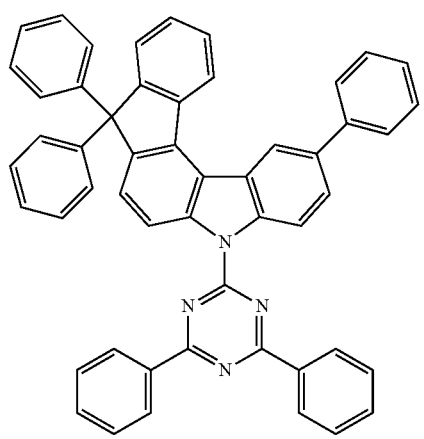
-continued
H2-449
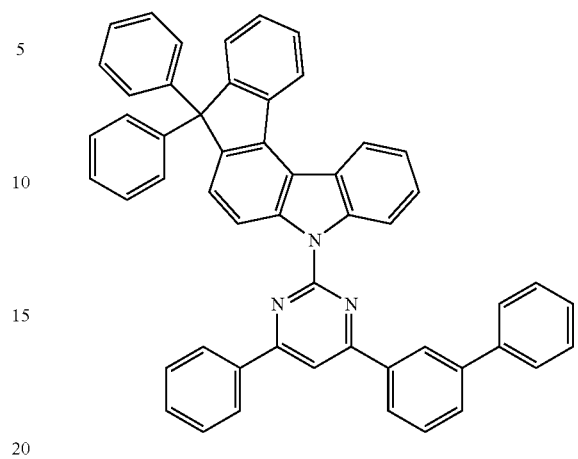
H2-450
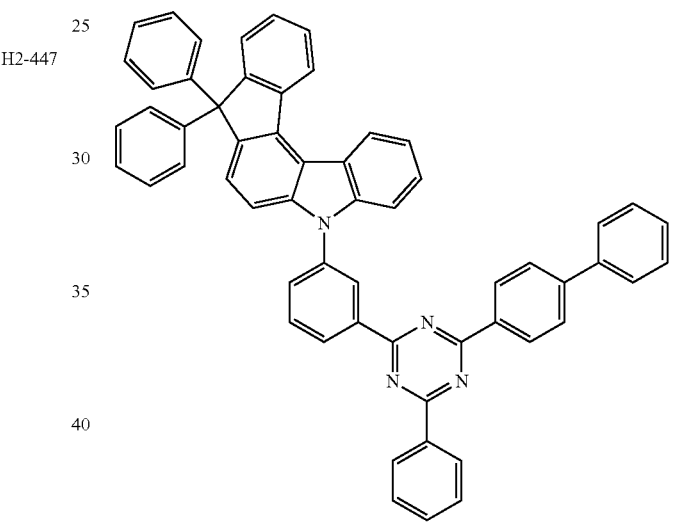
H2-451
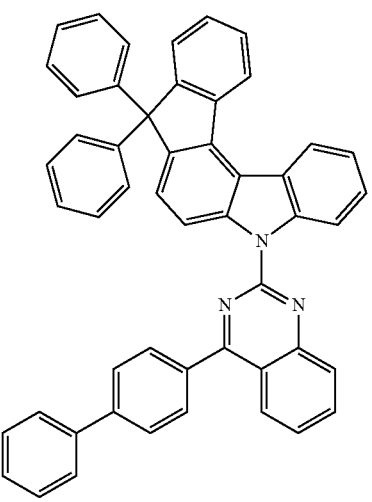

H2-452
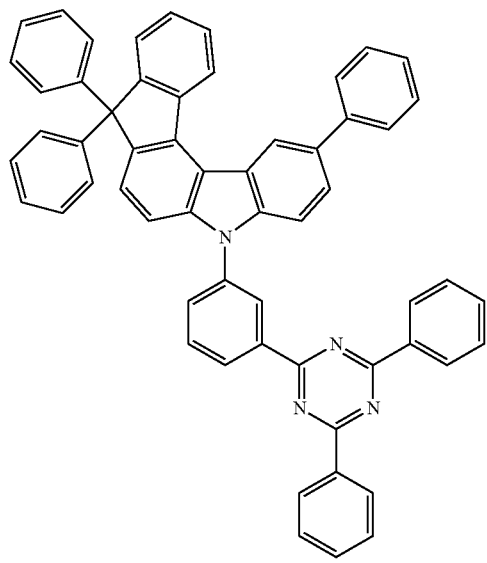
H2-454
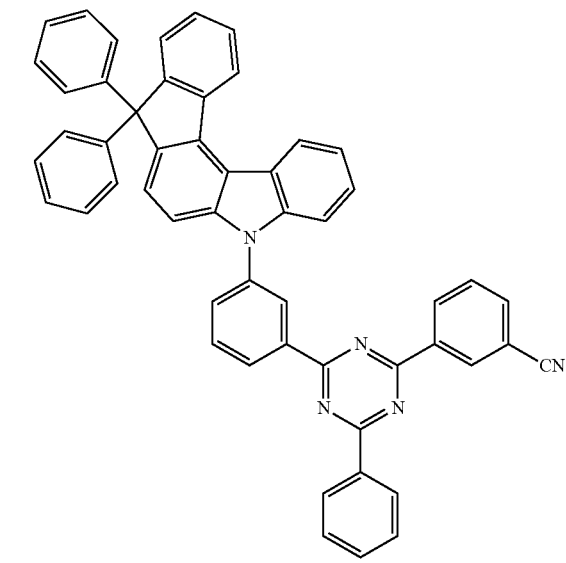
H2-455
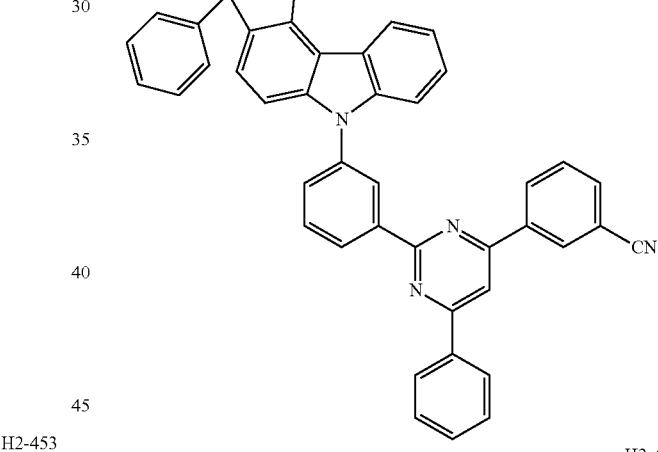
H2-453
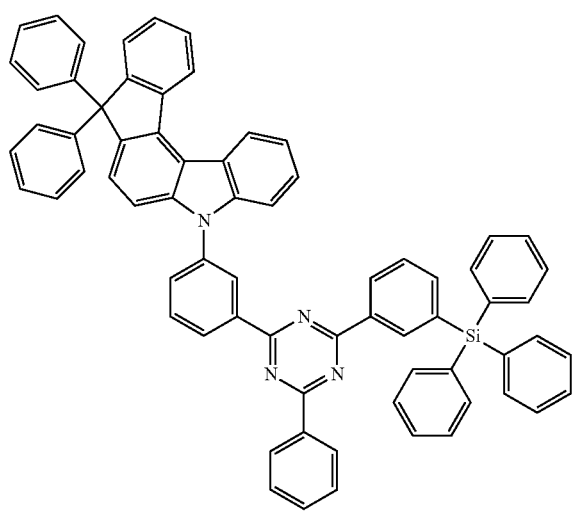
H2-456
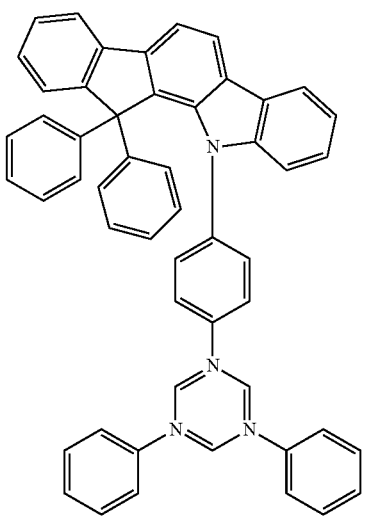

H2-457
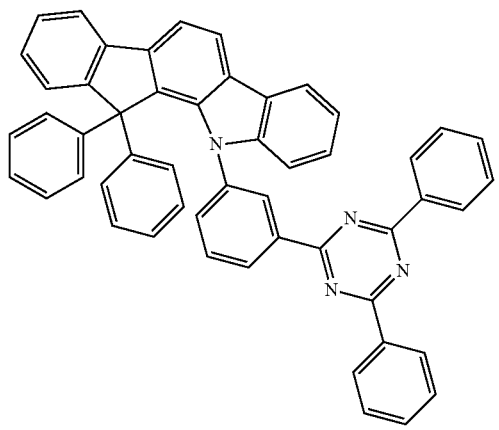
H2-458
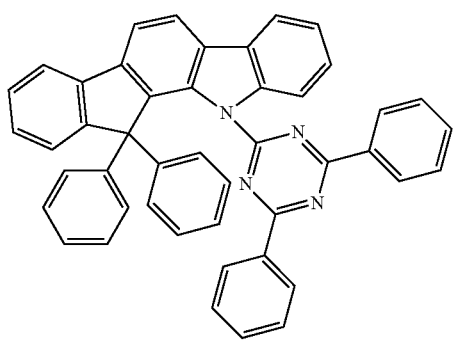
H2-459
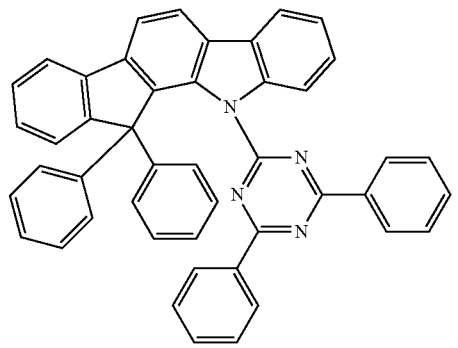
H2-460
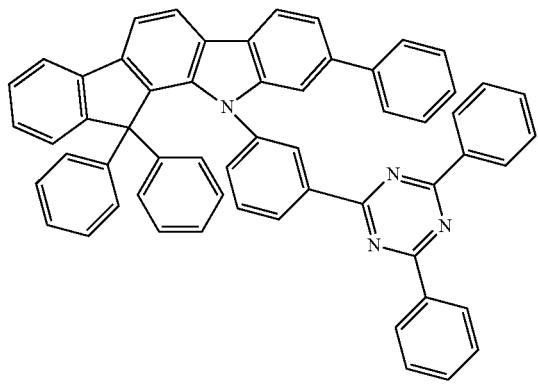
H2-461
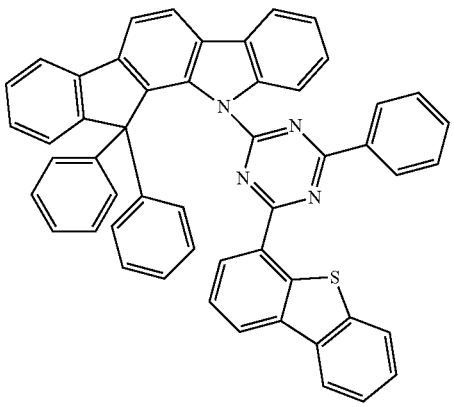
H2-462
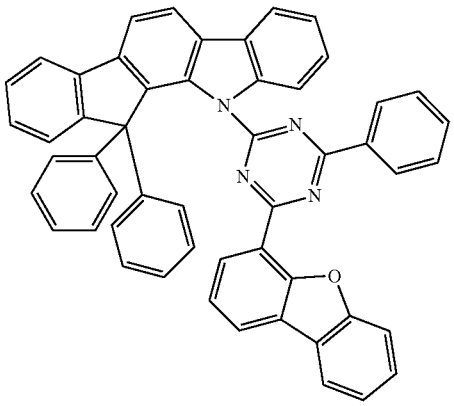
H2-463
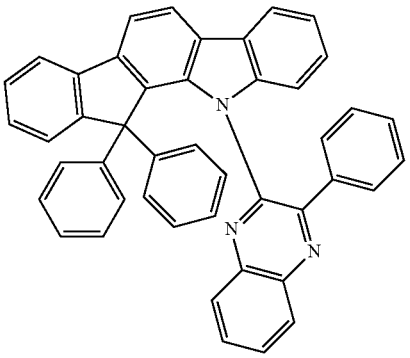
H2-464
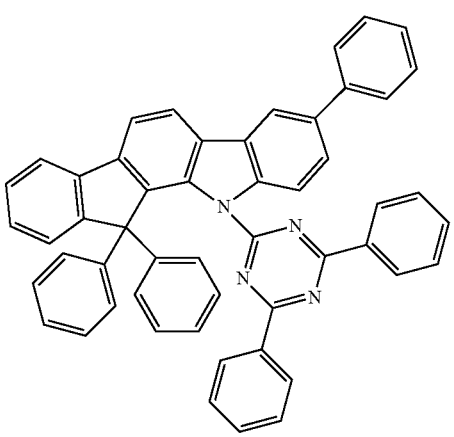

-continued
H2-465
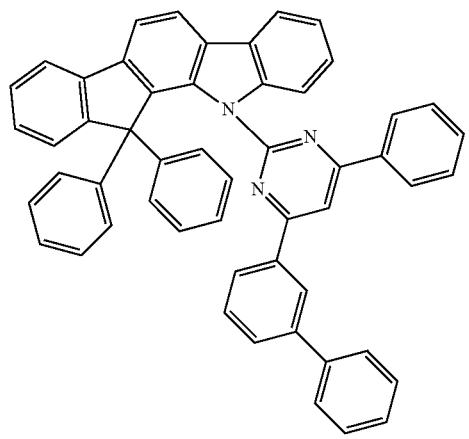
H2-466
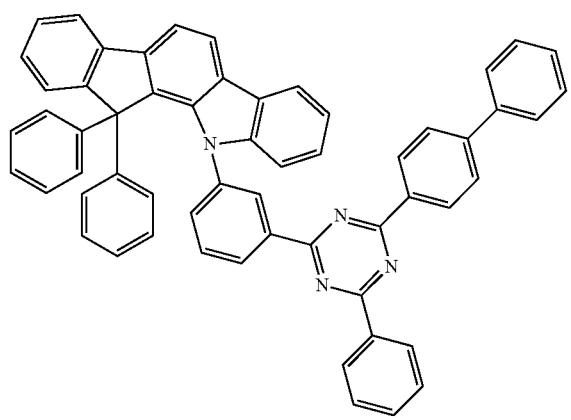
H2-467
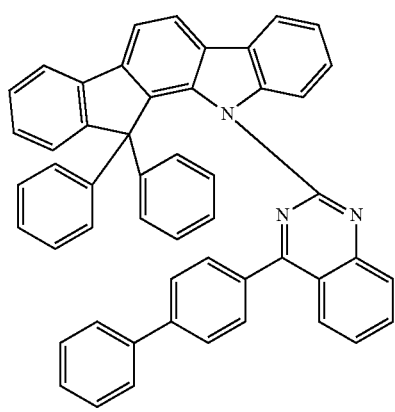
-continued
H2-468
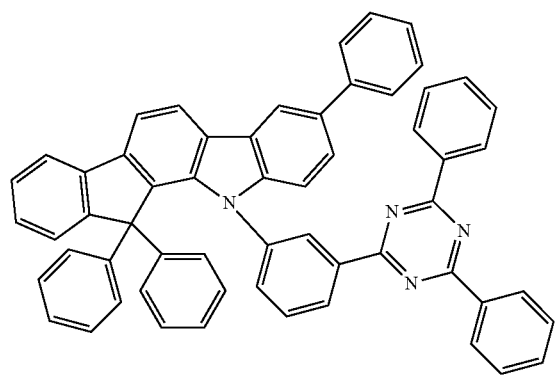
H2-469
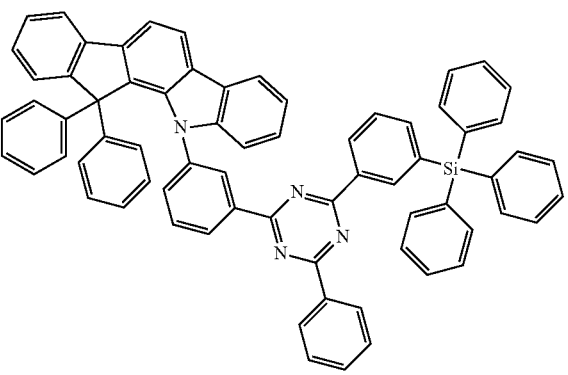
H2-470
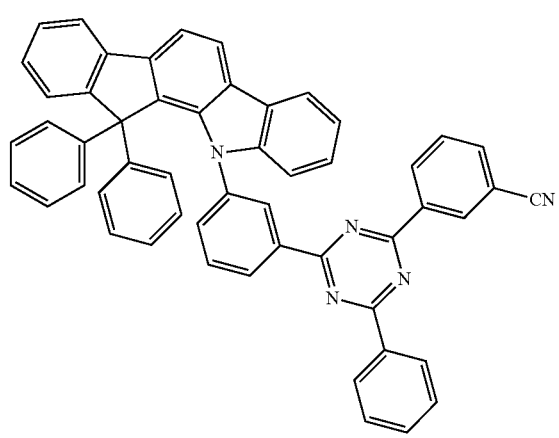

535
-continued
H2-471
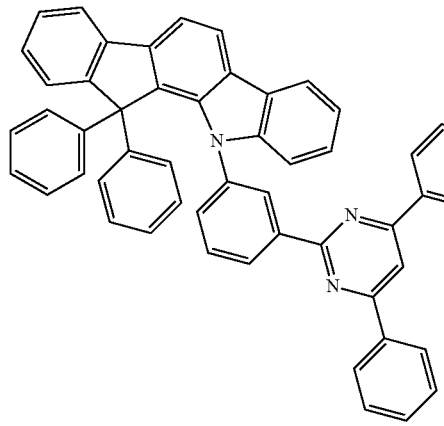
H2-472
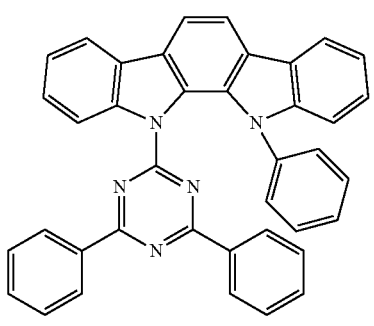
H2-473
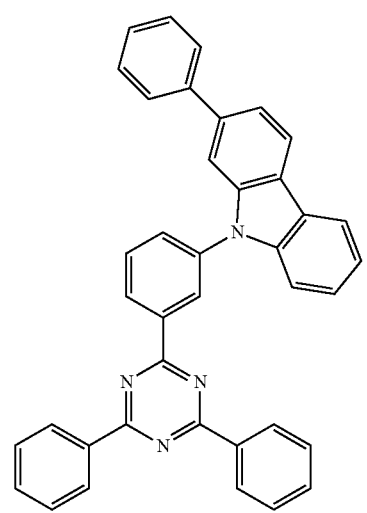
536
-continued
H2-475
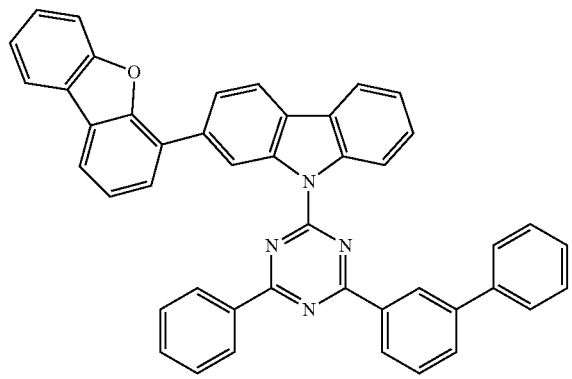
H2-476
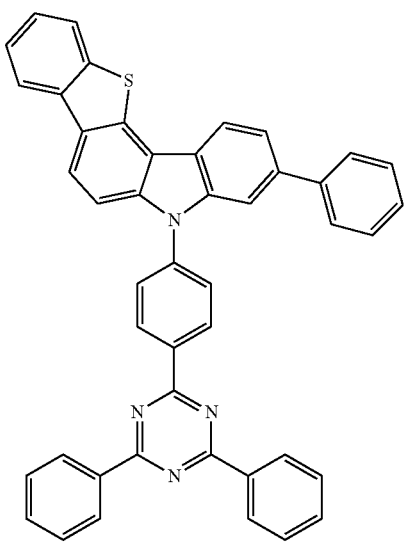
H2-477
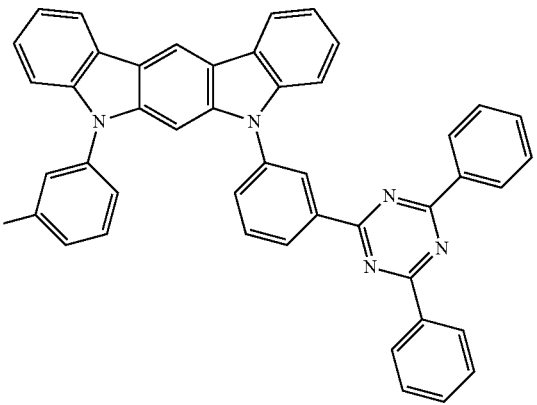

H2-478
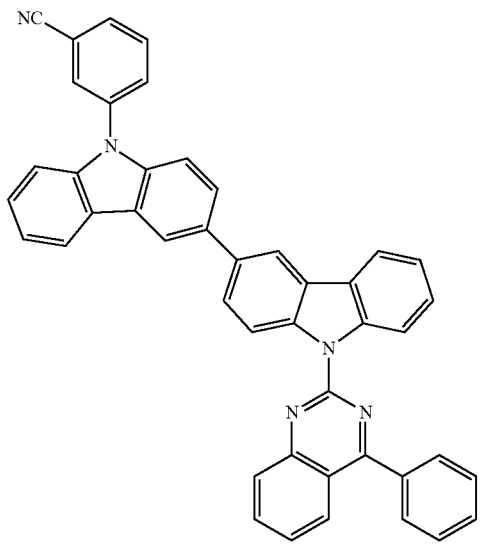
H2-479
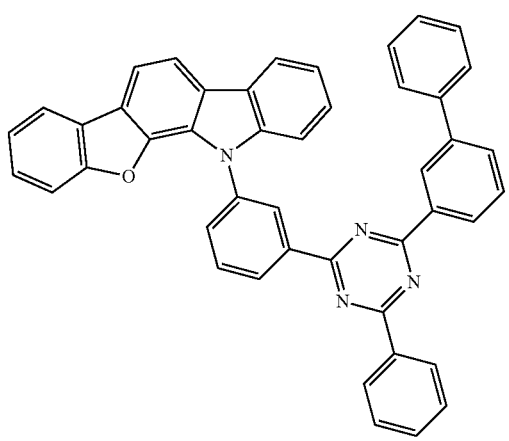
H2-480
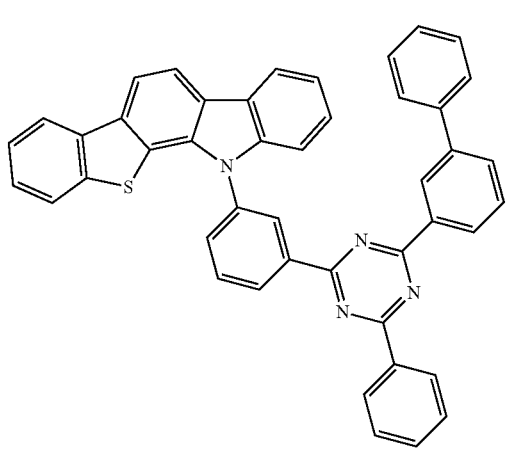
H2-481
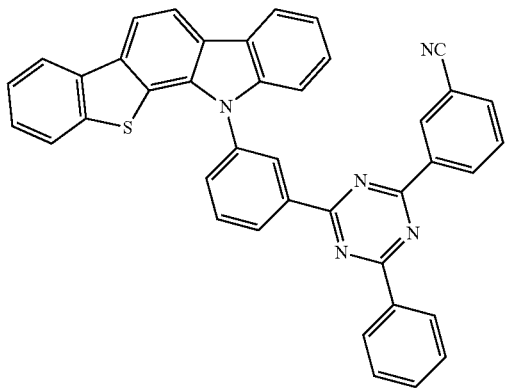
H2-482
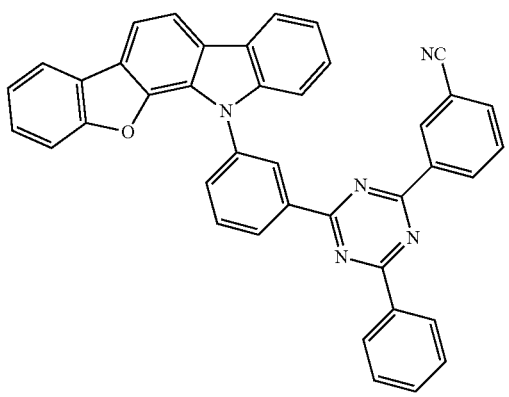
H2-483
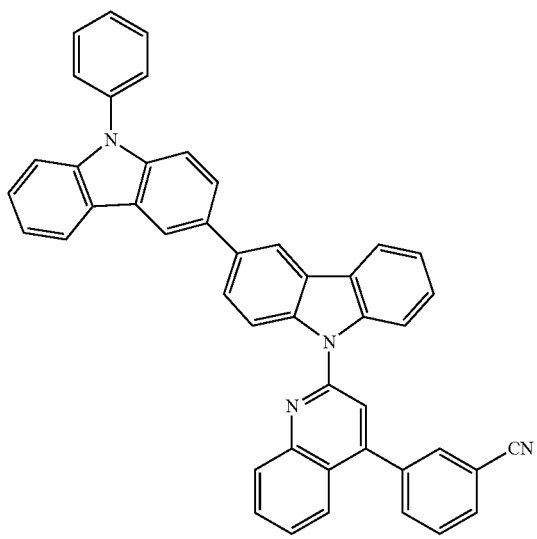

H2-484
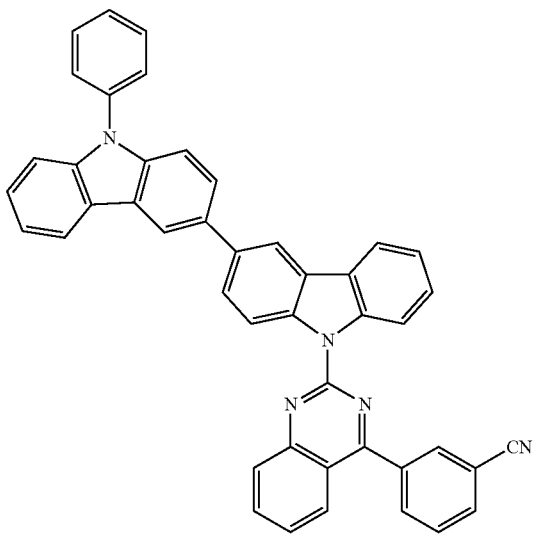
H2-485
H2-486
H2-487
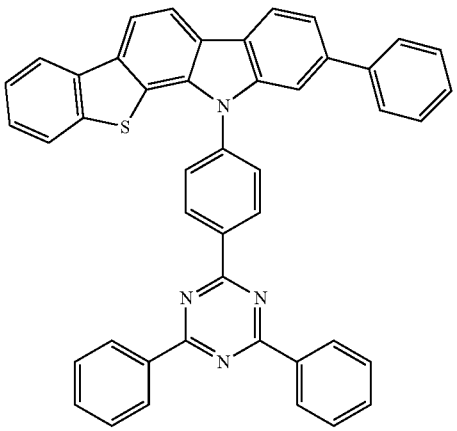
H2-488
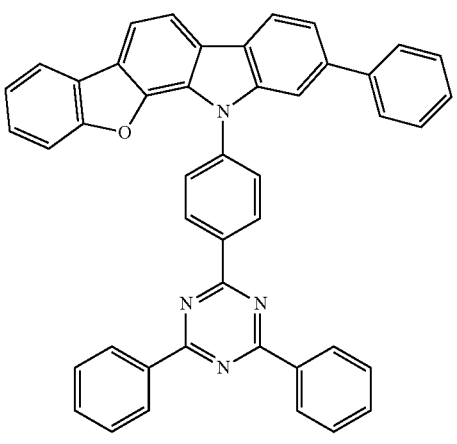
H2-489
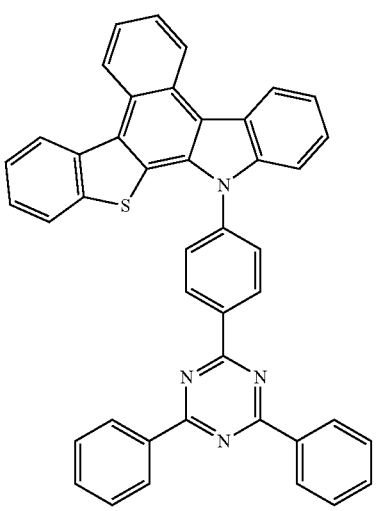

H2-490

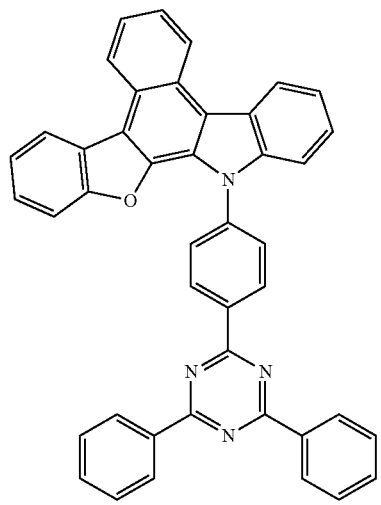

H2-491

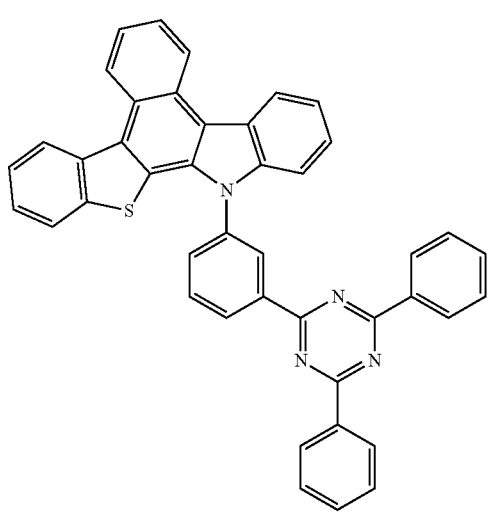

H2-492

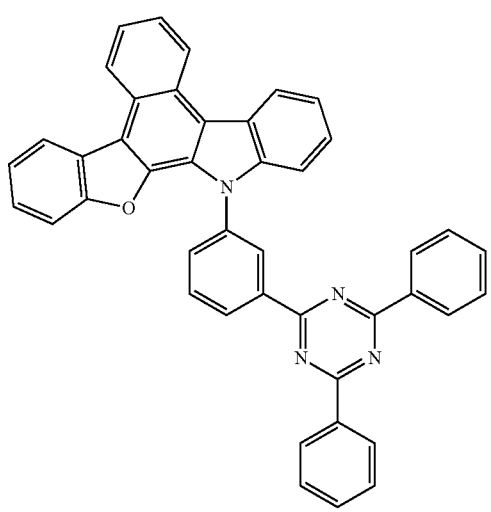

H2-493

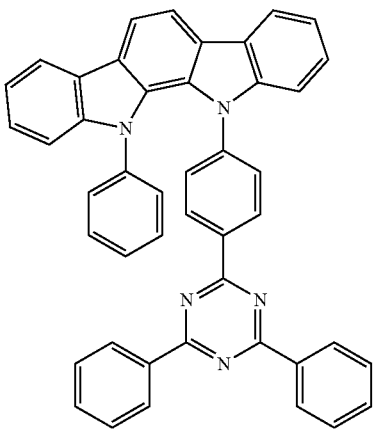

H2-494

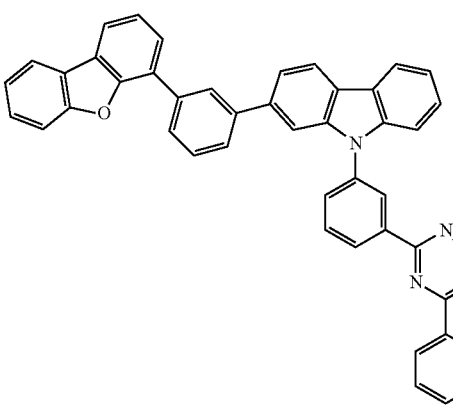

H2-495

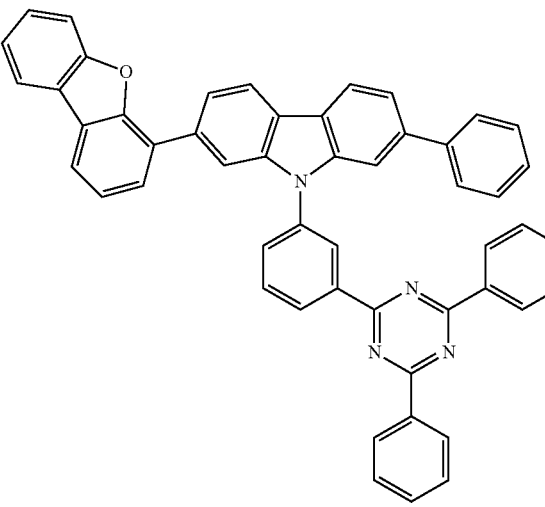

The organic electroluminescent device according to the present invention comprises an anode, a cathode, and at least one organic layer between the anode and the cathode. The organic layer comprises a light-emitting layer, and the light-emitting layer comprises a host and a phosphorescent dopant. The host material comprises plural host compounds, at least a first host compound of the plural host compounds is represented by formula 1, and a second host compound is represented by formula 2.

The light-emitting layer is a layer from which light is emitted, and can be a single layer or a multi-layer of which two or more layers are stacked. In the light-emitting layer, it is preferable that the doping concentration of the dopant compound based on the host compound is less than 20 wt %.

The organic layer comprises a light-emitting layer, and may further comprise at least one layer selected from the group consisting of a hole injection layer, a hole transport layer, an electron transport layer, an electron injection layer, an interlayer, a hole blocking layer, and an electron blocking layer.

According to the organic electroluminescent device of the present invention, the weight ratio of the first host material to the second host material is in the range of 1:99 to 99:1.

The dopant is preferably at least one phosphorescent dopant. The dopant materials applied to the organic electroluminescent device according to the present invention are not limited, but may be preferably selected from metallated complex compounds of iridium, osmium, copper, and platinum, more preferably selected from ortho-metallated complex compounds of iridium, osmium, copper and platinum, and even more preferably ortho-metallated iridium complex compounds.

The phosphorescent dopant is preferably selected from compounds represented by the following formulas 101 to 103.

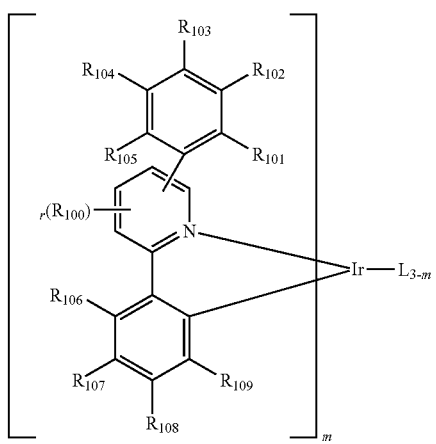

(101)

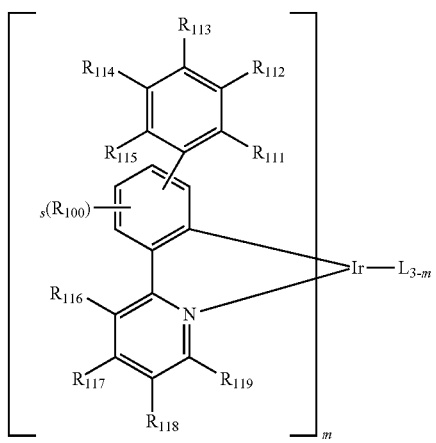

(102)

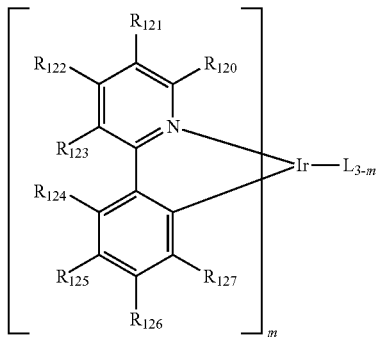

(103)

wherein L is selected from the following structures:

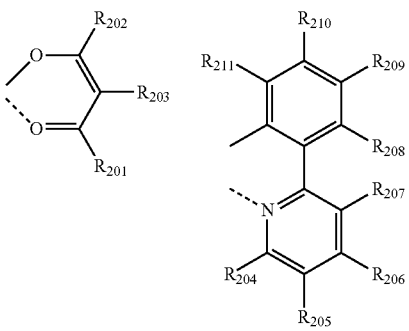

$R_{100}$ represents hydrogen, a substituted or unsubstituted (C1-C30)alkyl, or a substituted or unsubstituted (C3-C30) cycloalkyl;

$R_{101}$ to $R_{109}$, and $R_{111}$ to $R_{123}$ each independently represent hydrogen, deuterium, a halogen, a (C1-C30)alkyl unsubstituted or substituted with a halogen(s), a cyano, a substituted or unsubstituted (C1-C30)alkoxy, a substituted or unsubstituted (C6-C30)aryl, or a substituted or unsubstituted (C3-C30)cycloalkyl; adjacent substituents of $R_{106}$ to $R_{109}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl; and adjacent substituents of $R_{120}$ to $R_{123}$ may be linked to each other to form a substituted or unsubstituted fused ring, e.g., quinoline unsubstituted or substituted with halogen, alkyl, or aryl;

$R_{124}$ to $R_{127}$ each independently represent hydrogen, deuterium, a halogen, a substituted or unsubstituted (C1-C30) alkyl, or a substituted or unsubstituted (C6-C30)aryl; and adjacent substituents of $R_{124}$ to $R_{127}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

$R_{201}$ to $R_{211}$ each independently represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30) aryl; and adjacent substituents of $R_{208}$ to $R_{211}$ may be linked to each other to form a substituted or unsubstituted fused ring, e.g., fluorene unsubstituted or substituted with alkyl, dibenzothiophene unsubstituted or substituted with alkyl, or dibenzofuran unsubstituted or substituted with alkyl;

r and s each independently represent an integer of 1 to 3; where r or s is an integer of 2 or more, each of $R_{100}$ may be the same or different; and
m represents an integer of 1 to 3.
Specifically, the phosphorescent dopant materials include the following:
D-1
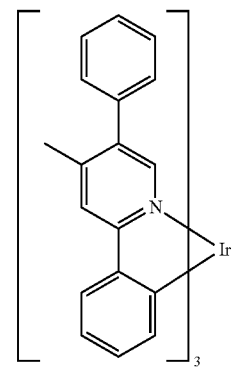
D-2
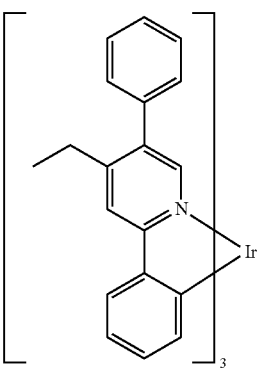
D-3
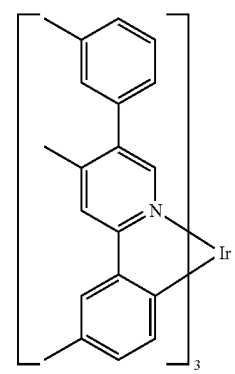
D-4
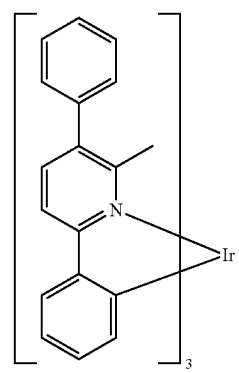
D-5
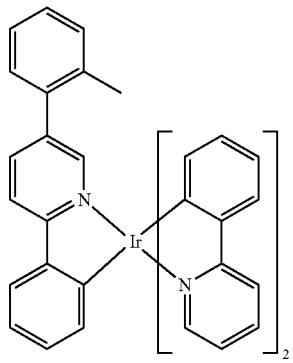
D-6
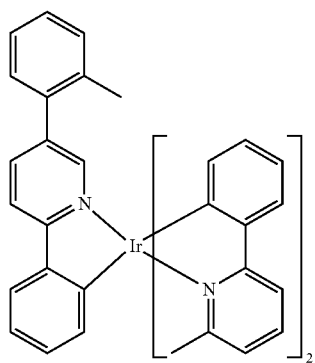
D-7
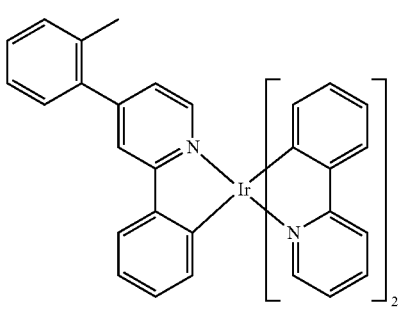
D-8
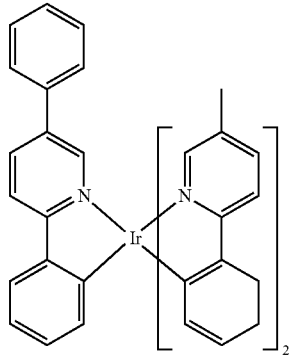

D-9
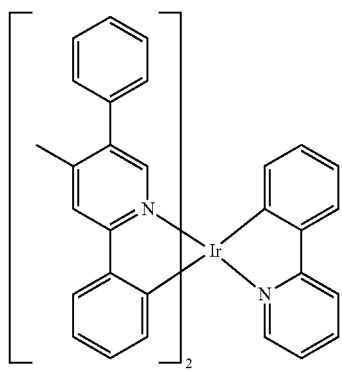
D-10
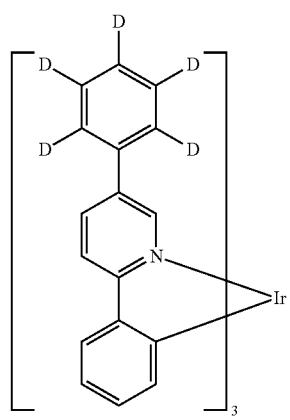
D-11
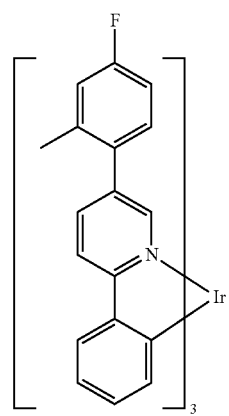
D-12
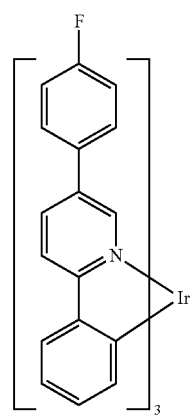
D-13
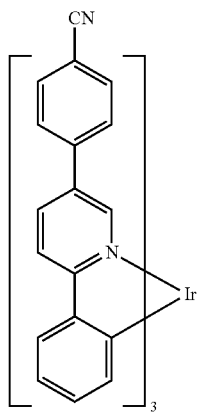
D-14
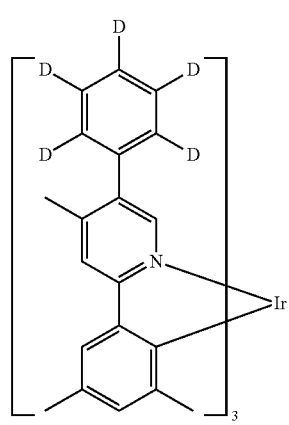
D-15
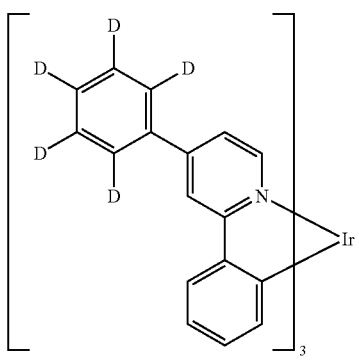
D-16
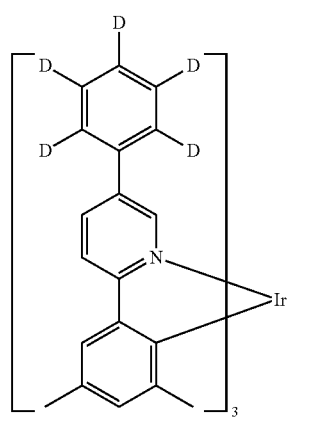

549
-continued
D-17
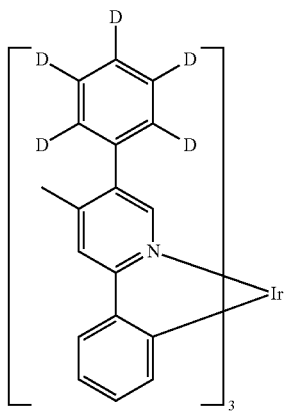
D-18
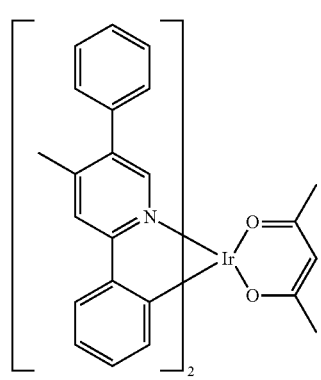
D-19
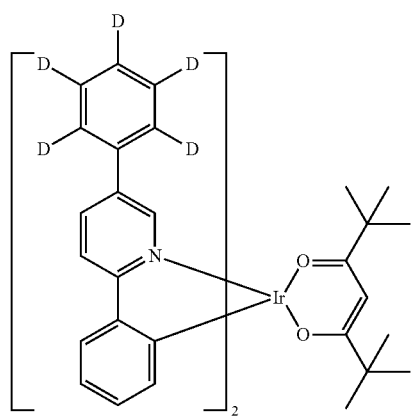
D-20
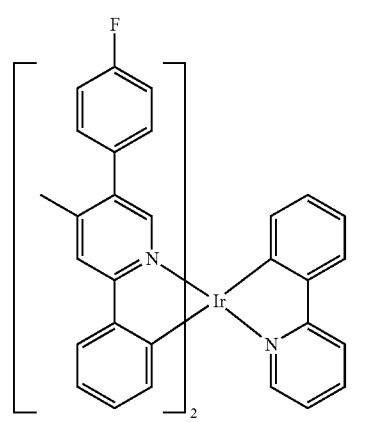
550
-continued
D-21
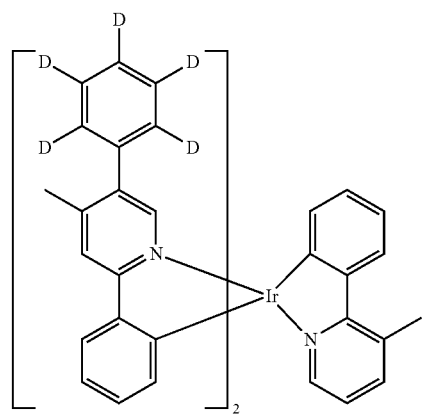
D-22
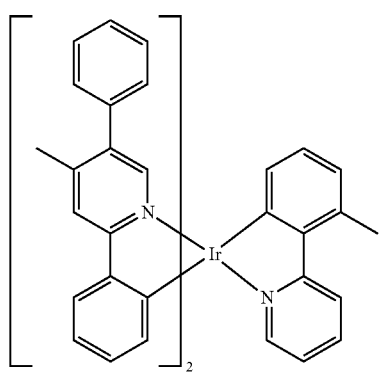
D-23
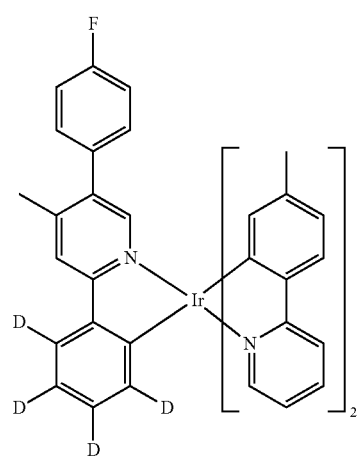

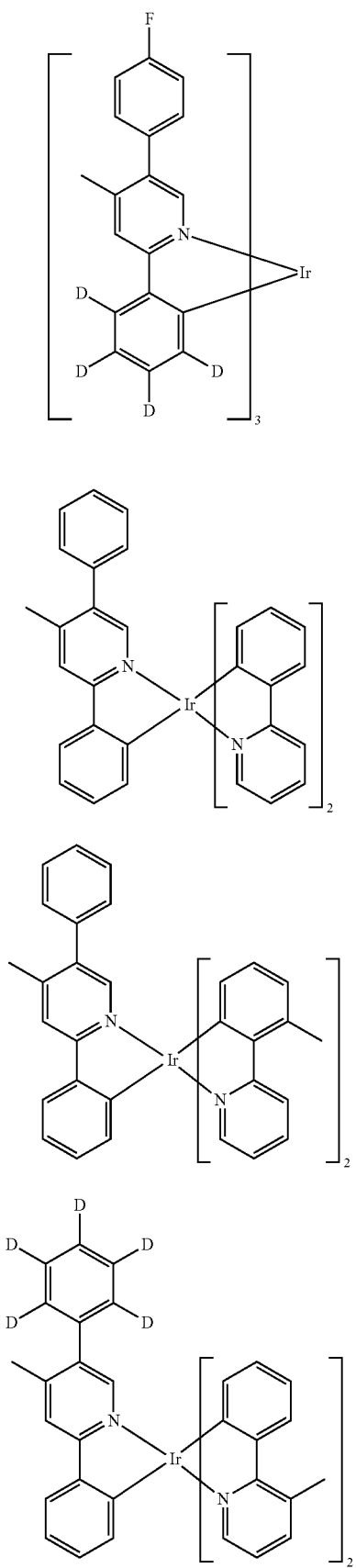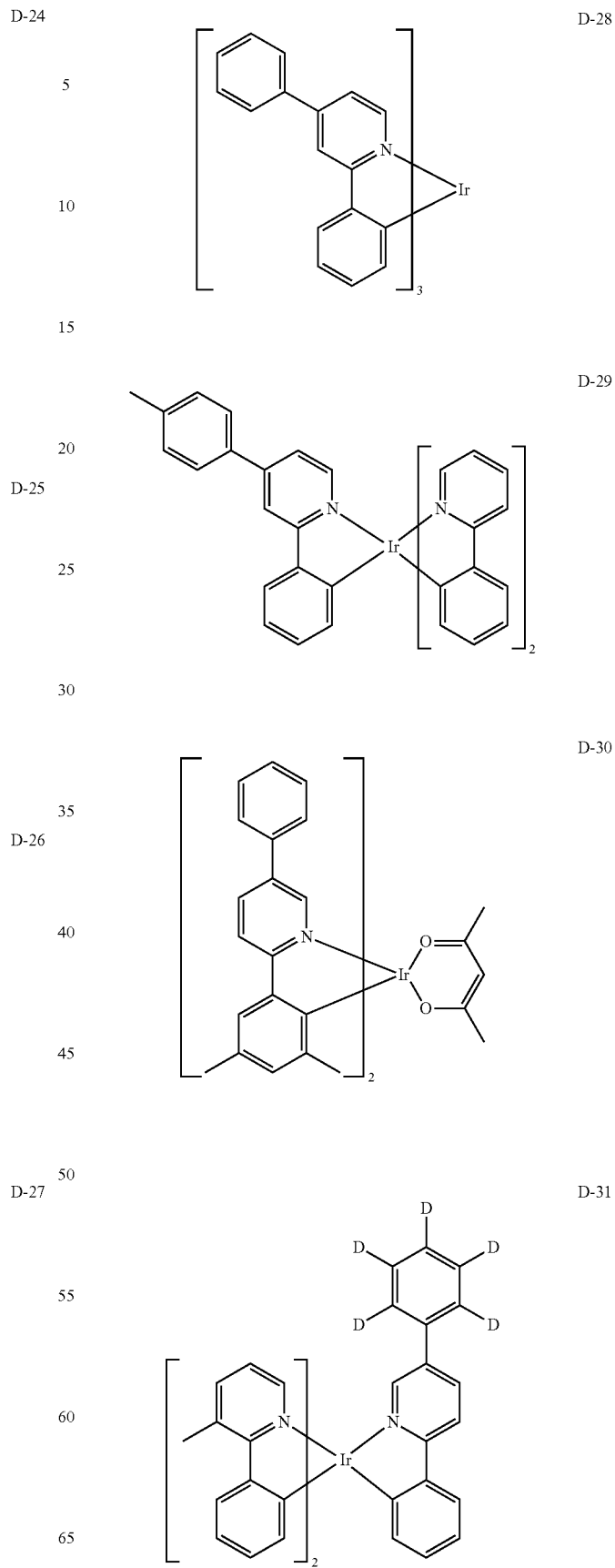

D-32
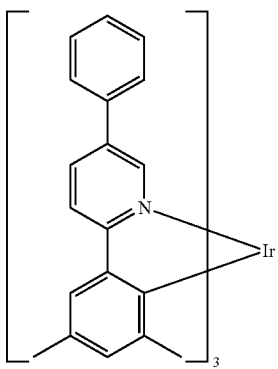
D-36
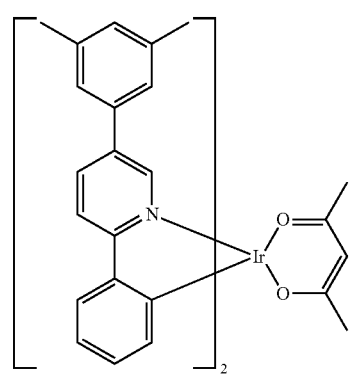
D-33
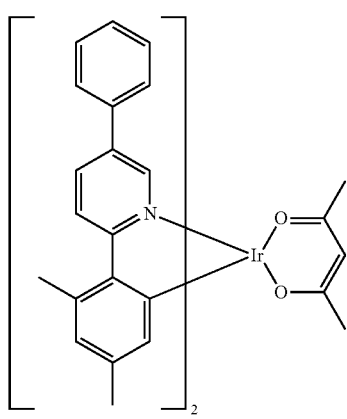
D-37
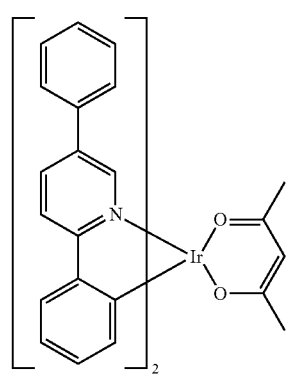
D-34
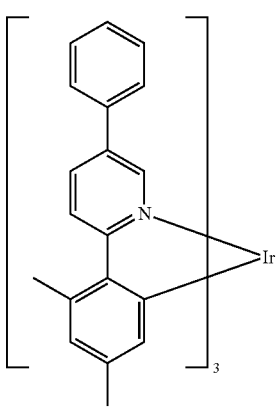
D-38
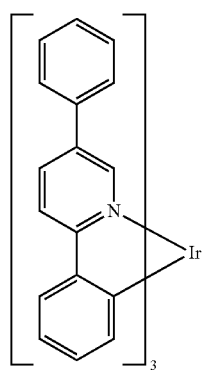
D-35
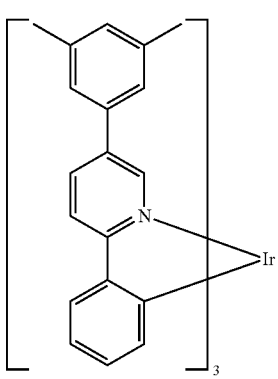
D-39
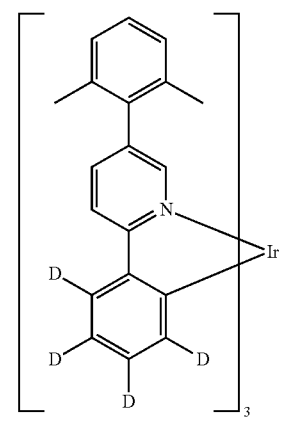

D-40
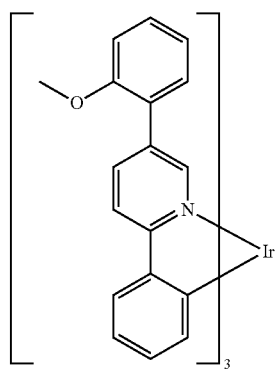
D-41
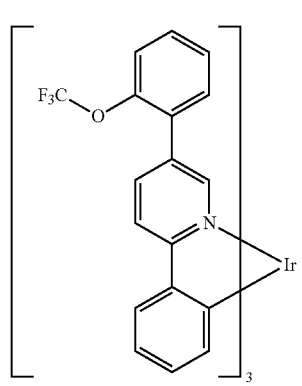
D-42
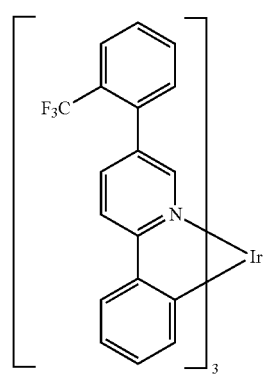
D-43
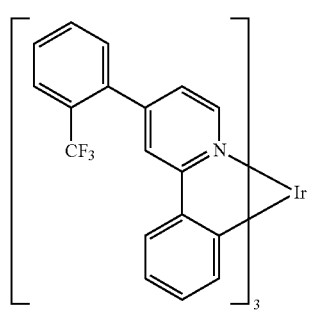
D-44
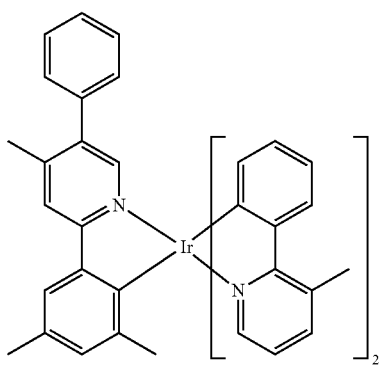
D-45
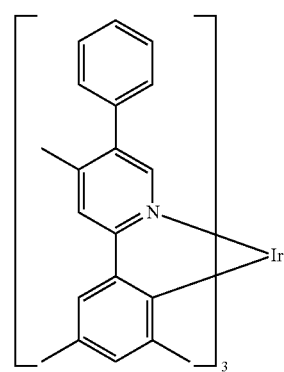
D-46
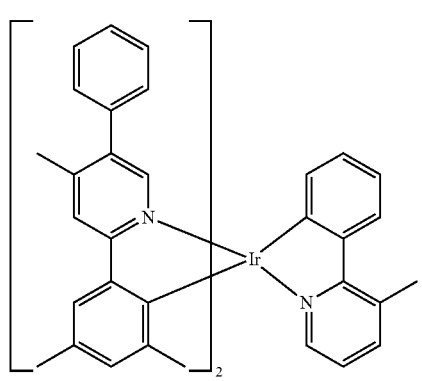
D-47
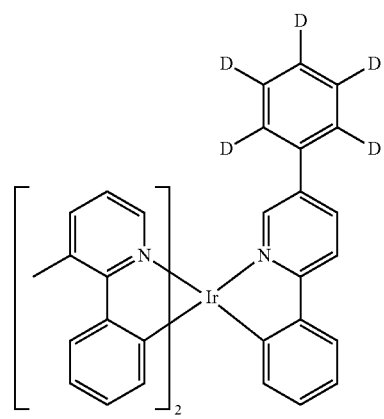

-continued
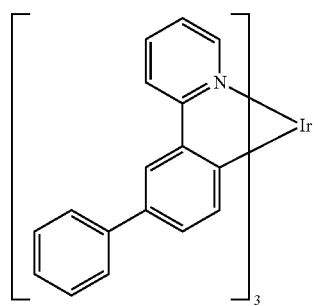
D-48
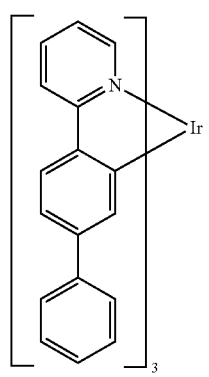
D-49
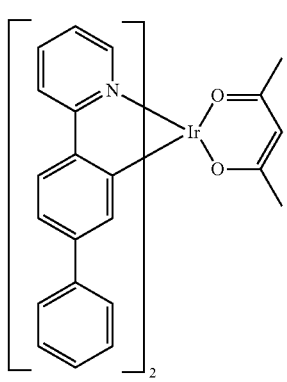
D-50
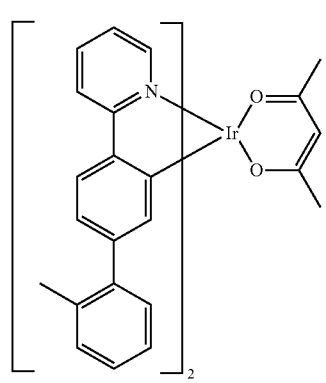
D-51
-continued
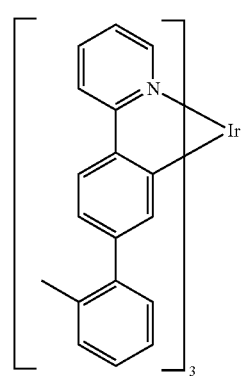
D-52
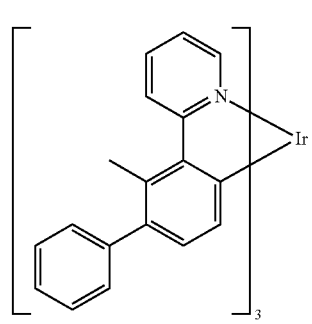
D-53
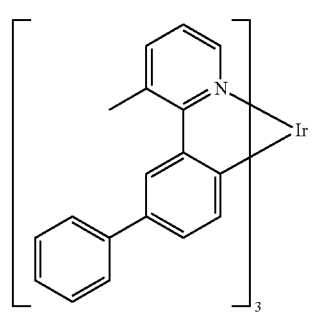
D-54
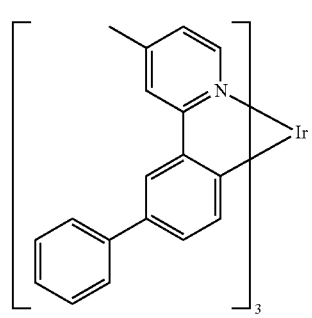
D-55
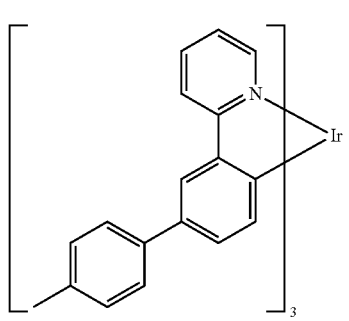
D-56

-continued
D-57
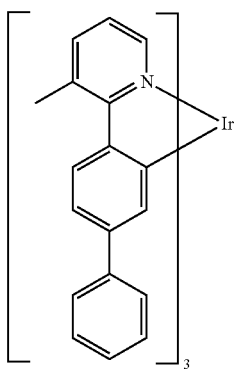
D-58
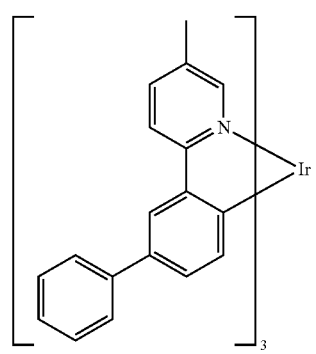
D-59
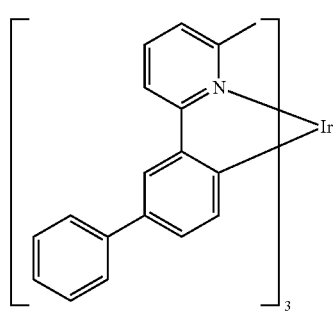
D-60
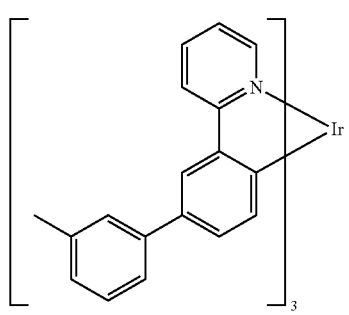
-continued
D-61
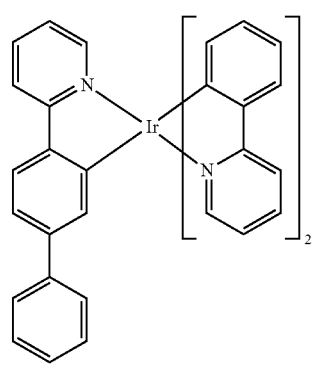
D-62
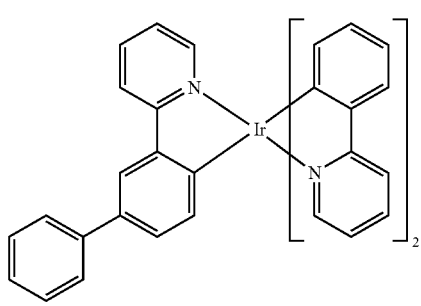
D-63
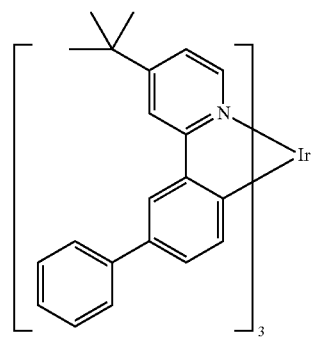
D-64
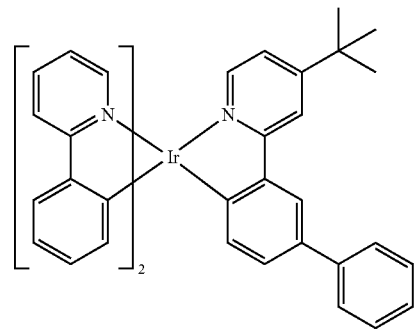

D-65
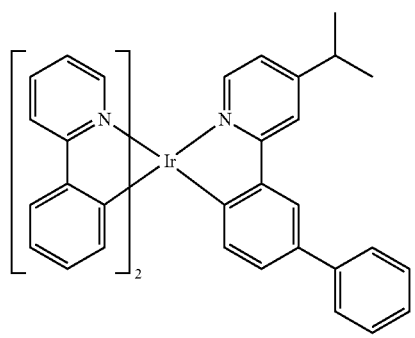
D-66
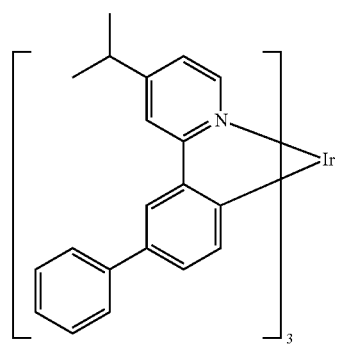
D-67
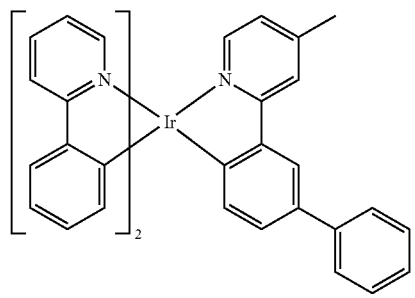
D-68
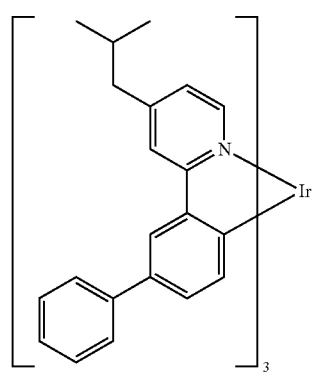
D-69
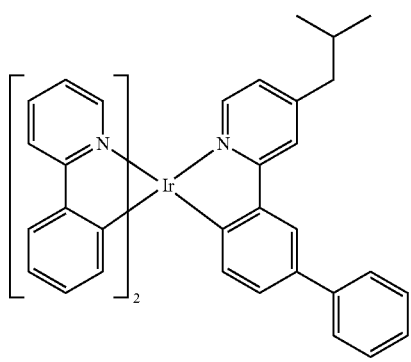
D-70
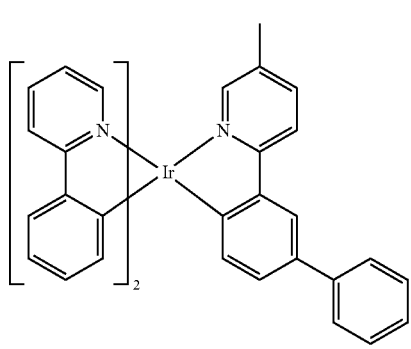
D-71
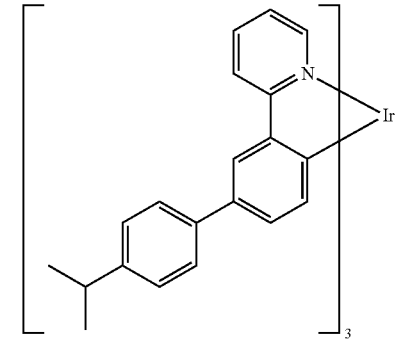
D-72
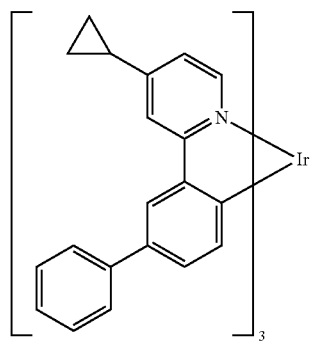

D-73 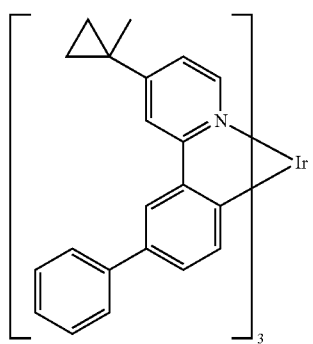
D-74 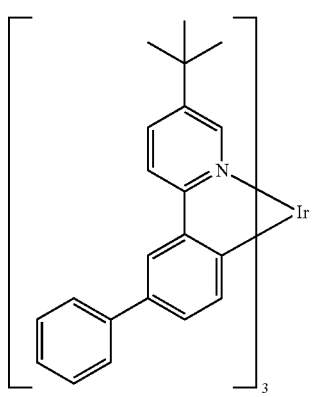
D-75 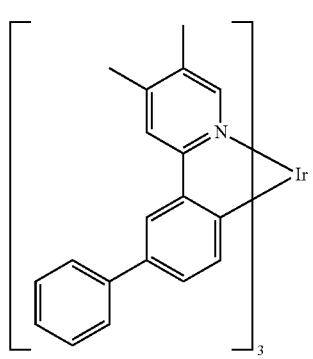
D-76 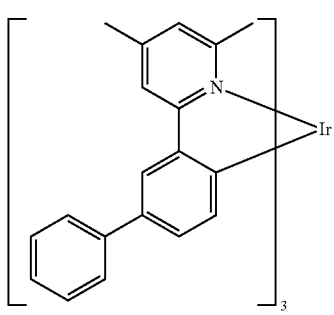
D-77 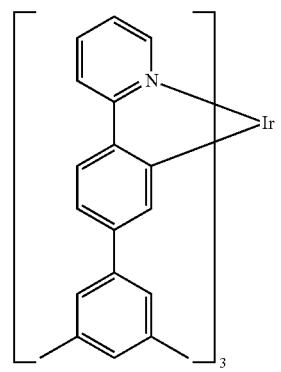
D-78 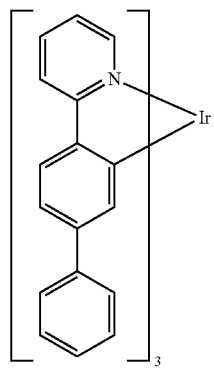
D-79 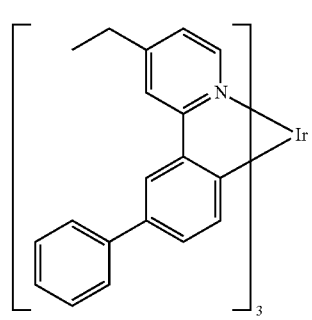
D-80 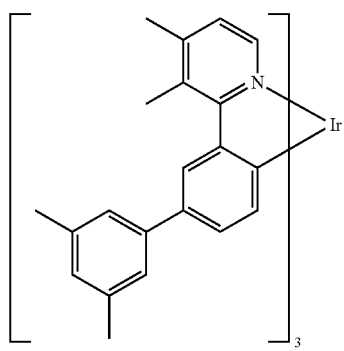

D-81
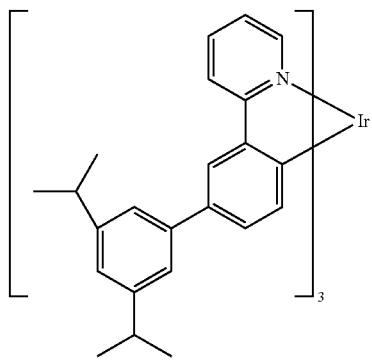
D-82
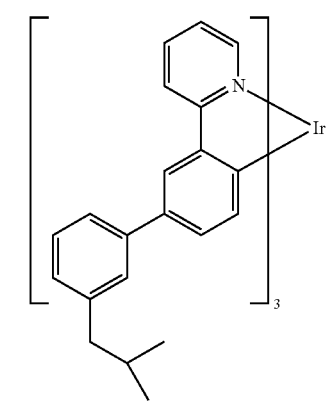
D-83
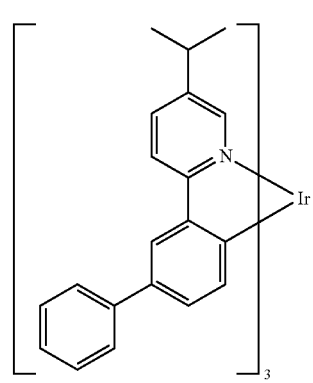
D-84
D-85
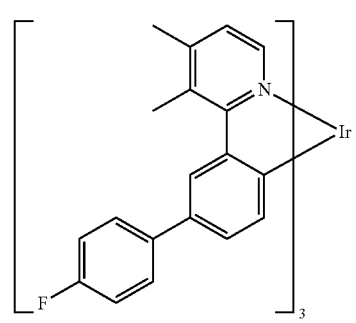
D-86
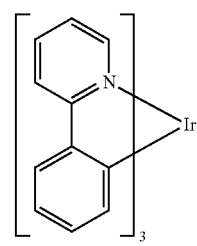
D-87
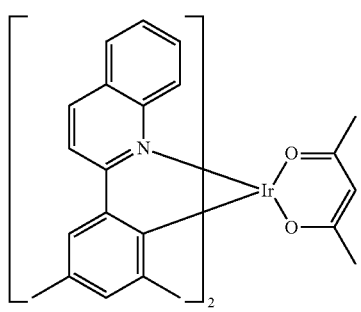
D-88
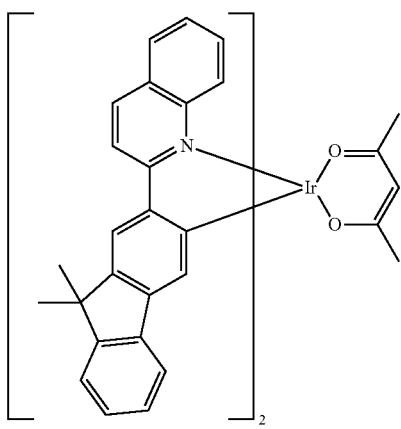
D-89
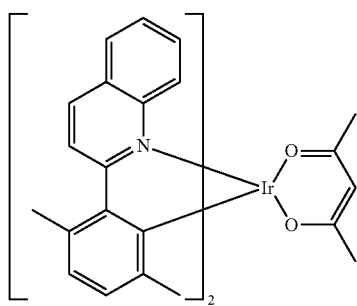

-continued
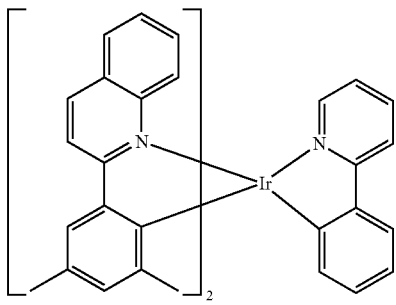
D-90
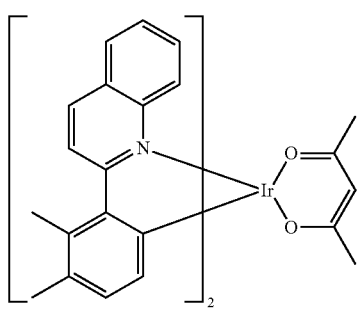
D-91
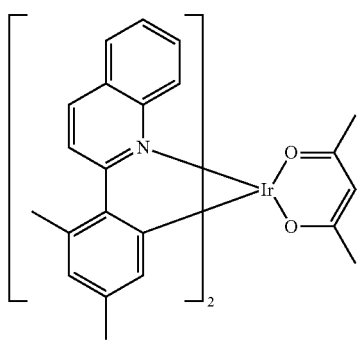
D-92
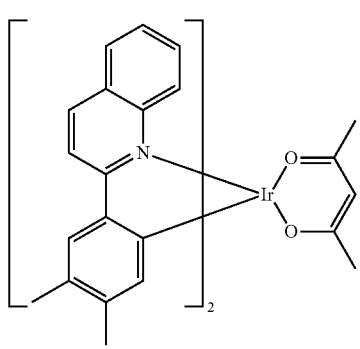
D-93
-continued
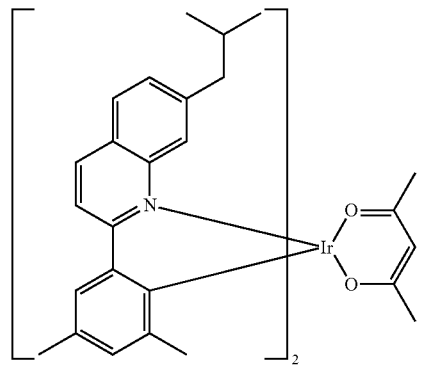
D-94
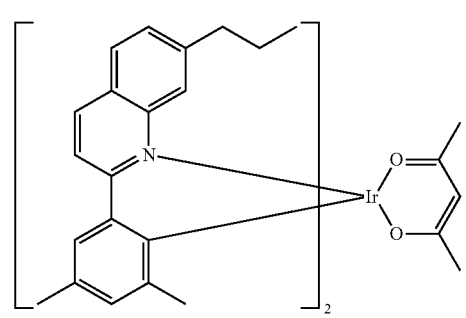
D-95
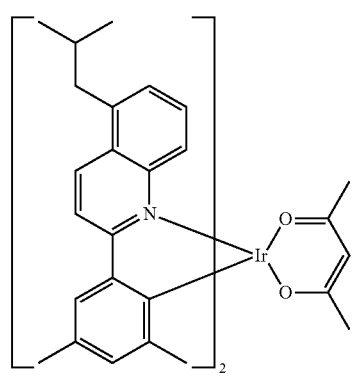
D-96
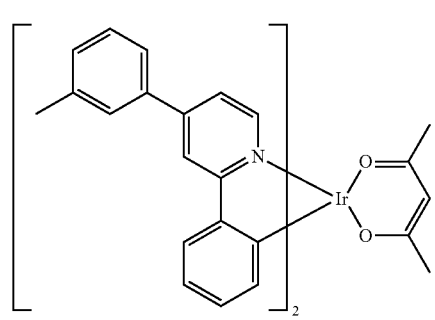
D-97

D-98
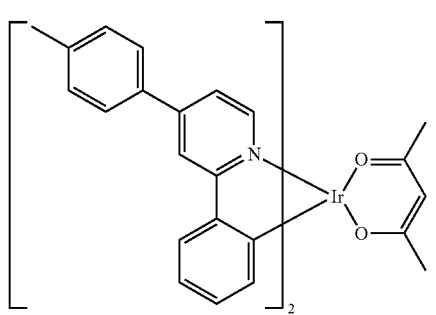
D-99
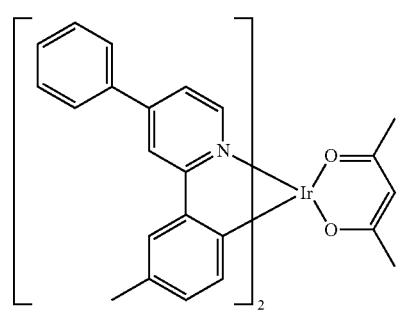
D-100
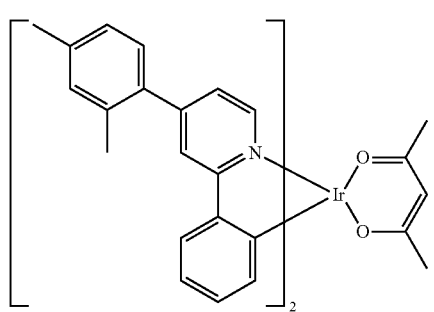
D-101
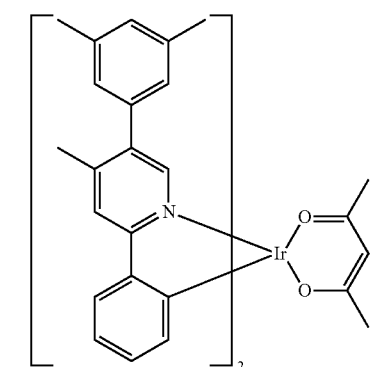
D-102
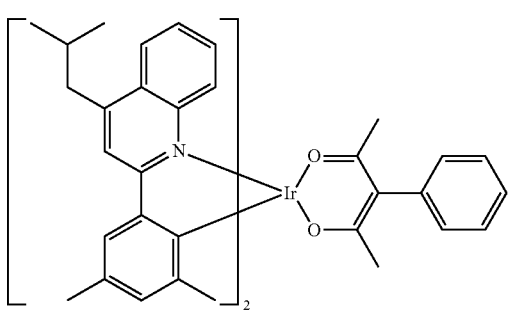
D-103
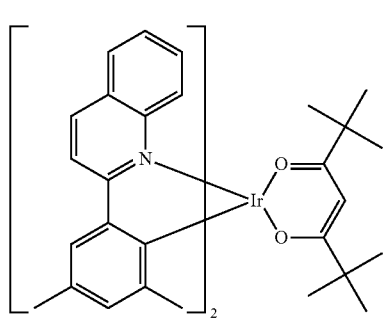
D-104
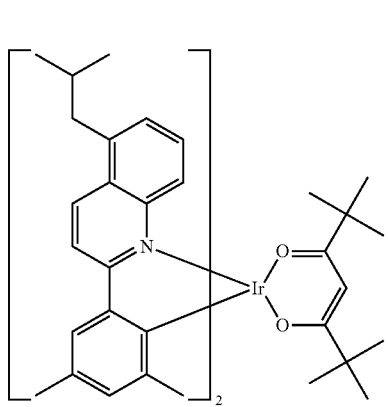
D-105
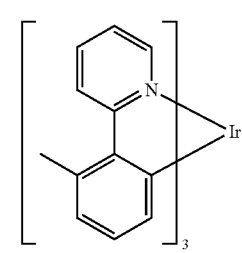
D-106
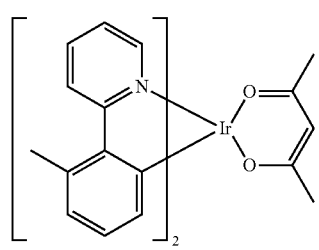
D-107
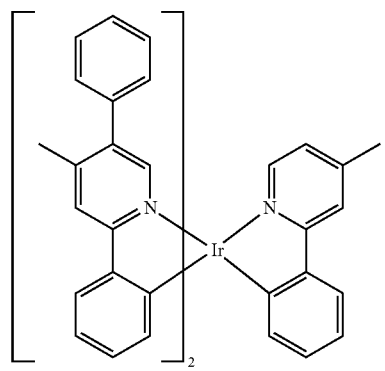

D-108
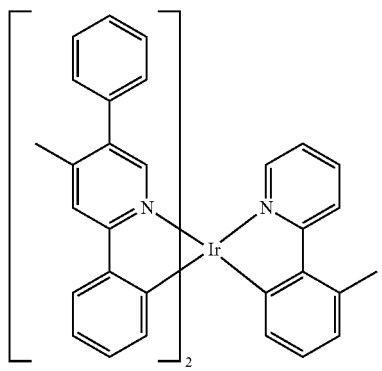
D-109
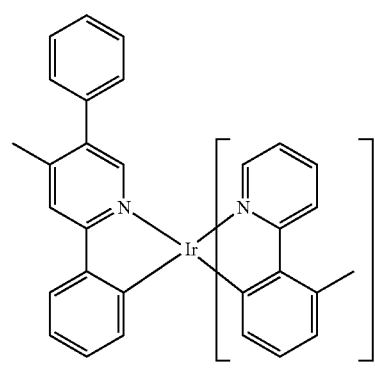
D-110
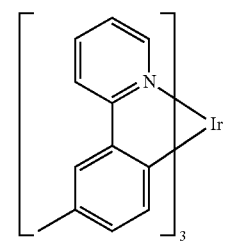
D-111
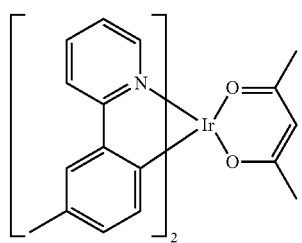
D-112
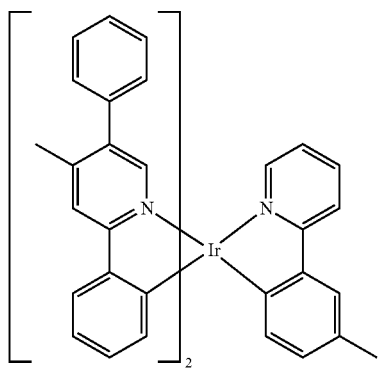
D-113
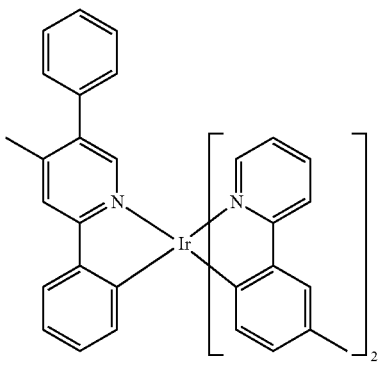
D-114
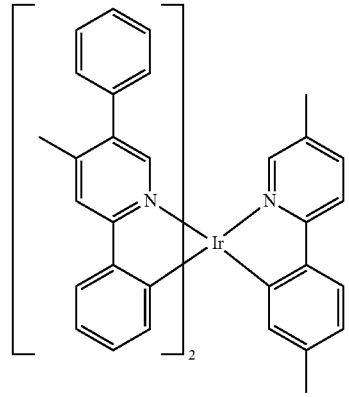
D-115
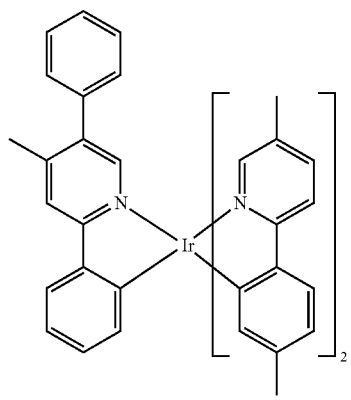
D-116
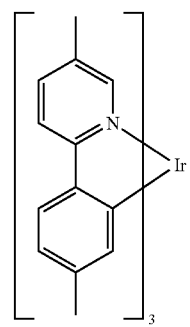

D-117
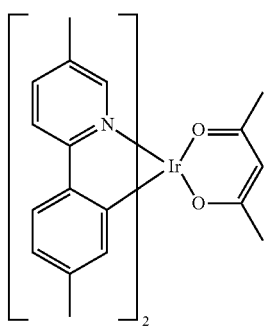
D-118
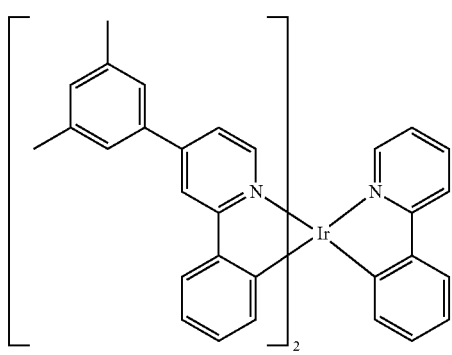
D-119
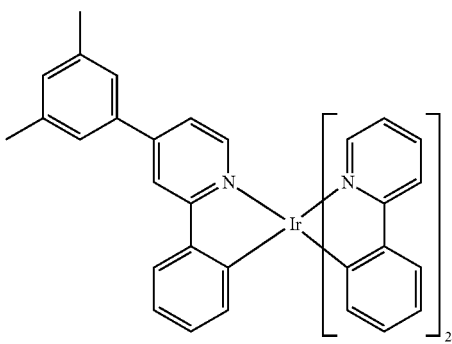
D-120
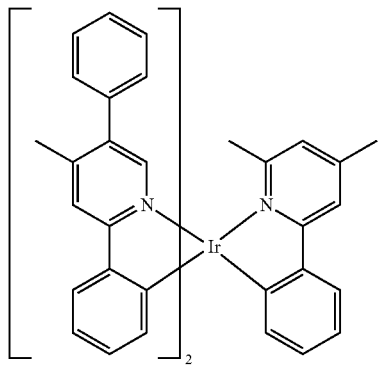
D-121
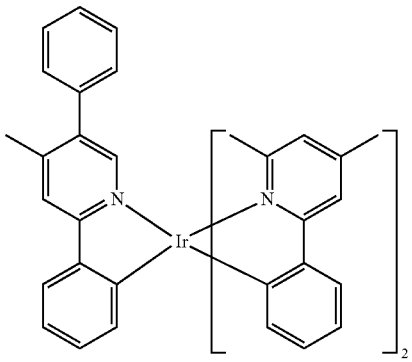
D-122
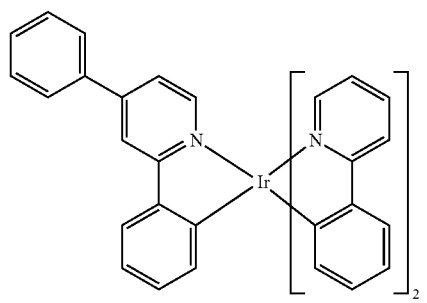
D-123
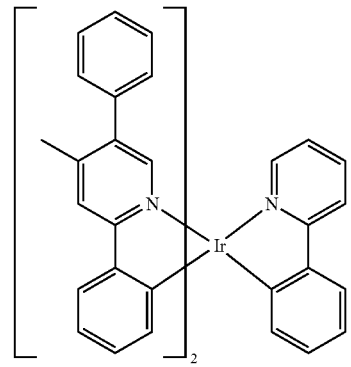
D-124
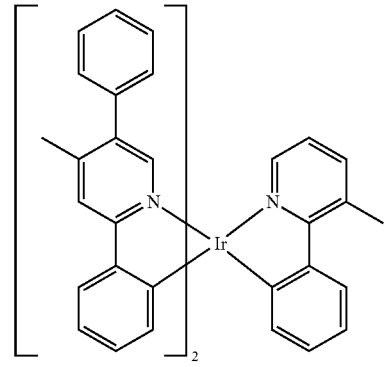

D-125
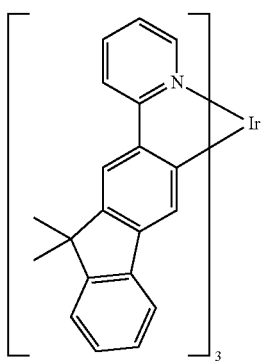
D-126
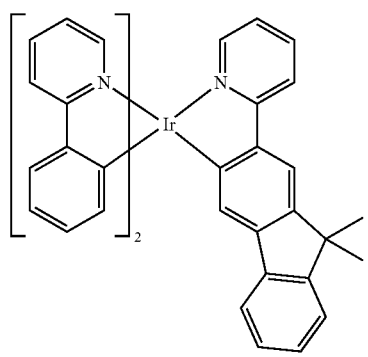
D-127
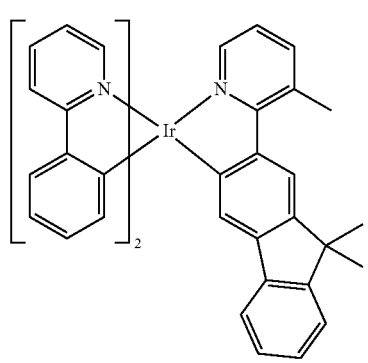
D-128
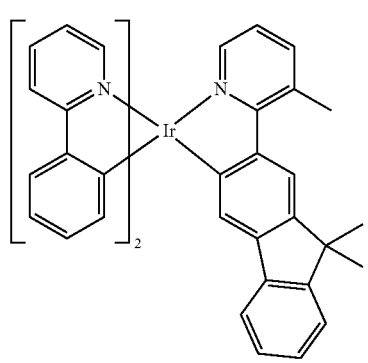
D-129
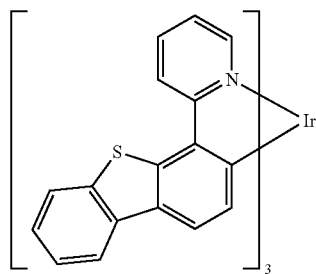
D-130
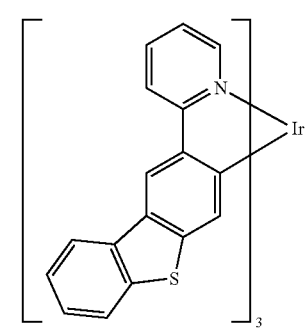
D-131
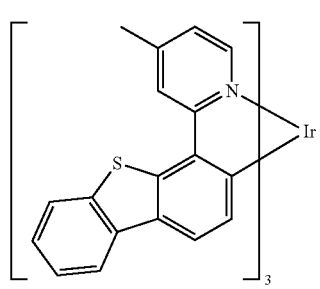
D-132
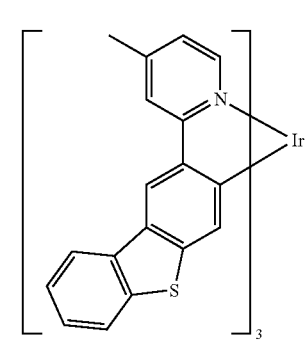
D-133
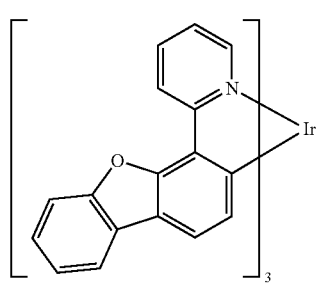

D-134 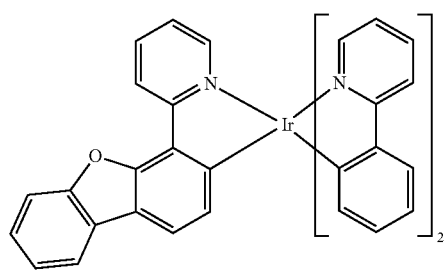
D-135 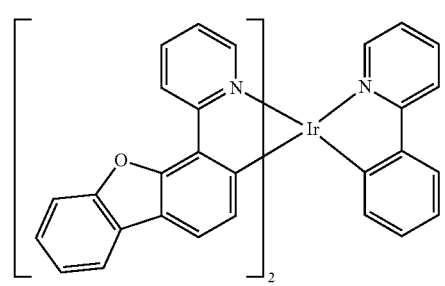
D-136 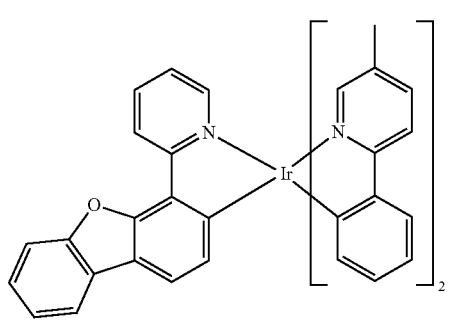
D-137 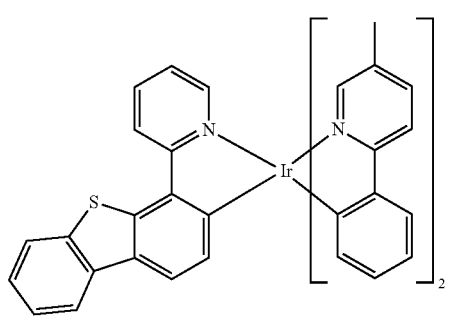
D-138 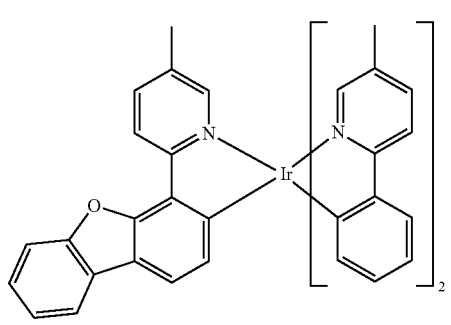
D-139 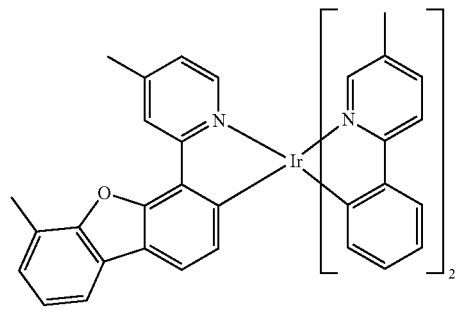
D-140 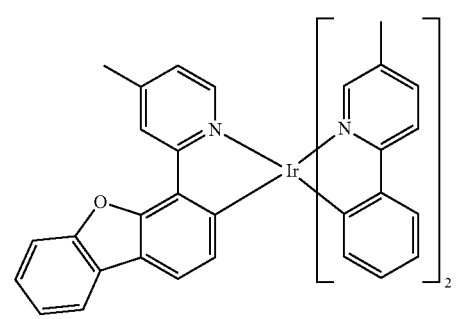
D-141 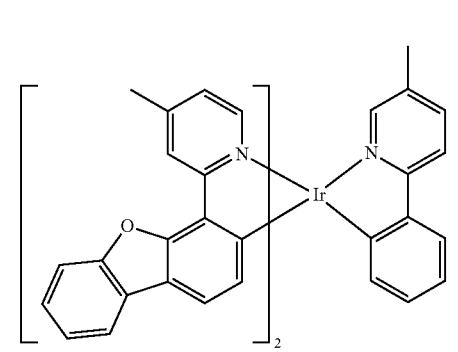
D-142 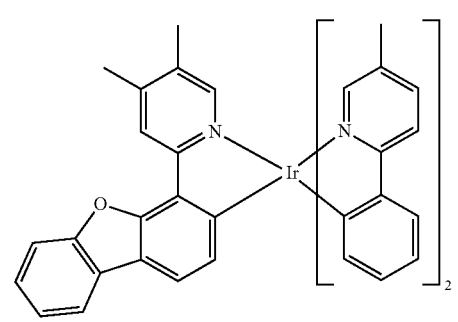
D-143 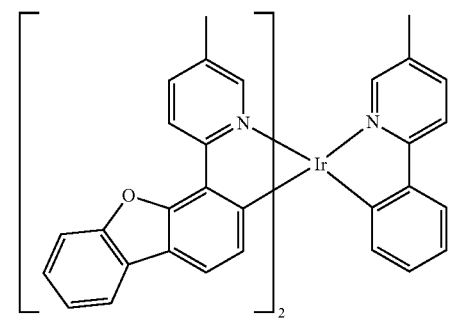

D-144
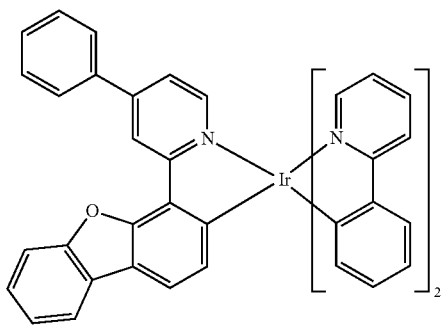
D-145
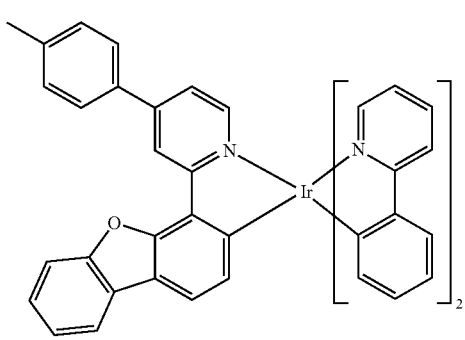
D-146
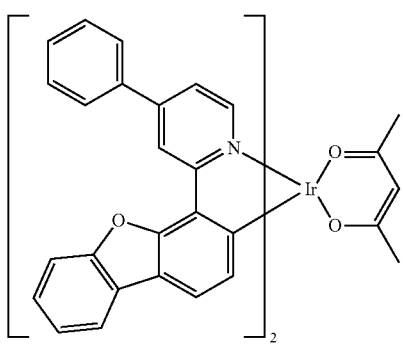
D-147
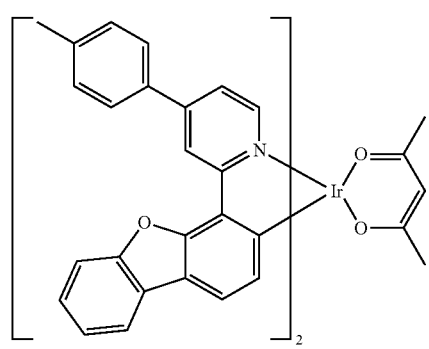
D-148
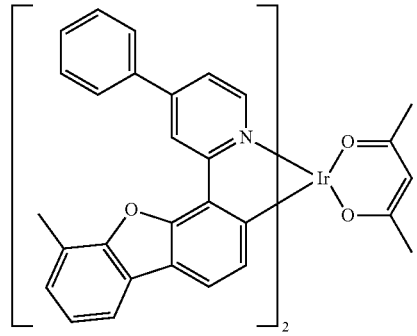
D-149
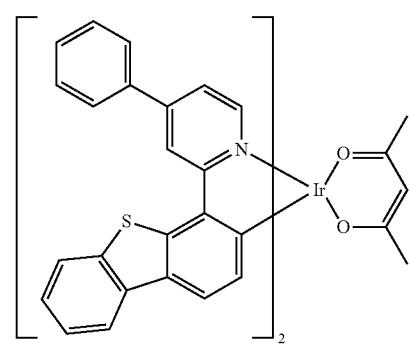
D-150
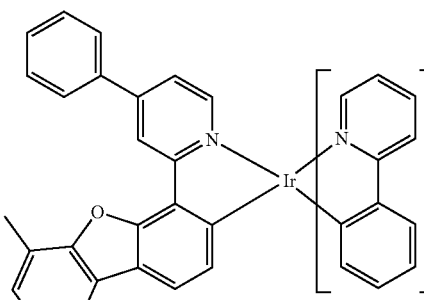
D-151
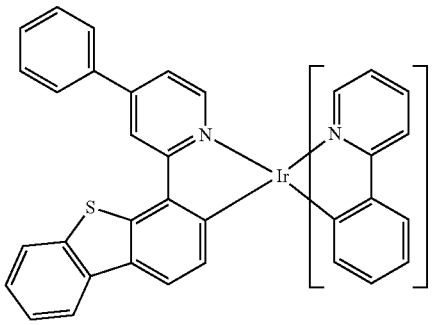
D-152
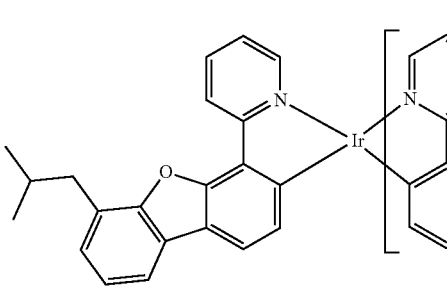

D-153
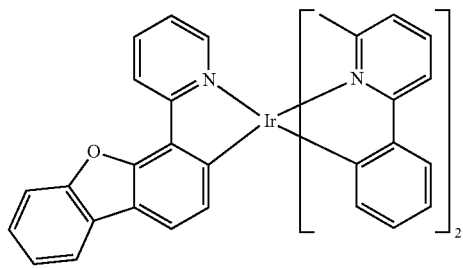
D-154
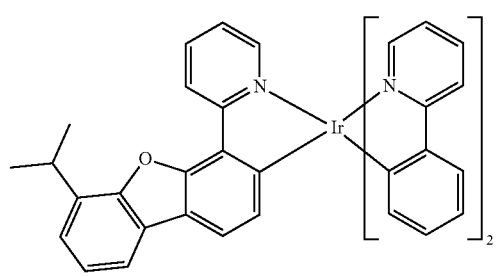
D-155
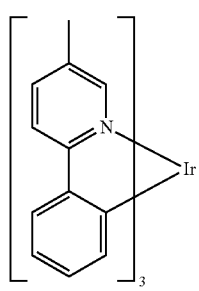
D-156
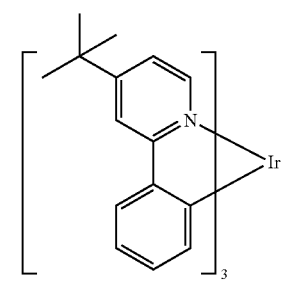
D-157
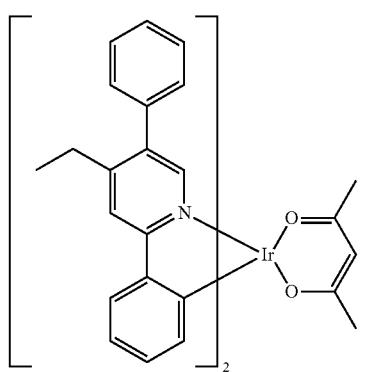
D-158
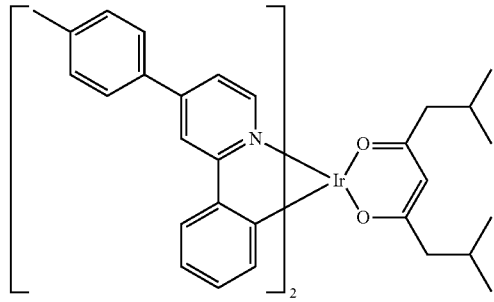
D-159
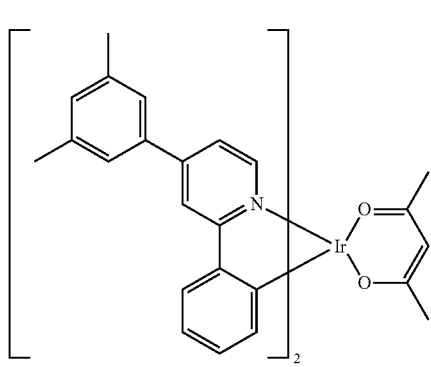
D-160
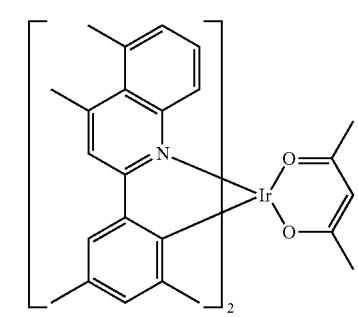
D-161
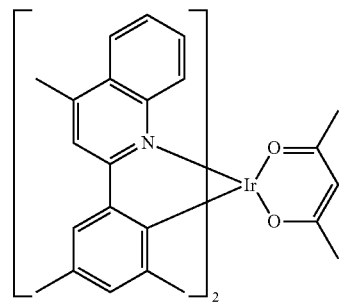
D-162
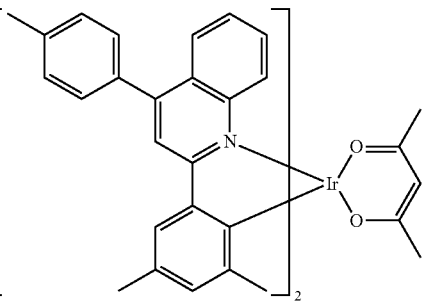

D-163
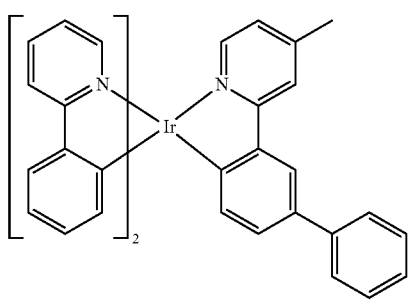
D-164
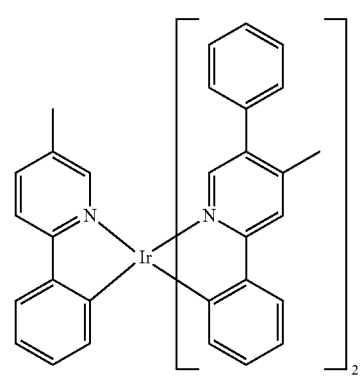
D-165
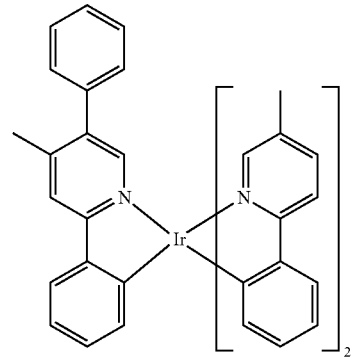
D-166
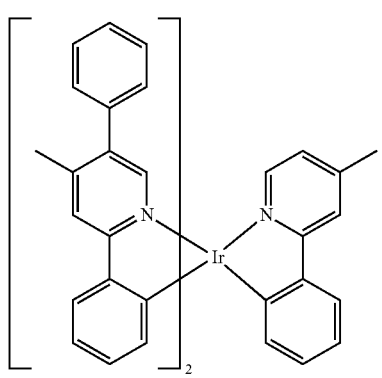
D-167
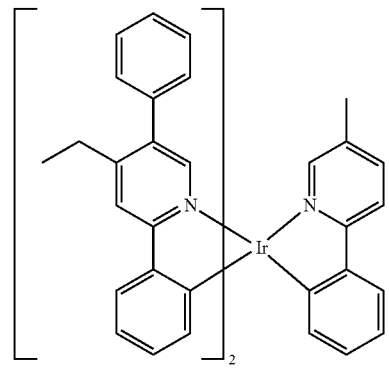
D-168
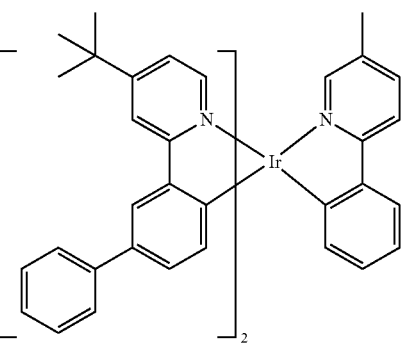
D-169
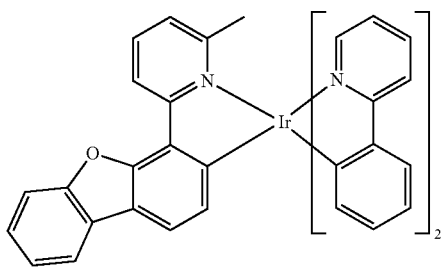
D-170
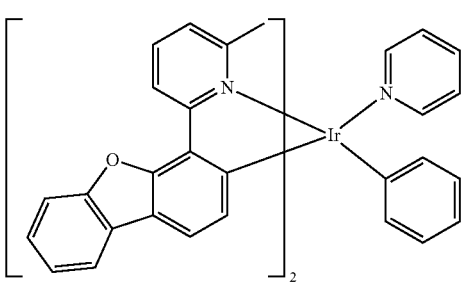
D-171

D-172
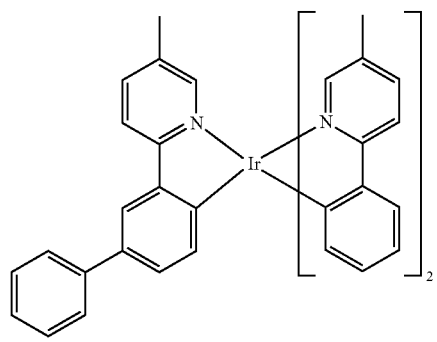
D-173
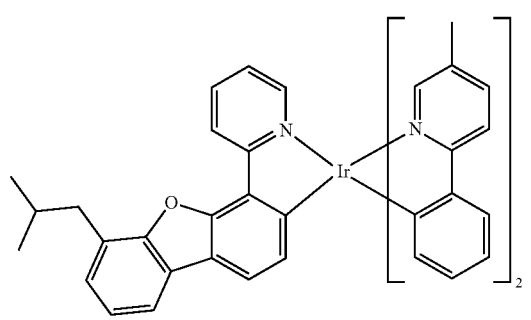
D-174
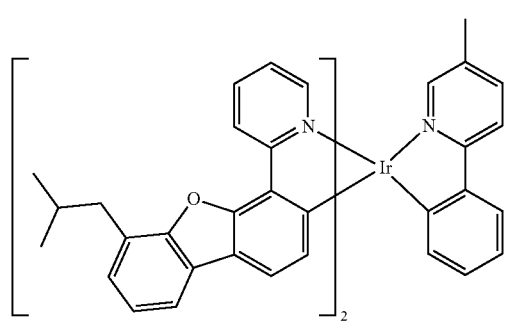
D-175
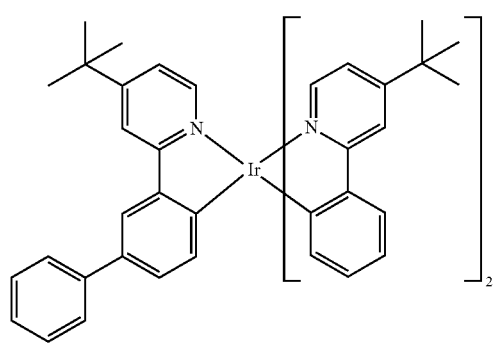
D-176
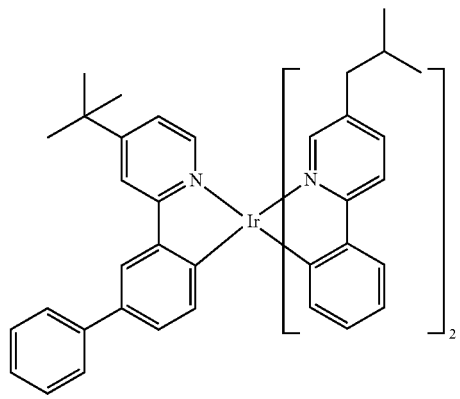
D-177
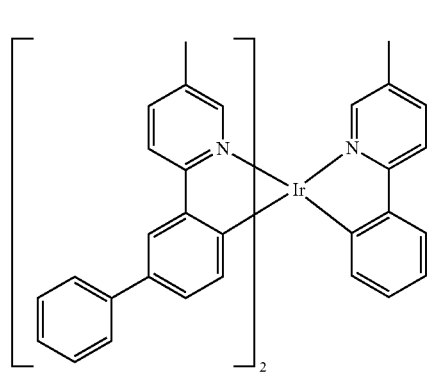
D-178
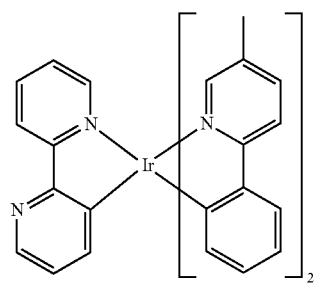
D-179
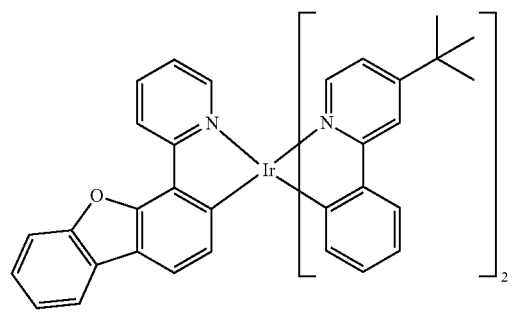

D-180
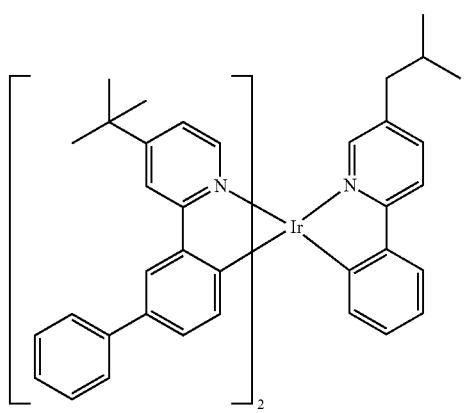
D-181
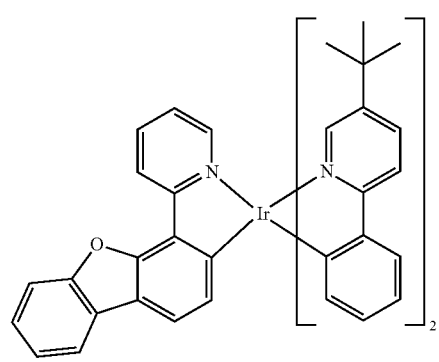
D-182
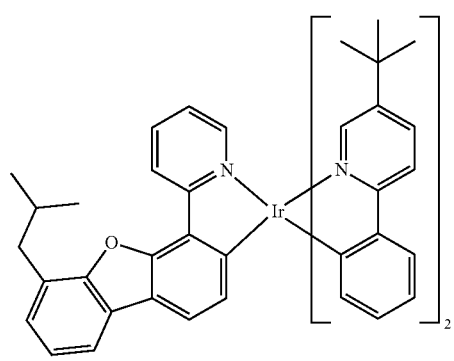
D-183
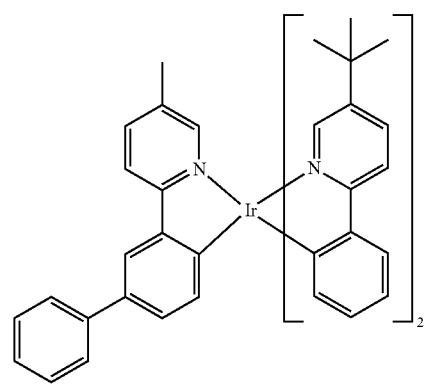
D-184
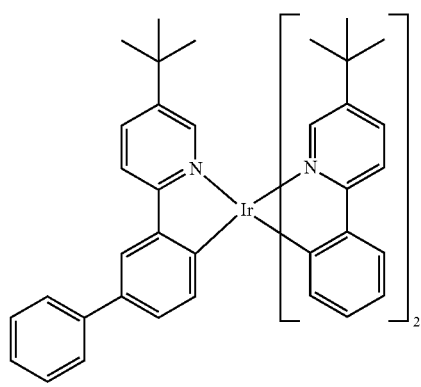
D-185
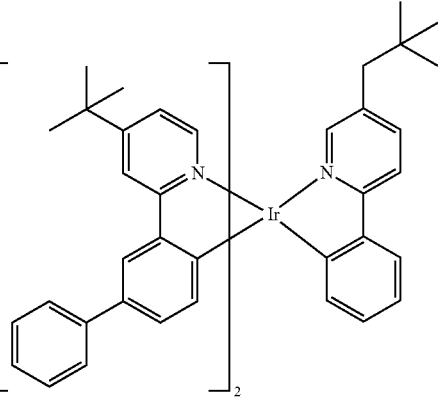
D-186
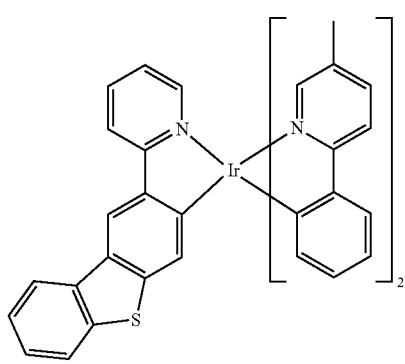
D-187
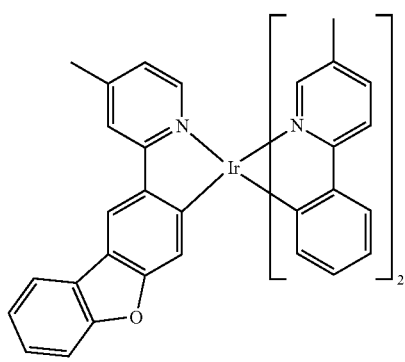

-continued
D-188
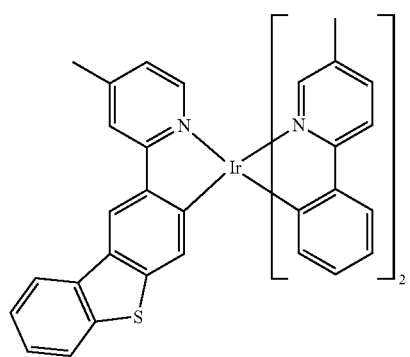
D-189
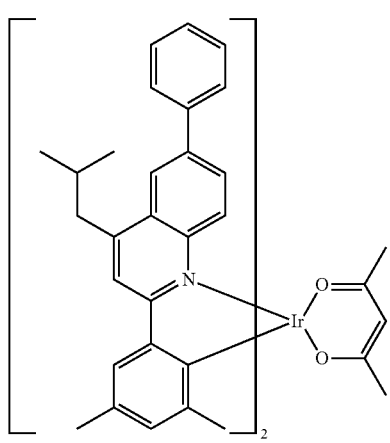
D-190
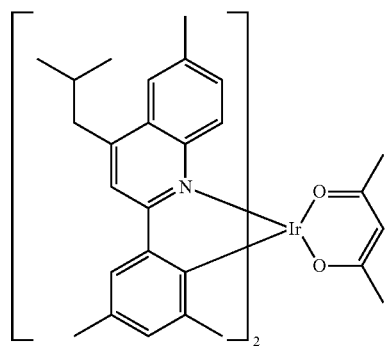
D-191
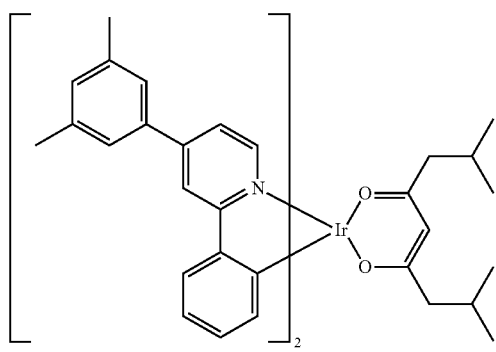
-continued
D-192
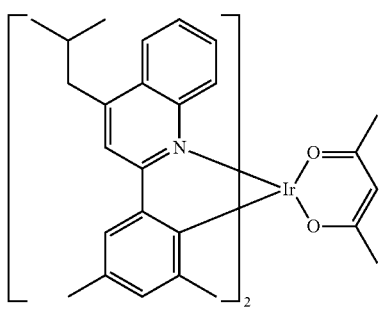
D-193
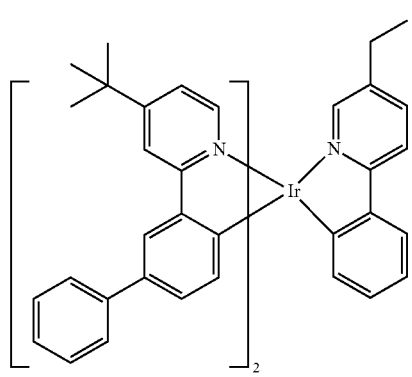
D-194
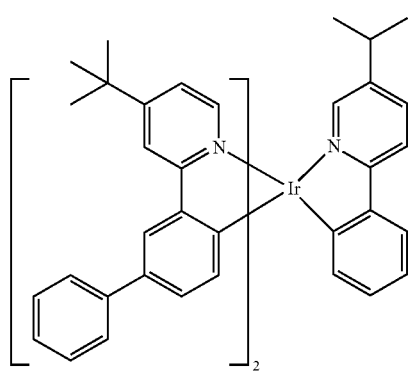
D-195
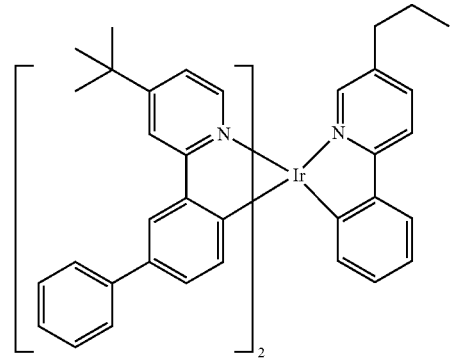

-continued

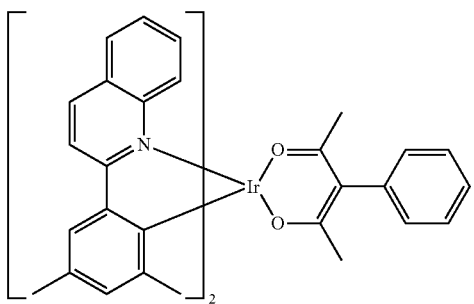
D-196

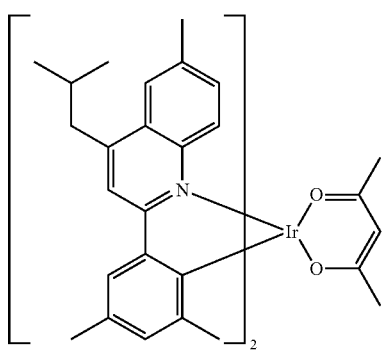
D-197

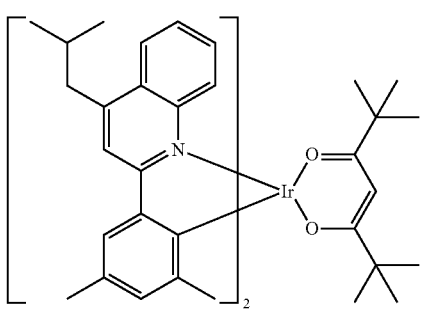
D-198

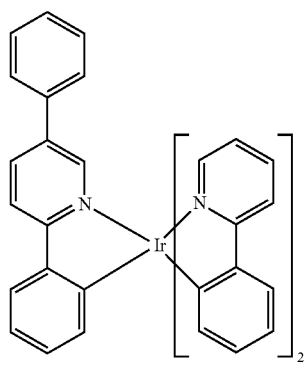
D-199

The organic electroluminescent device according to the present invention may further comprise at least one compound selected from the group consisting of arylamine-based compounds and styrylarylamine-based compounds in the organic layer.

In addition, in the organic electroluminescent device according to the present invention, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

According to the present invention, at least one layer (hereinafter, "a surface layer") is preferably placed on an inner surface(s) of one or both electrodes; selected from a chalcogenide layer, a metal halide layer and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x(1≤X≤2)$, $AlO_x(1≤X≤1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Between the anode and the light-emitting layer, a hole injection layer, a hole transport layer, an electron blocking layer, or a combination thereof can be used. Multi-layers can be used for the hole injection layer in order to lower the hole injection barrier (or hole injection voltage) from the anode to the hole transport layer or the electron blocking layer. Two compounds can be simultaneously used in each layer. The hole transport layer and the electron blocking layer can also be formed of multi-layers.

Between the light-emitting layer and the cathode, a layer selected from an electron buffer layer, a hole blocking layer, an electron transport layer, or an electron injection layer, or formed by a combination thereof can be used. Multi-layers can be used for the electron buffer layer in order to control the injection of the electrons and enhance the interfacial characteristics between the light-emitting layer and the electron injection layer. Two compounds can be simultaneously used in each layer. The hole blocking layer and the electron transport layer can also be formed of multi-layers, and each layer can comprise two or more compounds.

In the organic electroluminescent device according to the present invention, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an electroluminescent device having two or more electroluminescent layers and emitting white light.

In order to form each layer of the organic electroluminescent device of the present invention, dry film-forming methods such as vacuum evaporation, sputtering, plasma and ion plating methods, or wet film-forming methods such as ink jet printing, nozzle printing, slot coating, spin coating, dip coating, and flow coating methods can be used. The first and second host compounds of the present invention may be co-evaporated or mixture-evaporated.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Herein, a co-evaporation indicates a process for two or more materials to be deposited as a mixture, by introducing each of the two or more materials into respective crucible cells, and applying an electric current to the cells for each of the materials to be evaporated. Herein, a mixture-evaporation indicates a process for two or more materials to be deposited as a mixture, by mixing the two or more materials in one crucible cell before the deposition, and applying an electric current to the cell for the mixture to be evaporated.

By using the organic electroluminescent device of the present invention, a display system or a lighting system can be produced.

Hereinafter, the luminescent properties of the device comprising the host compound of the present invention will be explained in detail with reference to the following examples.

Device Examples 1-1 to 1-2: Preparation of an OLED Device Wherein the First Host Compound and the Second Host Compound of the Present Invention are Co-Evaporated An OLED device was produced using the organic electroluminescent compound according to the present invention. A transparent electrode indium tin oxide (ITO) thin film (10 Ω/sq) on a glass substrate for an organic light-emitting diode (OLED) device (Geomatec) was subjected to an ultrasonic washing with acetone, ethanol, and distilled water, sequentially, and then was stored in isopropanol. The ITO substrate was then mounted on a substrate holder of a vacuum vapor depositing apparatus. $N^4,N^{4'}$-diphenyl-$N^4$, $N^{4'}$-bis(9-phenyl-9H-carbazol-3-yl)-[1,1'-biphenyl]-4,4'-diamine (compound HI-1) was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. Next, 1,4,5,8,9,12-hexaazatriphenylene-hexacarbonitrile (compound HI-2) was introduced into another cell of said vacuum vapor depositing apparatus, and was evaporated by applying an electric current to the cell, thereby forming a second hole injection layer having a thickness of 3 nm on the first hole injection layer. N-([1,1'-biphenyl]-4-yl)-9,9-dimethyl-N-(4-(9-phenyl-9H-carbazol-3-yl)phenyl)-9H-fluorene-2-amine (compound HT-1) was then introduced into another cell of said vacuum vapor depositing apparatus, and was evaporated by applying an electric current to the cell, thereby forming a first hole transport layer having a thickness of 10 nm on the second hole injection layer. N-([1,1'-biphenyl]-4-yl)-N-(4-(9-(dibenzo[b,d]furan-4-yl)-9H-fluoren-9-yl)phenyl)-[1,1'-biphenyl]-4-amine (compound HT-2) was then introduced into another cell of said vacuum vapor depositing apparatus, and was evaporated by applying an electric current to the cell, thereby forming a second hole transport layer having a thickness of 30 nm on the first hole transport layer. Compound F-13 or F-31 and compound H2-125 were introduced into two cells of said vacuum vapor depositing apparatus as hosts, and compound D-136 was introduced into another cell as a dopant. The two host materials were evaporated at the same rate of 1:1, while the dopant was evaporated at a different rate from the host materials, so that the dopant was deposited in a doping amount of 15 wt % based on the total amount of the hosts and dopant to evaporate and form a light-emitting layer having a thickness of 40 nm on the second hole transport layer. 2,4-bis(9,9-dimethyl-9H-fluoren-2-yl)-6-(naphthalen-2-yl)-1,3,5-triazine (compound ET-1) and lithium quinolate (compound EI-1) were then introduced into two cells of the vacuum vapor depositing apparatus, respectively, and evaporated at a rate of 4:6 to form an electron transport layer having a thickness of 35 nm on the light-emitting layer. After depositing lithium quinolate (compound EI-1) as an electron injection layer having a thickness of 2 nm on the electron transport layer, an Al cathode having a thickness of 80 nm was deposited by another vacuum vapor deposition apparatus. Thus, an OLED device was produced. All the materials used for producing the OLED device were those purified by vacuum sublimation at $10^{-6}$ torr.

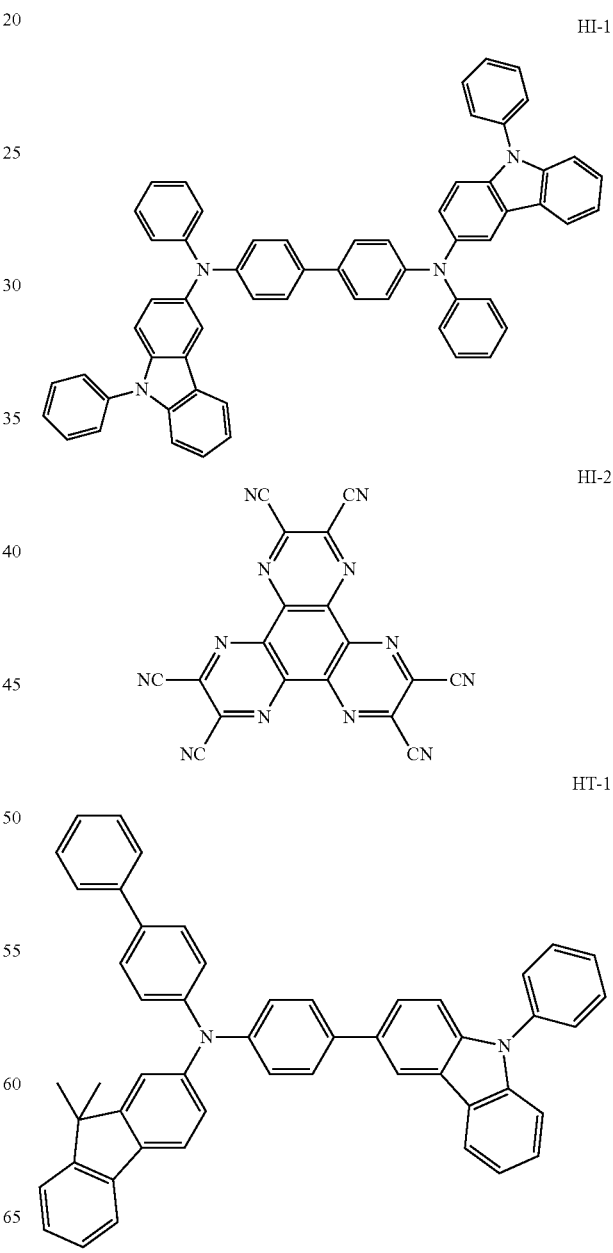

-continued

HT-2

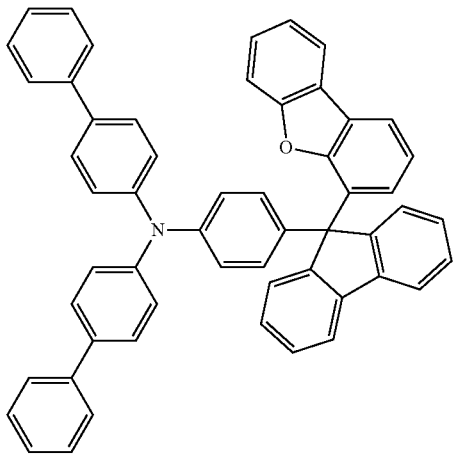

ET-1

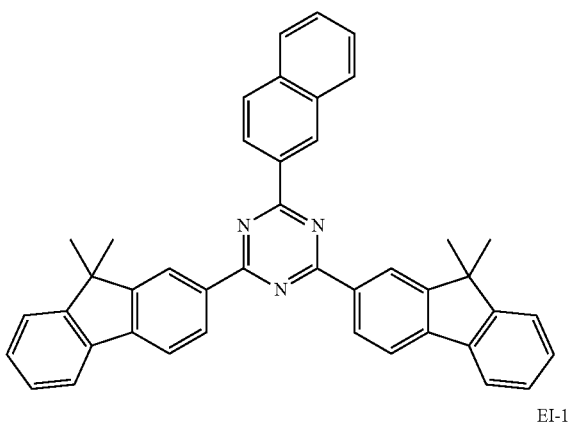

EI-1

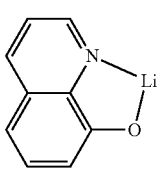

Comparative Example 1-1: Preparation of an OLED Device Comprising Only the First Host Compound of the Present Invention as a Host An OLED device was produced in the same manner as in Device Example 1-1, except for using only the first host compound as a host of the light-emitting layer.

Comparative Example 1-2: Preparation of an OLED Device Comprising Only the Second Host Compound of the Present Invention as a Host An OLED device was produced in the same manner as in Device Example 1-1, except for using only the second host compound as a host of the light-emitting layer.

A driving voltage at 1,000 nit, luminous efficiency, CIE color coordinate, and time taken to be reduced from 100% to 97% of the luminance at 15,000 nit and a constant current of OLEDs are shown in Table 1 below.

TABLE 1

|  | Host | Voltage (V) | Efficiency (cd/A) | Color coordinate (x, y) | T97 Lifespan [hr] |
|---|---|---|---|---|---|
| Device Example 1-1 | F-13: H2-125 | 3.1 | 51.3 | 0.327, 0.658 | 25 |
| Device Example 1-2 | F-31: H2-125 | 3.1 | 65.8 | 0.328, 0.657 | 30 |
| Comparative Example 1-1 | F-31 | 5.9 | 3.7 | 0.321, 0.660 | x |
| Comparative Example 1-2 | H2-125 | 3.0 | 64.9 | 0.337, 0.649 | 15 |

Device Examples 2-1 to 2-3: Preparation of an OLED Device Wherein the First Host Compound and the Second Host Compound of the Present Invention are Co-Evaporated An OLED device was produced in the same manner as in Device Example 1-1, except for evaporating the first hole transport layer of 40 nm thickness, not evaporating the second hole transport layer, using compound D-25 as a dopant of the light-emitting layer, and using the combination of the first host compound and the second host compound used as a host of the light-emitting layer as listed in Table 2 below.

Comparative Example 2-1: Preparation of an OLED Device Comprising Only the Second Host Compound of the Present Invention as a Host An OLED device was produced in the same manner as in Device Example 2-1, except for using the second host compound as a host of the light-emitting material as listed in Table 2 below.

A driving voltage at 1,000 nit, luminous efficiency, CIE color coordinate, and time taken to be reduced from 100% to 90% of the luminance at 15,000 nit and a constant current of OLEDs are shown in Table 2 below.

TABLE 2

|  | Host | Voltage (V) | Efficiency (cd/A) | Color coordinate (x, y) | T90 Lifespan [hr] |
|---|---|---|---|---|---|
| Device Example 2-1 | F-801: H2-32 | 2.9 | 46.5 | 0.306, 0.657 | 36 |
| Device Example 2-2 | F-30: H2-32 | 2.9 | 53.5 | 0.306, 0.657 | 63 |
| Device Example 2-3 | F-24: H2-32 | 2.9 | 53.3 | 0.305, 0.657 | 54 |
| Comparative Example 2-1 | H2-32 | 2.8 | 36.3 | 0.313, 0.653 | 18 |

The organic electroluminescent device of the present invention comprises a light-emitting layer comprising a host and a phosphorus dopant. The host consists of plural host compounds. At least a first host compound of the plural host compounds is a specific carbazole-(fused carbazole) derivative comprising an aryl, and a second host compound is a specific carbazole derivative comprising a nitrogen-containing heteroaryl. The organic electroluminescent device of the present invention maintains a high luminous efficiency while having a longer lifespan than conventional devices.

H2-308
H2-309
H2-310
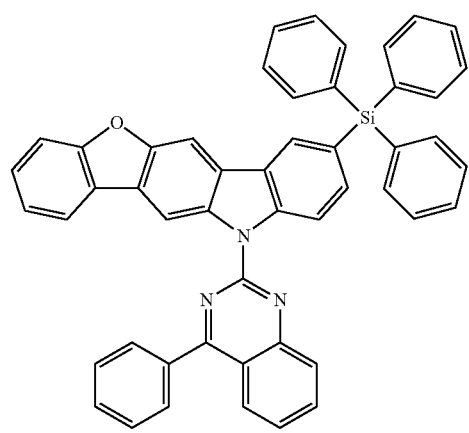
H2-311
H2-312
H2-313
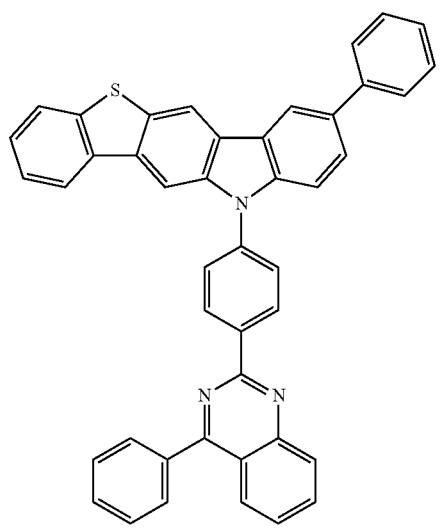
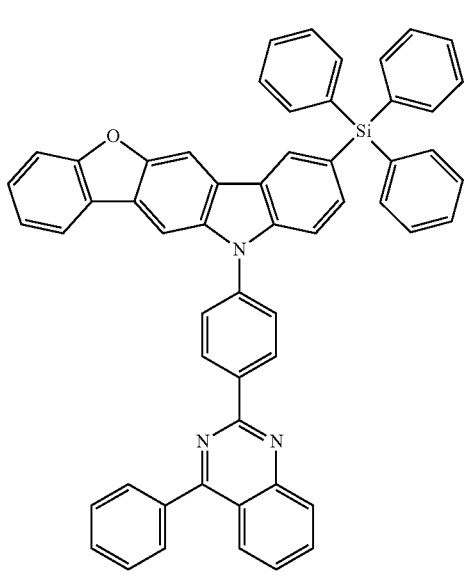
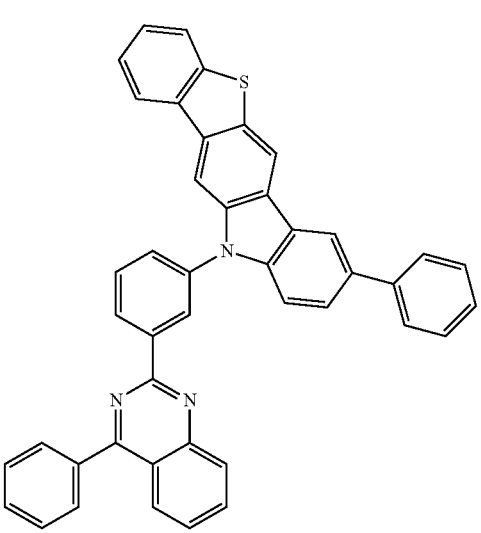

H2-314
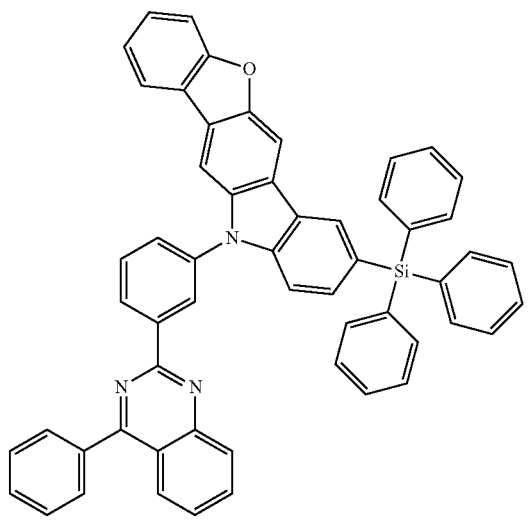
H2-317
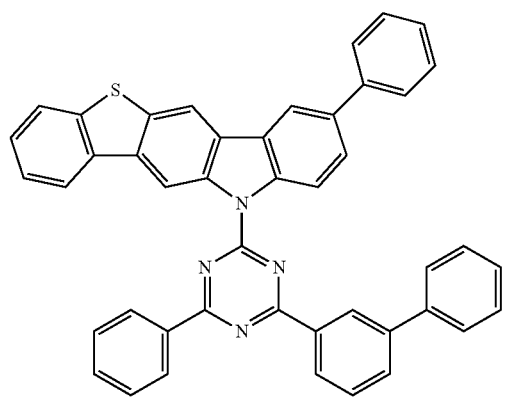
H2-315
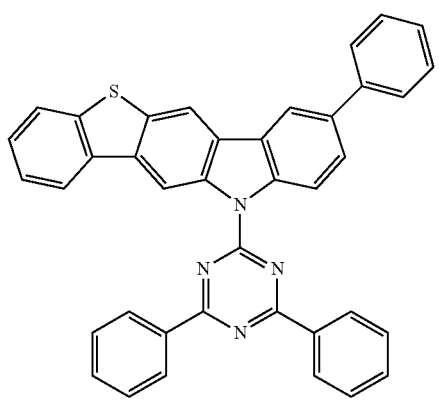
H2-318
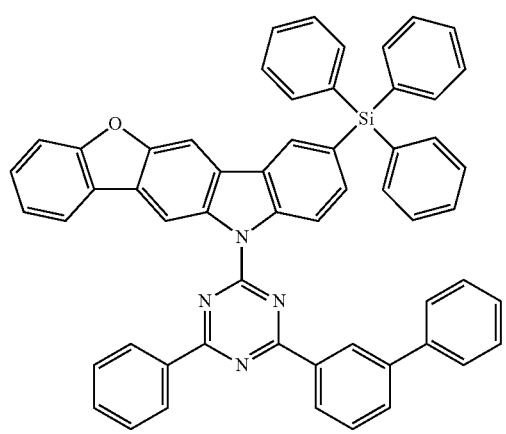
H2-316
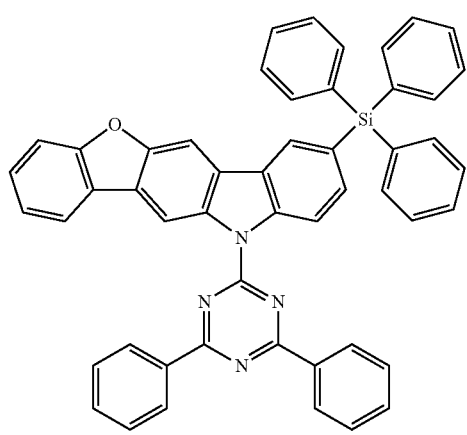
H2-319
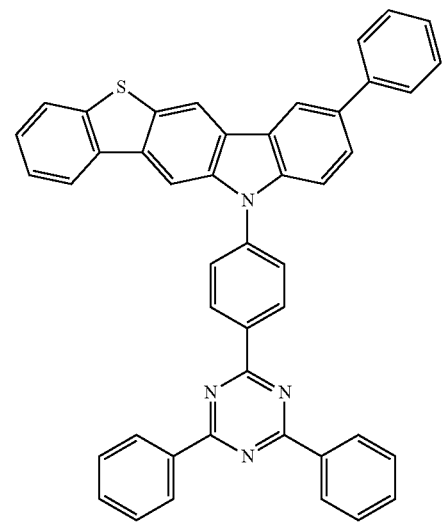

H2-320
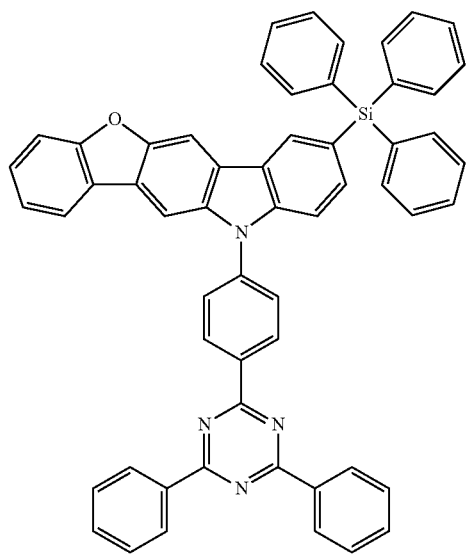
H2-321
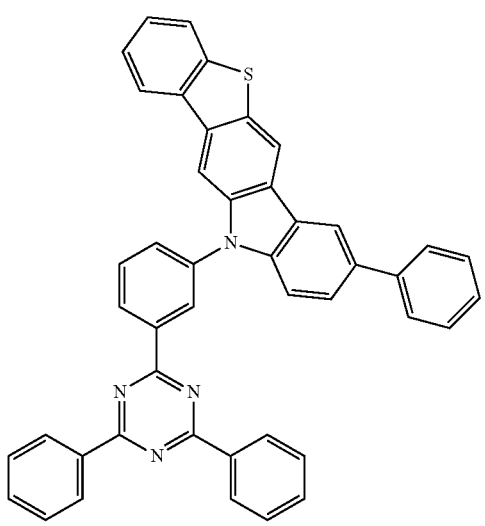
H2-322
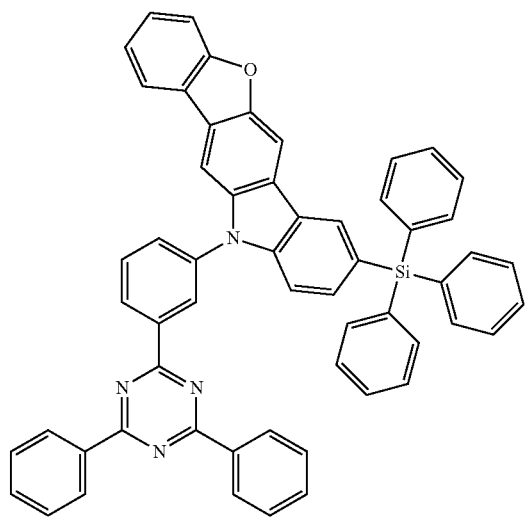
H2-323
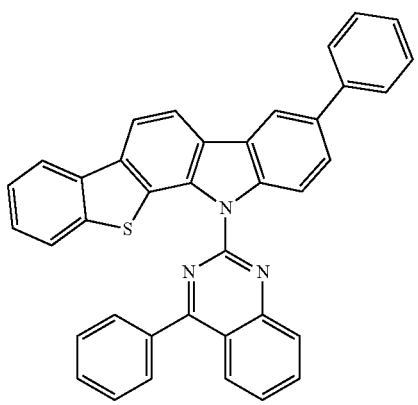
H2-324
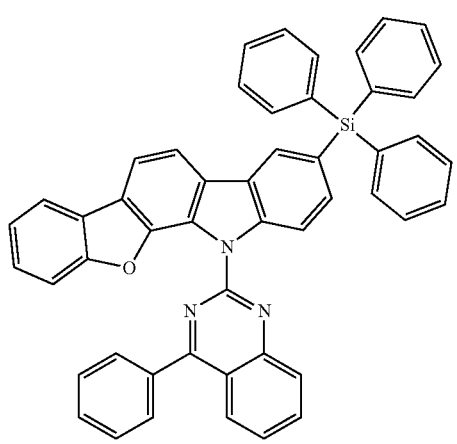
H2-325
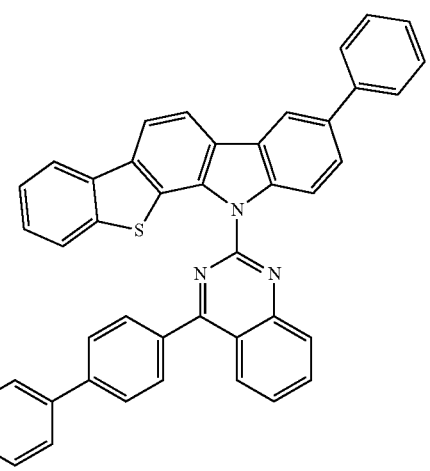

H2-326
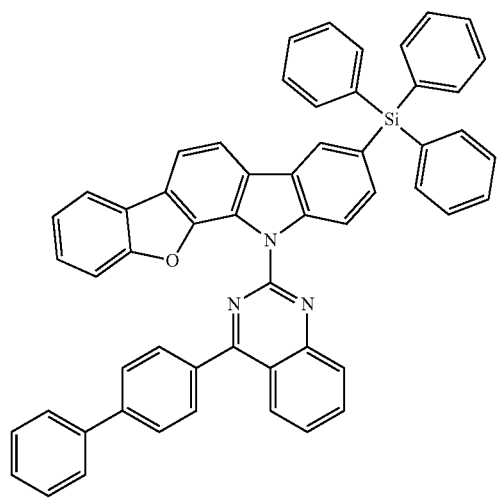
H2-327
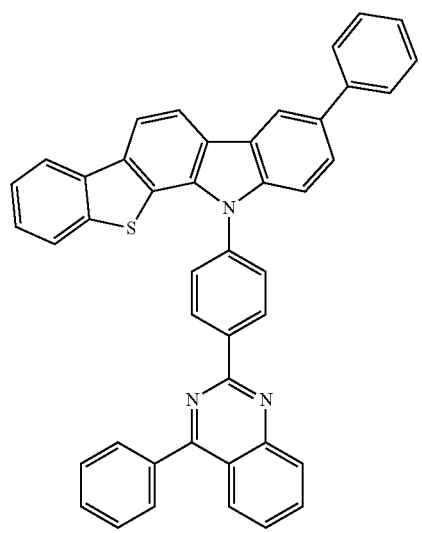
H2-328
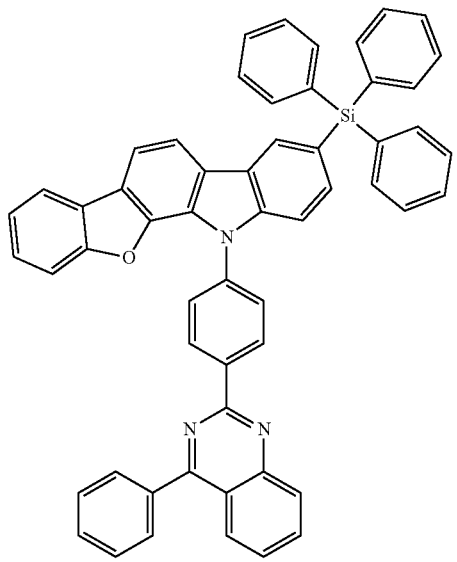
H2-329
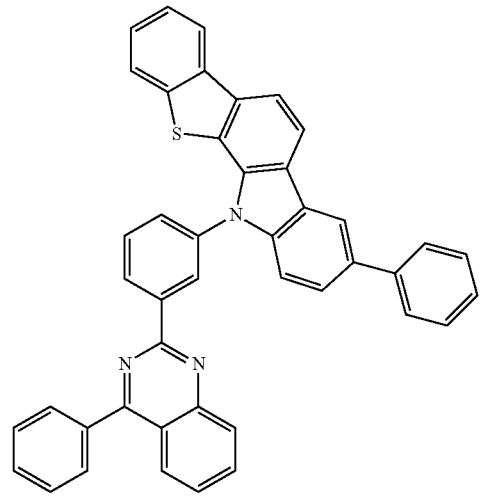
H2-330
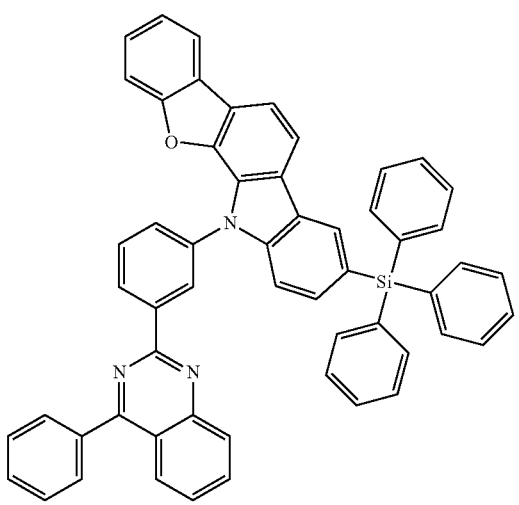
H2-331
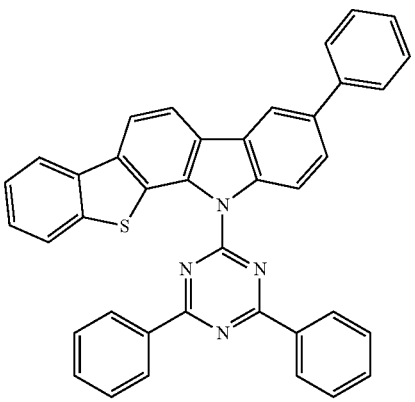

H2-332
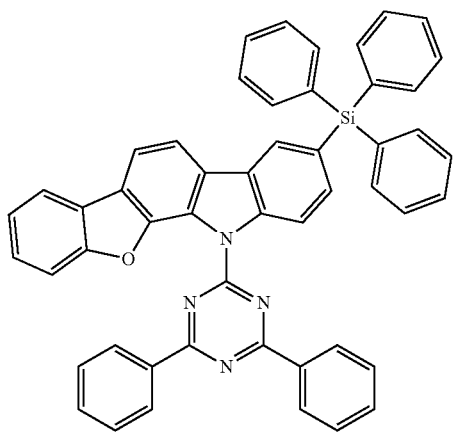
H2-333
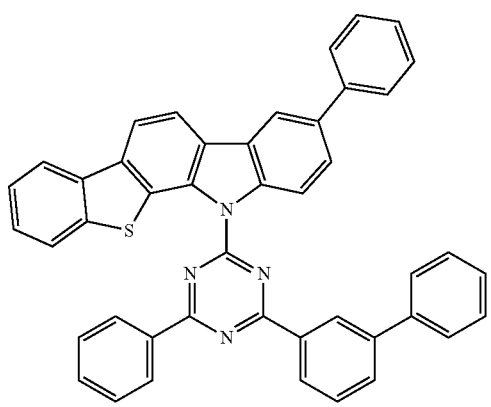
H2-334
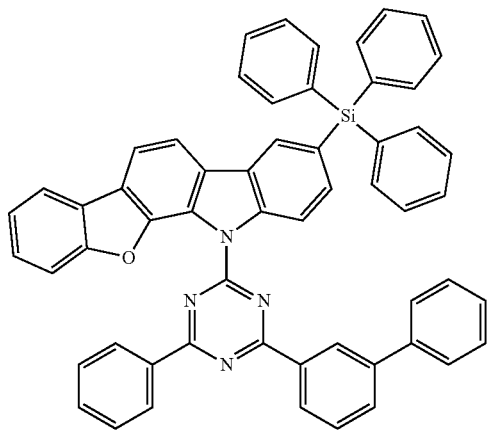
H2-335
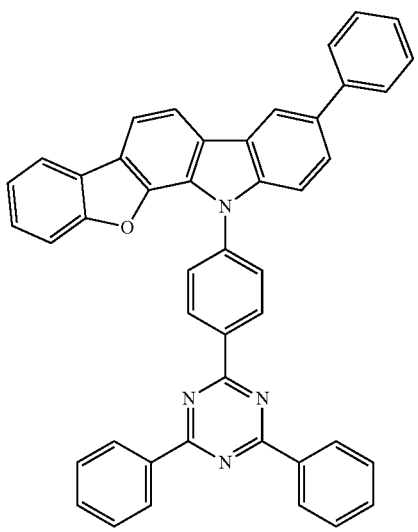
H2-336
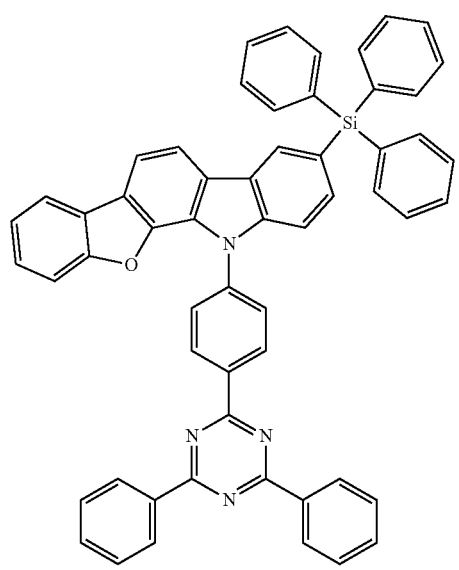
H2-337
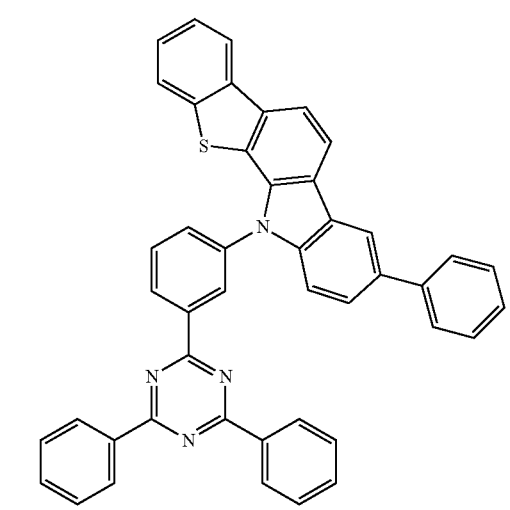

H2-338
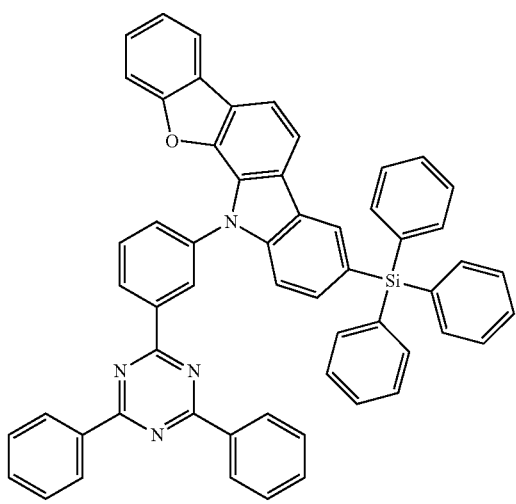
H2-341
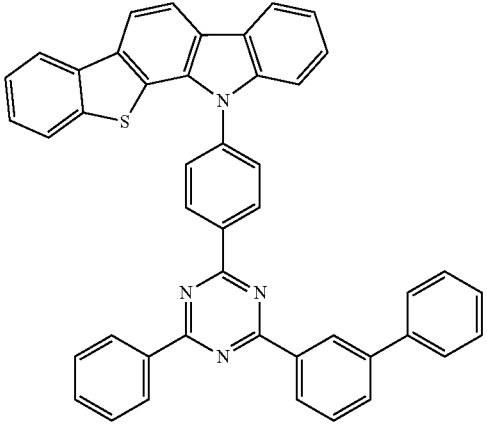
H2-339
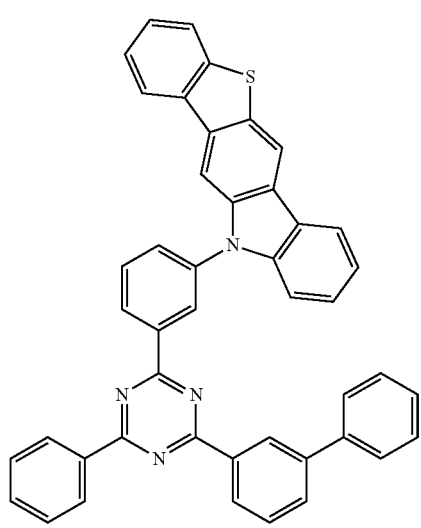
H2-342
H2-340
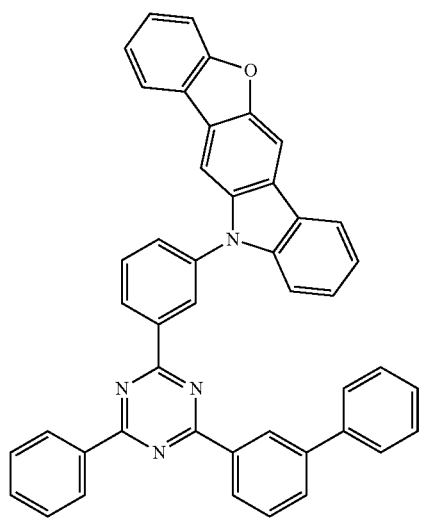
H2-343
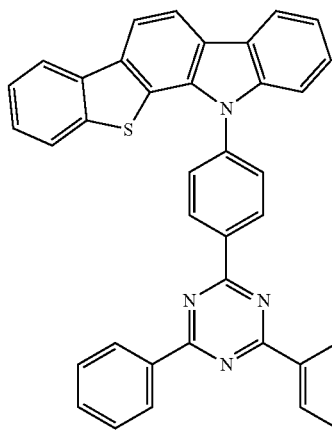

-continued
H2-344
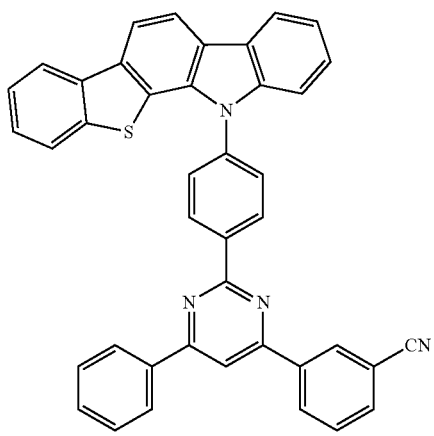
H2-345
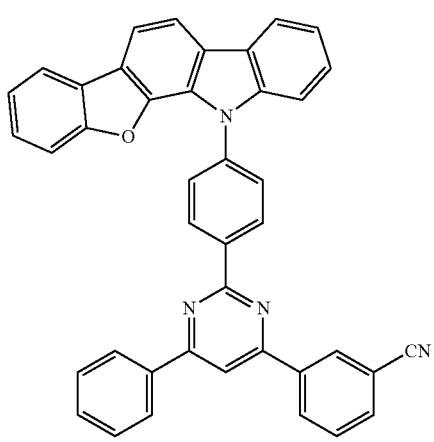
H2-346
-continued
H2-347
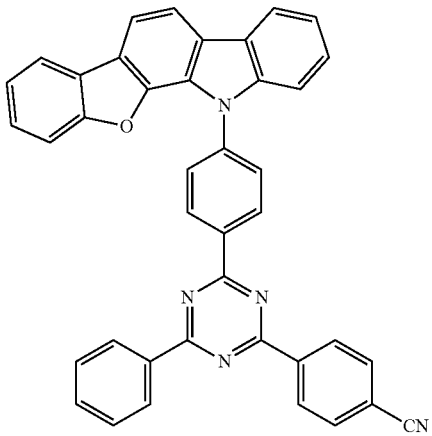
H2-348
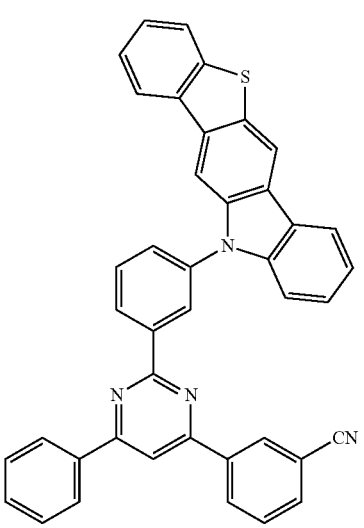
H2-349
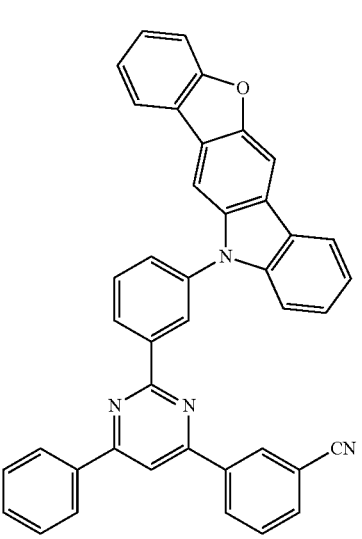

H2-350
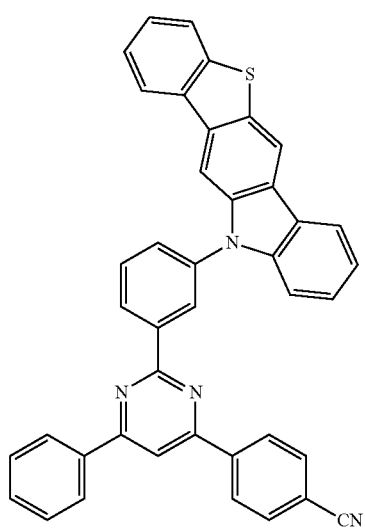
H2-351
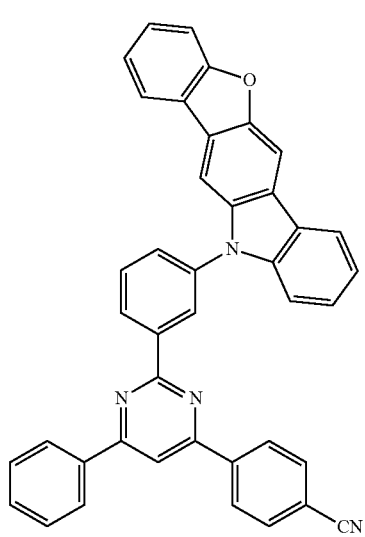
H2-352
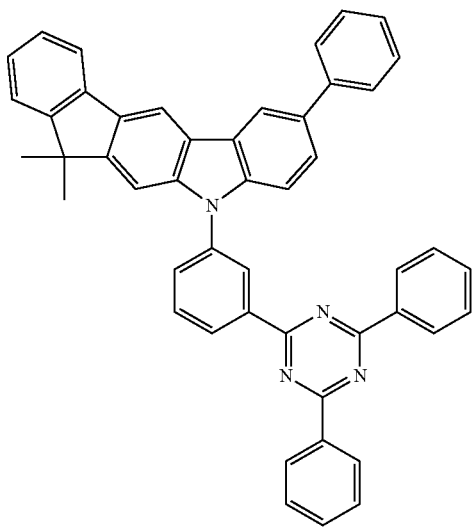
H2-353
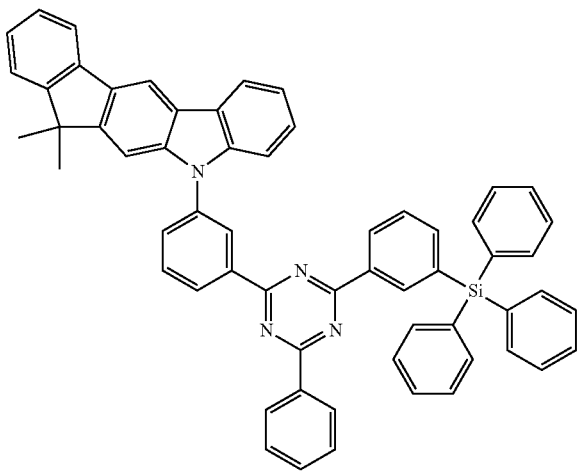
H2-354
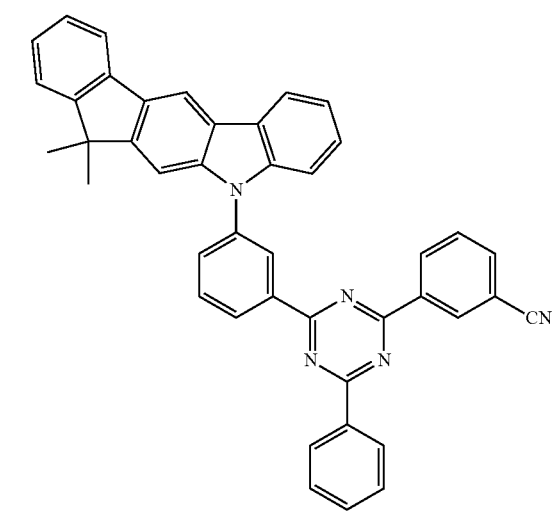
H2-355
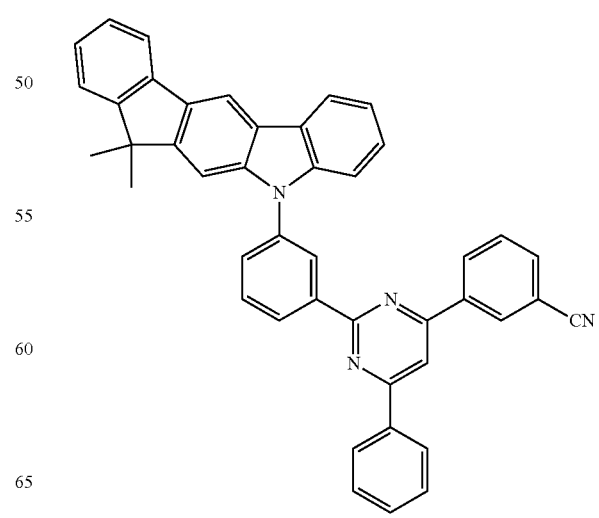

-continued
H2-356
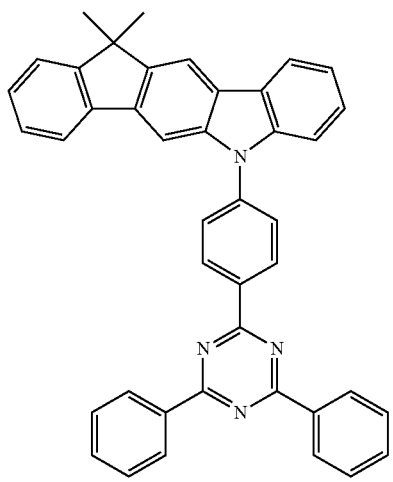
H2-357
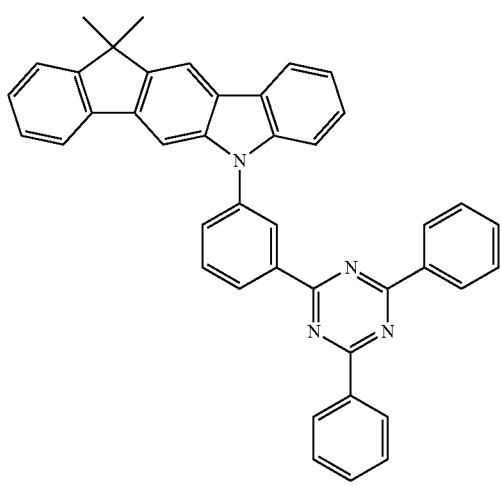
H2-358
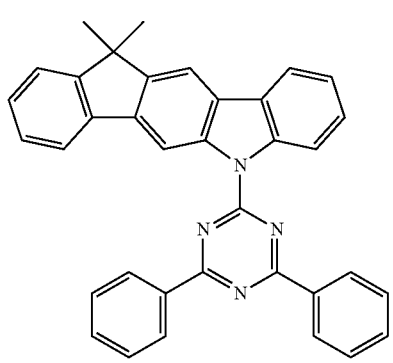
-continued
H2-359
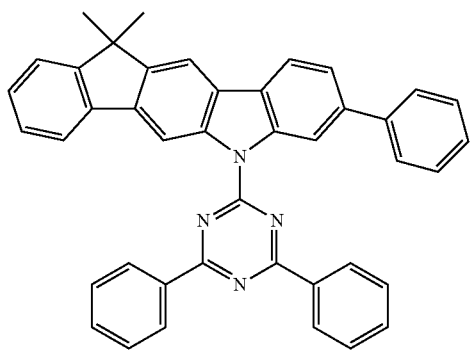
H2-360
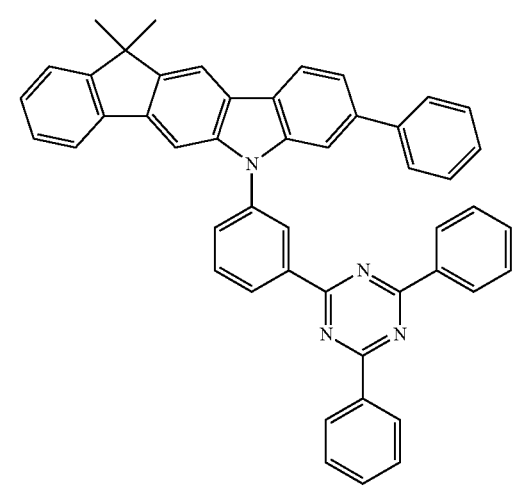
H2-361
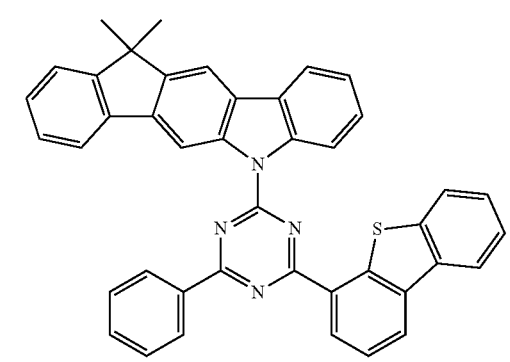
H2-362
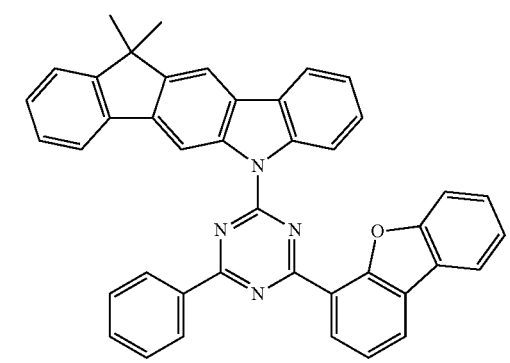

1103
-continued
H2-363
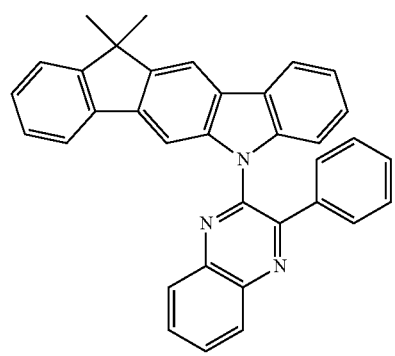
H2-364
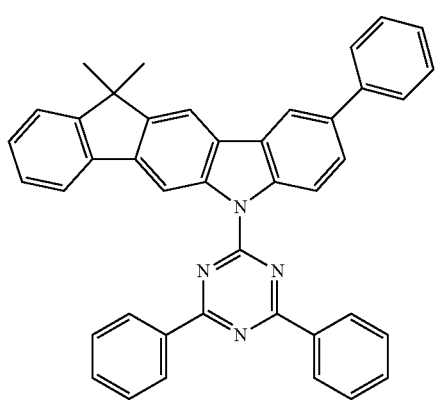
H2-365
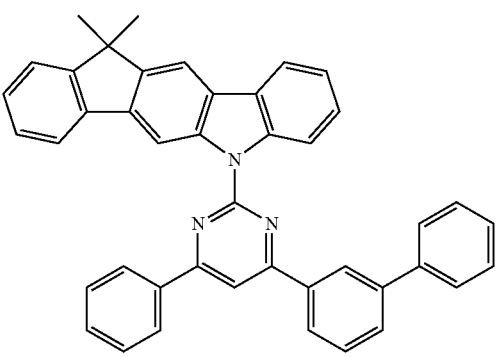
H2-366
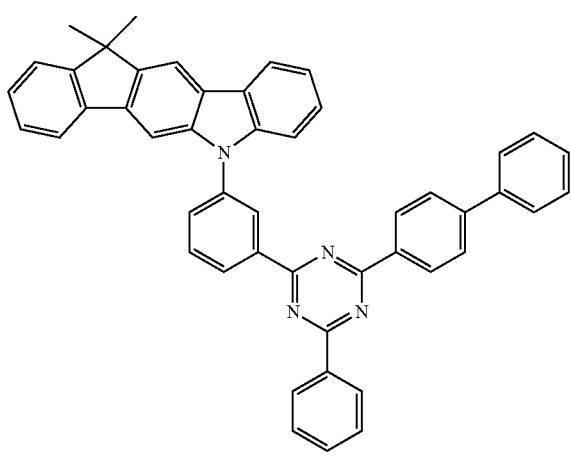
1104
-continued
H2-367
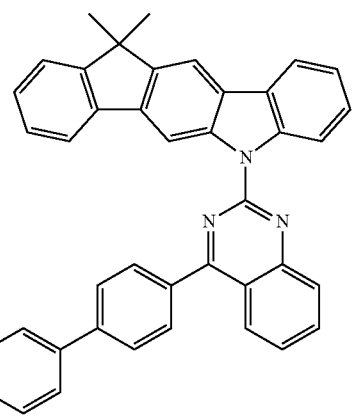
H2-368
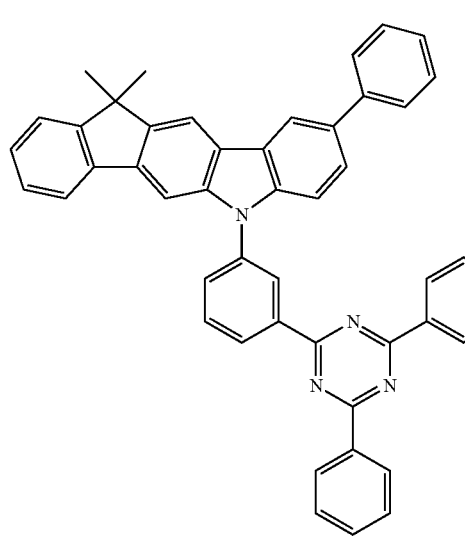
H2-369
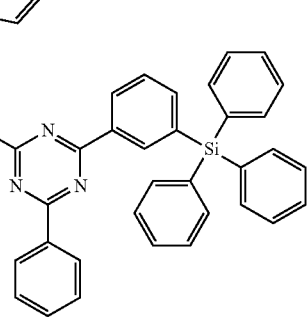

H2-370
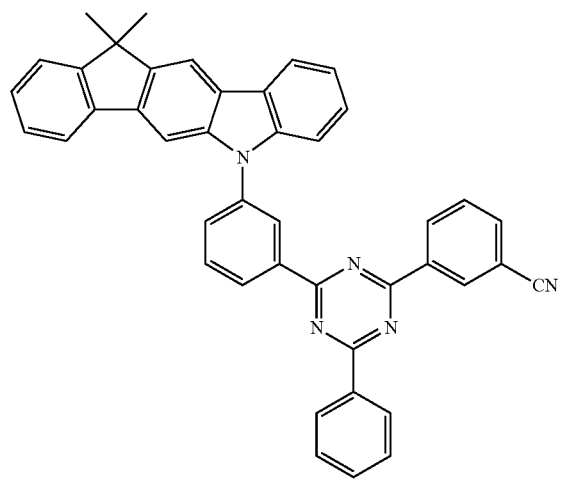
H2-371
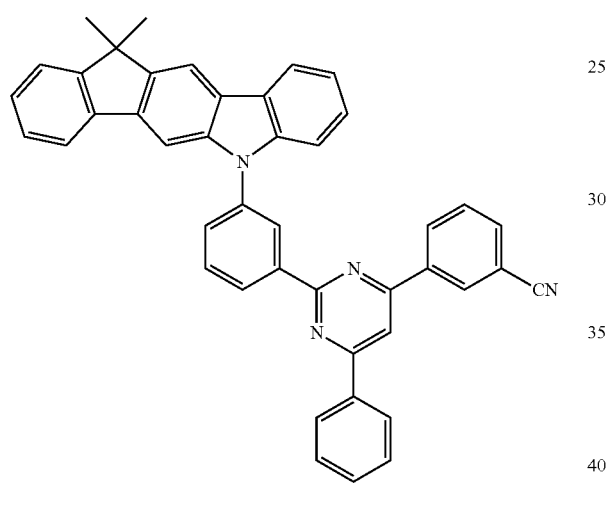
H2-372
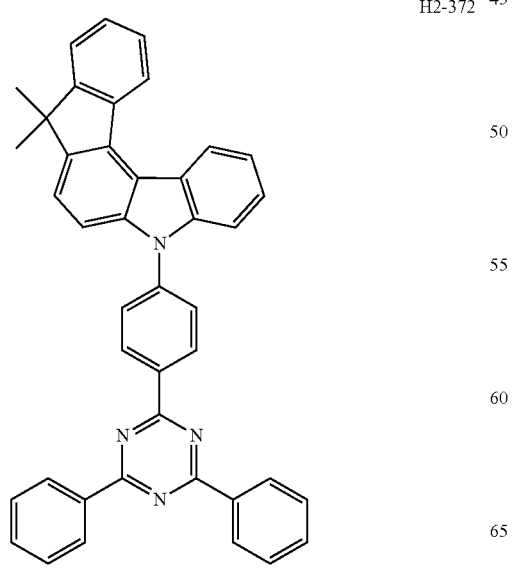
H2-373
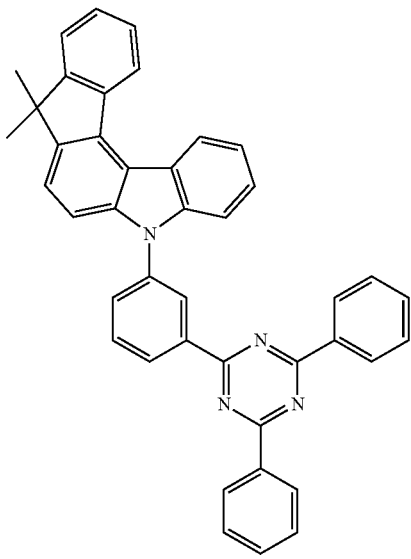
H2-374
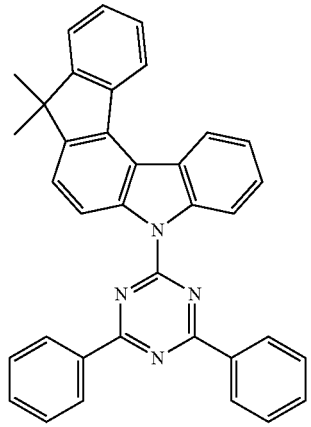
H2-375
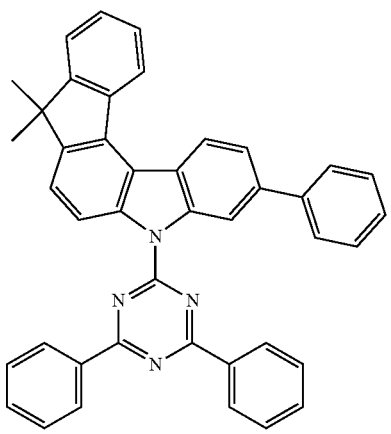

-continued
H2-376
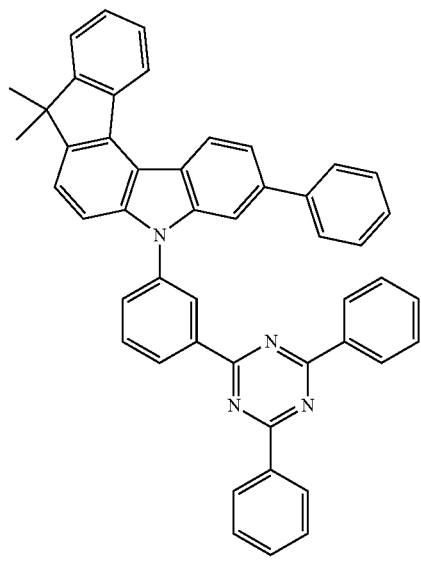
H2-377
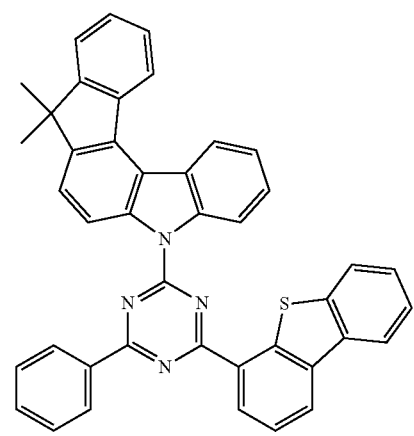
H2-378
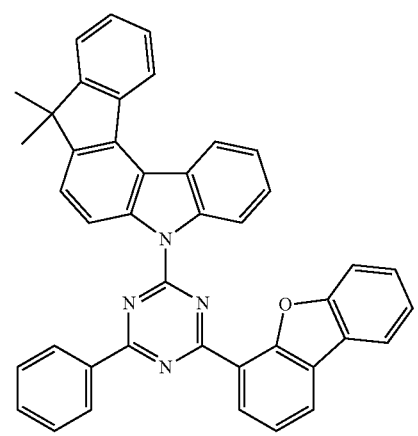
-continued
H2-379
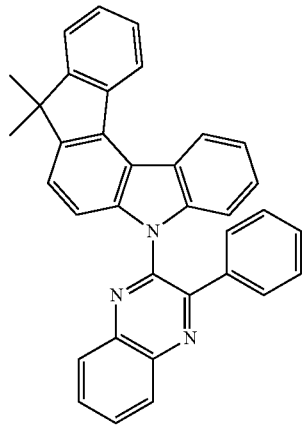
H2-380
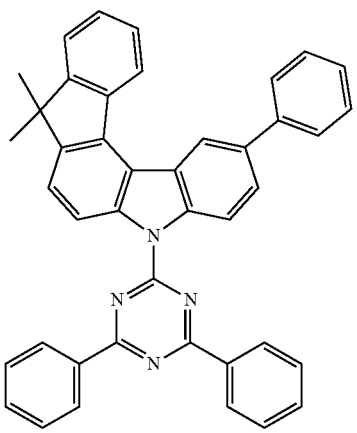
H2-381
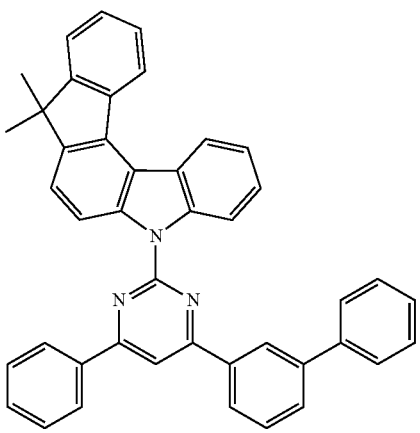

H2-382
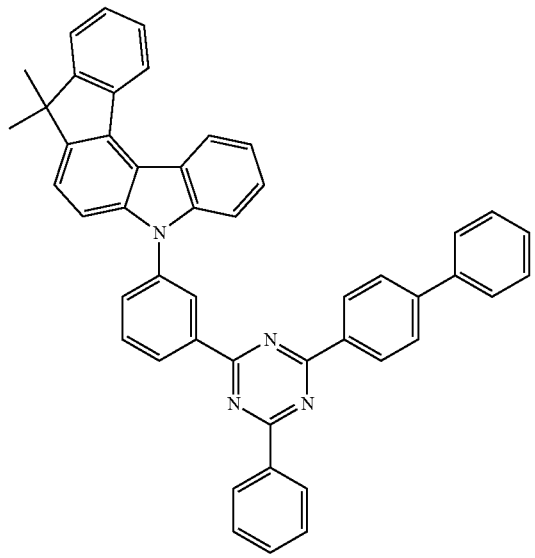
H2-385
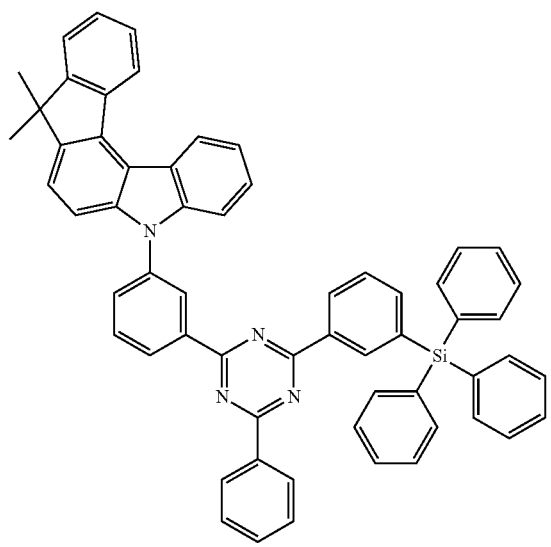
H2-383
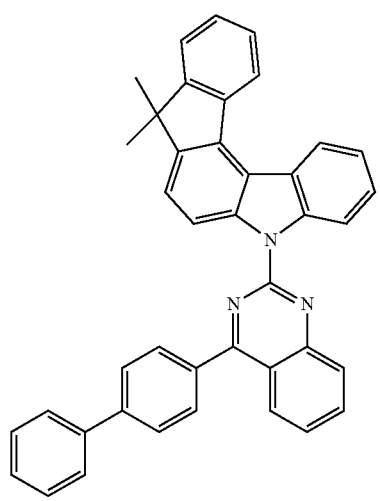
H2-384
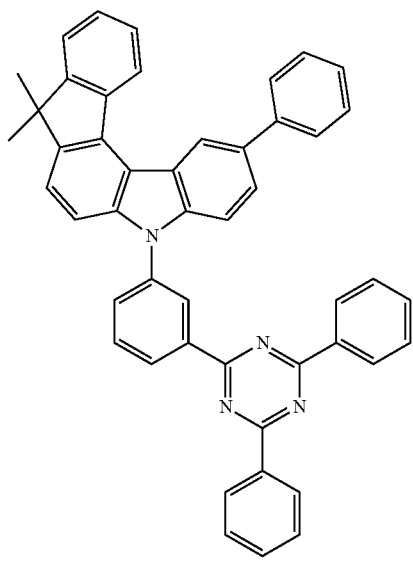
H2-386
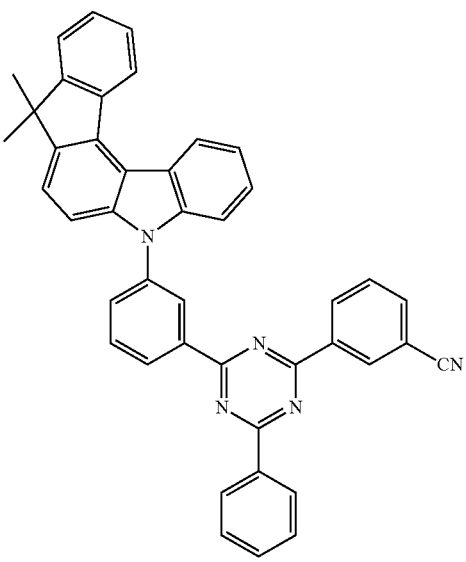

1111 -continued
H2-387
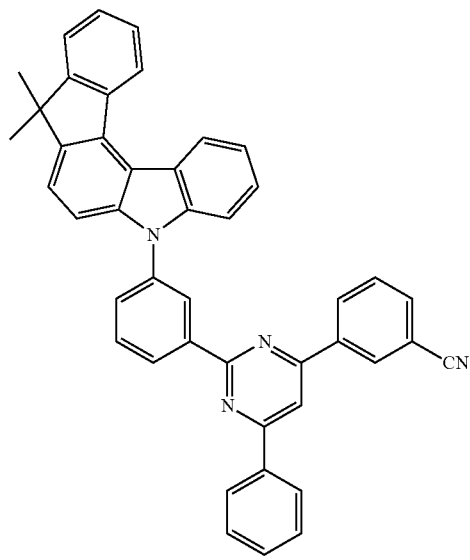
H2-388
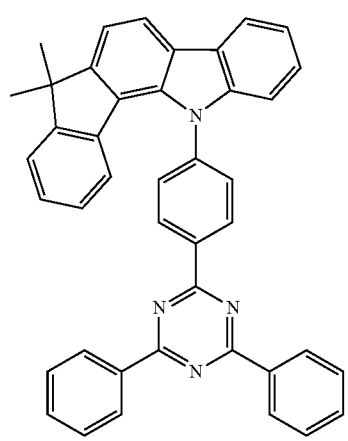
H2-389
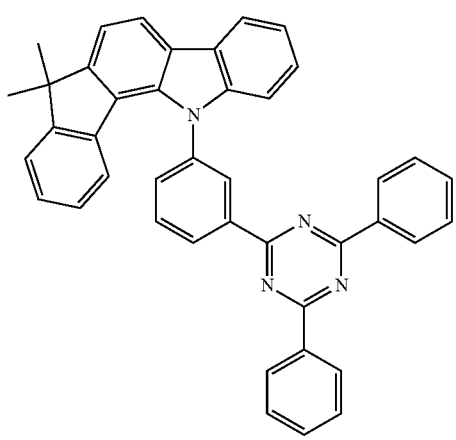
1112 -continued
H2-390
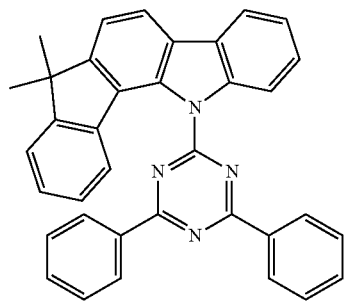
H2-391
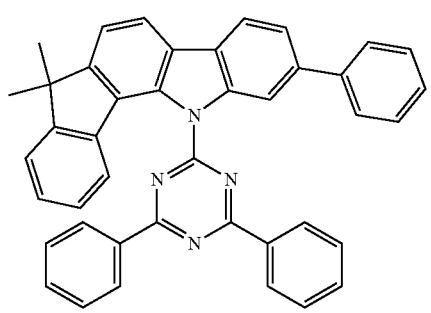
H2-392
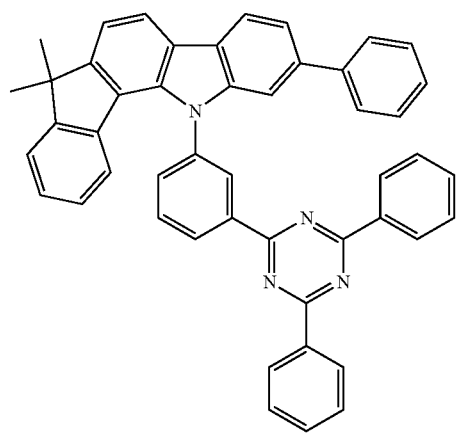
H2-393
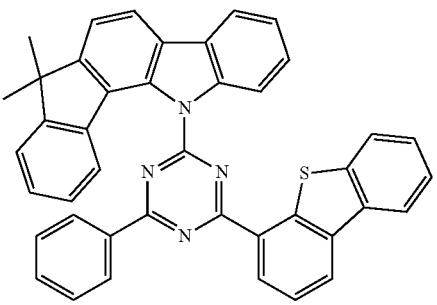
H2-394
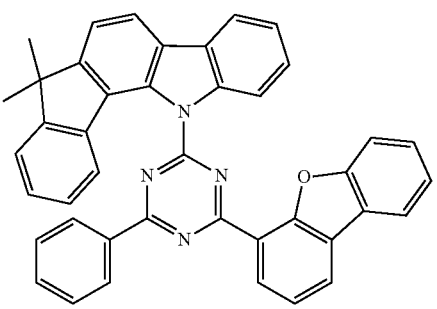

H2-395
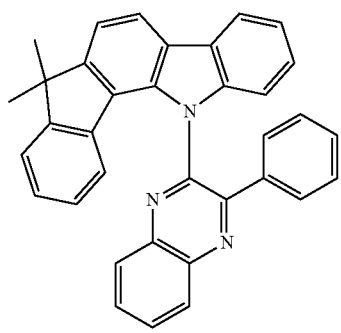
H2-399
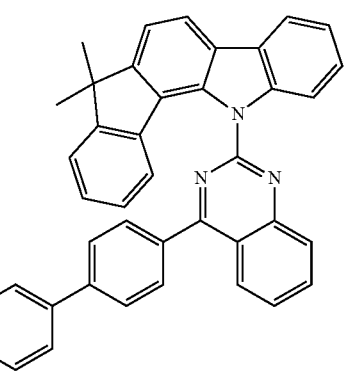
H2-396
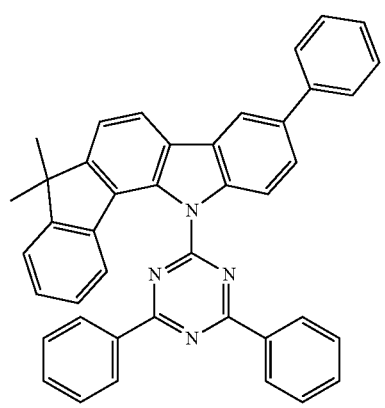
H2-400
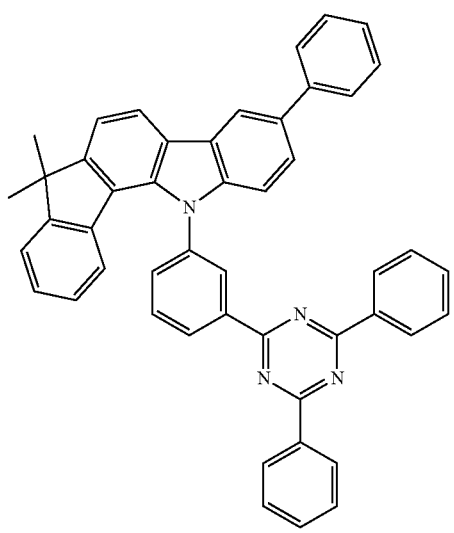
H2-397
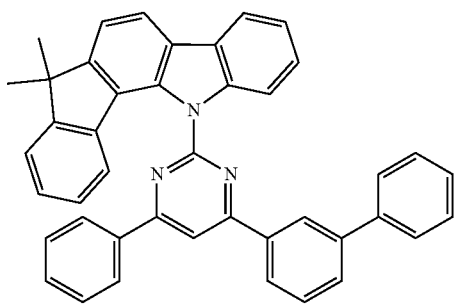
H2-398
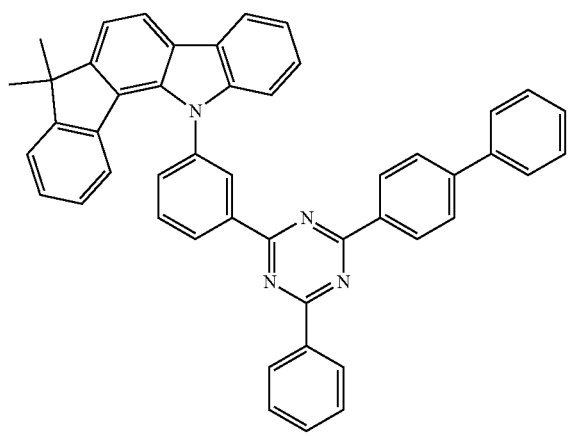
H2-401
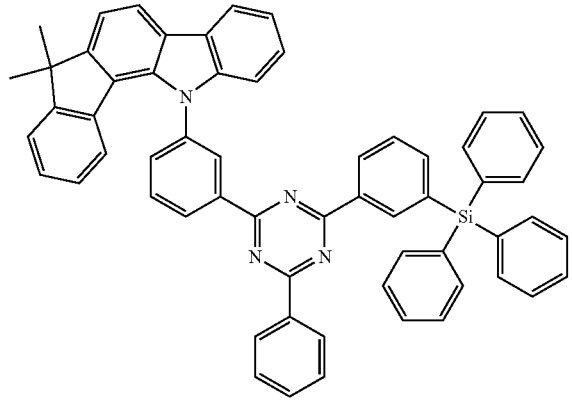

-continued
H2-402
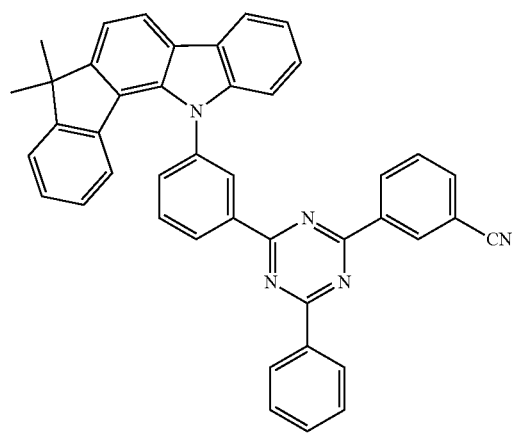
H2-403
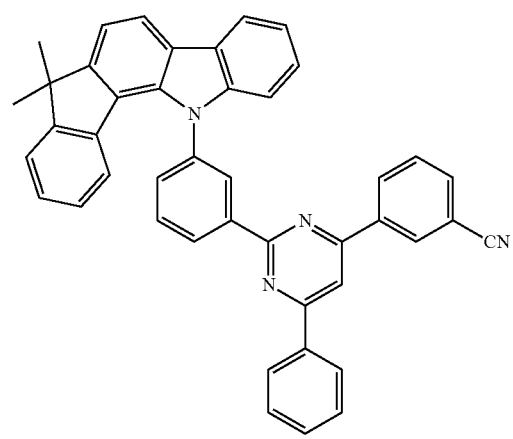
H2-404
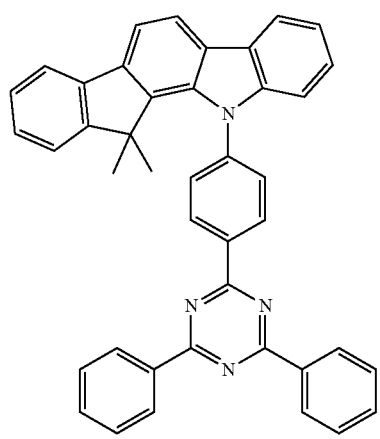
-continued
H2-405
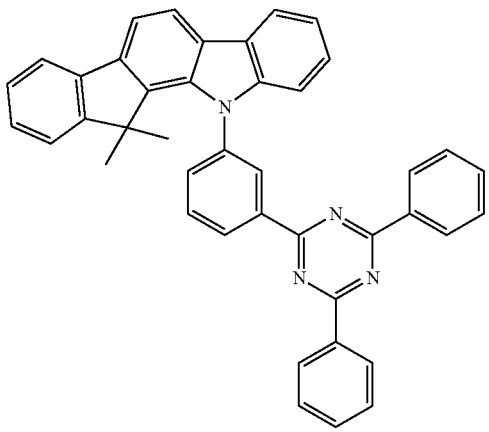
H2-406
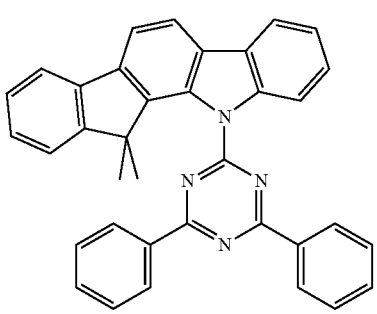
H2-407
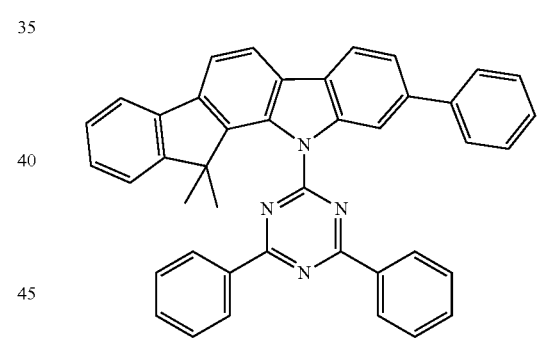
H2-408
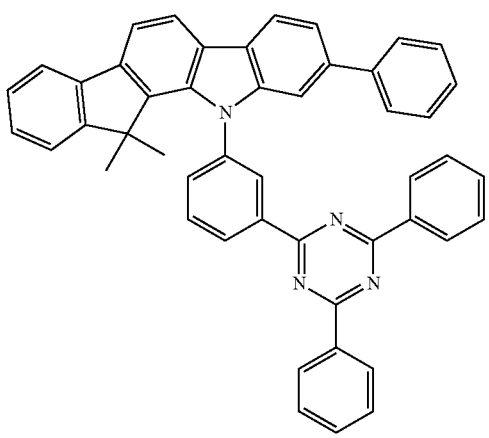

H2-409
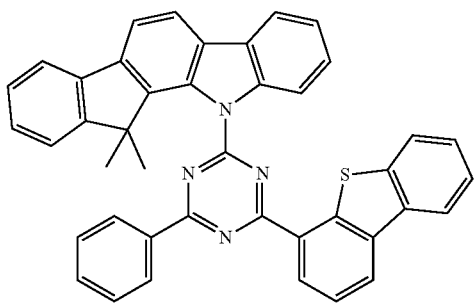
H2-410
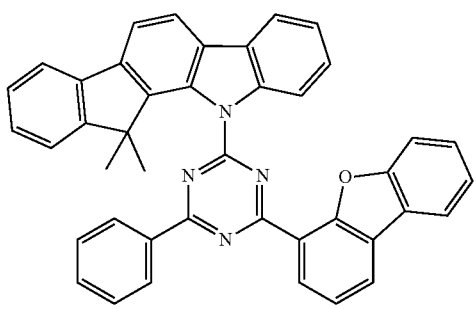
H2-411
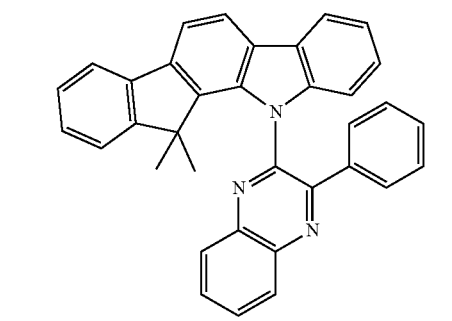
H2-412
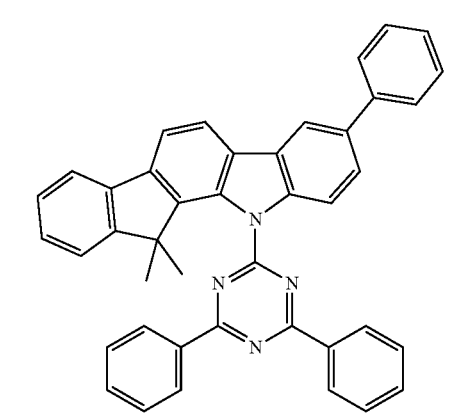
H2-413
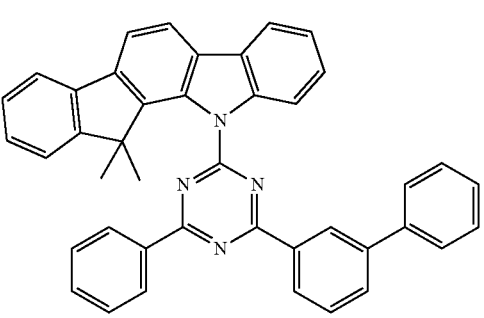
H2-414
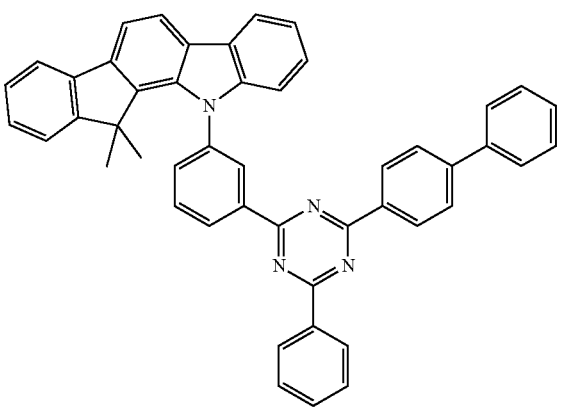
H2-415
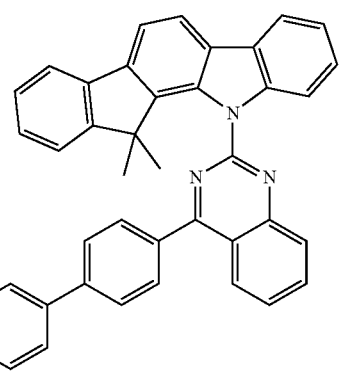
H2-416
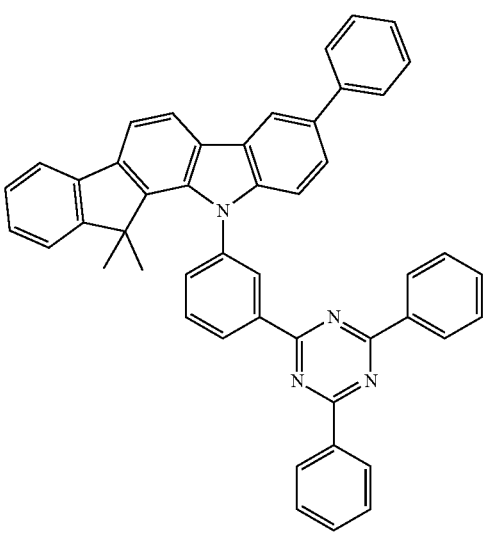

H2-417
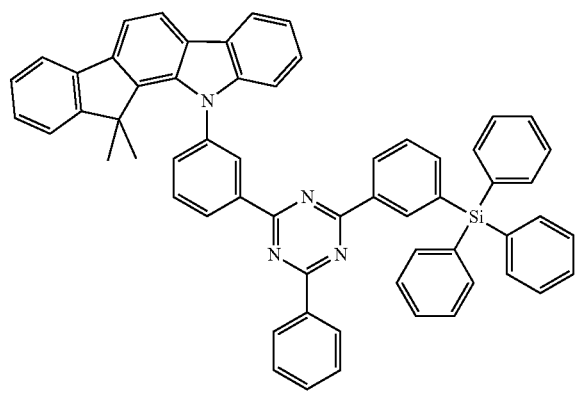
H2-418
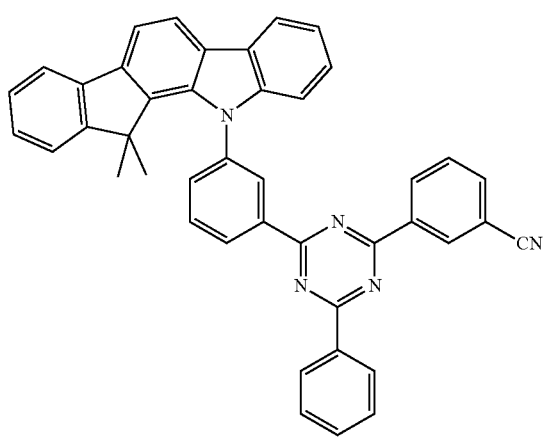
H2-419
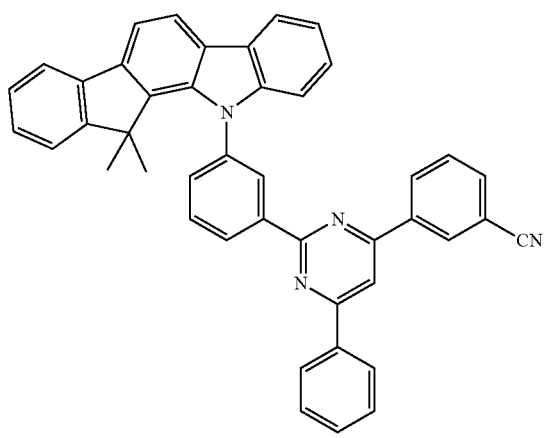
H2-420
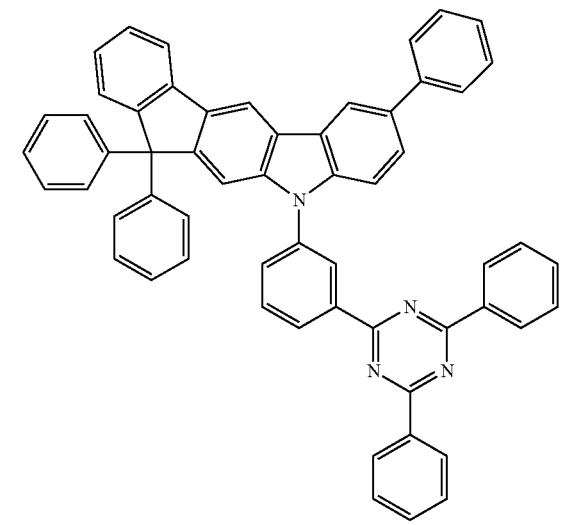
H2-421
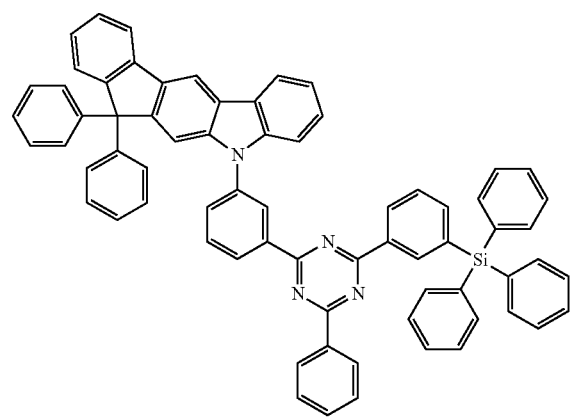
H2-422
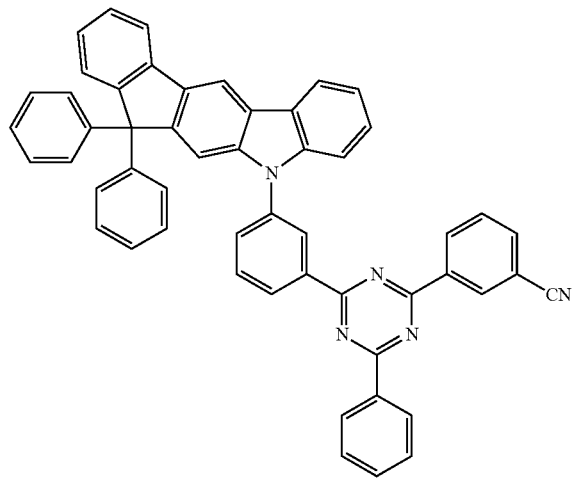

H2-423
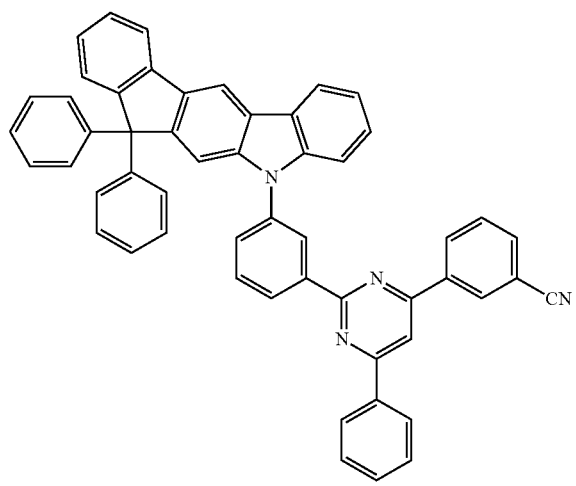
H2-426
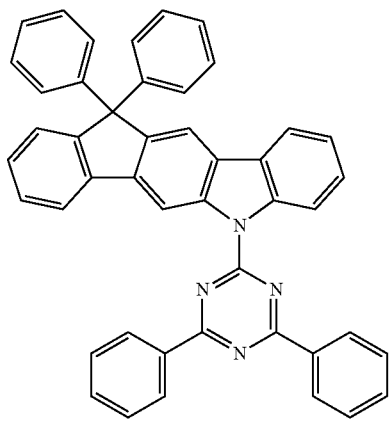
H2-424
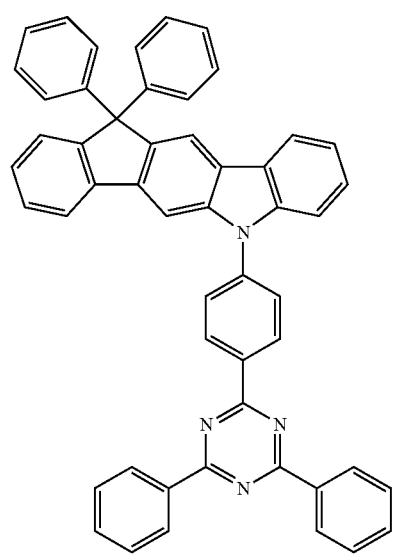
H2-427
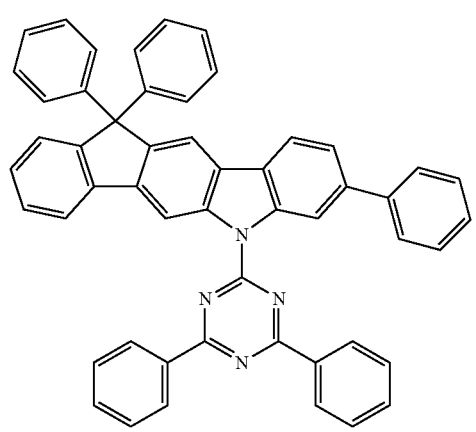
H2-425
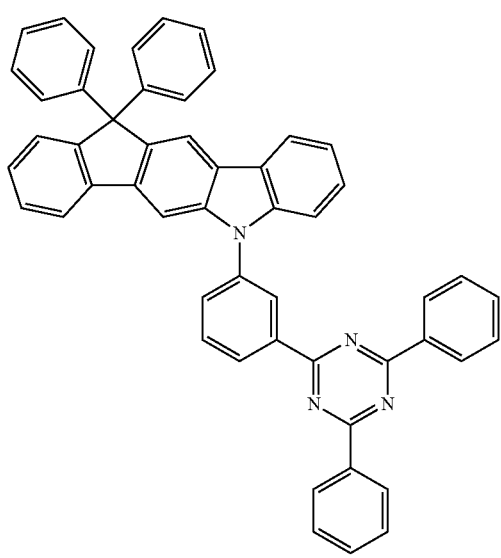
H2-428
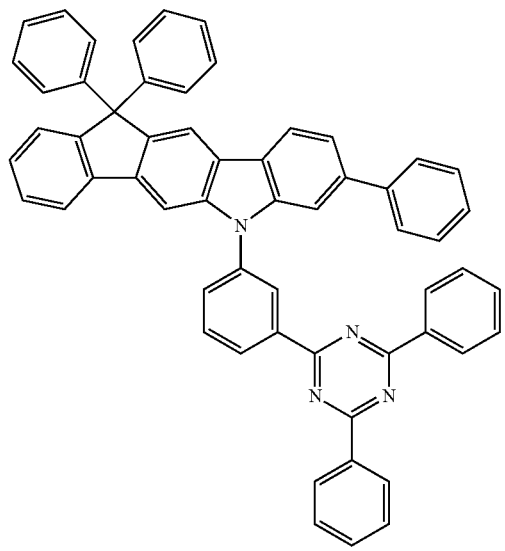

1123
-continued
H2-429
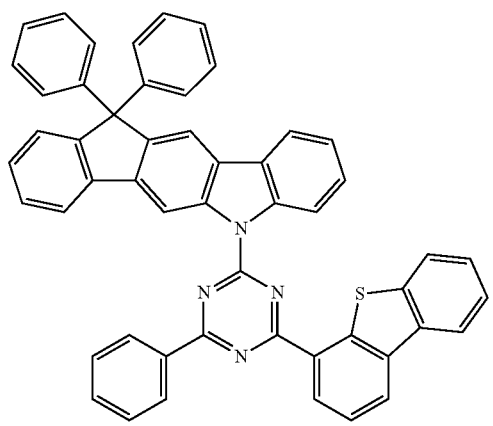
H2-430
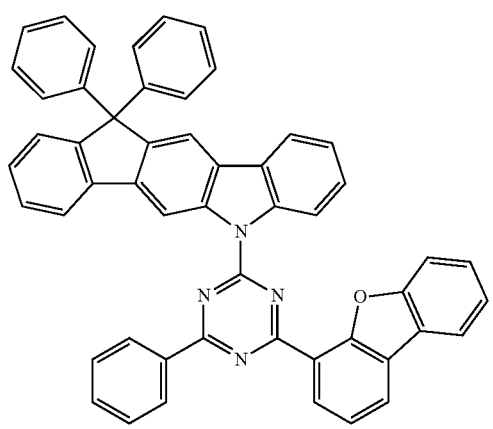
H2-431
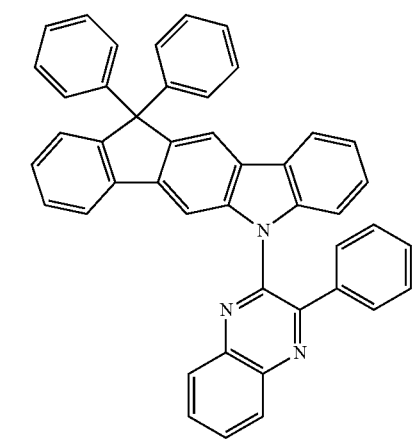
1124
-continued
H2-432
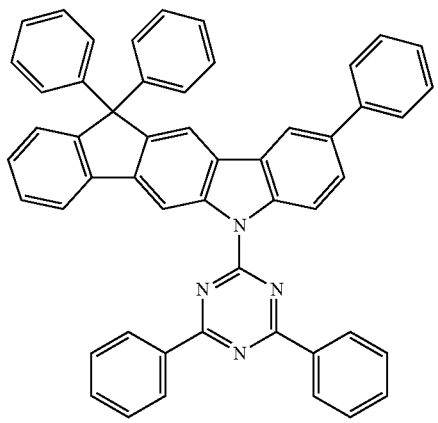
H2-433
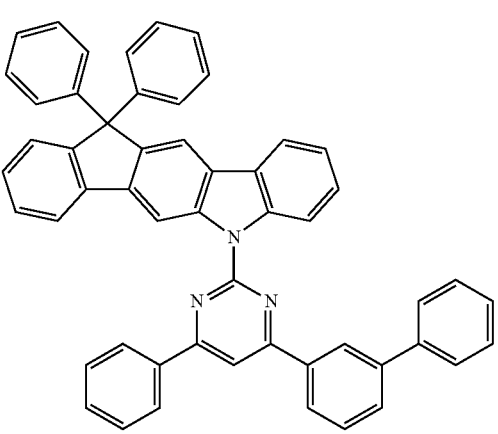
H2-434
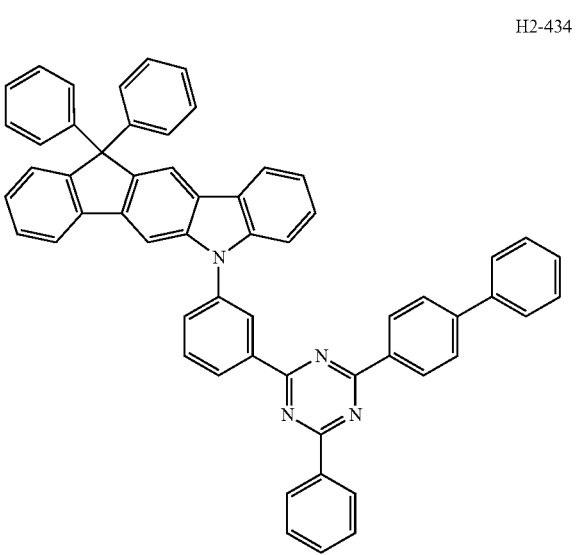

H2-435
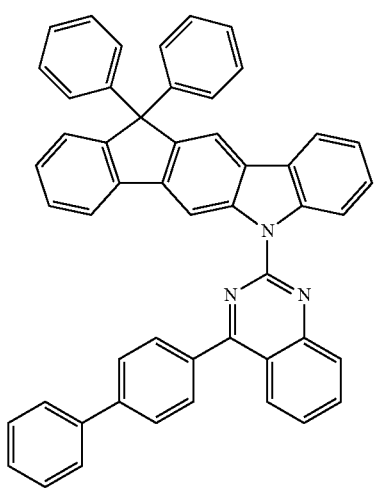
H2-438
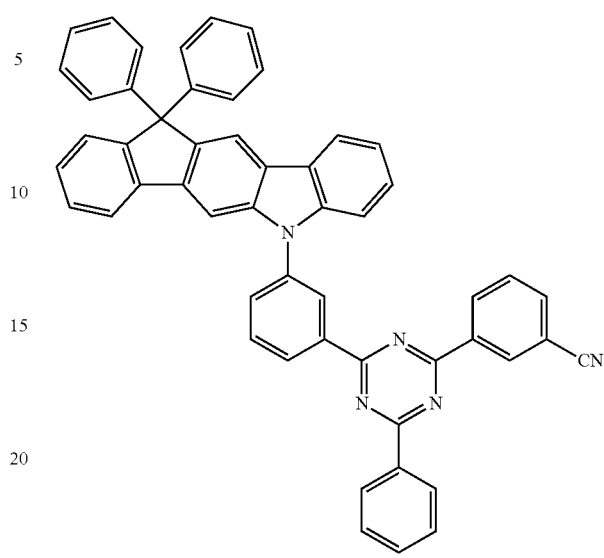
H2-436
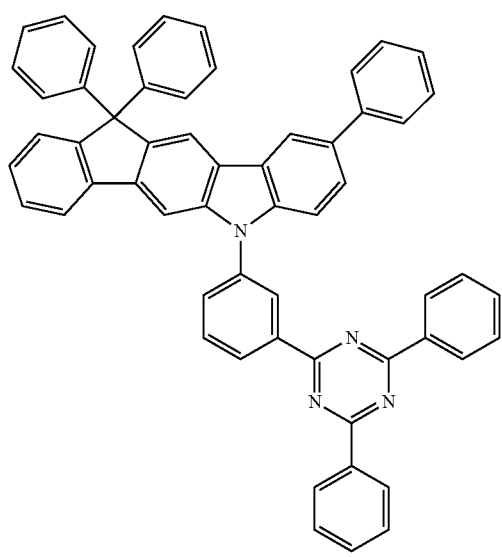
H2-437
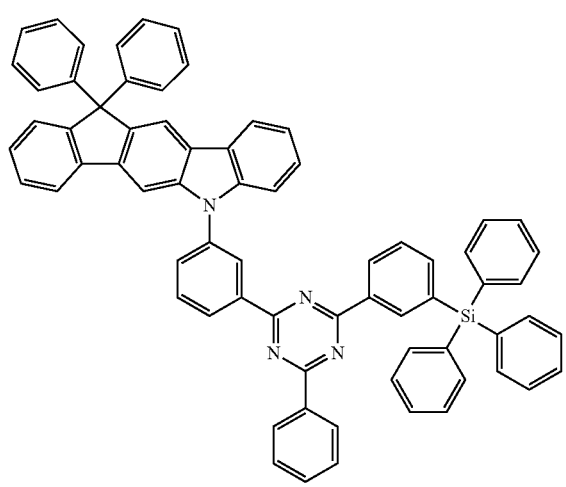
H2-439
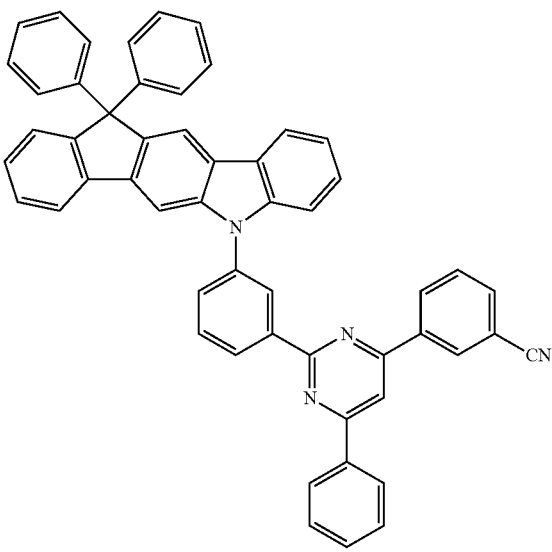

H2-440
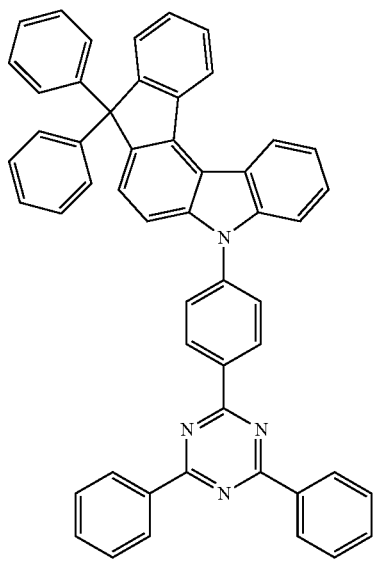
H2-441
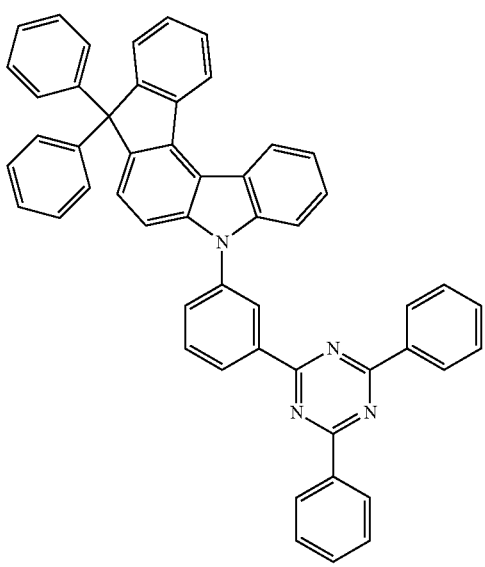
H2-442
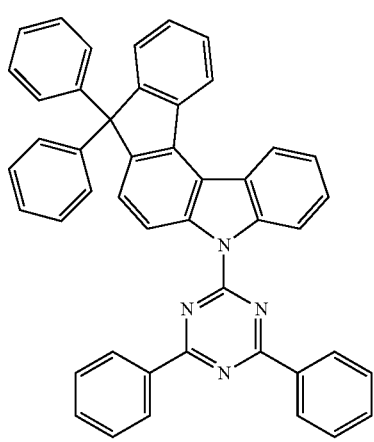
H2-443
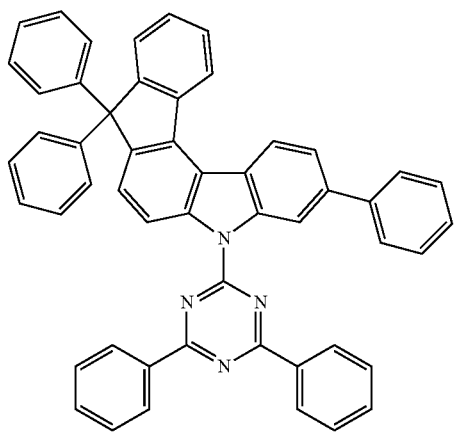
H2-444
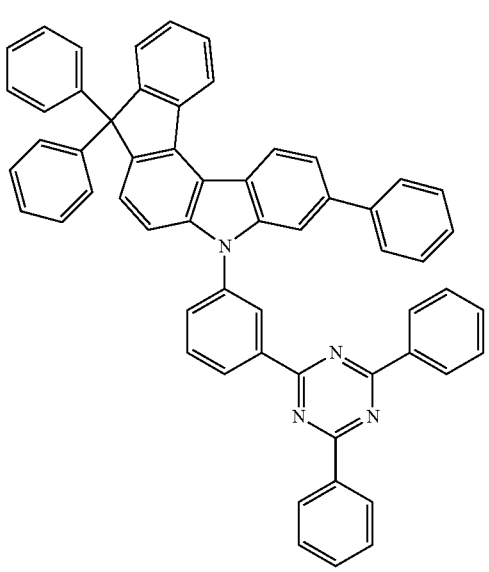
H2-445
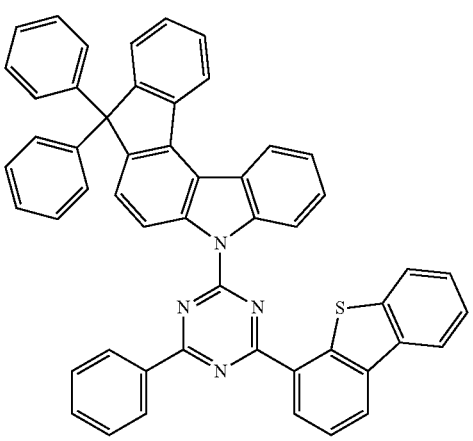

H2-446
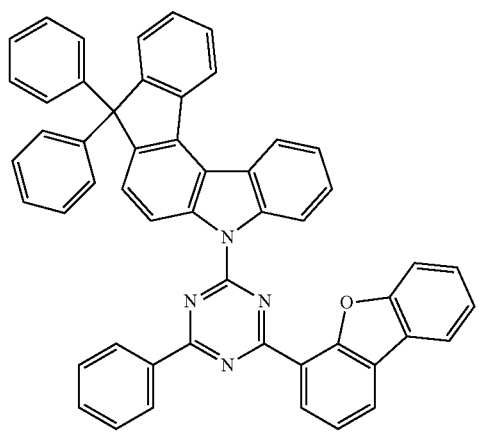
H2-449
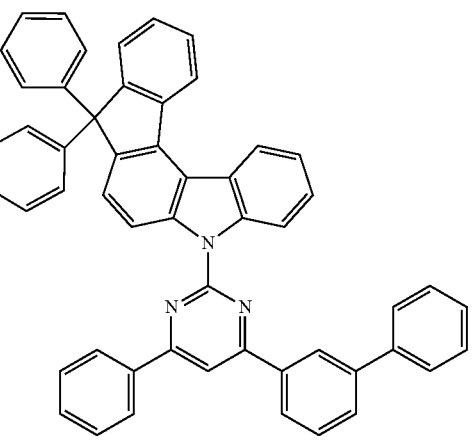
H2-447
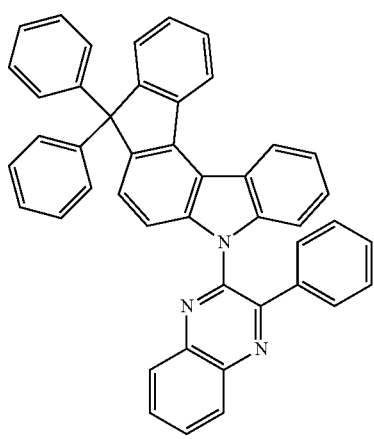
H2-450
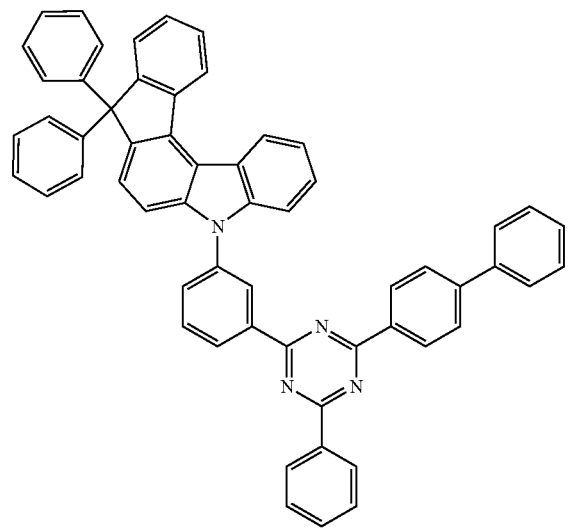
H2-448
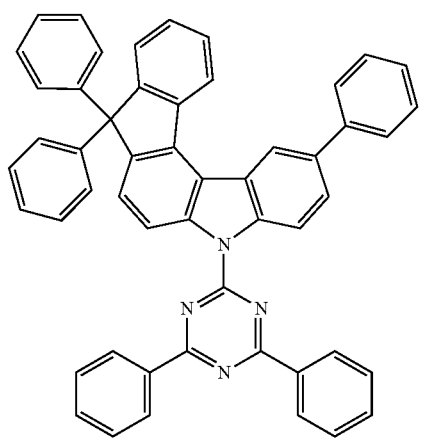
H2-451
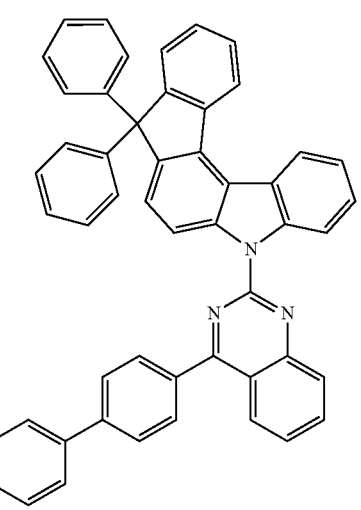

H2-452
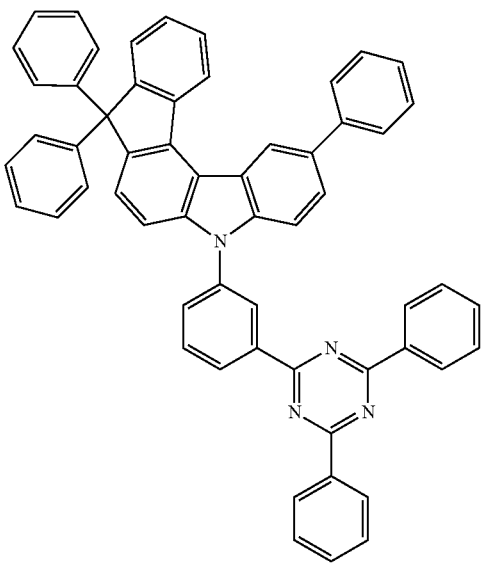
H2-455
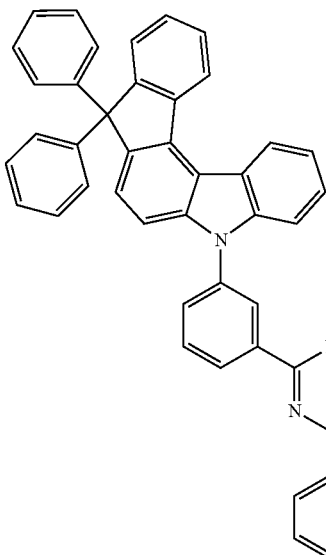
H2-453
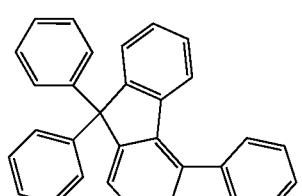
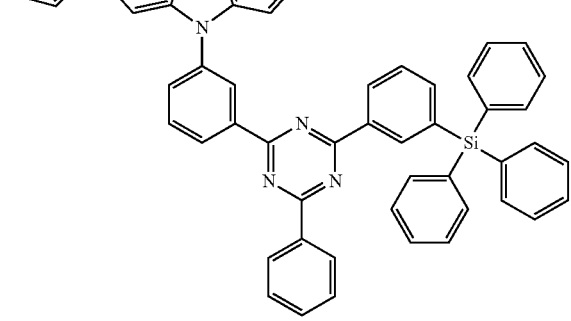
H2-456
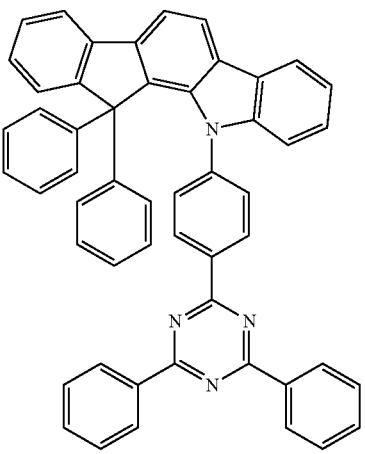
H2-454
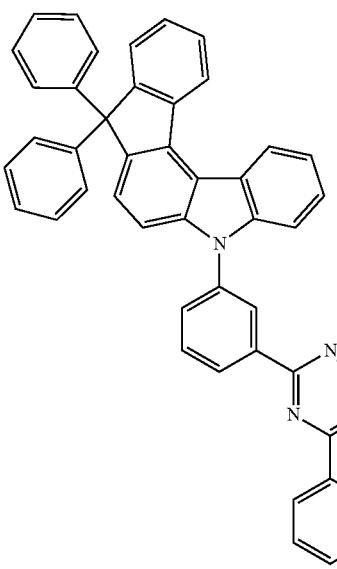
H2-457
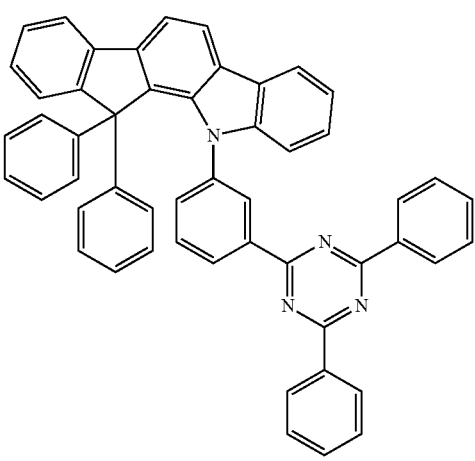

H2-458
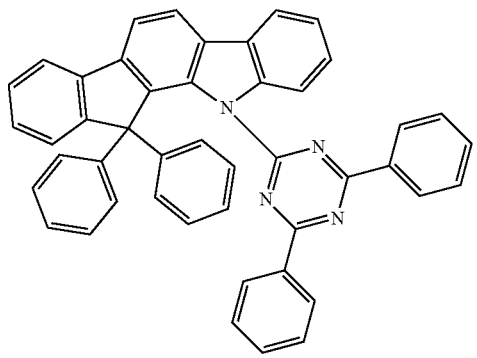
H2-459
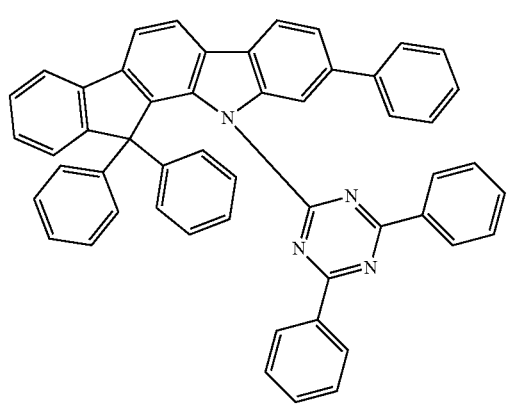
H2-460
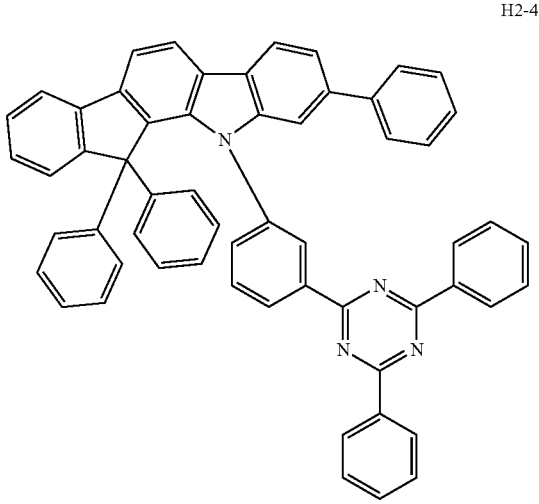
H2-461
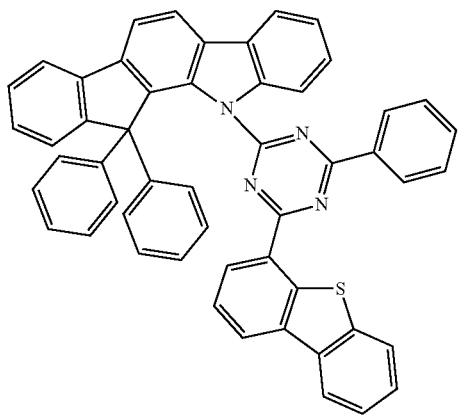
H2-462
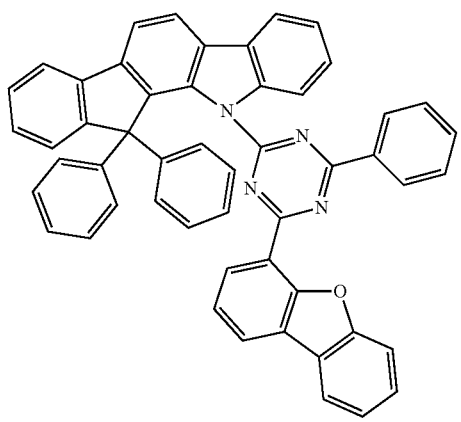
H2-463
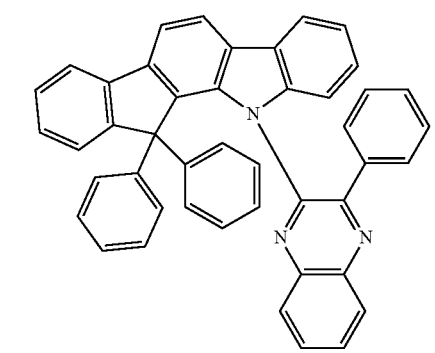
H2-464
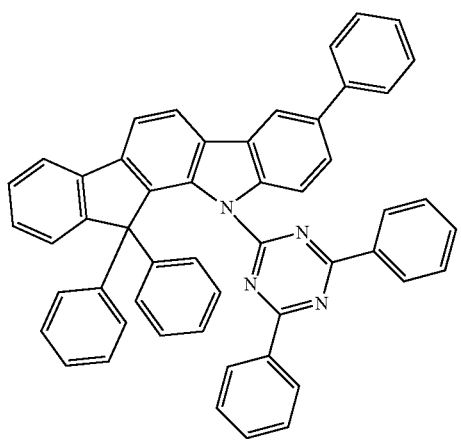

H2-465
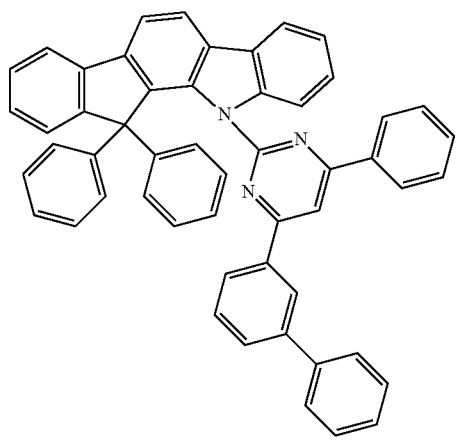
H2-468
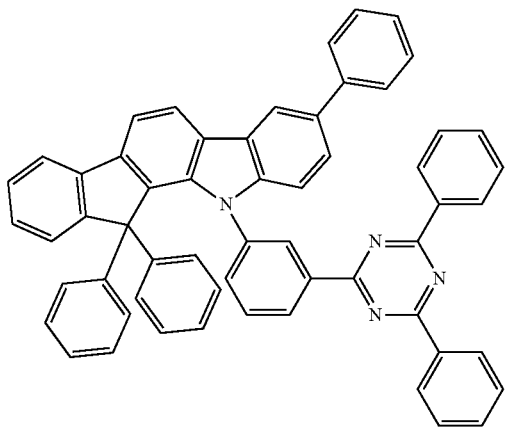
H2-466
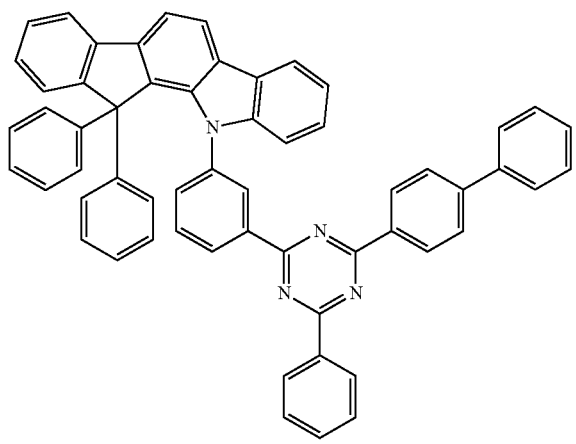
H2-469
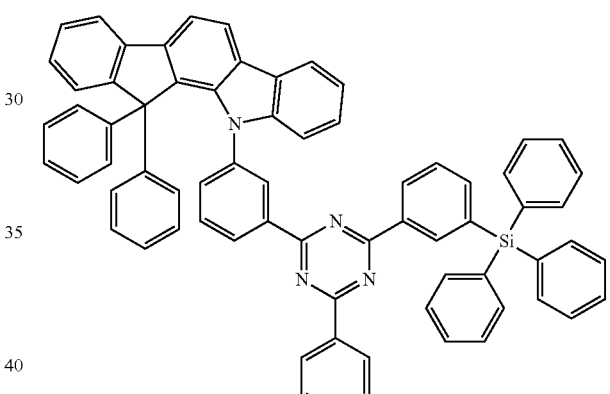
H2-467
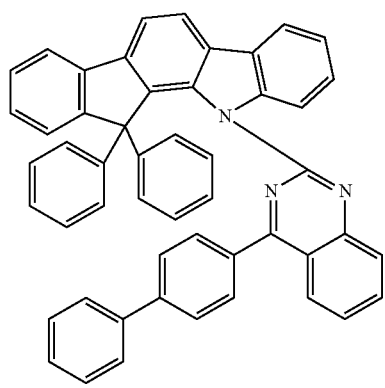
H2-470
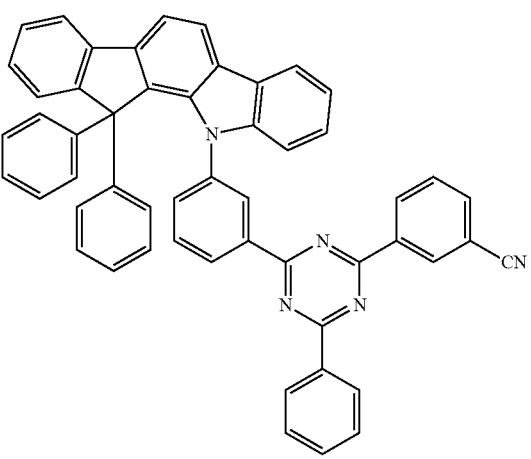

H2-471
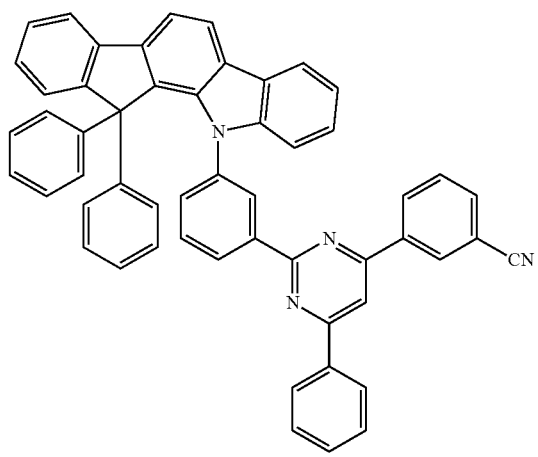
H2-472
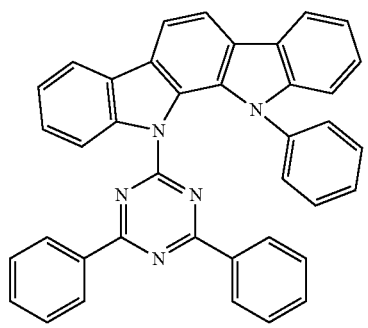
H2-473
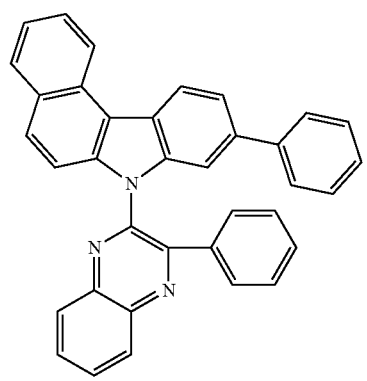
H2-474
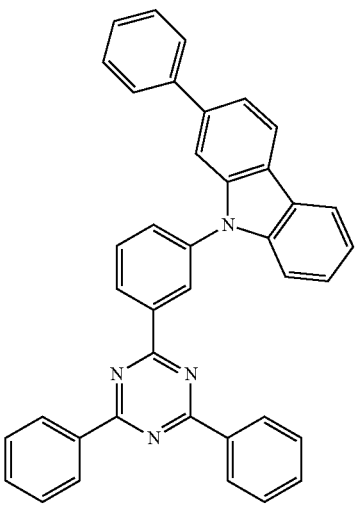
H2-475
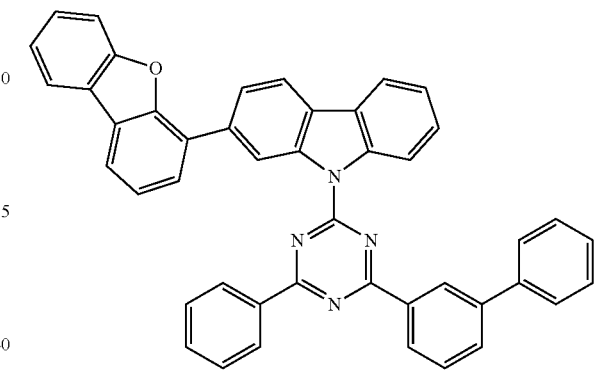
H2-476
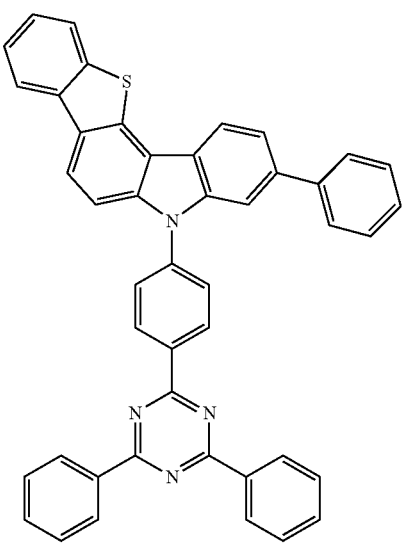

H2-477
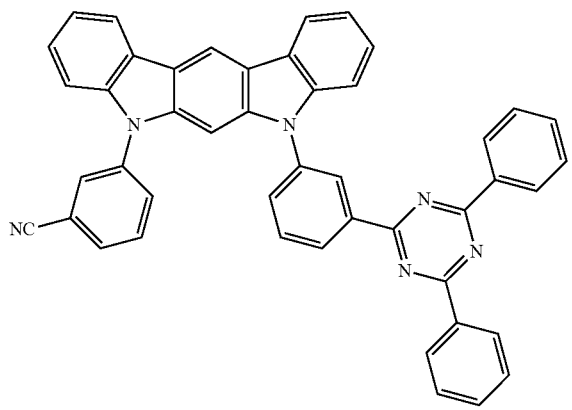
H2-480
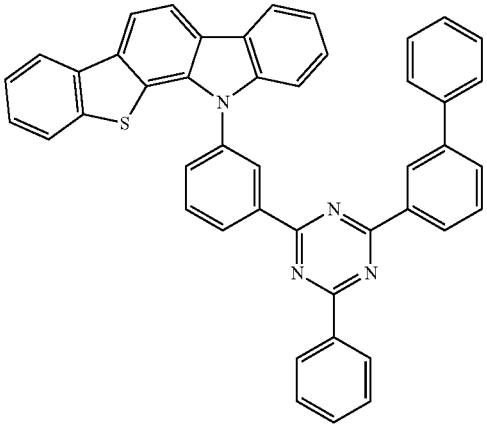
H2-478
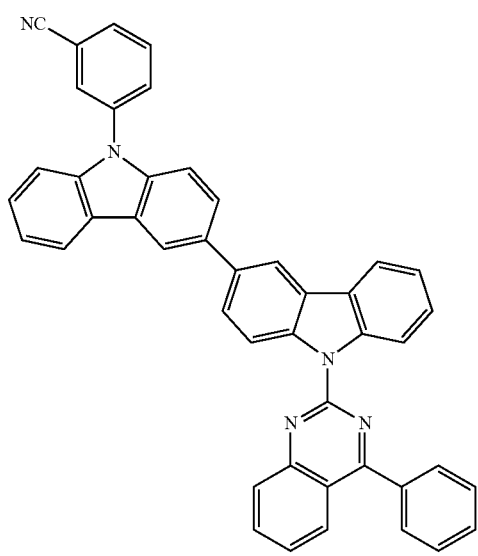
H2-481
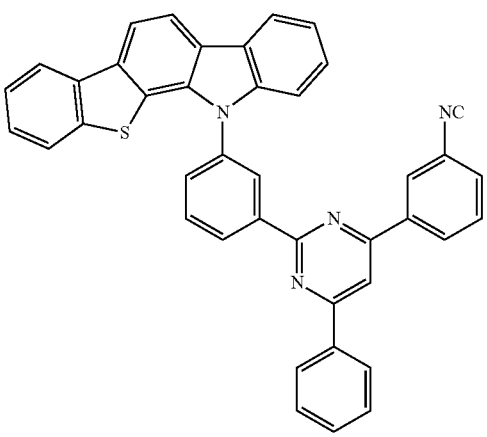
H2-479
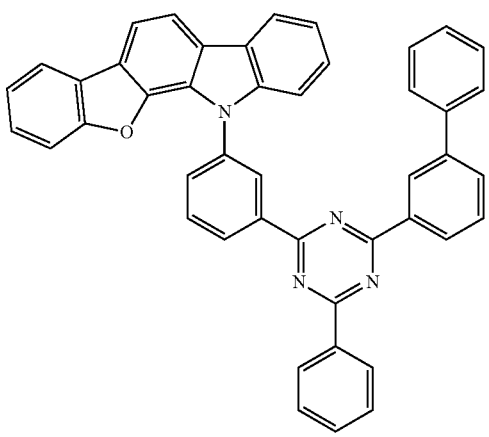
H2-482
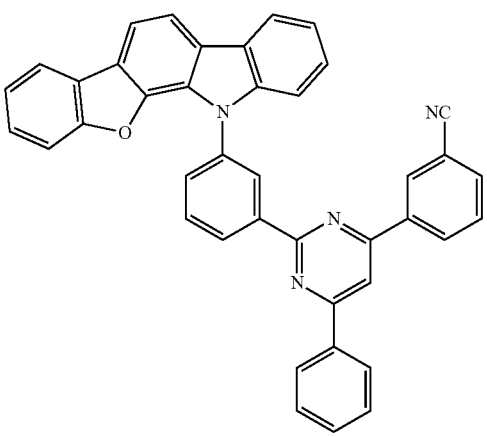

H2-483
H2-484
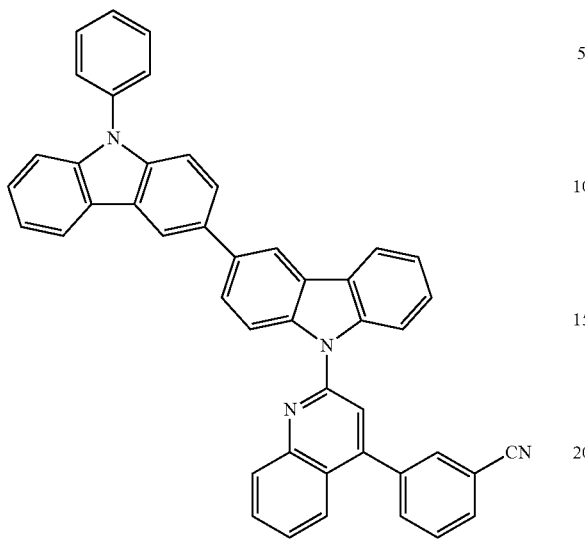
H2-486
H2-487
H2-488
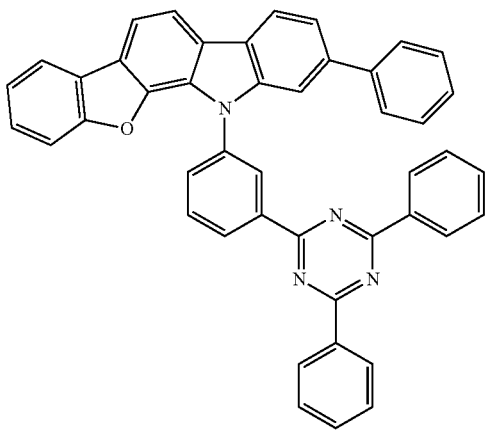
H2-485
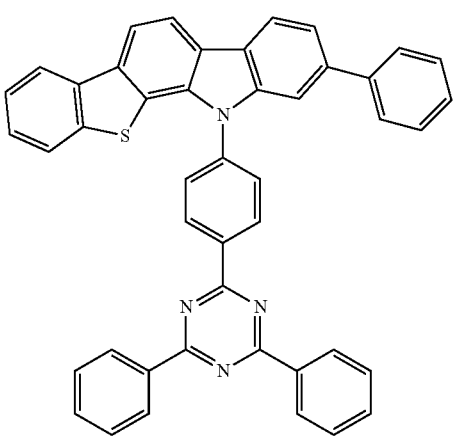
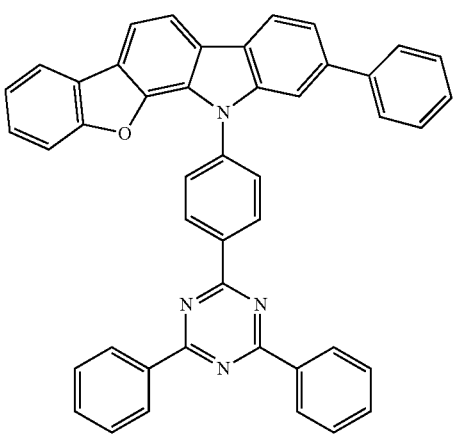

H2-489
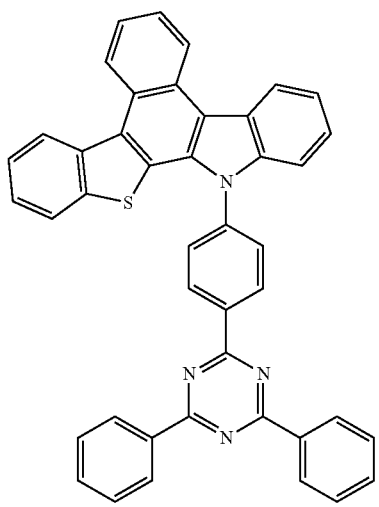
H2-492
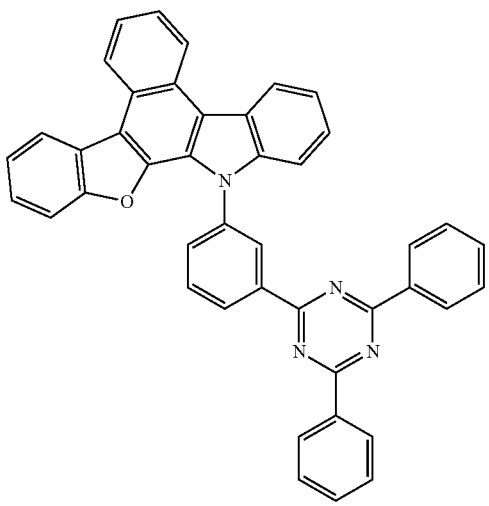
H2-490
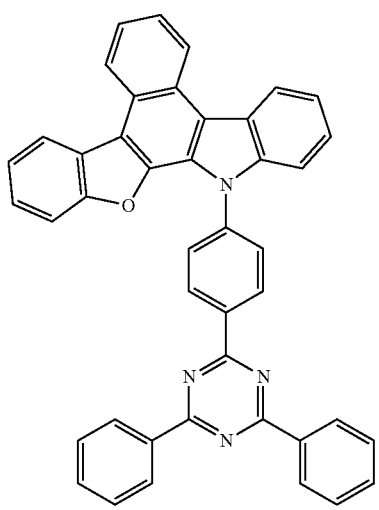
H2-493
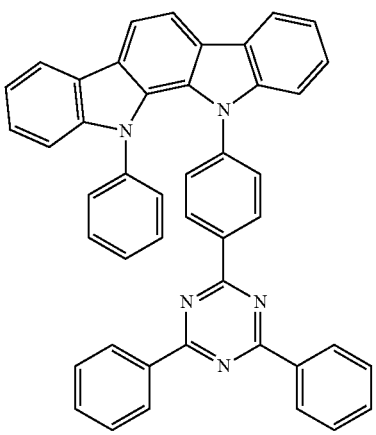
H2-491
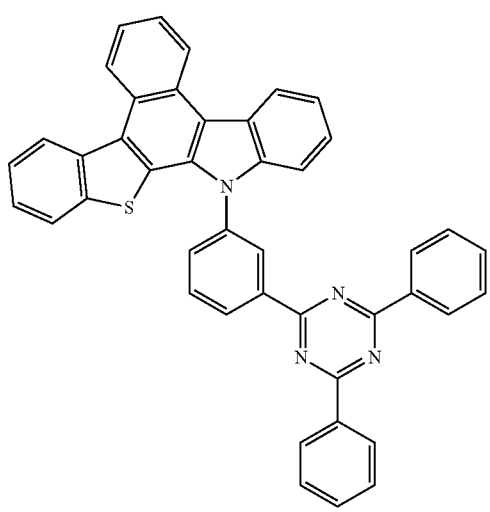
H2-494
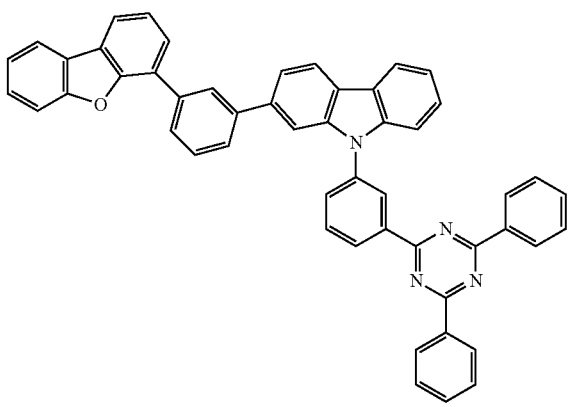
and H2-495
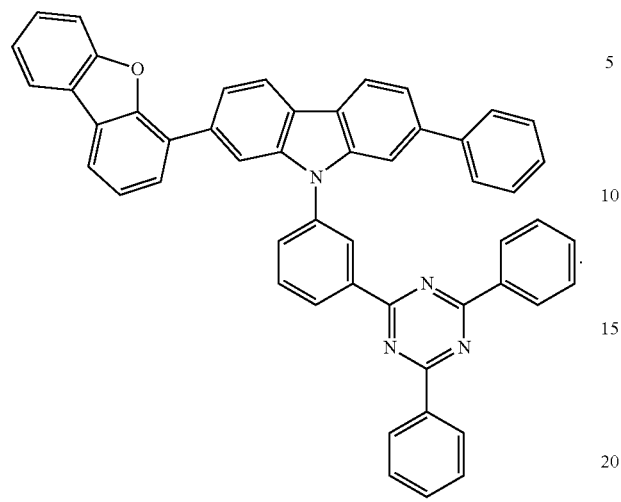

The invention claimed is:
1. An organic electroluminescent device comprising at least one light-emitting layer between an anode and a cathode, wherein the light-emitting layer comprises a host and a phosphorescent dopant; the host comprises plural host compounds; at least a first host compound of the plural host compounds is represented by the following formula 1; and a second host compound is represented by the following formula 2,

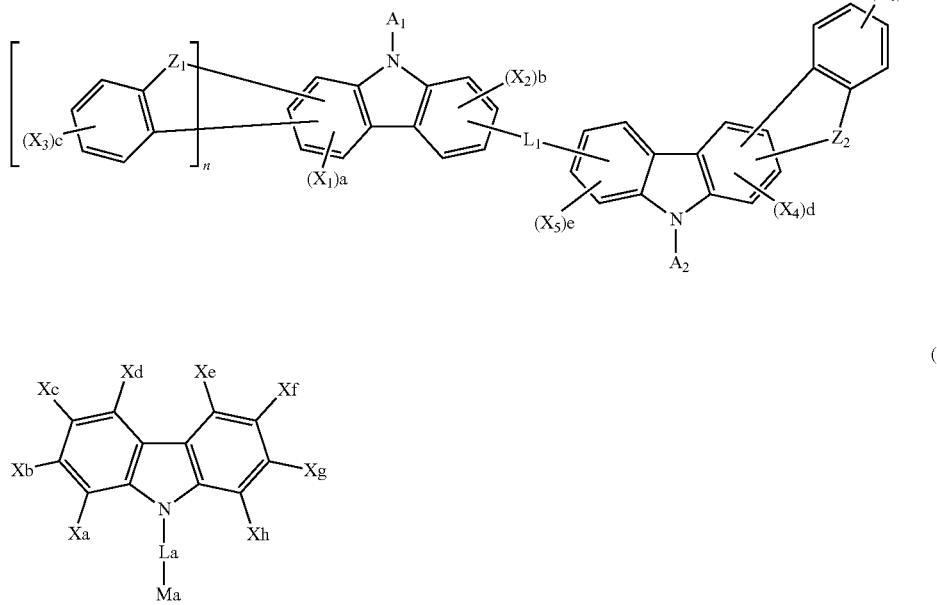

wherein
$A_1$ and $A_2$ each independently represent a substituted or unsubstituted (C6-C30)aryl;
n represents an integer of 0 or 1;
where n is 1, a 5-membered ring including $Z_1$ is fused with the phenyl ring of carbazole;
a 5-membered ring including $Z_2$ is fused with the phenyl ring of carbazole;
$L_1$ and La each independently represent a single bond, or a substituted or unsubstituted (C6-C30)arylene;
$Z_1$ and $Z_2$ each independently represent $CR_1R_2$, $NR_3$, O, or S;
$X_1$ to $X_6$, and $R_1$ to $R_3$ each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur;
Ma represents a substituted or unsubstituted 5- to 30-membered nitrogen-containing heteroaryl;
Xa to Xh each independently represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted mono- or polycyclic, (C3-C30) alicyclic or aromatic ring, whose carbon atom(s) may be replaced with at least one hetero atom selected from nitrogen, oxygen, and sulfur;
a and d each independently represent an integer of 1 to 2, b and e each independently represent an integer of 1 to 3, c and f each independently represent an integer of 1 to 4, where a, b, c, d, e, or f is an integer of 2 or more, each of $X_1$, each of $X_2$, each of $X_3$, each of $X_4$, each of $X_5$, and each of $X_6$ may be the same or different; and
the heteroaryl contains at least one hetero atom selected from B, N, O, S, Si, and P.
2. The organic electroluminescent device according to claim 1, wherein formula 1 is represented by one of the following formulas 3 to 6:

(3)
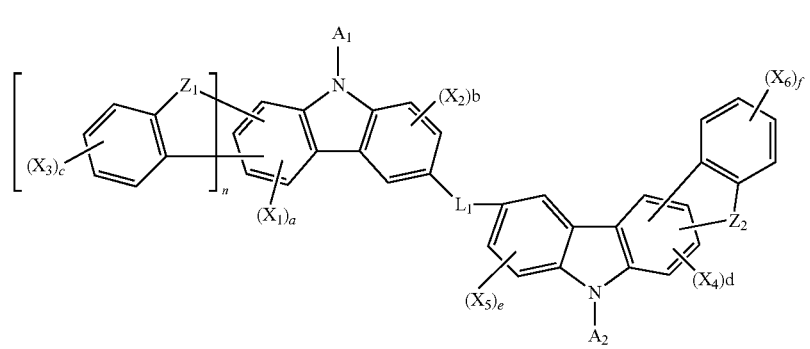
(4)
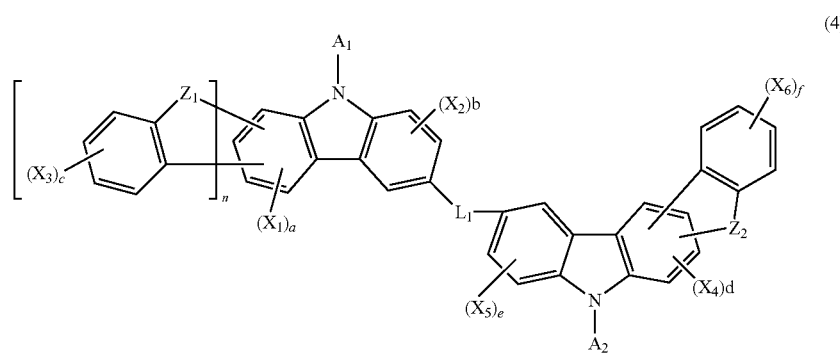
(5)
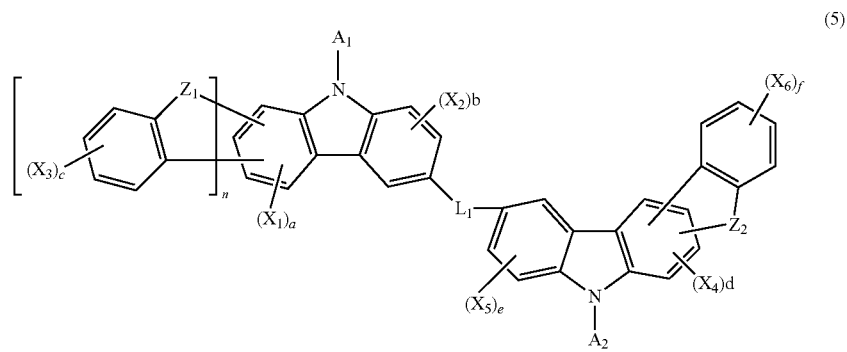
(6)
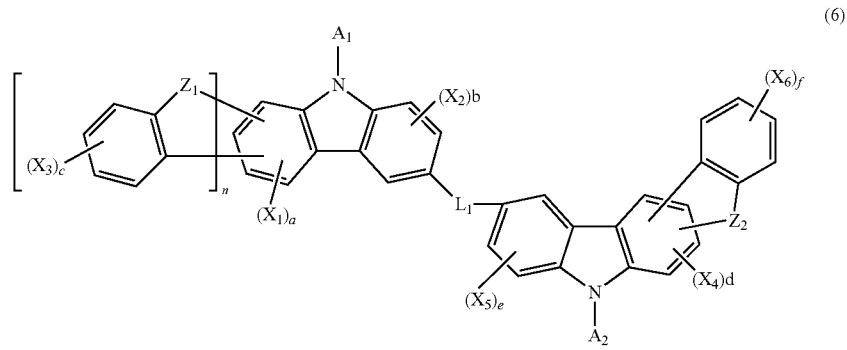

wherein
$A_1$, $A_2$, $Z_1$, $Z_2$, $L_1$, $X_1$ to $X_6$, and a to f are as defined in claim 1.
3. The organic electroluminescent device according to claim 1, wherein formula 1 is represented by one of the following formulas 7 to 36:
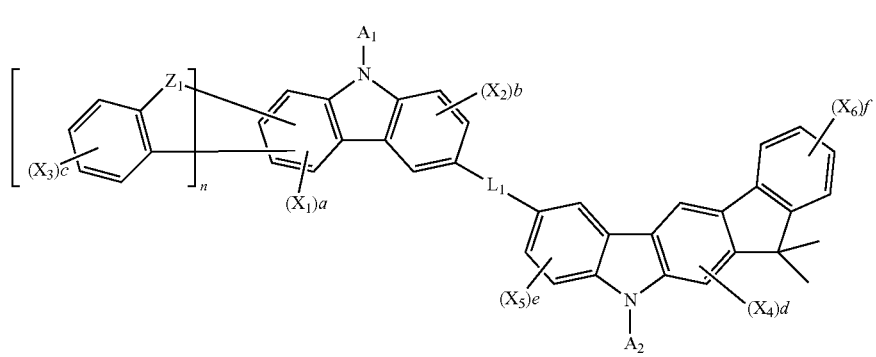
(7)
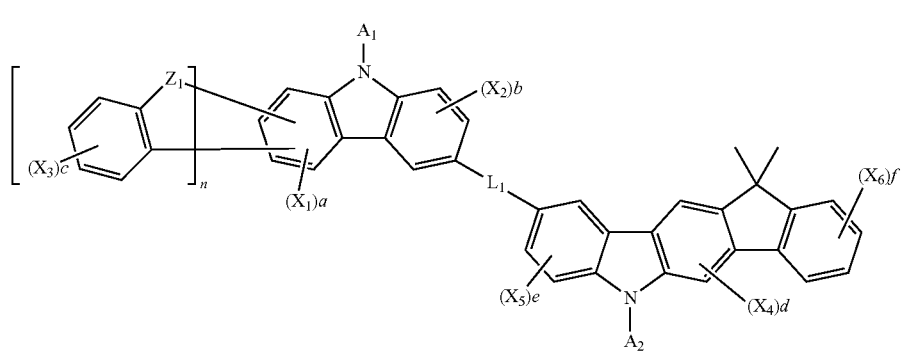
(8)
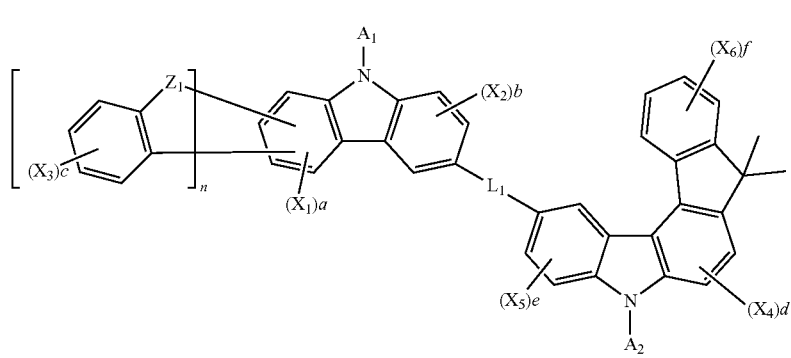
(9)
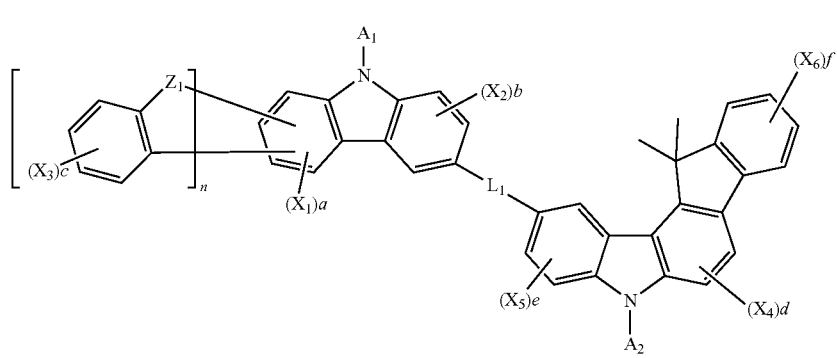
(10)

(11)
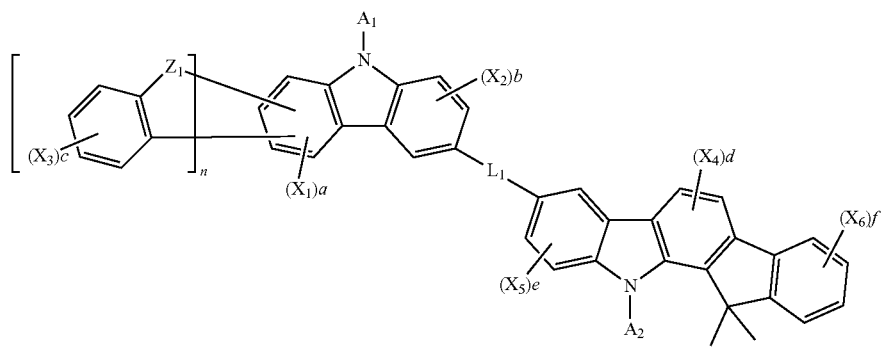
(12)
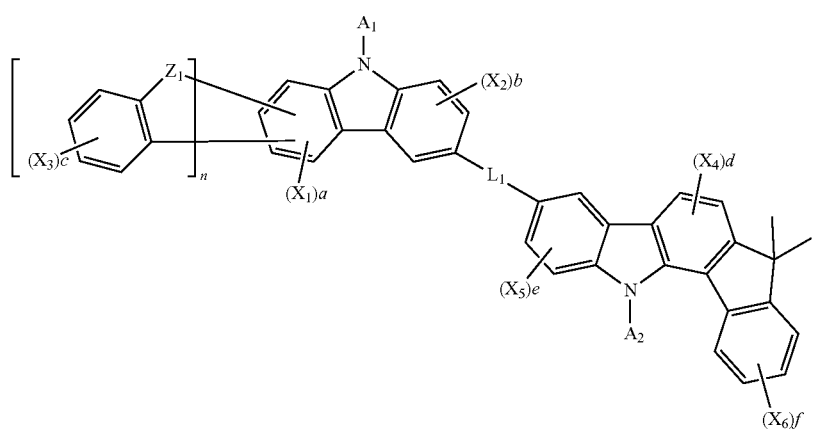
(13)
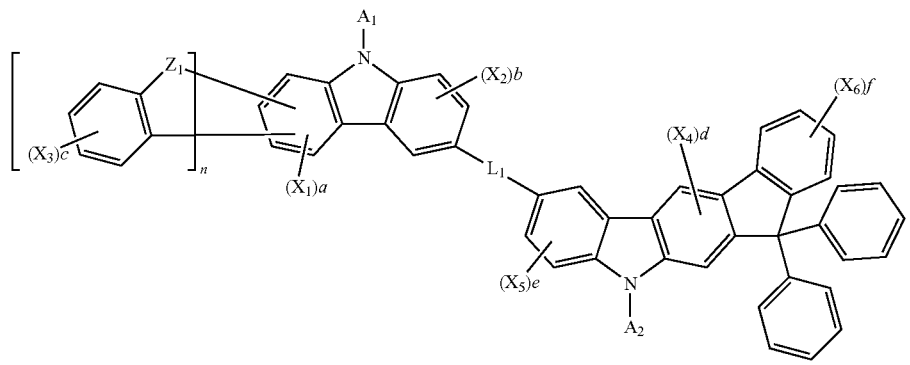
(14)
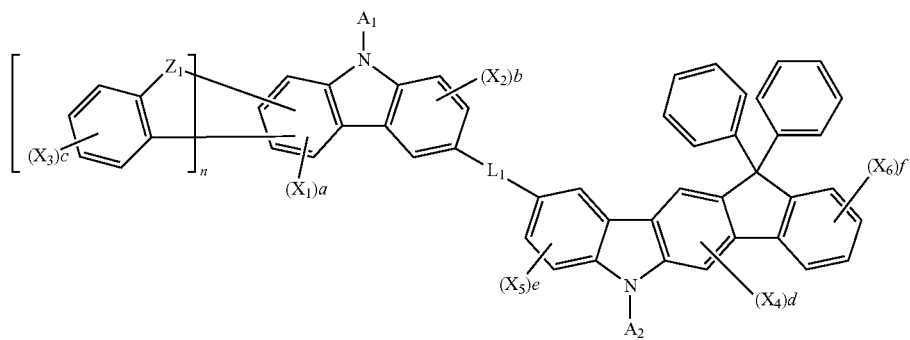

(15)
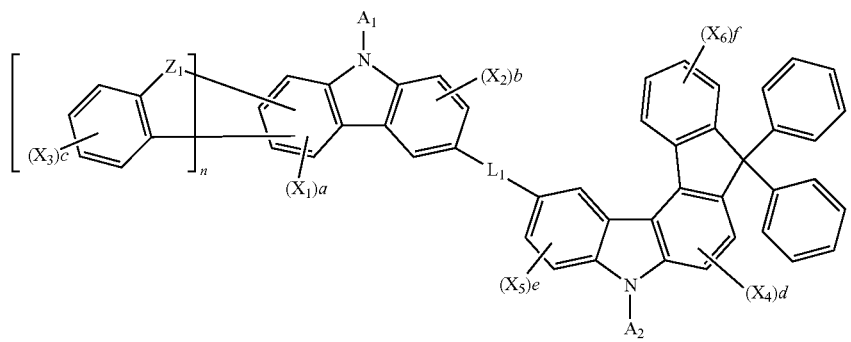
(16)
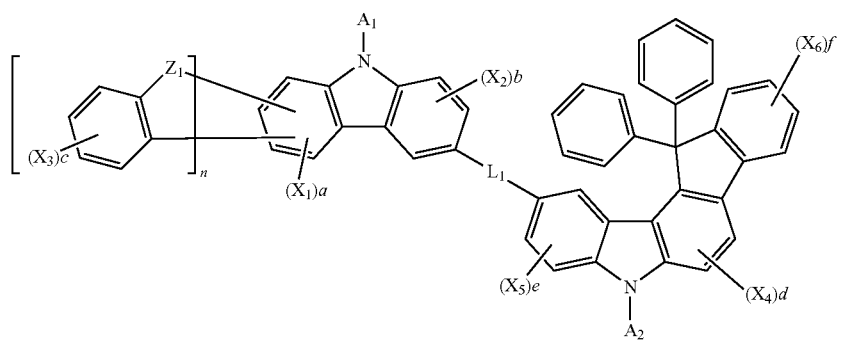
(17)
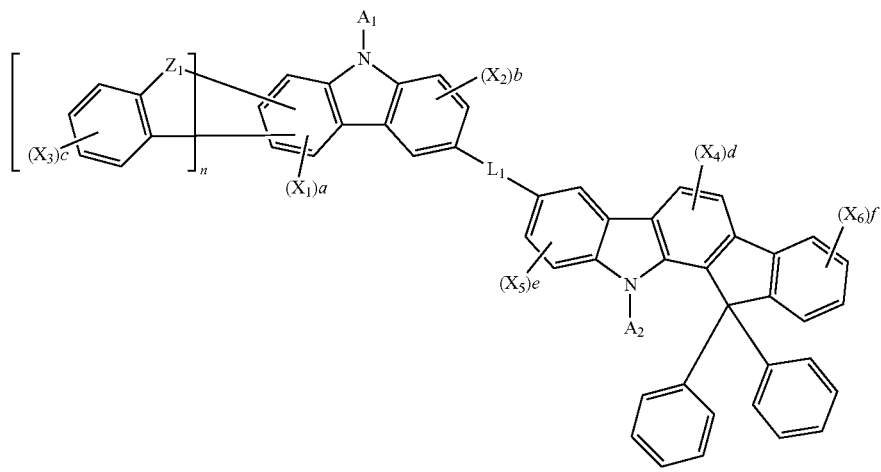
(18)
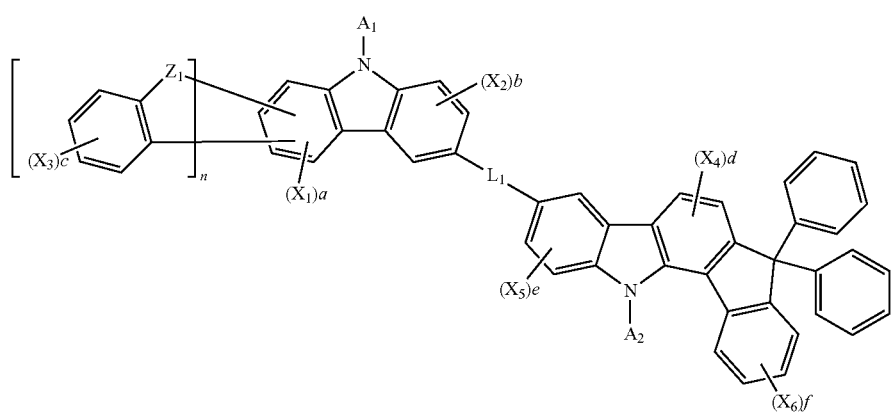

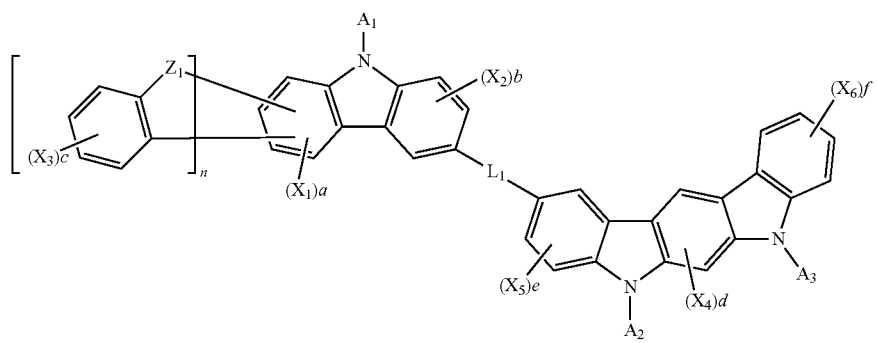
(19)
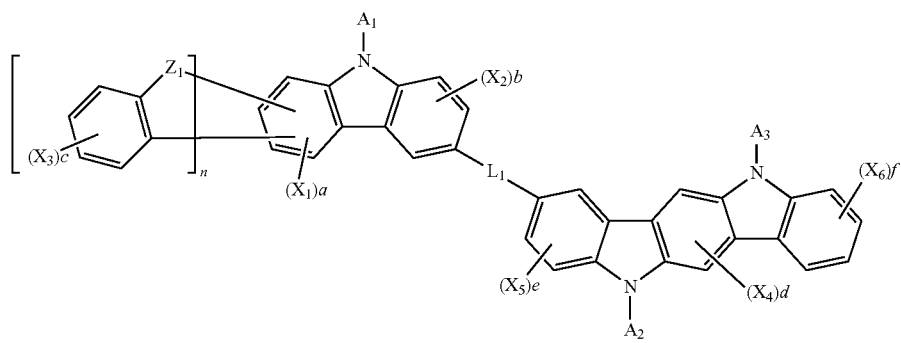
(20)
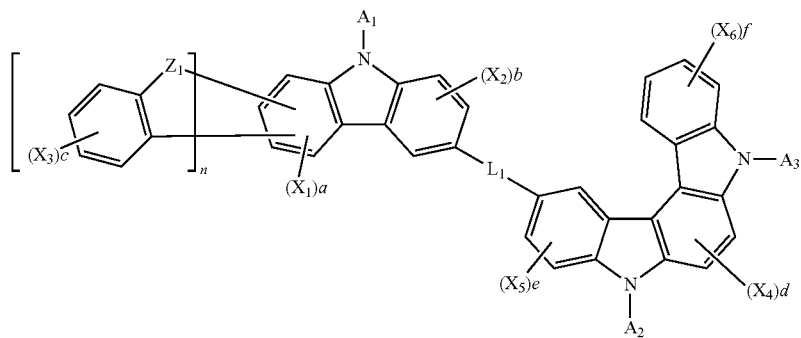
(21)
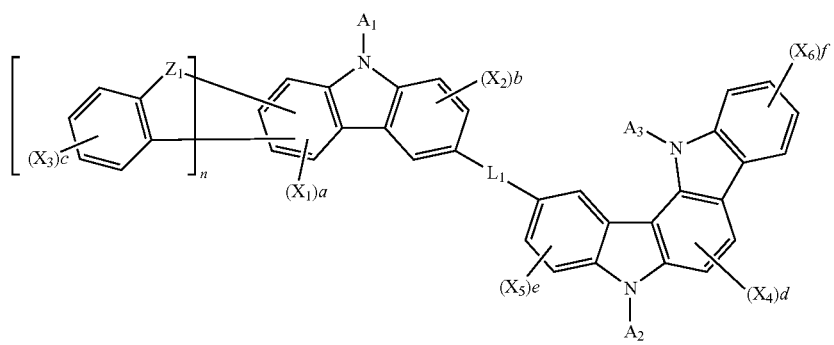
(22)

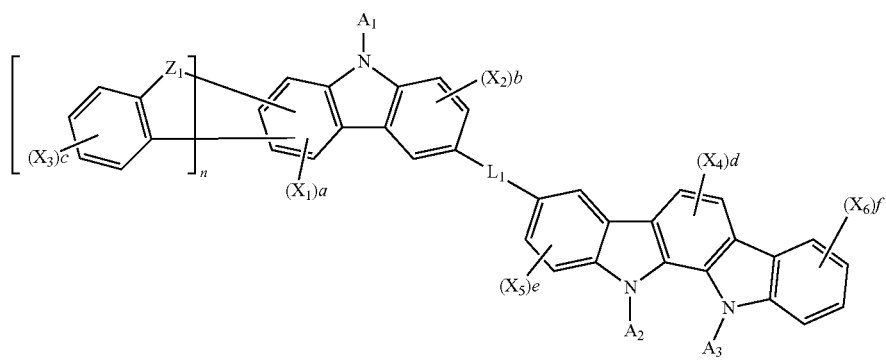
(23)
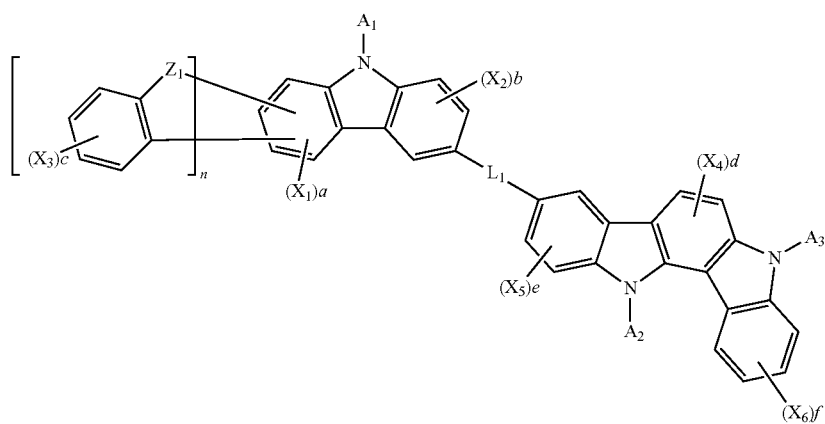
(24)
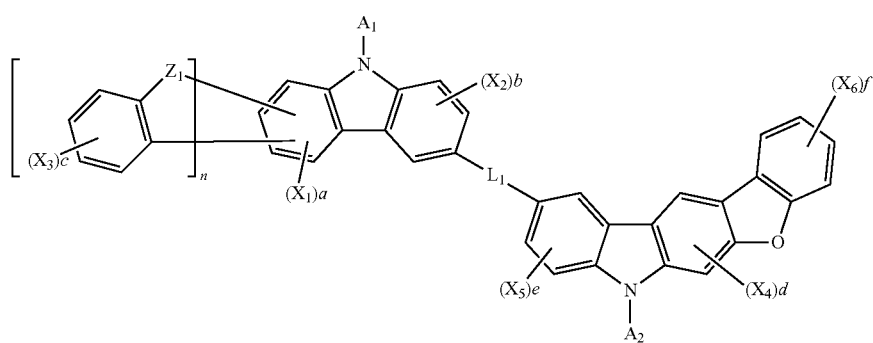
(25)
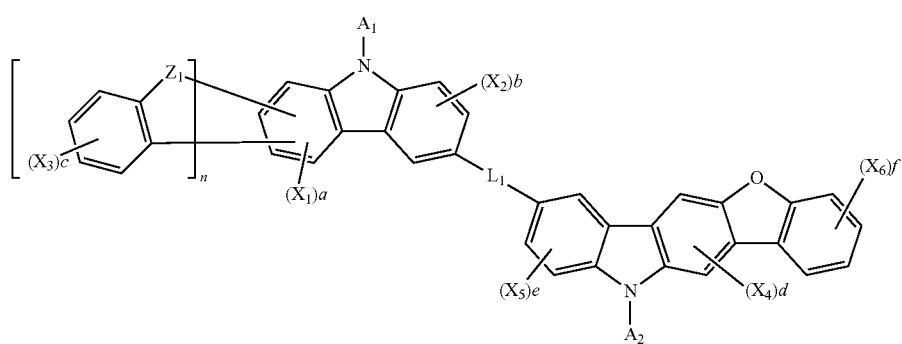
(26)

-continued
(27)
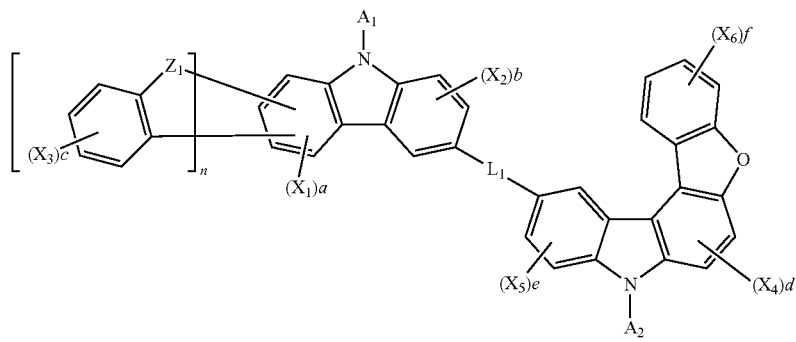
(28)
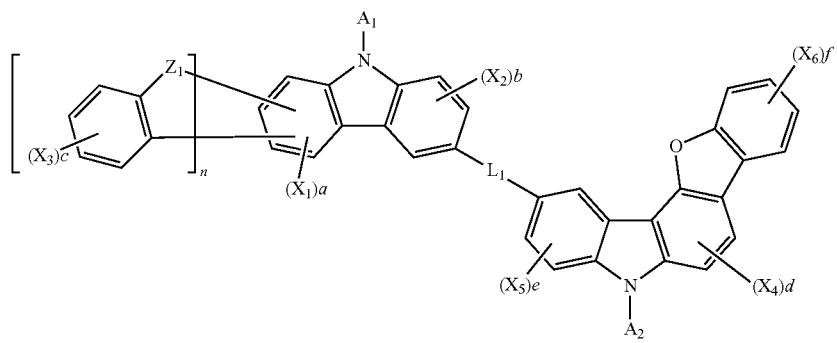
(29)
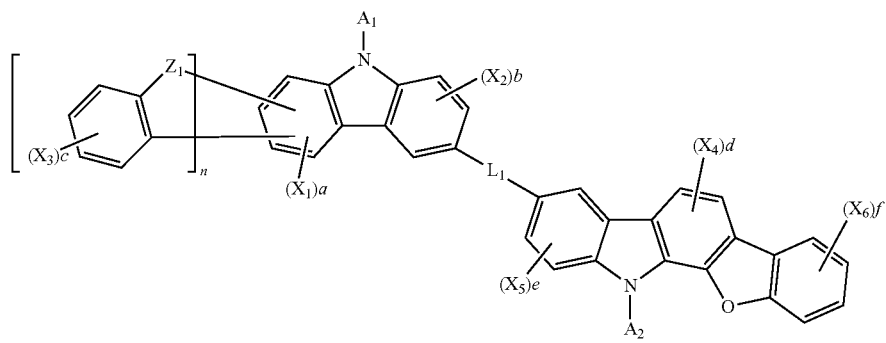
(30)
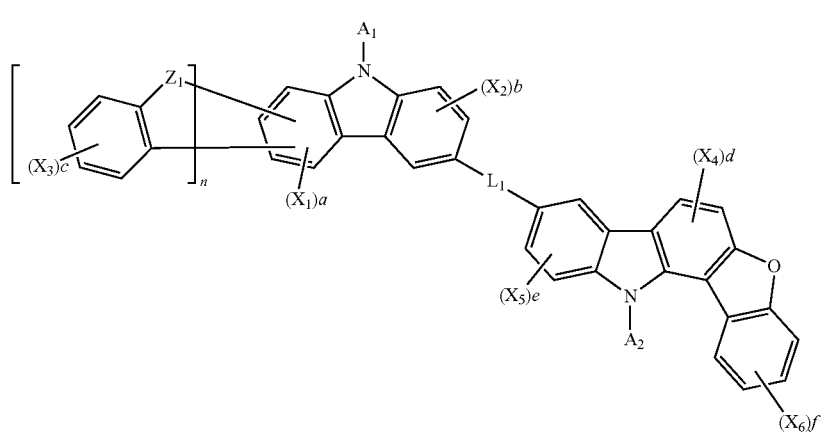

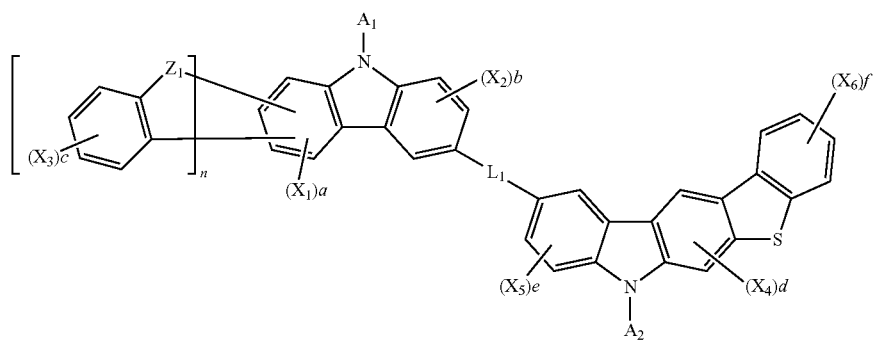
(31)
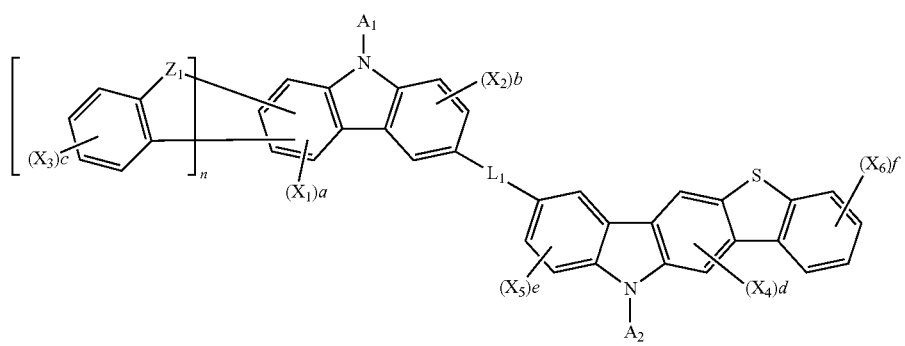
(32)
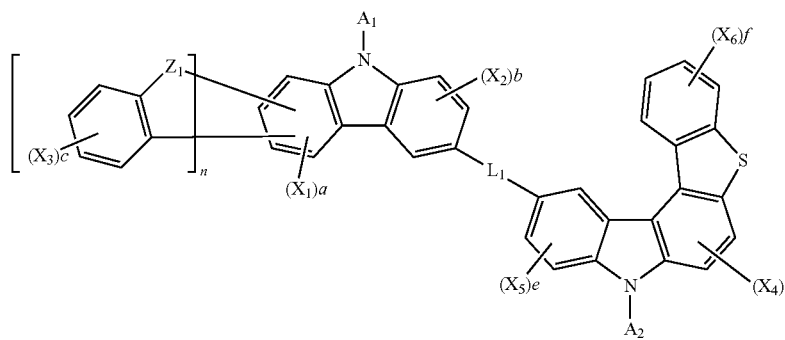
(33)
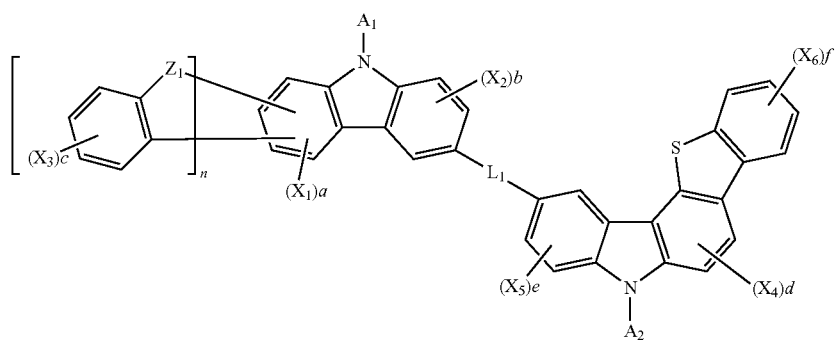
(34)

-continued
(35)
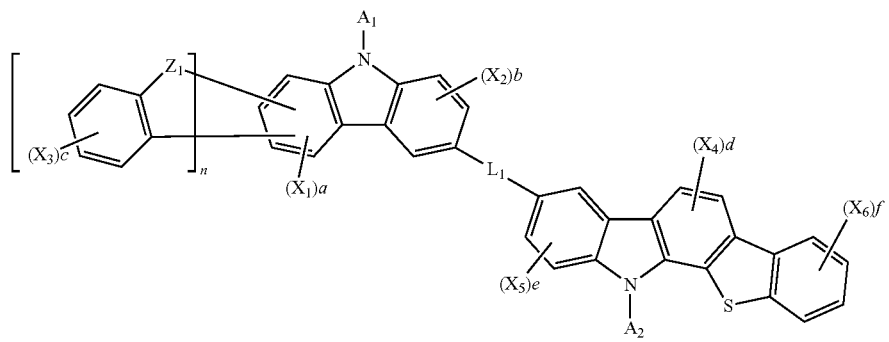
(36)
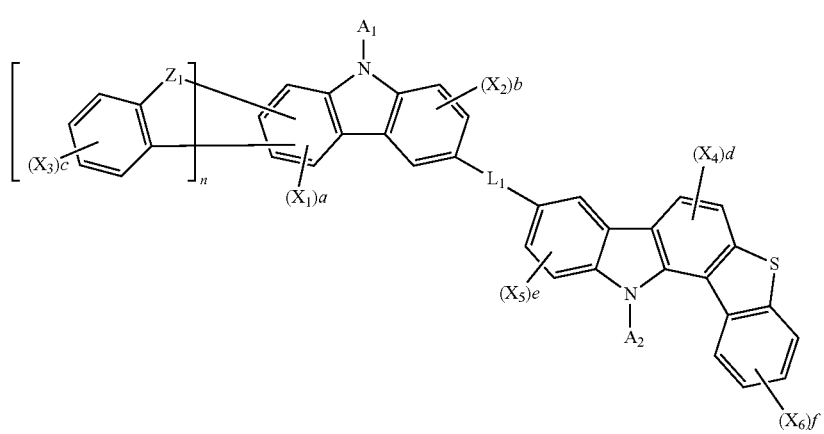
wherein
$A_1, A_2, Z_1, L_1, X_1$ to $X_b$, and a to f are as defined in claim 1.
4. The organic electroluminescent device according to claim 1, wherein in formulas 1 and 2, $L_1$ and La each independently represent a single bond, or one of the following formulas 37 to 49:
(37)
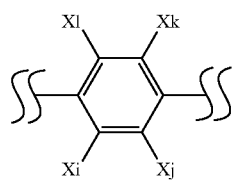
(38)
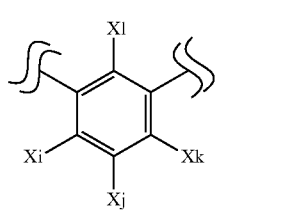
(39)
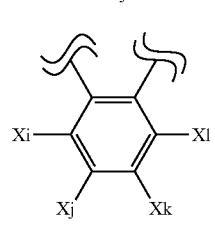
-continued
(40)
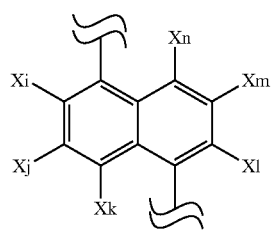
(41)
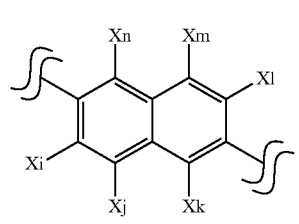
(42)

-continued

(43) 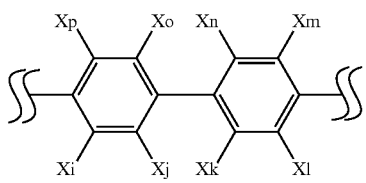

(44) 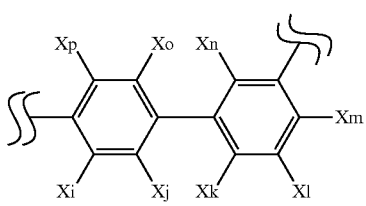

(45) 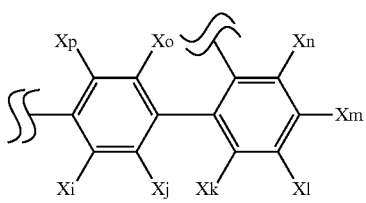

(46) 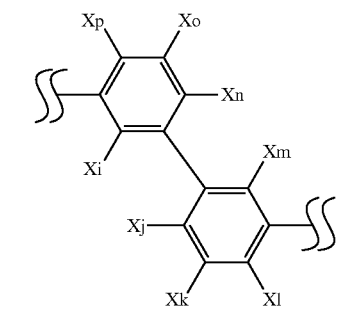

(47) 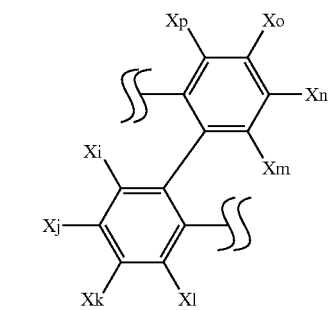

(48) 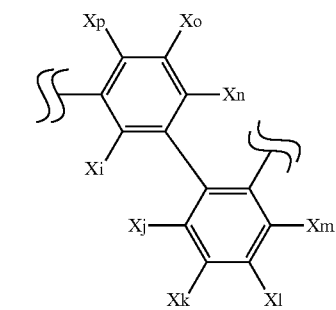

-continued

(49) 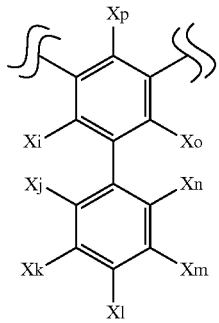

wherein
Xi to Xp each independently represent hydrogen, deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi (C6-C30)arylsilyl, a substituted or unsubstituted mono- or di-(C1-C30)alkylamino, or a substituted or unsubstituted mono- or di-(C6-C30)arylamino; or adjacent substituents may be linked to each other to form a substituted or unsubstituted, mono- or polycyclic, (C3-C30) alicyclic or aromatic ring, whose carbon atom(s) may be replaced with at least one hetero atom selected from nitrogen, oxygen, and sulfur.

5. The organic electroluminescent device according to claim 1, wherein in formula 1,
$A_1$ and $A_2$ each independently represent phenyl, biphenyl, terphenyl, naphthyl, naphthylphenyl, fluorenyl, phenanthrenyl, anthracenyl, indenyl, triphenylenyl, pyrenyl, tetracenyl, perylenyl, chrysenyl, naphthacenyl, or fluoranthenyl.

6. The organic electroluminescent device according to claim 1, wherein in formula 1,
$X_1$ to $X_6$, and $R_1$ to $R_3$ each independently represent hydrogen, a substituted or unsubstituted (C6-C18)aryl, an unsubstituted triphenylsilyl, a substituted or unsubstituted dibenzothiophene, or a substituted or unsubstituted dibenzofuran.

7. The organic electroluminescent device according to claim 1, wherein in formula 2,
Ma represents a monocyclic ring-type heteroaryl selected from the group consisting of a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, and a substituted or unsubstituted pyridazinyl, or a fused ring-type heteroaryl selected from the group consisting of a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, a substituted or unsubstituted quinoxalinyl, a substituted or unsubstituted carbazolyl, and a substituted or unsubstituted phenanthridinyl.

8. The organic electroluminescent device according to claim 1, wherein in formula 2,
Xa to Xh each independently represent hydrogen; a cyano; a (C6-C15)aryl unsubstituted or substituted with a 10- to 20-membered heteroaryl or a tri(C6-C10)arylsilyl; a 10- to 20-membered heteroaryl unsubstituted or substituted with a (C6-C12)aryl or a cyano (C6-C12)aryl; or an unsubstituted tri(C6-C10)arylsilyl; or adjacent substituents may be linked to each other to form a substituted or unsubstituted benzene, a substituted or unsubstituted indole, a substituted or unsubstituted benzoindole, a substituted or unsubstituted indene, a substituted or unsubstituted benzofuran, or a substituted or unsubstituted benzothiophene.

9. The organic electroluminescent device according to claim 1, wherein the compound represented by formula 1 is selected from the group consisting of:

F-1

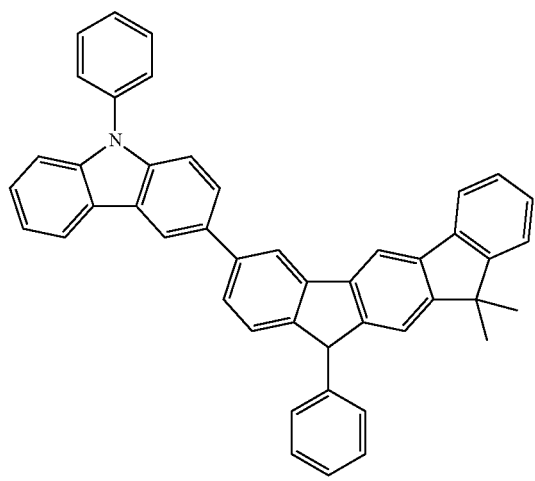

F-2

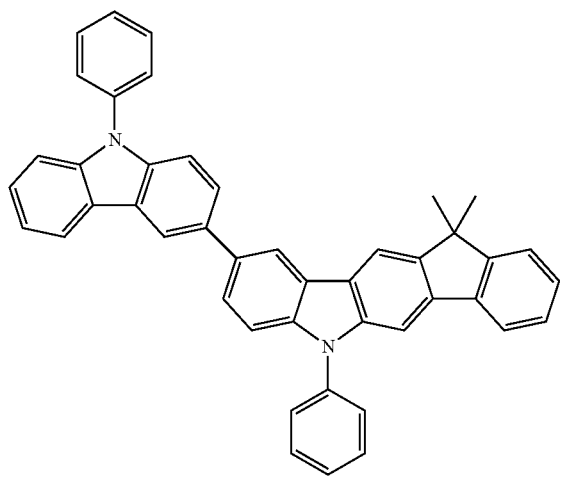

F-3

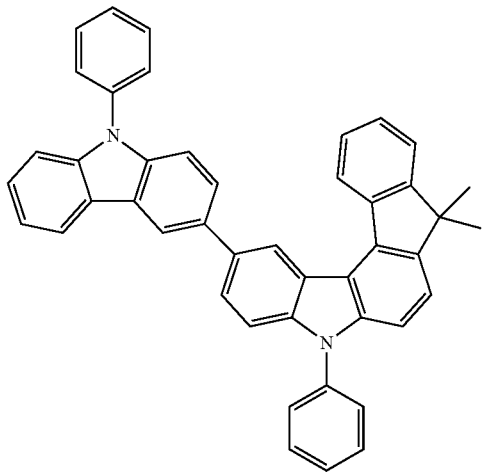

F-4

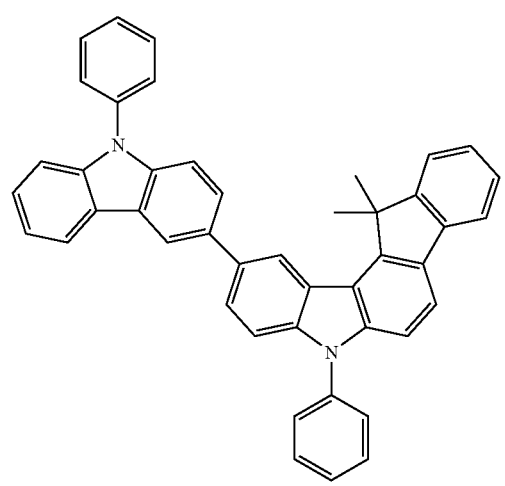

F-5

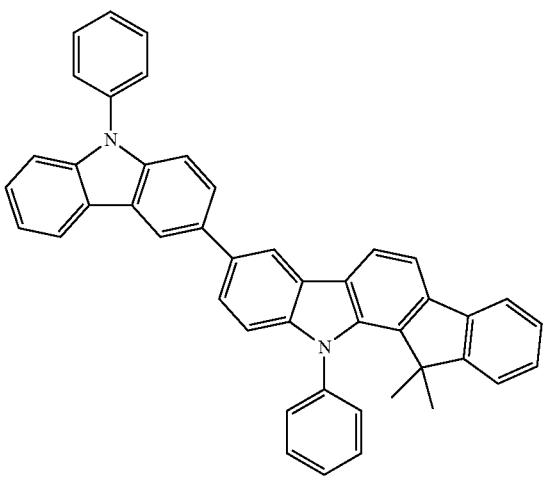

F-6
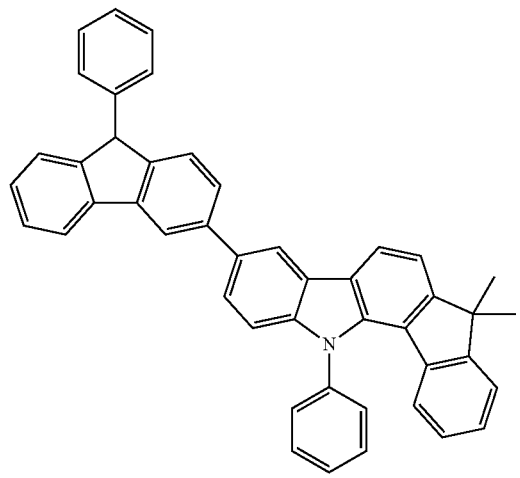
F-9
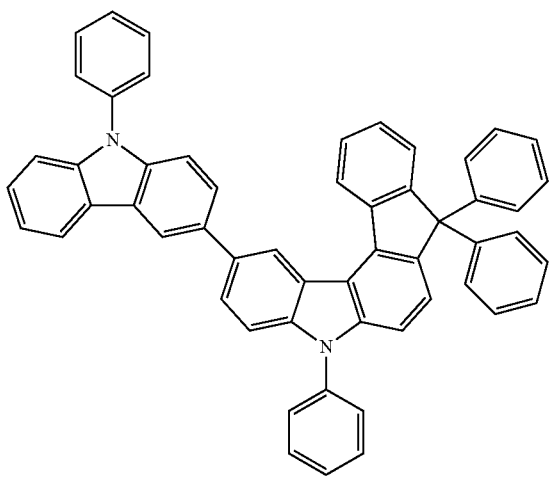
F-7
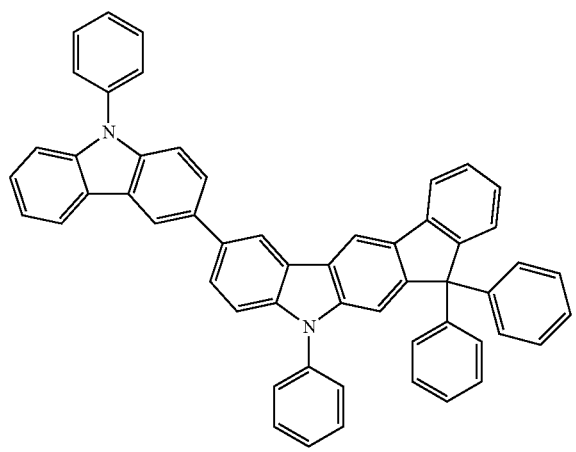
F-10
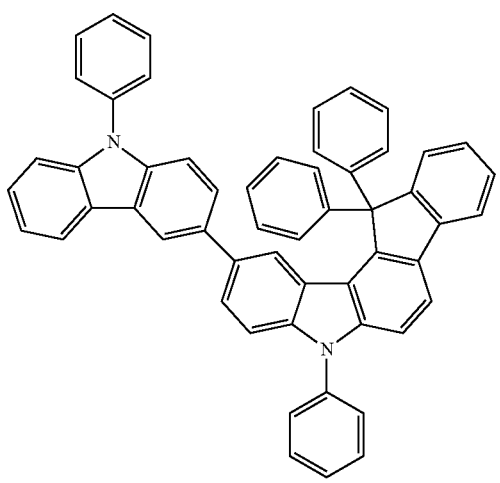
F-8
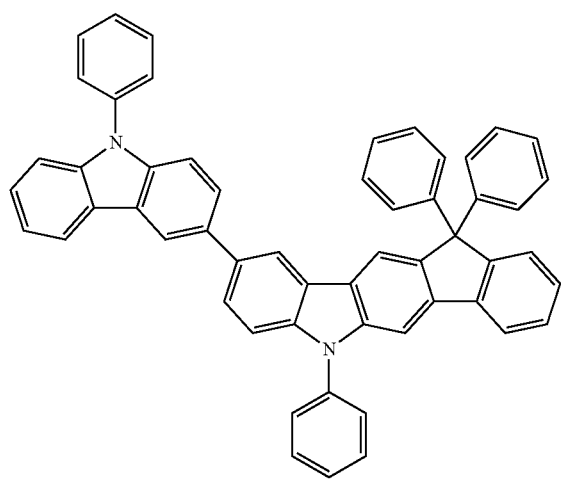
F-11
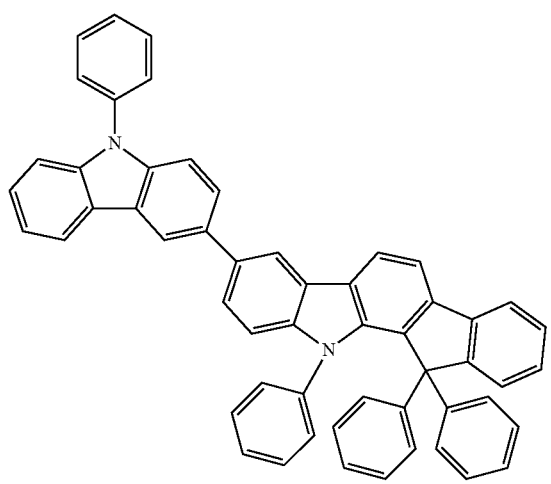

-continued
F-12
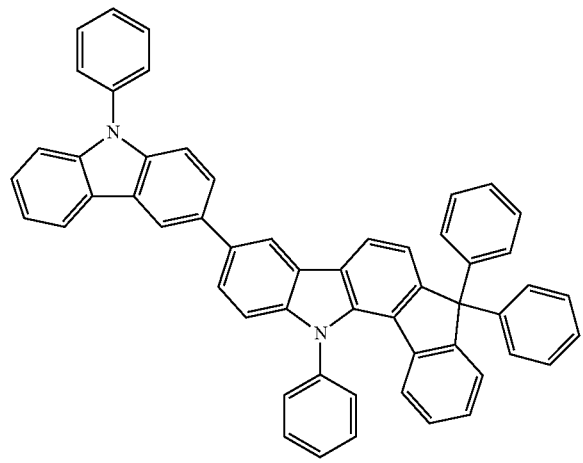
F-13
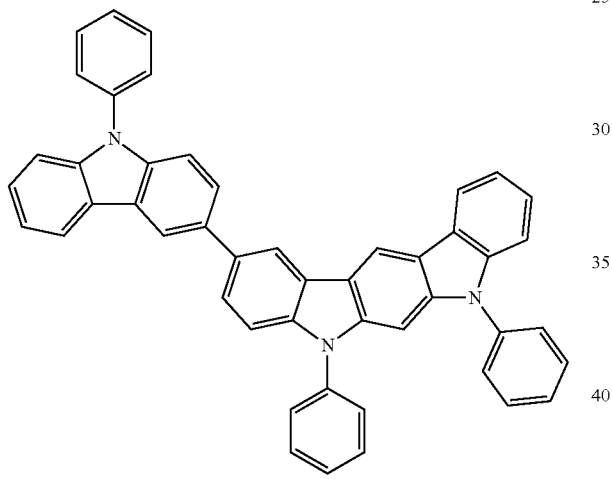
F-14
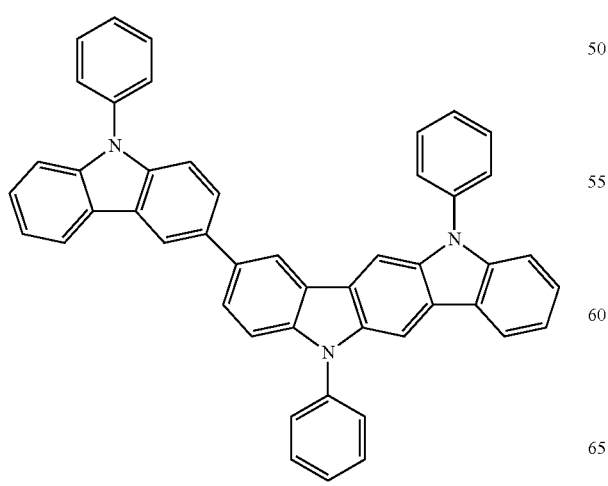
-continued
F-15
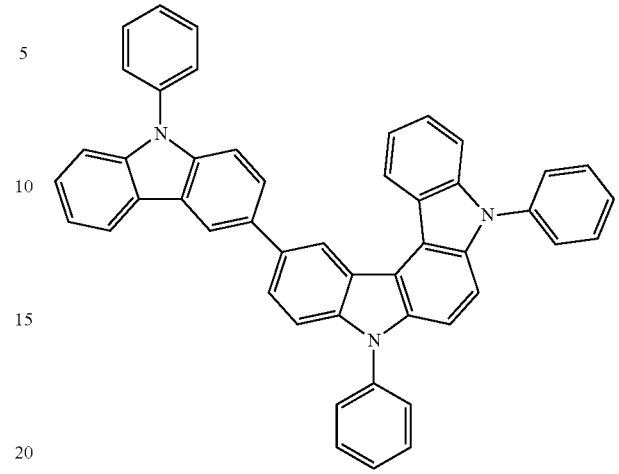
F-16
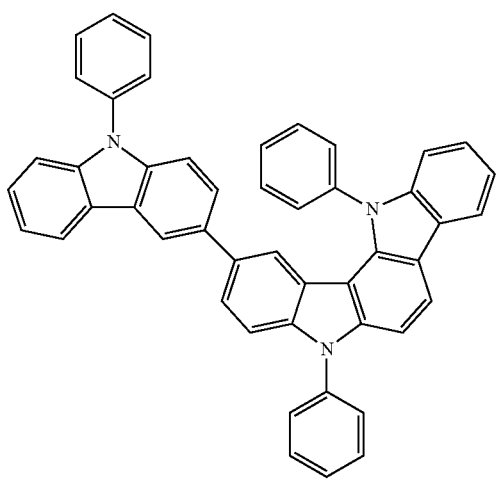
F-17
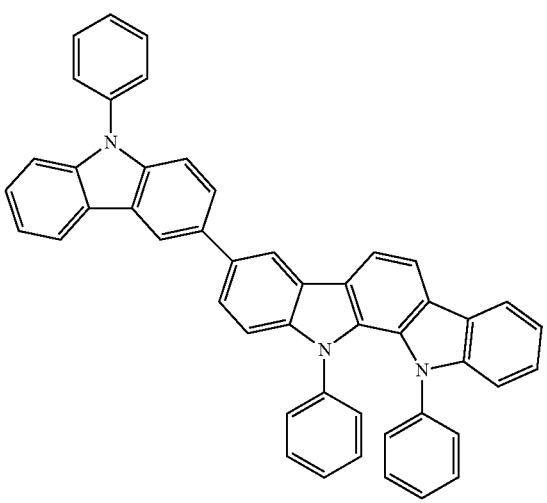

F-18
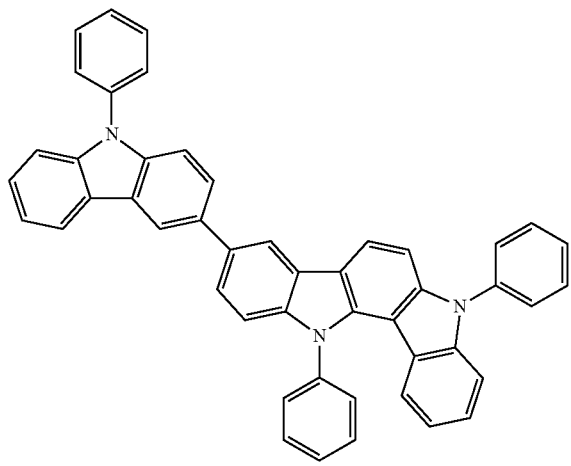
F-21
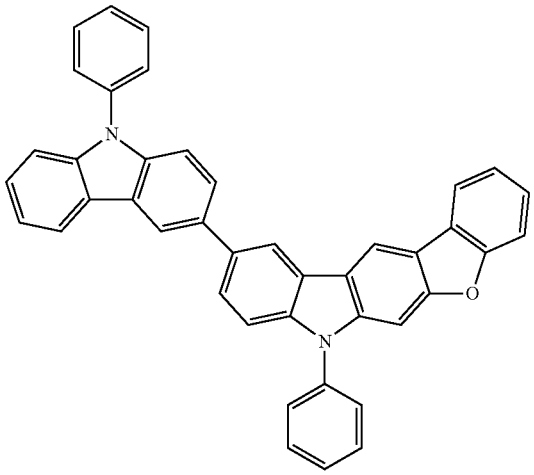
F-19
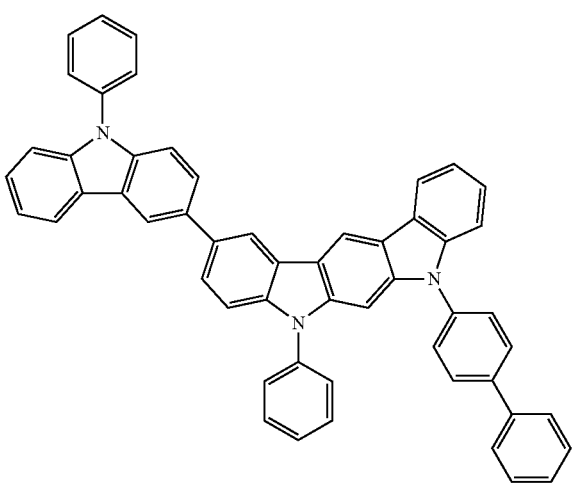
F-22
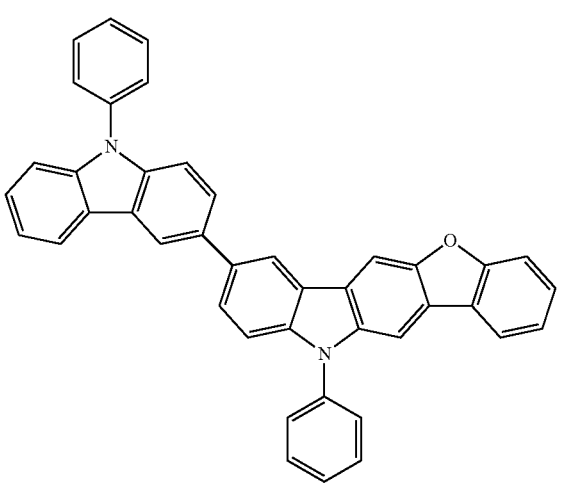
F-20
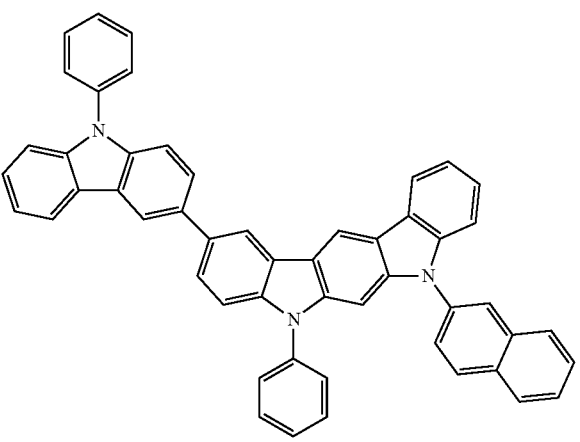
F-23
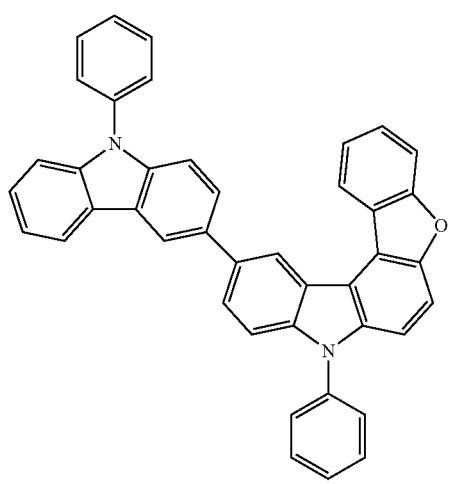

F-24
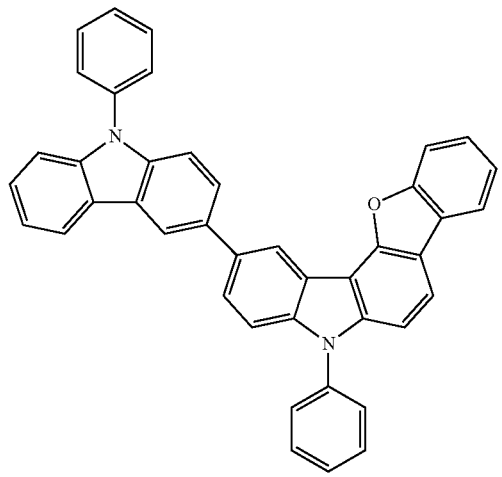
F-27
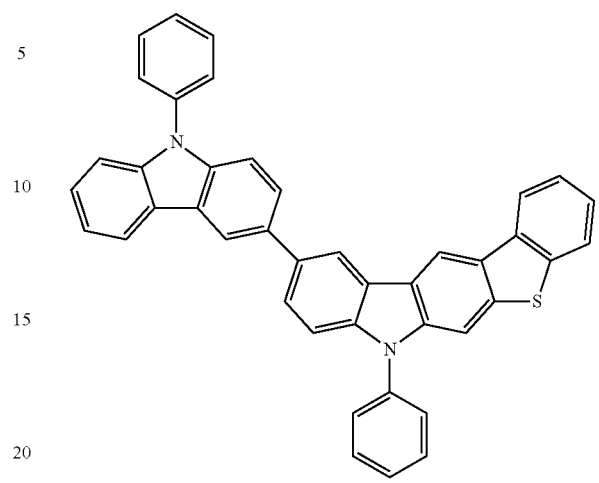
F-25
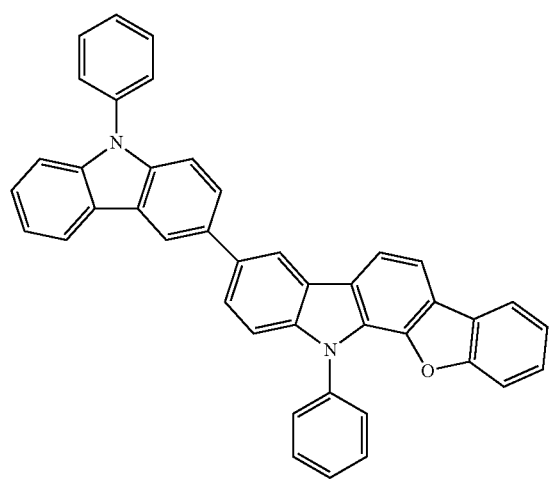
F-28
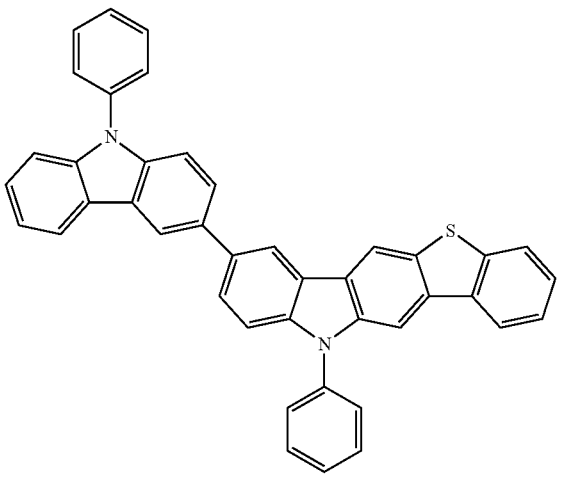
F-26
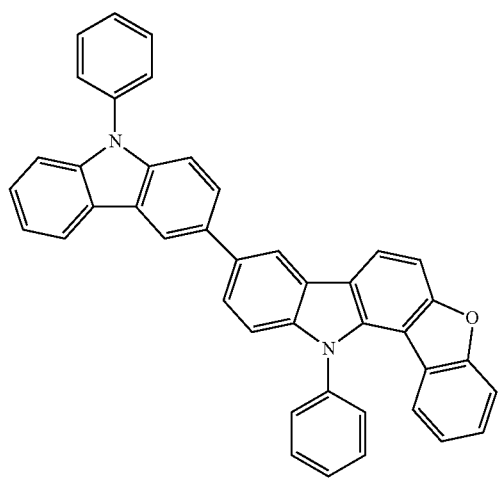
F-29
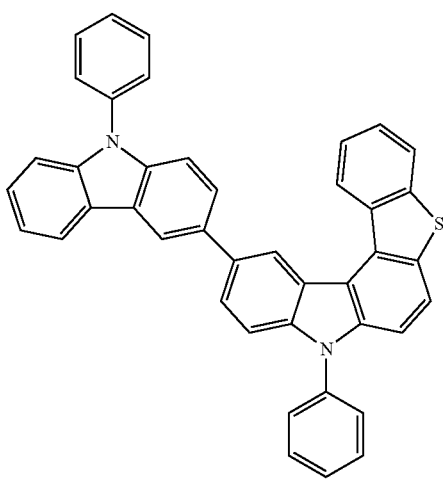

F-30
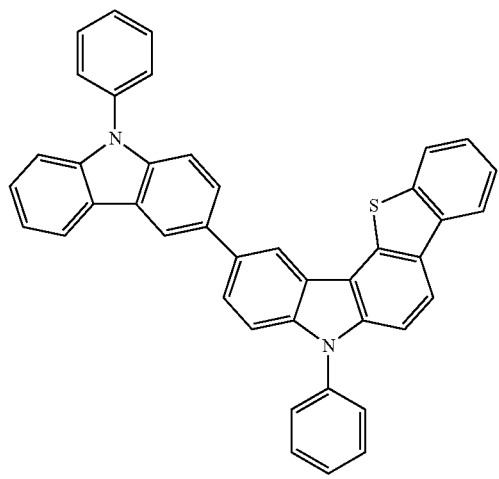
F-31
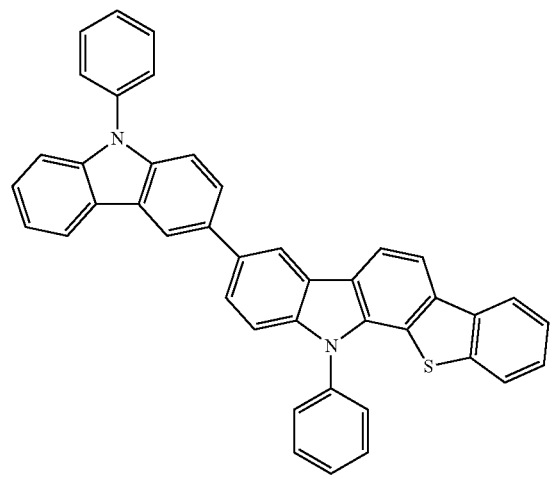
F-32
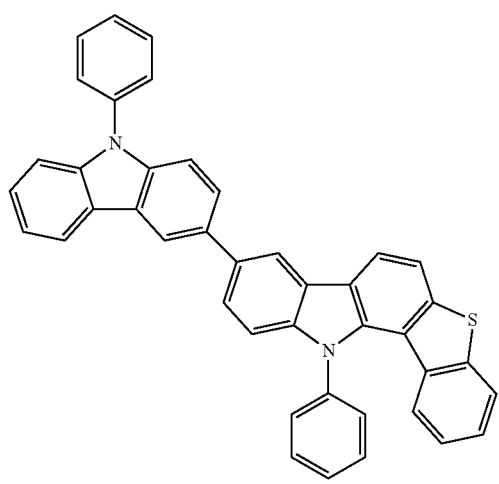
F-33
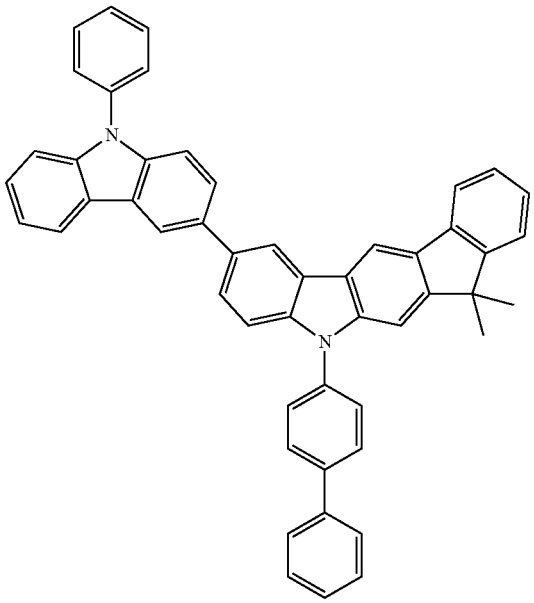
F-34
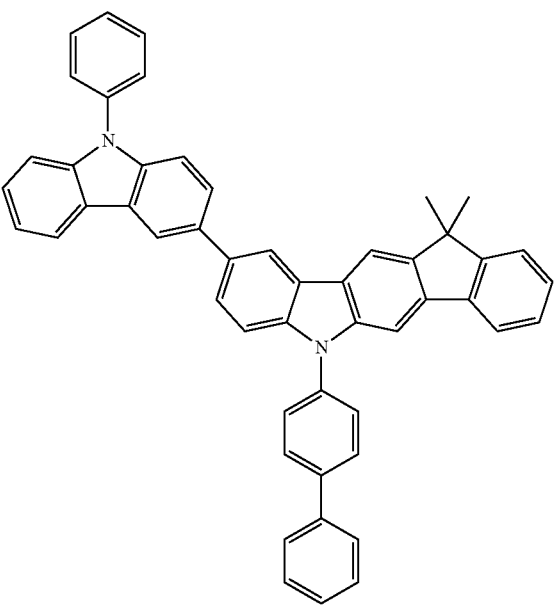

631
-continued
F-35
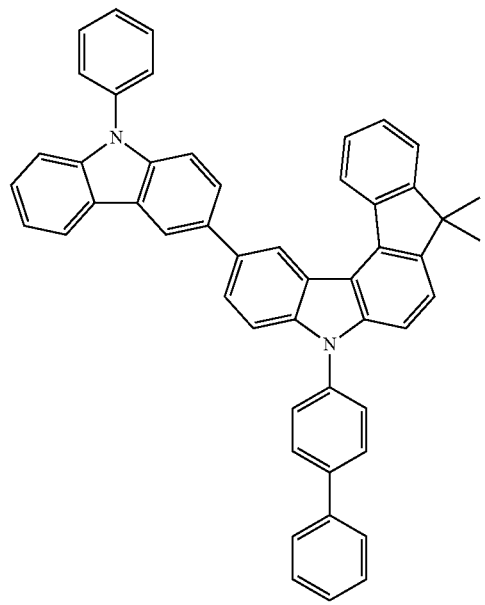
F-37
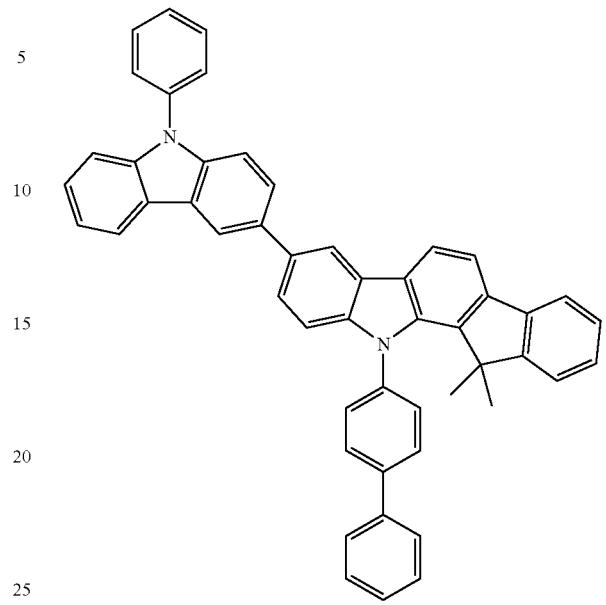
F-36
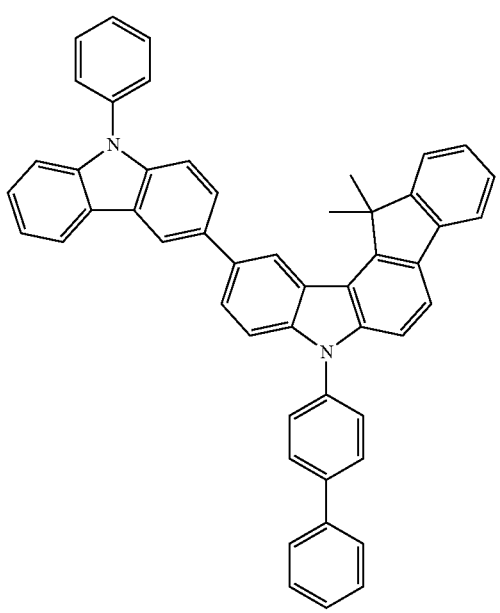
F-38
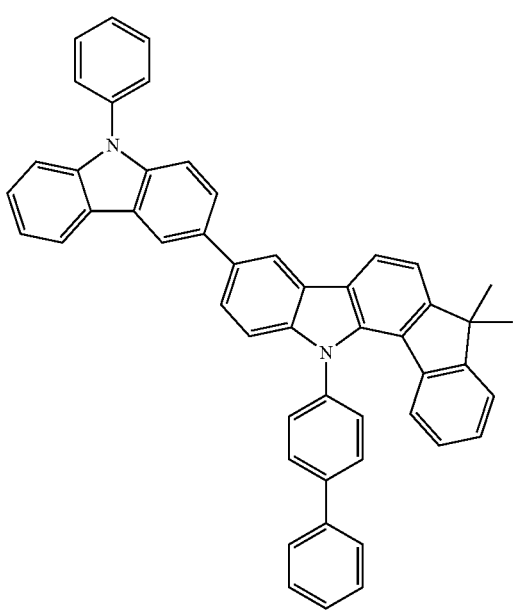

F-39
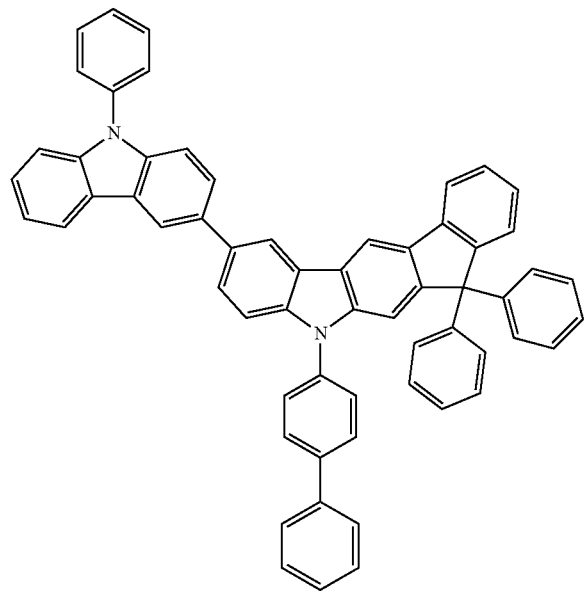
F-40
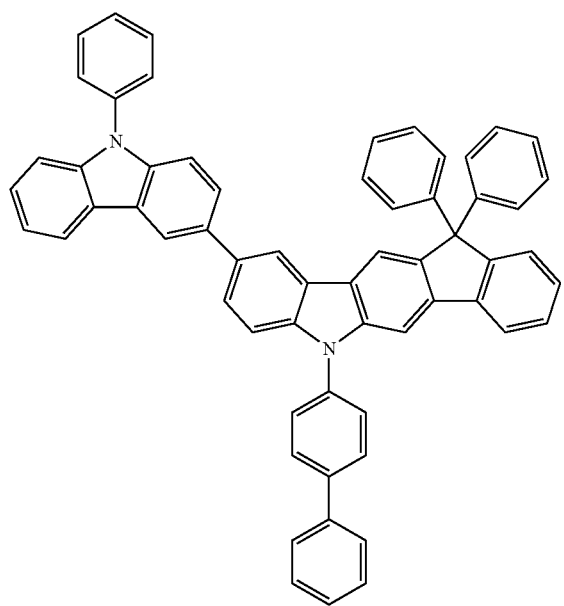
F-41
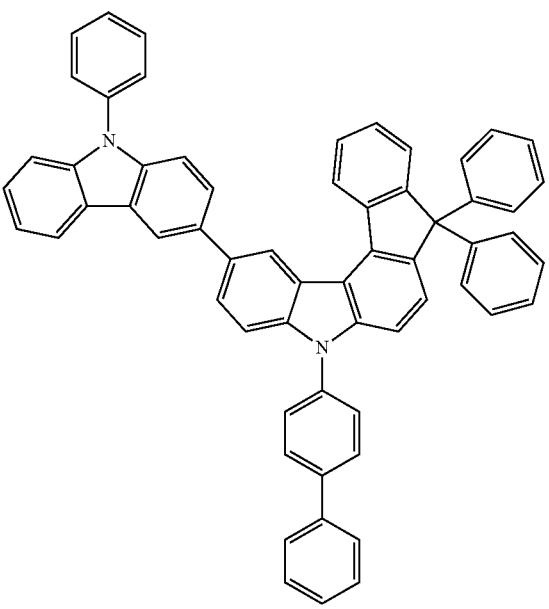
F-42
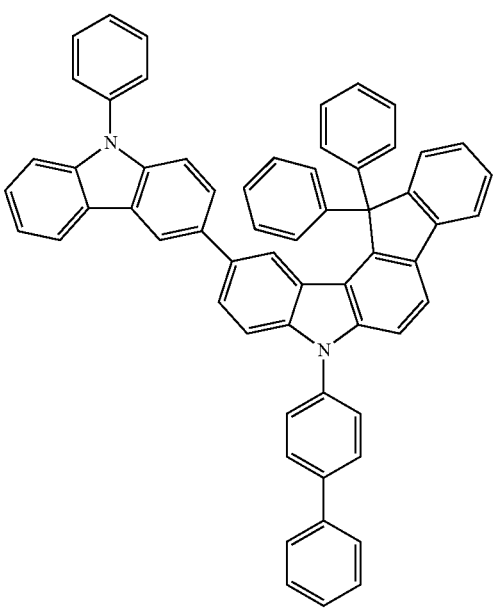

F-43
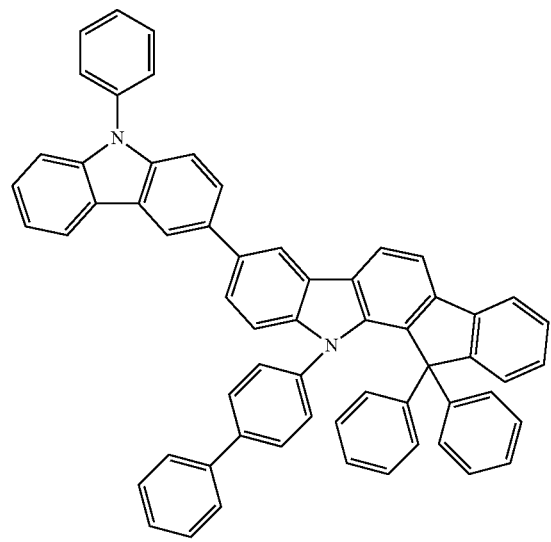
F-44
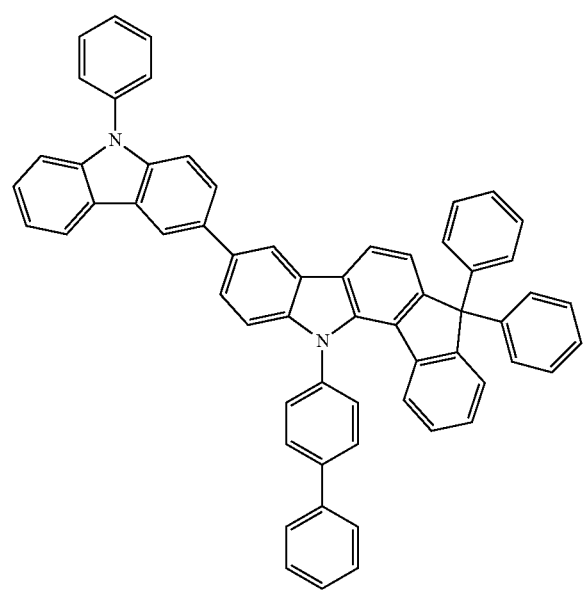
F-45
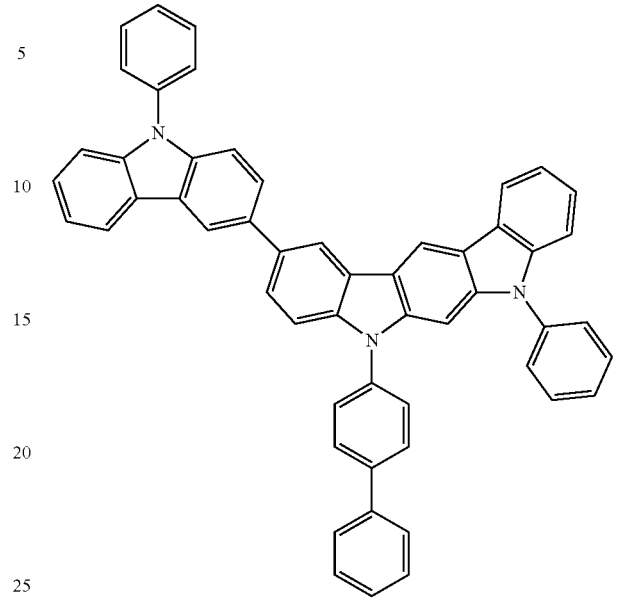
F-46
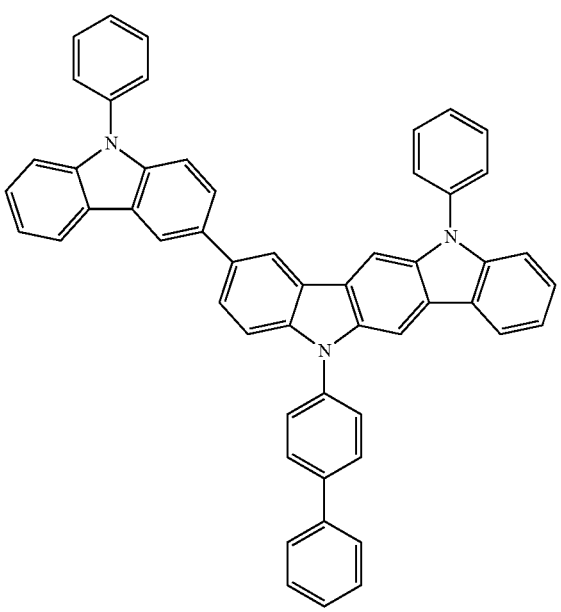

-continued
F-47
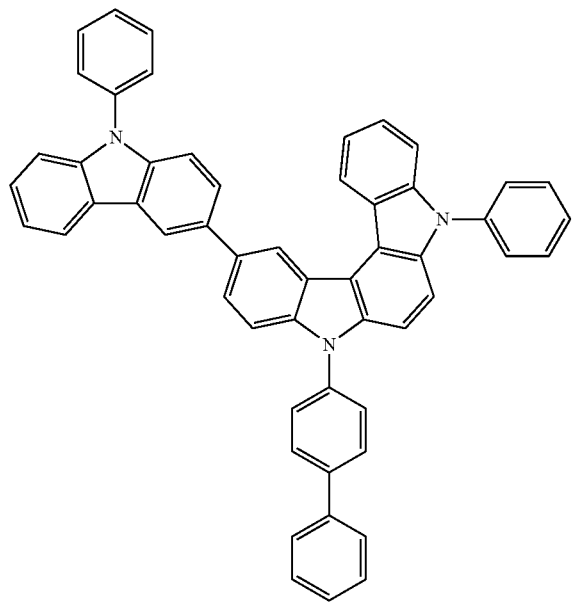
F-48
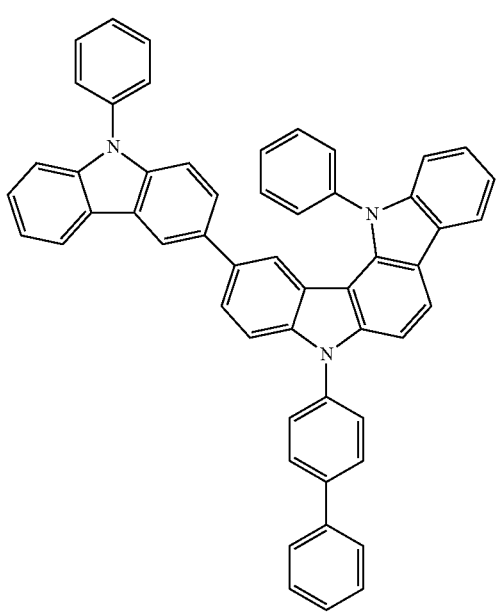
F-49
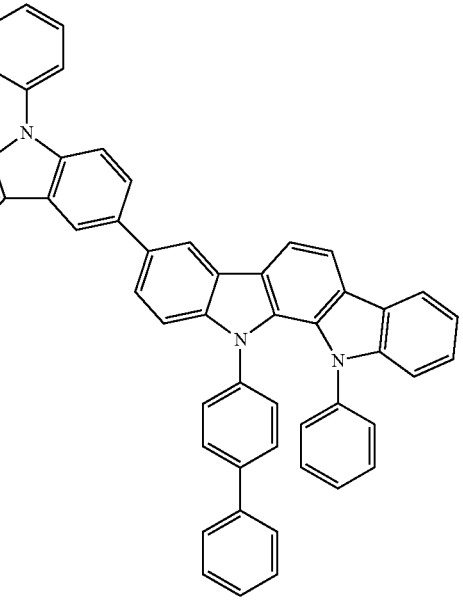
F-50
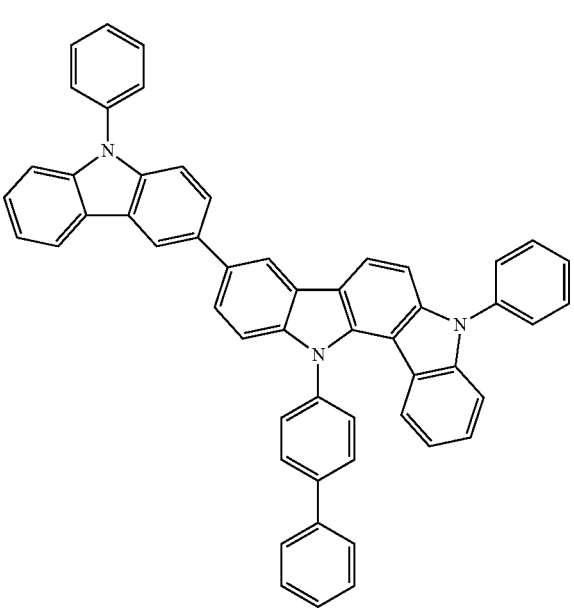

F-51
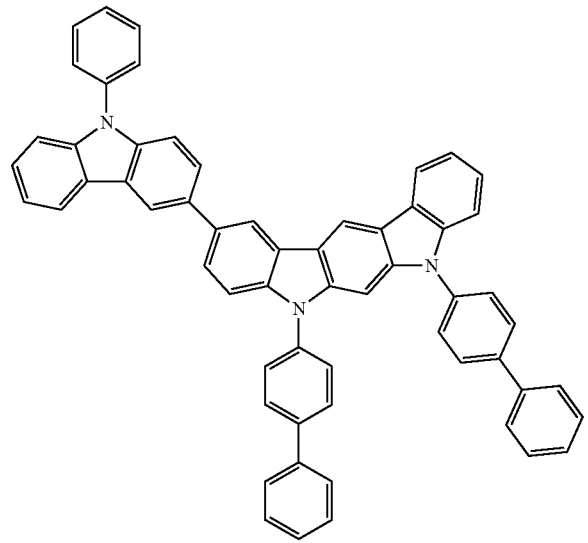
F-52
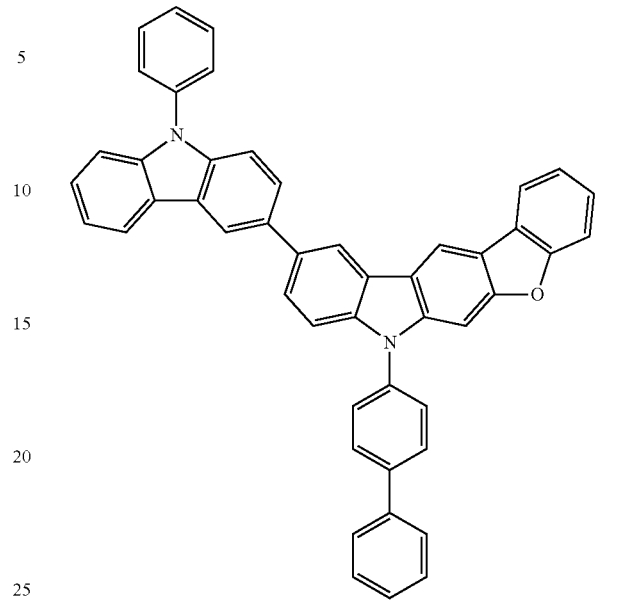
F-53
F-54
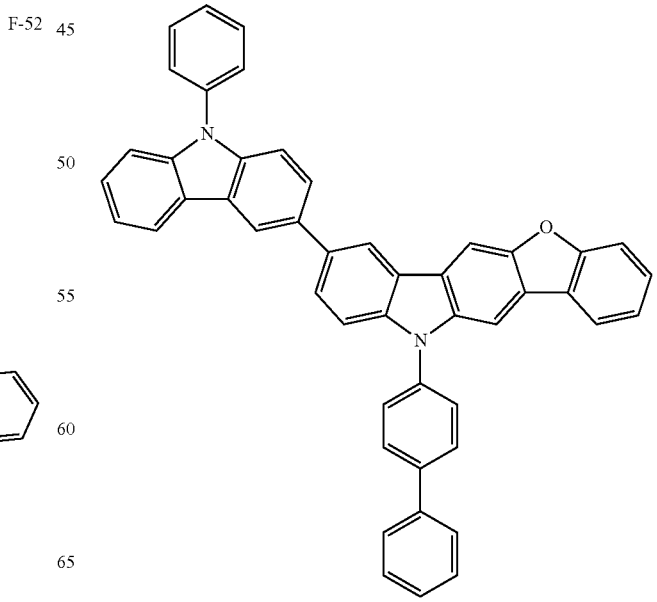

F-55
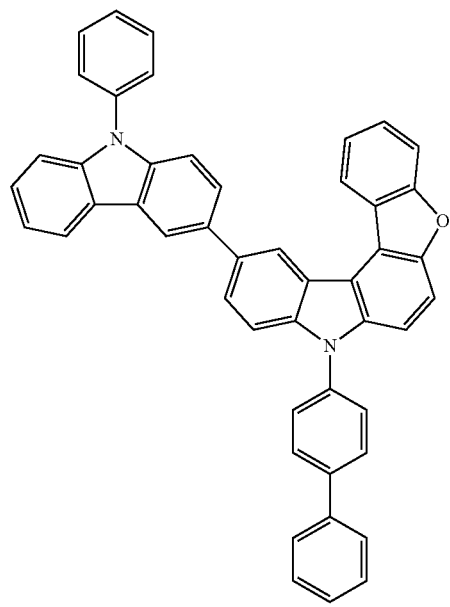
F-57
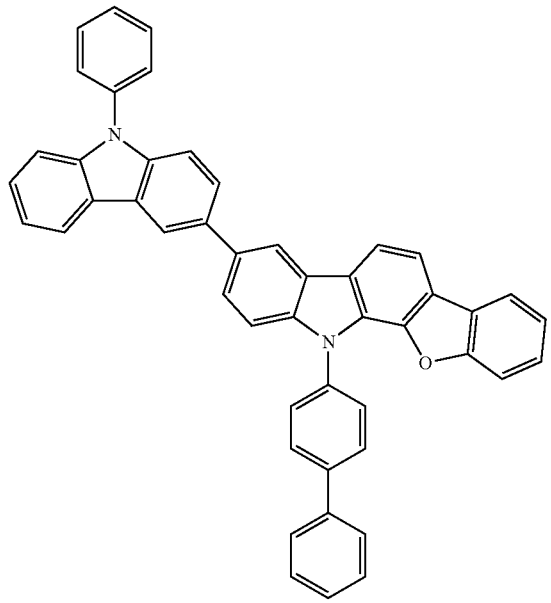
F-56
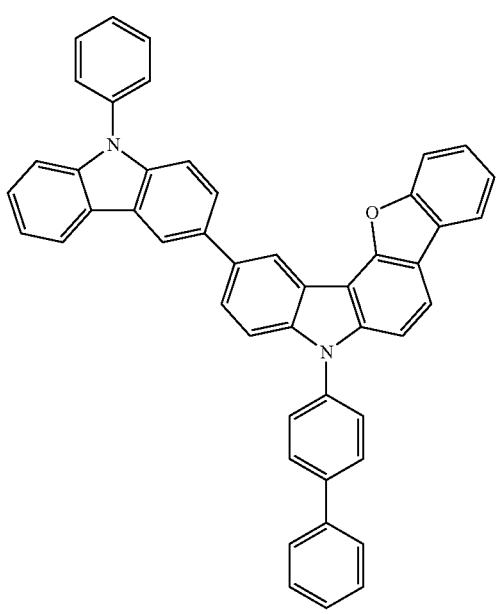
F-58
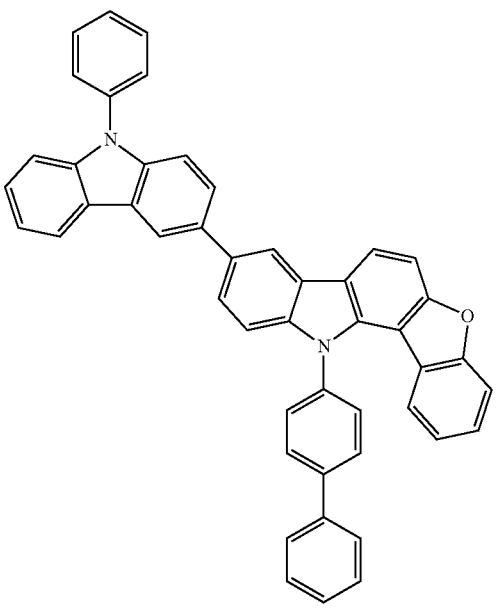

F-59
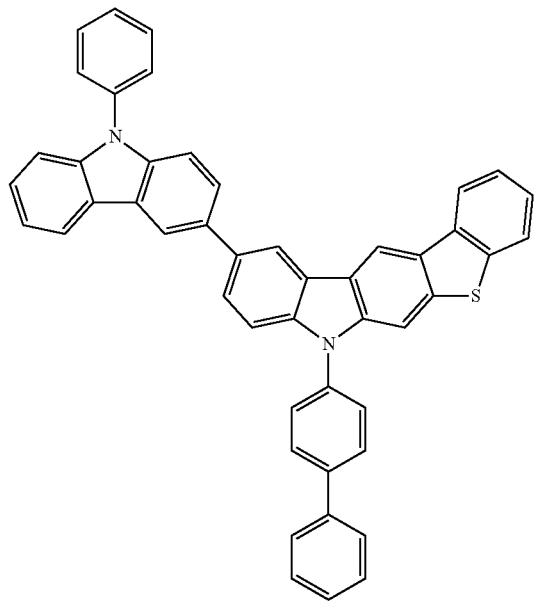
F-60
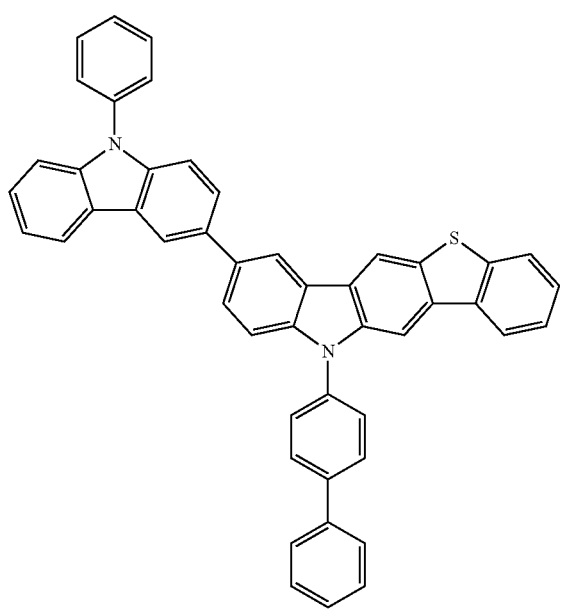
F-61
F-62

F-63
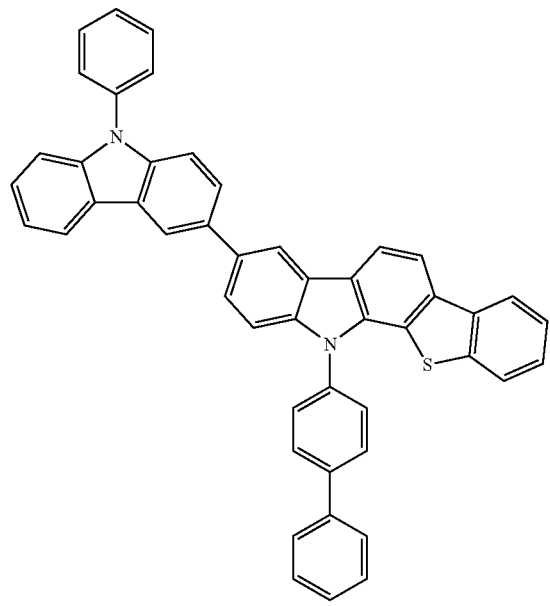
F-64
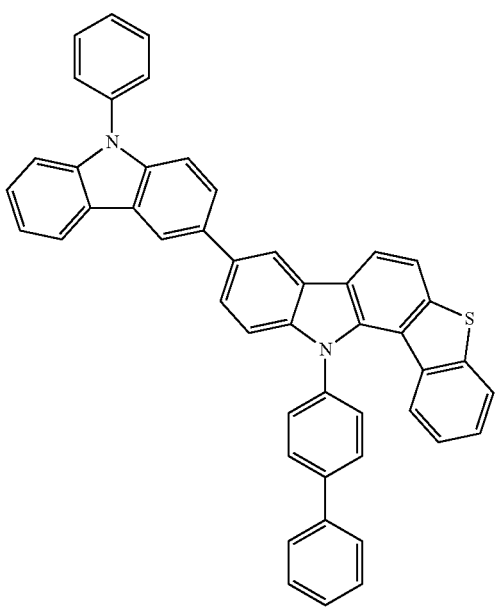
F-65
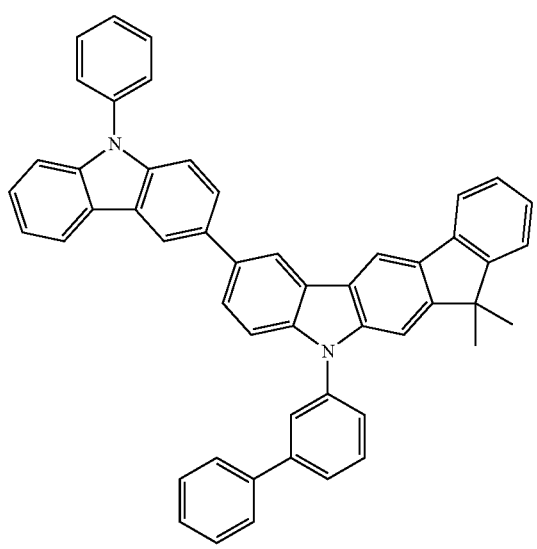
F-66
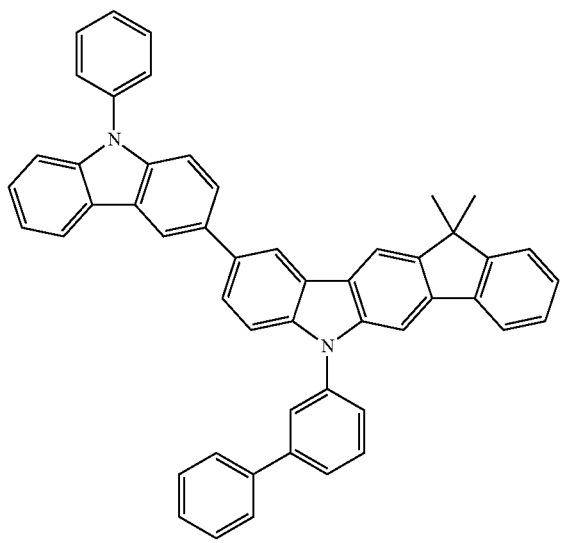

F-67
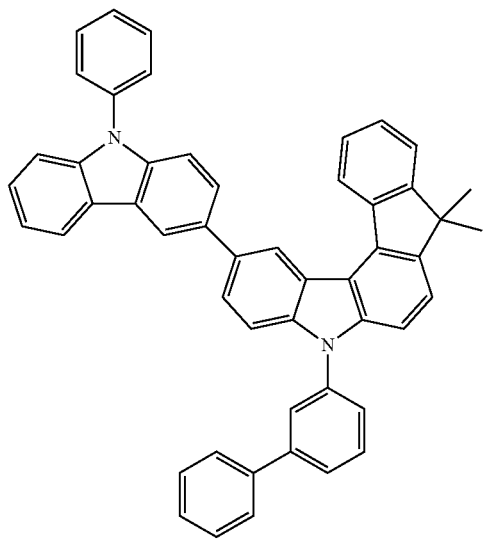
F-69
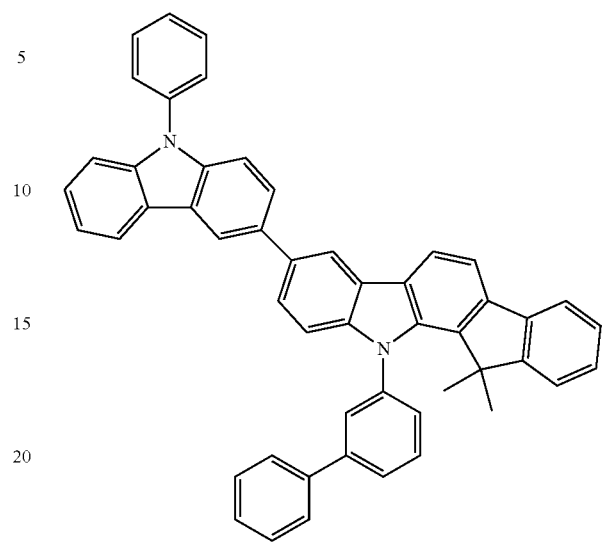
F-70
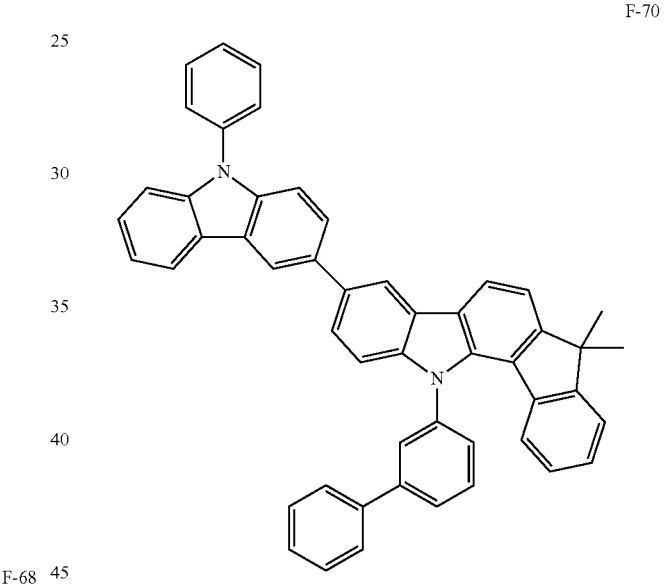
F-68
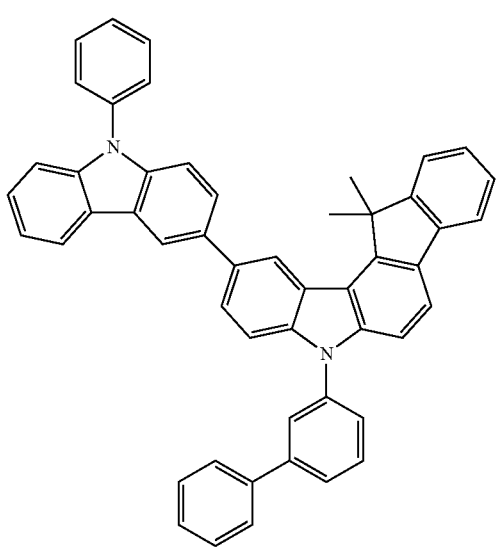
F-71
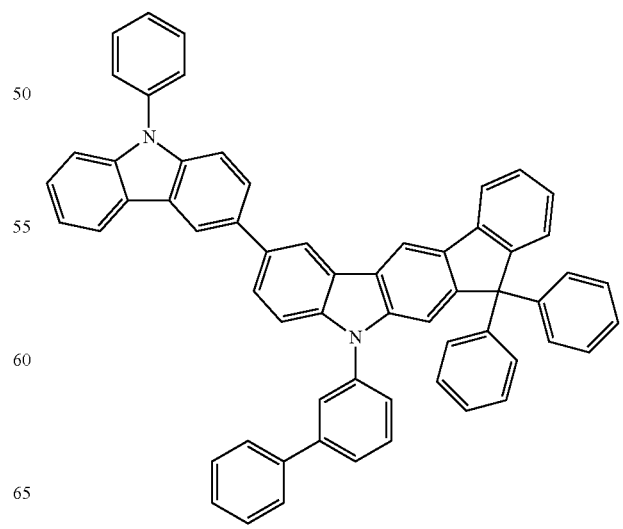

F-72
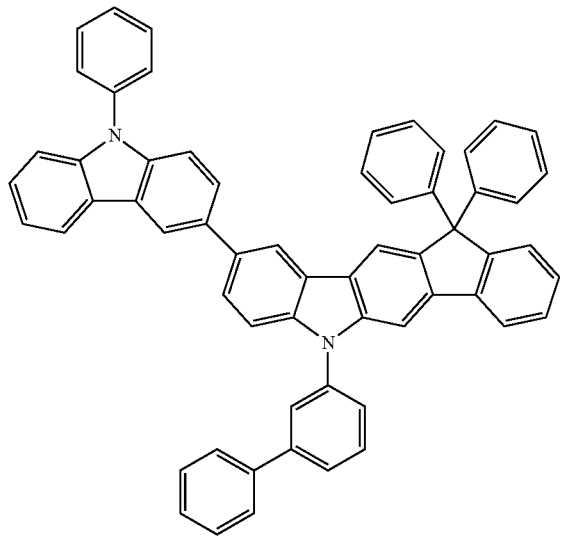
F-73
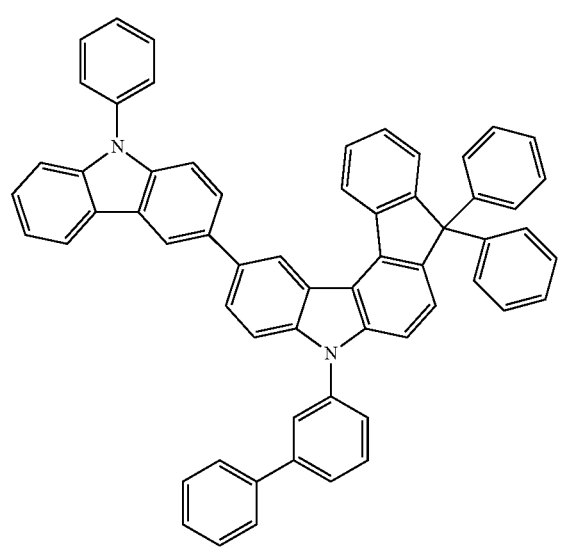
F-74
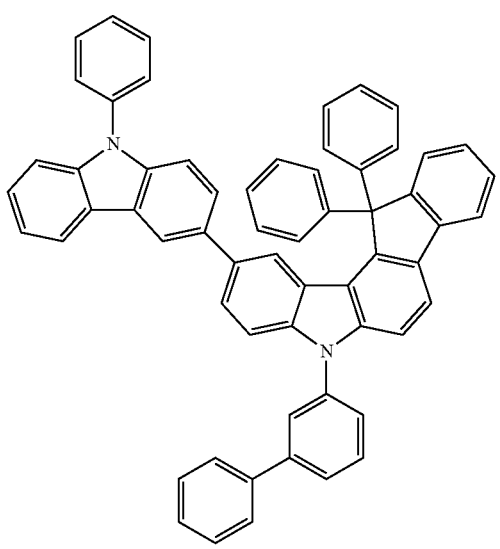
F-75
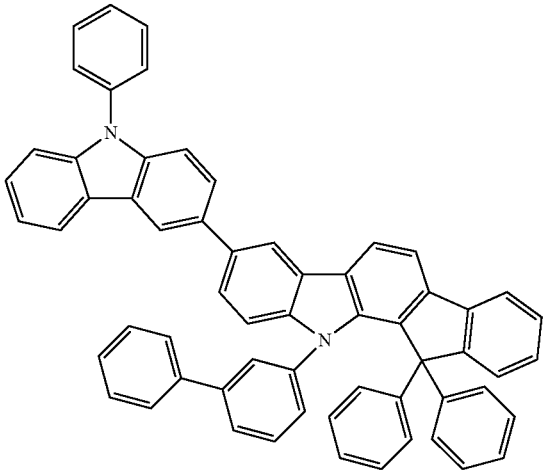
F-76
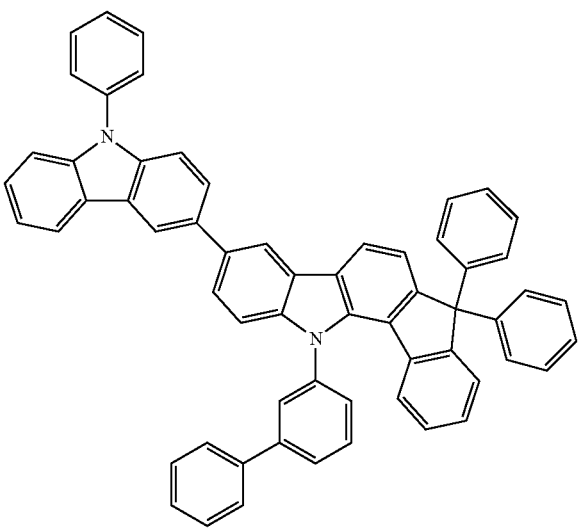
F-77
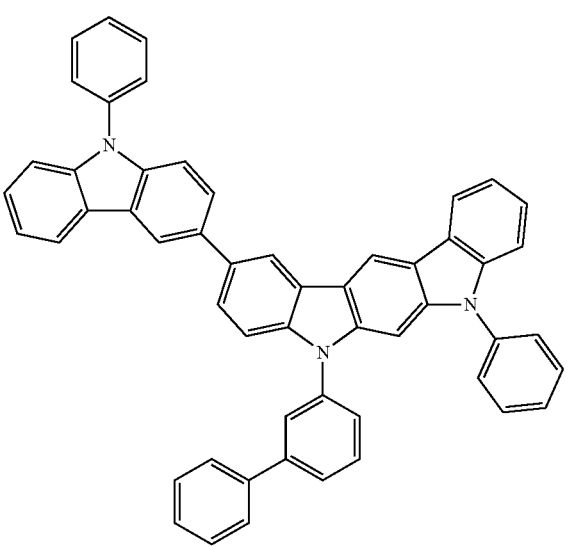

-continued
F-78
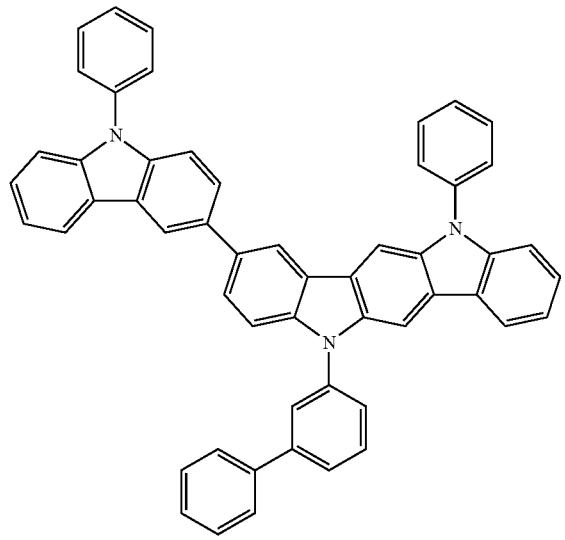
F-79
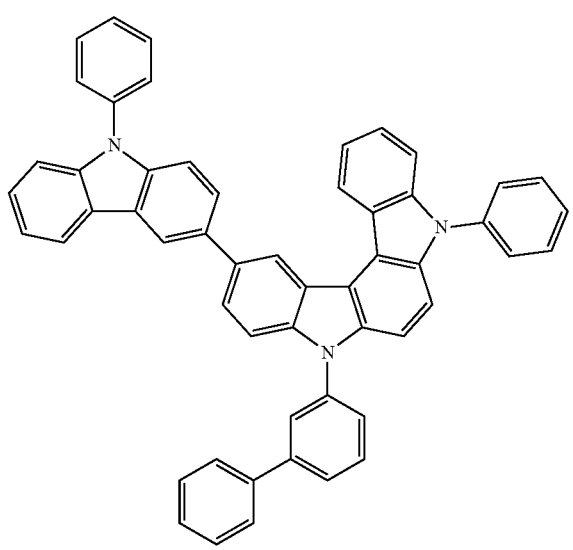
-continued
F-80
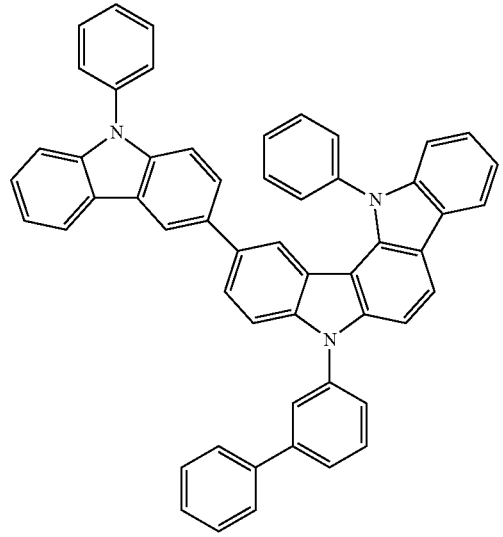
F-81
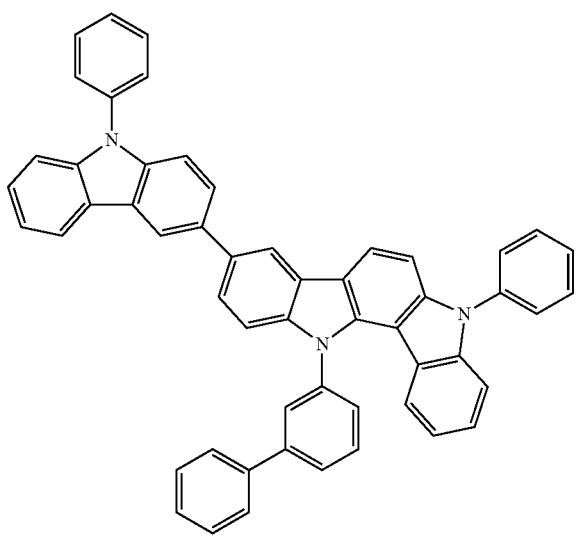
F-82

F-83
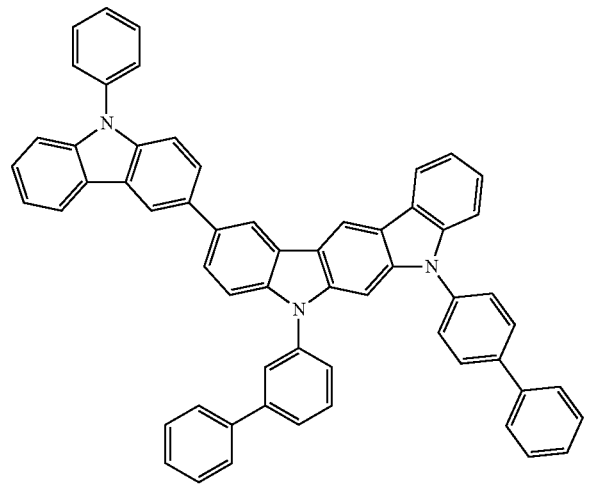
F-84
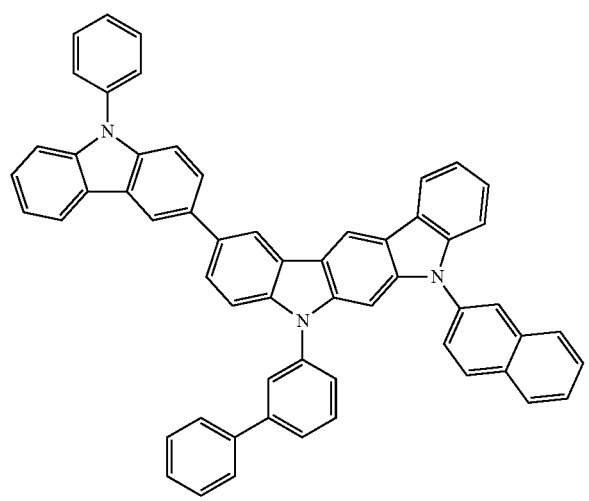
F-85
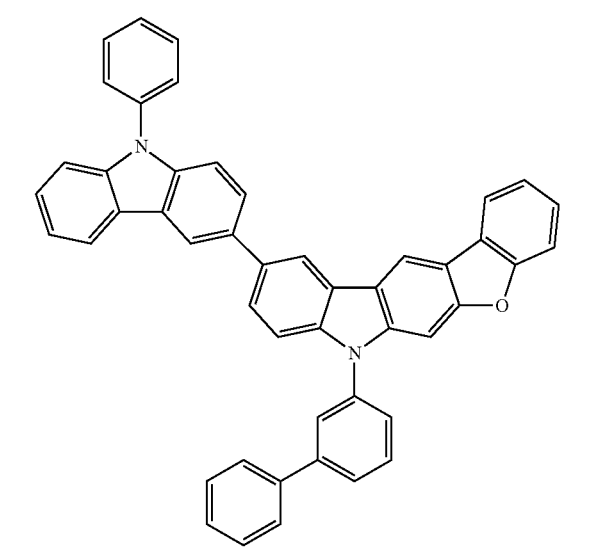
F-86
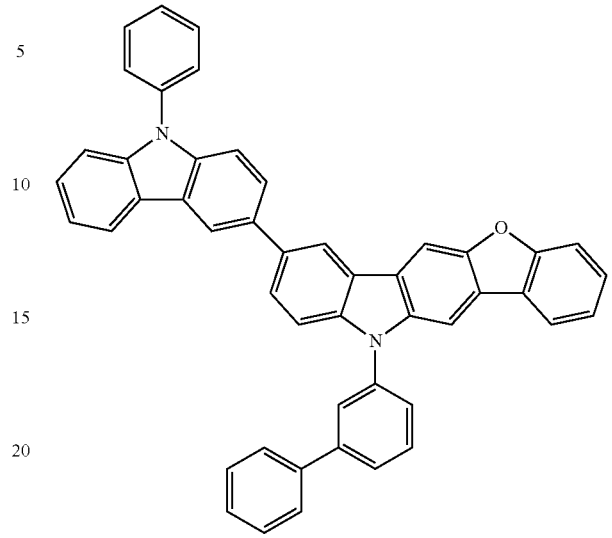
F-87
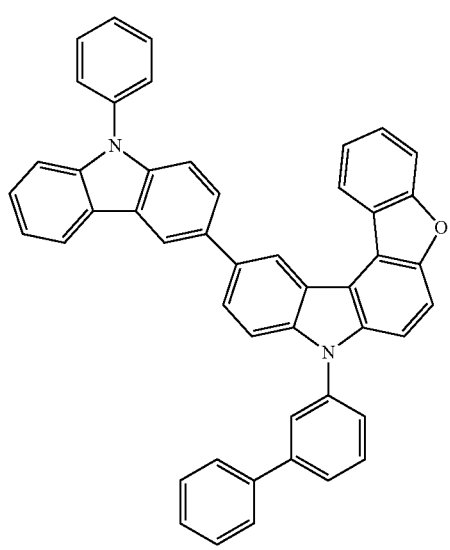
F-88
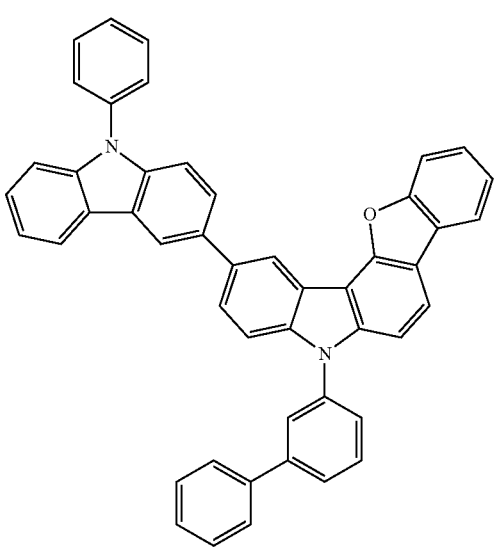

-continued
F-89
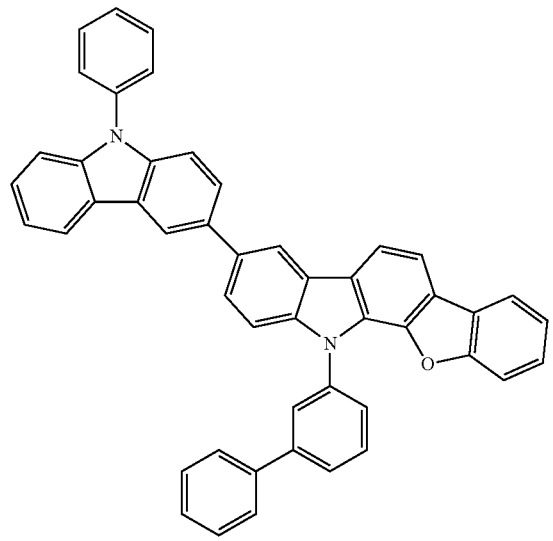
F-90
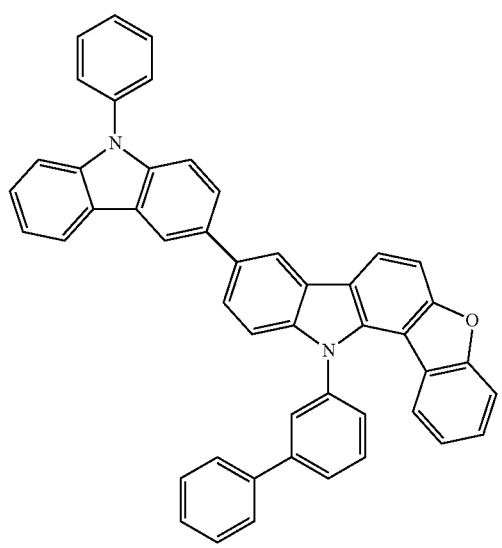
F-91
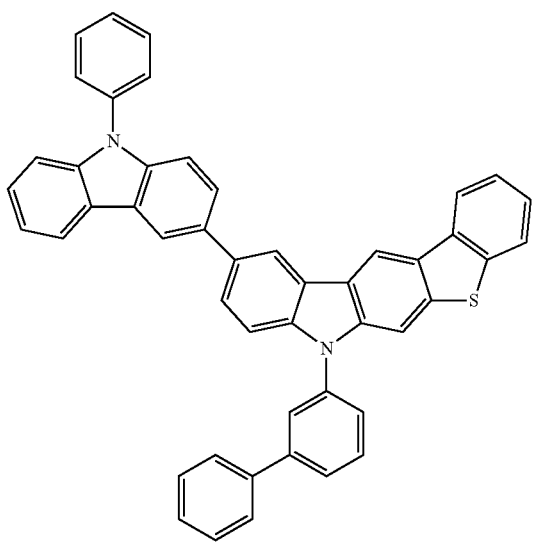
-continued
F-92
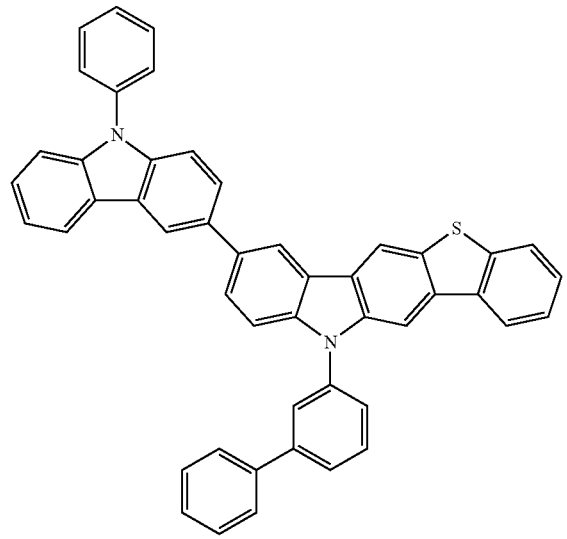
F-93
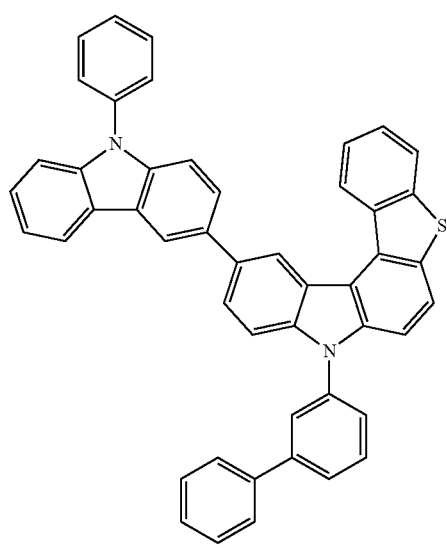
F-94
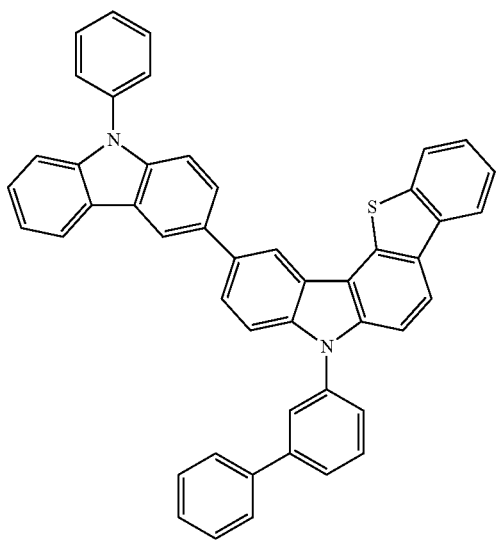

F-95
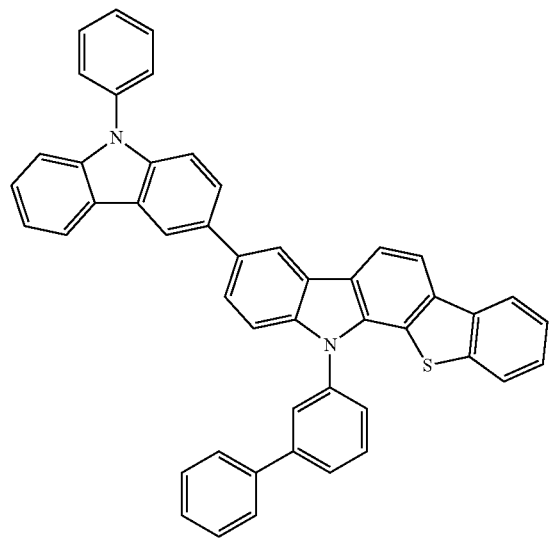
F-96
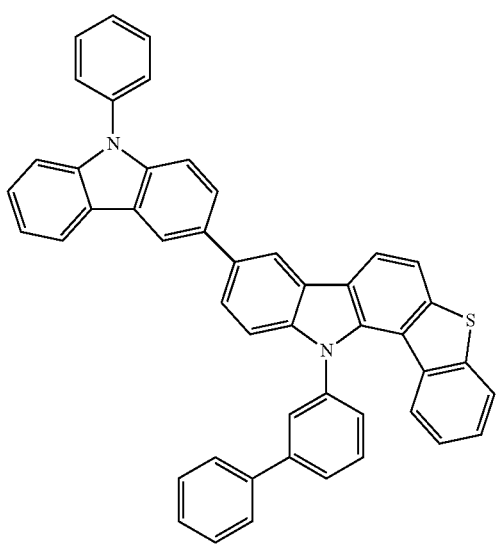
F-97
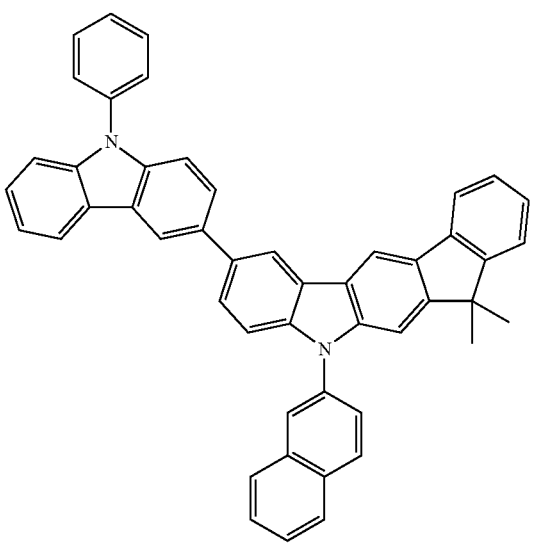
F-98
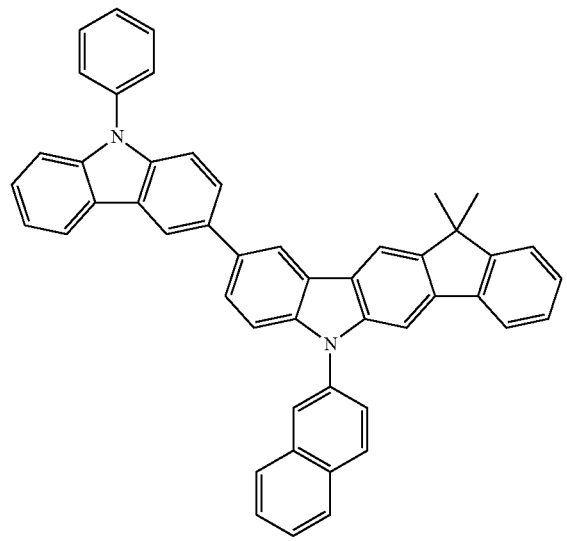
F-99
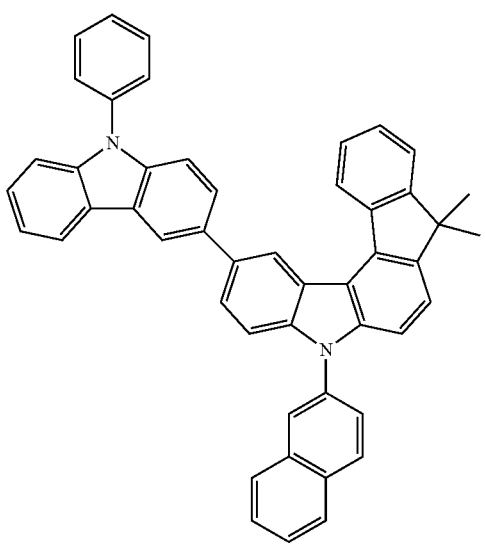

F-100
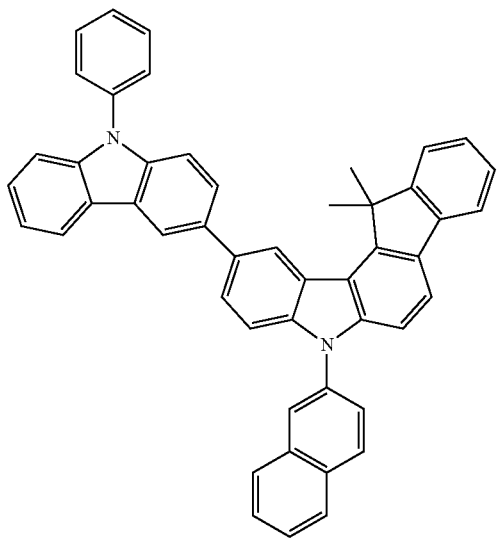
F-102
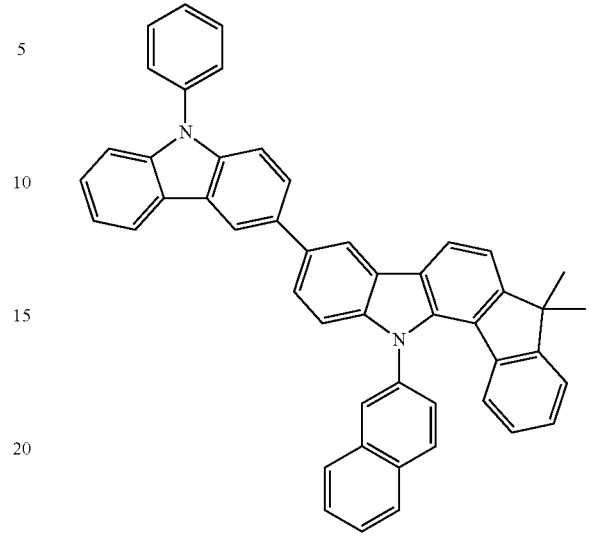
F-103
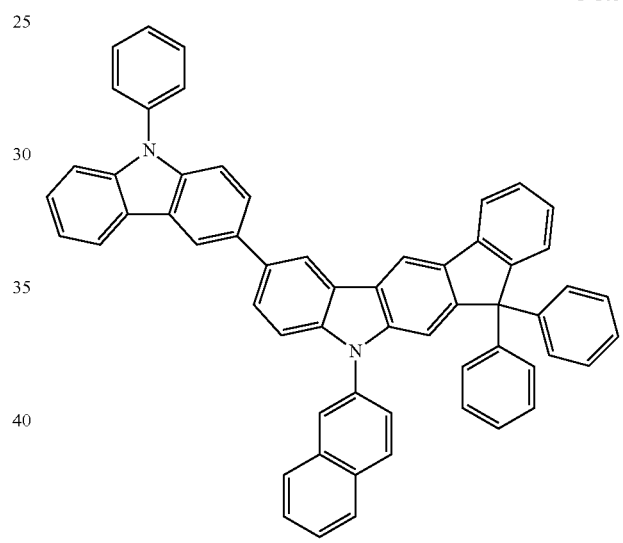
F-101
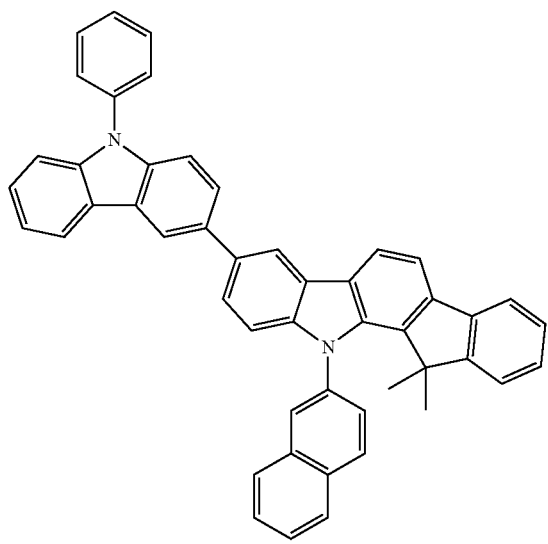
F-104
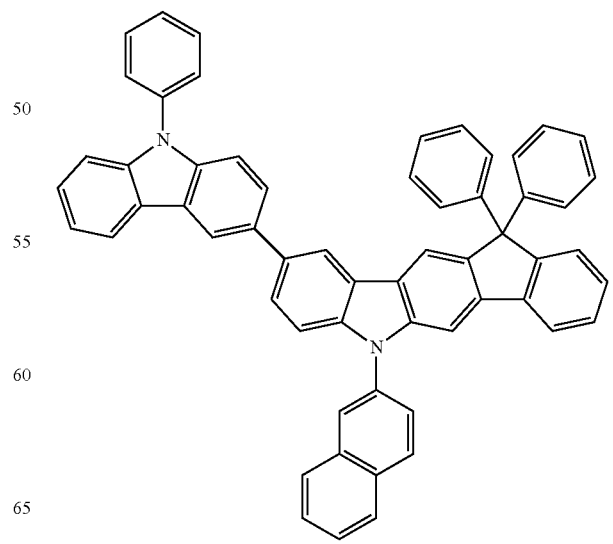

-continued
F-105
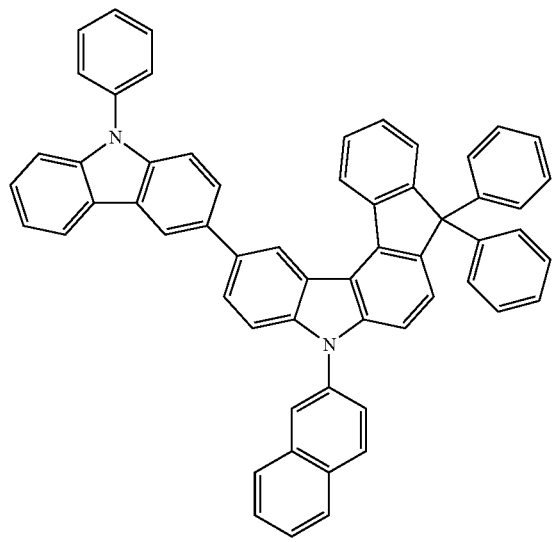
F-106
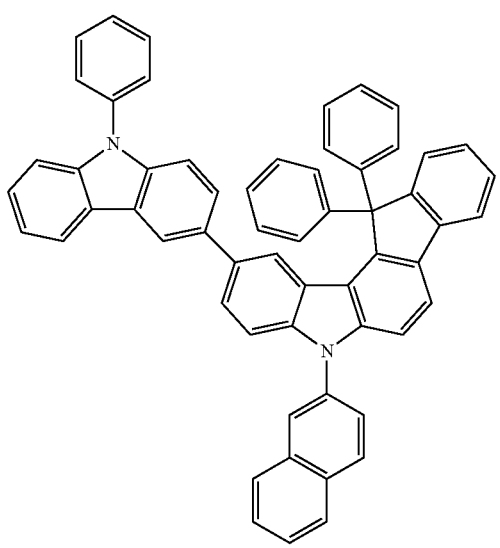
F-107
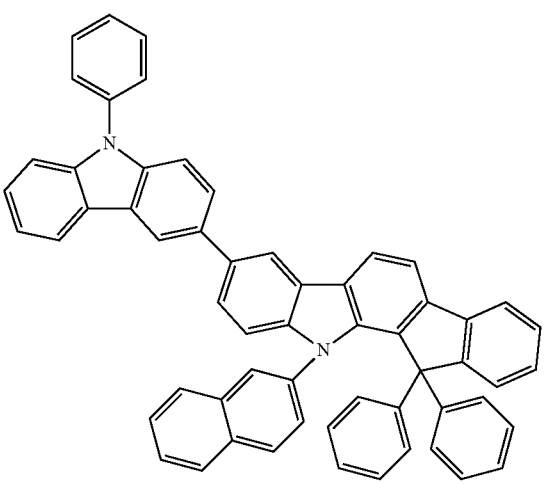
-continued
F-108
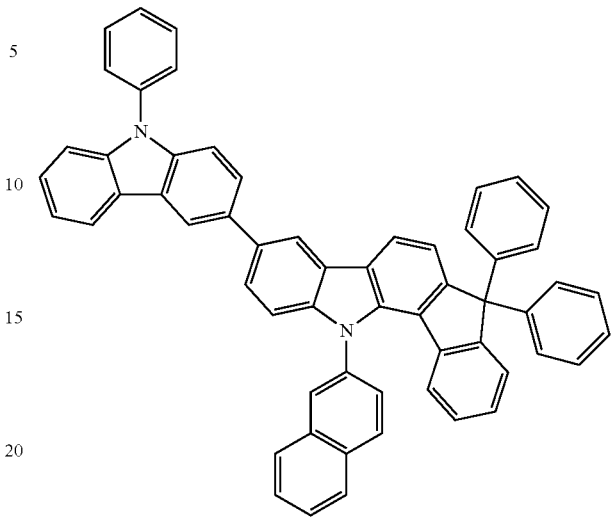
F-109
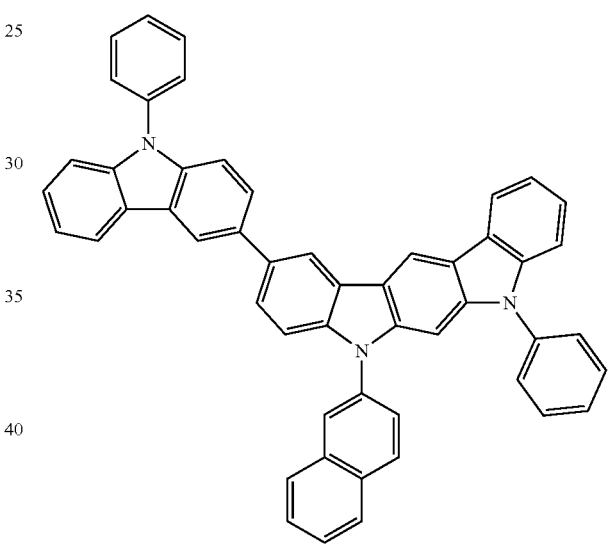
F-110
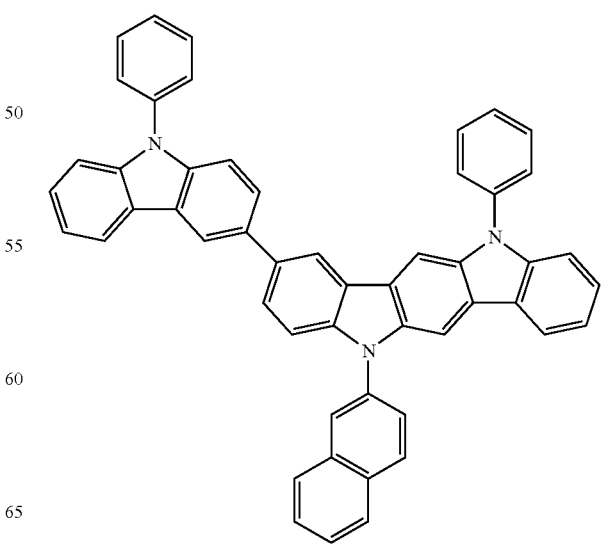

F-111
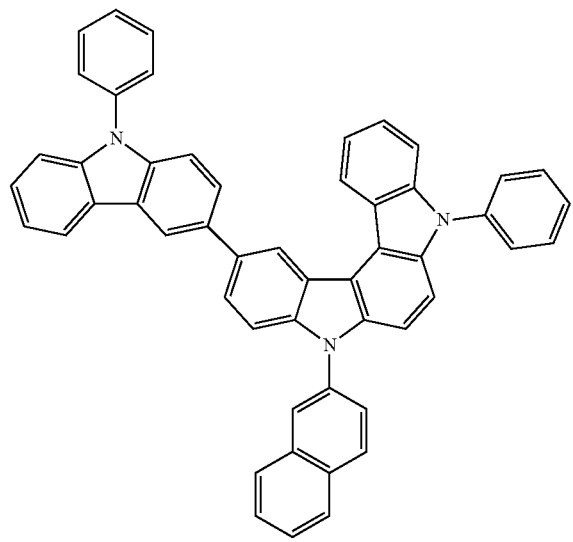
F-112
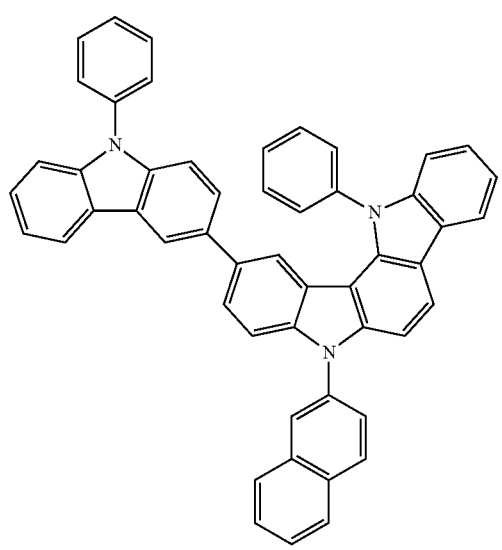
F-113
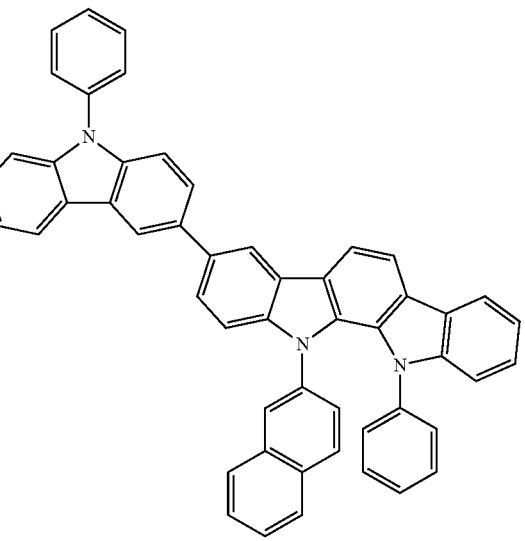
F-114
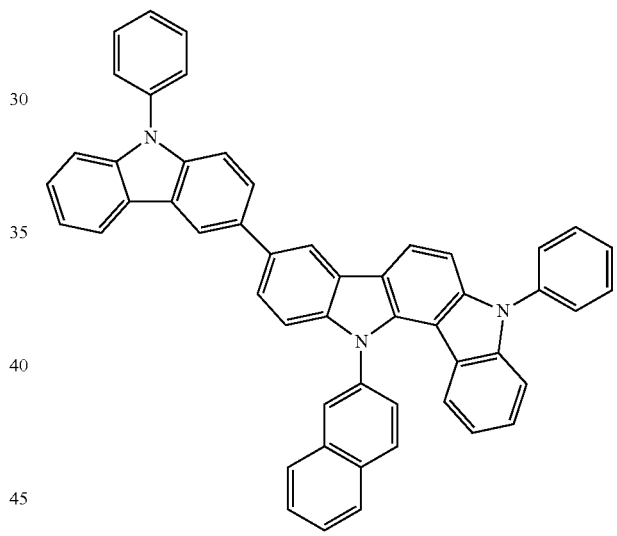
F-115
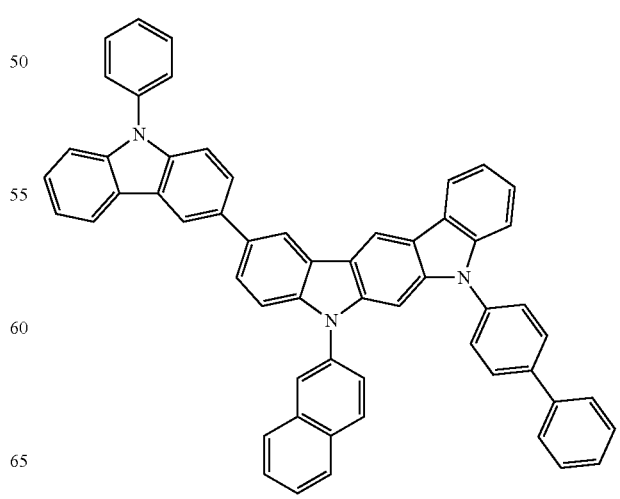

F-116
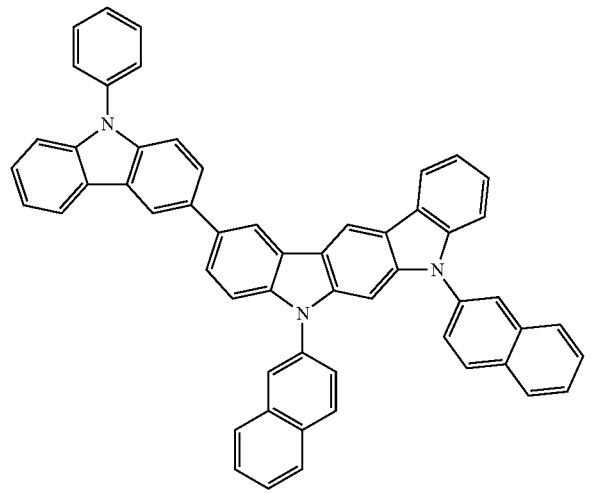
F-117
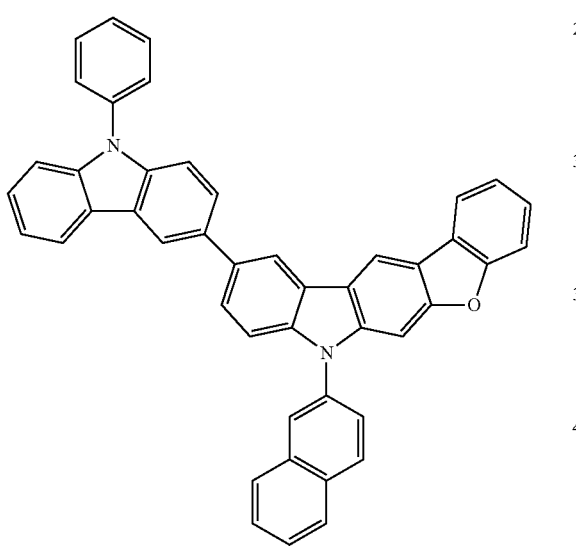
F-118
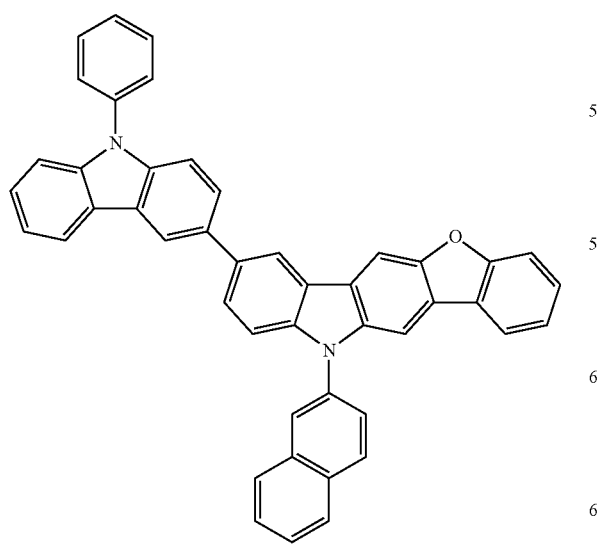
F-119
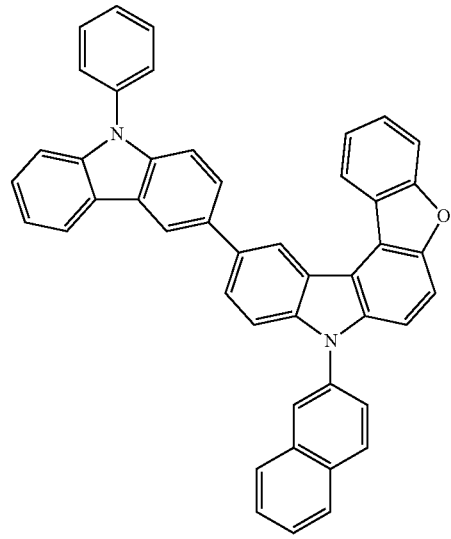
F-120
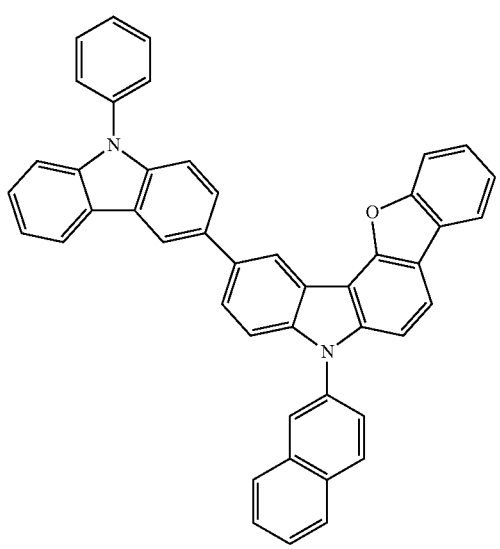
F-121
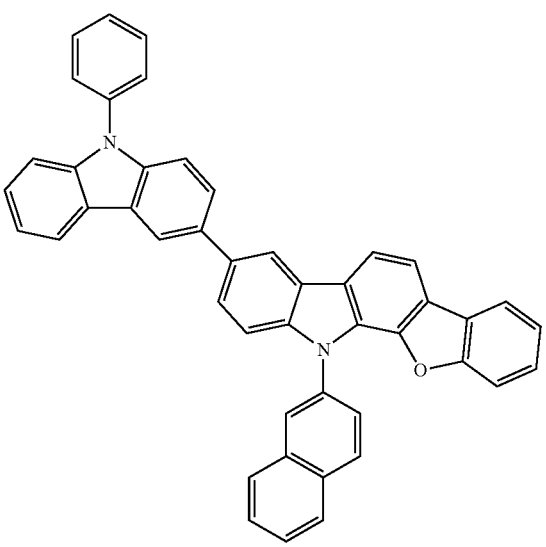

-continued
F-122
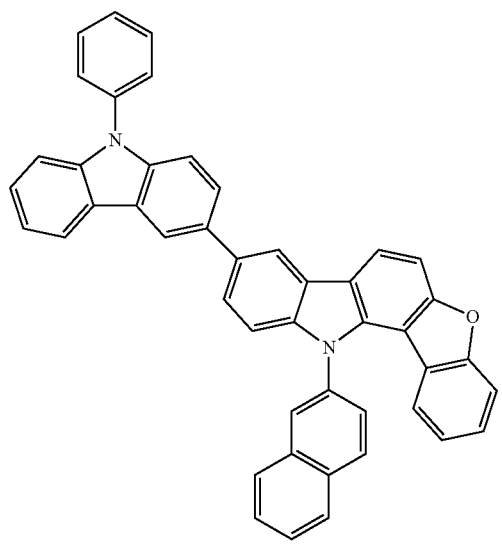
F-124
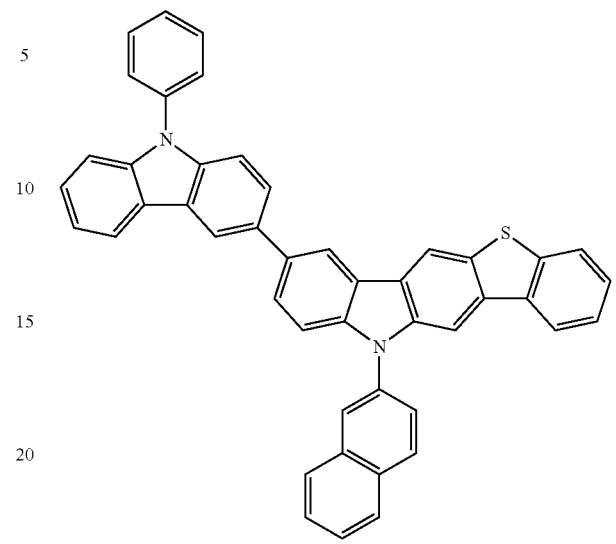
F-125
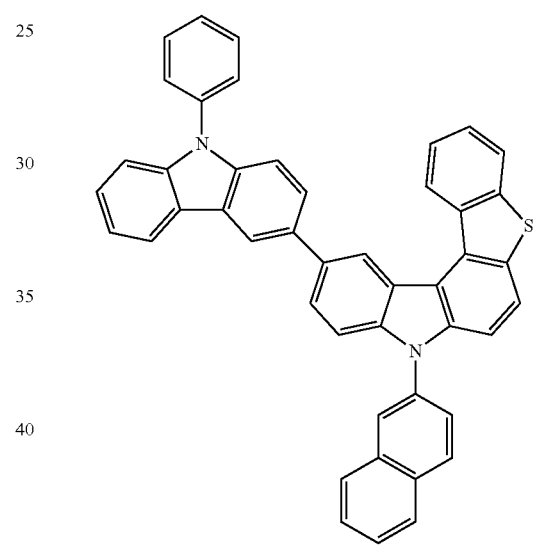
F-123
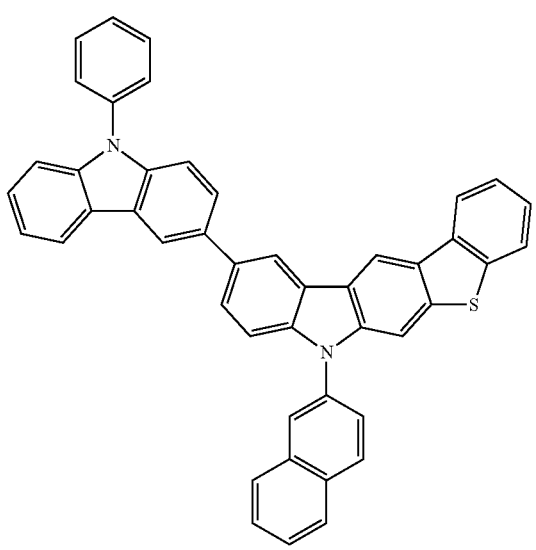
F-126
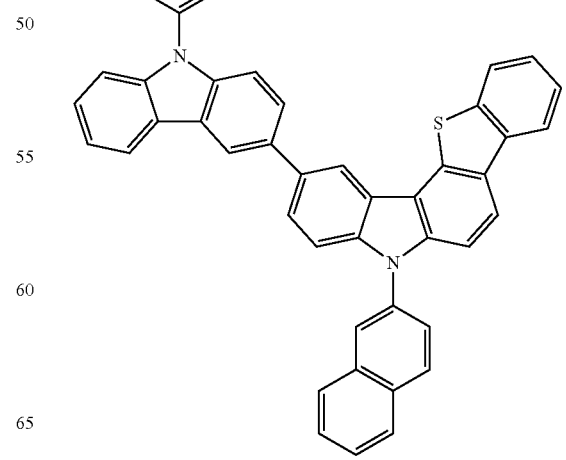

F-127
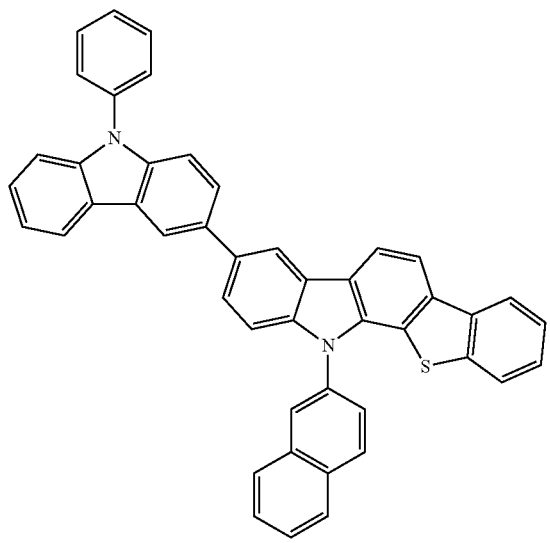
F-130
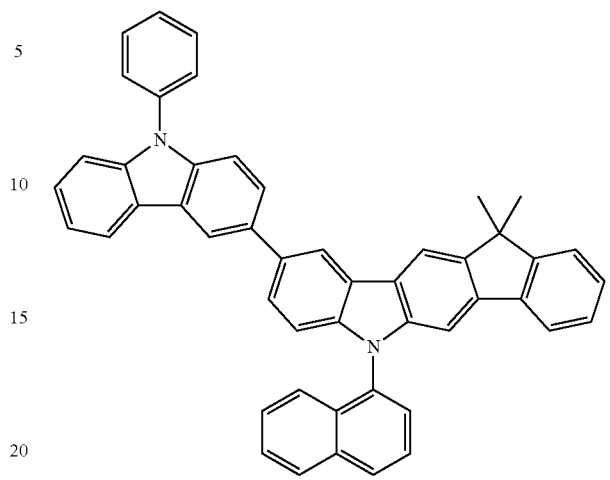
F-128
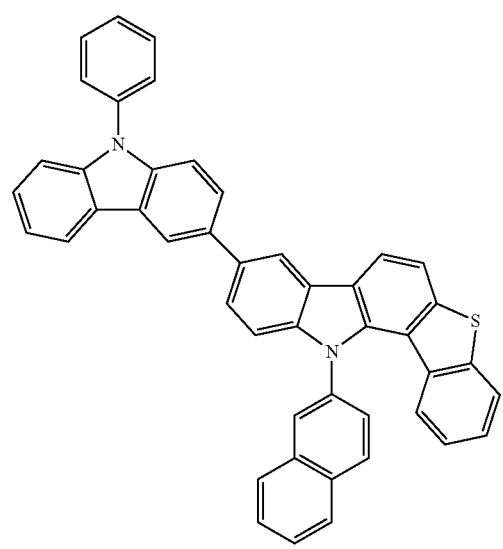
F-131
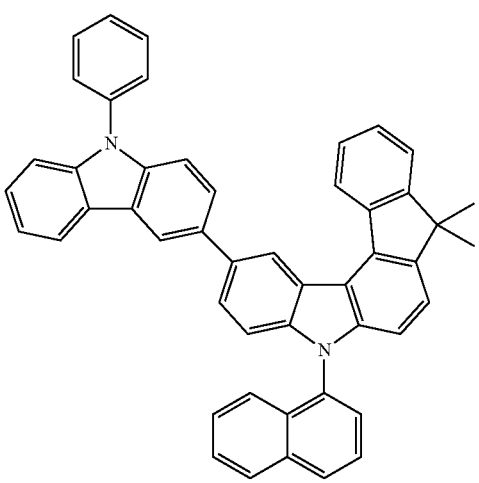
F-129
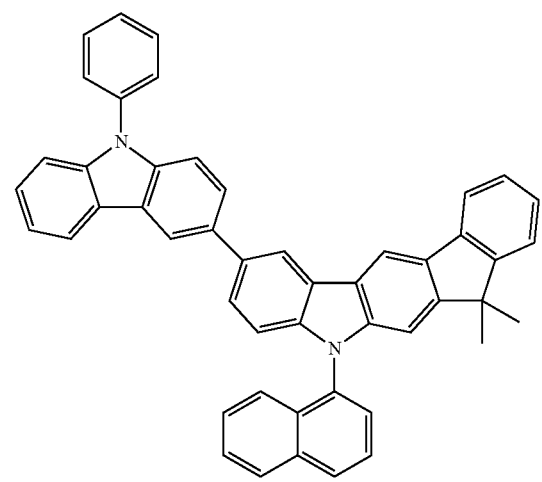
F-132
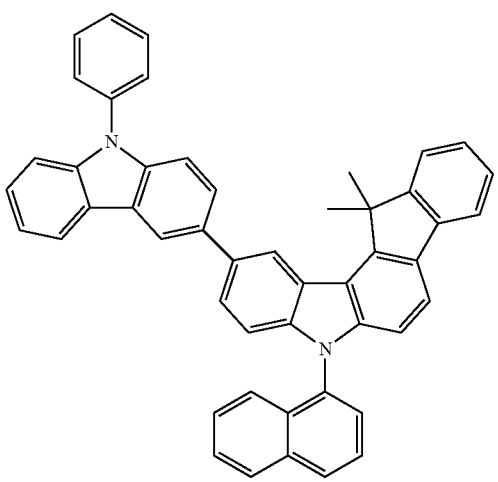

F-133
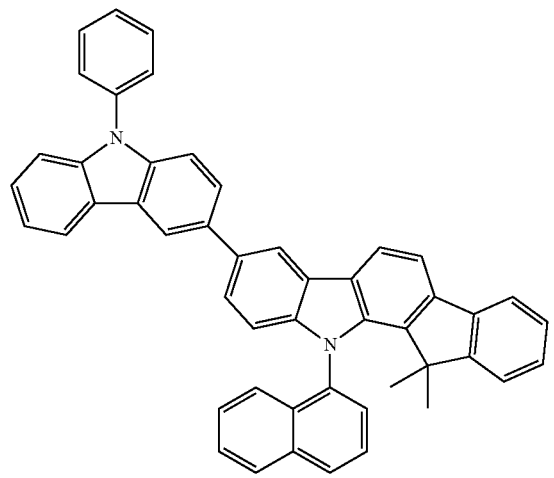
F-134
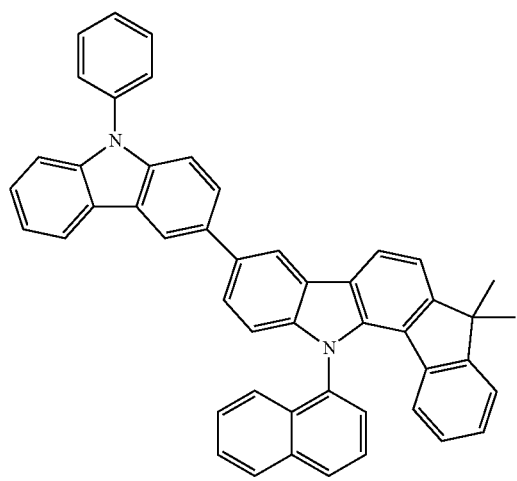
F-135
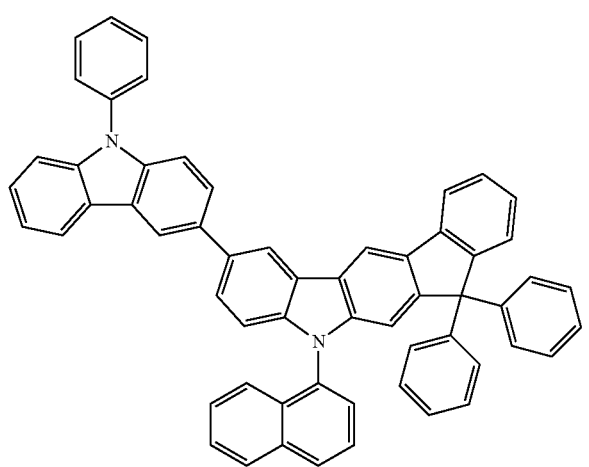
F-136
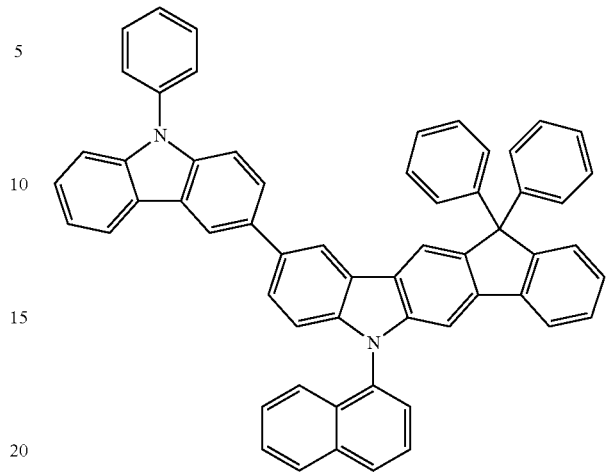
F-137
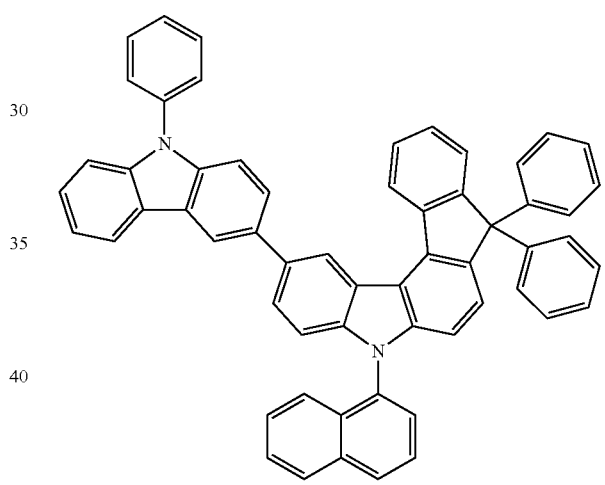
F-138
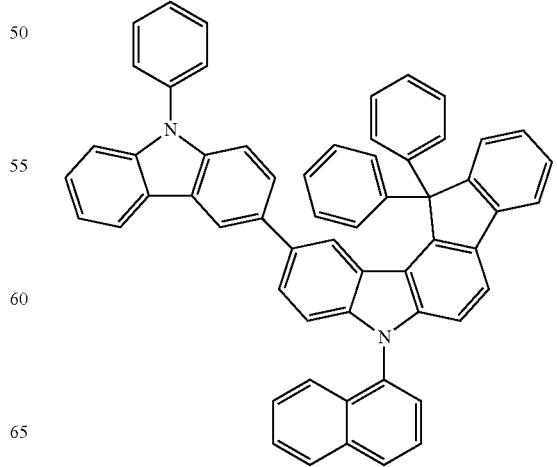

-continued
F-139
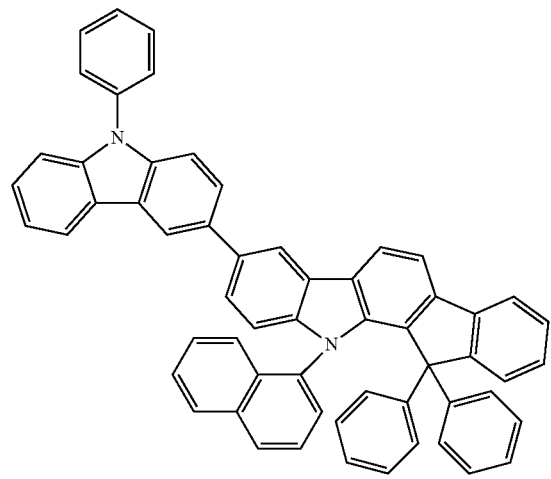
F-140
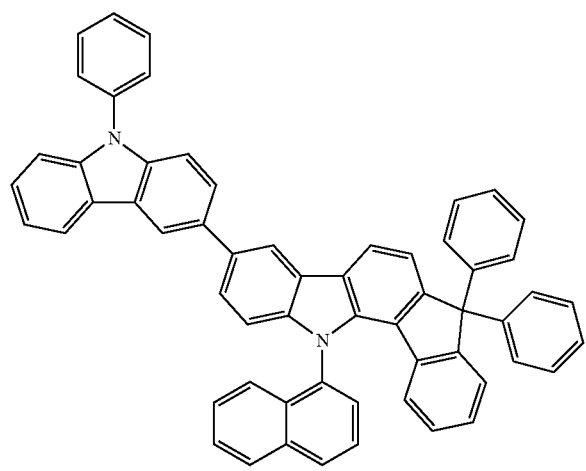
F-141
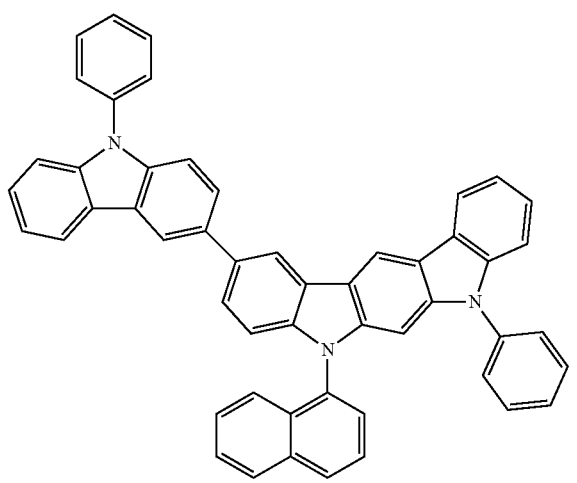
-continued
F-142
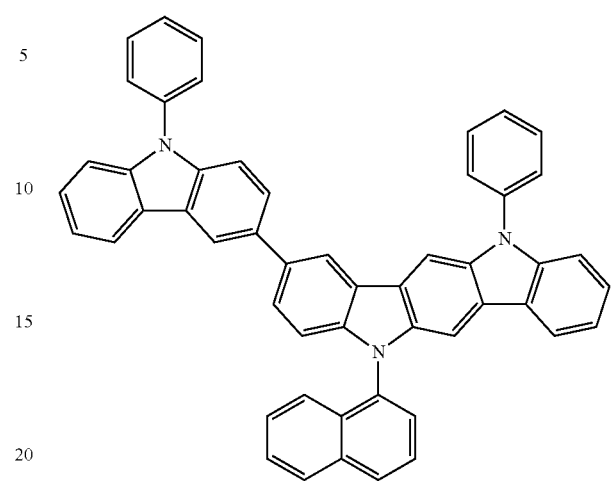
F-143
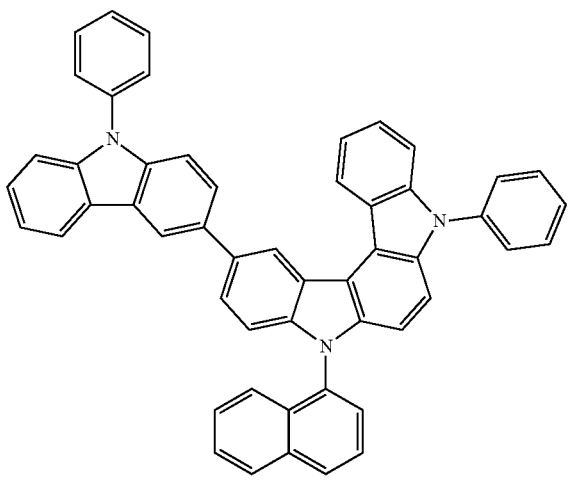
F-144
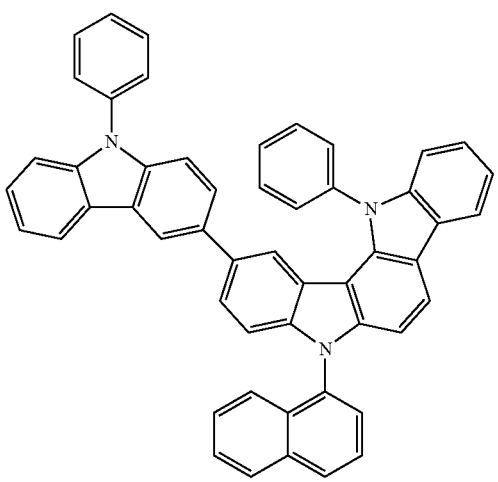

F-145
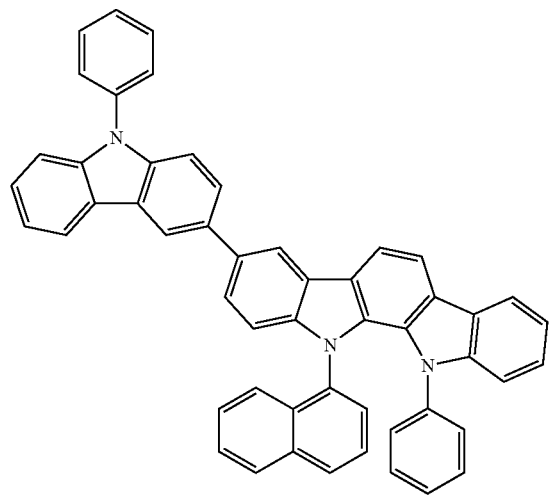
F-146
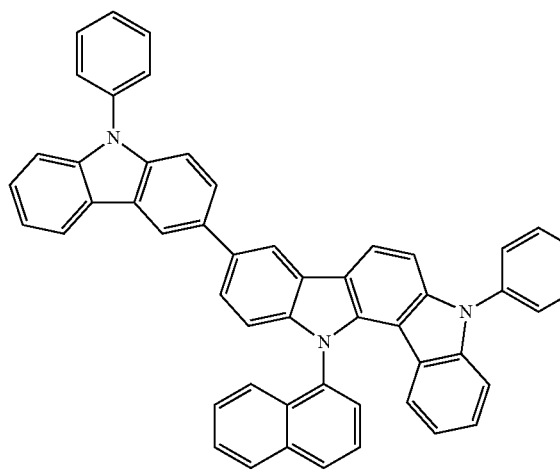
F-147
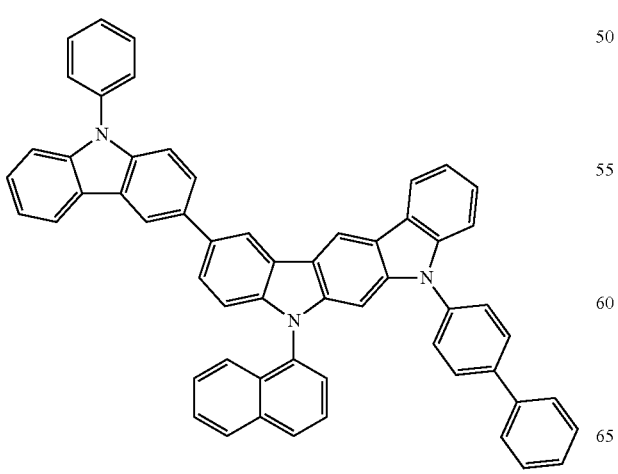
F-148
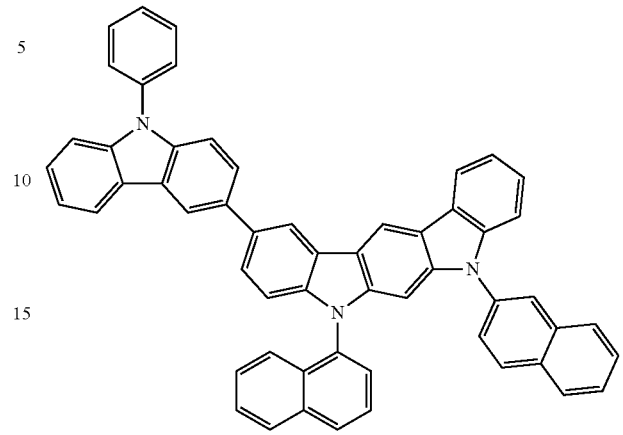
F-149
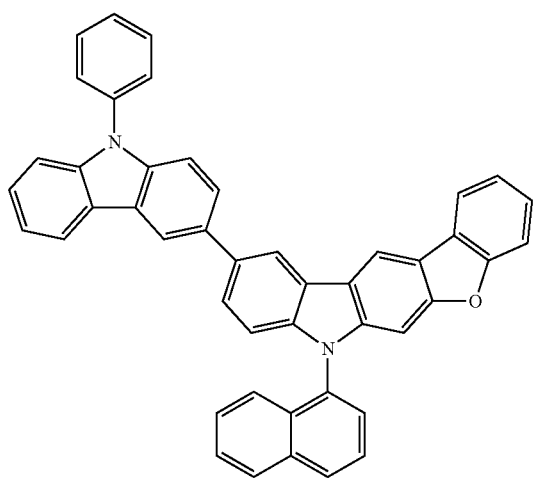
F-150
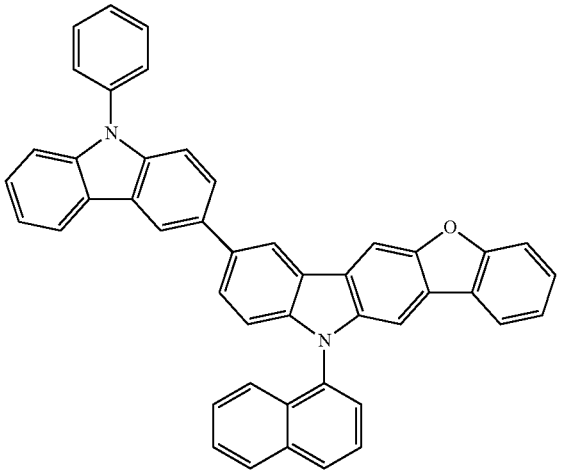

F-151
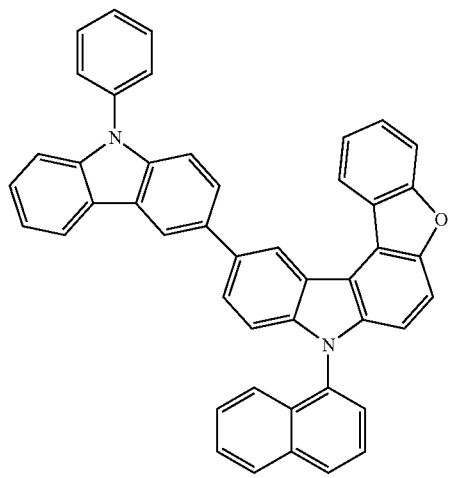
F-152
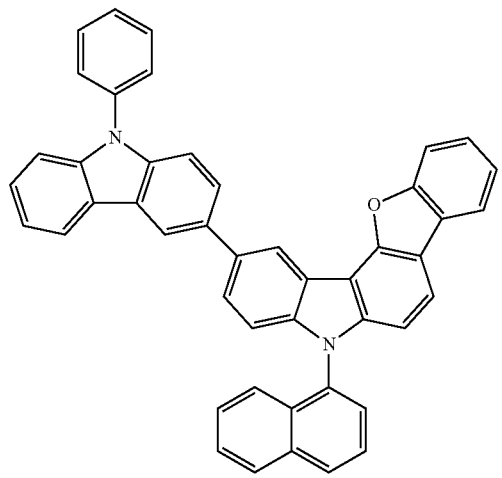
F-153
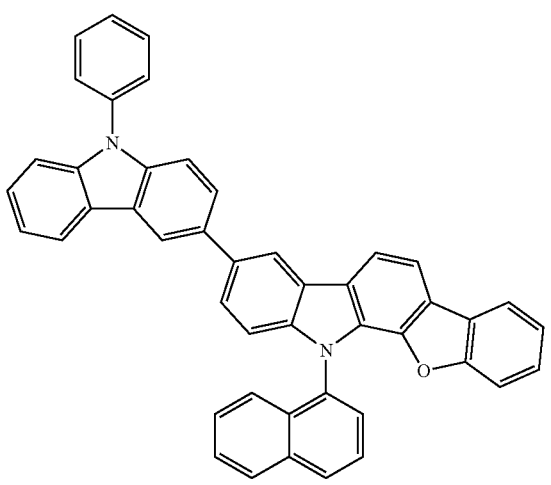
F-154
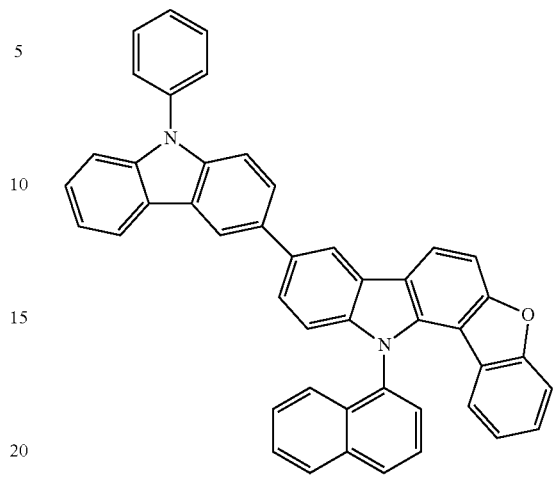
F-155
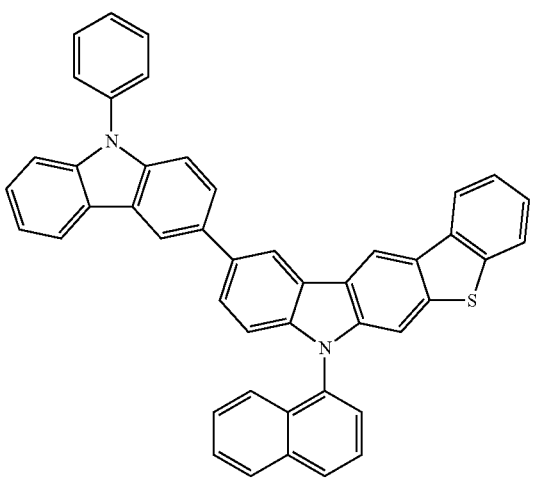
F-156
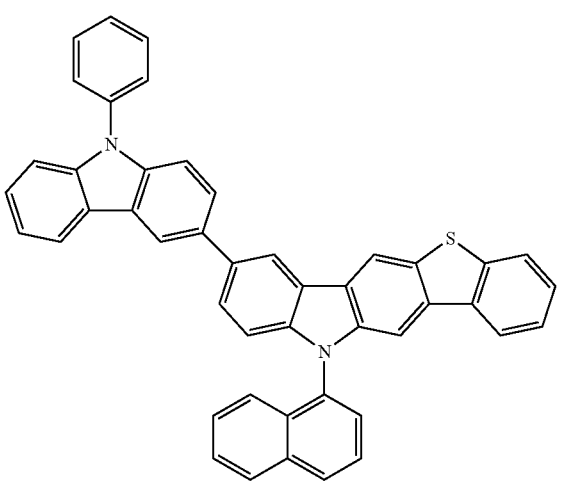

F-157
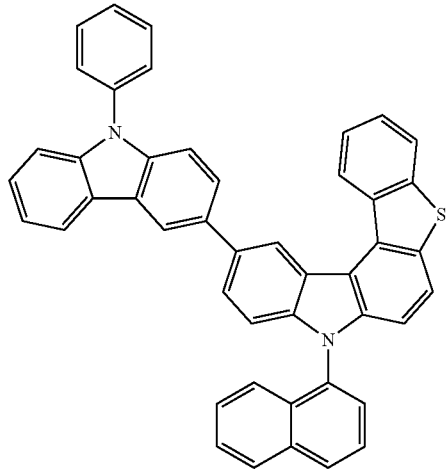
F-158
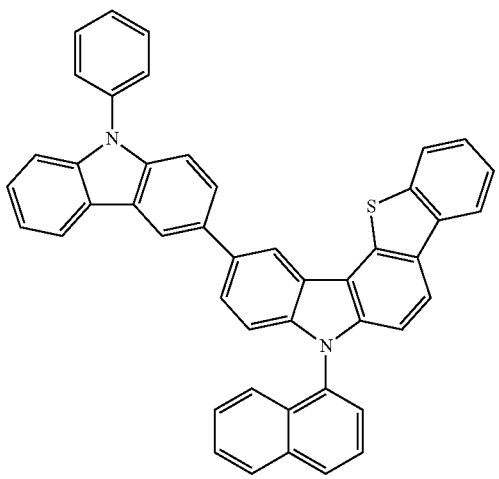
F-159
F-160
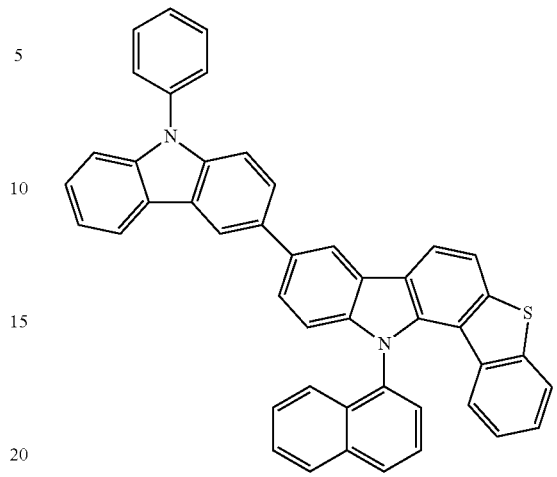
F-161
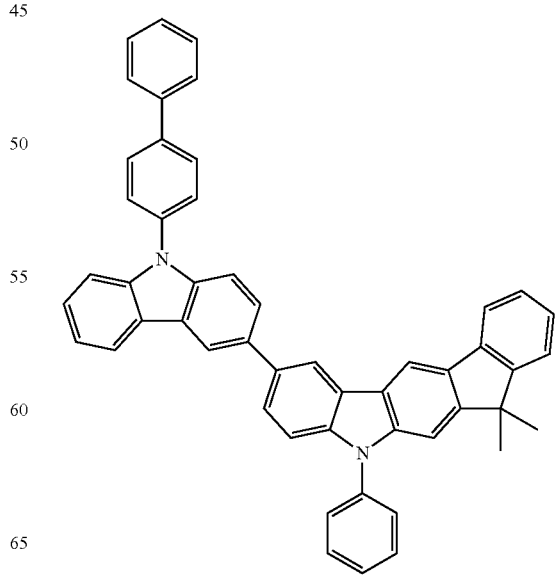

F-162
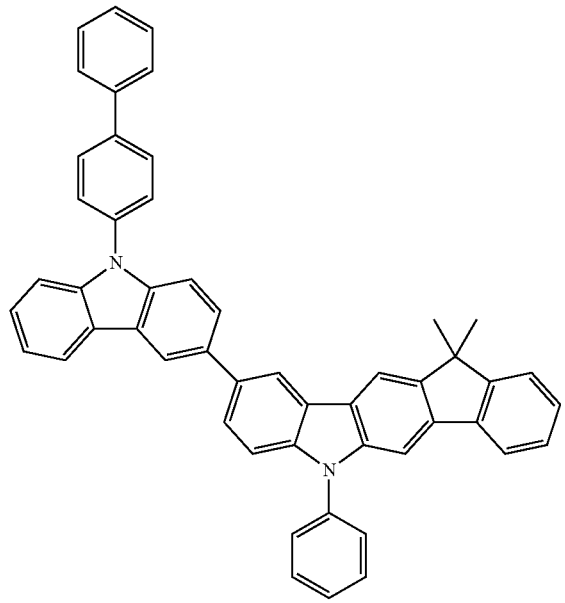
F-164
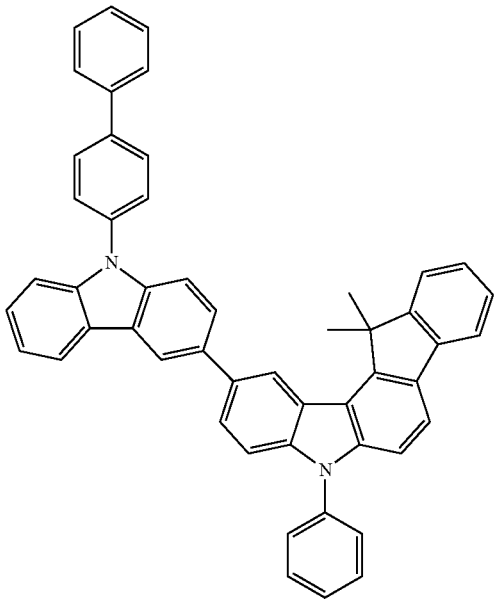
F-163
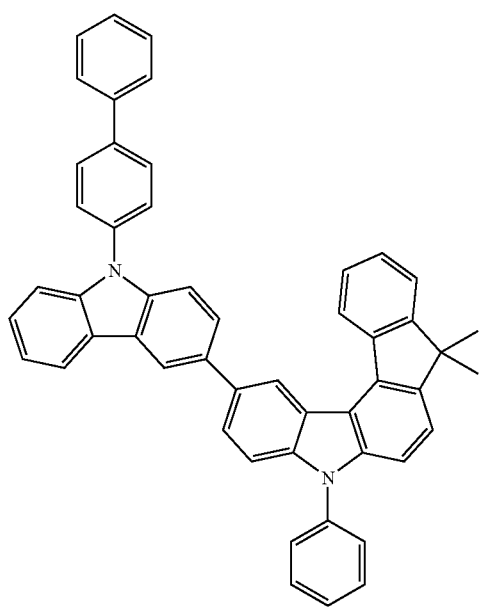
F-165
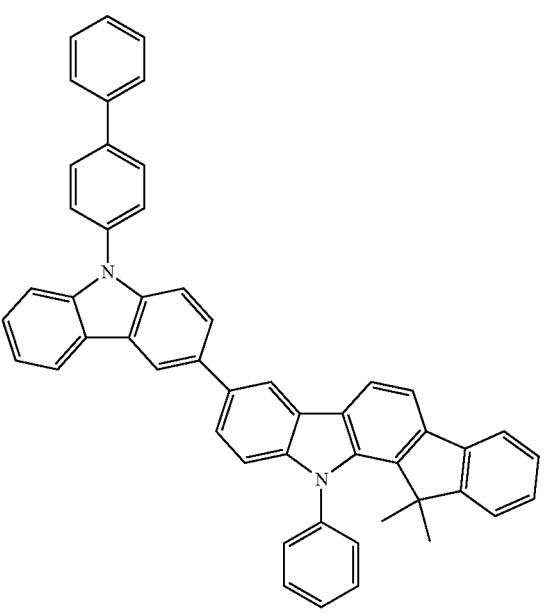

F-166
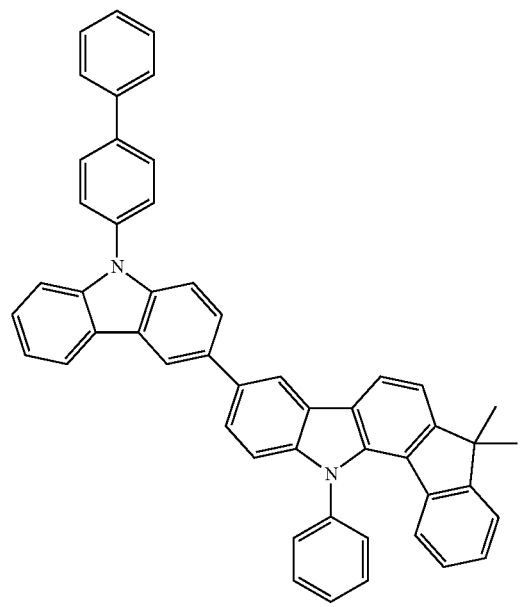
F-167
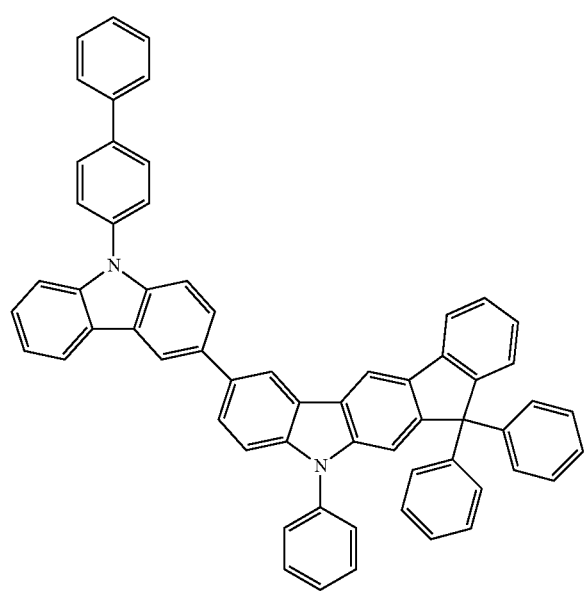
F-168
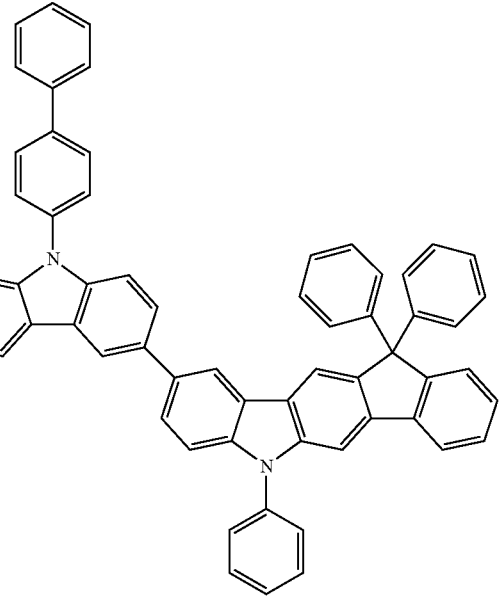
F-169
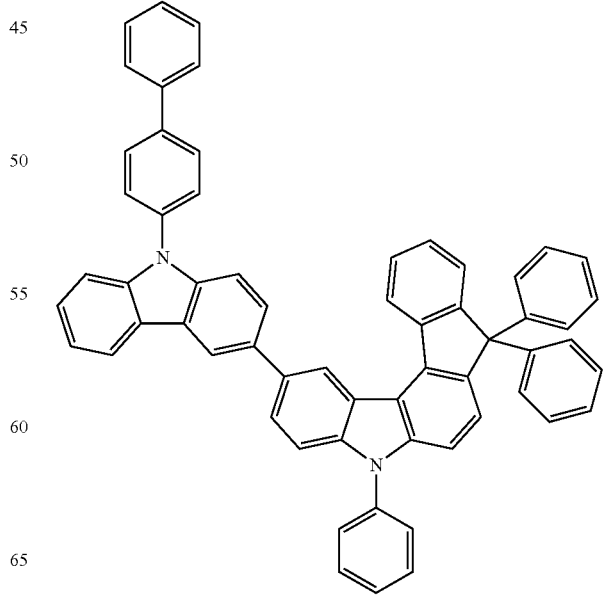

F-170
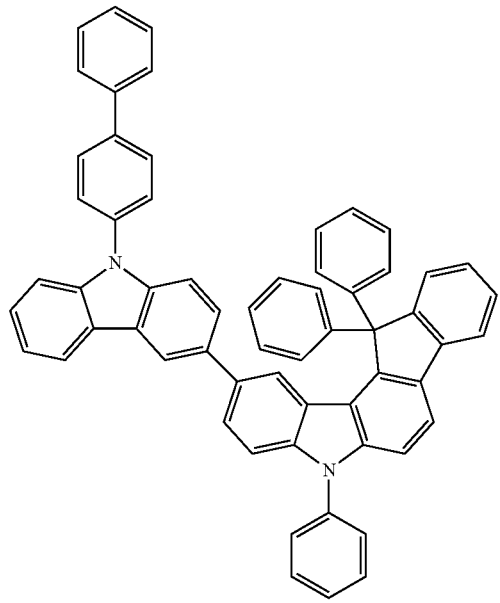
F-172
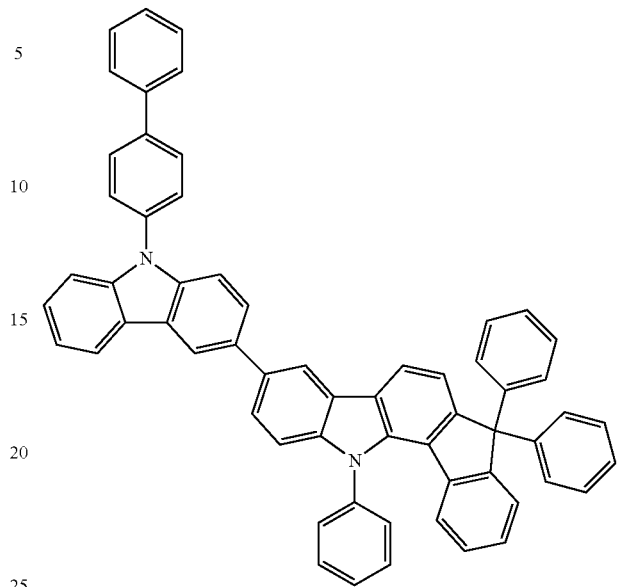
F-171
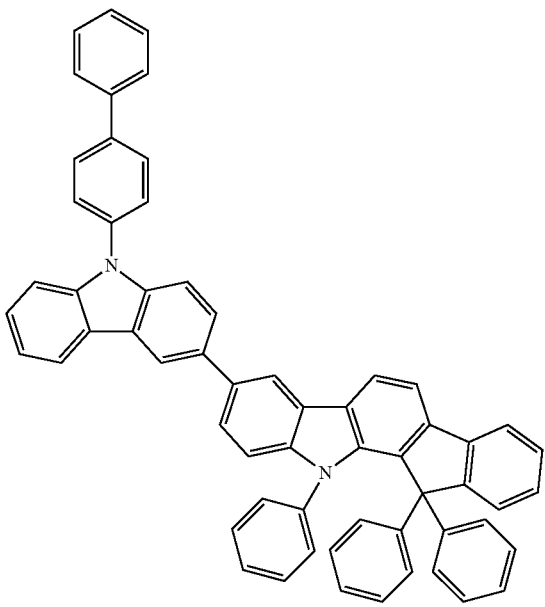
F-173
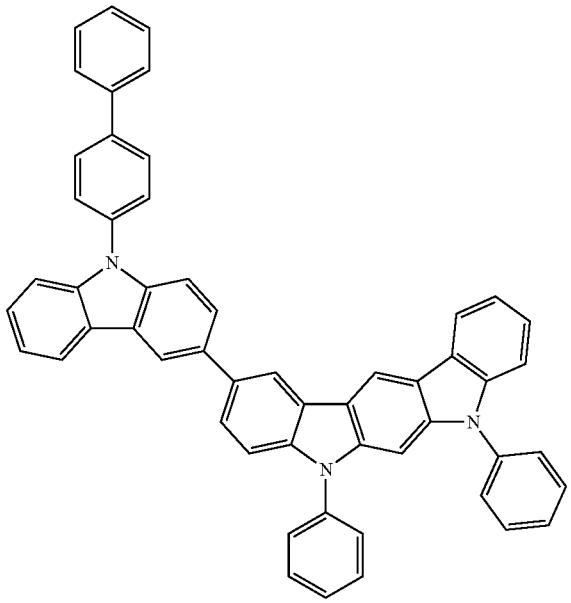

F-174
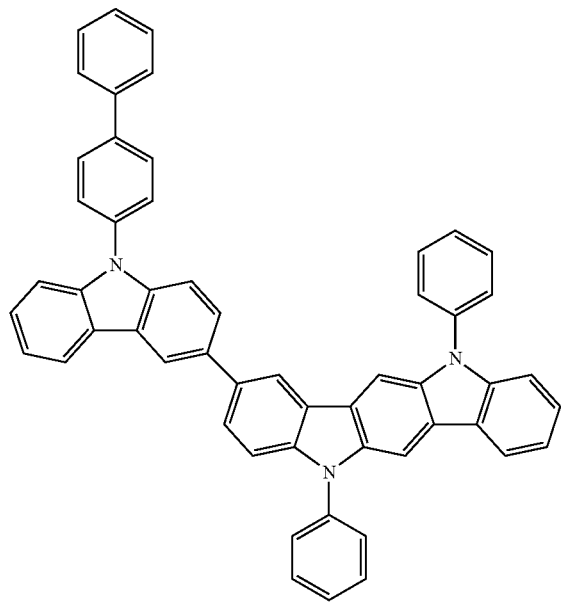
F-176
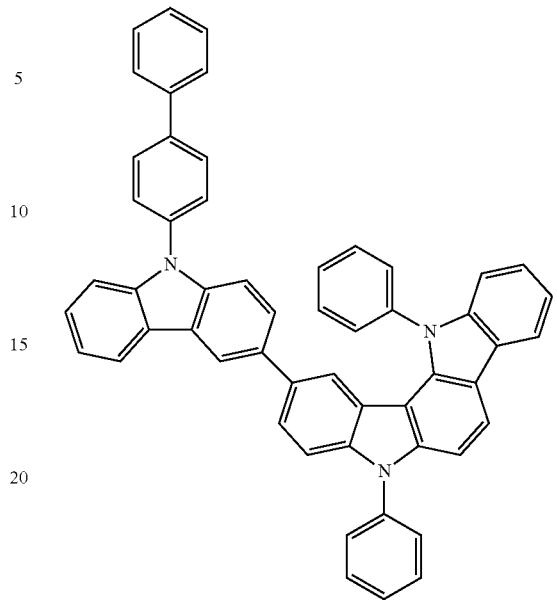
F-175
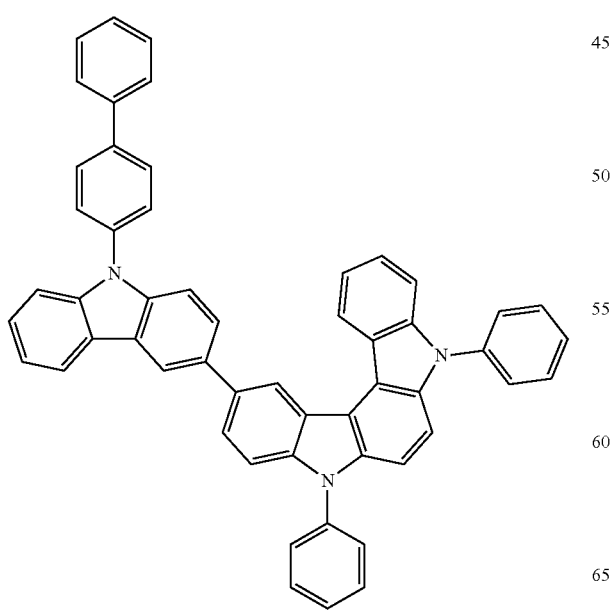
F-177
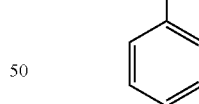

F-178
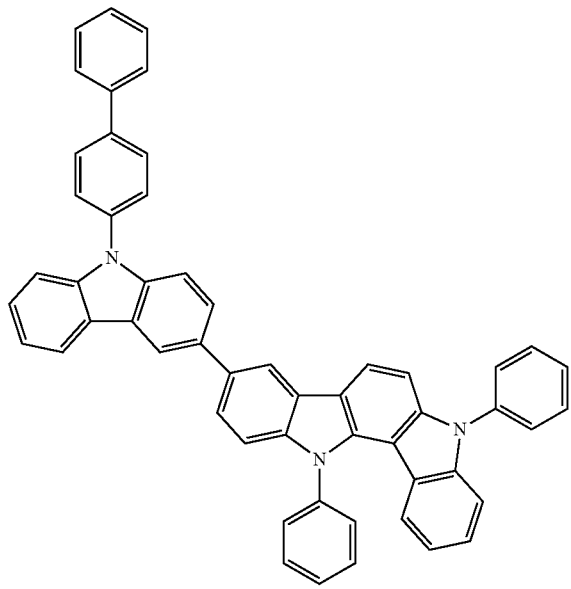
F-180
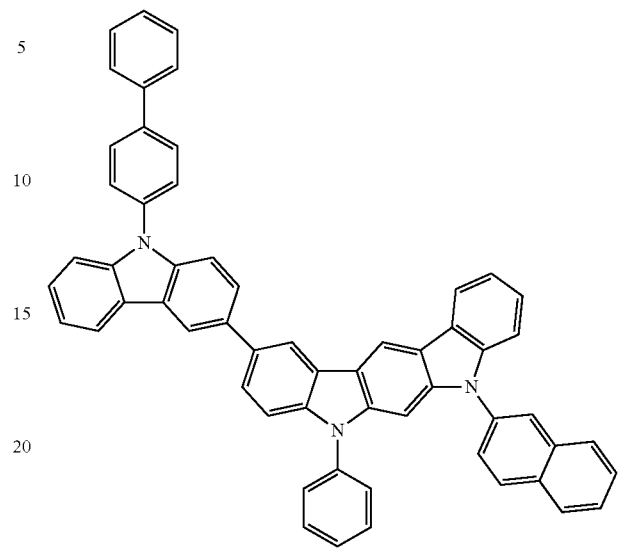
F-179
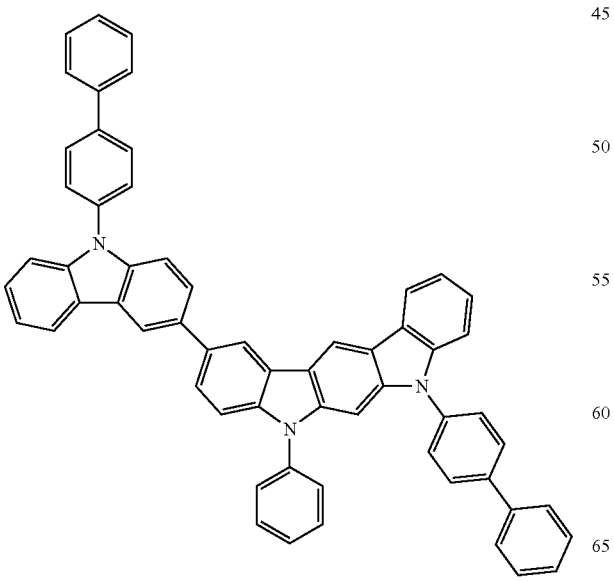
F-181
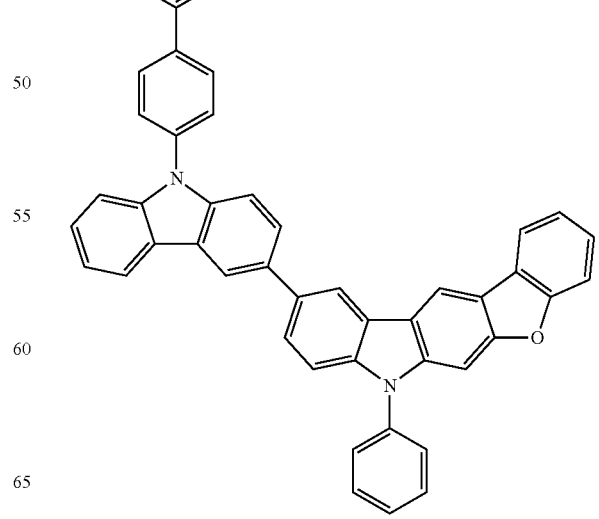

-continued
F-182
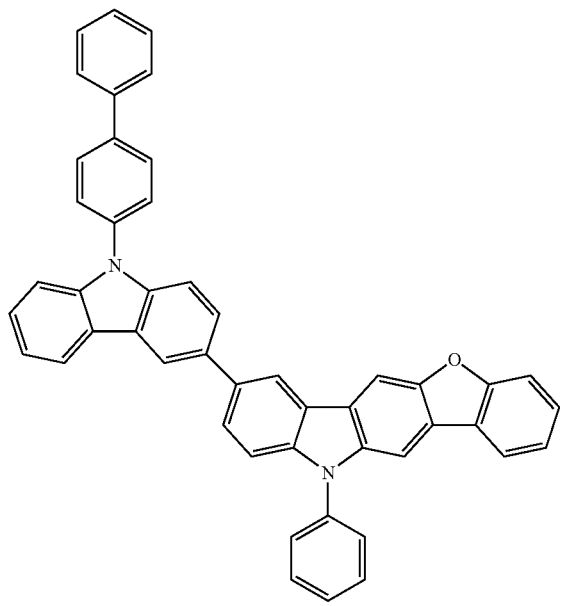
F-183
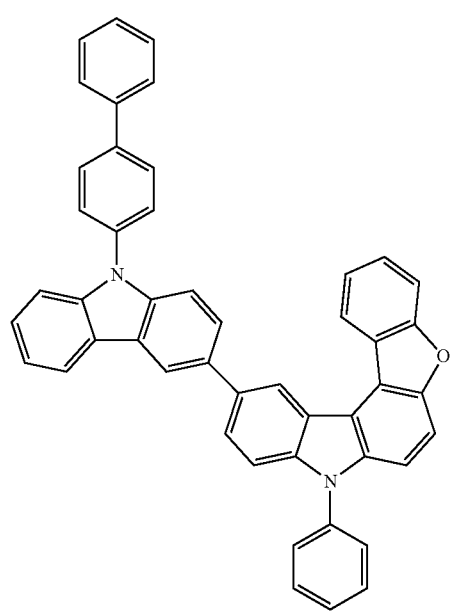
-continued
F-184
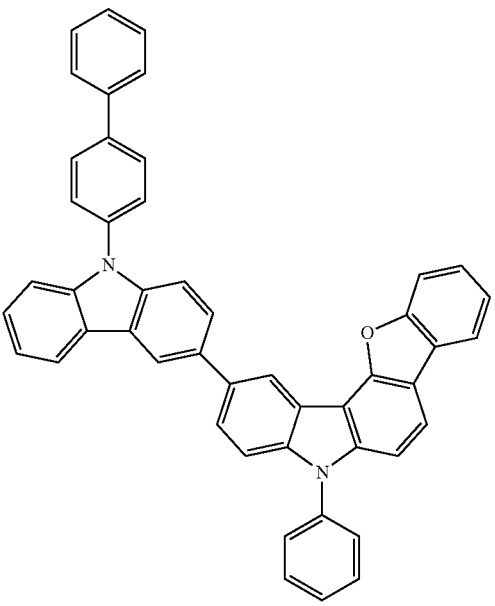
F-185
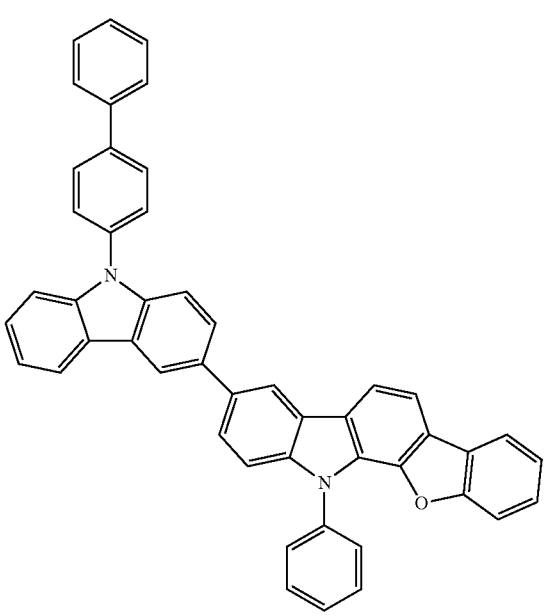

F-186
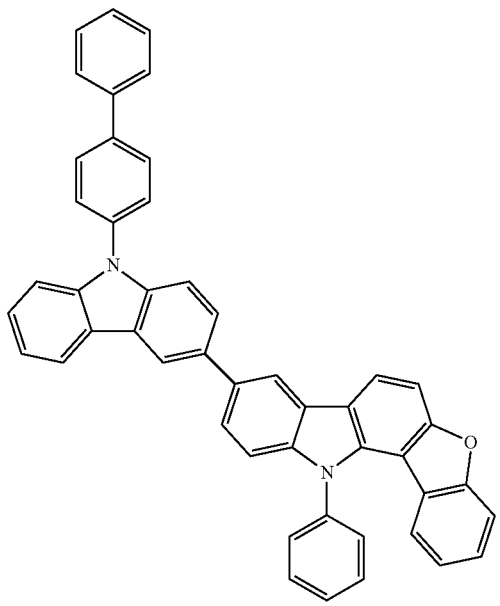
F-187
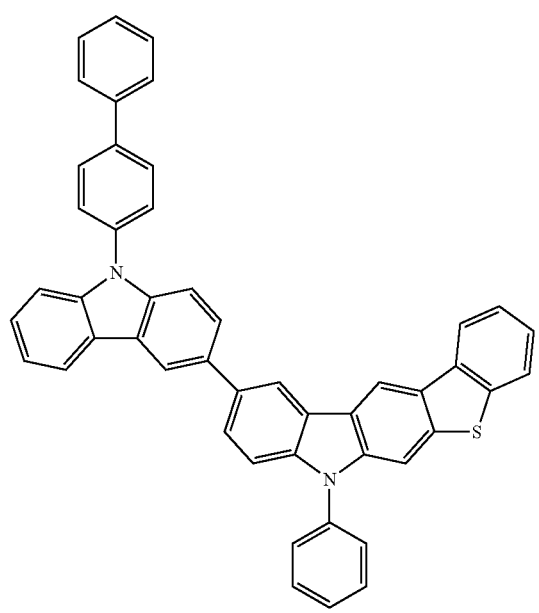
F-188
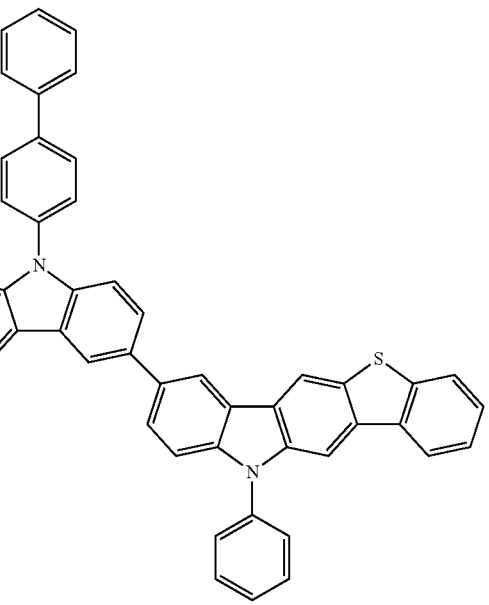
F-189
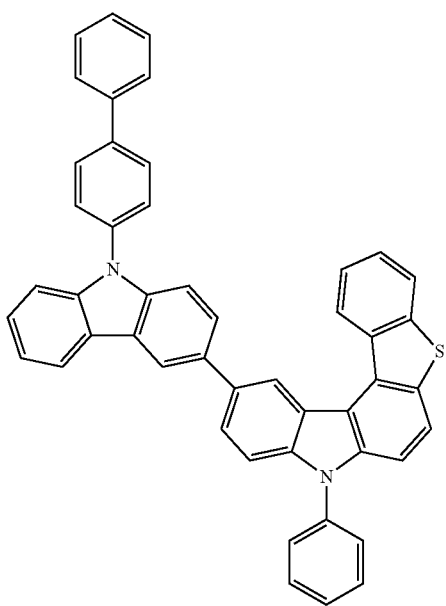

F-190
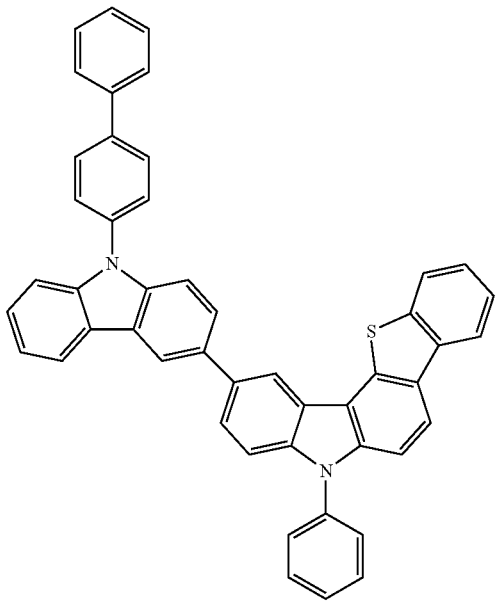
F-192
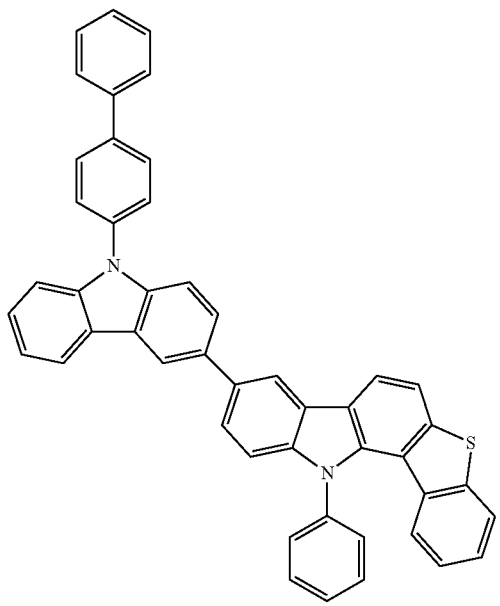
F-191
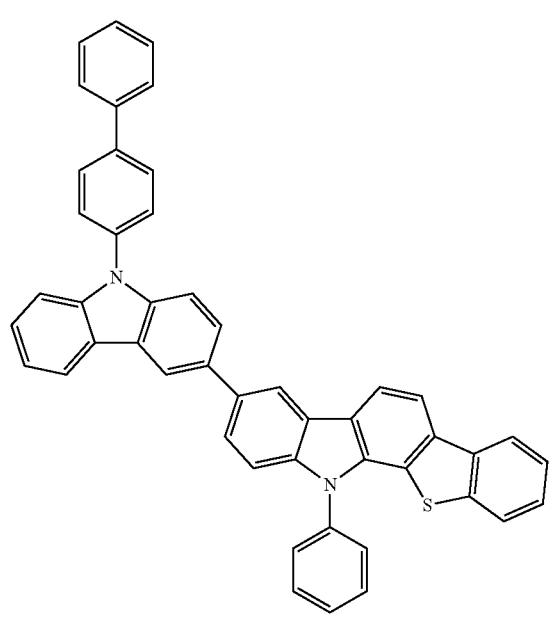
F-193
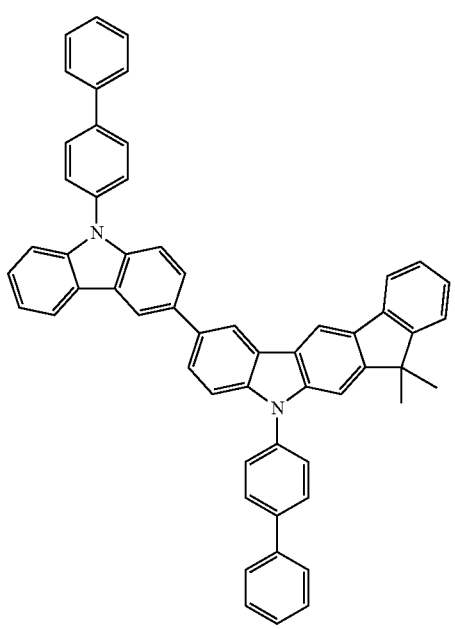

F-194
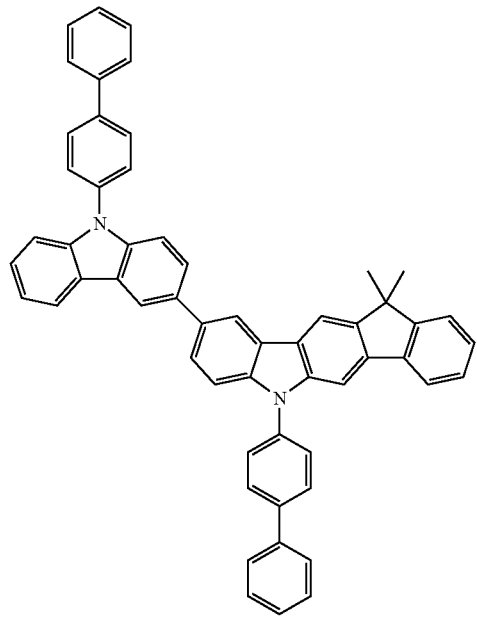
F-195
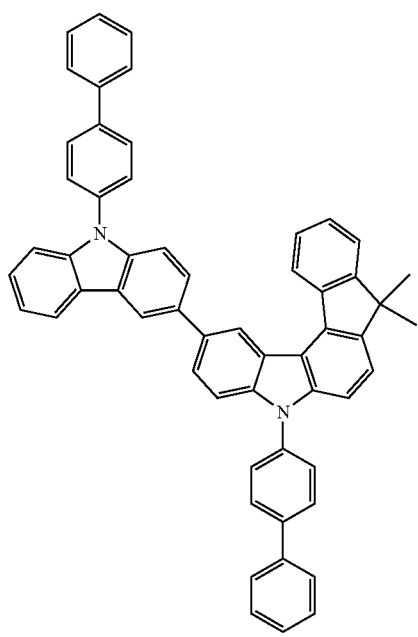
F-196
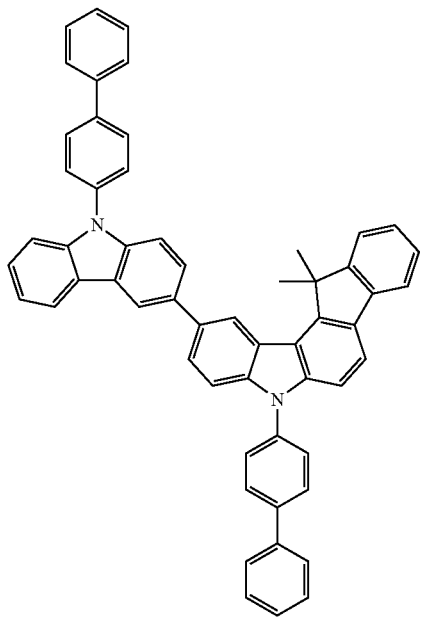
F-197
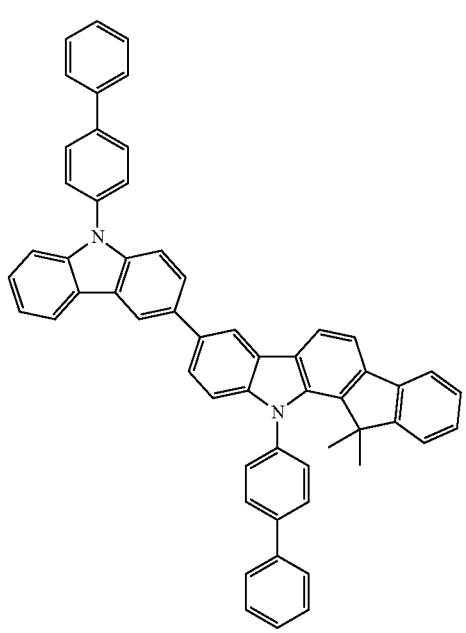

F-198
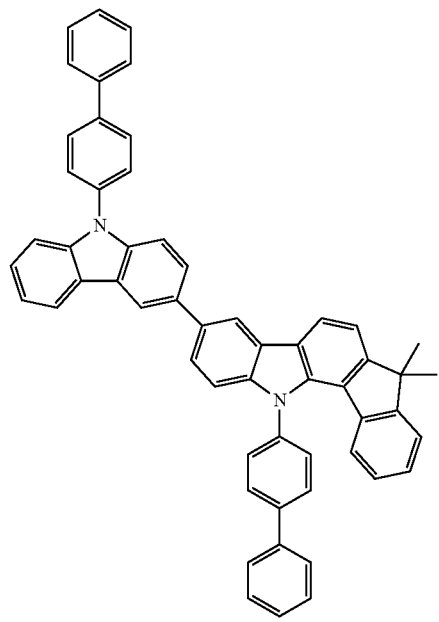
F-200
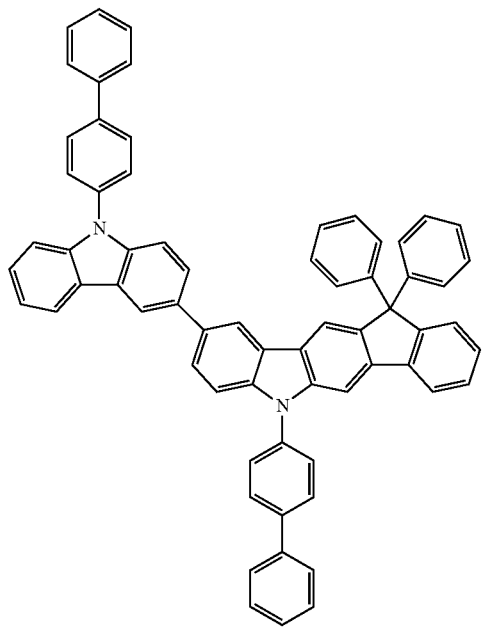
F-199
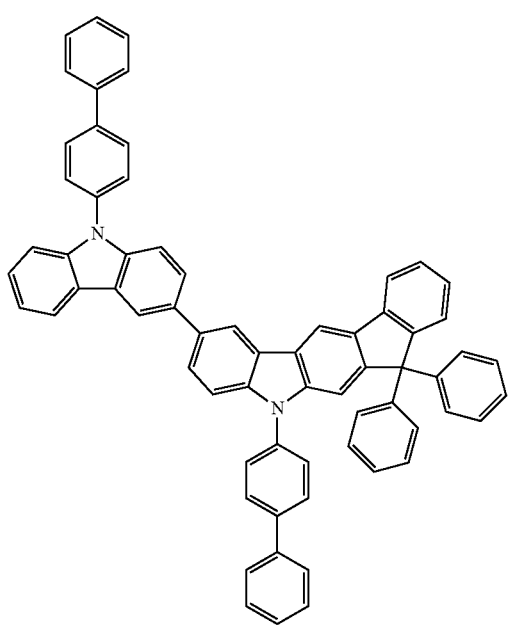
F-201
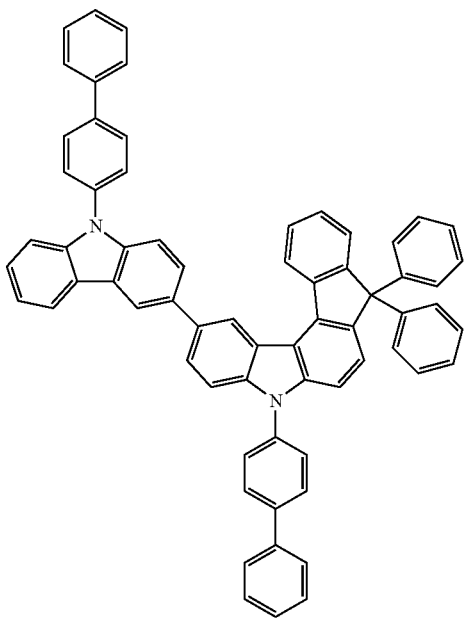

-continued
F-202
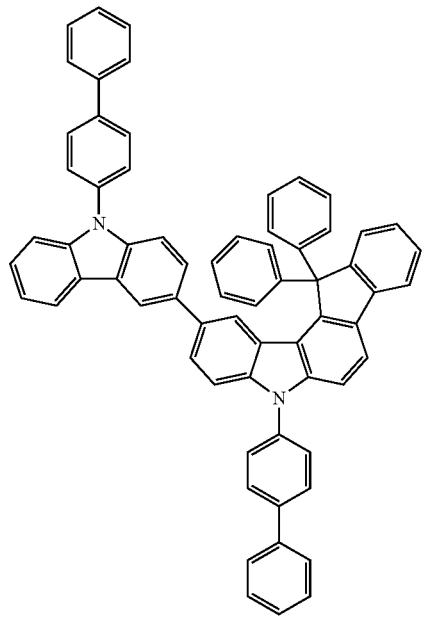
F-203
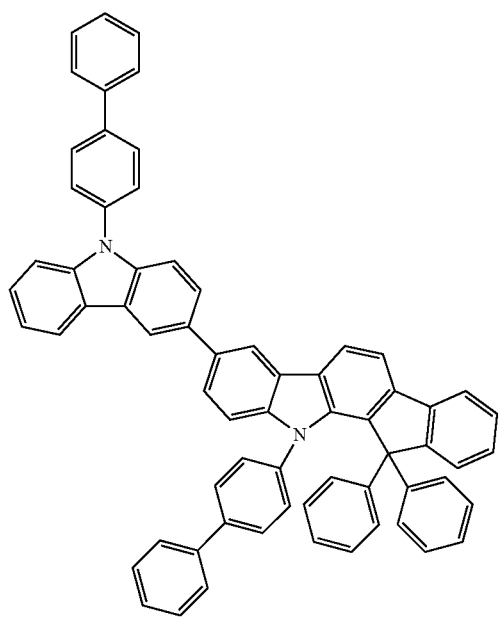
-continued
F-204
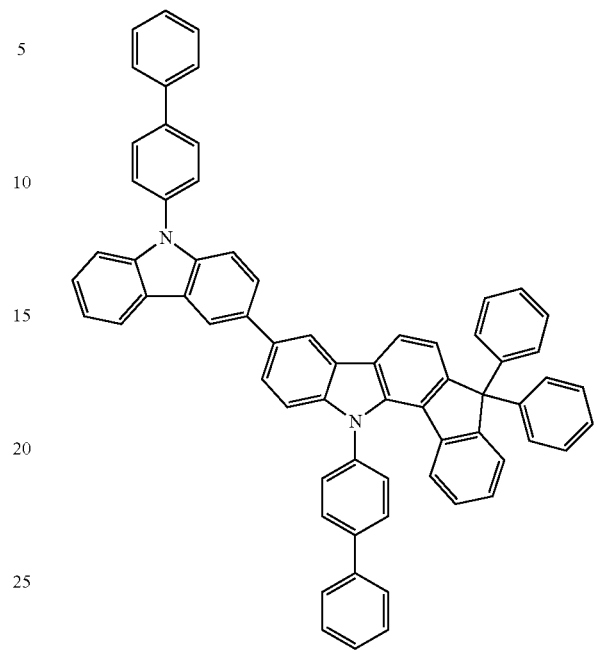
F-205
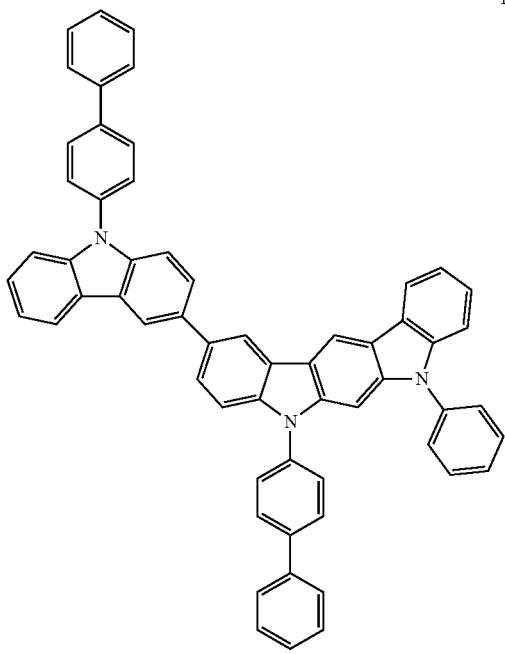

-continued
F-206
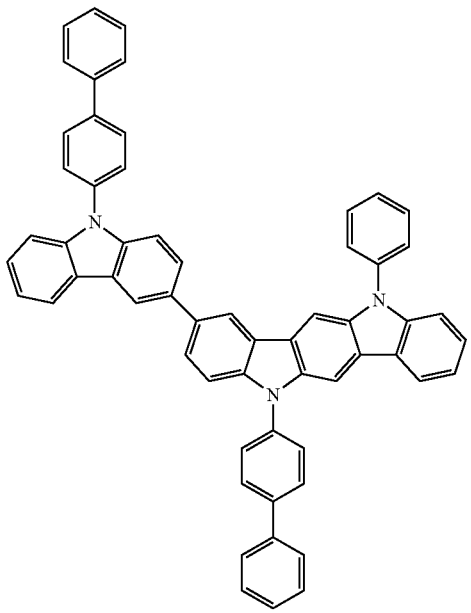
F-207
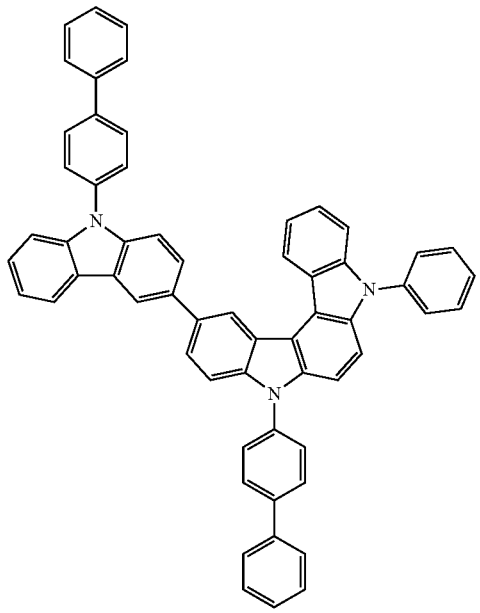
F-208
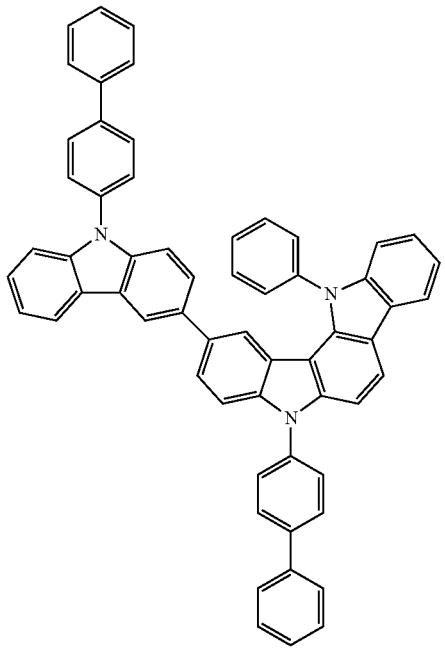
F-209
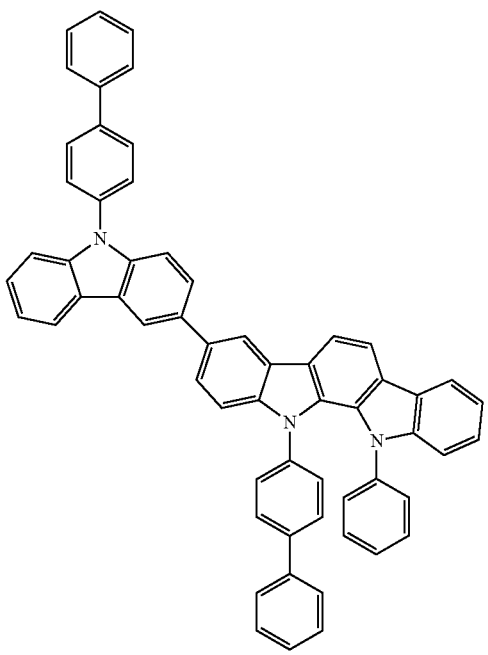

F-210
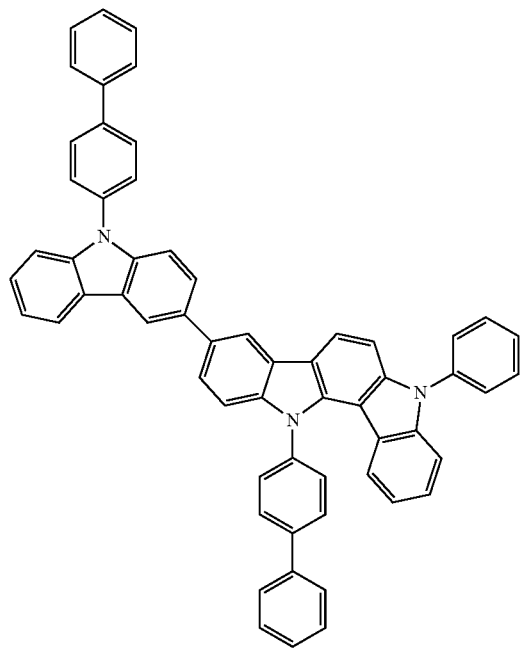
F-211
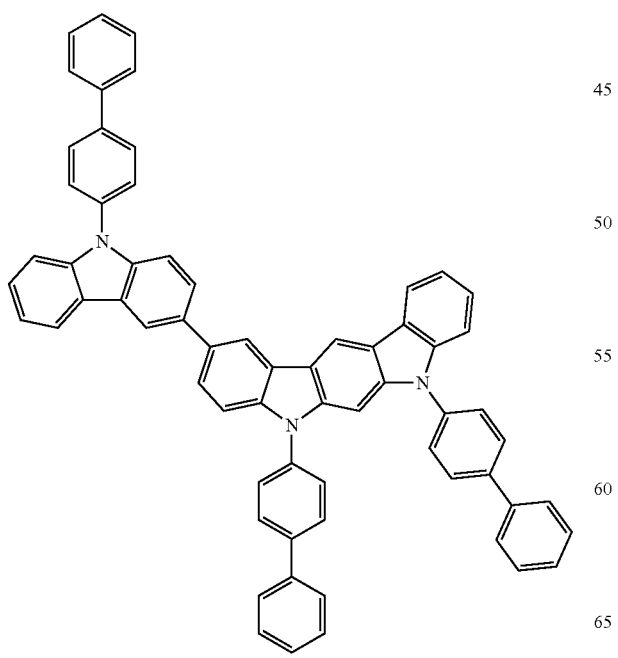
F-212
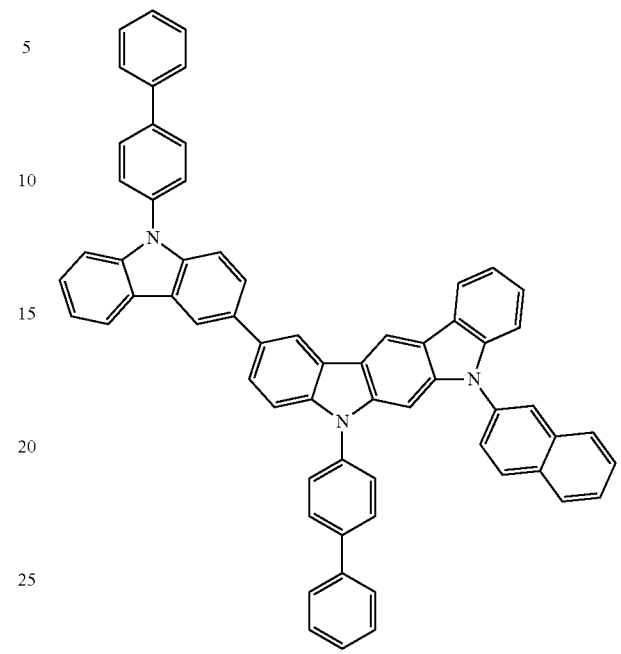
F-213
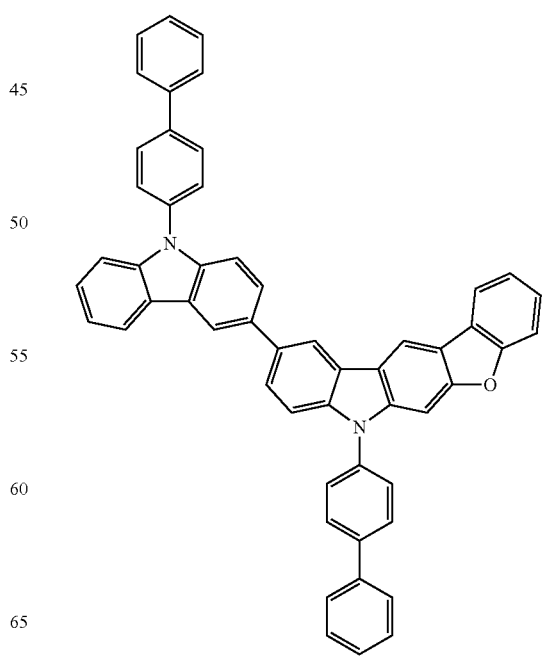

-continued
F-214
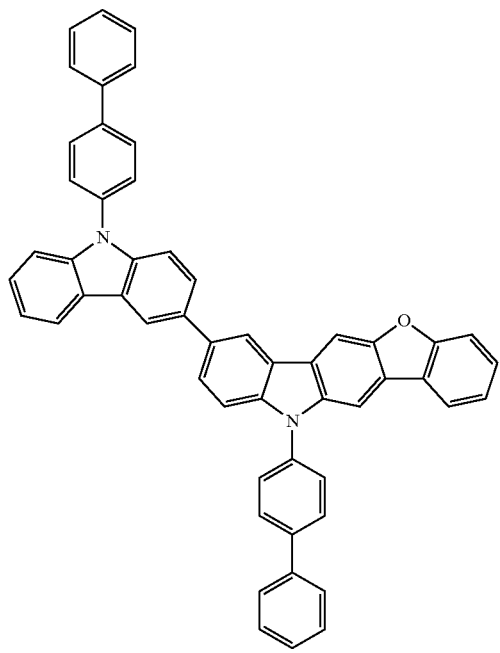
F-216
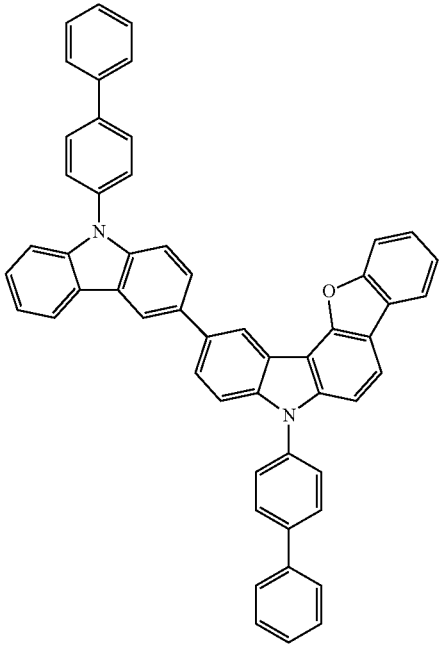
F-215
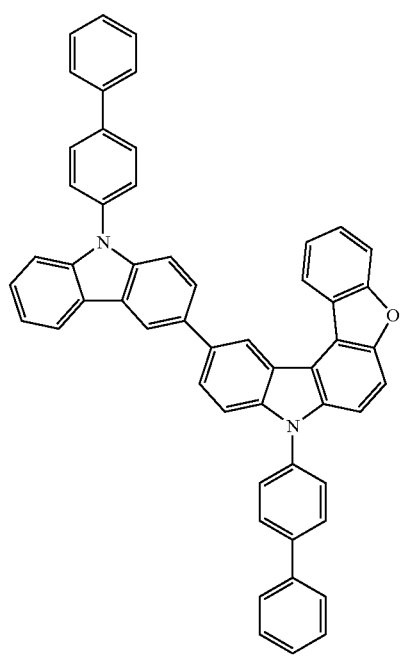
F-217
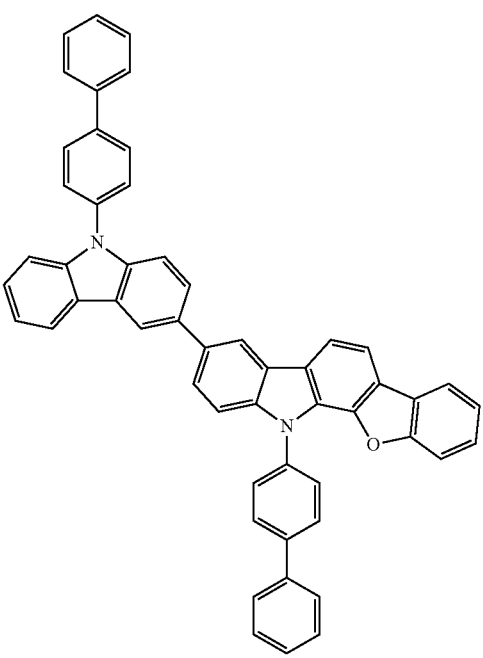

F-218
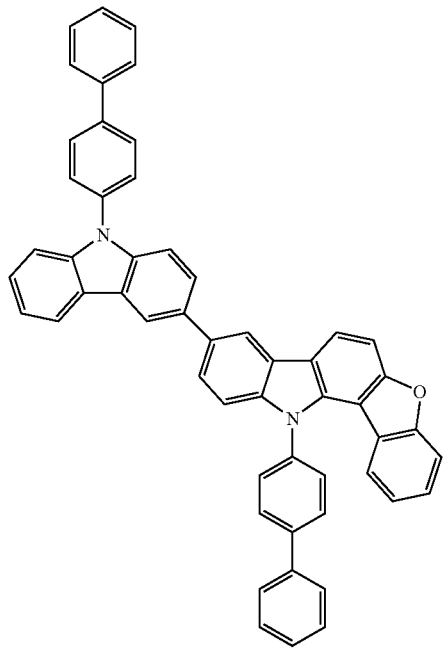
F-220
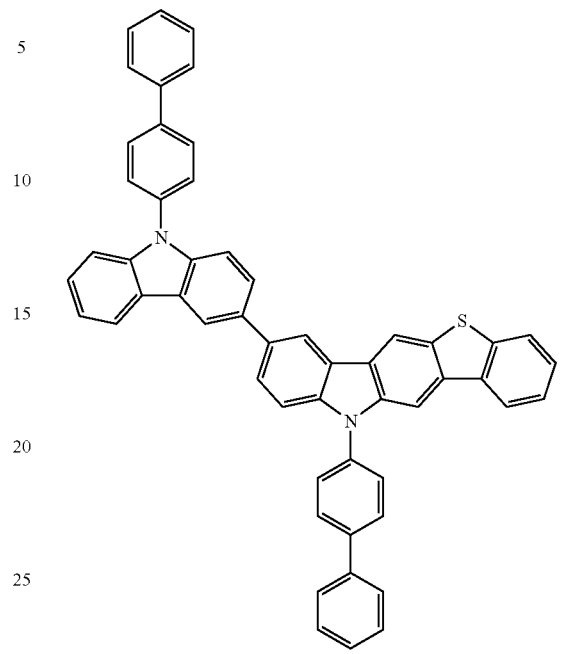
F-219
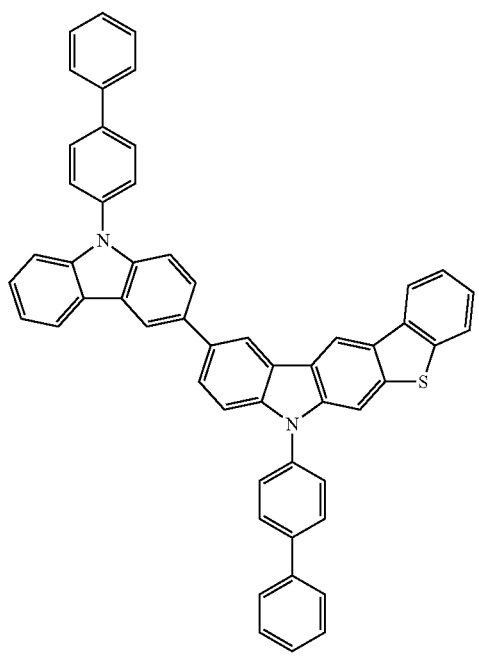
F-221
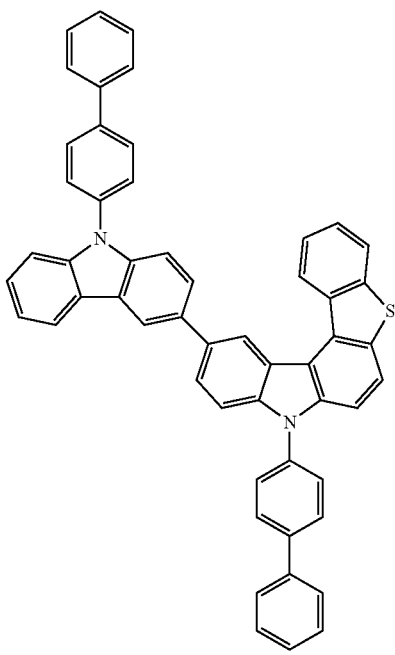

-continued
F-222
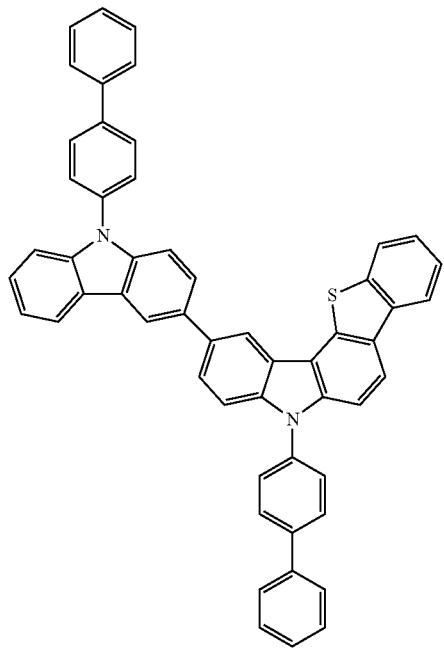
F-223
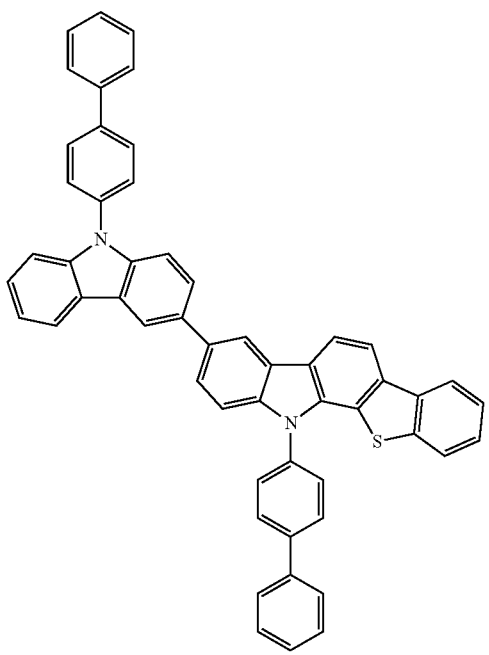
F-224
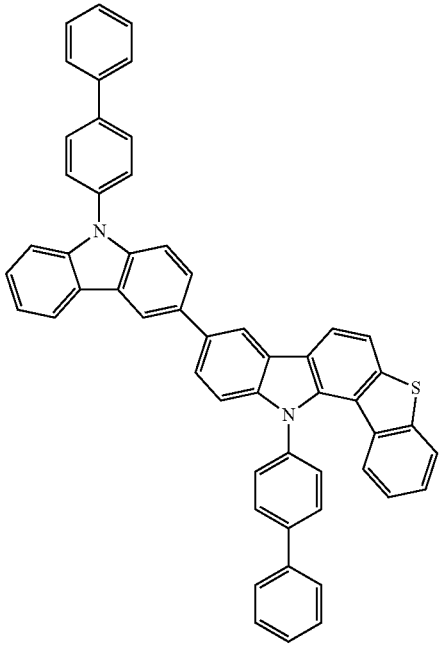
F-225
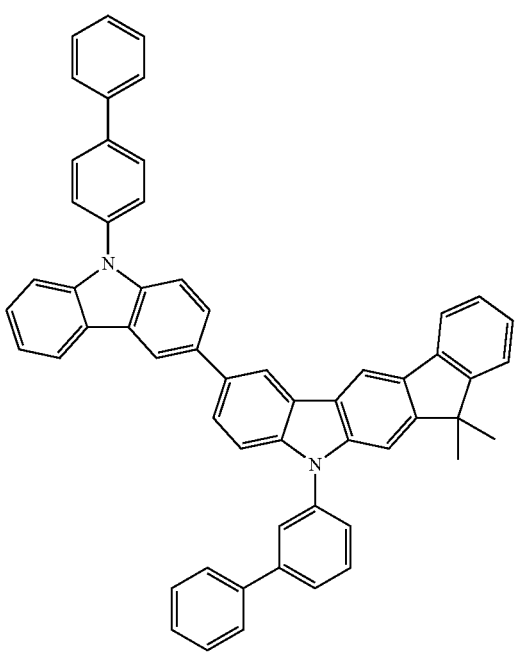

F-226
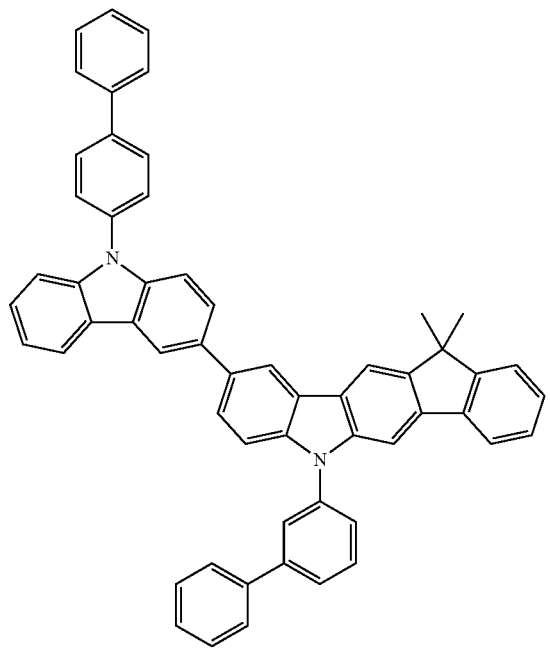
F-228
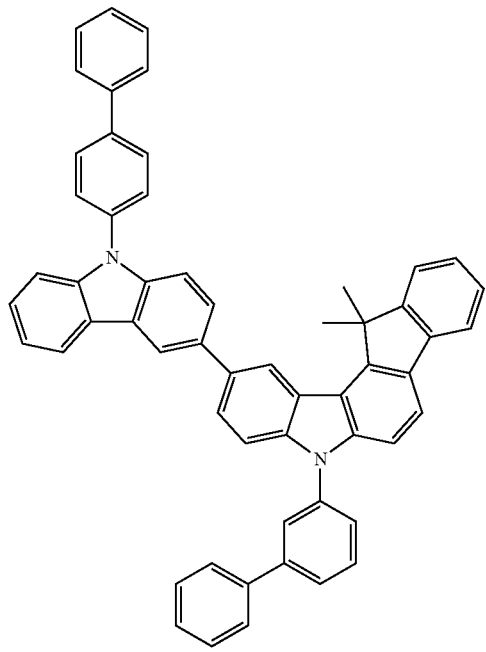
F-227
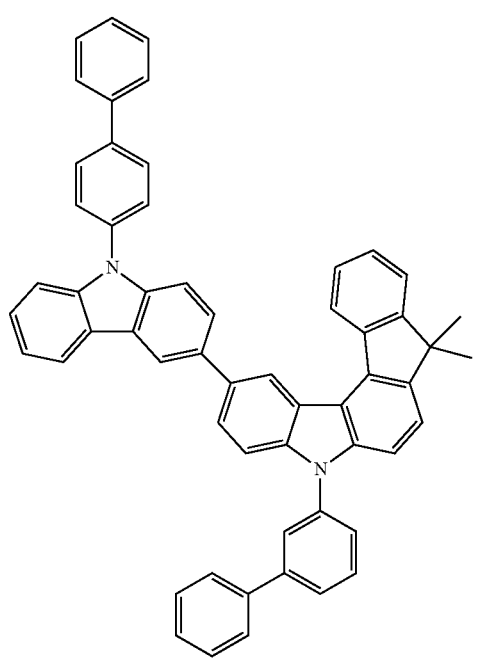
F-229
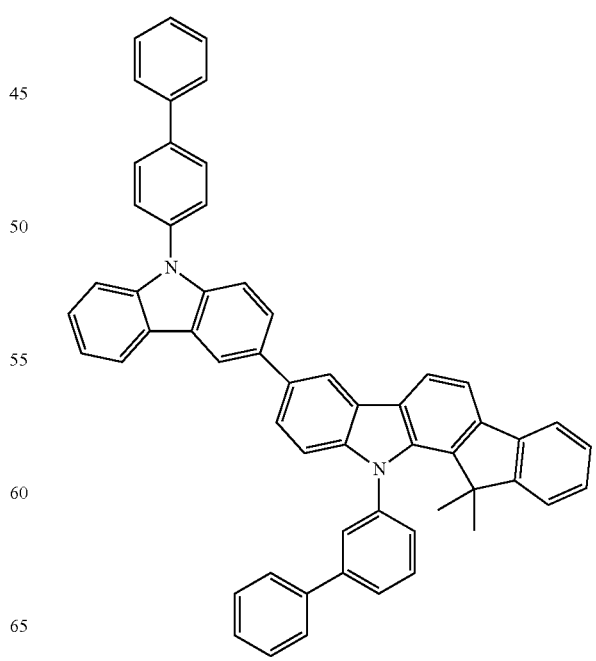

F-230
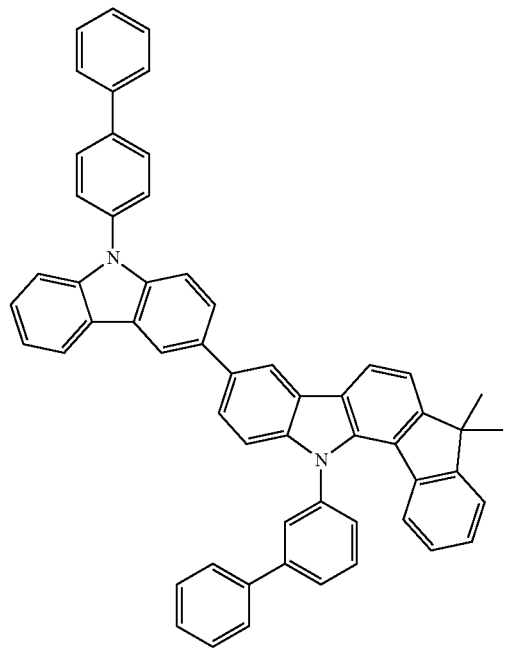
F-232
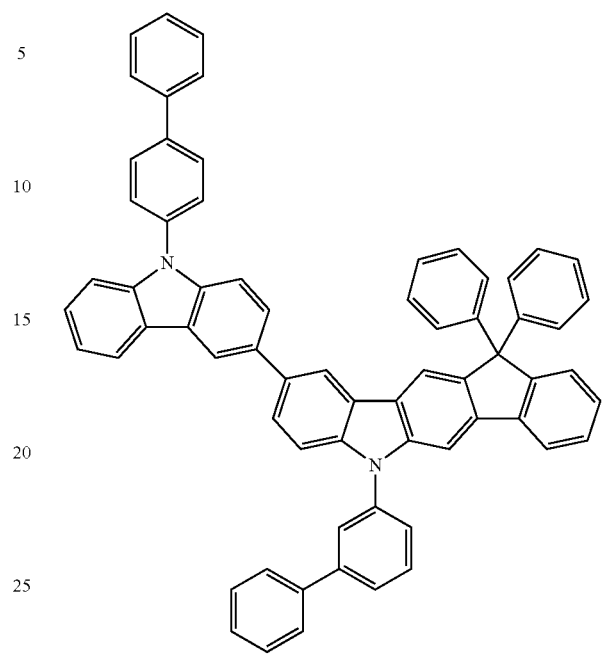
F-231
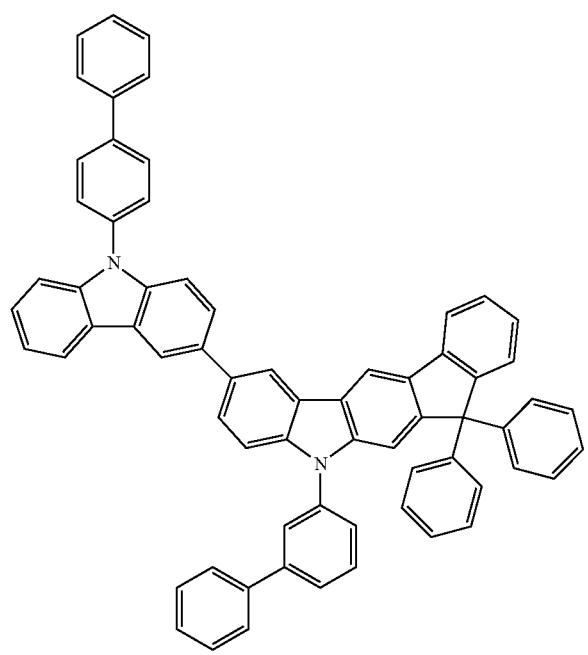
F-233
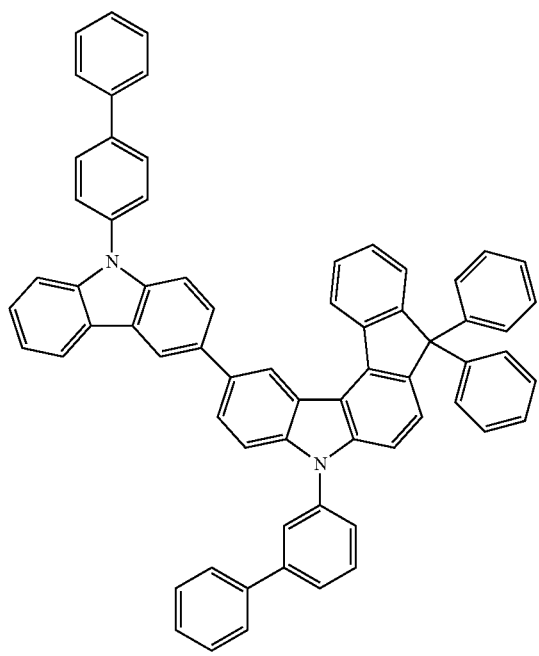

F-234
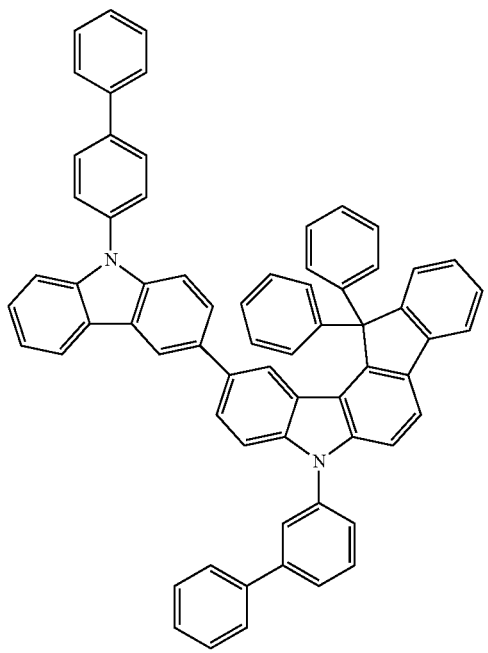
F-236
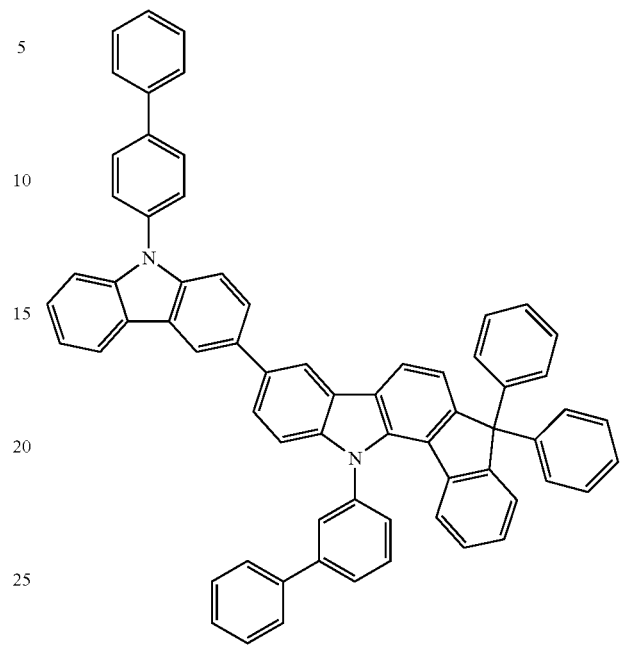
F-235
F-237
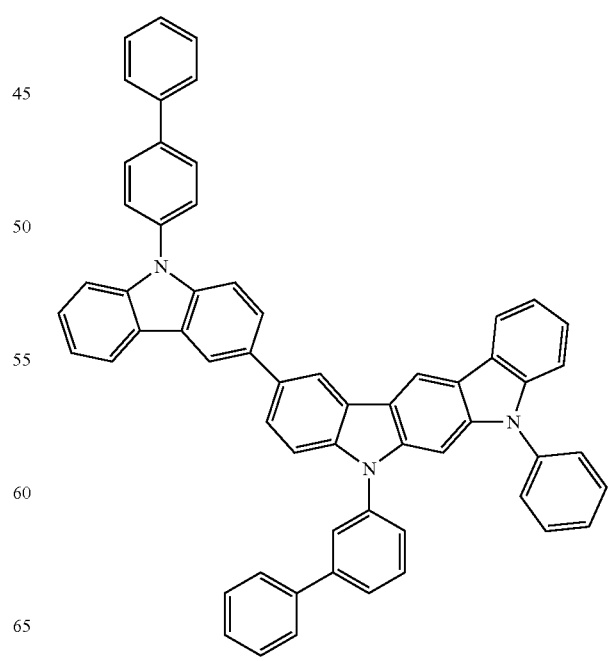

F-238
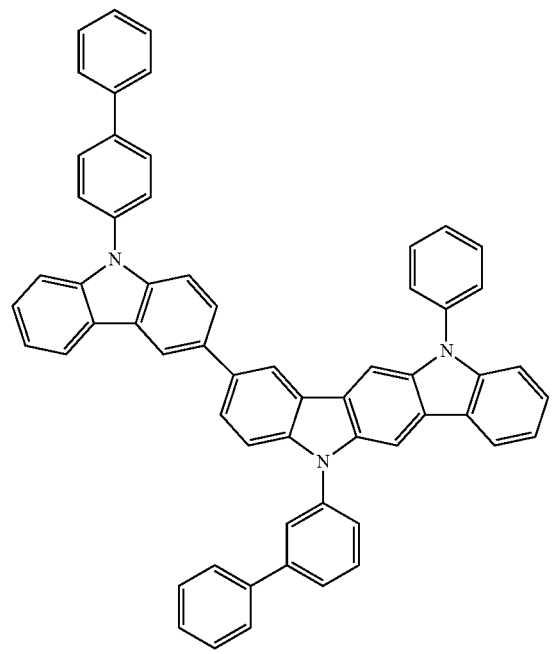
F-239
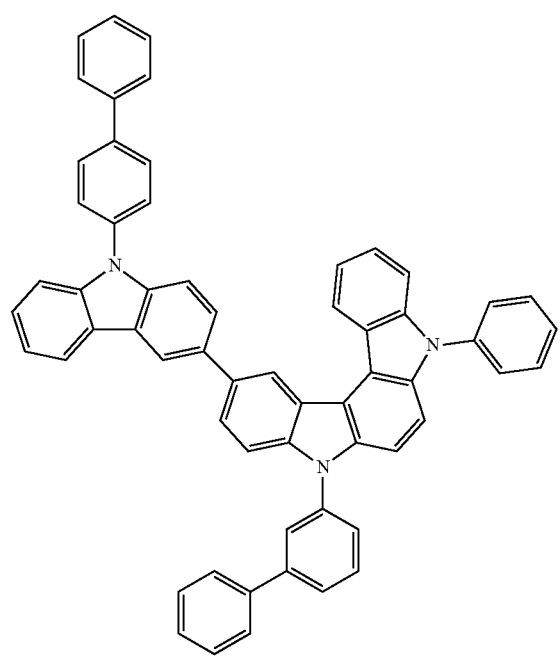
F-240
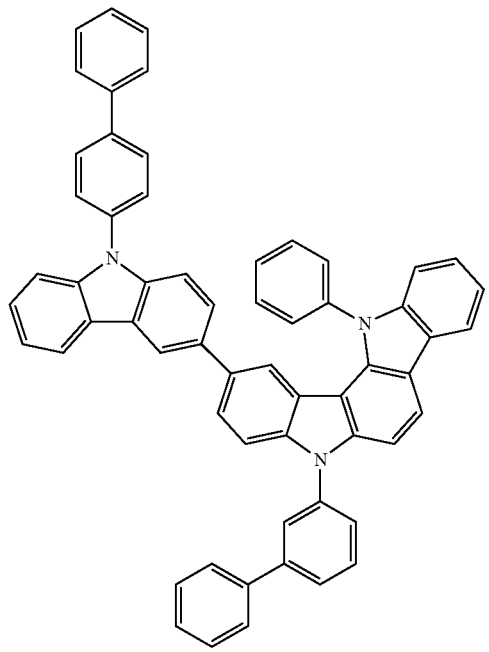
F-241
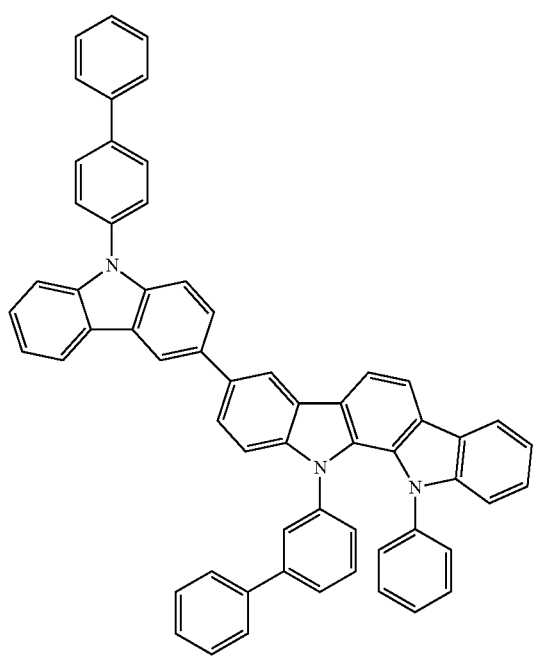

F-242
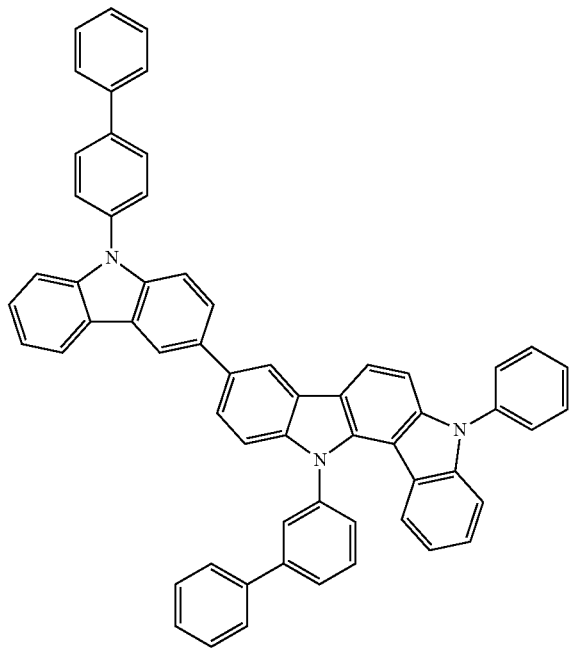
F-244
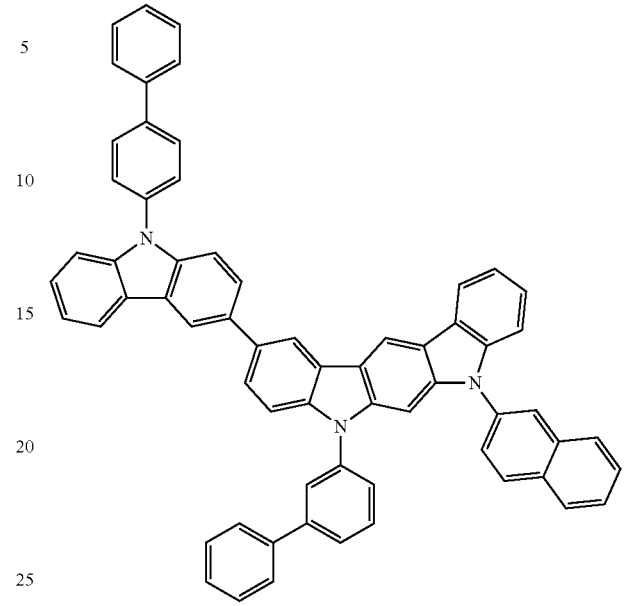
F-243
F-245
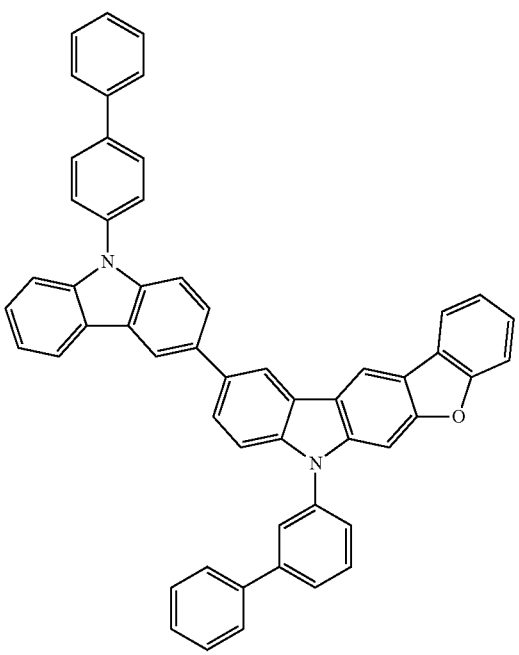

F-246
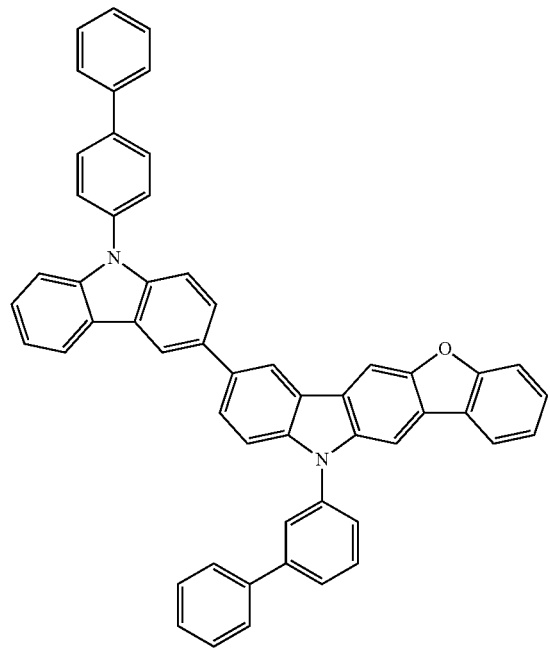
F-247
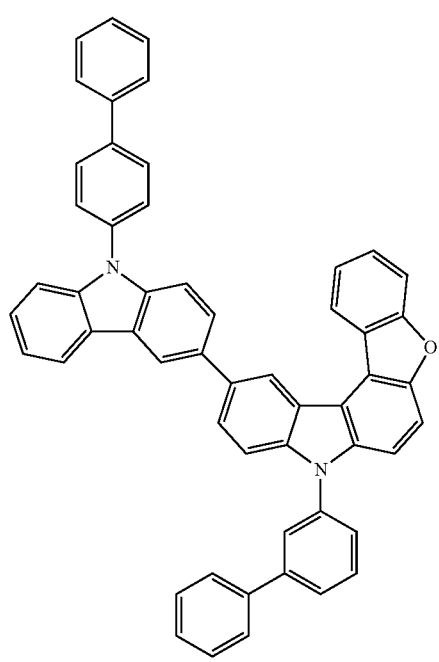
F-248
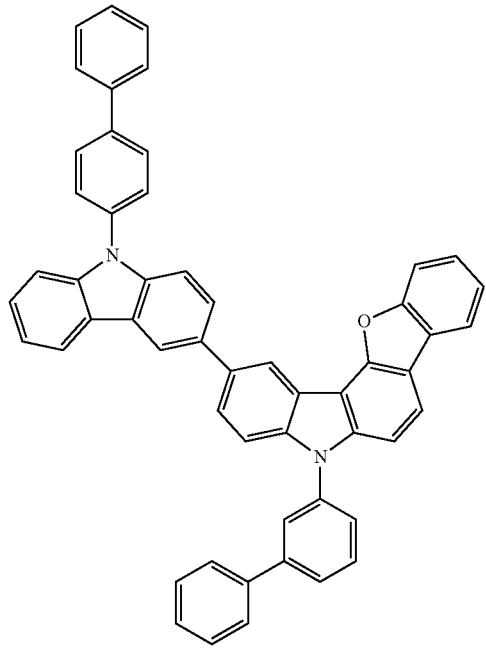
F-249
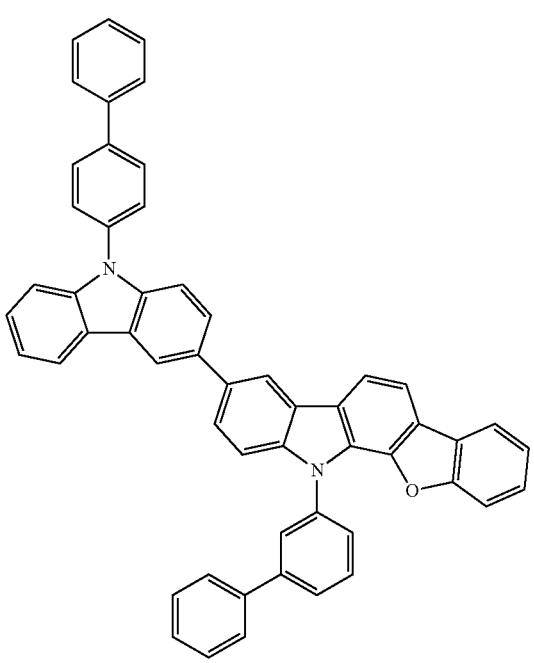

F-250
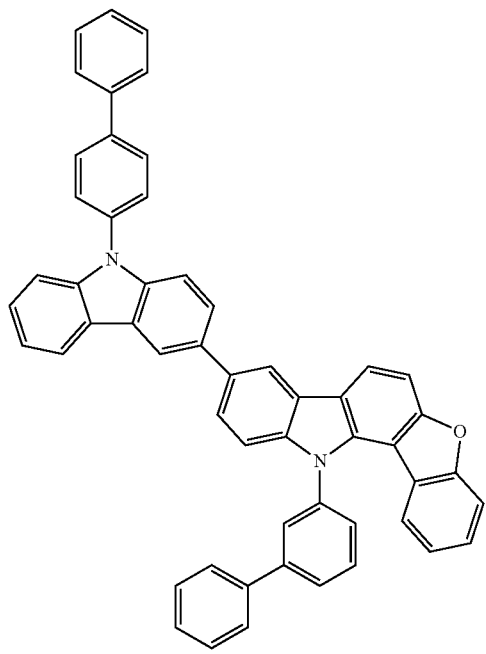
F-252
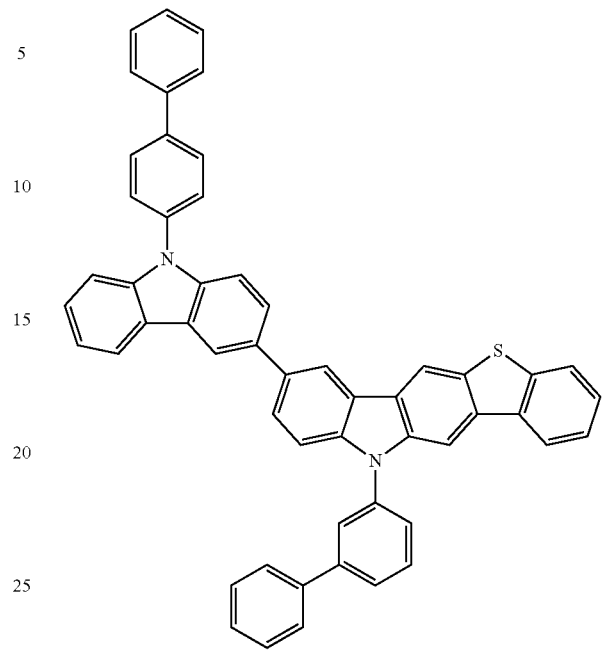
F-251
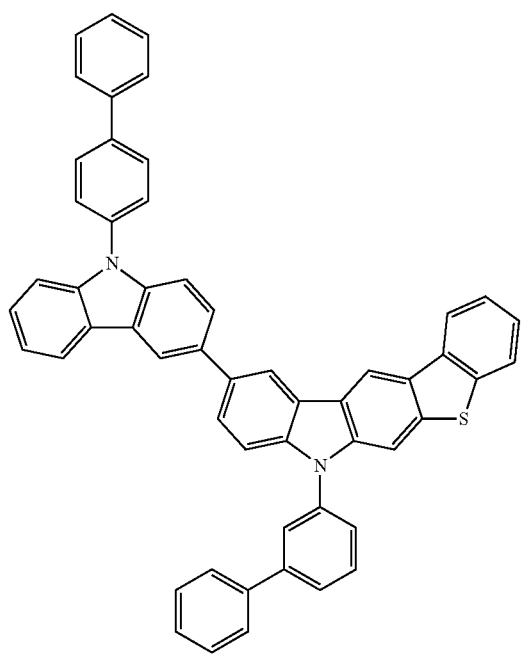
F-253
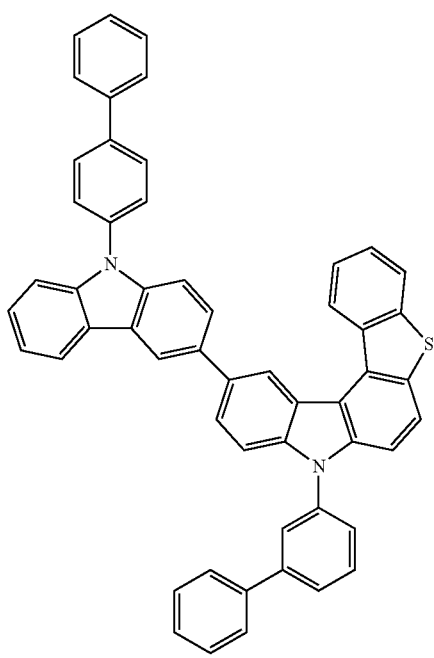

F-254
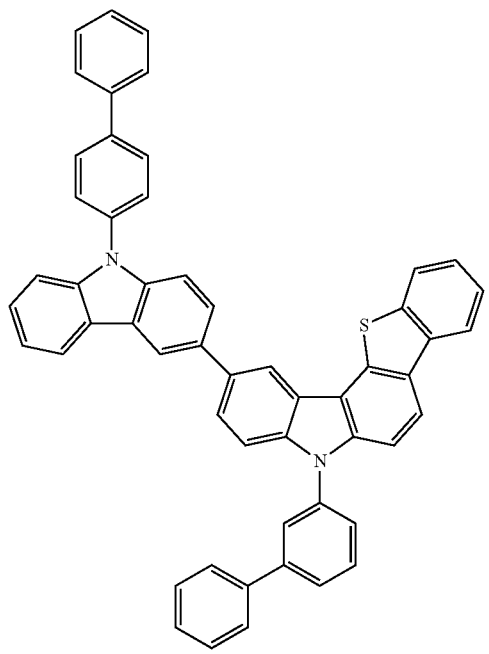
F-255
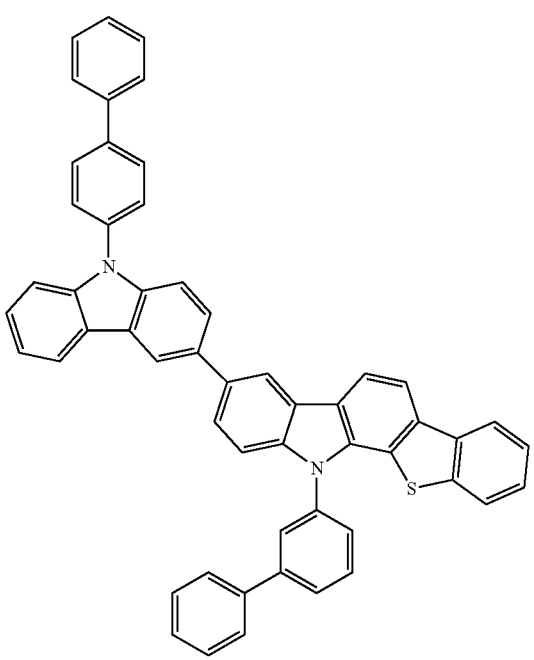
F-256
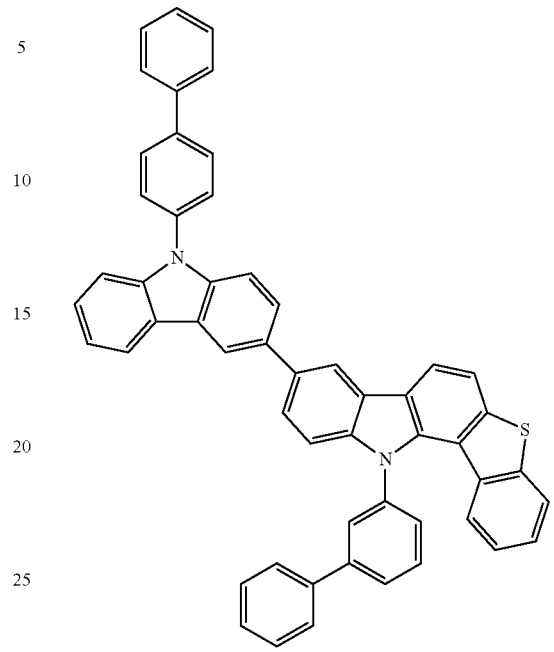
F-257
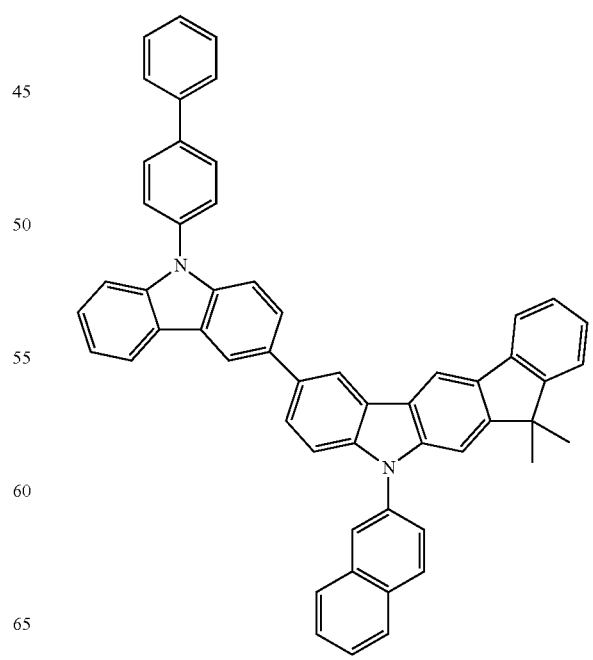

F-258
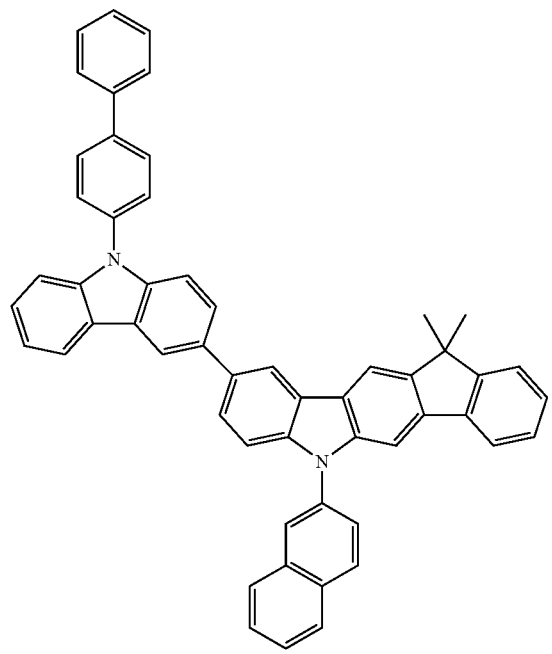
F-259
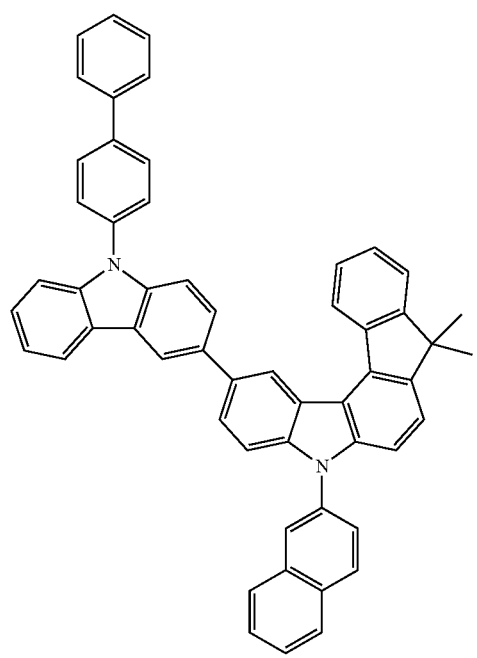
F-260
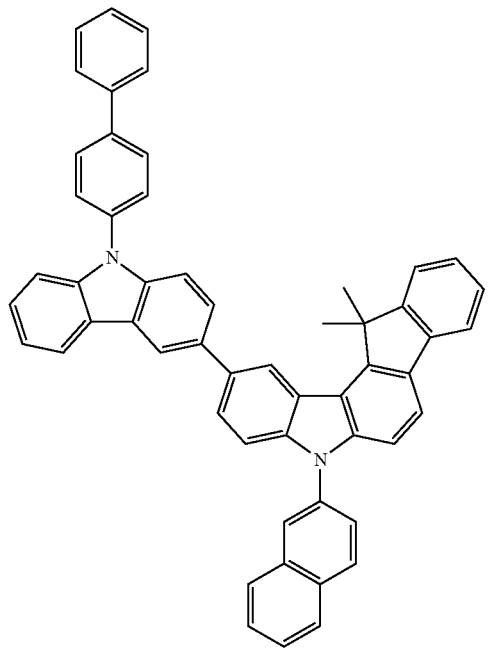
F-261
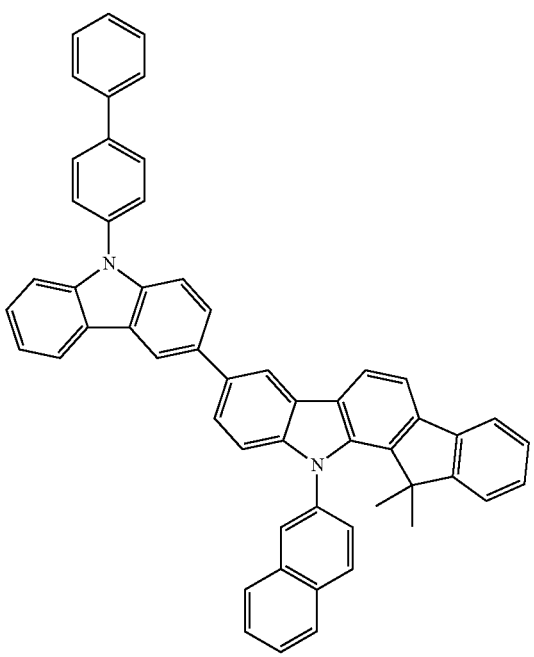

F-262
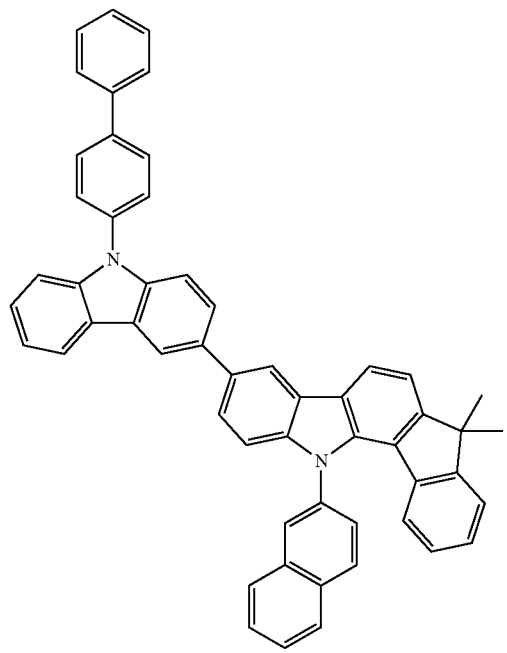
F-263
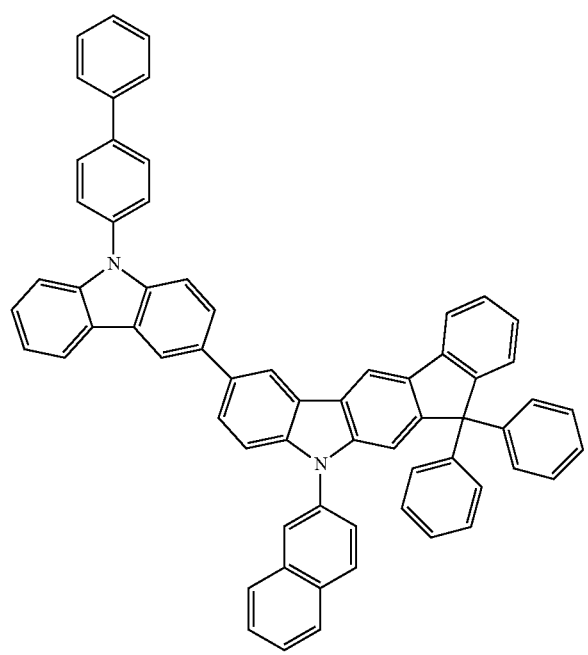
F-264
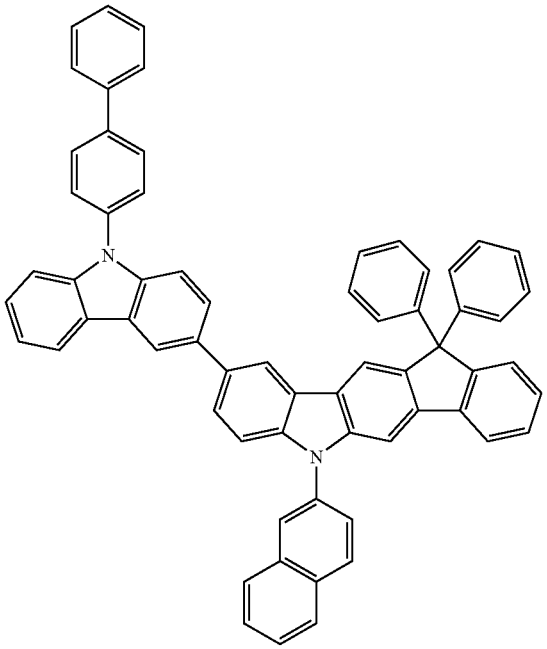
F-265
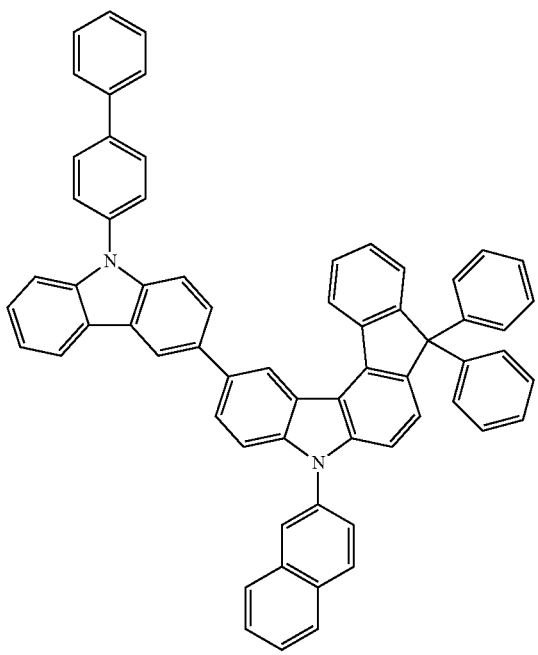

F-266
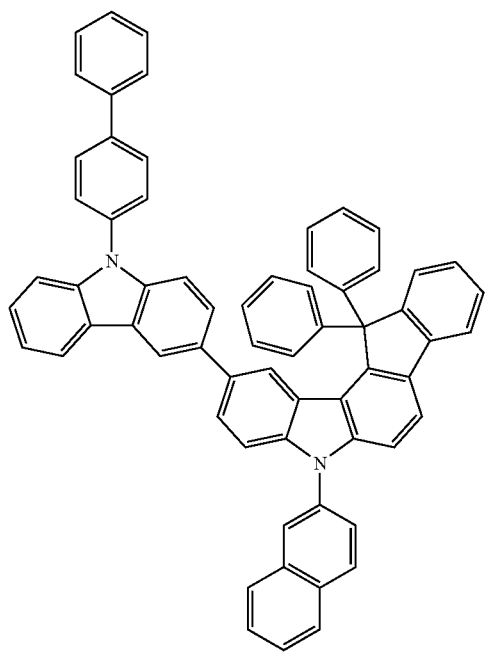
F-268
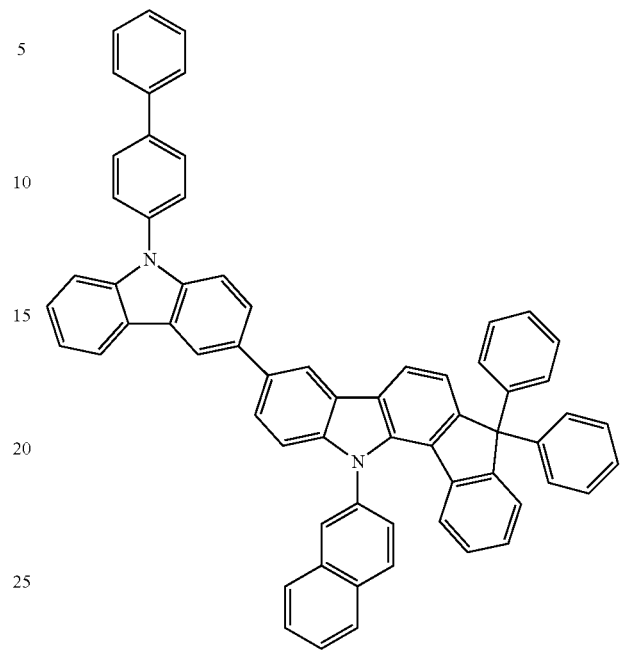
F-267
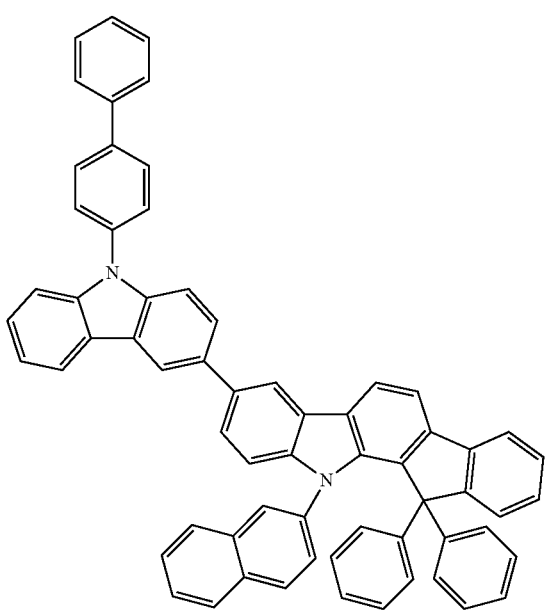
F-269
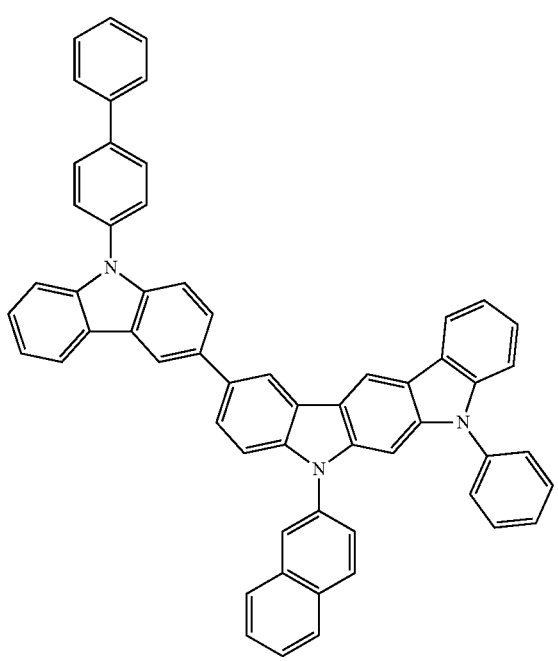

F-270
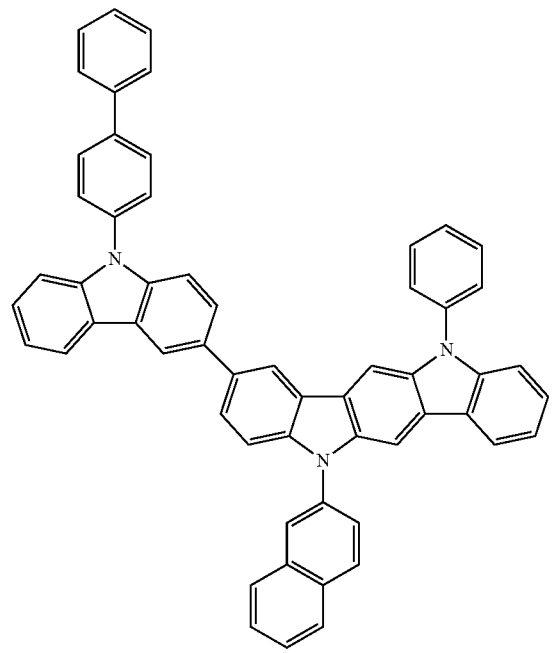
F-271
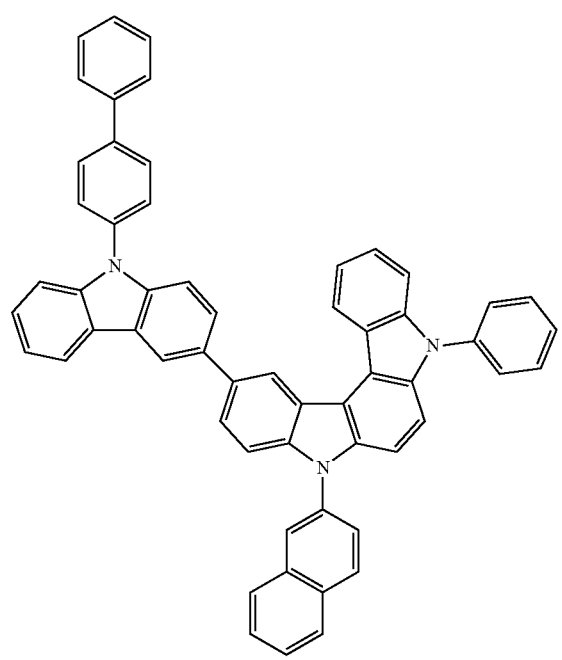
F-272
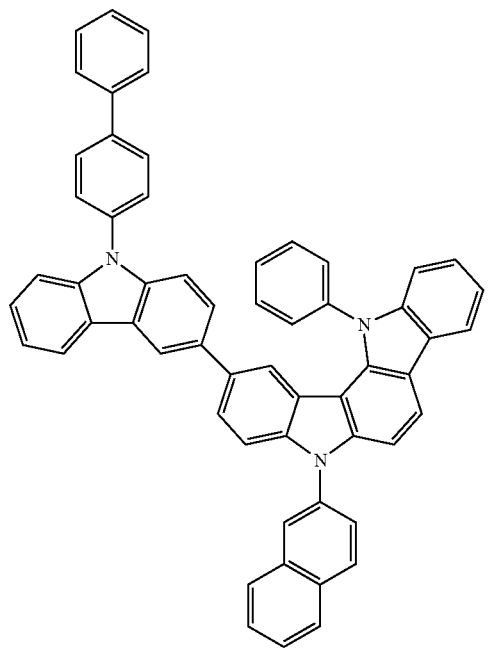
F-273
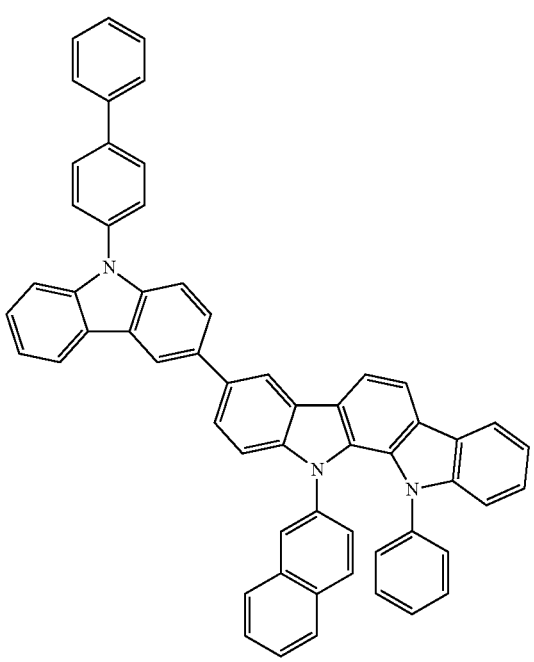

F-274
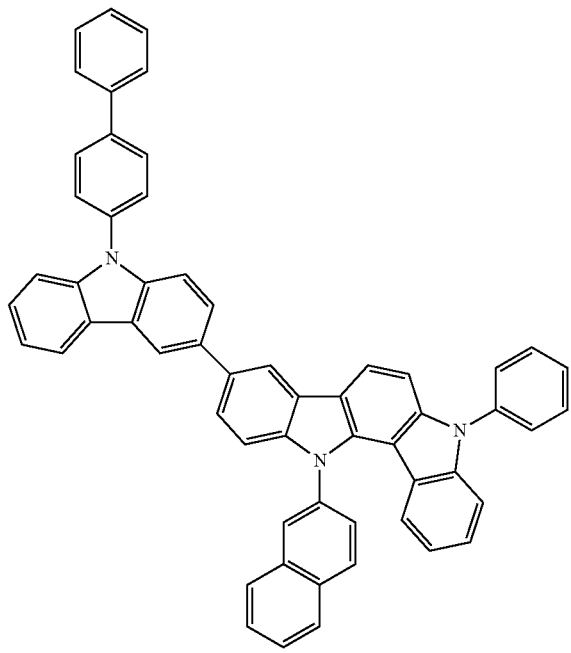
F-276
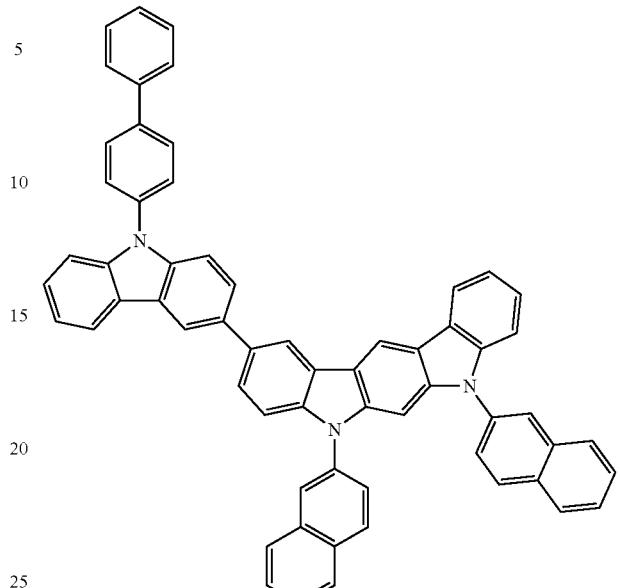
F-275
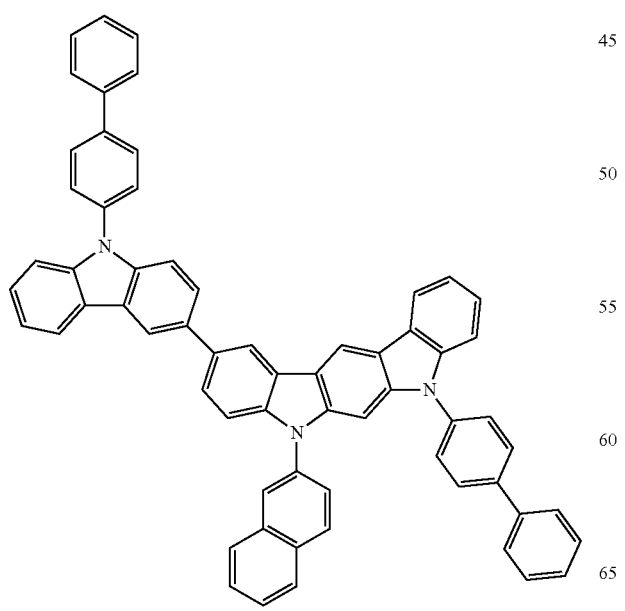
F-277
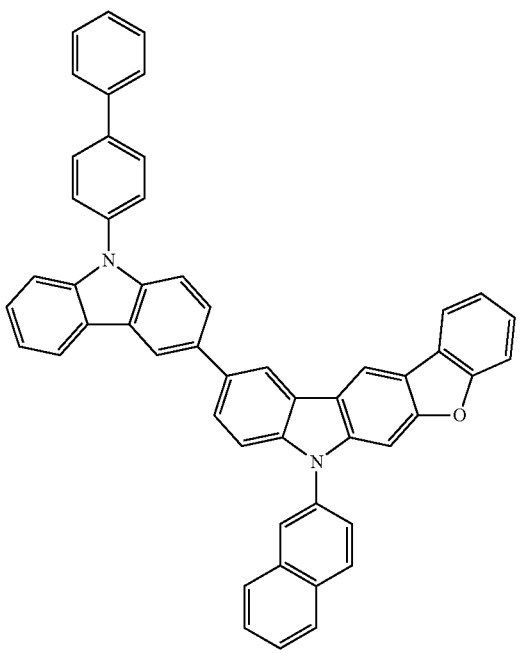

F-278
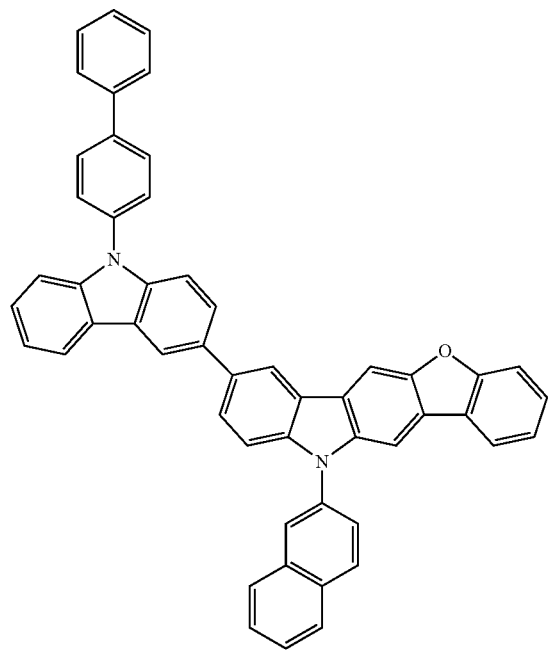
F-279
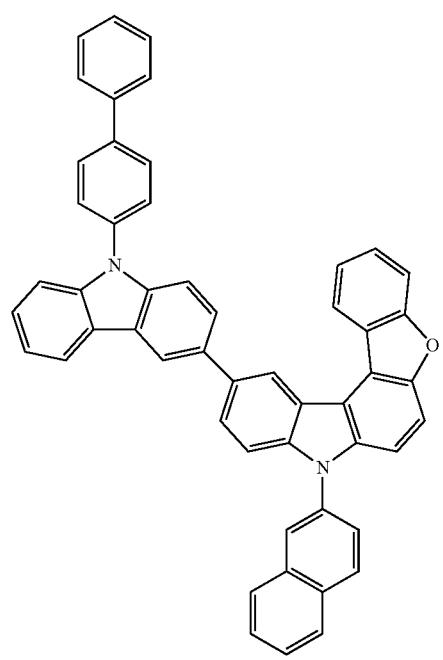
F-280
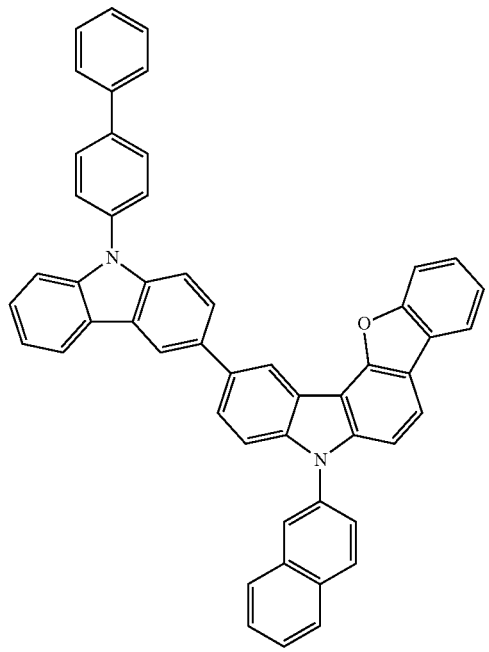
F-281
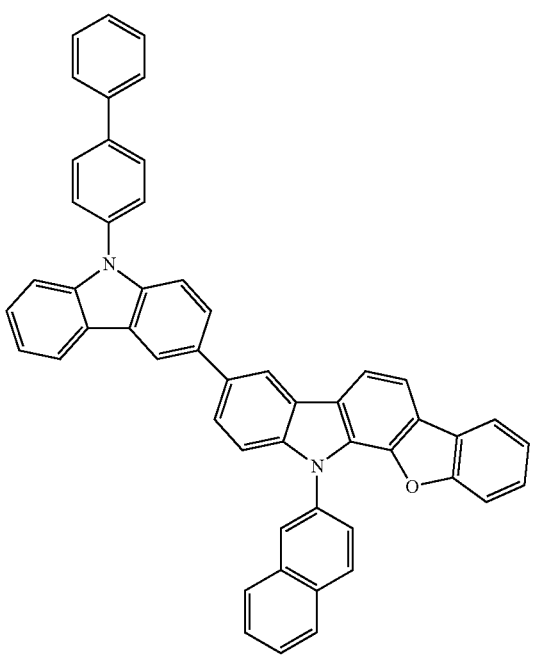

F-282
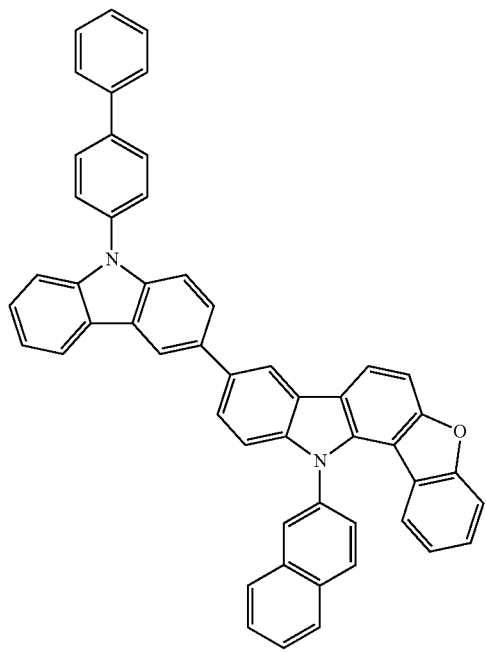
F-283
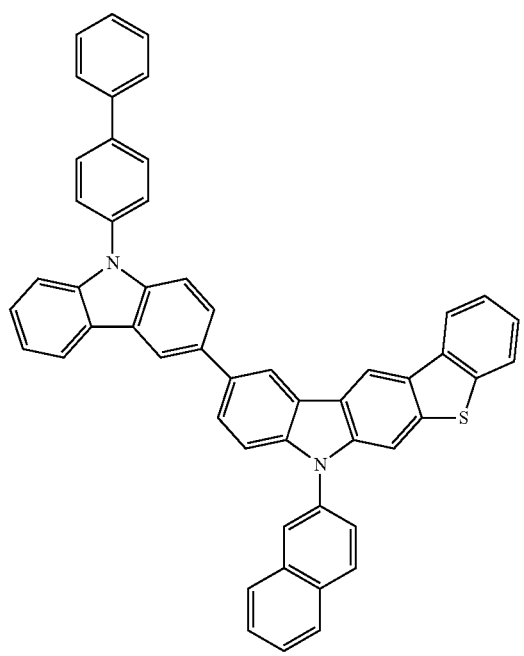
F-284
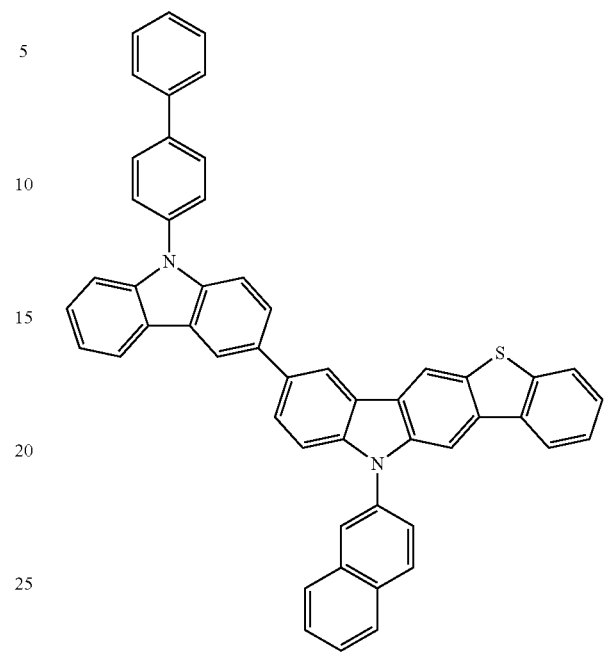
F-285
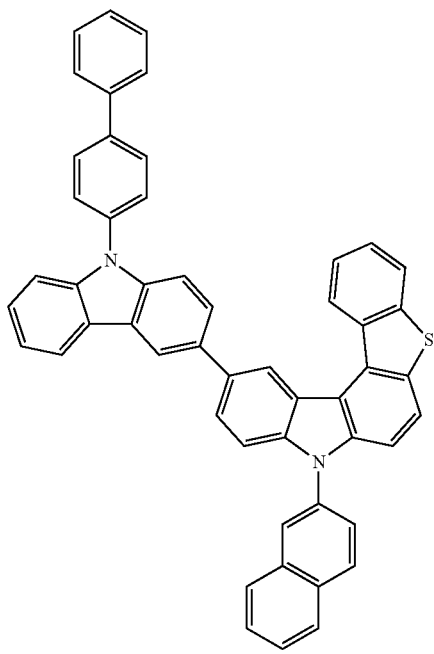

F-286
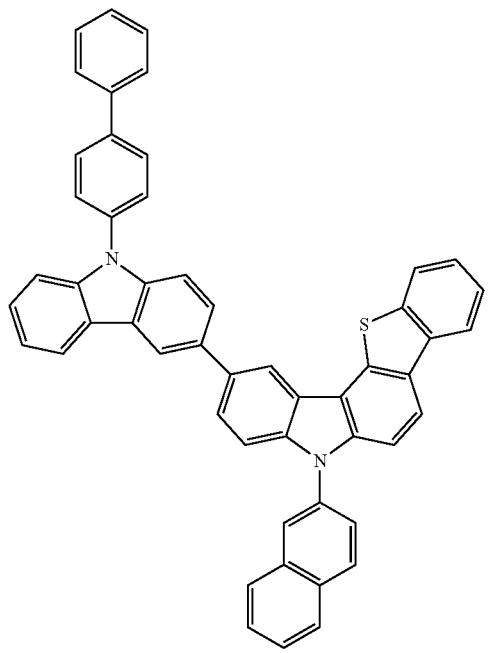
F-288
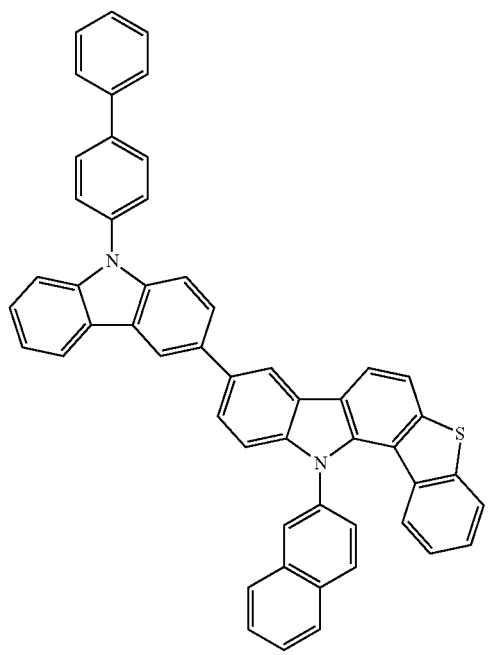
F-287
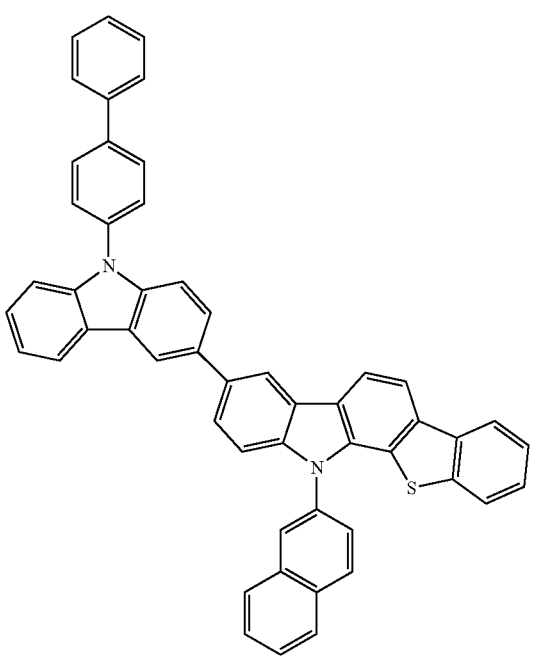
F-289
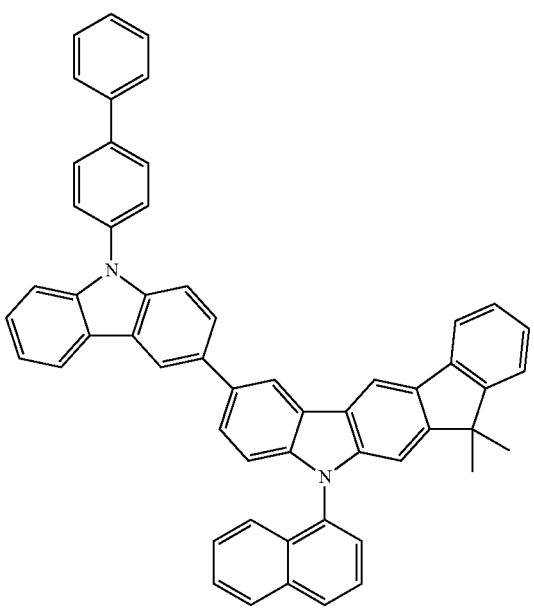

F-290
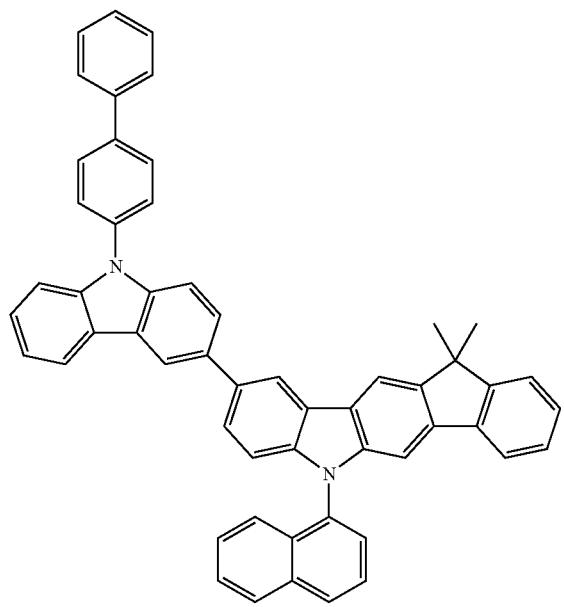
F-292
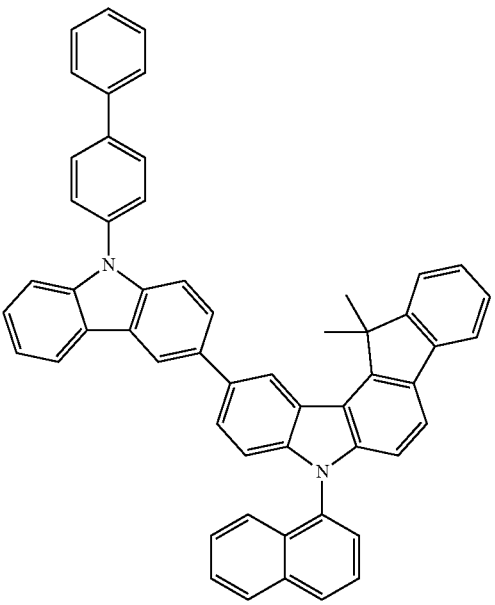
F-291
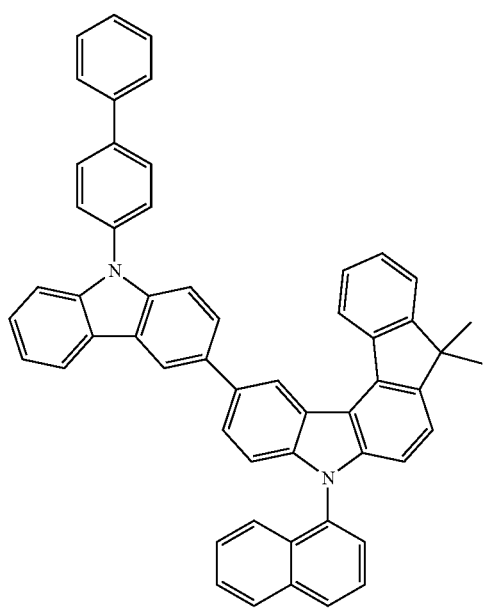
F-293
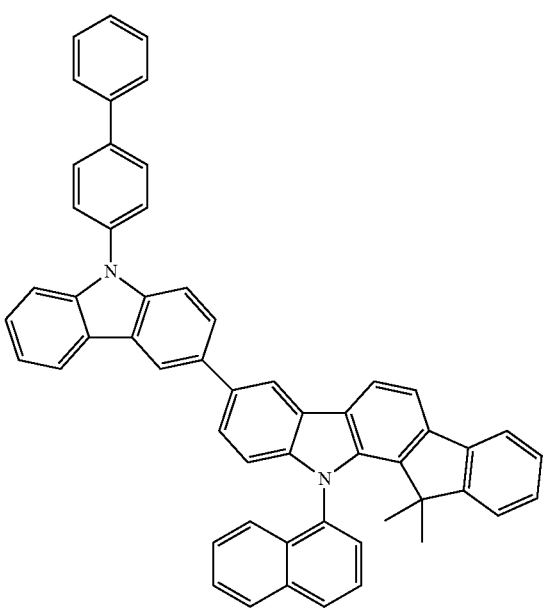

F-294
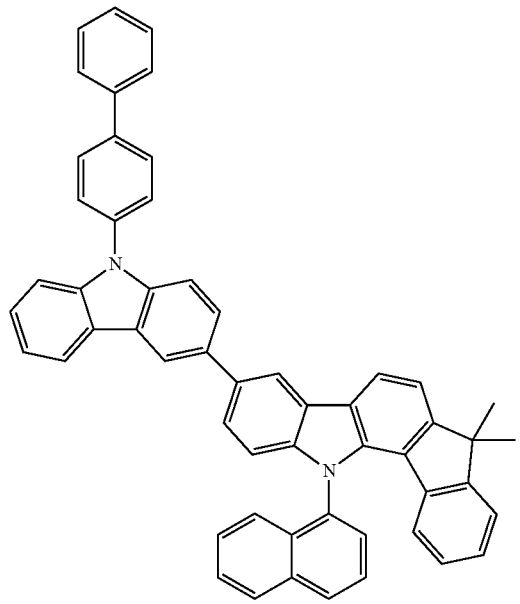
F-295
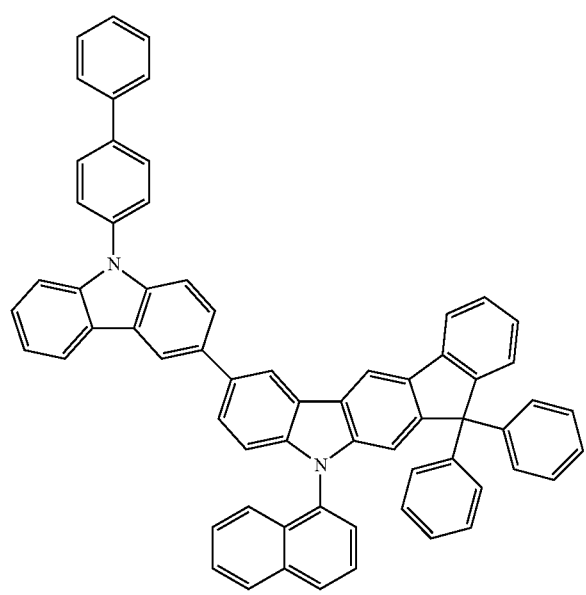
F-296
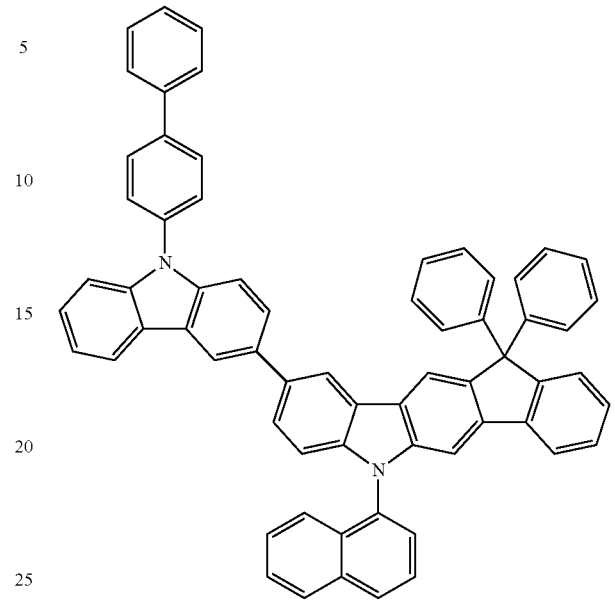
F-297
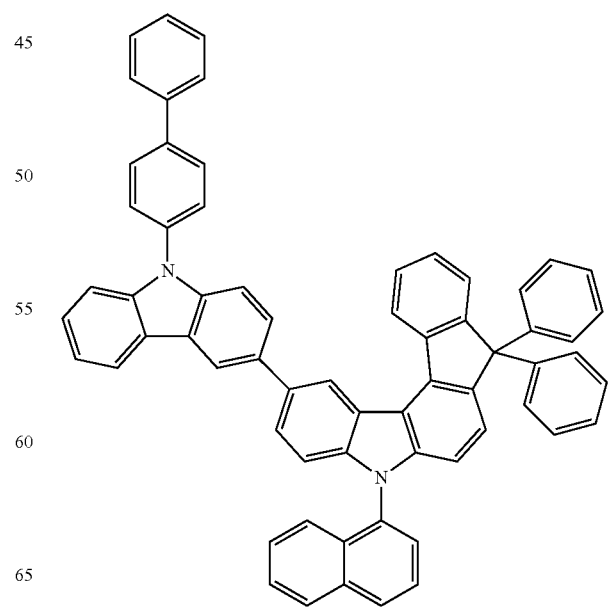

F-298
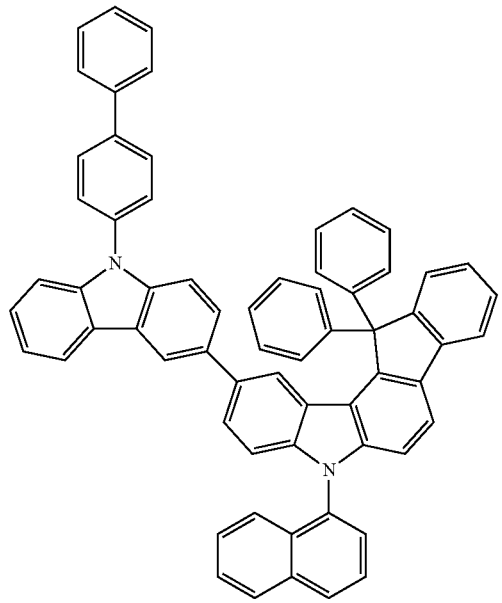
F-300
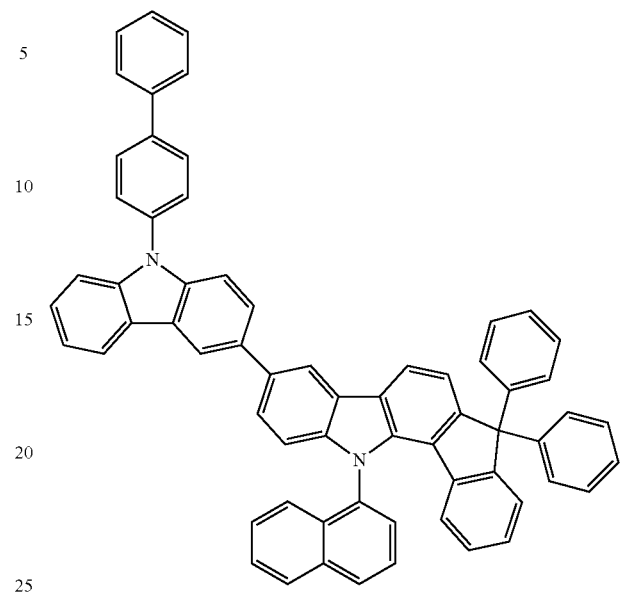
F-299
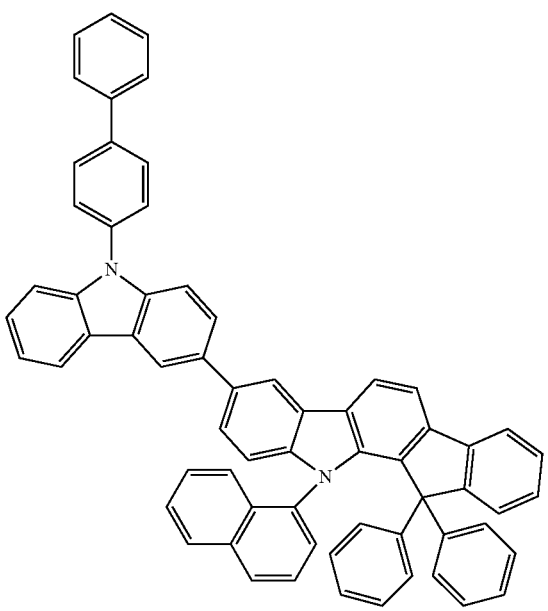
F-301
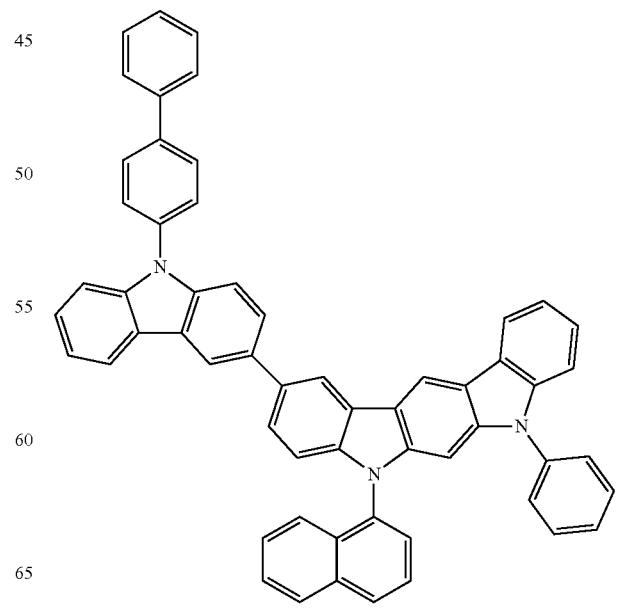

F-302
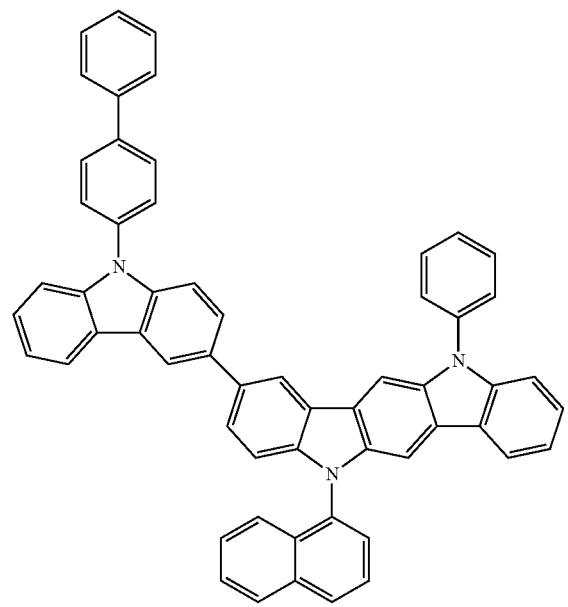
F-303
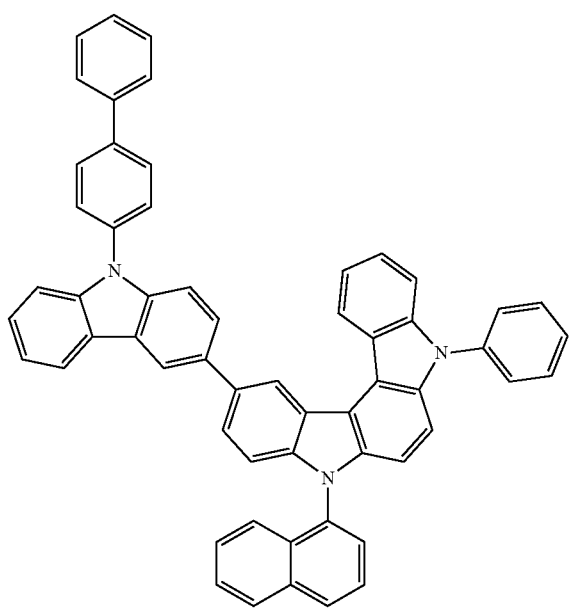
F-304
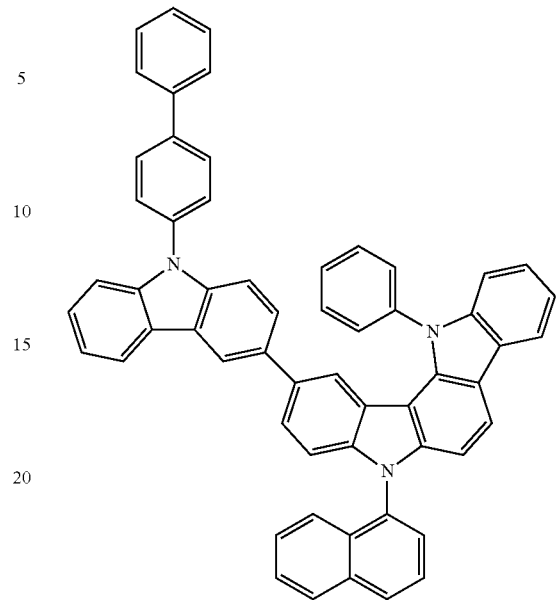
F-305
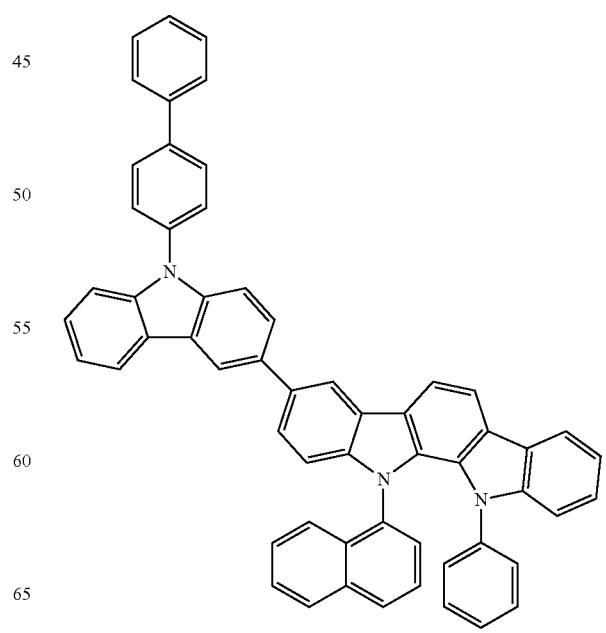

F-306
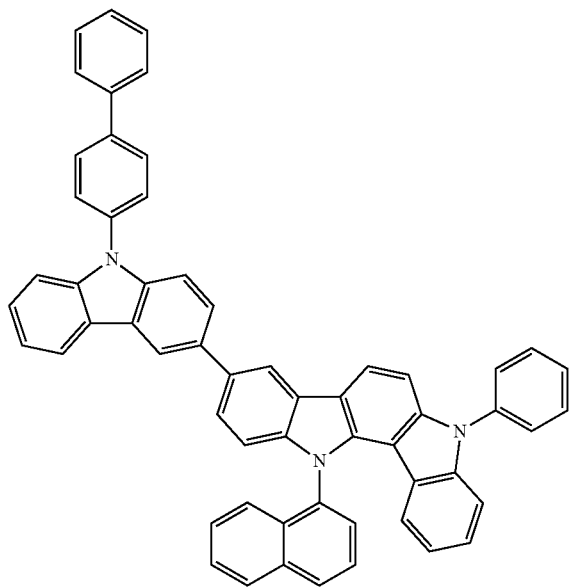
F-307
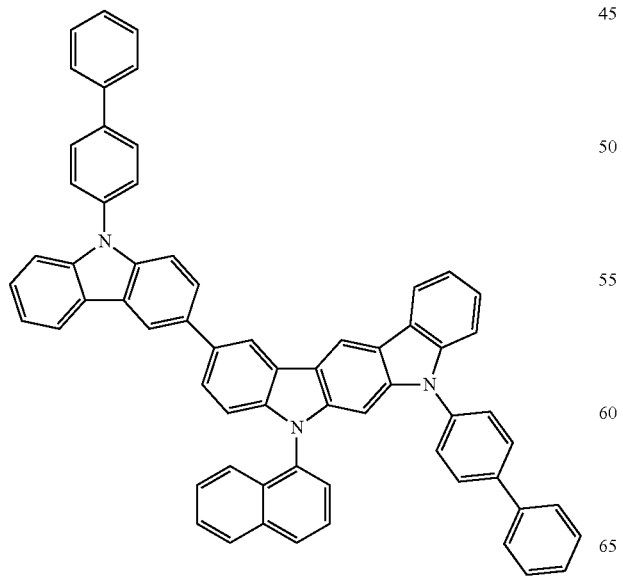
F-308
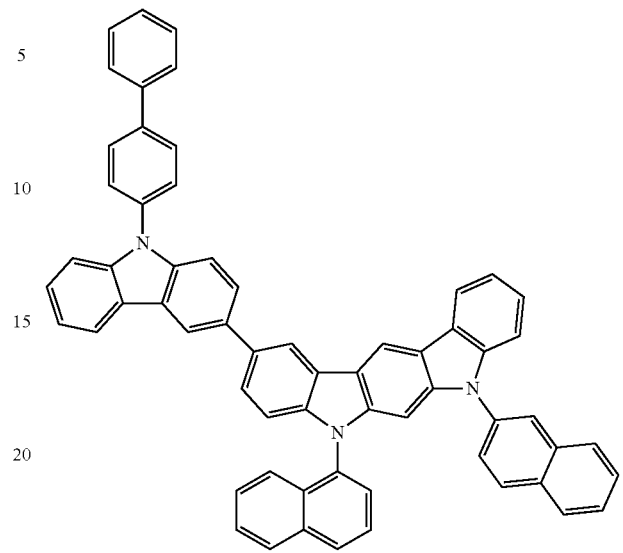
F-309
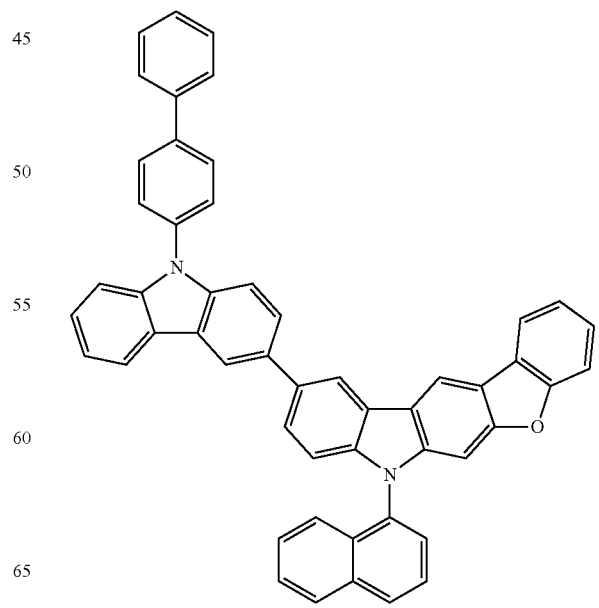

F-310
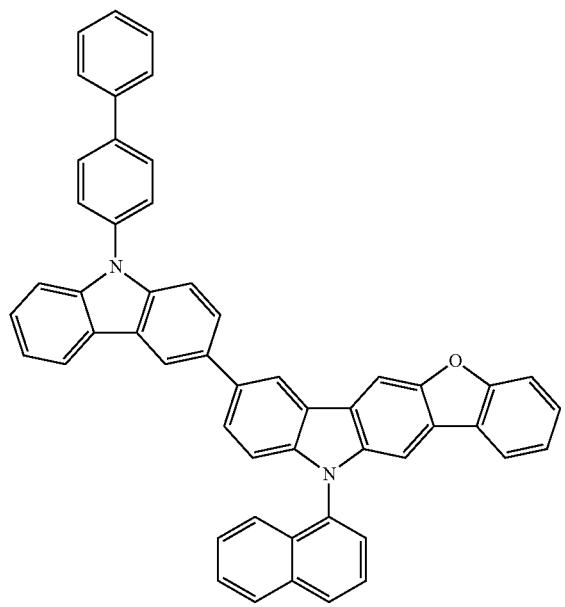
F-312
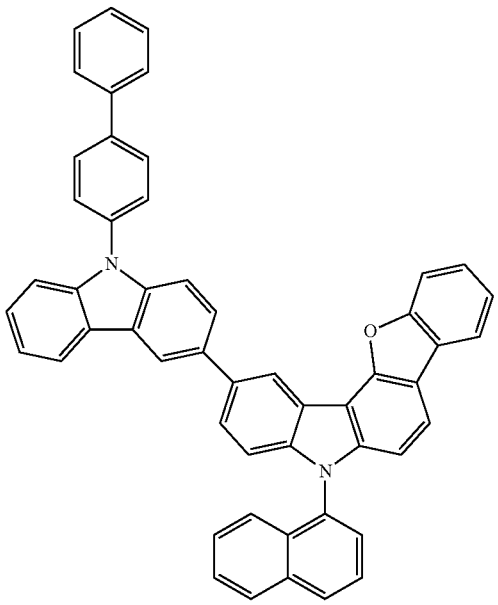
F-311
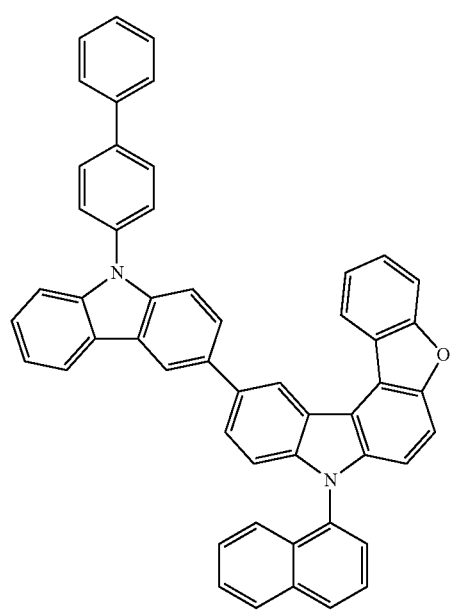
F-313
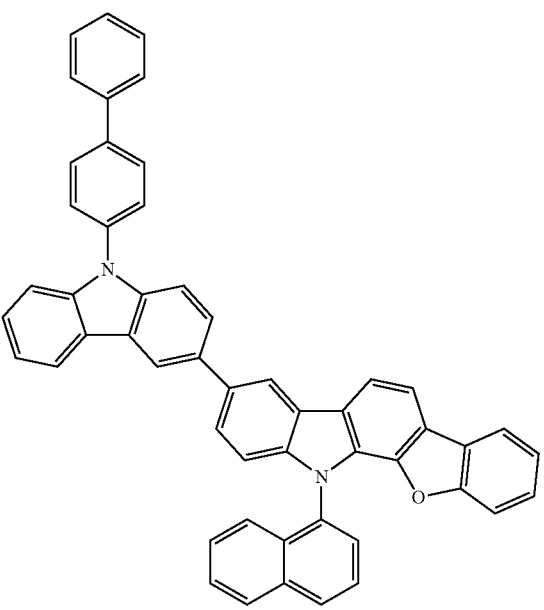

F-314
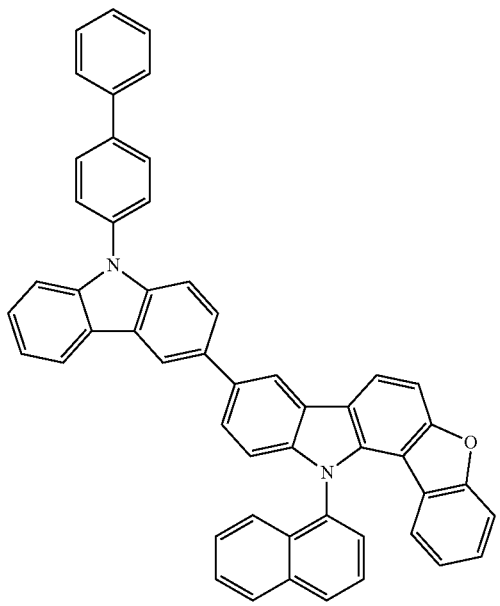
F-316
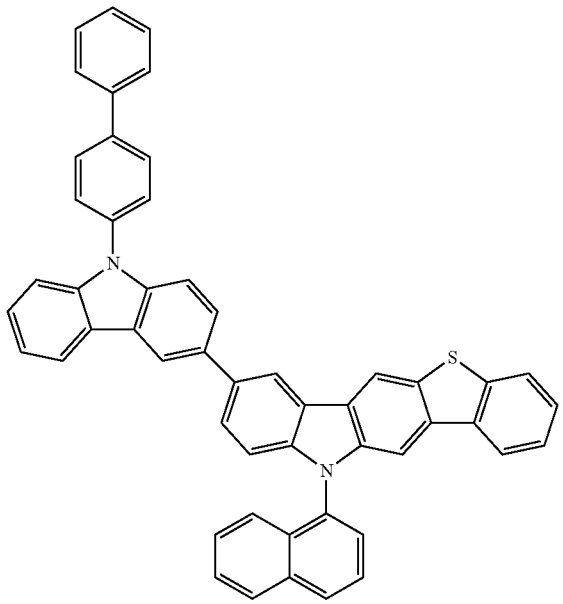
F-315
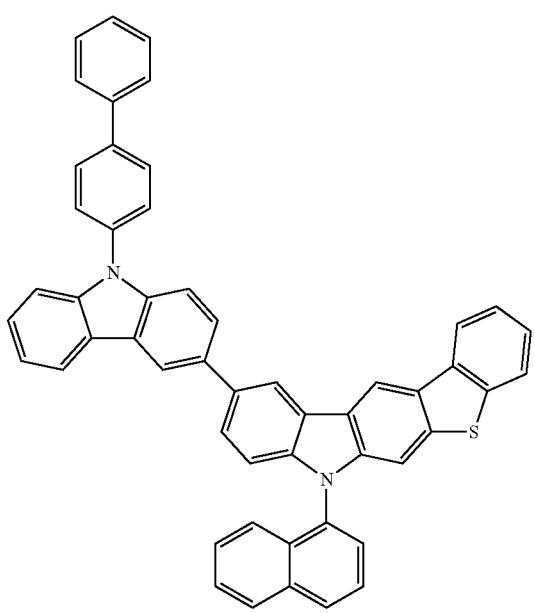
F-317
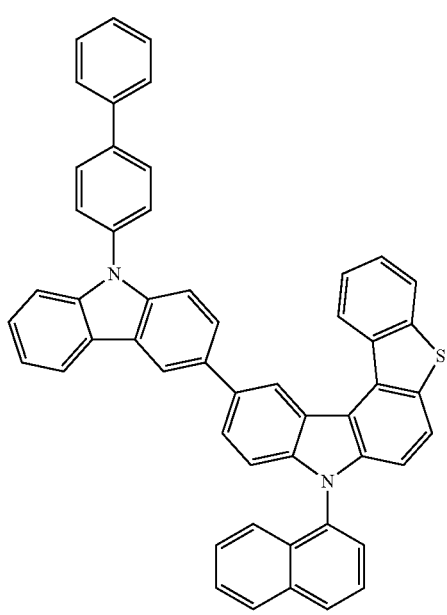

-continued
F-318
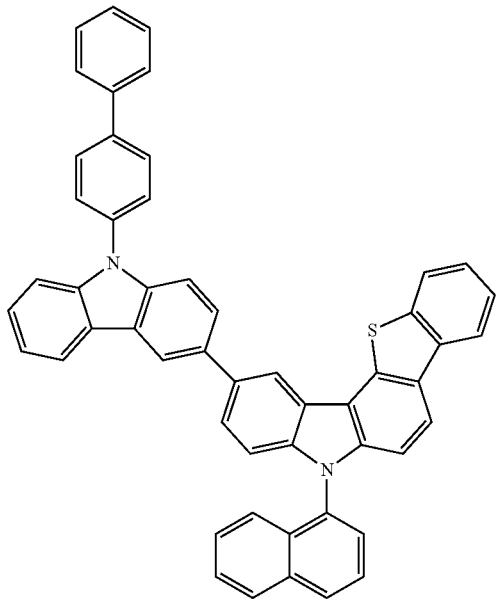
F-319
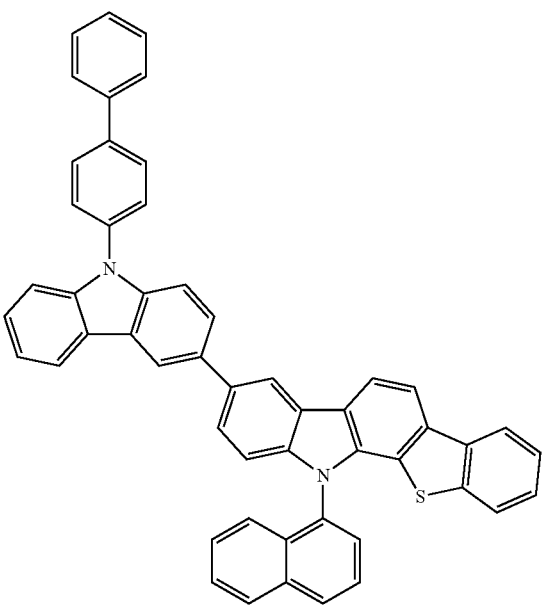
-continued
F-320
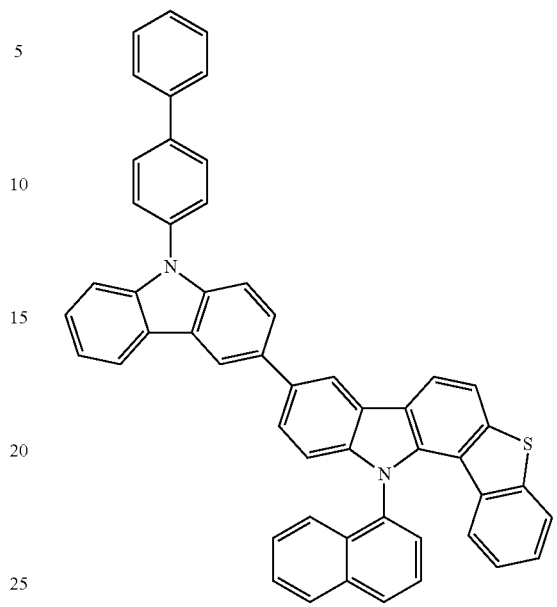
F-321
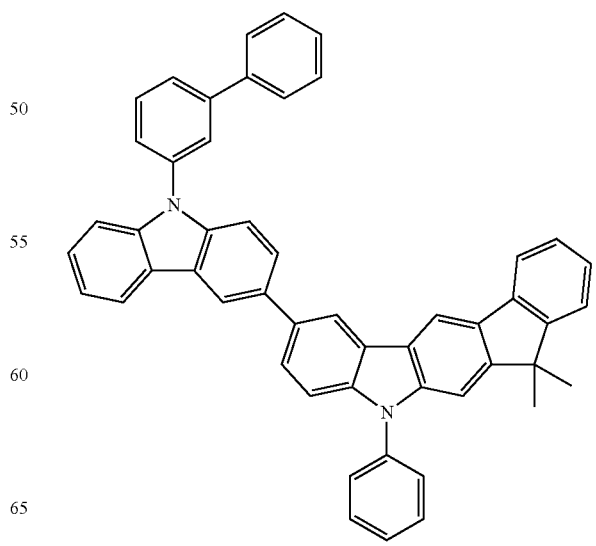

F-322
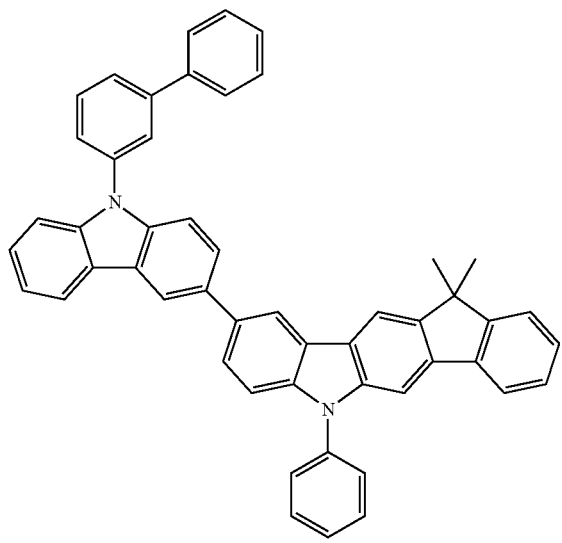
F-323
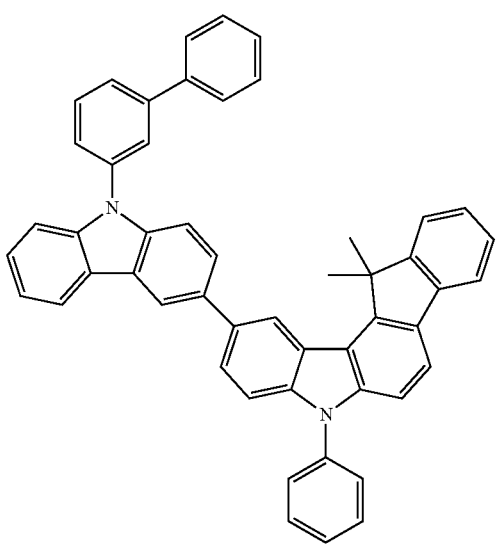
F-324
F-325
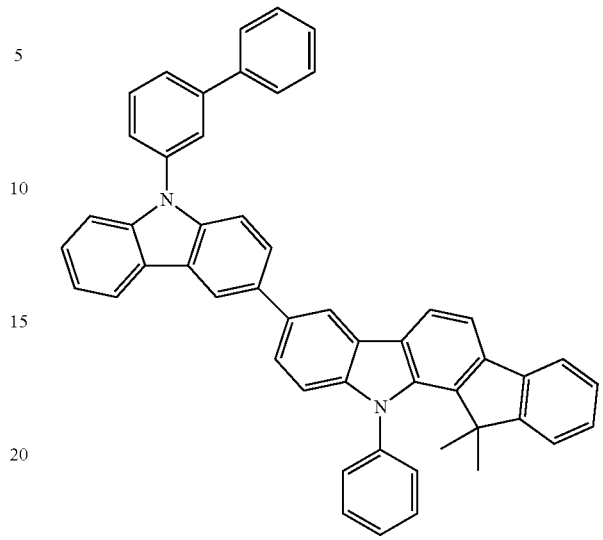
F-326
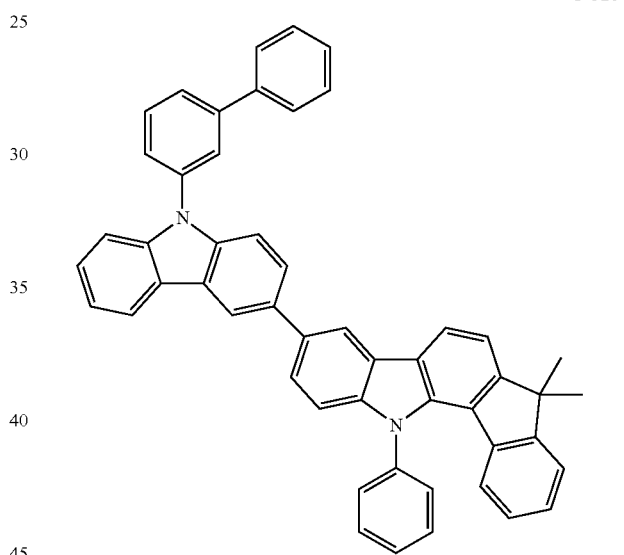
F-327
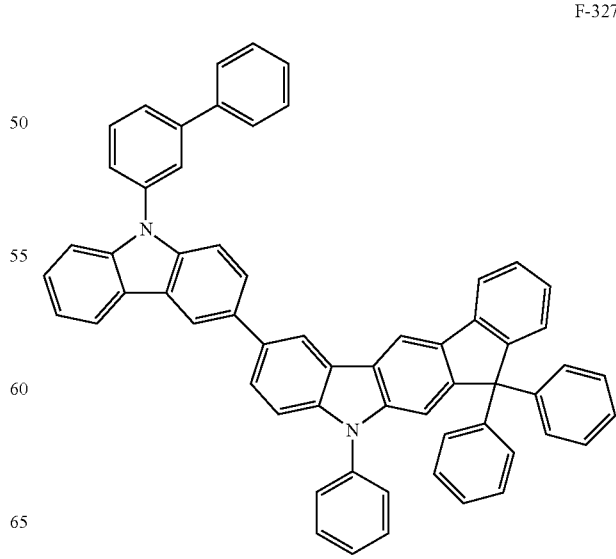

F-328
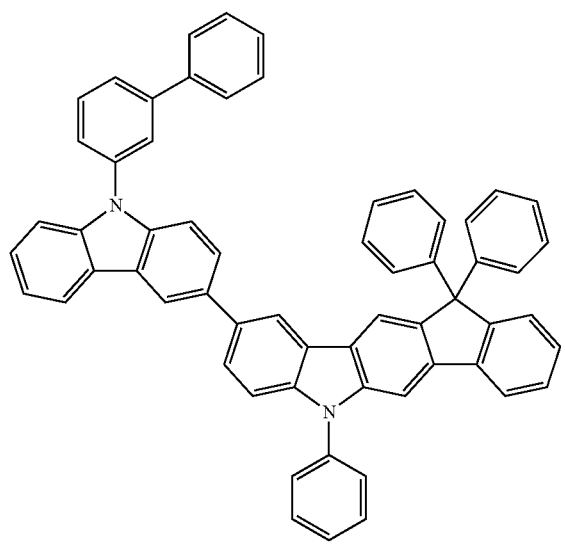
F-330
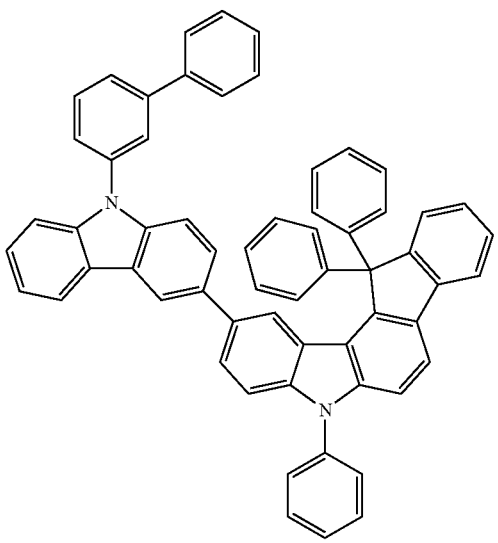
F-331
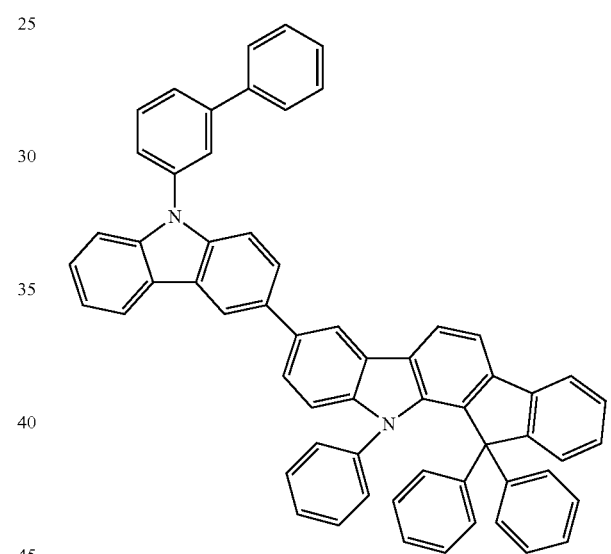
F-329
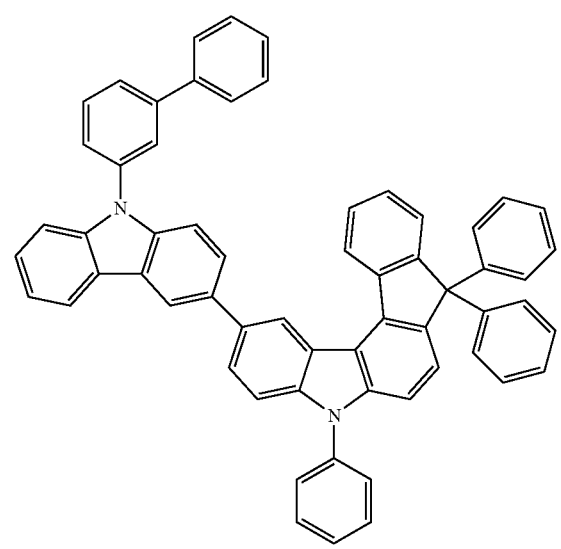
F-332
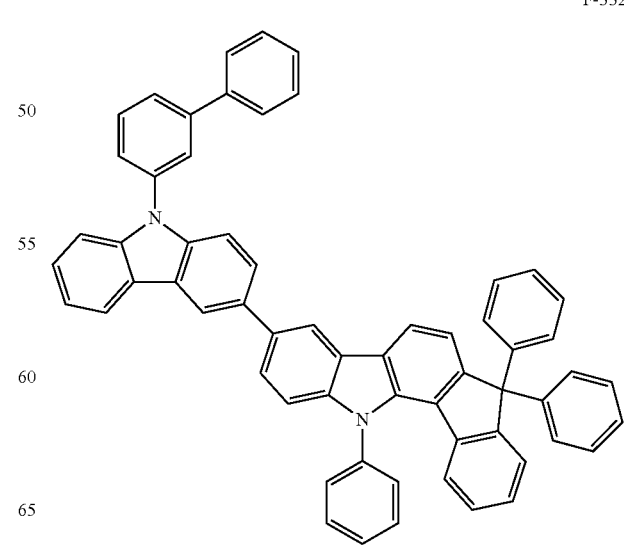

F-333
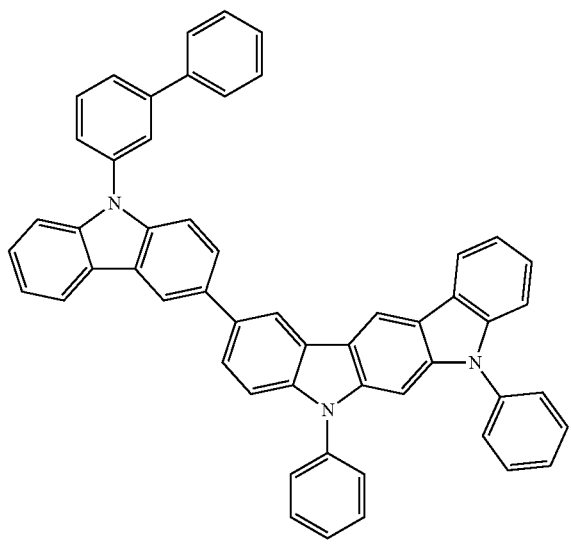
F-335
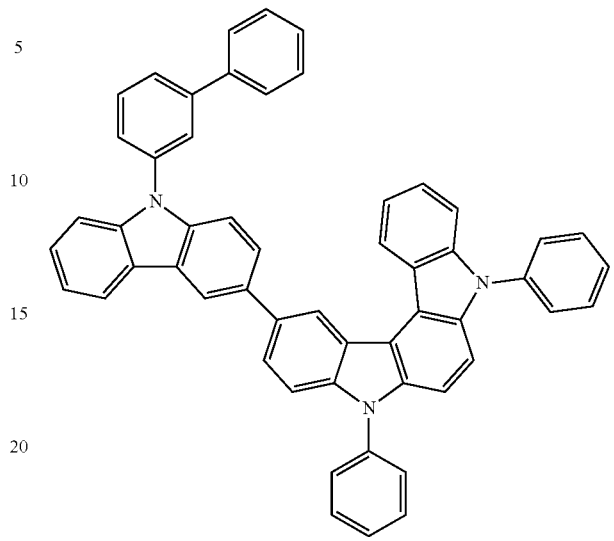
F-334
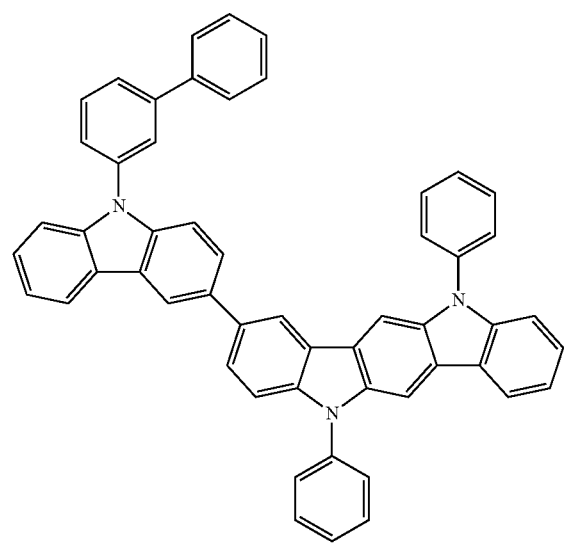
F-336
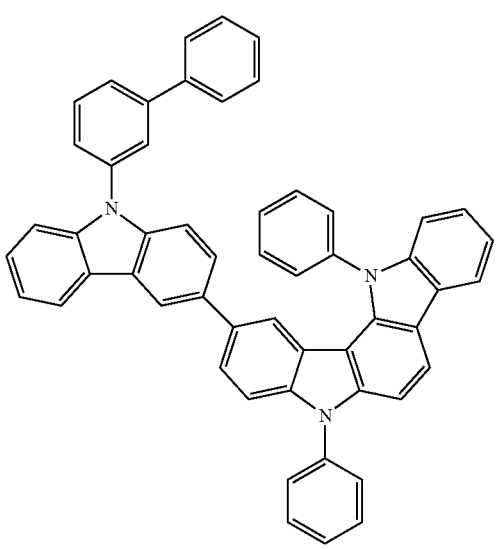

F-337
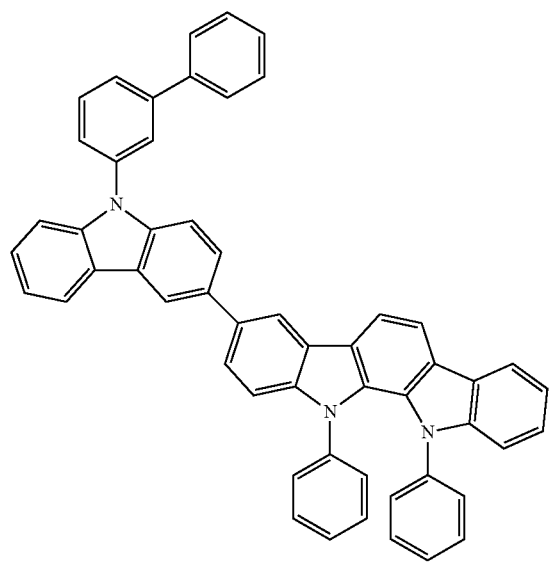
F-340
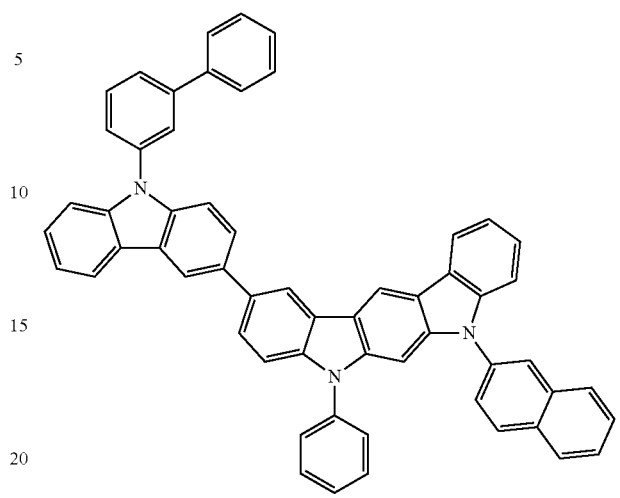
F-338
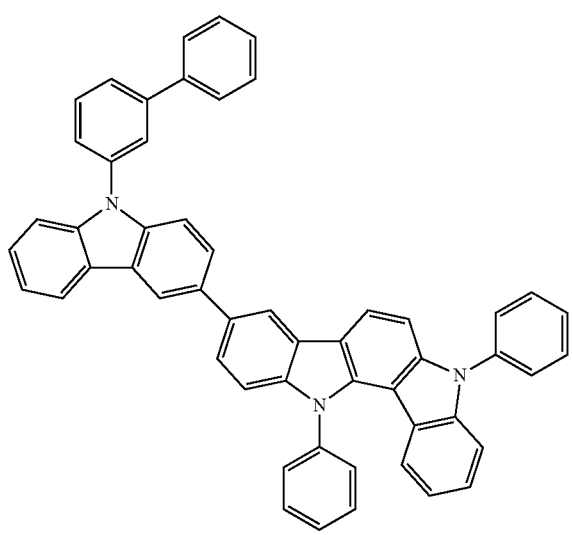
F-341
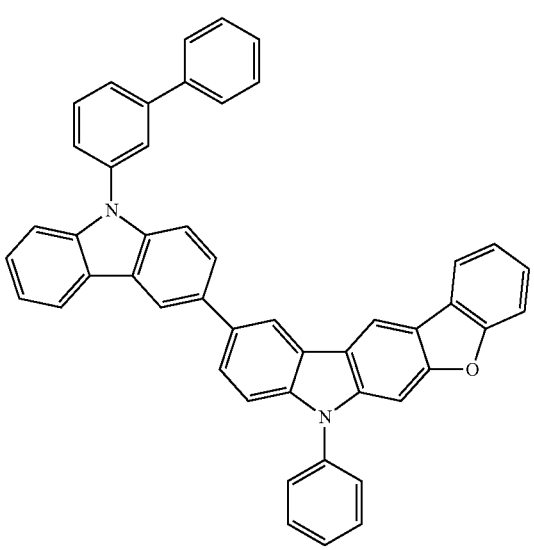
F-339
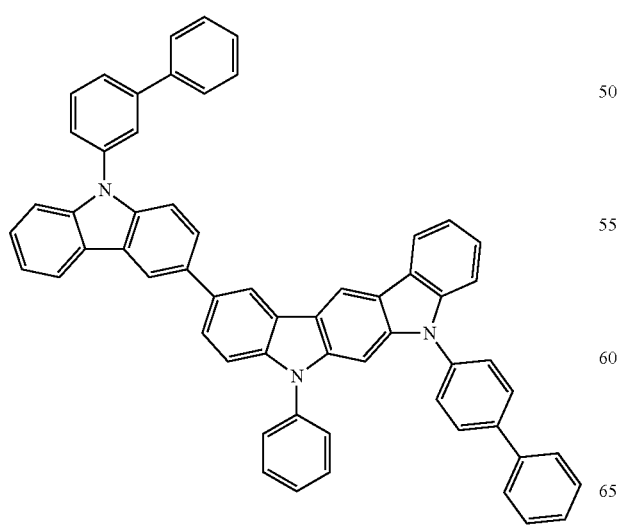
F-342

F-343
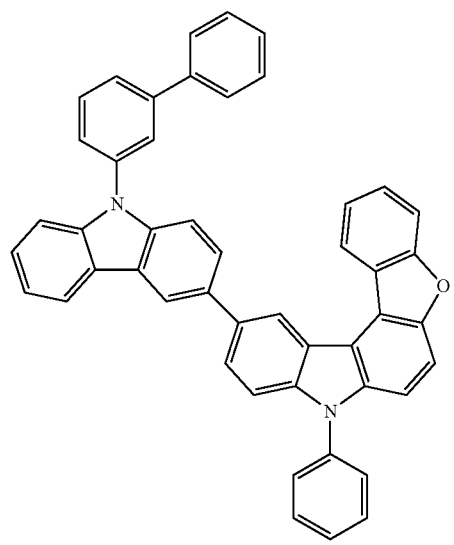
F-344
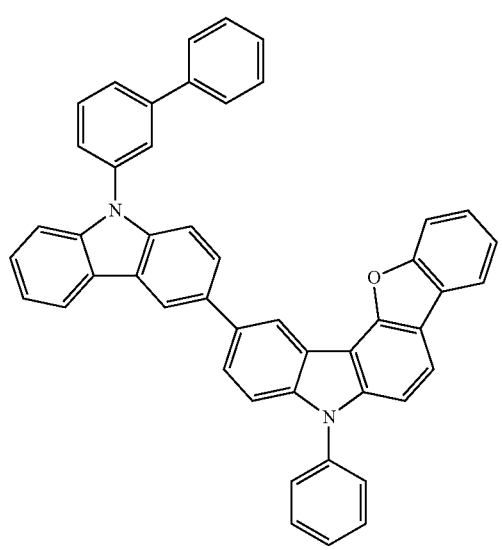
F-345
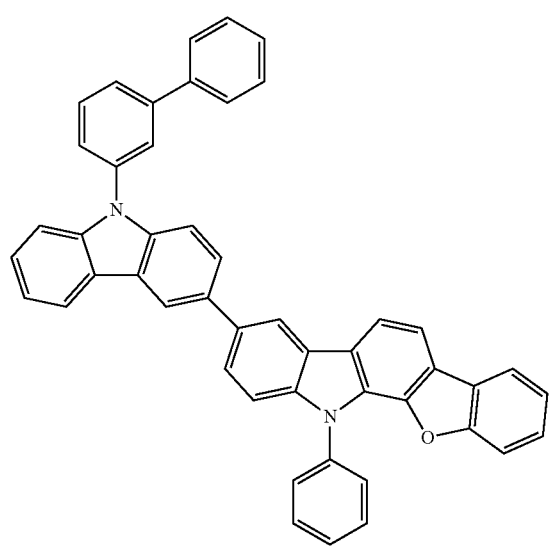
F-346
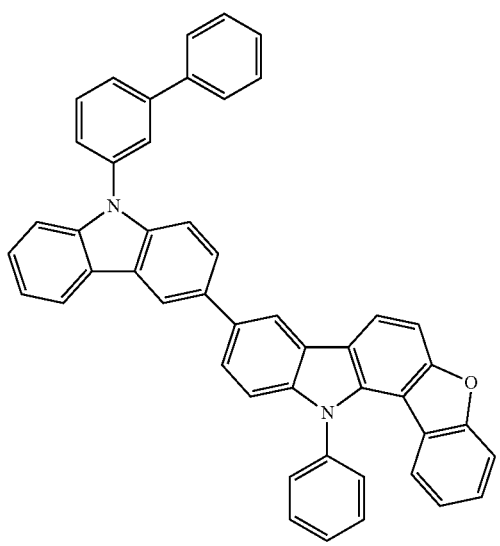
F-347
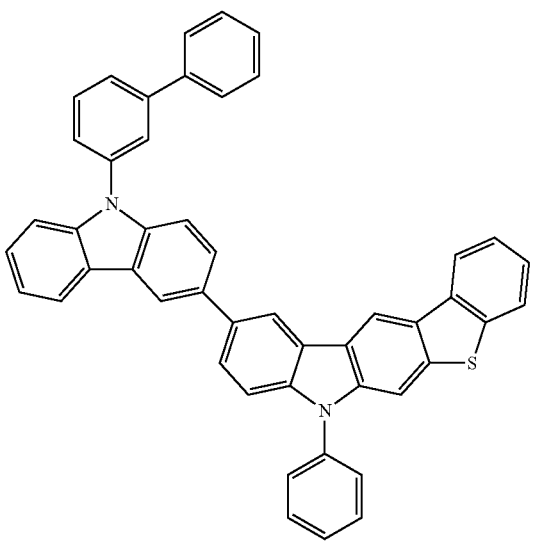

F-348
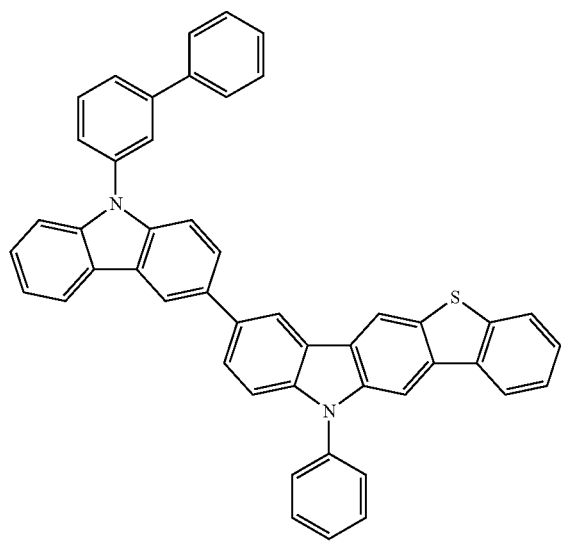
F-349
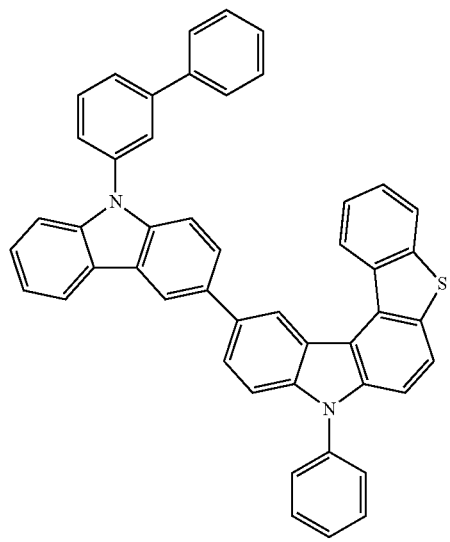
F-350
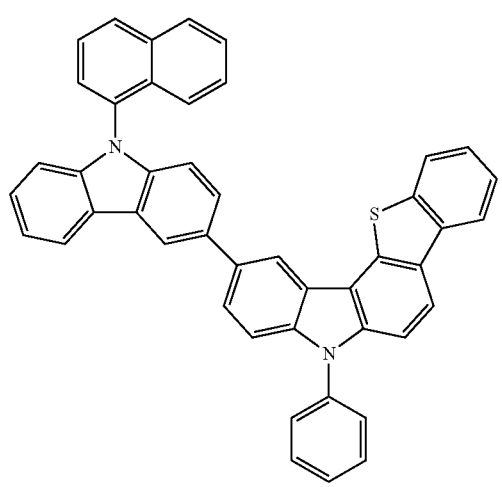
F-351
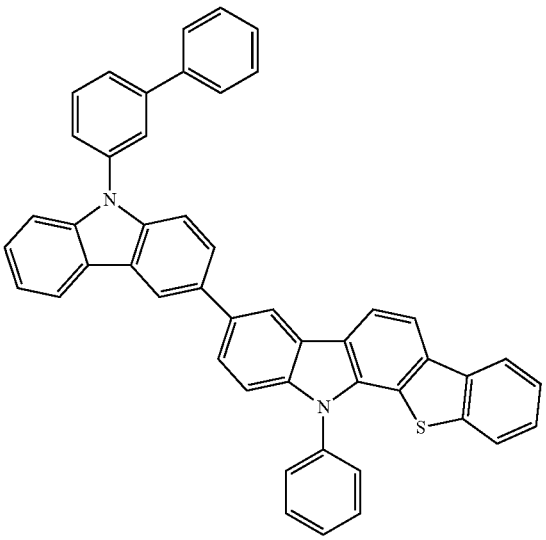
F-352
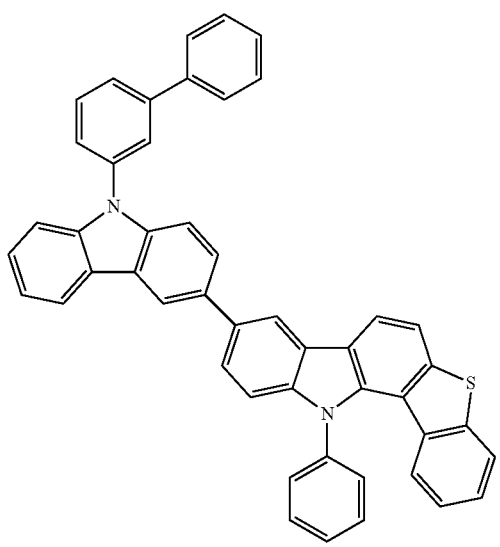

F-353
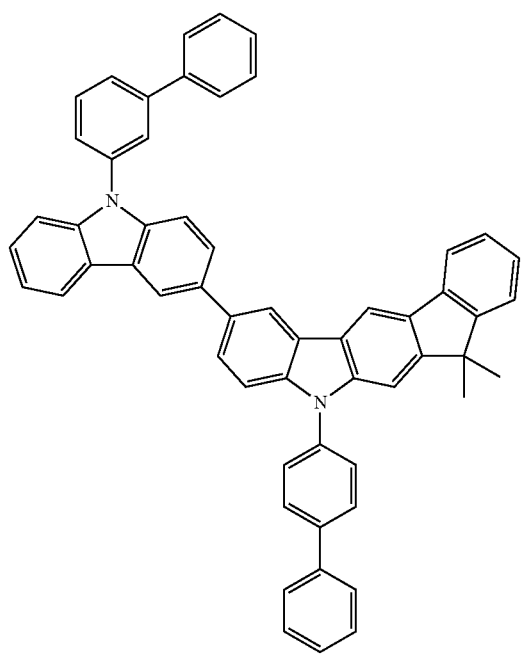
F-355
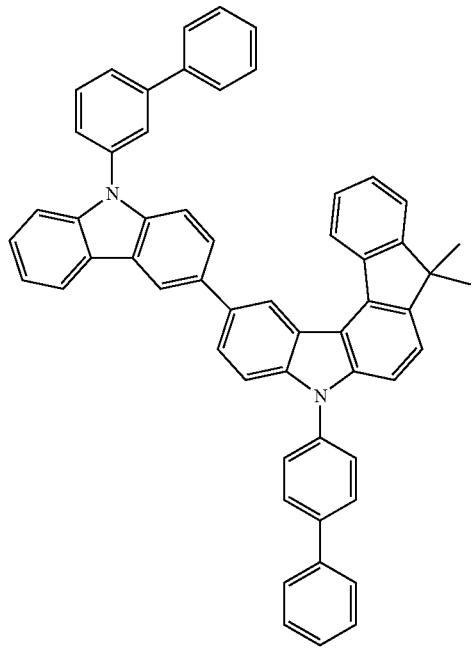
F-354
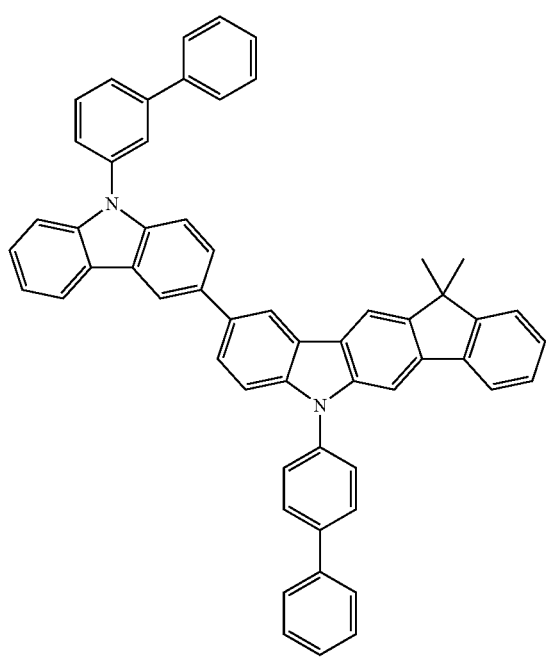
F-356
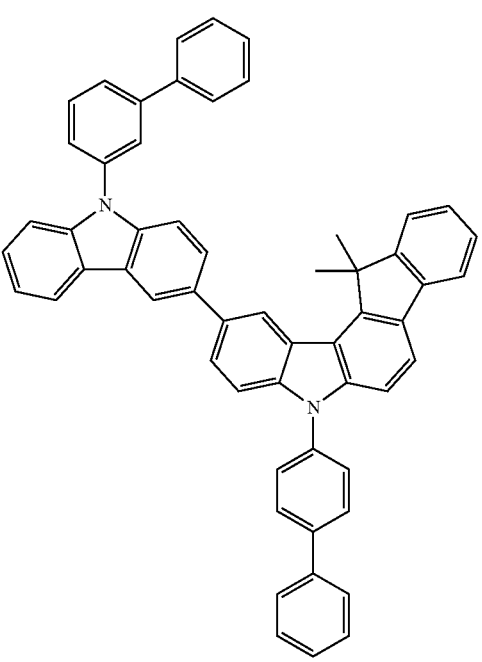

F-357
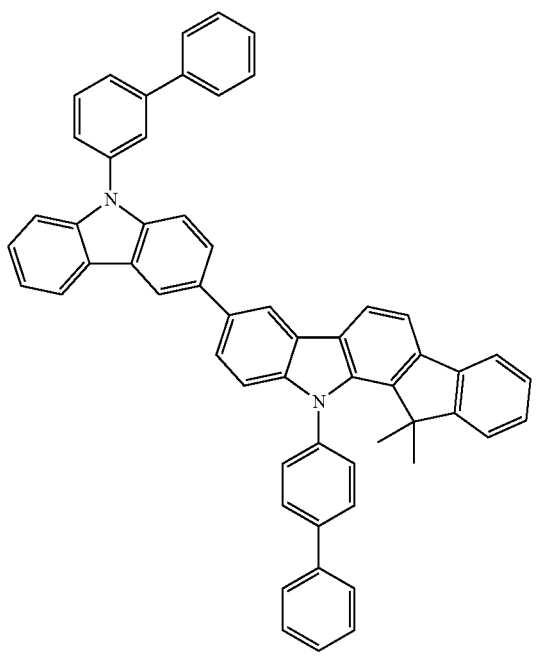
F-358
F-359
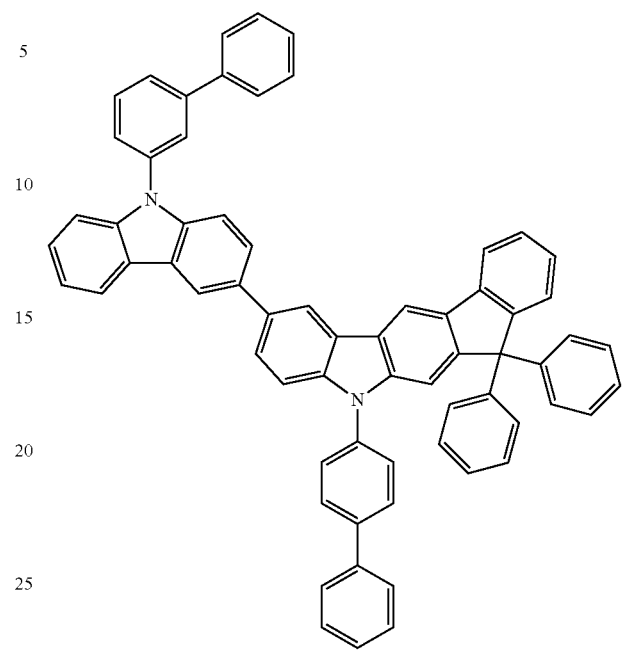
F-360
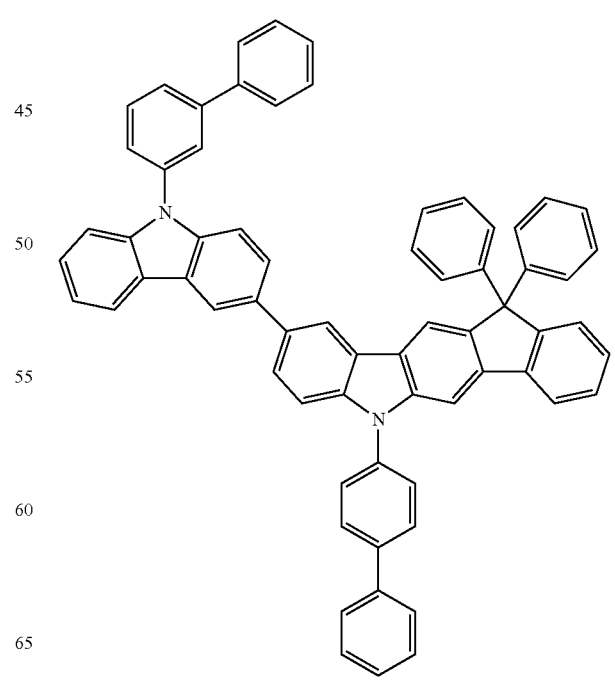

F-361
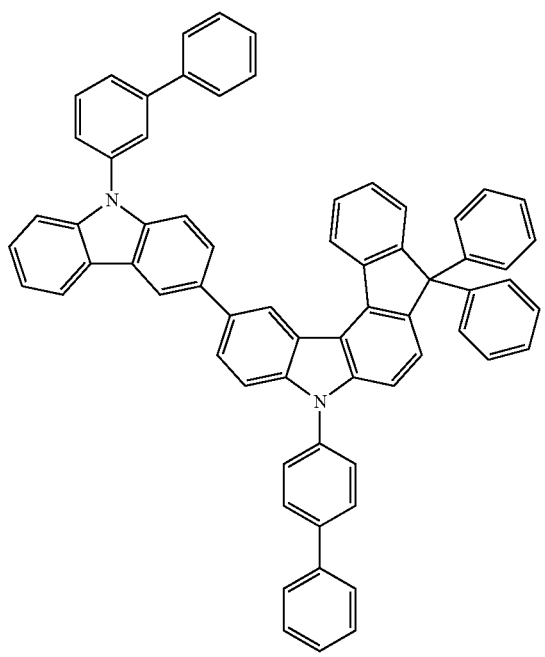
F-363
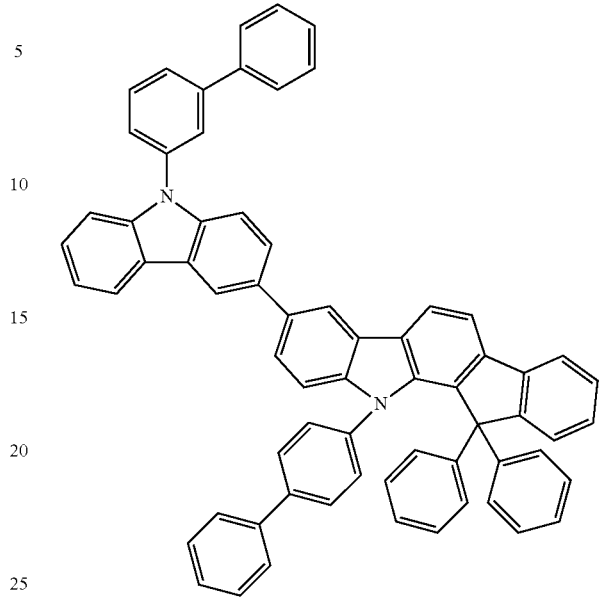
F-362
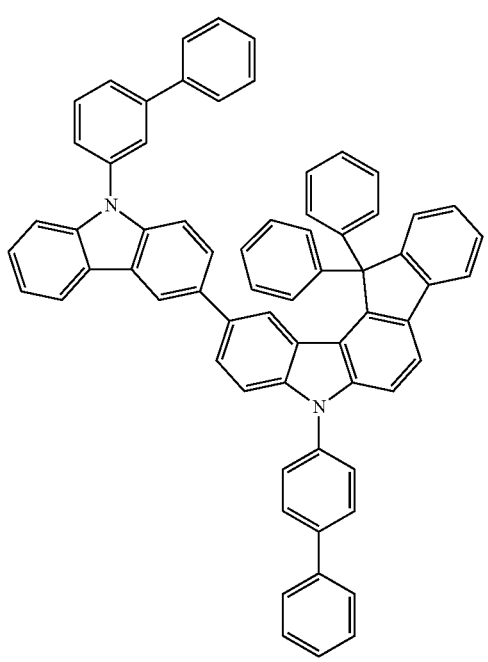
F-364
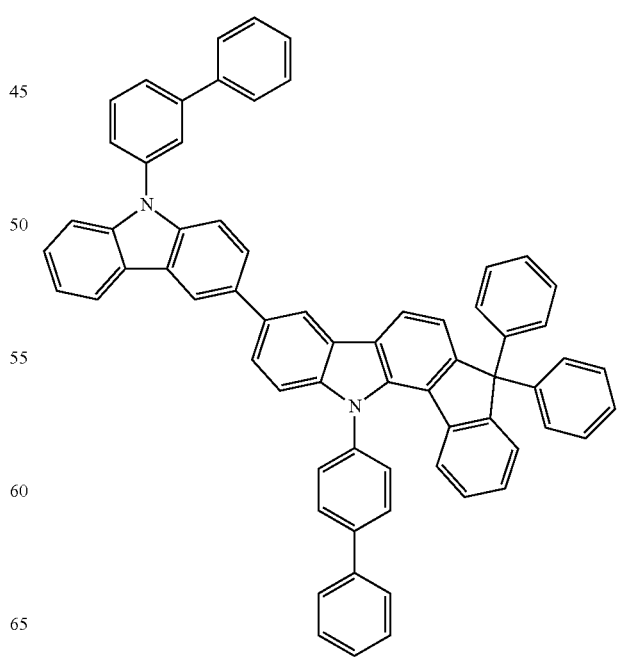

F-365
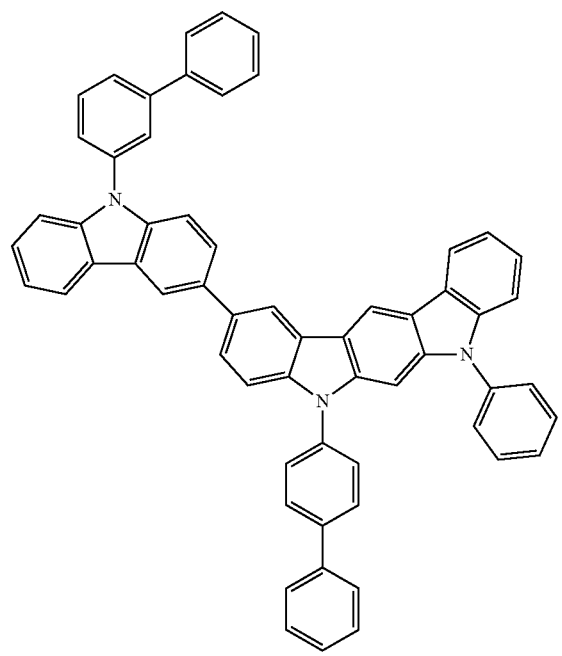
F-367
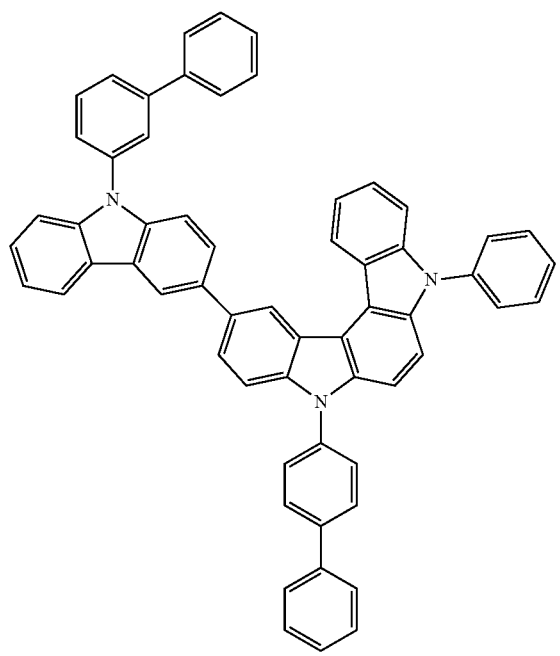
F-366
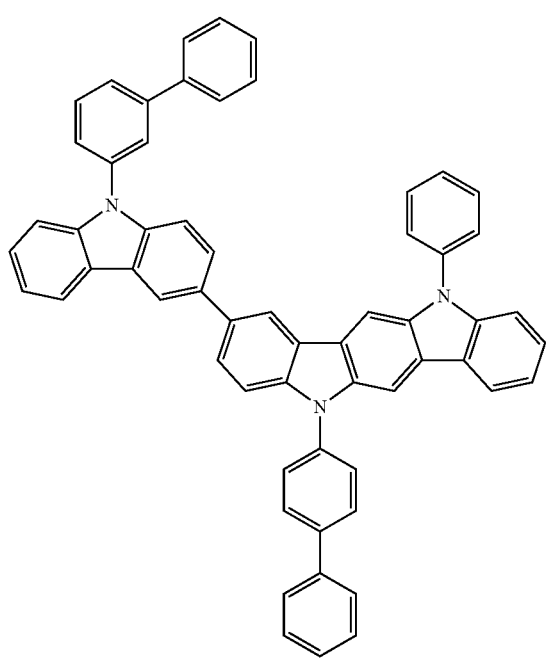
F-368
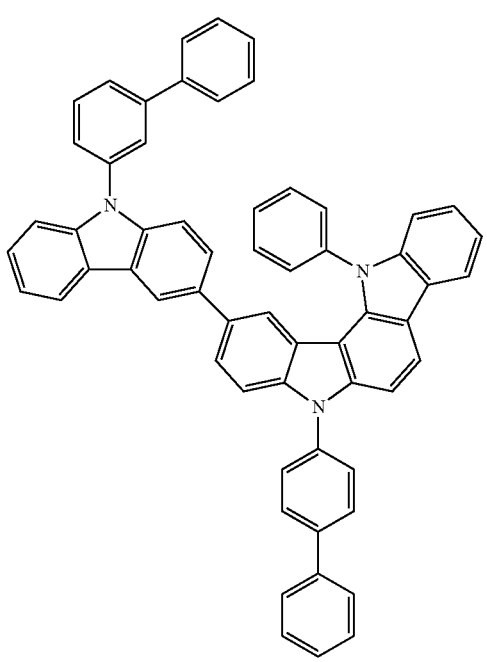

-continued
F-369
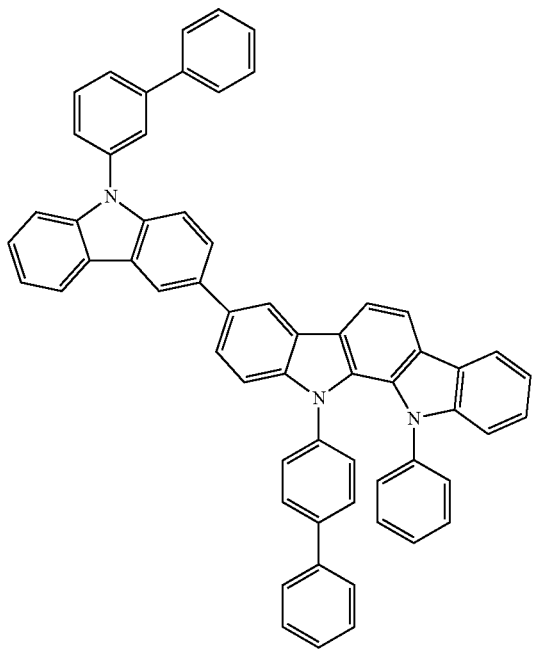
F-370
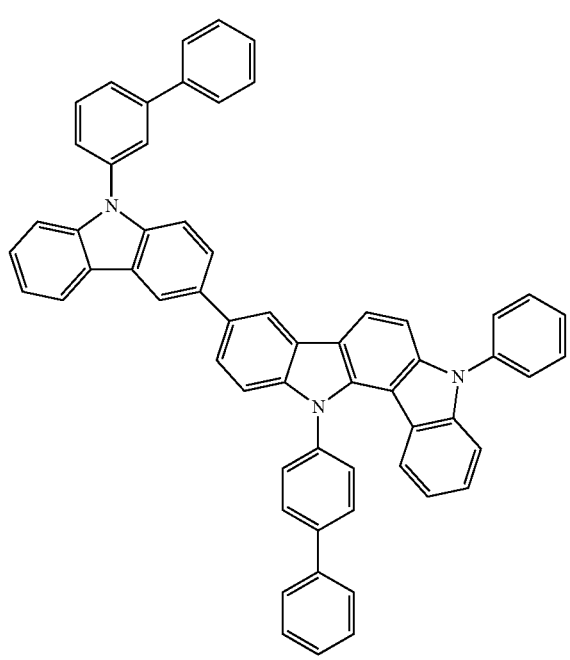
F-371
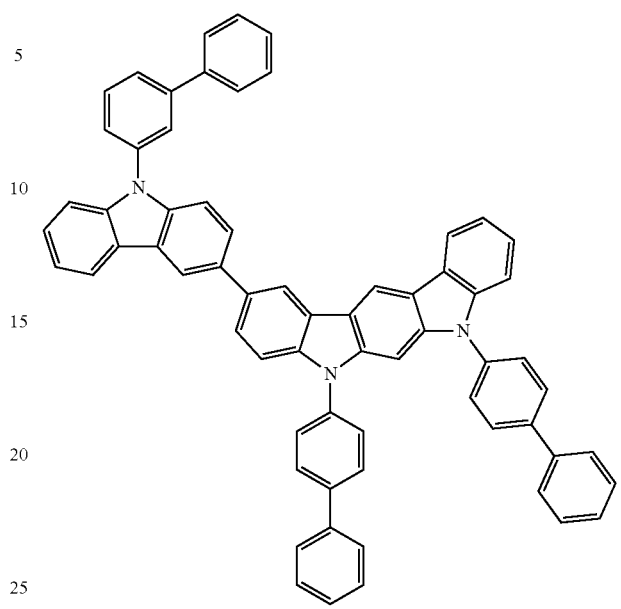
F-372
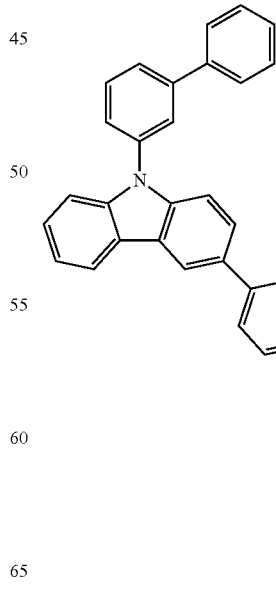

F-373
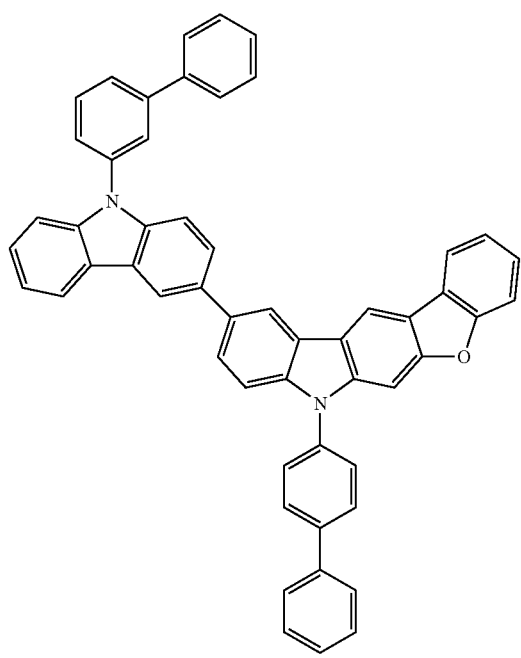
F-374
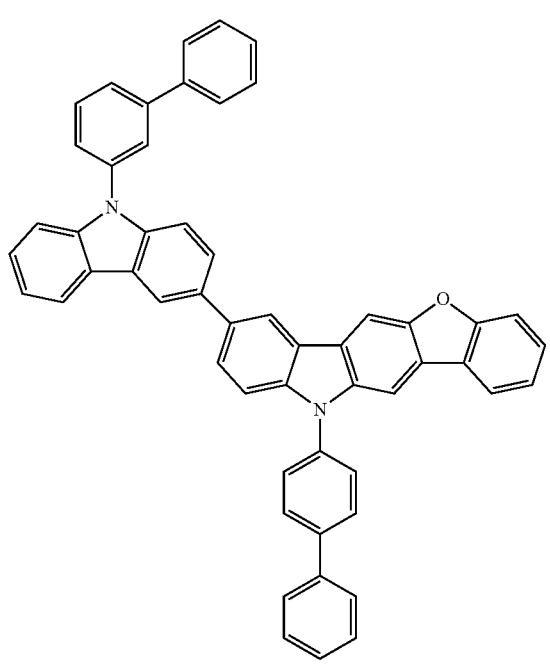
F-375
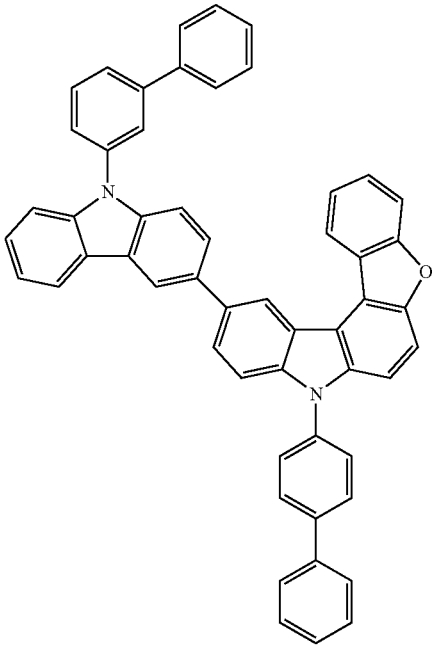
F-376
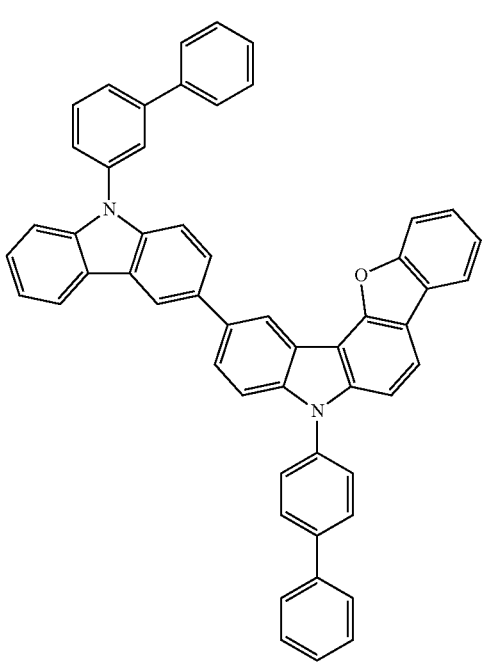

F-377
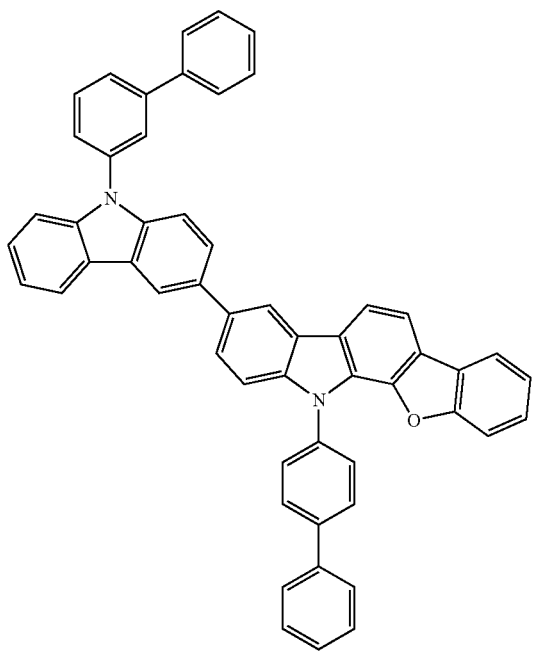
F-378
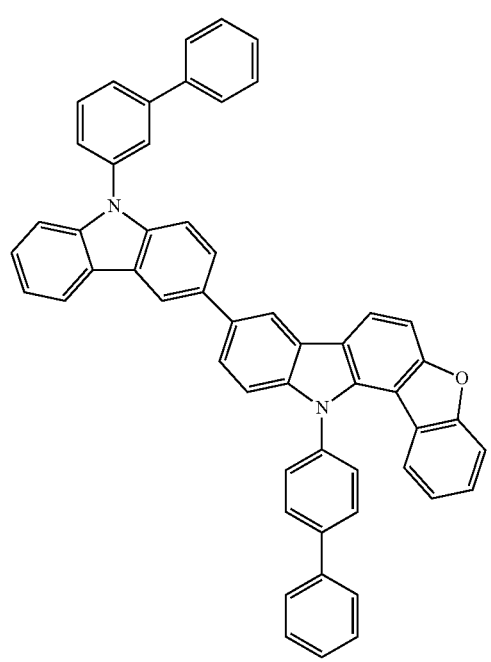
F-379
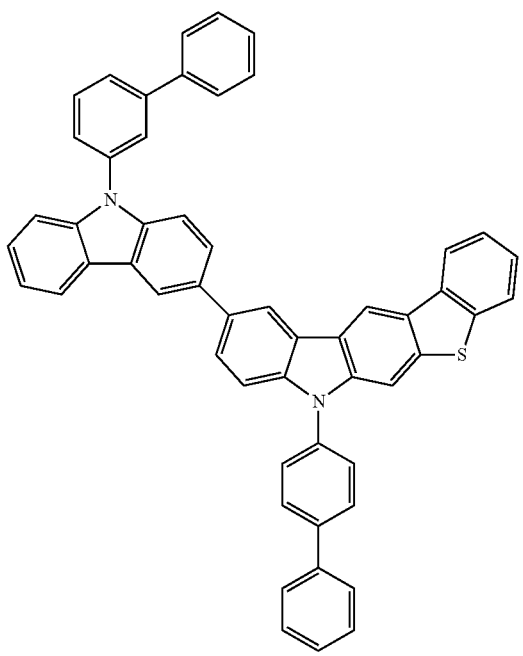
F-380
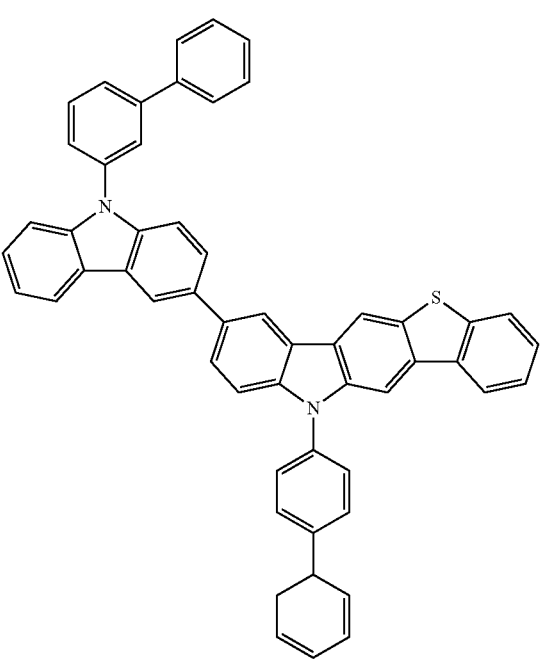

F-381
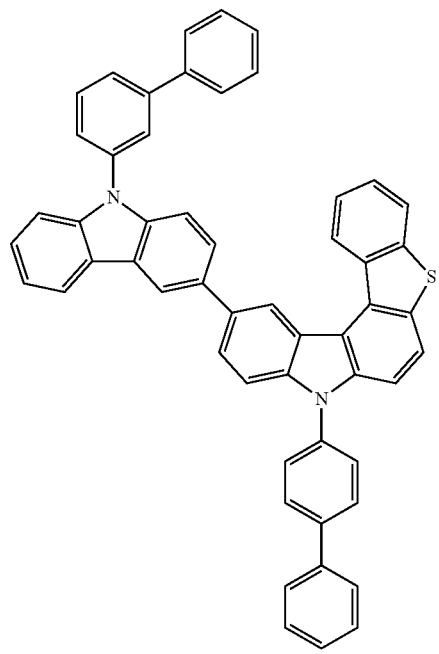
F-383
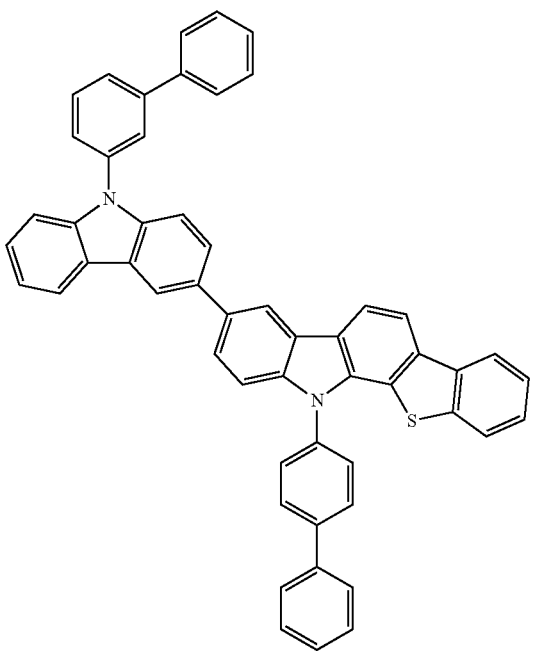
F-382
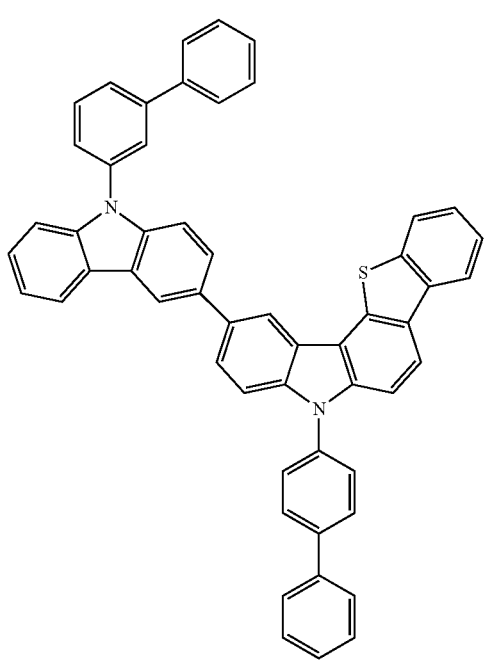
F-384
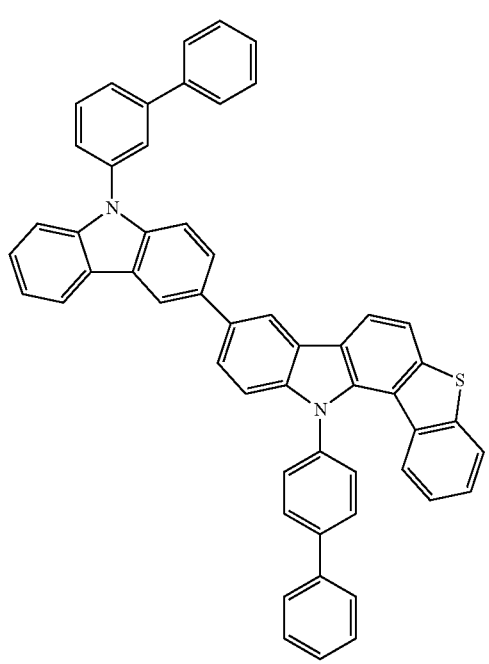

F-385
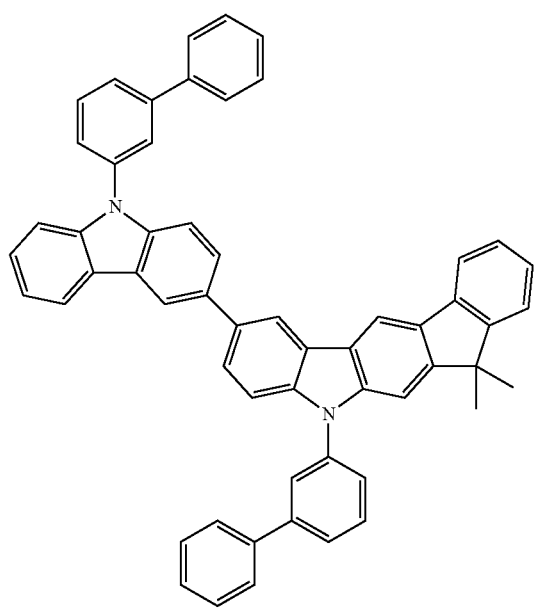
F-386
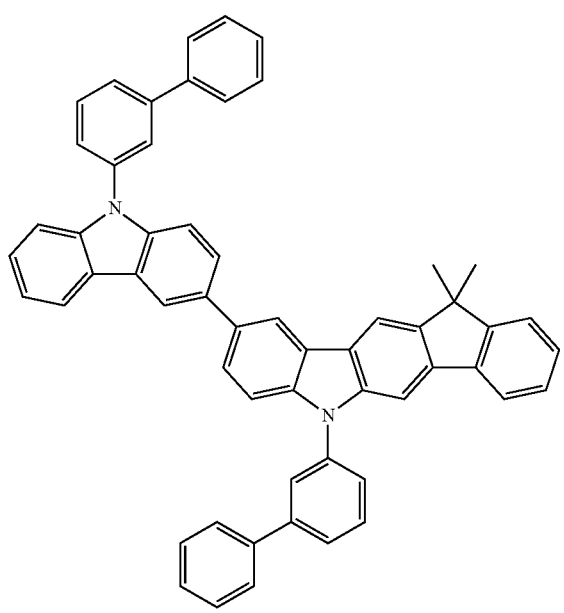
F-387
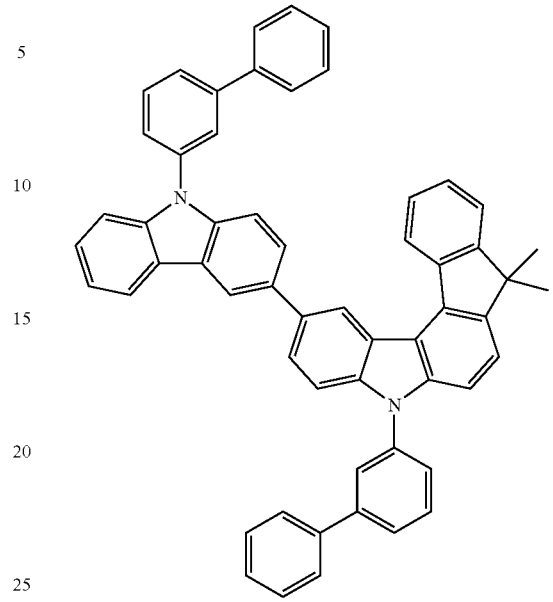
F-388
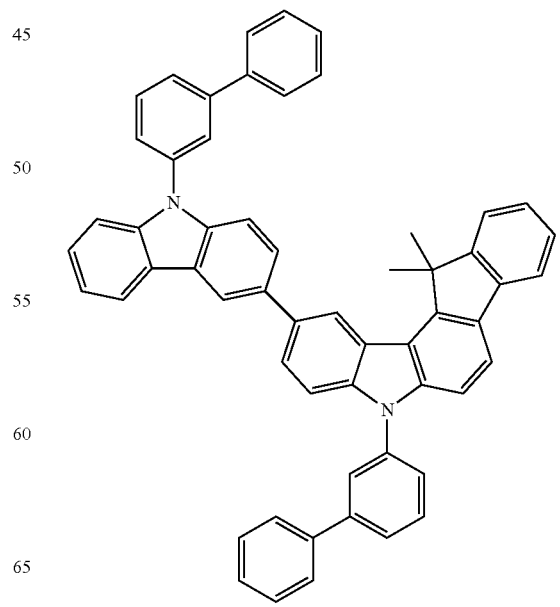

F-389
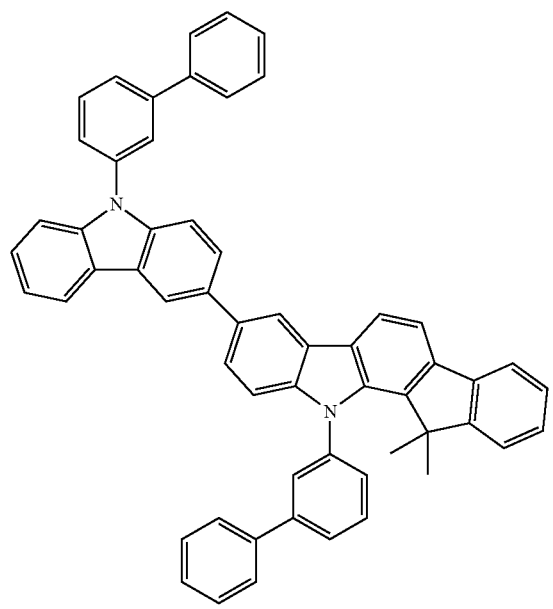
F-391
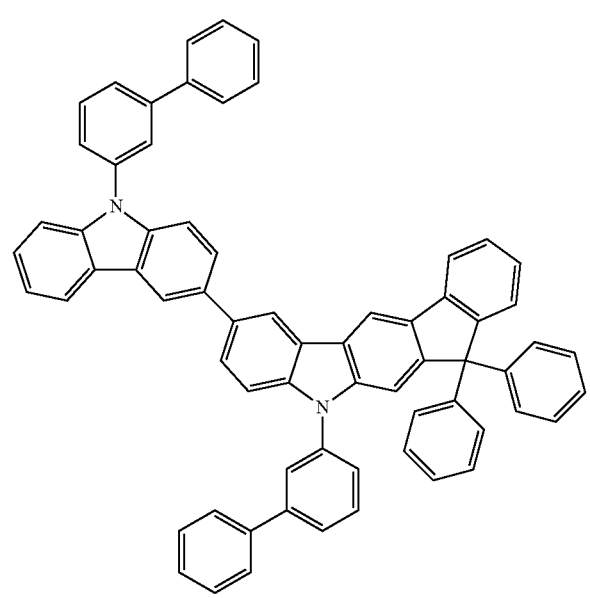
F-390
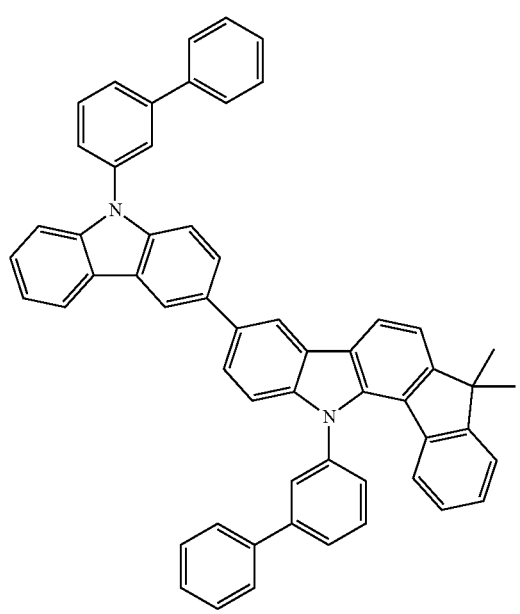
F-392

F-393
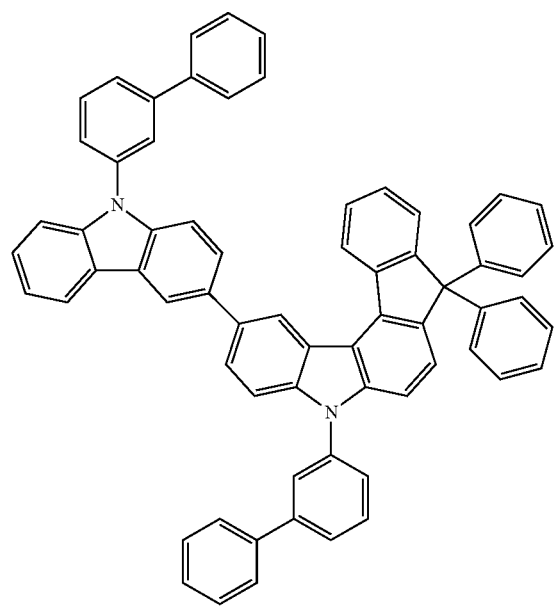
F-395
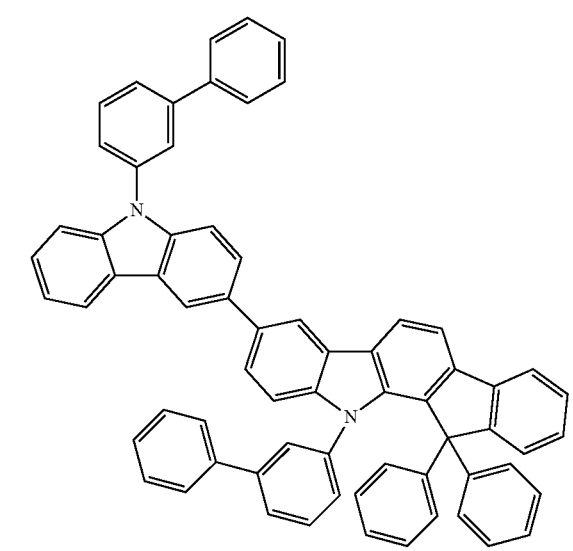
F-394
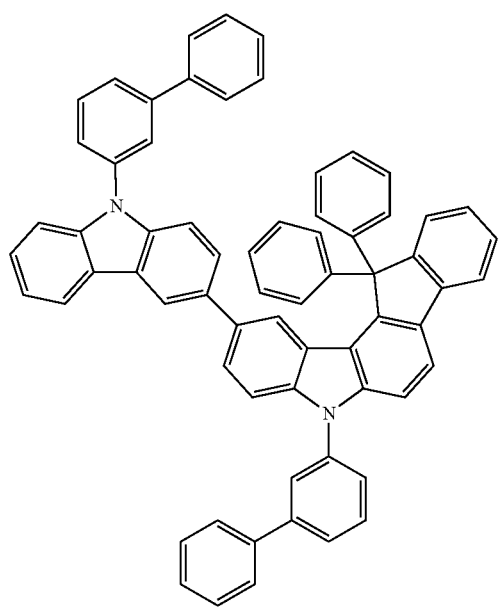
F-396
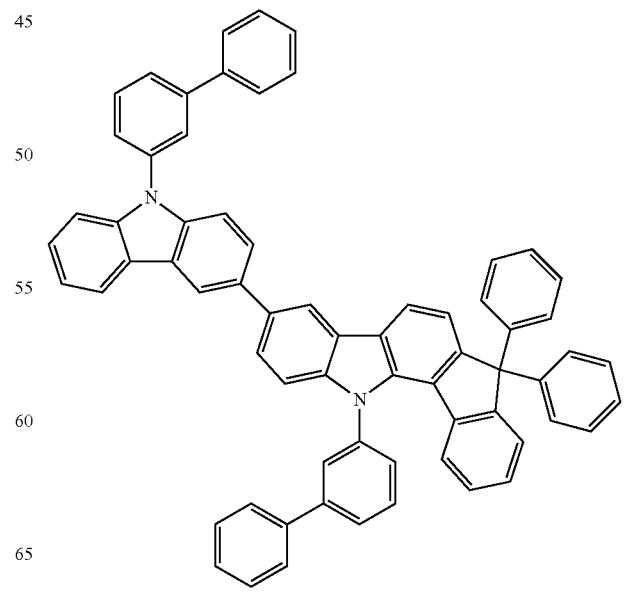

F-397
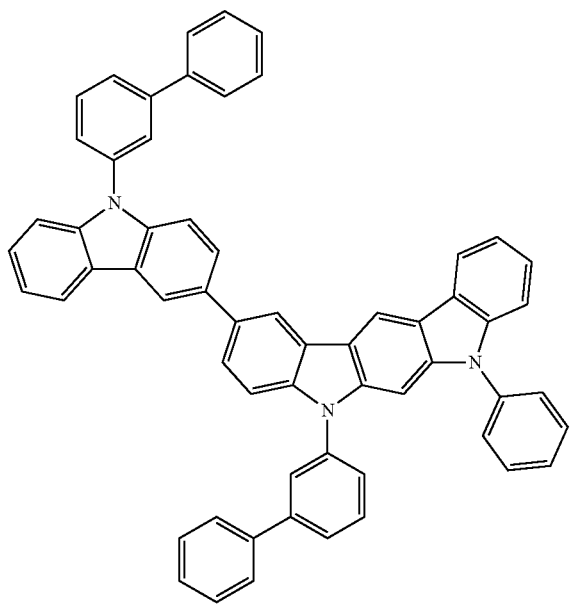
F-399
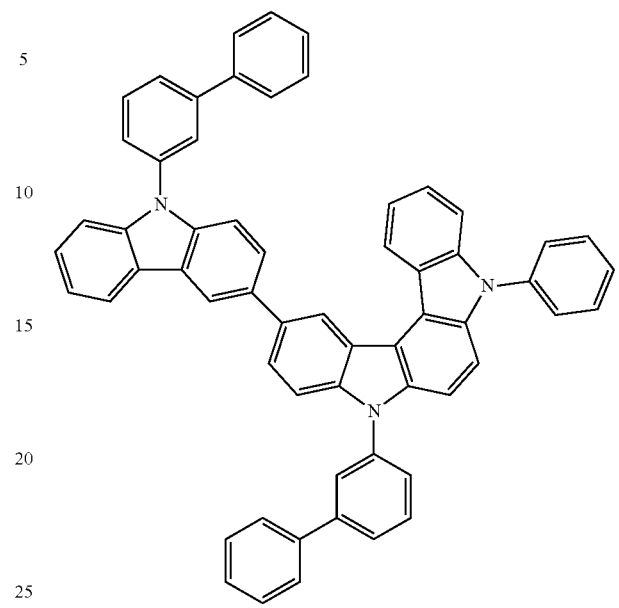
F-398
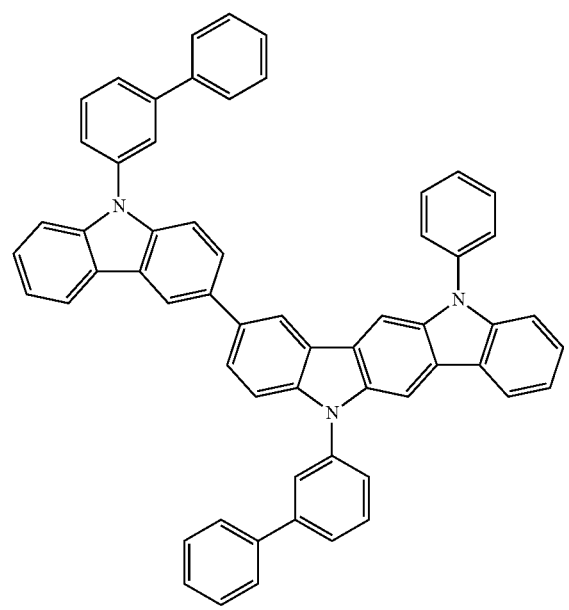
F-400
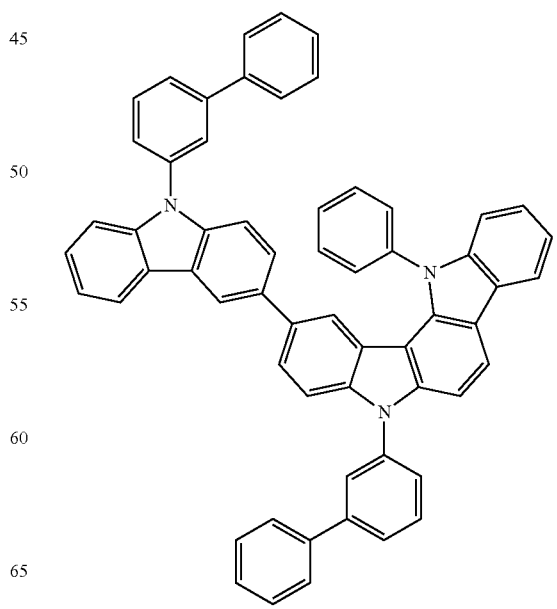

-continued
F-401
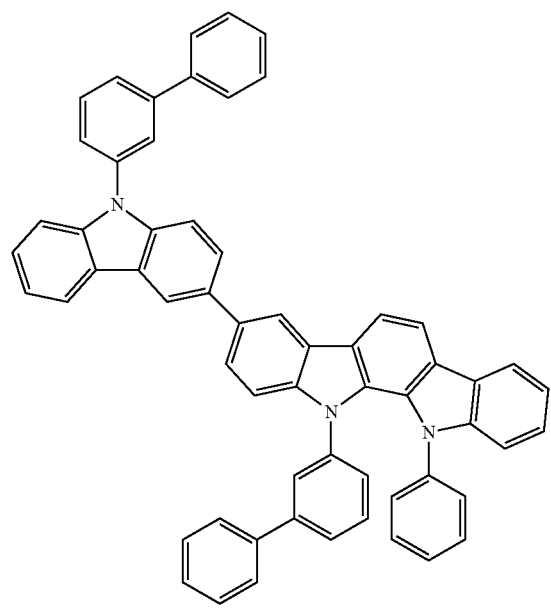
F-402
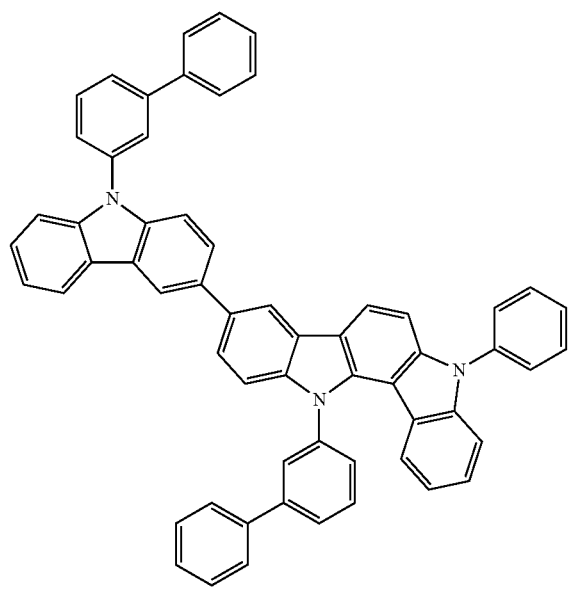
F-403
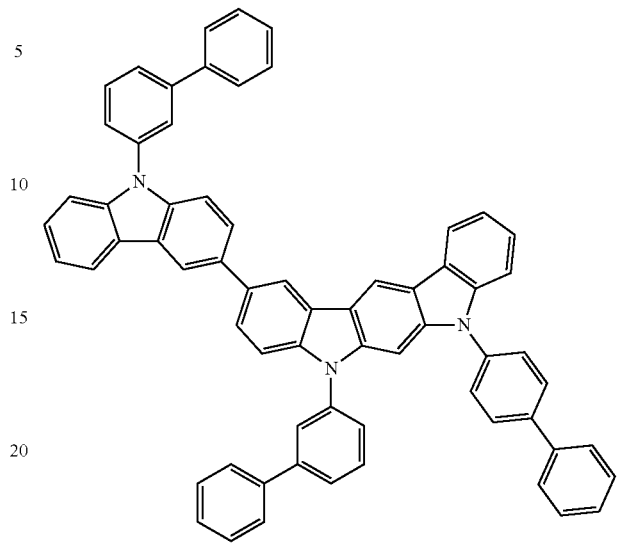
F-404
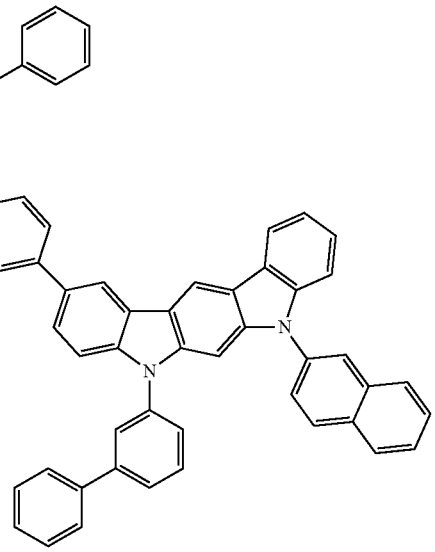

F-405
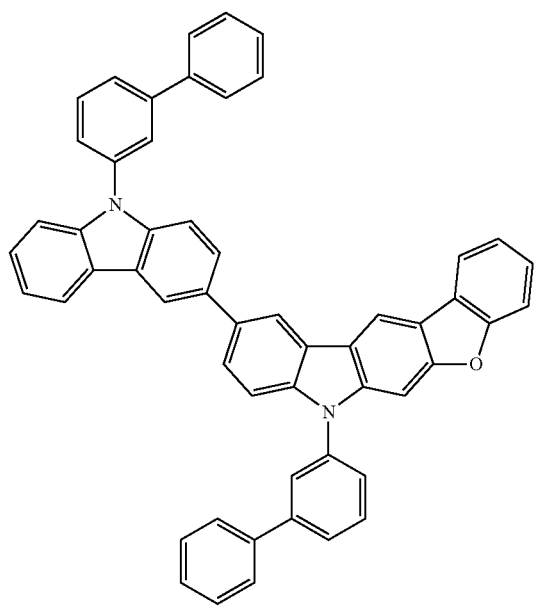
F-406
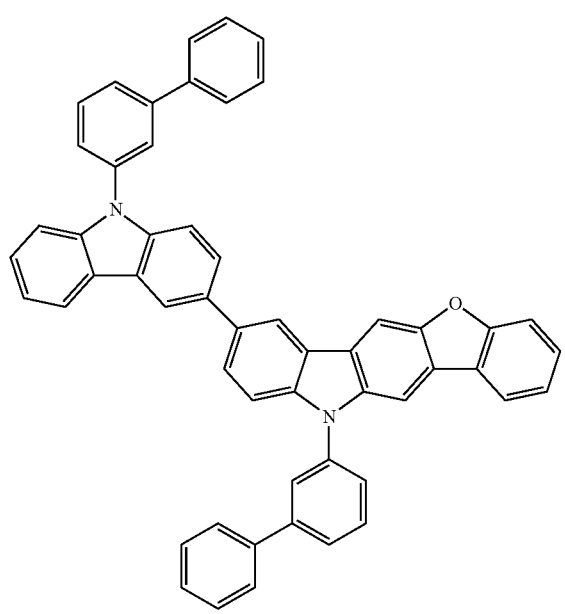
F-407
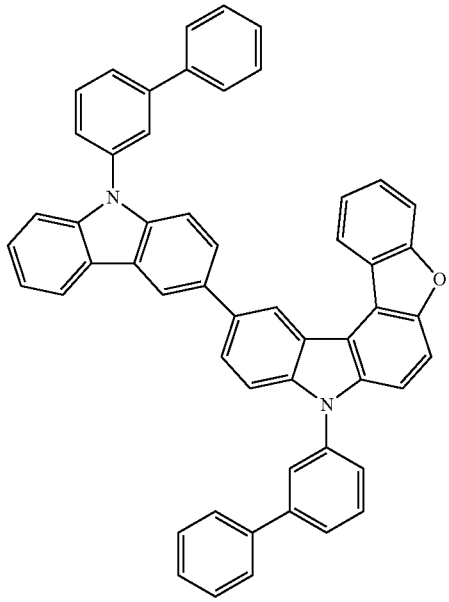
F-408

F-409
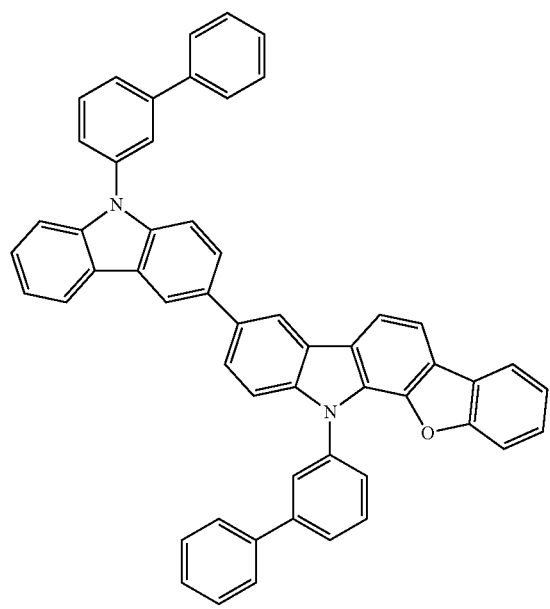
F-411
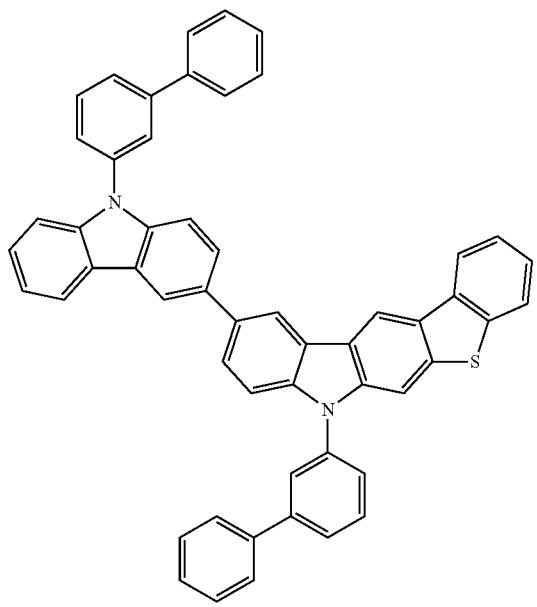
F-410
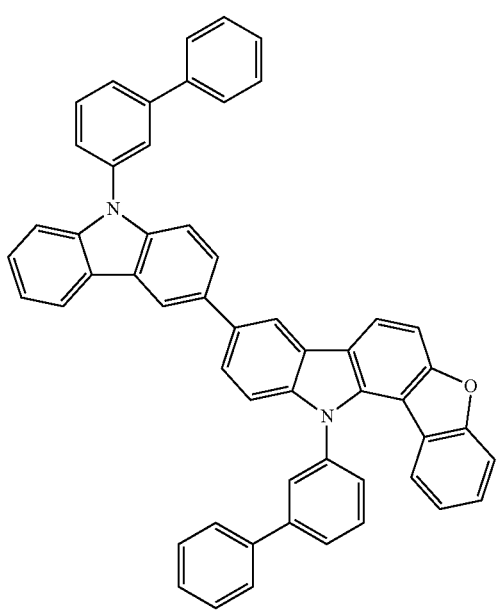
F-412
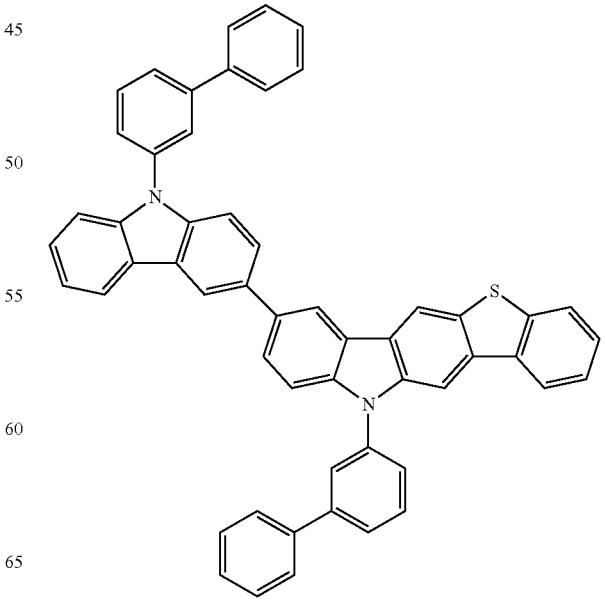

F-413
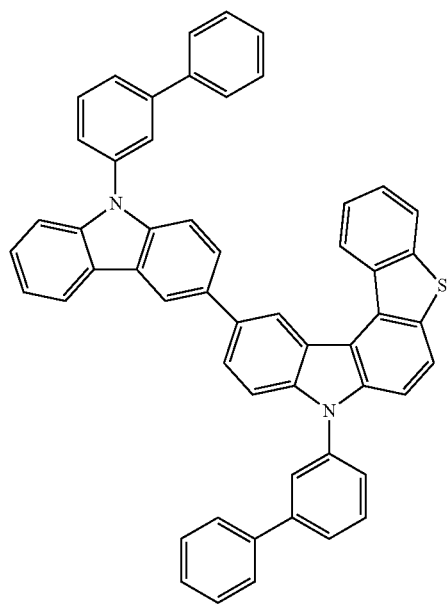
F-415
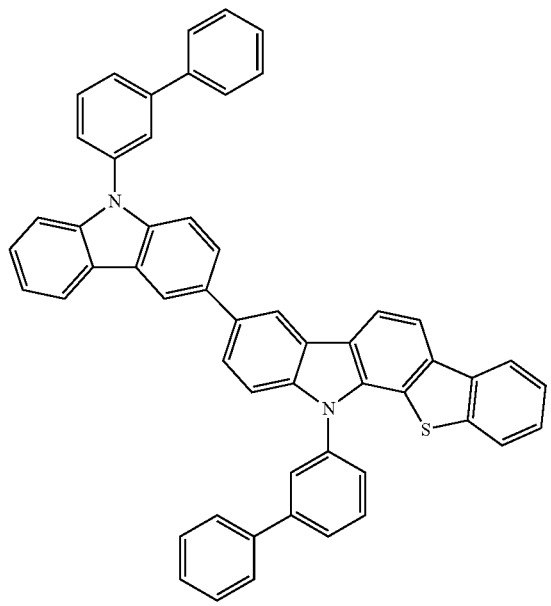
F-414
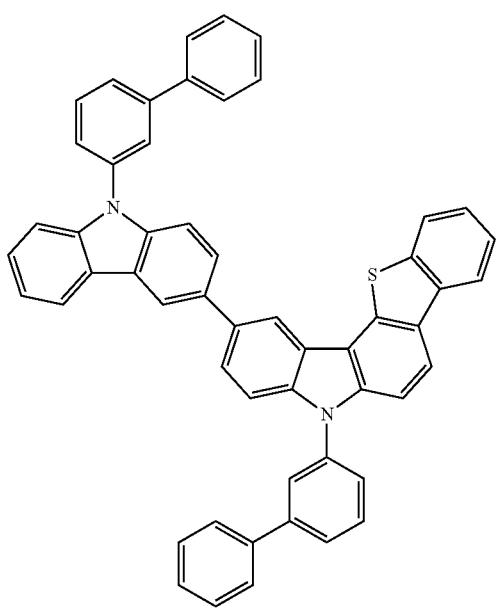
F-416
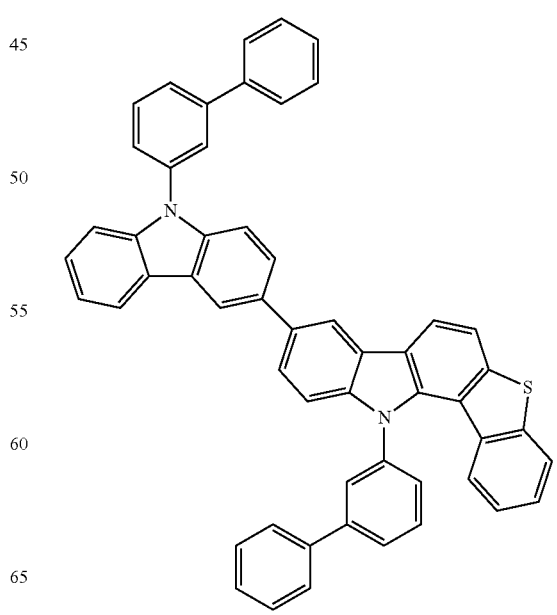

F-417
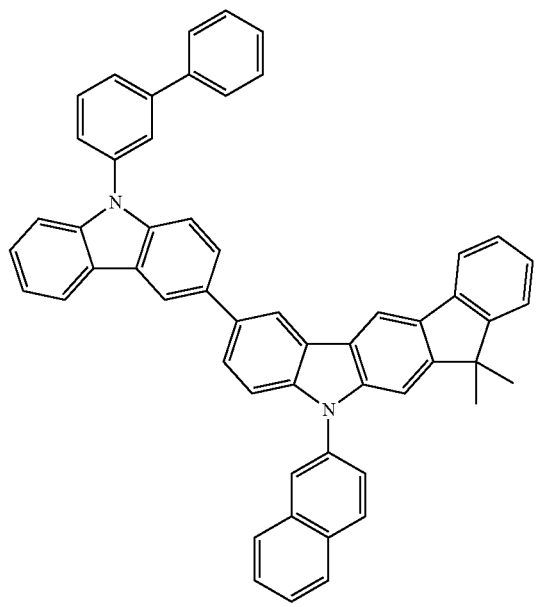
F-418
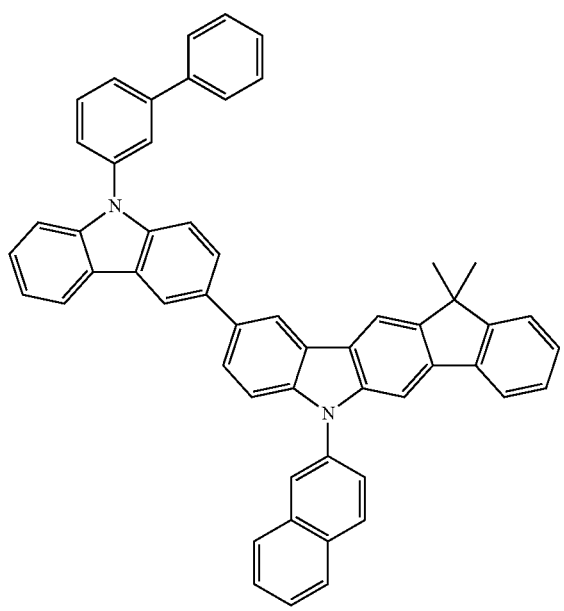
F-419
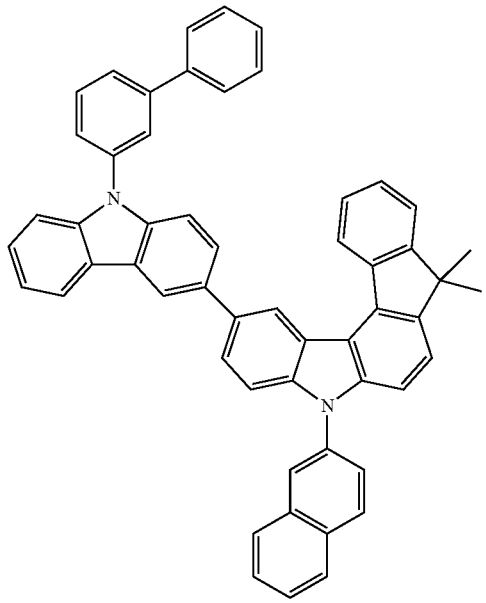
F-420
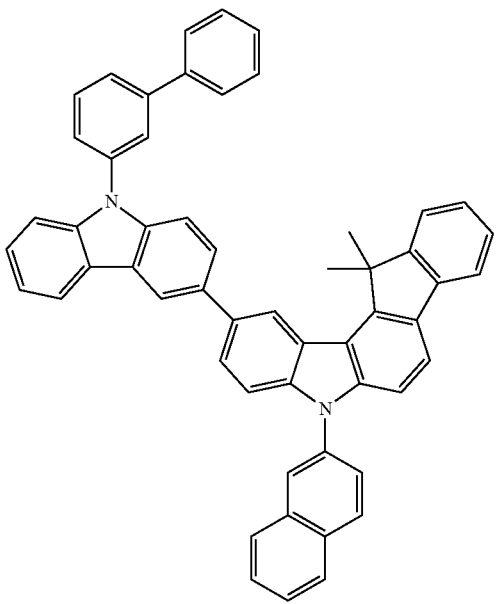

F-421
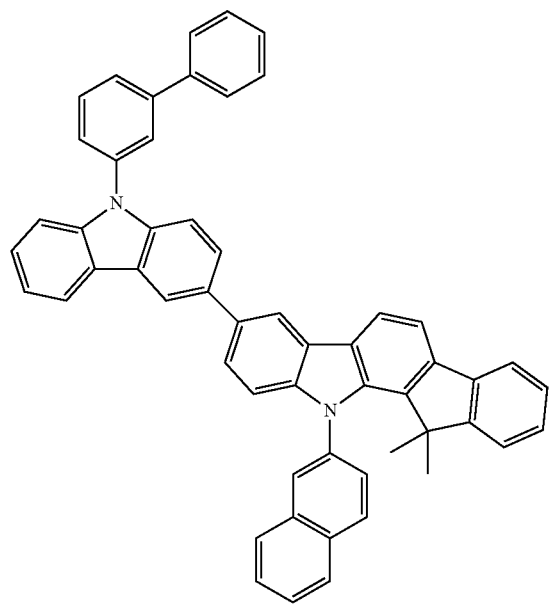
F-423
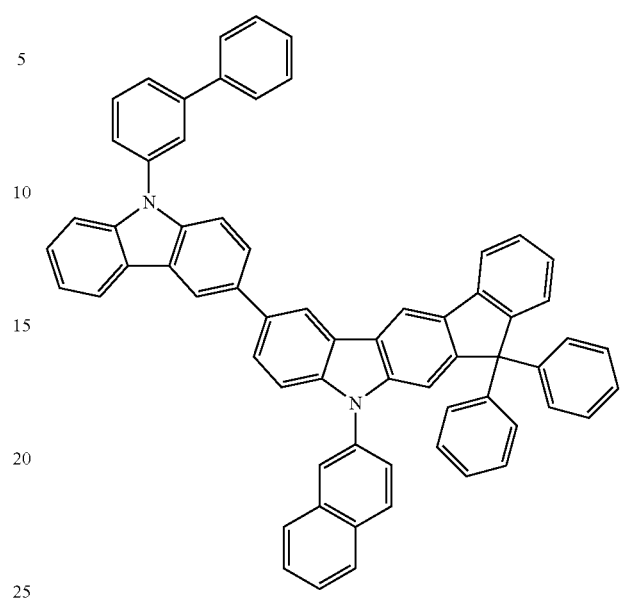
F-422
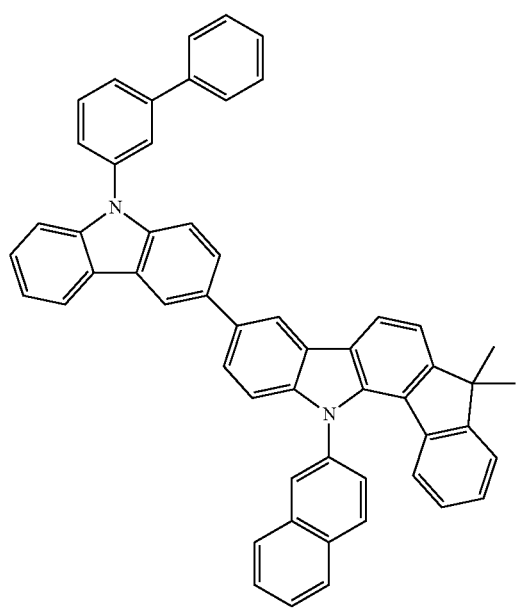
F-424
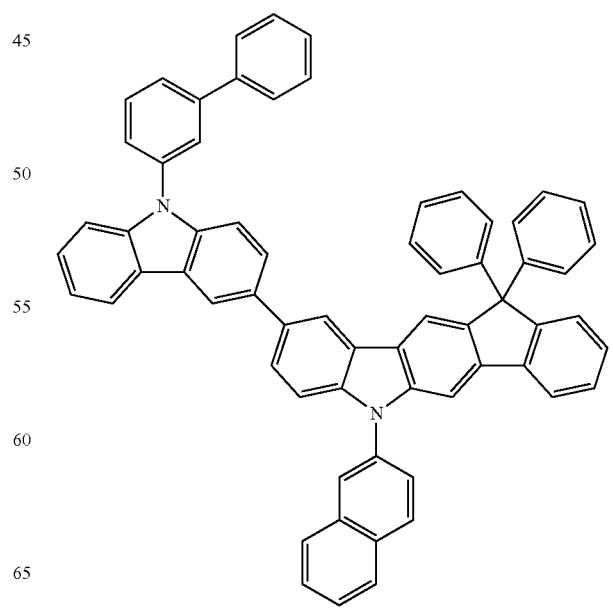

F-425
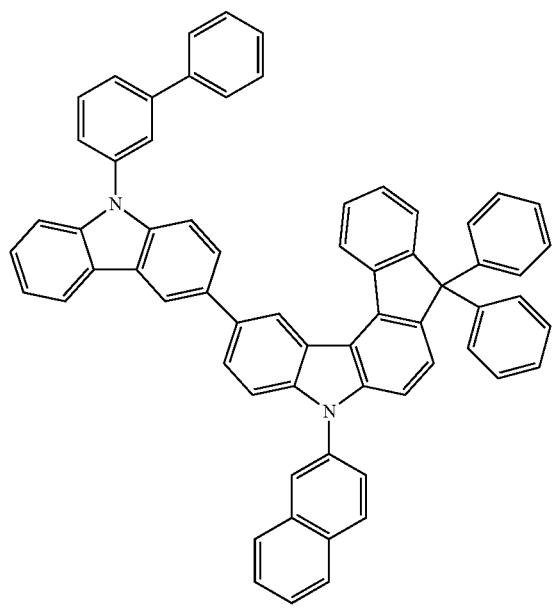
F-427
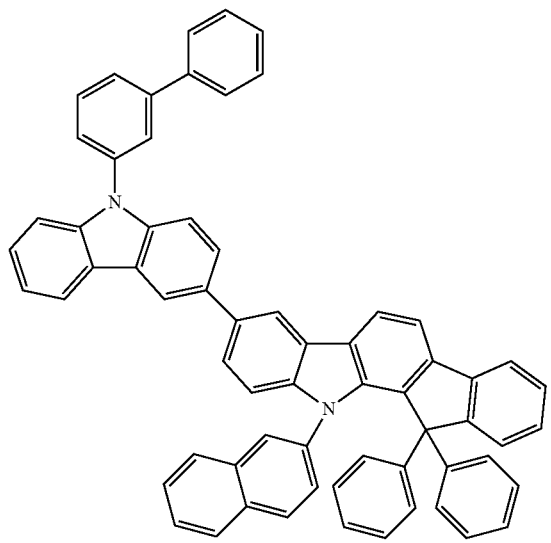
F-426
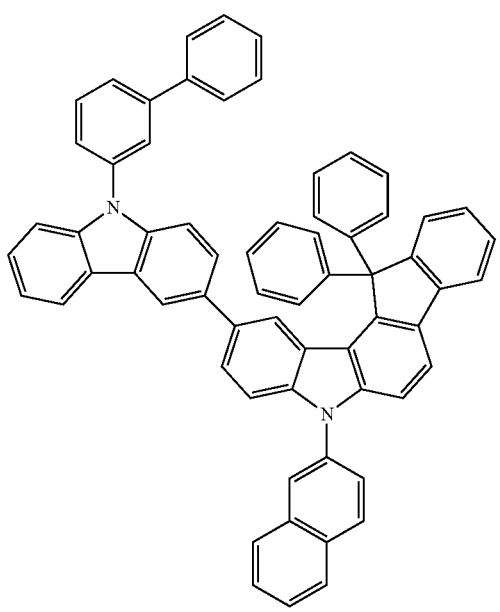
F-428

F-429
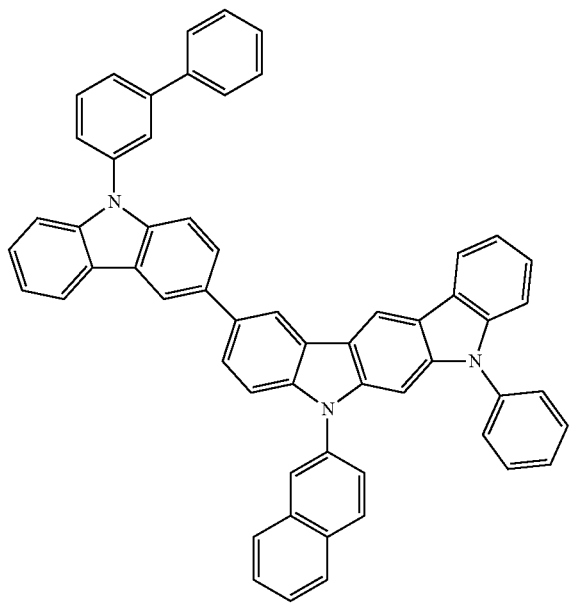
F-431
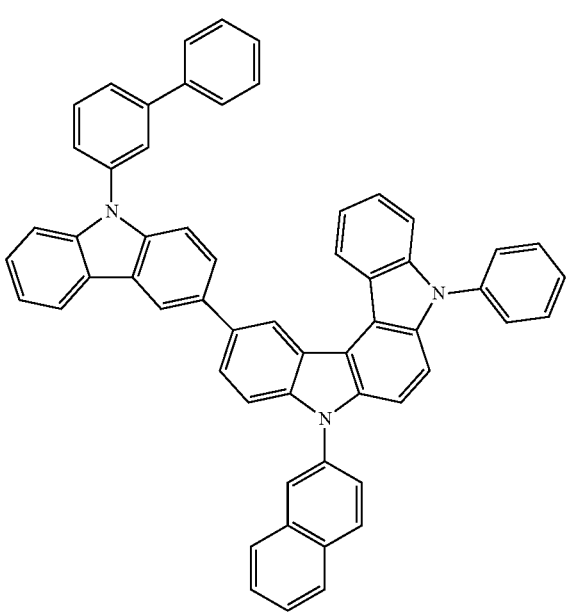
F-430
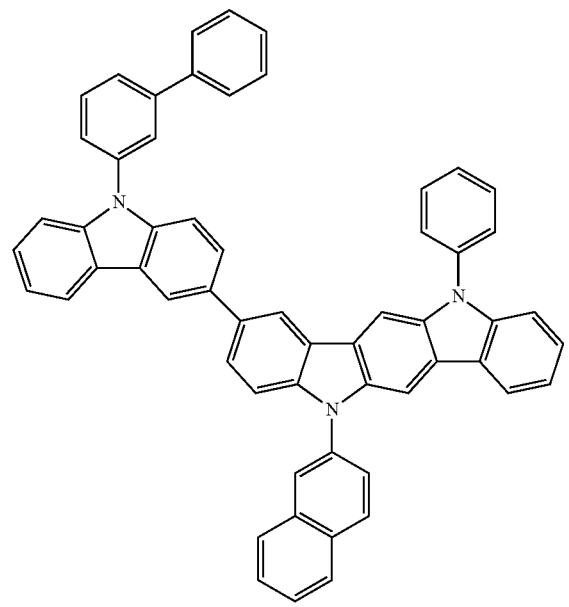
F-432
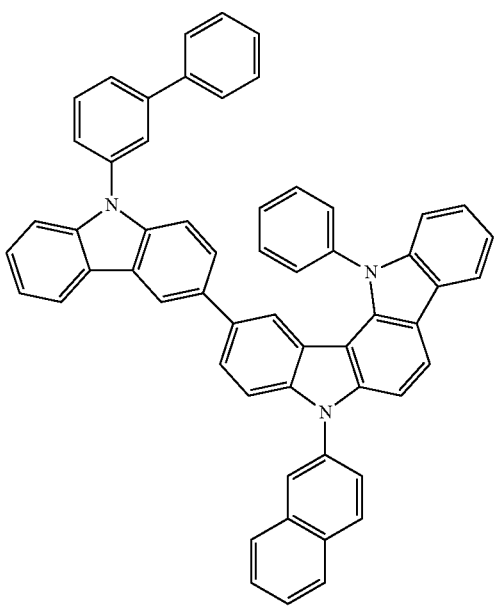

-continued
F-401
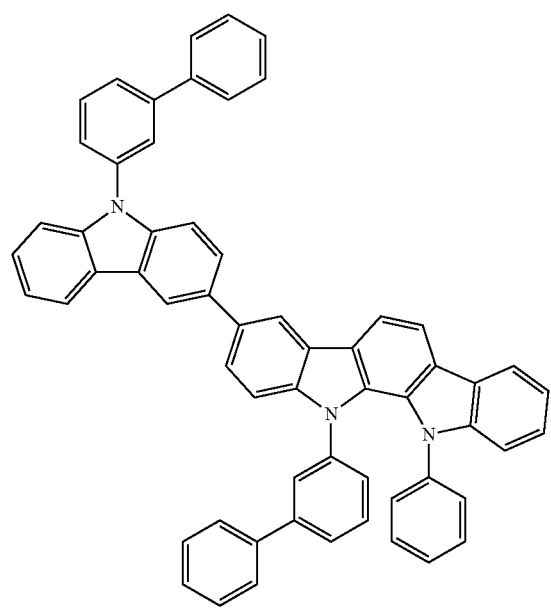
F-402
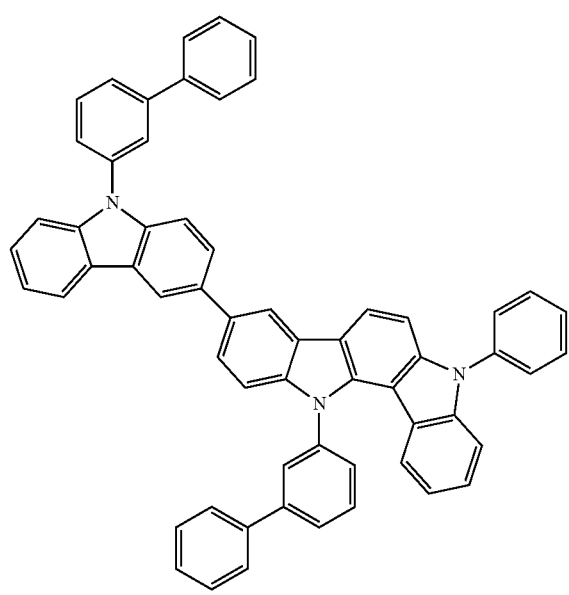
-continued
F-403
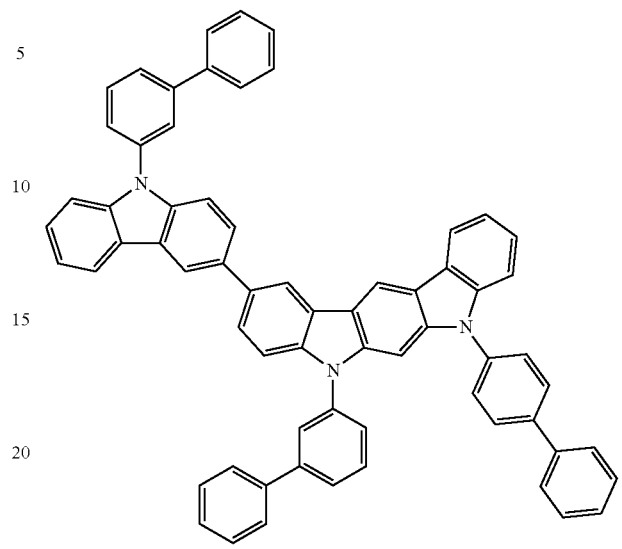
F-404
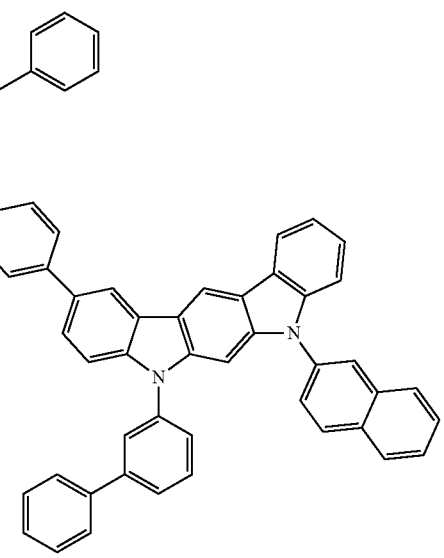

F-405
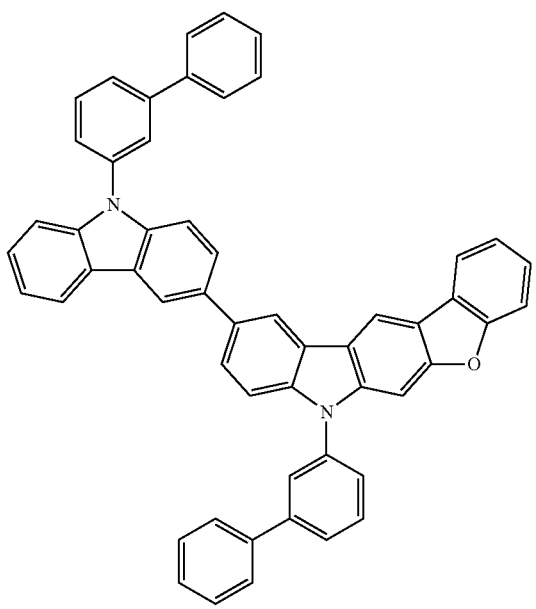
F-407
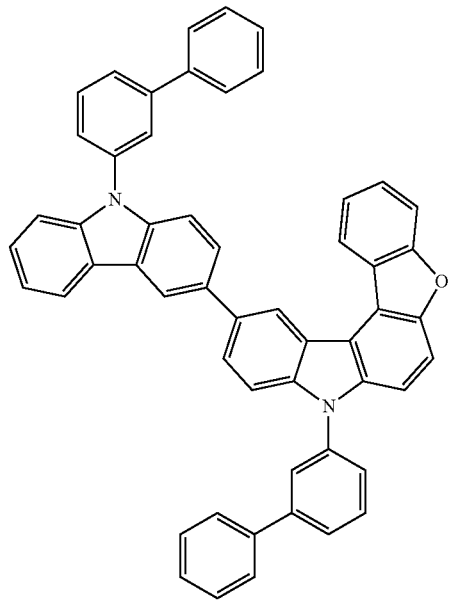
F-406
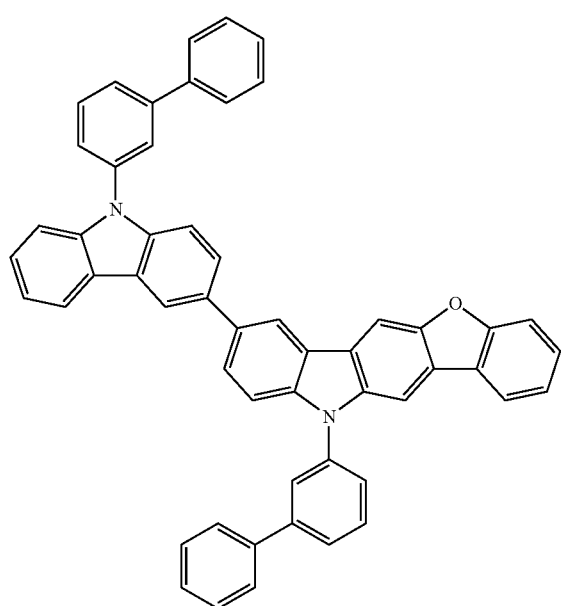
F-408
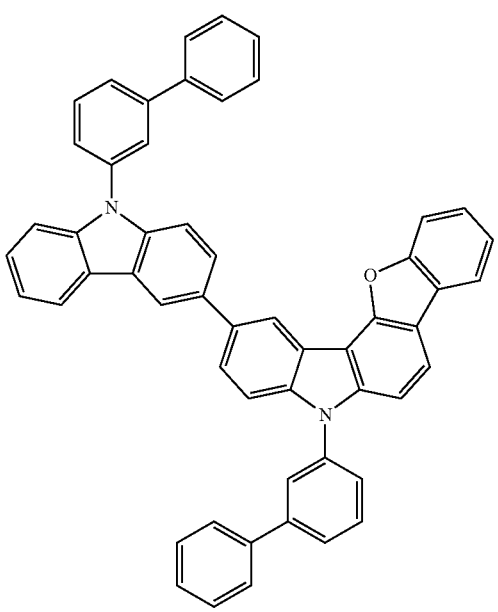

F-409
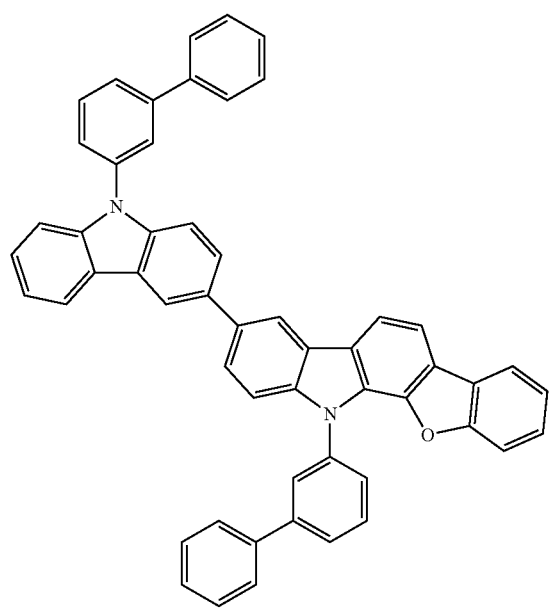
F-411
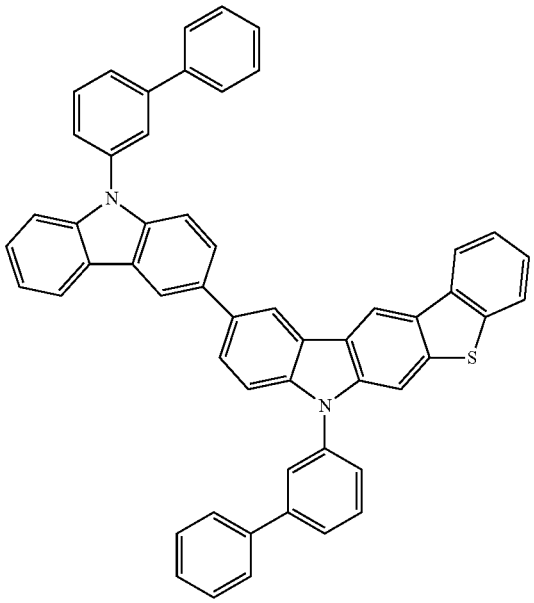
F-410
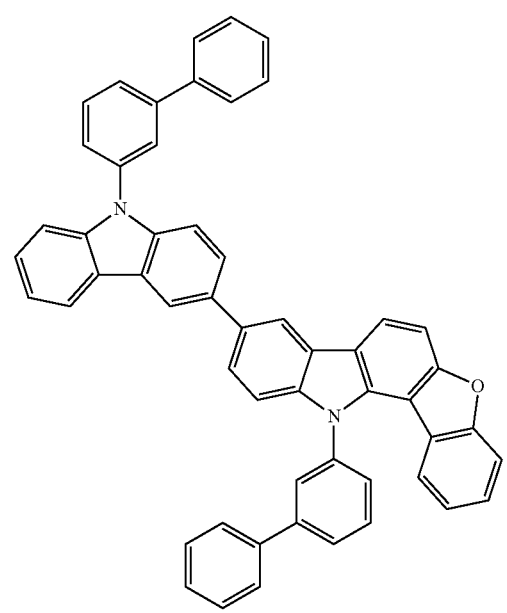
F-412
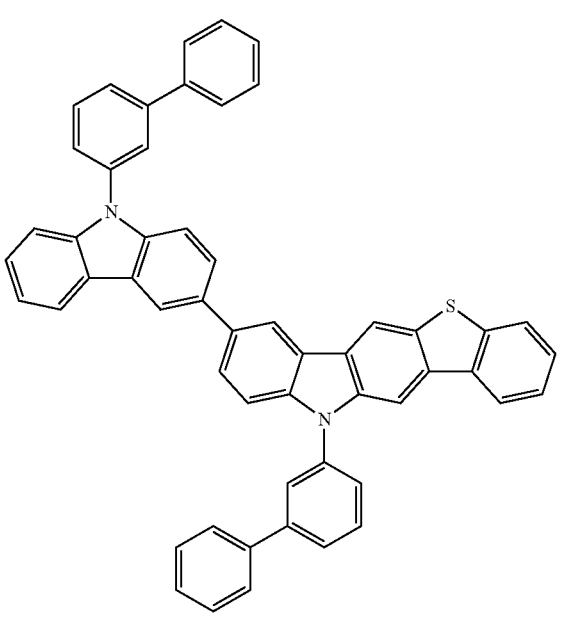

F-413
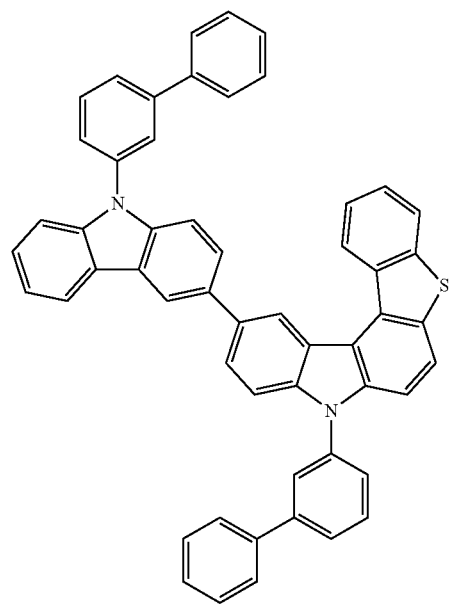
F-414
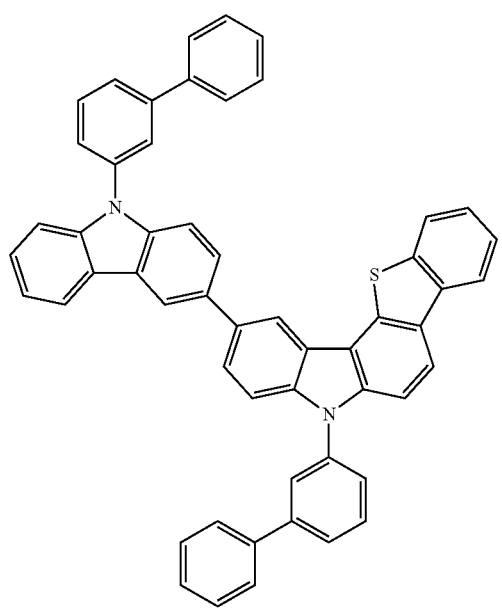
F-415
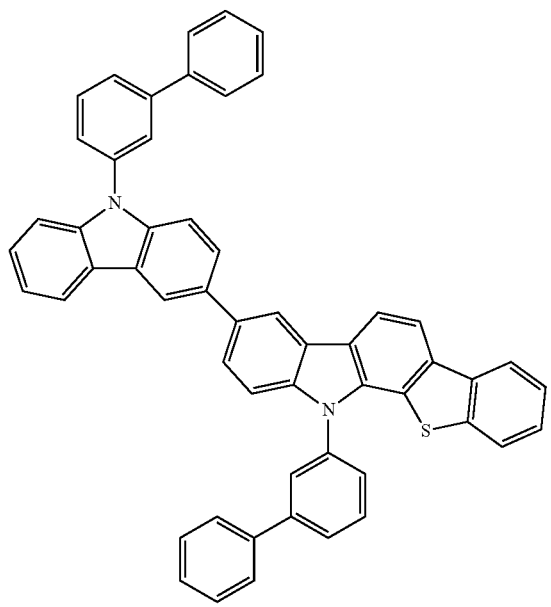
F-416

F-449
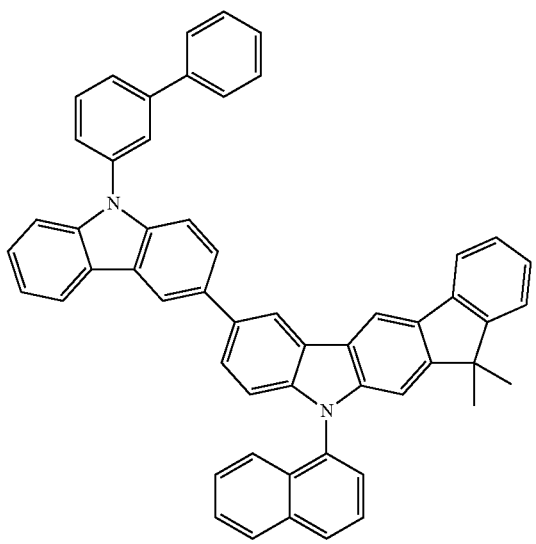
F-451
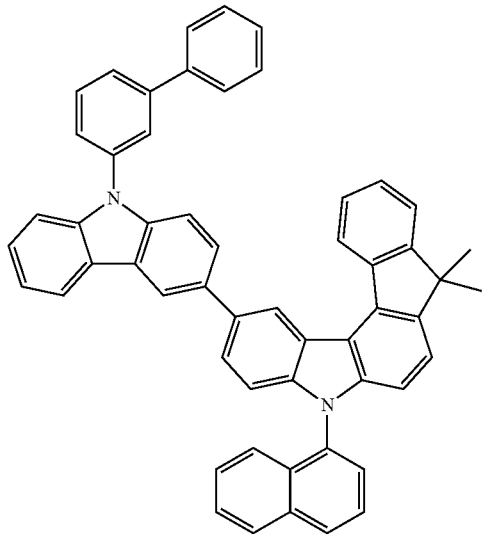
F-450
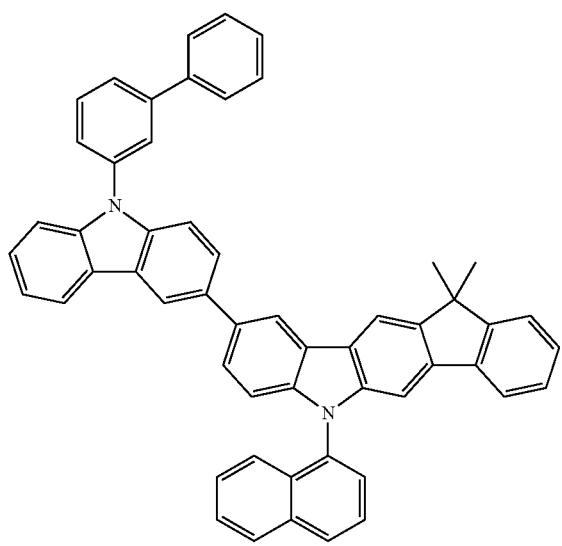
F-452
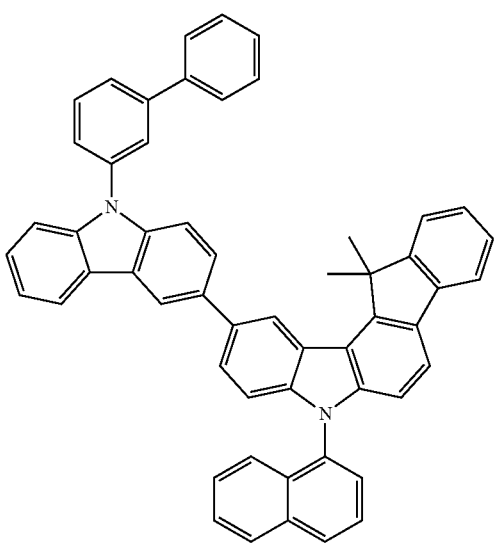

F-453
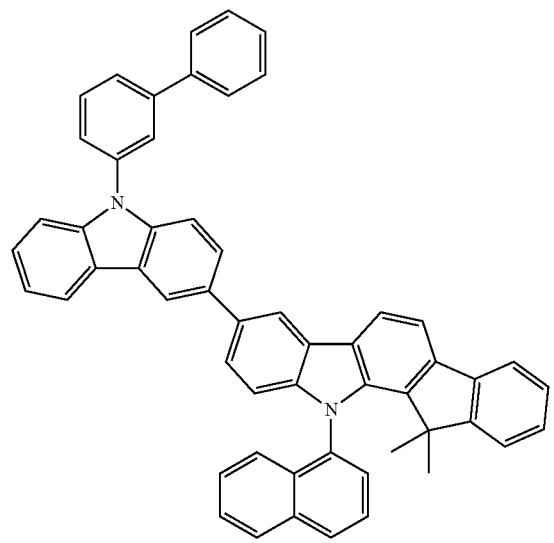
F-454
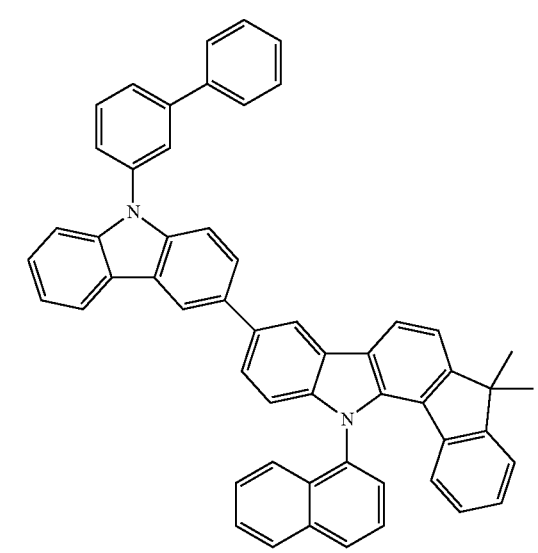
F-455
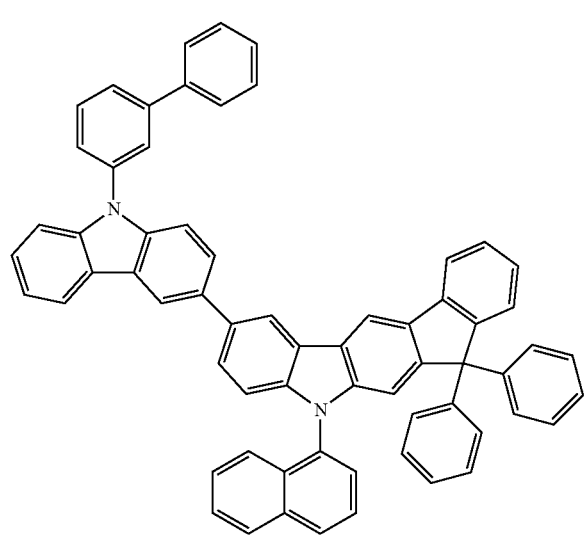
F-456
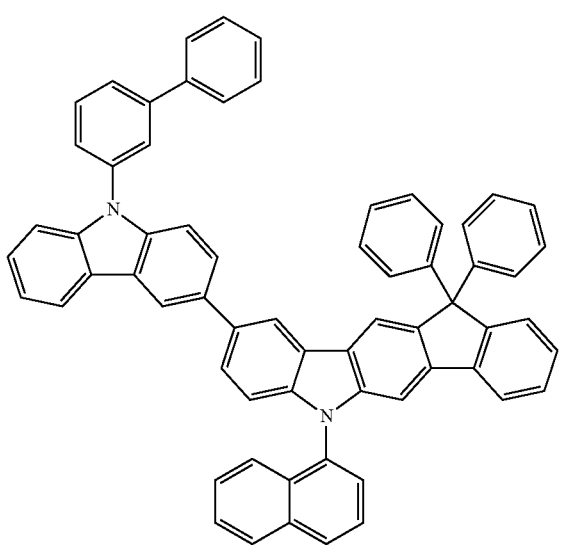
F-457
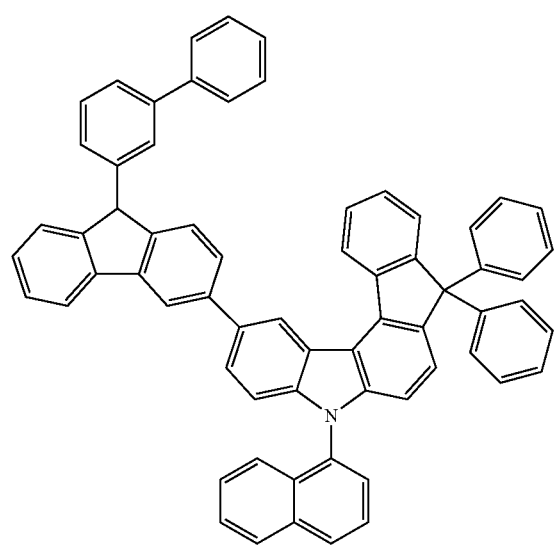

F-458
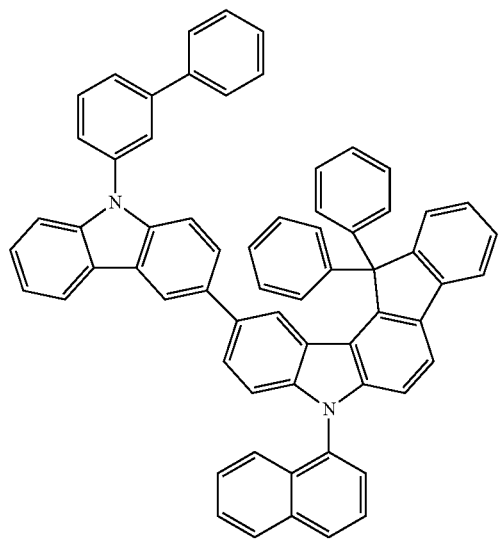
F-461
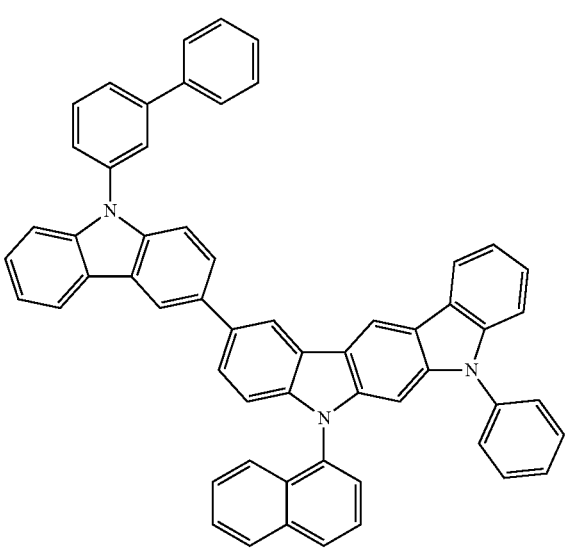
F-459
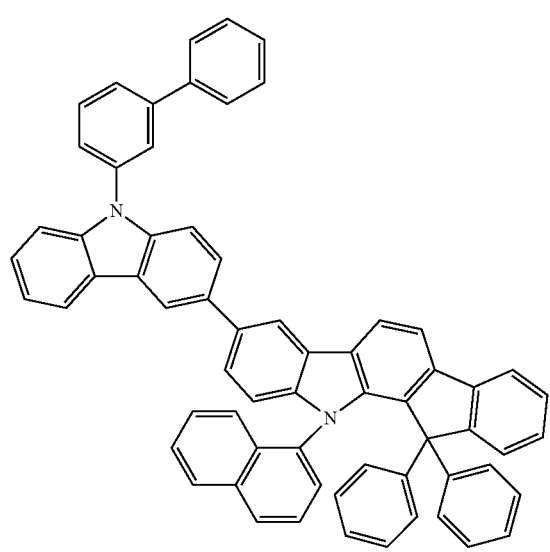
F-460
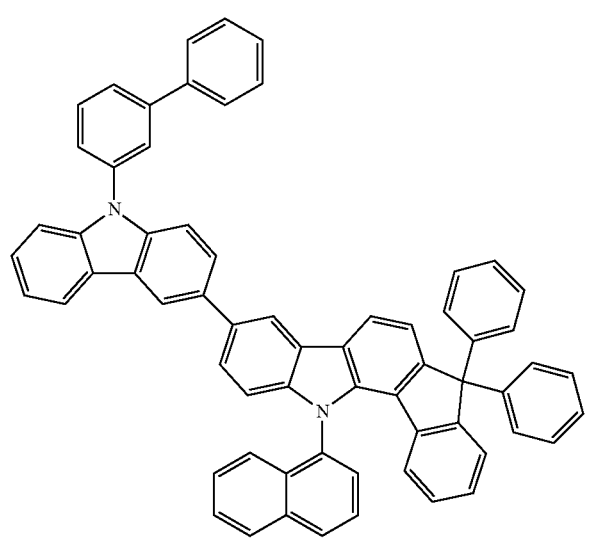
F-462
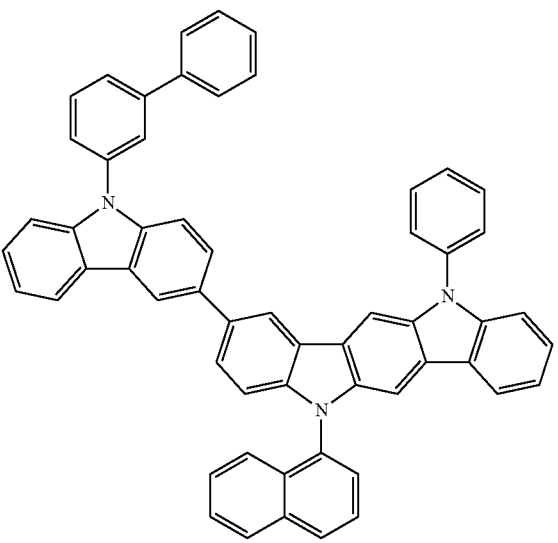

F-463
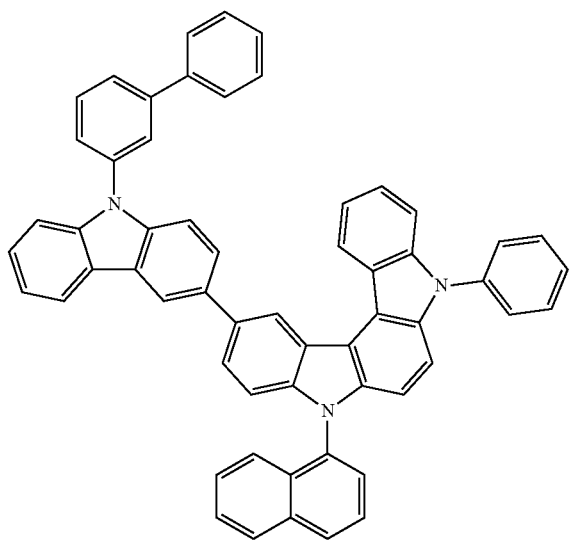
F-465
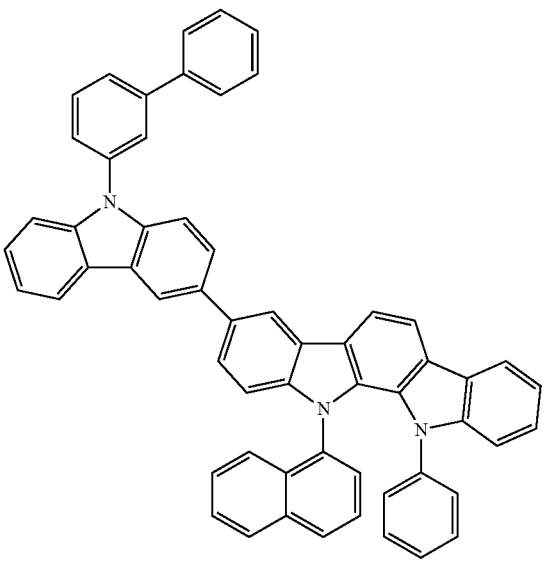
F-464
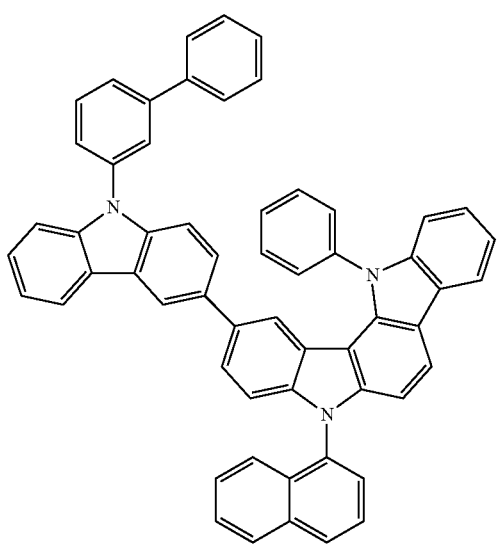
F-466
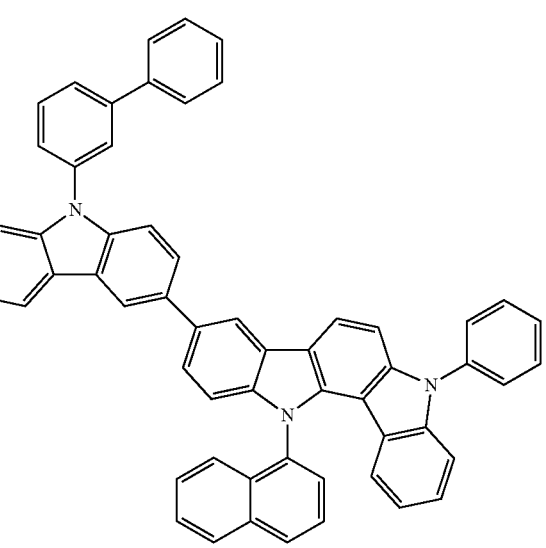

829
-continued
F-467
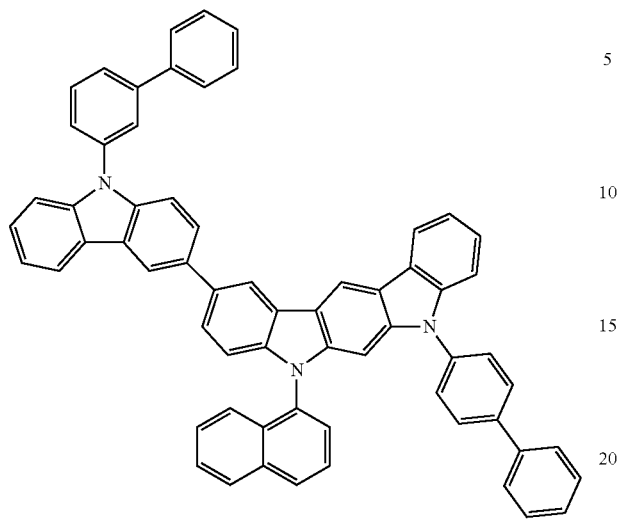
F-468
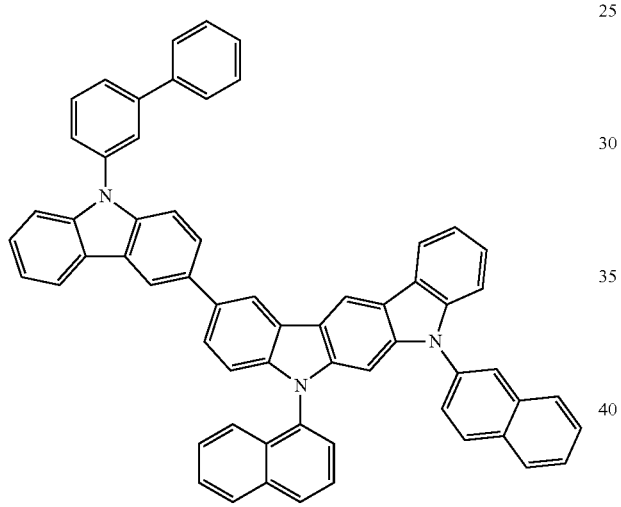
F-469
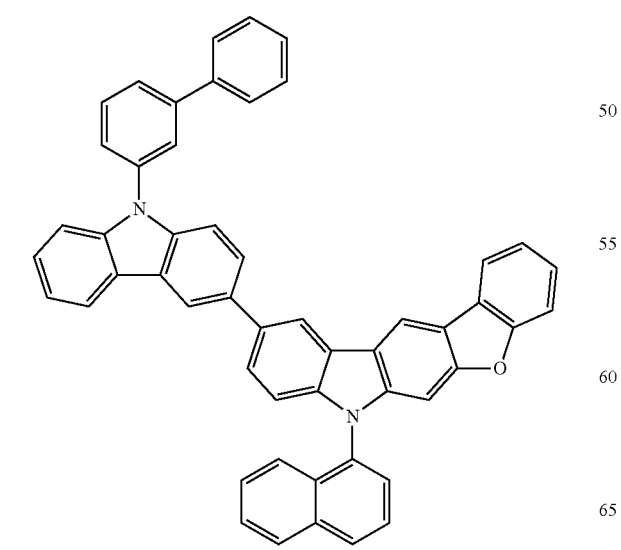
830
-continued
F-470
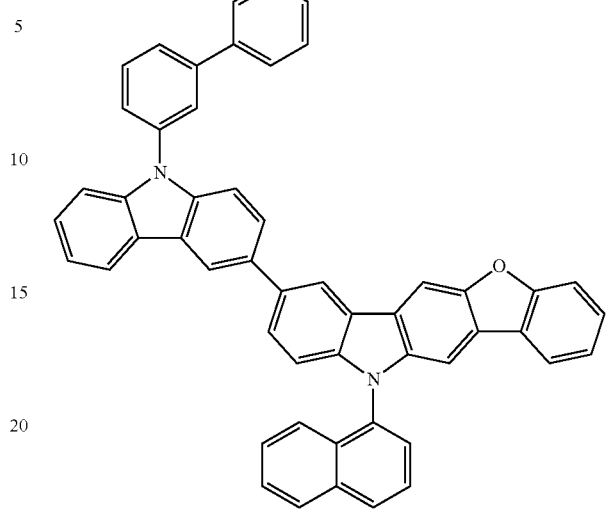
F-471
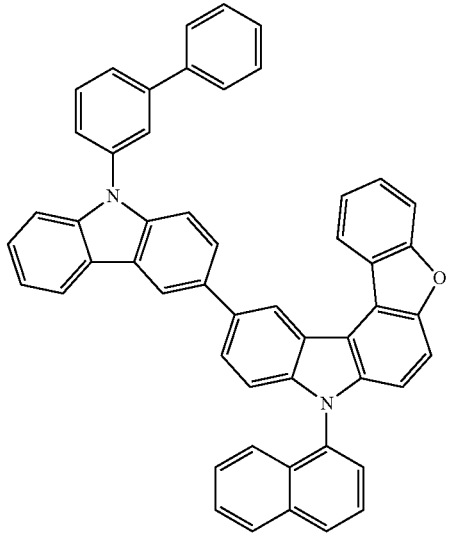
F-472
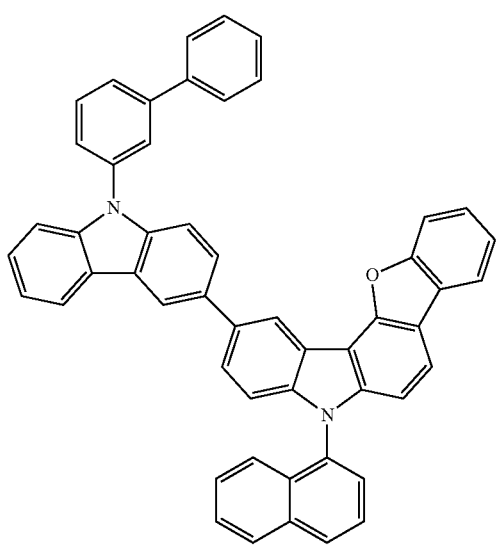

F-473
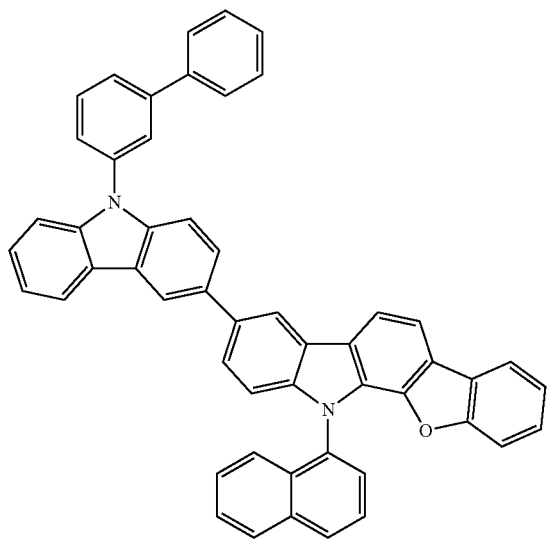
F-474
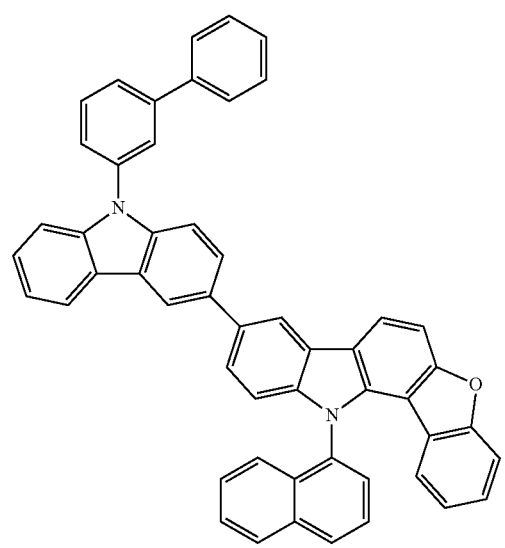
F-475
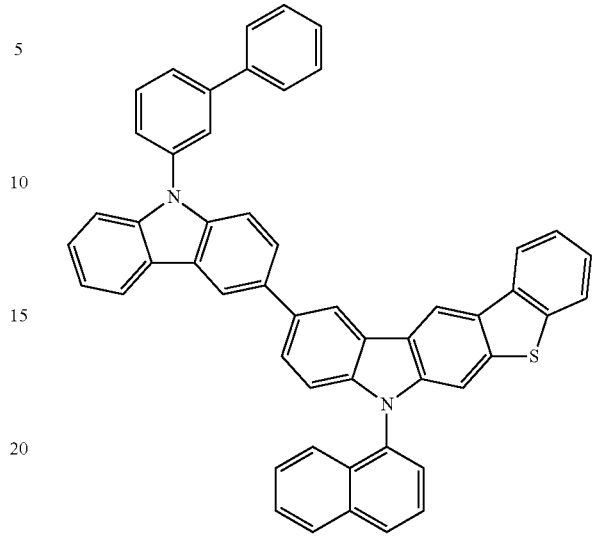
F-476
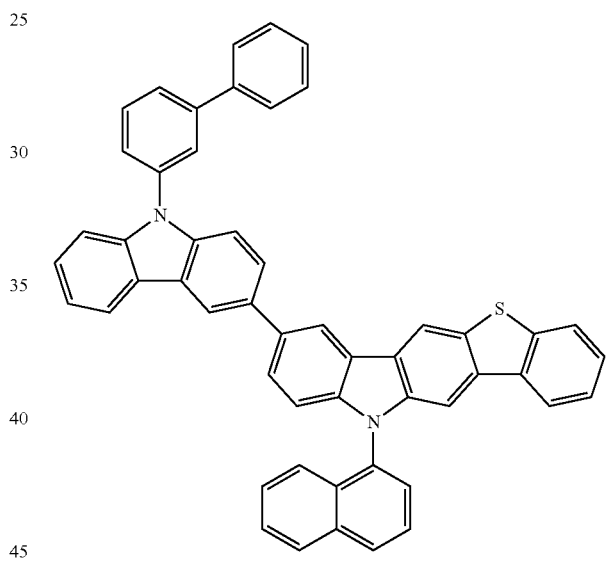
F-477

F-478
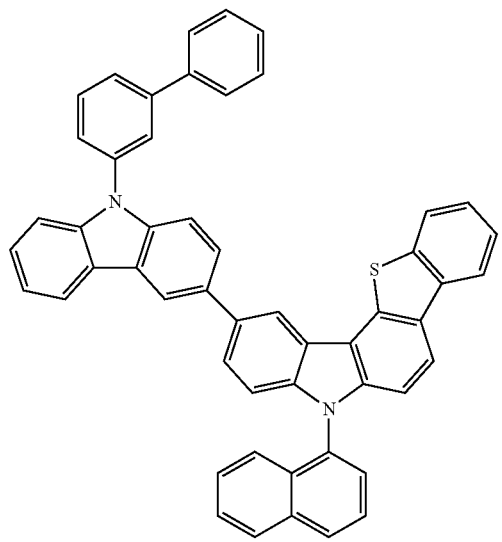
F-480
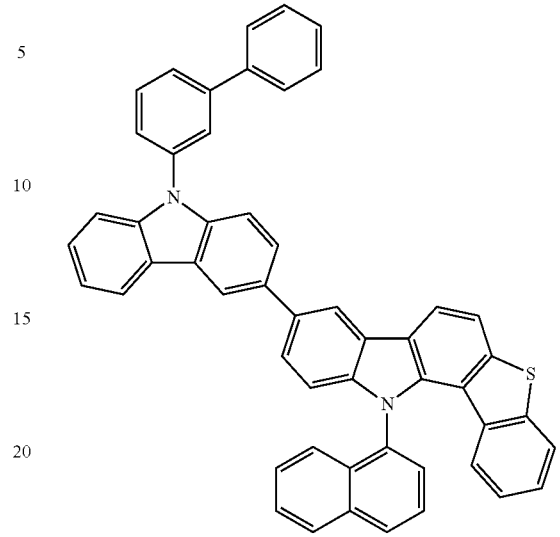
F-479
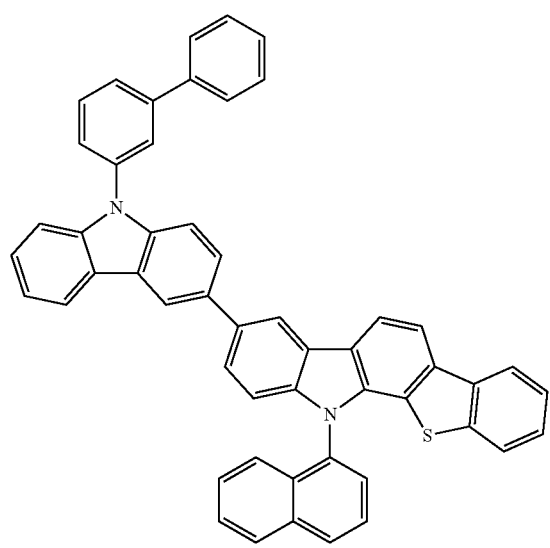
F-481
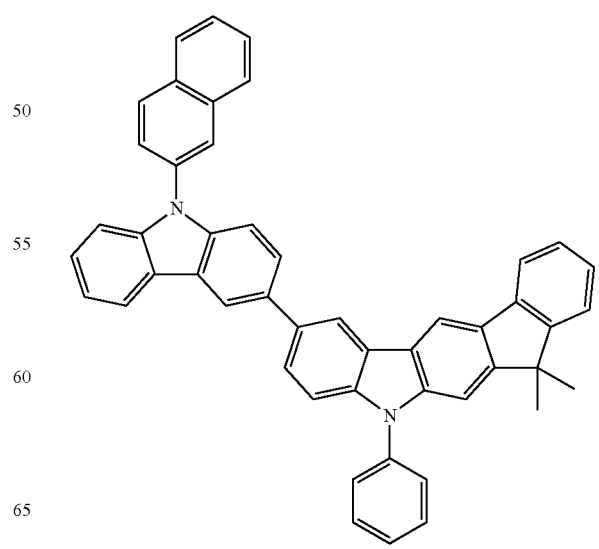

-continued
F-482
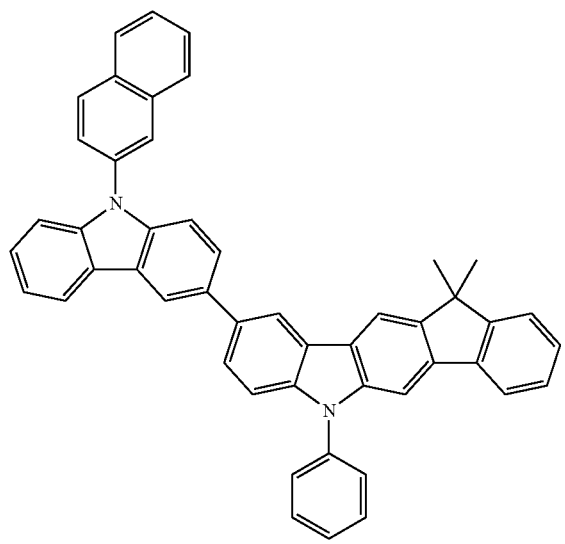
F-483
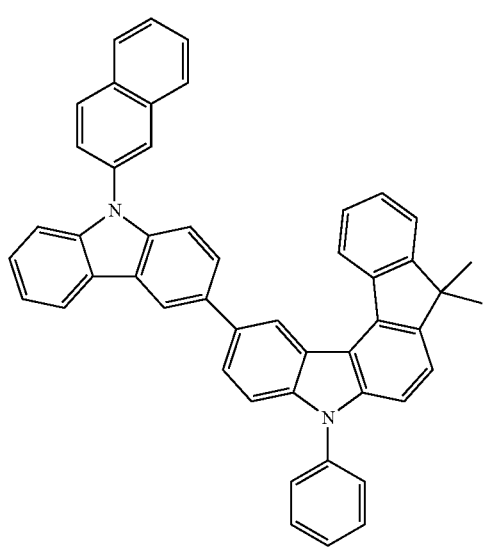
-continued
F-484
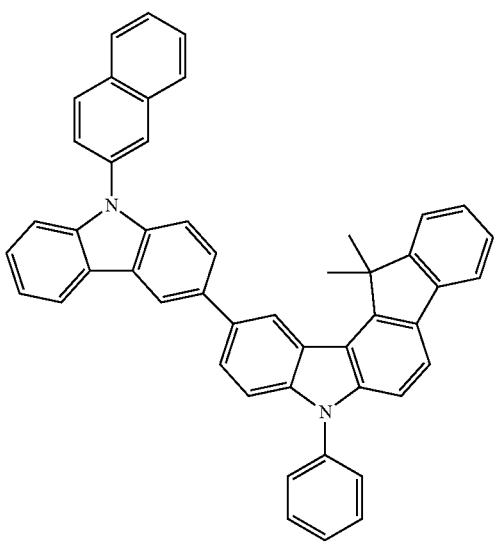
F-485
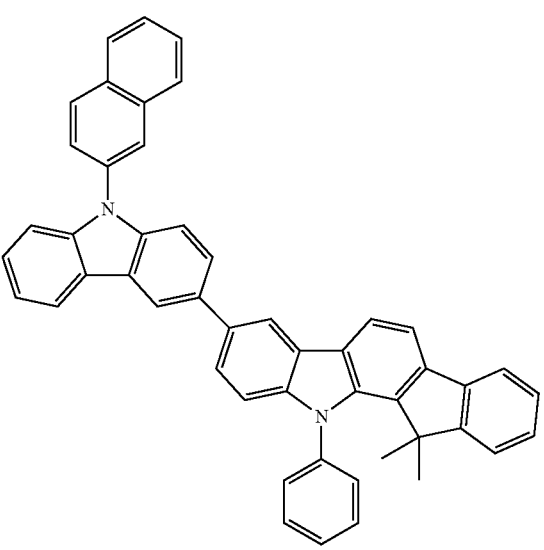

F-486
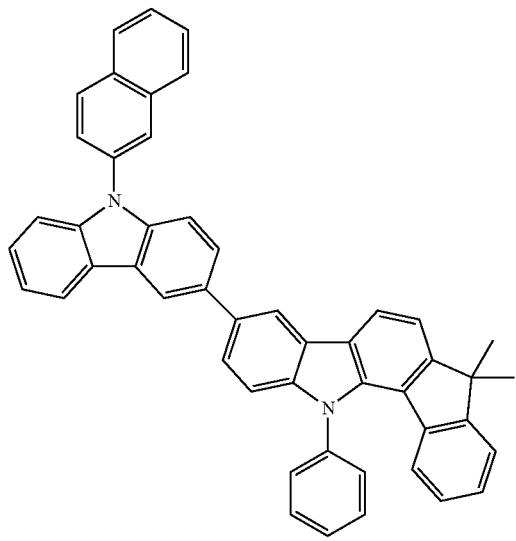
F-487
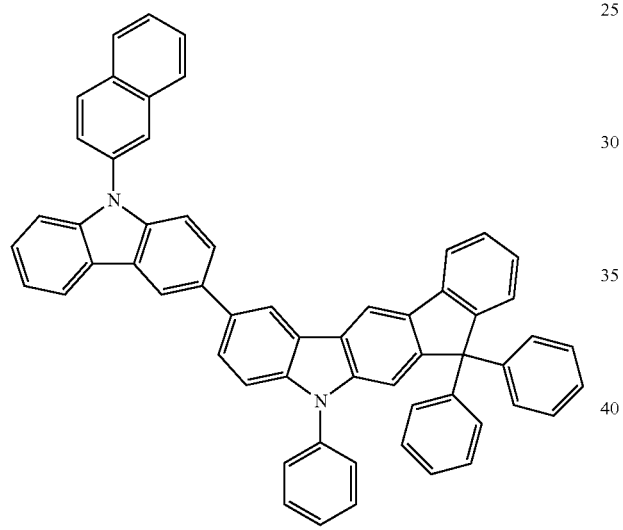
F-488
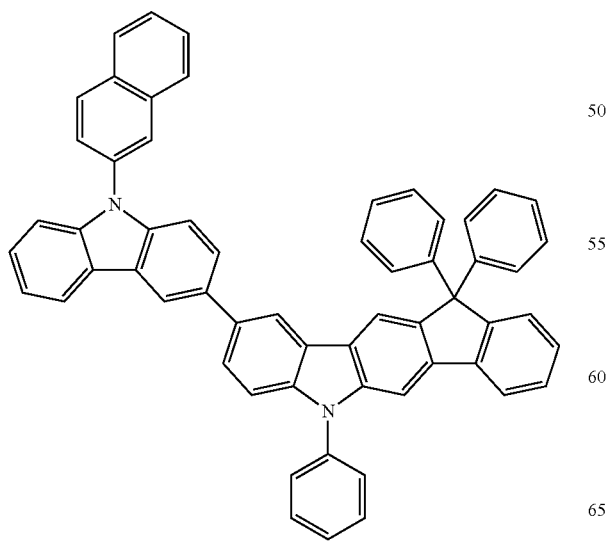
F-489
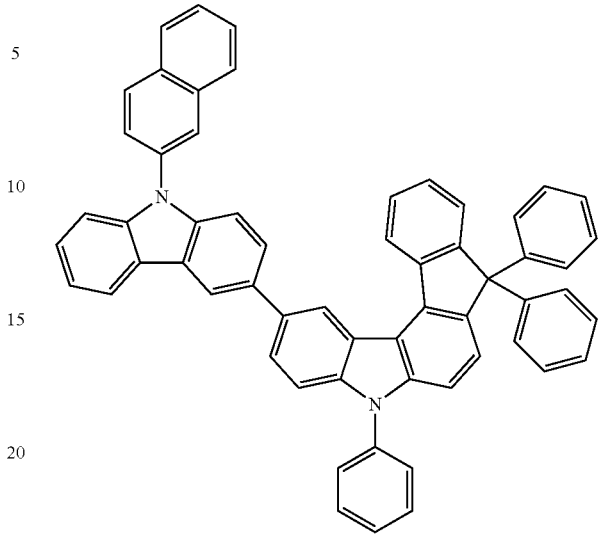
F-490
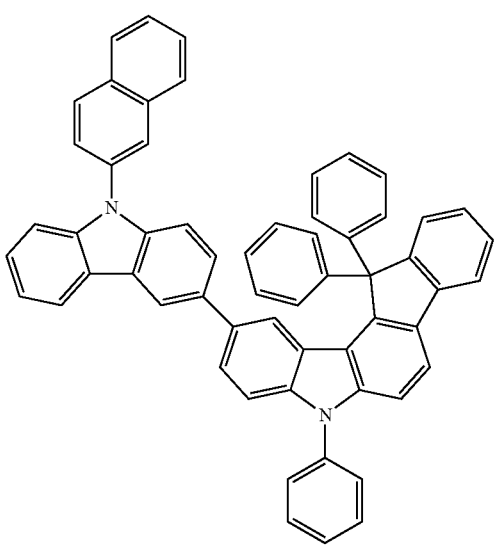

F-491
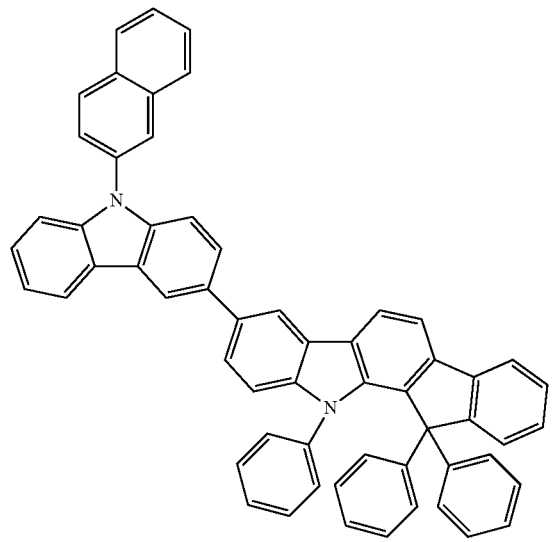
F-492
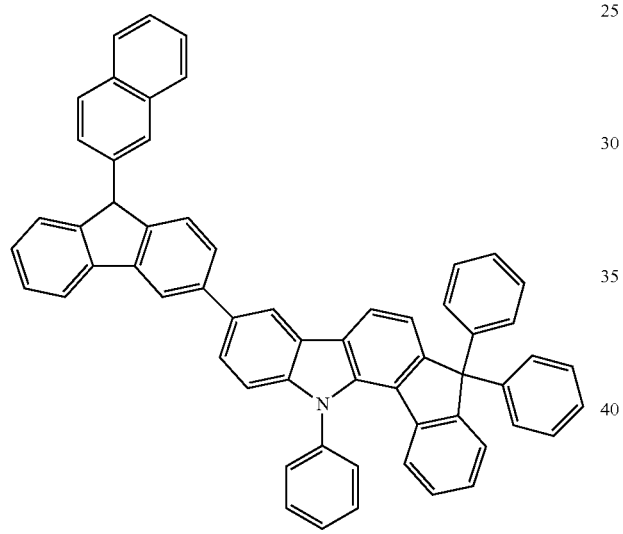
F-493
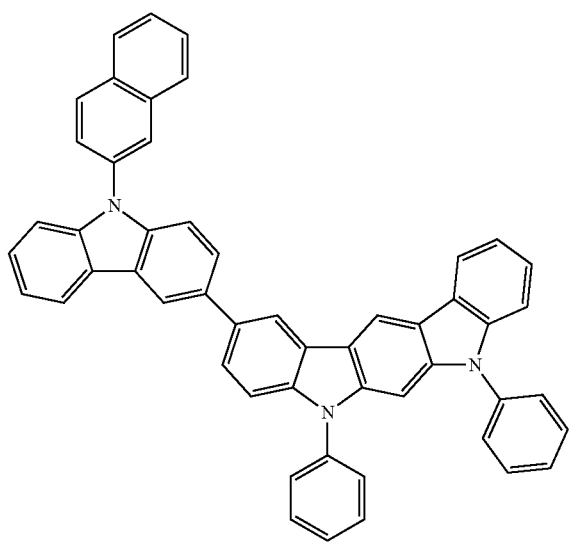
F-494
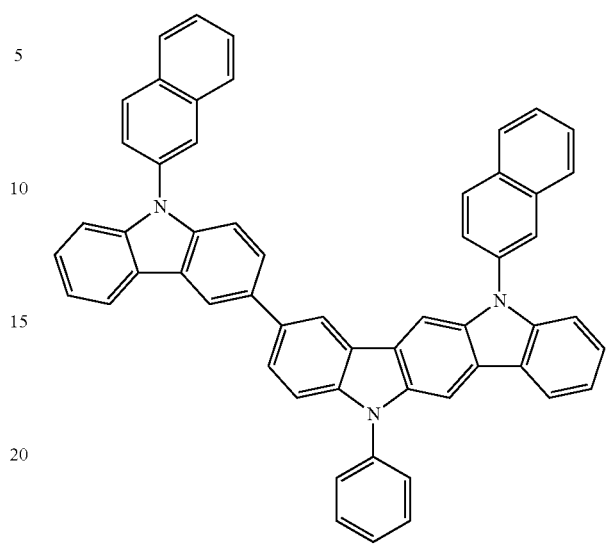
F-495
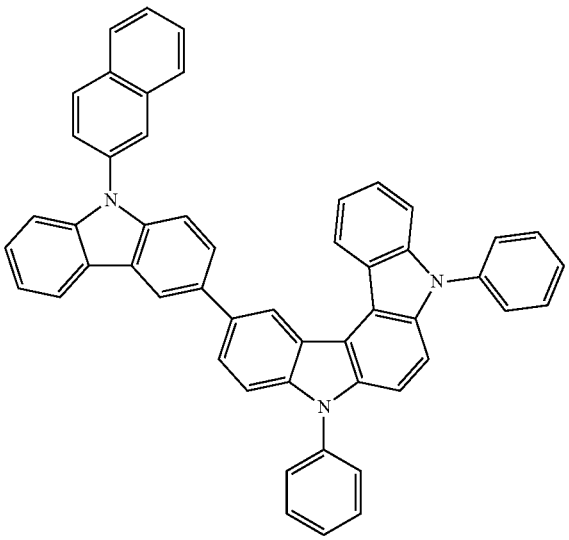

F-496
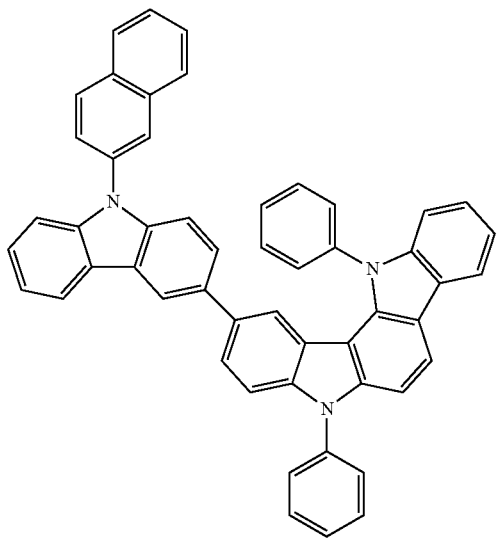
F-497
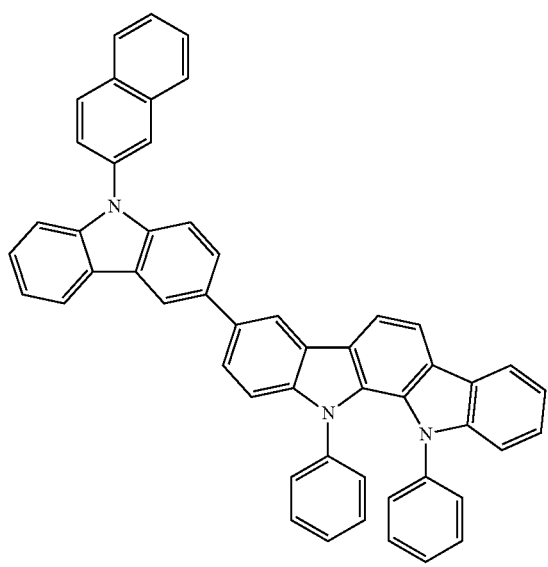
F-498
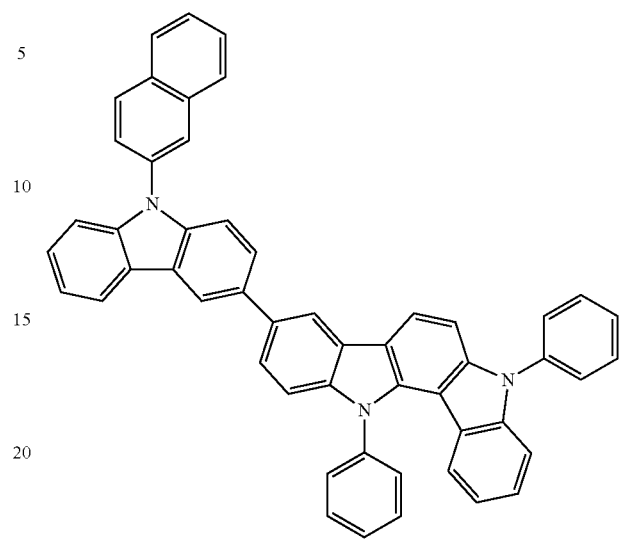
F-499
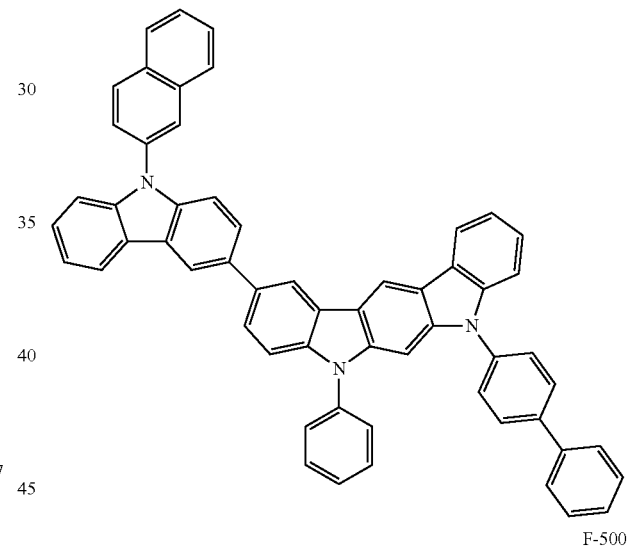
F-500
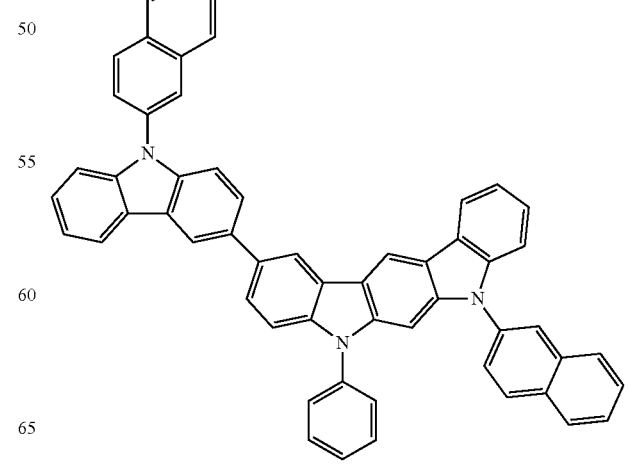

-continued
F-501
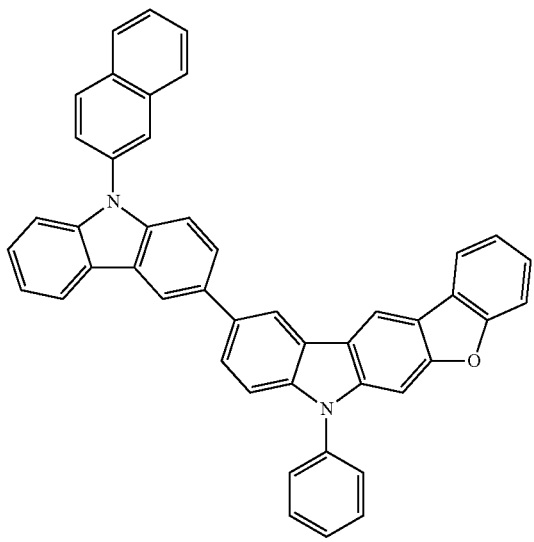
F-502
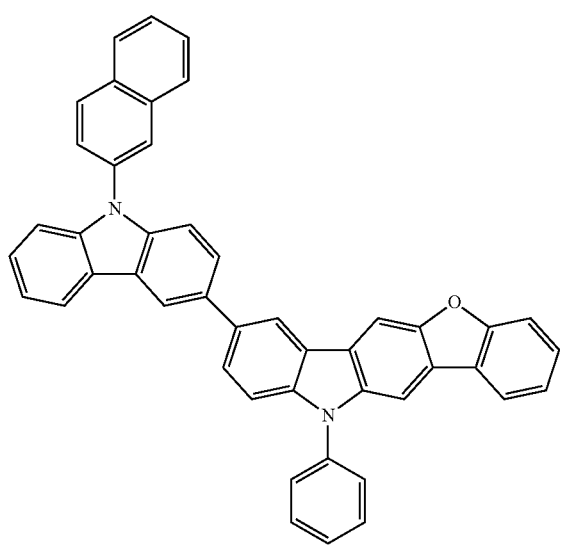
F-503
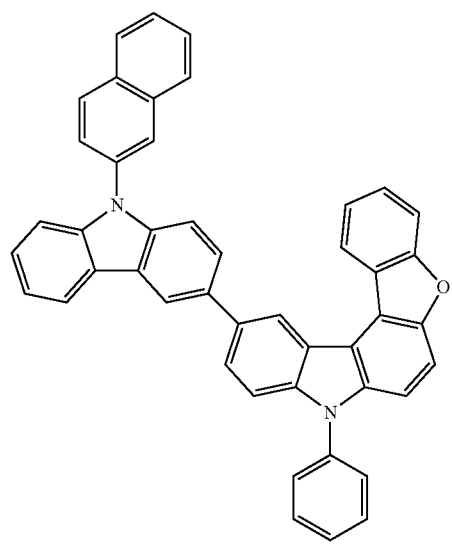
-continued
F-504
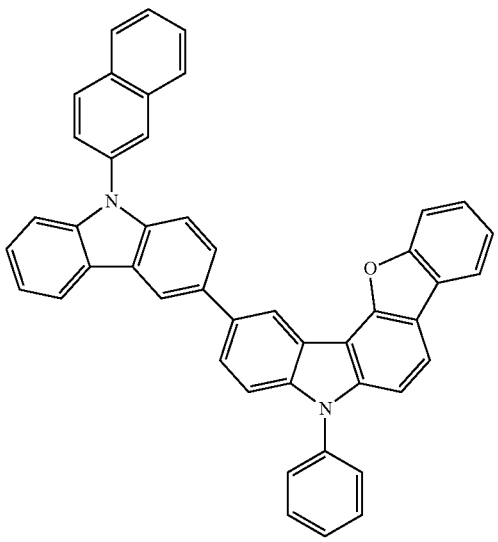
F-505
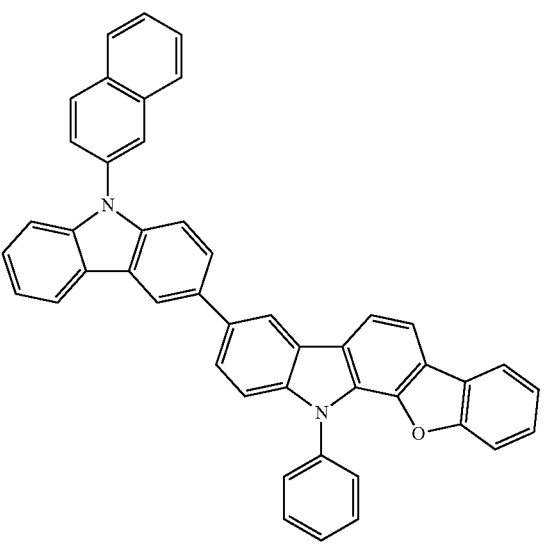

-continued
F-506
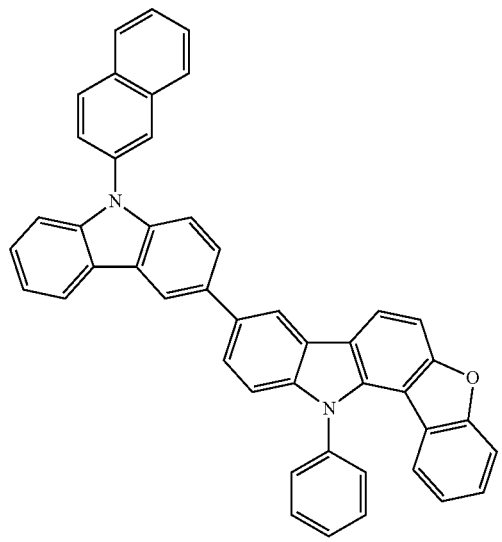
F-507
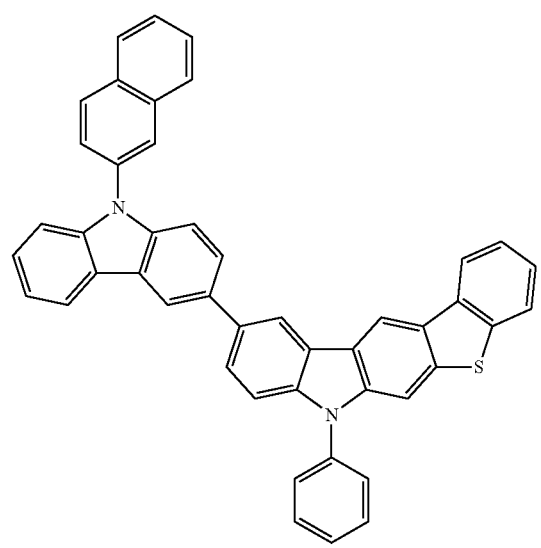
-continued
F-508
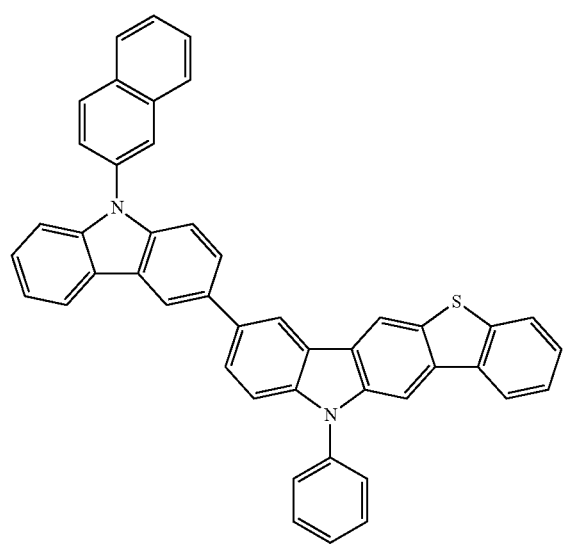
F-509
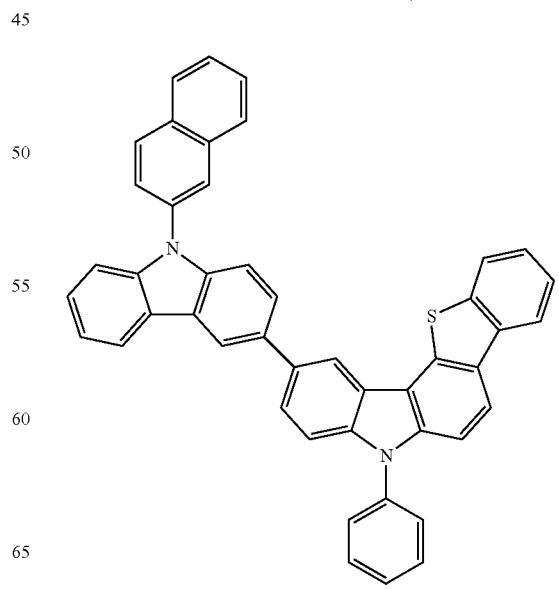
F-510

F-511
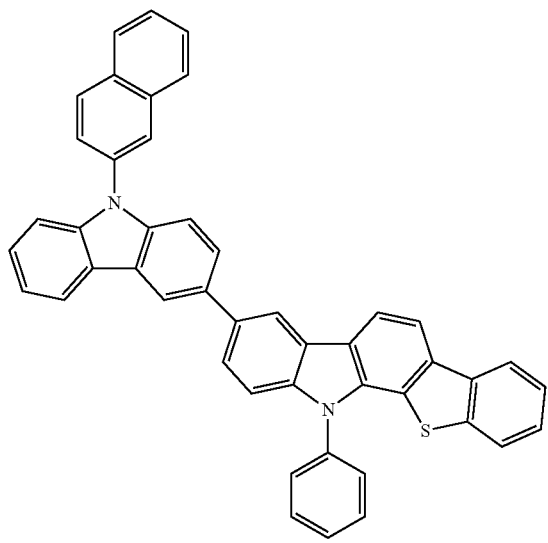
F-513
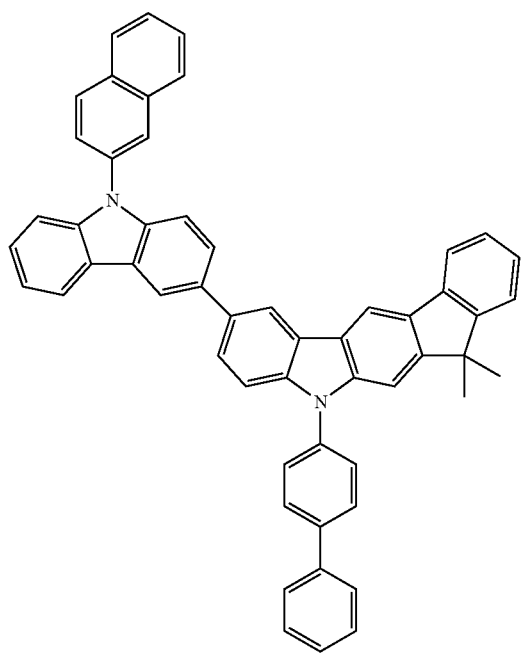
F-512
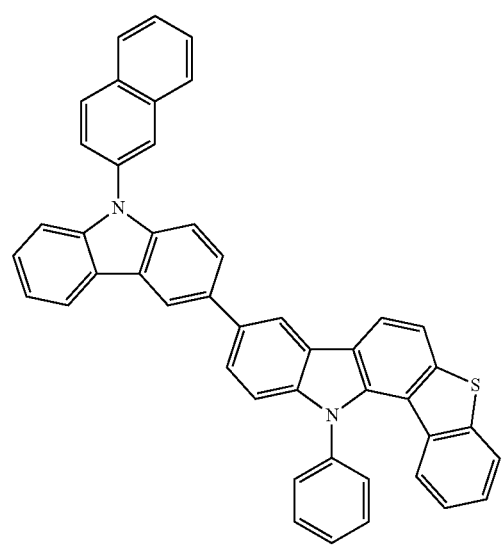
F-514
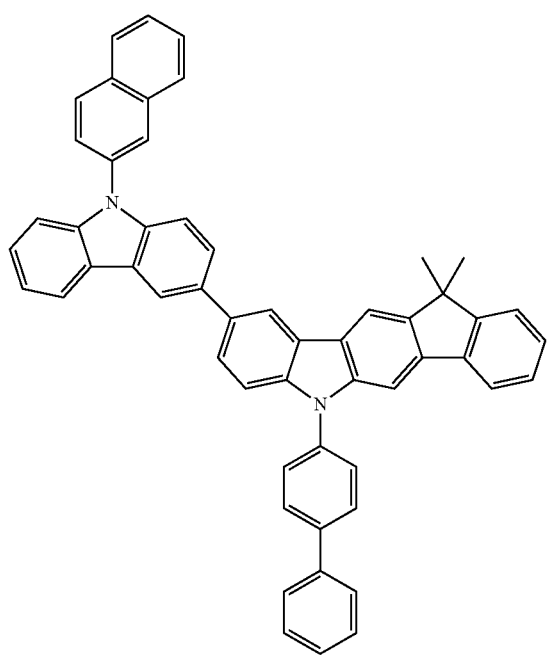

F-515
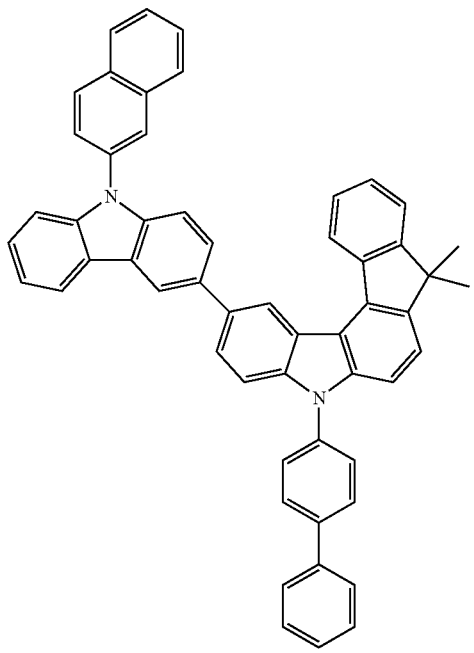
F-517
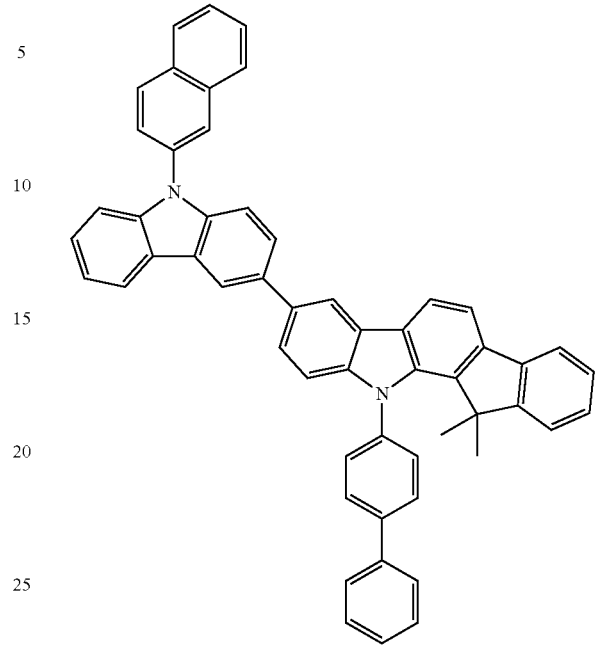
F-516
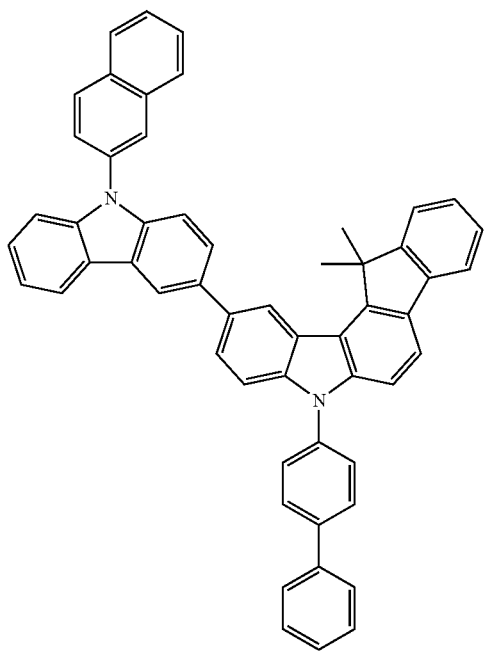
F-518
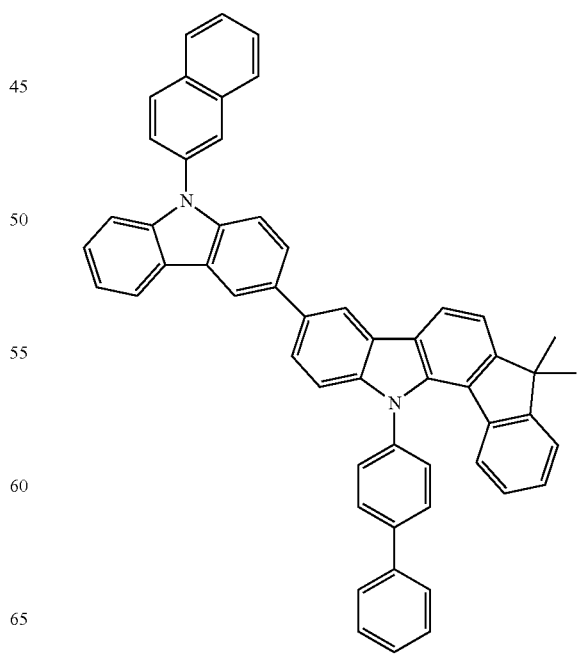

-continued
F-519
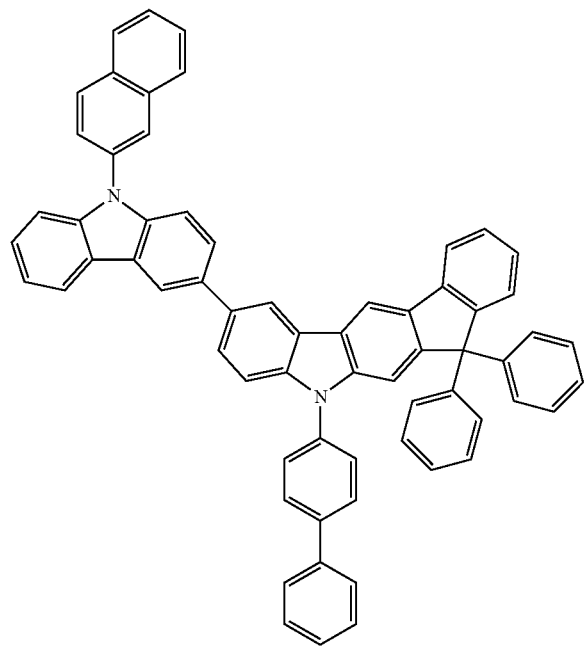
F-521
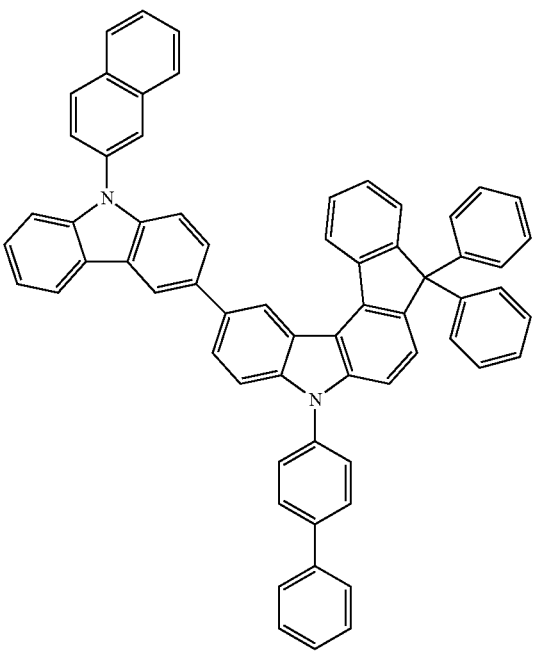
F-520
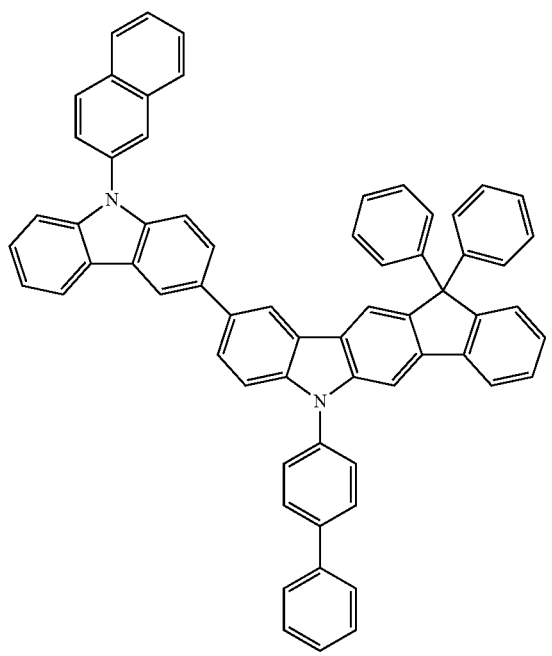
F-522
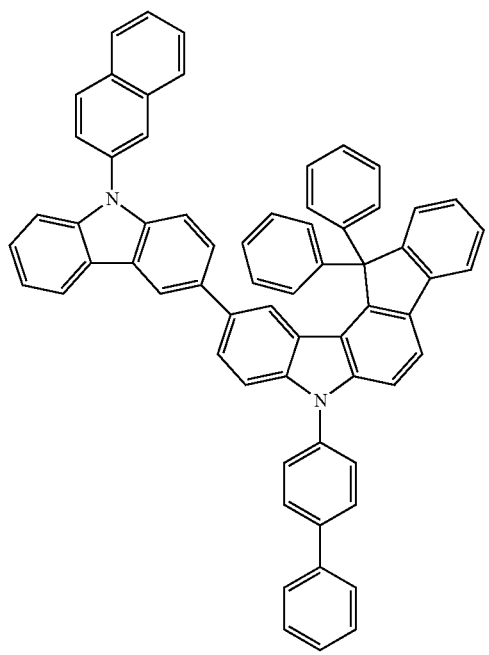

F-523
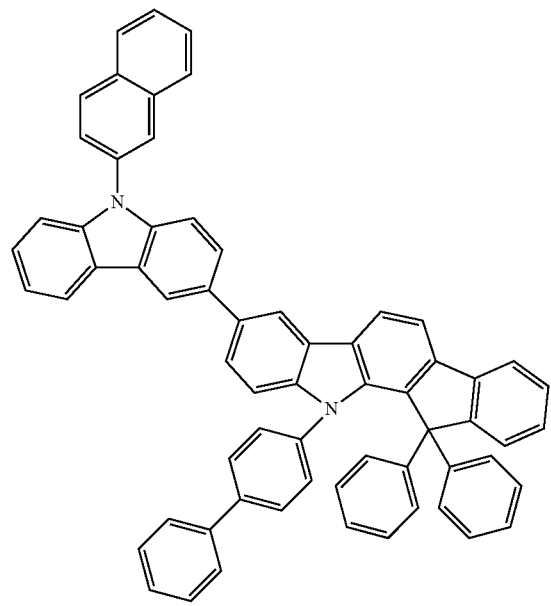
F-525
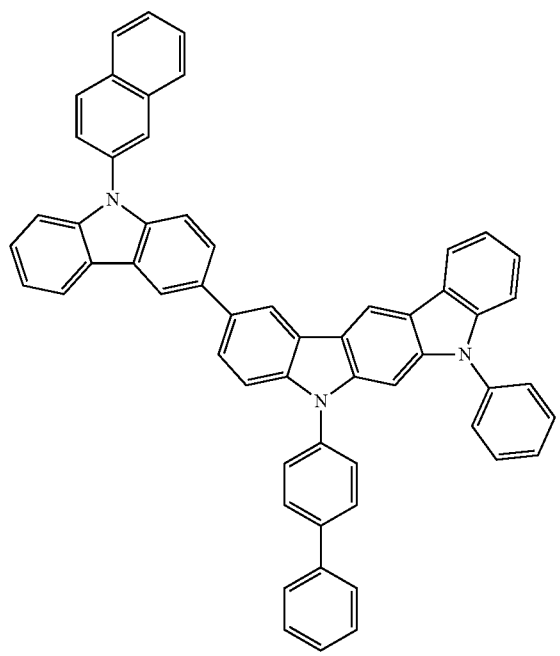
F-524
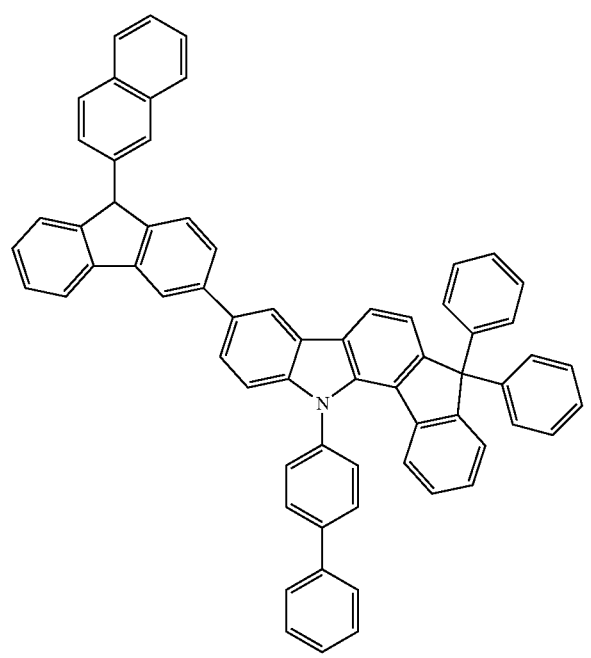
F-526
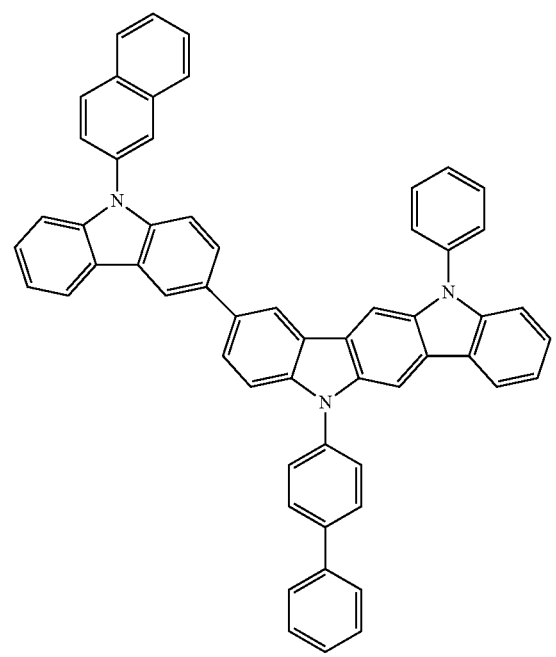

F-527
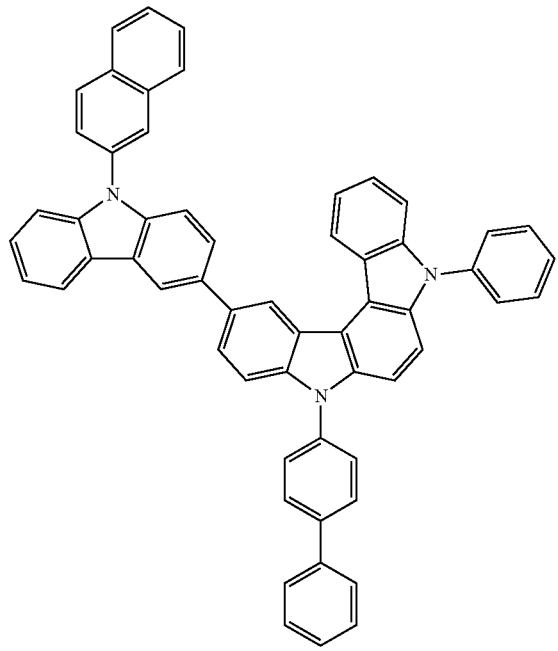
F-528
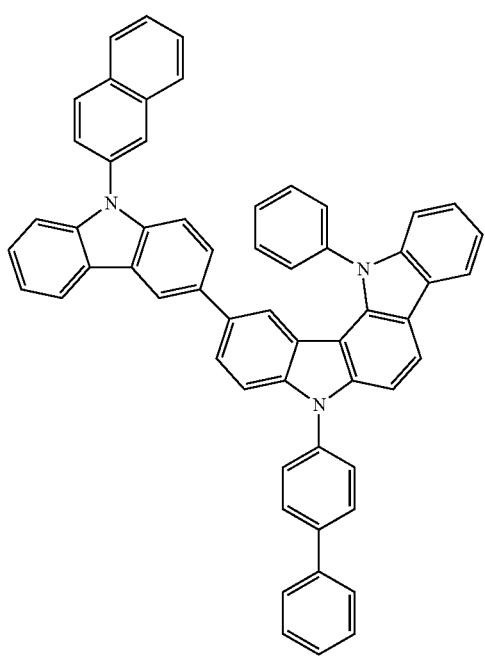
F-529
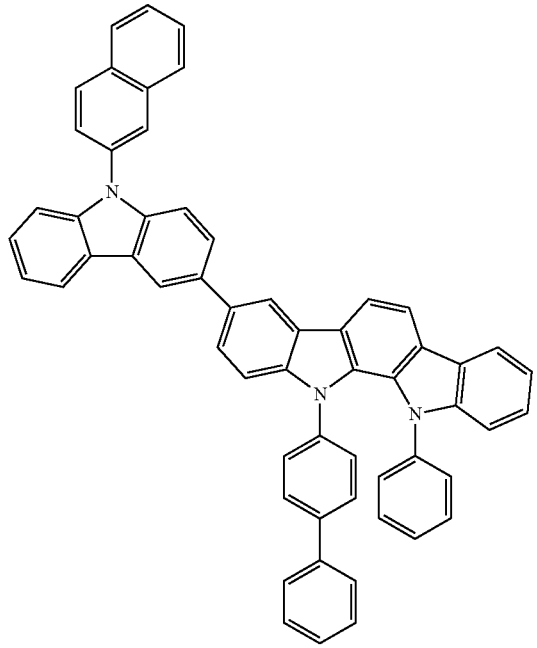
F-530
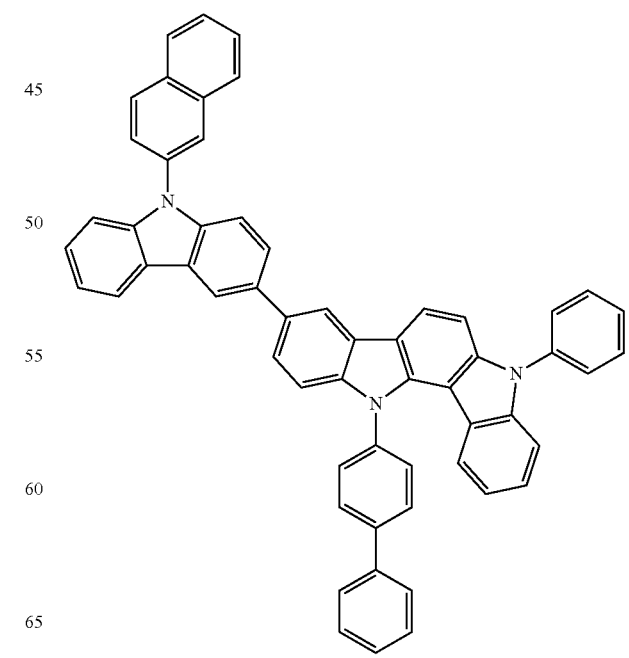

F-531
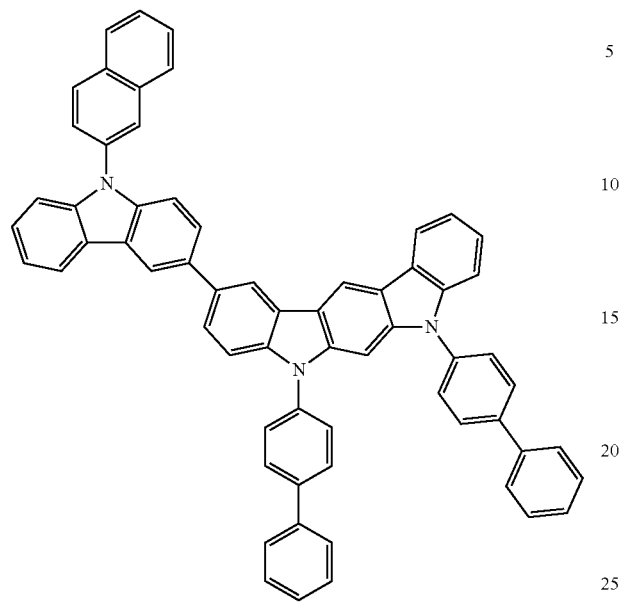
F-533
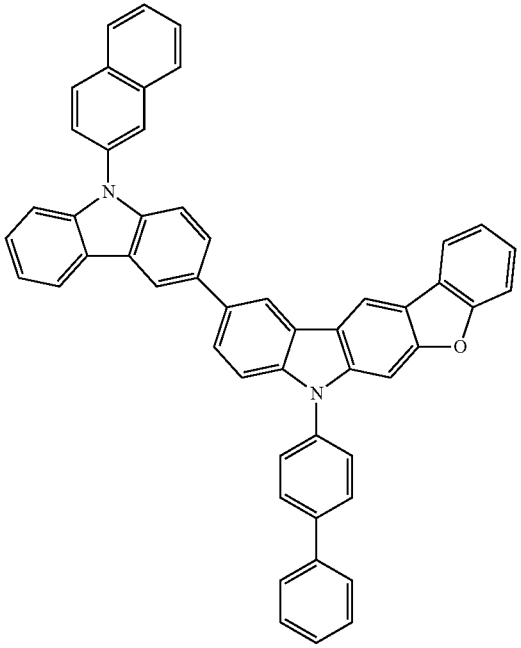
F-532
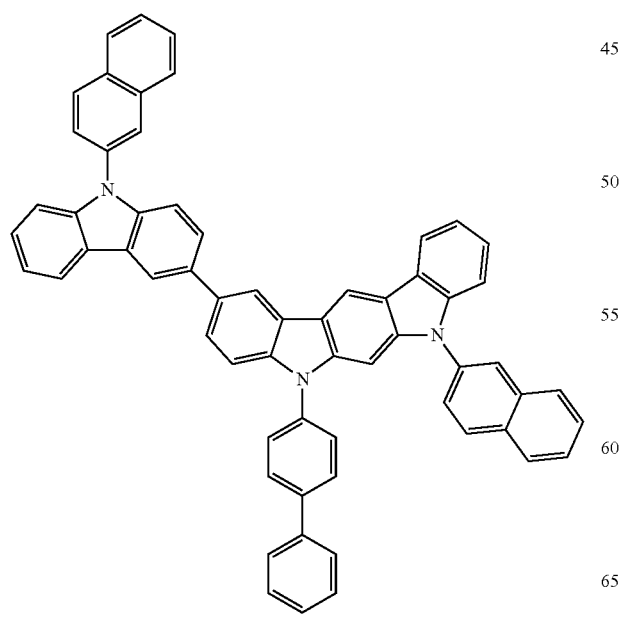
F-534
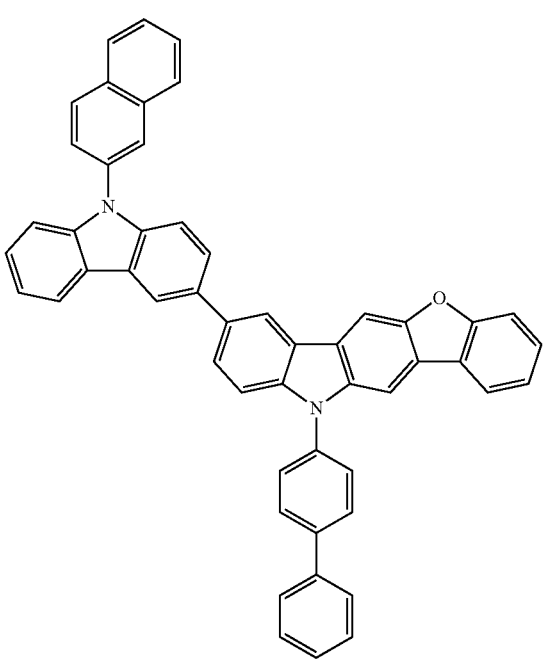

F-535
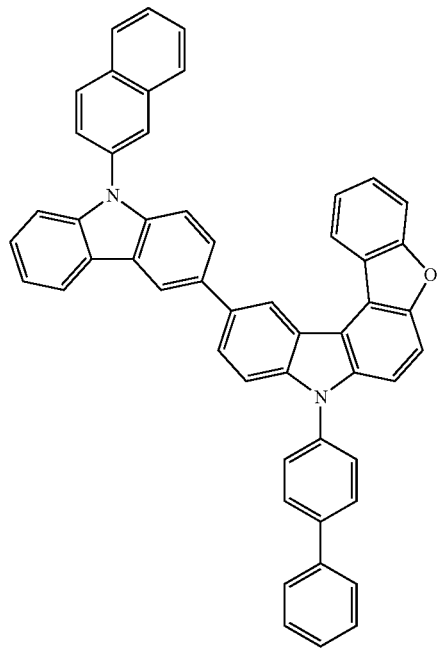
F-537
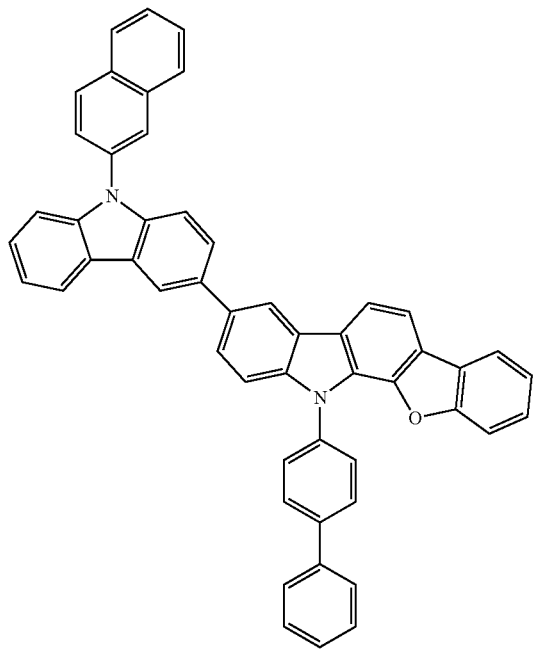
F-536
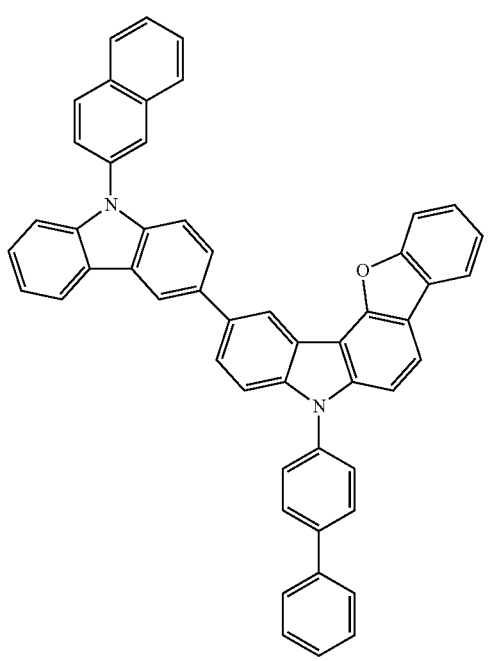
F-538
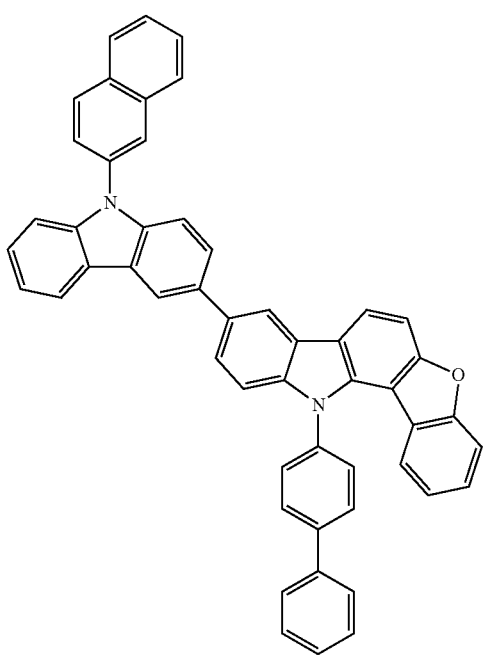

F-539
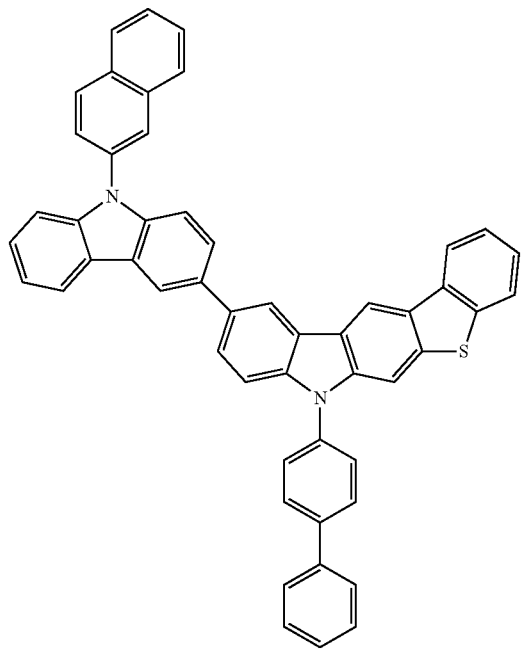
F-541
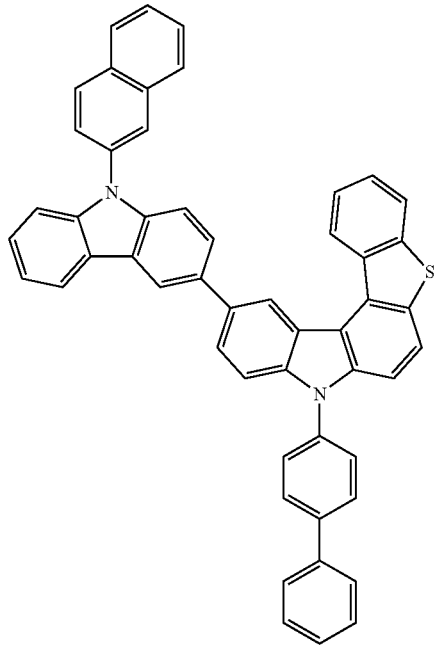
F-540
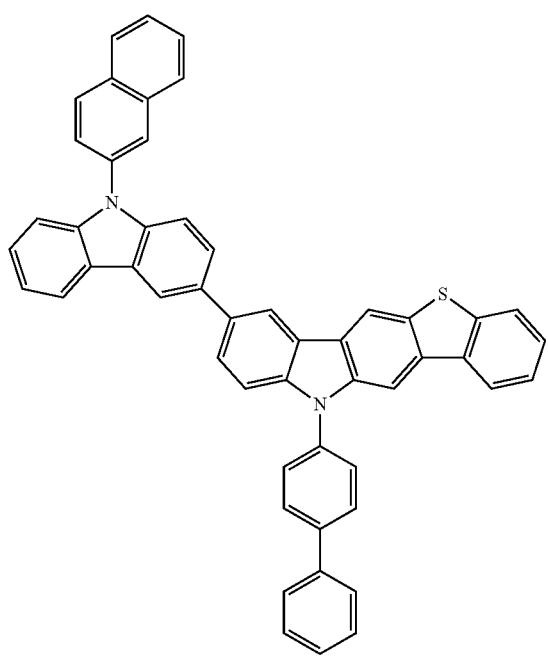
F-542
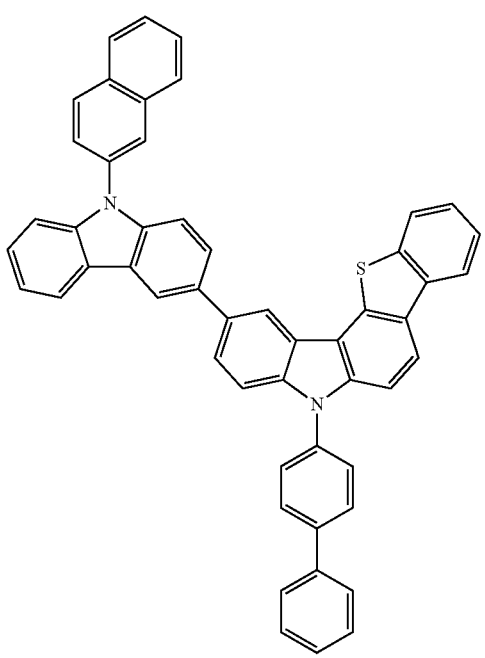

F-543
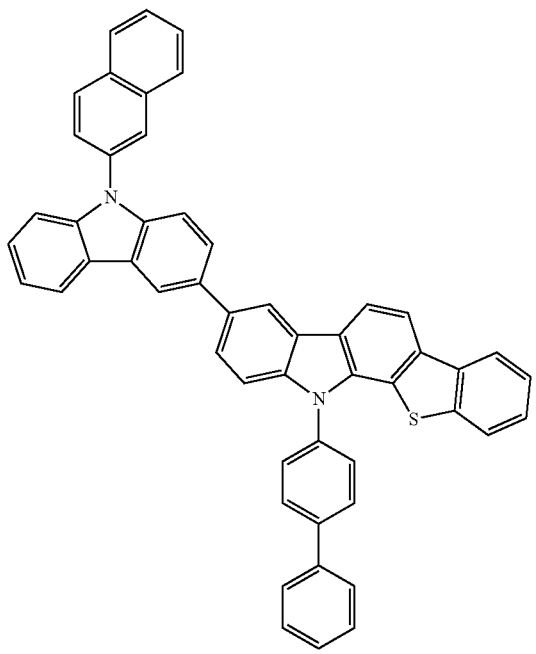
F-545
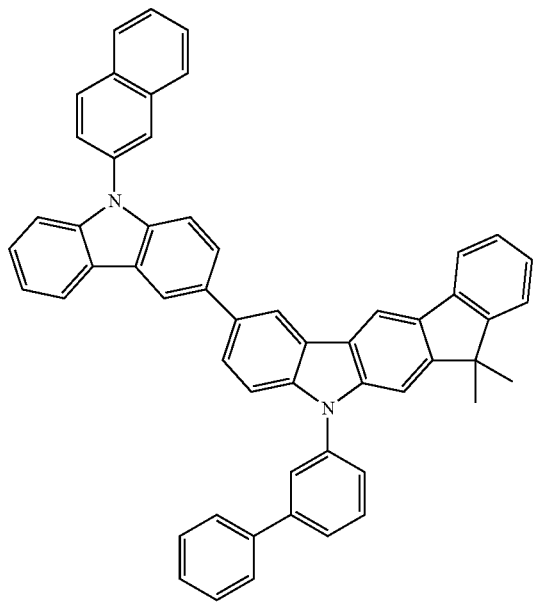
F-544
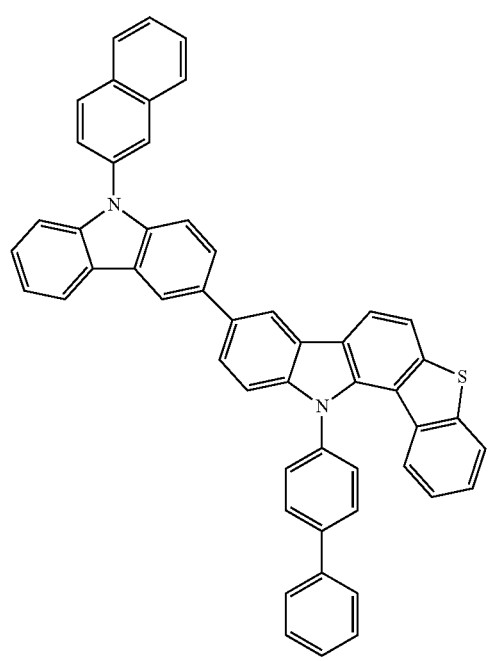
F-546
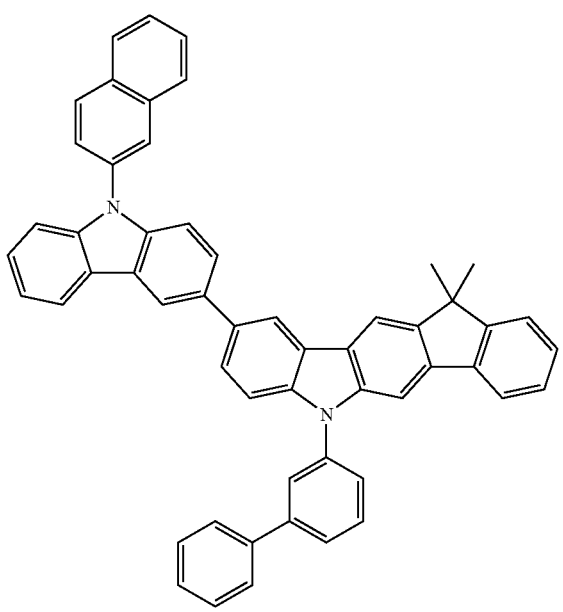

F-547
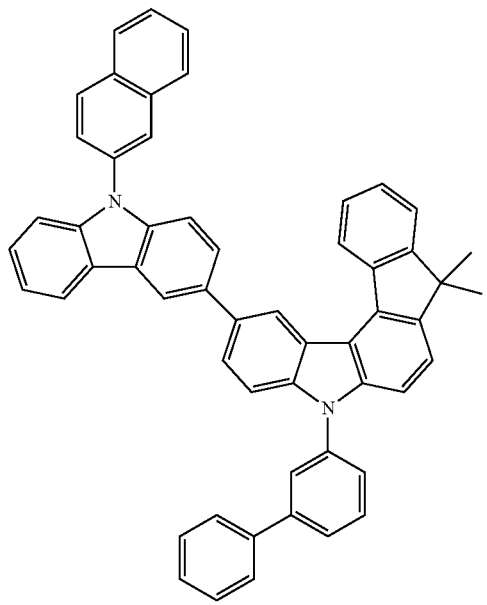
F-548
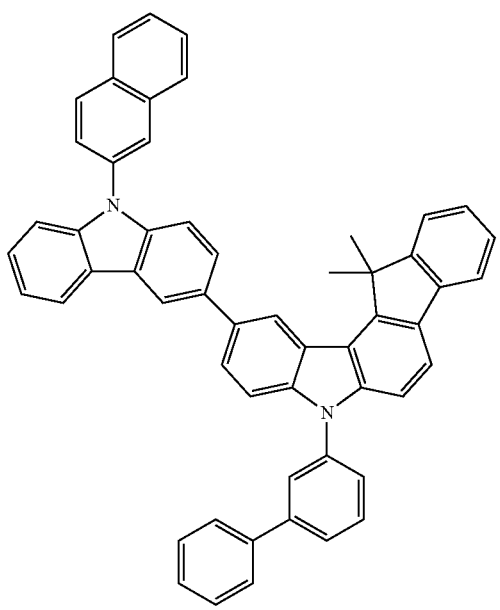
F-549
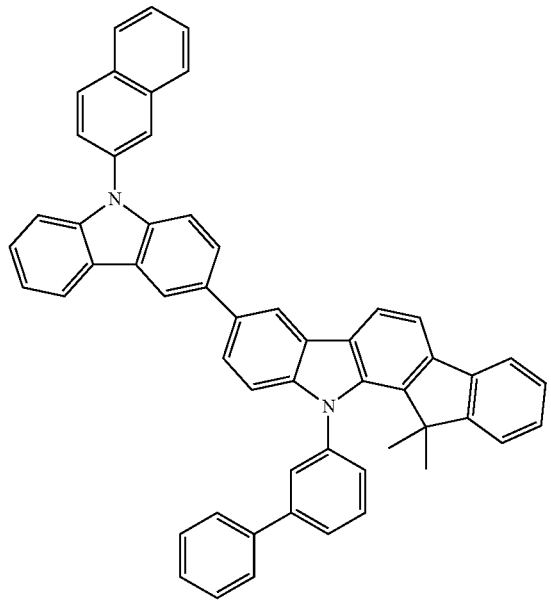
F-550
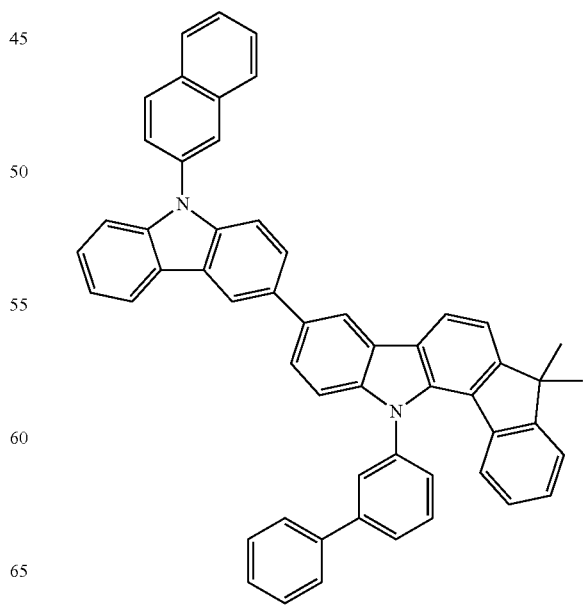

F-551
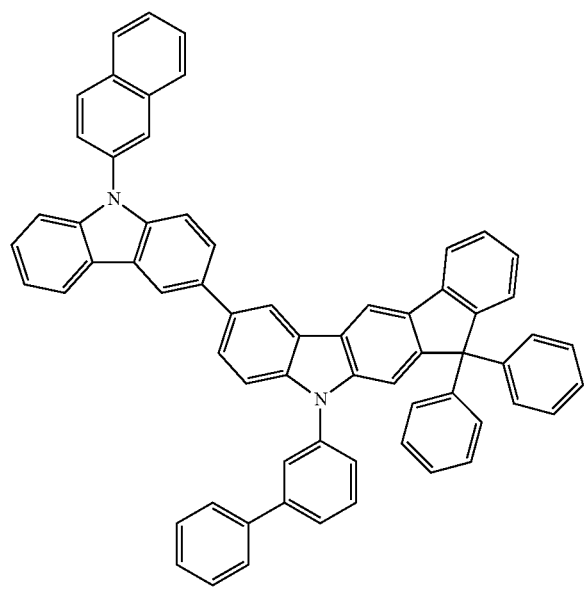
F-553
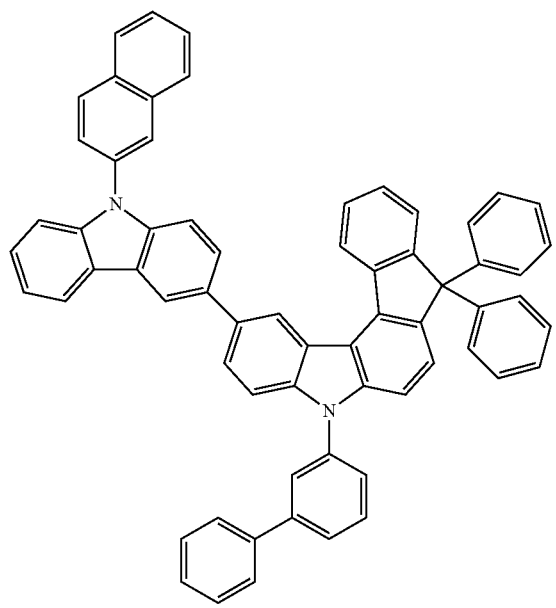
F-552
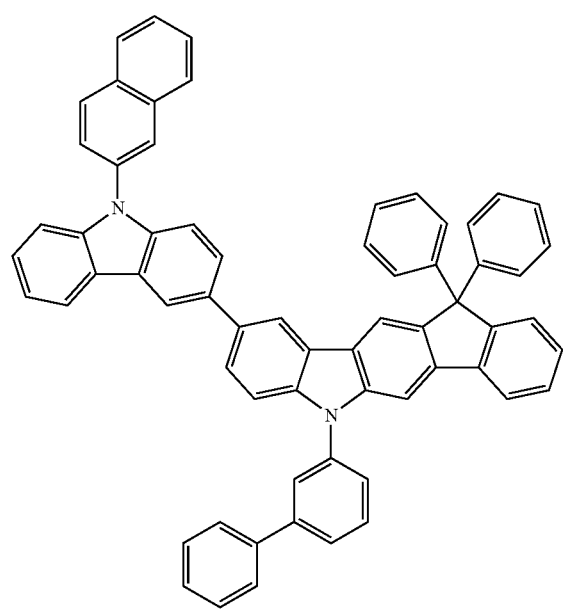
F-554
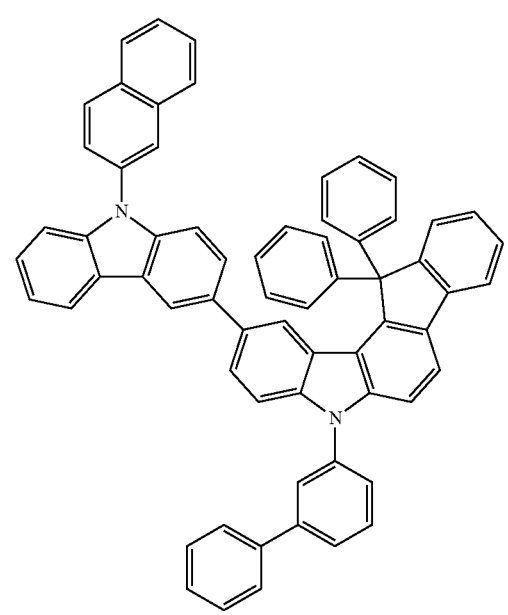

-continued
F-555
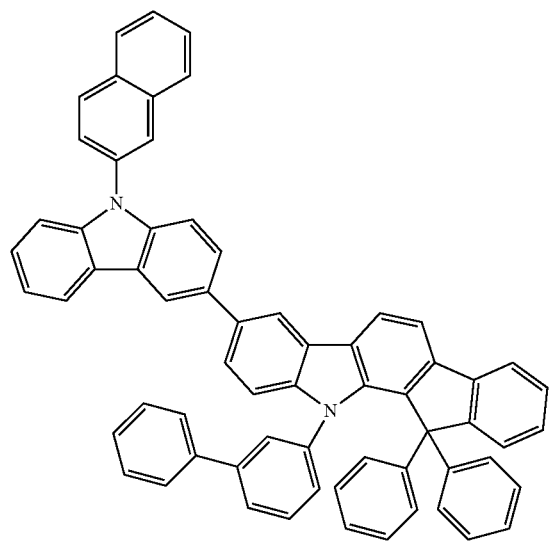
F-557
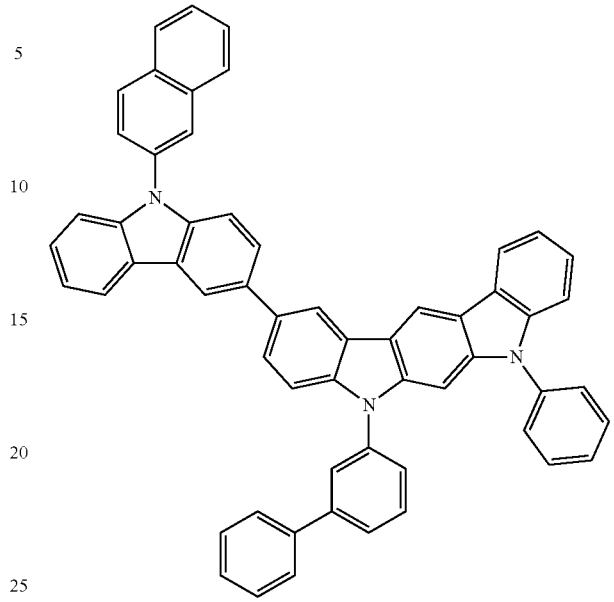
F-556
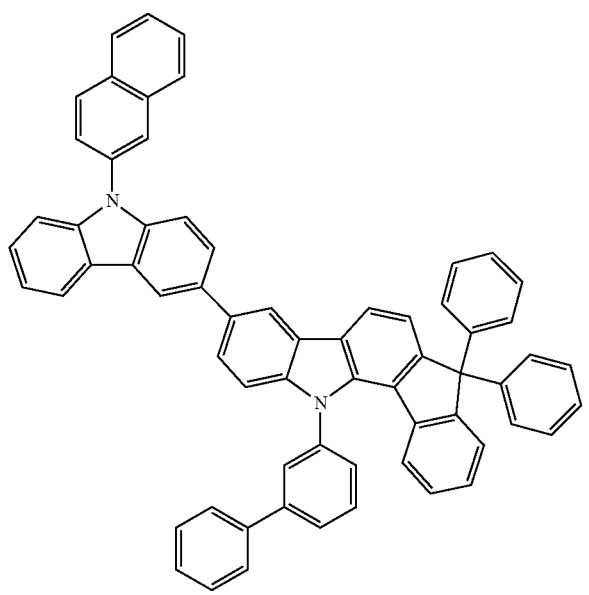
F-558
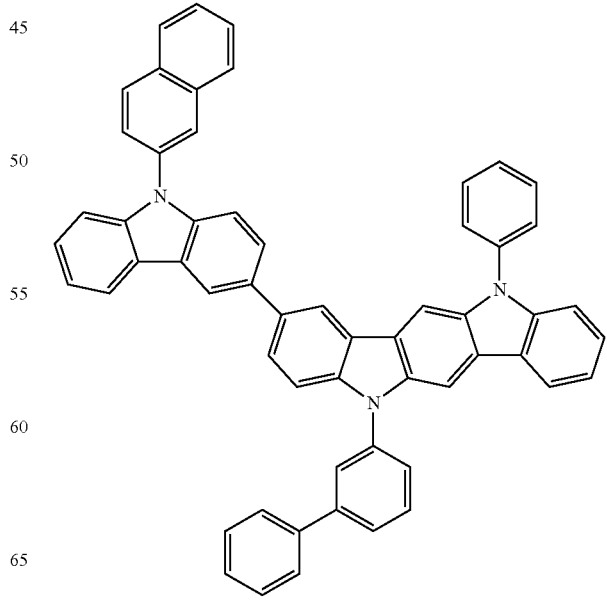

F-559
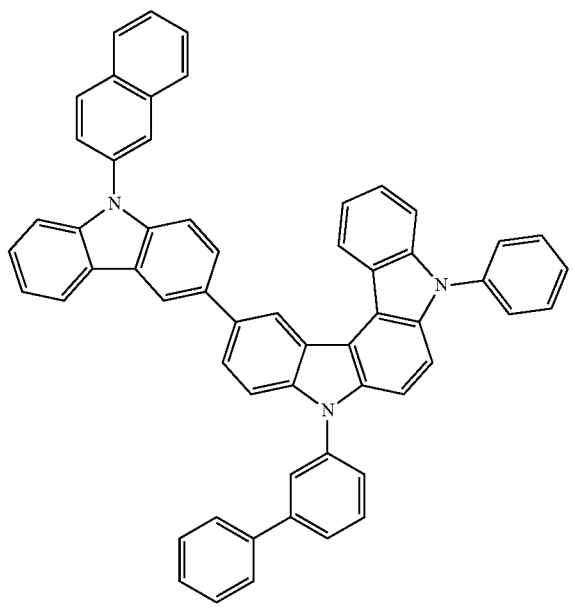
F-561
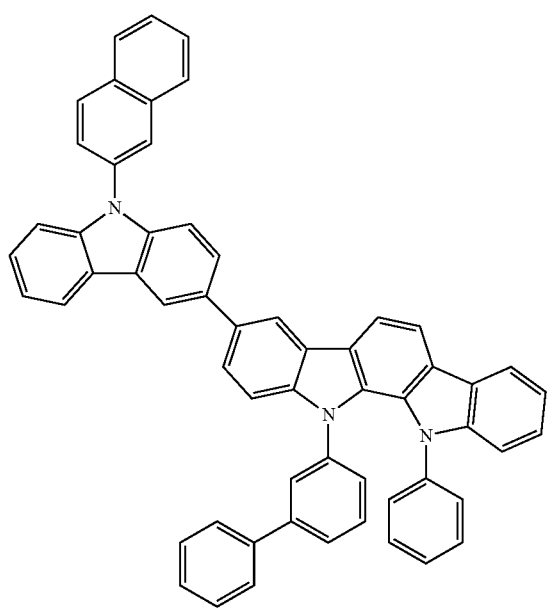
F-560
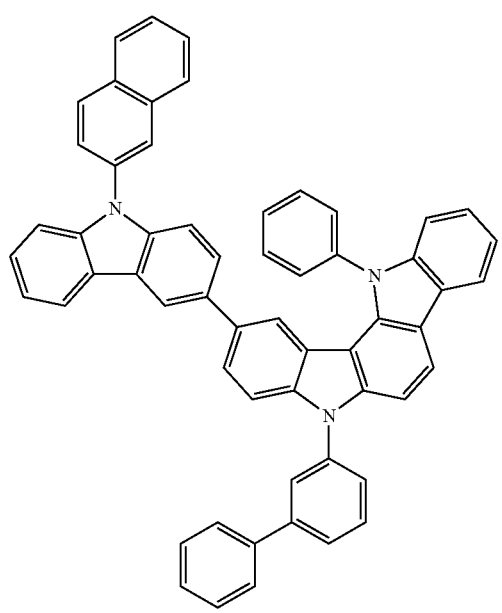
F-562
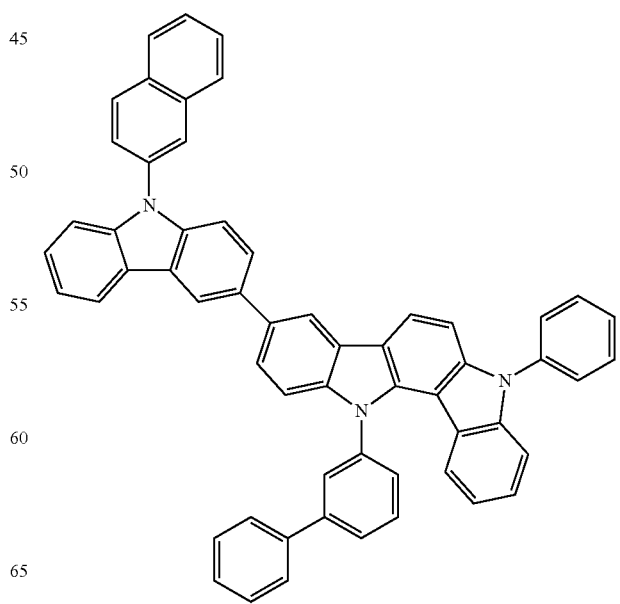

F-563
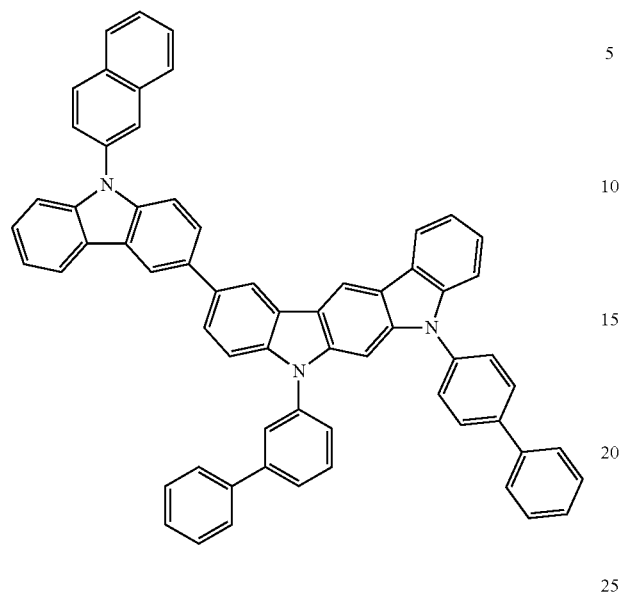
F-564
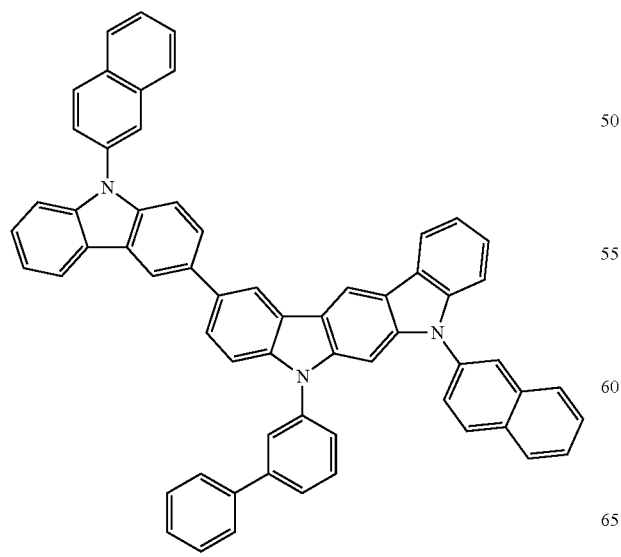
F-565
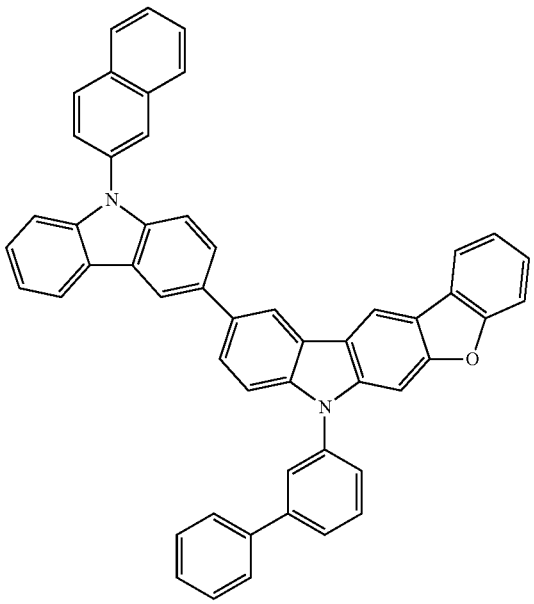
F-566
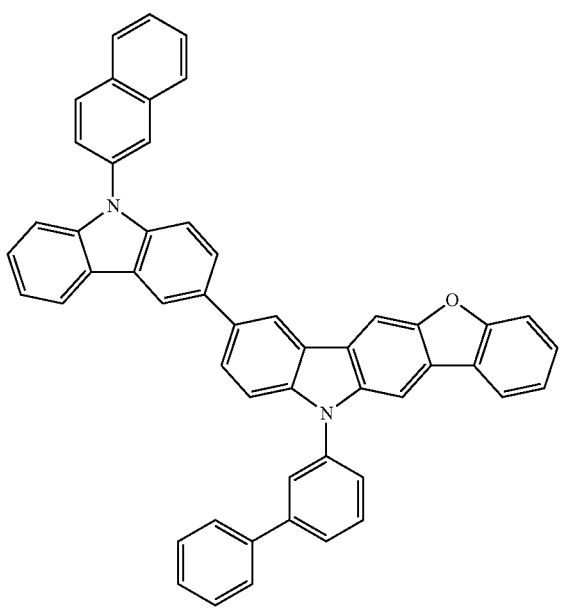

F-567
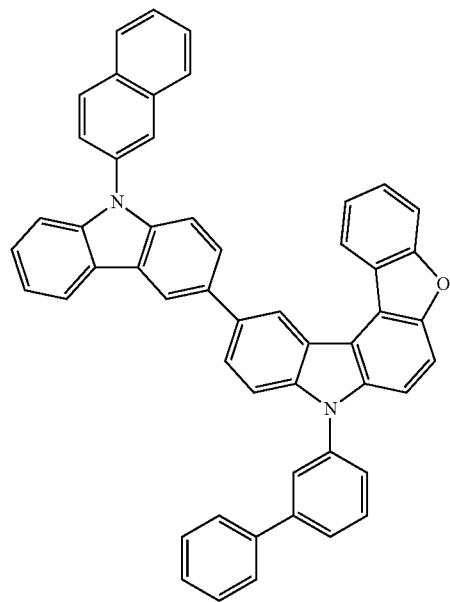
F-569
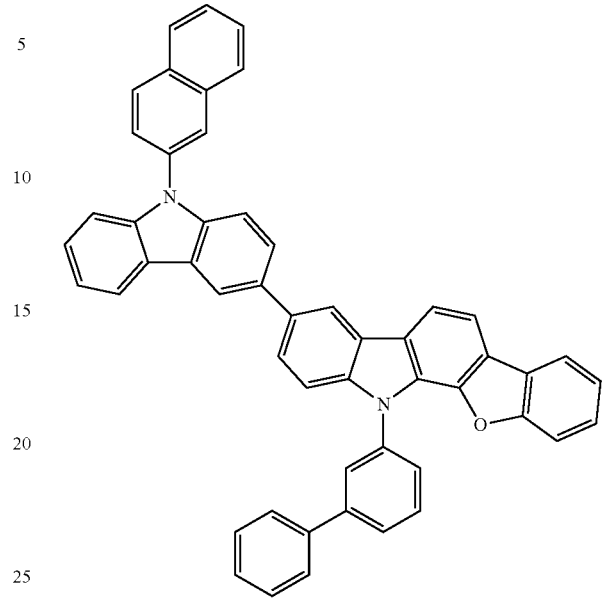
F-568
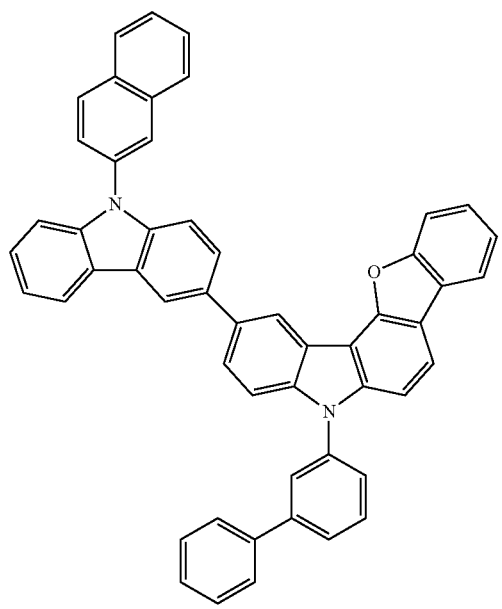
F-570
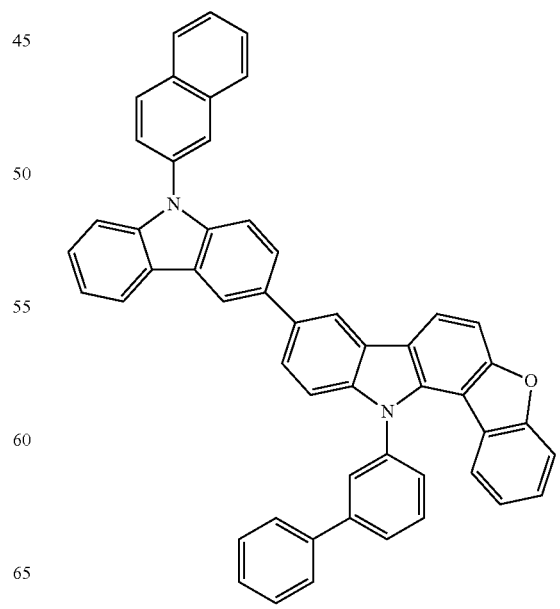

F-571
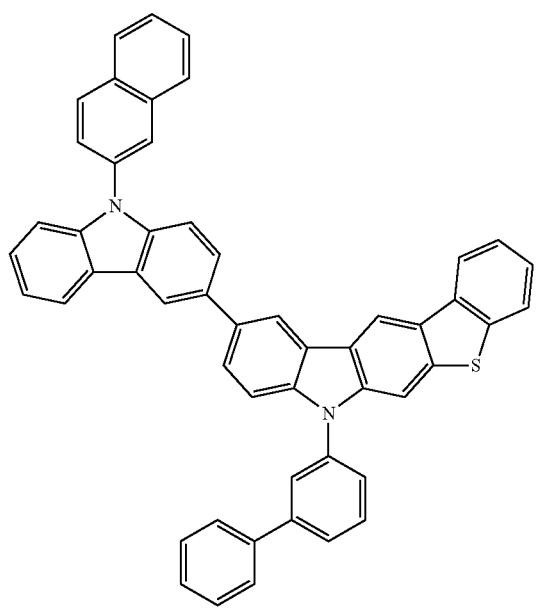
F-573
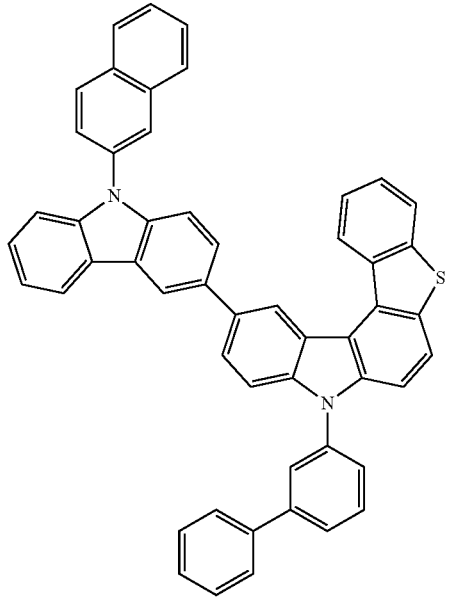
F-572
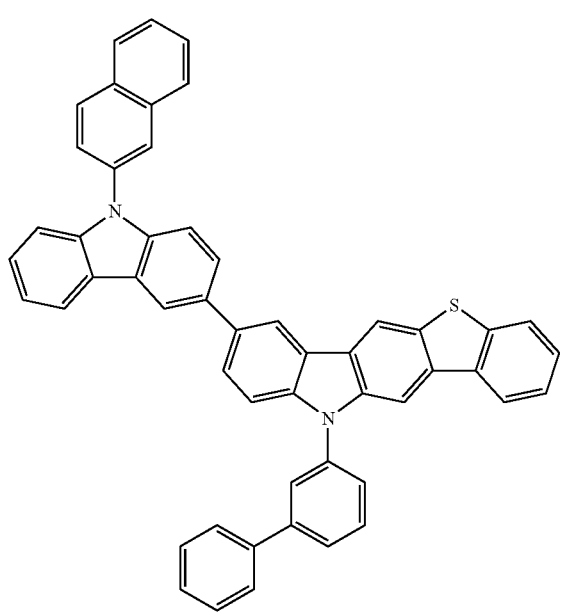
F-574

F-575
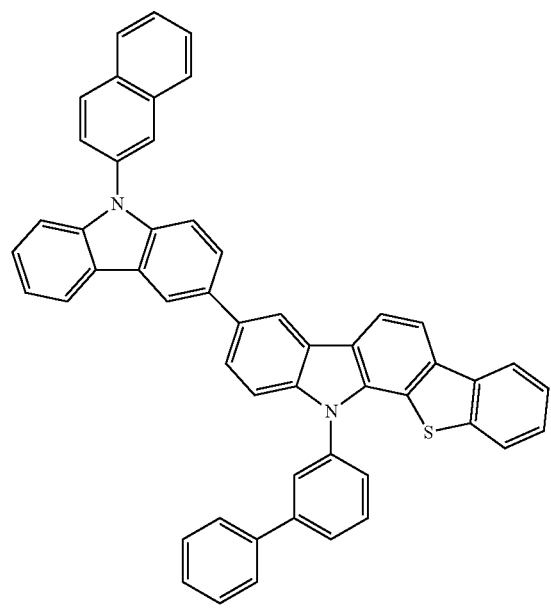
F-577
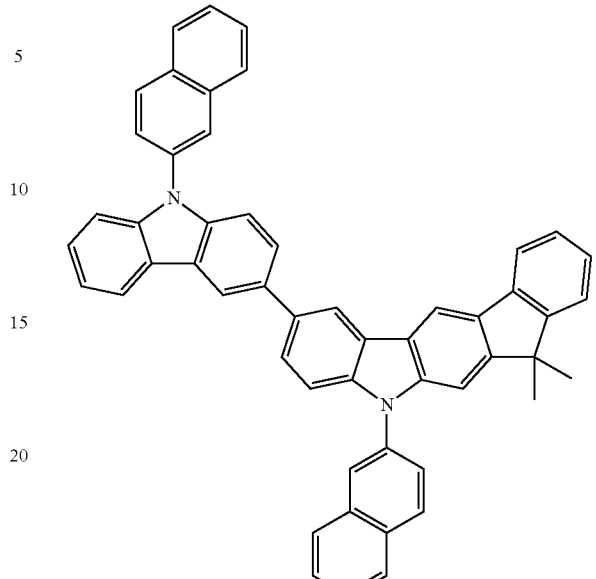
F-576
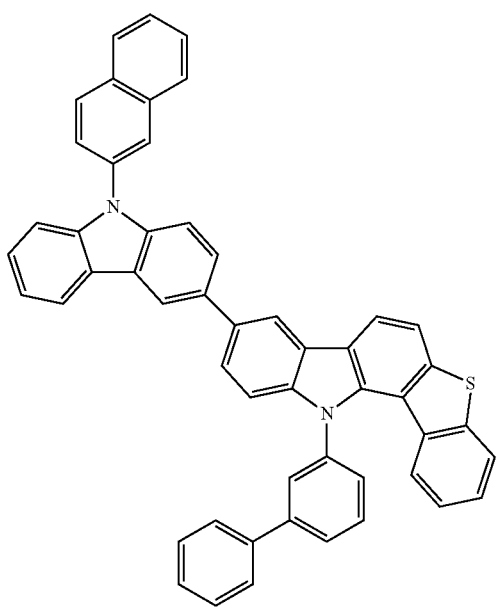
F-578
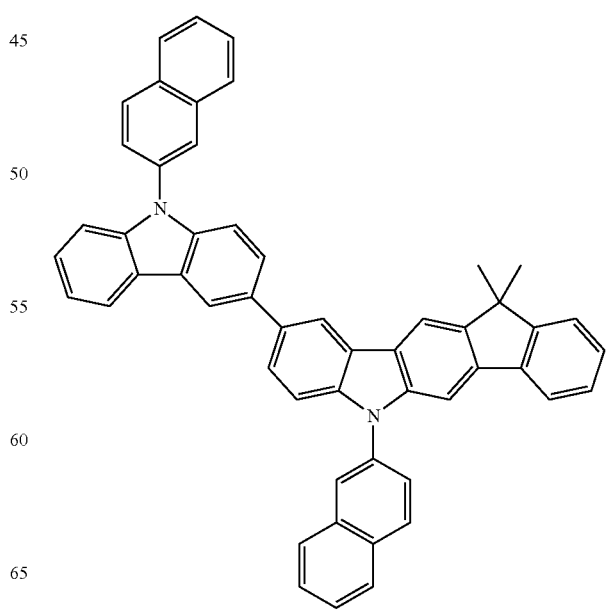

F-579
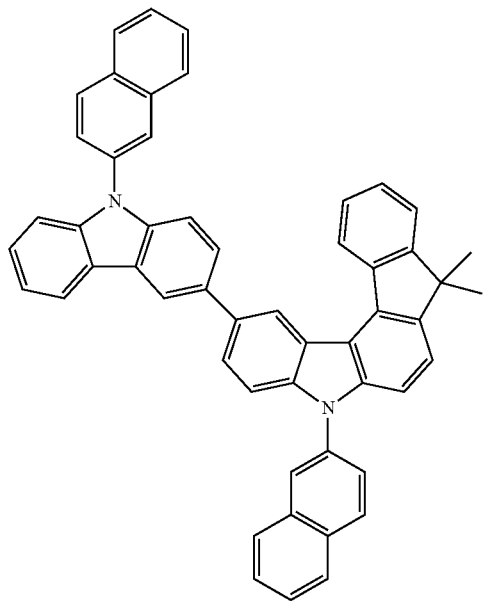
F-581
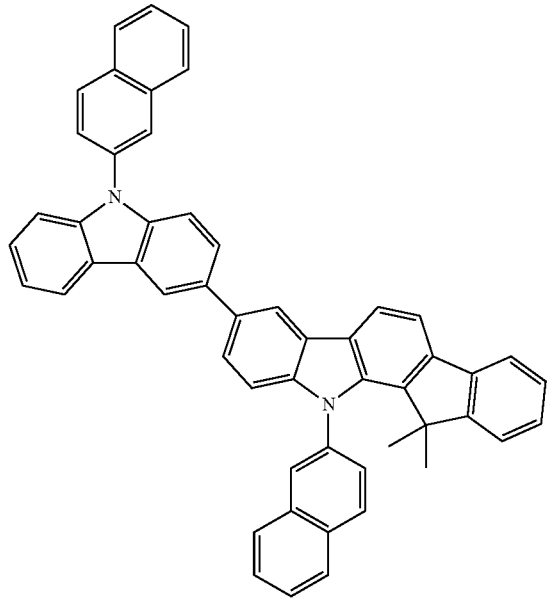
F-580
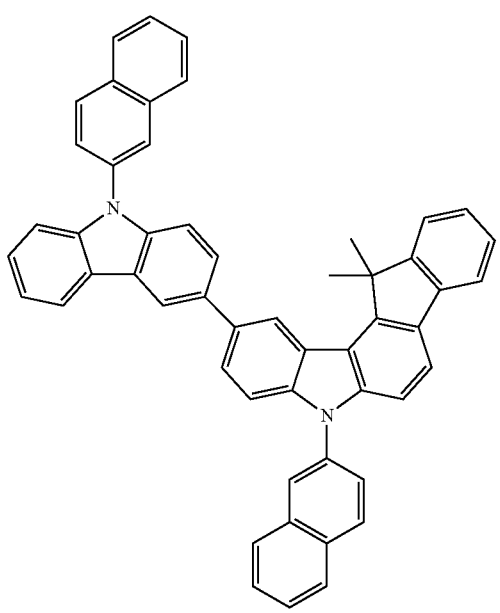
F-582
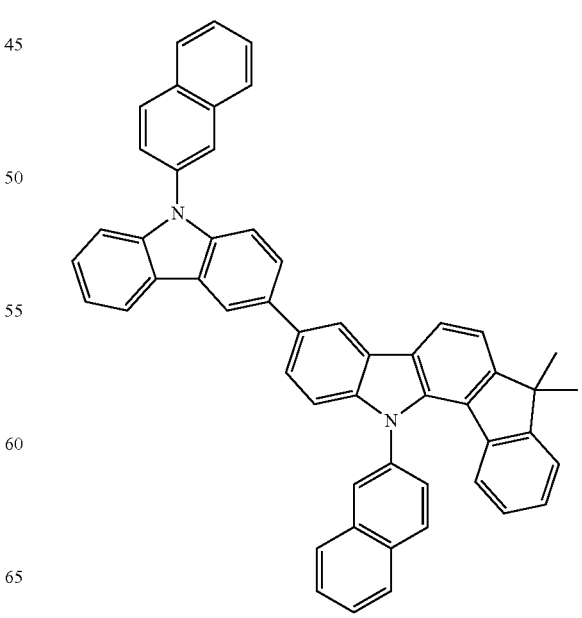

F-583
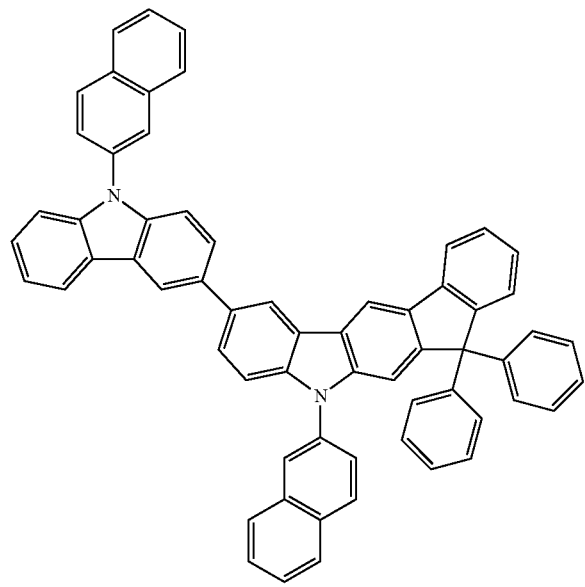
F-584
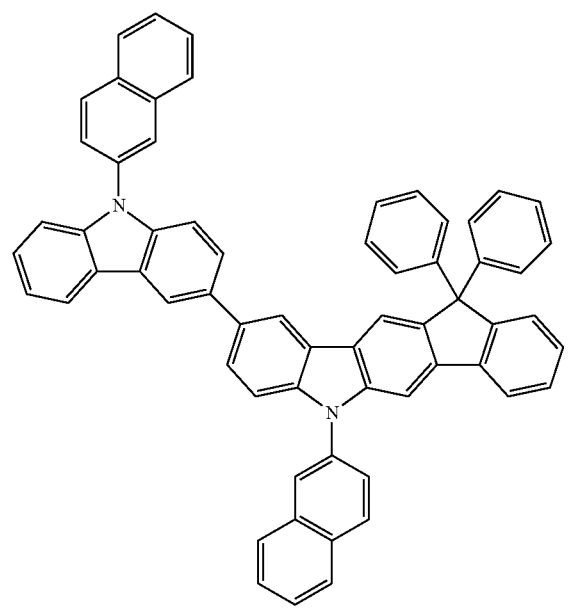
F-585
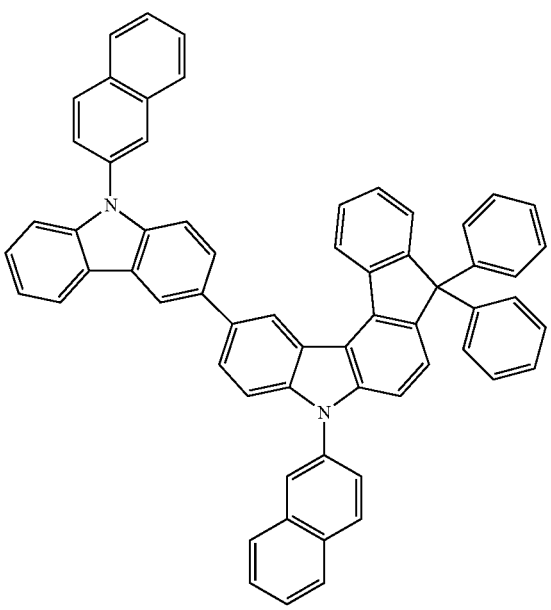
F-586

F-587
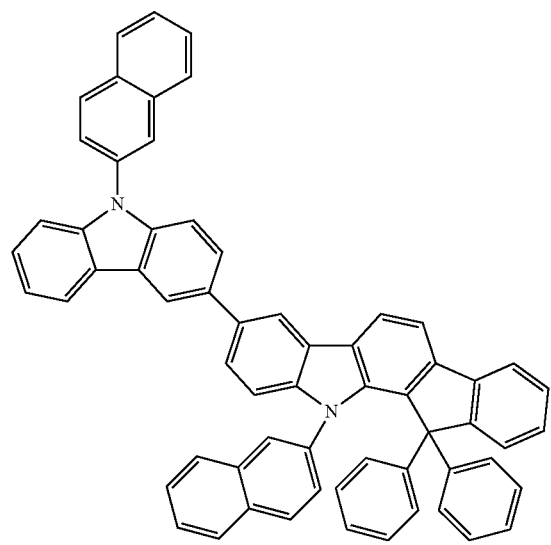
F-589
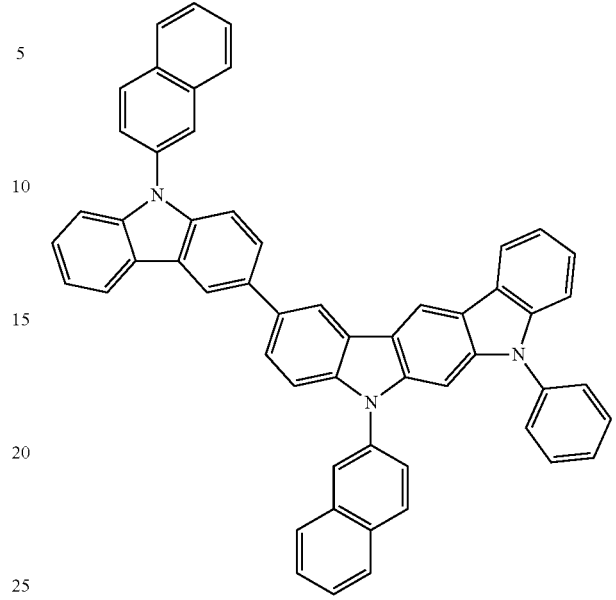
F-588
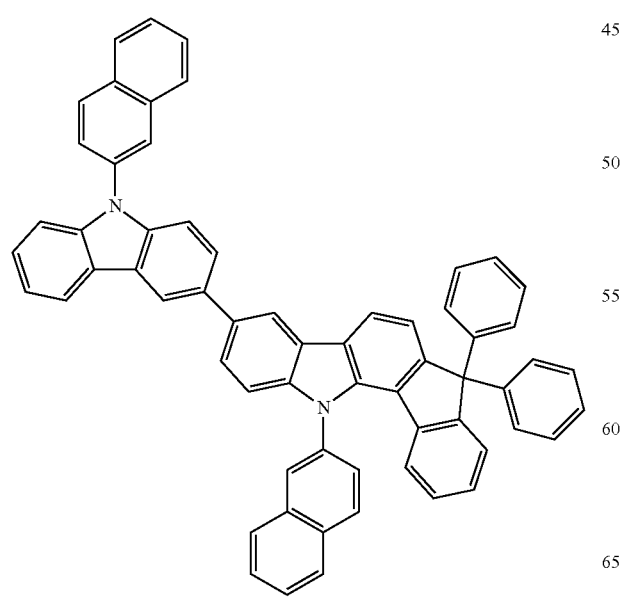
F-590
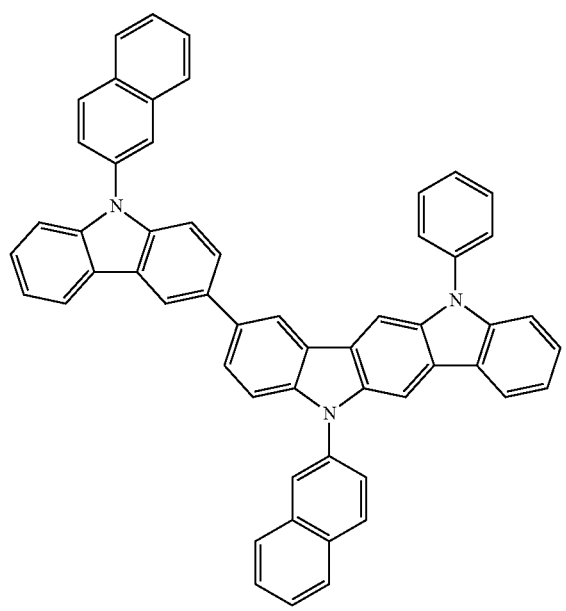

F-591
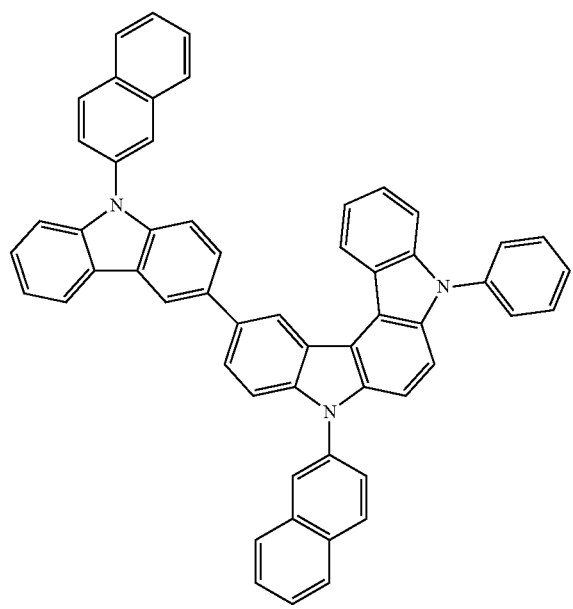
F-593
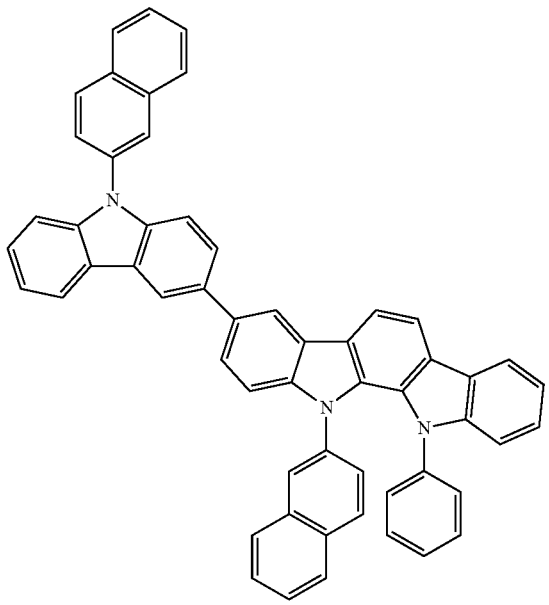
F-592
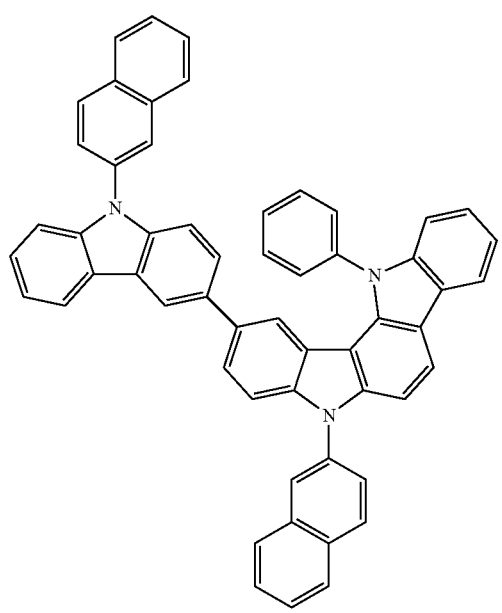
F-594
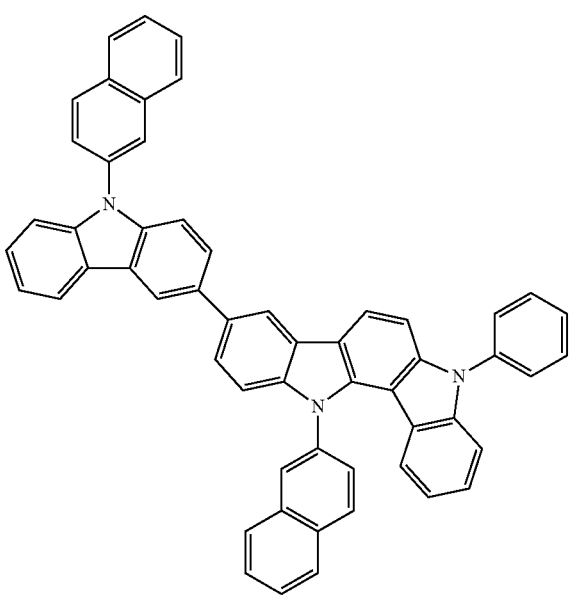

F-595
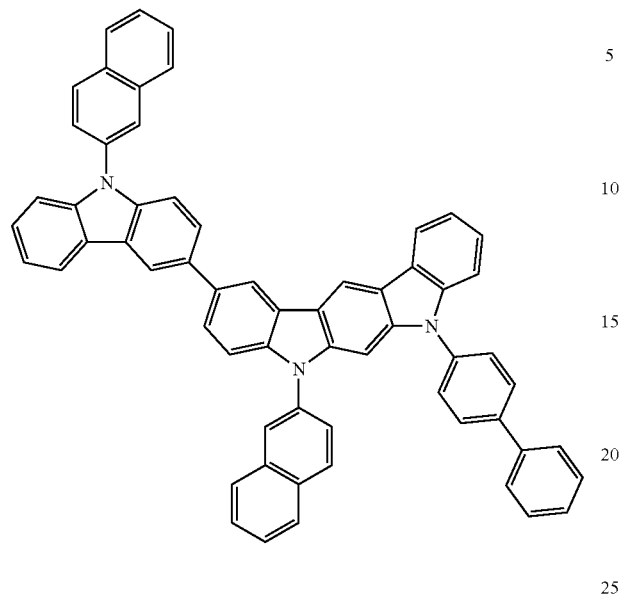
F-597
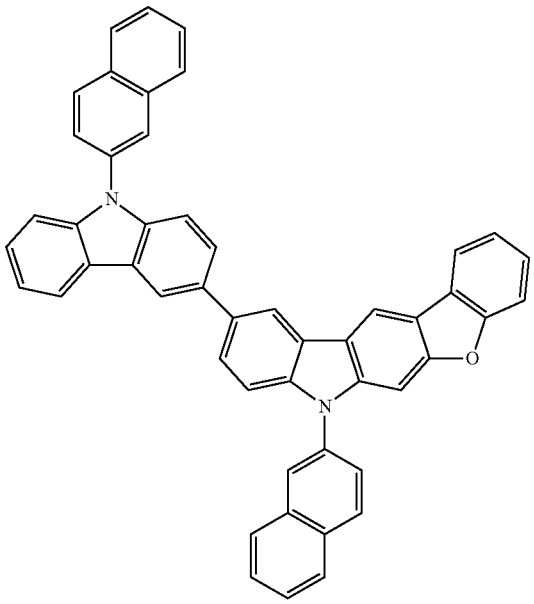
F-596
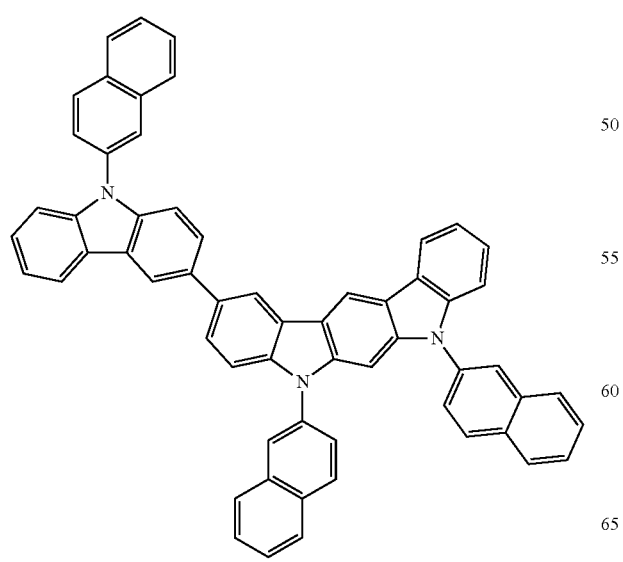
F-598
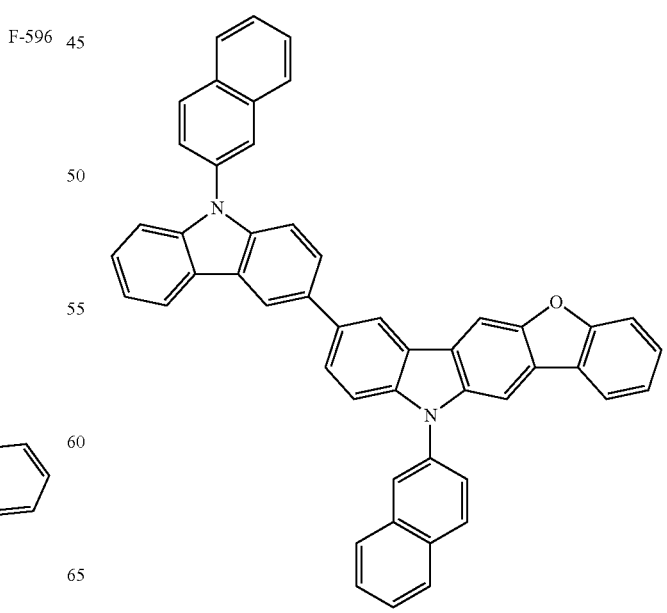

F-599
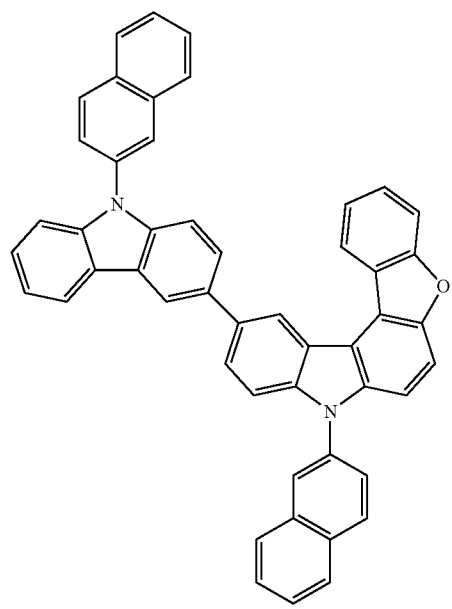
F-601
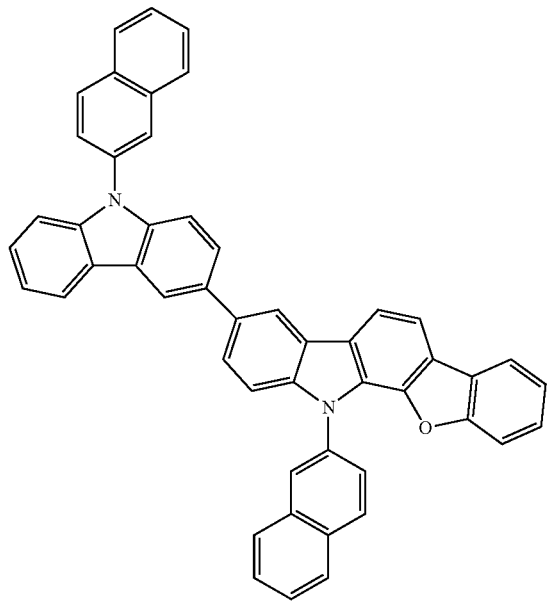
F-600
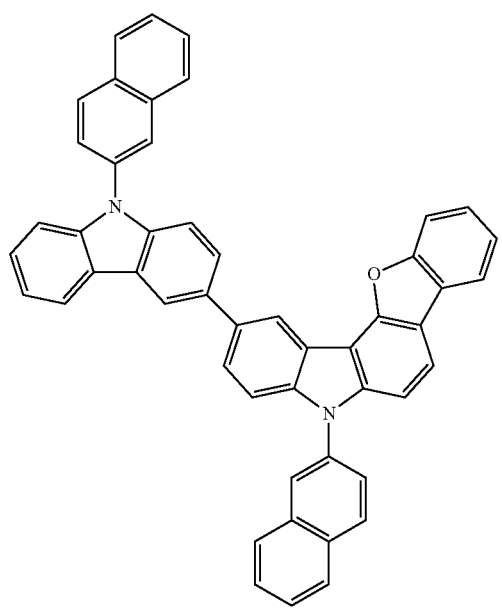
F-602
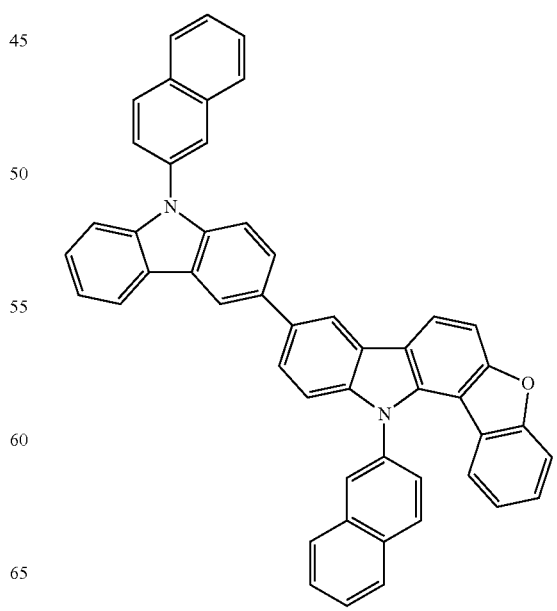

F-603
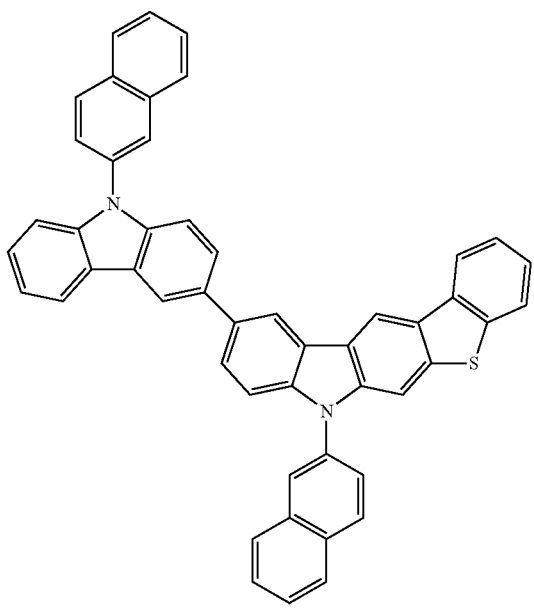
F-605
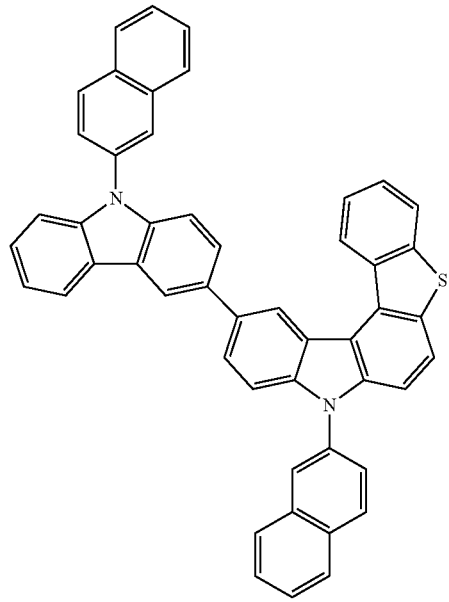
F-604
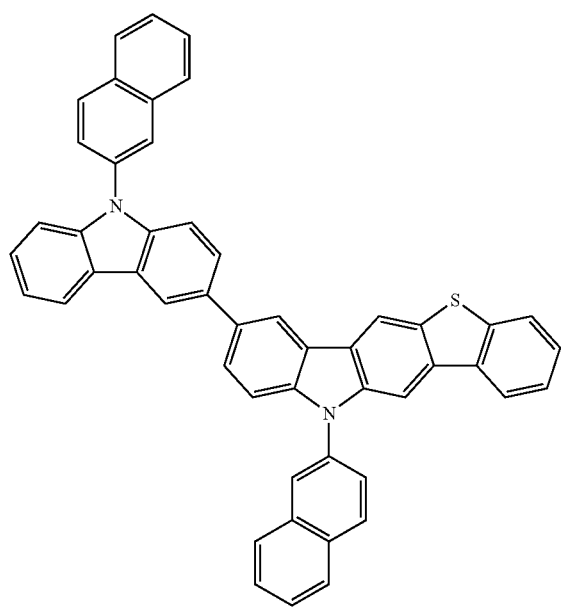
F-606
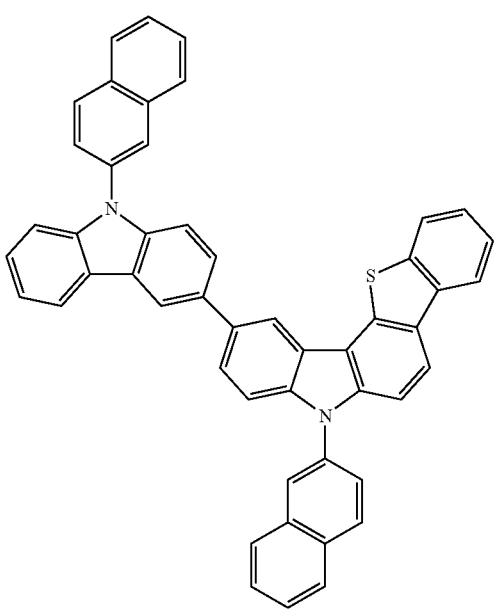

F-607
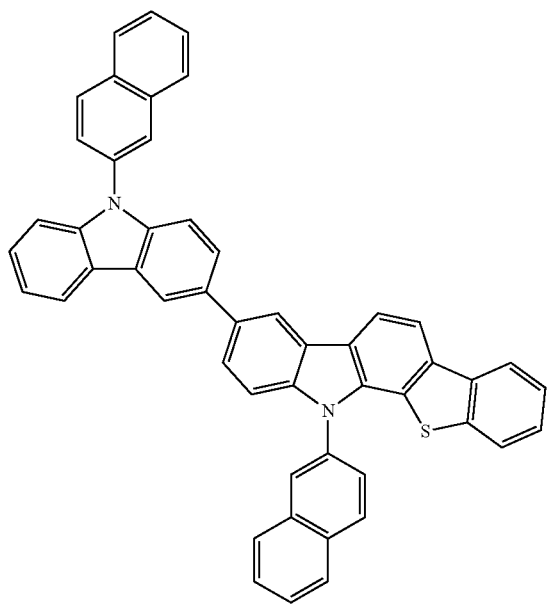
F-609
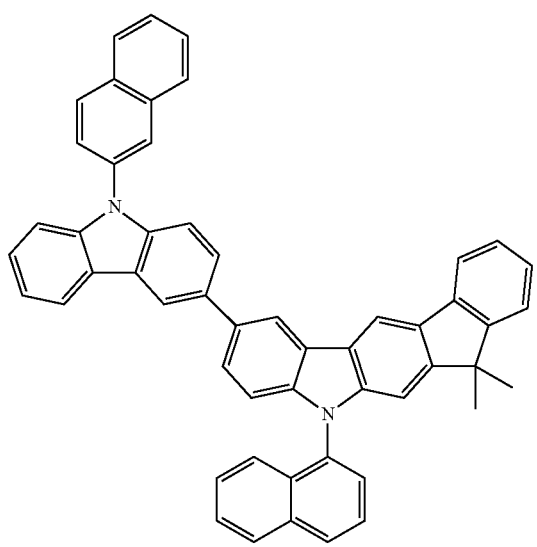
F-608
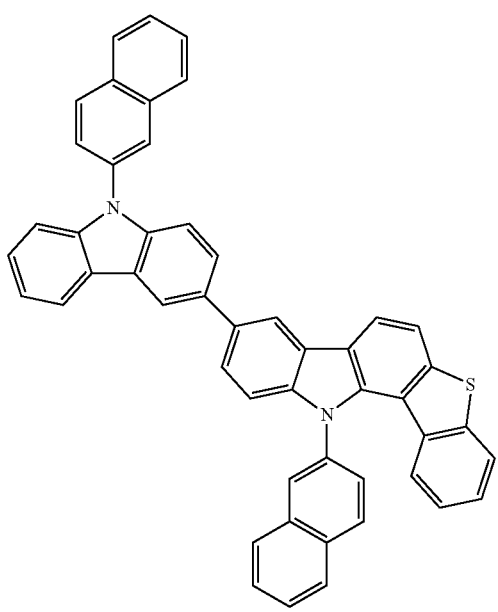
F-610
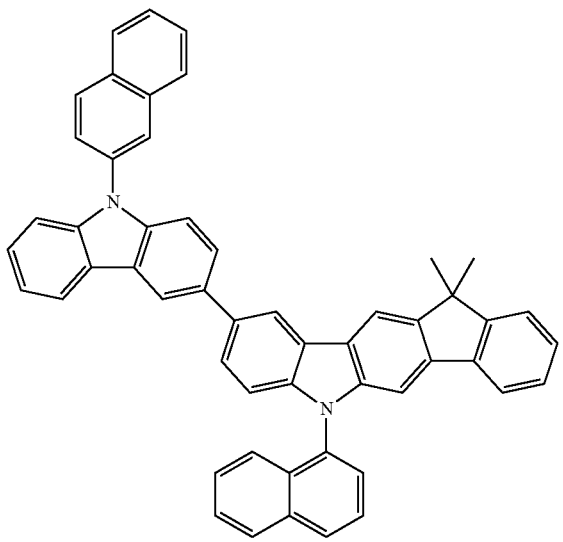

F-611
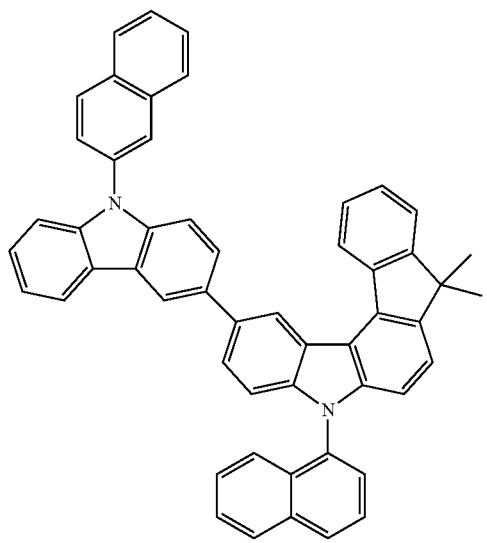
F-613
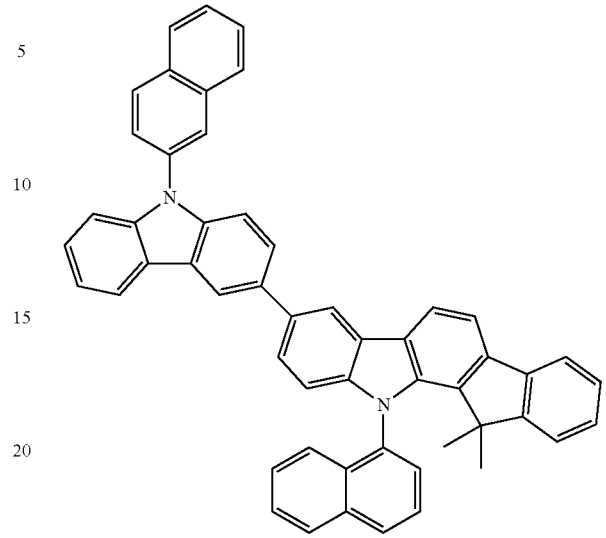
F-614
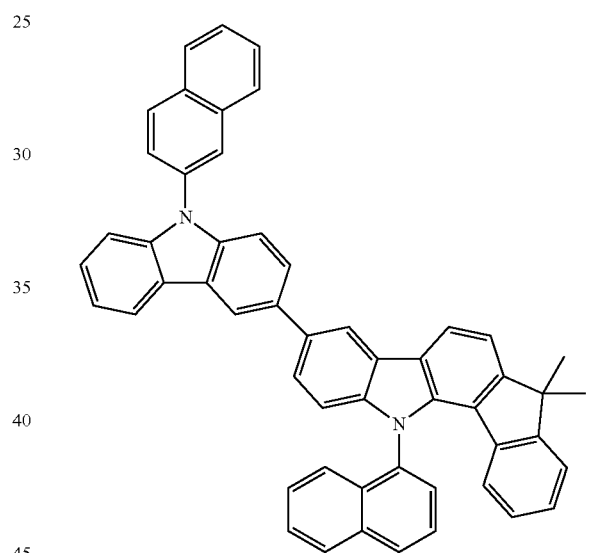
F-612
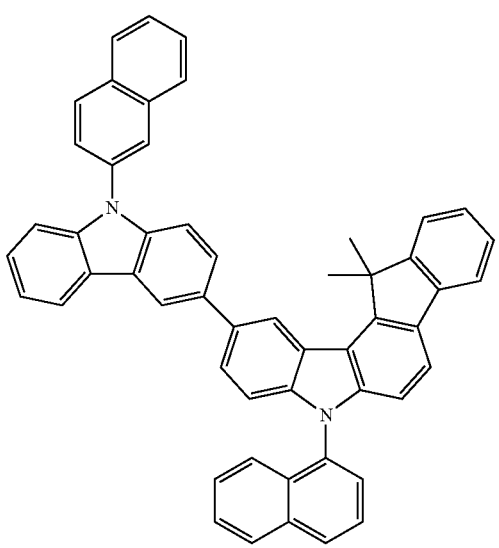
F-615
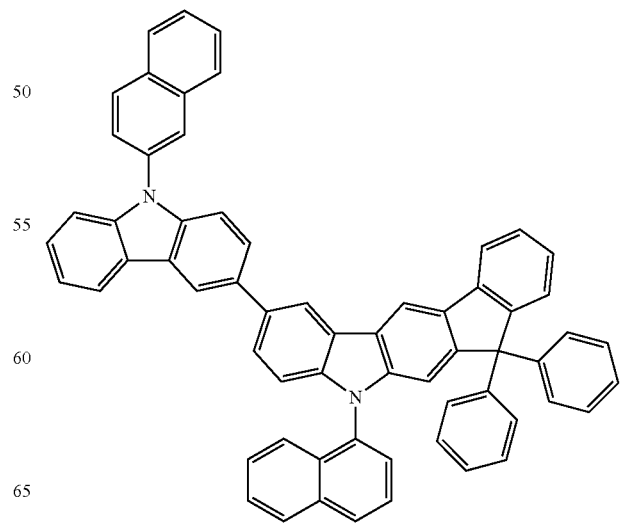

F-616
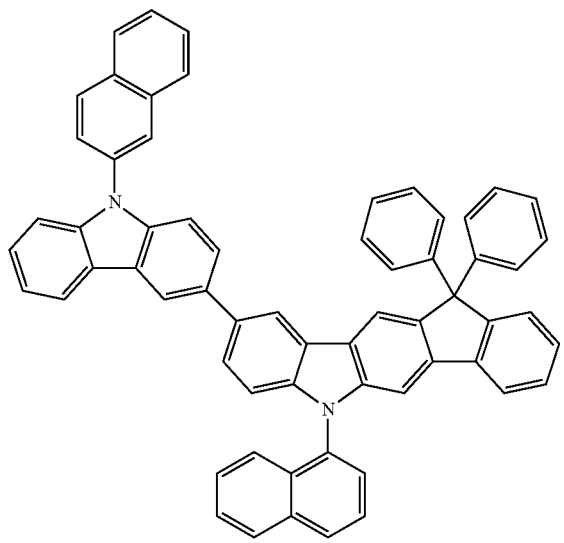
F-618
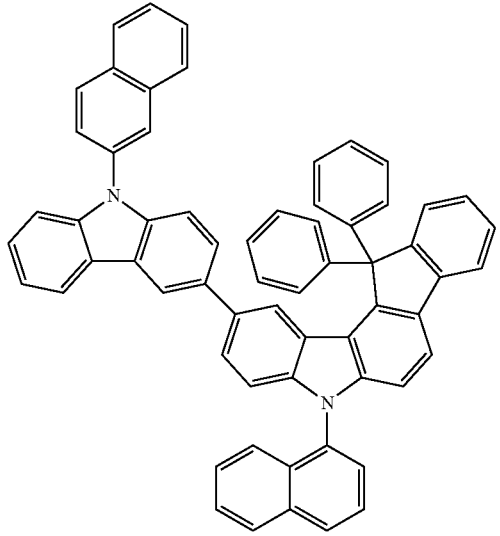
F-619
F-617
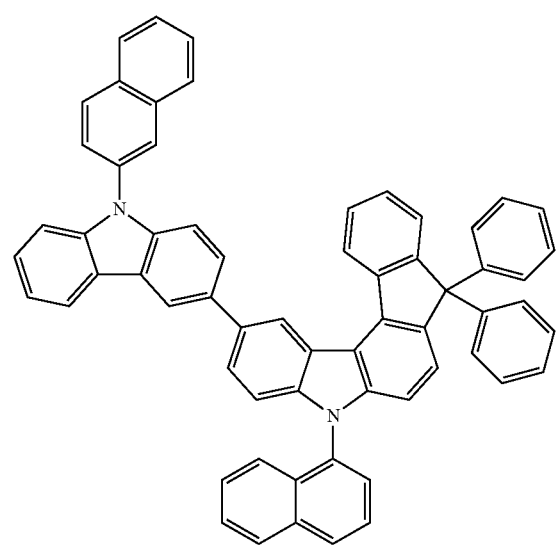
F-620
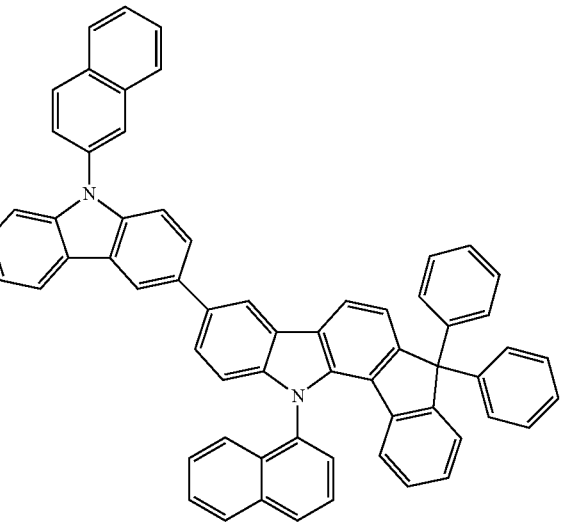

F-621
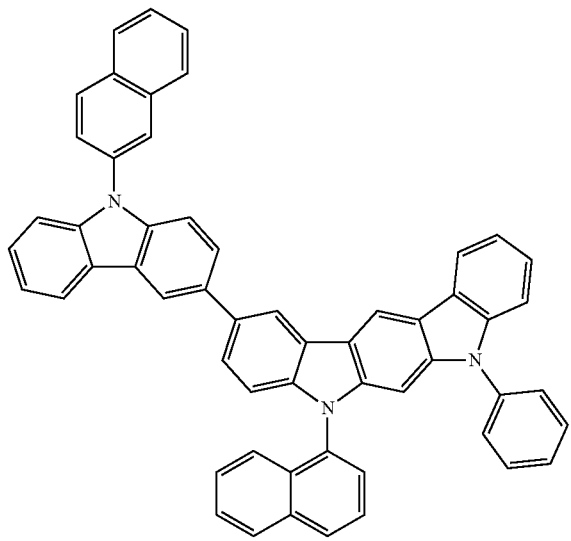
F-623
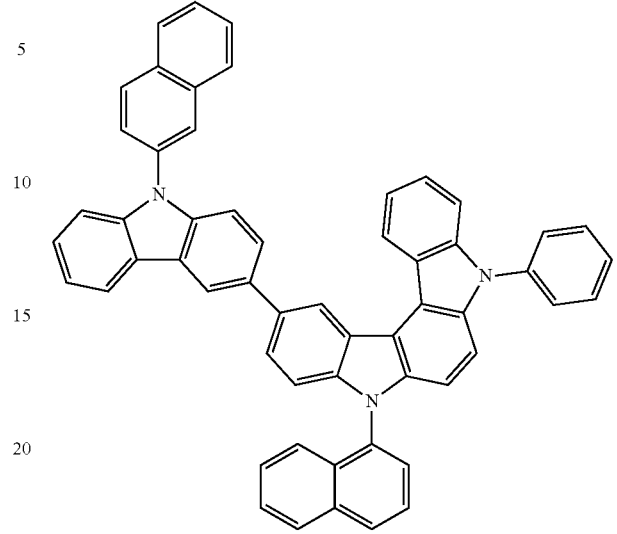
F-622
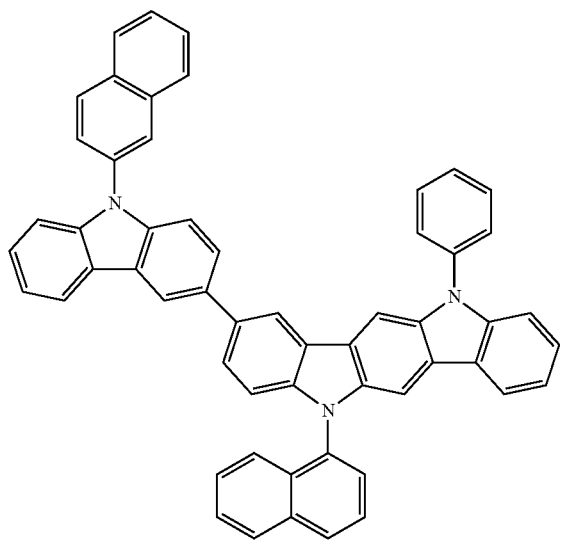
F-624
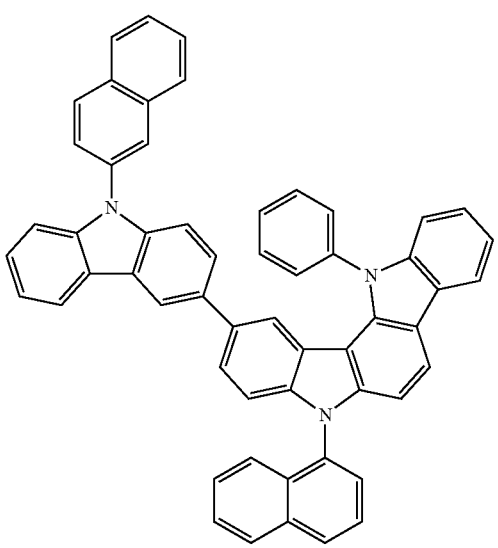

F-625
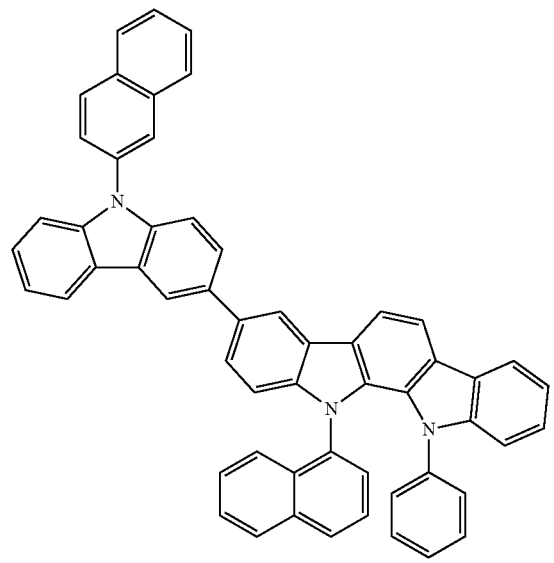
F-626
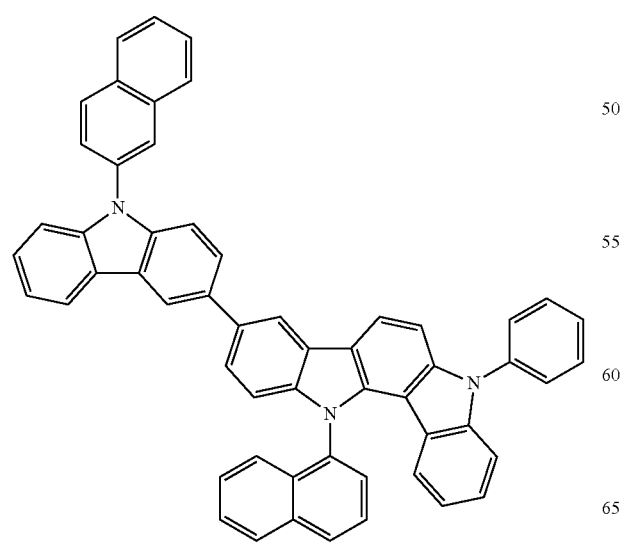
F-627
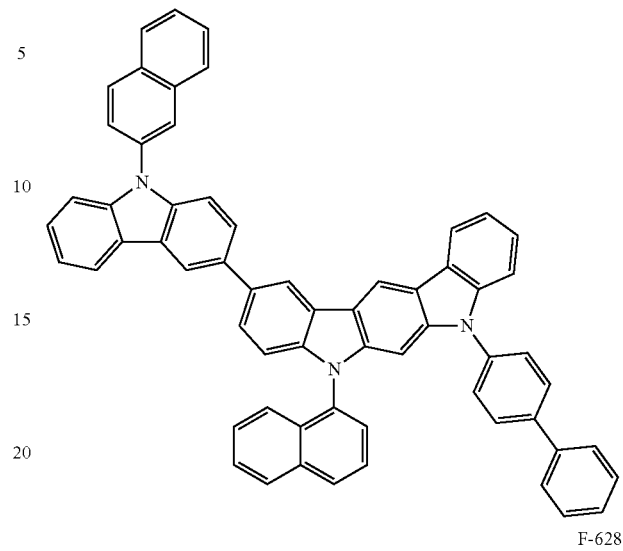
F-628
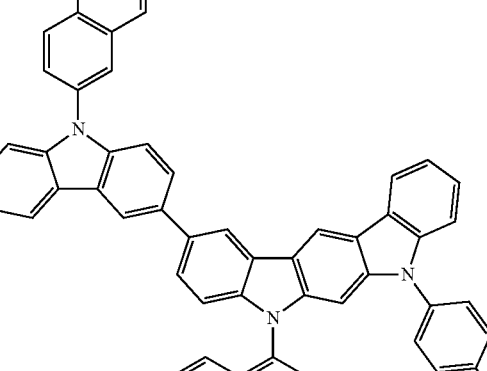
F-629
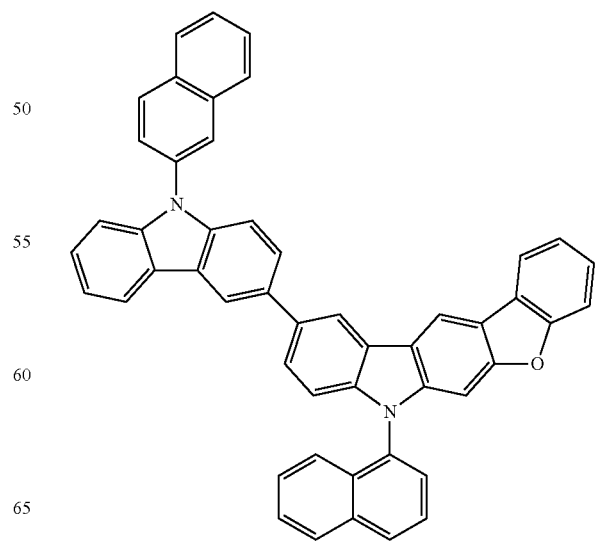

F-630
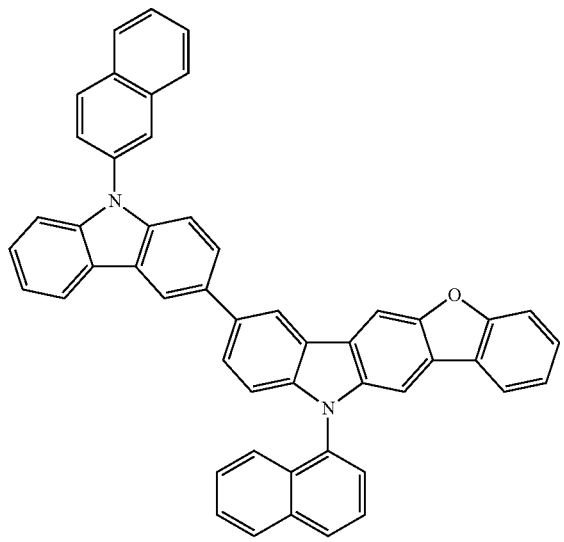
F-631
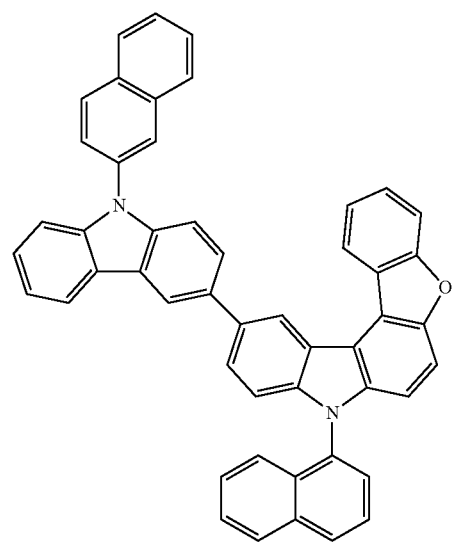
F-632
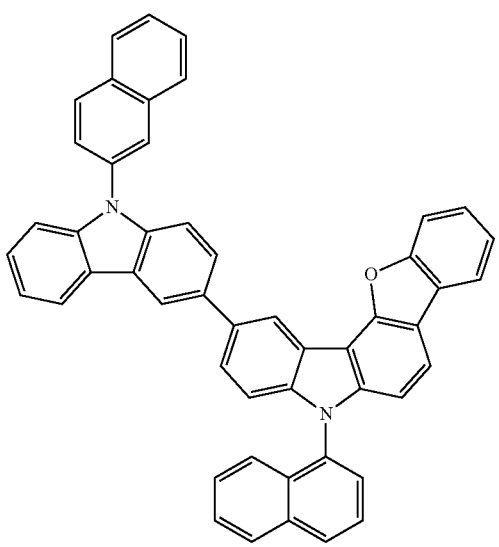
F-633
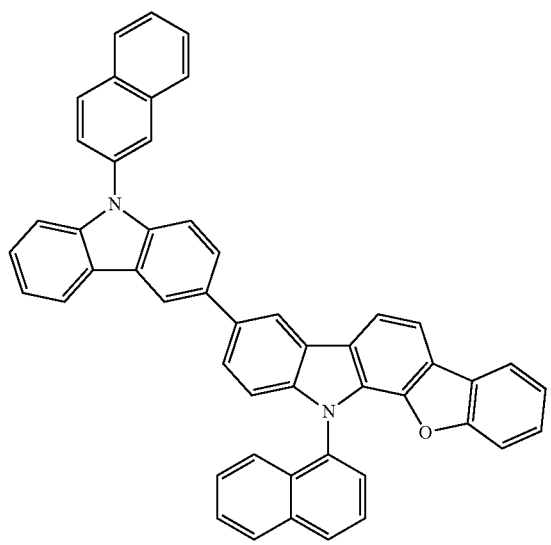
F-634
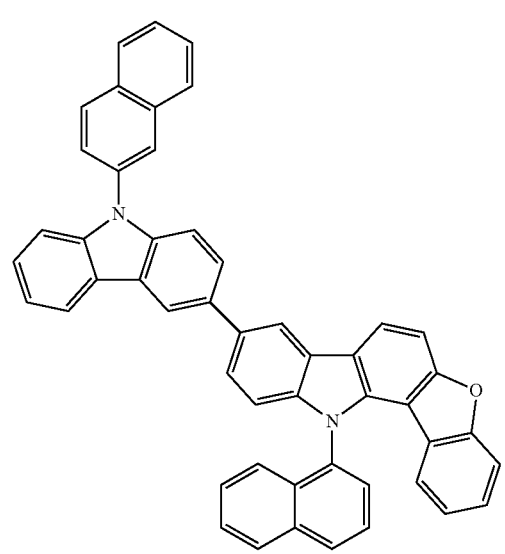
F-635
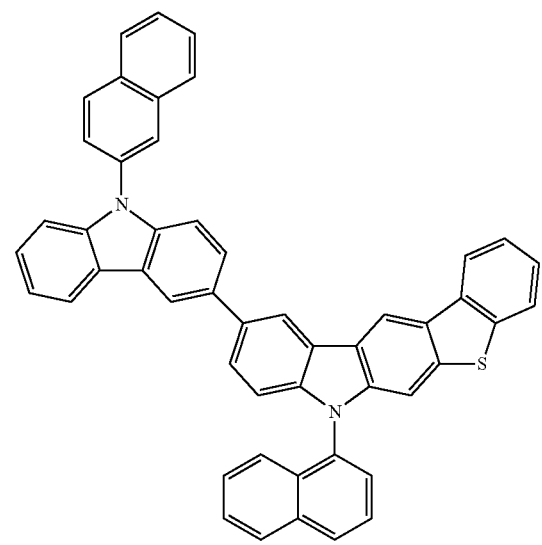

F-636
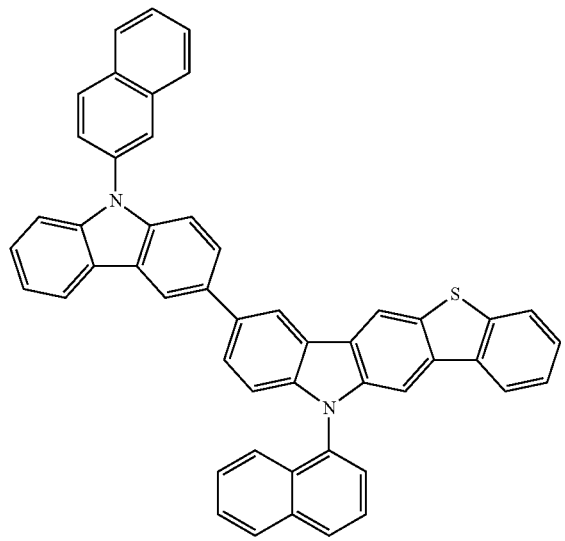
F-637
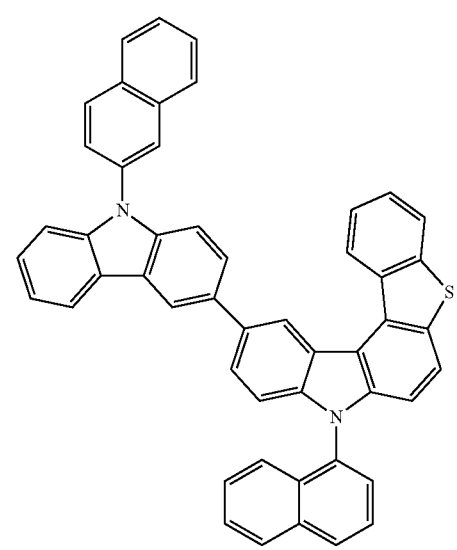
F-638
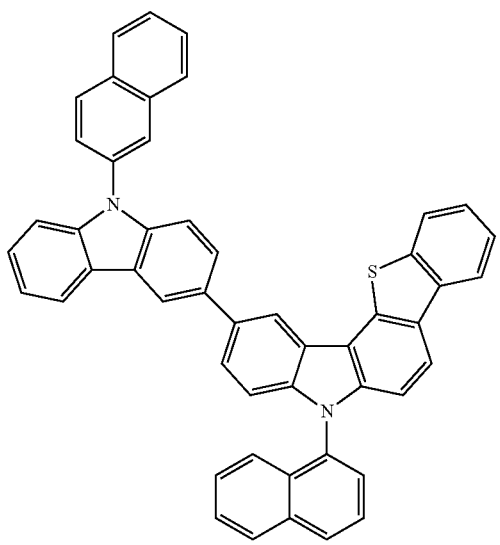
F-639
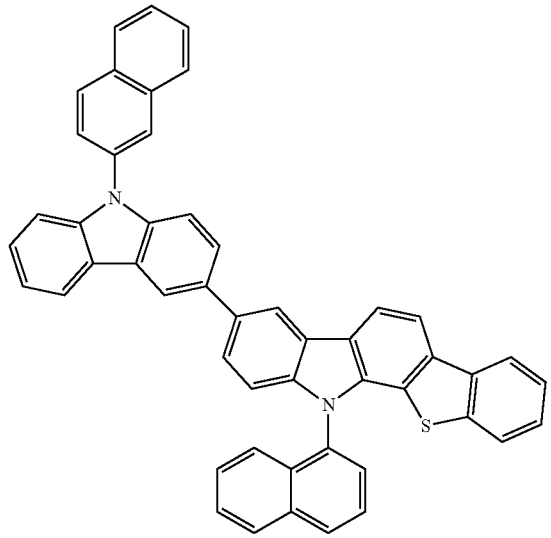
F-640
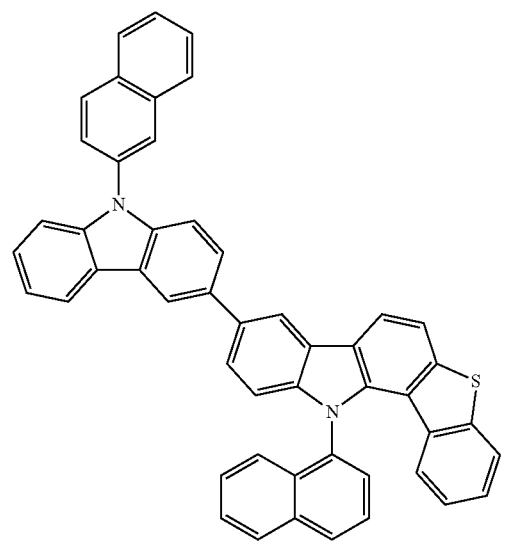
F-641
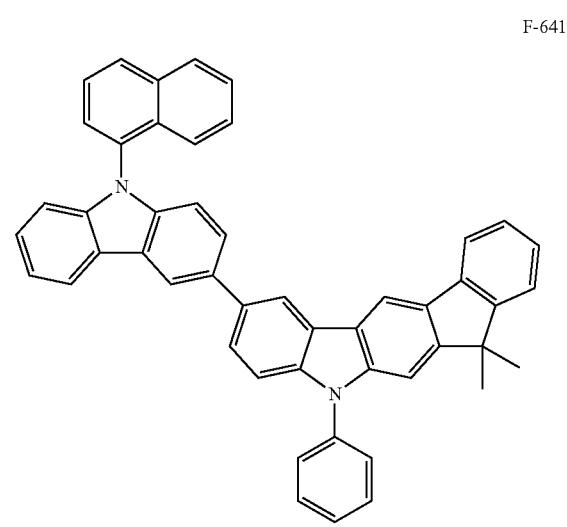

F-642
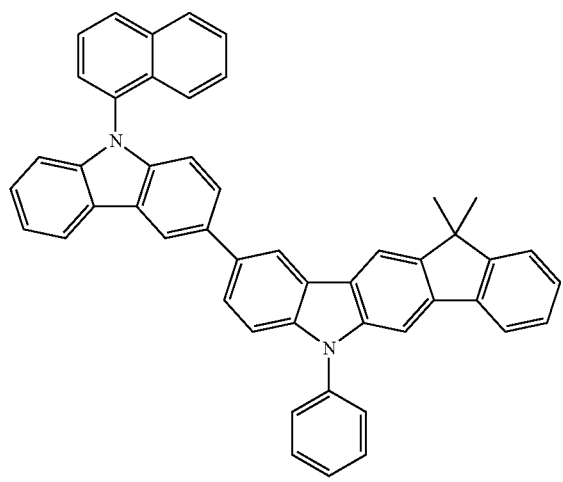
F-645
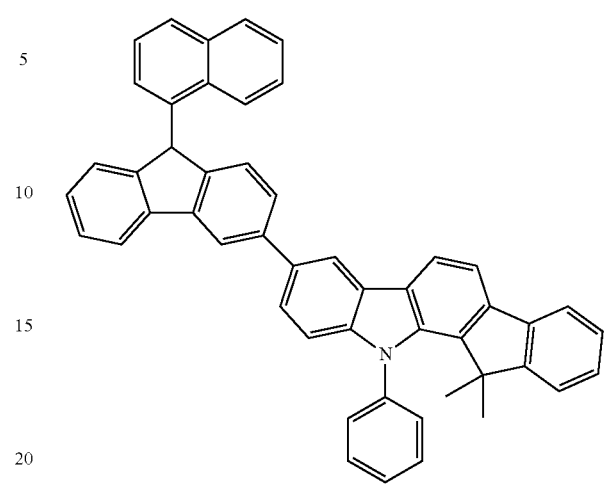
F-643
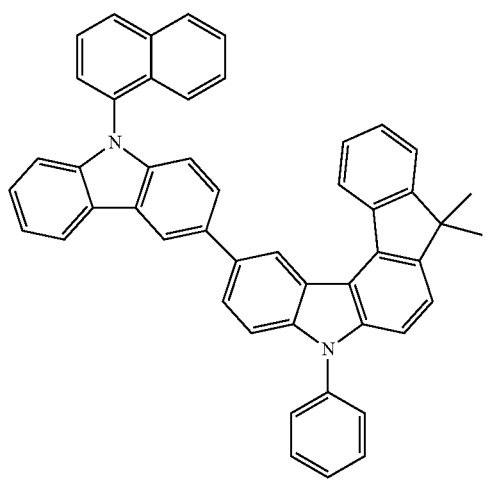
F-646
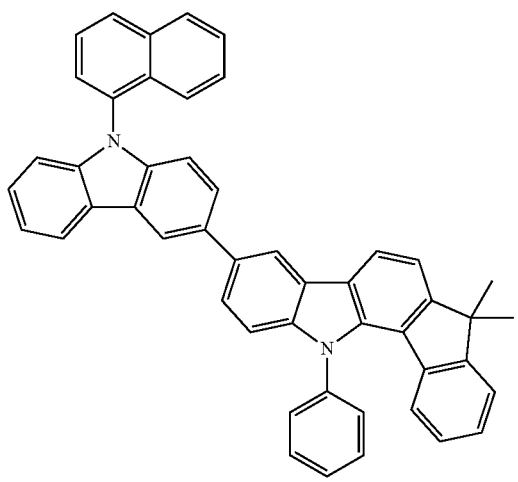
F-644
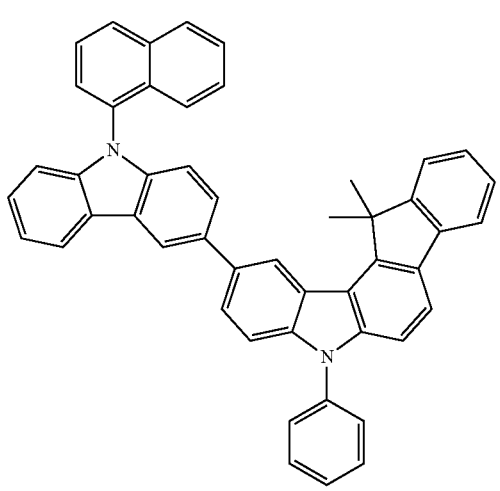
F-647
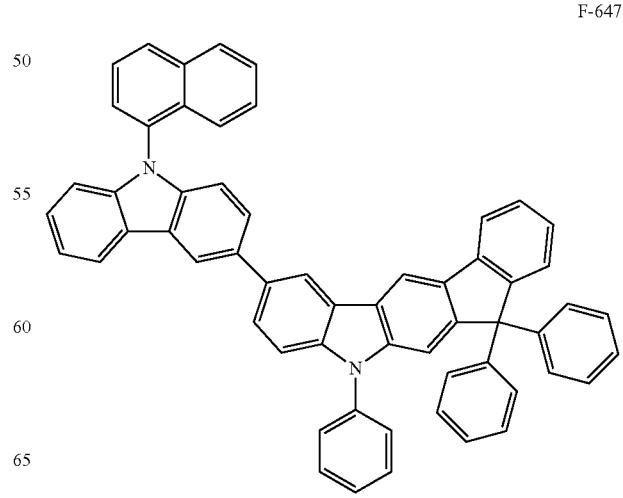

F-648
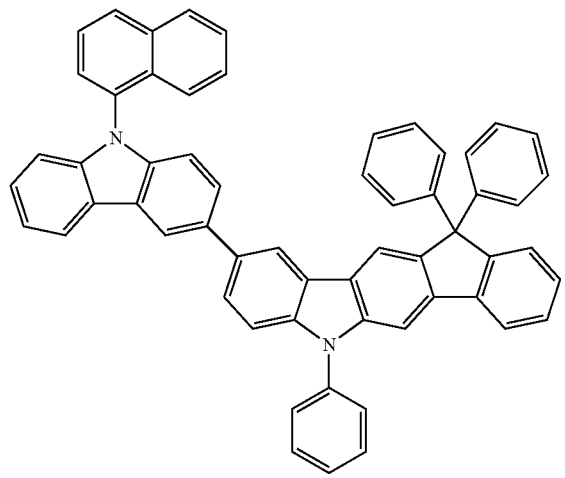
F-651
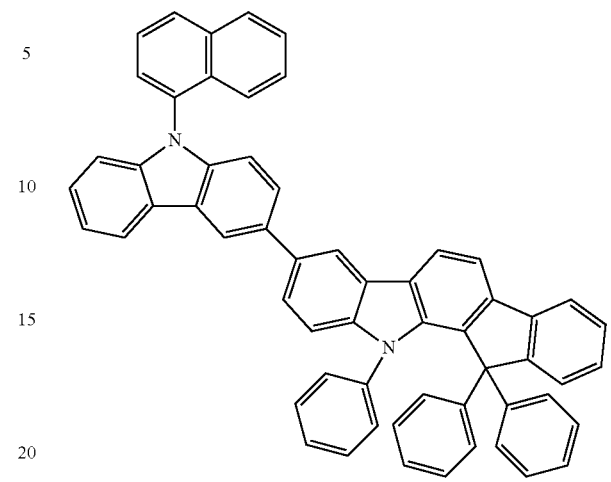
F-649
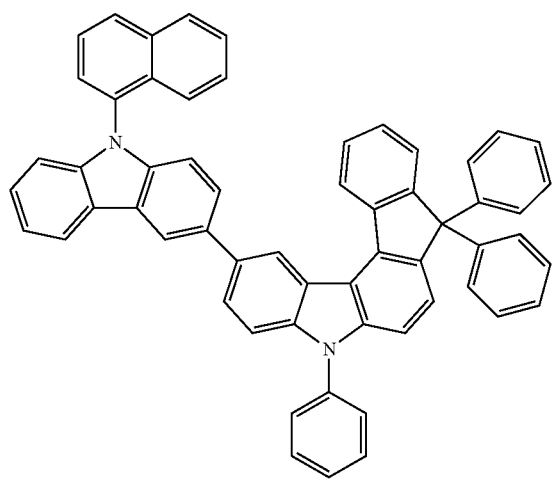
F-652
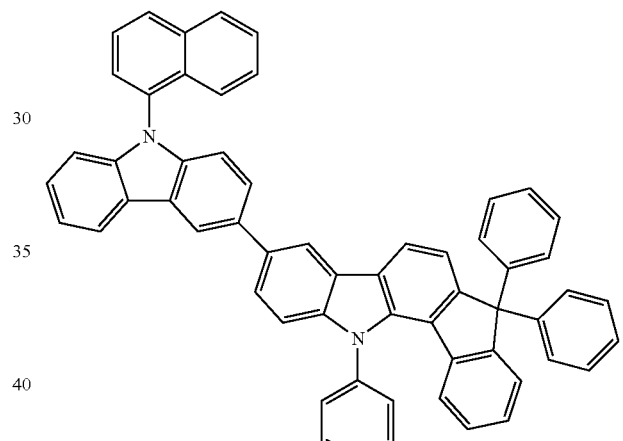
F-650
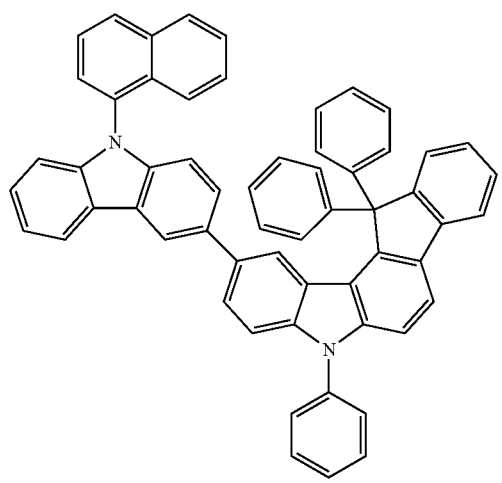
F-653
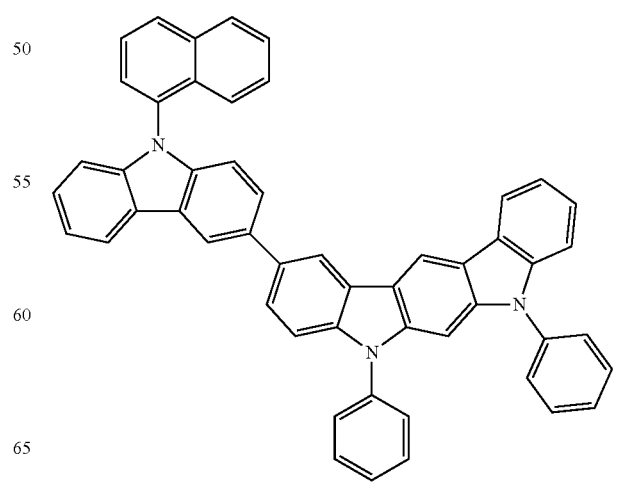

-continued
F-654
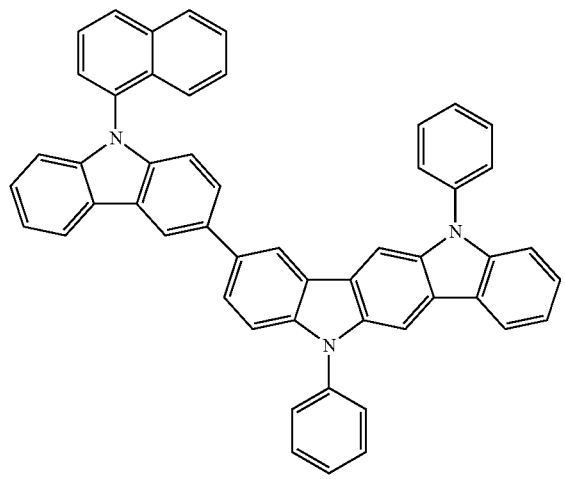
F-655
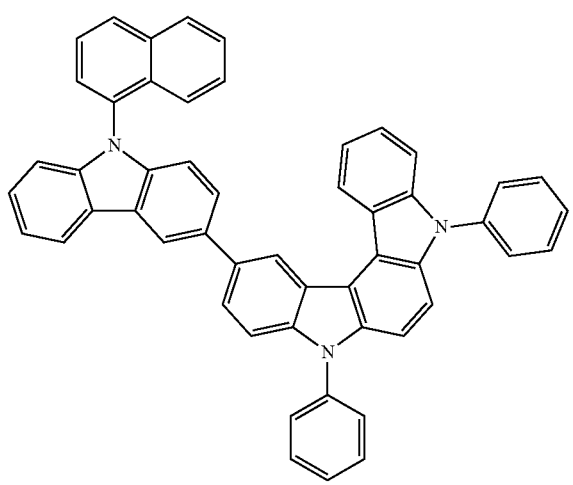
F-656
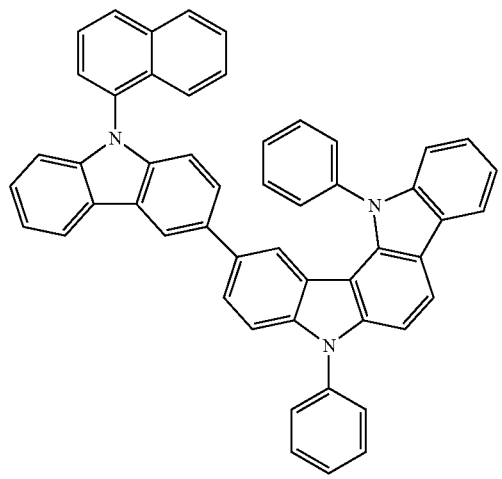
-continued
F-657
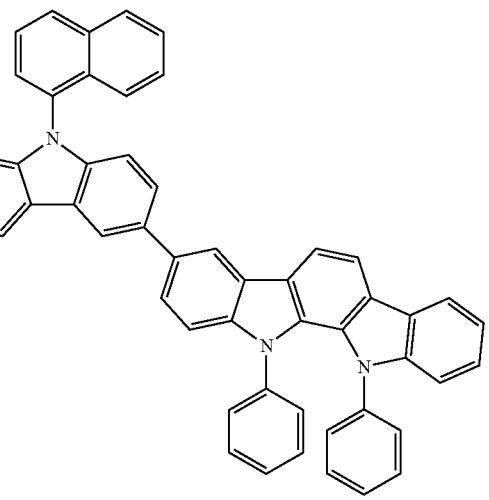
F-658
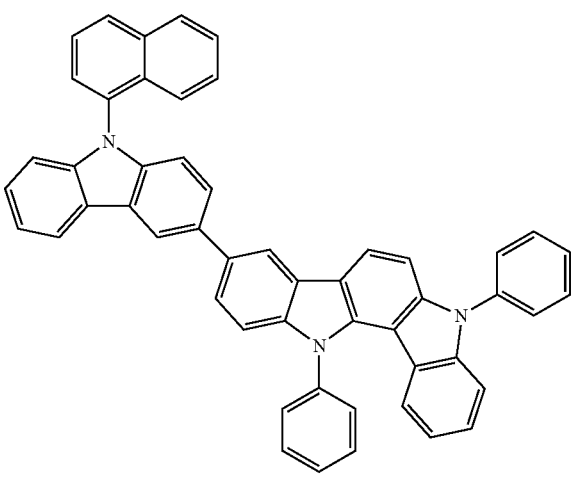
F-659
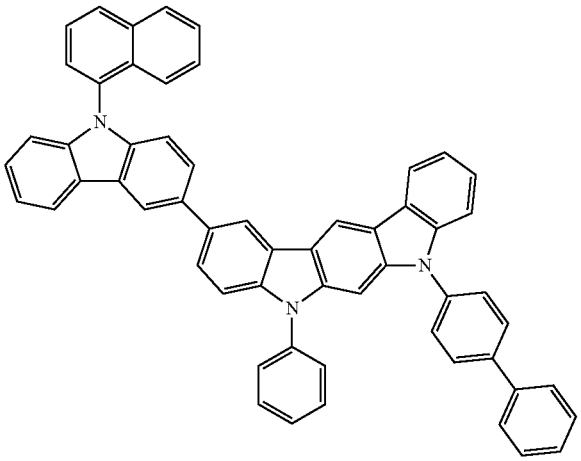

F-660
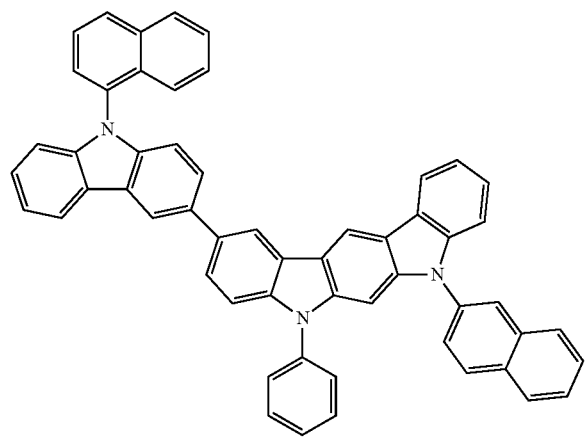
F-663
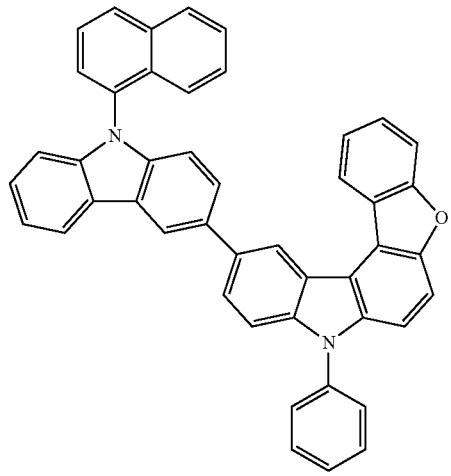
F-661
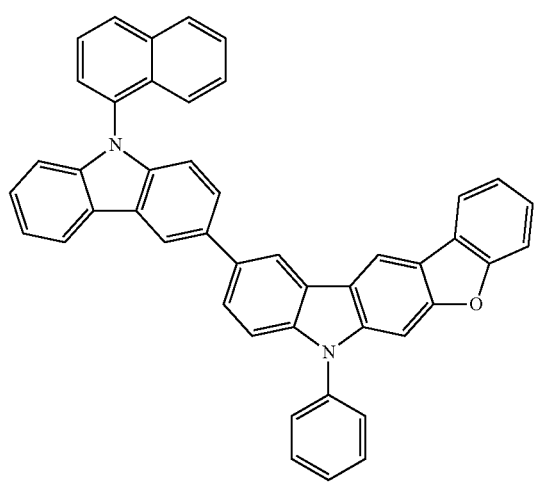
F-664
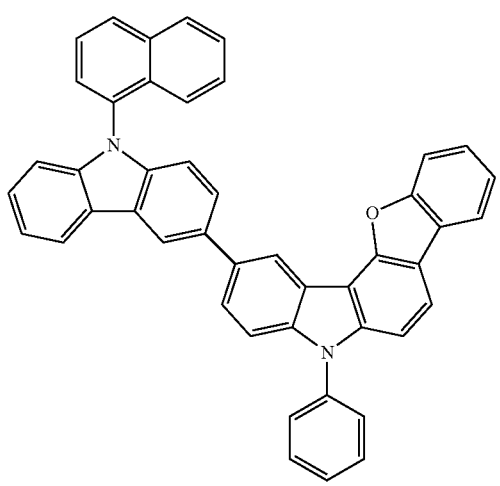
F-662
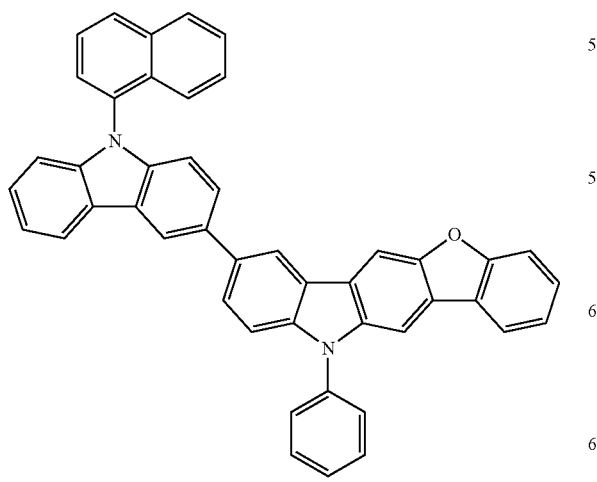
F-665
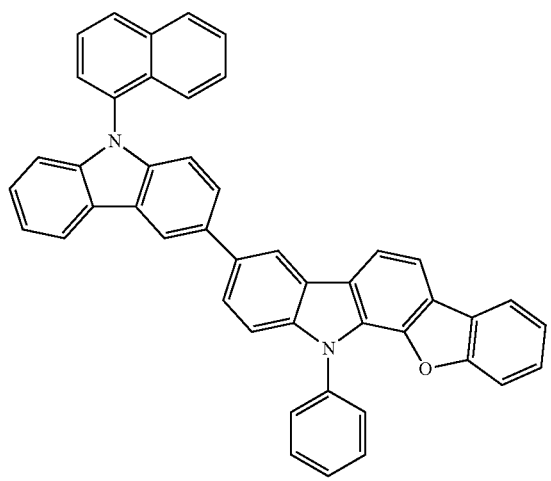

-continued
F-666
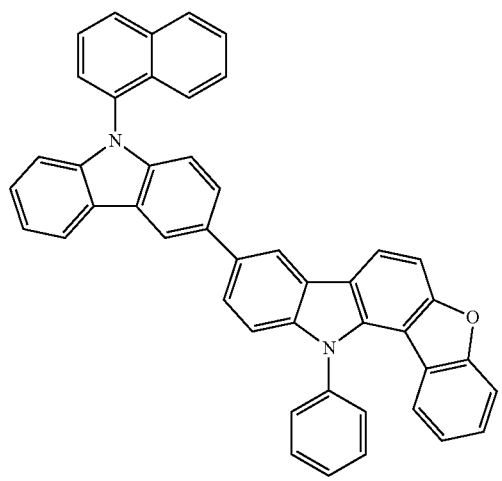
F-667
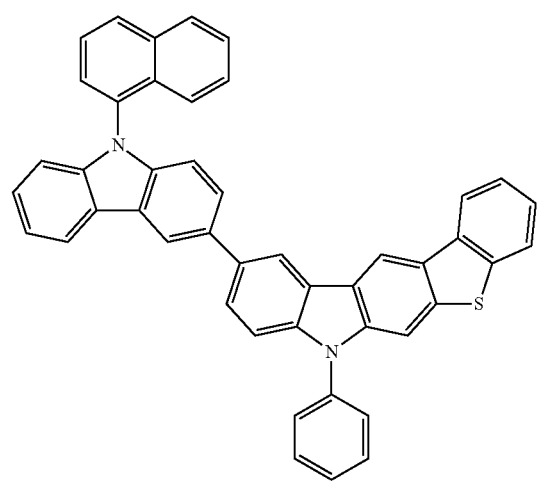
F-668
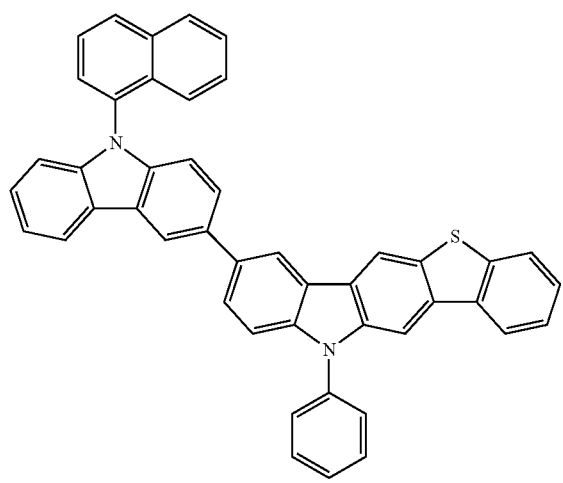
F-669
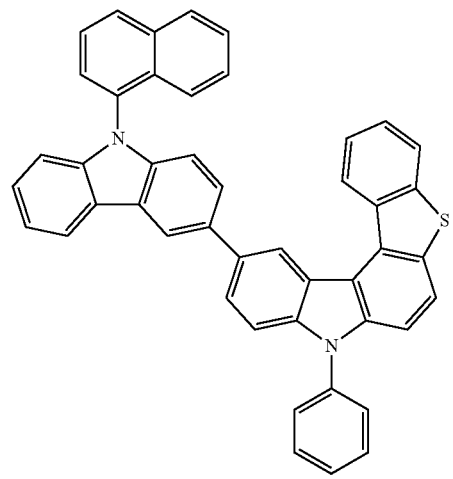
F-670
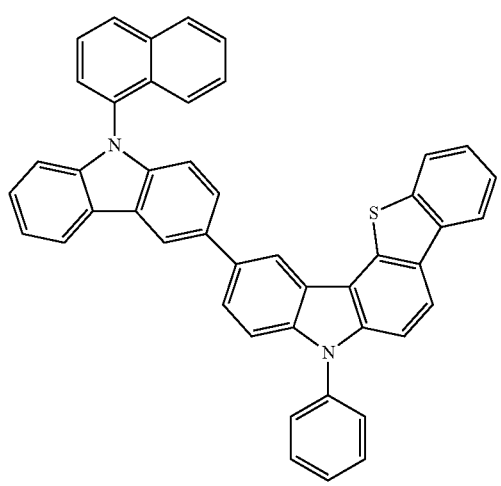
F-671
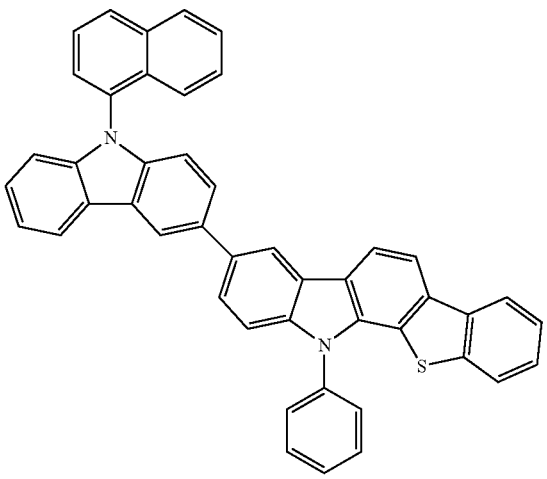

-continued
F-672
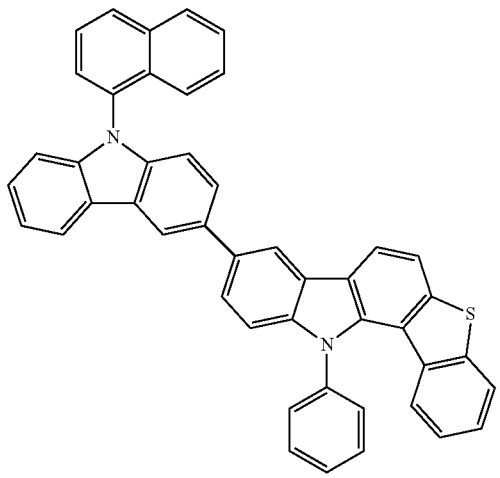
F-673
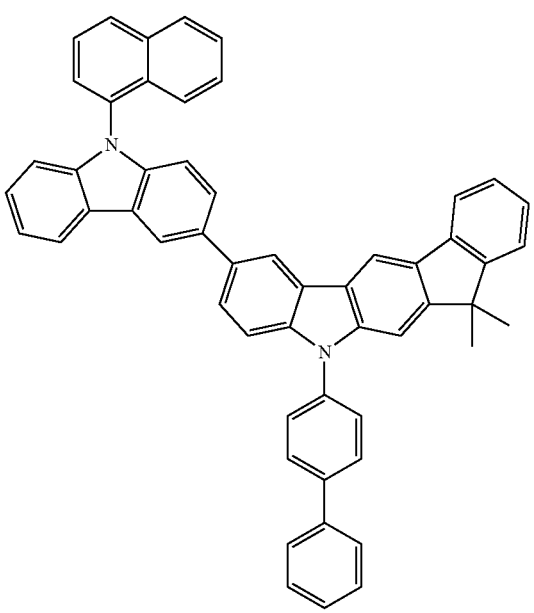
-continued
F-674
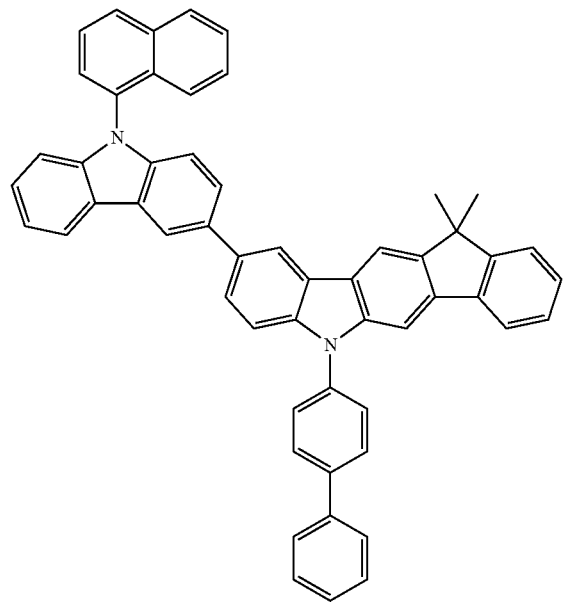
F-675
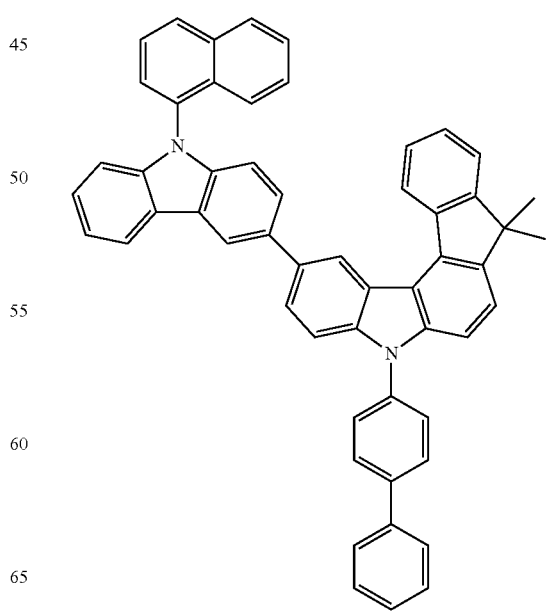

F-676
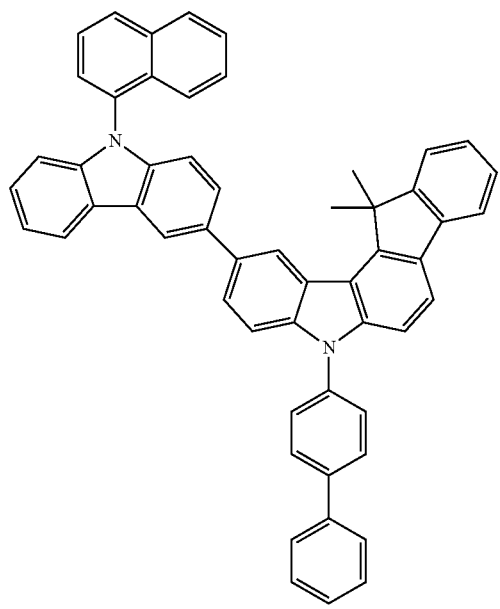
F-678
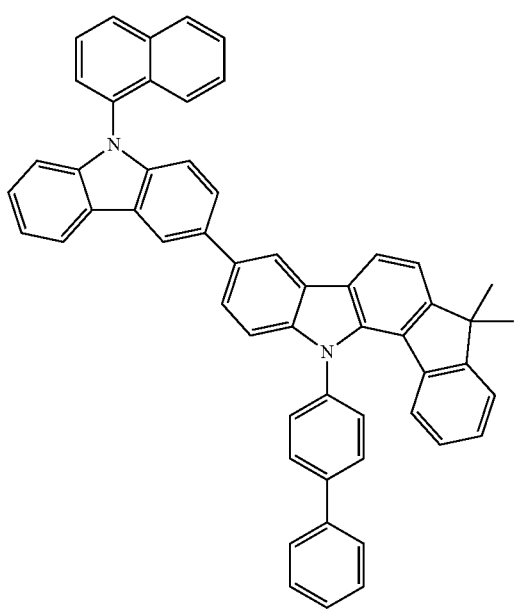
F-677
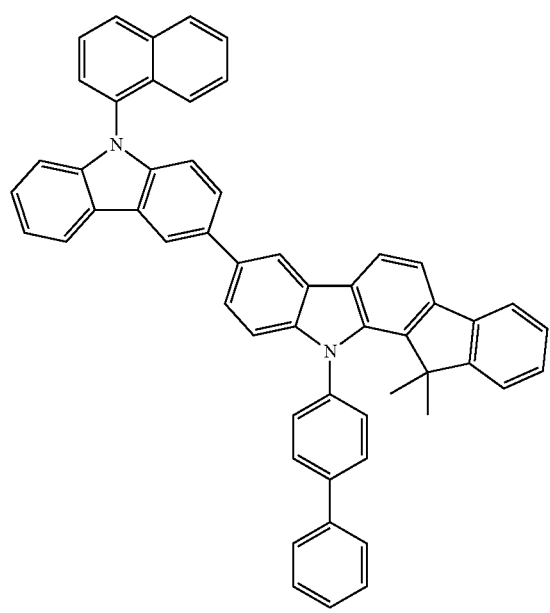
F-679
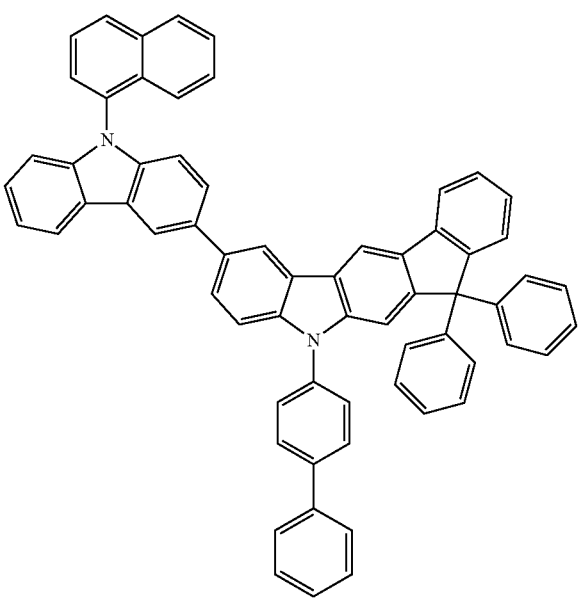

F-680
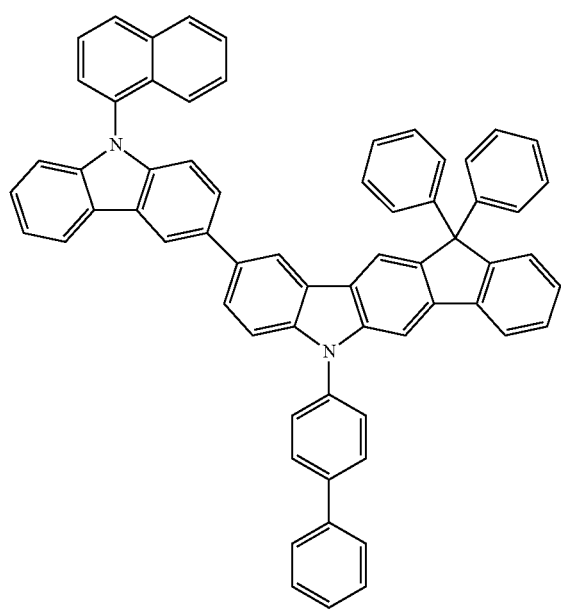
F-682
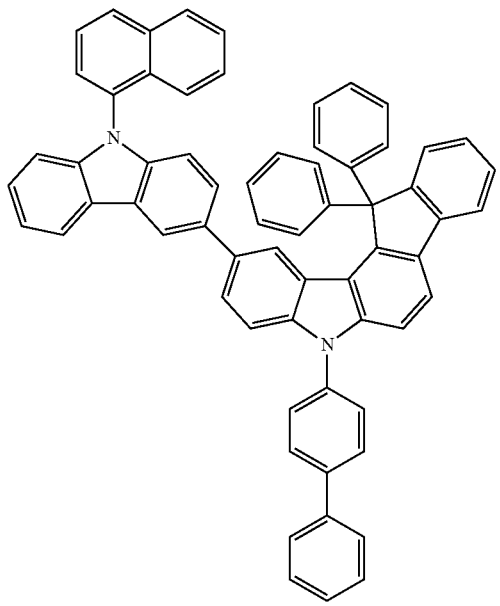
F-681
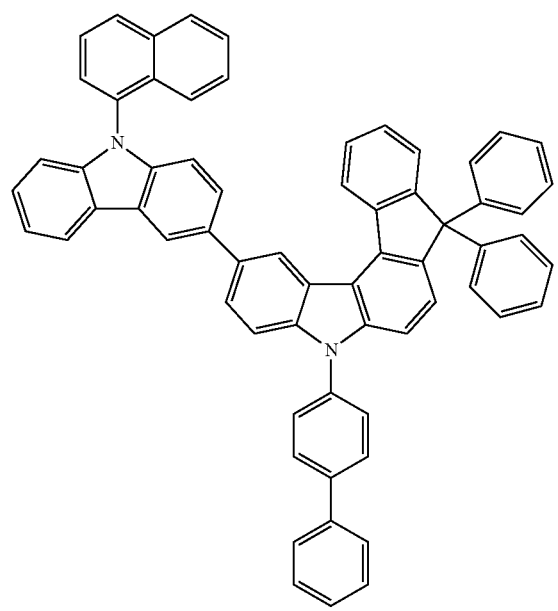
F-683
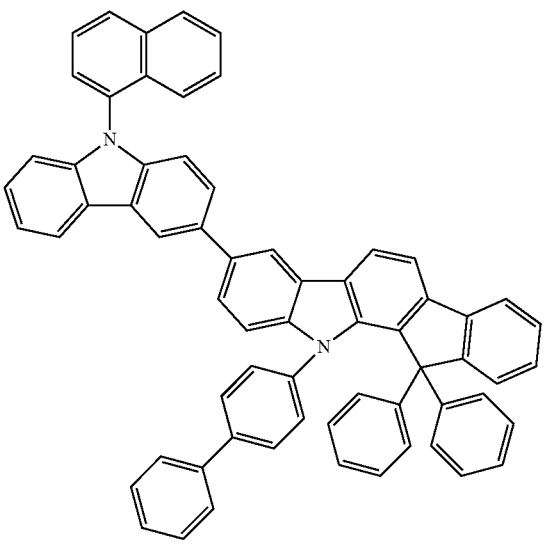

F-684
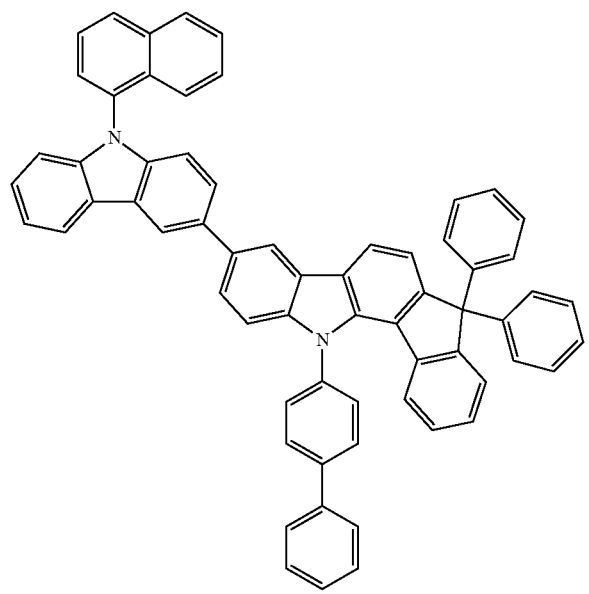
F-686
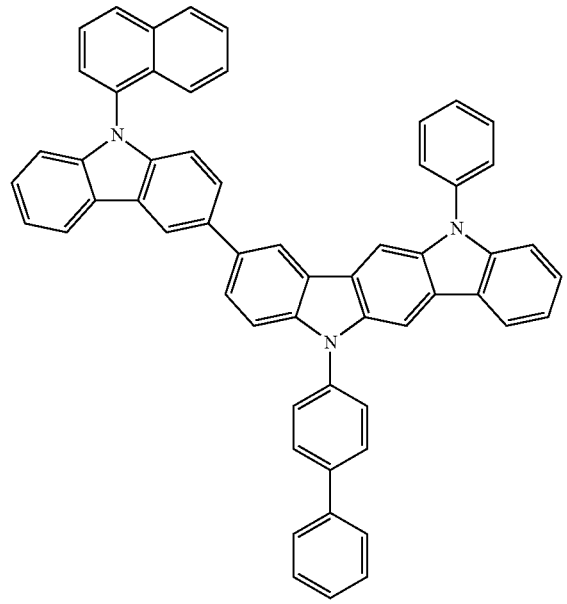
F-685
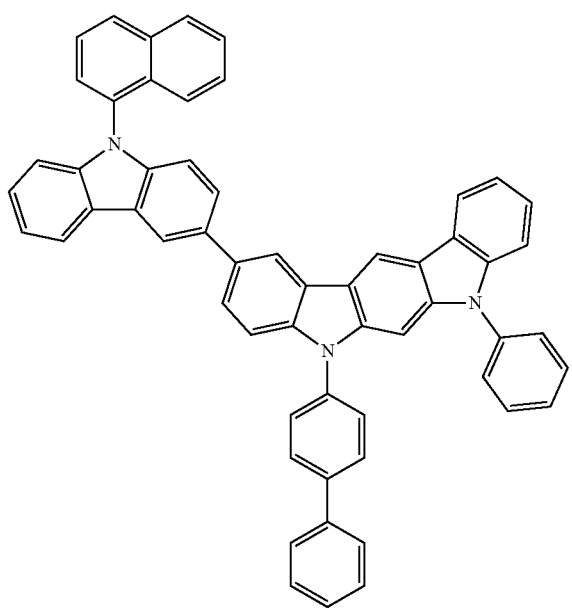
F-687
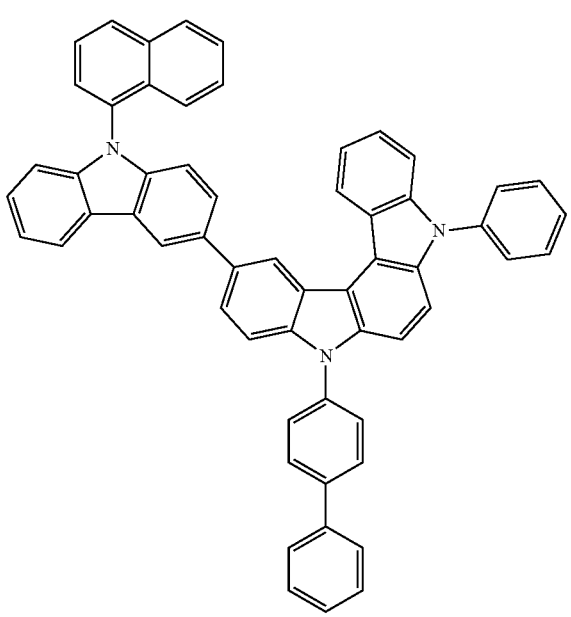

F-688
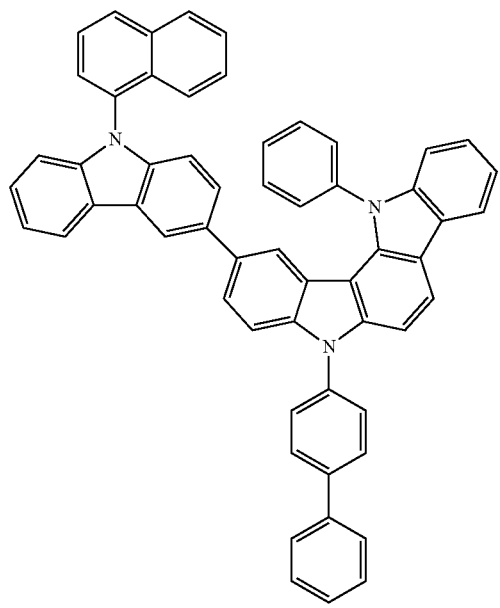
F-689
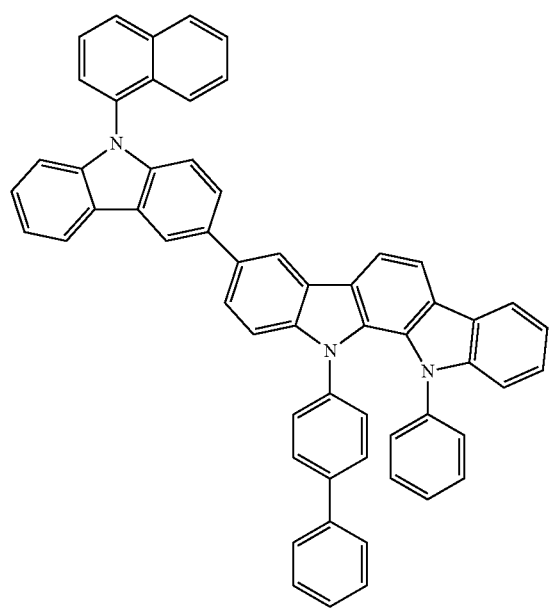
F-690
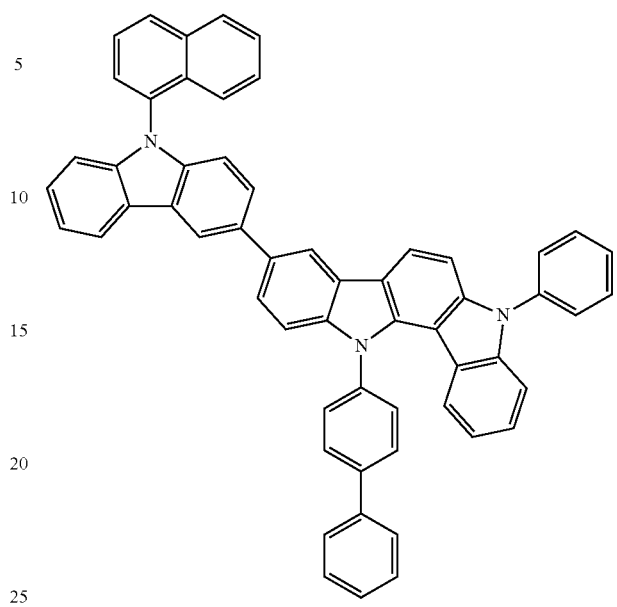
F-691
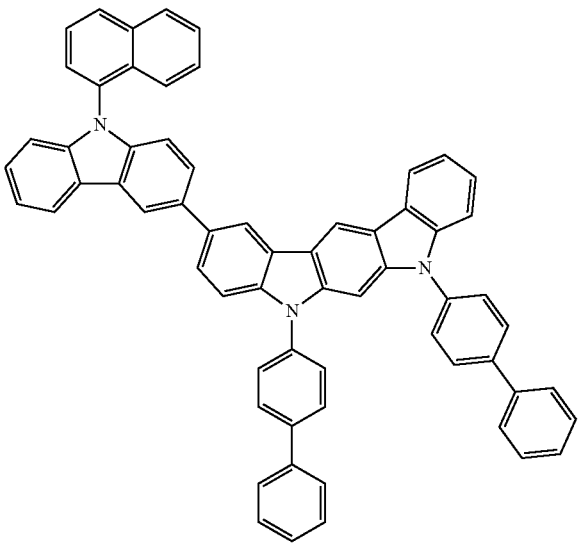

F-692
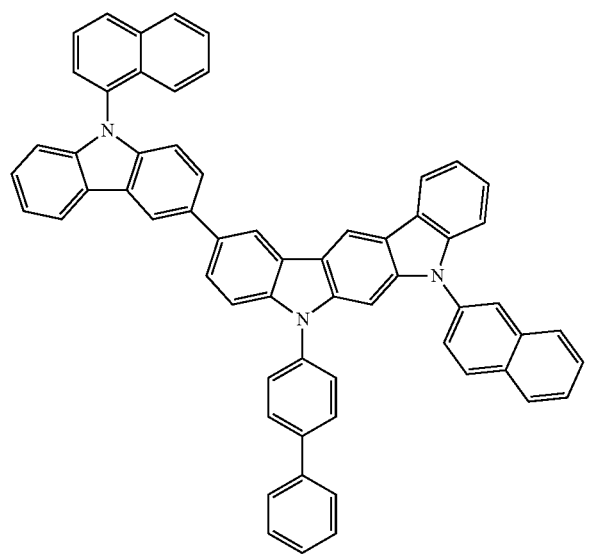
F-694
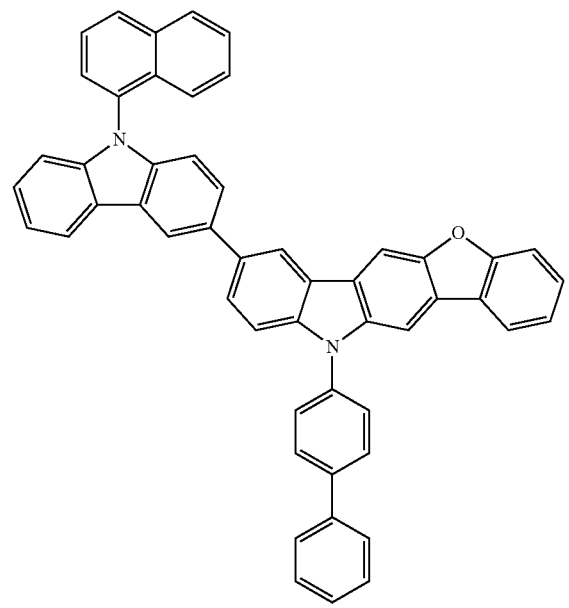
F-693
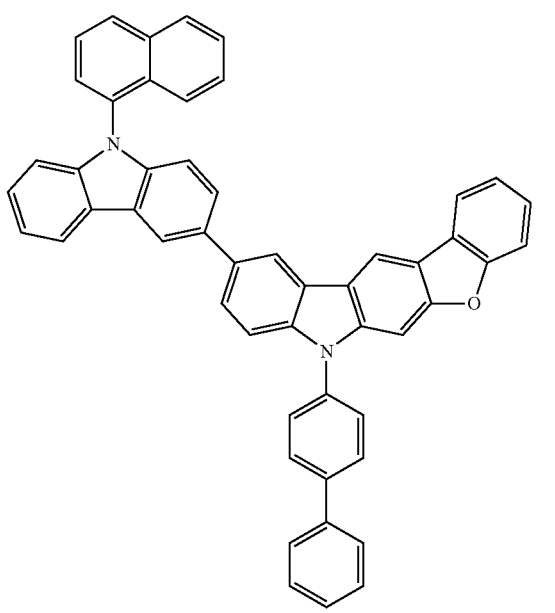
F-695
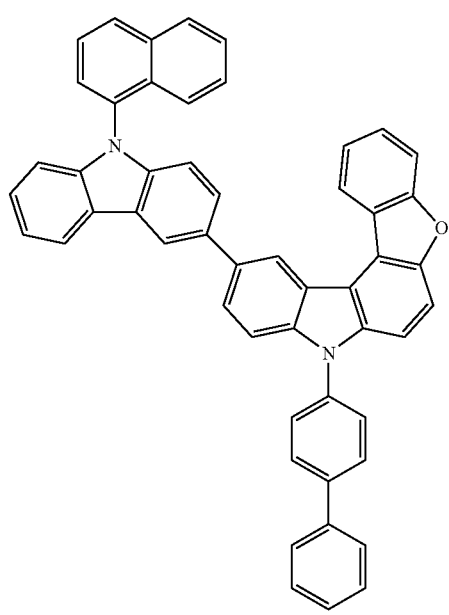

931
-continued
F-696
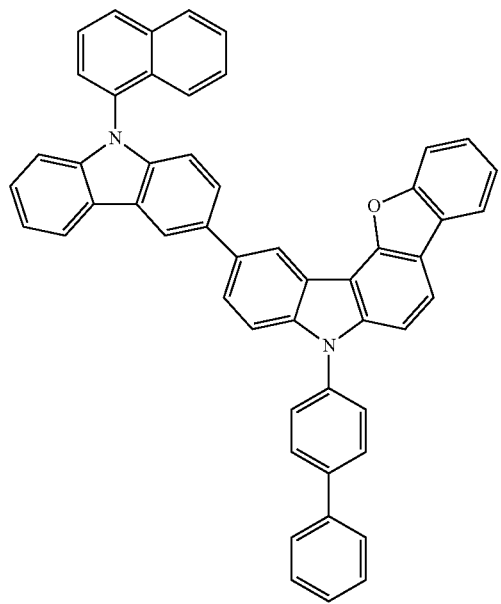
F-697
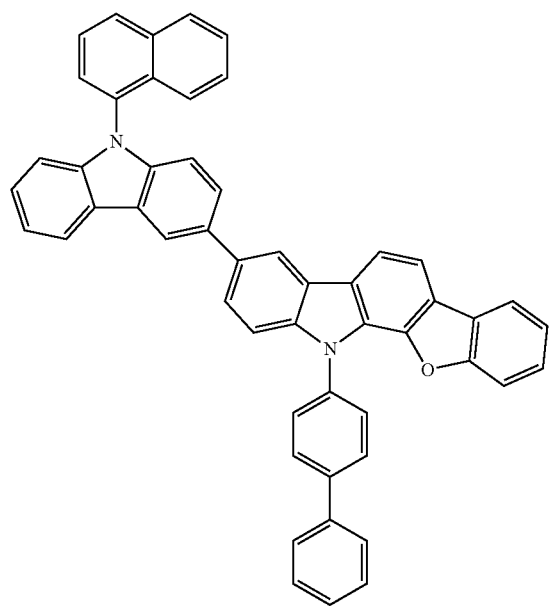
932
-continued
F-698
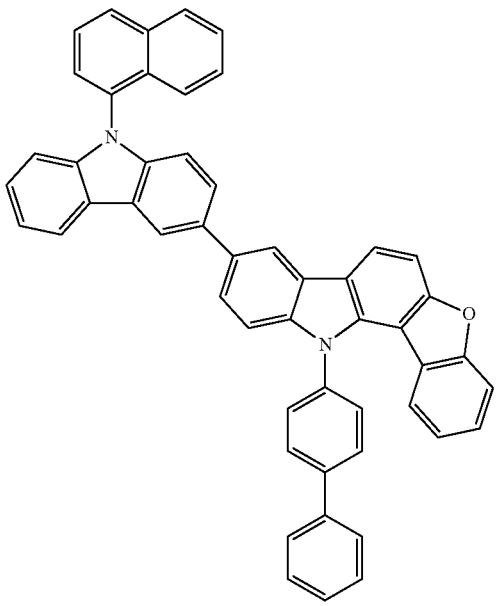
F-699
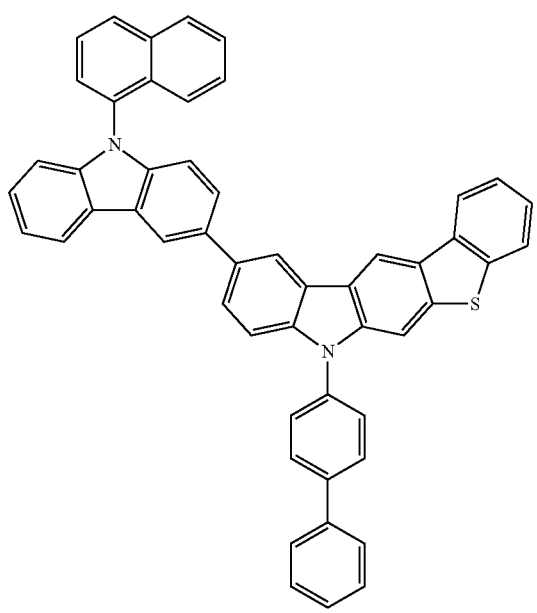

F-700
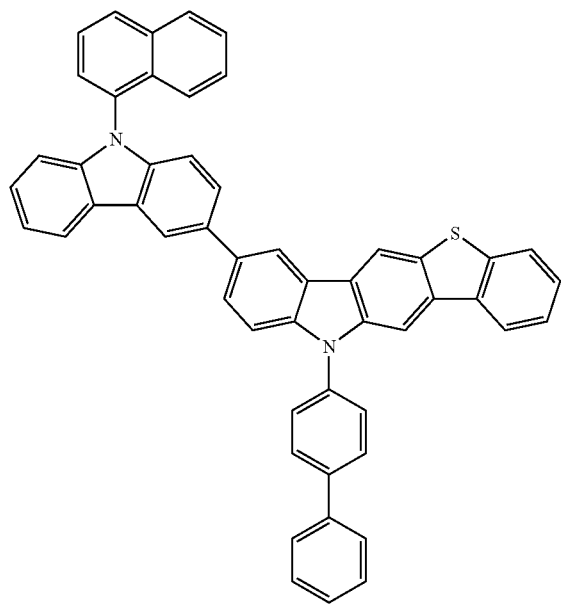
F-701
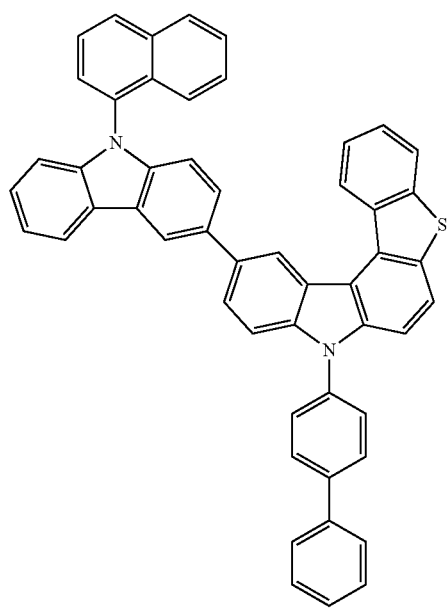
F-702
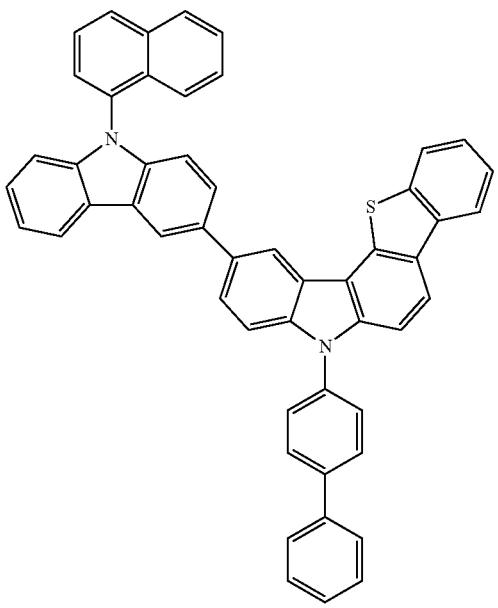
F-703
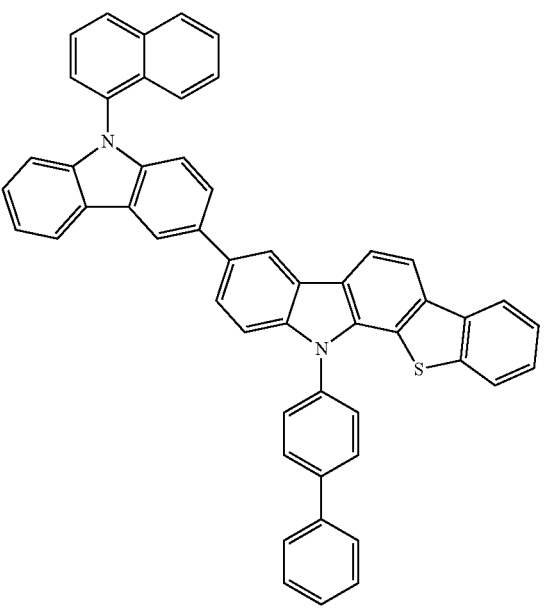

F-704
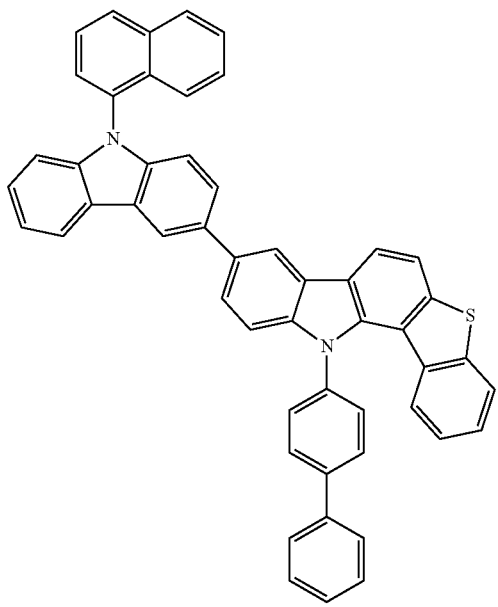
F-706
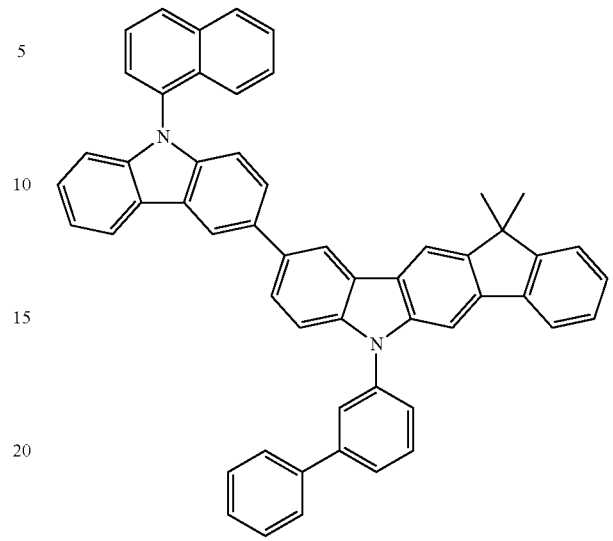
F-705
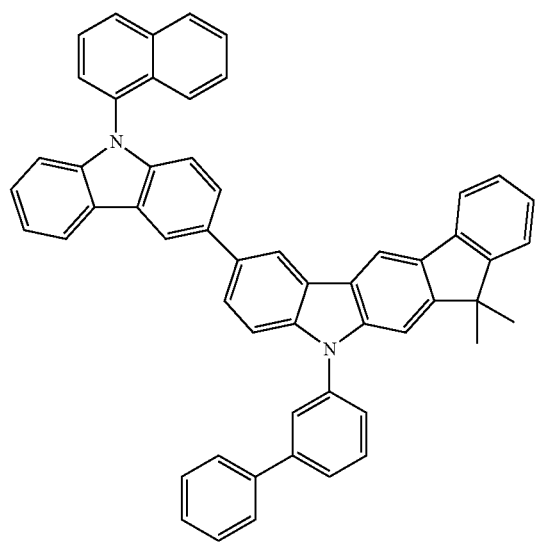
F-707
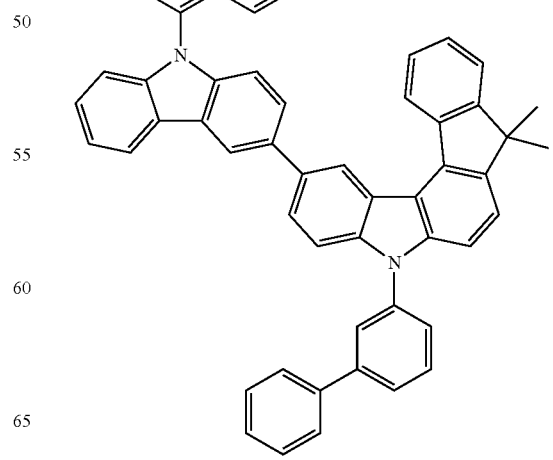

-continued
F-708
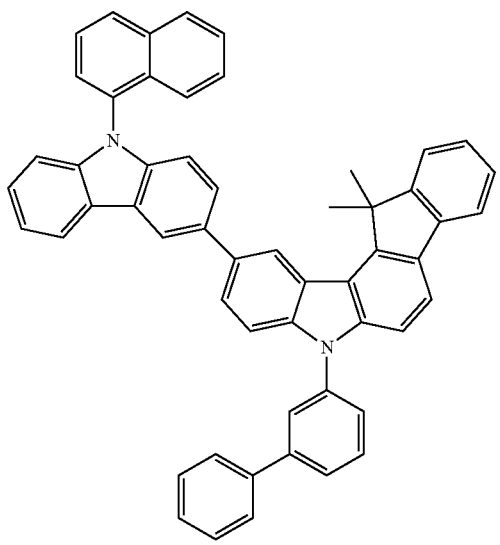
F-709
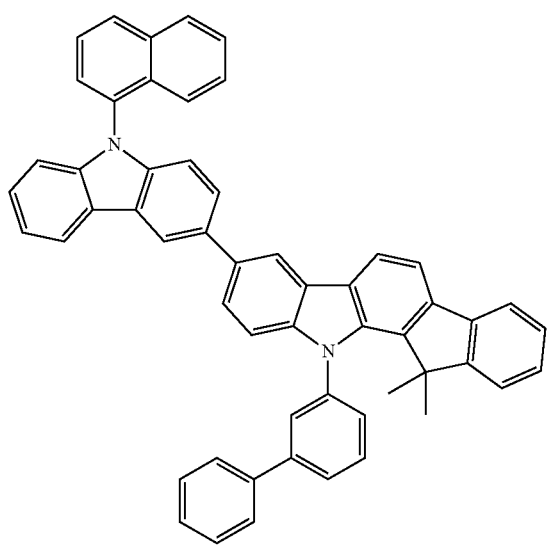
F-710
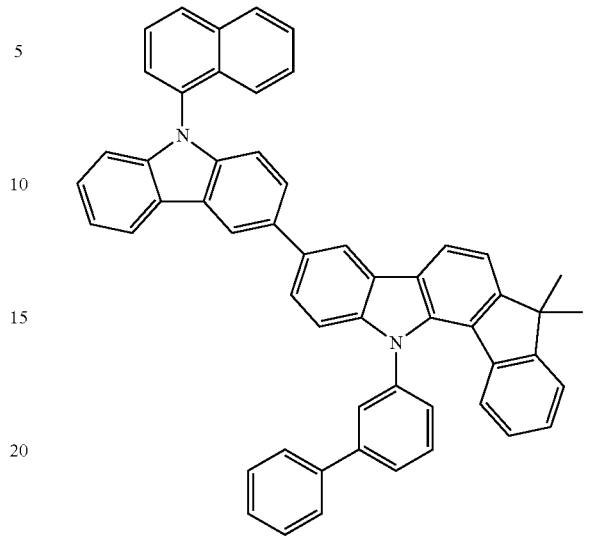
F-711
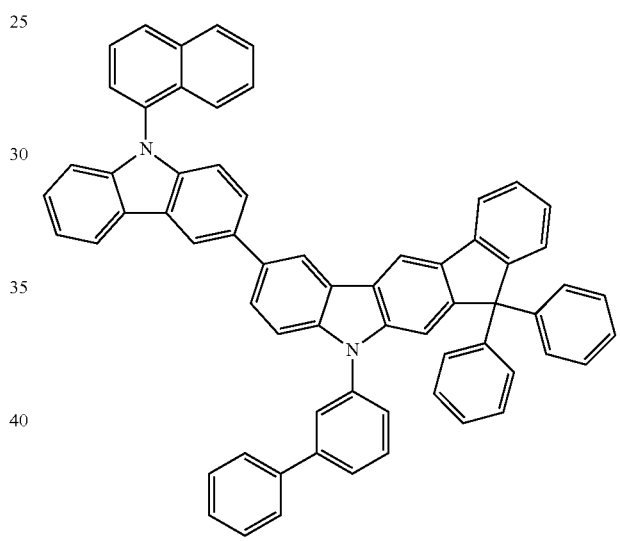
F-712
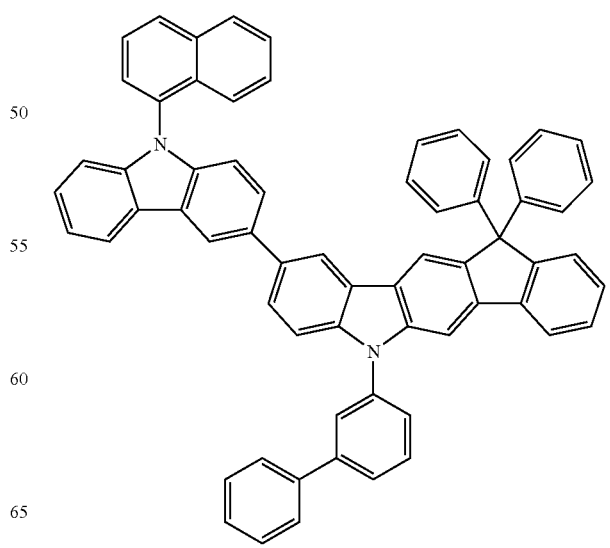

F-713
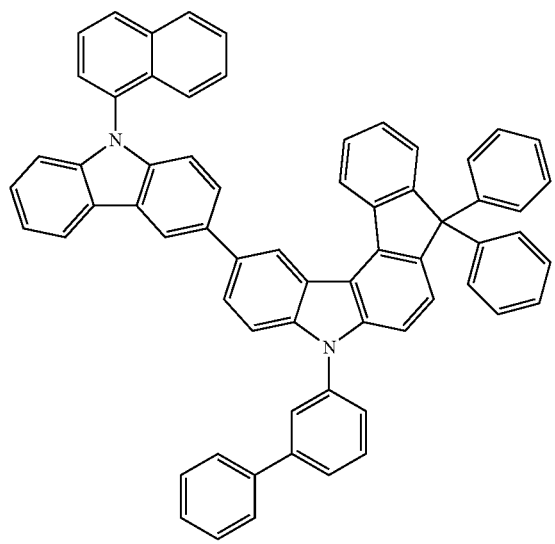
F-716
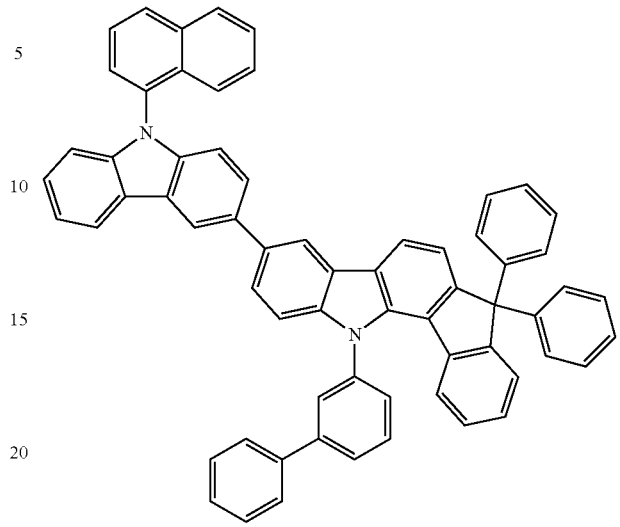
F-714
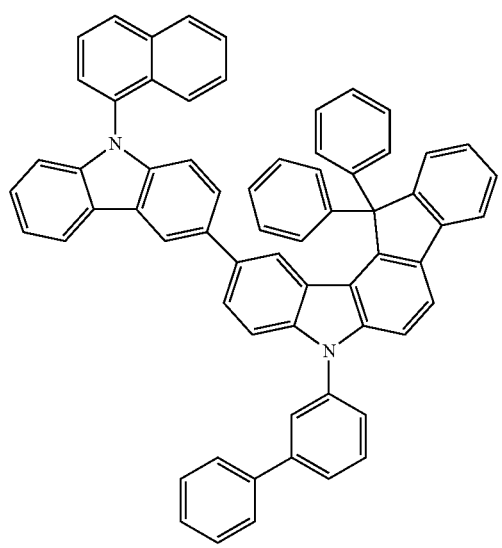
F-717
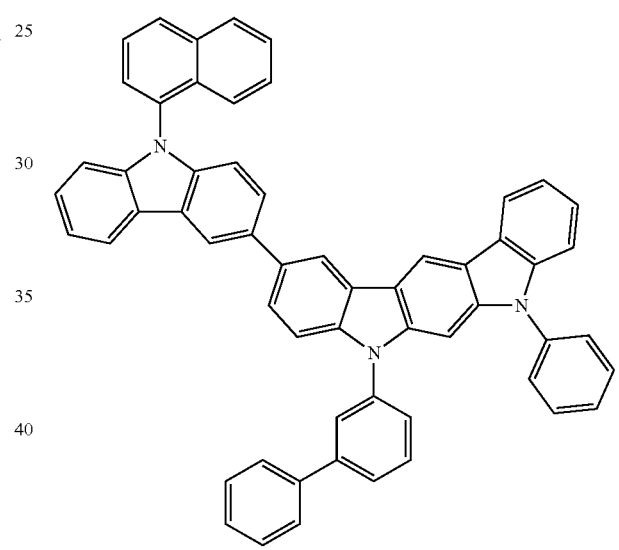
F-715
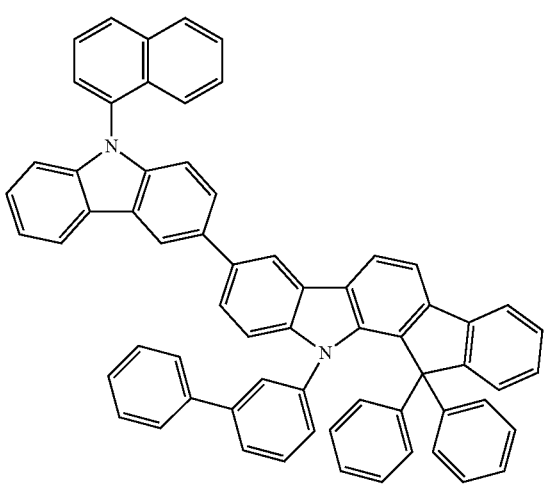
F-718
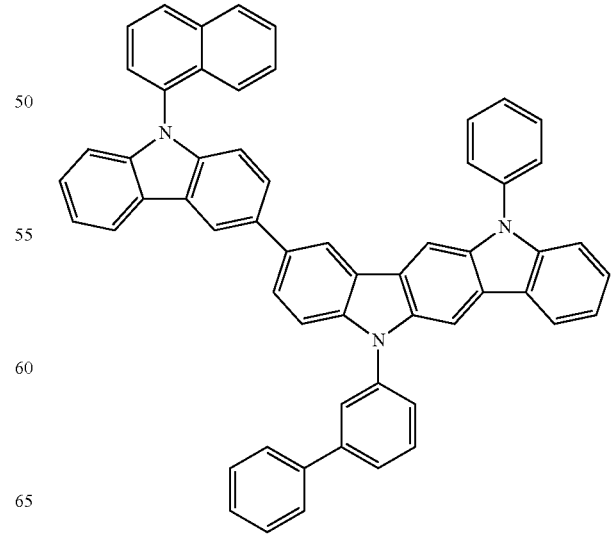

-continued
F-719
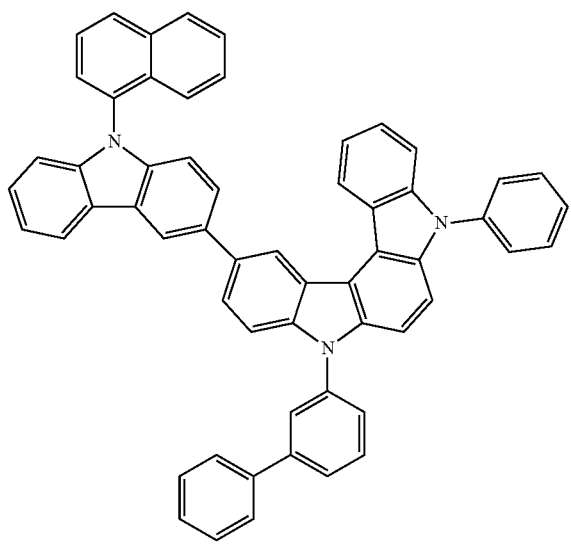
F-720
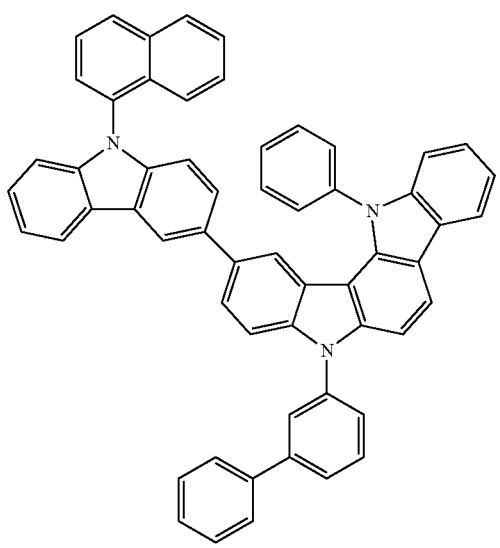
F-721
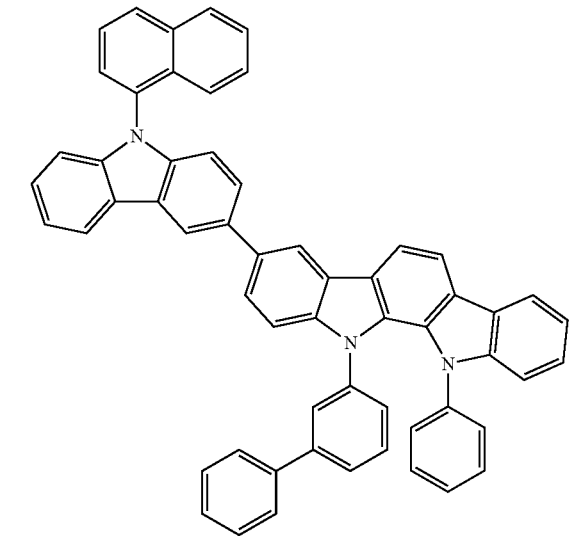
F-722
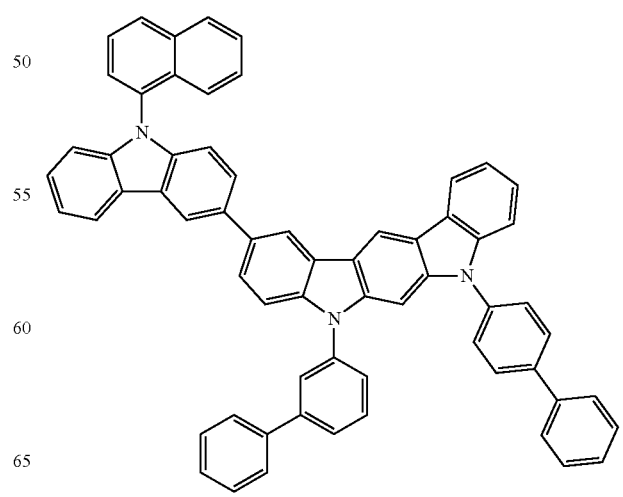
F-723

-continued
F-724
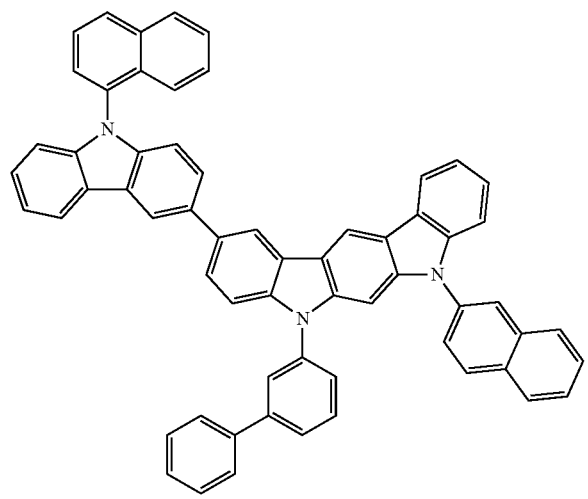
F-275
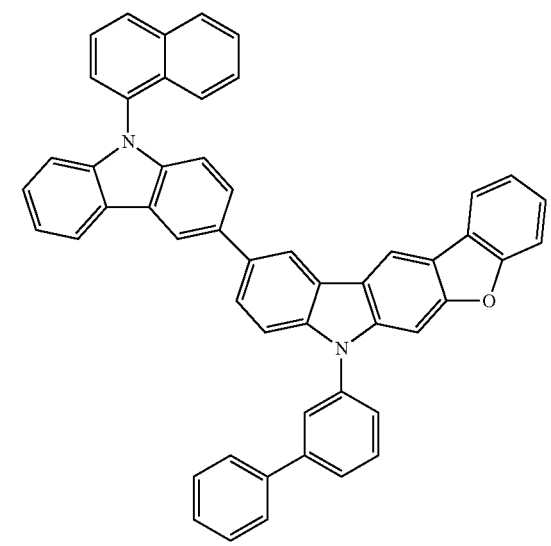
F-276
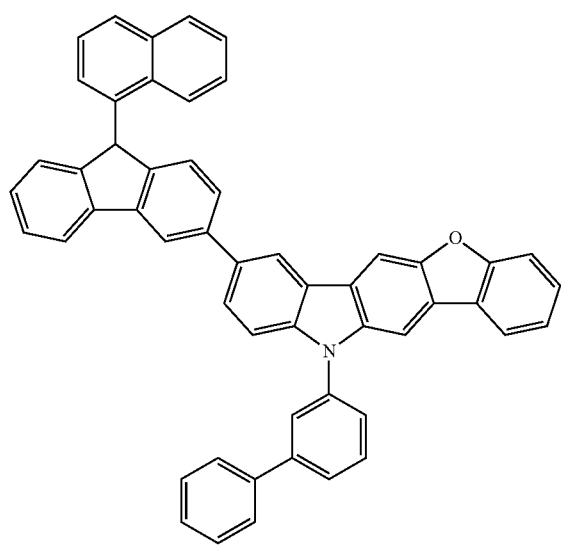
-continued
F-277
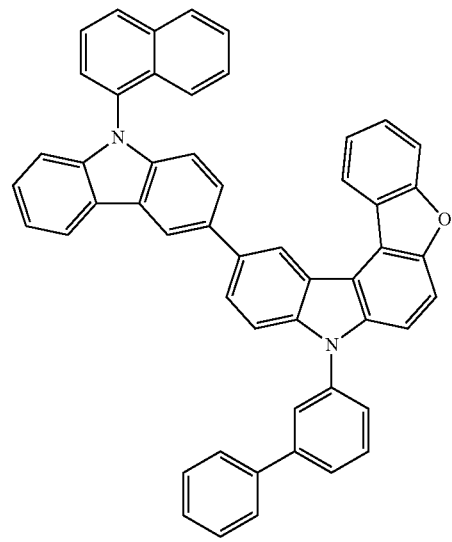
F-728
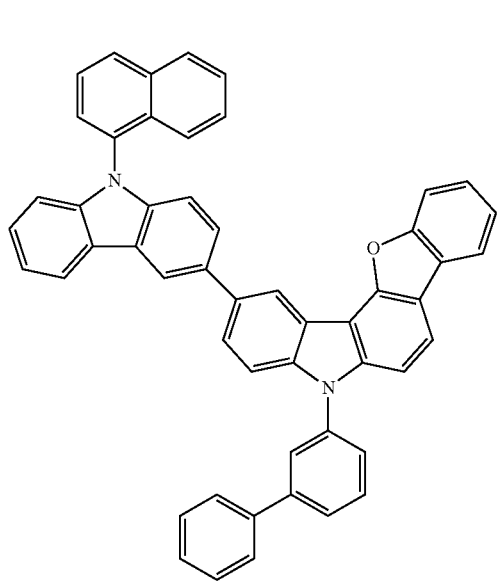
F-729
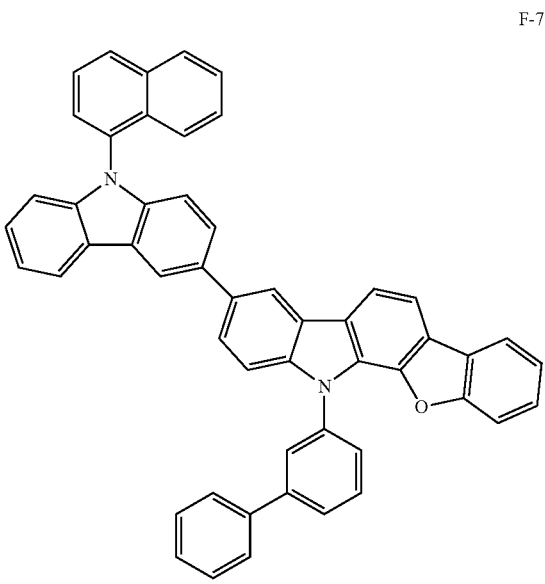

-continued
F-730
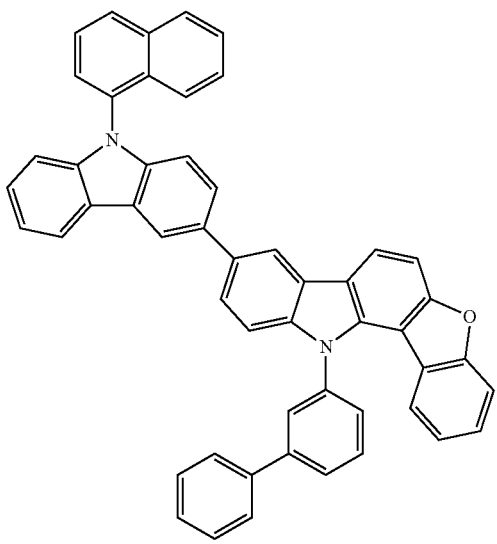
F-731
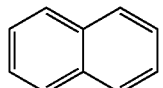
F-732
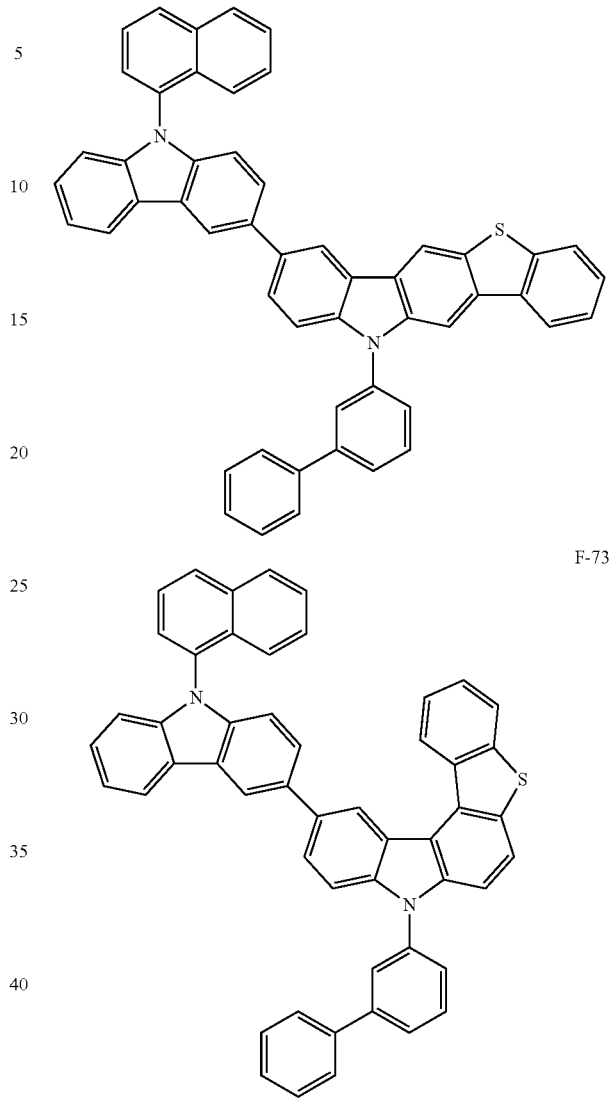
F-733
F-734

F-735
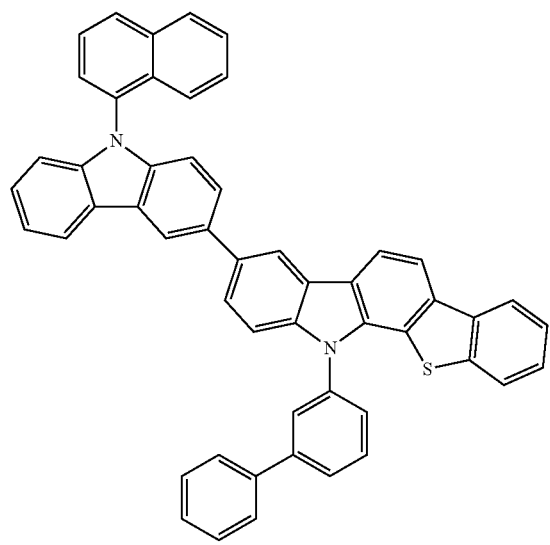
F-737
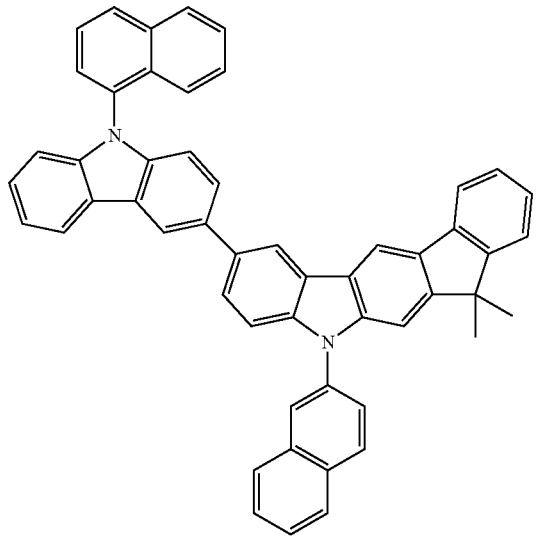
F-736
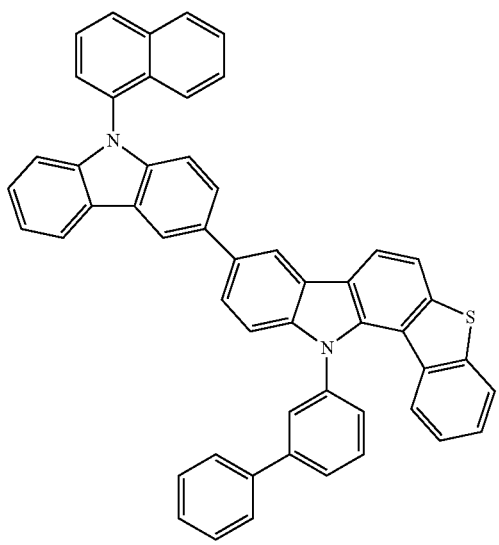
F-738
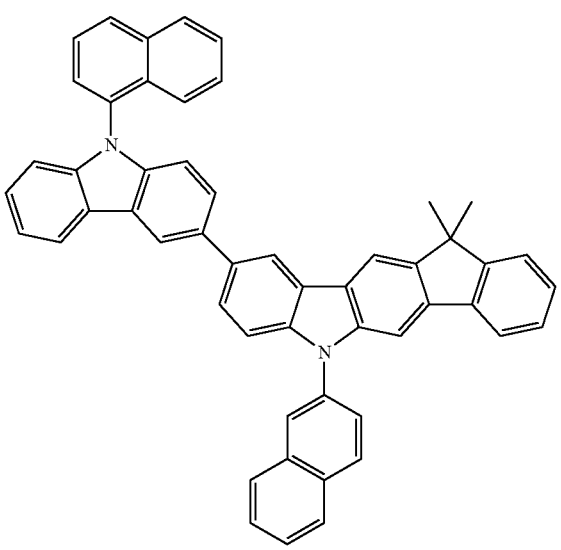

F-739
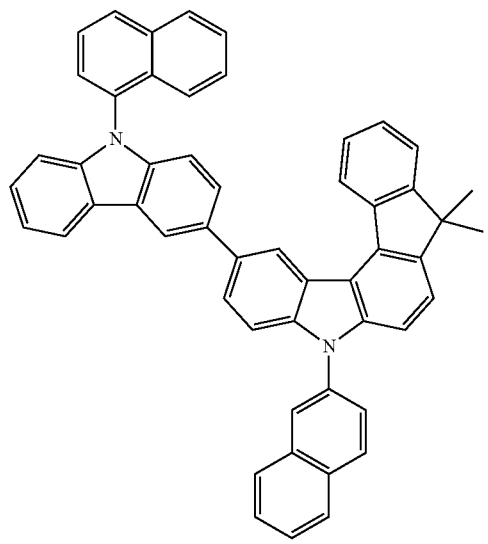
F-742
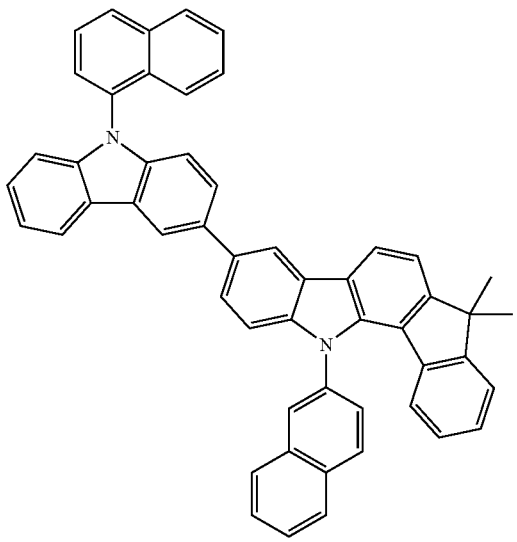
F-740
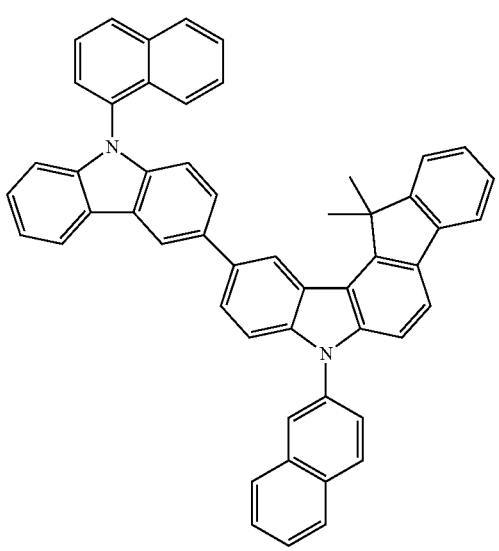
F-743
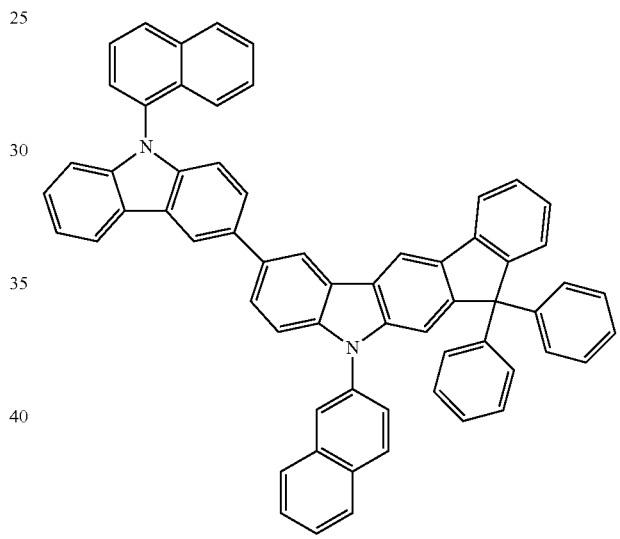
F-741
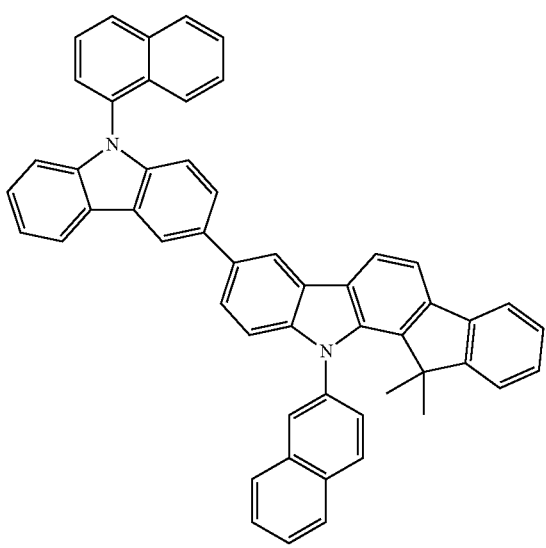
F-744
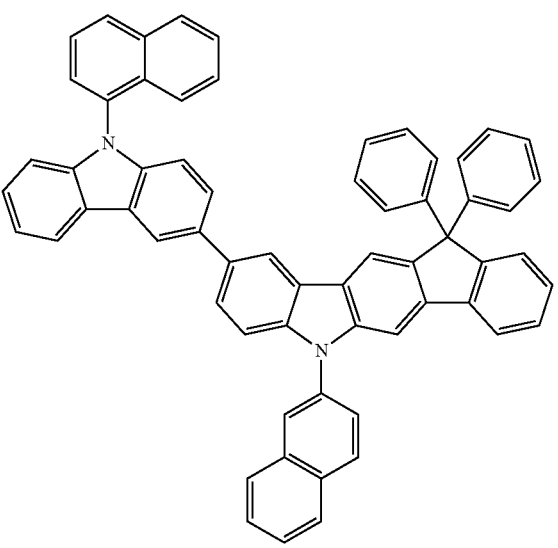

-continued
F-745
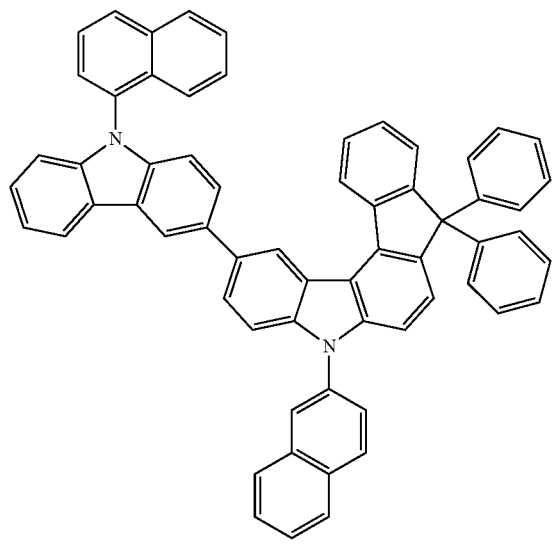
F-746
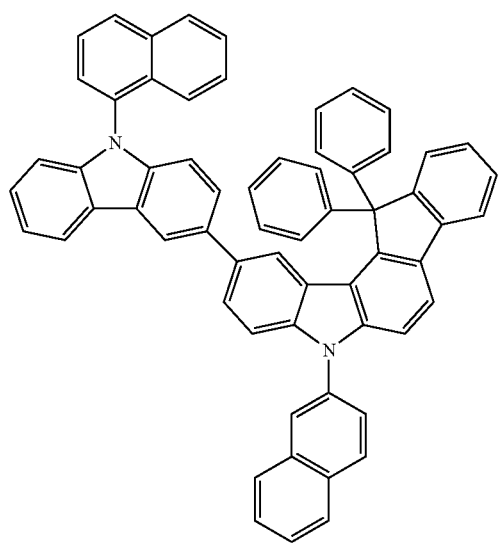
F-747
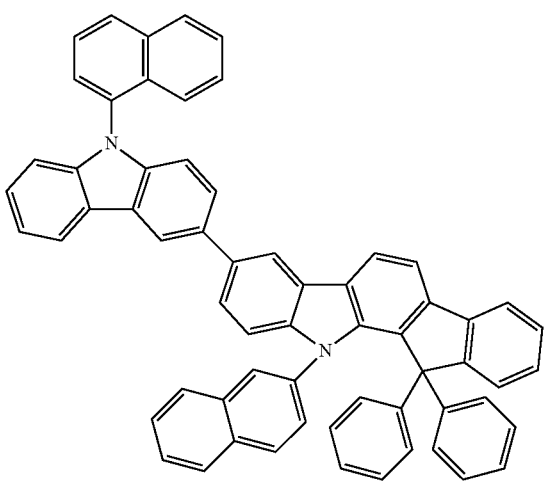
-continued
F-748
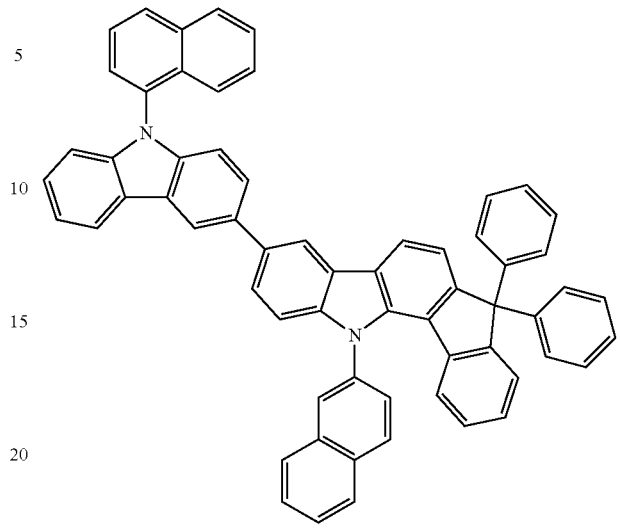
F-749
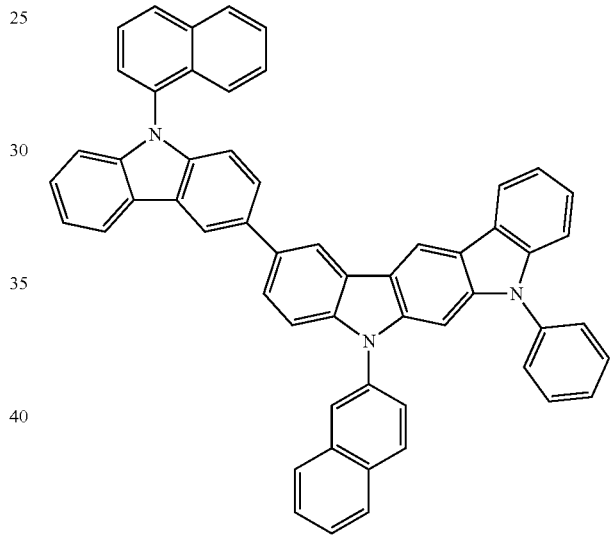
F-750
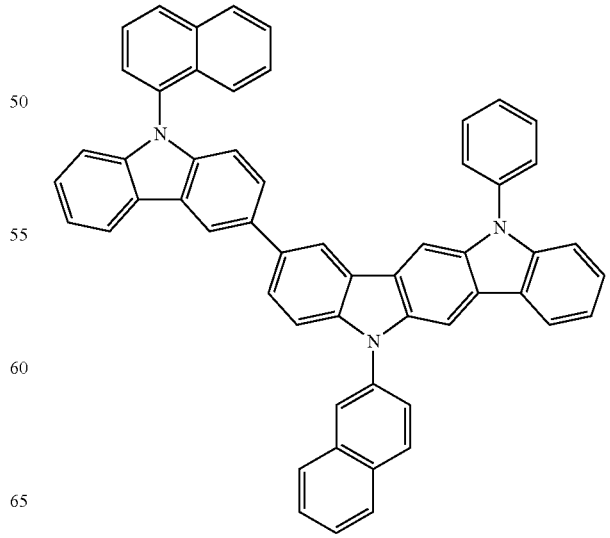

F-751
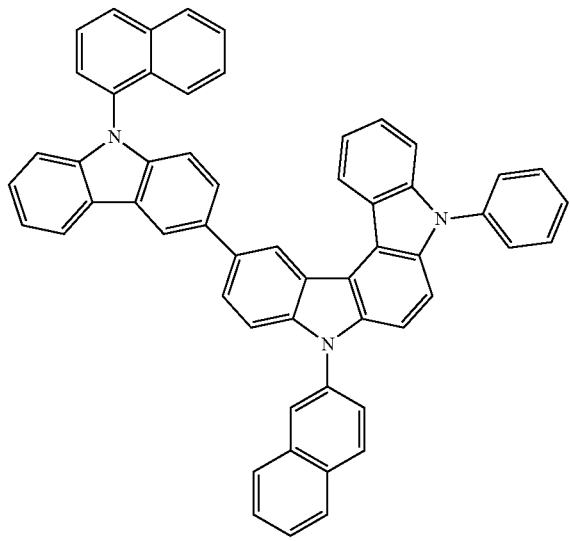
F-752
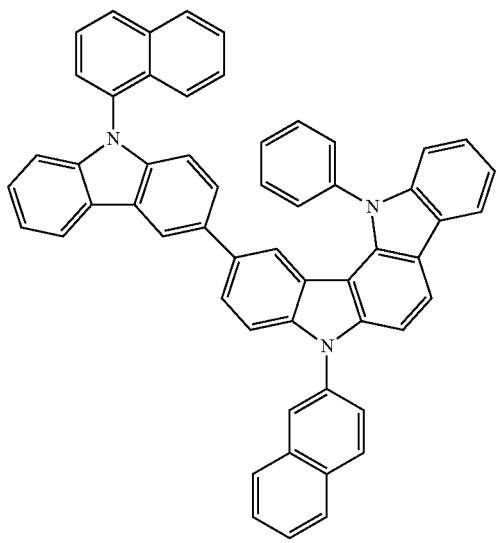
F-753
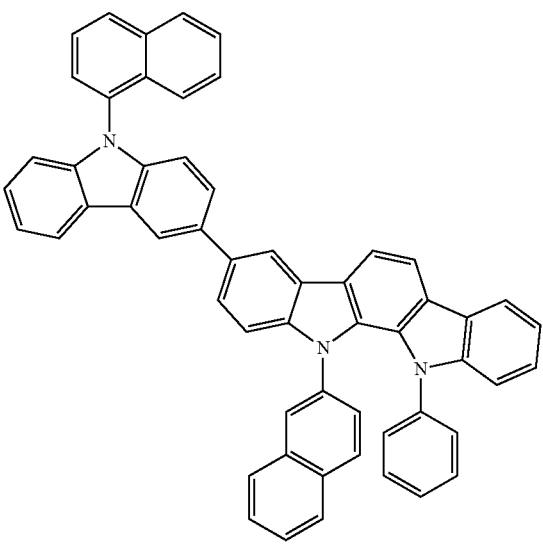
F-754
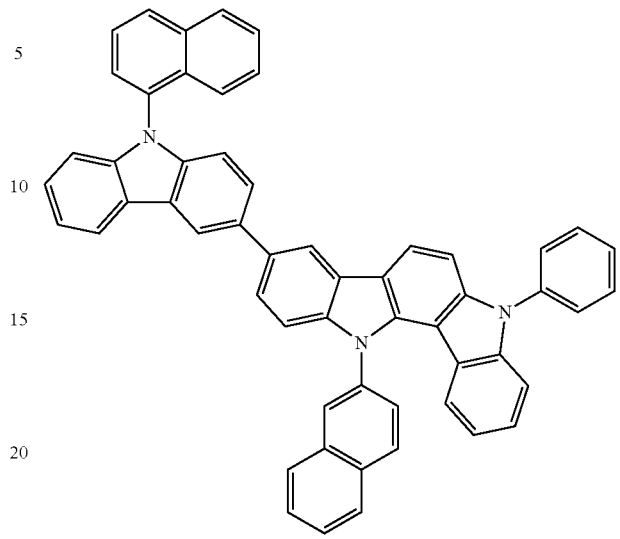
F-755
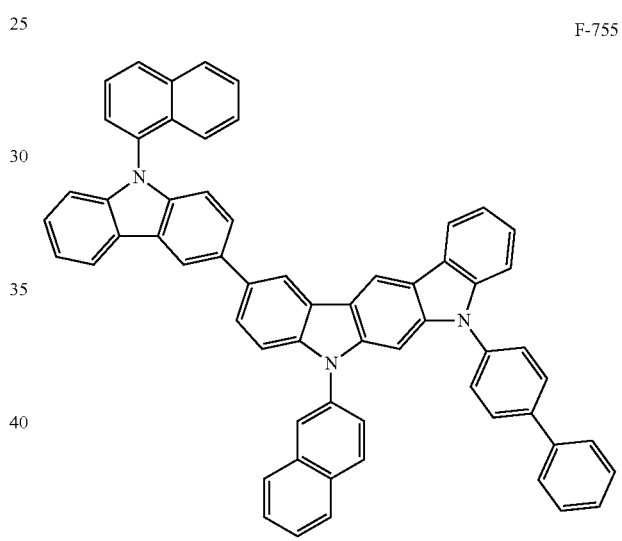
F-756
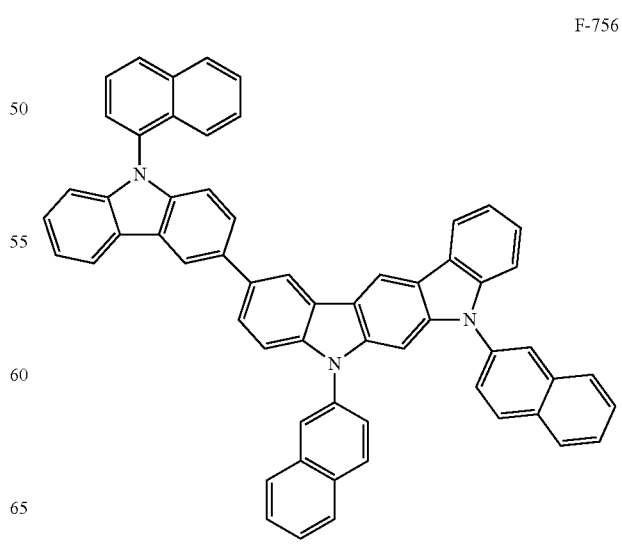

F-757
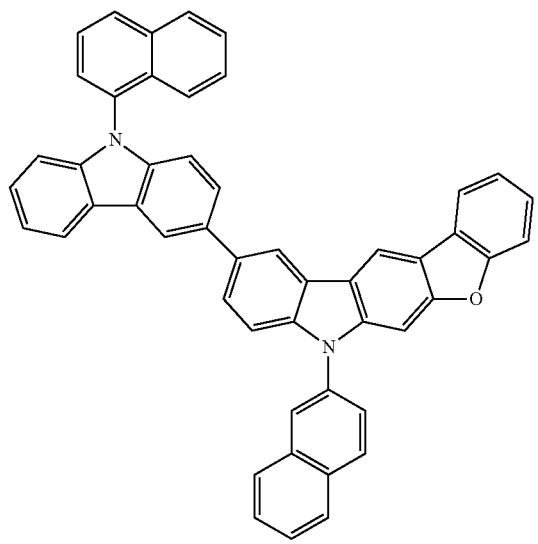
F-758
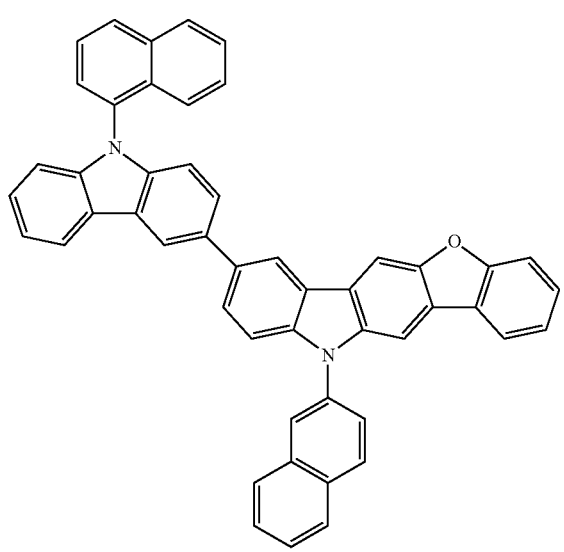
F-759
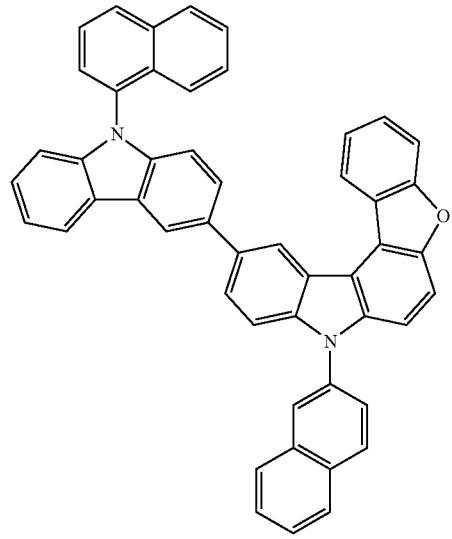
F-760
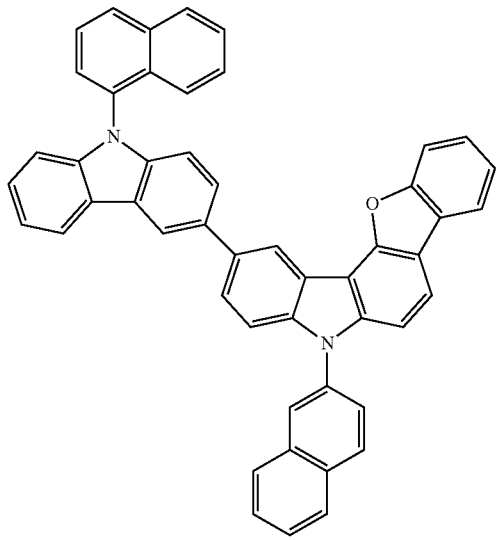
F-761
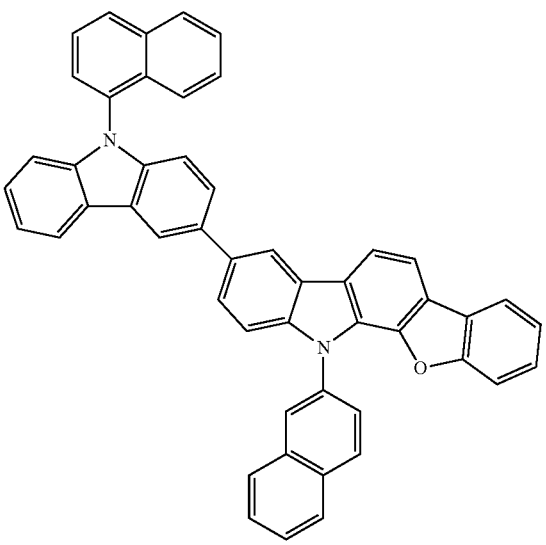
F-762
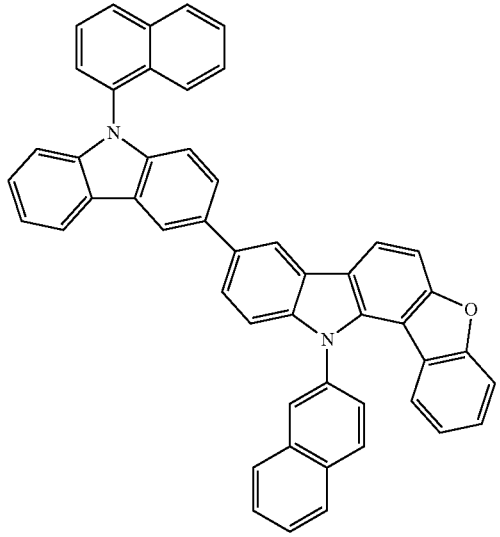

-continued
F-763
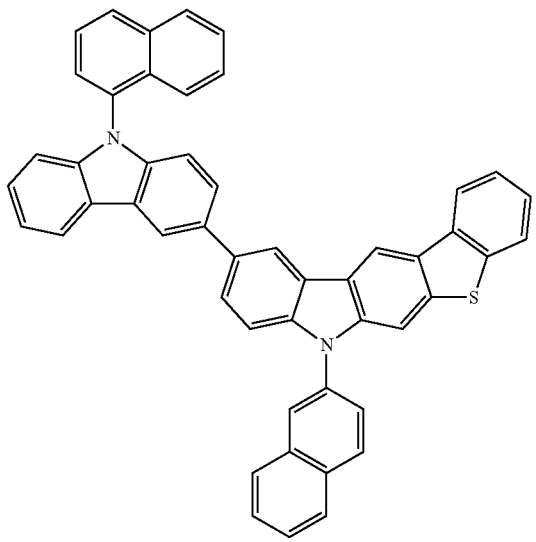
F-764
F-766
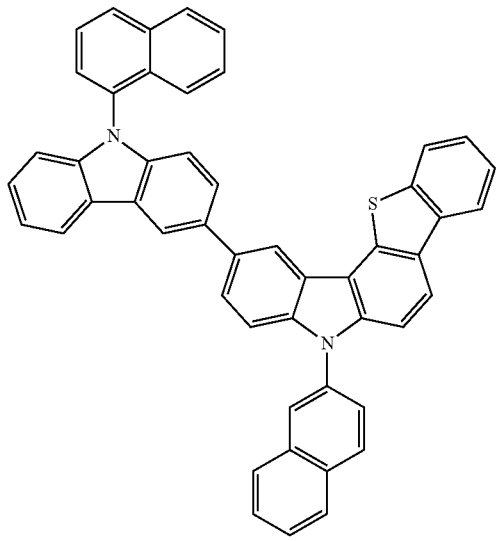
F-767
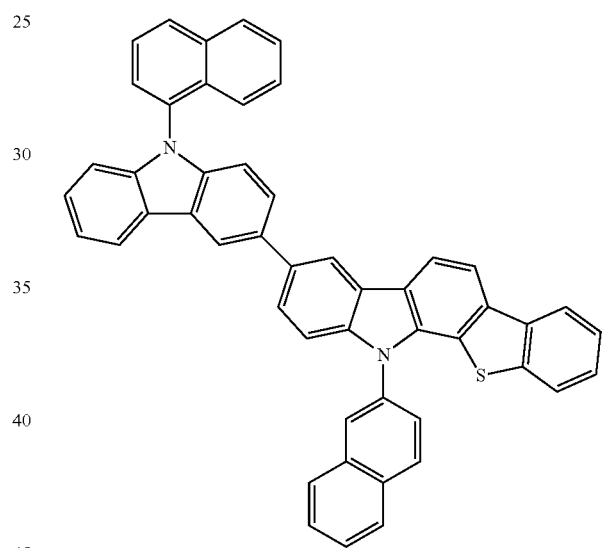
F-765
F-768
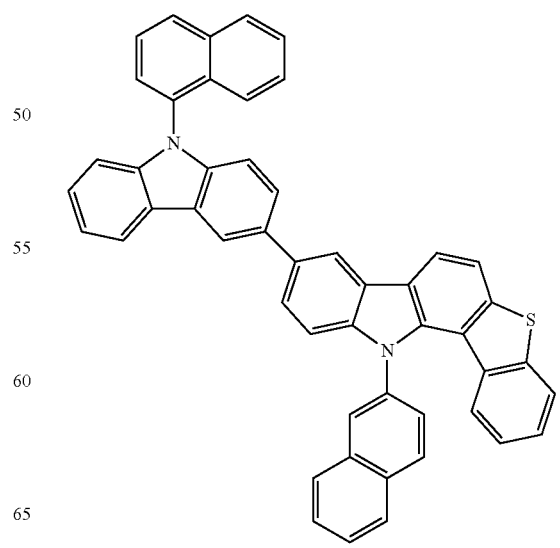

F-769
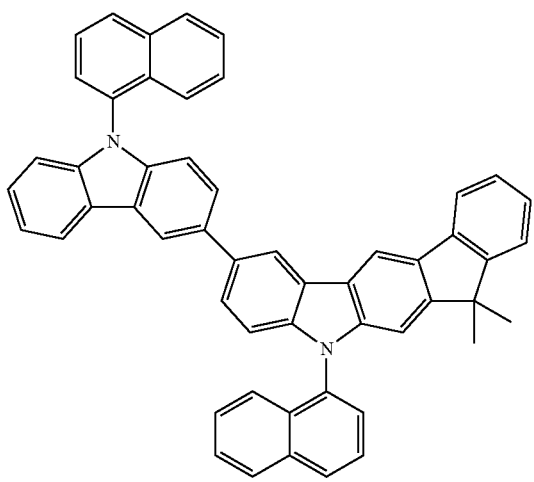
F-772
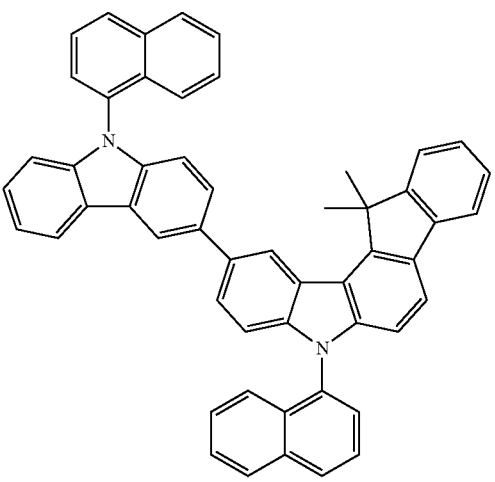
F-770
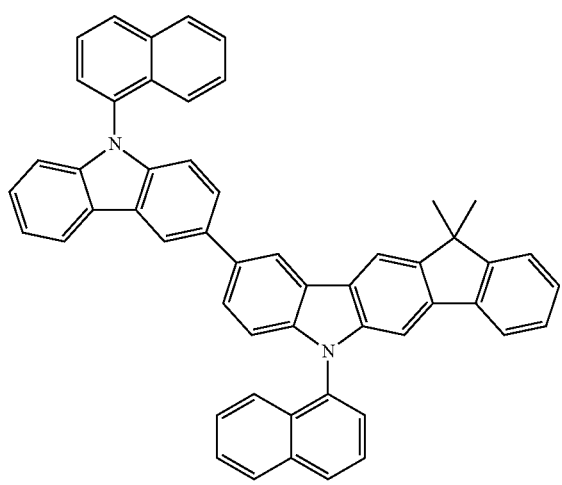
F-773
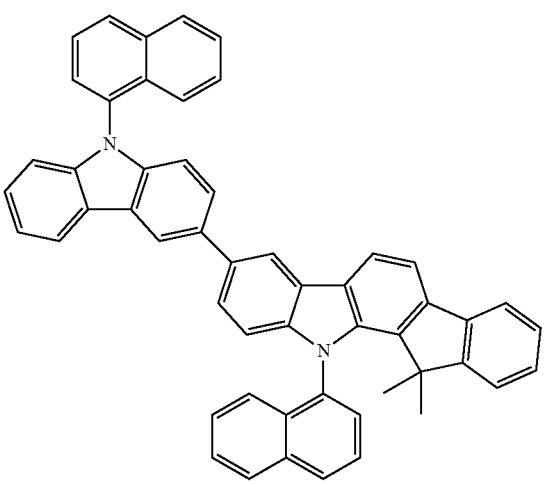
F-771
F-774
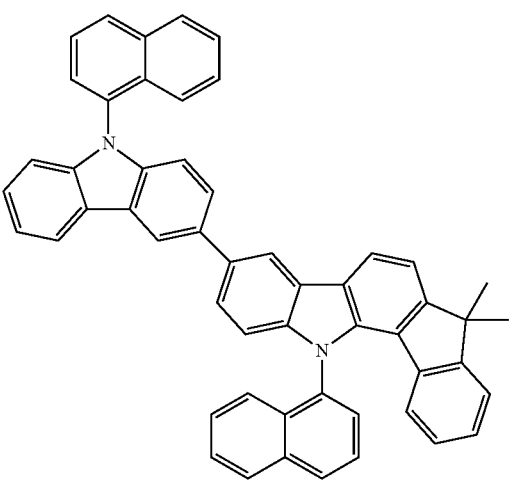

-continued
F-775
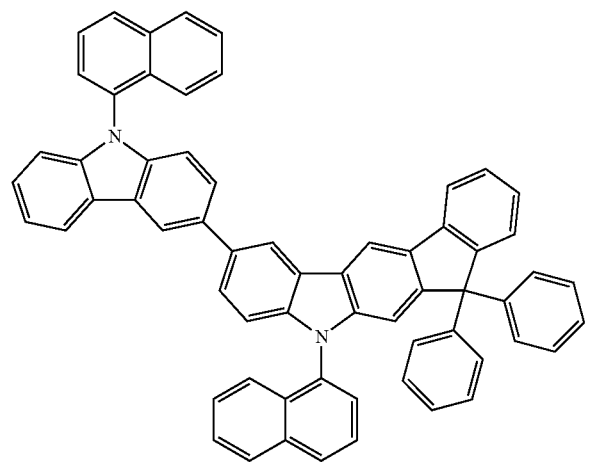
F-776
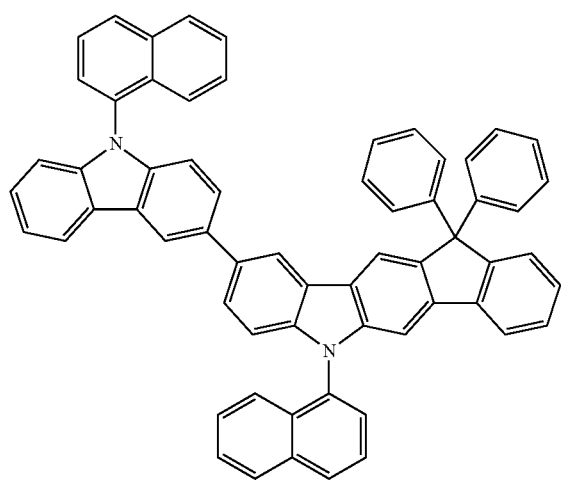
F-777
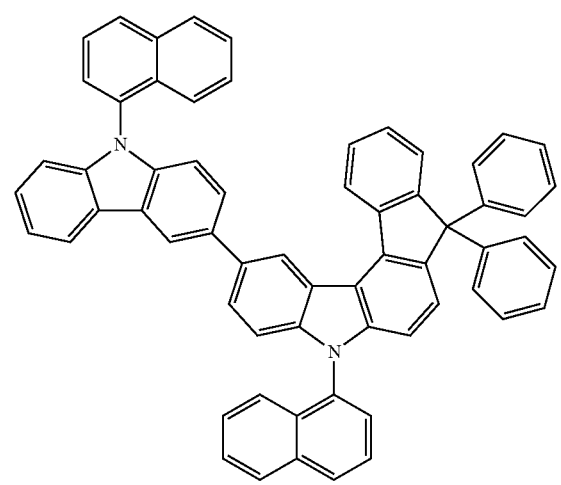
-continued
F-778
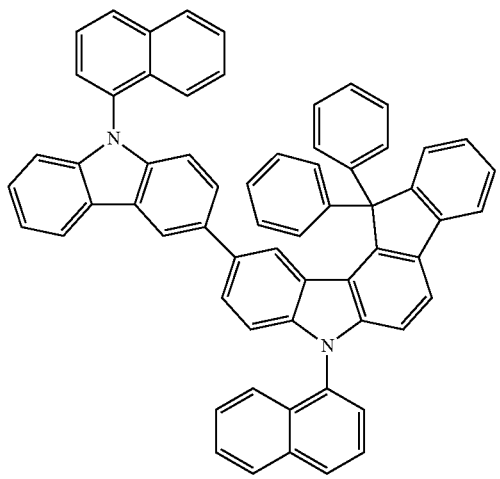
F-779
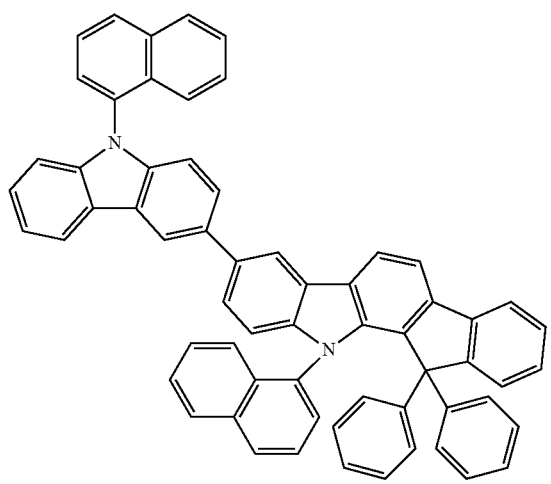
F-780
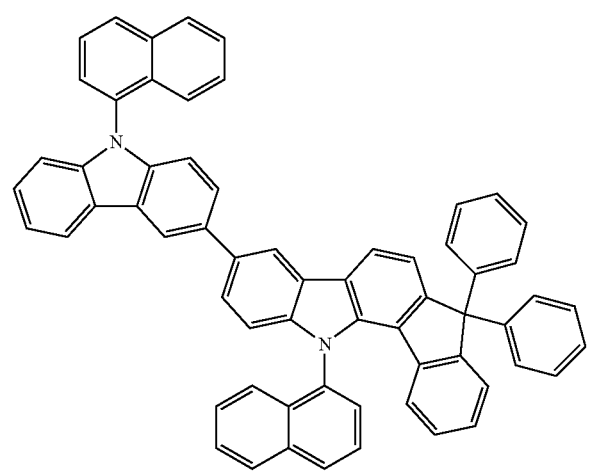

-continued
F-781
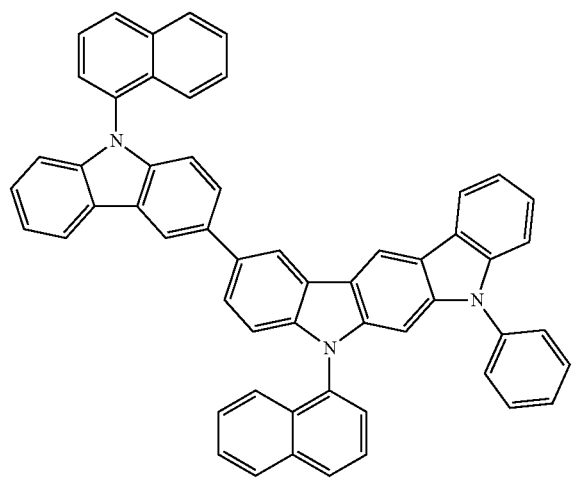
F-782
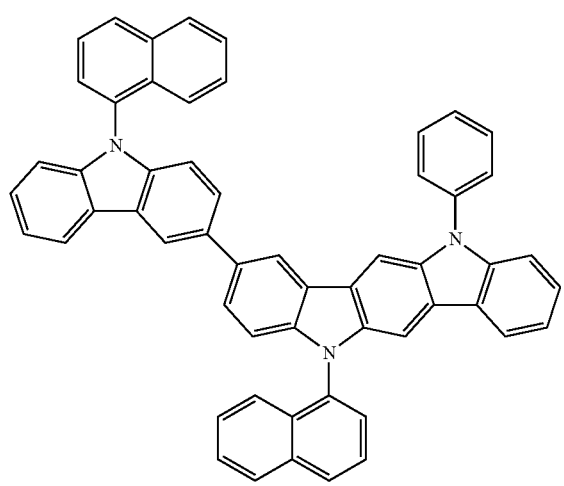
F-783
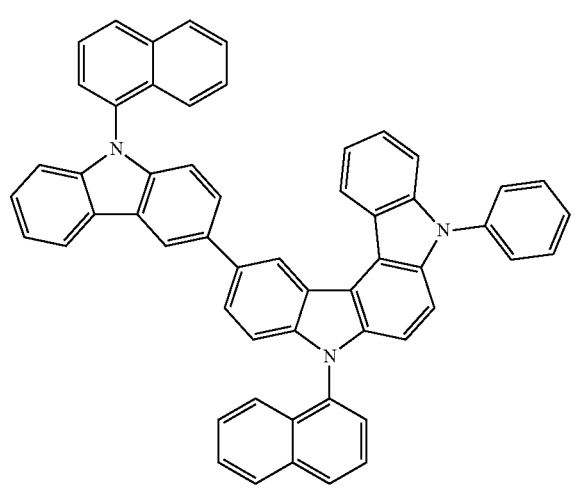
-continued
F-784
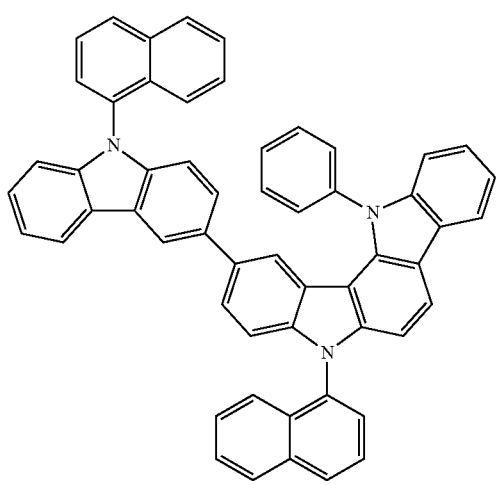
F-785
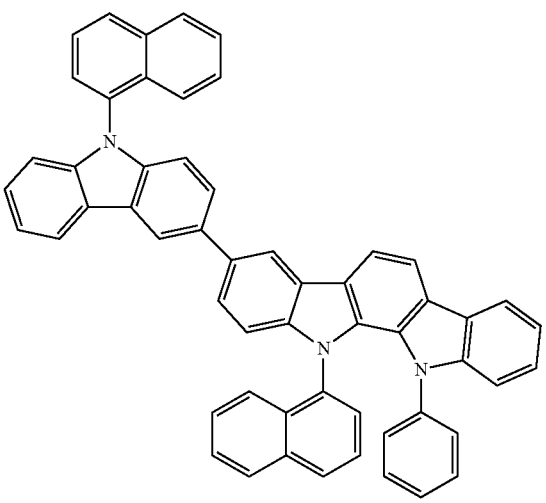
F-786
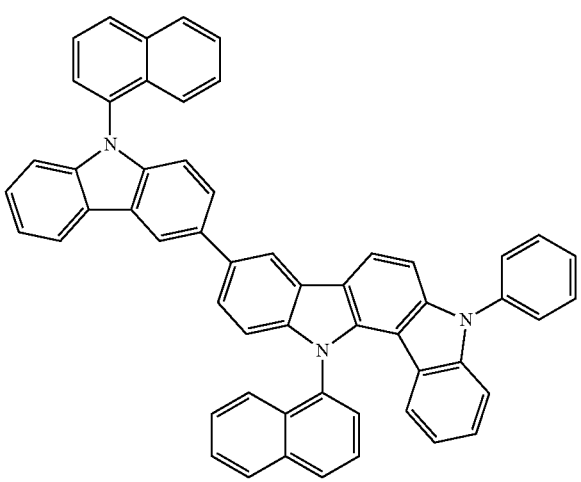

-continued
F-787
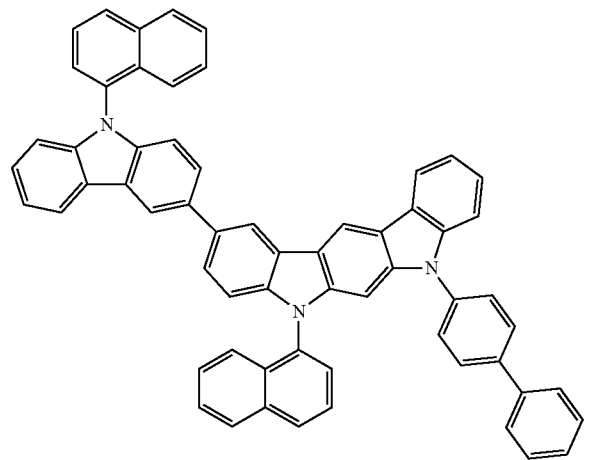
F-788
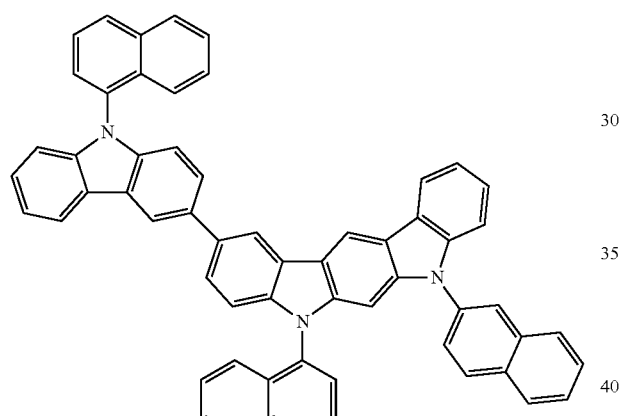
F-789
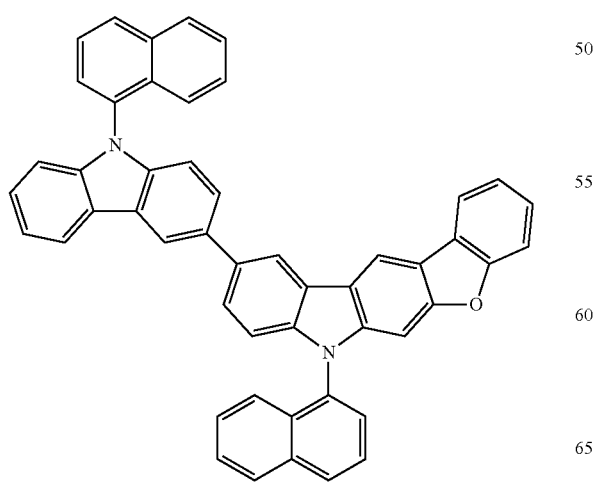
-continued
F-790
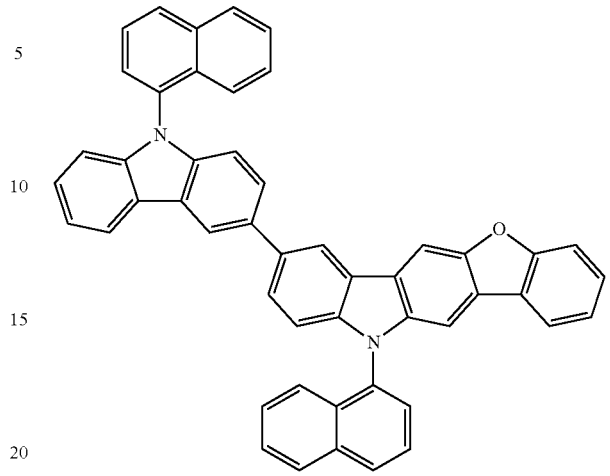
F-791
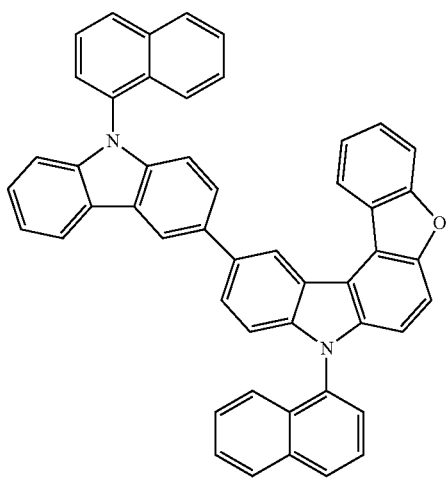
F-792
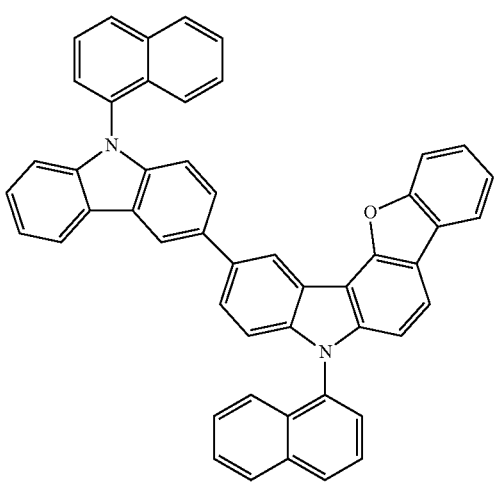

-continued
F-793
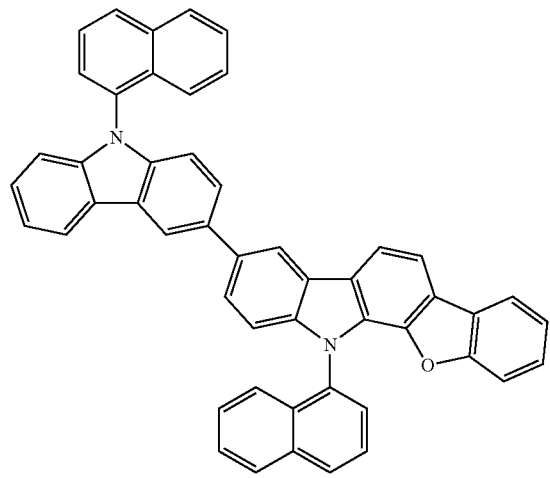
F-794
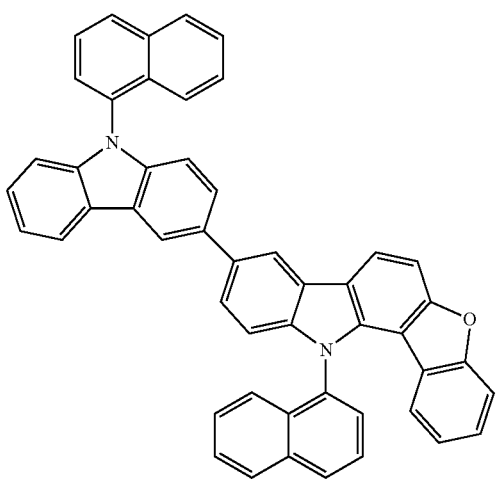
F-795
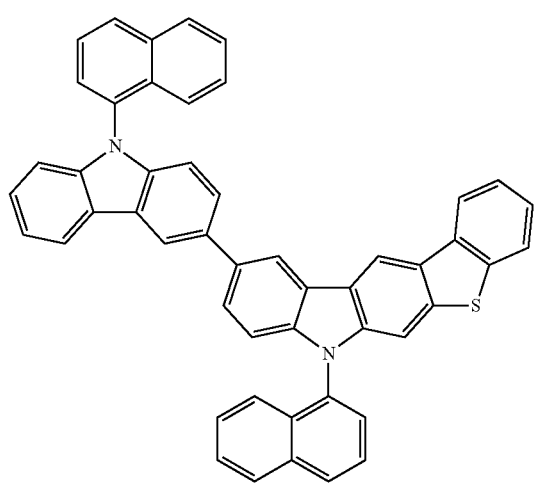
-continued
F-796
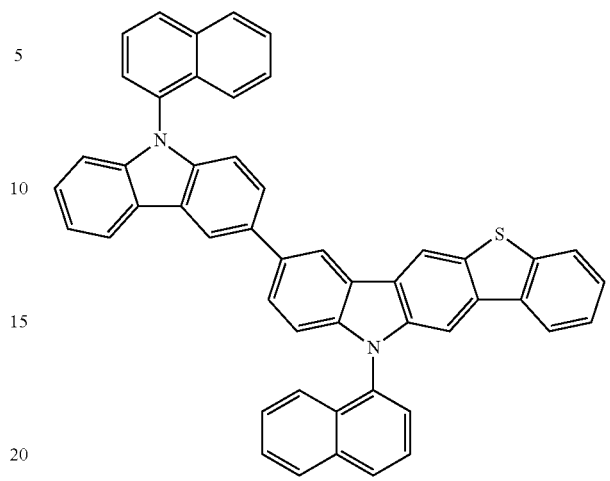
F-797
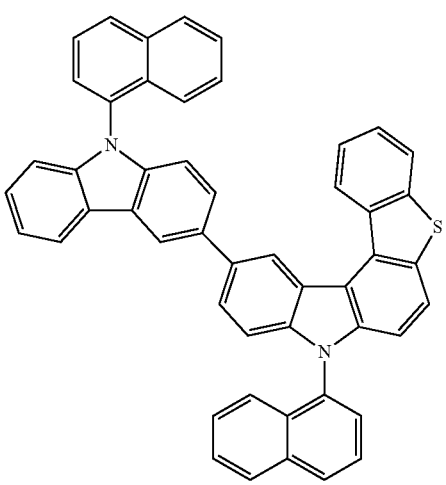
F-798
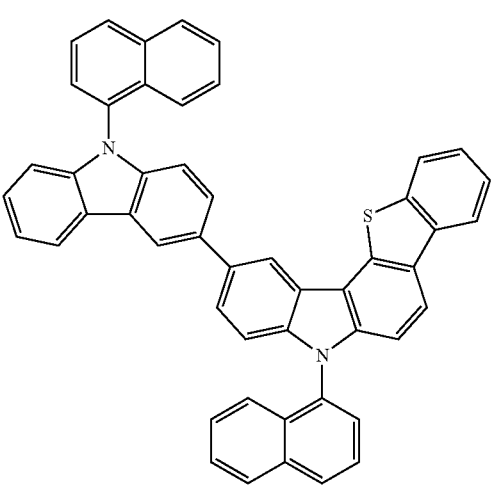

F-799
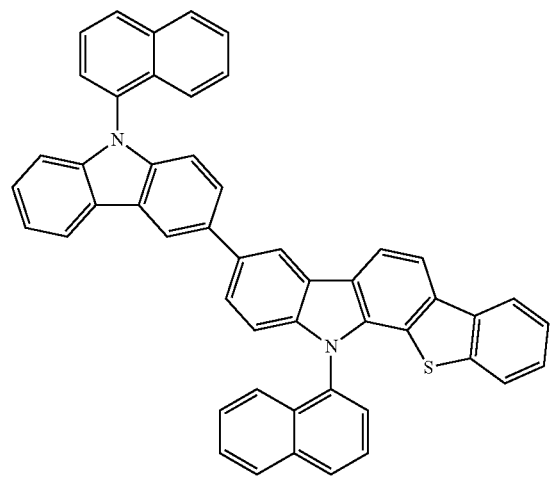
F-802
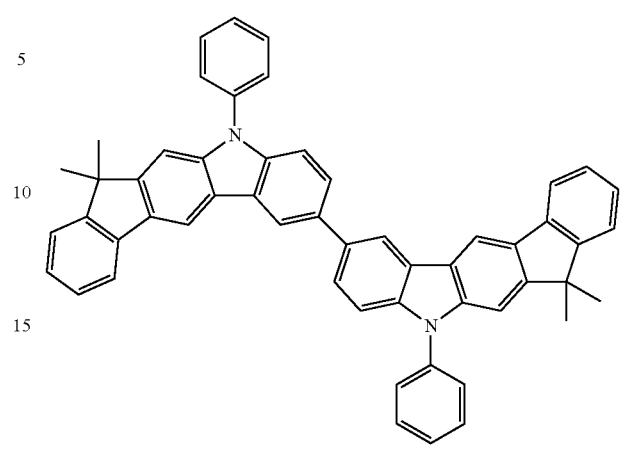
F-800
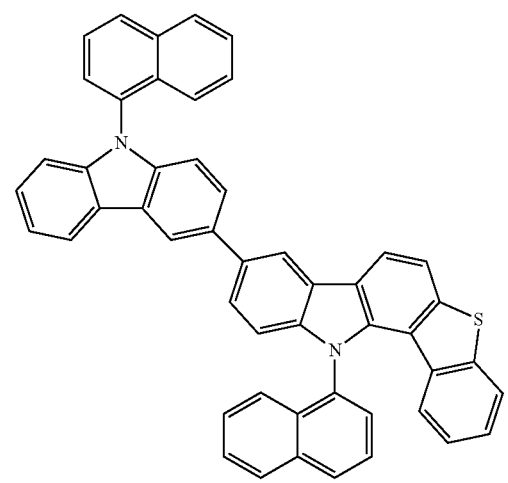
F-803
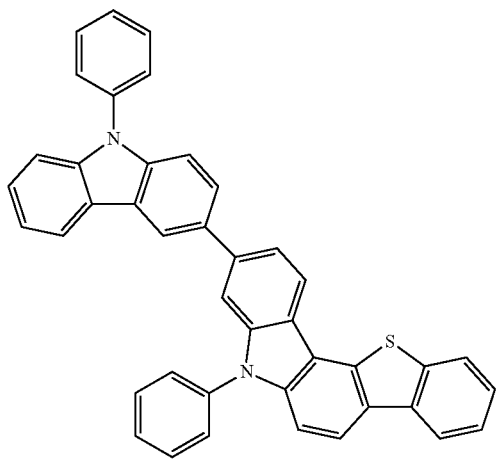
F-801
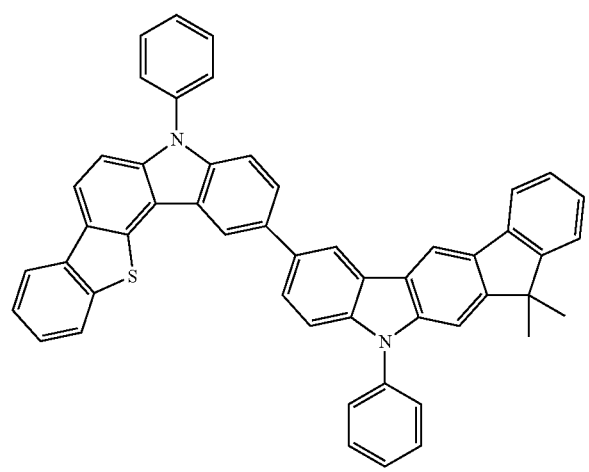
F-804
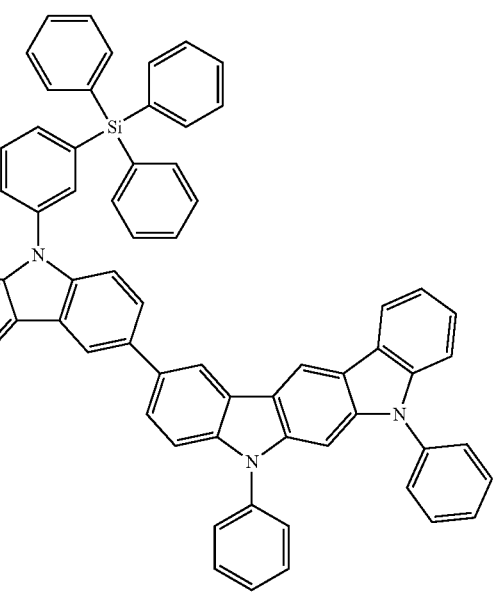

F-805
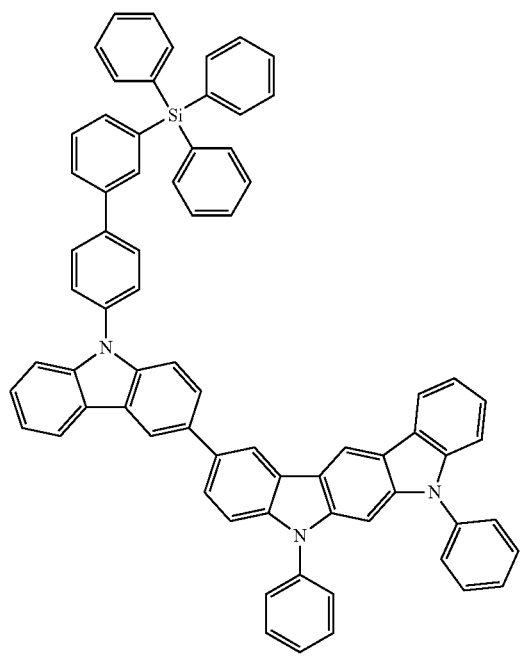
F-806
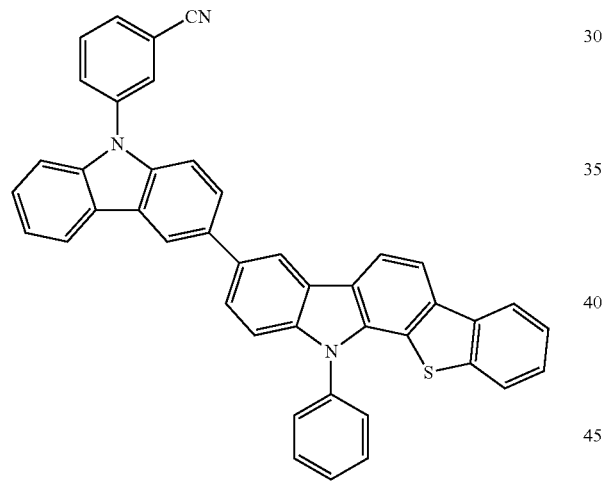
F-807
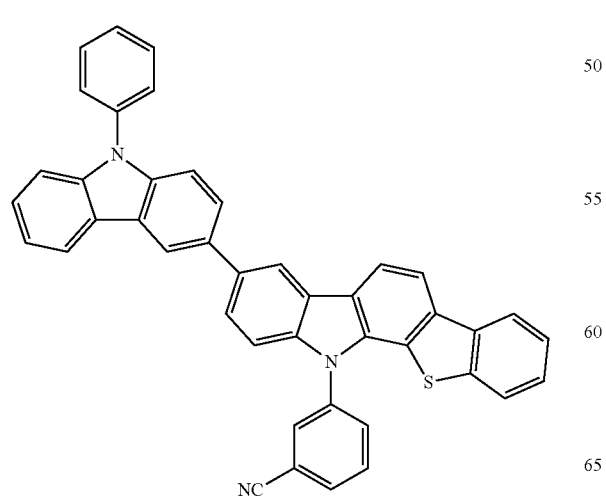
F-808
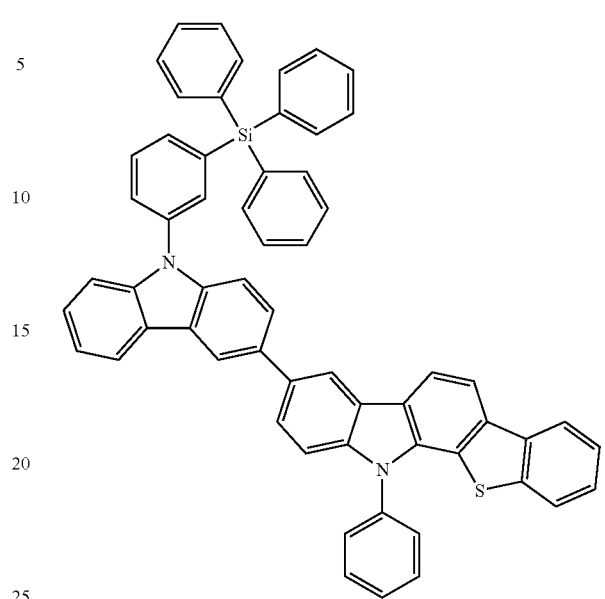
F-809
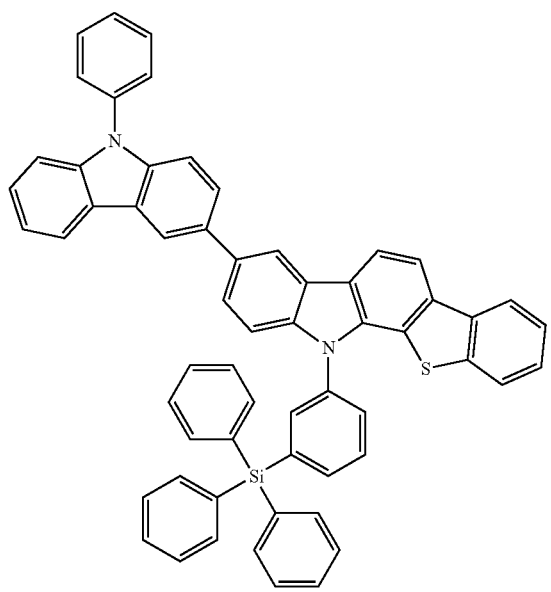

F-810
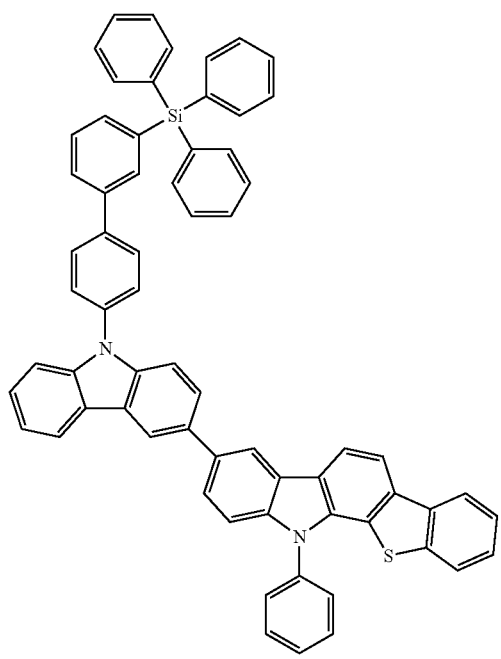
F-811
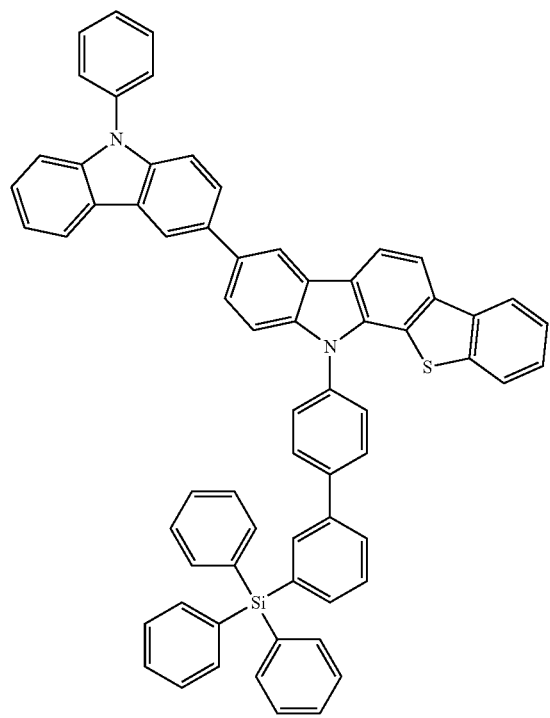
F-812
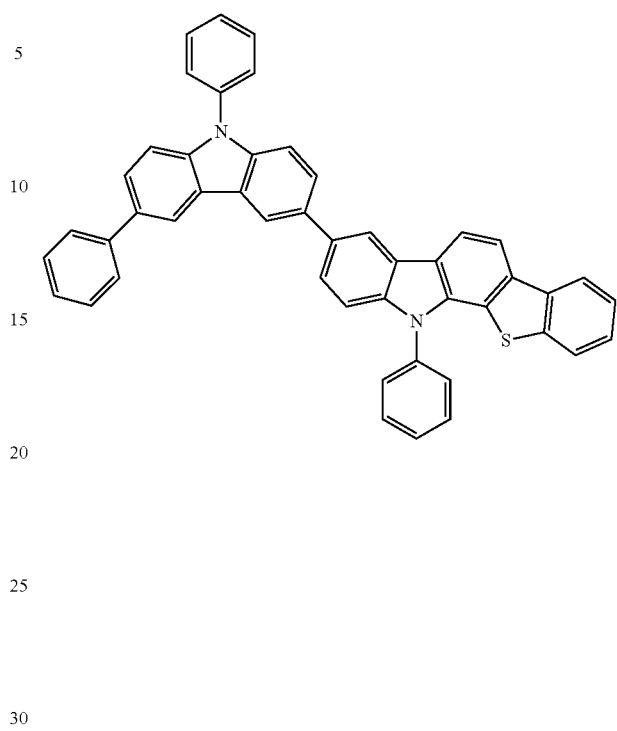
F-813
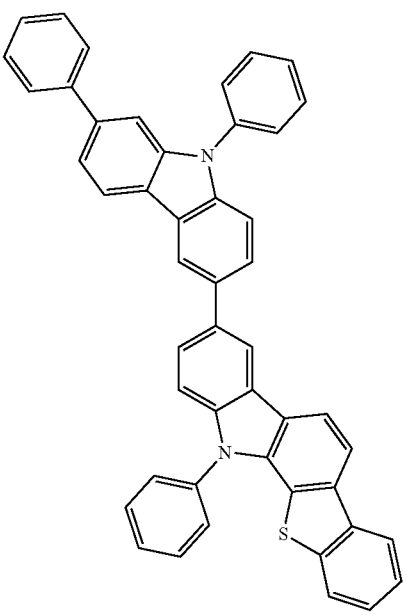

F-814
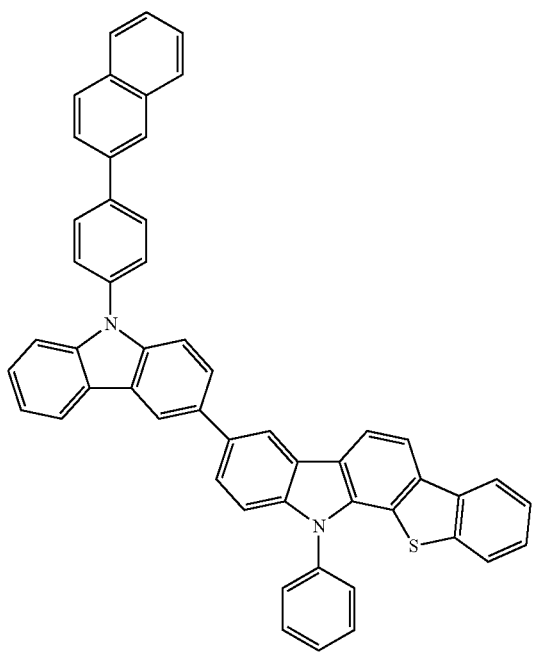
F-815
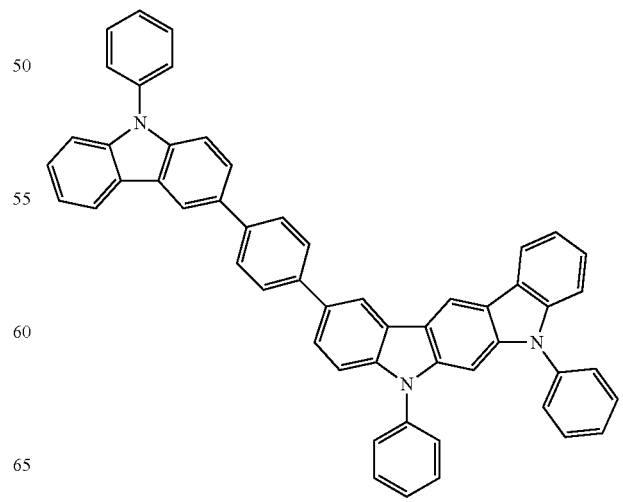
F-816
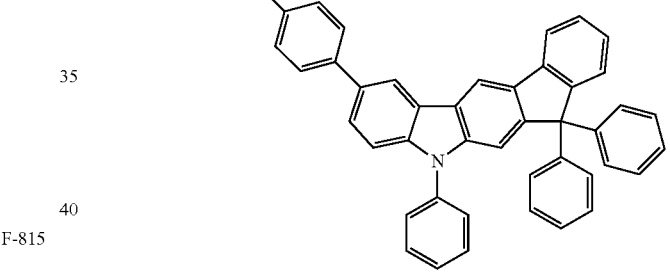
F-817
F-818

-continued
F-819
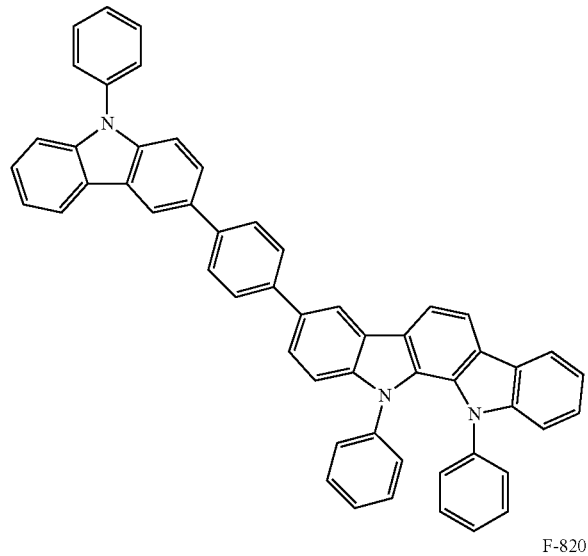
F-820
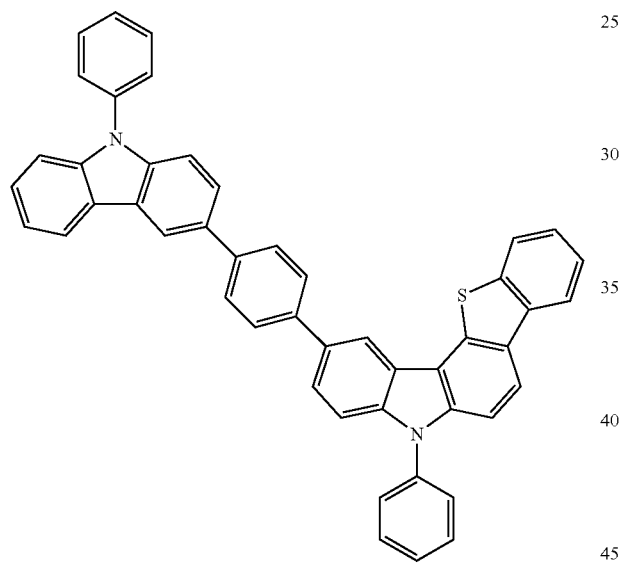
F-821
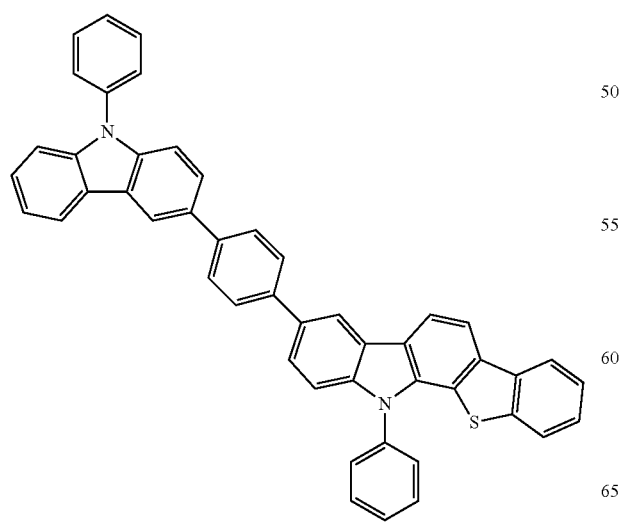
-continued
F-822
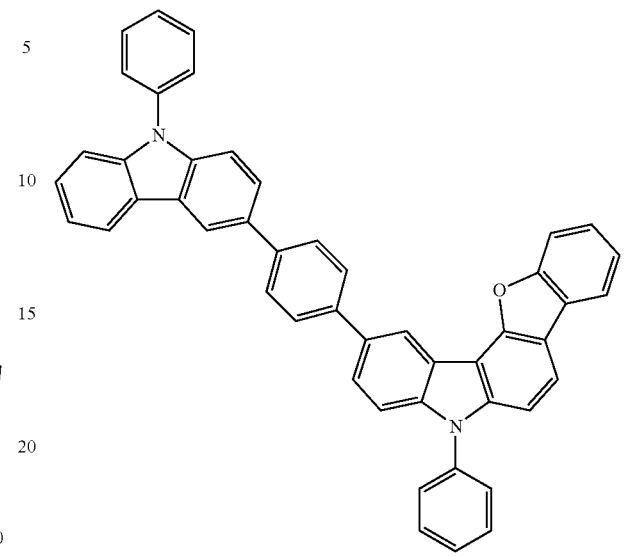
F-823
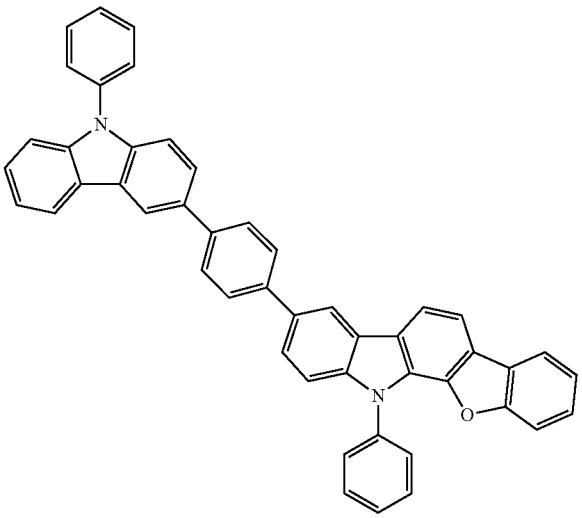
and -continued
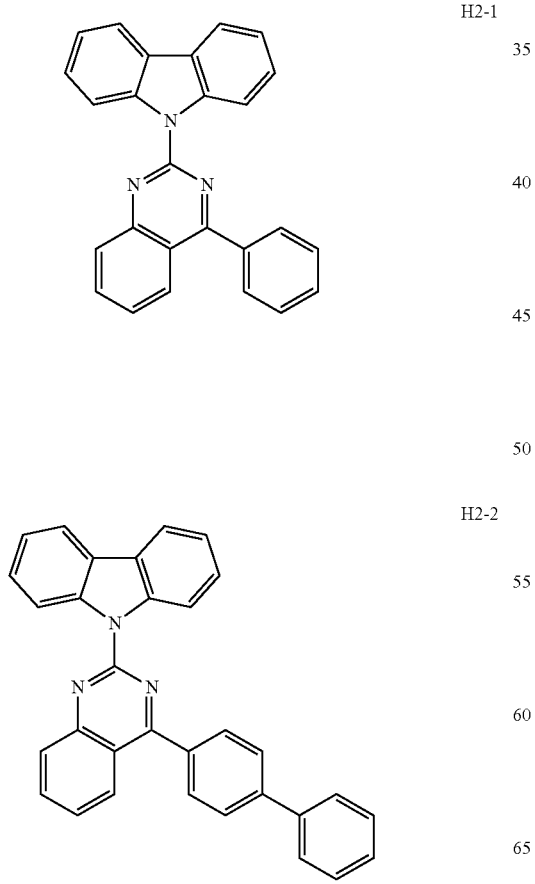
F-824
10. The organic electroluminescent device according to claim 1, wherein the compound represented by formula 2 is selected from the group consisting of:
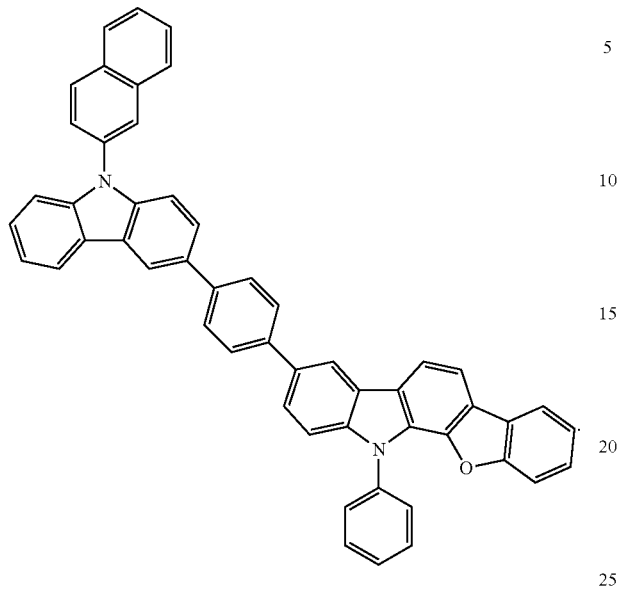
H2-1
H2-2
-continued
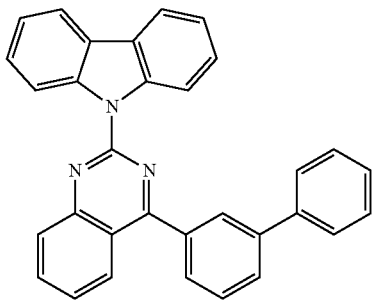
H2-3
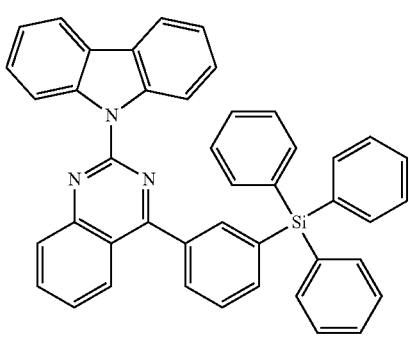
H2-4
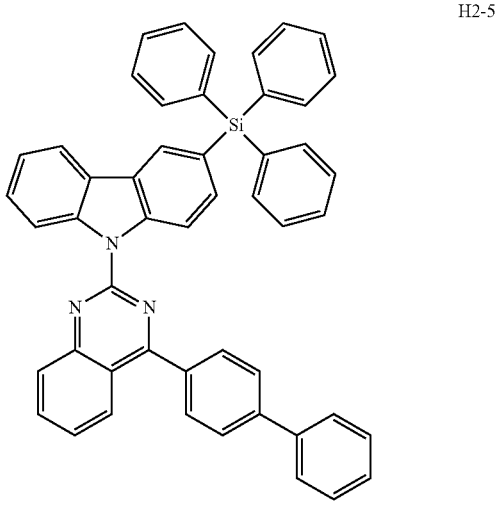
H2-5
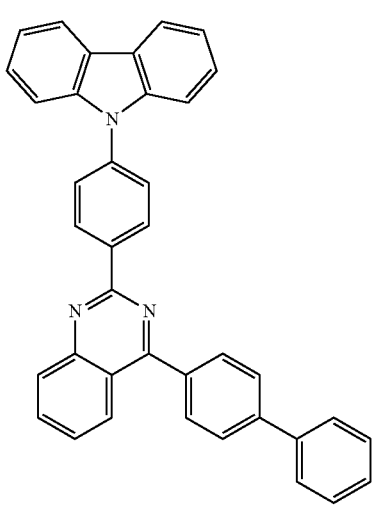
H2-6

H2-7
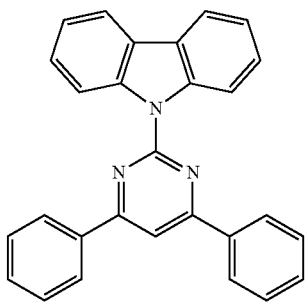
H2-8
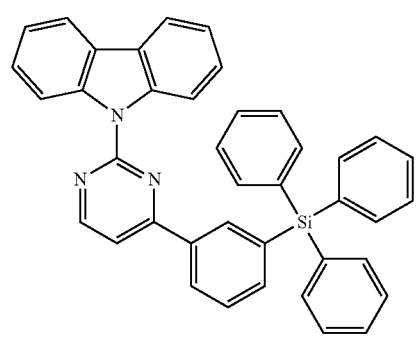
H2-9
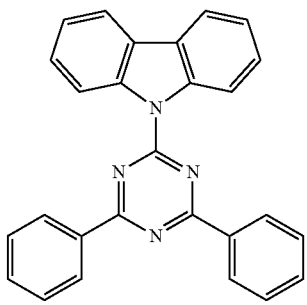
H2-10
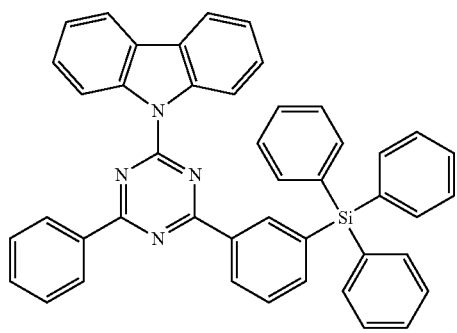
H2-11
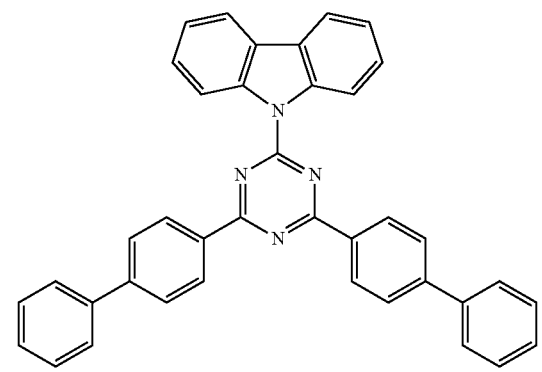
H2-12
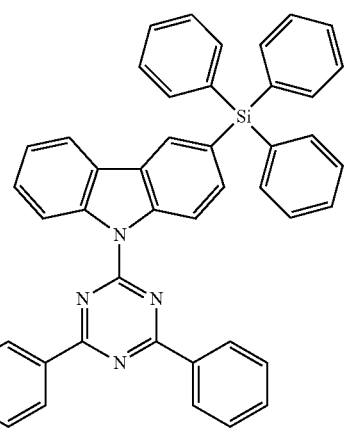
H2-13
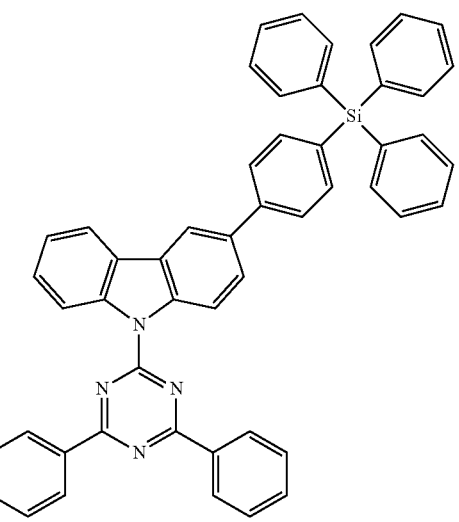

H2-14
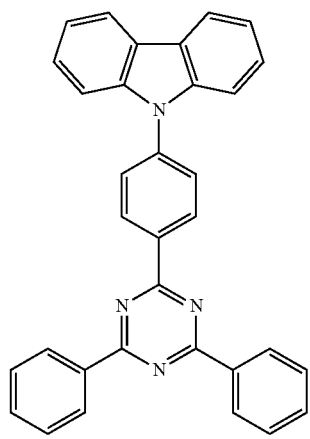
H2-15
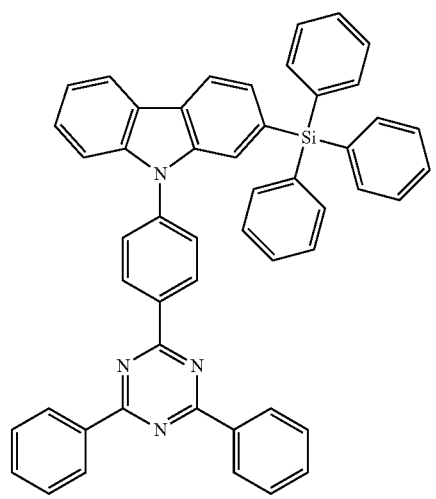
H2-16
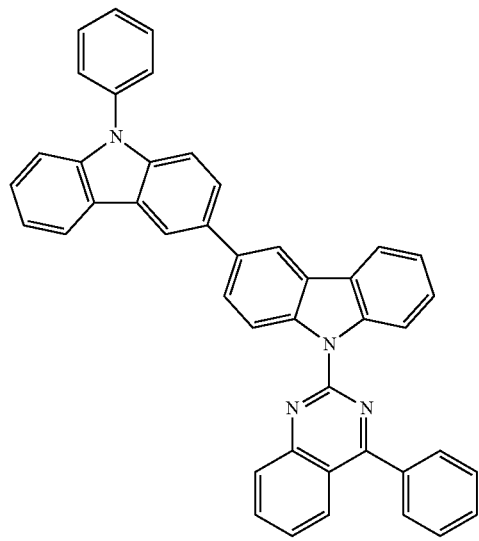
H2-17
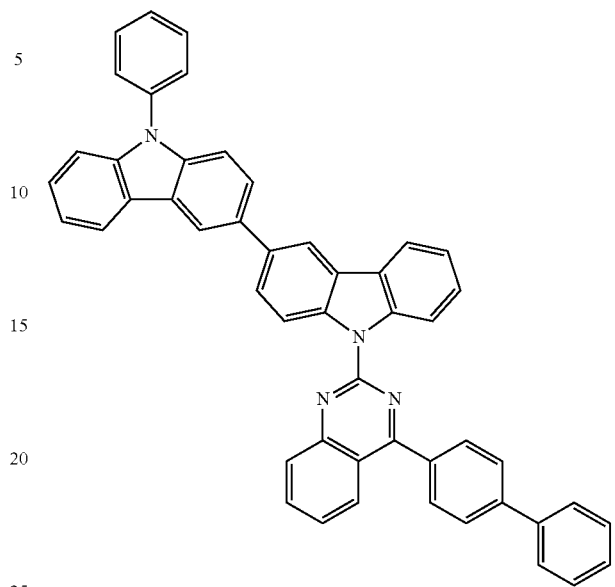
H2-18
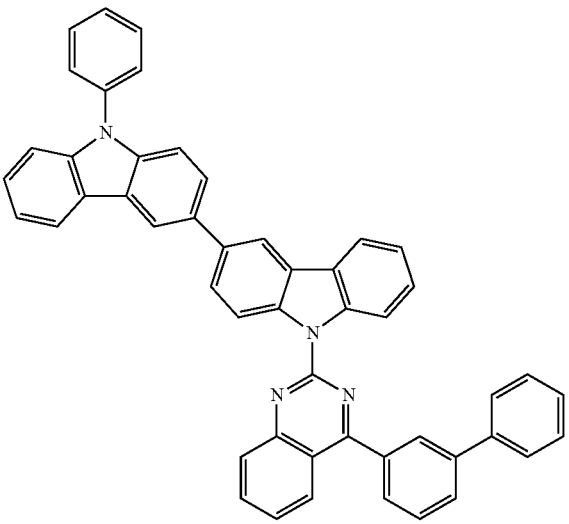

-continued
H2-19
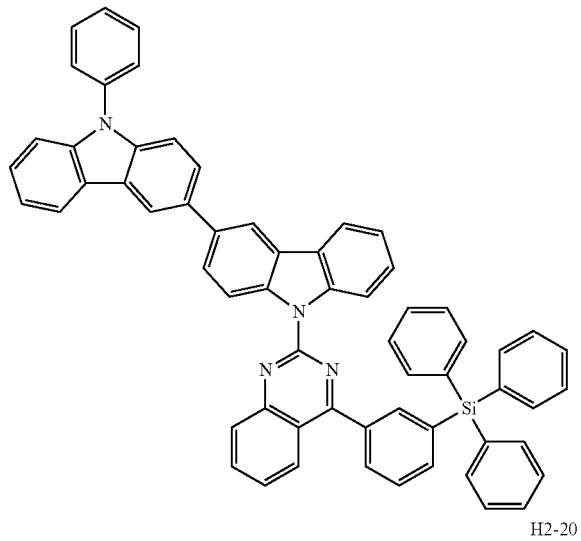
H2-22
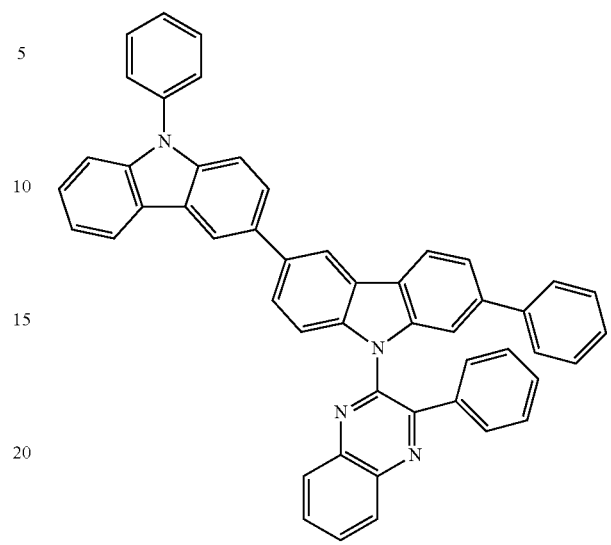
H2-20
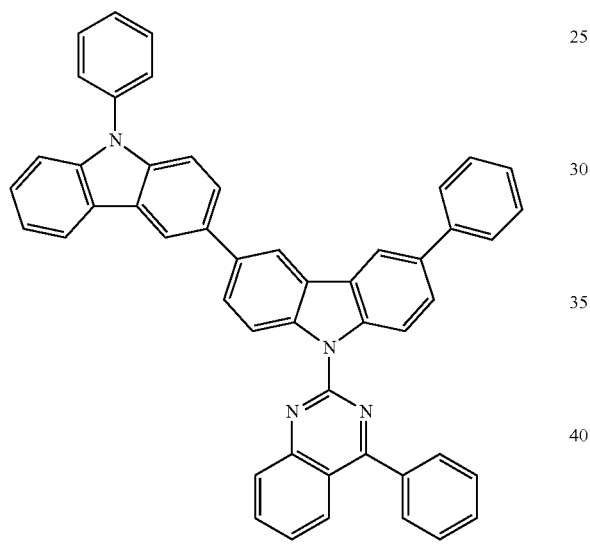
H2-21
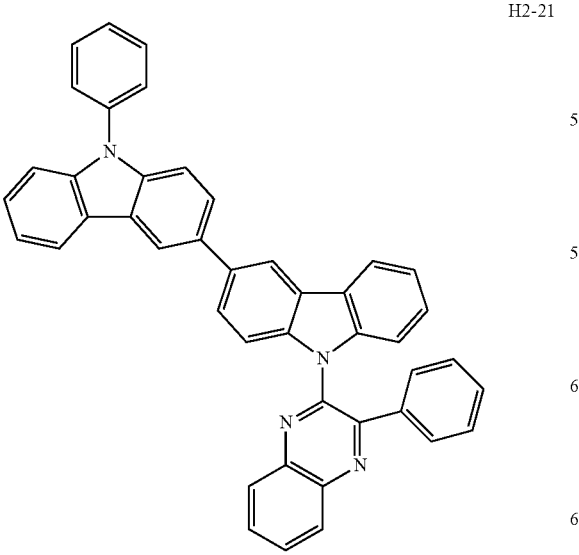
H2-23
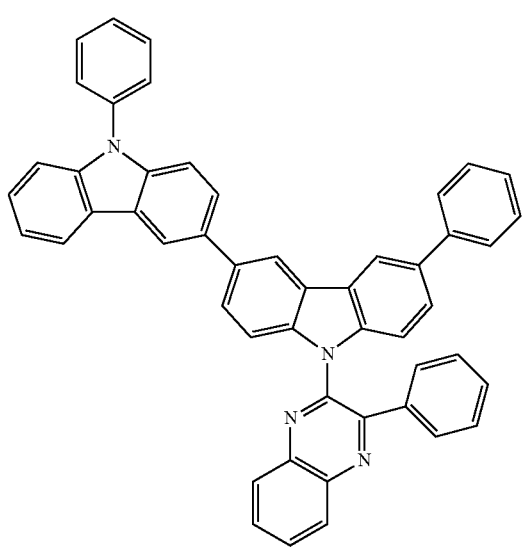

H2-24
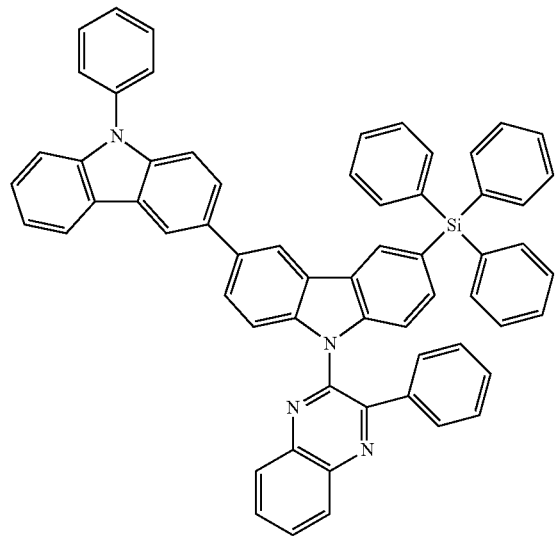
H2-25
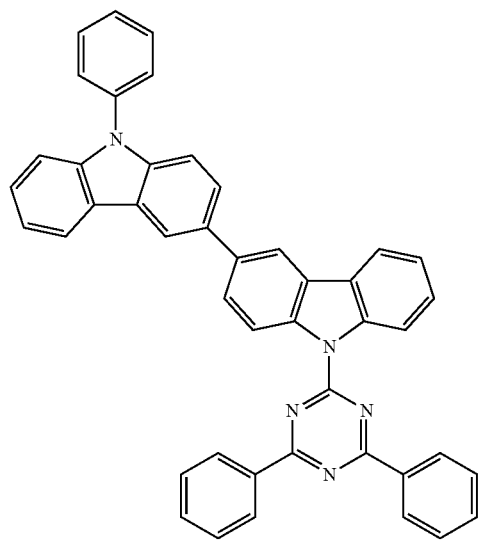
H2-26
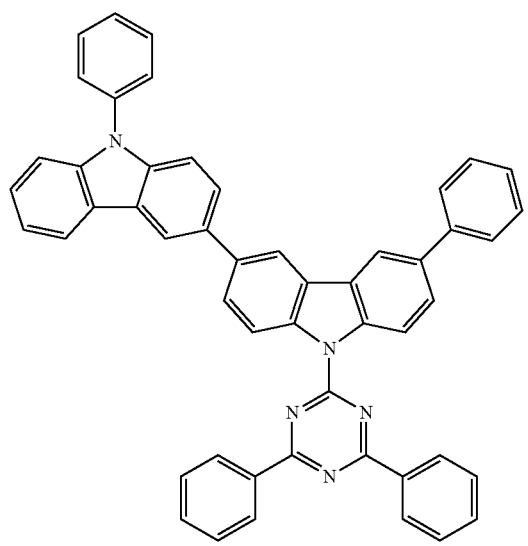
H2-27
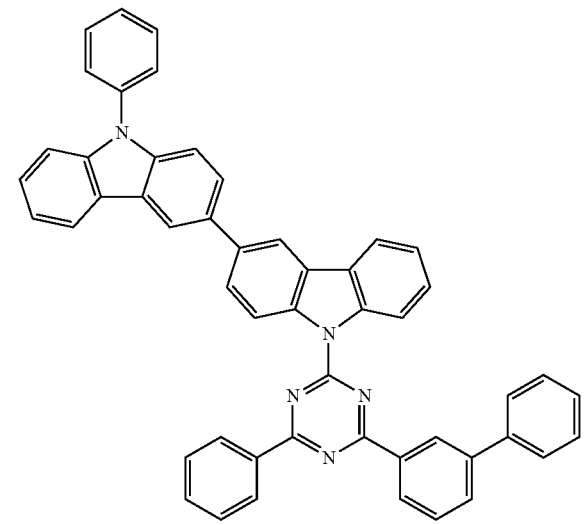
H2-28
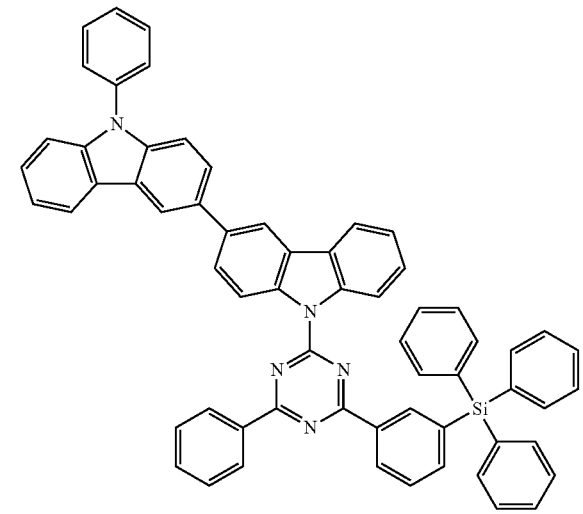

H2-29
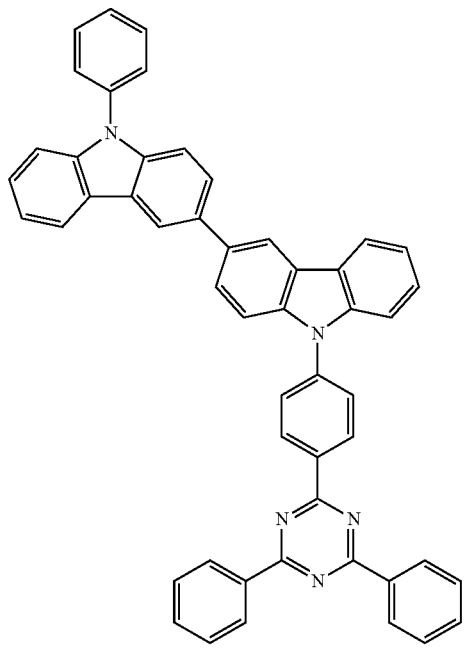
H2-30
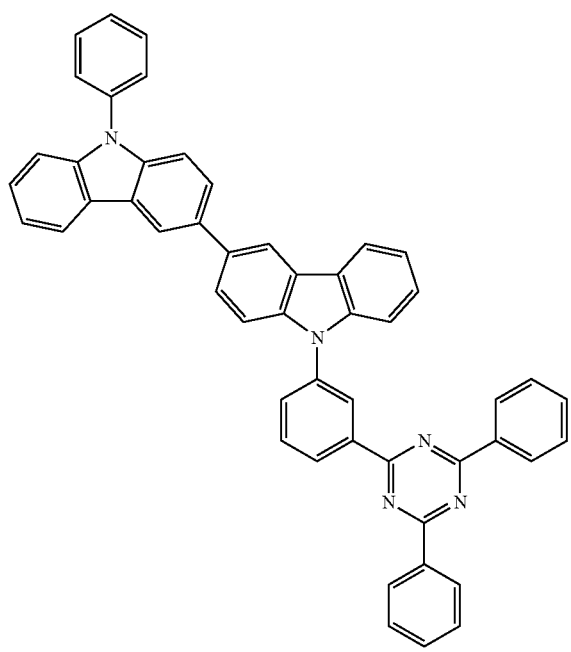
H2-31
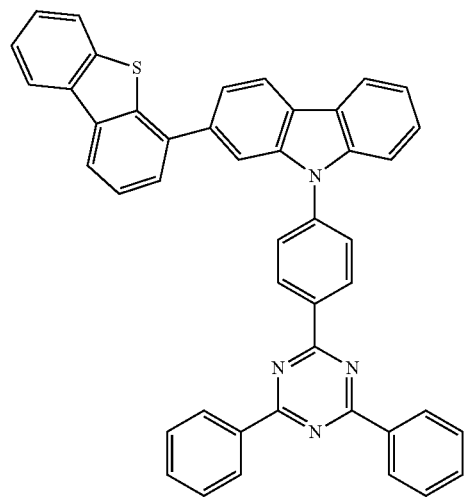
H2-32
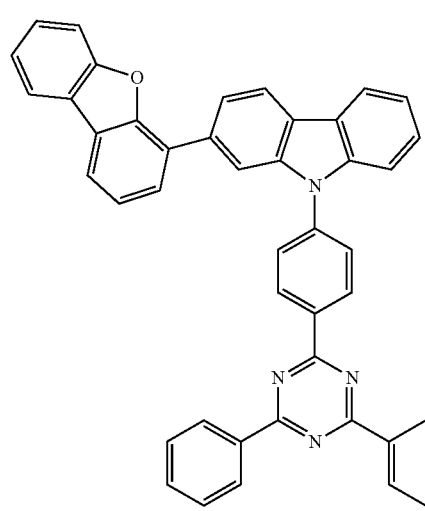
H2-33
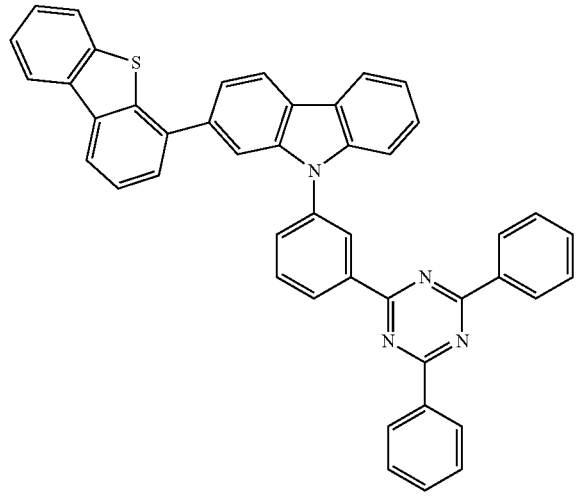

-continued
H2-34
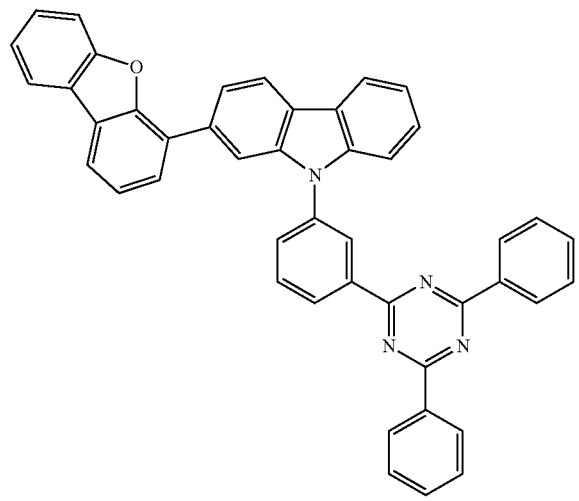
H2-35
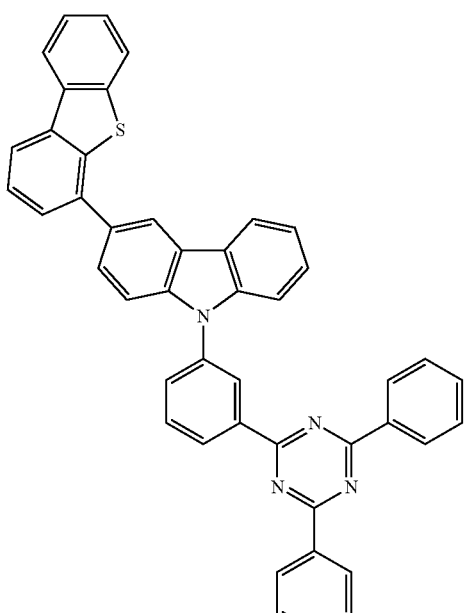
H2-36
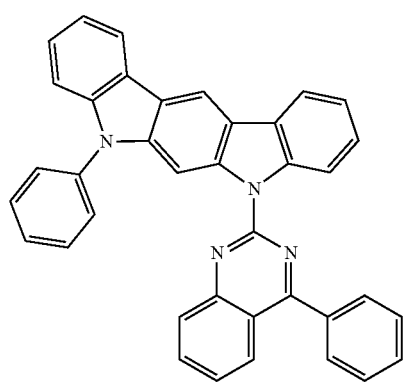
-continued
H2-37
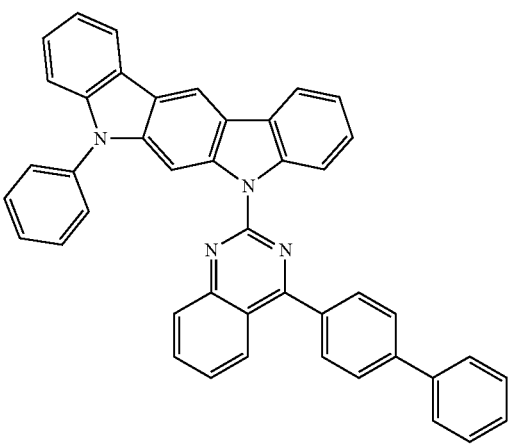
H2-38
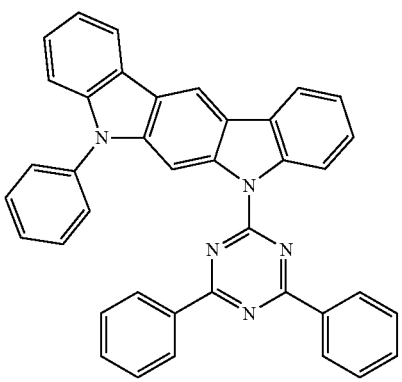
H2-39
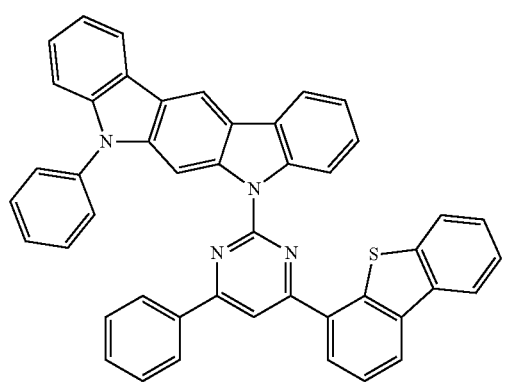

-continued
H2-40
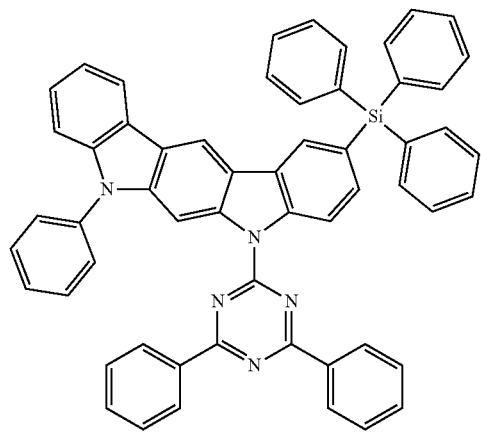
H2-41
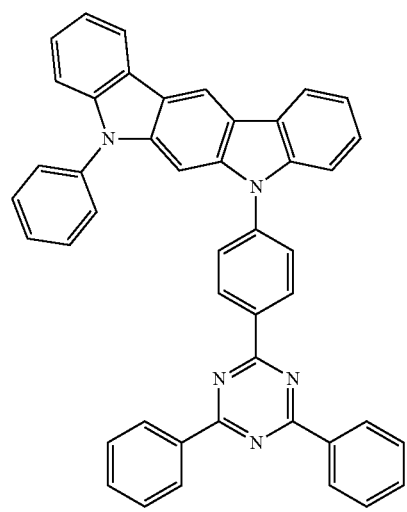
H2-42
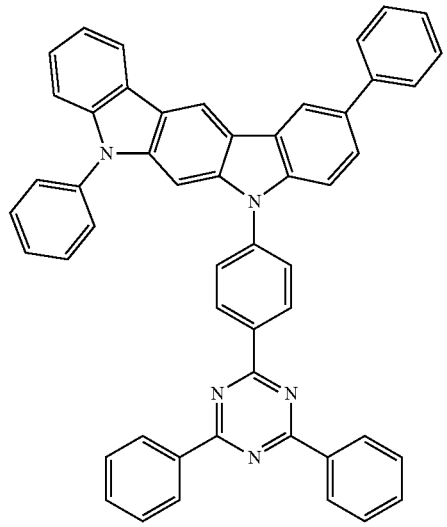
-continued
H2-43
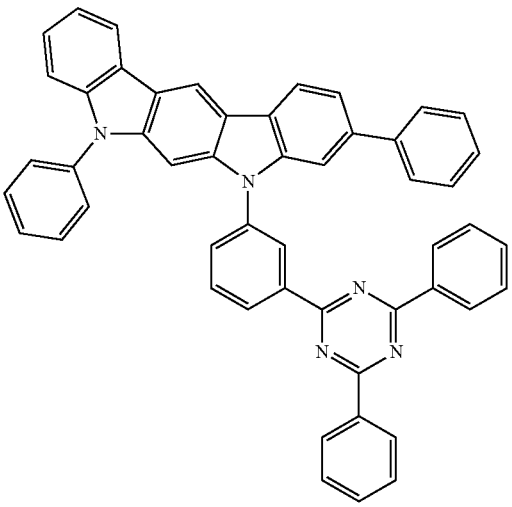
H2-44
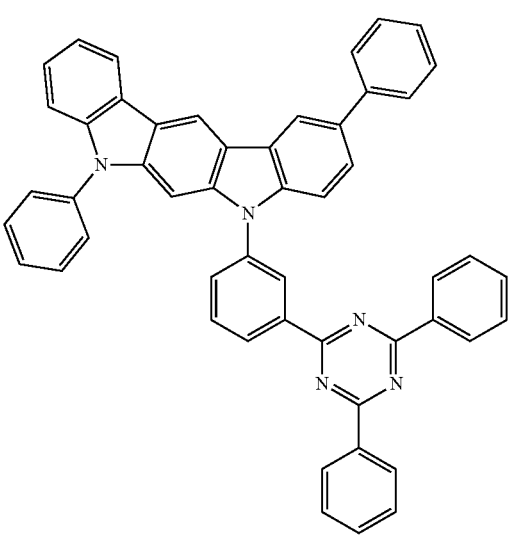
H2-45
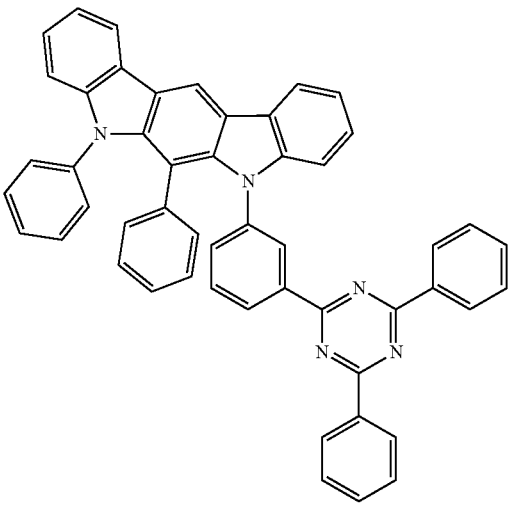

H2-46
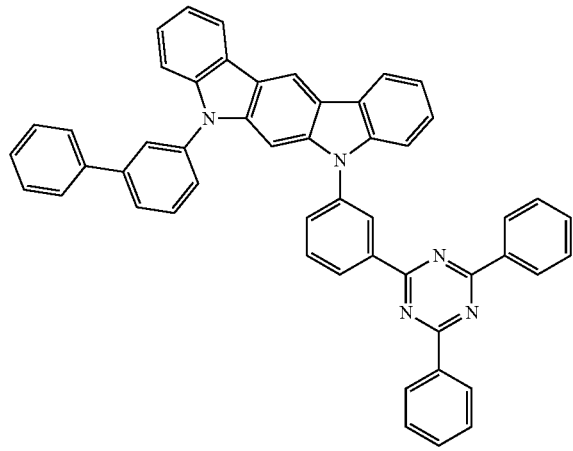
H2-47
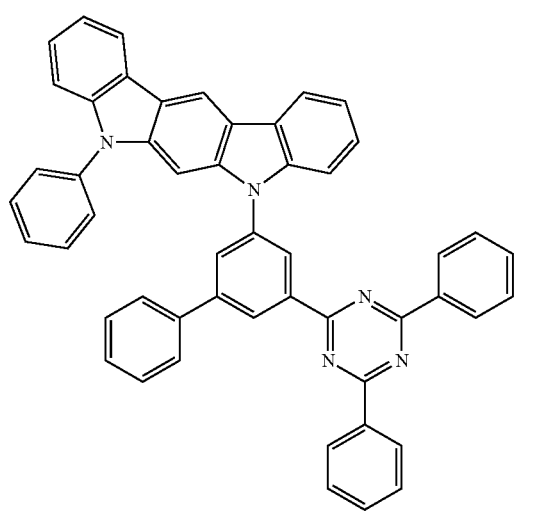
H2-48
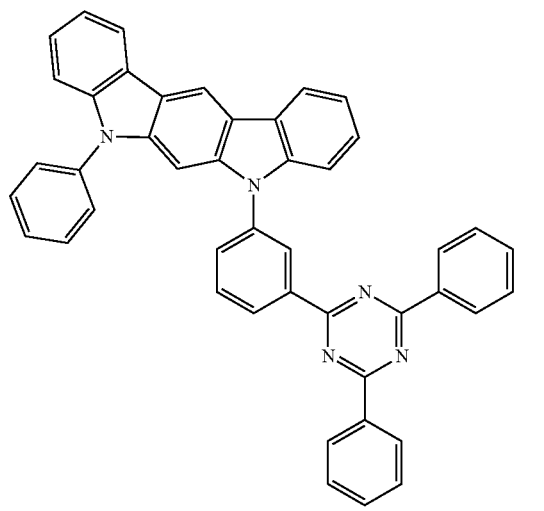
H2-49
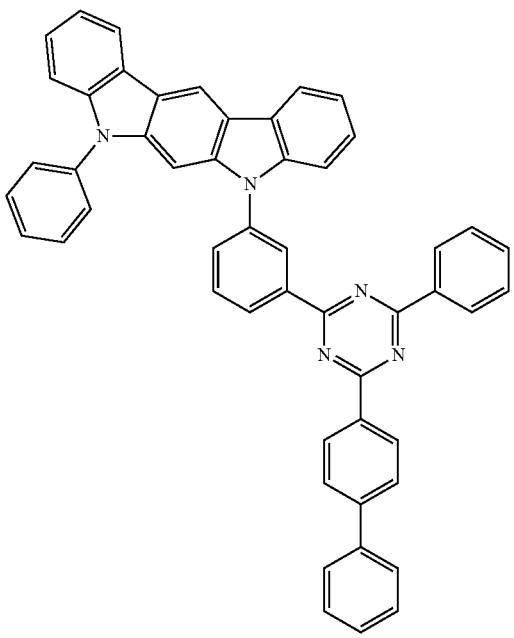
H2-50
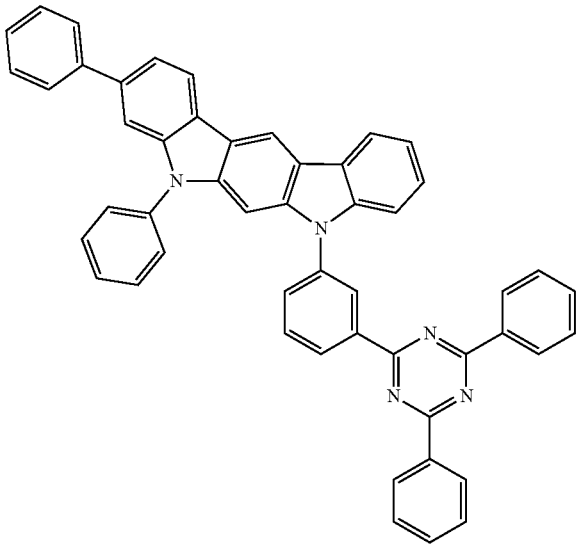

-continued
H2-51
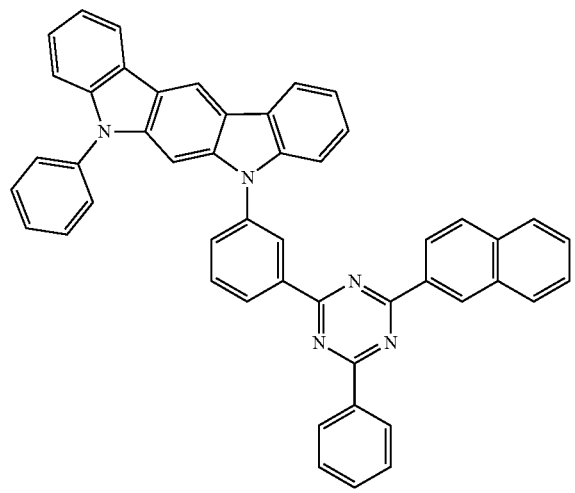
H2-52
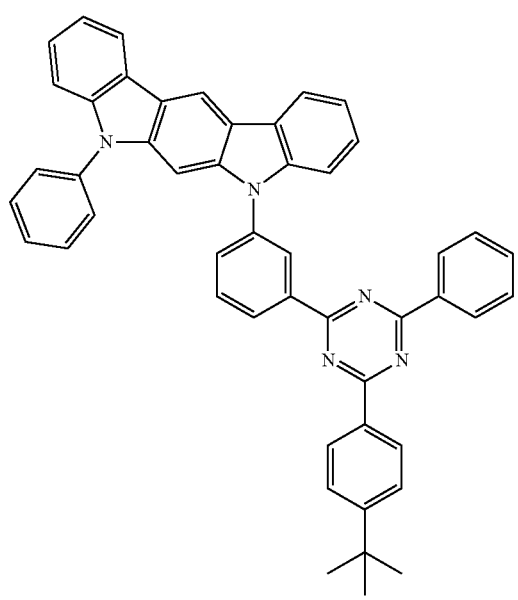
H2-53
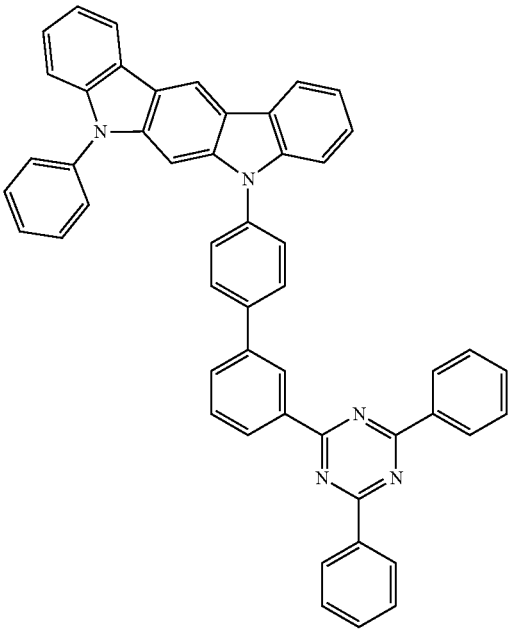
H2-54
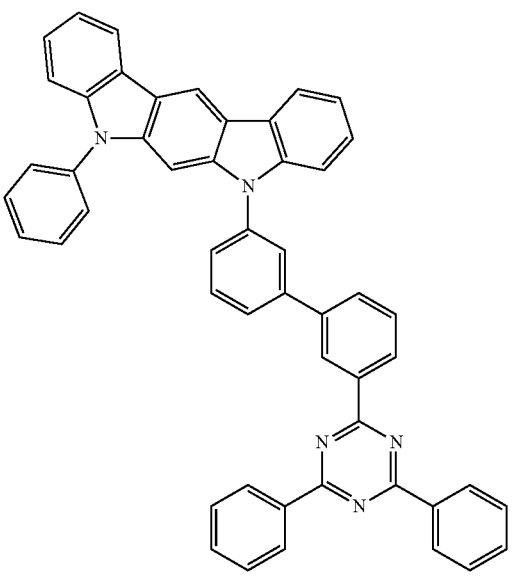

H2-55
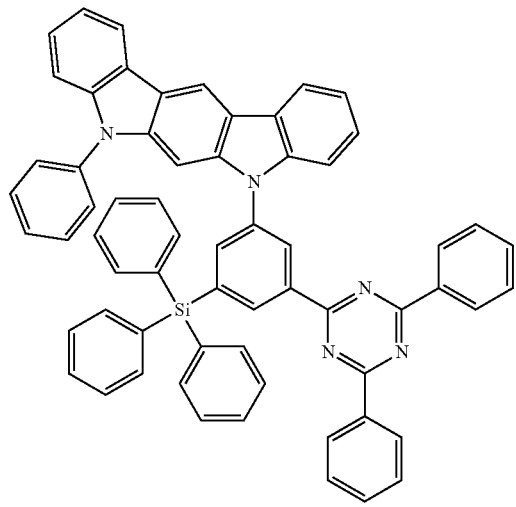
H2-58
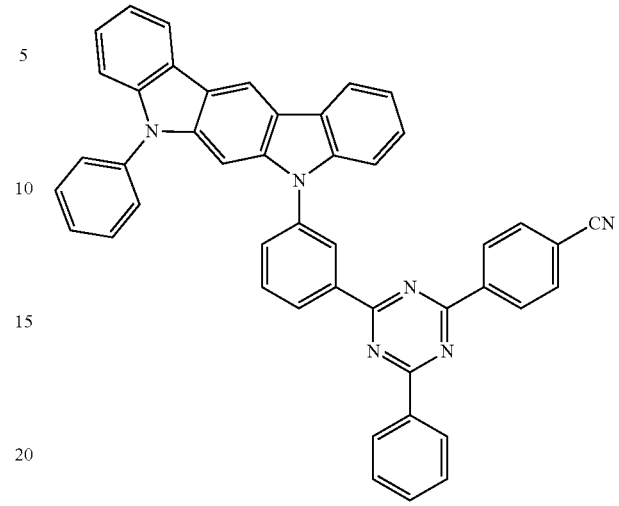
H2-56
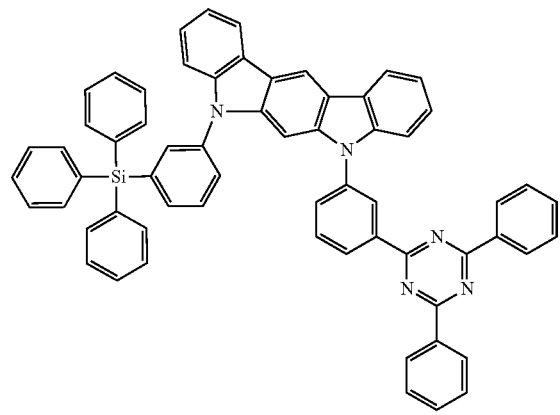
H2-59
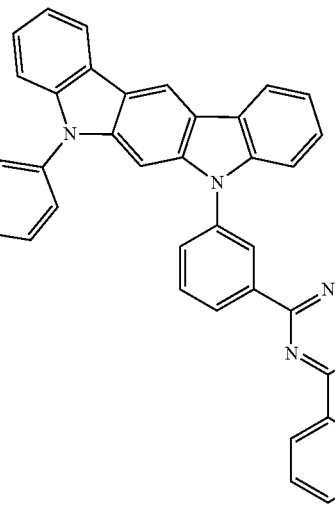
H2-57
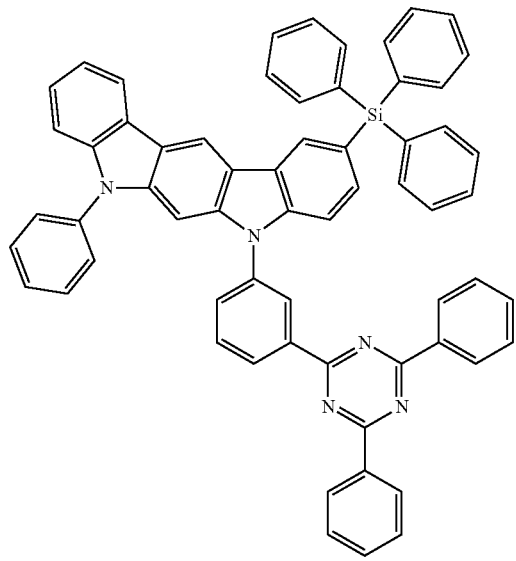
H2-60
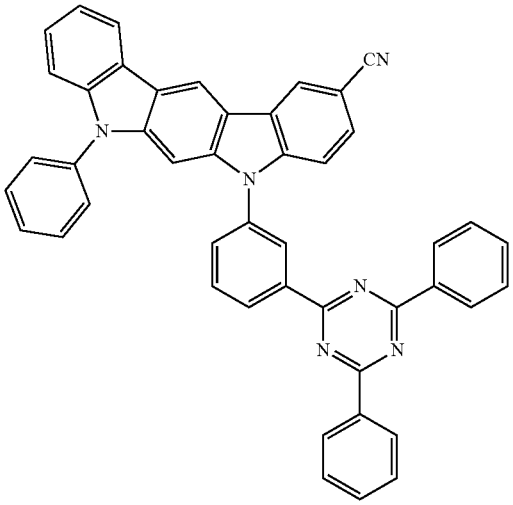

-continued
H2-61
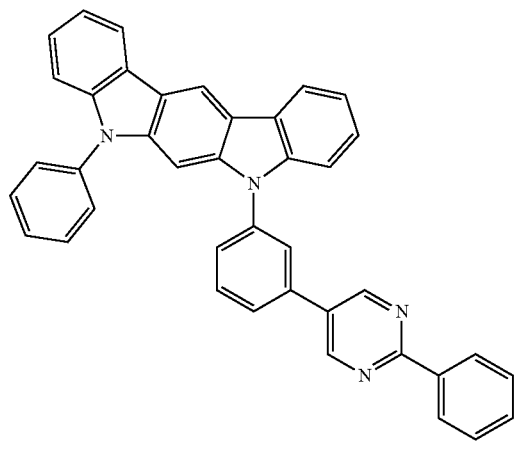
H2-62
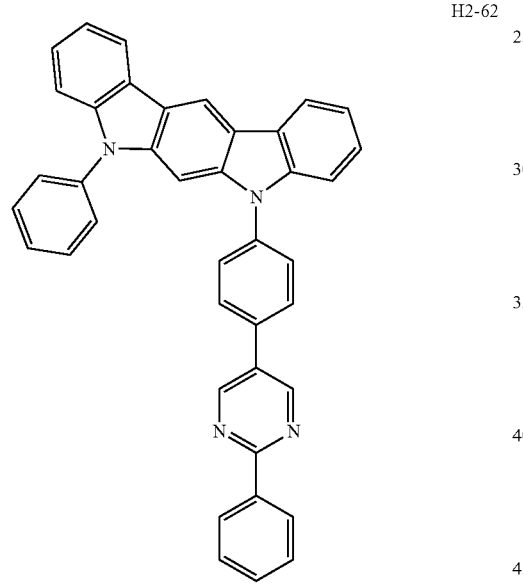
H2-63
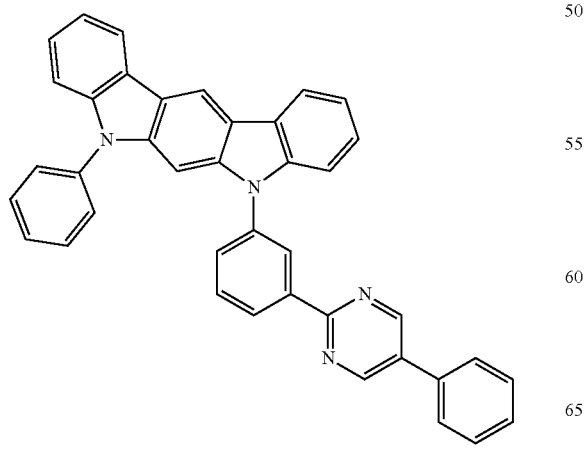
-continued
H2-64
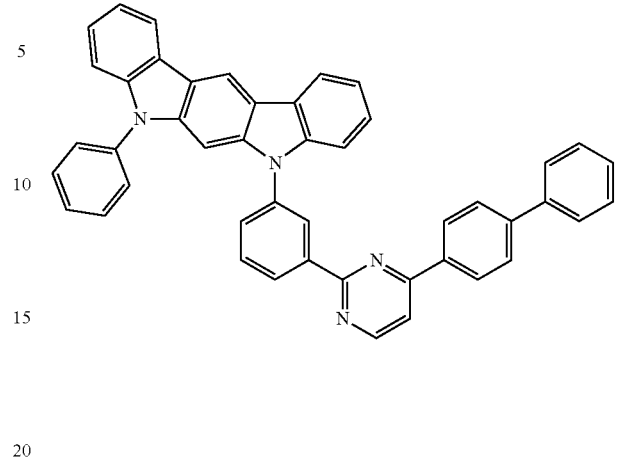
H2-65
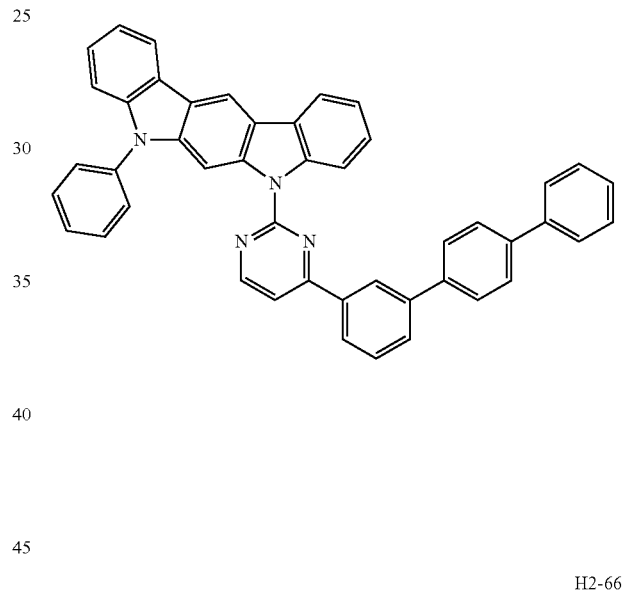
H2-66
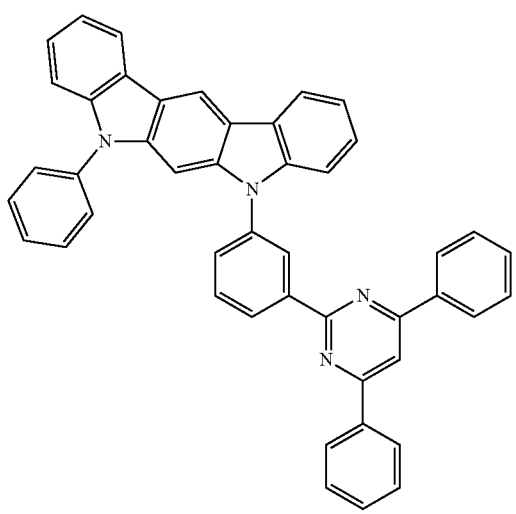

1003
-continued
H2-67
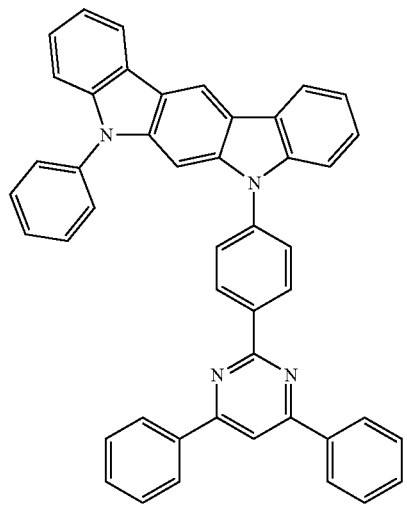
H2-68
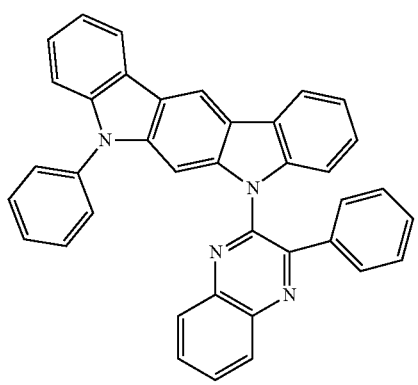
H2-69
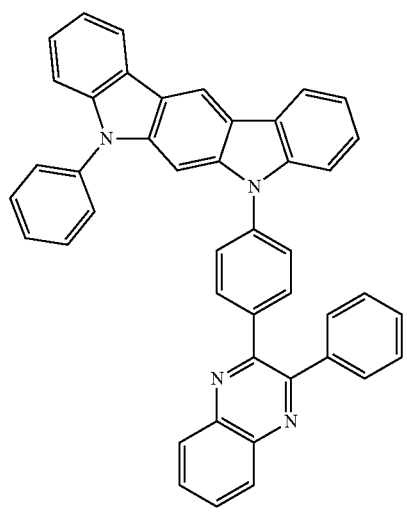
1004
-continued
H2-70
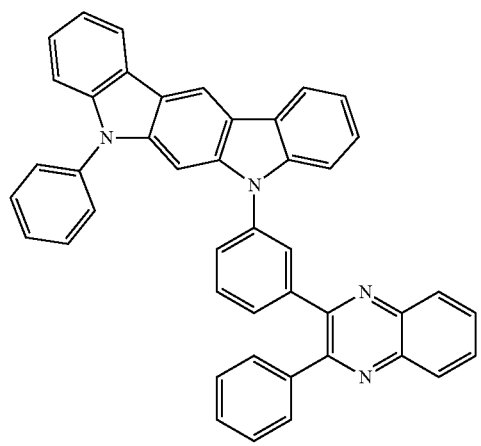
H2-71
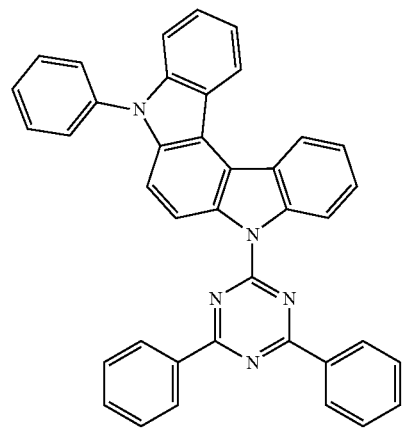
H2-72
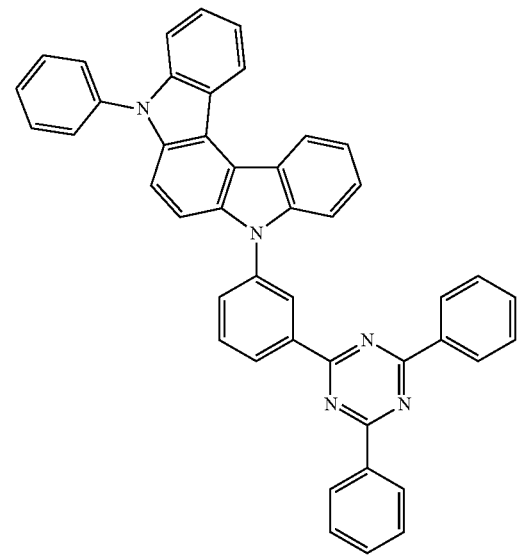

H2-73
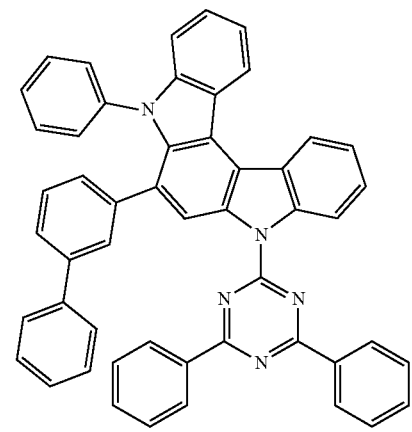
H2-74
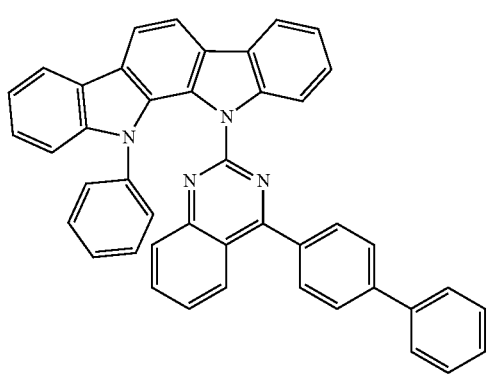
H2-75
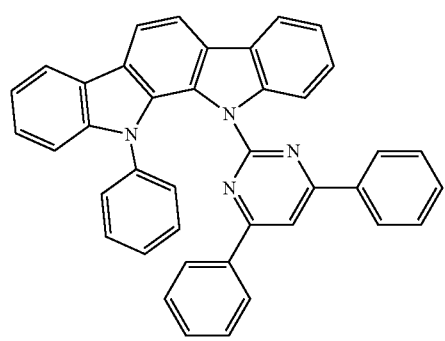
H2-76
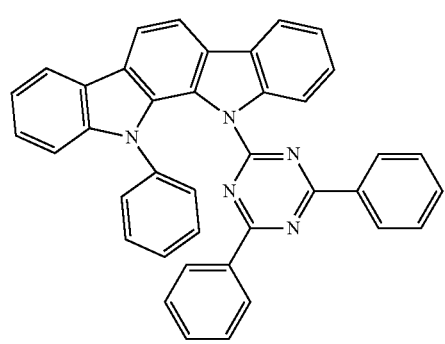
H2-77
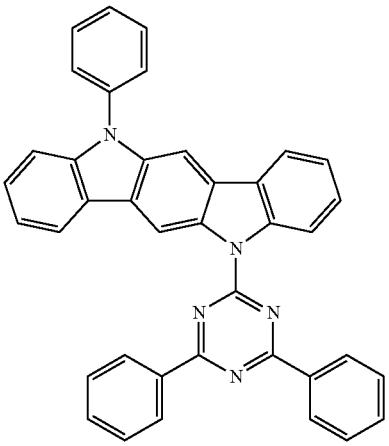
H2-78
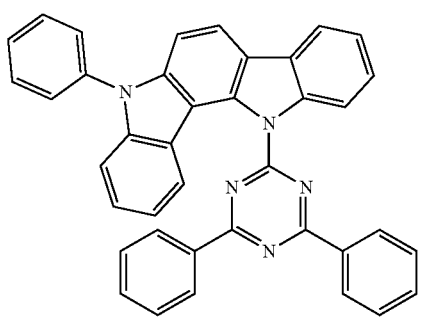
H2-79
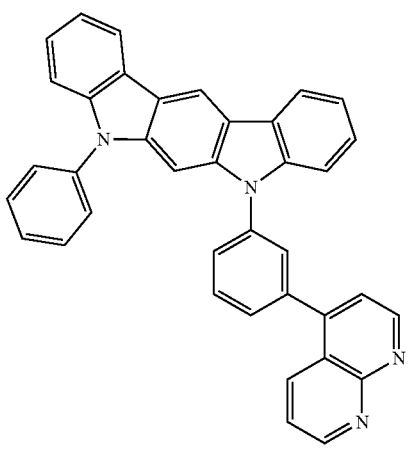
H2-80
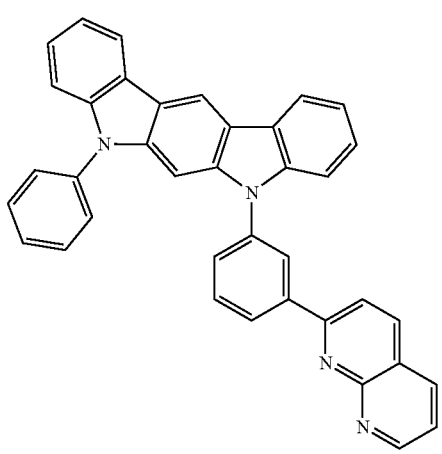

1007
-continued
H2-81
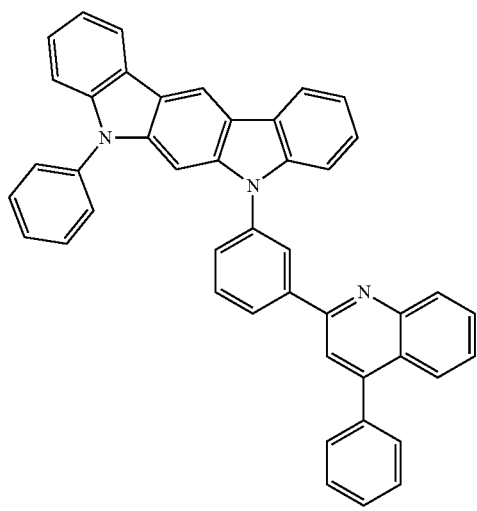
H2-82
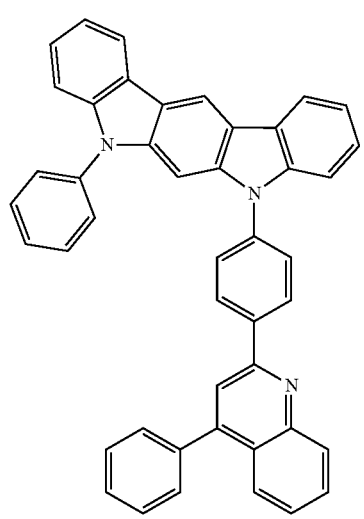
H2-83
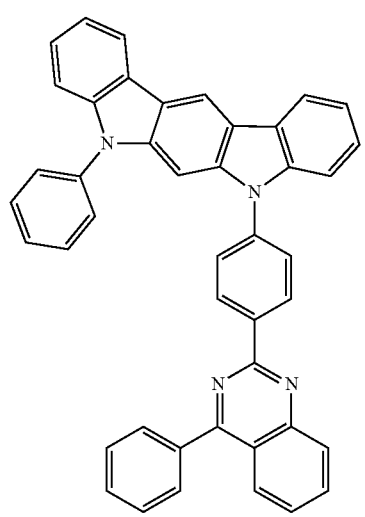
1008
-continued
H2-84
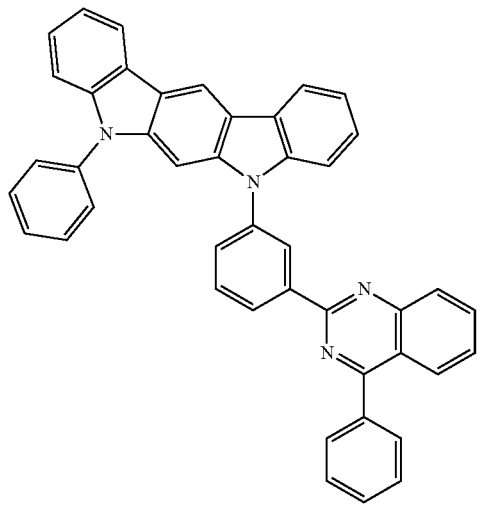
H2-85
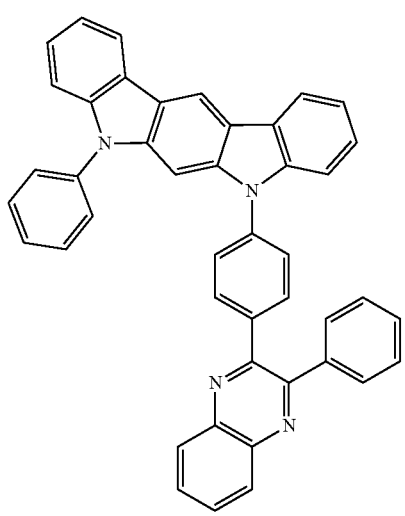
H2-86
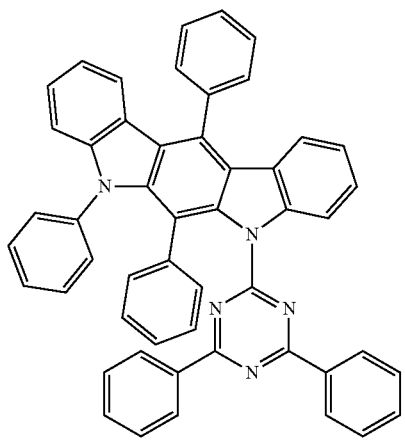

-continued
H2-87
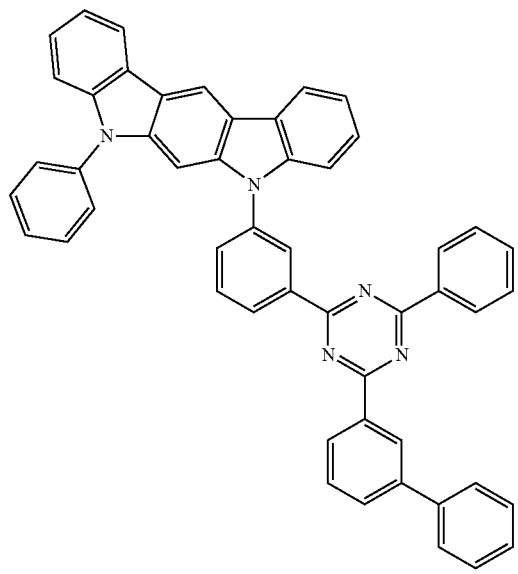
H2-88
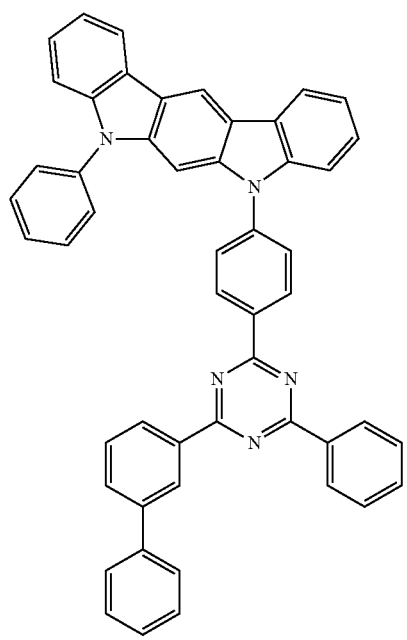
H2-89
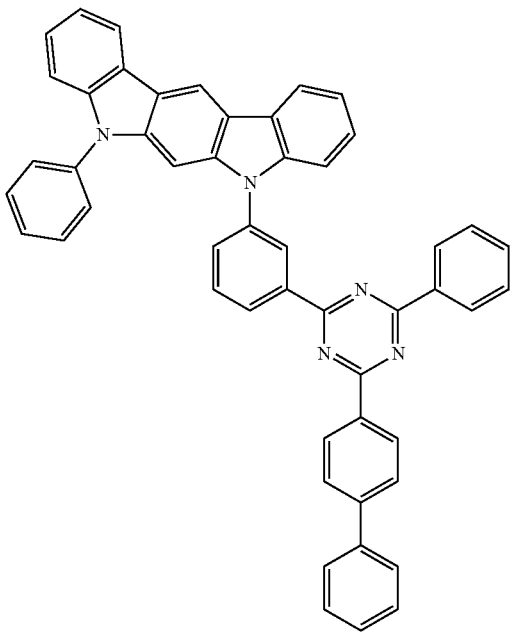
H2-90
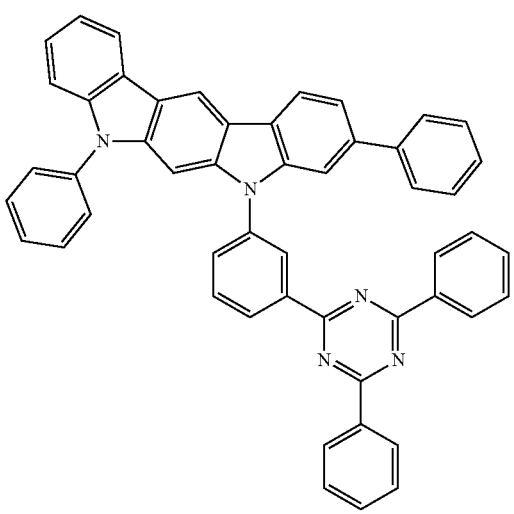

H2-91
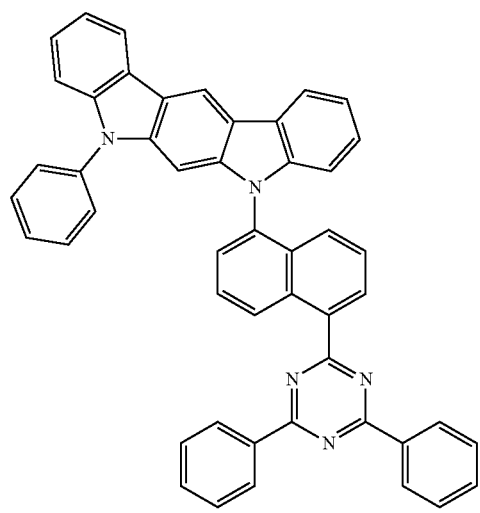
H2-92
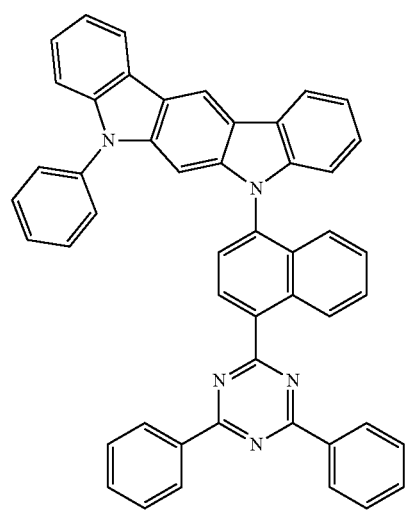
H2-93
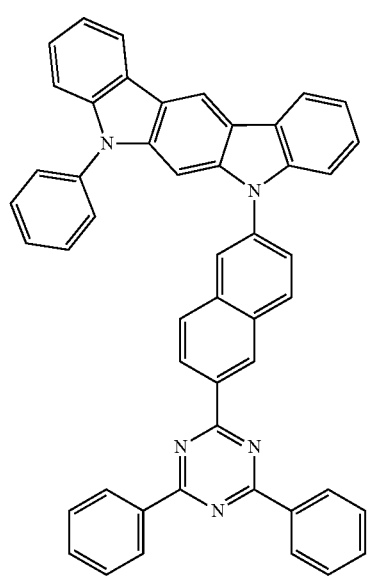
H2-94
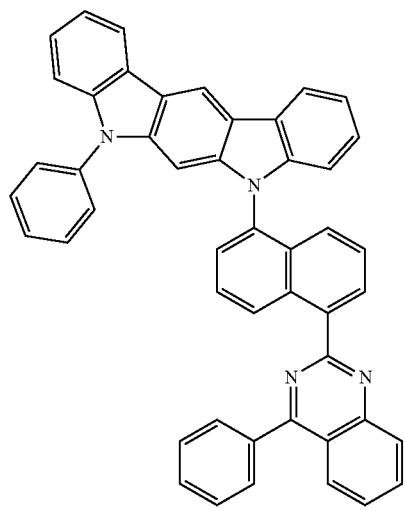
H2-95
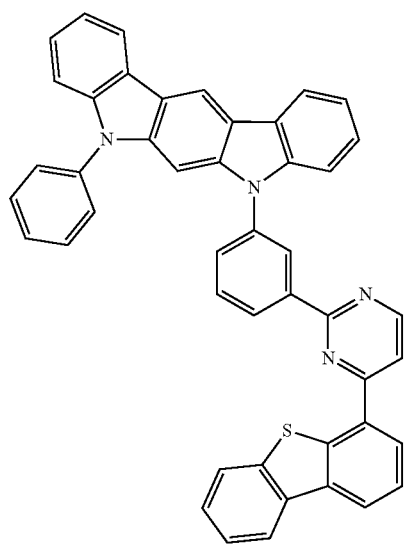
H2-96
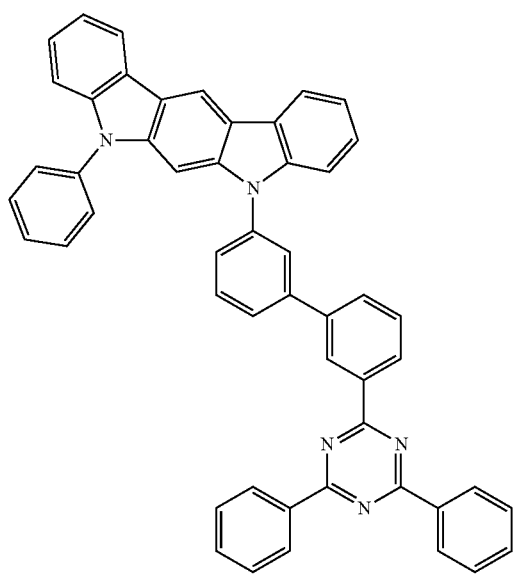

H2-97
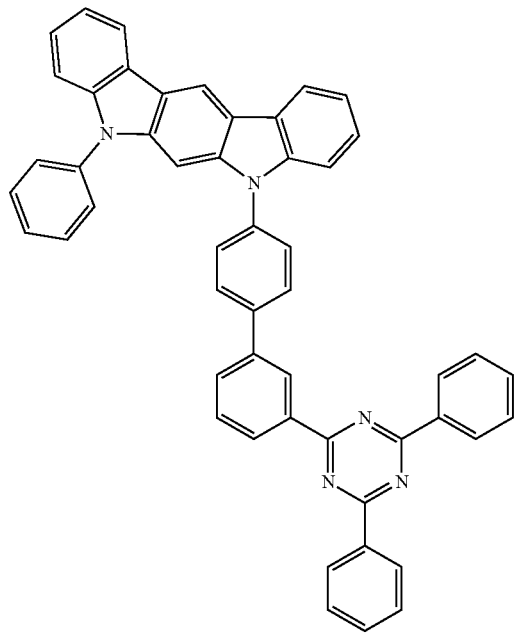
H2-98
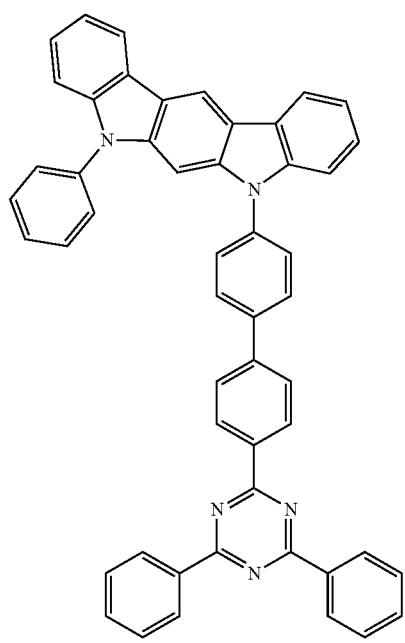
H2-99
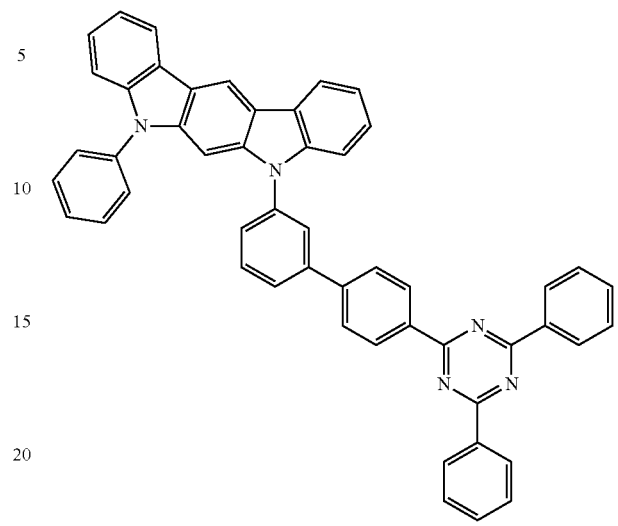
H2-100
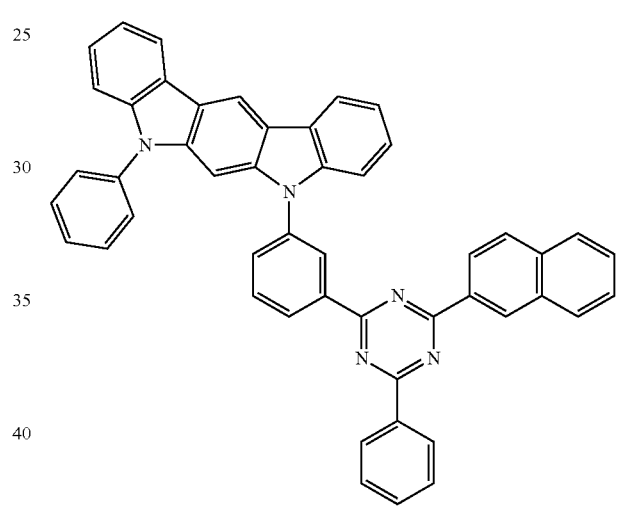
H2-101
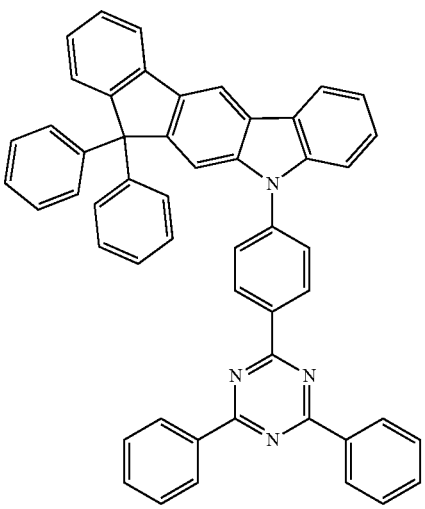

H2-102
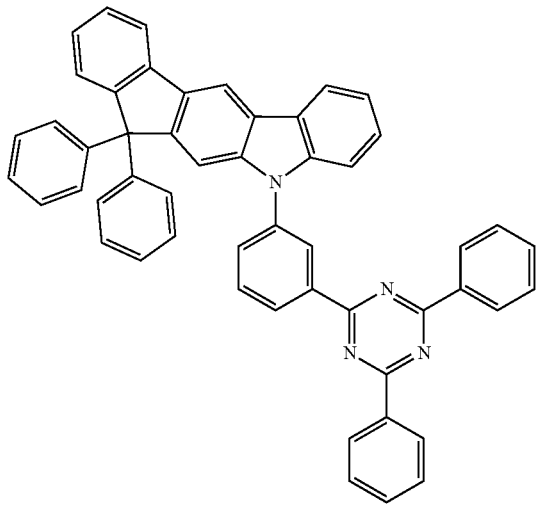
H2-105
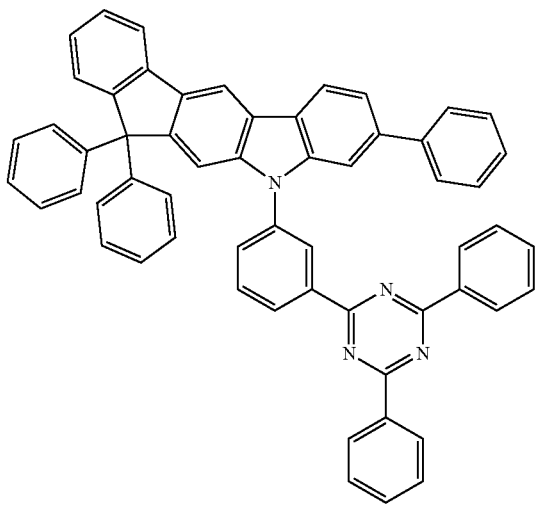
H2-103
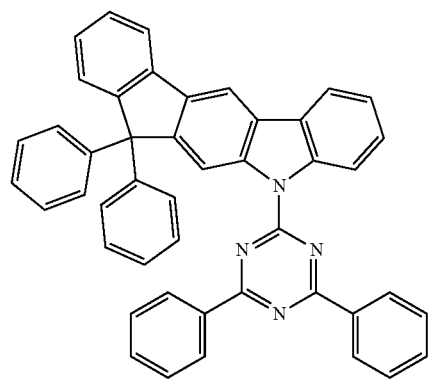
H2-106
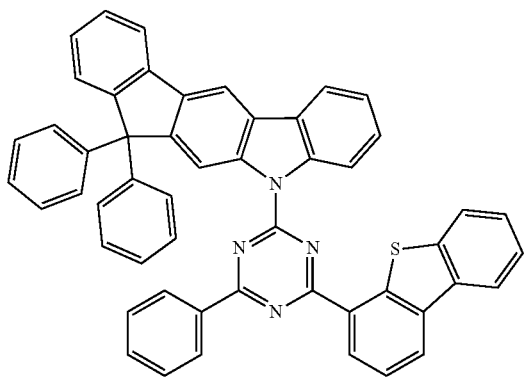
H2-104
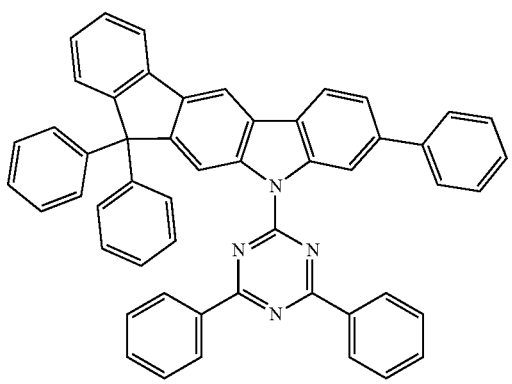
H2-107
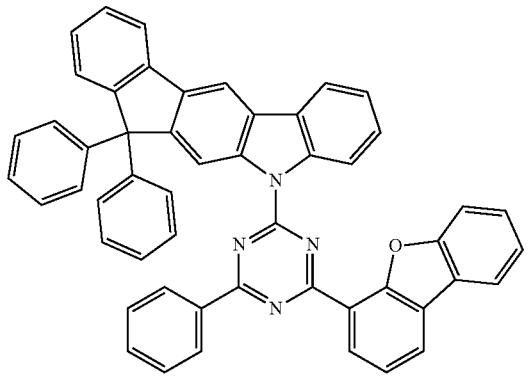

H2-108
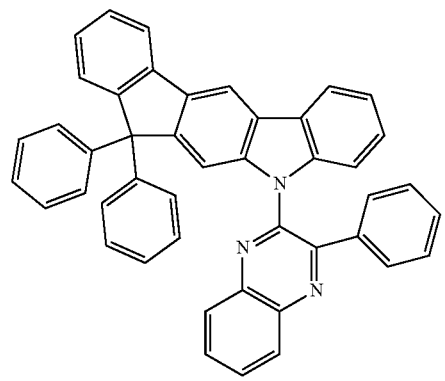
H2-109
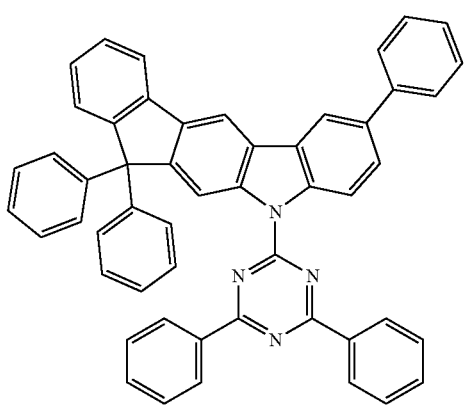
H2-110
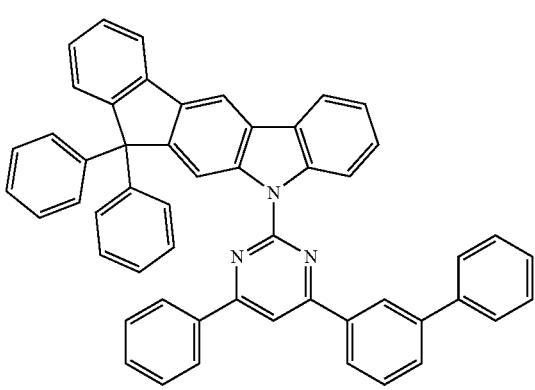
H2-111
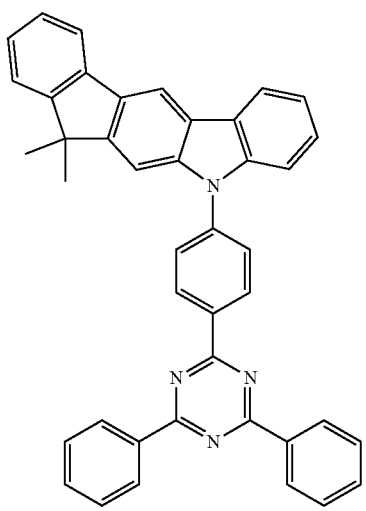
H2-112
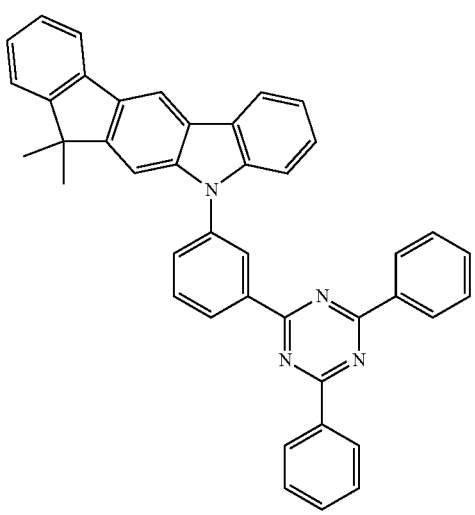
H2-113
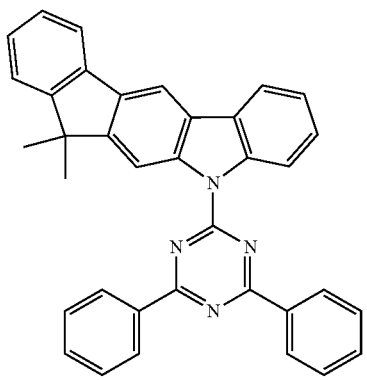

1019
-continued
H2-114
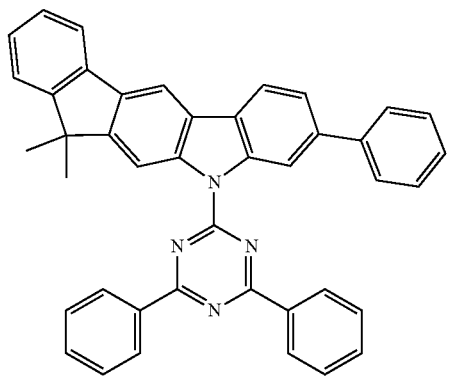
H2-115
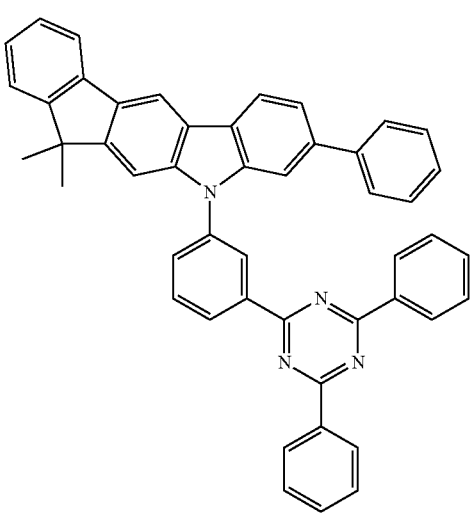
H2-116
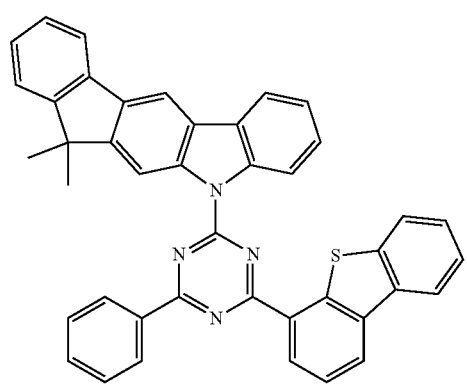
H2-117
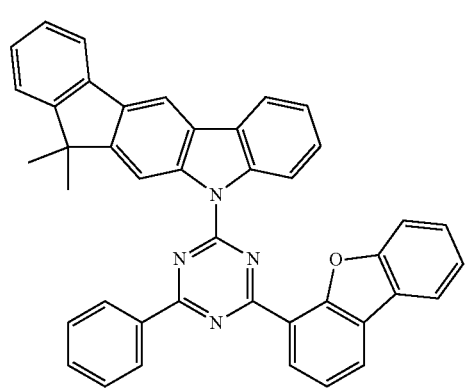
1020
-continued
H2-118
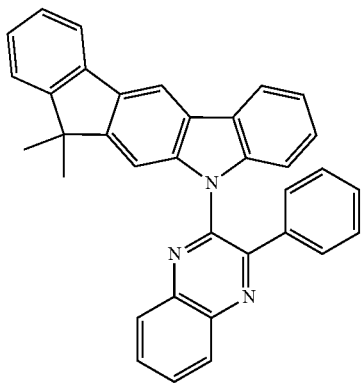
H2-119
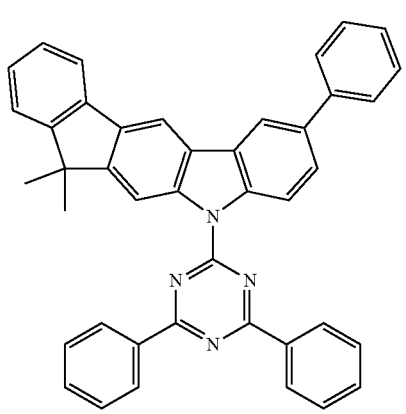
H2-120
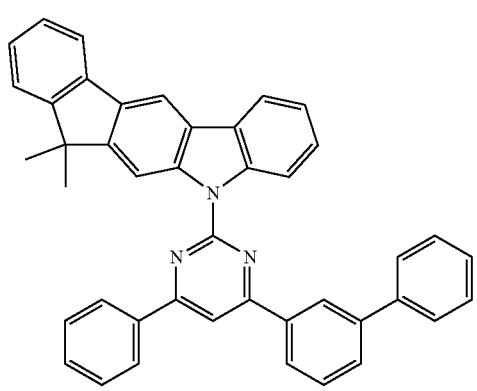
H2-121
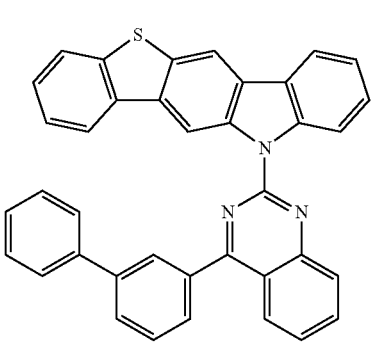

-continued
H2-122
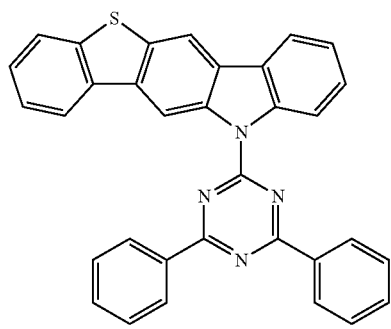
H2-123
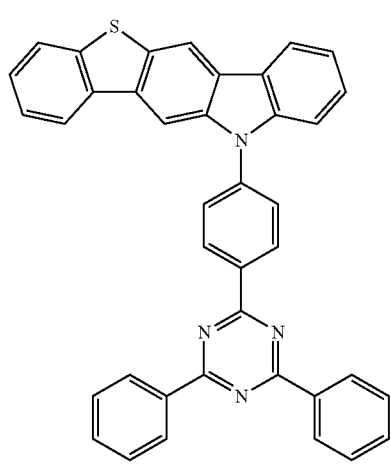
H2-124
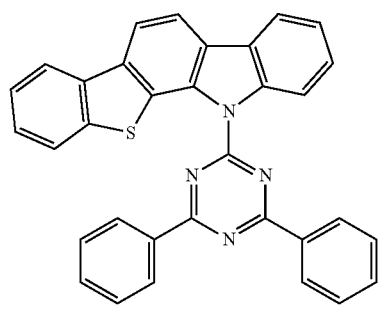
-continued
H2-126
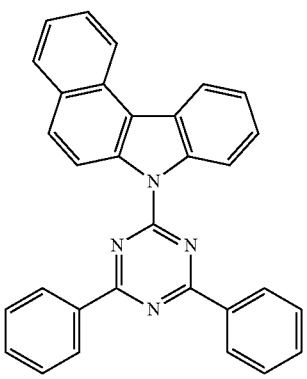
H2-127
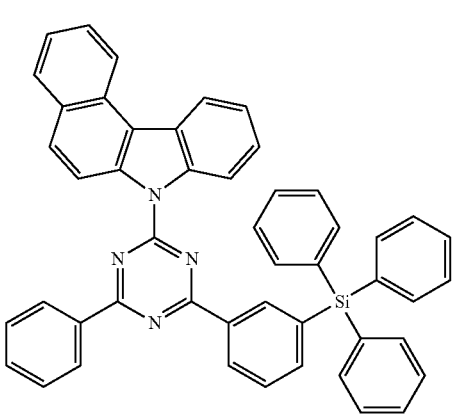
H2-125
H2-128
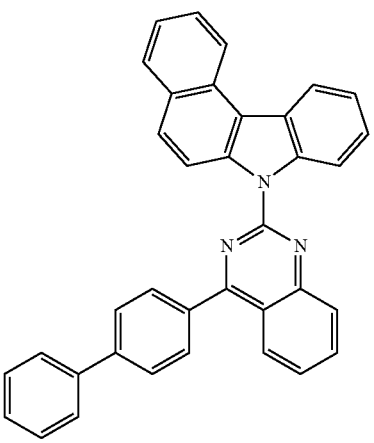

-continued
H2-129
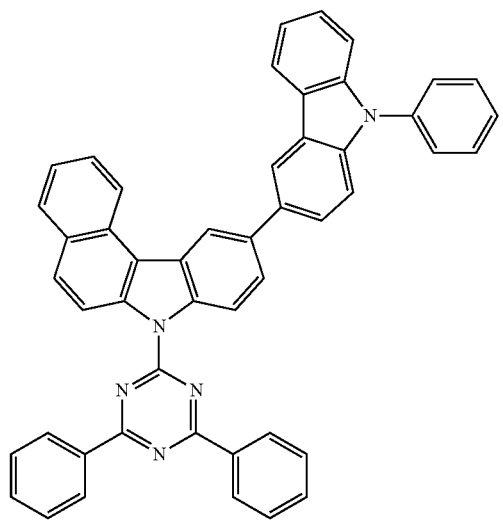
H2-130
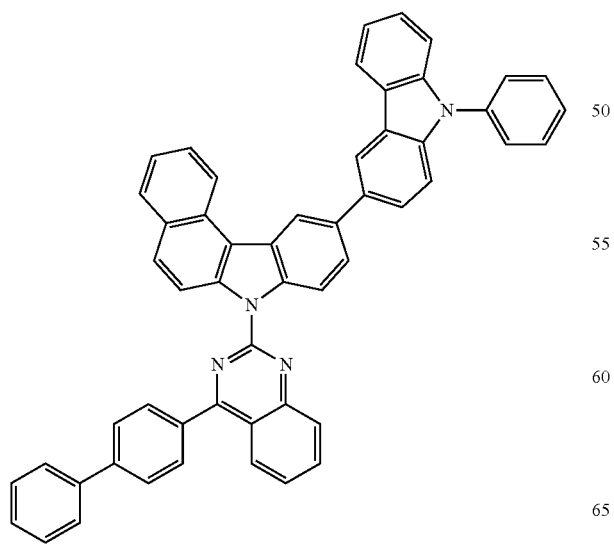
-continued
H2-131
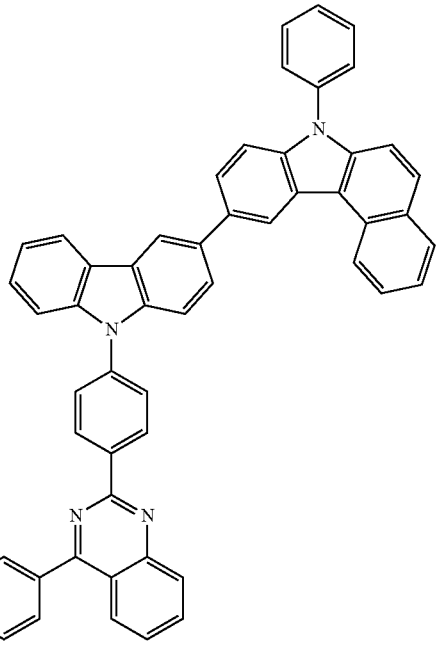
H2-132
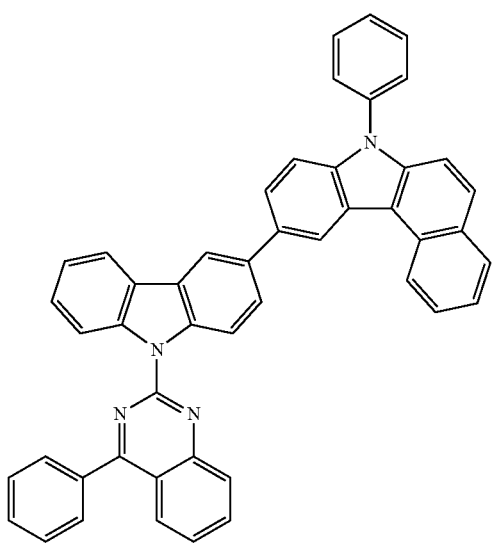

-continued
H2-133
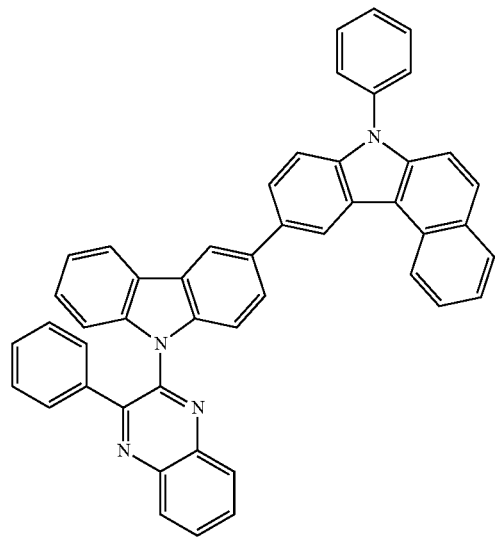
H2-134
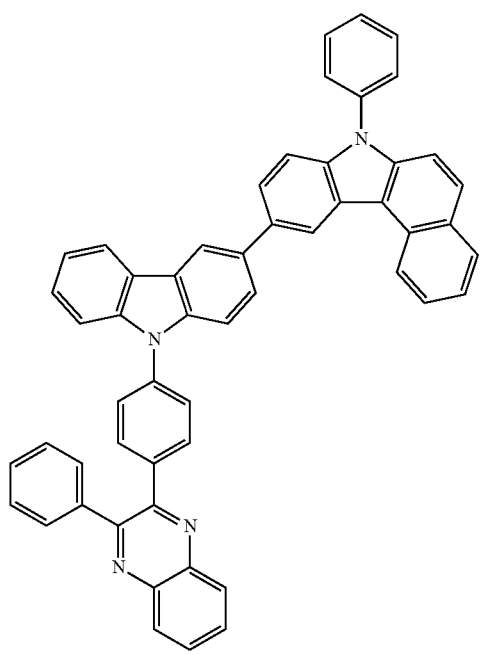
-continued
H2-135
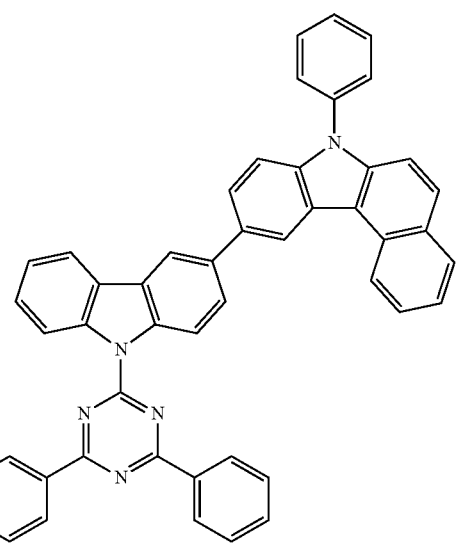
H2-136
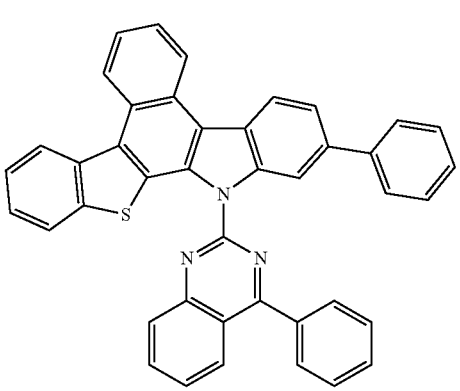
H2-137
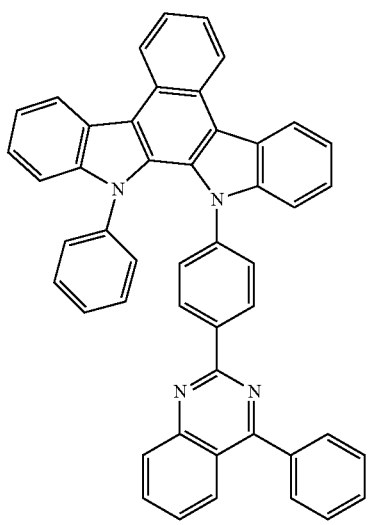

H2-138
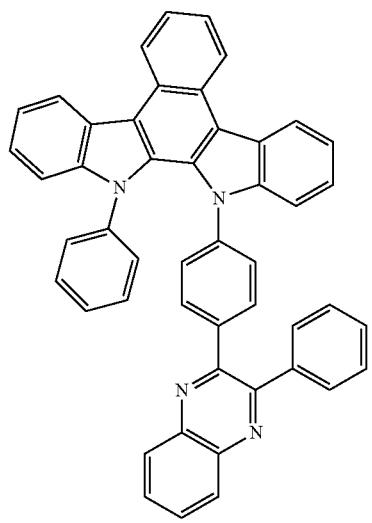
H2-139
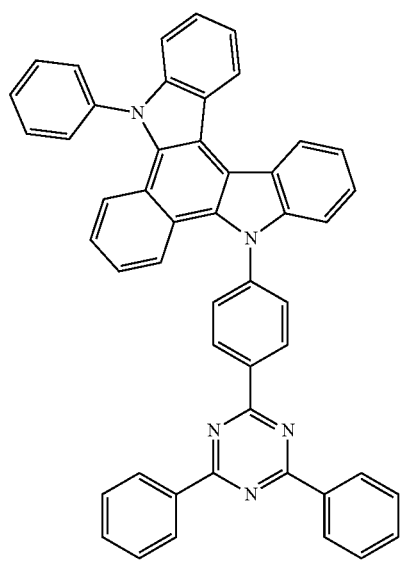
H2-140
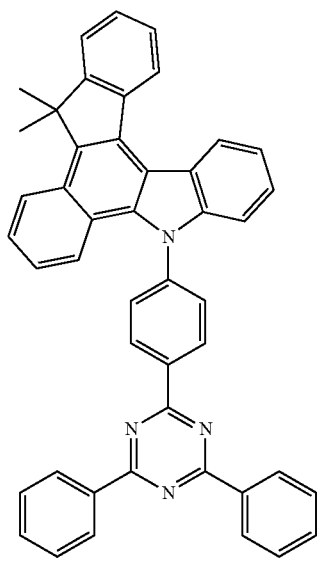
H2-141
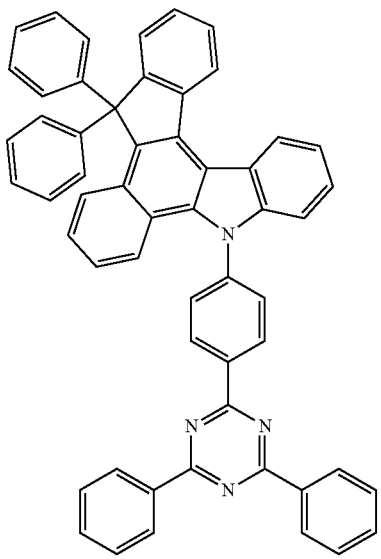
H2-142
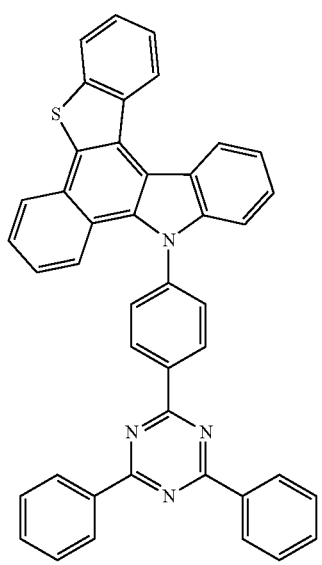
H2-143
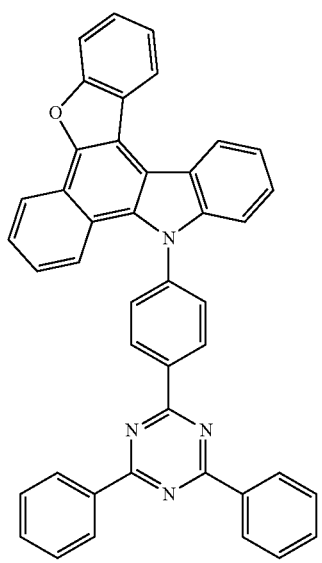

H2-144
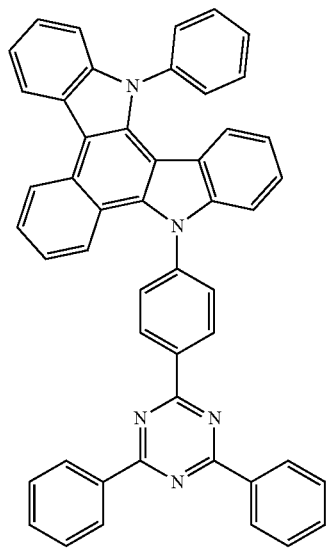
H2-145
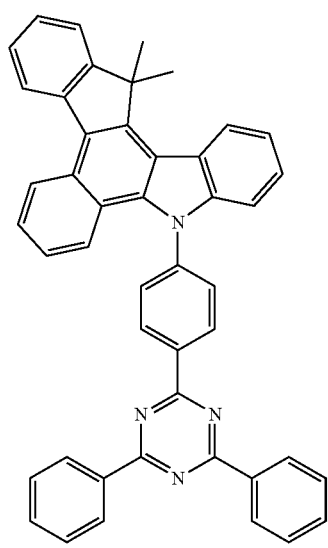
H2-146
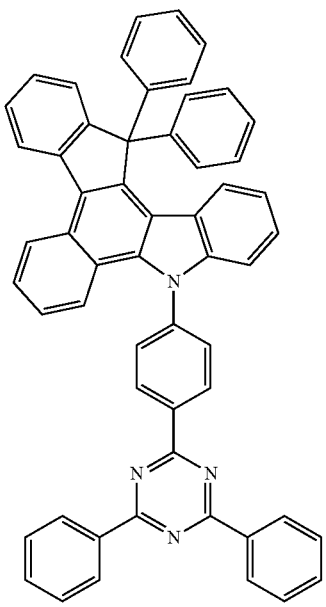
H2-147
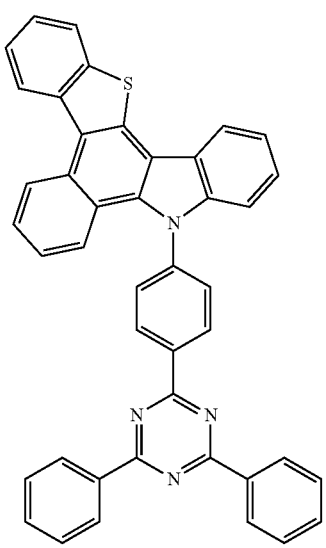

H2-148
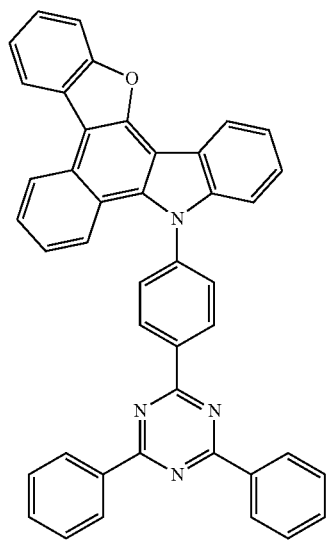
H2-149
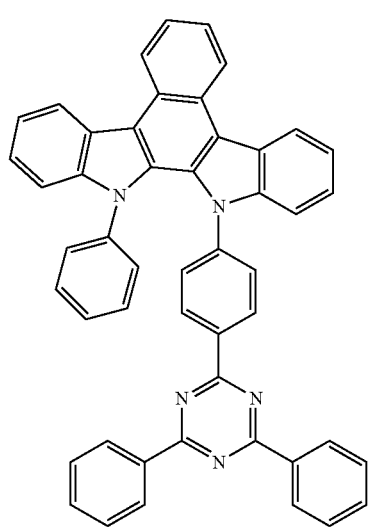
H2-150
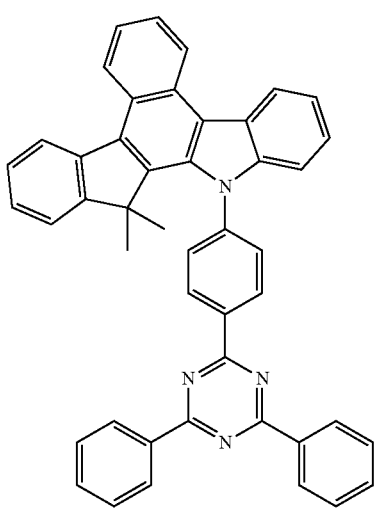
H2-151
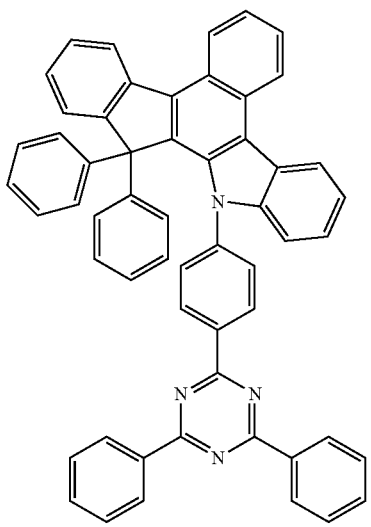
H2-152
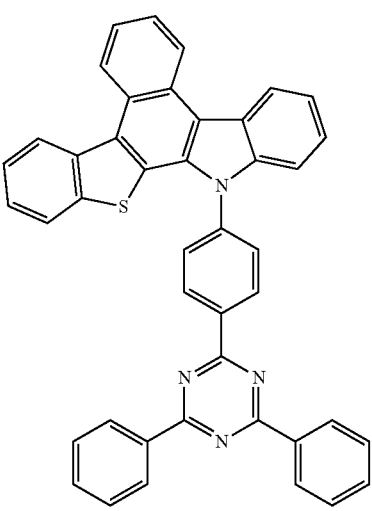
H2-153
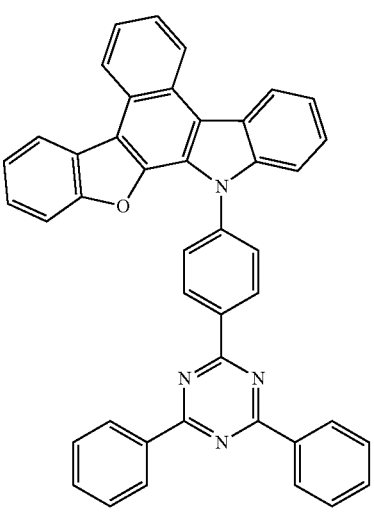

1033
-continued
H2-154
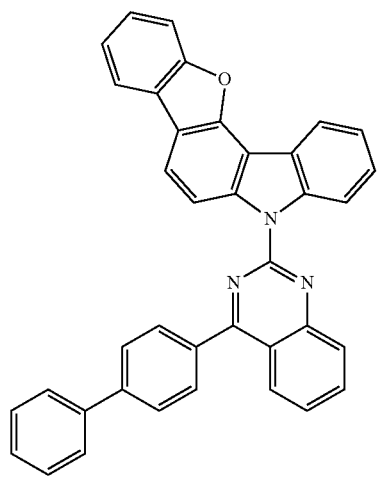
H2-155
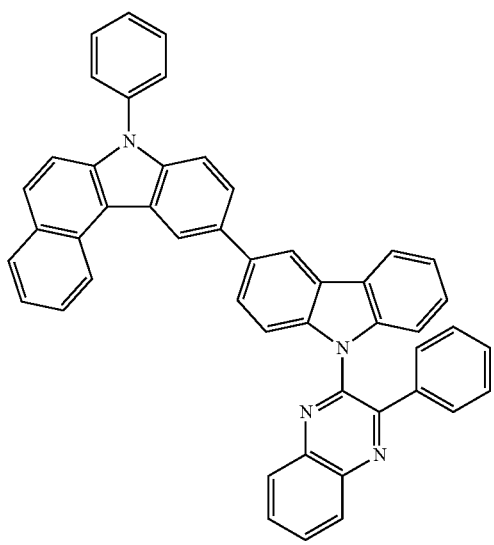
H2-156
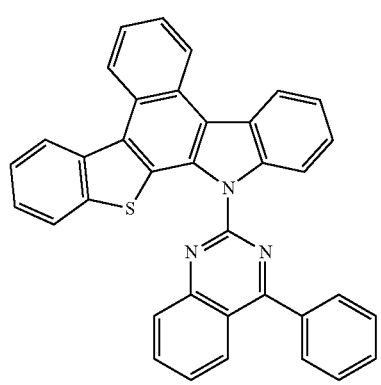
1034
-continued
H2-157
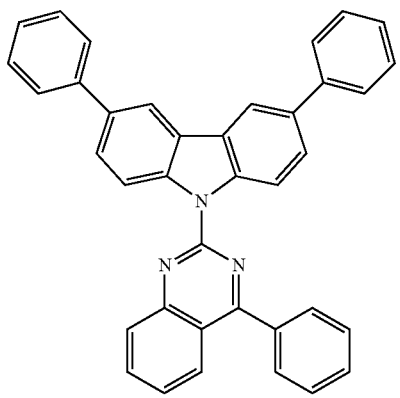
H2-158
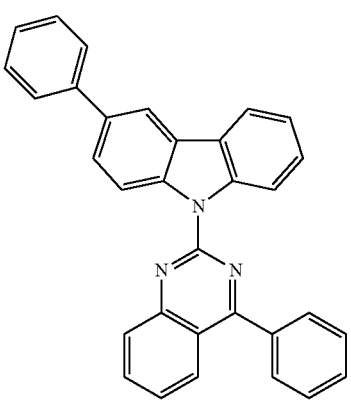
H2-159
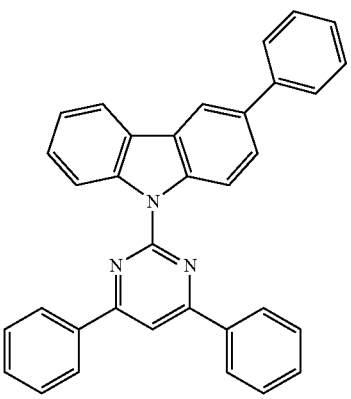
H2-160
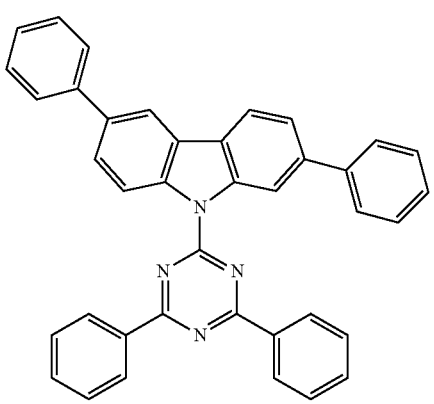

H2-161
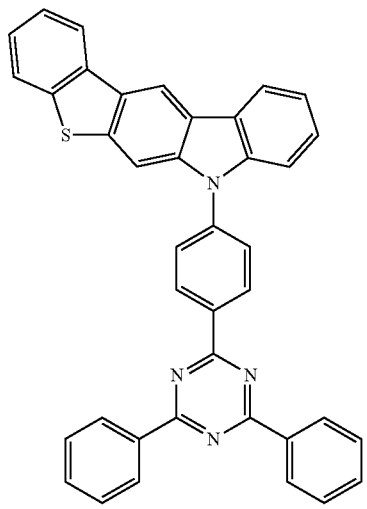
H2-162
H2-163
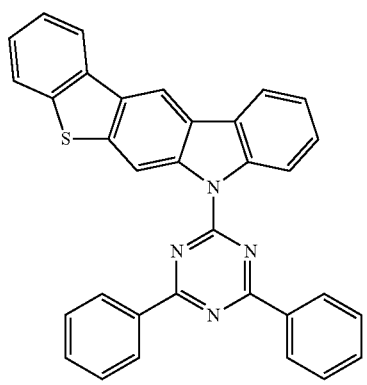
H2-164
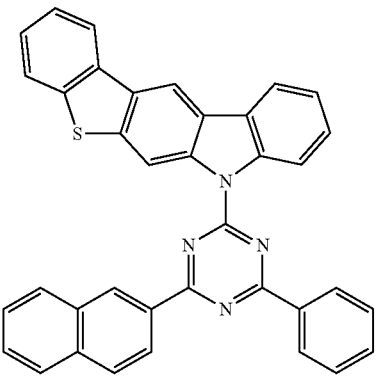
H2-165
H2-166
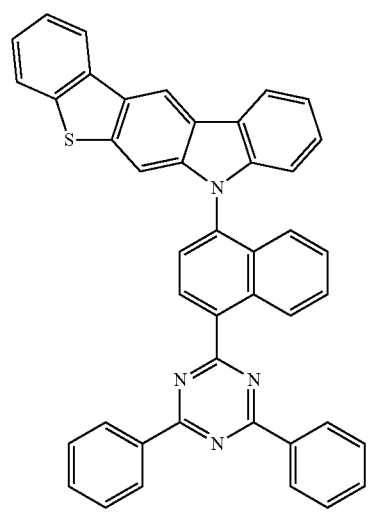

1037
-continued
H2-167
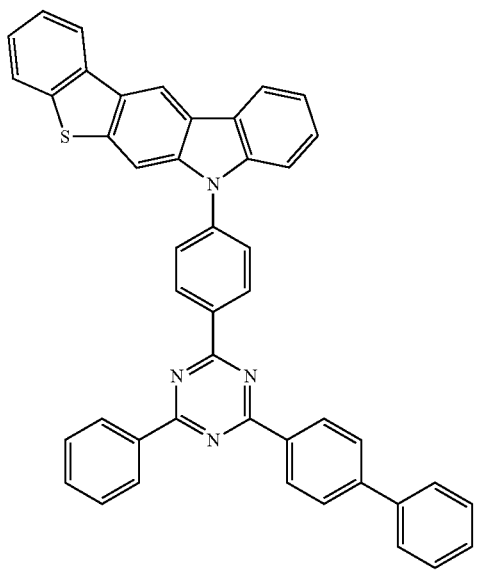
H2-168
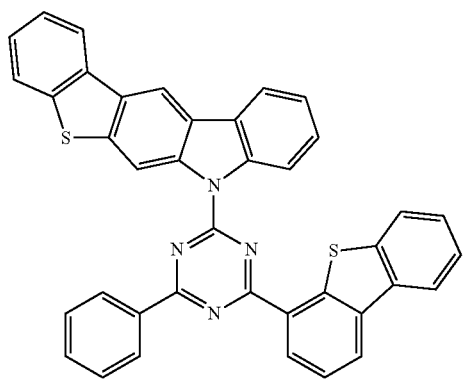
H2-169
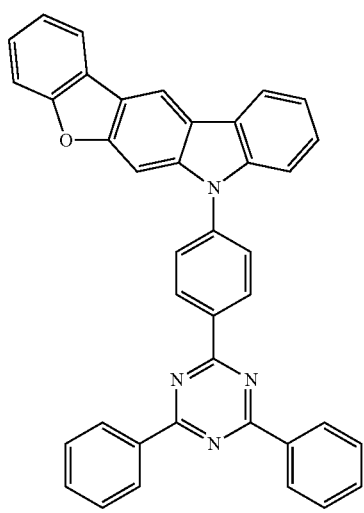
1038
-continued
H2-170
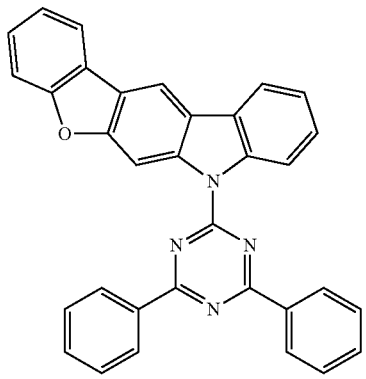
H2-171
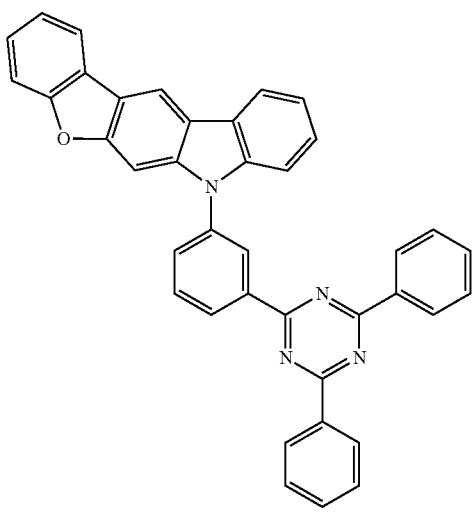
H2-172
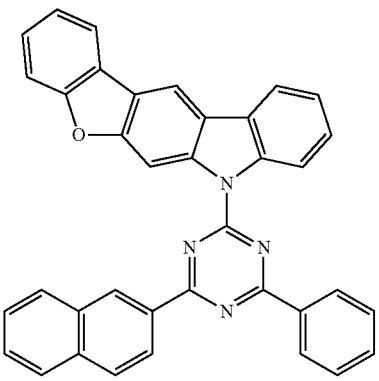

| 1039 -continued | 1040 -continued |
|---|---|
| H2-173 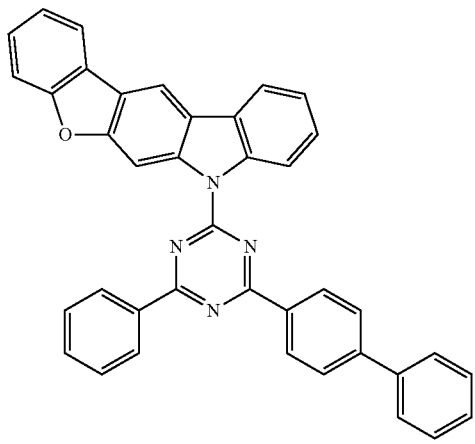 | H2-176 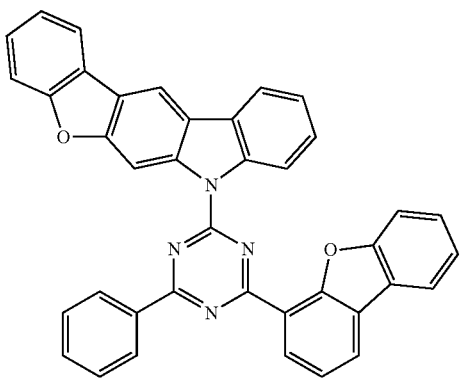 |
| H2-174 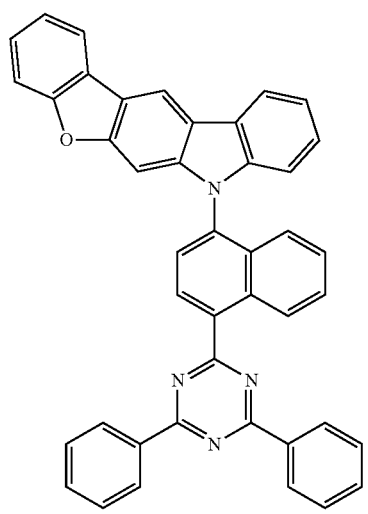 | H2-177 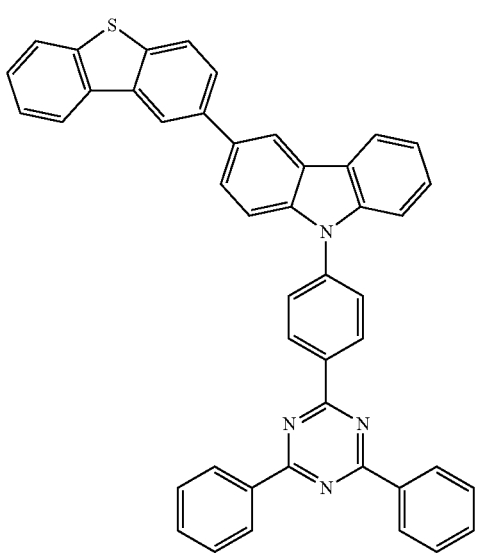 |
| H2-175 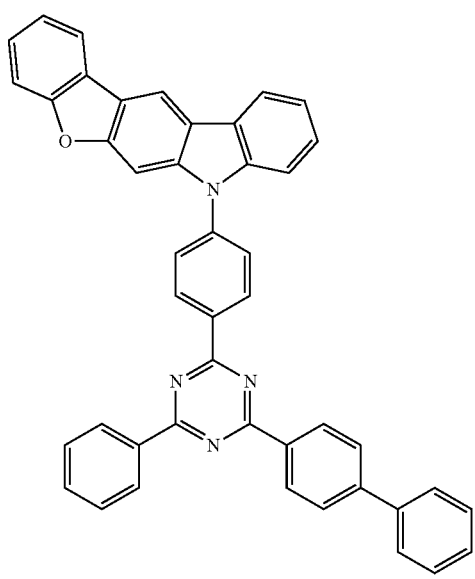 | H2-178 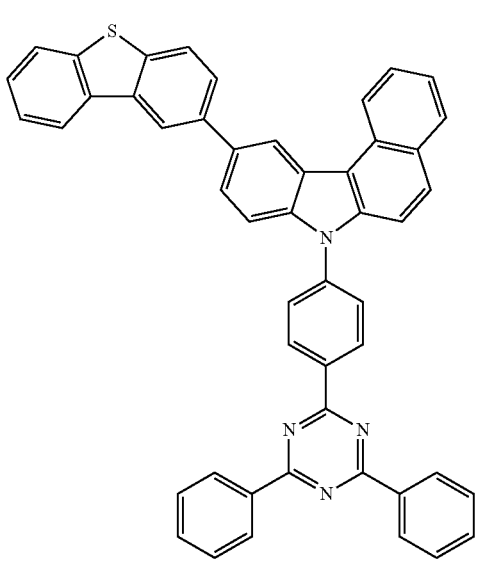 |

H2-179
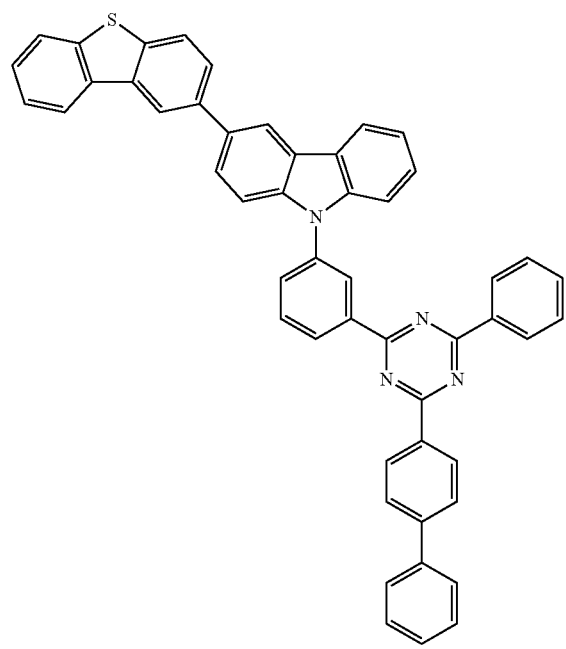
H2-181
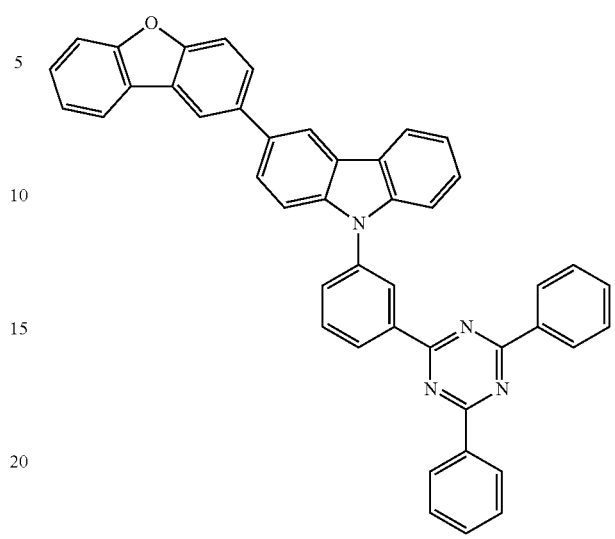
H2-182
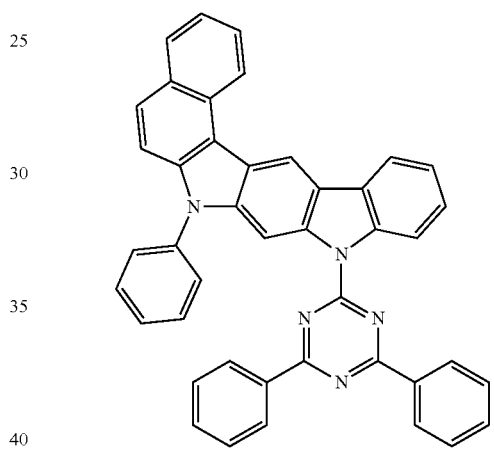
H2-180
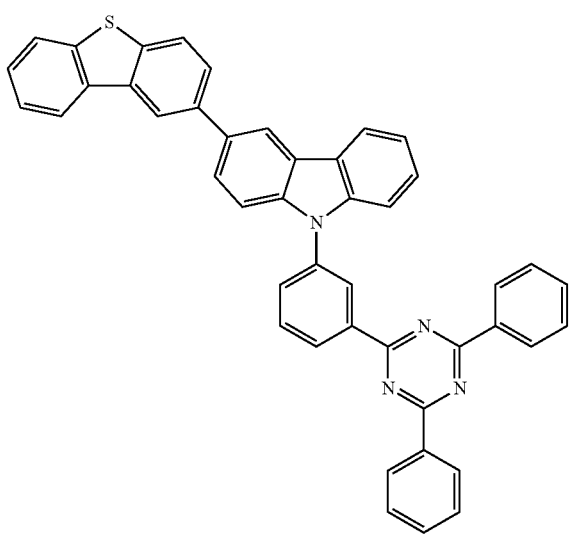
H2-183
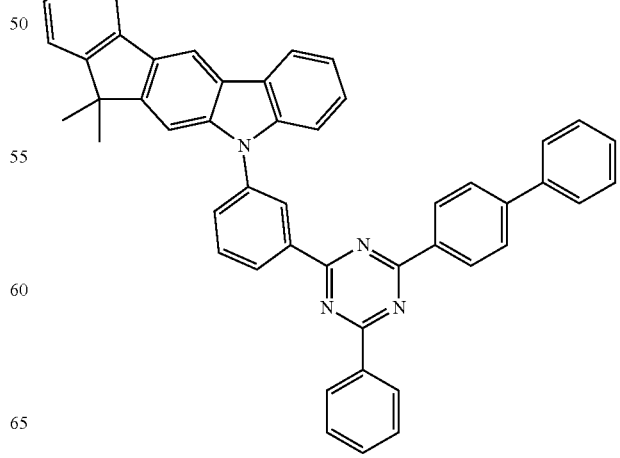

H2-184
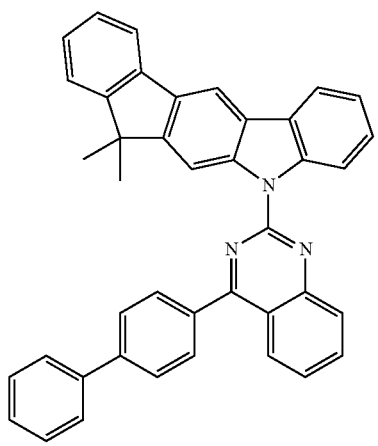
H2-185
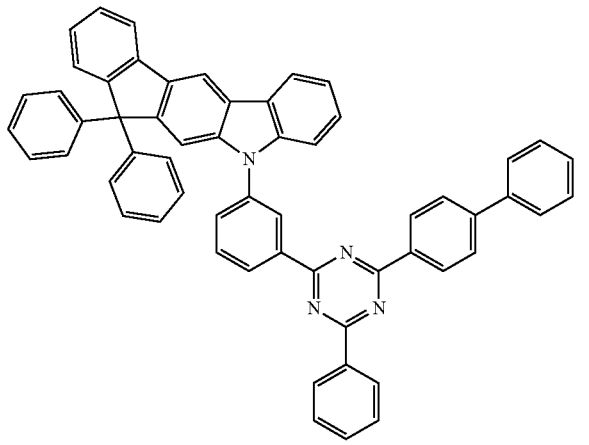
H2-186
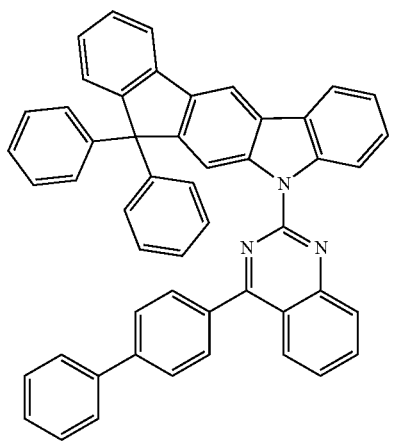
H2-187
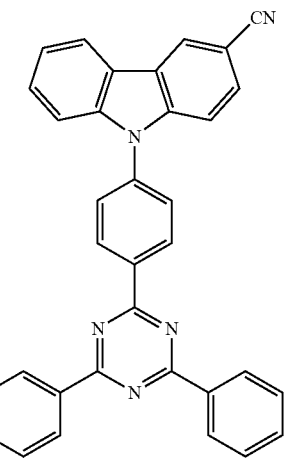
H2-188
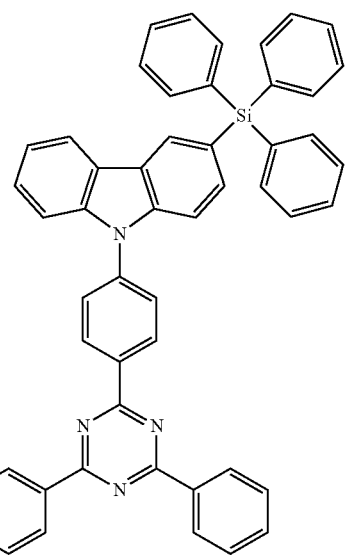
H2-189
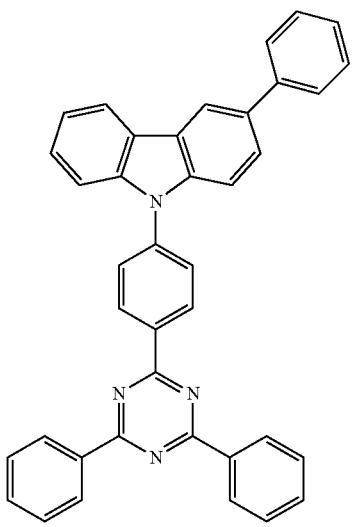

H2-190
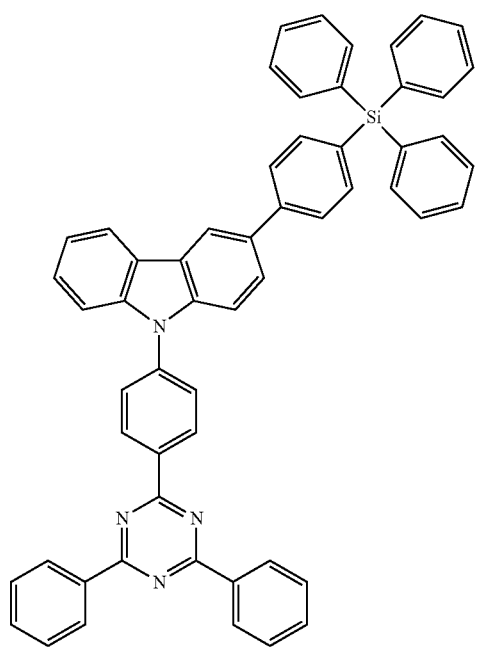
H2-193
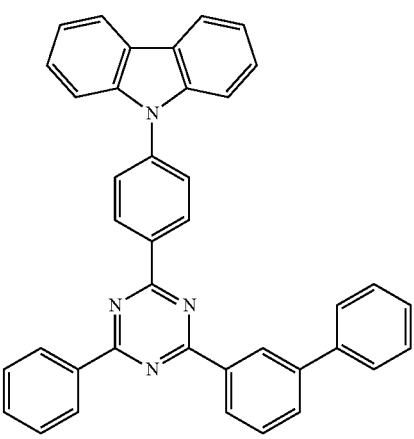
H2-191
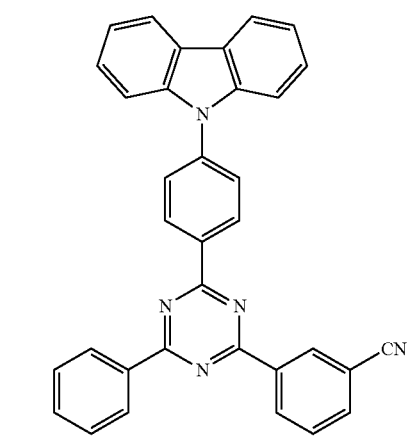
H2-194
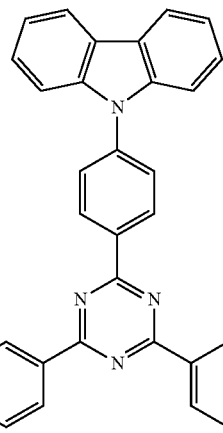
H2-192
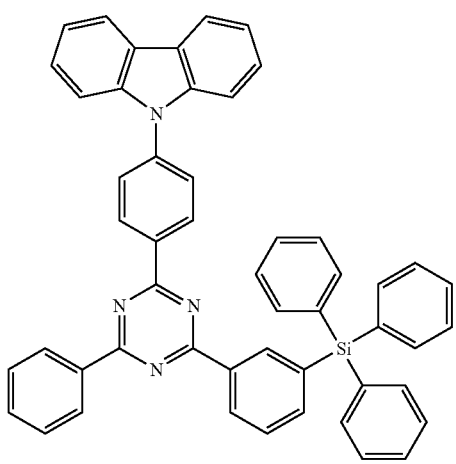
H2-195
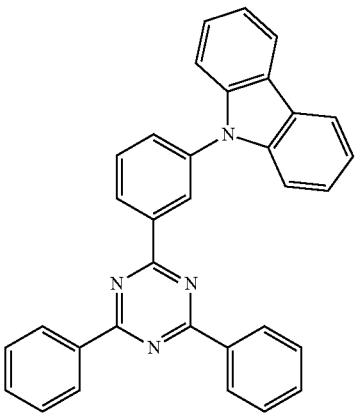

H2-196
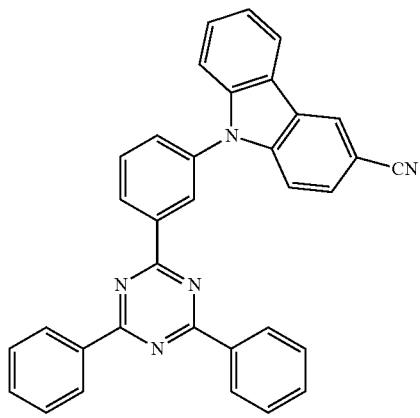
H2-197
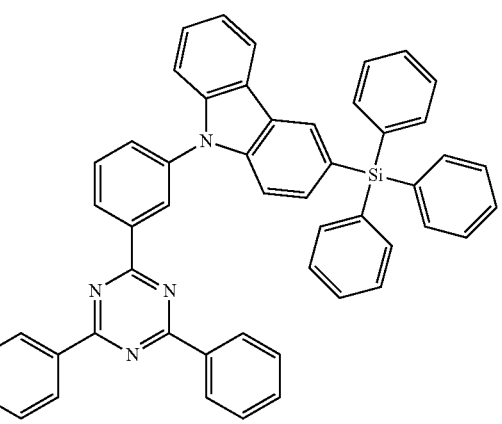
H2-198
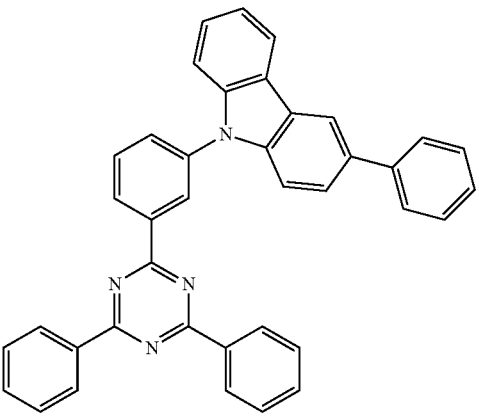
H2-199
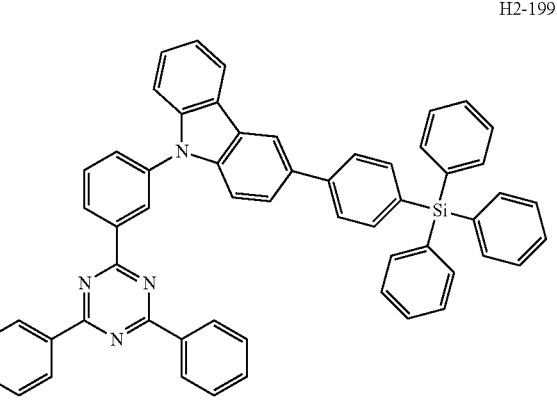
H2-200
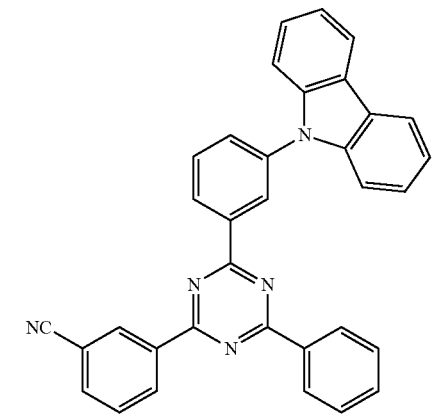
H2-201
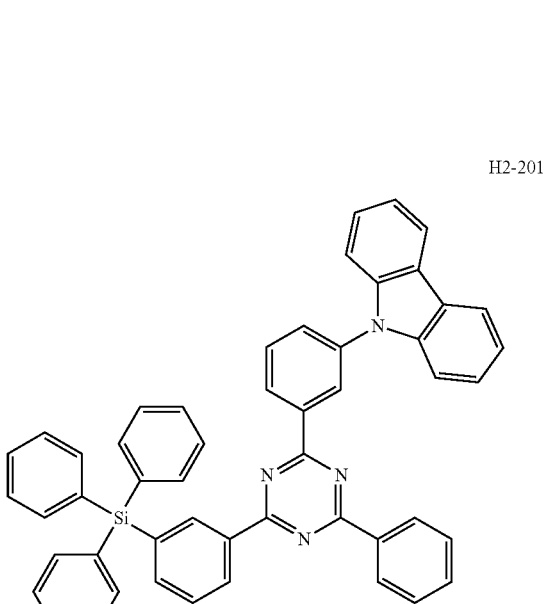
H2-202
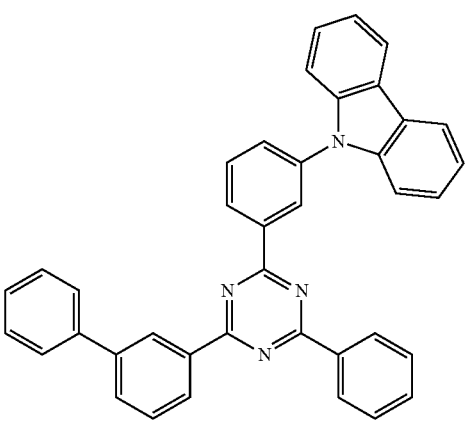

1049
H2-203
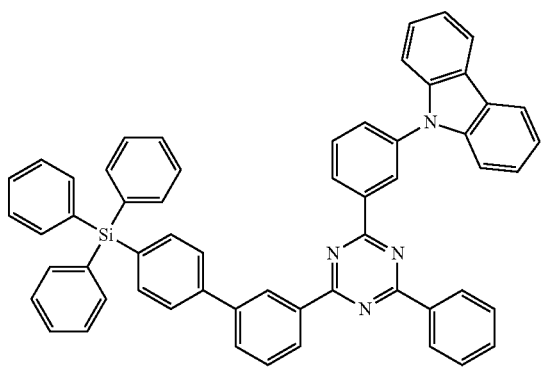
H2-204
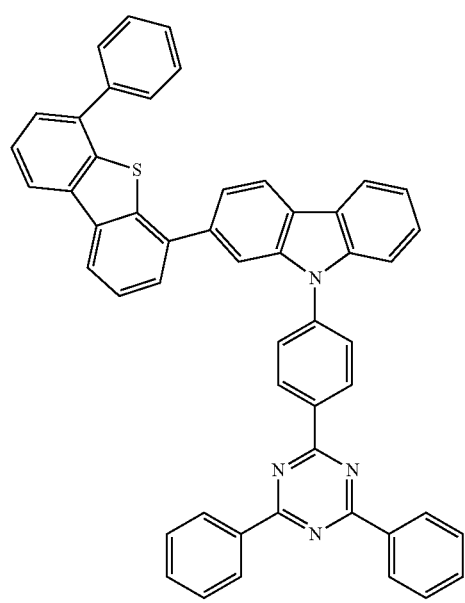
H2-205
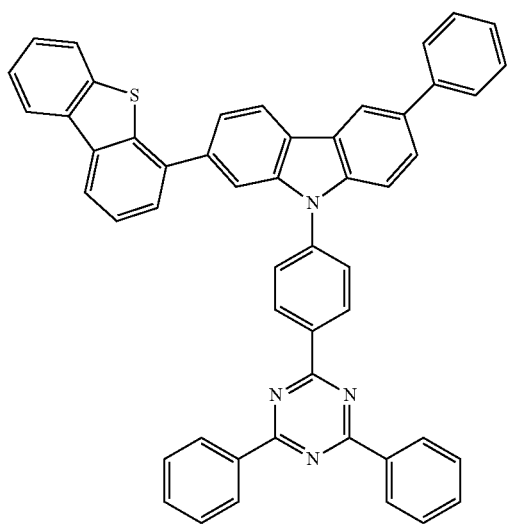
1050
H2-206
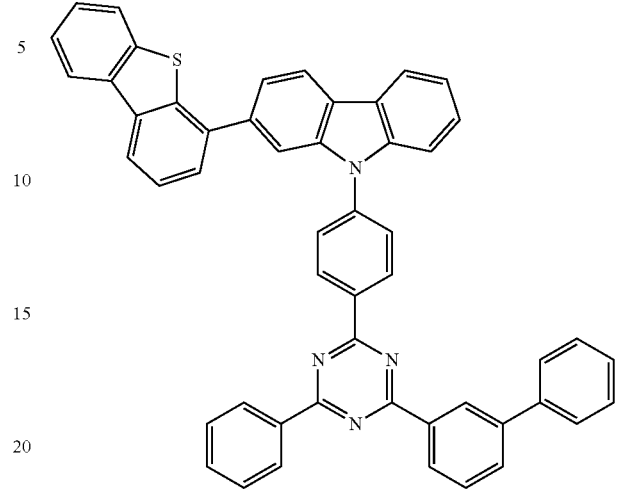
H2-207
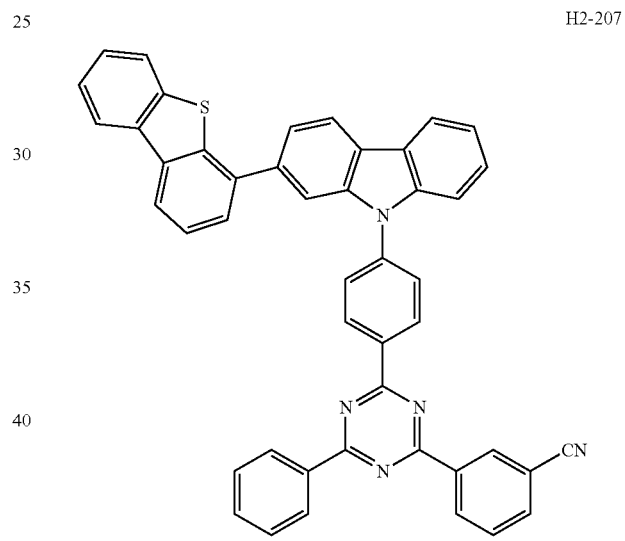
H2-208
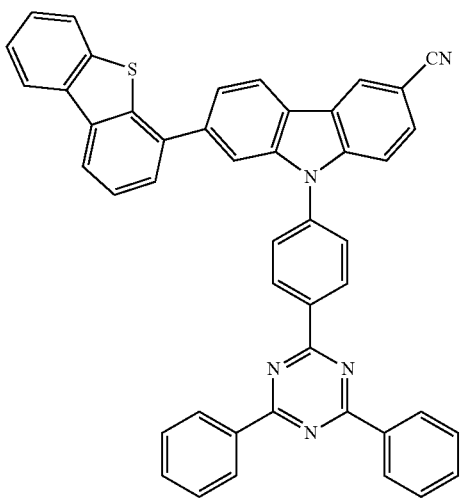

H2-209
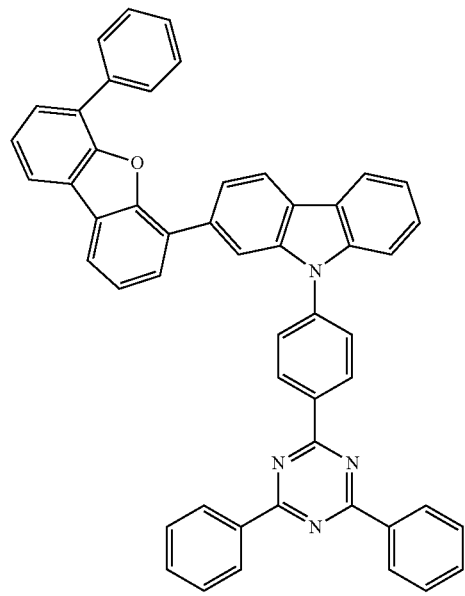
H2-210
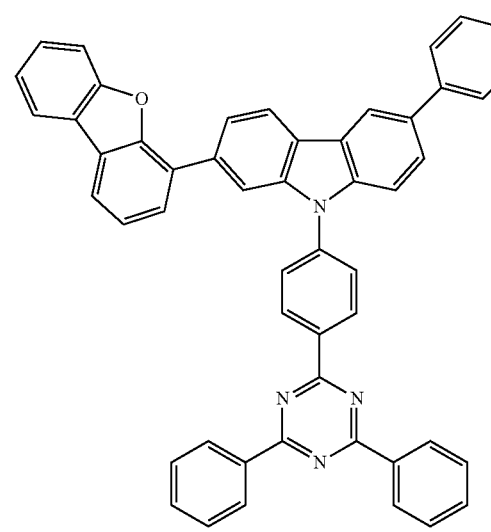
H2-211
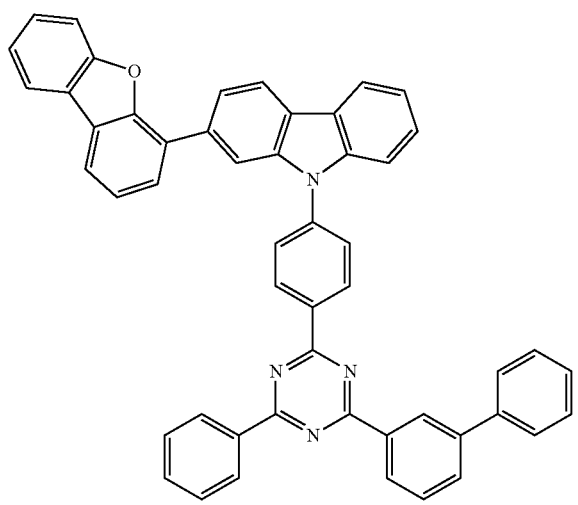
H2-212
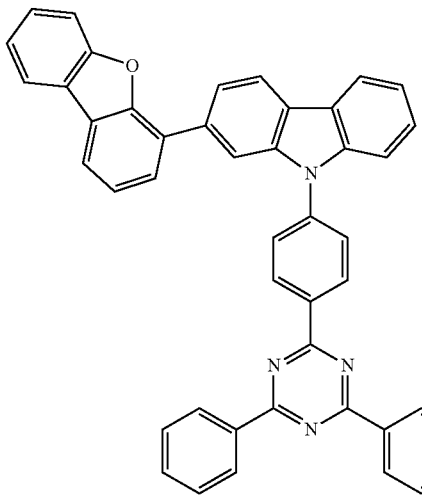
H2-213
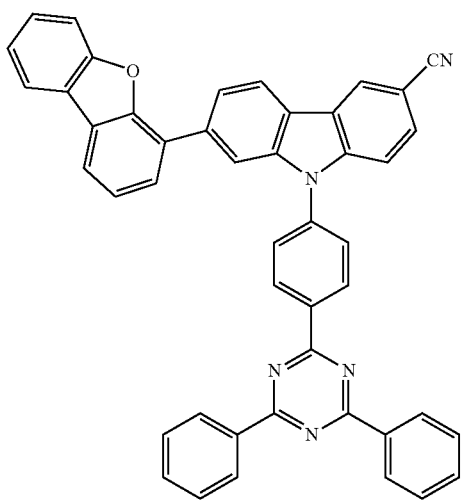
H2-214
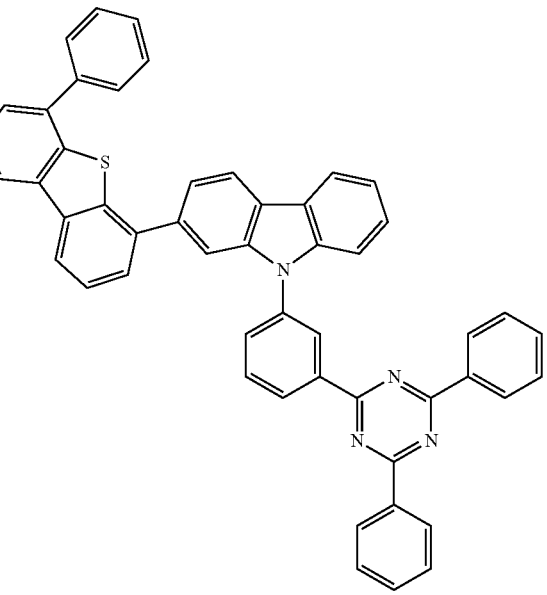

-continued
H2-215
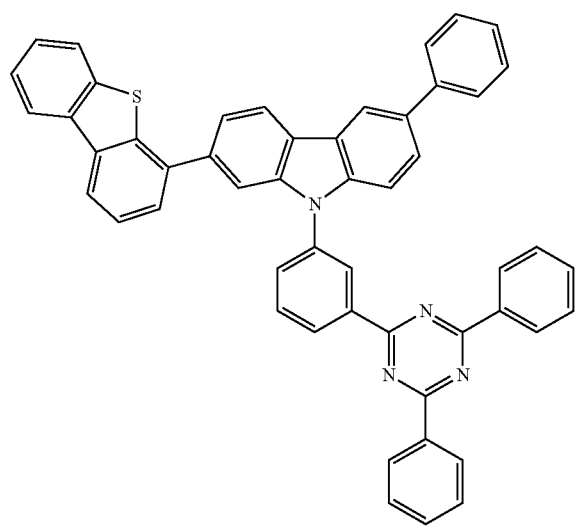
H2-216
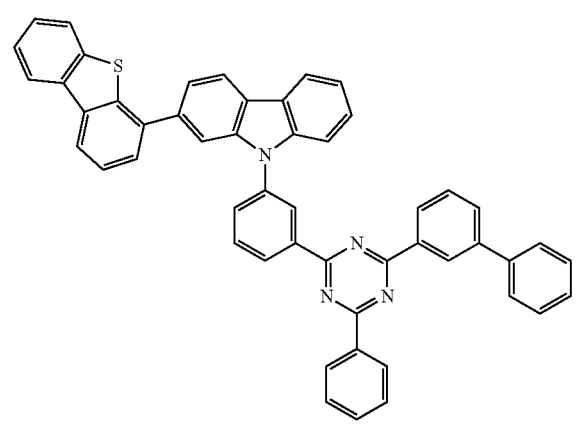
H2-217
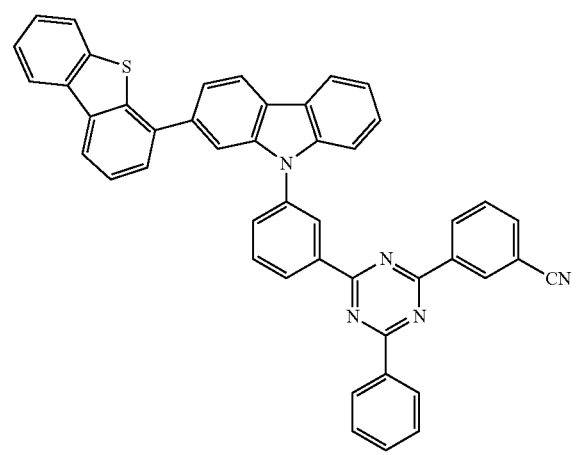
-continued
H2-218
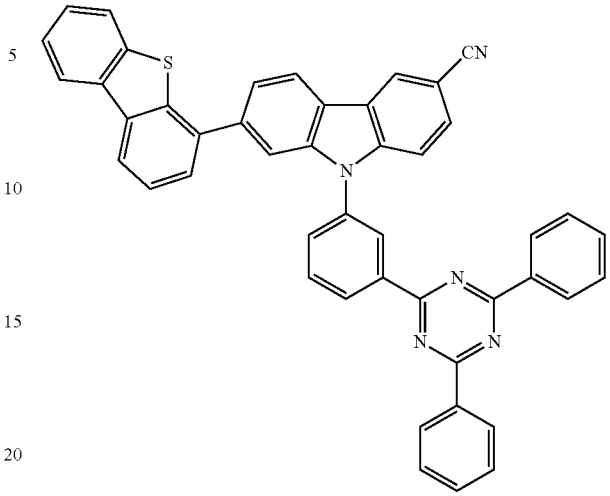
H2-219
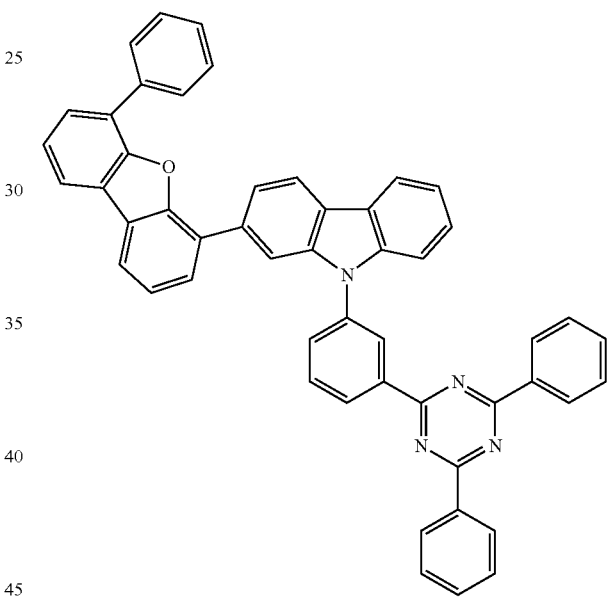
H2-220
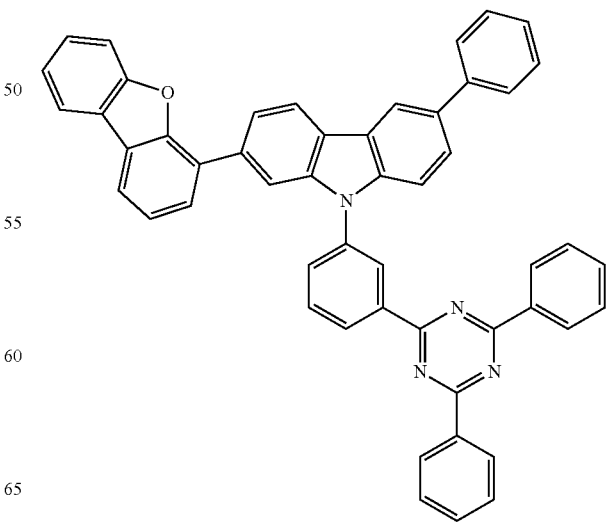

H2-221
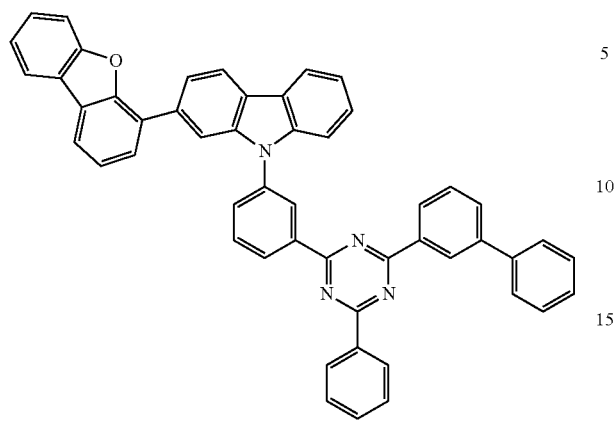
H2-222
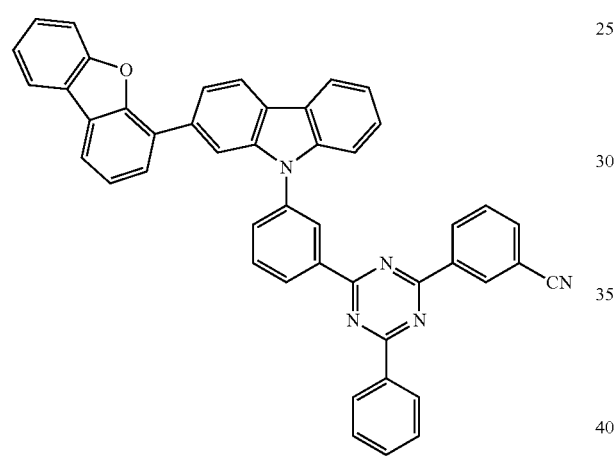
H2-223
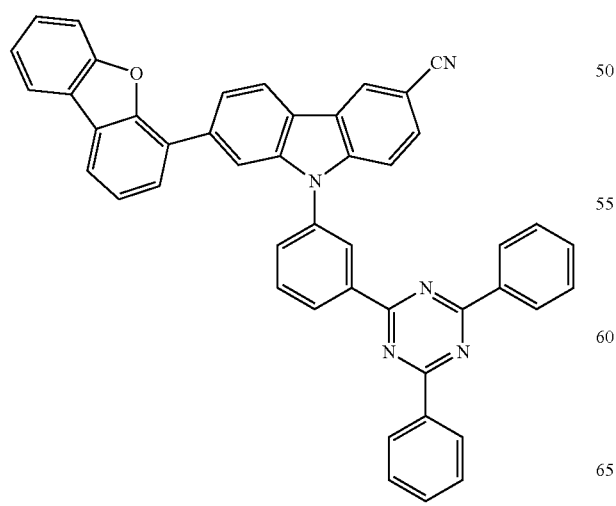
H2-224
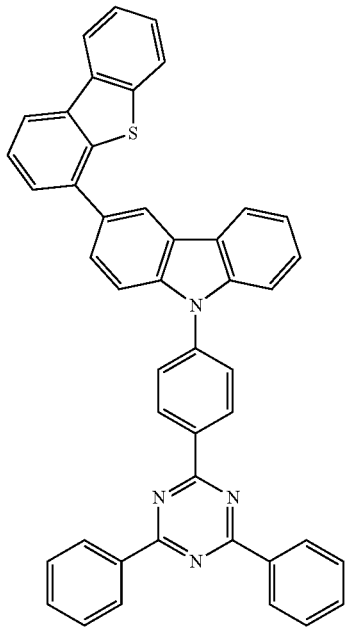
H2-225
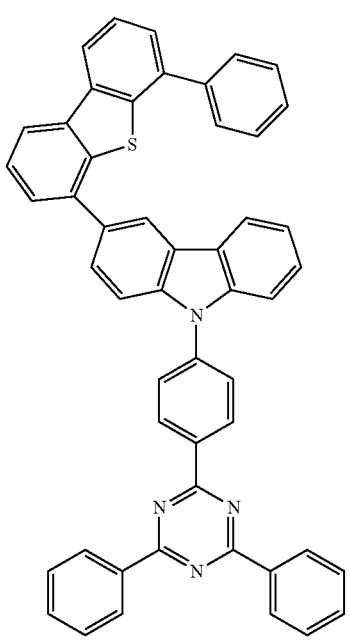

H2-226
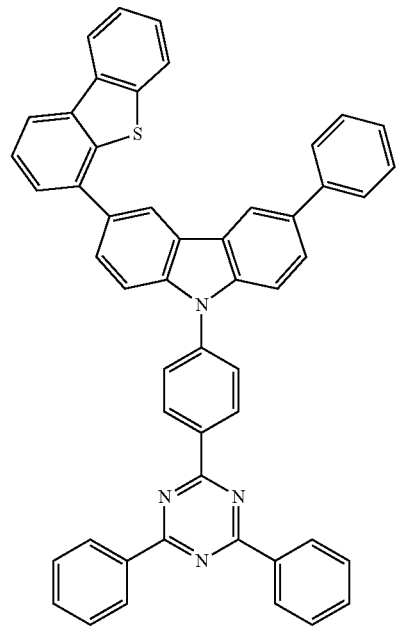
H2-228
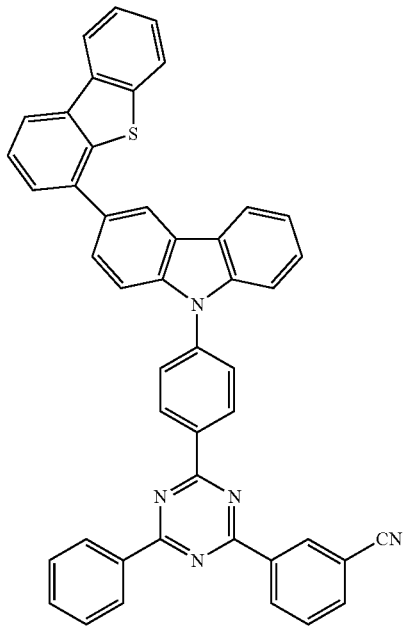
H2-227
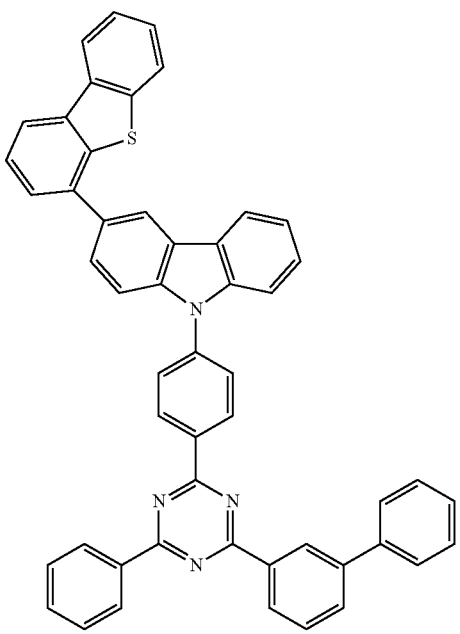
H2-229
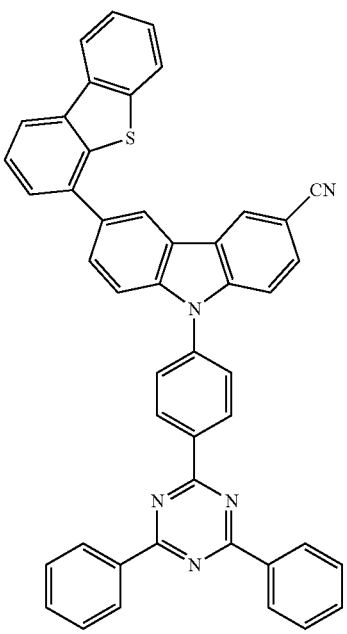

H2-230
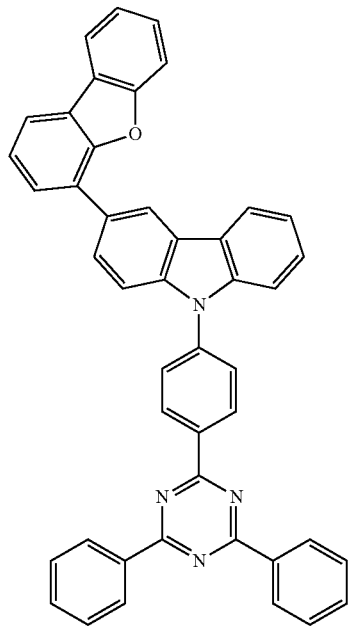
H2-232
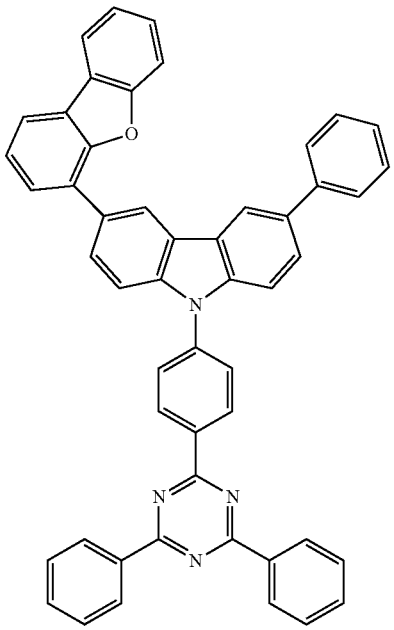
H2-231
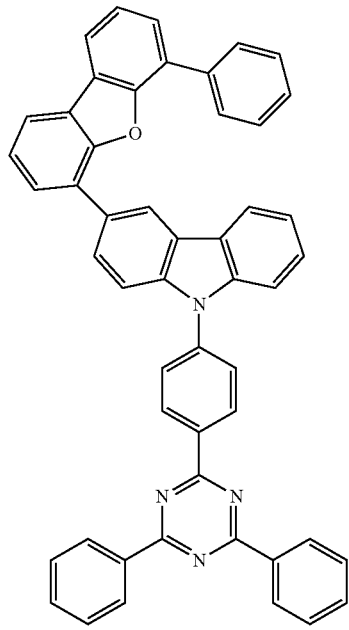
H2-233
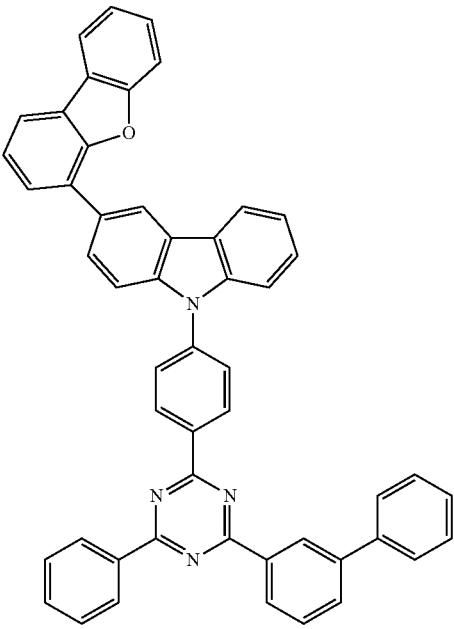

1061
-continued
H2-234
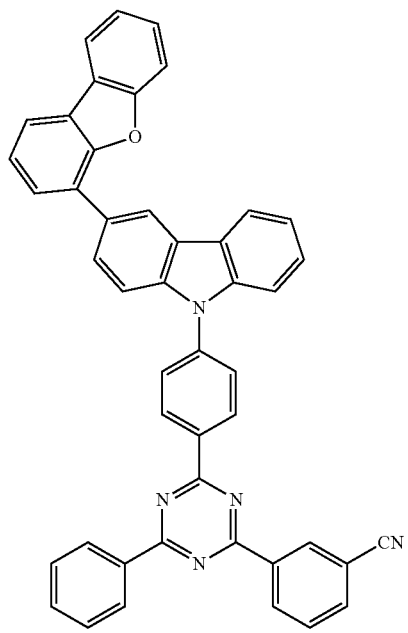
H2-235
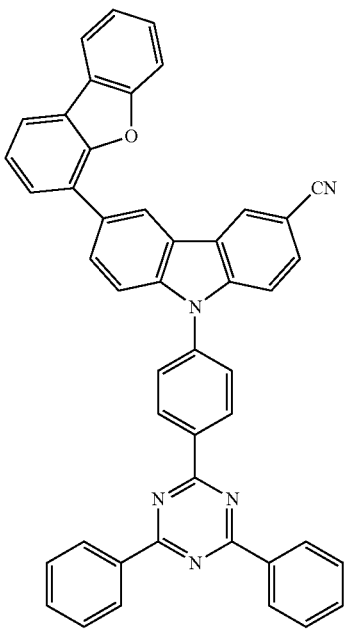
1062
-continued
H2-236
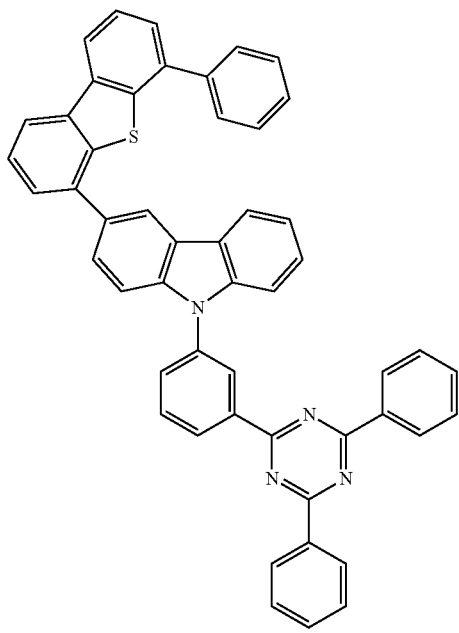
H2-237
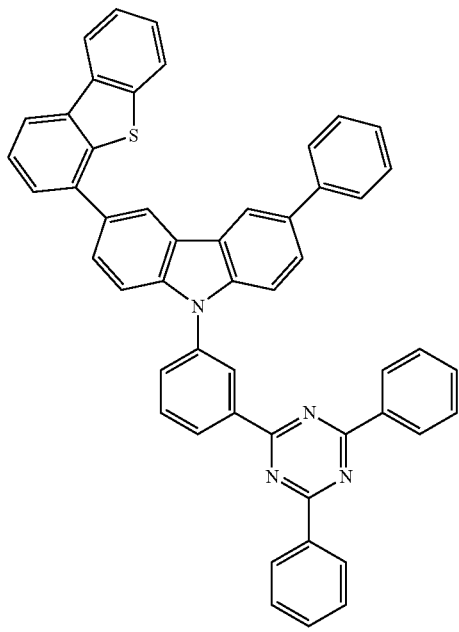

H2-238
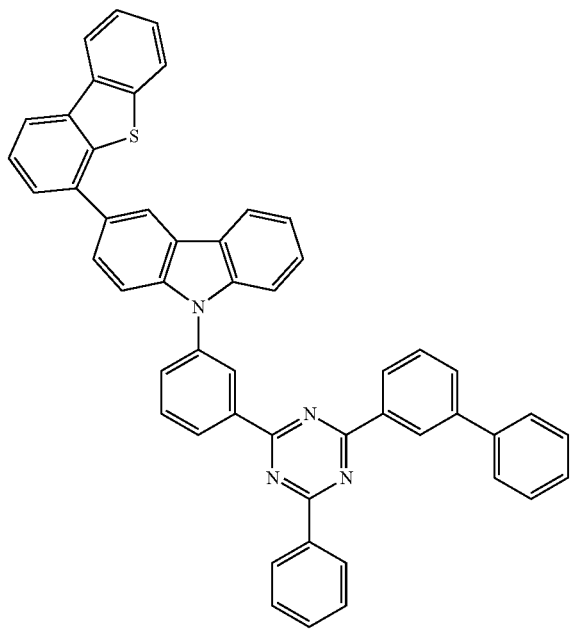
H2-240
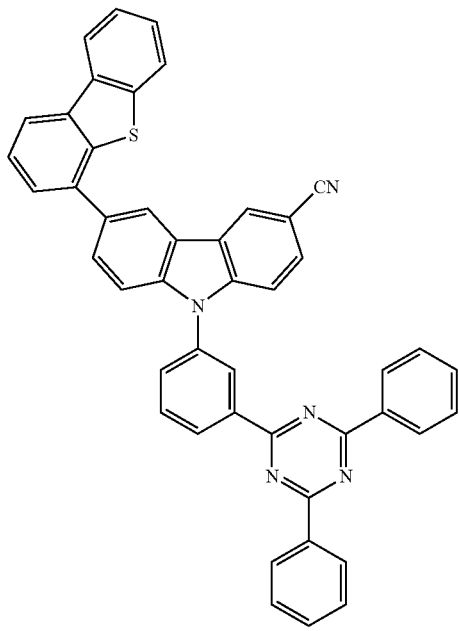
H2-239
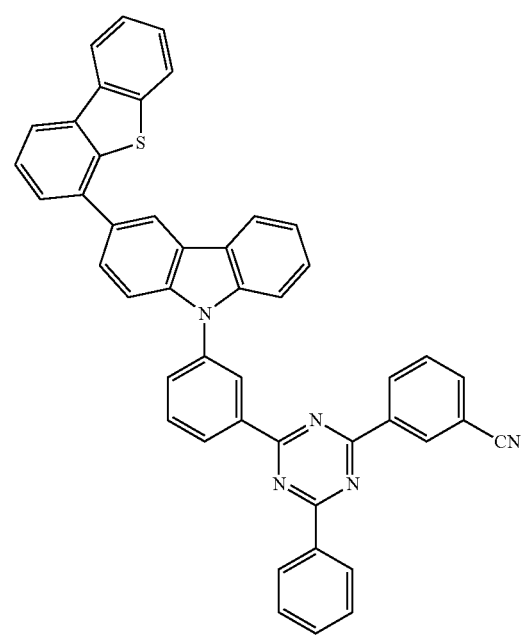
H2-241
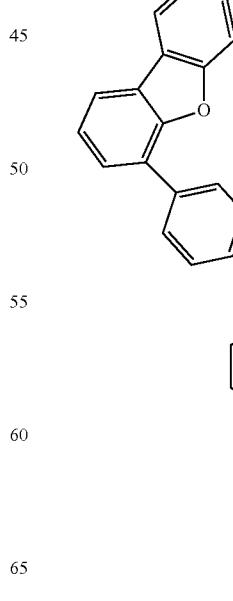

H2-242
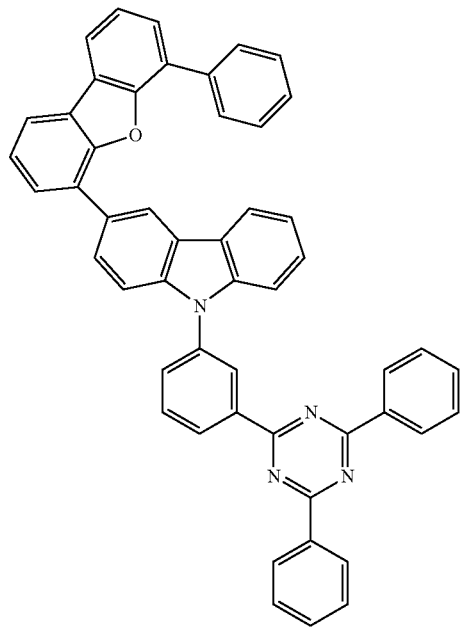
H2-243
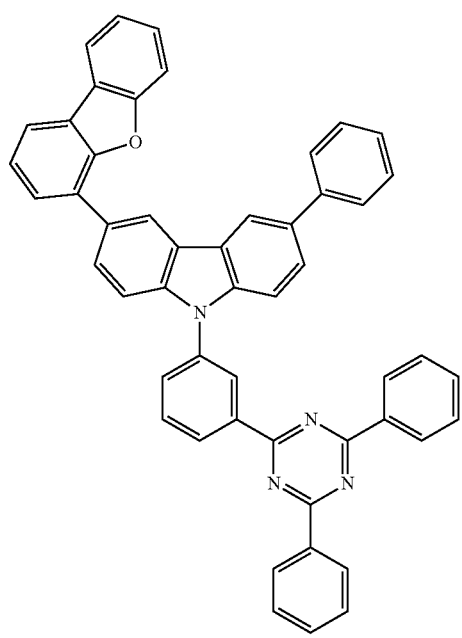
H2-244
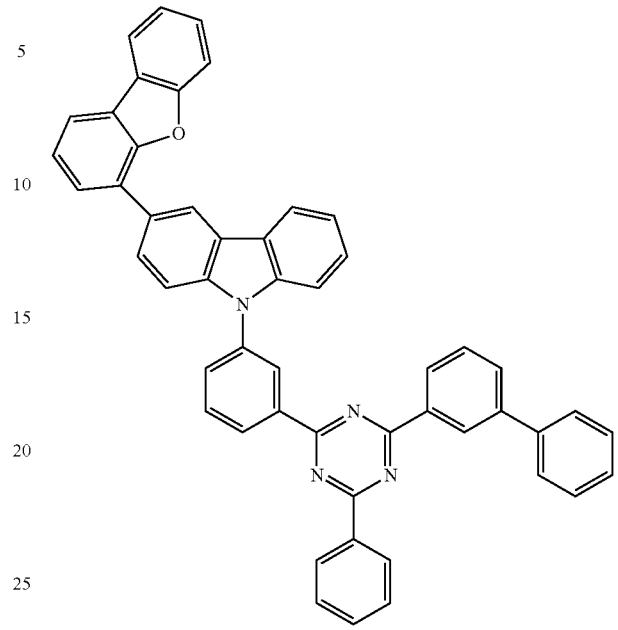
H2-245
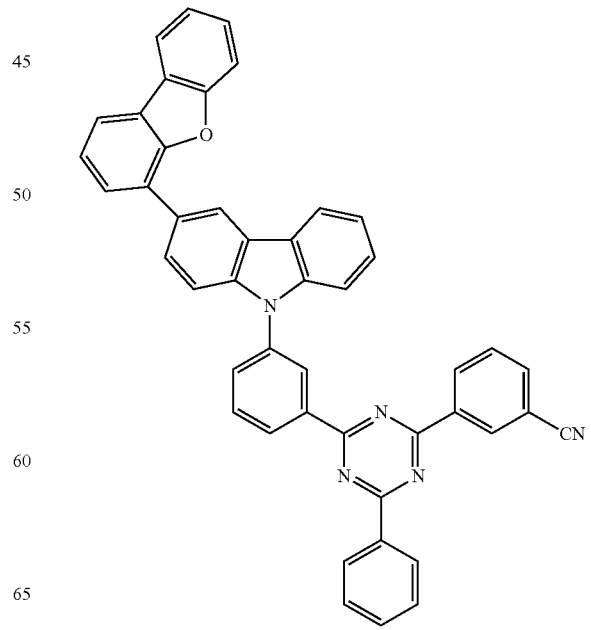

H2-246
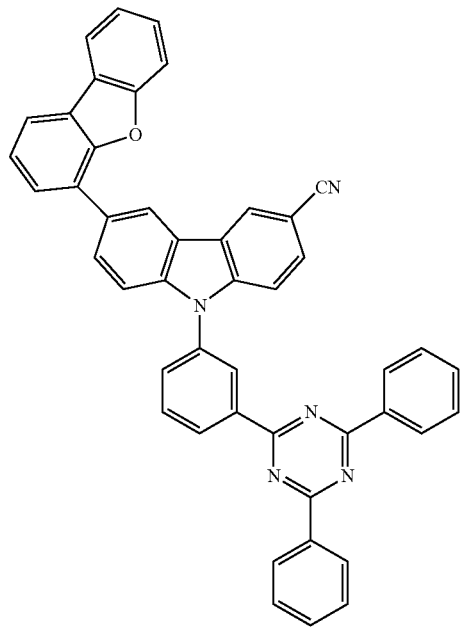
H2-247
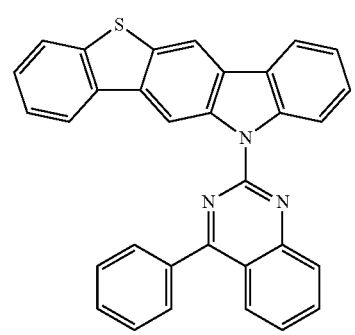
H2-248
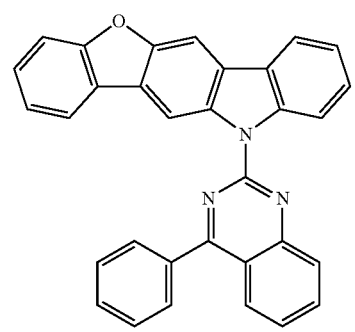
H2-249
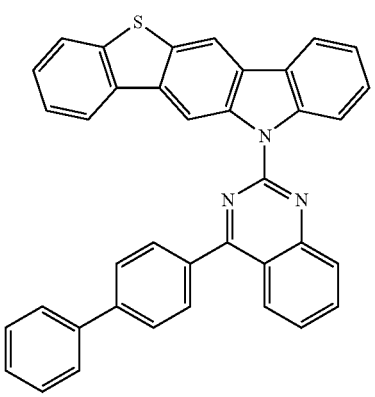
H2-250
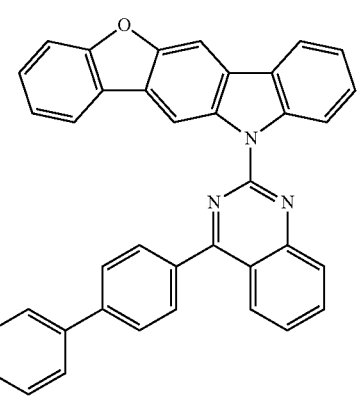
H2-251
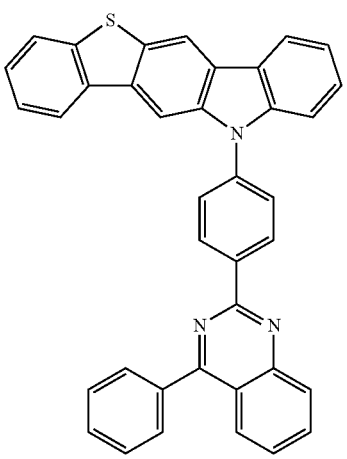

-continued
H2-252
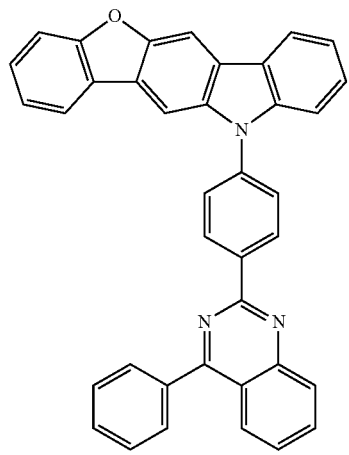
H2-253
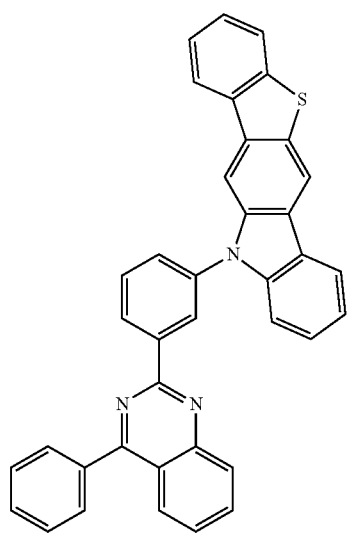
H2-254
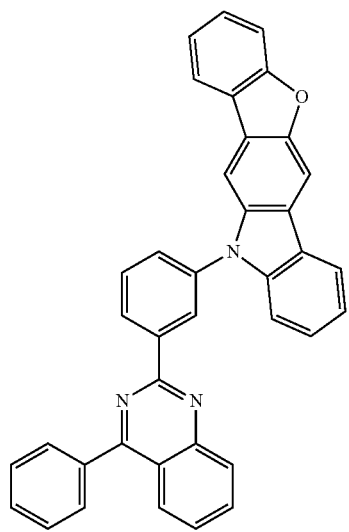
-continued
H2-255
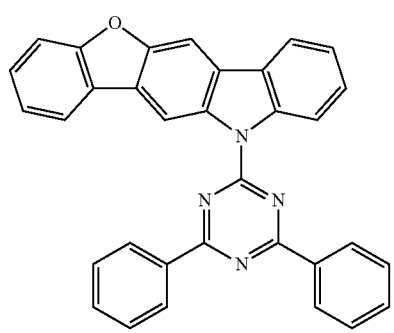
H2-256
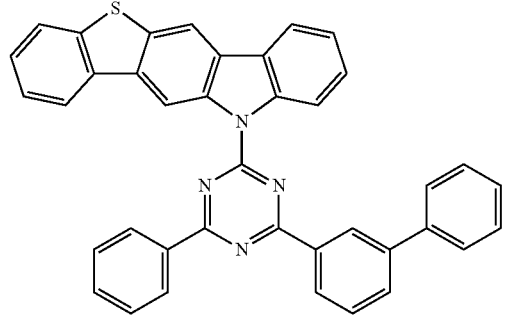
H2-257
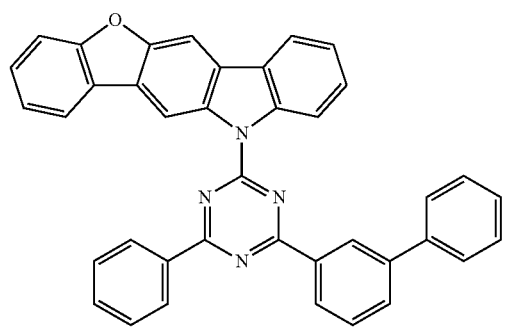
H2-258
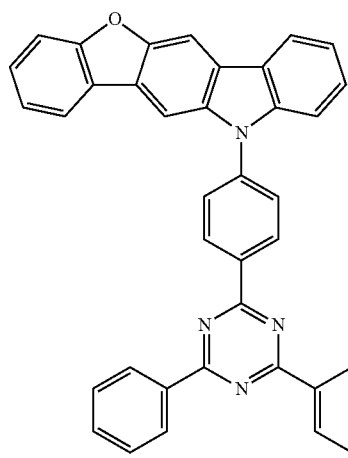

H2-259
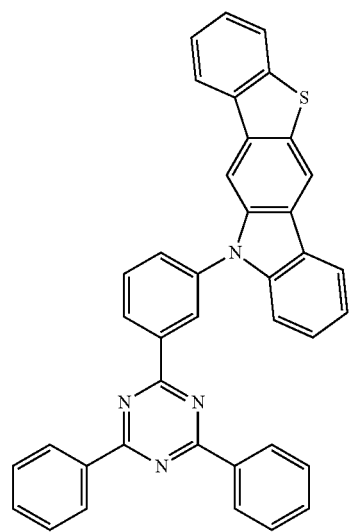
H2-260
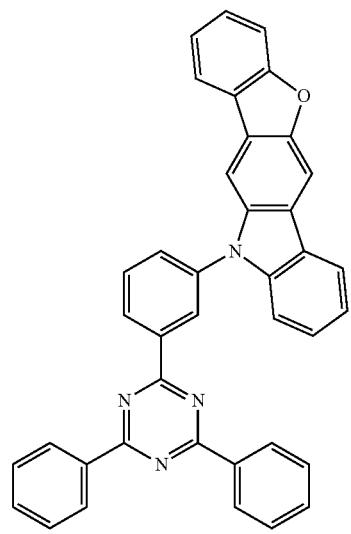
H2-261
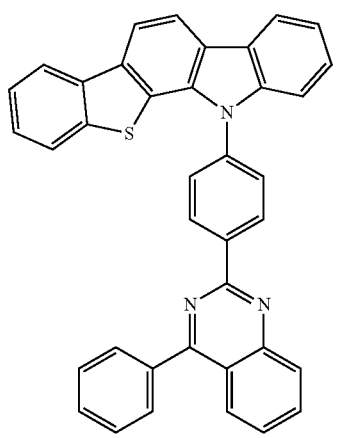
H2-262
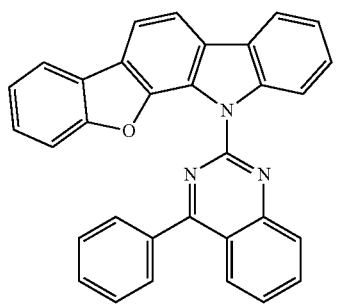
H2-263
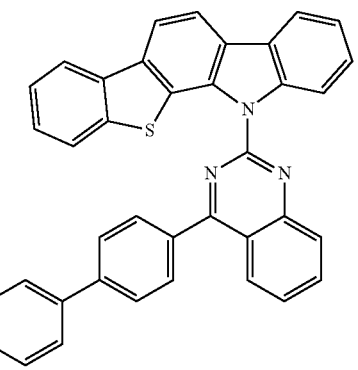
H2-264
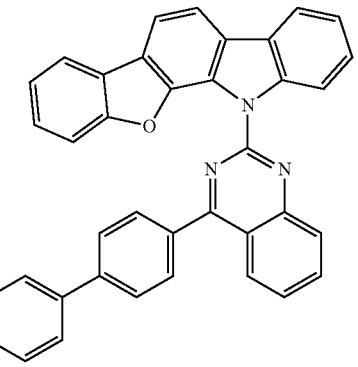
H2-265
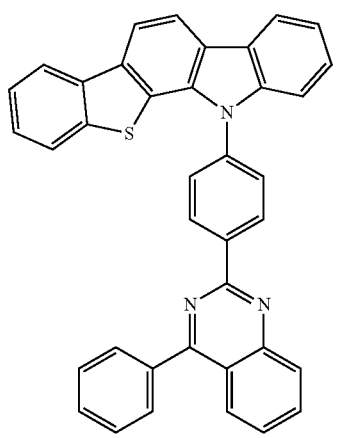

H2-266
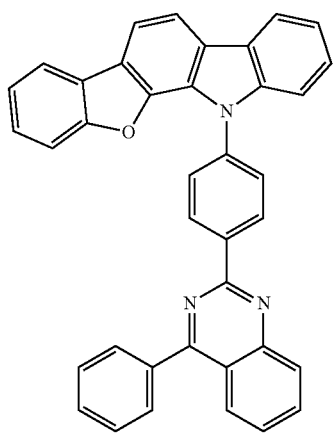
H2-267
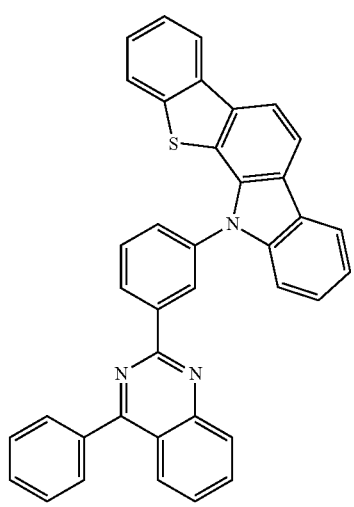
H2-268
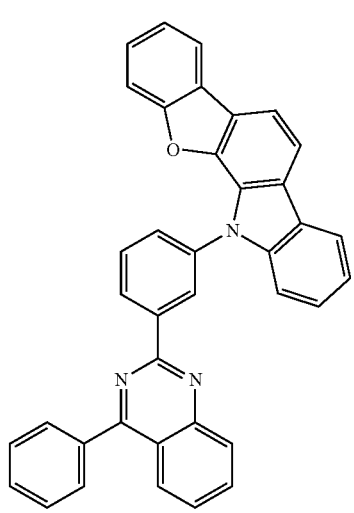
H2-269
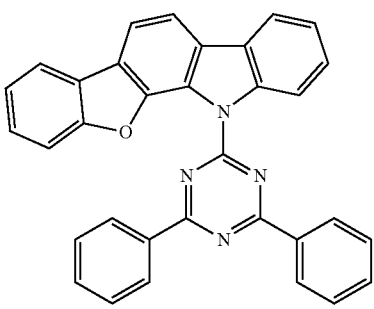
H2-270
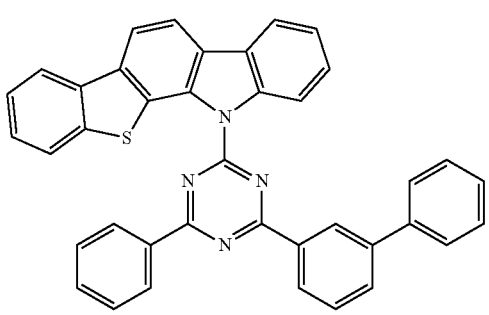
H2-271
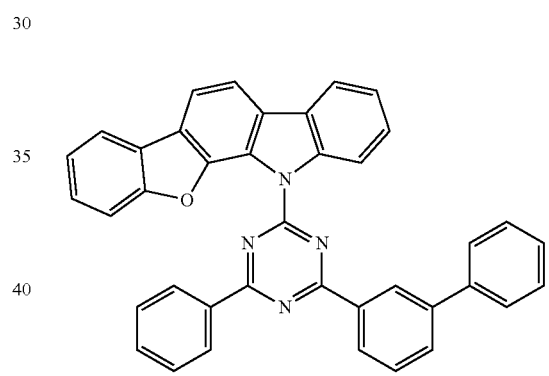
H2-272
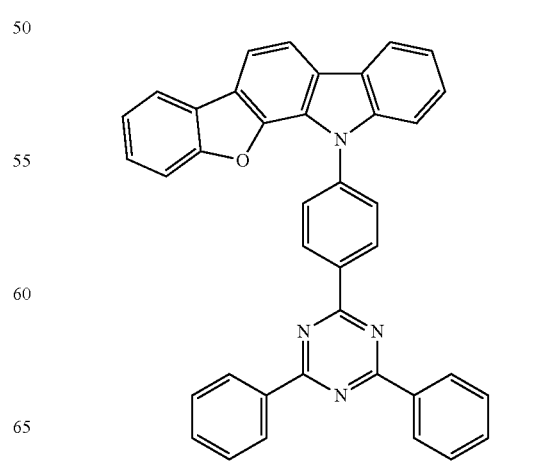

H2-273
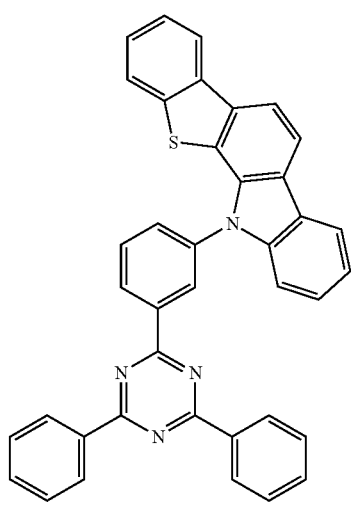
H2-274
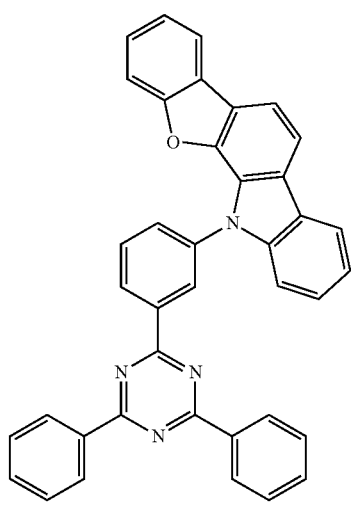
H2-275
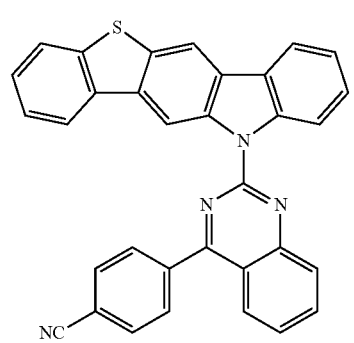
H2-276
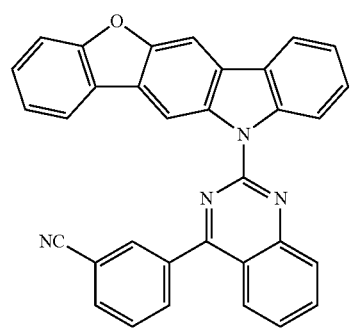
H2-277
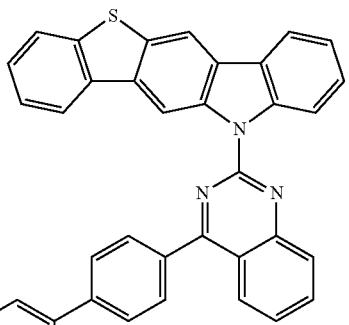
H2-278
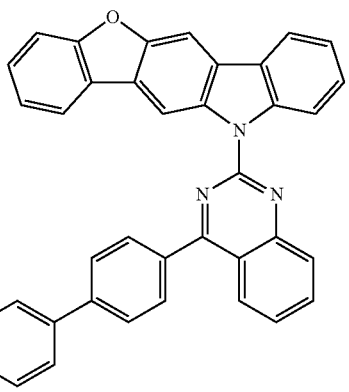
H2-279
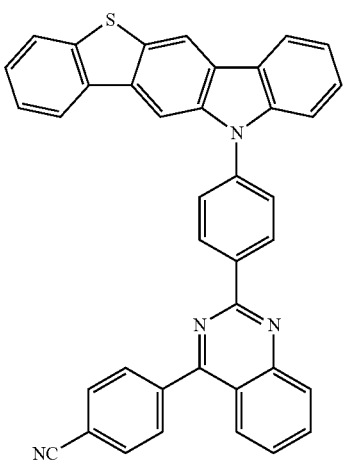

| 1077 -continued | 1078 -continued |
|---|---|
| H2-280 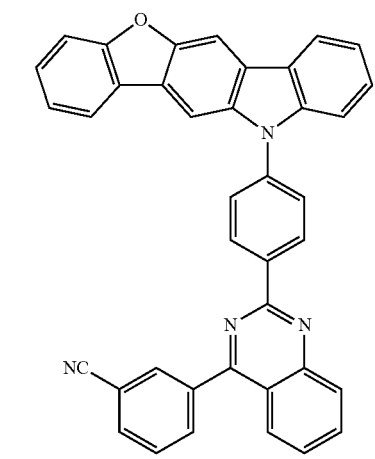 | H2-283 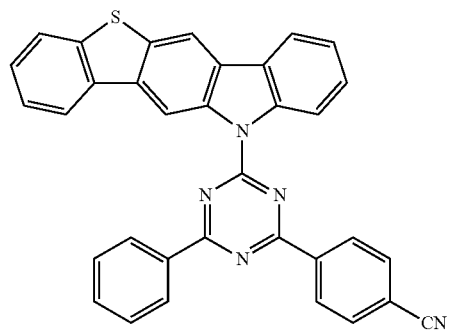 |
| H2-281 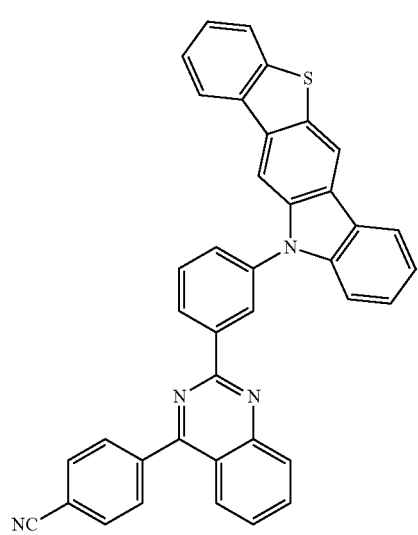 | H2-284 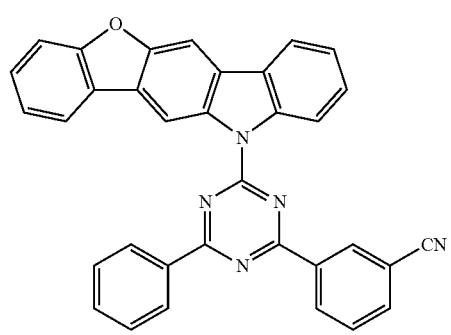 |
| H2-282 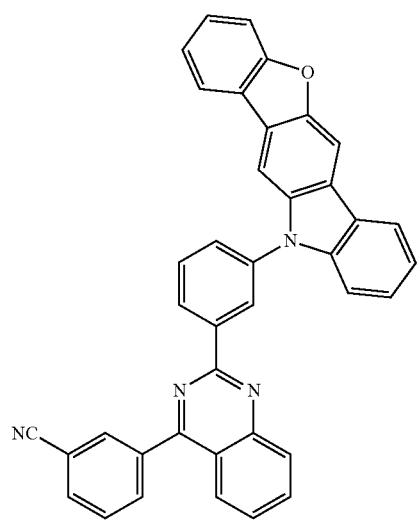 | H2-285 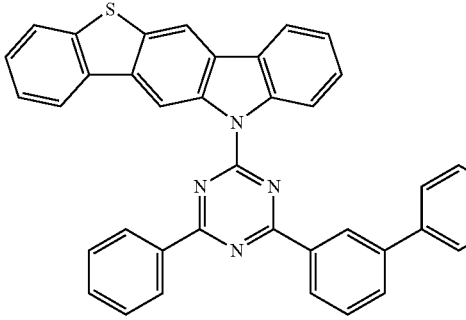 |
| | H2-286 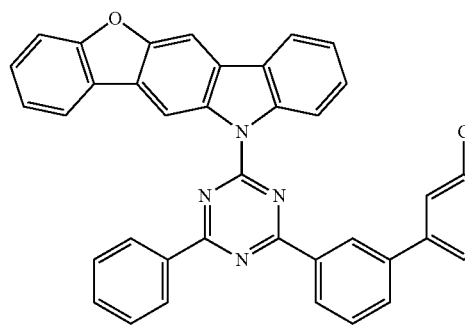 |

-continued
H2-287
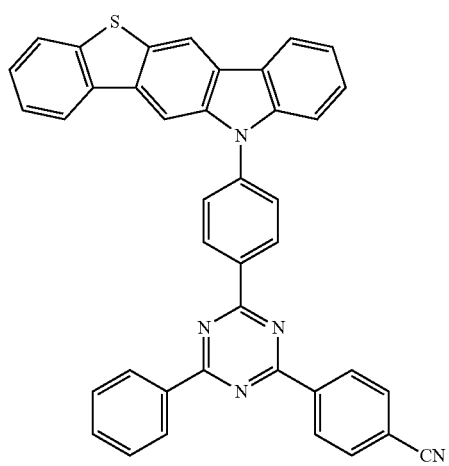
H2-288
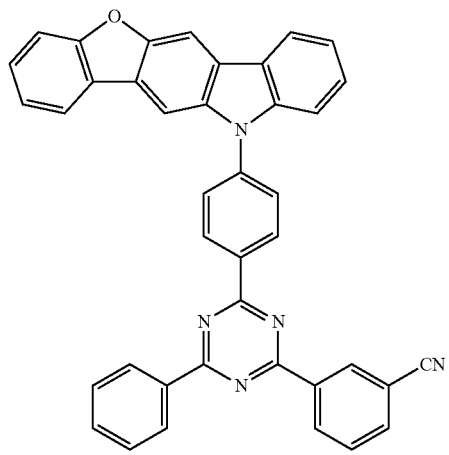
H2-289
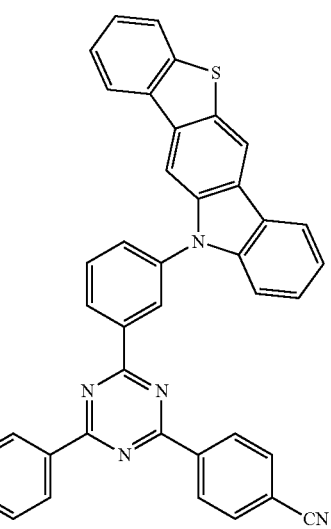
-continued
H2-290
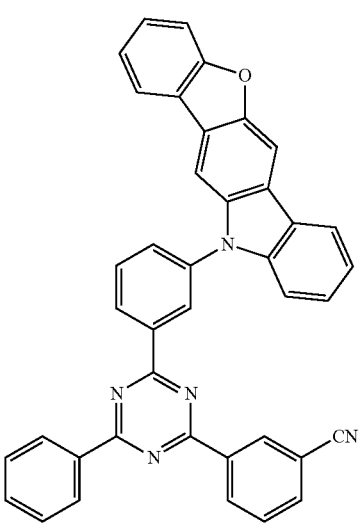
H2-291
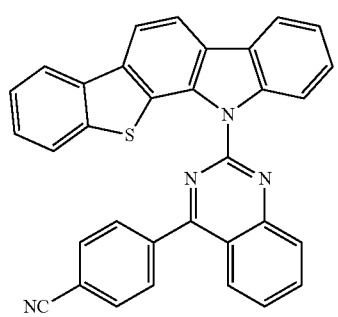
H2-292
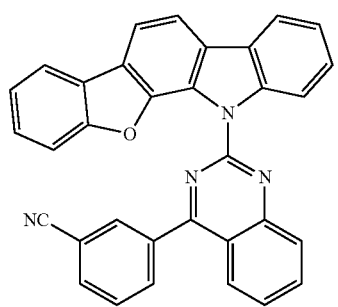
H2-293
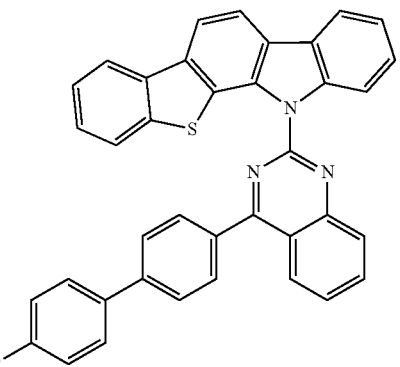

H2-294
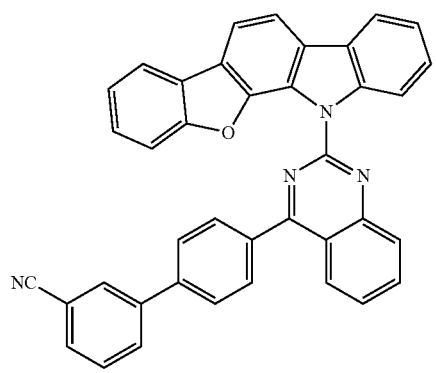
H2-295
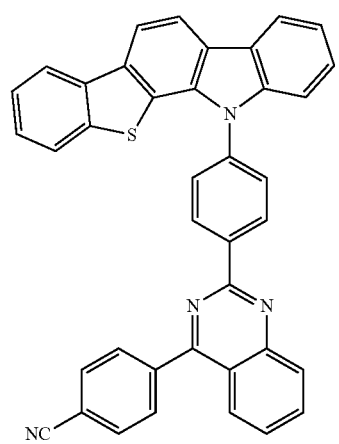
H2-296
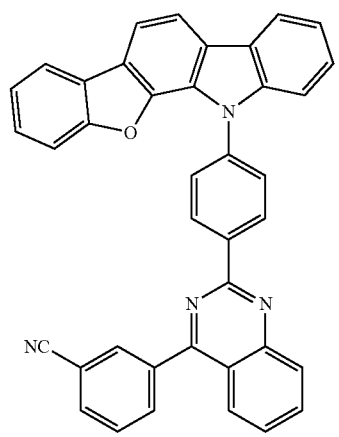
H2-297
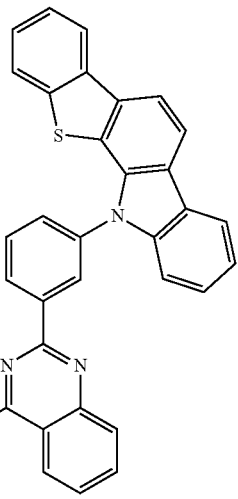
H2-298
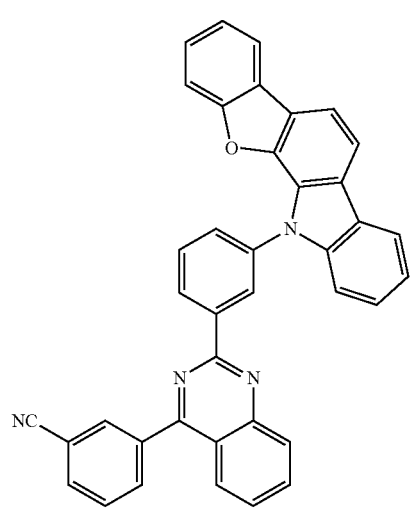
H2-299
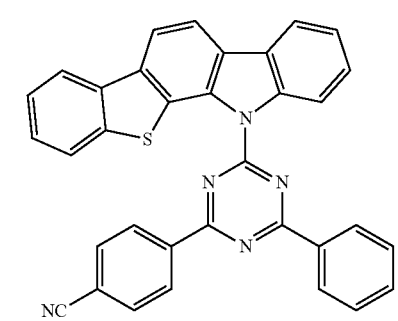
H2-300
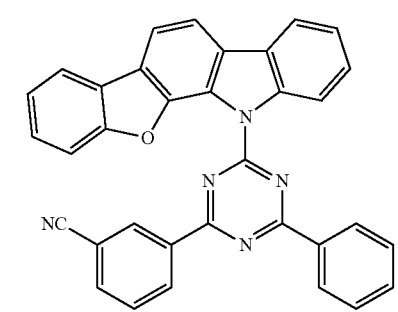

-continued
H2-301
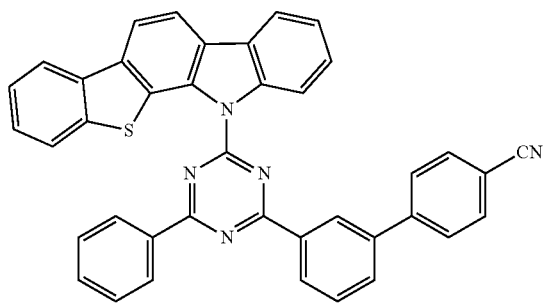
H2-302
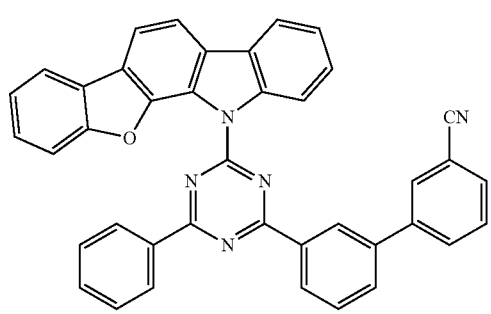
H2-303
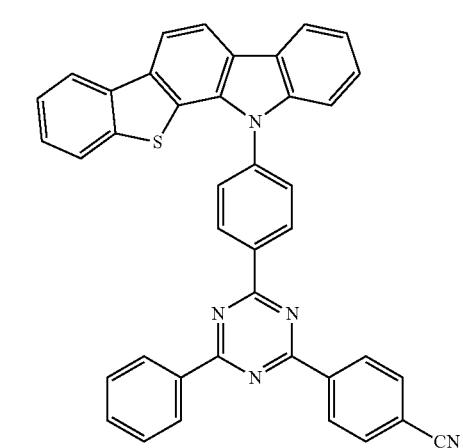
H2-304
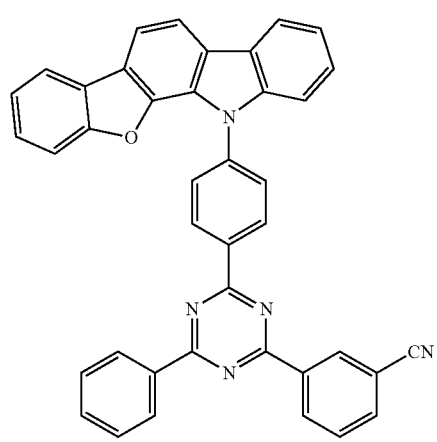
-continued
H2-305
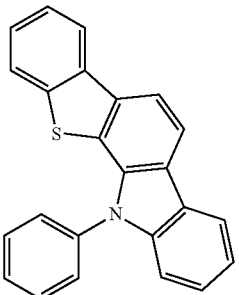
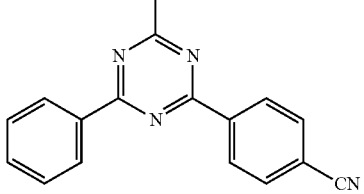
H2-306
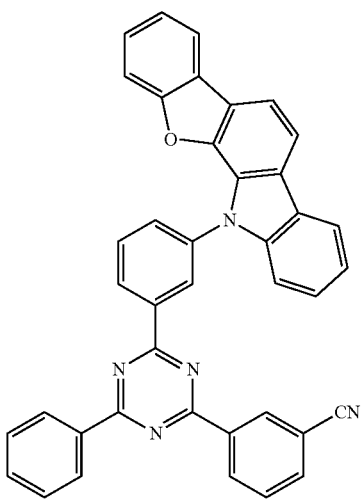
H2-307